United States Patent
Chan-Hui et al.

(10) Patent No.: US 12,410,243 B2
(45) Date of Patent: Sep. 9, 2025

(54) METHODS OF TREATING HIV-1 INFECTION UTILIZING BROADLY NEUTRALIZING HUMAN IMMUNODEFICIENCY VIRUS TYPE 1 (HIV-1) GP120-SPECIFIC MONOCLONAL ANTIBODIES

(71) Applicants: INTERNATIONAL AIDS VACCINE INITIATIVE, INC., New York, NY (US); THE SCRIPPS RESEARCH INSTITUTE, La Jolla, CA (US); THERACLONE SCIENCES INC., Seattle, WA (US)

(72) Inventors: Po-Ying Chan-Hui, Bellevue, WA (US); Katherine Doores, San Diego, CA (US); Michael Huber, Zurich (CH); Stephen Kaminsky, Bronx, NY (US); Steven Frey, Redmond, WA (US); Ole Olsen, Everett, WA (US); Jennifer Mitcham, Redmond, WA (US); Matthew Moyle, Redmond, WA (US); Sanjay K. Phogat, Frederick, MD (US); Dennis R. Burton, La Jolla, CA (US); Laura Majorie Walker, San Diego, CA (US); Pascal Raymond Georges Poignard, San Diego, CA (US); Wayne Koff, Stony Brook, NY (US); Melissa Danielle De Jean De St. Marcel Simek-Lemos, Brooklyn, NY (US)

(73) Assignees: International AIDS Vaccine Initiative, Inc., New York, NY (US); The Scripps Research Institute, La Jolla, CA (US); Theraclone Sciences Inc., Seattle, WA (US)

( * ) Notice: Subject to any disclaimer, the term of this patent is extended or adjusted under 35 U.S.C. 154(b) by 0 days.

(21) Appl. No.: 18/452,002

(22) Filed: Aug. 18, 2023

(65) Prior Publication Data
US 2024/0132578 A1  Apr. 25, 2024

Related U.S. Application Data

(63) Continuation of application No. 17/376,276, filed on Jul. 15, 2021, now Pat. No. 11,845,789, which is a continuation of application No. 16/591,175, filed on Oct. 2, 2019, now Pat. No. 11,319,362, which is a continuation of application No. 15/701,679, filed on
(Continued)

(51) Int. Cl.
C07K 16/10 (2006.01)
A61K 39/21 (2006.01)
A61K 39/00 (2006.01)
A61P 31/18 (2006.01)

(52) U.S. Cl.
CPC .......... *C07K 16/1063* (2013.01); *A61K 39/21* (2013.01); *C07K 16/1045* (2013.01); *A61K 2039/505* (2013.01); *A61P 31/18* (2018.01); *C07K 2317/21* (2013.01); *C07K 2317/33* (2013.01); *C07K 2317/34* (2013.01); *C07K 2317/51* (2013.01); *C07K 2317/515* (2013.01); *C07K 2317/56* (2013.01); *C07K 2317/565* (2013.01); *C07K 2317/76* (2013.01); *C07K 2317/92* (2013.01); *C12N 2740/16111* (2013.01); *C12N 2740/16122* (2013.01)

(58) Field of Classification Search
CPC ................................................ C07K 16/1063
See application file for complete search history.

(56) References Cited

U.S. PATENT DOCUMENTS

| 7,041,293 B1 | 5/2006 | Berman et al. |
| 8,840,890 B2 | 9/2014 | Lewis et al. |

(Continued)

FOREIGN PATENT DOCUMENTS

| WO | 2010/056898 | 5/2010 |
| WO | 2010/107939 | 9/2010 |

OTHER PUBLICATIONS

Kwong, P. D., et al., Oct. 2009, Mining the B Cell Repertoire for Broadly Neutralizing Monoclonal Antibodies to HIV-1, Cell Host & Microbe, 6:292-294.*

(Continued)

*Primary Examiner* — Jeffrey S Parkin
(74) *Attorney, Agent, or Firm* — Duane Morris LLP; Thomas J. Kowalski

(57) ABSTRACT

The invention provides a method for obtaining a broadly neutralizing antibody (bNab), including screening memory B cell cultures from a donor PBMC sample for neutralization activity against a plurality of HIV-1 species, cloning a memory B cell that exhibits broad neutralization activity; and rescuing a monoclonal antibody from that memory B cell culture. The resultant monoclonal antibodies may be characterized by their ability to selectively bind epitopes from the Env proteins in native or monomeric form, as well as to inhibit infection of HIV-1 species from a plurality of clades. Compositions containing human monoclonal anti-HIV antibodies used for prophylaxis, diagnosis and treatment of HIV infection are provided. Methods for generating such antibodies by immunization using epitopes from conserved regions within the variable loops of gp120 are provided. Immunogens for generating anti-HIV1 bNAbs are also provided. Furthermore, methods for vaccination using suitable epitopes are provided.

16 Claims, 111 Drawing Sheets
Specification includes a Sequence Listing.

Related U.S. Application Data

Sep. 12, 2017, now Pat. No. 10,836,811, which is a continuation of application No. 15/152,630, filed on May 12, 2016, now Pat. No. 10,087,239, which is a continuation of application No. 13/780,776, filed on Feb. 28, 2013, now Pat. No. 9,464,131, which is a continuation-in-part of application No. PCT/US2011/049880, filed on Aug. 31, 2011.

(60) Provisional application No. 61/515,548, filed on Aug. 5, 2011, provisional application No. 61/476,978, filed on Apr. 19, 2011, provisional application No. 61/386,940, filed on Sep. 27, 2010, provisional application No. 61/378,604, filed on Aug. 31, 2010.

(56) References Cited

U.S. PATENT DOCUMENTS

| | | | |
|---|---|---|---|
| 9,051,362 | B2 | 6/2015 | Chan et al. |
| 9,464,131 | B2 | 10/2016 | Chan-Hui et al. |
| 10,087,239 | B2 | 10/2018 | Chan-Hui et al. |
| 2008/0279879 | A1 | 11/2008 | Zolla-Pazner |
| 2010/0215691 | A1 | 8/2010 | Parks et al. |
| 2011/0044994 | A1 | 2/2011 | Chan et al. |
| 2011/0223615 | A1 | 9/2011 | Lewis et al. |

OTHER PUBLICATIONS

Brown, et al., Tolerance to single, but not multiple, amino acid replacements in antibody VH CDR2, J. Immunol. (1996) 156:3285-3291.

Fanning, et al., Development of the immunoglobulin repertoire, Clin. Immunol. Immunopath. (1996) 79(1):1-14.

Koefoed et al., Molecular characterization of the circulating anti-HIV-1 gp120-specific B cell repertoire using antibody phage display libraries generated from pre-selected HIV-1 gp120 binding PBLs, J. Immunol. Methods (2005) 297:187-201.

Pejchal, et al., Structure and function of broadly reactive antibody PG16 reveal an H3 subdomain that mediates potent neutralization of HIV-1, Proceedings of the National Academy of Sciences (Jun. 2010) 107(25):11483-11488.

Walker, et al., Broad and Potent Neutralizing Antibodies from an African Donor Reveal a New HIV-1 Vaccine Target, Science, American Association for the Advance of Science (Sep. 2009).

Walker et al., Broad neutralization coverage of HIV by multiple highly potent antibodies, Nature (Sep. 2011) 477 (7365):466-470.

Walker, et al., Supporting Online Material for Broad and Potent Neutralizing Antibodies from an African Donor Reveal a New HIV-1 Vaccine Target, Science (Sep. 2009).

Winkler, et al., Changing the antigen binding specificity by single point mutations of an anti-p24 (HIV-1) antibody, J. Immunol. (2000) 165:4505-4514.

European Search Report dated Apr. 21, 2017, which issued during prosecution of European Application No. 16206293.

Supplementary European Search Report corresponding to EP 11822530.9 dated May 20, 2014.

Partial European Search Report dated Jun. 22, 2015, issued in EP Application No. 14004015.5.

Communication regarding extended EP Search Report corresponding to EP 11822530.9 dated May 20, 2014.

Devin Sok, et al., The Effects of Somatic Hypermutation on Neutralization and Binding in the PGT121 Family of Broadly Neutralizing HIV Antibodies, PLOS Pathogens (Nov. 2013) vol. 9, Issue 11, e1003754, p. 1-20.

Extended European Search Report dated Jul. 17, 2019 issued in EP Application No. 19156884.9.

Franchini, G., and M. L. Bosch, Genetic relatedness of the human immunodeficiency viruses type 1 and 2 (HIV-1, HIV-2) and the simian immunodeficiency virus (SIV), Annal. NY Acad. Sci. (1989) 554(1):81-87.

Maartens, G., et al., HIV infection: epidemiology, pathogenesis, treatment, and prevention, The Lancet (Jul. 2014) 384:258-271.

Stevenson, M., HIV-1 pathogenesis, Nat. Med. (Jul. 2003) 9(7):853-860.

Linling He, et al., Toward a more accurate view of human B-cell repertoire by next-generation sequencing, unbiased repertoire capture and single-molecule barcoding, Scientific Reports vol. 4, No. 1, Oct. 27, 2014.

EP Examination Report issued Jul. 27, 2020 in corresponding Application No. EP2019156884.9.

Rosa, S. S., et al., mRNA vaccines manufacturing: Challenges and bottlenecks, Vaccine (2021) 39:2190-2200.

\* cited by examiner

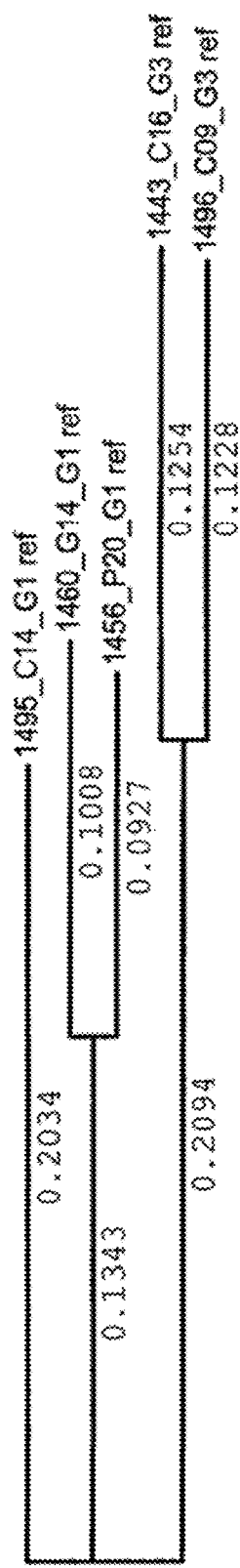
FIG. 1A    Heavy Chain Tree
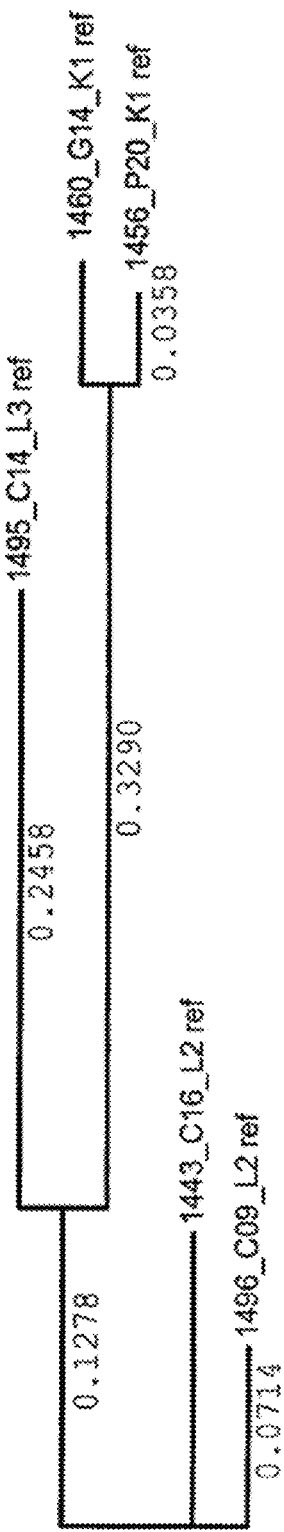
FIG. 1B    Light Chain Tree

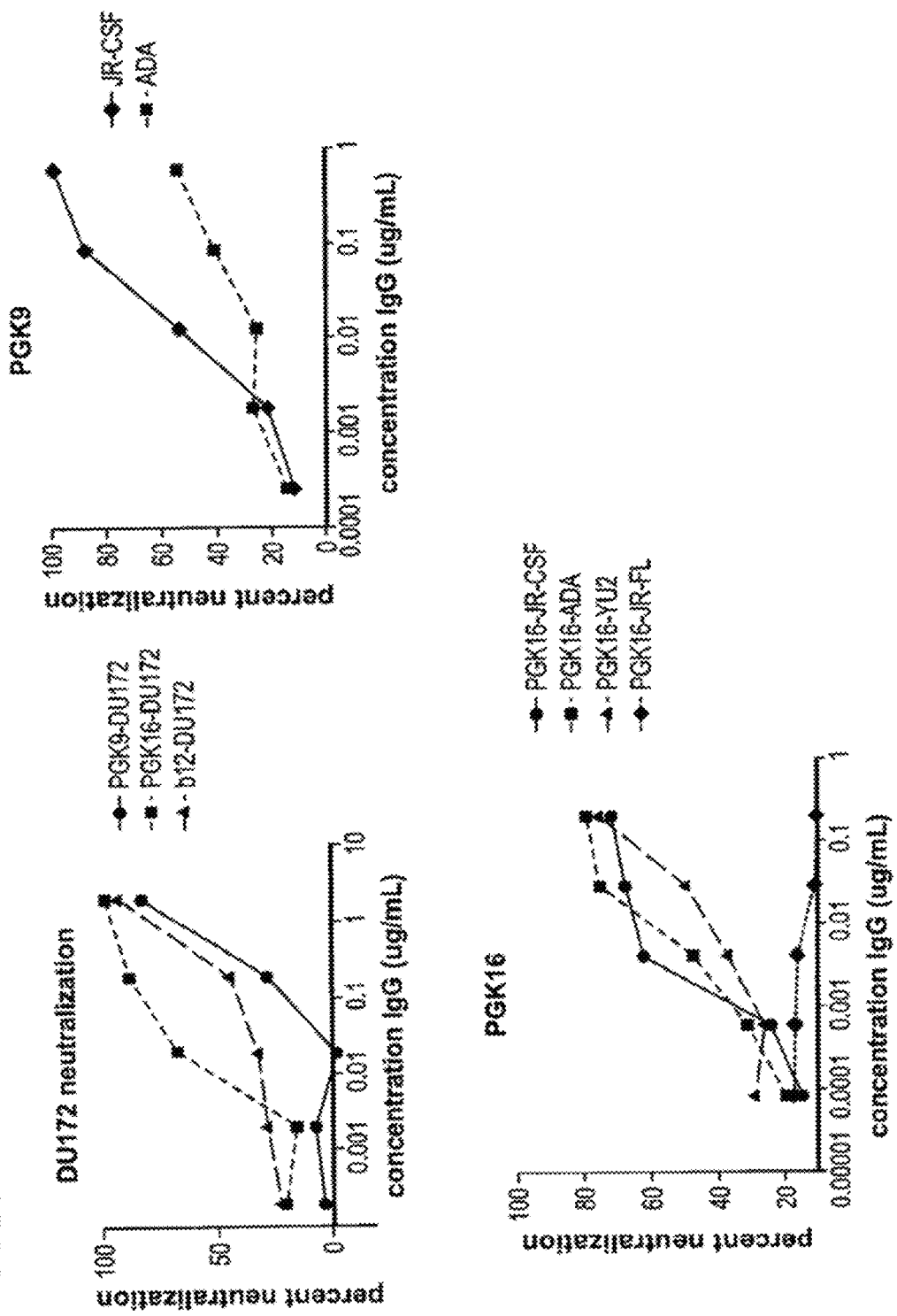
FIG. 4  PG9 and PG16 Neutralization Assays

FIG. 6 (continued)

— ● — PGK9-JR-FL gp120
— ■ — PGK16-JR-FL gp120
— ▲ — b12-JR-FL gp120
— ▼ — PGK16-JR-FL gp120 delta V1/V2
— ◆ — PGK16-JR-FL gp120
— ○ — b12-JR-FL gp120
— □ — PGK16-JR-FL gp120 deltaV3
— △ — PGK16-JR-FL gp120 deltaV3
— ▽ — b12-JR-FL gp120

FIG. 6 (continued)
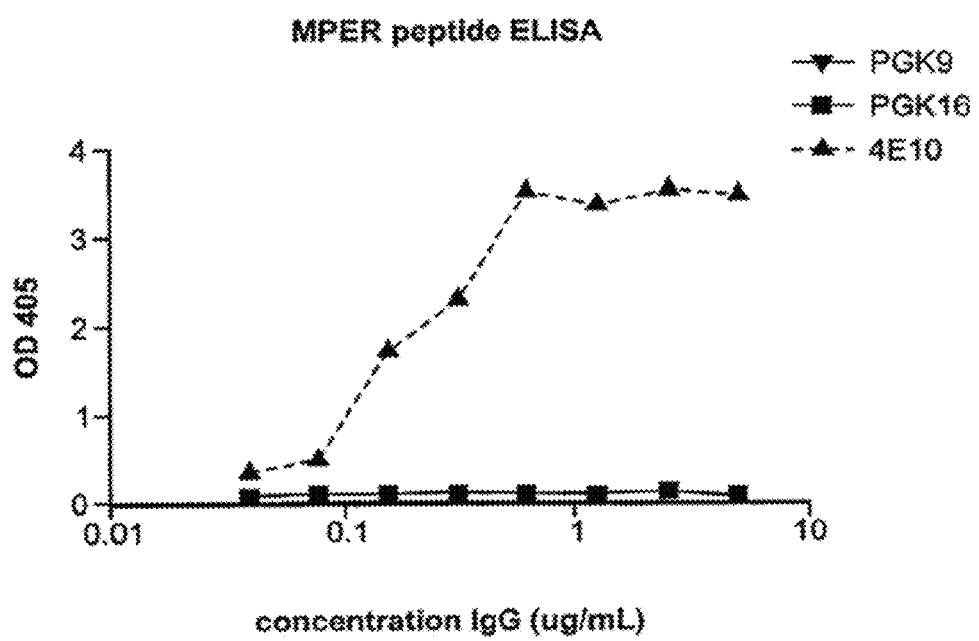
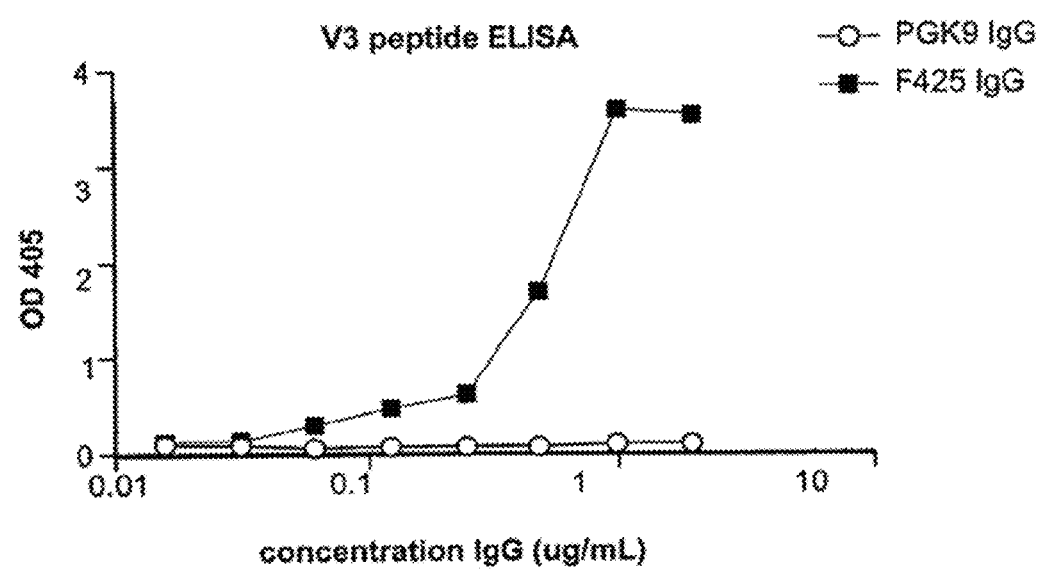

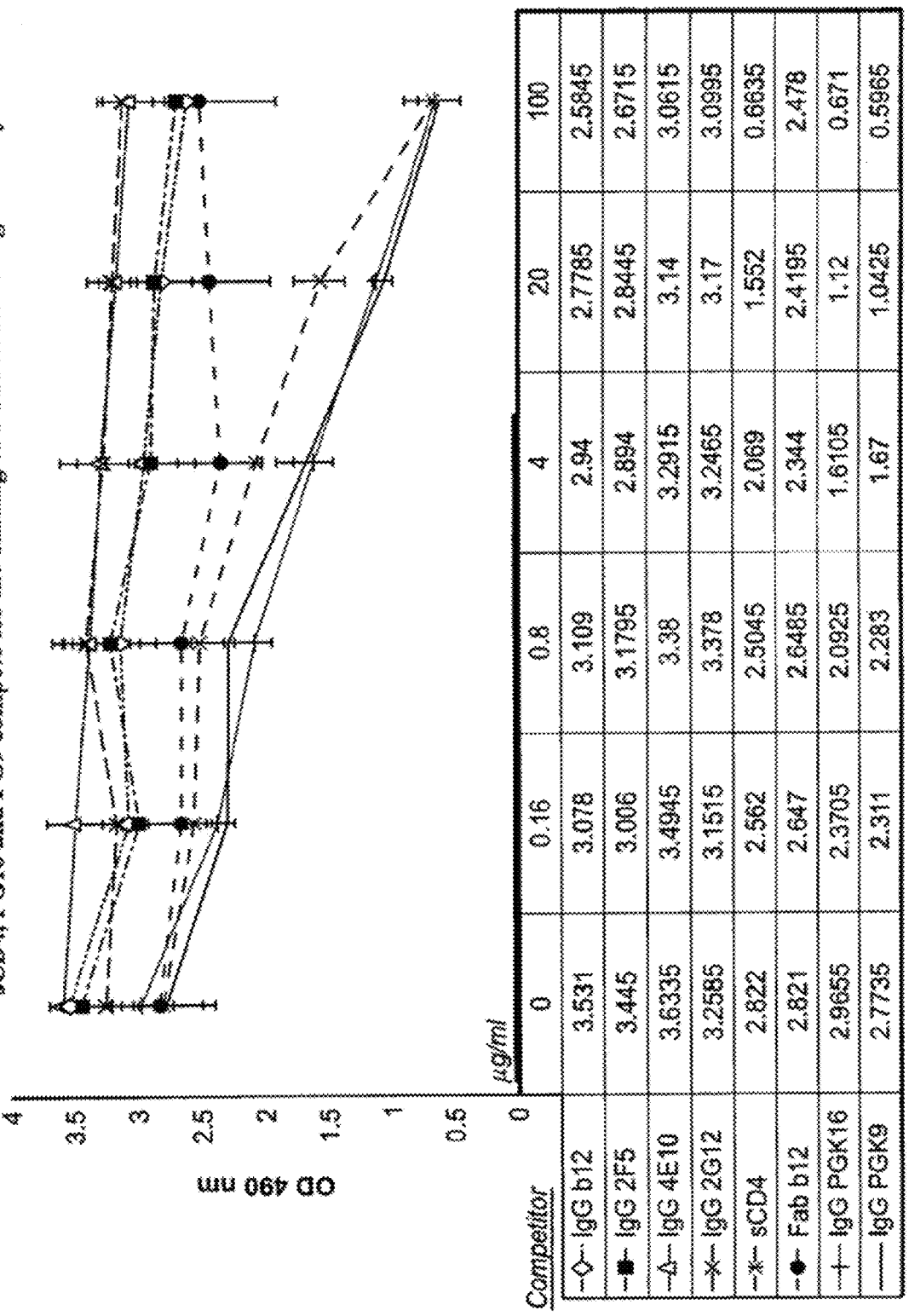

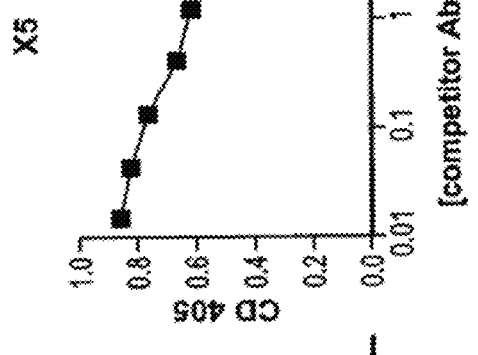
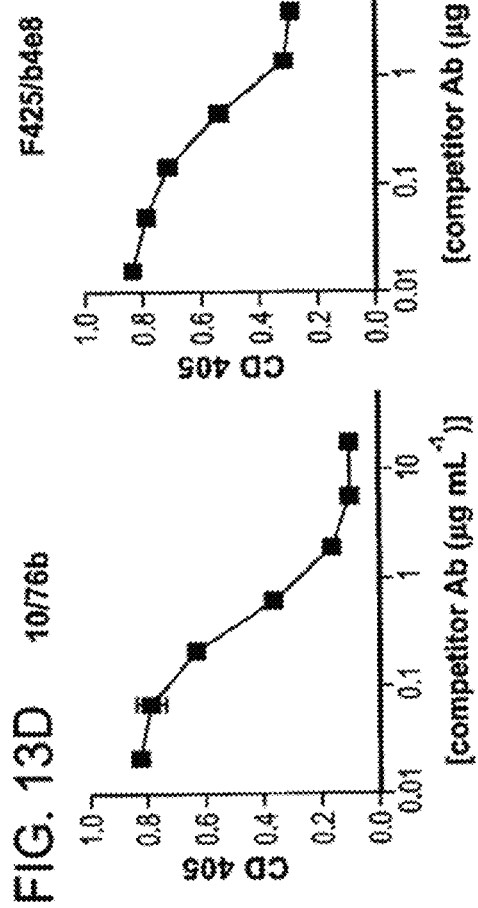
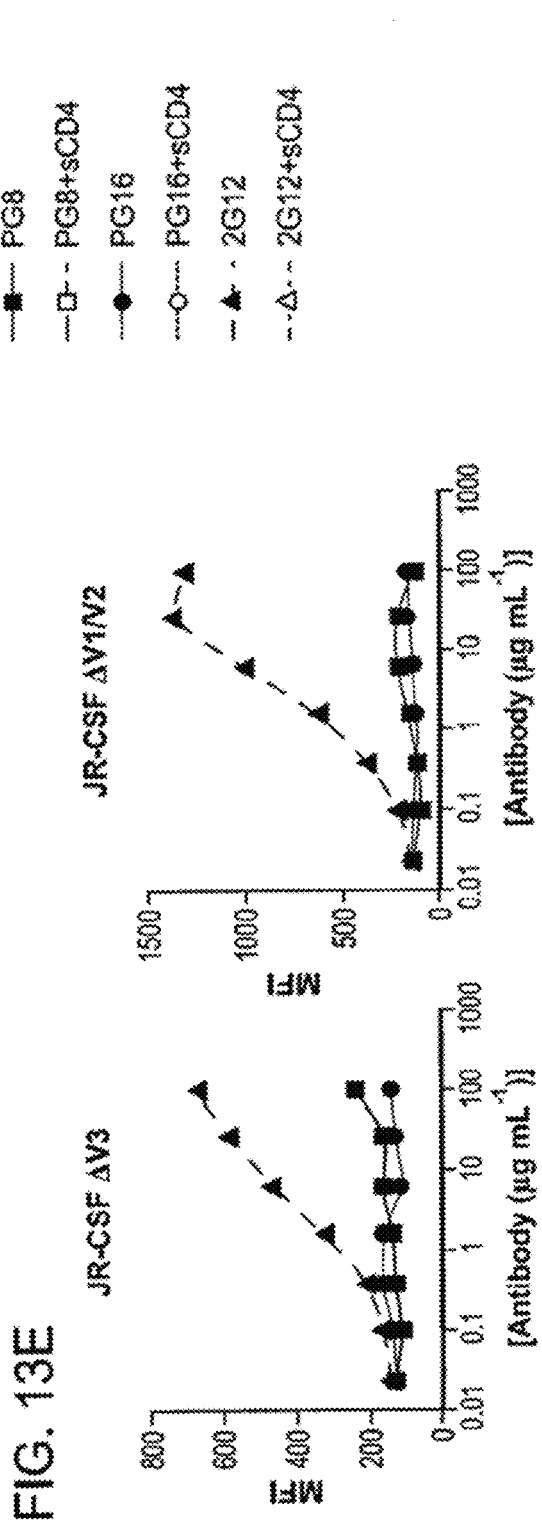
FIG. 13D
FIG. 13E

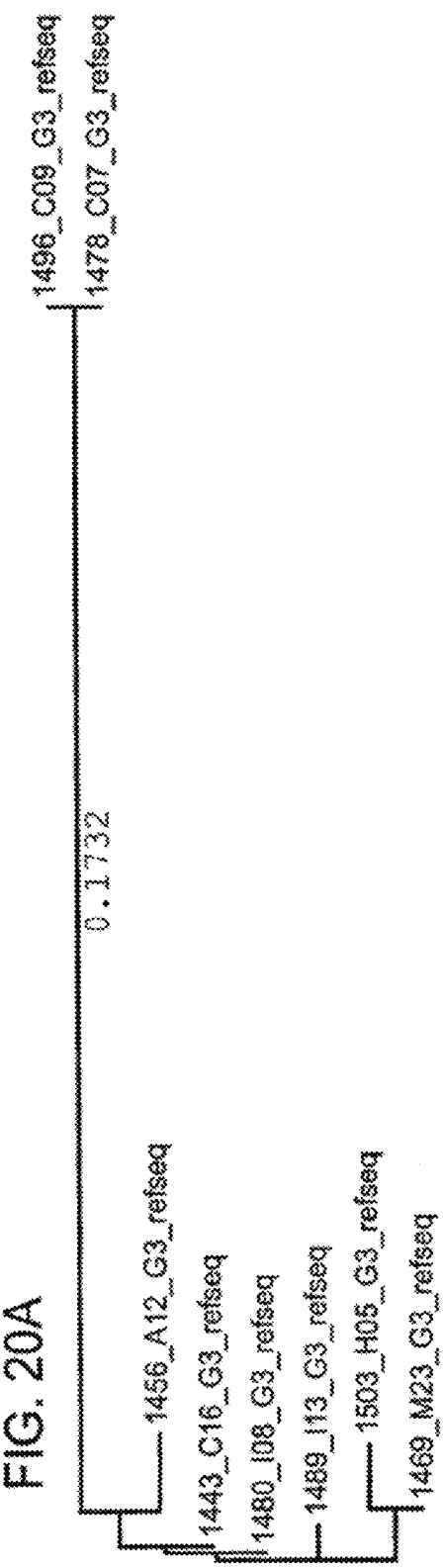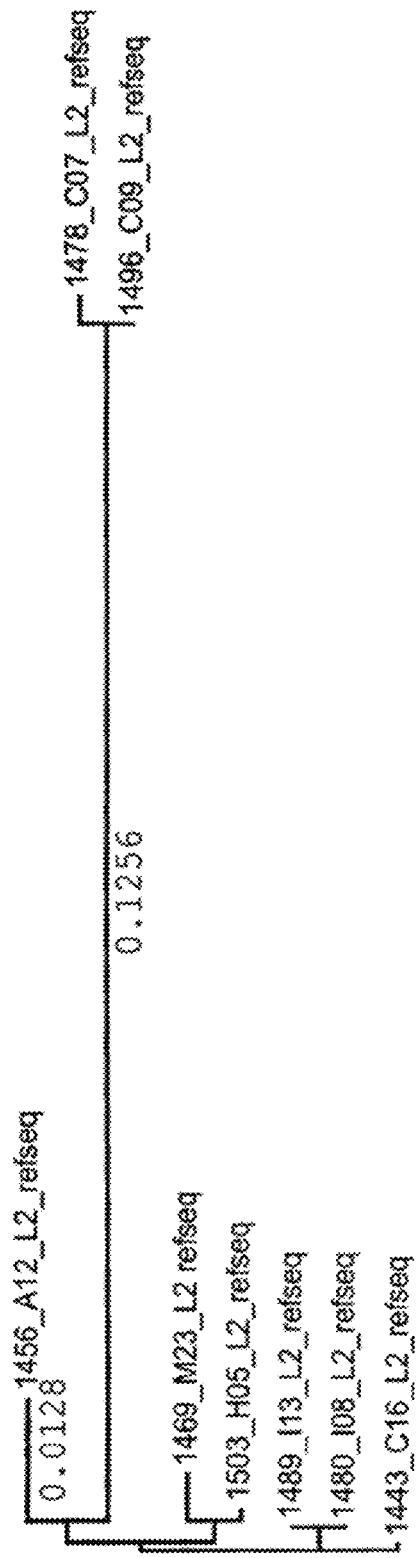
FIG. 20A
FIG. 20B

Number of HIV-Neutralizing Hits Detected in Primary Screening

Heavy Chain Variable Gene Relationship Tree

Light Chain Variable Gene Relationship Tree

FIGURE 44A
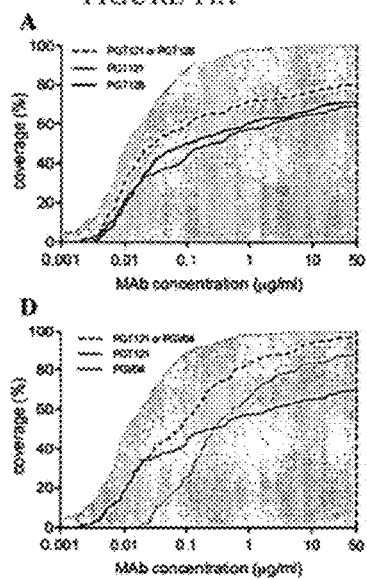
FIGURE 44B
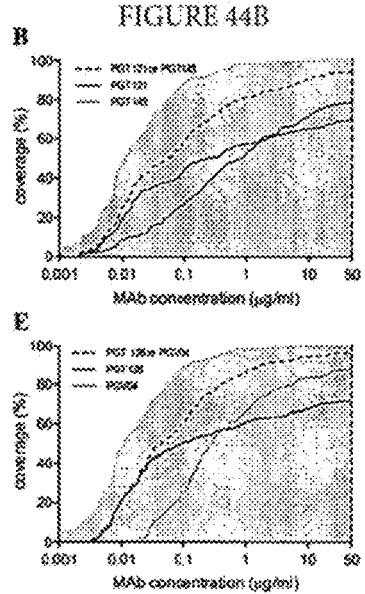
FIGURE 44C
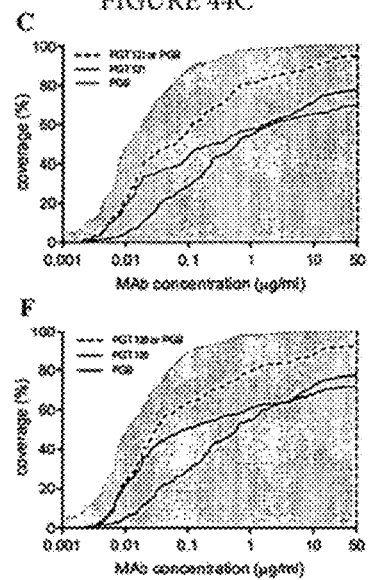
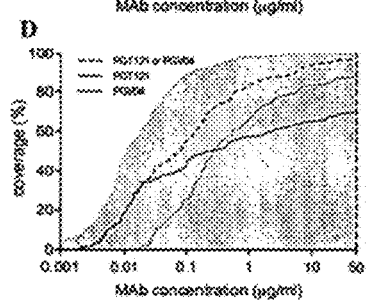
FIGURE 44D
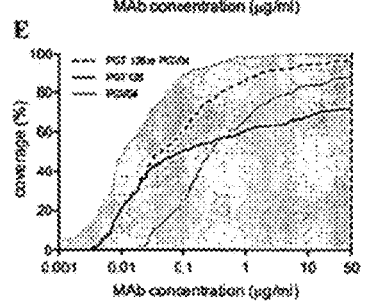
FIGURE 44E
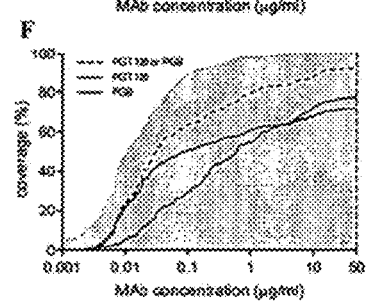
FIGURE 44F Kabat CDR sequences for the PG16 sister clones are highlighted in boxes (SEQ ID NO: 652-653).

Kabat CDR sequences for the PG16 sister clones are highlighted in boxes (SEQ ID NO: 654-655).

FIGURE 47

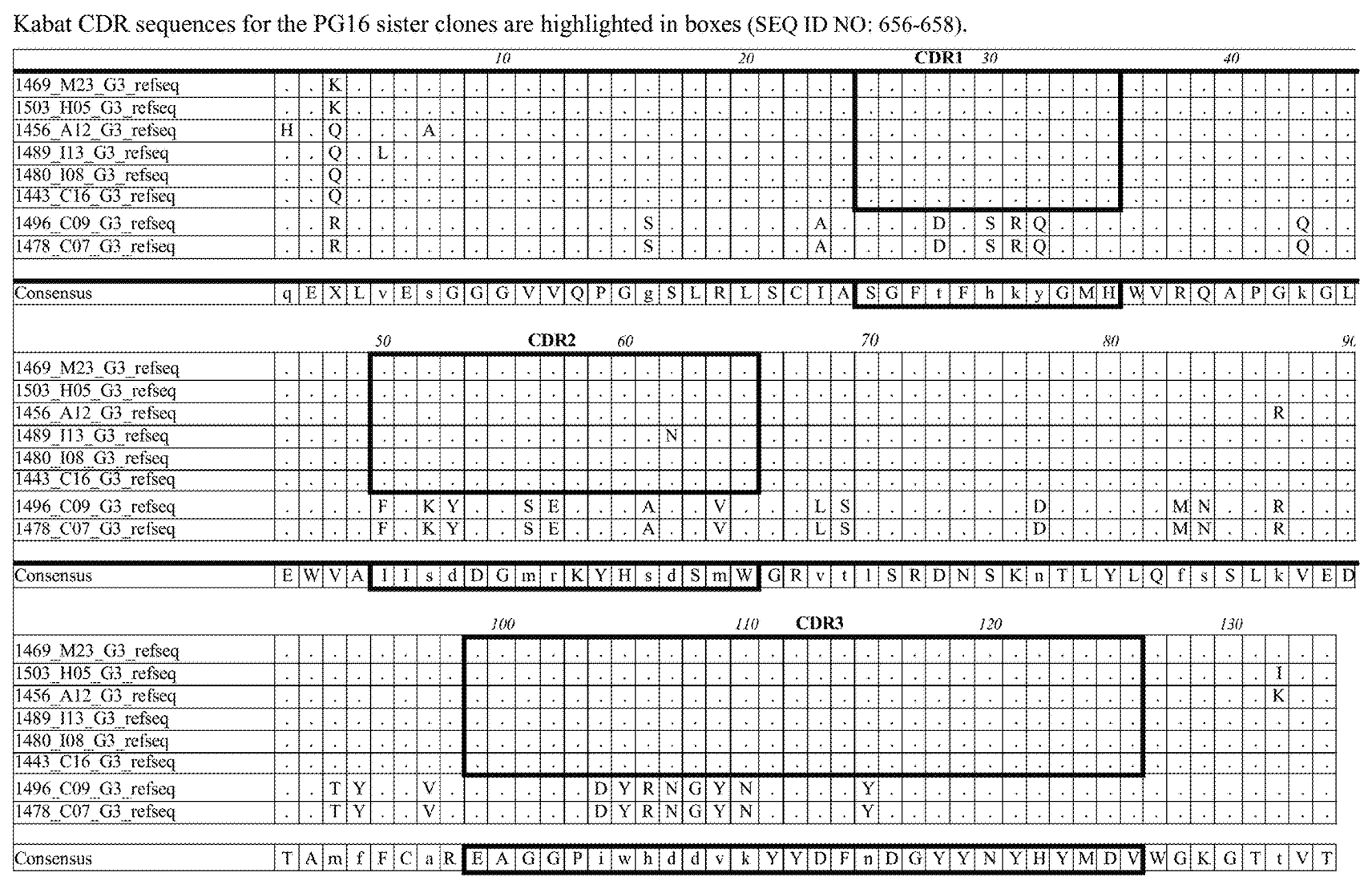

Kabat CDR sequences for the PG16 sister clones are highlighted in boxes (SEQ ID NO: 656-658).

FIGURE 48

Kabat CDR sequences for the PG16 sister clones are highlighted in black boxes (SEQ ID NO: 659-660).

| | | | | | | | | | | | | | | | | | | | | | | 10 | | | | | | | | | | | 20 | | | | | CDR1 | | | 30 | | | | | | | | | 40 | | | | | | | 50 | CDR2 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 1496_C09_L2_refseq | | | | | | | | | | | | | | | | | | | | | | | | | | | | | | | | | | | S | | | | | | | N | | | Y E | | | | | H | | | | | | | V I Y | | |
| 1478_C07_L2_refseq | | | | | | | | | | | | | | | | | | | | | | | | | | | | | | | | | | | S | | | | | | | N | | | Y E | | | | | H | | | | | | | V I Y | | |
| 1443_C16_L2_refseq | | | | | | | | | | | | | | | | | | | | | | | | | | | | | | | | | | | | | | | | | | | | | | | | | | | | | | | | | | | |
| 1480_I08_L2_refseq | | | | | | | | | | | | | | | | | | | | | | | | | | | | | | | | | | | | | | | | | | R | | | | | | | | | | | | | | | | |
| 1456_A12_L2_refseq | | | | | | | | | | | | | | | | | | | | | | | | | | | | | | | | | | | | | | | | | | | | | | | | | | | | | | | | | | | |
| 1469_M23_L2_refseq | | | | | | | | | | | | | | | | | | | | | | | | | | | | | | | | | | | | | | | | | | | | | | | | | | | | | | | | | R | | |
| 1489_I13_L2_refseq | | | | | | | | | | | | | | | | | | | | | | | | | | | | | | | | | | | | | | | | | | R | | | | | | | | | | | | | | | | |
| 1503_H05_L2_refseq | | | | | | | | | | | | | | | | | | | | | | | | | | | | | | | | | | | | | | | | | | R | | | | | | | | | | | | | | | | |
| Consensus | Q S A L T Q P A S V S G S P G Q t I T I S C N G T s D V G G f d s V S W Y Q Q s P G k A P K V m v f D V S |

| | | 60 | | | | | | | 70 | | | | | | | | 80 | | | | | | | 90 | | | | | | CDR3 100 | | | | | |
|---|---|---|---|---|---|---|---|---|---|---|---|---|---|---|---|---|---|---|---|---|---|---|---|---|---|---|---|---|---|---|---|---|---|---|---|---|
| 1496_C09_L2_refseq | K | | | V | | | | | | | | | | | | | | | | Q A | | | | | Y K | | | S T R R | | | V | | | L | |
| 1478_C07_L2_refseq | K | | | V | | | | | | | | | | | | | | | | Q A | | | | | Y K | | | S T R R | | | V | | | L | |
| 1443_C16_L2_refseq | | | | | | | | | | | | | | | | | | | | | | | | | | | | | | | | | | | | V |
| 1480_I08_L2_refseq | | | | M | | | | | | | | | | | | | | | | | | | | | | | | | | | | | | | | V |
| 1456_A12_L2_refseq | | | | | | | | | | | | | | | | | | | | | | | | | | | | | | | | | | | | L |
| 1469_M23_L2_refseq | | | | | | | | | | | | | | | | | | | | | | | | | | | | | | | | | | | | L |
| 1489_I13_L2_refseq | | | | | | | | | | | | | | | | | | | | | | | | | | | | | | | | | | | | V |
| 1503_H05_L2_refseq | | | | | | | | | | | | | | | | | | | | | | | | | | | | | | | | | | | | V |
| Consensus | h R P S G i S N R F S G S K S G N T A S L T I S G L h i E D E G D Y f C s S L T d r s h R j F G g g T K X T |

FIGURE 49

Antibody sequence characteristics.

Heavy Chain Sequences (SEQ ID NO: 143, 262, 171, 187, 203, 661, 336, 219, 350, 235, 252, 366, 279, 308, 380, 152, 164, 180, 196, 212, 228, 359, 245, 288, 389)

| Name | Donor | Putative V-gene | Putative J-gene | CDR3 length (amino acids) | CDR3 sequence (amino acids) | Somatic mutations (nucleotides) | Somatic mutations (amino acids) | Mutation frequency (nucleotides) | Mutation frequency (amino acids) | Insertions/Deletions (number of amino acids; positions) |
|---|---|---|---|---|---|---|---|---|---|---|
| PGT121 | 17 | IGHV4-59*01 | IGHJ6*03 | 24 | TLHGRAIYGMAPNRWFYFYMDV | 65 | 27 | 17% | 21% | |
| PGT122 | | | | | TKHGRRYGVVAFKEWFYFYMDV | 68 | 31 | 18% | 24% | |
| PGT123 | | | | | ALHGKNYGVALGLFYFYMDV | 79 | 35 | 21% | 27% | |
| PGT125 | 36 | IGHV4-39*07 | IGHJ3*02 | 19 | FDGEVLVNHWPKPAWVDL | 75 | 38 | 20% | 27% | +6 in CDR2 |
| PGT126 | | | | | FDGEVLVHDWPKPAWVDL | 67 | 30 | 17% | 23% | +6 in CDR2 |
| PGT127 | | | | | FGGEVVYEDWRPAWVDL | 58 | 30 | 15% | 23% | +6 in CDR2 |
| PGT128 | | | | | PGGEVLRYDWPKPAWVDL | 73 | 36 | 18% | 23% | +6 in CDR2 |
| PGT130 | | | | | SGGDLIYYEWQKPHWFSP | 83 | 42 | 22% | 14% | |
| PGT131 | | | | | SGGDLIYYEWNQKPHWFYP | 84 | 43 | 19% | 13% | |
| PGT135 | 39 | IGHV4-39*07 | IGHJ3*02 | 18 | HRHHDYRMLVEAGWFDV | 67 | 37 | 17% | 30% | +3 in CDR1 |
| PGT136 | | | | | HKYHDFRVVFVAGRWFDV | 68 | 33 | 15% | 25% | +5 in CDR3; +1 in CDR1 |
| PGT137 | | | | | HKYHDLNRVVRAGWFDP | 77 | 38 | 20% | 29% | +1 in CDR1 |
| PGT141 | 84 | IGHV1-3*01 | IGHJ6*02 | 31/32 | GSKHRLRDYVLYDDYGLNYQEWNDYLEFLDV | 51 | 29 | 12% | 22% | 0 or +1 in CDR3* |
| PGT142 | | | | | GSKHRLRDYVLYDDYGLNYQEWADYLEFLDV | 51 | 31 | 12% | 23% | 0 or +1 in CDR3* |
| PGT143 | | | | | GSKHRLRDYVLYDDYGLNYQEWNDYLEFLDV | 51 | 29 | 12% | 23% | 0 or +1 in CDR3* |
| PGT144 | | | | | GSKHRLRDYVLYDDYGLNQEWNDYLEFLDV | 59 | 32 | 14% | 24% | 0 or +1 in CDR3* |
| PGT145 | | | | | GSKHRLRDYTLYNEYGPTEEWGDYLATDV | 73 | 39 | 18% | 29% | -1 or 0 in CDR3* |

FIGURE 49 CONT'D

| Light Chain Sequences | | | | | | | | |
|---|---|---|---|---|---|---|---|---|
| Name | Donor | Putative V-gene[a] | Putative J-gene[a] | CDR3 length (amino acids)[b] | CDR3 sequence (amino acids) | Somatic mutations (nucleotides)[c] | Somatic mutations (amino acids)[c] | Mutation frequency (nucleotides)[c] | Mutation frequency (amino acids)[c] | Insertions/Deletions (number of amino acids/positions) |
| PGT121 | 17 | IGLV3-21*02 | IGLJ3*02 | 12 | HIWDSRVPIKWV | 56 | 31 | 18% | 30% | -7 in FR1;+1 in FR3 |
| PGT122 | | | | | HIWDSRPTKWV | 58 | 27 | 19% | 26% | -7 in FR1;+1 in FR3 |
| PGT123 | | | | | HTDARGGTSWV | 73 | 39 | 24% | 38% | -7 in FR1;+1 in FR3 |
| PGT125 | 36 | IGLV2-8*01 | IGLJ2*01 or IGLJ3*01 | 10 | GSLVGNWDV | 48 | 23 | 15% | 22% | |
| PGT126 | | | | | SSLVGNWDV | 28 | 14 | 9% | 13% | |
| PGT127 | | | | | SSLVGNWDV | 27 | 13 | 9% | 12% | |
| PGT128 | | | | | GSLVGNWDV | 37 | 14 | 9% | 14% | |
| PGT130 | | | | | SSLFGRWDV | 35 | 21 | 12% | 19% | |
| PGT131 | | | | | SSLSGRWDV | 44 | 23 | 12% | 22% | |
| PGT135 | 39 | IGKV3-15*01 | IGKJ1*01 | 9 | QQYKEWPIT | 51 | 29 | 16% | 28% | |
| PGT136 | | | | | QQYKEWPIT | 39 | 22 | 12% | 21% | |
| PGT137 | | | | | QQYKEWPIT | 35 | 19 | 11% | 18% | |
| PGT141 | 38 | IGKV2-28*01 or IGKV2D-28*01 | IGKJ1*01 | 9 | MQGLNEPWT | 46 | 23 | 14% | 23% | |
| PGT142 | | | | | MQGLNEPWT | 44 | 22 | 14% | 21% | |
| PGT143 | | | | | MQGLNEPWT | 46 | 24 | 14% | 22% | |
| PGT144 | | | | | MQGLNEPWT | 44 | 23 | 13% | 23% | |
| PGT145 | | | | | MQGLNEPWT | 52 | 26 | 16% | 24% | | a) Putative V- or J-gene of the common germline ancestor of each clonally related antibody cluster.
b) CDR3 lengths according to the Kabat definition.
c) Somatic mutations were counted over the whole variable region as nucleotides or amino acids differing from a putative germline sequence. For each cluster of clonally related antibodies, a germline sequence was composed of the putative V-gene, a consensus junction, the putative J-gene, and a consensus insertion where present. Sequences derived from 3' cloning primers were excluded from the frequency calculations.
d) Either an insertion in PGT141 to 144 or a deletion in PGT145.

Heavy Chain Variable Gene Alignment for PGT-121, PGT-122, PGT-123, PGT-125, PGT-126, PGT-130, PGT 135, and PGT-136. (SEQ ID NO: 662-673 from top to bottom)

Heavy Chain Variable Protein Alignment for PGT-121, PGT-122, PGT-123, PGT-125, PGT-126, PGT-130, PGT-135, and PGT-136. (SEQ ID NO: 674-684 from top to bottom)

| Sequence | 1–50 | 51–100 |
|---|---|---|
| PGT-121 4838 L96_VH | QMQLQESGPGLVKPSETLSLTCSVSGASI\*\*\*\*\*DSYWSWIRRSPGK | GLEWIGYVHKSG\*\*\*\*\*DTNYSPSLKSRVNLSLDTSKNQVSLSLYAATA |
| PGT-121 4873 E03_VH | QMQLQESGPGLVKPSETLSLTCSVSGASI\*\*\*\*\*DSYWSWIRRSPGK | GLEWIGYVHKSG\*\*\*\*\*DTNYSPSLKSRVNLSLDTSKNQVSLSLYAATA |
| PGT-122 4877 D15_VH | QVHLQESGPGLVKPSETLSLTCSVSGASI\*\*\*\*\*DNYWSWIRQPLGK | QPEWIGYVBDSG\*\*\*\*\*DTNYIPSLKSRVHLSLDKSKNLVSLRLTGVTA |
| PGT-123 4855 P08_VH | QLHLQESGPGLVKPPETLSLTCSVSGASIN\*\*\*\*\*DAYWSWIRQSPGK | RPEWVGYVBHSG\*\*\*\*\*DTNYNPSLKRRVTFSLDTAKNEVASLKLVDLTA |
| PGT-126 5141 B17_VH | QPQLQESGPGLVEASETLSLTCTVSGDSTA\*\*\*\*\*ACDYFWGWVRQPPGK | GLEWIGGILSHCAGYYNTGWTIYHNPSLKSRLTISLDTPKNQVFLKLNSVTA |

CDR1 and CDR2 regions indicated.

FIGURE 52

Light Chain Variable Gene Alignment for PGT-121, PGT-122, PGT-123, PGT-125, PGT-126, PGT-130, PGT-135, and PGT-136. (SEQ ID NO: 685-697 from top to bottom)

Light Chain Variable Protein Alignment for PGT-121, PGT-122, PGT-123, PGT-125, PGT-126, PGT-130, PGT-135, and PGT-136. (SEQ ID NO: 698-706 from top to bottom)

FIGURE 53 (Cont'd)

| I | F | G | V | D | K | R | P | P | G | V | P | D | R | F | S | G | S | R | S | * | * | * | G | T | T | A | S | L | T | V | S | R | L | Q | T | D | D | E | A | V | Y | Y | C | G | S | L | V | G | N |

FIGURE 53 (Cont'd)

|  |  | 110 |  |
|---|---|---|---|
| PGT-121_4838_L06_VL | V P T K W | V F G G | G T T L T V L |
| PGT-121_4873_E03_VL | V P T K W | V F G G | G T T L T V L |
| PGT-122_4877_D15_VL | R P T N W | V F G E | G T T L T V L |
| PGT-123_4858_P08_VL | G G T N W | V F D R | G T T L T V L |
| PGT-126_5141_B17_VL | * * * W | D V I F G G | G T K L T V L |
| PGT-125_5123_A06_VL | * * * W | D V I F G G | G T T L T V L |
| PGT-130_5147_N06_VL | * * * W | D V V F G G | G T K L T V L |
| PGT-135_5343_B08_VL | * * * P | * * R T F G Q | G T K V D I K |
| PGT-135_5344_E16_VL | * * * P | * * R T F G Q | G T K V D I K |
| PGT-136_5329_C19_VL | * * * P | * * R T F G Q | G T K V D I K |
| PGT-136_5366_P21_VL | * * * P | * * R T F G Q | G T K Y D I K |
| Consensus | X p t X X X | F g X G T k | l t v l |

FIGURE 54

Heavy Chain Variable Gene Alignment for PGT-141, PGT-142, PGT-143, and PGT-144. (SEQ ID NO: 707-712 from top to bottom)

Heavy Chain Variable Protein Alignment for PGT-141, PGT-142, PGT-143, and PGT-144. (SEQ ID NO: 717-720 from top to bottom)

FIGURE 55 (Cont'd)

| | | | | | | | | | | | | | | 120 | | | | | | | | | | | 140 | |
|---|---|---|---|---|---|---|---|---|---|---|---|---|---|---|---|---|---|---|---|---|---|---|---|---|---|---|
| PGT-141 Translation of 4964_G22_G1_refseq | W | N | D | Y | L | E | F | L | D | V | W | G | H | G | T | A | V | T | V | S | S |
| PGT-141 Translation of 4983_K13_G1_refseq | W | N | D | Y | L | L | F | L | D | V | W | G | H | G | T | A | V | T | V | S | S |
| PGT-142 Translation of 4995_E20_G1_refseq | W | N | D | Y | L | E | F | L | D | V | W | G | H | G | T | A | V | T | V | S | S |
| PGT-143 Translation of 4989_N08_G1_refseq | W | N | D | Y | L | E | F | L | D | V | W | G | H | G | T | A | I | V | V | S | S |
| PGT-144 Translation of 4977_K23_G1_refseq | W | N | D | Y | L | E | F | L | D | V | W | G | H | G | T | A | V | T | V | S | S |
| Consensus | W | N | D | Y | L | E | F | L | D | V | W | G | H | G | T | A | V | T | V | S | S |

FIGURE 56

Light Chain Variable Gene Alignment for PGT-141, PGT 142, PGT-143, and PGT-144. (SEQ ID NO: 713-716 from top to bottom).

Light Chain Variable Protein Alignment for PGT-141, PGT 142, PGT-143, and PGT-144. (SEQ ID NO: 721-724 from top to bottom).

METHODS OF TREATING HIV-1 INFECTION UTILIZING BROADLY NEUTRALIZING HUMAN IMMUNODEFICIENCY VIRUS TYPE 1 (HIV-1) GP120-SPECIFIC MONOCLONAL ANTIBODIES

RELATED APPLICATIONS AND INCORPORATION BY REFERENCE

This application is a continuation of U.S. application Ser. No. 17/376,276 filed Jul. 15, 2021, now allowed, which is a continuation of U.S. application Ser. No. 16/591,175 filed Oct. 2, 2019, now U.S. Pat. No. 11,319,362, which issued on May 3, 2022, which is a continuation of U.S. application Ser. No. 15/701,679 filed Sep. 12, 2017, now U.S. Pat. No. 10,836,811, which issued on Nov. 17, 2020, which is a continuation of U.S. application Ser. No. 15/152,630 filed May 12, 2016, now U.S. Pat. No. 10,087,239, which issued on Oct. 2, 2018, which is a continuation of U.S. application Ser. No. 13/780,776 filed Feb. 28, 2013, now U.S. Pat. No. 9,464,131, which issued on Oct. 11, 2016, which is a continuation-in-part application of international patent application Serial No. PCT/US2011/049880 filed Aug. 31, 2011, which published as PCT Publication No. WO 2012/030904 on Mar. 8, 2012, which claims priority to U.S. Provisional Patent Application Serial Nos. 61/378,604 filed Aug. 31, 2010, 61/386,940 filed Sep. 27, 2010, 61/476,978 filed Apr. 19, 2011 and 61/515,548 filed Aug. 5, 2011.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

GOVERNMENT SUPPORT

This invention was made with Government support under Grant Nos. AI033292 and AI084817 awarded by the National Institutes of Health. This invention was also made in part with Government Support under Grant No. GPH G 00 06 00006 00 awarded by the U.S. Agency for International Development ("USAID"). The Government has certain rights in the invention.

SEQUENCE STATEMENT

The instant application contains a Sequence Listing which has been submitted electronically in XML format and is hereby incorporated by reference in its entirety. Said XML copy, was amended on Jan. 9, 2023, is named Y7991_10001.xml and is 11,128,824 bytes in size.

FIELD OF THE INVENTION

The present invention relates generally to therapy, diagnosis and monitoring of human immunodeficiency virus (HIV) infection. The invention is more specifically related to human neutralizing monoclonal antibodies specific for HIV-1, such as broad and potent neutralizing monoclonal antibodies specific for HIV-1 and their manufacture and use. Broad neutralization suggests that the antibodies can neutralize HIV-1 isolates from different individuals. Such antibodies are useful in pharmaceutical compositions for the prevention and treatment of HIV, and for the diagnosis and monitoring of HIV infection and for design of HIV vaccine immunogens.

BACKGROUND OF THE INVENTION

AIDS was first reported in the United States in 1981 and has since become a major worldwide epidemic. AIDS is caused by the human immunodeficiency virus, or HIV. By killing or damaging cells of the body's immune system, HIV progressively destroys the body's ability to fight infections and certain cancers. People diagnosed with AIDS may get life-threatening diseases called opportunistic infections. These infections are caused by microbes such as viruses or bacteria that usually do not make healthy people sick. HIV is spread most often through unprotected sex with an infected partner. HIV also is spread through contact with infected blood. The human immunodeficiency virus (HIV) is the cause of acquired immune deficiency syndrome (AIDS) (Barre-Sinoussi, F., et al., 1983, Science 220:868-870; Gallo, R., et al., 1984, Science 224:500-503). There are currently 1.25 million people in the US infected with HIV-induced acquired immunodeficiency syndrome according to a Center for Disease Control report. The epidemic is growing most rapidly among minority populations and is a leading killer of African-American males ages 25 to 44. According, AIDS affects nearly seven times more African Americans and three times more Hispanics than whites. In recent years, an increasing number of African-American women and children are being affected by HIV/AIDS. With over 40 million people infected worldwide, the current global HIV pandemic ranks among the greatest infectious disease scourges in human history.

There is therefore a need for the efficient identification and production of neutralizing antibodies effective against multiple clades and strains of HIV as well as the elucidation of the target and antigenic determinants to which such antibodies bind.

Citation or identification of any document in this application is not an admission that such document is available as prior art to the present invention.

SUMMARY OF THE INVENTION

The present invention provides a novel method for isolating potent, broadly neutralizing monoclonal antibodies against HIV. Peripheral Blood Mononuclear Cells (PBMCs) are obtained from an HIV-infected donor selected for HIV-1 neutralizing activity in the plasma, and memory B cells are isolated for culture in vitro. The B cell culture supernatants may then be screened by a primary neutralization assay in a high throughput format, and B cell cultures exhibiting neutralizing activity may be selected for rescue of monoclonal antibodies. It is surprisingly observed that neutralizing antibodies obtained by this method do not always exhibit gp120 or gp41 binding at levels that correlate with neutralization activity. The method of the invention therefore allows identification of novel antibodies with cross-clade neutralization properties.

The present invention provides human monoclonal antibodies specifically directed against HIV. In certain embodiments, the invention provides human anti-HIV monoclonal antibodies including, but not limited to, 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_101 (PGT-137), 4993_K13 (PGT-141), 4995 E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and 6881_N05 (PGT-158) and sister clones thereof. For instance, an exemplary sister clone of the 1443_C16 (PG16) (TCN-116) antibody is the 1503 H05 (PG16) (TCN-119) antibody, the 1456 A12 (PG16) (TCN-117) antibody, the 1469 M23 (PG16) (TCN-118) antibody, the 1489_I13 (PG16) (TCN-120) antibody, or the 1480_I08 (PG16) antibody.

Specifically, the invention provides an isolated anti-HIV antibody, wherein said antibody may have heavy chain with three CDRs which may comprise an amino acid sequence selected from the group consisting of the amino acid sequences of KYGMH (SEQ ID NO: 88), LISDDGMRKYHSDSMWG (SEQ ID NO: 89), and EAGGPIWHDDVKYYDFNDGYYNYHYMDV (SEQ ID NO: 6), and a light chain with three CDRs that include an amino acid sequence selected from the group consisting of the amino acid sequences of NGTSSDVGGFDSVS (SEQ ID NO: 97), DVSHRPS (SEQ ID NO: 95), and SSLTDRSHRI (SEQ ID NO: 41).

The invention provides an isolated anti-HIV antibody, wherein said antibody may have a heavy chain with three CDRs which may comprise an amino acid sequence selected from the group consisting of the amino acid sequences of GFTFHK (SEQ ID NO: 266), LISDDGMRKY (SEQ ID NO: 267), and EAGGPIWHDDVKYYDFNDGYYNYHYMDV (SEQ ID NO: 6), and a light chain with three CDRs that include an amino acid sequence selected from the group consisting of the amino acid sequences of NGTSSDVGGFDSVS (SEQ ID NO: 97), DVSHRPS (SEQ ID NO: 95), and SSLTDRSHRI (SEQ ID NO: 41).

The invention provides an isolated anti-HIV antibody, wherein said antibody may have a heavy chain with three CDRs which may comprise an amino acid sequence selected from the group consisting of the amino acid sequences of KYGMH (SEQ ID NO: 88), LISDDGMRKYHSDSMWG (SEQ ID NO: 89), and EAGGPIWHDDVKYYDFNDGYYNYHYMDV (SEQ ID NO: 6), and a light chain with three CDRs that include an amino acid sequence selected from the group consisting of the amino acid sequences of NGTRSDVGGFDSVS (SEQ ID NO: 92), DVSHRPS (SEQ ID NO: 95), and SSLTDRSHRI (SEQ ID NO: 41).

The invention provides an isolated anti-HIV antibody, wherein said antibody may have a heavy chain with three CDRs which may comprise an amino acid sequence selected from the group consisting of the amino acid sequences of GFTFHK (SEQ ID NO: 266), LISDDGMRKY (SEQ ID NO: 267), and EAGGPIWHDDVKYYDFNDGYYNYHYMDV (SEQ ID NO: 6), and a light chain with three CDRs that include an amino acid sequence selected from the group consisting of the amino acid sequences of NGTRSDVGGFDSVS (SEQ ID NO: 92), DVSHRPS (SEQ ID NO: 95), and SSLTDRSHRI (SEQ ID NO: 41).

The invention provides an isolated anti-HIV antibody, wherein said antibody may have a heavy chain with three CDRs which may comprise an amino acid sequence selected from the group consisting of the amino acid sequences of KYGMH (SEQ ID NO: 88), LISDDGMRKYHSDSMWG (SEQ ID NO: 89), and EAGGPIWHDDVKYYDFNDGYYNYHYMDV (SEQ ID NO: 6), and a light chain with three CDRs that include an amino acid sequence selected from the group consisting of the amino acid sequences of NGTSRDVGGFDSVS (SEQ ID NO: 93), DVSHRPS (SEQ ID NO: 95), and SSLTDRSHRI (SEQ ID NO: 41).

The invention provides an isolated anti-HIV antibody, wherein said antibody may have a heavy chain with three CDRs which may comprise an amino acid sequence selected from the group consisting of the amino acid sequences of GFTFHK (SEQ ID NO: 266), LISDDGMRKY (SEQ ID NO: 267), and EAGGPIWHDDVKYYDFNDGYYNYHYMDV (SEQ ID NO: 6), and a light chain with three CDRs that include an amino acid sequence selected from the group consisting of the amino acid sequences of NGTSRDVGGFDSVS (SEQ ID NO: 93), DVSHRPS (SEQ ID NO: 95), and SSLTDRSHRI (SEQ ID NO: 41).

The invention provides an isolated anti-HIV antibody, wherein said antibody may have a heavy chain with three CDRs which may comprise an amino acid sequence selected from the group consisting of the amino acid sequences of KYGMH (SEQ ID NO: 88), LISDDGMRKYHSNSMWG (SEQ ID NO: 98), and EAGGPIWHDDVKYYDFNDGYYNYHYMDV (SEQ ID NO: 6), and a light chain with three CDRs that include an amino acid sequence selected from the group consisting of the amino acid sequences of NGTSSDVGGFDSVS (SEQ ID NO: 97), DVSHRPS (SEQ ID NO: 95), and SSLTDRSHRI (SEQ ID NO: 41).

The invention provides an isolated anti-HIV antibody, wherein said antibody may have a heavy chain with three CDRs which may comprise an amino acid sequence selected from the group consisting of the amino acid sequences of SYAFT (SEQ ID NO: 104), MVTPIFGEAKYSQRFEG (SEQ ID NO: 105), and DRRAVPIATDNWLDP (SEQ ID NO: 9), and a light chain with three CDRs that include an amino acid sequence selected from the group consisting of the amino acid sequences of RASQTINNYLN (SEQ ID NO: 107), GASNLQN (SEQ ID NO: 108), and QQSFSTPRT (SEQ ID NO: 42).

The invention provides an isolated anti-HIV antibody, wherein said antibody may have a heavy chain with three CDRs which may comprise an amino acid sequence selected from the group consisting of the amino acid sequences of GGTFSS (SEQ ID NO: 268), MVTPIFGEAK (SEQ ID NO: 269), and DRRAVPIATDNWLDP (SEQ ID NO: 9), and a light chain with three CDRs that include an amino acid sequence selected from the group consisting of the amino acid sequences of RASQTINNYLN (SEQ ID NO: 107), GASNLQN (SEQ ID NO: 108), and QQSFSTPRT (SEQ ID NO: 42).

The invention provides an isolated anti-HIV antibody, wherein said antibody may have a heavy chain with three CDRs which may comprise an amino acid sequence selected from the group consisting of the amino acid sequences of SYAFS (SEQ ID NO: 110), MITPVFGETKYAPRFQG (SEQ ID NO: 111), and DRRVVPMATDNWLDP (SEQ ID NO: 8), and a light chain with three CDRs that include an amino acid sequence selected from the group consisting of the amino acid sequences of RASQTIHTYLN (SEQ ID NO: 113), GASTLQS (SEQ ID NO: 114), and QQSYSTPRT (SEQ ID NO: 43).

The invention provides an isolated anti-HIV antibody, wherein said antibody may have a heavy chain with three CDRs which may comprise an amino acid sequence selected from the group consisting of the amino acid sequences of GGAFSS (SEQ ID NO: 270), MITPVFGETK (SEQ ID NO: 271), DRRVVPMATDNWLDP (SEQ ID NO: 8), and a light chain with three CDRs that include an amino acid sequence selected from the group consisting of the amino acid sequences of RASQTIHTYLN (SEQ ID NO: 113), GASTLQS (SEQ ID NO: 114), and QQSYSTPRT (SEQ ID NO: 43).

The invention provides an isolated anti-HIV antibody, wherein said antibody may have a heavy chain with three CDRs which may comprise an amino acid sequence selected from the group consisting of the amino acid sequences of DYYLH (SEQ ID NO: 116), LIDPENGEARYAEKFQG (SEQ ID NO: 117), GAVGADSGSWFDP (SEQ ID NO: 10), and a light chain with three CDRs that include an amino acid sequence selected from the group consisting of the amino acid sequences of SGSKLGDKYVS (SEQ ID NO: 120), ENDRRPS (SEQ ID NO: 121), QAWETTTTFVF (SEQ ID NO: 44).

The invention provides an isolated anti-HIV antibody, wherein said antibody may have a heavy chain with three CDRs which may comprise an amino acid sequence selected from the group consisting of the amino acid sequences of GYSFID (SEQ ID NO: 102), LIDPENGEAR (SEQ ID NO: 103), GAVGADSGSWFDP (SEQ ID NO: 10), and a light chain with three CDRs that include an amino acid sequence selected from the group consisting of the amino acid sequences of SGSKLGDKYVS (SEQ ID NO: 120), ENDRRPS (SEQ ID NO: 121), QAWETTTTFVF (SEQ ID NO: 44).

The invention provides an isolated anti-HIV antibody, wherein said antibody may have a heavy chain with three CDRs which may comprise an amino acid sequence selected from the group consisting of the amino acid sequences of RQGMI-1 (SEQ ID NO: 123), FIKYDGSEKYHADSVWG (SEQ ID NO: 124), and EAGGPDYRNGY-NYYDFYDGYYNYHYMDV (SEQ ID NO: 7), and a light chain with three CDRs that include an amino acid sequence selected from the group consisting of the amino acid sequences of NGTSNDVGGYESVS (SEQ ID NO: 126), DVSKRPS (SEQ ID NO: 127), and KSLTSTRRRV (SEQ ID NO: 45).

The invention provides an isolated anti-HIV antibody, wherein said antibody may have a heavy chain with three CDRs which may comprise an amino acid sequence selected from the group consisting of the amino acid sequences of GFDFSR (SEQ ID NO: 118), FIKYDGSEKY (SEQ ID NO: 272), and EAGGPDYRNGYNYYDFYDGYYNYHYMDV (SEQ ID NO: 7), and a light chain with three CDRs that include an amino acid sequence selected from the group consisting of the amino acid sequences of NGTSNDVG-GYESVS (SEQ ID NO: 126), DVSKRPS (SEQ ID NO: 127), and KSLTSTRRRV (SEQ ID NO: 45).

The invention provides an isolated anti-HIV antibody, wherein said antibody may have a heavy chain with three CDRs including an amino acid sequence selected from the group consisting of the amino acid sequences of DSYWS (SEQ ID NO: 90), YVHKSGDTNYSPSLKS (SEQ ID NO: 265), TLHGRRIYGIVAFNEWFTYFYMDV (SEQ ID NO: 143), and a light chain with three CDRs that include an amino acid sequence selected from the group consisting of the amino acid sequences of GEKSLGSRAVQ (SEQ ID NO: 150), NNQDRPS (SEQ ID NO: 151), HIWDSRVPTKWV (SEQ ID NO: 152).

The invention provides an isolated anti-HIV antibody, wherein said antibody may have a heavy chain with three CDRs including an amino acid sequence selected from the group consisting of the amino acid sequences of GASISD (SEQ ID NO: 144), YVHKSGDTN (SEQ ID NO: 145), TLHGRRIYGIVAFNEWFTYFYMDV (SEQ ID NO: 143), and a light chain with three CDRs that include an amino acid sequence selected from the group consisting of the amino acid sequences of GEKSLGSRAVQ (SEQ ID NO: 150), NNQDRPS (SEQ ID NO: 151), HIWDSRVPTKWV (SEQ ID NO: 152).

The invention provides an isolated anti-HIV antibody, wherein said antibody may havea heavy chain with three CDRs including an amino acid sequence selected from the group consisting of the amino acid sequences of DNYWS (SEQ ID NO: 261), YVHDSGDTNYNPSLKS (SEQ ID NO: 157), and TKHGRRIYGVVAFKEWFTYFYMDV (SEQ ID NO: 262), and a light chain with three CDRs that include an amino acid sequence selected from the group consisting of the amino acid sequences of GEESLGSRSVI (SEQ ID NO: 162), NNNDRPS (SEQ ID NO: 163), and HIWDSRRPTNWV (SEQ ID NO: 164).

The invention provides an isolated anti-HIV antibody, wherein said antibody may have a heavy chain with three CDRs including an amino acid sequence selected from the group consisting of the amino acid sequences of GTLVRD (SEQ ID NO: 263), YVHDSGDTN (SEQ ID NO: 264), and TKHGRRIYGVVAFKEWFTYFYMDV (SEQ ID NO: 262), and a light chain with three CDRs that include an amino acid sequence selected from the group consisting of the amino acid sequences of GEESLGSRSVI (SEQ ID NO: 162), NNNDRPS (SEQ ID NO: 163), and HIWDSRRPTNWV (SEQ ID NO: 164).

The invention provides an isolated anti-HIV antibody, wherein said antibody may have a heavy chain with three CDRs including an amino acid sequence selected from the group consisting of the amino acid sequences of DAYWS (SEQ ID NO: 169), YVHHSGDTNYNPSLKR (SEQ ID NO: 170), and ALHGKRIYGIVALGELFTYFYMDV (SEQ ID NO: 171), and a light chain with three CDRs that include an amino acid sequence selected from the group consisting of the amino acid sequences of GKESIGSRAVQ (SEQ ID NO: 178), NNQDRPA (SEQ ID NO: 179), and HIYDARGGTNWV (SEQ ID NO: 180).

The invention provides an isolated anti-HIV antibody, wherein said antibody may have a heavy chain with three CDRs including an amino acid sequence selected from the group consisting of the amino acid sequences of GASIND (SEQ ID NO: 172), YVHHSGDTN (SEQ ID NO: 173), and ALHGKRIYGIVALGELFTYFYMDV (SEQ ID NO: 171), and a light chain with three CDRs that include an amino acid sequence selected from the group consisting of the amino acid sequences of GKESIGSRAVQ (SEQ ID NO: 178), NNQDRPA (SEQ ID NO: 179), and HIYDARGGTNWV (SEQ ID NO: 180).

The invention provides an isolated anti-HIV antibody, wherein said antibody may have a heavy chain with three CDRs including an amino acid sequence selected from the group consisting of the amino acid sequences of ACTYFWG (SEQ ID NO: 185), SLSHCQSFWGSGWTFHNPSLKS (SEQ ID NO: 186), and FDGEVLVYNHWPKPAWVDL (SEQ ID NO: 187), and a light chain with three CDRs that include an amino acid sequence selected from the group consisting of the amino acid sequences of NGTATNFVS (SEQ ID NO: 194), GVDKRPP (SEQ ID NO: 195), and GSLVGNWDVI (SEQ ID NO: 196).

The invention provides an isolated anti-HIV antibody, wherein said antibody may have a heavy chain with three CDRs including an amino acid sequence selected from the group consisting of the amino acid sequences of GESTGACT (SEQ ID NO: 188), SLSHCQSFWGSGWTF (SEQ ID NO: 189), and FDGEVLVYNHWPKPAWVDL (SEQ ID NO: 187), and a light chain with three CDRs that include an amino acid sequence selected from the group consisting of the amino acid sequences of NGTATNFVS (SEQ ID NO: 194), GVDKRPP (SEQ ID NO: 195), and GSLVGNWDVI (SEQ ID NO: 196).

The invention provides an isolated anti-HIV antibody, wherein said antibody may have a heavy chain with three CDRs including an amino acid sequence selected from the group consisting of the amino acid sequences of ACDYFWG (SEQ ID NO: 201), GLSHCAGYYNTGWT-YHNPSLKS (SEQ ID NO: 202), and FDGEVLVYHDWPKPAWVDL (SEQ ID NO: 203), and a light chain with three CDRs that include an amino acid sequence selected from the group consisting of the amino acid sequences of TGTSNRFVS (SEQ ID NO: 210), GVNKRPS (SEQ ID NO: 211), and SSLVGNWDVI (SEQ ID NO: 212).

The invention provides an isolated anti-HIV antibody, wherein said antibody may have a heavy chain with three CDRs including an amino acid sequence selected from the group consisting of the amino acid sequences of GDSTAACD (SEQ ID NO: 204), GLSHCAGYYNTGWTY (SEQ ID NO: 205), and FDGEVLVYHDWPKPAWVDL (SEQ ID NO: 203), and a light chain with three CDRs that include an amino acid sequence selected from the group consisting of the amino acid sequences of TGTSNRFVS (SEQ ID NO: 210), GVNKRPS (SEQ ID NO: 211), and SSLVGNWDVI (SEQ ID NO: 212).

The invention provides an isolated anti-HIV antibody, wherein said antibody may have a heavy chain with three CDRs including an amino acid sequence selected from the group consisting of the amino acid sequences of TGHYYWG (SEQ ID NO: 217), HIHYTTAVLHNPSLKS (SEQ ID NO: 218), and SGGDILYYYEWQKPHWFSP (SEQ ID NO: 219), and a light chain with three CDRs that include an amino acid sequence selected from the group consisting of the amino acid sequences of NGTSS-DIGGWNFVS (SEQ ID NO: 226), EVNKRPS (SEQ ID NO: 227), and SSLFGRWDVV (SEQ ID NO: 228).

The invention provides an isolated anti-HIV antibody, wherein said antibody may have a heavy chain with three CDRs including an amino acid sequence selected from the group consisting of the amino acid sequences of GES-INTGH (SEQ ID NO: 220), HIHYTTAVL (SEQ ID NO: 221), and SGGDILYYYEWQKPHWFSP (SEQ ID NO: 219), and a light chain with three CDRs that include an amino acid sequence selected from the group consisting of the amino acid sequences of NGTSSDIGGWNFVS (SEQ ID NO: 226), EVNKRPS (SEQ ID NO: 227), and SSLFGRWDVV (SEQ ID NO: 228).

The invention provides an isolated anti-HIV antibody, wherein said antibody may have a heavy chain with three CDRs including an amino acid sequence selected from the group consisting of the amino acid sequences of GGEWGDKDYHWG (SEQ ID NO: 233), SIHWRGTTHYKESLRR (SEQ ID NO: 234), and HRHHDVFMLVPIAGWFDV (SEQ ID NO: 235), and a light chain with three CDRs that include an amino acid sequence selected from the group consisting of the amino acid sequences of RASQNINKNLA (SEQ ID NO: 243), ETYSKIA (SEQ ID NO: 244), and QQYEEWPRT (SEQ ID NO: 245).

The invention provides an isolated anti-HIV antibody, wherein said antibody may have a heavy chain with three CDRs including an amino acid sequence selected from the group consisting of the amino acid sequences of GDSIR-GGEWGDKD (SEQ ID NO: 236), SIHWRGTTH (SEQ ID NO: 237), and HRHHDVFMLVPIAGWFDV (SEQ ID NO: 235), and a light chain with three CDRs that include an amino acid sequence selected from the group consisting of the amino acid sequences of RASQNINKNLA (SEQ ID NO: 243), ETYSKIA (SEQ ID NO: 244), and QQYEE-WPRT (SEQ ID NO: 245).

The invention provides an isolated anti-HIV antibody, wherein said antibody may have a heavy chain with three CDRs including an amino acid sequence selected from the group consisting of the amino acid sequences of GTDW-GENDFHYG (SEQ ID NO: 250), SIHWR-GRTTHYKTSFRS (SEQ ID NO: 251), HKYHDI-FRVVPVAGWFDP (SEQ ID NO: 252), and a light chain with three CDRs that include an amino acid sequence selected from the group consisting of the amino acid sequences of RASQNVKNNLA (SEQ ID NO: 259), DAS-SRAG (SEQ ID NO: 260), QQYEEWPRT (SEQ ID NO: 245).

The invention provides an isolated anti-HIV antibody, wherein said antibody may have a heavy chain with three CDRs including an amino acid sequence selected from the group consisting of the amino acid sequences of GGSMRGTDWGEND (SEQ ID NO: 253), SIHWRGRTTH (SEQ ID NO: 254), HKYHDIFRVVPVAGWFDP (SEQ ID NO: 252), and a light chain with three CDRs that include an amino acid sequence selected from the group consisting of the amino acid sequences of RASQNVKNNLA (SEQ ID NO: 259), DASSRAG (SEQ ID NO: 260), QQYEEWPRT (SEQ ID NO: 245).

The invention provides an isolated anti-HIV antibody, wherein said antibody may have a heavy chain with three CDRs which may comprise an amino acid sequence selected from the group consisting of the amino acid sequences of KYDVH (SEQ ID NO: 277), WMSHEGDKTESAQRFKG (SEQ ID NO: 278), and GSKHRLRDYVLYDD-YGLINYQEWNDYLEFLDV (SEQ ID NO: 279), and a light chain with three CDRs that include an amino acid sequence selected from the group consisting of the amino acid sequences of SSTQSLRHSNGANYLA (SEQ ID NO: 286), LGSQRAS (SEQ ID NO: 287), and MQGLNRPWT (SEQ ID NO: 288).

The invention provides an isolated anti-HIV antibody, wherein said antibody may have a heavy chain with three CDRs which may comprise an amino acid sequence selected from the group consisting of the amino acid sequences of GNTFSK (SEQ ID NO: 280), WMSHEGDKTE (SEQ ID NO: 281), GSKHRLRDYVLYDDYGLINYQEWNDYLE-FLDV (SEQ ID NO: 279), and a light chain with three CDRs that include an amino acid sequence selected from the group consisting of the amino acid sequences of SSTQSLRHSN-GANYLA (SEQ ID NO: 286), LGSQRAS (SEQ ID NO: 287), and MQGLNRPWT (SEQ ID NO: 288).

The invention provides an isolated anti-HIV antibody, wherein said antibody may have a heavy chain with three CDRs which may comprise an amino acid sequence selected from the group consisting of the amino acid sequences of KYDVH (SEQ ID NO: 277), WISHERDKTESAQRFKG (SEQ ID NO: 293), GSKHRLRDYVLYDD-YGLINYQEWNDYLEFLDV (SEQ ID NO: 279), and a light chain with three CDRs that include an amino acid sequence selected from the group consisting of the amino acid sequences of SSTQSLRHSNGANYLA (SEQ ID NO: 286), LGSQRAS (SEQ ID NO: 287), and MQGLNRPWT (SEQ ID NO: 288).

The invention provides an isolated anti-HIV antibody, wherein said antibody may have a heavy chain with three CDRs which may comprise an amino acid sequence selected from the group consisting of the amino acid sequences of GNTFSK (SEQ ID NO: 280), WISHERDKTE (SEQ ID NO: 294), GSKHRLRDYVLYDDYGLINYQEWNDYLE-FLDV (SEQ ID NO: 279), and a light chain with three CDRs that include an amino acid sequence selected from the group consisting of the amino acid sequences of SSTQSLRHSN-GANYLA (SEQ ID NO: 286), LGSQRAS (SEQ ID NO: 287), and MQGLNRPWT (SEQ ID NO: 288).

The invention provides an isolated anti-HIV antibody, wherein said antibody may have a heavy chain with three CDRs which may comprise an amino acid sequence selected from the group consisting of the amino acid sequences of KYDVH (SEQ ID NO: 277), WMSHEGDKTESAQRFKG (SEQ ID NO: 278), and GSKHRLRDYVLYDD-YGLINYQEWNDYLEFLDV (SEQ ID NO: 279), and a light chain with three CDRs that include an amino acid sequence selected from the group consisting of the amino acid sequences of TSTQSLRHSNGANYLA (SEQ ID NO: 303), LGSQRAS (SEQ ID NO: 287), and MQGLNRPWT (SEQ ID NO: 288).

The invention provides an isolated anti-HIV antibody, wherein said antibody may have a heavy chain with three CDRs which may comprise an amino acid sequence selected from the group consisting of the amino acid sequences of GNTFSK (SEQ ID NO: 280), WMSHEGDKTE (SEQ ID NO: 281), and GSKHRLRDYVLYDDYGLINYQEWNDYLE-FLDV (SEQ ID NO: 279), and a light chain with three CDRs that include an amino acid sequence selected from the group consisting of the amino acid sequences of TSTQSLRHSN-GANYLA (SEQ ID NO: 303), LGSQRAS (SEQ ID NO: 287), and MQGLNRPWT (SEQ ID NO: 288).

The invention provides an isolated anti-HIV antibody, wherein said antibody may have a heavy chain with three CDRs which may comprise an amino acid sequence selected from the group consisting of the amino acid sequences of KYDVH (SEQ ID NO: 277), WMSHEGDKTESAQRFKG (SEQ ID NO: 278), GSKHRLRDYVLYDDYG-LINQQEWNDYLEFLDV (SEQ ID NO: 308), and a light chain with three CDRs that include an amino acid sequence selected from the group consisting of the amino acid sequences of TSTQSLRHSNGANYLA (SEQ ID NO: 303), LGSQRAS (SEQ ID NO: 287), and MQGLNRPWT (SEQ ID NO: 288).

The invention provides an isolated anti-HIV antibody, wherein said antibody may have a heavy chain with three CDRs which may comprise an amino acid sequence selected from the group consisting of the amino acid sequences of GNTFRK (SEQ ID NO: 309), WMSHEGDKTE (SEQ ID NO: 281), and GSKHRLRDYVLYDDYGLINQQEWN-DYLEFLDV (SEQ ID NO: 308), and a light chain with three CDRs that include an amino acid sequence selected from the group consisting of the amino acid sequences of TSTQSLRHSNGANYLA (SEQ ID NO: 303), LGSQRAS (SEQ ID NO: 287), and MQGLNRPWT (SEQ ID NO: 288).

The invention provides an isolated anti-HIV antibody, wherein said antibody may have a heavy chain with three CDRs which may comprise an amino acid sequence selected from the group consisting of the amino acid sequences of RCNYFWG (SEQ ID NO: 320), SLSHCRSYYNTDWT-YHNPSLKS (SEQ ID NO: 321), and FGGEVLVYRDWPKPAWVDL (SEQ ID NO: 322), and a light chain with three CDRs that include an amino acid sequence selected from the group consisting of the amino acid sequences of TGTSNNFVS (SEQ ID NO: 325), EVNKRPS (SEQ ID NO: 227), and SSLVGNWDVI (SEQ ID NO: 212).

The invention provides an isolated anti-HIV antibody, wherein said antibody may have a heavy chain with three CDRs which may comprise an amino acid sequence selected from the group consisting of the amino acid sequences of GDSTGRCN (SEQ ID NO: 323), SLSHCRSYYNTDWTY (SEQ ID NO: 324), and FGGEVLVYRDWPKPAWVDL (SEQ ID NO: 322), and a light chain with three CDRs that include an amino acid sequence selected from the group consisting of the amino acid sequences of TGTSNNFVS (SEQ ID NO: 325), EVNKRPS (SEQ ID NO: 227), and SSLVGNWDVI (SEQ ID NO: 212).

The invention provides an isolated anti-HIV antibody, wherein said antibody may have a heavy chain with three CDRs which may comprise an amino acid sequence selected from the group consisting of the amino acid sequences of ACNSFWG (SEQ ID NO: 326), SLSHCASYWNRGWT-YHNPSLKS (SEQ ID NO: 335), and FGGEVL-RYTDWPKPAWVDL (SEQ ID NO: 336), and a light chain with three CDRs that include an amino acid sequence selected from the group consisting of the amino acid sequences of TGTSNNFVS (SEQ ID NO: 325), (SEQ ID NO: 343), and (SEQ ID NO: 196).

The invention provides an isolated anti-HIV antibody, wherein said antibody may have a heavy chain with three CDRs which may comprise an amino acid sequence selected from the group consisting of the amino acid sequences of GDSTAACN (SEQ ID NO: 337), SLSHCASYWNRGWTY (SEQ ID NO: 338), and FGGEVLRYTDWPKPAWVDL (SEQ ID NO: 336), and a light chain with three CDRs that include an amino acid sequence selected from the group consisting of the amino acid sequences of TGTSNNFVS (SEQ ID NO: 325), DVNKRPS (SEQ ID NO: 343), and GSLVGNWDVI (SEQ ID NO: 196).

The invention provides an isolated anti-HIV antibody, wherein said antibody may have a heavy chain with three CDRs which may comprise an amino acid sequence selected from the group consisting of the amino acid sequences of TGHHYWG (SEQ ID NO: 348), HIHYNTAVLHNPALKS (SEQ ID NO: 349), and SGGDILYYIEWQKPHWFYP (SEQ ID NO: 350), and a light chain with three CDRs that include an amino acid sequence selected from the group consisting of the amino acid sequences of SGTGS-DIGSWNFVS (SEQ ID NO: 357), EVNRRRS (SEQ ID NO: 358), and SSLSGRWDIV (SEQ ID NO: 359).

The invention provides an isolated anti-HIV antibody, wherein said antibody may have a heavy chain with three CDRs which may comprise an amino acid sequence selected from the group consisting of the amino acid sequences of GDSINTGH (SEQ ID NO: 351), HIHYNTAVL (SEQ ID NO: 352), and SGGDILYYIEWQKPHWFYP (SEQ ID NO: 350), and a light chain with three CDRs that include an amino acid sequence selected from the group consisting of the amino acid sequences of SGTGSDIGSWNFVS (SEQ ID NO: 357), EVNRRRS (SEQ ID NO: 358), and SSLSGRWDIV (SEQ ID NO: 359).

The invention provides an isolated anti-HIV antibody, wherein said antibody may have a heavy chain with three CDRs which may comprise an amino acid sequence selected from the group consisting of the amino acid sequences of GGEWGDSDYHWG (SEQ ID NO: 364), SIHWRGTTHYNAPFRG (SEQ ID NO: 365), and HKYHDIVMVVPIAGWFDP (SEQ ID NO: 366), and a light chain with three CDRs that include an amino acid sequence selected from the group consisting of the amino acid sequences of RASQSVKNNLA (SEQ ID NO: 372), DTSSRAS (SEQ ID NO: 373), and QQYEEWPRT (SEQ ID NO: 245).

The invention provides an isolated anti-HIV antibody, wherein said antibody may have a heavy chain with three CDRs which may comprise an amino acid sequence selected from the group consisting of the amino acid sequences of GGSIRGGEWGDSD (SEQ ID NO: 367), SIHWRGTTH (SEQ ID NO: 237), and HKYHDIVMVVPIAGWFDP (SEQ ID NO: 366), and a light chain with three CDRs that include an amino acid sequence selected from the group consisting of the amino acid sequences of RASQSVKNNLA (SEQ ID NO: 372), DTSSRAS (SEQ ID NO: 373), and QQYEEWPRT (SEQ ID NO: 245).

The invention provides an isolated anti-HIV antibody, wherein said antibody may have a heavy chain with three CDRs which may comprise an amino acid sequence selected from the group consisting of the amino acid sequences of NHDVH (SEQ ID NO: 378), WMSHEGDKTGLAQKFQG (SEQ ID NO: 379), and GSKHRLRDYFLYNEYGPNYEEWGDYLATLDV (SEQ ID NO: 380), and a light chain with three CDRs that include an amino acid sequence selected from the group consisting of the amino acid sequences of KCSHSLQHSTGANYLA (SEQ ID NO: 387), LATHRAS (SEQ ID NO: 388), and MQGLHSPWT (SEQ ID NO: 389).

The invention provides an isolated anti-HIV antibody, wherein said antibody may have a heavy chain with three CDRs which may comprise an amino acid sequence selected from the group consisting of the amino acid sequences of GNSFSN (SEQ ID NO: 381), WMSHEGDKTG (SEQ ID NO: 382), and GSKHRLRDYFLYNEYGPNYEEWGDYLATLDV (SEQ ID NO: 380), and a light chain with three CDRs that include an amino acid sequence selected from the group consisting of the amino acid sequences of KCSHSLQHSTGANYLA (SEQ ID NO: 387), LATHRAS (SEQ ID NO: 388), and MQGLHSPWT (SEQ ID NO: 389).

The invention provides an isolated anti-HIV antibody, wherein said antibody may comprise a $V_H$_CDR1 region which may comprise the amino acid sequence of NYYWT (SEQ ID NO: 406); a $V_H$_CDR2 region which may comprise the amino acid sequence of YISDRETTTYNPSLNS (SEQ ID NO: 407); a $V_H$_CDR3 region which may comprise the amino acid sequence of ARRGQRIYGVVSFGEFFYYYYMDV (SEQ ID NO: 408); a $V_L$_CDR1 region which may comprise the amino acid sequence of GRQALGSRAVQ (SEQ ID NO: 415); a $V_L$ CDR2 region which may comprise the amino acid sequence of NNQDRPS (SEQ ID NO: 151); and a $V_L$_CDR3 region which may comprise the amino acid sequence of HMWDSRSGFSWS (SEQ ID NO: 416).

The invention provides an isolated anti-HIV antibody, wherein said antibody may comprise a $V_H$_CDR1 region which may comprise the amino acid sequence of GRFWS (SEQ ID NO: 421); a $V_H$_CDR2 region which may comprise the amino acid sequence of YFSDTDRSEYNPSLRS (SEQ ID NO: 422); a $V_H$_CDR3 region which may comprise the amino acid sequence of AQQGKRIYGIVSFGEFFYYYYMDA (SEQ ID NO: 423); a $V_L$_CDR1 region which may comprise the amino acid sequence of GERSRGSRAVQ (SEQ ID NO: 430); a $V_L$ CDR2 region which may comprise the amino acid sequence of NNQDRPA (SEQ ID NO: 179); and a $V_L$_CDR3 region which may comprise the amino acid sequence of HYWDSRSPISWI (SEQ ID NO: 431).

The invention provides an isolated anti-HIV antibody, wherein said antibody may comprise a $V_H$_CDR1 region which may comprise the amino acid sequence of GRFWS (SEQ ID NO: 421); a $V_H$_CDR2 region which may comprise the amino acid sequence of YFSDTDRSEYNPSLRS (SEQ ID NO: 422); a $V_H$_CDR3 region which may comprise the amino acid sequence of AQQGKRIYGIVSFGELFYYYYMDA (SEQ ID NO: 436); a $V_L$_CDR1 region which may comprise the amino acid sequence of GERSRGSRAVQ (SEQ ID NO: 430); a $V_L$ CDR2 region which may comprise the amino acid sequence of NNQDRPA (SEQ ID NO: 179); and a $V_L$_CDR3 region which may comprise the amino acid sequence of HYWDSRSPISWI (SEQ ID NO: 431).

The invention provides an isolated anti-HIV antibody, wherein said antibody may comprise a $V_H$_CDR1 region which may comprise the amino acid sequence of TGHHYWG (SEQ ID NO: 348); a $V_H$_CDR2 region which may comprise the amino acid sequence of HIHYNTAVLHNPALKS (SEQ ID NO: 349); a $V_H$_CDR3 region which may comprise the amino acid sequence of SGGDILYYNEWQKPHWFYP (SEQ ID NO: 445); a $V_L$_CDR1 region which may comprise the amino acid sequence of SGTASDIGSWNFVS (SEQ ID NO: 450); a $V_L$_CDR2 region which may comprise the amino acid sequence of EVNRRRS (SEQ ID NO: 358); and a $V_L$ CDR3 region which may comprise the amino acid sequence of SSLSGRWDIV (SEQ ID NO: 359).

The invention provides an isolated anti-HIV antibody, wherein said antibody may comprise a $V_H$_CDR1 region which may comprise the amino acid sequence of ACDYFWG (SEQ ID NO: 201); a $V_H$_CDR2 region which may comprise the amino acid sequence of SLSHCAGYYNSGWTYHNPSLKS (SEQ ID NO: 455); a $V_H$_CDR3 region which may comprise the amino acid sequence of FGGDVLVYHDWPKPAWVDL (SEQ ID NO: 456); a $V_L$_CDR1 region which may comprise the amino acid sequence of TGNINNFVS (SEQ ID NO: 458); a $V_L$ CDR2 region which may comprise the amino acid sequence of GVNKRPS (SEQ ID NO: 211); and a $V_L$_CDR3 region which may comprise the amino acid sequence of GSLAGNWDVV (SEQ ID NO: 459).

The invention provides an isolated anti-HIV antibody, wherein said antibody may comprise a $V_H$_CDR1 region which may comprise the amino acid sequence of GCDYFWG (SEQ ID NO: 464); a $V_H$_CDR2 region which may comprise the amino acid sequence of GLSHCAGYYNTGWTYHNPSLKS (SEQ ID NO: 202); a $V_H$_CDR3 region which may comprise the amino acid sequence of FDGEVLVYNDWPKPAWVDL (SEQ ID NO: 465); a $V_L$_CDR1 region which may comprise the amino acid sequence of TGTSNNFVS (SEQ ID NO: 325); a $V_L$ CDR2 region which may comprise the amino acid sequence of GVNKRPS (SEQ ID NO: 211); and a $V_L$_CDR3 region which may comprise the amino acid sequence of GSLVGNWDVI (SEQ ID NO: 196).

The invention provides an isolated anti-HIV antibody, wherein said antibody may comprise a $V_H$_CDR1 region which may comprise the amino acid sequence of KYPMY (SEQ ID NO: 475); a $V_H$_CDR2 region which may comprise the amino acid sequence of AISGDAWHVVYSNSVQG (SEQ ID NO: 476); a $V_H$_CDR3 region which may comprise the amino acid sequence of MFQESGPPRLDRWSGRNYYYYSGMDV (SEQ ID NO: 477); a $V_L$ CDR1 region which may comprise the amino acid sequence of KSSESLRQSNGKTSLY (SEQ ID NO: 484); a $V_L$_CDR2 region which may comprise the amino acid sequence of EVSNRFS (SEQ ID NO: 485); and a $V_L$_CDR3 region which may comprise the amino acid sequence of MQSKDFPLT (SEQ ID NO: 486).

The invention provides an isolated anti-HIV antibody, wherein said antibody may comprise a $V_H$_CDR1 region which may comprise the amino acid sequence of KYPMY (SEQ ID NO: 475); a $V_H$_CDR2 region which may comprise the amino acid sequence of AISADAWHVVYSGSVQG (SEQ ID NO: 491); a $V_H$_CDR3 region which may comprise the amino acid sequence of MFQESGPPRFDSWSGRNYYYYSGMDV (SEQ ID NO: 492); a $V_L$ CDR1 region which may comprise the amino acid sequence of KSSQSLRQSNGKTSLY (SEQ ID NO: 498); a $V_L$_CDR2 region which may comprise the amino acid sequence of EVSNRFS (SEQ ID NO: 485); and a $V_L$_CDR3 region which may comprise the amino acid sequence of (MQSKDFPLT (SEQ ID NO: 486).

The invention provides an isolated anti-HIV antibody, wherein said antibody may comprise a $V_H$_CDR1 region which may comprise the amino acid sequence of KRHIVIH (SEQ ID NO: 503); a $V_H$_CDR2 region which may comprise the amino acid sequence of VISSDAIHVDYASSVRG (SEQ ID NO: 504); a $V_H$_CDR3 region which may comprise the amino acid sequence of DRDGYGPPQIQTWSGRYLHLYSGIDA (SEQ ID NO: 505); a $V_L$_CDR1 region which may comprise the amino acid sequence of KSSQSLRQSNGKTYLY (SEQ ID NO: 512); a $V_L$_CDR2 region which may comprise the amino acid sequence of EVSIRFS (SEQ ID NO: 513); and a $V_L$_CDR3 region which may comprise the amino acid sequence of MQSKDFPLT (SEQ ID NO: 486).

The invention provides an isolated anti-HIV antibody, wherein said antibody may comprise a $V_H$_CDR1 region which may comprise the amino acid sequence of KYPMY (SEQ ID NO: 475); a $V_H$_CDR2 region which may comprise the amino acid sequence of AISADAWHVDYAASVKD (SEQ ID NO: 518); a $V_H$_CDR3 region which may comprise the amino acid sequence of NIEEFSVPQFDSWSGRSYYHYFGMDV (SEQ ID NO: 519); a $V_L$ CDR1 region which may comprise the amino acid sequence of SSSESLGRGDGRTYLH (SEQ ID NO: 526); a $V_L$_CDR2 region which may comprise the amino acid sequence of EVSTRFS (SEQ ID NO: 527); and a $V_L$_CDR3 region which may comprise the amino acid sequence of MQSRDFPIT (SEQ ID NO: 528).

The invention provides an isolated anti-HIV antibody, wherein said antibody may comprise a $V_H$_CDR1 region which may comprise the amino acid sequence of EYPMY (SEQ ID NO: 533); a $V_H$_CDR2 region which may comprise the amino acid sequence of AISADAWHVDYAGSVRG (SEQ ID NO: 534); a $V_H$_CDR3 region which may comprise the amino acid sequence of DGEEHKVPQLHSWSGRNLYHYTGFDV (SEQ ID NO: 535); a $V_L$ CDR1 region which may comprise the amino acid sequence of KSSQSVRQSDGKTFLY (SEQ ID NO: 541); a $V_L$_CDR2 region which may comprise the amino acid sequence of EGSSRFS (SEQ ID NO: 542); and a $V_L$_CDR3 region which may comprise the amino acid sequence of LQTKDFPLT (SEQ ID NO: 543).

The invention provides an isolated anti-HIV antibody, wherein said antibody may comprise a $V_H$_CDR1 region which may comprise the amino acid sequence of QYPMY (SEQ ID NO: 548); a $V_H$_CDR2 region which may comprise the amino acid sequence of AISADAWHVDYPGSVRG (SEQ ID NO: 549); a $V_H$_CDR3 region which may comprise the amino acid sequence of DGEEHKVPQLHSWSGRNLYHYTGFDV (SEQ ID NO: 535); a $V_L$ CDR1 region which may comprise the amino acid sequence of KSSQTVRQSDGKTFLY (SEQ ID NO: 555); a $V_L$_CDR2 region which may comprise the amino acid sequence of EGSNRFS (SEQ ID NO: 556); and a $V_L$_CDR3 region which may comprise the amino acid sequence of LQTKDFPLT (SEQ ID NO: 543).

The invention provides an isolated anti-HIV antibody, wherein said antibody may comprise a $V_H$_CDR1 region which may comprise the amino acid sequence of QYPMY (SEQ ID NO: 548); a $V_H$_CDR2 region which may comprise the amino acid sequence of AISADAWHVDYAGSVRG (SEQ ID NO: 534); a $V_H$_CDR3 region which may comprise the amino acid sequence of DGEEHEVPQLHSWSGRNLYHYTGVDI (SEQ ID NO: 561); a $V_L$ CDR1 region which may comprise the amino acid sequence of KSSQSLRQSDGKTFLY (SEQ ID NO: 567); a $V_L$_CDR2 region which may comprise the amino acid sequence of EASNRFS (SEQ ID NO: 568); and a $V_L$_CDR3 region which may comprise the amino acid sequence of MQTKDFPLT (SEQ ID NO: 569).

The invention provides an isolated anti-HIV antibody, wherein said antibody may comprise a $V_H$_CDR1 region which may comprise the amino acid sequence of KYPMY (SEQ ID NO: 475); a $V_H$_CDR2 region which may comprise the amino acid sequence of AISADAWHVDYPGSVRG (SEQ ID NO: 549); a $V_H$_CDR3 region which may comprise the amino acid sequence of DGEEHEVPQLHSWSGRNLYHYTGVDV (SEQ ID NO: 574); a $V_L$ CDR1 region which may comprise the amino acid sequence of KSSQSVRQSDGKTFLY (SEQ ID NO: 541); a $V_L$_CDR2 region which may comprise the amino acid sequence of EASKRFS (SEQ ID NO: 580); and a $V_L$_CDR3 region which may comprise the amino acid sequence of MQTKDFPLT (SEQ ID NO: 569).

The invention also provides an isolated anti-HIV antibody, wherein said antibody has a heavy chain with three CDRs including an amino acid sequence selected from the group consisting of the amino acid sequences of KYGMH (SEQ ID NO: 88), LISDDGMRKYHSDSMWG (SEQ ID NO: 89), EAGGPIWHDDVKYYDFNDGYYNYHYMDV (SEQ ID NO: 6), SYAFT (SEQ ID NO: 104), MVTPIFGEAKYSQRFEG (SEQ ID NO: 105), DRRAVPIATDNWLDP (SEQ ID NO: 9), SYAFS (SEQ ID NO: 110), MITPVFGETKYAPRFQG (SEQ ID NO: 111), DRRVVPMATDNWLDP (SEQ ID NO: 8), DYYLH (SEQ ID NO: 116), LIDPENGEARYAEKFQG (SEQ ID NO: 117), GAVGADSGSWFDP (SEQ ID NO: 10), RQGMH (SEQ ID NO: 123), FIKYDGSEKYHADSVWG (SEQ ID NO: 124), EAGGPDYRNGYNYYDFYDGYYNYHYMDV (SEQ ID NO: 7), LISDDGMRKYHSNSMWG (SEQ ID NO: 98), DSYWS (SEQ ID NO: 90), YVHKSGDTNYSPSLKS (SEQ ID NO: 265), TLHGRRIYGIVAFNEWFTYFYMDV (SEQ ID NO: 143), DNYWS (SEQ ID NO: 261), YVHDSGDTNYNPSLKS (SEQ ID NO: 157), TKHGRRIYGVVAFKEWFTYFYMDV (SEQ ID NO: 262), DAYWS (SEQ ID NO: 169), YVHHSGDTNYNPSLKR (SEQ ID NO: 170), ALHGKRIYGIVALGELFTYFYMDV (SEQ ID NO: 171), ACTYFWG (SEQ ID NO: 185), SLSHCQSFWGSGWTFHNPSLKS (SEQ ID NO: 186), FDGEVLVYNHWPKPAWVDL (SEQ ID NO: 187), ACDYFWG (SEQ ID NO: 201), GLSHCAGYYNTGWT-YHNPSLKS (SEQ ID NO: 202), FDGEVLVYHDWPKPAWVDL (SEQ ID NO: 203), TGHYYWG (SEQ ID NO: 217), HIHYTTAVLHNPSLKS (SEQ ID NO: 218), SGGDILYYYEWQKPHWFSP (SEQ ID NO: 219), GGEWGDKDYHWG (SEQ ID NO: 233), SIHWRGTTHYKESLRR (SEQ ID NO: 234), HRHHDVFMLVPIAGWFDV (SEQ ID NO: 235), GTDW-GENDFHYG (SEQ ID NO: 250), SIHWR-GRTTHYKTSFRS (SEQ ID NO: 251), HKYHDI-FRVVPVAGWFDP (SEQ ID NO: 252), KYDVH (SEQ ID NO: 277), WMSHEGDKTESAQRFKG (SEQ ID NO: 278), GSKHRLRDYVLYDDYGLINYQEWNDYLEFLDV (SEQ ID NO: 279), WISHERDKTESAQRFKG (SEQ ID NO: 293), and GSKHRLRDYVLYDDYGLINQQEWN-DYLEFLDV (SEQ ID NO: 308), wherein said antibody binds to and neutralizes HIV-1. Optionally, this antibody has a light chain with three CDRs that include an amino acid sequence selected from the group consisting of the amino acid sequences of

NGTSSDVGGFDSVS, (SEQ ID NO: 97)

DVSHRPS, (SEQ ID NO: 95)

SSLTDRSHRI, (SEQ ID NO: 41)

RASQTINNYLN, (SEQ ID NO: 107)

GASNLQN, (SEQ ID NO: 108)

QQSFSTPRT, (SEQ ID NO: 42)

RASQTIHTYLN, (SEQ ID NO: 113)

GASTLQS, (SEQ ID NO: 114)

QQSYSTPRT, (SEQ ID NO: 43)

SGSKLGDKYVS, (SEQ ID NO: 120)

ENDRRPS, (SEQ ID NO: 121)

QAWETTTTTFVF, (SEQ ID NO: 44)

NGTSNDVGGYESVS, (SEQ ID NO: 126)

DVSKRPS, (SEQ ID NO: 127)

KSLTSTRRRV, (SEQ ID NO: 45)

NGTRSDVGGFDSVS, (SEQ ID NO: 92)

NGTSRDVGGFDSVS, (SEQ ID NO: 93)

GEKSLGSRAVQ, (SEQ ID NO: 150)

NNQDRPS, (SEQ ID NO: 151)

HIWDSRVPTKWV, (SEQ ID NO: 152)

GEESLGSRSVI, (SEQ ID NO: 162)

NNNDRPS, (SEQ ID NO: 163)

HIWDSRRPTNWV, (SEQ ID NO: 164)

GKESIGSRAVQ, (SEQ ID NO: 178)

NNQDRPA, (SEQ ID NO: 179)

HIYDARGGTNWV, (SEQ ID NO: 180)

NGTATNFVS, (SEQ ID NO: 194)

GVDKRPP, (SEQ ID NO: 195)

GSLVGNWDVI, (SEQ ID NO: 196)

TGTSNRFVS, (SEQ ID NO: 210)

GVNKRPS, (SEQ ID NO: 211)

SSLVGNWDVI, (SEQ ID NO: 212)

NGTSSDIGGWNFVS, (SEQ ID NO: 226)

EVNKRPS, (SEQ ID NO: 227)

SSLFGRWDVV, (SEQ ID NO: 228)

RASQNINKNLA, (SEQ ID NO: 243)

ETYSKIA, (SEQ ID NO: 244)

QQYEEWPRT, (SEQ ID NO: 245)

RASQNVKNNLA, (SEQ ID NO: 259)

DASSRAG, (SEQ ID NO: 260)

SSTQSLRHSNGANYLA, (SEQ ID NO: 286)

LGSQRAS, and (SEQ ID NO: 287)

MQGLNRPWT, and (SEQ ID NO: 288)

TSTQSLRHSNGANYLA. (SEQ ID NO: 303)

The invention provides an isolated anti-HIV antibody, wherein said antibody has a light chain with three CDRs that include an amino acid sequence selected from the group consisting of the amino acid sequences of NGTSSDVGGFDSVS (SEQ ID NO: 97), DVSHRPS (SEQ ID NO: 95), SSLTDRSHRI (SEQ ID NO: 41), RASQTINNYLN (SEQ ID NO: 107), GASNLQN (SEQ ID NO: 108), QQSFSTPRT (SEQ ID NO: 42), RASQTIHTYLN (SEQ ID NO: 113), GASTLQS (SEQ ID NO: 114), QQSYSTPRT (SEQ ID NO: 43), SGSKLGDKYVS (SEQ ID NO: 120), ENDRRPS (SEQ ID NO: 121), QAWETTTTFVF (SEQ ID NO: 44), NGTSNDVGGYESVS (SEQ ID NO: 126), DVSKRPS (SEQ ID NO: 127), KSLTSTRRRV (SEQ ID NO: 45), NGTRSDVGGFDSVS (SEQ ID NO: 92), NGTSRDVGGFDSVS (SEQ ID NO: 93), GEKSLGSRAVQ (SEQ ID NO: 150), NNQDRPS (SEQ ID NO: 151), HIWDSRVPTKWV (SEQ ID NO: 152), GEESLGSRSVI (SEQ ID NO: 162), NNNDRPS (SEQ ID NO: 163), HIWDSRRPTNWV (SEQ ID NO: 164), GKESIGSRAVQ (SEQ ID NO: 178), NNQDRPA (SEQ ID NO: 179), HIYDARGGTNWV (SEQ ID NO: 180), NGTATNFVS (SEQ ID NO: 194), GVDKRPP (SEQ ID NO: 195), GSLVGNWDVI (SEQ ID NO: 196), TGTSNRFVS (SEQ ID NO: 210), GVNKRPS (SEQ ID NO: 211), SSLVGNWDVI (SEQ ID NO: 212), NGTSSDIGGWNFVS (SEQ ID NO: 226), EVNKRPS (SEQ ID NO: 227), SSLFGRWDVV (SEQ ID NO: 228), RASQNINKNLA (SEQ ID NO: 243), ETYSKIA (SEQ ID NO: 244), QQYEEWPRT (SEQ ID NO: 245), RASQNVKNNLA (SEQ ID NO: 259), DASSRAG (SEQ ID NO: 260), SSTQSLRHSNGANYLA (SEQ ID NO: 286), LGSQRAS (SEQ ID NO: 287), and MQGLNRPWT (SEQ ID NO: 288), and TSTQSLRHSNGANYLA (SEQ ID NO: 303), wherein said antibody binds to and neutralizes HIV-1.

The invention provides an isolated anti-HIV antibody, wherein said antibody has a heavy chain with three CDRs which may comprise an amino acid sequence selected from the group consisting of the amino acid sequences of GFTFHK (SEQ ID NO: 266), LISDDGMRKY (SEQ ID NO: 267), and EAGGPIWHDDVKYYDFNDGYYNYHYMDV (SEQ ID NO: 6), GGTFSS (SEQ ID NO: 268), MVTPIFGEAK (SEQ ID NO: 269), and DRRAVPIATDNWLDP (SEQ ID NO: 9), GGAFSS (SEQ ID NO: 270), MITPVFGETK (SEQ ID NO: 271), DRRVVPMATDNWLDP (SEQ ID NO: 8), GYSFID (SEQ ID NO: 102), LIDPENGEAR (SEQ ID NO: 103), GAVGADSGSWFDP (SEQ ID NO: 10), GFDFSR (SEQ ID NO: 118), FIKYDGSEKY (SEQ ID NO: 272), and EAGGPDYRNGYNYYDFYDGYYNYHYMDV (SEQ ID NO: 7), GASISD (SEQ ID NO: 144), YVHKSGDTN (SEQ ID NO: 145), TLHGRRIYGIVAFNEWFTYFYMDV (SEQ ID NO: 143), GTLVRD (SEQ ID NO: 263), YVHDSGDTN (SEQ ID NO: 264), TKHGRRIYGVVAFKEWFTYFYMDV (SEQ ID NO: 262), GASIND (SEQ ID NO: 172), YVHHSGDTN (SEQ ID NO: 173), ALHGKRIYGIVALGELFTYFYMDV (SEQ ID NO: 171), GESTGACT (SEQ ID NO: 188), SLSHCQSFWGSGWTF (SEQ ID NO: 189), FDGEVLVYNHWPKPAWVDL (SEQ ID NO: 187), GDSTAACD (SEQ ID NO: 204), GLSHCAGYYNTGWTY (SEQ ID NO: 205), FDGEVLVYHDWPKPAWVDL (SEQ ID NO: 203), GESINTGH (SEQ ID NO: 220), HIHYTAVL (SEQ ID NO: 221), SGGDILYYYEWQKPHWFSP (SEQ ID NO: 219), GDSIRGGEWGDKD (SEQ ID NO: 236), SIHWRGTTH (SEQ ID NO: 237), HRHHDVFMLVPIAGWFDV (SEQ ID NO: 235), GGSMRGTDWGEND (SEQ ID NO: 253), SIHWRGRTTH (SEQ ID NO: 254), HKYHDIFRVVPVAGWFDP (SEQ ID NO: 252), GNTFSK (SEQ ID NO: 280), WMSHEGDKTE (SEQ ID NO: 281), GSKHRLRDYVLYDDYGLINYQEWNDYLEFLDV (SEQ ID NO: 279), WISHERDKTE (SEQ ID NO: 294), GNTFRK (SEQ ID NO: 309), and GSKHRLRDYVLYDDYGLINQQEWNDYLEFLDV (SEQ ID NO: 308), wherein said antibody binds to and neutralizes HIV-1. Optionally, this antibody has a light chain with three CDRs that include an amino acid sequence selected from the group consisting of the amino acid sequences of

```
                                       (SEQ ID NO: 97)
NGTSSDVGGFDSVS, (SEQ ID NO: 95)
DVSHRPS, (SEQ ID NO: 41)
SSLTDRSHRI, (SEQ ID NO: 107)
RASQTINNYLN, (SEQ ID NO: 108)
GASNLQN, (SEQ ID NO: 42)
QQSFSTPRT, (SEQ ID NO: 113)
RASQTIHTYLN, (SEQ ID NO: 114)
GASTLQS, (SEQ ID NO: 43)
QQSYSTPRT, (SEQ ID NO: 120)
SGSKLGDKYVS, (SEQ ID NO: 121)
ENDRRPS, (SEQ ID NO: 44)
QAWETTTTFVF, (SEQ ID NO: 126)
NGTSNDVGGYESVS, (SEQ ID NO: 127)
DVSKRPS, (SEQ ID NO: 45)
KSLTSTRRRV, (SEQ ID NO: 92)
NGTRSDVGGFDSVS, (SEQ ID NO: 93)
NGTSRDVGGFDSVS, (SEQ ID NO: 150)
GEKSLGSRAVQ, (SEQ ID NO: 151)
NNQDRPS, (SEQ ID NO: 152)
HIWDSRVPTKWV, (SEQ ID NO: 162)
GEESLGSRSVI, (SEQ ID NO: 163)
NNNDRPS,
```

-continued

HIWDSRRPTNWV, (SEQ ID NO: 164)

GKESIGSRAVQ, (SEQ ID NO: 178)

NNQDRPA, (SEQ ID NO: 179)

HIYDARGGTNWV, (SEQ ID NO: 180)

NGTATNFVS, (SEQ ID NO: 194)

GVDKRPP, (SEQ ID NO: 195)

GSLVGNWDVI, (SEQ ID NO: 196)

TGTSNRFVS, (SEQ ID NO: 210)

GVNKRPS, (SEQ ID NO: 211)

SSLVGNWDVI, (SEQ ID NO: 212)

NGTSSDIGGWNFVS, (SEQ ID NO: 226)

EVNKRPS, (SEQ ID NO: 227)

SSLFGRWDVV, (SEQ ID NO: 228)

RASQNINKNLA, (SEQ ID NO: 243)

ETYSKIA, (SEQ ID NO: 244)

QQYEEWPRT, (SEQ ID NO: 245)

RASQNVKNNLA, (SEQ ID NO: 259)

DASSRAG, (SEQ ID NO: 260)

SSTQSLRHSNGANYLA, (SEQ ID NO: 286)

LGSQRAS, and (SEQ ID NO: 287)

MQGLNRPWT, and (SEQ ID NO: 288)

TSTQSLRHSNGANYLA. (SEQ ID NO: 303)

Moreover, the invention provides an isolated anti-HIV antibody or fragment thereof, wherein said antibody includes: (a) a $V_H$_CDR1 region including the amino acid sequence of SEQ ID NO: 88, 104, 110, 116, 123, 90, 261, 169, 185, 201, 217, 233, 250, or 277; (b) a $V_H$_CDR2 region including the amino acid sequence of SEQ ID NO: 98, 89, 105, 111, 117, 124, 265, 157, 170, 186, 202, 218, 234, 251, 278, or 293; and (c) a $V_H$_CDR3 region including the amino acid sequence of SEQ ID NO: 6, 9, 8, 10, 7, 143, 262, 171, 187, 203, 219, 235, 252, 279, or 308; wherein said antibody binds to and neutralizes HIV-1. This antibody may further includes: (a) a $V_L$_CDR1 region including the amino acid sequence of SEQ ID NO: 93, 92, 97, 94, 107, 113, 120, 126, 150, 162, 178, 194, 210, 226, 243, 259, 286 or 303; (b) a $V_L$_CDR2 region including the amino acid sequence of SEQ ID NO: 95, 108, 114, 121, 127, 151, 163, 179, 195, 211, 227, 244, 260, or 287; and (c) a $V_L$_CDR3 region including the amino acid sequence of SEQ ID NO: 41, 42, 43, 44, 45, 152, 164, 180, 196, 212, 228, 245, or 288.

Alternatively, the invention provides an isolated anti-HIV antibody or fragment thereof, wherein said antibody includes: (a) a $V_H$_CDR1 region including the amino acid sequence of SEQ ID NO: 266, 268, 270, 201, 118, 144, 263, 172, 188, 204, 220, 236, 253, 280 or 309; (b) a $V_H$_CDR2 region including the amino acid sequence of SEQ ID NO: 267, 269, 271, 103, 272, 145, 264, 173, 189, 205, 221, 237, 254, 281, or 294; and (c) a $V_H$_CDR3 region including the amino acid sequence of SEQ ID NO: 6, 9, 8, 10, 7, 143, 262, 171, 187, 203, 219, 235, 252, 279, or 308; wherein said antibody binds to and neutralizes HIV-1. This antibody may further include: (a) a $V_L$ CDR1 region including the amino acid sequence of SEQ ID NO: 93, 92, 97, 94, 107, 113, 120, 126, 150, 162, 178, 194, 210, 226, 243, 259, 286 or 303; (b) a $V_L$_CDR2 region including the amino acid sequence of SEQ ID NO: 95, 108, 114, 121, 127, 151, 163, 179, 195, 211, 227, 244, 260, or 287; and (c) a $V_L$_CDR3 region including the amino acid sequence of SEQ ID NO: 41, 42, 43, 44, 45, 152, 164, 180, 196, 212, 228, 245, or 288.

The invention provides an isolated fully human monoclonal anti-HIV antibody including: a) a heavy chain sequence including the amino acid sequence of SEQ ID NO: 31 and a light chain sequence including amino acid sequence SEQ ID NO: 32, or b) a heavy chain sequence including the amino acid sequence of SEQ ID NO: 33 and a light chain sequence including amino acid sequence SEQ ID NO: 34, or c) a heavy chain sequence including the amino acid sequence of SEQ ID NO: 35 and a light chain sequence which may comprise amino acid sequence SEQ ID NO: 36, or d) a heavy chain sequence including the amino acid sequence of SEQ ID NO: 37 and a light chain sequence including amino acid sequence SEQ ID NO: 38, or e) a heavy chain sequence including the amino acid sequence of SEQ ID NO: 39 and a light chain sequence including amino acid sequence SEQ ID NO: 40, or f) a heavy chain sequence including the amino acid sequence of SEQ ID NO: 140 and a light chain sequence including amino acid sequence SEQ ID NO: 96, or g) a heavy chain sequence including the amino acid sequence of SEQ ID NO: 48 and a light chain sequence including amino acid sequence SEQ ID NO: 51, or h) a heavy chain sequence including the amino acid sequence of SEQ ID NO: 54 and a light chain sequence including amino acid sequence SEQ ID NO: 57, or i) a heavy chain sequence including the amino acid sequence of SEQ ID NO: 60 and a light chain sequence including amino acid sequence SEQ ID NO: 32, or j) a heavy chain sequence which may comprise the amino acid sequence of SEQ ID NO: 79 and a light chain sequence which may comprise amino acid sequence SEQ ID NO: 149, or k) a heavy chain sequence which may comprise the amino acid sequence of SEQ ID NO: 156 and a light chain sequence which may comprise amino acid sequence SEQ ID NO: 161, or l) a heavy chain sequence which may comprise the amino acid sequence of SEQ ID NO: 168 and a light chain sequence which may comprise amino acid sequence SEQ ID NO: 177, or m) a heavy chain sequence which may comprise the amino acid sequence of SEQ ID NO: 184 and a light chain sequence which may comprise amino acid sequence SEQ ID NO: 193, or n) a heavy chain sequence which may comprise the amino acid sequence of SEQ ID NO: 200 and a light chain sequence which may comprise amino acid sequence SEQ ID NO: 209, or o) a heavy chain sequence which may comprise the amino acid sequence of SEQ ID NO: 216 and a light chain sequence which may comprise amino acid sequence SEQ ID NO: 225, or p) a heavy chain sequence which may comprise the amino acid sequence of SEQ ID NO: 232 and a light chain sequence which may comprise amino acid sequence SEQ ID NO: 242 or q) a heavy chain sequence which may comprise the amino acid sequence of SEQ ID NO: 249 and a light chain sequence which may comprise amino acid sequence SEQ ID NO: 258 or r) a heavy chain sequence which may comprise the amino acid sequence of SEQ ID NO: 276 and a light chain sequence which may comprise amino acid sequence SEQ ID NO: 285 or s) a heavy chain sequence which may comprise the amino acid sequence of SEQ ID NO: 292 and a light chain sequence which may comprise amino acid sequence SEQ ID NO: 285 or t) a heavy chain sequence which may comprise the amino acid sequence of SEQ ID NO: 298 and a light chain sequence which may comprise amino acid sequence SEQ ID NO: 302 or u) a heavy chain sequence which may comprise the amino acid sequence of SEQ ID NO: 307 and a light chain sequence which may comprise amino acid sequence SEQ ID NO: 313 or v) a heavy chain sequence which may comprise the amino acid sequence of SEQ ID NO: 319 and a light chain sequence which may comprise amino acid sequence SEQ ID NO: 330 or w) a heavy chain sequence which may comprise the amino acid sequence of SEQ ID NO: 334 and a light chain sequence which may comprise amino acid sequence SEQ ID NO: 393 or x) a heavy chain sequence which may comprise the amino acid sequence of SEQ ID NO: 347 and a light chain sequence which may comprise amino acid sequence SEQ ID NO: 356 or y) a heavy chain sequence which may comprise the amino acid sequence of SEQ ID NO: 363 and a light chain sequence which may comprise amino acid sequence SEQ ID NO: 397 or z) a heavy chain sequence which may comprise the amino acid sequence of SEQ ID NO: 401 and a light chain sequence which may comprise amino acid sequence SEQ ID NO: 386, or aa) a heavy chain sequence which may comprise the amino acid sequence of SEQ ID NO: 405 and a light chain sequence which may comprise amino acid sequence SEQ ID NO: 414, or ab) a heavy chain sequence which may comprise the amino acid sequence of SEQ ID NO: 420 and a light chain sequence which may comprise amino acid sequence SEQ ID NO: 429, or ac) a heavy chain sequence which may comprise the amino acid sequence of SEQ ID NO: 435 and a light chain sequence which may comprise amino acid sequence SEQ ID NO: 440, or ad) a heavy chain sequence which may comprise the amino acid sequence of SEQ ID NO: 444 and a light chain sequence which may comprise amino acid sequence SEQ ID NO: 449, or ae) a heavy chain sequence which may comprise the amino acid sequence of SEQ ID NO: 454 and a light chain sequence which may comprise amino acid sequence SEQ ID NO: 584, or af) a heavy chain sequence which may comprise the amino acid sequence of SEQ ID NO: 463 and a light chain sequence which may comprise amino acid sequence SEQ ID NO: 470, or ag) a heavy chain sequence which may comprise the amino acid sequence of SEQ ID NO: 474 and a light chain sequence which may comprise amino acid sequence SEQ ID NO: 483, or ah) a heavy chain sequence which may comprise the amino acid sequence of SEQ ID NO: 490 and a light chain sequence which may comprise amino acid sequence SEQ ID NO: 497, or ai) a heavy chain sequence which may comprise the amino acid sequence of SEQ ID NO: 502 and a light chain sequence which may comprise amino acid sequence SEQ ID NO: 511, or aj) a heavy chain sequence which may comprise the amino acid sequence of SEQ ID NO: 517 and a light chain sequence which may comprise amino acid sequence SEQ ID NO: 525, or ak) a heavy chain sequence which may comprise the amino acid sequence of SEQ ID NO: 532 and a light chain sequence which may comprise amino acid sequence SEQ ID NO: 540, or al) a heavy chain sequence which may comprise the amino acid sequence of SEQ ID NO: 547 and a light chain sequence which may comprise amino acid sequence SEQ ID NO: 554, or am) a heavy chain sequence which may comprise the amino acid sequence of SEQ ID NO: 560 and a light chain sequence which may comprise amino acid sequence SEQ ID NO: 566.

The invention provides a composition including any one of the isolated anti-HIV antibodies described herein.

Optionally, an anti-HIV human monoclonal antibody of the invention is isolated from a B-cell from an HIV-1-infected human donor. In some embodiments, the antibody is effective in neutralizing a plurality of different clades of HIV. In some embodiments, the antibody is effective in neutralizing a plurality of different strain within the same Glade of HIV-1. In some embodiments, the neutralizing antibody binds to the HIV envelope proteins gp120, or gp41 or envelope protein on HIV-1 pseudovirions or expressed on transfected or infected cell surfaces. In some embodiments, the neutralizing antibody does not bind to recombinant or monomeric envelope proteins gp120, or gp41 or envelope protein on HIV-1 pseudovirions or expressed on transfected or infected cell surfaces but binds to natural trimeric forms of the HIV-1 Env proteins.

The present invention provides human monoclonal antibodies wherein the antibodies are potent, broadly neutralizing antibody (bNAb). In some embodiments, a broadly neutralizing antibody is defined as a bNAb that neutralizes HIV-1 species belonging to two or more different clades. In some embodiments the different clades are selected from the group consisting of clades A, B, C, D, E, AE, AG, G or F. In some embodiments the HIV-1 strains from two or more clades comprise virus from non-B clades.

In some embodiments, a broadly neutralizing antibody is defined as a bNAb that neutralizes at least 60% of the HIV-1 strains listed in Tables 18A-18F. In some embodiments, at least 70%, or at least 80%, or at least 90% of the HIV-1 strains listed in Tables 18A-18F are neutralized.

In some embodiments, a potent, broadly neutralizing antibody is defined as a bNAb that displays a potency of neutralization of at least a plurality of HIV-1 species with an IC50 value of less than 0.2 µg/mL. In some embodiments the potency of neutralization of the HIV-1 species has an IC50 value of less than 0.15 µg/mL, or less than 0.10 µg/mL, or less than 0.05 µg/mL. A potent, broadly neutralizing antibody is also defined as a bNAb that displays a potency of neutralization of at least a plurality of HIV-1 species with an IC90 value of less than 2.0 µg/mL. In some embodiments the potency of neutralization of the HIV-1 species has an IC90 value of less than 1.0 µg/mL, or less than 0.5 µg/mL.

Exemplary monoclonal antibodies that neutralize HIV-1 include 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19

(PGT-136), 5366_P21 (PGT-136), 4964_G22 (PGT-141), 5345_I01 (PGT-137), 4993_K13 (PGT-141), 4995_E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and 6881_N05 (PGT-158) described herein. Alternatively, the monoclonal antibody is an antibody that binds to the same epitope as 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_I01 (PGT-137), 4993_K13 (PGT-141), 4995_E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), or 6881_N05 (PGT-158). Specifically, monoclonal antibodies PG9 and PG16 are broad and potent neutralizing antibodies. The antibodies are respectively referred to herein as HIV antibodies.

The invention provides a number of isolated human monoclonal antibodies, wherein each said monoclonal antibody binds to HIV-1 infected or transfected cells; and binds to HIV-1 virus. A neutralizing antibody having potency in neutralizing HIV-1, or a fragment thereof is provided. In some embodiments a neutralizing antibody of the invention exhibits higher neutralization index and/or a higher affinity for binding to the envelope proteins gp120, or gp41 than anti-HIV mAbs known in the art, such as the mAb b12. (Burton D R et al., Science Vol. 266. no. 5187, pp. 1024-1027). Exemplary monoclonal antibodies 1496_C09 (PG9), 1443_C16 (PG16), 1456_P20 (PG20), 1460_G14 (PGG14), and 1495_C14 (PGC14) exhibit binding to the envelope glycoprotein gp120, but not gp41, in an ELISA assay, however gp120 binding does not always correlate with neutralization activity against specific strains of HIV-1. In some embodiments, monoclonal antibodies, for example 1443_C16 (PG16) and 1496_C09 (PG9), display none or weak gp120 binding activity against a particular strain but bind to HIV-1 trimer on transfected or infected cell surface and/or virion and exhibit broad and potent neutralization activity against that strain of HIV-1.

In one aspect the antibody is a monoclonal antibody which may comprise one or more polypeptides selected from the group consisting of 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_I01 (PGT-137), 4993_K13 (PGT-141), 4995_E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and 6881_N05 (PGT-158); which may comprise a heavy chain selected from the group consisting of the heavy chain of 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123_A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_I01 (PGT-137), 4993_K13 (PGT-141), 4995 E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and 6881_N05 (PGT-158); which may comprise a heavy chain which may comprise a CDR selected from the group consisting of the CDRs of the heavy chain of 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123_A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_I01 (PGT-137), 4993_K13 (PGT-141), 4995 E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and 6881_N05 (PGT-158); which may comprise a light chain selected from the group consisting of the light chain of 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_I01 (PGT-137), 4993_K13 (PGT-141), 4995 E20 (PGT-142), 4980_N08 (PGT-143), 4970_K22 (PGT-144), 4995_P16 (PGT-145), 4835_F12 (PGT-124), 4869-K15 (PGT-133), 4876_M06

(PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and 6881_N05 (PGT-158); which may comprise a light chain which may comprise a CDR selected from the group consisting of the CDRs of the light chain of 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_I01 (PGT-137), 4993_K13 (PGT-141), 4995_E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and 6881_N05 (PGT-158).

The invention relates to an antibody or a fragment thereof, such as Fab, Fab', F(ab')2 and Fv fragments that binds to an epitope or immunogenic polypeptide capable of binding to an antibody selected from 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_101 (PGT-137), 4993_K13 (PGT-141), 4995_E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and 6881_N05 (PGT-158).

The invention also relates to immunogenic polypeptides encoding such epitopes.

Nucleic acid molecules encoding such antibodies, and vectors and cells carrying such nucleic acids are also provided.

The invention relates to a pharmaceutical composition which may comprise at least one antibody or fragment as recited herein, together with a pharmaceutically acceptable carrier.

The invention relates to a method of immunizing, preventing or inhibiting HIV infection or an HIV-related disease which may comprise the steps of identifying a patient in need of such treatment and administering to said patient a therapeutically effective amount of at least one monoclonal antibody as recited herein.

In a further aspect the HIV antibodies according to the invention are linked to a therapeutic agent or a detectable label.

Additionally, the invention provides methods for stimulating an immune response, treating, preventing or alleviating a symptom of an HIV viral infection by administering an HIV antibody to a subject In another aspect, the invention provides methods of administering the HIV antibody of the invention to a subject prior to, and/or after exposure to an HIV virus. For example, the HIV antibody of the invention is used to treat or prevent HIV infection. The HIV antibody is administered at a dose sufficient to promote viral clearance or eliminate HIV infected cells.

Also included in the invention is a method for determining the presence of an HIV virus infection in a patient, by contacting a biological sample obtained from the patient with an HIV antibody; detecting an amount of the antibody that binds to the biological sample; and comparing the amount of antibody that binds to the biological sample to a control value.

The invention further provides a diagnostic kit which may comprise an HIV monoclonal antibody.

The invention relates to a broadly neutralizing antibody (bNAb) wherein the antibody neutralizes at least one member of each Glade with a potency greater than that of the bNAbs b12, 2G12, 2F5 and 4E10 respectively.

The invention relates to a broadly neutralizing antibody (bNAb) wherein the antibody binds or does not bind monomeric gp120 or gp41 proteins of the HIV-1 env gene. The antibody binds with higher affinity to trimeric forms of the HIV-1 Env expressed on a cell surface than to the monomeric gp120 or artificially trimerized gp140. In some aspects, the antibody binds with high affinity to uncleaved HIV-1 gp160 trimers on a cell surface.

The invention relates to a broadly neutralizing antibody (bNAb) wherein the antibody binds an epitope within the variable loop of gp120, wherein the epitope may comprise the conserved regions of V2 and V3 loops of gp120, wherein the epitope may comprise N-glycosylation site at residue Asn-160 within the V2 loop of gp120, wherein the antibody binds an epitope presented by a trimeric spike of gp120 on a cell surface, wherein the epitope is not presented when gp120 is artificially trimerized. In some embodiments, the antibody does not neutralize the HIV-1 in the absence of N-glycosylation site at residue Asn-160 within the V2 loop of gp120.

The invention relates to a broadly neutralizing antibody (bNAb) selected from the group consisting of PG16 and PG9. Moreover, the invention relates to a broadly neutralizing antibody (bNAb) selected from the group consisting of 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_101 (PGT-137), 4993_K13 (PGT-141), 4995_E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and 6881_N05 (PGT-158).

The invention relates to an antigen or an immunogenic polypeptide, or a vaccine which may comprise such antigen or immunogenic polypeptide, for producing a broadly neutralizing antibody (bNAb) by an immune response, the antigen which may comprise an epitope within the variable loop of gp120 according to the invention.

The invention relates to method for passive or active immunization of an individual against a plurality of HIV-1 species across one or more clades, the method which may comprise: providing a broadly neutralizing antibody (bNAb) wherein the bNAb neutralizes HIV-1 species belonging to two or more clades, and further wherein the potency of neutralization of at least one member of each Glade is determined by an IC50 value of less than 0.005 µg/mL. In some embodiments, the antibody is selected from the group consisting of PG9 and PG16. Alternatively, or in addition, the antibody is selected from the group consisting of 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456 P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_101 (PGT-137), 4993_K13 (PGT-141), 4995_E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and 6881_N05 (PGT-158).

In some embodiments, the antibody is produced by active immunization with an antigen which may comprise an epitope within the variable loop of gp120, wherein the epitope may comprise the conserved regions of V2 and V3 loops of gp120 or, wherein the epitope may comprise an N-glycosylation site at residue Asn-160 within the V2 loop of gp120. In some aspects, the epitope is presented by a trimeric spike of gp120 on a cell surface, and the epitope is not presented when gp120 is monomeric or artificially trimerized.

The invention provides a method for obtaining a broadly neutralizing human monoclonal antibody, the method including: (a) screening memory B cell cultures from a donor PBMC sample for a broad neutralization activity against a plurality of HIV-1 species; (b) cloning a memory B cell that exhibits broad neutralization activity; and then (c) rescuing the monoclonal antibody from the clonal memory B cell culture that exhibits broad neutralization activity. In one embodiment the method, the screening step includes screening polyclonal transfectants for neutralization activity prior to the cloning step of monoclonal transfection. In this embodiment, the screening step is optionally repeated following monoclonal transfection. Finally, in this embodiment, the DNA sequence of the monoclonal antibody is determined as part of the rescue step. Exemplary antibodies that are generated using this embodiment include, but are not limited to, 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_101 (PGT-137), 4993_K13 (PGT-141), 4995_E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and 6881_N05 (PGT-158).

Alternatively, or in addition, the screening step includes determining variable gene sequences from selected B cell wells by deep sequencing, which is optionally followed by sequence alignment to cluster related antibodies. In this alternative embodiment, following the screening step, a monoclonal transfection is performed as part of the cloning step. Subsequently, in this alternative embodiment, monoclonal transfectants are screened for neutralization activity against an HIV virus from one or more clades. Exemplary antibodies that are generated using this embodiment include, but are not limited to, 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_101 (PGT-137), 4993_K13 (PGT-141), 4995 E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and 6881_N05 (PGT-158).

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

FIG. 1A is a schematic tree diagram of Clustal W-aligned variable region sequences of heavy chains of the monoclonal antibodies.

FIG. 1B is a schematic tree diagram of Clustal W-aligned variable region sequences of light chains of the monoclonal antibodies.

FIG. 10A is a graph depicting the results of a competitive binding assay using monoclonal antibodies sCD4, PG16 and PG9, wherein the claimed antibodies compete for the binding of monoclonal antibody 1443_C16 (PG16) to pseudovirus but control antibodies b12, 2G12, 2F5 and 4E10 do not competitively bind to the pseudovirus.

FIG. 13A-13E is a series of graphs depicting the mapping the PG9 and PG16 epitopes. Competitor antibody is indicated at the top of each graph. 2G12 is included to control for cell surface Env expression. A: PG9 and PG16 compete with each other for cell surface Env binding and neither antibody competes with the CD4bs antibody b12 for Env binding. B: Ligation of cell surface Env with sCD4 diminishes binding of PG9 and PG16. 2G12 is included to control for CD4-induced shedding of gp120. C: sCD4 inhibits binding of PG9 to artificially trimerized gp140YU-2 as determined by ELISA. D: PG9 competes with 10/76b (anti-V2), F425/b4e8 (anti-V3) and X5 (CD4i) for gp120 binding in competition ELISA assays. E: PG9 and PG16 fail to bind variable loop deleted HIV-1JR-CSF variants expressed on the surface of 293T cells.

FIG. 20A is a tree diagram illustrating the correlation of the heavy chain of 1443_C16 sister clones to the heavy chain of 1496_C09 at the nucleotide level.

FIG. 20B is a tree diagram illustrating the correlation of the light chain of 1443_C16 sister clones to the light chain of 1496_C09 at the nucleotide level.

FIG. 44A-44M is a series of graphs depicting the percent of viruses covered by single MAbs (solid lines) or by at least one of the MAbs in dual combinations (dashed black lines) dependent on individual concentrations. The grey area in all panels is the coverage of 26 MAbs tested on the 162-virus panel (PGT121-123, PGT125-128, PGT130-131, PGT135-137, PGT141-145, PG9, PG16, PGC14, VRC01, PGV04, b12, 2G12, 4E10, 2F5) and depicts the theoretical maximal achievable coverage known to date.

FIG. 47 is an alignment of heavy chain protein sequences of the variable domain of 1443_C16 sister clones to 1443_C16 and 1496_C09 (SEQ ID NO: 656-658).

FIG. 48 is an alignment of light chain protein sequences of the variable domain of 1443_C16 sister clones to 1443_C16 and 1496_C09 (SEQ ID NO: 659-660).

FIG. 49 is a table showing antibody sequence characteristics of MAbs PGT121-123, PGT125-128, PGT130-131, PGT135-137, PGT141-145 (SEQ ID NO: 143, 262, 171, 187, 203, 661, 336, 219, 350, 235, 252, 366, 279, 308, 380, 152, 164, 180, 196, 212, 228, 359, 245, 288, 389).

FIG. 55 is is a table showing heavy chain variable protein alignment for PGT-141, PGT-142, PGT-143, and PGT-144 (SEQ ID NO: 717-720 from top to bottom).

FIG. 56 is a table showing light chain variable gene alignment for PGT-141, PGT 142, PGT-143, and PGT-144 (SEQ ID NO: 713-716 from top to bottom).

FIG. 57 is a table showing light chain variable protein alignment for PGT-141, PGT 142, PGT-143, and PGT-144 (SEQ ID NO: 721-724 from top to bottom).

DETAILED DESCRIPTION OF THE INVENTION

Figure 2:
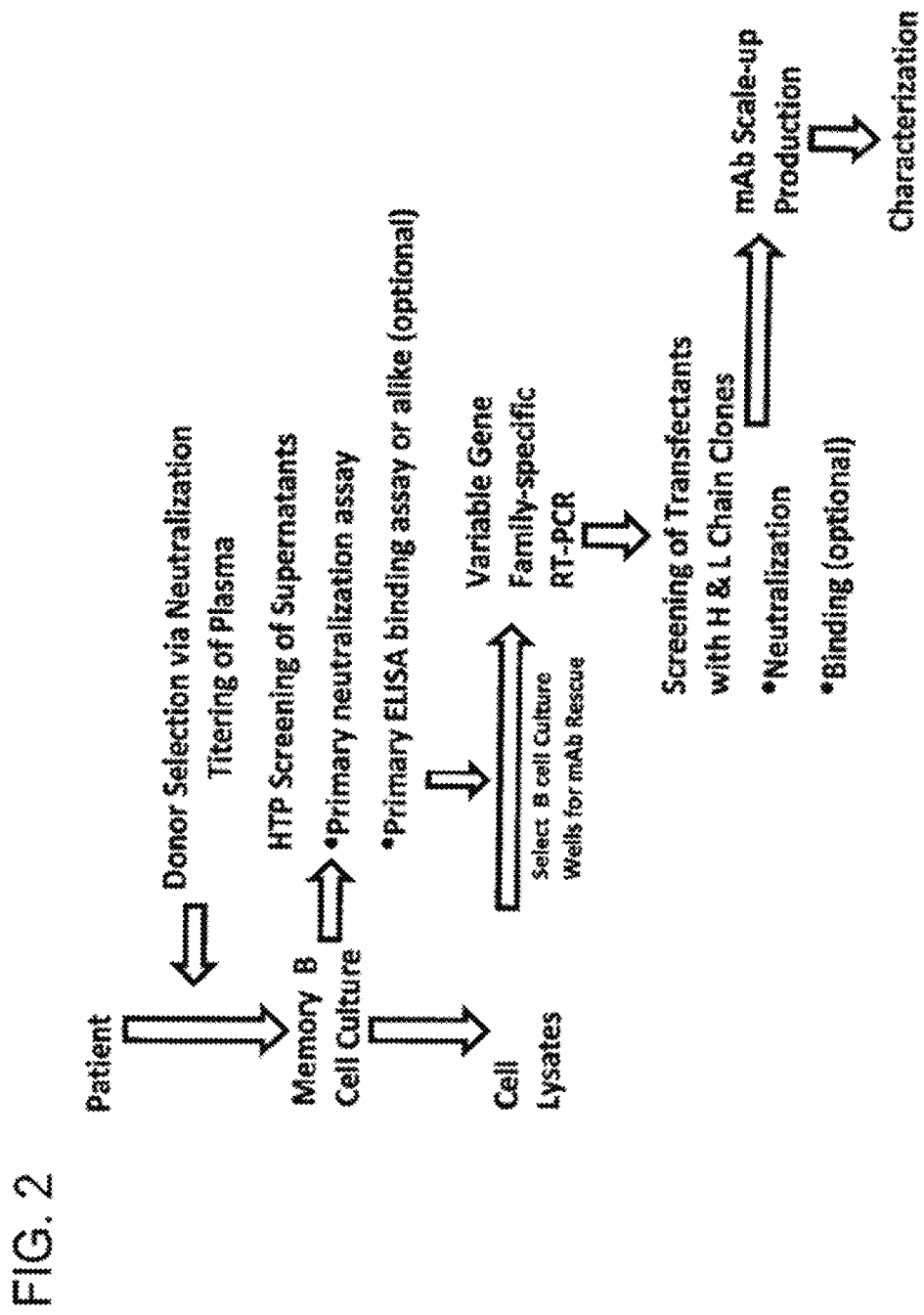
FIG. 2 is a flow chart of the process for isolation of monoclonal antibodies according to the invention.

In the sera of human immunodeficiency virus type 1 (HIV-1) infected patients, anti-virus antibodies can be detected over a certain period after infection without any clinical manifestations of the acquired immunodeficiency syndrome (AIDS). At this state of active immune response, high numbers of antigen-specific B-cells are expected in the circulation. These B-cells are used as fusion partners for the generation of human monoclonal anti-HIV antibodies. One major drawback to finding a vaccine composition suitable for more reliable prevention of human individuals from HIV-1 infection and/or for more successful therapeutic treatment of infected patients is the ability of the HIV-1 virus to escape antibody capture by genetic variation, which very often renders the remarkable efforts of the researchers almost useless. Such escape mutants may be characterized by a change of only one or several of the amino acids within one of the targeted antigenic determinants and may occur, for example, as a result of spontaneous or induced mutation. In addition to genetic variation, certain other properties of the HIV-1 envelope glycoprotein makes it difficult to elicit neutralizing antibodies making generation of undesirable non-neutralizing antibodies a major concern (see, Phogat S K and Wyatt R T, Curr Pharm Design 2007; 13(2):213-227).

HIV-1 is among the most genetically diverse viral pathogens. Of the three main branches of the HIV-1 phylogenetic tree, the M (main), N (new), and O (outlier) groups, group M viruses are the most widespread, accounting for over 99% of global infections. This group is presently divided into nine distinct genetic subtypes, or clades (A through K), based on full-length sequences. Env is the most variable HIV-1 gene, with up to 35% sequence diversity between clades, 20% sequence diversity within clades, and up to 10% sequence diversity in a single infected person (Shankarappa, R. et al. 1999. J. Virol. 73:10489-10502). Clade B is dominant in Europe, the Americas, and Australia. Clade C is common in southern Africa, China, and India and presently infects more people worldwide than any other Glade (McCutchan, F E. 2000. Understanding the genetic diversity of HIV-1. AIDS 14(Suppl. 3): S31-S44). Clades A and D are prominent in central and eastern Africa.

Neutralizing antibodies (NAbs) against viral envelope proteins (Env) provide adaptive immune defense against human immunodeficiency virus type 1 (HIV-1) exposure by blocking the infection of susceptible cells (Kwong P D et al., 2002. Nature 420: 678-682). The efficacy of vaccines against several viruses has been attributed to their ability to elicit NAbs. However, despite enormous efforts, there has been limited progress toward an effective immunogen for HIV-1. (Burton, D. R. 2002. Nat. Rev. Immunol. 2:706-713).

HIV-1 has evolved with an extensive array of strategies to evade antibody-mediated neutralization. (Barouch, D. H. Nature 455, 613-619 (2008); Kwong, P. D. & Wilson, I. A. Nat Immunol 10, 573-578 (2009); Karlsson Hedestam, G. B., et al. Nat Rev Microbiol 6, 143-155 (2008)). However, broadly neutralizing antibodies (bNAbs) develop over time in a proportion of HIV-1 infected individuals. (Leonidas Stamatatos, L. M., Dennis R Burton, and John Mascola. Nature Medicine (E-Pub: Jun. 14, 2009); PMID: 19525964.) A handful of broadly neutralizing monoclonal antibodies have been isolated from Glade B infected donors. (Burton, D. R., et al. Science 266, 1024-1027 (1994); Trkola, A., et al. J Virol 69, 6609-6617 (1995); Stiegler, G., et al. AIDS Res Hum Retroviruses 17, 1757-1765 (2001)). These antibodies tend to display less breadth and potency against non-Glade B viruses, and they recognize epitopes on the virus that have so far failed to elicit broadly neutralizing responses when incorporated into a diverse range of immunogens. (Phogat, S. & Wyatt, R. Curr Pharm Design 13, 213-227 (2007); Montero, M., van Houten, N. E., Wang, X. & Scott, J. K. Microbiol Mol Biol Rev 72, 54-84, table of contents (2008); Scanlan, C. N., Offer, J., Zitzmann, N. & Dwek, R. A. Nature 446, 1038-1045 (2007)). Despite the enormous diversity of the human immunodeficiency virus (HIV), all HIV viruses known to date interact with the same cellular receptors (CD4 and/or a co-receptor, CCRS or CXCR4). Most neutralizing antibodies bind to functional regions involved in receptor interactions and cell membrane fusion. However, the vast majority of neutralizing antibodies isolated to date do not recognize more than one Glade, therefore exhibiting limited protective efficacy in vitro or in vivo. (See Binley J M et al., 2004. J. Virol. 78(23):13232-13252). The rare broadly neutralizing human monoclonal antibodies (mAbs) that have been isolated from HIV+Glade B-infected human donors bind to products of the env gene of HIV-1, gp120 and the transmembrane protein gp41. (Parren, P W et al. 1999. AIDS 13:S137-S162). However, a well-known characteristic of the HIV-1 envelope glycoprotein is its extreme variability. It has been recognized that even relatively conserved epitopes on HIV-1, such as the CD4 binding site, show some variability between different isolates (Poignard, P., et al., Ann. Rev. Immunol. (2001) 19:253-274). Even an antibody targeted to one of these conserved sites can be expected to suffer from a reduced breadth of reactivity across multiple different isolates.

The few cross-clade reactive monoclonal antibodies known to date have been isolated by processes involving generation of panels of specific viral antibodies from peripheral blood lymphocytes (PBLs) of HIV-infected individuals, either via phage display, or via conventional immortalization techniques such as hybridoma or Epstein Barr virus transformation, electrofusion and the like. These are selected based on reactivity in vitro to HIV-1 proteins, followed by testing for HIV neutralization activity.

An antibody phage surface expression system was used to isolate the cross-clade neutralizing Fab (fragment, antigen binding) b12 occurring in a combinatorial library. The Fab b12 was screened by panning for envelope glycoprotein gp120 binding activity and neutralizing activity against the HIV-1 (HXBc2) isolate was observed. (Roben P et al., J. Virol. 68(8): 4821-4828(1994); Barbas C F et al., Proc. Natl. Acad. Sci. USA Vol. 89, pp. 9339-9343, (1992); Burton D P et al., Proc. Natl. Acad. Sci. USA Vol. 88, pp. 10134-10137 (1991)).

Human B cell immortalization was used to isolate the cross-clade neutralizing monoclonal antibodies 2G12, 2F5, and 4E10 from HIV-infected individuals. The monoclonal antibody 2G12 binds to a glycotope on the gp120 surface glycoprotein of HIV-1 and had been shown to display broad neutralizing patterns. (Trkola A., et al., J. Virol. 70(2):1100-1108 (1996), Buchacher, A., et al., 1994. AIDS Res. Hum. Retroviruses 10:359-369). The monoclonal antibody 2F5 which had been shown to bind a sequence within the external domain of the gp41 envelope glycoprotein of HIV-1 was found to have broad neutralization properties. (Conley A J Proc. Natl. Acad. Sci. USA Vol. 91, pp. 3348-3352 (1994); Muster T et al., J. Virol. 67(11):6642-6647 (1993); Buchacher A et al., 1992, Vaccines 92:191-195). The monoclonal antibody 4E10, which binds to a novel epitope C terminal of the ELDKWA sequence in gp41 recognized by 2F5, has also been found to have potent cross-clade neutralization activity. (Buchacher, A., et al., 1994. AIDS Res. Hum. Retroviruses 10:359-369; Stiegler, G., et al., 2001. AIDS Res. Hum. Retroviruses 17(18): 1757-1765)).

Other studies on antibody neutralization of HIV-1 (Nara, P. L., et al. (1991) FASEB J. 5:2437-2455.) focused on a single linear epitope in the third hypervariable region of the viral envelope glycoprotein gp120 known as the V3 loop. Antibodies to this loop are suggested to neutralize by inhibiting fusion of viral and cell membranes. However there is sequence variability within the loop and neutralizing antibodies are sensitive to sequence variations outside the loop (Albert J. et al., (1990) AIDS 4, 107-112). Hence anti-V3 loop antibodies are often strain-specific and mutations in the loop in vivo may provide a mechanism for viral escape from antibody neutralization. There is some indication that not all neutralizing antibodies act by blocking the attachment of virus, since a number of mouse monoclonal antibodies inhibiting CD4 binding to gp120 are either non-neutralizing (Lasky L A, et al., (1987) Cell 50:975-985.) or only weakly neutralizing (Sun N., et al., (1989) J. Virol. 63, 3579-3585).

It is widely accepted that such a vaccine will require both T-cell mediated immunity as well as the elicitation of a broadly neutralizing antibody (bNAb) response. (Barouch, D. H. Nature 455, 613-619 (2008); Walker, B. D. & Burton, D. R. Science 320, 760-764 (2008); Johnston, M. I. & Fauci, A. S. N Engl J Med 356, 2073-2081 (2007)). All of the known bNAbs provide protection in the best available primate models (Veazey, R. S., et al. Nat Med 9, 343-346 (2003); Hessell, A. J., et al. PLoS Pathog 5, e1000433 (2009); Parren, P. W., et al. J Virol 75, 8340-8347 (2001); Mascola, J. R. Vaccine 20, 1922-1925 (2002); Mascola, J. R., et al. Nat Med 6, 207-210 (2000); Mascola, J. R., et al. J Virol 73, 4009-4018 (1999)). Therefore, broadly neutralizing antibodies (bNAbs) are considered to be the types of antibodies that should be elicited by a vaccine. Unfortunately, existing immunogens, often designed based on these bNAbs, have failed to elicit NAb responses of the required breadth and potency. Therefore, it is of high priority to identify new bNAbs that bind to epitopes that may be more amenable to incorporation into immunogens for elicitation of NAb responses.

The present invention provides a novel method for isolating novel broad and potent neutralizing monoclonal antibodies against HIV. The method involves selection of a PBMC donor with high neutralization titer of antibodies in the plasma. B cells are screened for neutralization activity prior to rescue of antibodies. Novel broadly neutralizing antibodies are obtained by emphasizing neutralization as the initial screen.

The invention relates to potent, broadly neutralizing antibody (bNAb) wherein the antibody neutralizes HIV-1 species belonging to two or more clades, and further wherein the potency of neutralization of at least one member of each Glade is determined by an IC50 value of less than 0.2 µg/mL. In some aspects, the clades are selected from Clade A, Clade B, Clade C, Clade D and Clade A E. In some aspects, the HIV-1 belonging two or more clades are non-Clade B viruses. In some aspects, the broadly neutralizing antibody neutralizes at least 60% of the HIV-1 strains listed in Tables 18A-18F. In some embodiments, at least 70%, or at least 80%, or at least 90% of the HIV-1 strains listed in Tables 18A-18F are neutralized.

The invention relates to potent, broadly neutralizing antibody (bNAb) wherein the antibody neutralizes HIV-1 species with a potency of neutralization of at least a plurality of HIV-1 species with an IC50 value of less than 0.2 µg/mL. In some embodiments the potency of neutralization of the HIV-1 species has an IC50 value of less than 0.15 µg/mL, or less than 0.10 µg/mL, or less than 0.05 µg/mL. In some aspects, a potent, broadly neutralizing antibody is defined as a bNAb that displays a potency of neutralization of at least a plurality of HIV-1 species with an IC90 value of less than 2.0 µg/mL. In some embodiments the potency of neutralization of the HIV-1 species has an IC90 value of less than 1.0 µg/mL, or less than 0.5 µg/mL.

Figure 4:
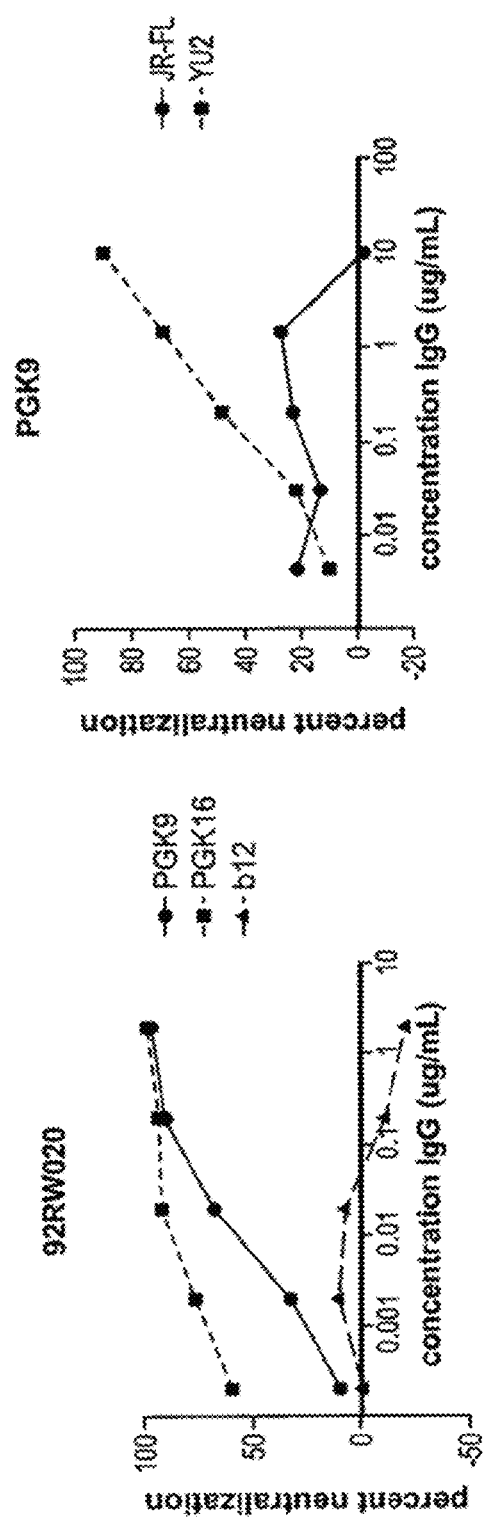
FIG. 4 is a series of graphs depicting the neutralization activity of monoclonal antibodies 1443_C16 (PG16) and 1496_C09 (PG9) to additional pseudoviruses not included in Tables 17A and 17B.

An exemplary method is illustrated in the schematic shown in FIG. 4. Peripheral Blood Mononuclear Cells (PBMCs) were obtained from an HIV-infected donor selected for HIV-1 neutralizing activity in the plasma. Memory B cells were isolated and B cell culture supernatants were subjected to a primary screen of neutralization assay in a high throughput format. Optionally, HIV antigen binding assays using ELISA or like methods were also used as a screen. B cell lysates corresponding to supernatants exhibiting neutralizing activity were selected for rescue of monoclonal antibodies by standard recombinant methods.

In one embodiment, the recombinant rescue of the monoclonal antibodies involves use of a B cell culture system as described in Weitcamp J-H et al., J. Immunol. 171:4680-4688 (2003). Any other method for rescue of single B cells clones known in the art also may be employed such as EBV immortalization of B cells (Traggiai E., et al., Nat. Med. 10(8):871-875 (2004)), electrofusion (Buchacher, A., et al., 1994. AIDS Res. Hum. Retroviruses 10:359-369), and B cell hybridoma (Karpas A. et al., Proc. Natl. Acad. Sci. USA 98:1799-1804 (2001).

In some embodiments, monoclonal antibodies were rescued from the B cell cultures using variable chain gene-specific RT-PCR, and transfectant with combinations of H and L chain clones were screened again for neutralization and HIV antigen binding activities. mAbs with neutralization properties were selected for further characterization.

A novel high-throughput strategy was used to screen IgG-containing culture screening supernatants from approximately 30,000 activated memory B cells from a Glade A infected donor for recombinant, monomeric gp120JR-CSF and gp41HxB2 (Env) binding as well as neutralization activity against HIV-1JR-CSF and HIV-1SF162 (See Table 1).

TABLE 1

| Memory B cell Screening. | |
|---|---|
| Total number of wells screened | 23,328 |
| Number of sIgG⁺ memory B cells screened | 30,300 |
| gp120 ELISA hits | 411 (1.36%) |
| gp41 ELISA hits | 167 (0.55%) |
| SF162 neutralization hits | 401 (1.32%) |
| JR-CSF neutralization hits | 401 (1.32%) |

Figure 3A:
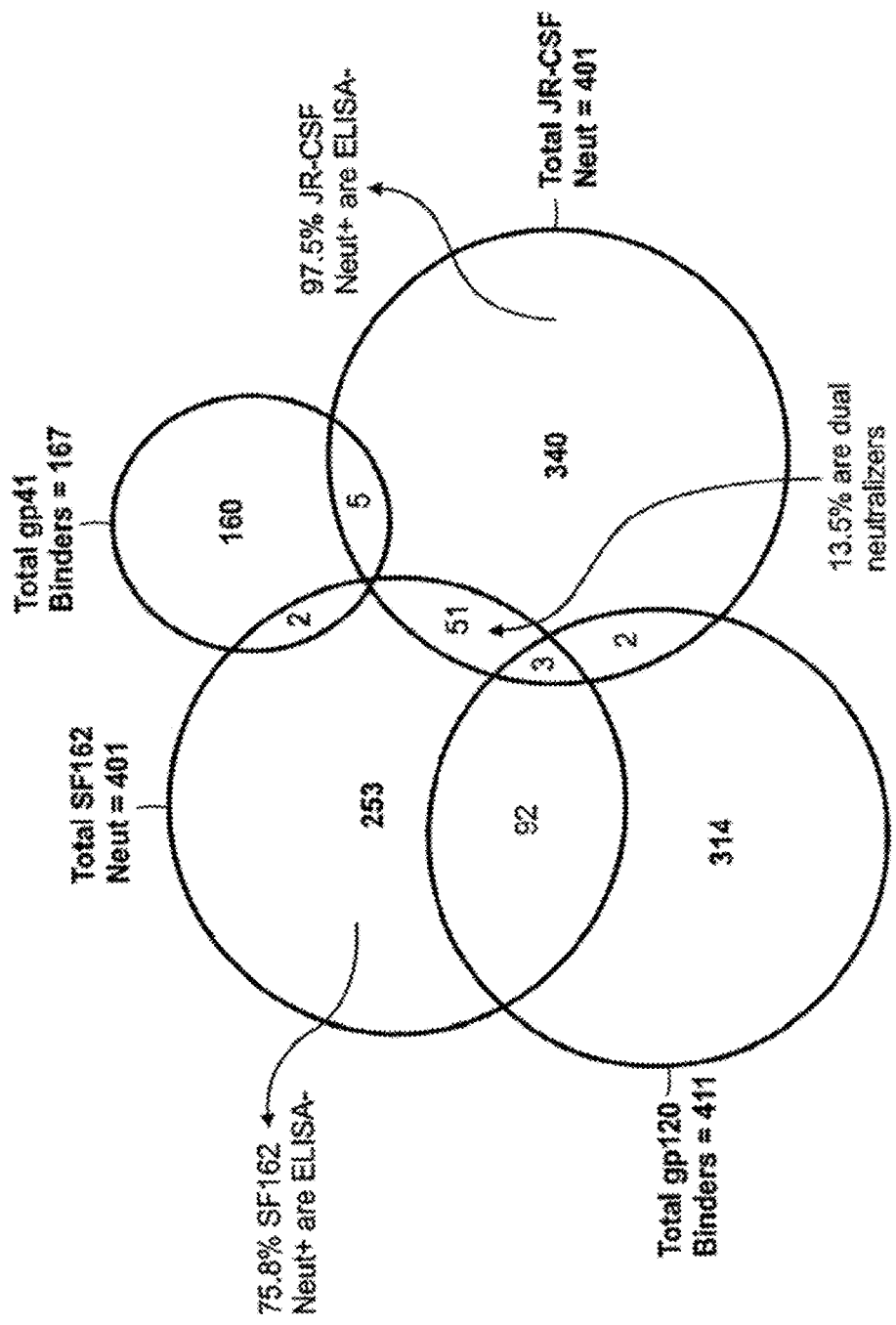
FIG. 3A is a schematic diagram that summarizes the screening results for neutralization and HIV-env protein (gp120 and gp41) binding assays from which B cell cultures were selected for antibody rescue and the monoclonal antibodies 1496_C09 (PG9), 1443_C16 (PG16), 1456_P20 (PG20), 1460_G14 (PGG14), and 1495_C14 (PGC14) were derived. A neutralization index value Of 1.5 was used as a cut-off.
Figure 3B:
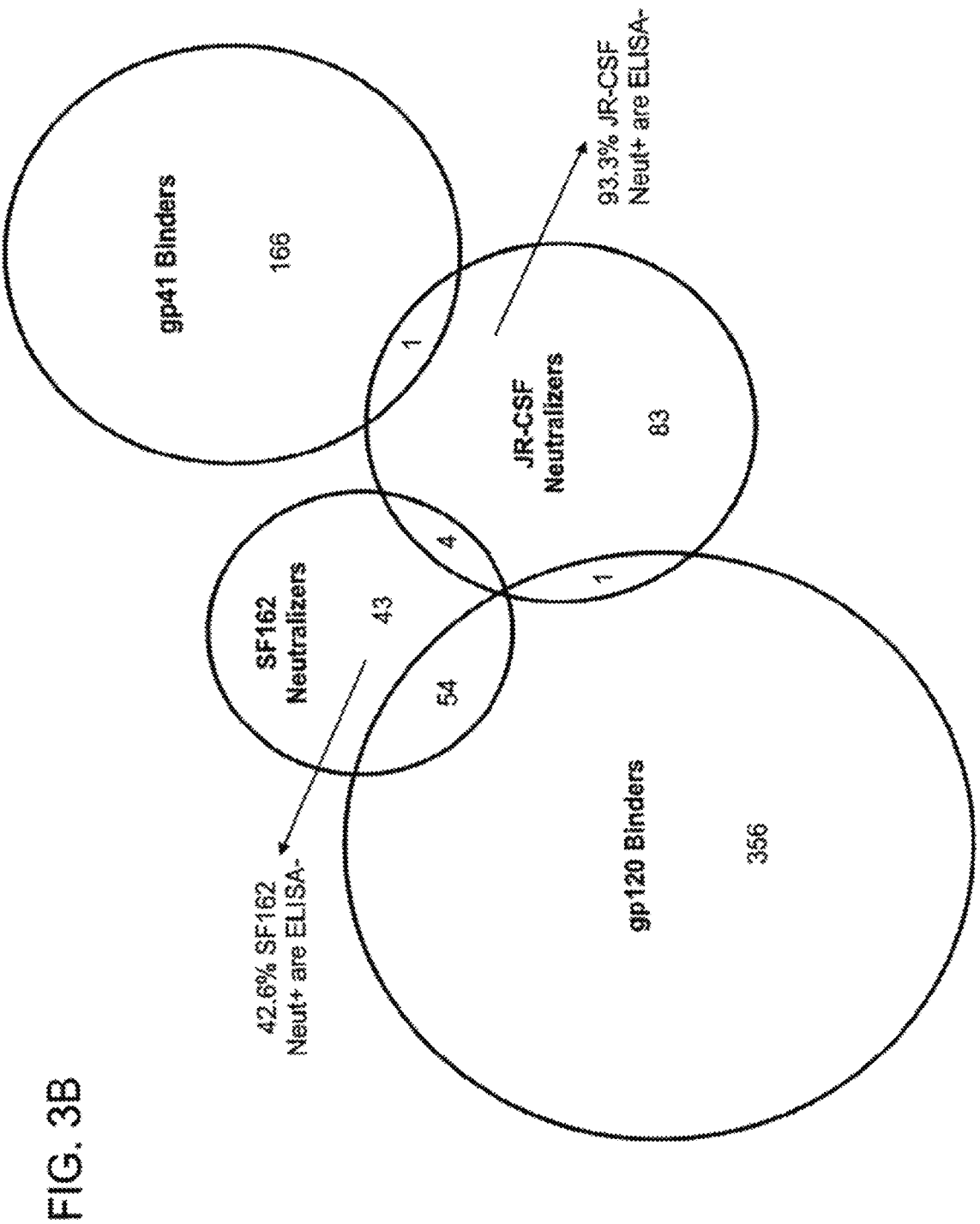
FIG. 3B is a schematic diagram that summaries the neutralizing activity and HIV-env protein (gp120 and gp41) binding activities of the monoclonal antibodies 1496_C09 (PG9), 1443_C16 (PG16), 1456_P20 (PG20), 1460_G14 (PGG14), and 1495_C14 (PGC14) as determined by ELISA assays among the B cell supernatants using a neutralization index cut-off value of 2.0. The neutralization index was expressed as the ratio of normalized relative luminescence units (RLU) of SIVmac239 to that of test viral strain derived from the same test B cell culture supernatant. The cut-off values used to distinguish neutralizing hits were determined by the neutralization index of a large number of negative control wells containing B cell culture supernatants derived from healthy donors.

Unexpectedly, a large proportion of the B cell supernatants that neutralized HIV-1JR-CSF did not bind monomeric gp120JR-CSF or gp41HxB2, and there were only a limited number of cultures that neutralized both viruses (FIG. 3B). Antibody genes were rescued from five B cell cultures selected for differing functional profiles; one bound to gp120 and only neutralized HIV-1SF162, two bound to gp120 and weakly neutralized both viruses, and two potently neutralized HIV-1JR-CSF, failed to neutralize HIV-1SF162, and did not bind to monomeric gp120 or gp41. Five antibodies identified according to these methods are disclosed herein. The antibodies were isolated from a human sample obtained through International AIDS Vaccine Initiative's (IAVI's) Protocol G, and are produced by the B cell cultures referred to as 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456 P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19

(PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_101 (PGT-137), 4993_K13 (PGT-141), 4995_E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and 6881_N05 (PGT-158). Antibodies referred to as 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_101 (PGT-137), 4993_K13 (PGT-141), 4995_E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and 6881_N05 (PGT-158), were isolated from the corresponding B cell cultures. These antibodies have been shown to neutralize HIV in vitro.

Analysis of the antibody variable genes revealed that two antibody pairs were related by somatic hypermutation and that two of the somatic variants contained unusually long CDRH3 loops (Table 2). Long CDRH3 loops have previously been associated with polyreactivity. (Ichiyoshi, Y. & Casali, P. J Exp Med 180, 885-895 (1994)). The antibodies were tested against a panel of antigens and the antibodies were confirmed to be not polyreactive.

TABLE 2

Sequence Analysis of mAb Variable Genes

| Clone | Germline IGVL[a] | Germline IGVH[a] | CDRL3[b] | SEQ ID NO: | CDRH3[b] | SEQ ID NO: |
|---|---|---|---|---|---|---|
| PG16 | VL2-14*01 | VH3-33*05 | SSLTDRSHRIF | 1 | EAGGPIWHDDV KYYDFNDGYYN YHYMDV | 6 |
| PG9 | VL2-14*01 | VH3-33*05 | KSLTSTRRRVF | 2 | EAGGPDYRNGY NYYDFYDGYYN YHYMDV | 7 |
| PGG14 | VK1-39*01 | VH1-69*12 | SYSTPRTF | 3 | DRRVVPMATDN WLDP | 8 |
| PG20 | VK2-14*01 | VH1-69*12 | SFSTPRTF | 4 | DRRAVPIATDN WLDP | 9 |
| PGC14 | VL3-1*01 | VH1-24*01 | AWETTTTFV FF | 5 | GAVGADSGSWF DP | 10 |

[a]Germ line gene sequences were determined using the IMGT database, which is publicly available at imgt.cines.fr. "L" and "K" refer to lambda and kappa chains, respectively,
[b]Bolded amino acids denote differences between somatic variants.

TABLE 3A

Heavy Chain Gene Usage Summary

| mAb ID | mAb Specificity | V-Gene & allele | V-Gene identity | J-Gene & allele | J-Gene identity | CDR3 |
|---|---|---|---|---|---|---|
| 1443_C16 | ELISA-negative | IGHV3-33*05 | 85.07% (245/288 nt) | IGHJ6*03 | 85.48% (53/62 nt) | AREAGGPIWHDDVKY YDFNDGYYNYHYMDV (SEQ ID NO: 46) |
| 1456_P20 | gp120 | IGHV1-69*11 or IGHV1-69*12 | 85.07% (245/288 nt) | IGHJ5*02 | 88.24% (45/51 nt) | ARDRRAVPIATDNWL DP (SEQ ID NO: 47) |
| 1460_G14 | gp120 | IGHV1-69*11 or IGHV1-69*12 | 86.11% (248/288 nt) | IGHJ5*02 | 86.27% (44/51 nt) | TRDRRVVPMATDNWL DP (SEQ ID NO: 48) |

TABLE 3A-continued

Heavy Chain Gene Usage Summary

| mAb ID | mAb Specificity | V-Gene & allele | V-Gene identity | J-Gene & allele | J-Gene identity | CDR3 |
|---|---|---|---|---|---|---|
| 1495_C14 | gp120 | IGHV1-f*01 | 88.89% (256/288 nt) | IGHJ5*02 | 84.31% (43/51 nt) | AAGAVGADSGSWFDP (SEQ ID NO: 49) |
| 1496_C09 | ELISA-negative | IGHV3-33*05 | 85.07% (245/288 nt) | IGHJ6*03 | 83.87% (52/62 nt) | VREAGGPDYRNGYNYYDFYDGYYNYHYMDV (SEQ ID NO: 50) |

TABLE 3B

Light Chain Gene Usage Summary

| mAb ID | mAb Specificity | V-Gene and allele | V-gene identity | J-GENE and allele | J-Gene identity | CDR3 | SEQ ID NO: |
|---|---|---|---|---|---|---|---|
| 1443_C16 | ELISA-negative | IGLV2-14*01 | 88.19% (254/288 nt) | IGLJ2*01. or IGLJ3*01 or IGLJ3*02 | 83.33% (30/36 nt) | SSLTDRSHRI | 41 |
| 1456_P20 | gp120 | IGKV1-39*01, or IGKV1D-39*01 | 92.11% (257/279 nt) | IGKJ5*01 | 92.11% (35/38 nt) | QQSFSTPRT | 42 |
| 1460_G14 | gp120 | IGKV1-39*01, or IGKV1D-39*01 | 92.11% (257/279 nt) | IGKJ5*01 | 89.47% (34/38 nt) | QQSYSTPRT | 43 |
| 1495_C14 | gp120 | IGLV3-1*01 | 88.89% (248/279 nt) | IGLJ2*01. or IGLJ3*01 | 86.84% (33/38 nt) | QAWETTTTTFVF | 44 |
| 1496_C09 | ELISA-negative | IGLV2-14*01 | 91.32% (263/288 nt) | IGLJ3*02 | 86.11% (31/36 nt) | KSLTSTRRRV | 45 |

The broadly neutralizing antibodies from 1443_C16 (PG16) and 1496_C09 (PG9) clones obtained by this method did not exhibit soluble gp120 or gp41 binding at levels that correlate with neutralization activity. The method of the invention therefore allows identification of novel antibodies with broad cross-clade neutralization properties regardless of binding activities in an ELISA screen. Further characterization of PG16 and PG9 is disclosed herein.

All five antibodies were first tested for neutralization activity against a multi-clade 16-pseudovirus panel (Table 4). Two of the antibodies that bound to monomeric gp120 in the initial screen (PGG14 and PG20) did not show substantial neutralization breadth or potency against any of the viruses tested, and the third antibody that bound to gp120 (PGC14) neutralized 4/16 viruses with varying degrees of potency. In contrast, the two antibodies that failed to bind recombinant Env in the initial screen (PG9 and PG16) neutralized a large proportion of the viruses at sub-microgram per ml concentrations. PG9 and PG16 neutralized non-clade B viruses with greater breadth than three out of the four existing bNAbs. This is significant considering that the majority of HIV-1 infected individuals worldwide are infected with non-clade B viruses.

TABLE 4

Neutralization Profiles of Rescued mAbs

| | | IC50 (μg/mL) | | | | |
|---|---|---|---|---|---|---|
| | Isolate | PGC14 | PG9 | PG16 | PGG14 | P20 |
| Clade A | 94UG103 | >50 | 0.17 | 0.008 | >50 | >50 |
| | 92RW020 | 28.60 | 0.06 | 0.004[a] | >50 | 50 |
| | 93UG077 | >50 | >50 | >50 | >50 | >50 |
| Clade B | 92BR020 | 0.64 | >50 | >50 | >50 | >50 |
| | APV-13 | >50 | >50 | >50 | >50 | >50 |
| | JRCSF | >50 | <0.0025 | <0.0025 | >50 | >50 |
| | APV-17 | >50 | 26.45 | >50 | >50 | >50 |
| | APV-6 | 7.41 | 0.09 | 0.08[a] | >50 | 25.770 |
| Clade C | 93IN905 | >50 | N/A | 0.10[a] | >50 | >50 |
| | IAVI-C18 | >50 | 0.05 | 0.007 | >50 | >50 |
| | IAVI-C22 | >50 | N/A | 0.069[a] | >50 | >50 |
| | IAVI-C3 | 9.50 | 12.91 | 14.80 | >50 | >50 |
| Clade D | 92UG024 | >50 | 10.96 | >50 | >50 | >50 |
| | 92UG005 | >50 | >50 | >50 | >50 | >50 |

TABLE 4-continued

Neutralization Profiles of Rescued mAbs

IC50 (µg/mL)

| | Isolate | PGC14 | PG9 | PG16 | PGG14 | P20 |
|---|---|---|---|---|---|---|
| CRF01_AE | 92TH021 | >50 | 0.11 | 0.13[a] | >50 | >50 |
| | CMU02 | >50 | >50 | >50 | >50 | >50 |
| negative control | aMLV | >50 | >50 | >50 | >50 | >50 |

[a]Plateau observed in curve.

Table 17A shows neutralization profiles (IC50 values) of monoclonal antibodies 1443_C16 (PG16), 1456_P20 (PG20), 1460_G14 (PGG14), 1495_C14 (PGC14) and 1496_C09 (PG9) and the known cross-clade neutralizing antibodies b12, 2G12, 2F5 and 4E10 on a diverse panel of 16 HIV pseudoviruses from different clades. 1443_C16 (PG16) and 1496_C09 (PG9) neutralize HIV-1 species from Clades A, B, C, D and CRF01_AE with better potency for most viral strains tested than known and generally accepted broad and potent neutralizing antibodies. However, neutralization profiles of individual species of HIV-1 belonging to these clades vary between 1443_C16 (PG16) and 1496_C09 (PG9) and the known cross-clade neutralizing antibodies b12, 2G12, 2F5 and 4E10. 1495_C14 (PGC14) neutralizes fewer HIV-1 species from Clades A, B and C comparable to other neutralizing antibodies. Table 17B shows IC90 values of the monoclonal antibodies 1443_C16 (PG16) and 1496_C09 (PG9) and the known cross-clade neutralizing antibodies b12, 2G12, 2F5 and 4E10 on the same panel of pseudoviruses. FIG. 4 shows neutralization activities of monoclonal antibodies 1443_C16 (PG16) and 1496_C09 (PG9) to six other HIV pseudoviruses (YU2, Bal, ADA, DU172, DU422, and ZM197) for clades B and C not included in Tables 17A and 17B.

PG9, PG16, and PGC14 were next evaluated on a large multi-clade pseudovirus panel consisting of 162 viruses to further assess the neutralization breadth and potency of these three antibodies (Tables 5A-5B, Tables 18A-18F and Tables 19A-19B). The bNAbs b12, 2G12, 2F5, and 4E10, as well as the donor's serum, were also included in the panel for comparison. Overall, PG9 neutralized 127 out of 162 and PG16 neutralized 119 out of 162 viruses with a potency that frequently considerably exceeded that noted for the four control bNAbs.

The median IC50 and IC90 values for neutralized viruses across all clades were an order of magnitude lower for PG9 and PG16 than any of the four existing bNAbs (Table 5A, Tables 18A-18F and Tables 19A-19B). Both mAbs showed overall greater neutralization breadth than b12, 2G12, and 2F5 (Table 5B, Tables 18A-18F and Tables 19A-19B). At low antibody concentrations, PG9 and PG16 also demonstrated greater neutralization breadth than 4E10 (Table 5B). Furthermore, both mAbs potently neutralized one virus (IAVI-C18) that exhibits resistance to all four existing bNAbs (Tables 18A-18F). The mAb neutralization curves reveal that, whereas the PG9 neutralization curves usually exhibit sharp slopes, the neutralization curves for PG16 sometimes exhibit gradual slopes or plateaus at less than 100% neutralization. Although neutralization curves with similar profiles have been reported previously (W. J. Honnen et al., J Virol 81, 1424 (February, 2007), A. Pinter et al., J Virol 79, 6909 (June, 2005)), the mechanism for this is not well understood.

Comparison of the neutralization profile of the serum with the neutralization profile of PG9, PG16 and PGC14 revealed that these three antibodies could recapitulate the breadth of the serum neutralization in most cases (Tables 18A-18F). For example, almost all of the viruses that were neutralized by the serum with an IC50>1:500 were neutralized by PG9 and/or PG16 at <0.05 µg/mL. The one case where this did not occur was against HIV-1SF162, but this virus was potently neutralized by PGC14. Despite the fact that PG9 and PG16 are somatic variants, they exhibited different degrees of potency against a number of the viruses tested. For instance, PG9 neutralized HIV-16535.30 approximately 185 times more potently than PG16, and PG16 neutralized HIV-1MGRM-AG-001 approximately 440 times more potently than PG9. In some cases, the two antibodies also differed in neutralization breadth; PG9 neutralized nine viruses that were not affected by PG16, and PG16 neutralized two viruses that were not affected by PG9. Based on these results, it is postulated that broad serum neutralization might be mediated by somatic antibody variants that recognize slightly different epitopes and display varying degrees of neutralization breadth and potency against any given virus. In the face of an evolving viral response, it seems reasonable that the immune system might select for these types of antibodies.

Comparison of the neutralization profile of the serum with the neutralization profile of PG9, PG16 and PGC14 revealed that these three antibodies could recapitulate the breadth of the serum neutralization in most cases. For example, almost all of the viruses that were neutralized by the serum with an IC50>1:1000 were neutralized by PG9 and/or PG16 at <0.005 µg/mL. The one case where this did not occur was against HIV-1SF162, but this virus was potently neutralized by PGC14. Tables 5(a) and 5(b) show the neutralization activities—breadth and potency, respectively—of PG9, PG16, and PGC14 as well as four control bNAbs as measured by IC50 values. Tables 19A-19B show results of the same analysis using IC90 values.

TABLE 5(A)

Neutralization Potency of mAbs

Median IC$_{50}$ (µg/mL) against viruses neutralized with an IC$_{50}$ <50 µg/mL

| Clade[a] | # viruses | b12 | 2G12 | 2F5 | 4E10 | PG9 | PG16 | PGC14 |
|---|---|---|---|---|---|---|---|---|
| A | 27 | 6.98 | 17.10 | 5.70 | 6.20 | 0.16 | 0.11 | 41.59 |
| B | 31 | 0.80 | 0.82 | 2.41 | 5.22 | 0.43 | 0.70 | 21.88 |
| C | 27 | 6.46 | 2.93 | 31.51 | 2.97 | 0.22 | 0.25 | 11.97 |

TABLE 5(A)-continued

Neutralization Potency of mAbs

| Clade[a] | # viruses | Median IC$_{50}$ (μg/mL) against viruses neutralized with an IC$_{50}$ <50 μg/mL | | | | | | |
|---|---|---|---|---|---|---|---|---|
| | | b12 | 2G12 | 2F5 | 4E10 | PG9 | PG16 | PGC14 |
| D | 25 | 1.47 | 7.71 | 3.17 | 4.60 | 0.10 | 0.02 | 38.57 |
| CRF01_AE | 10 | 21.53 | >50 | 0.26 | 0.51 | 0.08 | 0.03 | >50 |
| CRF_AG | 10 | 10.40 | 0.95 | 0.64 | 1.42 | 0.80 | 0.03 | 45.10 |
| G | 15 | 3.07 | 31.03 | 1.24 | 1.44 | 0.29 | 1.21 | >50 |
| F | 15 | >50 | 9.23 | 1.78 | 2.30 | 0.09 | 0.08 | 25.71 |
| Total | 162 | 2.82 | 2.43 | 2.30 | 3.24 | 0.22 | 0.15 | 25.99 |

Boxes are color colded as follows: white, median potency >50 μg/mL; light grey, median potency between 2 and 20 μg/mL; medium grey, median potencybetween 0.2 and 2 μg/mL; dark grey, median potency <0.2 μg/mL.
[a] CRF_07BC and CRF_08BC viruses are not included in the clade analysis because there was only one virus tested from each of these clades.

TABLE 5(B)

Neutralization Breadth of mAbs

| Clade[a] | # viruses | b12 | 2G12 | 2F5 | 4E10 | PG9 | PG16 | PGC14 |
|---|---|---|---|---|---|---|---|---|
| | | % viruses neutralized with an IC$_{50}$ <50 μg/mL | | | | | | |
| A | 27 | 30 | 37 | 74 | 96 | 85 | 85 | 11 |
| B | 31 | 58 | 71 | 68 | 97 | 74 | 74 | 29 |
| C | 27 | 33 | 11 | 7 | 96 | 78 | 78 | 19 |
| D | 25 | 48 | 24 | 56 | 96 | 76 | 60 | 8 |
| CRF01_AE | 10 | 30 | 0 | 89 | 100 | 100 | 100 | 0 |
| CRF_AG | 10 | 30 | 50 | 80 | 100 | 80 | 60 | 10 |
| G | 15 | 13 | 20 | 80 | 100 | 87 | 73 | 7 |
| F | 15 | 0 | 21 | 87 | 100 | 67 | 64 | 13 |
| Total | 162 | 35 | 32 | 60 | 98 | 79 | 73 | 15 |
| | | % viruses neutralized with an IC$_{50}$ <1.0 μg/mL | | | | | | |
| A | 27 | 0 | 4 | 4 | 0 | 70 | 63 | 0 |
| B | 31 | 32 | 39 | 23 | 0 | 45 | 42 | 3 |
| C | 27 | 7 | 0 | 0 | 11 | 56 | 48 | 0 |
| D | 25 | 12 | 8 | 12 | 8 | 48 | 44 | 0 |
| CRF01_AE | 10 | 11 | 0 | 88 | 80 | 70 | 70 | 0 |
| CRF_AG | 10 | 10 | 30 | 60 | 30 | 40 | 50 | 0 |
| G | 15 | 0 | 0 | 27 | 0 | 60 | 33 | 0 |
| F | 15 | 0 | 14 | 13 | 28 | 80 | 79 | 0 |
| Total | 162 | 11 | 12 | 19 | 12 | 57 | 51 | 1 |

Boxes are color coded as follows: white, no viruses neutralized; black, 1 to 30% of viruses neutralized; light grey, 30 to 60% of viruses neutralized: medium grey, 60 to 90% of viruses neutralized: dark grey, 90 to 100% of viruses neutralized.
[a] CRF_07BC and CRF_08BC viruses are not included in the clade analysis because there was only one virus tested from each of these clades.

Despite the fact that PG9 and PG16 are somatic variants, they exhibited different degrees of potency against a number of the viruses tested. For instance, PG9 neutralized the virus 6535.30 about 100 times more potently than PG16, and PG16 neutralized the virus MGRM-AG-001 about 3000 times more potently than PG9. In some cases, the two antibodies also differed in neutralization breadth; PG9 neutralized seven viruses that were not neutralized by PG16, and PG16 neutralized three viruses that were not neutralized by PG9. Without being bound by theory, it appears that broad serum neutralization might be mediated by somatic variants that recognize slightly different epitopes and display varying degrees of neutralization breadth and potency against any given virus. In the face of an evolving viral response, the immune system likely selects for these types of antibodies.

Figure 5:
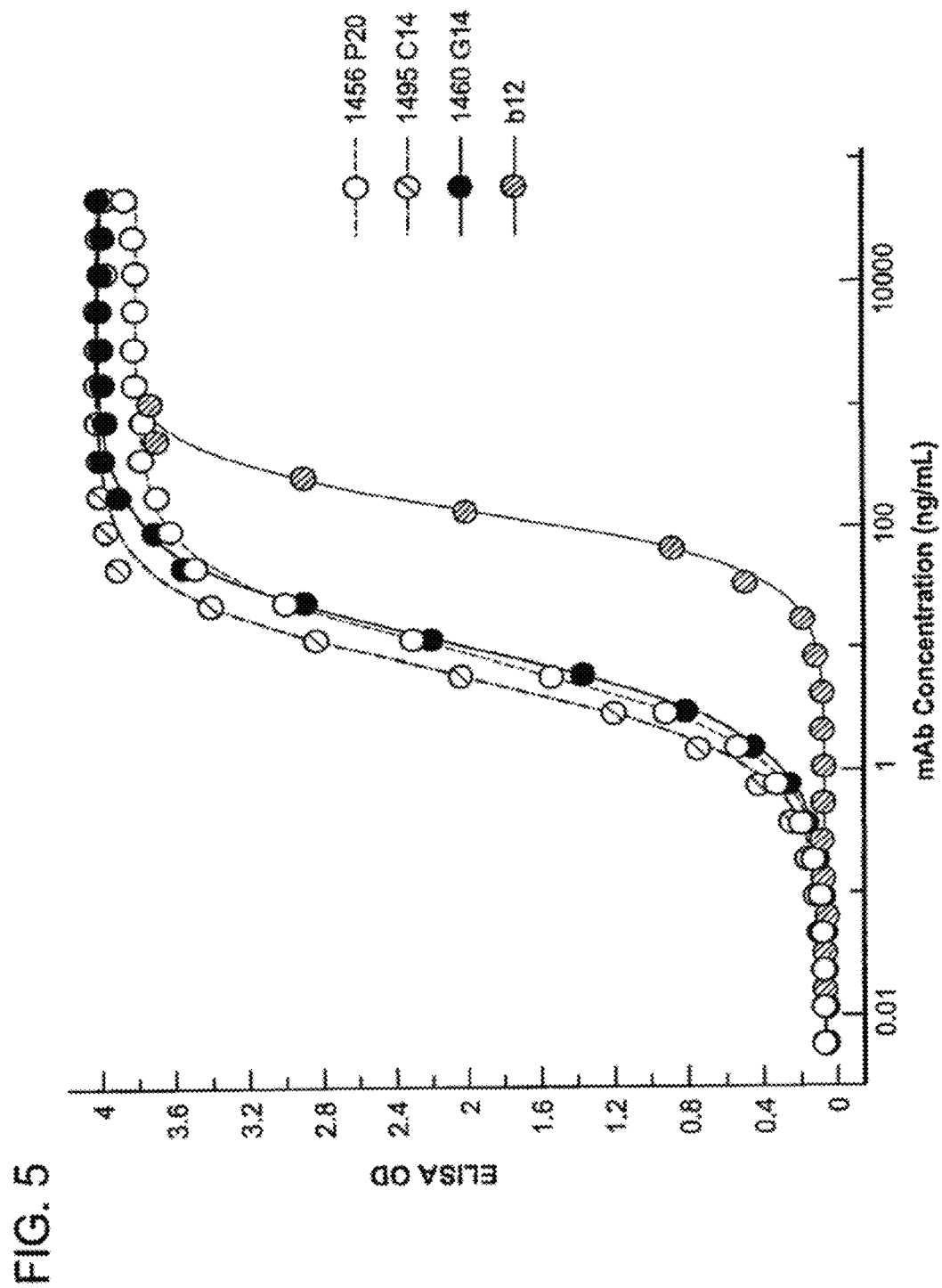
FIG. 5 is a graph depicting the dose response curves of 1456_P20 (PG20), 1495_C14 (PGC14) and 1460_G14 (PGG14) binding to recombinant gp120 in ELISA as compared to control anti-gp120 (b12). Data is presented as average OD values of triplicate ELISA wells obtained on the same plate.
Figure 6:
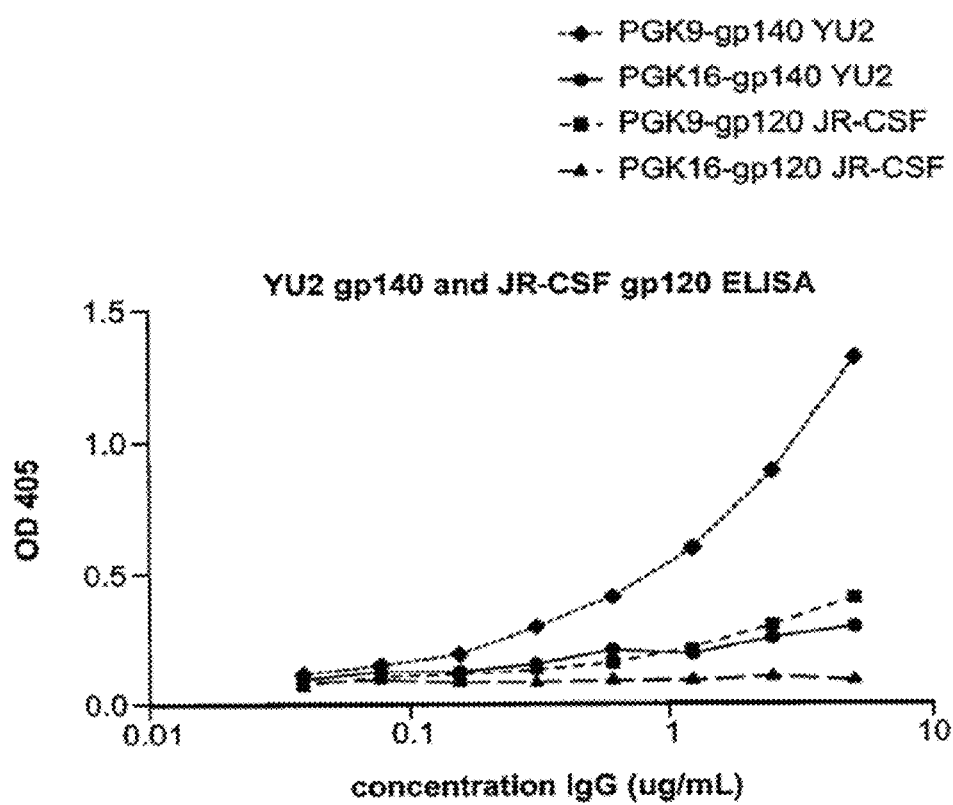
FIG. 6 is a series of graphs depicting the results from ELISA binding assays of monoclonal antibodies 1443_C16 (PG16) and 1496_C09 (PG9) to HIV-1 YU2 gp140, JR-CSFgp120, membrane-proximal external regions (MPER) peptide of gp41 and V3 polypeptide.

The antibodies were also tested for ability to bind soluble recombinant HIV envelope proteins. FIG. 5 shows dose response curves of 1456_P20 (PG20), 1495_C14 (PGC14) and 1460_G14 (PGG14) binding to recombinant gp120 in ELISA as compared to control anti-gp120 (b12). FIG. 6 shows ELISA binding assays of monoclonal antibodies 1443_C16 (PG16) and 1496_C09 (PG9) to HIV-1 strain YU2 gp140 and JR-CSF gp120, the membrane proximal region (MPER) of HIV-1 envelope glycoprotein gp41, and the V3 polypeptide. PG-9 binds to YU2 gp140 (IC50~20-40 nM), YU2 gp120 and weakly binds to JR-CSF gp120. However, PG16 weakly binds Yu2 gp120, but not the soluble form of HIV-1 envelope glycoprotein, gp120 JR-CSF. Neither mAb binds to JR-FL gp120, JR-FL gp140, MPER peptide of gp41 or V3 peptide.

Figure 7:
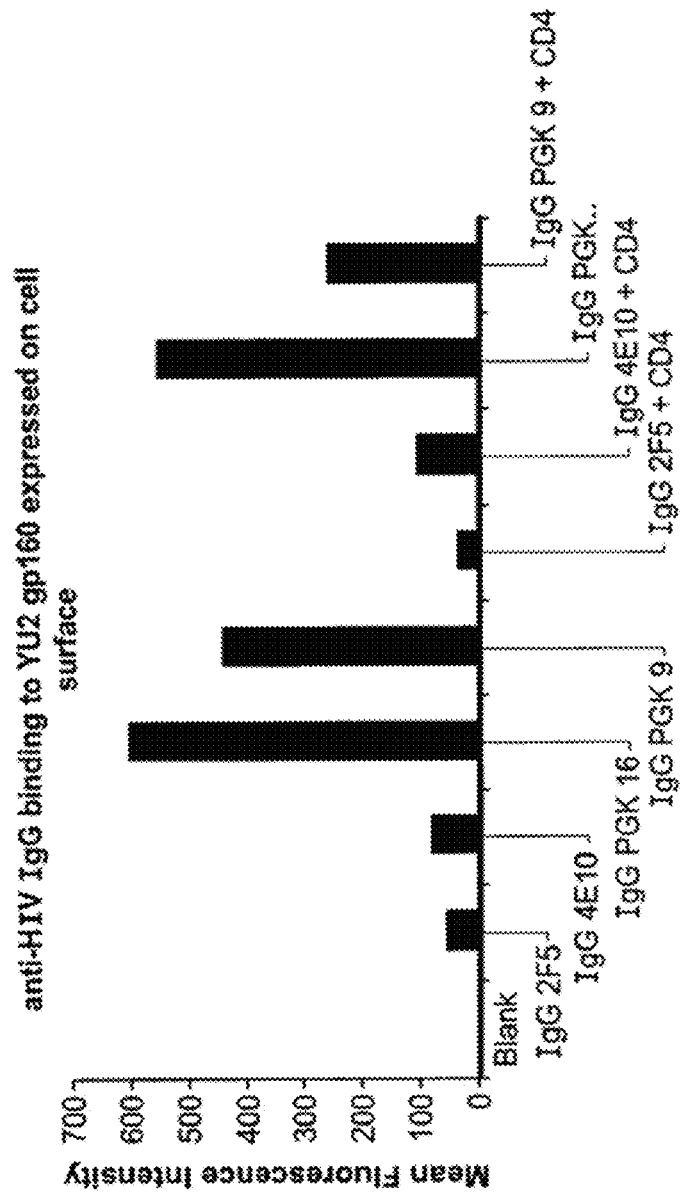
FIG. 7 is a graph depicting the results of a binding assay using monoclonal antibodies 1443_C16 (PG16) and 1496_C09 (PG9) to HIV-1 YU2 gp160 expressed on the cell surface in the presence and absence of soluble CD4 (sCD4).

FIG. 7 shows binding of monoclonal antibodies 1443_C16 (PG16) and 1496_C09 (PG9) to HIV-1 YU2 gp160 expressed on the cell surface in the presence and absence of sCD4. Competitive inhibition of the binding by sCD4 indicates that the binding of monoclonal antibody 1496_C09 to HIV-1 envelope protein gp160 expressed on the cell surface is presumably affected due to the conformational changes induced by sCD4. The data further suggest that 1443_C16 (PG16) and 1496_C09 (PG9) exhibit relatively stronger binding to trimeric forms of the HIV-1 Env (gp160 and gp140) than to the monomeric gp120.

Figure 8:
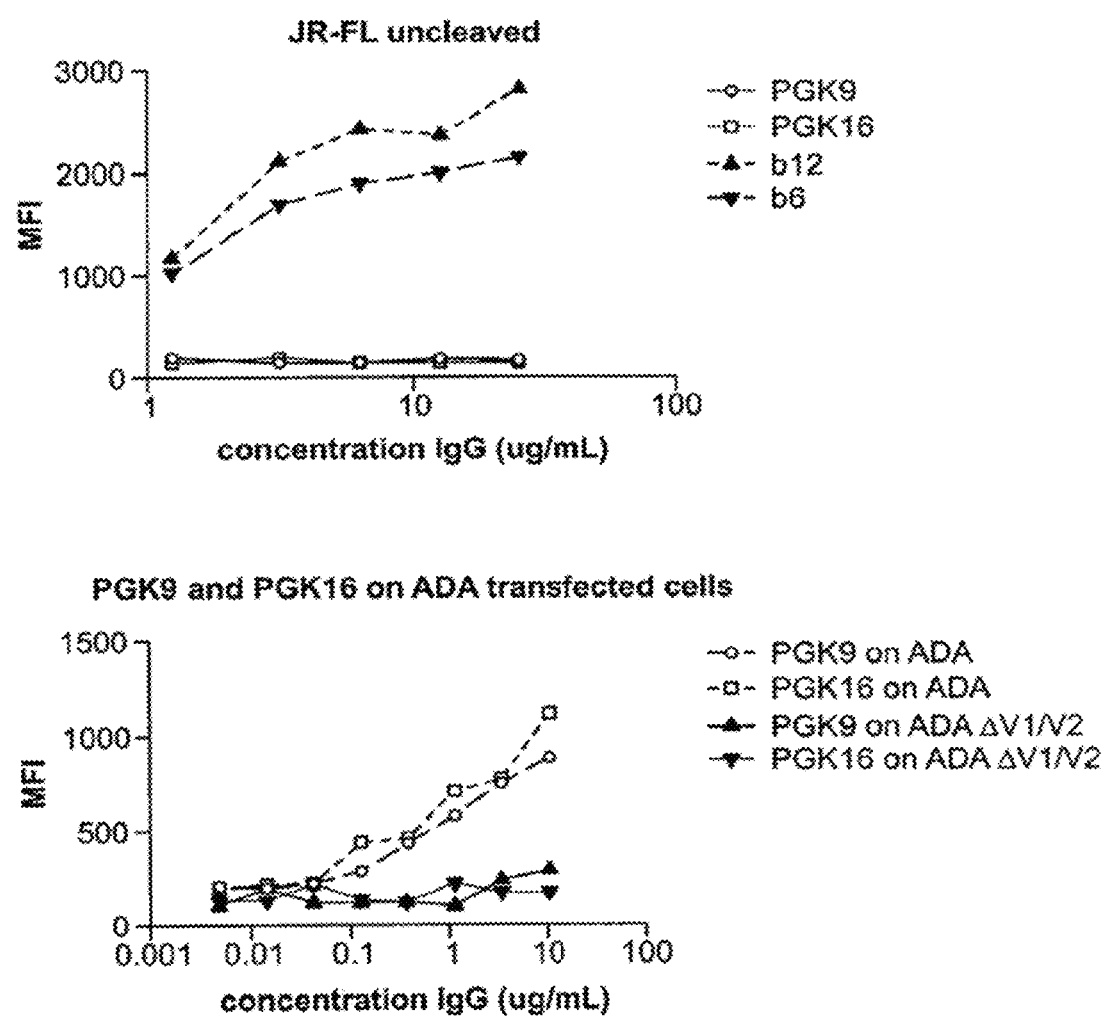
FIG. 8 is a graph depicting the results of a binding assay using monoclonal antibodies 1443_C16 (PG16) and 1496_C09 (PG9) to HIV-1 gp160 transfected cells.
Figure 8:
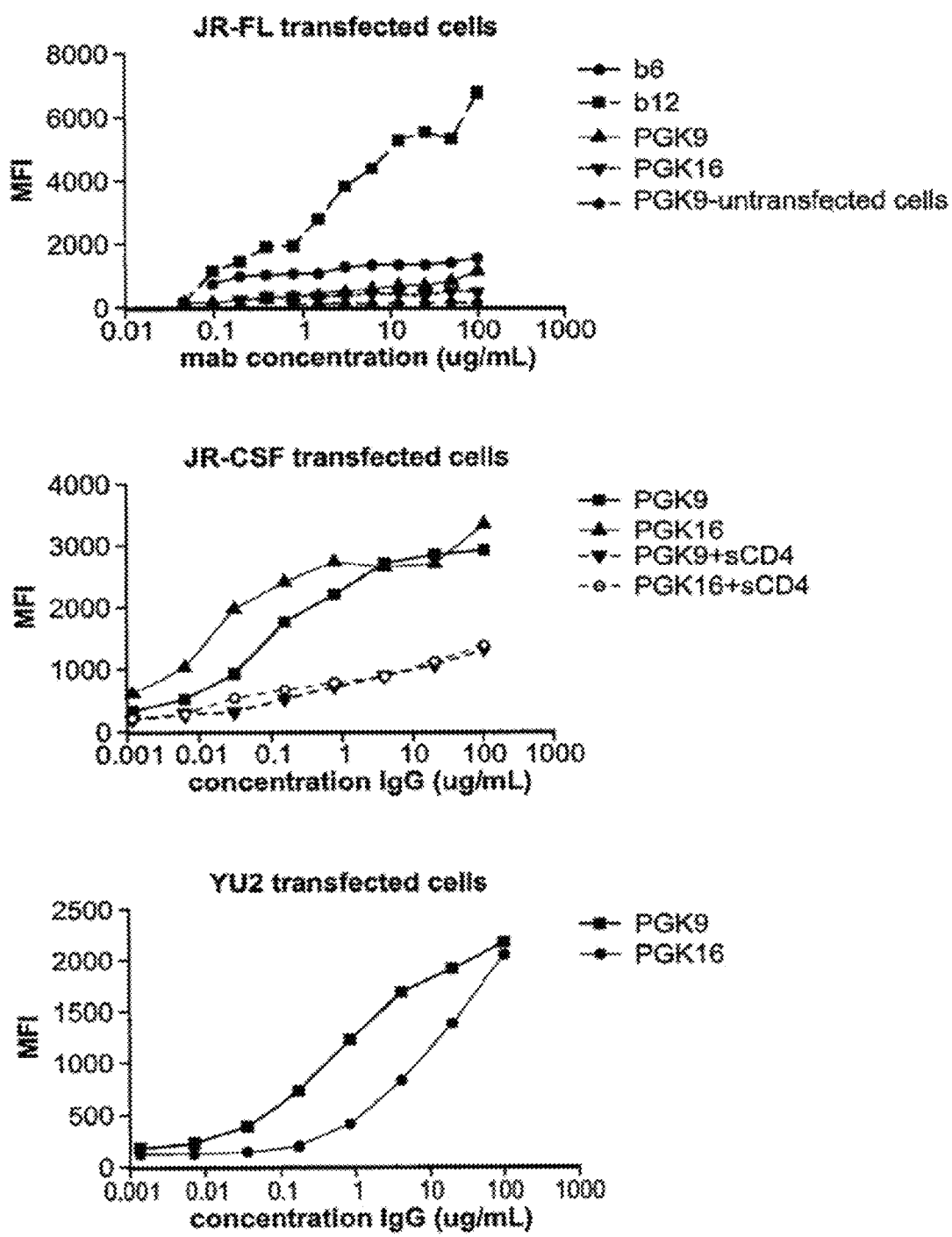

FIG. 8 shows binding of monoclonal antibodies 1443_C16 (PG16) and 1496_C09 (PG9) to HIV-1 transfected cells. PG9 and PG16 do not bind untransfected cells. PG9 and PG16 bind JR-CSF, ADA, and YU2 gp160 transfected cells. PG9 and PG16 do not bind JR-FL gp160 transfected cells (cleaved or uncleaved). PG9 and PG16 do not bind ADA AV1/AV2 transfected cells. PG9 and PG16 binding to JR-CSF gp160 transfected cells is inhibited by sCD4.

Figure 9:
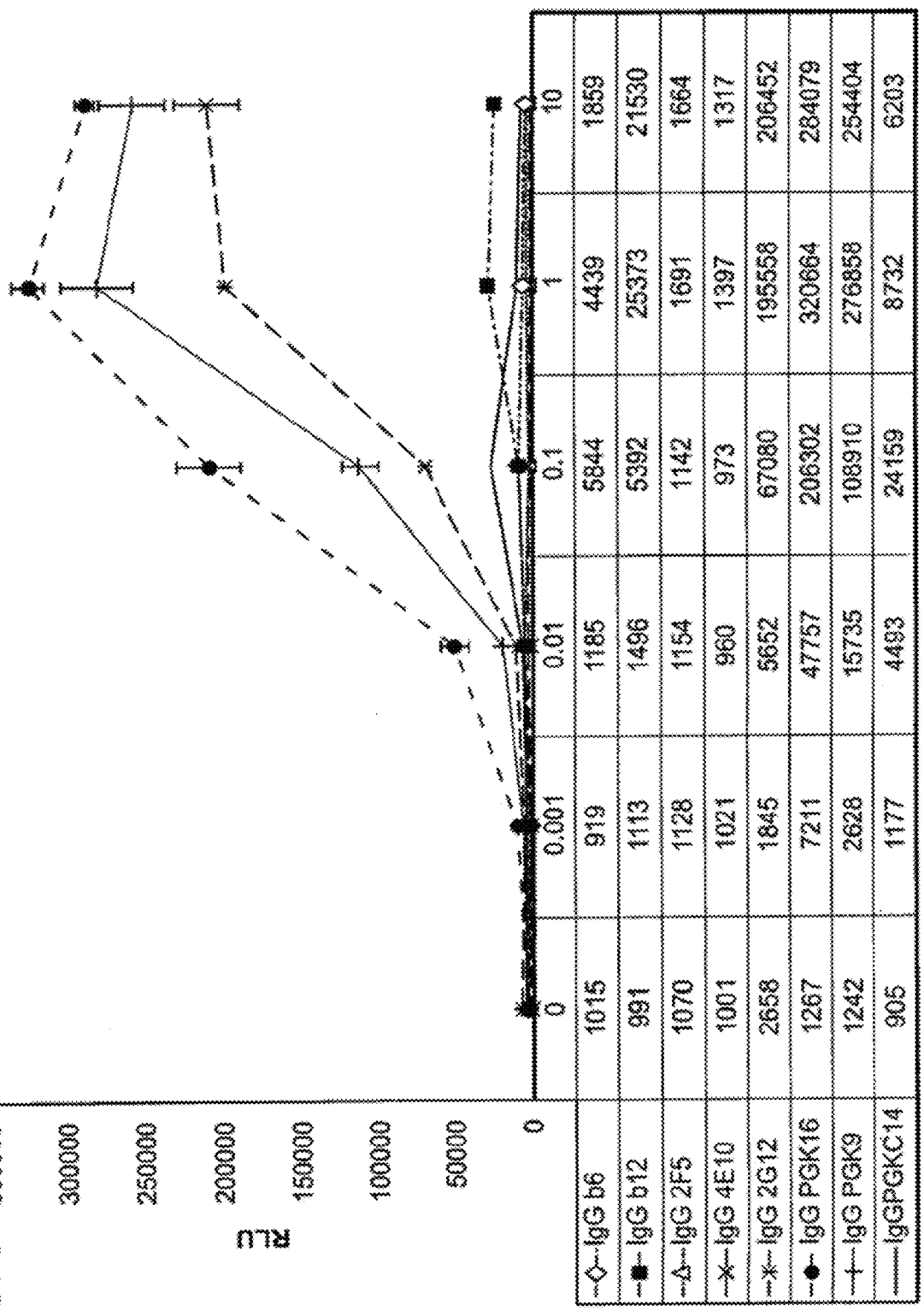
FIG. 9 is a series of graphs depicting the results of a capture assay. The data describe capturing of entry-competent JRCSF pseudovirus by neutralizing monoclonal antibodies 1443_C16 (PG16) and 1496_C09 (PG9) in a dose-dependent manner.

FIG. 9 shows the capturing of entry-competent JR-CSF pseudovirus by neutralizing monoclonal antibodies 1443_C16 (PG16) and 1496_C09 (PG9) in a dose-dependent manner. The ability of both antibodies to capture JR-CSF pseudovirus is higher than IgG b12 but comparable to IgG 2G12. It is postulated that the capture may be mediated by the binding of the mAbs to the HIV-1 Env on the virions.

Figure 10B:
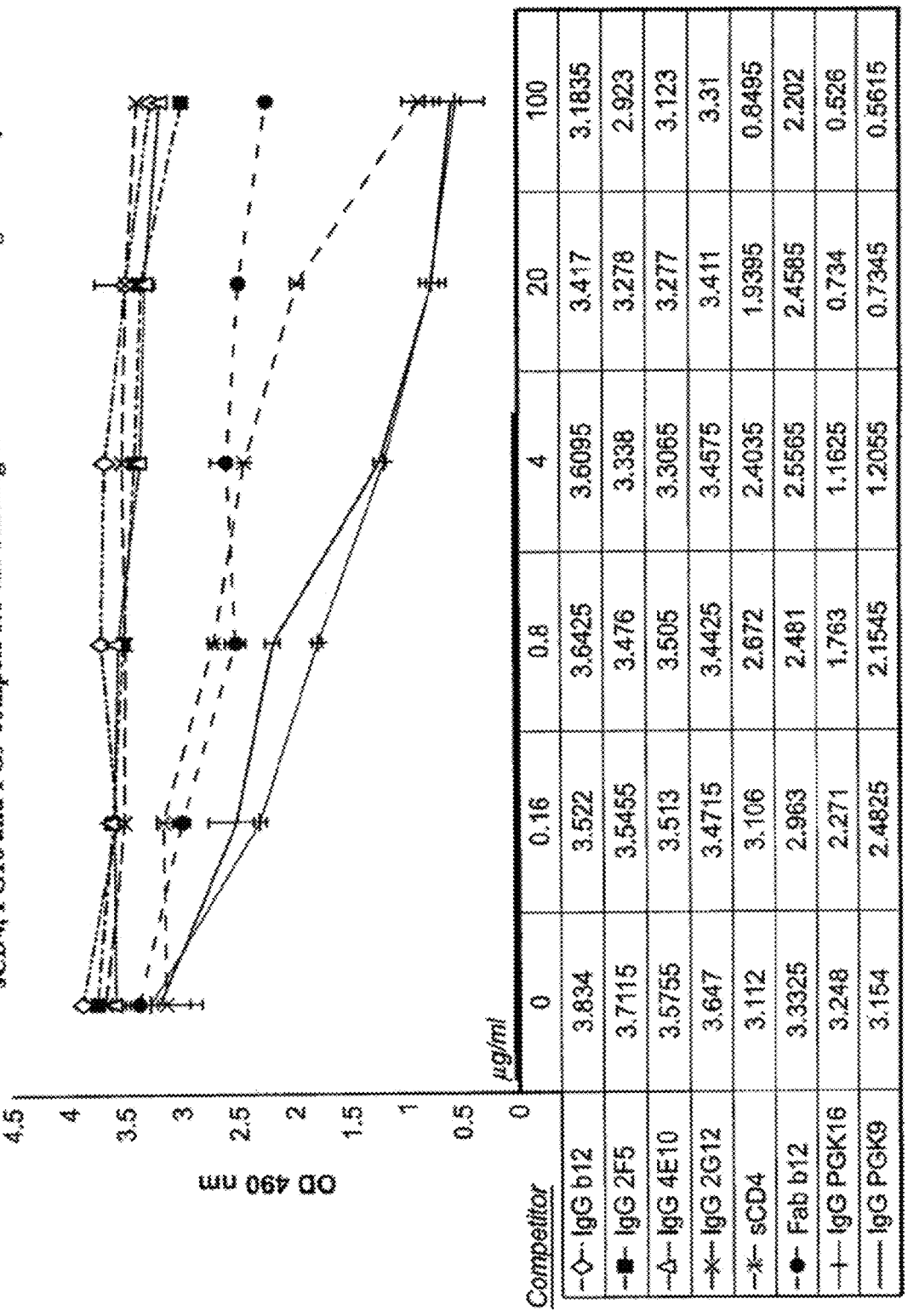
FIG. 10B is a graph depicting the results of a competitive binding assay using monoclonal antibodies sCD4, PG16 and PG9, wherein the claimed antibodies compete for the binding of monoclonal antibody 1496_C09 (PG9) to pseudovirus but control antibodies b12, 2G12, 2F5 and 4E10 do not competitively bind to the pseudovirus.

FIG. 10A shows that sCD4, PG16 and PG9 compete for the binding of monoclonal antibody 1443_C16 (PG16) to JR-CSF pseudovirus but b12, 2G12, 2F5 and 4E10 do not. FIG. 10B shows sCD4, PG16 and PG9 compete for the binding of monoclonal antibody 1496_C09 (PG9) to JR-CSF pseudovirus but b12, 2G12, 2F5 and 4E10 do not. This suggests that the PG16 and PG9 mAbs bind gp120 at a site different from those bound by b12 and 2G12. PG9 and PG16 binding to HIV-1 envelope protein is competitively inhibited by sCD4. Given that the MAbs are not inhibited by the CD4 binding site MAb b12, this suggests that PG9 and PG16 are binding to an epitope that is unavailable for sCD4 binding to gp120 as a result of conformational changes. The inability of PG9 and PG16 to bind monomeric gp120JR-CSF or gp41HxB2 in the initial screen while potently neutralizing HIV-1JR-CSF suggests that the epitope targeted by these antibodies is preferentially expressed on trimeric HIV envelope protein. The ability of PG9 and PG16 to bind monomeric gp120 from several different strains, artificially trimerized gp140 constructs, and trimeric Env expressed on the surface of transfected cells respectively, was compared. Although both antibodies bound with high affinity to cell surface Env, PG16 did not bind to any of the soluble gp120 or gp140 constructs and PG9 bound only weakly to monomeric gp120 and trimerized gp140 from certain strains (FIG. 11). It has been previously shown that a substantial fraction of cell surface Env is comprised of uncleaved gp160 molecules. (Pancera, M. & Wyatt, R. Virology 332, 145-156 (2005)). That PG9 and PG16 do not exhibit exclusive specificity for native HIV-1 trimers was confirmed by the fact that both antibodies bound with high affinity to cleavage-defective HIV-1YU2 trimers expressed on the surface of transfected cells (FIG. 12).

Figure 13A:
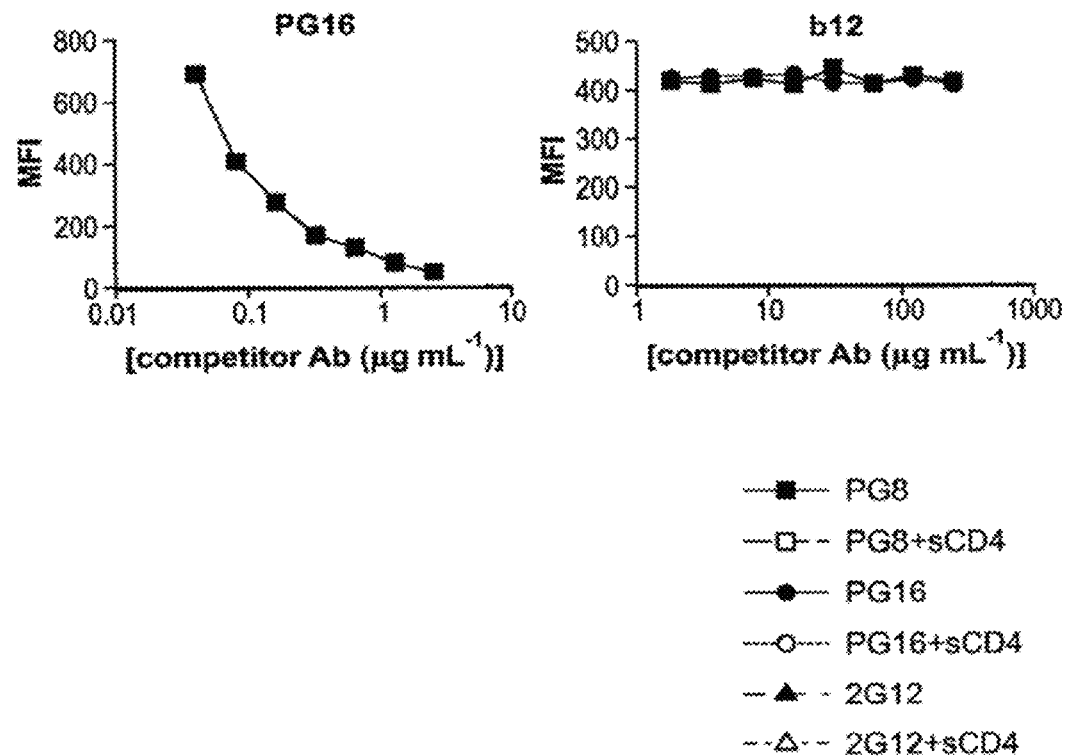
Figure 13B:
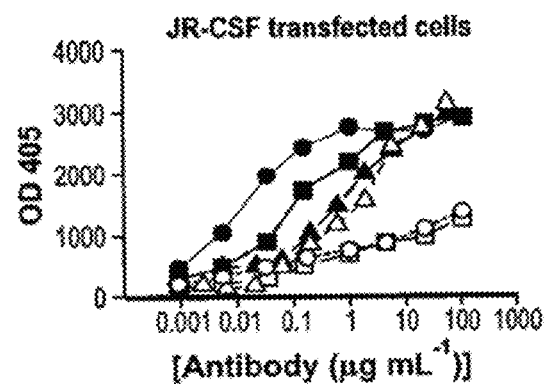
Figure 13C:
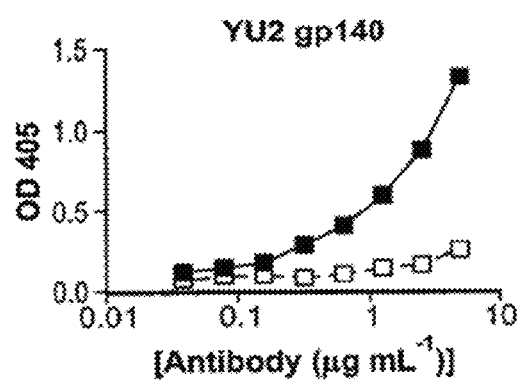

The epitopes recognized by PG9 and PG16 were investigated. Since the PG9 and PG16 antibodies are somatic variants, they recognize the same or overlapping epitopes. Both antibodies cross-competed for binding to HIV-1JR-CSF transfected cells (FIG. 13A). Ligation of monomeric gp120 or cell surface Env with soluble CD4 diminished binding of both PG9 and PG16, although neither antibody competed with CD4-binding site antibodies for trimer binding (FIG. 13A-13C). This result suggests that CD4-induced conformational changes cause a loss of the epitope targeted by the antibodies.

Figure 14:
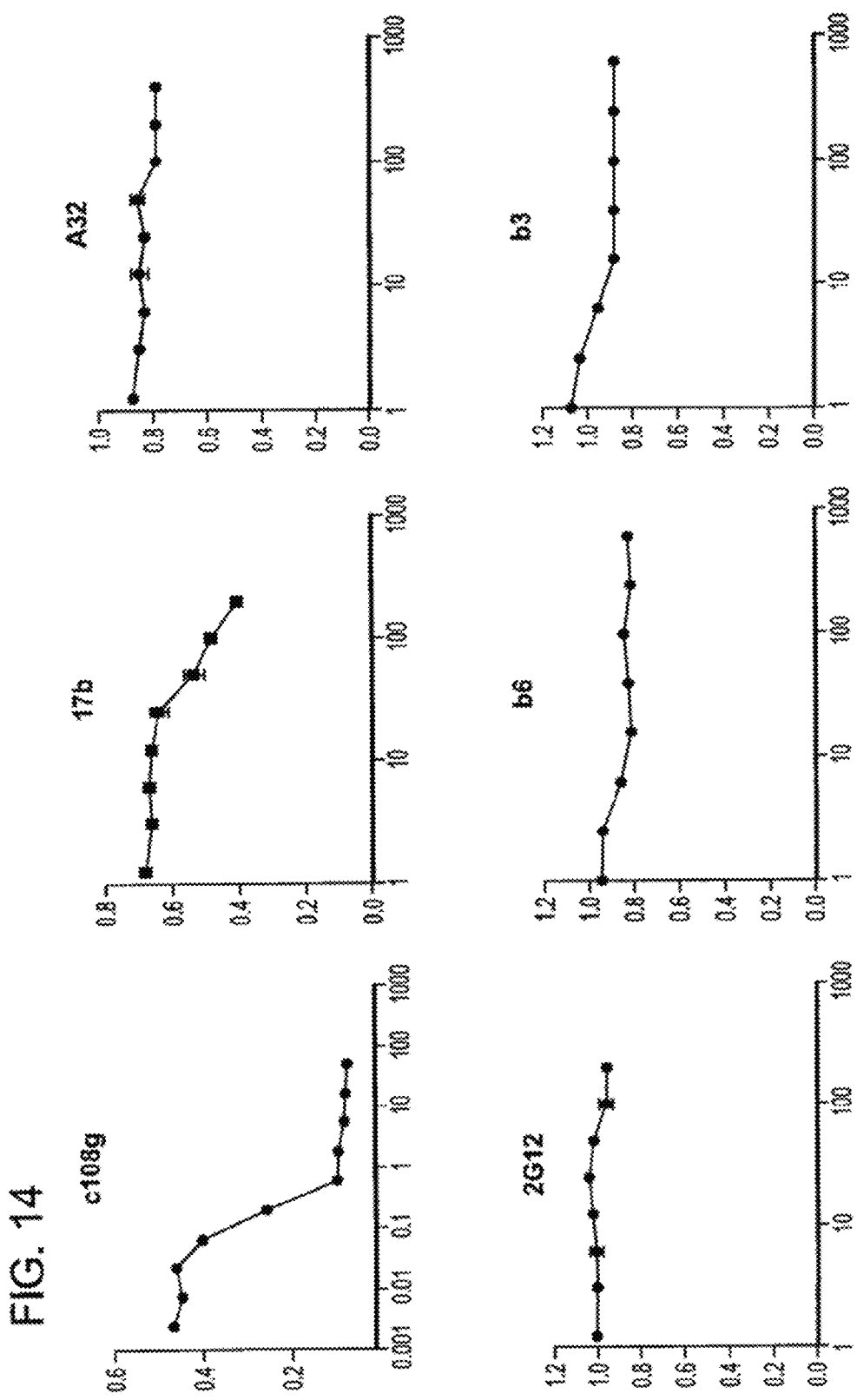
FIG. 14 is a series of graphs depicting the results of competition ELISA assays using the monoclonal antibody PG9.

Since PG9 bound well enough to gp120 from certain isolates to generate ELISA binding curves, competition ELISAs were performed with PG9 using a panel of neutralizing and non-neutralizing antibodies. These data revealed that PG9 cross-competed with anti-V2, anti-V3, and to a lesser extent, CD4i antibodies for gp120. (FIGS. 13D and 14).

Neither PG9 nor PG16 bound to V1/V2 or V3 deleted HIV-1JR-CSF variants expressed on the surface of transfected cells, further suggesting contributions of variable loops in forming their epitopes (FIG. 13E).

To dissect the fine specificity of PG9 and PG16, alanine scanning was performed using a large panel of HIV-1JR-CSF Env alanine mutants that have been described previously (Pantophlet, R., et al. J Virol 77, 642-658 (2003); Pantophlet, R., et al. J Virol 83, 1649-1659 (2009); Darbha, R., et al. Biochemistry 43, 1410-1417 (2004); Scanlan, C. N., et al. J Virol 76, 7306-7321 (2002)) as well as several new alanine mutants. Pseudoviruses incorporating single Env alanine mutations were generated, and PG9 and PG16 were tested for neutralization activity against each mutant pseudovirus. Mutations that resulted in viral escape from PG9 and PG16 neutralization were considered important for formation of the PG9 and PG16 epitopes (Tables 12 and 13).

Based on these criteria, and consistent with the competition experiments, residues that form the epitopes recognized by PG9 and PG16 appear to be located in conserved regions of the V2 and V3 loops of gp120. Certain co-receptor binding site mutations also had an effect on PG9 and PG16 neutralization, albeit to a lesser extent. Generally, PG9 and PG16 were dependent on the same residues, although PG16 was more sensitive to mutations located in the tip of the V3 loop than PG9. Interestingly, although neither antibody bound to wild-type HIV-1JR-FL transfected cells, a D to K mutation at position 168 in the V2 loop of HIV-1JR-FL generated high-affinity PG9 and PG16 recognition (Tables 18A-18F). N156 and N160, sites of V2 N-glycosylation, also appear to be critical in forming the epitope since substitutions at these positions resulted in escape from PG9 and PG16 neutralization. Deglycosylation of gp120 abolished binding of PG9 (FIG. 16), confirming that certain glycans may be important in forming the epitope.

Figure 17:
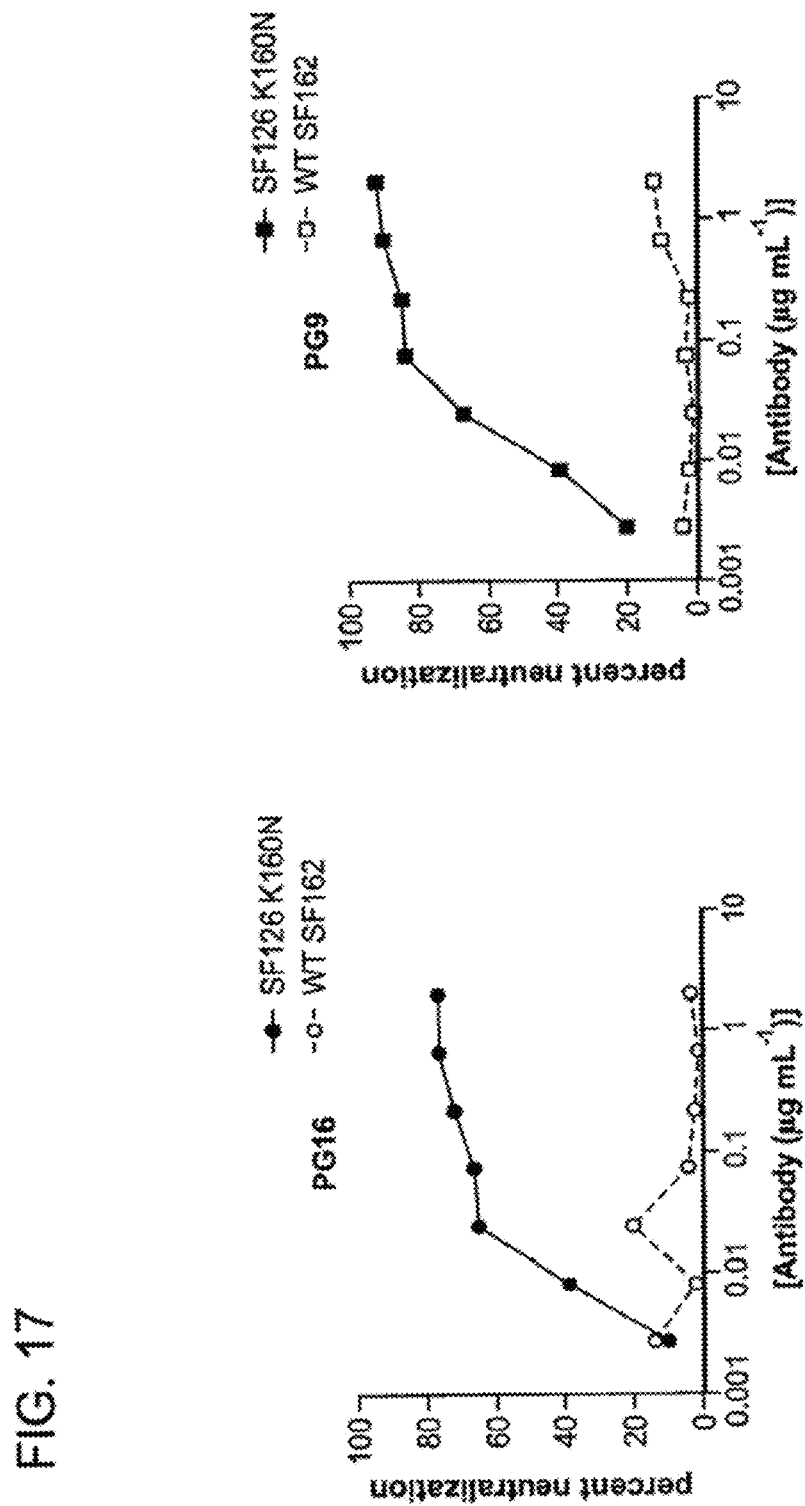
FIG. 17 is a series of graphs depicting the neutralization activity of PG9 and PG16 against HIV-1SF162 and HIV-1SF162 K160N, which was determined using a single-round replication luciferase reporter assay of pseudotyped virus.

HIV-1 SF162 contains a rare N to K polymorphism at position 160, and mutation of this residue to an Asn renders this isolate sensitive to PG9 and PG16 (FIG. 17).

Figure 18:
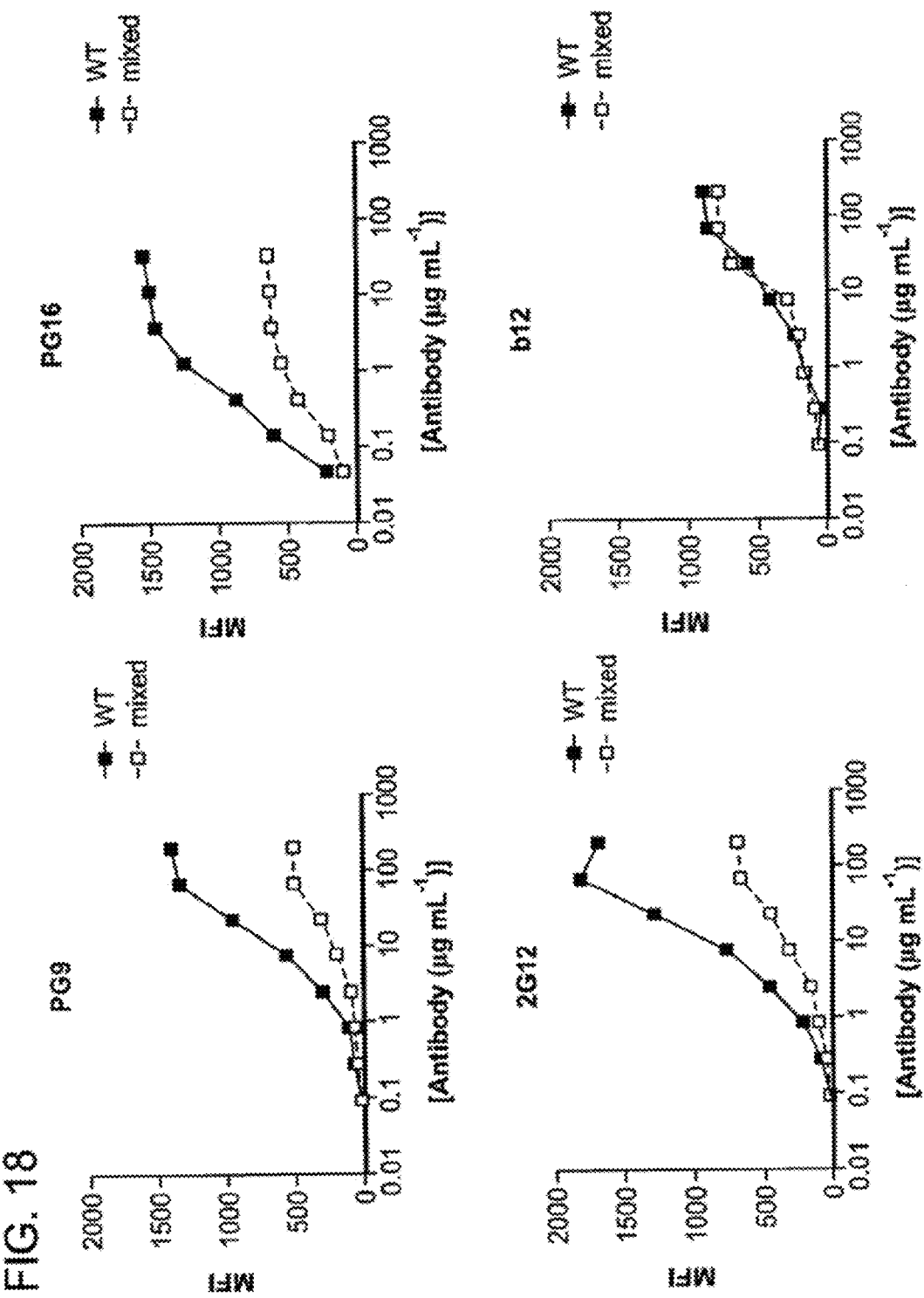
FIG. 18 is a series of graphs depicting the binding of PG9 and PG16 to mixed trimers. Alanine substitutions at positions 160 and 299 were introduced into HIV-1YU2 Env to abolish binding of PG9 and PG16. An alanine substitution at position 295 was also introduced into the same construct to abrogate binding of 2G12. Co-transfection of 293T cells with WT and mutant plasmids in a 1:2 ratio resulted in the expression of 29% mutant homotrimers, 44% heterotrimers with two mutant subunits, 23% heterotrimers with one mutant subunit, and 4% wild-type homotrimers.
Figure 19:
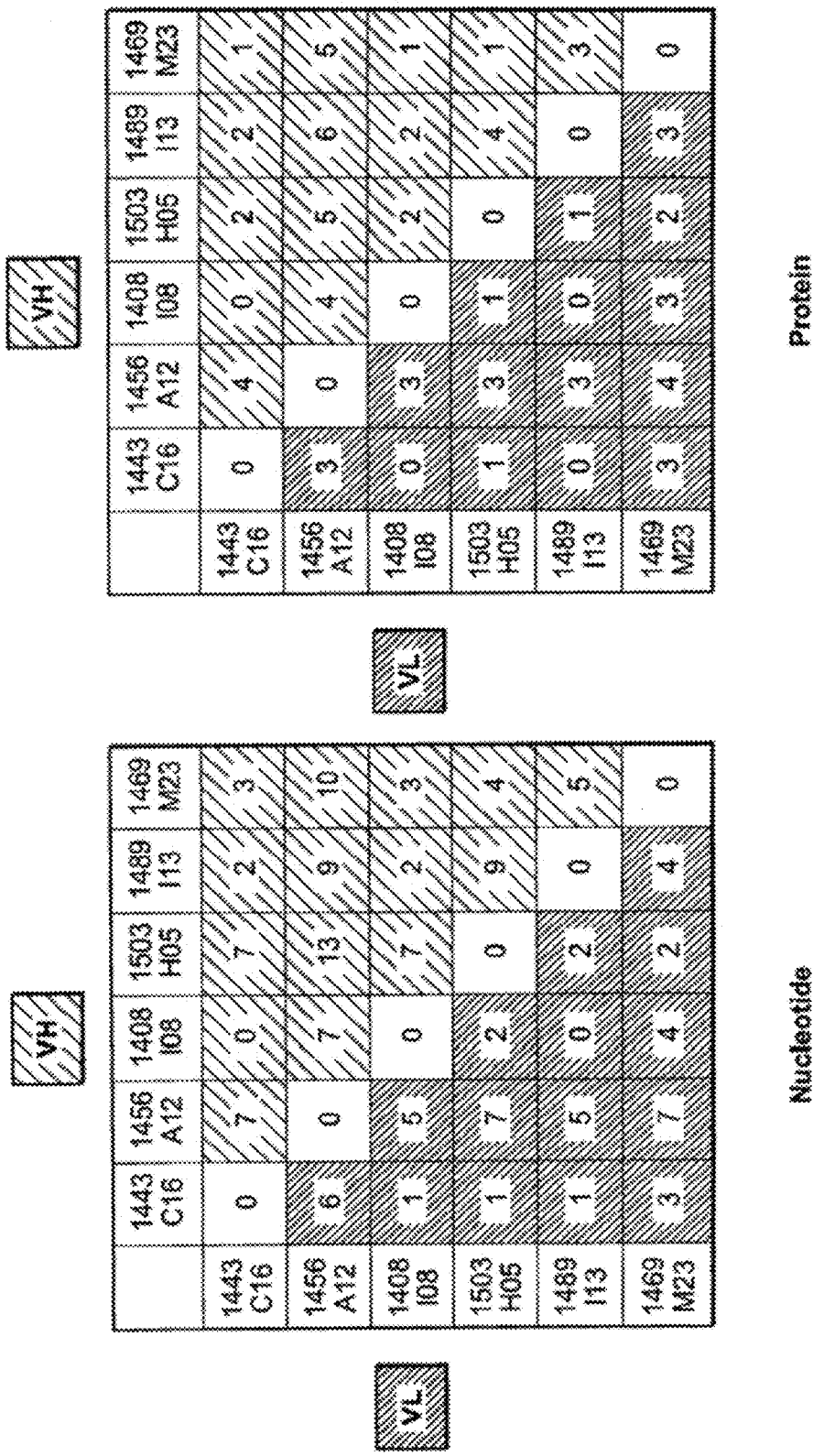
FIG. 19 is a series of graphical depictions of the number of nucleotide or amino acid differences in the heavy chain sequences of sister clones of 1443_C16 (PG16) among each other. Note that the single nucleotide difference of 1408_I08 translates into an identical protein sequence of 1443_C16. The nucleotide sequence of the 1408_I08 light chain is identical to the nucleotide sequence of the light chain of 1443_C16.
Figure 21A:
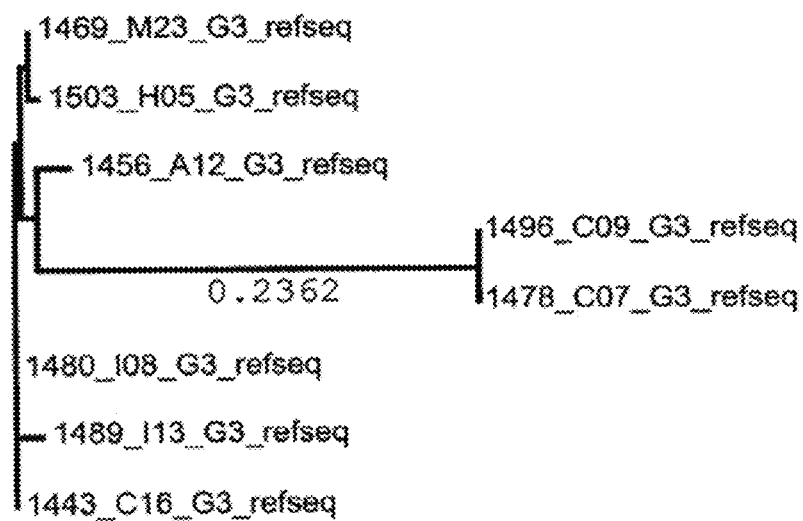
FIG. 21A is a tree diagram illustrating the correlation of the heavy chain of 1443_C16 sister clones to the heavy chain of 1496_C09 at the protein level.
Figure 21B:
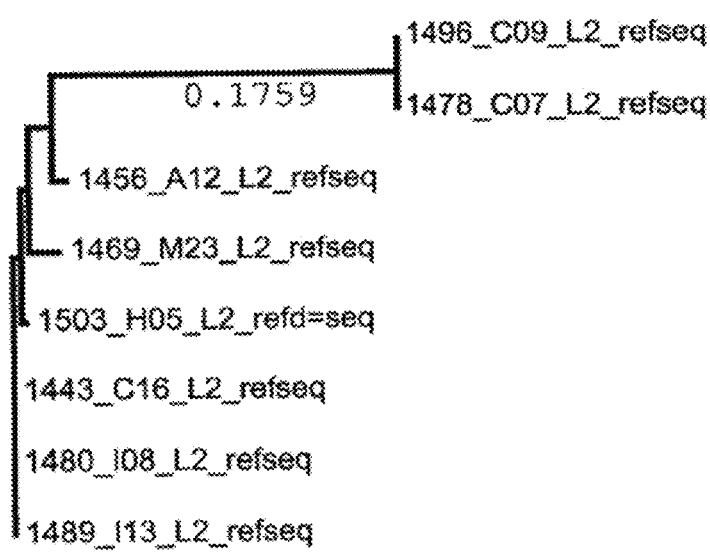
FIG. 21B is a tree diagram illustrating the correlation of the light chain of 1443_C16 sister clones to the light chain of 1496_C09 at the protein level.
Figure 22:
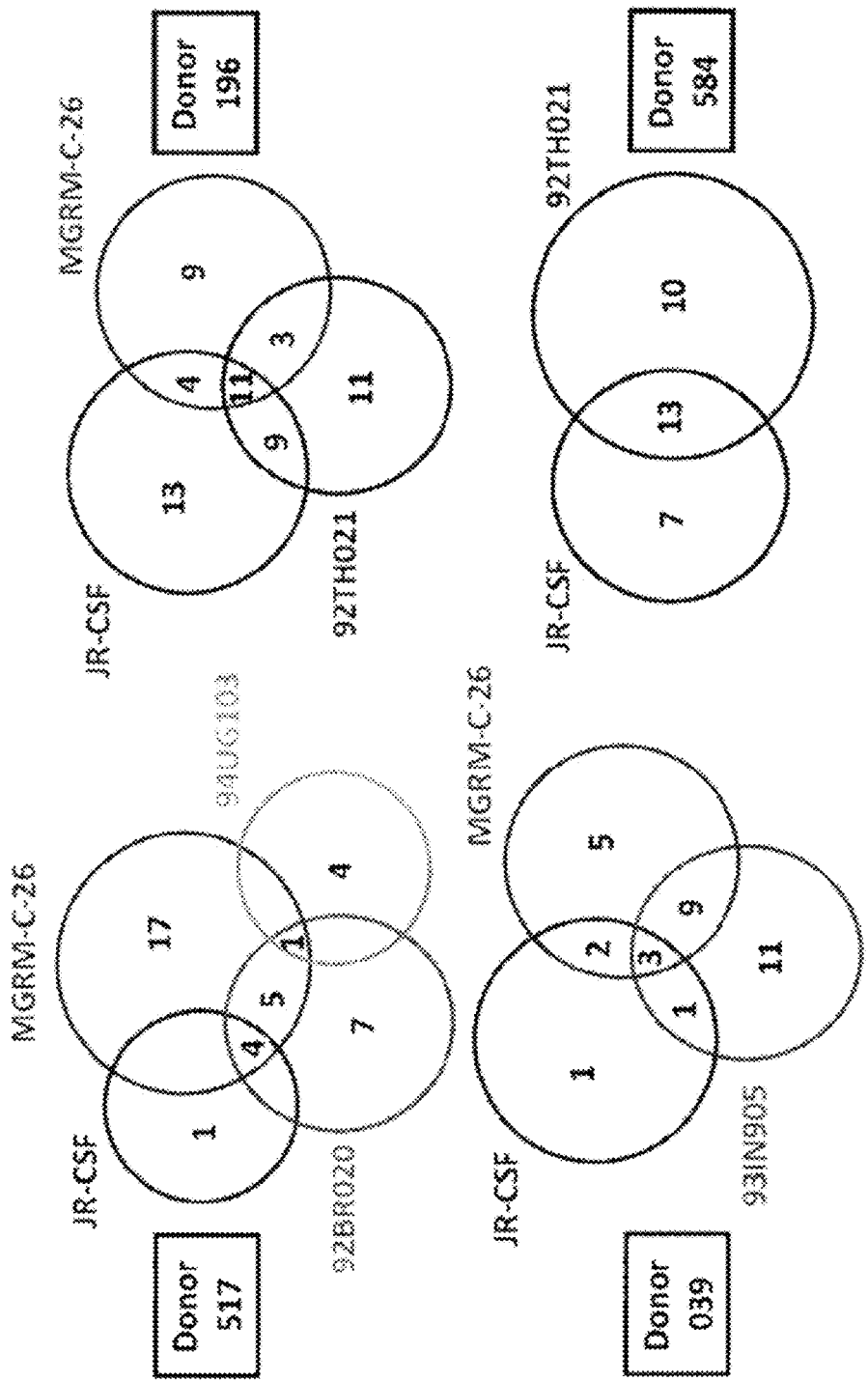
FIG. 22 is a Venn diagram depicting the viruses used in primary HIV-neutralization screening (JR-CSF, MGRM-C-26, 92BR020, 94UG103, 93IN905, 92TH021) and the number of neutralizing antibodies identified using these viruses alone, or in the demonstrated combinations. The results of screening antibodies isolated from B-cell cultures established from four human donors (#517, 039, 196, and 584) are shown.
Figure 23:
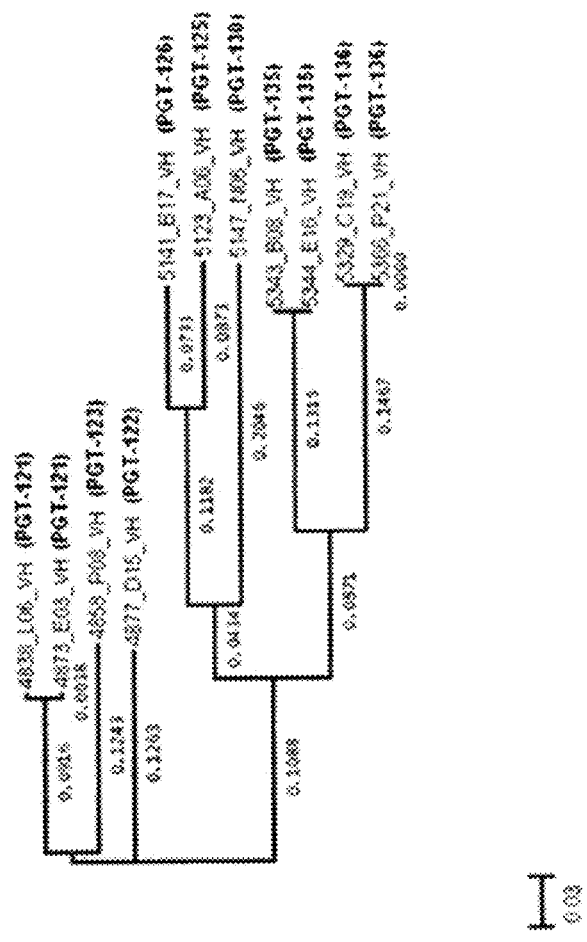
FIG. 23 is a tree diagram illustrating the relationships between the heavy chain variable gene sequences of antibodies PGT-121, PGT-122, PGT-123, PGT-125, PGT-126, PGT-130, PGT-135, and PGT-136. Scale bar=0.03. A value of zero demonstrates that an identical antibody was produced by two separate B-cell clones. Antibodies are less closely-related as the provided values increase.
Figure 24:
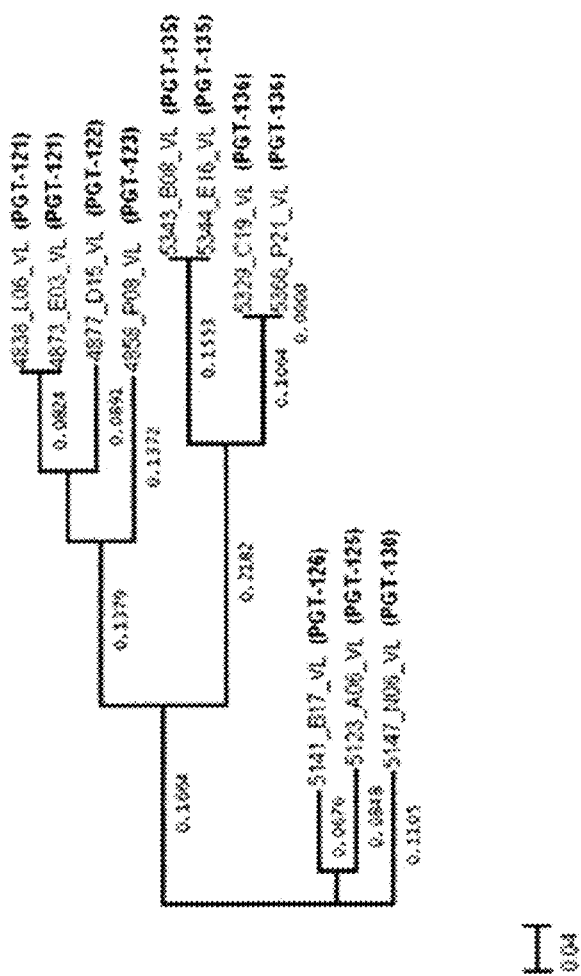
FIG. 24 is a tree diagram illustrating the relationships between the light chain variable gene sequences of antibodies PGT-121, PGT-122, PGT-123, PGT-125, PGT-126, PGT-130, PGT-135, and PGT-136. Scale bar=0.04. A value of zero demonstrates that an identical antibody was produced by two separate B-cell clones. Antibodies are less closely-related as the provided values increase.

The preferential binding of PG9 and PG16 to native trimers could either be a consequence of gp120 subunit cross-linking or recognition of a preferred oligomeric gp120 conformation. To address this question, the binding profiles of PG9 and PG16 to mixed HIV-1YU2 trimers were examined, in which two gp120 subunits containing point mutations abolished binding of the two antibodies. A third substitution that abrogates binding of 2G12, which binds with high affinity to both monomeric gp120 and trimeric Env, was also introduced into the same construct as an internal control. Cell surface binding analysis revealed that all three antibodies bound to the mixed trimers with similar apparent affinity as to wild-type trimers and all saturated at a similar lower level (FIG. 18). This result suggests that the preference of PG9 and PG16 for trimeric Env is due to gp120 subunit presentation in the context of the trimeric spike rather than gp120 cross-linking.

It has been shown that NAbs that bind to epitopes encompassing parts of the V2 or both the V2 and V3 domains can exhibit potency comparable to that of PG9 and PG16, although these antibodies have thus far displayed strong strain-specificity. (Honnen, W. J., et al. J Virol 81, 1424-1432 (2007); Gorny, M. K., et al.. J Virol 79, 5232-5237 (2005)). Importantly, the epitopes recognized by these antibodies have been shown to differ from that of the Glade B consensus sequence only by single amino acid substitutions, which suggested the existence of a relatively conserved structure within the V2 domain. (Honnen, W. J., et al. J Virol 81, 1424-1432 (2007)). The results observed with PG9 and PG16 confirm that this region serves as a potent neutralization target and demonstrates that antibodies that recognize conserved parts of V2 and V3 can possess broad reactivity.

The invention is based on novel monoclonal antibodies and antibody fragments that broadly and potently neutralize HIV infection. In some embodiments, these monoclonal antibodies and antibody fragments have a particularly high potency in neutralizing HIV infection in vitro across multiple clades or across a large number of different HIV species. Such antibodies are desirable, as only low concentrations are required to neutralize a given amount of virus. This facilitates higher levels of protection while administering lower amounts of antibody. Human monoclonal antibodies and the immortalized B cell clones that secrete such antibodies are included within the scope of the invention.

The invention provides methods for using high throughput functional screening to select neutralizing antibodies with unprecedented breadth and potency. The invention relates to other potent and broadly neutralizing antibodies that can be developed using the same methods. In particular, the invention relates to potent, broadly neutralizing antibodies against different strains of HIV, wherein the bNAbs bind poorly to recombinant forms of Env. The invention provides two neutralizing antibodies, PG9 and PG16, with broad neutralizing activities particularly against non-clade B isolates. The invention provides vaccine-induced antibodies of high specificity that provide protection against a diverse range of the most prevalent isolates of HIV circulating worldwide. The invention provides antibodies with very high and broad neutralization potency, such as that exhibited by PG9 and PG16 in vitro, which provides protection at relatively modest serum concentrations, and are generated by vaccination unlike the broad NAbs known in the art. The invention provides immunogens that can be designed that focus the immune response on conserved regions of variable loops in the context of the trimeric spike of the gp120 subunit of the Env protein.

The invention also relates to the characterization of the epitope to which the antibodies bind and the use of that epitope in raising an immune response.

The invention also relates to various methods and uses involving the antibodies of the invention and the epitopes to which they bind. For example, monoclonal antibodies according to the invention can be used as therapeutics. In some aspects, the monoclonal antibodies are used for adjuvant therapy. Adjuvant therapy refers to treatment with the therapeutic monoclonal antibodies, wherein the adjuvant therapy is administered after the primary treatment to increase the chances of a cure or reduce the statistical risk of relapse.

The invention provides novel monoclonal or recombinant antibodies having particularly high potency in neutralizing HIV. The invention also provides fragments of these recombinant or monoclonal antibodies, particularly fragments that retain the antigen-binding activity of the antibodies, for example which retain at least one complementarity determining region (CDR) specific for HIV proteins. In this specification, by "high potency in neutralizing HIV" is meant that an antibody molecule of the invention neutralizes HIV in a standard assay at a concentration lower than antibodies known in the art.

Preferably, the antibody molecule of the present invention can neutralize at a concentration of 0.16 μg/ml or lower (i.e. 0.15, 0.125, 0.1, 0.075, 0.05, 0.025, 0.02, 0.016, 0.015, 0.0125, 0.01, 0.0075, 0.005, 0.004 or lower), preferably 0.016 μg/ml or lower (an antibody concentration of $10^{-8}$ or lower, preferably $10^{-9}$ M or lower, preferably 10-10 M or lower, i.e. 10-11 M, 10-12 M, 10-13 M or lower). This means that only very low concentrations of antibody are required for 50% neutralization of a clinical isolate of HIV in vitro. Potency can be measured using a standard neutralization assay as described in the art.

The antibodies of the invention are able to neutralize HIV. Monoclonal antibodies can be produced by known procedures, e.g., as described by R. Kennet et al. in "Monoclonal Antibodies and Functional Cell Lines; Progress and Applications". Plenum Press (New York), 1984. Further materials and methods applied are based on known procedures, e.g., such as described in J. Virol. 67:6642-6647, 1993.

These antibodies can be used as prophylactic or therapeutic agents upon appropriate formulation, or as a diagnostic tool.

A "neutralizing antibody" is one that can neutralize the ability of that pathogen to initiate and/or perpetuate an infection in a host and/or in target cells in vitro. The invention provides a neutralizing monoclonal human antibody, wherein the antibody recognizes an antigen from HIV.

Preferably an antibody according to the invention is a novel monoclonal antibody referred to herein as 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_I01 (PGT-137), 4993_K13 (PGT-141), 4995_E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and 6881_N05 (PGT-158). These antibodies were initially isolated from human samples and are produced by the B cell cultures referred to as 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_I01 (PGT-137), 4993_K13 (PGT-141), 4995 E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and 6881_N05 (PGT-158). These antibodies have been shown to neutralize HIV in vitro. 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_I01 (PGT-137), 4993_K13 (PGT-141), 4995_E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and 6881_N05 (PGT-158) have been shown to have broad, potent HIV neutralizing activity.

The CDRs of the antibody heavy chains are referred to as CDRH1, CDRH2 and CDRH3, respectively. Similarly, the CDRs of the antibody light chains are referred to as CDRL1, CDRL2 and CDRL3, respectively. The position of the CDR amino acids is defined according to the IMGT numbering system as: CDR1—IMGT positions 27 to 38, CDR2—IMGT positions 56 to 65 and CDR3—IMGT positions 105 to 117. (Lefranc, M P. et al. 2003 IMGT unique numbering for immunoglobulin and T cell receptor variable regions and Ig superfamily V-like domains. Dev Comp Immunol. 27(1):

55-77; Lefranc, M P. 1997. Unique database numbering system for immunogenetic analysis. Immunology Today, 18:509; Lefranc, M P. 1999. The IMGT unique numbering for Immunoglobulins, T cell receptors and Ig-like domains. The Immunologist, 7:132-136.)

The amino acid sequences of the CDR3 regions of the light and heavy chains of the antibodies are shown in Tables 3A and 3B.

A phylogram is a branching diagram (tree) assumed to be an estimate of phylogeny, branch lengths are proportional to the amount of inferred evolutionary change. Tree diagrams of the five heavy chains and the five light chains were prepared using ClustalW (Larkin M. A., Blackshields G., Brown N. P., Chenna R., McGettigan P. A., McWilliam H., Valentin F., Wallace I. M., Wilm A., Lopez R., Thompson J. D., Gibson T. J. and Higgins D. G. Bioinformatics 23(21): 2947-2948 (2007); Higgins D G et al. Nucleic Acids Research 22: 4673-4680. (1994)) and are shown in FIGS. 1A and 1B respectively.

The sequences of the antibodies were determined, including the sequences of the variable regions of the Gamma heavy and Kappa or Lambda light chains of the antibodies designated 1496_C09 (PG9), 1443_C16 (PG16), 1456_P20 (PG20), 1460_G14 (PGG14), and 1495_C14 (PGC14). In addition, the sequence of each of the polynucleotides encoding the antibody sequences was determined. Shown below are the polypeptide and polynucleotide sequences of the gamma heavy chains and kappa light chains, with the signal peptides at the N-terminus (or 5' end) and the constant regions at the C-terminus (or 3' end) of the variable regions, which are shown in bolded text.

1443_C16 (PG16) (TCN-116) gamma heavy chain
nucleotide sequence: 1443 C16 γ3 coding
sequence (variable region in bold)
(SEQ ID NO: 11)
ATGGAGTTTGGGCTGAGCTGGGTTTTCCTCGCAACTCTGTTAAGAGT
TGTGAAGTGT**CAGGAACAACTGGTGGAGTCTGGGGGAGGCGTGGTCC
AGCCGGGGGGGTCCCTGAGACTCTCCTGTTTAGCGTCTGGATTCACG
TTTCACAAATATGGCATGCACTGGGTCCGCCAGGCTCCAGGCAAGGG
CCTGGAGTGGGTGGCACTCATCTCAGATGACGGAATGAGGAAATATC
ATTCAGACTCCATGTGGGGCCGAGTCACCATCTCCAGAGACAATTCC
AAGAACACTCTTTATCTGCAATTCAGCAGCCTGAAAGTCGAAGACAC
GGCTATGTTCTTCTGTGCGAGAGAGGCTGGTGGGCCAATCTGGCATG
ACGACGTCAAATATTACGATTTTAATGACGGCTACTACAACTACCAC
TACATGGACGTCTGGGGCAAGGGGACCACGGTCACCGTCTCGAGC**GC
CTCCACCAAGGGCCCATCGGTCTTCCCCCTGGCACCCTCCTCCAAGA
GCACCTCTGGGGGCACAGCGGCCCTGGGCTGCCTGGTCAAGGACTAC
TTCCCCGAACCGGTGACGGTGTCGTGGAACTCAGGCGCCCTGACCAG
CGGCGTGCACACCTTCCCGGCTGTCCTACAGTCCTCAGGACTCTACT
CCCTCAGCAGCGTGGTGACCGTGCCCTCCAGCAGCTTGGGCACCCAG
ACCTACATCTGCAACGTGAATCACAAGCCCAGCAACACCAAGGTGGA
CAAGAGAGTTGAGCCCAAATCTTGTGACAAAACTCACACATGCCCAC
CGTGCCCAGCACCTGAACTCCTGGGGGGACCGTCAGTCTTCCTCTTC
CCCCCAAAACCCAAGGACACCCTCATGATCTCCCGGACCCCTGAGGT
CACATGCGTGGTGGTGGACGTGAGCCACGAAGACCCTGAGGTCAAGT
TCAACTGGTACGTGGACGGCGTGGAGGTGCATAATGCCAAGACAAAG
CCGCGGGAGGAGCAGTACAACAGCACGTACCGTGTGGTCAGCGTCCT
CACCGTCCTGCACCAGGACTGGCTGAATGGCAAGGAGTACAAGTGCA
AGGTCTCCAACAAAGCCCTCCCAGCCCCCATCGAGAAAACCATCTCC
AAAGCCAAAGGGCAGCCCCGAGAACCACAGGTGTACACCCTGCCCCC
ATCCCGGGAGGAGATGACCAAGAACCAGGTCAGCCTGACCTGCCTGG
TCAAAGGCTTCTATCCCAGCGACATCGCCGTGGAGTGGGAGAGCAAT
GGGCAGCCGGAGAACAACTACAAGACCACGCCTCCCGTGCTGGACTC
CGACGGCTCCTTCTTCCTCTATAGCAAGCTCACCGTGGACAAGAGCA
GGTGGCAGCAGGGGAACGTCTTCTCATGCTCCGTGATGCATGAGGCT
CTGCACAACCACTACACGCAGAAGAGCCTCTCCCTGTCTCCGGGTAA
ATGA 1443_C16 (PG16) (TCN-116) gamma heavy chain
variable region nucleotide sequence:
(SEQ ID NO: 99)
CAGGAACAACTGGTGGAGTCTGGGGGAGGCGTGGTCCAGCCGGGGGG
GTCCCTGAGACTCTCCTGTTTAGCGTCTGGATTCACGTTTCACAAAT
ATGGCATGCACTGGGTCCGCCAGGCTCCAGGCAAGGGCCTGGAGTGG
GTGGCACTCATCTCAGATGACGGAATGAGGAAATATCATTCAGACTC
CATGTGGGGCCGAGTCACCATCTCCAGAGACAATTCCAAGAACACTC
TTTATCTGCAATTCAGCAGCCTGAAAGTCGAAGACACGGCTATGTTC
TTCTGTGCGAGAGAGGCTGGTGGGCCAATCTGGCATGACGACGTCAA
ATATTACGATTTTAATGACGGCTACTACAACTACCACTACATGGACG
TCTGGGGCAAGGGGACCACGGTCACCGTCTCGAGC 1443_C16 (PG16) (TCN-116) gamma heavy chain
amino acid sequence: expressed protein with
variable region in bold.
(SEQ ID NO: 12)
**QEQLVESGGGVVQPGGSLRLSCLASGFTFHKYGMHWVRQAPGKGLEW
VALISDDGMRKYHSDSMWGRVTISRDNSKNTLYLQFSSLKVEDTAMF
FCAREAGGPIWHDDVKYYDFNDGYYNYHYMDVWGKGTTVTVSS**ASTK
GPSVFPLAPSSKSTSGGTAALGCLVKDYFPEPVTVSWNSGALTSGVH
TFPAVLQSSGLYSLSSVVTVPSSSLGTQTYICNVNHKPSNTKVDKRV
EPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVL
HQDWLNGKEYKCKVSNKALPAPIEKTISKAKGQPREPQVYTLPPSRE
EMTKNQVSLTCLVKGFYPSDIAVEWESNGQPENNYKTTPPVLDSDGS
FFLYSKLTVDKSRWQQGNVFSCSVMHEALHNHYTQKSLSLSPGK 1443_C16 (PG16) (TCN-116) gamma heavy chain
variable region amino acid sequence: (Kabat
CDRs underlined, Chothia CDRs in bold italics)
(SEQ ID NO: 31)
QEQLVESGGGVVQPGGSLRLSCLAS*GFTFHK*YGMHWVRQAPGKGLEWVA<u>L
ISDDGMRKY</u>HSDSMWGRVTISRDNSKNTLYLQFSSLKVEDTAMFFCAR***EAG
GPIWHDDVKYYDFNDGYYNYHYMDV***WGKGTTVTVSS 1443_C16 (PG16) (TCN-116) gamma heavy chain
Kabat CDRs:
CDR 1:
(SEQ ID NO: 88)
KYGMH

CDR 2:
(SEQ ID NO: 89)
LISDDGMRKYHSDSMWG

CDR 3:
(SEQ ID NO: 6)
EAGGPIWHDDVKYYDENDGYYNYHYMDV

1443_C16 (PG16) (TCN-116) gamma heavy chain
Chothia CDRs:
CDR 1:
(SEQ ID NO: 266)
GFTFHK

CDR 2:
(SEQ ID NO: 267)
LISDDGMRKY

CDR 3:
(SEQ ID NO: 6)
EAGGPIWHDDVKYYDFNDGYYNYHYMDV

1443_C16 (PG16) (TCN-116) lambda light chain
nucleotide sequence: 1443_C16 22
coding sequence (variable region in bold)
(SEQ ID NO: 13)
ATGGCCTGGGCTCTGCTATTCCTCACCCTCTTCACTCAGGGCACAGGGTC
CTGGGGC**CAGTCTGCCCTGACTCAGCCTGCCTCCGTGTCTGGGTCTCCTG
GACAGACGATCACCATCTCCTGCAATGGAACCAGCAGTGACGTTGGTGGA
TTTGACTCTGTCTCCTGGTACCAACAATCCCAGGGAAAGCCCCCAAAGT
CATGGTTTTTGATGTCAGTCATCGGCCCTCAGGTATCTCTAATCGCTTCT
CTGGCTCCAAGTCCGGCAACACGGCCTCCCTGACCATCTCTGGGCTCCAC
ATTGAGGACGAGGGCGATTATTTCTGCTCTTCACTGACAGACAGAAGCCA
TCGCATATTCGGCGGCGGGACCAAGGTGACCGTTCTA**GGTCAGCCCAAGG
CTGCCCCCTCGGTCACTCTGTTCCCGCCCTCCTCTGAGGAGCTTCAAGCC
AACAAGGCCACACTGGTGTGTCTCATAAGTGACTTCTACCCGGGAGCCGT
GACAGTGGCCTGGAAGGCAGATAGCAGCCCCGTCAAGGCGGGAGTGGAGA

```
1443_C16 (PG16) (TCN-116) lambda light chain
variable region nucleotide sequence:
                              (SEQ ID NO: 100)
CAGTCTGCCCTGACTCAGCCTGCCTCCGTGTCTGGGTCTCCTGGACAGAC
GATCACCATCTCCTGCAATGGAACCAGCAGTGACGTTGGTGGATTTGACT
CTGTCTCCTGGTACCAACAATCCCAGGGAAAGCCCCCAAAGTCATGGTT
TTTGATGTCAGTCATCGGCCCTCAGGTATCTCTAATCGCTTCTCTGGCTC
CAAGTCCGGCAACACGGCCTCCCTGACCATCTCTGGGCTCCACATTGAGG
ACGAGGGCGATTATTTCTGCTCTTCACTGACAGACAGAAGCCATCGCATA
TTCGGCGGCGGGACCAAGGTGACCGTTCTA 1443_C16 (PG16) (TCN-116) lambda light chain
amino acid sequence: expressed protein with
variable region in bold.
                              (SEQ ID NO: 14)
**QSALTQPASVSGSPGQTITISCNGTSSDVGGFDSVSWYQQSPGKAPKVMV
FDVSHRPSGISNRFSGSKSGNTASLTISGLHIEDEGDYFCSSLTDRSHRI
FGGGTKVTVL**GQPKAAPSVTLFPPSSEELQANKATLVCLISDFYPGAVTV
AWKADSSPVKAGVETTTPSKQSNNKYAASSYLSLTPEQWKSHKSYSCQVT
HEGSTVEKTVAPTECS 1443_C16 (PG16) (TCN-116) lambda light chain
variable region amino acid sequence:
(Kabat CDRs underlined, Chothia CDRs in
bold italics)
                              (SEQ ID NO: 32)
QSALTQPASVSGSPGQTITISC*__NGTSSDVGGFDSVS__*WYQQSPGKAPKVMVF
*__DVSHRPS__*GISNRFSGSKSGNTASLTISGLHIEDEGDYFC
*__SSLTDRSHRI__*FGGGTKVTVL 1443_C16 (PG16) (TCN-116) lambda light chain
Kabat CDRs:
CDR 1:
                              (SEQ ID NO: 97)
NGTSSDVGGFDSVS

CDR 2:
                              (SEQ ID NO: 95)
DVSHRPS

CDR 3:
                              (SEQ ID NO: 41)
SSLTDRSHRI

1443_C16 (PG16) (TCN-116) lambda light chain
Chothia CDRs:
CDR 1:
                              (SEQ ID NO: 97)
NGTSSDVGGFDSVS

CDR 2:
                              (SEQ ID NO: 95)
DVSHRPS

CDR 3:
                              (SEQ ID NO: 41)
SSLTDRSHRI

1456_P20 (PG20) gamma heavy chain nucleotide
sequence: 1456_P20 γ1 coding sequence
(variable region in bold)
                              (SEQ ID NO: 15)
ATGGACTGGATTTGGAGGTTCCTCTTTGTGGTGGCAGCAGCTACAGGTGT
CCAGTCC**CAGGTCCGCCTGGTACAGTCTGGGCCTGAGGTGAAGAAGCCTG
GGTCCTCGGTGACGGTCTCCTGCCAGGCTTCTGGAGGCACCTTCAGCAGT
TATGCTTTCACCTGGGTGCGCCAGGCCCCCGGACAAGGTCTTGAGTGGTT
GGGCATGGTCACCCCAATCTTTGGTGAGGCCAAGTACTCACAAAGATTCG
AGGGCAGAGTCACCATCACCGCGGACGAATCCACGAGCACAACCTCCATA
GAATTGAGAGGCCTGACATCCGAAGACACGGCCATTTATTACTGTGCGCG
AGATCGGCGCGGTTCCAATTGCCACGGACAACTGGTTAGACCCCTGGGG
GCCAGGGGACCCTGGTCACCGTCTCGAG**CGCCTCCACCAAGGGCCCATCG
GTCTTCCCCCTGGCACCCTCCTCCAAGAGCACCTCTGGGGGCACAGCGGC
CCTGGGCTGCCTGGTCAAGGACTACTTCCCCGAACCGGTGACGGTGTCGT
GGAACTCAGGCGCCCTGACCAGCGGCGTGCACACCTTCCCGGCTGTCCTA
CAGTCCTCAGGACTCTACTCCCTCAGCAGCGTGGTGACCGTGCCCTCCAG
CAGCTTGGGCACCCAGACCTACATCTGCAACGTGAATCACAAGCCCAGCA
ACACCAAGGTGGACAAGAGAGTTGAGCCCAAATCTTGTGACAAAACTCAC
ACATGCCCACCGTGCCCAGCACCTGAACTCCTGGGGGGACCGTCAGTCTT
CCTCTTCCCCCCAAAACCCAAGGACACCCTCATGATCTCCCGGACCCCTG
AGGTCACATGCGTGGTGGTGGACGTGAGCCACGAAGACCCTGAGGTCAAG
TTCAACTGGTACGTGGACGGCGTGGAGGTGCATAATGCCAAGACAAAGCC
GCGGGAGGAGCAGTACAACAGCACGTACCGTGTGGTCAGCGTCCTCACCG
TCCTGCACCAGGACTGGCTGAATGGCAAGGAGTACAAGTGCAAGGTCTCC
AACAAAGCCCTCCCAGCCCCCATCGAGAAAACCATCTCCAAAGCCAAAGG
GCAGCCCCGAGAACCACAGGTGTACACCCTGCCCCCATCCCGGGAGGAGA
TGACCAAGAACCAGGTCAGCCTGACCTGCCTGGTCAAAGGCTTCTATCCC
AGCGACATCGCCGTGGAGTGGGAGAGCAATGGGCAGCCGGAGAACAACTA
CAAGACCACGCCTCCCGTGCTGGACTCCGACGGCTCCTTCTTCCTCTATA
GCAAGCTCACCGTGGACAAGAGCAGGTGGCAGCAGGGGAACGTCTTCTCA
TGCTCCGTGATGCATGAGGCTCTGCACAACCACTACACGCAGAAGAGCCT
CTCCCTGTCTCCGGGTAAATGA 1456_P20 (PG20) gamma heavy chain variable region
nucleotide sequence:
                              (SEQ ID NO: 101)
CAGGTCCGCCTGGTACAGTCTGGGCCTGAGGTGAAGAAGCCTGGGTCCTC
GGTGACGGTCTCCTGCCAGGCTTCTGGAGGCACCTTCAGCAGTTATGCTT
TCACCTGGGTGCGCCAGGCCCCCGGACAAGGTCTTGAGTGGTTGGGCATG
GTCACCCCAATCTTTGGTGAGGCCAAGTACTCACAAAGATTCGAGGGCAG
AGTCACCATCACCGCGGACGAATCCACGAGCACAACCTCCATAGAATTGA
GAGGCCTGACATCCGAAGACACGGCCATTTATTACTGTGCGCGAGATCGG
CGCGGTTCCAATTGCCACGGACAACTGGTTAGACCCCTGGGGCCAGGG
GACCCTGGTCACCGTCTCGAGC 1456_P20 (PG20) gamma heavy chain amino acid
sequence: expressed protein withvariable region in
bold.
                              (SEQ ID NO: 16)
**QVRLVQSGPEVKKPGSSVTVSCQASGGTFSSYAFTWVRQAPGQGLEWLGM
VTPIFGEAKYSQRFEGRVTITADESTSTTSIELRGLTSEDTAIYYCARDR
RAVPIATDNWLDPWGQGTLVTVSS**ASTKGPSVFPLAPSSKSTSGGTAALG
CLVKDYFPEPVTVSWNSGALTSGVHTFPAVLQSSGLYSLSSVVTVPSSSL
GTQTYICNVNHKPSNTKVDKRVEPKSCDKTHTCPPCPAPELLGGPSVFLF
PPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSL
SPGK 1456_P20 (PG20) gamma heavy chain variable region
amino acid sequence: (Kabat CDRs underlined,
Chothia CDRs in bold italics)
                              (SEQ ID NO: 33)
QVRLVQSGPEVKKPGSSVTVSCQAS*__GGTFSS__*__YAFT__WVRQAPGQGLEWLG
*__MVTPIFGEAK__*__YSQRFEG__RVTITADESTSTTSIELRGLTSEDTAIYYC
AR*__DRRAVPIATDNWLDP__*WGQGTLVTVSS 1456_P20 (PG20) gamma heavy chain Kabat CDRs:
CDR 1:
                              (SEQ ID NO: 104)
SYAFT

CDR 2:
                              (SEQ ID NO: 105)
MVTPIFGEAKYSQRFEG

CDR 3:
                              (SEQ ID NO: 9)
DRRAVPIATDNWLDP

1456_P20 (PG20) gamma heavy chain Chothia CDRs:
CDR 1:
                              (SEQ ID NO: 268)
GGTFSS

CDR 2:
                              (SEQ ID NO: 269)
MVTPIFGEAK

CDR 3:
                              (SEQ ID NO: 9)
DRRAVPIATDNWLDP
```

1456_P20 (PG20) kappa light chain nucleotide sequence: 1456_P20 κ1 coding sequence (variable region in bold)
(SEQ ID NO: 17)
ATGGACATGAGGGTCCCCGCTCAGCTCCTGGGGCTCCTGCTACTCTGGCT
CCGAGGTGCCAGATGT**GACATCCAGTTGACCCAGTCTCCATCCTCCCTGT
CTGCATCTGTTGGCGACAGAGTCTCCATCACTTGCCGGGCGAGTCAGACC
ATTAACAACTACTTAAATTGGTATCAACAGACACCCGGGAAAGCCCCTAA
ACTCCTGATCTATGGTGCCTCCAATTTGCAAAATGGGGTCCCATCAAGGT
TCAGCGGCAGTGGCTCTGGGACAGACTTCACTCTCACCATCAGCAGTCTG
CAACCTGAGGATTTTGCAACTTACTACTGTCAACAGAGTTTCAGTACTCC
GAGGACCTTCGGCCAAGGGACACGACTGGATATTAAA**CGTACGGTGGCTG
CACCATCTGTCTTCATCTTCCCGCCATCTGATGAGCAGTTGAAATCTGGA
ACTGCCTCTGTTGTGTGCCTGCTGAATAACTTCTATCCCAGAGAGGCCAA
AGTACAGTGGAAGGTGGATAACGCCCTCCAATCGGGTAACTCCCAGGAGA
GTGTCACAGAGCAGGACAGCAAGGACAGCACCTACAGCCTCAGCAGCACC
CTGACGCTGAGCAAAGCAGACTACGAGAAACACAAAGTCTACGCCTGCGA
AGTCACCCATCAGGGCCTGAGCTCGCCCGTCACAAAGAGCTTCAACAGGG
GAGAGTGTTAG 1456_P20 (PG20) kappa light chain variable region nucleotide sequence:
(SEQ ID NO: 106)
GACATCCAGTTGACCCAGTCTCCATCCTCCCTGTCTGCATCTGTTGGCGA
CAGAGTCTCCATCACTTGCCGGGCGAGTCAGACCATTAACAACTACTTAA
ATTGGTATCAACAGACACCCGGGAAAGCCCCTAAACTCCTGATCTATGGT
GCCTCCAATTTGCAAAATGGGGTCCCATCAAGGTTCAGCGGCAGTGGCTC
TGGGACAGACTTCACTCTCACCATCAGCAGTCTGCAACCTGAGGATTTTG
CAACTTACTACTGTCAACAGAGTTTCAGTACTCCGAGGACCTTCGGCCAA
GGGACACGACTGGATATTAAA 1456_P20 (PG20) kappa light chain amino acid sequence: expressed protein with variable region in bold.
(SEQ ID NO: 18)
**DIQLTQSPSSLSASVGDRVSITCRASQTINNYLNWYQQTPGKAPKLLIYGA
SNLQNGVPSRFSGSGSGTDFTLTISSLQPEDFATYYCQQSFSTPRTFGQGT
RLDIK**RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC 1456_P20 (PG20) kappa light chain variable region amino acid sequence: (Kabat CDRs underlined, Chothia CDRs in bold italics)
(SEQ ID NO: 34)
DIQLTQSPSSLSASVGDRVSITC<u>*RASQTINNYLN*</u>WYQQTPGKAPKLLIY
<u>*GASNLQN*</u>GVPSRFSGSGSGTDFTLTISSLQPEDFATYYC
<u>*QQSFSTPRT*</u>FGQGTRLDIK 1456_P20 (PG20) kappa light chain Kabat CDRs:
CDR 1:
(SEQ ID NO: 107)
RASQTINNYLN

CDR 2:
(SEQ ID NO: 108)
GASNLQN

CDR 3:
(SEQ ID NO: 42)
QQSFSTPRT

1456_P20 (PG20) kappa light chain Chothia CDRs:
CDR 1:
(SEQ ID NO: 107)
RASQTINNYLN

CDR 2:
(SEQ ID NO: 108)
GASNLQN

CDR 3:
(SEQ ID NO: 42)
QQSFSTPRT

1460_G14 (PGG14) gamma heavy chain nucleotide sequence: 1460_G14 γ1 coding sequence (variable region in bold)
(SEQ ID NO: 19)
ATGGACTGGATTTGGAGGTTCCTCTTGGTGGTGGCAGCAGCTACAGGTGT
CCAGTCC**CAGGTCCTGCTGGTGCAGTCTGGGACTGAGGTGAAGAAGCCTG
GGTCCTCGGTGAAGGTCTCCTGTCAGGCTTCTGGAGGCGCCTTCAGTAGT
TATGCTTTCAGCTGGGTGCGACAGGCCCCTGGACAGGGGCTTGAATGGAT
GGGCATGATCACCCCTGTCTTTGGTGAGACTAAATATGCACCGAGGTTCC
AGGGCAGACTCACACTTACCGCGGAAGAATCCTTGAGCACCACCTACATG
GAATTGAGAAGCCTGACATCTGATGACACGGCCTTTTATTATTGTACGAG
AGATCGGCGCGTAGTTCCAATGGCCACAGACAACTGGTTAGACCCCTGGG
GCCAGGGGACGCTGGTCACCGTCTCGAGC**GCCTCCACCAAGGGCCCATCG
GTCTTCCCCCTGGCACCCTCCTCCAAGAGCACCTCTGGGGGCACAGCGGC
CCTGGGCTGCCTGGTCAAGGACTACTTCCCCGAACCGGTGACGGTGTCGT
GGAACTCAGGCGCCCTGACCAGCGGCGTGCACACCTTCCCGGCTGTCCTA
CAGTCCTCAGGACTCTACTCCCTCAGCAGCGTGGTGACCGTGCCCTCCAG
CAGCTTGGGCACCCAGACCTACATCTGCAACGTGAATCACAAGCCCAGCA
ACACCAAGGTGGACAAGAGAGTTGAGCCCAAATCTTGTGACAAAACTCAC
ACATGCCCACCGTGCCCAGCACCTGAACTCCTGGGGGGACCGTCAGTCTT
CCTCTTCCCCCCAAAACCCAAGGACACCCTCATGATCTCCCGGACCCCTG
AGGTCACATGCGTGGTGGTGGACGTGAGCCACGAAGACCCTGAGGTCAAG
TTCAACTGGTACGTGGACGGCGTGGAGGTGCATAATGCCAAGACAAAGCC
GCGGGAGGAGCAGTACAACAGCACGTACCGTGTGGTCAGCGTCCTCACCG
TCCTGCACCAGGACTGGCTGAATGGCAAGGAGTACAAGTGCAAGGTCTCC
AACAAAGCCCTCCCAGCCCCCATCGAGAAAACCATCTCCAAAGCCAAAGG
GCAGCCCCGAGAACCACAGGTGTACACCCTGCCCCCATCCCGGGAGGAGA
TGACCAAGAACCAGGTCAGCCTGACCTGCCTGGTCAAAGGCTTCTATCCC
AGCGACATCGCCGTGGAGTGGGAGAGCAATGGGCAGCCGGAGAACAACTA
CAAGACCACGCCTCCCGTGCTGGACTCCGACGGCTCCTTCTTCCTCTATA
GCAAGCTCACCGTGGACAAGAGCAGGTGGCAGCAGGGGAACGTCTTCTCA
TGCTCCGTGATGCATGAGGCTCTGCACAACCACTACACGCAGAAGAGCCT
CTCCCTGTCTCCGGGTAAATGA 1460_G14 (PGG14) gamma heavy chain variable region nucleotide sequence:
(SEQ ID NO: 109)
CAGGTCCTGCTGGTGCAGTCTGGGACTGAGGTGAAGAAGCCTGGGTCCTC
GGTGAAGGTCTCCTGTCAGGCTTCTGGAGGCGCCTTCAGTAGTTATGCTT
TCAGCTGGGTGCGACAGGCCCCTGGACAGGGGCTTGAATGGATGGGCATG
ATCACCCCTGTCTTTGGTGAGACTAAATATGCACCGAGGTTCCAGGGCAG
ACTCACACTTACCGCGGAAGAATCCTTGAGCACCACCTACATGGAATTGA
GAAGCCTGACATCTGATGACACGGCCTTTTATTATTGTACGAGAGATCGG
CGCGTAGTTCCAATGGCCACAGACAACTGGTTAGACCCCTGGGGCCAGGG
GACGCTGGTCACCGTCTCGAGC 1460_G14 gamma heavy chain amino acid sequence: expressed protein with variableregion in bold.
(SEQ ID NO: 20)
**QVLLVQSGTEVKKPGSSVKVSCQASGGAFSSYAFSWVRQAPGQGLEWMGM
ITPVFGETKYAPRFQGRLTLTAEESLTTYMELRSLTSDDTAFYYCTRDR
RVVPMATDNWLDP**WGQGTLVTVSSASTKGPSVFPLAPSSKSTSGGTAALG
CLVKDYFPEPVTVSWNSGALTSGVHTFPAVLQSSGLYSLSSVVTVPSSSL
GTQTYICNVNHKPSNTKVDKRVEPKSCDKTHTCPPCPAPELLGGPSVFLF
PPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSL
SPG 1460_G14 gamma heavy chain variable region amino acid sequence: (Kabat CDRs underlined, Chothia CDRs in bold italics)
(SEQ ID NO: 35)
QVLLVQSGTEVKKPGSSVKVSCQAS*GGAFSS*<u>SYAFS</u>WVRQAPGQGLEWMG
*MITPVFGETK*<u>YAPRFQG</u>RLTLTAEESLTTYMELRSLTSDDTAFYYC
TR<u>*DRRVVPMATDNWLDP*</u>WGQGTLVTVSS 1460_G14 gamma heavy chain Kabat CDRs:
CDR 1:
(SEQ ID NO: 110)
SYAFS

CDR 2:
(SEQ ID NO: 111)
MITPVFGETKYAPRFQG

CDR 3:
(SEQ ID NO: 8)
DRRVVPMATDNWLDP

1460_G14 gamma heavy chain Chothia CDRs:
CDR 1:
(SEQ ID NO: 270)
GGAFSS

CDR 2:
(SEQ ID NO: 271)
MITPVFGETK

CDR 3:
(SEQ ID NO: 8)
DRRVVPMATDNWLDP

1460_G14 (PGG14) kappa light chain nucleotide
sequence: 1460_G14 κ1 coding sequence
(variable region in bold)
(SEQ ID NO: 21)
ATGGACATGAGGGTCCCCGCTCAGCTCCTGGGGCTCCTGCTCCTCTGGCT
CCGAGGTGCCACATGTGACATCCAGTTGACCCAGTCTCCATCCTCCCTGT
CTGCATCTGTAGGAGACAGGGTCACCGTCACTTGCCGGGCGAGTCAGACC
ATACACACCTATTTAAATTGGTATCAGCAAATTCCAGGAAAAGCCCCTAA
GCTCCTGATCTATGGTGCCTCCACCTTGCAAAGTGGGGTCCCGTCAAGGT
TCAGTGGCAGTGGATCTGGGACAGATTTCACTCTCACCATCAACAGTCTC
CAACCTGAGGACTTTGCAACTTACTACTGTCAACAGAGTTACAGTACCCC
AAGGACCTTCGGCCAAGGGACACGACTGGATATTAAACGTACGGTGGCTG
CACCATCTGTCTTCATCTTCCCGCCATCTGATGAGCAGTTGAAATCTGGA
ACTGCCTCTGTTGTGTGCCTGCTGAATAACTTCTATCCCAGAGAGGCCAA
AGTACAGTGGAAGGTGGATAACGCCCTCCAATCGGGTAACTCCCAGGAGA
GTGTCACAGAGCAGGACAGCAAGGACAGCACCTACAGCCTCAGCAGCACC
CTGACGCTGAGCAAAGCAGACTACGAGAAACACAAAGTCTACGCCTGCGA
AGTCACCCATCAGGGCCTGAGCTCGCCCGTCACAAAGAGCTTCAACAGGG
GAGAGTGTTAG 1460_G14 (PGG14) kappa light chain variable region
nucleotide sequence:
(SEQ ID NO: 112)
GACATCCAGTTGACCCAGTCTCCATCCTCCCTGTCTGCATCTGTAGGAGA
CAGGGTCACCGTCACTTGCCGGGCGAGTCAGACCATACACACCTATTTAA
ATTGGTATCAGCAAATTCCAGGAAAAGCCCCTAAGCTCCTGATCTATGGT
GCCTCCACCTTGCAAAGTGGGGTCCCGTCAAGGTTCAGTGGCAGTGGATC
TGGGACAGATTTCACTCTCACCATCAACAGTCTCCAACCTGAGGACTTTG
CAACTTACTACTGTCAACAGAGTTACAGTACCCCAAGGACCTTCGGCCAA
GGGACACGACTGGATATTAAA 1460_G14 kappa light chain amino acid sequence:
expressed protein with variable region in bold.
(SEQ ID NO: 22)
**DIQLTQSPSSLSASVGDRVTVTCRASQTIHTYLNWYQQIPGKAPKLLIYG
ASTLQSGVPSRFSGSGSGTDFTLTINSLQPEDFATYYCQQSYSTPRTFGQ
GTRLDIK**RTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC 1460_G14 kappa light chain variable region amino
acid sequence: (Kabat CDRs underlined, Chothia
CDRs in bold italics)
(SEQ ID NO: 36)
DIQLTQSPSSLSASVGDRVTVTC*RASQTIHTYLN*WYQQIPGKAPKLLIY
*GASTLQS*GVPSRFSGSGSGTDFTLTINSLQPEDFATYYC
*QQSYSTPRT*FGQGTRLDIK 1460_G14 kappa light chain Kabat CDRs:
CDR 1:
(SEQ ID NO: 113)
RASQTIHTYLN

CDR 2:
(SEQ ID NO: 114)
GASTLQS

CDR 3:
(SEQ ID NO: 43)
QQSYSTPRT

1460_G14 kappa light chain Chothia CDRs:
CDR 1:
(SEQ ID NO: 113)
RASQTIHTYLN

CDR 2:
(SEQ ID NO: 114)
GASTLQS

CDR 3:
(SEQ ID NO: 43)
QQSYSTPRT

1495_C14 (PGC14) gamma heavy chain nucleotide
sequence: 1495_C14 γ1 coding sequence
(variable region in bold)
(SEQ ID NO: 23)
ATGGACTGGATTTGGAGGATCCTCCTCTTGGTGGCAGCAGCTACAGGCAC
CCTCGCC**GACGGCCACCTGGTTCAGTCTGGGGTTGAGGTGAAGAAGACTG
GGGCTACAGTCAAAATCTCCTGCAAGGTTTCTGGATACAGCTTCATCGAC
TACTACCTTCATTGGGTGCAACGGGCCCCTGGAAAAGGCCTTGAGTGGGT
GGGACTTATTGATCCTGAAAATGGTGAGGCTCGATATGCAGAGAAGTTCC
AGGGCAGAGTCACCATAATCGCGGACACGTCTATAGATACAGGCTACATG
GAAATGAGGAGCCTGAAATCTGAGGACACGGCCGTGTATTTCTGTGCAGC
AGGTGCCGTGGGGGCTGATTCCGGGAGCTGGTTCGACCCCTGGGGCCAGG
GAACTCTGGTCACCGTCTCGAGC**GCCTCCACCAAGGGCCCATCGGTCTTC
CCCCTGGCACCCTCCTCCAAGAGCACCTCTGGGGGCACAGCGGCCCTGGG
CTGCCTGGTCAAGGACTACTTCCCCGAACCGGTGACGGTGTCGTGGAACT
CAGGCGCCCTGACCAGCGGCGTGCACACCTTCCCGGCTGTCCTACAGTCC
TCAGGACTCTACTCCCTCAGCAGCGTGGTGACCGTGCCCTCCAGCAGCTT
GGGCACCCAGACCTACATCTGCAACGTGAATCACAAGCCCAGCAACACCA
AGGTGGACAAGAGAGTTGAGCCCAAATCTTGTGACAAAACTCACACATGC
CCACCGTGCCCAGCACCTGAACTCCTGGGGGGACCGTCAGTCTTCCTCTT
CCCCCCAAAACCCAAGGACACCCTCATGATCTCCCGGACCCCTGAGGTCA
CATGCGTGGTGGTGGACGTGAGCCACGAAGACCCTGAGGTCAAGTTCAAC
TGGTACGTGGACGGCGTGGAGGTGCATAATGCCAAGACAAAGCCGCGGGA
GGAGCAGTACAACAGCACGTACCGTGTGGTCAGCGTCCTCACCGTCCTGC
ACCAGGACTGGCTGAATGGCAAGGAGTACAAGTGCAAGGTCTCCAACAAA
GCCCTCCCAGCCCCCATCGAGAAAACCATCTCCAAAGCCAAAGGGCAGCC
CCGAGAACCACAGGTGTACACCCTGCCCCCATCCCGGGAGGAGATGACCA
AGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGAC
CACGCCTCCCGTGCTGGACTCCGACGGCTCCTTCTTCCTCTATAGCAAGC
TCACCGTGGACAAGAGCAGGTGGCAGCAGGGGAACGTCTTCTCATGCTCC
GTGATGCATGAGGCTCTGCACAACCACTACACGCAGAAGAGCCTCTCCCT
GTCTCCGGGTAAATGA 1495_C14 (PGC14) gamma heavy chain variable region
nucleotide sequence:
(SEQ ID NO: 115)
GACGGCCACCTGGTTCAGTCTGGGGTTGAGGTGAAGAAGACTGGGGCTAC
AGTCAAAATCTCCTGCAAGGTTTCTGGATACAGCTTCATCGACTACTACC
TTCATTGGGTGCAACGGGCCCCTGGAAAAGGCCTTGAGTGGGTGGGACTT
ATTGATCCTGAAAATGGTGAGGCTCGATATGCAGAGAAGTTCCAGGGCAG
AGTCACCATAATCGCGGACACGTCTATAGATACAGGCTACATGGAAATGA
GGAGCCTGAAATCTGAGGACACGGCCGTGTATTTCTGTGCAGCAGGTGCC
GTGGGGGCTGATTCCGGGAGCTGGTTCGACCCCTGGGGCCAGGGAACTCT
GGTCACCGTCTCGAGC 1495_C14 (PGC14) gamma heavy chain amino acid
sequence: expressed protein with variable region
in bold.
(SEQ ID NO: 24)
**DGHLVQSGVEVKKTGATVKISCKVSGYSFIDYYLHWVQRAPGKGLEWVGL
IDPENGEARYAEKFQGRVTIIADTSIDTGYMEMRSLKSEDTAVYFCAAGA
VGADSGSWFDPWGQGTLVTVSS**ASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKRVEPKSCDKTHTCPPCPAPELLGGPSVFLFPP
KPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSP
GK 1495_C14 (PGC14) gamma heavy chain variable region amino acid sequence: (Kabat CDRs underlined, Chothia CDRs in bold italics)

(SEQ ID NO: 37)
DGHLVQSGVEVKKTGATVKISCKVS*GYSFID*YYLHWVQRAPGKGLEWVG
LIDPENGEARYAEKFQGRVTIIADTSIDTGYMEMRSLKSEDTAVYFCA
*RGAVGADSGSWFDP*WGQGTLVTVSS

1495_C14 gamma heavy chain Kabat CDRs:
CDR 1:
(SEQ ID NO: 116)
DYYLH

CDR 2:
(SEQ ID NO: 117)
LIDPENGEARYAEKFQG

CDR 3:
(SEQ ID NO: 10)
GAVGADSGSWFDP

1495_C14 gamma heavy chain Chothia CDRs:
CDR 1:
(SEQ ID NO: 102)
GYSFID

CDR 2:
(SEQ ID NO: 103)
LIDPENGEAR

CDR 3:
(SEQ ID NO: 10)
GAVGADSGSWFDP

1495_C14 (PGC14) lambda light chain nucleotide sequence: 1495_C14 λ3 coding sequence (variable region in bold)
(SEQ ID NO: 25)
ATGGCCTGGATCCCTCTCTTCCTCGGCGTCCTTGCTTACTGCACAGATTC
CGTAGT**CTCCTATGAACTGACTCAGCCACCCTCAGTGTCCGTGTCCCAG
GACAGACAGCCAGCATCACCTGTTCTGGATCTAAATTGGGGGATAAAATAT
GTTTCCTGGTATCAACTGAGGCCAGGCCAGTCCCCCATACTGGTCATGTA
TGAAAATGACAGGCGGCCCTCCGGGATCCCTGAGCGATTCTCCGGTTCCA
ATTCTGGCGACACTGCCACTCTGACCATCAGCGGGACCCAGGCTTTGGAT
GAGGCTGACTTCTACTGTCAGGCGTGGGAGACCACCACCACCACTTTTGT
TTTCTTCGGCGGAGGGACCCAGCTGACCGTTCTA**GGTCAGCCCAAGGCTG
CCCCCTCGGTCACTCTGTTCCCGCCCTCCTCTGAGGAGCTTCAAGCCAAC
AAGGCCACACTGGTGTGTCTCATAAGTGACTTCTACCCGGGAGCCGTGAC
AGTGGCCTGGAAGGCAGATAGCAGCCCCGTCAAGGCGGGAGTGGAGACCA
CCACACCCTCCAAACAAAGCAACAACAAGTACGCGGCCAGCAGCTACCTG
AGCCTGACGCCTGAGCAGTGGAAGTCCCACAAAAGCTACAGCTGCCAGGT
CACGCATGAAGGGAGCACCGTGGAGAAGACAGTGGCCCCCTACAGAATGTT
CATAG 1495_C14 (PGC14) lambda light chain variable region nucleotide sequence:
(SEQ ID NO: 119)
TCCTATGAACTGACTCAGCCACCCTCAGTGTCCGTGTCCCCAGGACAGAC
AGCCAGCATCACCTGTTCTGGATCTAAATTGGGGGATAAAATATGTTTCCT
GGTATCAACTGAGGCCAGGCCAGTCCCCCATACTGGTCATGTATGAAAAT
GACAGGCGGCCCTCCGGGATCCCTGAGCGATTCTCCGGTTCCAATTCTGG
CGACACTGCCACTCTGACCATCAGCGGGACCCAGGCTTTGGATGAGGCTG
ACTTCTACTGTCAGGCGTGGGAGACCACCACCACCACTTTTGTTTTCTTC
GGCGGAGGGACCCAGCTGACCGTTCTA 1495_C14 (PGC14) lambda light chain amino acid sequence: expressed protein with variable region in bold.
(SEQ ID NO: 26)
**SYELTQPPSVSVSPGQTASITCSGSKLGDKYVSWYQLRPGQSPILVMYEN
DRRPSGIPERFSGSNSGDTATLTISGTQALDEADFYCQAWETTTTTFVFF
GGGTQLTVL**GQPKAAPSVTLFPPSSEELQANKATLVCLISDFYPGAVTVA
WKADSSPVKAGVETTTPSKQSNNKYAASSYLSLTPEQWKSHKSYSCQVTH
EGSTVEKTVAPTECS 1495_C14 (PGC14) lambda light chain variable region amino acid sequence: (Kabat CDRs underlined, Chothia CDRs in bold italics)
(SEQ ID NO: 38)
SYELTQPPSVSVSPGQTASITC*SGSKLGDKYVS*WYQLRPGQSPILVMY
*ENDRRPS*GIPERFSGSNSGDTATLTISGTQALDEADFYCF
*QAWETTTTTFVF*GGGTQLTVL 1495_C14 (PGC14) lambda light chain Kabat CDRs:
CDR 1:
(SEQ ID NO: 120)
SGSKLGDKYVS

CDR 2:
(SEQ ID NO: 121)
ENDRRPS

CDR 3:
(SEQ ID NO: 44)
QAWETTTTTFVF

1495_C14 (PGC14) lambda light chain Chothia CDRs:
CDR 1:
(SEQ ID NO: 120)
SGSKLGDKYVS

CDR 2:
(SEQ ID NO: 121)
ENDRRPS

CDR 3:
(SEQ ID NO: 44)
QAWETTTTTFVF

1496_C09 (PG9) (TCN-109) gamma heavy chain nucleotide sequence: 1496_C09 γ3 coding sequence (variable region in bold)
(SEQ ID NO: 27)
ATGGAGTTTGGGCTGAGCTGGGTTTTCCTCGTTGCTCTTTCTTAAGAGGTGT
CCAGTGT**CAGCGATTAGTGGAGTCTGGGGGAGGCGTGGTCCAGCCTGGGT
CGTCCCTGAGACTCTCCTGTGCAGCGTCCGGATTCGACTTCAGTAGACAA
GGCATGCACTGGGTCCGCCAGGCTCCAGGCCAGGGGCTGGAGTGGGTGGC
ATTTATTAAATATGATGGAAGTGAGAAATATCATGCTGACTCCGTATGGG
GCCGACTCAGCATCTCCAGAGACAATTCCAAGGATACGTTTATCTCCAA
ATGAATAGCCTGAGAGTCGAGGACACGGCTACATATTTTTGTGTGAGAGA
GGCTGGTGGGCCCGACTACCGTAATGGGTACAACTATTACGATTTCTATG
ATGGTTATTATAACTACCACTATATGGACGTCTGGGGCAAAGGGACCACG
GTCACCGTCTCGAGC**GCCTCCACCAAGGGCCCATCGGTCTTCCCCCTGGC
ACCCTCCTCCAAGAGCACCTCTGGGGGCACAGCGGCCCTGGGCTGCCTGG
TCAAGGACTACTTCCCCGAACCGGTGACGGTGTCGTGGAACTCAGGCGCC
CTGACCAGCGGCGTGCACACCTTCCCGGCTGTCCTACAGTCCTCAGGACT
CTACTCCCTCAGCAGCGTGGTGACCGTGCCCTCCAGCAGCTTGGGCACCC
AGACCTACATCTGCAACGTGAATCACAAGCCCAGCAACACCAAGGTGGAC
AAGAGAGTTGAGCCCAAATCTTGTGACAAAACTCACACATGCCCACCGTG
CCCAGCACCTGAACTCCTGGGGGGACCGTCAGTCTTCCTCTTCCCCCCAA
AACCCAAGGACACCCTCATGATCTCCCGGACCCCTGAGGTCACATGCGTG
GTGGTGGACGTGAGCCACGAAGACCCTGAGGTCAAGTTCAACTGGTACGT
GGACGGCGTGGAGGTGCATAATGCCAAGACAAAGCCGCGGGAGGAGCAGT
ACAACAGCACGTACCGTGTGGTCAGCGTCCTCACCGTCCTGCACCAGGAC
TGGCTGAATGGCAAGGAGTACAAGTGCAAGGTCTCCAACAAAGCCCTCCC
AGCCCCCATCGAGAAAACCATCTCCAAAGCCAAAGGGCAGCCCCGAGAAC
CACAGGTGTACACCCTGCCCCCATCCCGGGAGGAGATGACCAAGAACCAG
GTCAGCCTGACCTGCCTGGTCAAAGGCTTCTATCCCAGCGACATCGCCGT
GGAGTGGGAGAGCAATGGGCAGCCGGAGAACAACTACAAGACCACGCCTC
CCGTGCTGGACTCCGACGGCTCCTTCTTCCTCTATAGCAAGCTCACCGTG
GACAAGAGCAGGTGGCAGCAGGGGAACGTCTTCTCATGCTCCGTGATGCA
TGAGGCTCTGCACAACCACTACACGCAGAAGAGCCTCTCCCTGTCTCCGG
GTAAATGA 1496_C09 (PG9) (TCN-109) gamma heavy chain variable region nucleotide sequence:
(SEQ ID NO: 122)
CAGCGATTAGTGGAGTCTGGGGGAGGCGTGGTCCAGCCTGGGTCGTCCCT
GAGACTCTCCTGTGCAGCGTCCGGATTCGACTTCAGTAGACAAGGCATGC
ACTGGGTCCGCCAGGCTCCAGGCCAGGGGCTGGAGTGGGTGGCATTTATT
AAATATGATGGAAGTGAGAAATATCATGCTGACTCCGTATGGGGCCGACT
CAGCATCTCCAGAGACAATTCCAAGGATACGTTTATCTCCAAATGAATA
GCCTGAGAGTCGAGGACACGGCTACATATTTTTGTGTGAGAGAGGCTGGT
GGGCCCGACTACCGTAATGGGTACAACTATTACGATTTCTATGATGGTTA
TTATAACTACCACTATATGGACGTCTGGGGCAAAGGGACCACGGTCACCG
TCTCGAGC 1496_C09 (PG9) (TCN-109) gamma heavy chain amino acid sequence: expressed protein with variable region in bold.

(SEQ ID NO: 28)
QRLVESGGGVVQPGSSLRLSCAASGFDFSRQGMHWVRQAPGQGLEWVAFI
KYDGSEKYHADSVWGRLSISRDNSKDTLYLQMNSLR VEDTATYFCVREA
GGPDYRNGYNYYDFYDGYYNYHYMDVWGKGTTVTVSSASTKGPSVFPLAP
SSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCP
APELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPA
PIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHE
ALHNHYTQKSLSLSPGK

1496_C09 (PG9) (TCN-109) gamma heavy chain variable region amino acid sequence: (Kabat CDRs underlined, Chothia CDRs in bold italics)

(SEQ ID NO: 39)
QRLVESGGGVVQPGSSLRLSCAAS*GFDGSR*QGMHWVRQAPGQGLEWVA
F*IKYDGSEKY*HADSVWGRLSISRDNSKDTLYLQMNSLRVEDTATYFC
VR*EAGGPDYRNGYNYYDFYDGYYNYHYMDV*WGKGTTVTVSS

1496_C09 (PG9) (TCN-109) gamma heavy chain Kabat CDRs:
CDR 1:

(SEQ ID NO: 123)
RQGMH

CDR 2:

(SEQ ID NO: 124)
FIKYDGSEKYHADSVWG

CDR 3:

(SEQ ID NO: 7)
EAGGPDYRNGYNYYDFYDGYYNYHYMDV

1496_C09 (PG9) (TCN-109) gamma heavy chain Chothia CDRs:
CDR 1:

(SEQ ID NO: 118)
GFDFSR

CDR 2:

(SEQ ID NO: 272)
FIKYDGSEKY

CDR 3:

(SEQ ID NO: 7)
EAGGPDYRNGYNYYDFYDGYYNYHYMDV

1496_C09 (PG9) (TCN-109) lambda light chain nucleotide sequence: 1496_C09 λ2 coding sequence (variable region in bold)

(SEQ ID NO: 29)
ATGGCCTGGGCTCTGCTTTTCCTCACCCTCCTCACTCAGGGCACAGGGTC
CTGGGCCCAGTCTGCCCTGACTCAGCCTGCCTCCGTGTCTGGGTCTCCTG
GACAGTCGATCACCATCTCCTGCAATGGAACCAGCAATGATGTTGGTGGC
TATGAATCTGTCTCCTGGTACCAACAACATCCCGGCAAAGCCCCCAAAGT
CGTGATTTATGATGTCAGTAAACGGCCCTCAGGGGTTTCTAATCGCTTCT
CTGGCTCCAAGTCCGGCAACACGGCCTCCCTGACCATCTCTGGGCTCCAG
GCTGAGGACGAGGGTGACTATTACTGCAAGTCTCGACAAGCACGAGACTG
TCGGGTTTTCGGCACTGGGACCAAGCTGACCGTTCTAGGTCAGCCCAAGG
CTGCCCCCTCGGTCACTCTGTTCCCGCCCTCCTCTGAGGAGCTTCAAGCC
AACAAGGCCACACTGGTGTGTCTCATAAGTGACTTCTACCCGGGAGCCGT
GACAGTGGCCTGGAAGGCAGATAGCAGCCCCGTCAAGGCGGGAGTGGAGA
CCACCACACCCTCCAAACAAAGCAACAACAAGTACGCGGCCAGCAGCTAC
CTGAGCCTGACGCCTGAGCAGTGGAAGTCCCACAAAAGCTACAGCTGCCA
GGTCACGCATGAAGGGAGCACCGTGGAGAAGACAGTGGCCCCTACAGAAT
GTTCATAG

1496_C09 (PG9) (TCN-109) lambda light chain variable region nucleotide sequence:

(SEQ ID NO: 125)
CAGTCTGCCCTGACTCAGCCTGCCTCCGTGTCTGGGTCTCCTGGACAGTC
GATCACCATCTCCTGCAATGGAACCAGCAATGATGTTGGTGGCTATGAAT
CTGTCTCCTGGTACCAACAACATCCCGGCAAAGCCCCCAAAGTCGTGATT
TATGATGTCAGTAAACGGCCCTCAGGGGTTTCTAATCGCTTCTCTGGCTC
CAAGTCCGGCAACACGGCCTCCCTGACCATCTCTGGGCTCCAGGCTGAGG
ACGAGGGTGACTATTACTGCAAGTCTCTGACAAGCACGAGACGTCGGGTT
TTCGGCACTGGGACCAAGCTGACCGTTCTA

1496_C09 (PG9) (TCN-109) lambda light chain amino acid sequence: expressed protein with variable region in bold.

(SEQ ID NO: 30)
**QSALTQPASVSGSPGQSITISCNGTSNDVGGYESVSWYQQHPGKAPKVVI
YDVSKRPSGVSNRFSGSKSGNTASLTISGLQAEDEGDYYCKSLTSTRRRV
FGTGTKLTVL**GQPKAAPSVTLFPPSSEELQANKATLVCLISDFYPGAVTV
AWKADSSPVKAGVETTTPSKQSNNKYAASSYLSLTPEQWKSHKSYSCQVT
HEGSTVEKTVAPTECS

1496_C09 (PG9) (TCN-109) lambda light chain variable region amino acid sequence: (Kabat CDRs underlined, Chothia CDRs in bold italics)

(SEQ ID NO: 40)
QSALTQPASVSGSPGQSITISC*NGTSNDVGGYESVS*WYQQHPGKAPKV
VIY*DV SKRPS*GVSNRFSGSKSGNTASLTISGLQAEDEGDYYC
*KSLTSTRRRV*FGTGTKLTVL

1496_C09 (PG9) (TCN-109) lambda light chain Kabat CDRs:
CDR 1:

(SEQ ID NO: 126)
NGTSNDVGGYESVS

CDR 2:

(SEQ ID NO: 127)
DVSKRPS

CDR 3:

(SEQ ID NO: 45)
KSLTSTRRRV

1496_C09 (PG9) (TCN-109) lambda light chain Chothia CDRs:
CDR 1:

(SEQ ID NO: 126)
NGTSNDVGGYESVS

CDR 2:

(SEQ ID NO: 127)
DVSKRPS

CDR 3:

(SEQ ID NO: 45)
KSLTSTRRRV

The 1443_C16 (PG16) antibody includes a heavy chain variable region (SEQ ID NO: 31), encoded by the nucleic acid sequence shown in SEQ ID NO: 99, and a light chain variable region (SEQ ID NO: 32) encoded by the nucleic acid sequence shown in SEQ ID NO: 100.

The heavy chain CDRs of the 1443_C16 (PG16) antibody have the following sequences per Kabat definition: KYGMH (SEQ ID NO: 88), LISDDGMRKYHSDSMWG (SEQ ID NO: 89), and EAGGPIWHDDVKYYDFNDGYYNYHYMDV (SEQ ID NO: 6). The light chain CDRs of the 1443_C16 (PG16) antibody have the following sequences per Kabat definition: NGTSSDVGGFDSVS (SEQ ID NO: 97), DVSHRPS (SEQ ID NO: 95), and SSLTDRSHRI (SEQ ID NO: 41).

The heavy chain CDRs of the 1443_C16 (PG16) antibody have the following sequences per Chothia definition: GFTFHK (SEQ ID NO: 266), LISDDGMRKY (SEQ ID NO: 267), and EAGGPIWHDDVKYYDFNDGYYNYHYMDV (SEQ ID NO: 6). The light chain CDRs of the 1443_C16 (PG16) antibody have the following sequences per Chothia definition: NGTSSDVGGFDSVS (SEQ ID NO: 97), DVSHRPS (SEQ ID NO: 95), and SSLTDRSHRI (SEQ ID NO: 41).

The 1456_P20 (PG20) antibody includes a heavy chain variable region (SEQ ID NO: 33), encoded by the nucleic acid sequence shown in SEQ ID NO: 101, and a light chain variable region (SEQ ID NO: 34) encoded by the nucleic acid sequence shown in SEQ ID NO: 106.

The heavy chain CDRs of the 1456 P20 (PG20) antibody have the following sequences per Kabat definition: SYAFT (SEQ ID NO: 104), MVTPIFGEAKYSQRFEG (SEQ ID NO: 105), and DRRAVPIATDNWLDP (SEQ ID NO: 9). The light chain CDRs of the 1456 P20 (PG20) antibody have the following sequences per Kabat definition: RASQTIN-NYLN (SEQ ID NO: 107), GASNLQN (SEQ ID NO: 108), and QQSFSTPRT (SEQ ID NO: 42).

The heavy chain CDRs of the 1456 P20 (PG20) antibody have the following sequences per Chothia definition: GGTFSS (SEQ ID NO: 268), MVTPIFGEAK (SEQ ID NO: 269), and DRRAVPIATDNWLDP (SEQ ID NO: 9). The light chain CDRs of the 1456 P20 (PG20) antibody have the following sequences per Chothia definition: RASQTIN-NYLN (SEQ ID NO: 107), GASNLQN (SEQ ID NO: 108), and QQSFSTPRT (SEQ ID NO: 42).

The 1460_G14 (PGG14) antibody includes a heavy chain variable region (SEQ ID NO: 35), encoded by the nucleic acid sequence shown in SEQ ID NO: 109, and a light chain variable region (SEQ ID NO: 36) encoded by the nucleic acid sequence shown in SEQ ID NO: 112.

The heavy chain CDRs of the 1460_G14 (PGG14) antibody have the following sequences per Kabat definition: SYAFS (SEQ ID NO: 110), MITPVFGETKYAPRFQG (SEQ ID NO: 111), and DRRVVPMATDNWLDP (SEQ ID NO: 8). The light chain CDRs of the 1460_G14 (PGG14) antibody have the following sequences per Kabat definition: RASQTIHTYLN (SEQ ID NO: 113), GASTLQS (SEQ ID NO: 114), QQSYSTPRT (SEQ ID NO: 43).

The heavy chain CDRs of the 1460_G14 (PGG14) antibody have the following sequences per Chothia definition: GGAFSS (SEQ ID NO: 270), MITPVFGETK (SEQ ID NO: 271), DRRVVPMATDNWLDP (SEQ ID NO: 8). The light chain CDRs of the 1460_G14 (PGG14) antibody have the following sequences per Chothia definition: RASQTIHTYLN (SEQ ID NO: 113), GASTLQS (SEQ ID NO: 114), QQSYSTPRT (SEQ ID NO: 43).

The 1495_C14 (PGC14) antibody includes a heavy chain variable region (SEQ ID NO: 37), encoded by the nucleic acid sequence shown in SEQ ID NO: 115, and a light chain variable region (SEQ ID NO: 38) encoded by the nucleic acid sequence shown in SEQ ID NO: 119.

The heavy chain CDRs of the 1495_C14 (PGC14) antibody have the following sequences per Kabat definition: DYYLH (SEQ ID NO: 116), LIDPENGEARYAEKFQG (SEQ ID NO: 117), GAVGADSGSWFDP (SEQ ID NO: 10). The light chain CDRs of the 1495_C14 (PGC14) antibody have the following sequences per Kabat definition: SGSK-LGDKYVS (SEQ ID NO: 120), ENDRRPS (SEQ ID NO: 121), and QAWETTTTFVF (SEQ ID NO: 44).

The heavy chain CDRs of the 1495_C14 (PGC14) antibody have the following sequences per Chothia definition: GYSFID (SEQ ID NO: 102), LIDPENGEAR (SEQ ID NO: 103), GAVGADSGSWFDP (SEQ ID NO: 10). The light chain CDRs of the 1495_C14 (PGC14) antibody have the following sequences per Chothia definition: SGSK-LGDKYVS (SEQ ID NO: 120), ENDRRPS (SEQ ID NO: 121), and QAWETTTTFVF (SEQ ID NO: 44).

The 1496_C09 (PG9) antibody includes a heavy chain variable region (SEQ ID NO: 39), encoded by the nucleic acid sequence shown in SEQ ID NO: 122, and a light chain variable region (SEQ ID NO: 40) encoded by the nucleic acid sequence shown in SEQ ID NO: 125.

The heavy chain CDRs of the 1496_C09 (PG9) antibody have the following sequences per Kabat definition: RQGMH (SEQ ID NO: 123), FIKYDGSEKYHADSVWG (SEQ ID NO: 124), and EAGGPDYRNGYNYYDFYDGYYNY-HYMDV (SEQ ID NO: 7). The light chain CDRs of the 1496_C09 (PG9) antibody have the following sequences per Kabat definition: NGTSNDVGGYESVS (SEQ ID NO: 126), DVSKRPS (SEQ ID NO: 127), and KSLTSTRRRV (SEQ ID NO: 45).

The heavy chain CDRs of the 1496_C09 (PG9) antibody have the following sequences per Chothia definition: GFDFSR (SEQ ID NO: 118), FIKYDGSEKY (SEQ ID NO: 272), and EAGGPDYRNGYNYYDFYDGYYNYHYMDV (SEQ ID NO: 7). The light chain CDRs of the 1496_C09 (PG9) antibody have the following sequences per Chothia definition: NGTSNDVGGYESVS (SEQ ID NO: 126), DVSKRPS (SEQ ID NO: 127), and KSLTSTRRRV (SEQ ID NO: 45).

TABLE 6A

Heavy Chain Variable Region Protein Alignment

```
                              10                        20
1495_C14_G1 ref D G H L  V Q S G  V  E V K K  T G A T V K  I S C K V  S
1460_G14_G1 ref Q V L L  V Q S G  T  E V K K  P G S S V K  V S C Q A  S
1456_P20_G1 ref Q V R L  V Q S G  P  E V K K  P G S S V T  V S C Q A  S
1443_C16_G3 ref Q E Q L  V E S G  G  G V V Q  P G G S L R  L S C L A  S
1496_C09_G3 ref Q - R L  V E S G  G  G V V Q  P G S S L R  L S C A A  S 30                        40                  50
1495_C14_G1 ref G Y S  F  I D Y Y  L  H W V Q R  A P G K G  L E W V G  L
1460_G14_G1 ref G G A  F  S S Y A  F  S W V R Q  A P G Q G  L E W M G  M
1456_P20_G1 ref G G T  F  S S Y A  F  T W V R Q  A P G Q G  L E W L G  M
1443_C16_G3 ref G F T  F  H K Y G  M  H W V R Q  A P G K G  L E W V A  L
1496_C09_G3 ref G F D  F  S R Q G  M  H W V R Q  A P G Q G  L E W V A  F 60                        70
1495_C14_G1 ref I D P  E  N G E A  R  Y A E K F  Q G R V T  I I A D T  S
1460_G14_G1 ref I T P  V  F G E T  K  Y A P R F  Q G R L T  L T A E E  S
1456_P20_G1 ref V T P  I  F G E A  K  Y S Q R F  E G R V T  I T A D E  S
1443_C16_G3 ref I S D  D  G M R K  Y  H S D S M  W G R V T  I S R D N  S
1496_C09_G3 ref I K Y  D  G S E K  Y  H A D S V  W G R L S  I S R D N  S 80                        90                      100
1495_C14_G1 ref I D T  G  Y M E M  R  S L K S E  D T A V Y  F C A A G  -
1460_G14_G1 ref L S T  T  Y M E L  R  S L T S D  D T A F Y  Y C T R D  R
1456_P20_G1 ref T S T  T  S I E L  R  G L T S E  D T A I Y  Y C A R D  R
```

TABLE 6A-continued

Heavy Chain Variable Region Protein Alignment

```
1443_C16_G3 ref K N T L  Y L Q F  S  S L K V E  D T A M F  F C A R E  A
1496_C09_G3 ref K D T L  Y L Q M  N  S L R V E  D T A T Y  F C V R E  A 110                    120
1495_C14_G1 ref - - - -  - - - -  -  - - - - -  A V G A D  S G S W F  D
1460_G14_G1 ref R - - -  - - - -  -  - - - - -  V V P M A  T D N W L  D
1456_P20_G1 ref R - - -  - - - -  -  - - - - -  A V P I A  T D N W L  D
1443_C16_G3 ref G G P I  W H D D  V  K Y Y D F  N D G Y Y  N Y H Y M  D
1496_C09_G3 ref G G P D  Y R N G  Y  N Y Y D F  Y D G Y Y  N Y H Y M  D 130
                        1495_C14_G1 ref P W G Q G T  L V T V S  S
                        1460_G14_G1 ref P W G Q G T  L V T V S  S
                        1456_P20_G1 ref P W G Q G T  L V T V S  S
                        1443_C16_G3 ref V W G K G T  T V T V S  S
                        1496_C09_G3 ref V W G K G T  T V T V S  S
```

TABLE 6B

Light Chain Variable Region Protein Alignment

```
                                  10                      20
1495_C14_L3 ref S Y E L T Q - P P  S V S V S  P G Q T A S  I T C
1460_G14_K1 ref D I Q L T Q S P S  S L S A S  V G D R V T  V T C
1456_P20_K1 ref D I Q L T Q S P S  S L S A S  V G D R V S  I T C
1443_C16_L2 ref Q S A L T Q - P A  S V S G S  P G Q T I T  I S C
1496_C09_L2 ref Q S A L T Q - P A  S V S G S  P G Q S I T  I S C 30                     40
1495_C14_L3 ref S G S K - - - L G  D K Y V S  W Y Q L R P  G Q S
1460_G14_K1 ref R A S Q T - - - I  H T Y L N  W Y Q Q I P  G K A
1456_P20_K1 ref R A S Q T - - - I  N N Y L N  W Y Q Q T P  G K A
1443_C16_L2 ref N G T S S D V G G  F D S V S  W Y Q Q S P  G K A
1496_C09_L2 ref N G T S N D V G G  Y E S V S  W Y Q Q H P  G K A 50                      60
1495_C14_L3 ref P I L V M Y E N D  R P S G I P  E R F S G S N
1460_G14_K1 ref P K L L I Y G A S  T L Q S G V P  S R F S G S G
1456_P20_K1 ref P K L L I Y G A S  N L Q N G V P  S R F S G S G
1443_C16_L2 ref P K V M V F D V S  H R P S G I S  N R F S G S K
1496_C09_L2 ref P K V V I Y D V S  K R P S G V S  N R F S G S K 70                      80                90
1495_C14_L3 ref S G D T A T L T I  S G T Q A L D  E A D F Y C Q
1460_G14_K1 ref S G T D F T L T I  N S L Q P E D  F A T Y Y C Q
1456_P20_K1 ref S G T D F T L T I  S S L Q P E D  F A T Y Y C Q
1443_C16_L2 ref S G N T A S L T I  S G L H I E D  E G D Y F C S
1496_C09_L2 ref S G N T A S L T I  S G L Q A E D  E G D Y Y C K 100                 110
1495_C14_L3 ref A W E T T T T T F  V F F G G G T  Q L T V L  G
1460_G14_K1 ref Q - - - S Y S T P  R T F G Q G T  R L D I K  -
1456_P20_K1 ref Q - - - S F S T P  R T F G Q G T  R L D I K  -
1443_C16_L2 ref S - - L T D R S H  R I F G G G T  K V T V L  G
1496_C09_L2 ref S - - L T S T R R  R V F G T G T  K L T V L  G
```

The sequences of sister clones to human monoclonal antibody 1443_C16 (PG16) were determined, including the sequences of the variable regions of the Gamma heavy and Kappa or Lambda light chains. In addition, the sequence of each of the polynucleotides encoding the antibody sequences was determined. Shown below are the polypeptide and polynucleotide sequences of the gamma heavy chains and kappa light chains, with the signal peptides at the N-terminus (or 5' end) and the constant regions at the C-terminus (or 3' end) of the variable regions, which are shown in bolded text.

1469_M23 (PG16)(TCN-118) gamma heavy chain nucleotide sequence: 1469_M23 γ3 coding sequence (variable region in bold)

(SEQ ID NO: 138)

ATGGAGTTTGGGCTGAGCTGGGTTTTCCTCGCAACTCTGTTAAGAGTTGTGAAGTG
**TCAGGAAAAACTGGTGGAGTCTGGGGGAGGCGTGGTCCAGCC
GGGGGGGTCCCTGAGACTCTCCTGTTTAGCGTCTGGATTCACCTTTC
ACAAATATGGCATGCACTGGGTCCGCCAGGCTCCAGGCAAGGGCCTG
GAGTGGGTGGCACTCATCTCAGATGACGGAATGAGGAAATATCATTC**

```
AGACTCCATGTGGGGCCGAGTCACCATCTCCAGAGACAATTCCAAGA
ACACTCTATATCTGCAATTCaGCAGCCTGAAAGTCGAAGACACGGCTA
TGTTCTTCTGTGCGAGAGAGGCTGGTGGGCCAATCTGGCATGACGAC
GTCAAATATTACGATTTTAATGACGGCTACTACAACTACCACTACATG
GACGTCTGGGGCAAGGGGACCACGGTCACCGtCTCCTCAGCGTCGACC
AAGGGCCCATCGGTCTTCCCTCTGGCACCATCATCCAAGTCGACCTCTGG
GGGCACAGCGGCCCTGGGCTGCCTGGTCAAGGACTACTTCCCCGAACCGG
TGACGGTGTCGTGGAACTCAGGCGCCCTGACCAGCGGCGTGCACACCTTC
CCGGCTGTCCTACAGTCCTCAGGACTCTACTCCCTCAGCAGCGTGGTGAC
CGTGCCCTCCAGCAGCTTGGGCACCCAGACCTACATCTGCAACGTGAATC
ACAAGCCCAGCAACACCAAGGTGGACAAGAGAGTTGAGCCCAAATCTTG
TGACAAAACTCACACATGCCCACCGTGCCCAGCACCTGAACTCCTGGGGG
GACCGTCAGTCTTCCTCTTCCCCCCAAAACCCAAGGACACCCTCATGATCT
CCCGGACCCCTGAGGTCACATGCGTGGTGGTGGACGTGAGCCACGAAGA
CCCTGAGGTCAAGTTCAACTGGTACGTGGACGGCGTGGAGGTGCATAATG
CCAAGACAAAGCCGCGGGAGGAGCAGTACAACAGCACGTACCGTGTGGT
CAGCGTCCTCACCGTCCTGCACCAGGACTGGCTGAATGGCAAGGAGTACA
AGTGCAAGGTCTCCAACAAAGCCCTCCCAGCCCCCATCGAGAAAACCATC
TCCAAAGCCAAAGGGCAGCCCCGAGAACCACAGGTGTACACCCTGCCCC
CATCCCGGGAGGAGATGACCAAGAACCAGGTCAGCCTGACCTGCCTGGTC
AAAGGCTTCTATCCCAGCGACATCGCCGTGGAGTGGGAGAGCAATGGGC
AGCCGGAGAACAACTACAAGACCACGCCTCCCGTGCTGGACTCCGACGG
CTCCTTCTTCCTCTATAGCAAGCTCACCGTGGACAAGAGCAGGTGGCAGC
AGGGGAACGTCTTCTCATGCTCCGTGATGCATGAGGCTCTGCACAACCAC
TACACGCAGAAGAGCCTCTCCCTGTCTCCGGGTAAATGA

1469_M23 (PG16) (TCN-118) gamma heavy chain variable region nucleotide
sequence:
                                                   (SEQ ID NO: 128)
CAGGAAAAACTGGTGGAGTCTGGGGGAGGCGTGGTCCAGCCGGGGGGT
CCCTGAGACTCTCCTGTTTAGCGTCTGGATTCACCTTTCACAAATATGGCA
TGCACTGGGTCCGCCAGGCTCCAGGCAAGGGCCTGGAGTGGGTGGCACTC
ATCTCAGATGACGGAATGAGGAAATATCATTCAGACTCCATGTGGGGCCG
AGTCACCATCTCCAGAGACAATTCCAAGAACACTCTATATCTGCAATTCaG
CAGCCTGAAAGTCGAAGACACGGCTATGTTCTTCTGTGCGAGAGAGGCTG
GTGGGCCAATCTGGCATGACGACGTCAAATATTACGATTTTAATGACGGC
TACTACAACTACCACTACATGGACGTCTGGGGCAAGGGGACCACGGTCAC
CGtCTCCTCA 1469_M23 (PG16)(TCN-118) gamma heavy chain amino acid sequence: expressed
protein with variable region in bold.
                                                   (SEQ ID NO: 139)
QEKLVESGGGVVQPGGSLRLSCLASGFTFHKYGMHWVRQAPGKGLEW
VALISDDGMRKYHSDSMWGRVTISRDNSKNTLYLQFSSLKVEDTAMFFC
AREAGGPIWHDDVKYYDFNDGYYNYHYMDVWGKGTTVTVSSASTKGPS
VFPLAPSSKSTSGGTAALGCLVKDYFPEPVTSWNSGALTSGVHTFPAVLQSS
GLYSLSSVVTVPSSSLGTQTYICNVNHKPSNTKVDKRVEPKSCDKTHTCPPCP
APELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHY
TQKSLSLSPGK 1469_M23 (PG16) (TCN-118) gamma heavy chain variable region amino acid
sequence: (Kabat CDRs underlined, Chothia CDRs in bold italics)
                                                   (SEQ ID NO: 140)
QEKLVESGGGVVQPGGSLRLSCLAS***GFTFHK***YGMHWVRQAPGKGLEWVA<u>L
ISDDGMRKY</u>HSDSMWGRVTISRDNSKNTLYL<u>QFSSLKVEDTAMFFCAREAG
GPIWHDDVKYYIFNDGYYNYHYMDV</u>WGKGTTVTVSS 1469_M23 (PG16)(TCN-118) gamma heavy chain Kabat CDRs:
                                                   (SEQ ID NO: 88)
CDR 1: KYGMH (SEQ ID NO: 89)
CDR 2: LISDDGMRKYHSDSMWG (SEQ ID NO: 6)
CDR 3: EAGGPIWHDDVKYYDFNDGYYNYHYMDV 1469_M23 (PG16)(TCN-118) gamma heavy chain Chothia CDRs:
                                                   (SEQ ID NO: 266)
CDR 1: GFTFHK (SEQ ID NO: 267)
CDR 2: LISDDGMRKY (SEQ ID NO: 6)
CDR 3: EAGGPIWHDDVKYYDENDGYYNYHYMDV
```

-continued

1469_M23(PG16)(TCN-118) lambda light chain nucleotide sequence: 1469_M23 λ2 coding sequence (variable region in bold)

(SEQ ID NO: 141)

ATGGCCTGGGCTCTGCTATTCCTCACCCTCTTCACTCAGGGCACAGGGTCC
TGGGGC**CAGTCTGCCCTGACTCAGCCTGCCTCCGTGTCTGGGTCTCCT
GGACAGACGATCACCATCTCCTGCAATGGAACCAGAAGTGACGTTGG
TGGATTTGACTCTGTCTCCTGGTACCAACAATCCCAGGGAGAGCCC
CCAAAGTCATGGTTTTTGATGTCAGTCATCGGCCCTCAGGTATCTCTA
ATCGCTTCTCTGGCTCCAAGTCCGGCAACACGGCCTCCCTGACCATC
TCTGGGCTCCACATTGAGGACGAGGGCGATTATTTCTGCTCTTCACT
GACAGACAGAAGCCATCGCATATTCGGCGGCGGGACCAAGCTGACC
GTTCTA**GGTCAGCCCAAGGCTGCCCCCTCGGTCACTCTGTTCCCGCCCTC
CTCTGAGGAGCTTCAAGCCAACAAGGCCACACTGGTGTGTCTCATAAGTG
ACTTCTACCCGGGAGCCGTGACAGTGGCCTGGAAGGCAGATAGCAGCCCC
GTCAAGGCGGGAGTGGAGACCACCACACCCTCCAAACAAAGCAACAACA
AGTACGCGGCCAGCAGCTACCTGAGCCTGACGCCTGAGCAGTGGAAGTCC
CACAAAAGCTACAGCTGCCAGGTCACGCATGAAGGGAGCACCGTGGAGA
AGACAGTGGCCCCTACAGAATGTTCATAG

1469_M23 (PG16)(TCN-118) lambda light chain variable region nucleotide sequence:

(SEQ ID NO: 129)

CAGTCTGCCCTGACTCAGCCTGCCTCCGTGTCTGGGTCTCCTGGACAGACG
ATCACCATCTCCTGCAATGGAACCAGAAGTGACGTTGGTGGATTTGACTC
TGTCTCCTGGTACCAACAATCCCAGGGAGAGCCCCCAAAGTCATGGTTT
TTGATGTCAGTCATCGGCCCTCAGGTATCTCTAATCGCTTCTCTGGCTCCA
AGTCCGGCAACACGGCCTCCCTGACCATCTCTGGGCTCCACATTGAGGAC
GAGGGCGATTATTTCTGCTCTTCACTGACAGACAGAAGCCATCGCATATT
CGGCGGCGGGACCAAGCTGACCGTTCTA

1469_M23 (PG16) (TCN-118) lambda light chain amino acid sequence: expressed protein with variable region in bold.

(SEQ ID NO: 142)

**QSALTQPASVSGSPGQTITISCNGTRSDVGGFDSVSWYQQSPGRAPKVMV
FDVSHRPSGISNRFSGSKSGNTASLTISGLHIEDEGDYFCSSLTDRSHRIFG
GGTKLTVL**GQPKAAPSVTLFPPSSEELQANKATLVCLISDFYPGAVTVAWKA
DSSPVKAGVETTTPSKQSNNKYAASSYLSLTPEQWKSHKSYSCQVTHEGSTV
EKTVAPTECS

1469_M23 (PG16) (TCN-118) lambda light chain variable region amino acid sequence: (Kabat CDRs underlined, Chothia CDRs in bold italics)

(SEQ ID NO: 96)

QSALTQPASVSGSPGQTITISC*NGTRSDVGGFDSVS*WYQQSPGRAPKVMVF***D
VSHRPS*GISNRFSGSKSGNTASLTISGLHIEDEGDYFC*SSLTDRSHRI***FGGGTKL
TVL

1469_M23 (PG16)(TCN-118) lambda light chain Kabat CDRs:

(SEQ ID NO: 92)

CDR 1: NGTRSDVGGFDSVS (SEQ ID NO: 95)

CDR 2: DVSHRPS (SEQ ID NO: 41)

CDR 3: SSLTDRSHRI

1469_M23(PG16)(TCN-118) lambda light chain Chothia CDRs:

(SEQ ID NO: 92)

CDR 1: NGTRSDVGGFDSVS (SEQ ID NO: 95)

CDR 2: DVSHRPS (SEQ ID NO: 41)

CDR 3: SSLTDRSHRI

1456_A12 (PG16)(TCN-117) gamma heavy chain nucleotide sequence: 1456_A12 γ3 coding sequence (variable region in bold)

(SEQ ID NO: 46)

ATGGAGTTTGGGCTGAGCTGGGTTTTCCTCGCAACTCTGTTAAGAGTTGTG
AAGTGT**CACGAACAACTGGTGGAGGCCGGGGGAGGCGTGGTCCAGC
CGGGGGGGTCCCTGAGACTCTCCTGTTTAGCGTCTGGATTCACGTTT
CACAAATATGGCATGCACTGGGTCCGCCAGGCTCAGGCAAGGGCCT
GGAGTGGGTGGCACTCATCTCAGATGACGGAATGAGGAAATATCATT
CAGACTCCATGTGGGGCCGAGTCACCATCTCCAGAGACAATTCCAAG
AACACTCTTTATCTGCAATTCAGCAGCCTGAGAGTCGAAGACACGGC
TATGTTCTTCTGTGCGAGAGGCCGGTGGGCCAATCTGGCATGACG
ACGTCAAATATTACGATTTTAATGACGGCTACTACAACTATCACTACA
TGGACGTCTGGGCAAGGGGACCAAGGTCACCGTCTCCTCAG**CGTCG
ACCAAGGGCCCATCGGTCTTCCCTCTGGCACCATCATCCAAGTCGACCTCT
GGGGGCACAGCGGCCCTGGGCTGCCTGGTCAAGGACTACTTCCCCGAACC
GGTGACGGTGTCGTGGAACTCAGGCGCCCTGACCAGCGGCGTGCACACCT

-continued
```
TCCCGGCTGTCCTACAGTCCTCAGGACTCTACTCCCTCAGCAGCGTGGTGA
CCGTGCCCTCCAGCAGCTTGGGCACCCAGACCTACATCTGCAACGTGAAT
CACAAGCCCAGCAACACCAAGGTGGACAAGAGAGTTGAGCCCAAATCTT
GTGACAAAACTCACACATGCCCACCGTGCCCAGCACCTGAACTCCTGGGG
GGACCGTCAGTCTTCCTCTTCCCCCCAAAACCCAAGGACACCCTCATGAT
CTCCCGGACCCCTGAGGTCACATGCGTGGTGGTGGACGTGAGCCACGAAG
ACCCTGAGGTCAAGTTCAACTGGTACGTGGACGGCGTGGAGGTGCATAAT
GCCAAGACAAAGCCGCGGGAGGAGCAGTACAACAGCACGTACCGTGTGG
TCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCAT
CTCCAAAGCCAAAGGGCAGCCCCGAGAACCACAGGTGTACACCCTGCCC
CCATCCCGGGAGGAGATGACCAAGAACCAGGTCAGCCTGACCTGCCTGGT
CAAAGGCTTCTATCCCAGCGACATCGCCGTGGAGTGGGAGAGCAATGGG
CAGCCGGAGAACAACTACAAGACCACGCCTCCCGTGCTGGACTCCGACG
GCTCCTTCTTCCTCTATAGCAAGCTCACCGTGGACAAGAGCAGGTGGCAG
CAGGGGAACGTCTTCTCATGCTCCGTGATGCATGAGGCTCTGCACAACCA
CTACACGCAGAAGAGCCTCTCCCTGTCTCCGGGTAAATGA
```

1456_A12 (PG16) (TCN-117) gamma heavy chain variable region nucleotide sequence:
(SEQ ID NO: 130)
```
CACGAACAACTGGTGGAGGCCGGGGGAGGCGTGGTCCAGCCGGGGGGT
CCCTGAGACTCTCCTGTTTAGCGTCTGGATTCACGTTTCACAAATATGGCA
TGCACTGGGTCCGCCAGGCTCCAGGCAAGGGCCTGGAGTGGGTGGCACTC
ATCTCAGATGACGGAATGAGGAAATATCATTCAGACTCCATGTGGGGCCG
AGTCACCATCTCCAGAGACAATTCCAAGAACACTCTTTATCTGCAATTCA
GCAGCCTGAGAGTCGAAGACACGGCTATGTTCTTCTGTGCGAGAGAGGCC
GGTGGGCCAATCTGGCATGACGACGTCAAATATTACGATTTTAATGACGG
CTACTACAACTATCACTACATGGACGTCTGGGGCAAGGGGACCAAGGTCA
CCGTCTCCTCA
```

1456_A12 (PG16)(TCN-117) gamma heavy chain amino acid sequence: expressed protein with variable region in bold.
(SEQ ID NO: 47)

HEQLVEAGGGVVQPGGSLRLSCLASGFTFHKYGMHWVRQAPGKGLEW
VALISDDGMRKYHSDSMWGRVTISRDNSKNTLYLQFSSLRVEDTAMFFC
AREAGGPIWHDDVKYYDFNDGYYNYHYMDVWGKGTKVTVSSASTKGPS
VFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCP
APELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHY
TQKSLSLSPGK

1456_A12 (PG16) (TCN-117) gamma heavy chain variable region amino acid sequence: (Kabat CDRs underlined, Chothia CDRs in bold italics)
(SEQ ID NO: 48)

HEQLVEAGGGVVQPGGSLRLSCLAS*GFTFHK*YGMHWVRQAPGKGLEWVA*L*
*ISDDGMRKY*HSDSMWGRVTISRDNSKNTLYLQFSSLRVEDTAMFFCAR*EAG*
*GPIWHDDVKYYD*FNDGYYNYHYMDVWGKGTKVTVSS

1456_A12 (PG16)(TCN-117) gamma heavy chain Kabat CDRs:
(SEQ ID NO: 88)
CDR 1: KYGMH (SEQ ID NO: 89)
CDR 2: LISDDGMRKYHSDSMWG (SEQ ID NO: 6)
CDR 3: EAGGPIWHDDVKYYDFNDGYYNYHYMDV 1456_A12 (PG16)(TCN-117) gamma heavy chain Chothia CDRs:
(SEQ ID NO: 266)
CDR 1: GFTFHK (SEQ ID NO: 267)
CDR 2: LISDDGMRKY (SEQ ID NO: 6)
CDR 3: EAGGPIWHDDVKYYDFNDGYYNYHYMDV 1456_A12 (PG16)(TCN-117) lambda light chain nucleotide sequence: 1456_A12 λ2 coding sequence (variable region in bold)
(SEQ ID NO: 49)
ATGGCCTGGGCTTGCTATTCCTCACCCTCTTCACTCAGGGCACAGGGTCCT
GGGGCCCAGTCTGCCCTGACTCAGCCTGCCTCCGTGTCTGGGTCTCCT
GGACAGACGATCACCATCTCCTGCAATGGAACCAGCCGTGACGTTGG
TGGATTTGACTCTGTCCTGGTATCAACAATCCCCAGGGAAAGCCC
CCAAAGTCTATGGTTTTTGATGTCAGTCATCGGCCCTCAGGTATGTCTA
ATCGCTTCTCTGGCTCCAAGTCCGGCAACACGGCCTCCCTGACCATT

-continued

TCTGGGCTCCACATTGAGGACGAGGGCGATTATTTCTGCTCTTCATT
GACAGACAGAAGCCATCGCATATTCGGCGGCGGGACCAAGCTGACC
GTTCTAGGTCAGCCCAAGGCTGCCCCTCGGTCACTCTGTTCCCGCCCTC
CTCTGAGGAGCTTCAAGCCAACAAGGCCACACTGGTGTGTCTCATAAGTG
ACTTCTACCCGGGAGCCGTGACAGTGGCCTGGAAGGCAGATAGCAGCCCC
GTCAAGGCGGGAGTGGAGACCACCACACCCTCCAAACAAAGCAACAACA
AGTACGCGGCCAGCAGCTACCTGAGCCTGACGCCTGAGCAGTGGAAGTCC
CACAAAAGCTACAGCTGCCAGGTCACGCATGAAGGGAGCACCGTGGAGA
AGACAGTGGCCCCTACAGAATGTTCATAG

1456_A12 (PG16)(TCN-117) lambda light chain variable region nucleotide sequence:
(SEQ ID NO: 131)

CAGTCTGCCCTGACTCAGCCTGCCTCCGTGTCTGGGTCTCCTGGACAGACG
ATCACCATCTCCTGCAATGGAACCAGCCGTGACGTTGGTGGATTTGACTCT
GTCTCCTGGTATCAACAATCCCCAGGGAAAGCCCCCAAAGTCATGGTTTT
TGATGTCAGTCATCGGCCCTCAGGTATGTCTAATCGCTTCTCTGGCTCCAA
GTCCGGCAACACGGCCTCCCTGACCATTTCTGGGCTCCACATTGAGGACG
AGGGCGATTATTTCTGCTCTTCATTGACAGACAGAAGCCATCGCATATTCG
GCGGCGGGACCAAGCTGACCGTTCTA

1456_A12 (PG16)(TCN-117) lambda light chain amino acid sequence: expressed
protein with variable region in bold.
(SEQ ID NO: 50)

**QSALTQPASVSGSPGQTITISCNGTSRDVGGFDSVSWYQQSPGKAPKVMV
FDVSHRPSGMSNRFSGSKSGNTASLTISGLHIEDEGDYFCSSLTDRSHRIF
GGGTKLTVL**GQPKAAPSVTLFPPSSEELQANKATLVCLISDFYPGAVTVAW
KADSSPVKAGVETTTPSKQSNNKYAASSYLSLTPEQWKSHKSYSCQVTHEGS
TVEKTVAPTECS

1456_A12 (PG16) (TCN-117) lambda light chain variable region amino acid
sequence: (Kabat CDRs underlined, Chothia CDRs in bold italics)
(SEQ ID NO: 51)

QSALTQPASVSGSPGQTITISC*NGTSRDVGGFDSVS*WYQQSPGKAPKVMVF***D
VSHRPS*GMSNRFSGSKSGNTASLTISGLHIEDEGDYFC*SSLTDRSHRI***FGGGTK
LTVL

1456_A12 (PG16)(TCN-117) lambda light chain Kabat CDRs:
(SEQ ID NO: 93)
CDR 1: NGTSRDVGGFDSVS (SEQ ID NO: 95)
CDR 2: DVSHRPS (SEQ ID NO: 41)
CDR 3: SSLTDRSHRI 1456_A12 (PG16)(TCN-117) lambda light chain Chothia CDRs:
(SEQ ID NO: 93)
CDR 1: NGTSRDVGGFDSVS (SEQ ID NO: 95)
CDR 2: DVSHRPS (SEQ ID NO: 41)
CDR 3: SSLTDRSHRI 1503_H05 (PG16)(TCN-119) gamma heavy chain nucleotide sequence: 1503_H05 γ3
coding sequence (variable region in bold)
(SEQ ID NO: 52)

ATGGAGTTTGGCTGAGCTGGGTTTTCCTCGCAACTCTGTTAAGAGTTGTGA
AGTGTC**AGGAAAAACTGGTGGAGTCTGGGGGAGGCGTGGTCCAGCCG
GGGGGGTCCCTGAGACTCTCCTGTTTAGCGTCTGGATTCACCTTTCA
CAAATATGGCATGCACTGGGTCCGCCAGGCTCCAGGCAAGGGCCTGG
AGTGGGTGGCACTCATCTCAGATGACGGAATGAGGAAATATCATTCA
GACTCCATGTGGGGCCGAGTCACCATCTCCAGAGACAATTCCAAGAA
CACTTTATATCTGCAATTCAGCAGCCTGAAAGTCGAAGCACGGCTA
TGTTCTTCTGTGCGAGAGAGGCTGGTGGGCCAATCTGGCATGACGAC
GTCAAATATTACGATTTTAATGACGGCTACTACAATTACCACTACATG
GACGTCTGGGGCAAGGGGACCATTGTCACCGTCTCCTCA**GCGTCGAC
CAAGGGCCCATCGGTCTTCCCTCTGGCACCATCATCAAGTCGACCTCTG
GGGGCACAGCGGCCCTGGGCTGCCTGGTCAAGGACTACTTCCCCGAACCG
GTGACGGTGTCGTGGAACTCAGGCGCCCTGACCAGCGGCGTGCACACCTT
CCCGGCTGTCCTACAGTCCTCAGGACTCTACTCCCTCAGCAGCGTGGTGA
CCGTGCCCTCCAGCAGCTTGGGCACCCAGACCTACATCTGCAACGTGAAT
CACAAGCCCAGCAACACCAAGGTGGACAAGAGAGTTGAGCCCAAATCTT
GTGACAAAACTCACACATGCCCACCGTGCCCAGCACCTGAACTCCTGGGG
GGACCGTCAGTCTTCCTCTTCCCCCCAAAACCCAAGGACACCCTCATGAT
CTCCCGGACCCCTGAGGTCACATGCGTGGTGGTGGACGTGAGCCACGAAG
ACCCTGAGGTCAAGTTCAACTGGTACGTGGACGGCGTGGAGGTGCATAAT
GCCAAGACAAAGCCGCGGGAGGAGCAGTACAACAGCACGTACCGTGTGG
TCAGCGTCCTCACCGTCCTGCACCAGGACTGGCTGAATGGCAAGGAGTAC

-continued
```
AAGTGCAAGGTCTCCAACAAAGCCCTCCCAGCCCCCATCGAGAAAACCAT
CTCCAAAGCCAAAGGGCAGCCCCGAGAACCACAGGTGTACACCCTGCCC
CCATCCCGGGAGGAGATGACCAAGAACCAGGTCAGCCTGACCTGCCTGGT
CAAAGGCTTCTATCCCAGCGACATCGCCGTGGAGTGGGAGAGCAATGGG
CAGCCGGAGAACAACTACAAGACCACGCCTCCCGTGCTGGACTCCGACG
GCTCCTTCTTCCTCTATAGCAAGCTCACCGTGGACAAGAGCAGGTGGCAG
CAGGGGAACGTCTTCTCATGCTCCGTGATGCATGAGGCTCTGCACAACCA
CTACACGCAGAAGAGCCTCTCCCTGTCTCCGGGTAAATGA
```

1503_H05 (PG16) (TCN-119) gamma heavy chain variable region nucleotide sequence:

(SEQ ID NO: 132)
```
CAGGAAAAACTGGTGGAGTCTGGGGGAGGCGTGGTCCAGCCGGGGGGT
CCCTGAGACTCTCCTGTTTAGCGTCTGGATTCACCTTTCACAAATATGGCA
TGCACTGGGTCCGCCAGGCTCCAGGCAAGGGCCTGGAGTGGGTGGCACTC
ATCTCAGATGACGGAATGAGGAAATATCATTCAGACTCCATGTGGGGCCG
AGTCACCATCTCCAGAGACAATTCCAAGAACACTTTATATCTGCAATTCA
GCAGCCTGAAAGTCGAAGACACGGCTATGTTCTTCTGTGCGAGAGAGGCT
GGTGGGCCAATCTGGCATGACGACGTCAAATATTACGATTTTAATGACGG
CTACTACAATTACCACTACATGGACGTCTGGGGCAAGGGGACCATTGTCA
CCGTCTCCTCA
```

1503_H05 (PG16)(TCN-119) gamma heavy chain amino acid sequence: expressed protein with variable region in bold.

(SEQ ID NO: 53)

QEKLVESGGGVVQPGGSLRLSCLASGFTFHKYGMHWVRQAPGKGLEW
VALISDDGMRKYHSDSMWGRVTISRDNSKNTLYLQFSSLKVEDTAMFFC
AREAGGPIWHDDVKYYDENDGYYNYHYMDVWGKGTIVTVSSASTKGPS
VFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCP
APELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHY
TQKSLSLSPGK.

1503_H05 (PG16) (TCN-119) gamma heavy chain variable region amino acid sequence: (Kabat CDRs underlined, Chothia CDRs in bold italics)

(SEQ ID NO: 54)

QEKLVESGGGVVQPGGSLRLSCLAS*GFTFHK*YGMHWVRQAPGKGLEWVA<u>L</u>
<u>*ISDDGMRKY*</u>HSDSMWGRVTISRDNSKNTLYLQFSSLKVEDTAMFFCAR*EAG*
*GPIWHDDVKYYDFNDGYYNYHYMDV*WGKGTIVTVSS

1503_H05 (PG16)(TCN-119) gamma heavy chain Kabat CDRs:

(SEQ ID NO: 88)
CDR 1: KYGMH (SEQ ID NO: 89)
CDR 2: LISDDGMRKYHSDSMWG (SEQ ID NO: 6)
CDR 3: EAGGPIWHDDVKYYDFNDGYYNYHYMDV

1503_H05 (PG16)(TCN-119) gamma heavy chain Chothia CDRs:

(SEQ ID NO: 266)
CDR 1: GFTFHK (SEQ ID NO: 267)
CDR 2: LISDDGMRKY (SEQ ID NO: 6)
CDR 3: EAGGPIWHDDVKYYDFNDGYYNYHYMDV

1503_H05 (PG16)(TCN-119) lambda light chain nucleotide sequence: 1503_H05 λ2 coding sequence (variable region in bold)

(SEQ ID NO: 55)
```
ATGGCCTGGGCTTGCTATTCCTCACCCTCTTCACTCAGGGCACAGGGTCCT
GGGGCCAGTCTGCCCTGACTCAGCCTGCCTCCGTGTCTGGGTCTCCT
GGACAGACGATCACCATCTCCTGCAATGGAACCAGAAGTGACGTTGG
TGGATTTGACTCTGTCTCCTGGTACCAACAATCCCCAGGGAAAGCCC
CCAAAGTCATGGTTTTTGATGTCAGTCATCGGCCCTCAGGTATCTCTA
ATCGCTTCTCTGGCTCCAAGTCCGGCAACACGGCCTCCCTGACCATC
TCTGGGCTCCACATTGAGGACGAGGGCGATTATTTCTGCTCTTCACT
GACAGACAGAAGCCATCGCATATTCGGCGGCGGGACCAAGGTGACC
GTTCTA
```
GGTCAGCCCAAGGCTGCCCCCTCGGTCACTCTGTTCCCGCCCTC
CTCTGAGGAGCTTCAAGCCAACAAGGCCACACTGGTGTGTCTCATAAGTG
ACTTCTACCCGGGAGCCGTGACAGTGGCCTGGAAGGCAGATAGCAGCCCC
GTCAAGGCGGGAGTGGAGACCACCACACCCTCCAAACAAAGCAACAACA
AGTACGCGGCCAGCAGCTACCTGAGCCTGACGCCTGAGCAGTGGAAGTCC
CACAAAAGCTACAGCTGCCAGGTCACGCATGAAGGGAGCACCGTGGAGA
AGACAGTGGCCCCTACAGAATGTTCATAG

-continued

1503_H05 (PG16)(TCN-119) lambda light chain variable region nucleotide sequence:
(SEQ ID NO: 133)
```
CAGTCTGCCCTGACTCAGCCTGCCTCCGTGTCTGGGTCTCCTGGACAGACG
ATCACCATCTCCTGCAATGGAACCAGAAGTGACGTTGGTGGATTTGACTC
TGTCTCCTGGTACCAACAATCCCCAGGGAAAGCCCCCAAAGTCATGGTTT
TTGATGTCAGTCATCGGCCCTCAGGTATCTCTAATCGCTTCTCTGGCTCCA
AGTCCGGCAACACGGCCTCCCTGACCATCTCTGGGCTCCACATTGAGGAC
GAGGGCGATTATTTCTGCTCTTCACTGACAGACAGAAGCCATCGCATATT
CGGCGGCGGGACCAAGGTGACCGTTCTA
```

1503_H05 (PG16) (TCN-119) lambda light chain amino acid sequence: expressed protein with variable region in bold.
(SEQ ID NO: 56)
QSALTQPASVSGSPGQTITISCNGTRSDVGGFDSVSWYQQSPGKAPKVMV
FDVSHRPSGISNRFSGSKSGNTASLTISGLHIEDEGDYFCSSLTDRSHRIFG
GGTKVTVLGQPKAAPSVTLFPPSSEELQANKATLVCLISDFYPGAVTVAWK
ADSSPVKAGVETTTPSKQSNNKYAASSYLSLTPEQWKSHKSYSCQVTHEGST
VEKTVAPTECS 1503_H05 (PG16)(TCN-119) lambda light chain variable region amino acid sequence:
(Kabat CDRs underlined, Chothia CDRs in bold italics)
(SEQ ID NO: 57)
QSALTQPASVSGSPGQTITISC*NGTRSDVGGFDSVS*WYQQSPGKAPKVMVF<u>D</u>
<u>VSHRPS</u>GISNRFSGSKSGNTASLTISGLHIEDEGDYFC*SSLTDRSHRI*FGGGTK
VTVL 1503_H05 (PG16)(TCN-119) lambda light chain Kabat CDRs:
(SEQ ID NO: 92)
CDR 1: NGTRSDVGGFDSVS (SEQ ID NO: 95)
CDR 2: DVSHRPS (SEQ ID NO: 41)
CDR 3: SSLTDRSHRI 1503_H05 (PG16)(TCN-119) lambda light chain Chothia CDRs:
(SEQ ID NO: 92)
CDR 1: NGTRSDVGGFDSVS (SEQ ID NO: 95)
CDR 2: DVSHRPS (SEQ ID NO: 41)
CDR 3: SSLTDRSHRI 1489_I13 (PG16)(TCN-120) gamma heavy chain nucleotide sequence: 1489_I13 γ3 coding sequence (variable region in bold)
(SEQ ID NO: 58)
```
ATGGAGTTTGGGCTGAGCTGGGTTTTCCTCGCAACTCTGTTAAGAGTTGTG
AAGTGTCAGGAACAACTGTTGGAGTCTGGGGGAGGCGTGGTCCAGCC
GGGGGGGTCCCTGAGACTCTCCTGTTTAGCGTCTGGATTCACGTTTC
ACAAATATGGCATGCACTGGGTCCGCCAGGCTCCAGGCAAGGGCCTG
GAGTGGGTGGCACTCATCTCAGATGACGGAATGAGGAAATATCATTC
AAACTCCATGTGGGGCCGAGTCACCATCTCCAGAGACAATTCCAAGA
ACACTCTTTATCTGCAATTCAGCAGCCTGAAAGTCGAAGACACGGCT
ATGTTCTTCTGTGCGAGAGAGGCTGGTGGGCCAATCTGGCATGACGA
CGTCAAATATTACGATTTTAATGACGGCTACTACAACTACCACTACAT
GGACGTCTGGGGCAAGGGGACCACGGTCACCGTCTCCTCAGCGTCGA
CCAAGGGCCCATCGGTCTTCCCTCTGGCACCATCATCCAAGTCGACCTCTG
GGGGCACAGCGGCCCTGGGCTGCCTGGTCAAGGACTACTTCCCCGAACCG
GTGACGGTGTCGTGGAACTCAGGCGCCCTGACCAGCGGCGTGCACACCTT
CCCGGCTGTCCTACAGTCCTCAGGACTCTACTCCCTCAGCAGCGTGGTGA
CCGTGCCCTCCAGCAGCTTGGGCACCCAGACCTACATCTGCAACGTGAAT
CACAAGCCCAGCAACACCAAGGTGGACAAGAGAGTTGAGCCCAAATCTT
GTGACAAAACTCACACATGCCCACCGTGCCCAGCACCTGAACTCCTGGGG
GGACCGTCAGTCTTCCTCTTCCCCCCAAAACCCAAGGACACCCTCATGAT
CTCCCGGACCCCTGAGGTCACATGCGTGGTGGTGGACGTGAGCCACGAAG
ACCCTGAGGTCAAGTTCAACTGGTACGTGGACGGCGTGGAGGTGCATAAT
GCCAAGACAAAGCCGCGGGAGGAGCAGTACAACAGCACGTACCGTGTGG
TCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCAT
CTCCAAAGCCAAAGGGCAGCCCCGAGAACCACAGGTGTACACCCTGCCC
CCATCCCGGGAGGAGATGACCAAGAACCAGGTCAGCCTGACCTGCCTGGT
CAAAGGCTTCTATCCCAGCGACATCGCCGTGGAGTGGGAGAGCAATGGG
CAGCCGGAGAACAACTACAAGACCACGCCTCCCGTGCTGGACTCCGACG
GCTCCTTCTTCCTCTATAGCAAGCTCACCGTGGACAAGAGCAGGTGGCAG
CAGGGGAACGTCTTCTCATGCTCCGTGATGCATGAGGCTCTGCACAACCA
CTACACGCAGAAGAGCCTCTCCCTGTCTCCGGGTAAATGA
```

-continued

1489_I13 (PG16)(TCN-120) gamma heavy chain variable region nucleotide sequence:
(SEQ ID NO: 134)
```
CAGGAACAACTGTTGGAGTCTGGGGGAGGCGTGGTCCAGCCGGGGGGT
CCCTGAGACTCTCCTGTTTAGCGTCTGGATTCACGTTTCACAAATATGGCA
TGCACTGGGTCCGCCAGGCTCCAGGCAAGGGCCTGGAGTGGGTGGCACTC
ATCTCAGATGACGGAATGAGGAAATATCATTCAAACTCCATGTGGGGCCG
AGTCACCATCTCCAGAGACAATTCCAAGAACACTCTTTATCTGCAATTCA
GCAGCCTGAAAGTCGAAGACACGGCTATGTTCTTCTGTGCGAGAGAGGCT
GGTGGGCCAATCTGGCATGACGACGTCAAATATTACGATTTTAATGACGG
CTACTACAACTACCACTACATGGACGTCTGGGGCAAGGGGACCACGGTCA
CCGTCTCCTCA
```

1489_I13 (PG16) (TCN-120) gamma heavy chain amino acid sequence: expressed
protein with variable region in bold.
(SEQ ID NO: 59)
QEQLLESGGGVVQPGGSLRLSCLASGFTFHKYGMHWVRQAPGKGLEW
VALISDDGMRKYHSNSMWGRVTISRDNSKNTLYLQFSSLKVEDTAMFFC
AREAGGPIWHDDVKYYDFNDGYYNYHYMDVWGKGTTVTVSSASTKGPS
VFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCP
APELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHY
TQKSLSLSPGK 1489_I13 (PG16) (TCN-120) gamma heavy chain variable region amino acid
sequence: (Kabat CDRs underlined, Chothia CDRs in bold italics)
(SEQ ID NO: 60)
QEQLLESGGGVVQPGGSLRLSCLAS*GFTFHK*YGMHWVRQAPGKGLEWVA<u>L
ISDDGMRKY</u>HSNSMWGRVTISRDNSKNTLYLQFSSLKVEDTAMFFCAR<u>**EAG
GPIWHDDVKYYDFNDGYYNYHYMDV**</u>WGKGTTVTVSS 1489_I13 (PG16)(TCN-120) gamma heavy chain Kabat CDRs:
(SEQ ID NO: 88)
CDR 1: KYGMH (SEQ ID NO: 98)
CDR 2: LISDDGMRKYHSNSMWG (SEQ ID NO: 6)
CDR 3: EAGGPIWHDDVKYYDFNDGYYNYHYMDV 1489_I13 (PG16)(TCN-120) gamma heavy chain Chothia CDRs:
(SEQ ID NO: 266)
CDR 1: GFTFHK (SEQ ID NO: 267)
CDR 2: LISDDGMRKY (SEQ ID NO: 6)
CDR 3: EAGGPIWHDDVKYYDFNDGYYNYHYMDV 1489_I13 (PG16)(TCN-120) lambda light chain nucleotide sequence: 1489_113 λ2
coding sequence (variable region in bold)
(SEQ ID NO: 61)
```
ATGGCCTGGGCTCTGCTATTCCTCACCCTCTTCACTCAGGGCACAGGGTCC
CGGGGCCAGTCTGCCCTGACTCAGCCTGCCTCCGTGTCTGGGTCTCCT
GGACAGACGATCACCATCTCCTGCAATGGAACCAGCAGTGACGTTGG
TGGATTTGACTCTGTCTCCTGGTATCAACAATCCCCAGGGAAAGCCC
CCAAAGTCATGGTTTTTGATGTCAGTCATCGGCCCTCAGGTATCTCTA
ATCGCTTCTCTGGCTCCAAGTCCGGCAACACGGCCTCCCTGACCATC
TCTGGGCTCCACATTGAGGACGAGGGCGATTATTTCTGCTCTTCACT
GACAGACAGAAGCCATCGCATATTCGGCGGCGGGACCAAGGTGACC
GTTCTAGGTCAGCCCAAGGCTGCCCCCTCGGTCACTCTGTTCCCGCCCTC
CTCTGAGGAGCTTCAAGCCAACAAGGCCACACTGGTGTGTCTCATAAGTG
ACTTCTACCCGGGAGCCGTGACAGTGGCCTGGAAGGCAGATAGCAGCCCC
GTCAAGGCGGGAGTGGAGACCACCACACCCTCCAAACAAAGCAACAACA
AGTACGCGGCCAGCAGCTACCTGAGCCTGACGCCTGAGCAGTGGAAGTCC
CACAAAAGCTACAGCTGCCAGGTCACGCATGAAGGGAGCACCGTGGAGA
AGACAGTGGCCCCTACAGAATGTTCATAG
```

1489_I13 (PG16) (TCN-120) lambda light chain variable region nucleotide sequence:
(SEQ ID NO: 135)
```
CAGTCTGCCCTGACTCAGCCTGCCTCCGTGTCTGGGTCTCCTGGACAGACG
ATCACCATCTCCTGCAATGGAACCAGCAGTGACGTTGGTGGATTTGACTC
TGTCTCCTGGTATCAACAATCCCCAGGGAAAGCCCCCAAAGTCATGGTTT
TTGATGTCAGTCATCGGCCCTCAGGTATCTCTAATCGCTTCTCTGGCTCCA
AGTCCGGCAACACGGCCTCCCTGACCATCTCTGGGCTCCACATTGAGGAC
GAGGGCGATTATTTCTGCTCTTCACTGACAGACAGAAGCCATCGCATATT
CGGCGGCGGGACCAAGGTGACCGTTCTA
```

-continued

1489_I13 (PG16) (TCN-120) lambda light chain amino acid sequence: expressed
protein with variable region in bold.

(SEQ ID NO: 14)

QSALTQPASVSGSPGQTITISCNGTSSDVGGFDSVSWYQQSPGKAPKVMV
FDVSHRPSGISNRFSGSKSGNTASLTISGLHIEDEGDYFCSSLTDRSHRIFG
GGTKVTVLGQPKAAPSVTLFPPSSEELQANKATLVCLISDFYPGAVTVAWK
ADSSPVKAGVETTTPSKQSNNKYAASSYLSLTPEQWKSHKSYSCQVTHEGST
VEKTVAPTECS

1489_I13 (PG16)(TCN-120) lambda light chain variable region amino acid sequence:
(Kabat CDRs underlined, Chothia CDRs in bold italics).

(SEQ ID NO: 32)

QSALTQPASVSGSPGQTITISC*NGTSSDVGGFDSVS*WYQQSPGKAPKVMVF*D*
*VSHRPS*GISNRFSGSKSGNTASLTISGLHIEDEGDYFC*SSLTDRSHRI*FGGGTK
VTVL

1489_I13 (PG16)(TCN-120) lambda light chain Kabat CDRs:

(SEQ ID NO: 97)

CDR 1: NGTSSDVGGFDSVS (SEQ ID NO: 95)

CDR 2: DVSHRPS (SEQ ID NO: 41)

CDR 3: SSLTDRSHRI

1489_I13 (PG16)(TCN-120) lambda light chain Chothia CDRs:

(SEQ ID NO: 97)

CDR 1: NGTSSDVGGFDSVS (SEQ ID NO: 95)

CDR 2: DVSHRPS (SEQ ID NO: 41)

CDR 3: SSLTDRSHRI

1480_I08 gamma heavy chain nucleotide sequence: 1480_I08 γ3 coding sequence
(variable region in bold)

(SEQ ID NO: 64)

ATGGAGTTTGGCTGAGCTGGGTTTTCCTCGCAACTCTGTTAAGAGTTGTGA
AGTGTCAGGAACAACTGGTGGAGTCTGGGGGAGGCGTGGTCCAGCCG
GGGGGGTCCCTGAGACTCTCCTGTTTAGCGTCTGGATTCACGTTTCA
CAAATATGGCATGCACTGGGTCCGCCAGGCTCCAGGCAAGGGCCTGG
AGTGGGTGGCACTCATCTCAGATGACGGAATGAGGAAATATCATTCA
GACTCCATGTGGGGCCGAGTCACCATCTCCAGAGACAATTCCAAGAA
CACTCTTTATCTGCAATTCAGCAGCCTGAAAGTCGAAGACACGGCTA
TGTTCTTCTGTGCGAGAGAGGCTGGTGGGCCAATCTGGCATGACGAC
GTCAAATATTACGATTTTAATGACGGCTACTACAACTACCACTACATG
GACGTCTGGGGCAAGGGGACCACGGTCACCGTCTCCTCAGCGTCGAC
CAAGGGCCCATCGGTCTTCCCTCTGGCACCATCATCCAAGTCGACCTCTG
GGGGCACAGCGGCCCTGGGCTGCCTGGTCAAGGACTACTTCCCCGAACCG
GTGACGGTGTCGTGGAACTCAGGCGCCCTGACCAGCGGCGTGCACACCTT
CCCGGCTGTCCTACAGTCCTCAGGACTCTACTCCCTCAGCAGCGTGGTGA
CCGTGCCCTCCAGCAGCTTGGGCACCCAGACCTACATCTGCAACGTGAAT
CACAAGCCCAGCAACACCAAGGTGGACAAGAGAGTTGAGCCCAAATCTT
GTGACAAAACTCACACATGCCCACCGTGCCCAGCACCTGAACTCCTGGGG
GGACCGTCAGTCTTCCTCTTCCCCCCAAAACCCAAGGACACCCTCATGAT
CTCCCGGACCCCTGAGGTCACATGCGTGGTGGTGGACGTGAGCCACGAAG
ACCCTGAGGTCAAGTTCAACTGGTACGTGGACGGCGTGGAGGTGCATAAT
GCCAAGACAAAGCCGCGGGAGGAGCAGTACAACAGCACGTACCGTGTGG
TCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCAT
CTCCAAAGCCAAAGGGCAGCCCCGAGAACCACAGGTGTACACCCTGCCC
CCATCCCGGGAGGAGATGACCAAGAACCAGGTCAGCCTGACCTGCCTGGT
CAAAGGCTTCTATCCCAGCGACATCGCCGTGGAGTGGGAGAGCAATGGG
CAGCCGGAGAACAACTACAAGACCACGCCTCCCGTGCTGGACTCCGACGG
GCTCCTTCTTCCTCTATAGCAAGCTCACCGTGGACAAGAGCAGGTGGCAG
CAGGGGAACGTCTTCTCATGCTCCGTGATGCATGAGGCTCTGCACAACCA
CTACACGCAGAAGAGCCTCTCCCTGTCTCCGGGTAAATGA

1480_I08 gamma heavy chain variable region nucleotide sequence:

(SEQ ID NO: 136)

CAGGAACAACTGGTGGAGTCTGGGGGAGGCGTGGTCCAGCCGGGGGGT
CCCTGAGACTCTCCTGTTTAGCGTCTGGATTCACGTTTCACAAATATGGCA
TGCACTGGGTCCGCCAGGCTCCAGGCAAGGGCCTGGAGTGGGTGGCACTC
ATCTCAGATGACGGAATGAGGAAATATCATTCAGACTCCATGTGGGGCCG
AGTCACCATCTCCAGAGACAATTCCAAGAACACTCTTTATCTGCAATTCA
GCAGCCTGAAAGTCGAAGACACGGCTATGTTCTTCTGTGCGAGAGAGGCT

-continued
```
GGTGGGCCAATCTGGCATGACGACGTCAAATATTACGATTTTAATGACGG
CTACTACAACTACCACTACATGGACGTCTGGGGCAAGGGGACCACGGTCA
CCGTCTCCTCA
```

1480_I08 gamma heavy chain amino acid sequence: expressed protein with variable
region in bold.

(SEQ ID NO: 65)

QEQLVESGGGVVQPGGSLRLSCLASGFTFHKYGMHWVRQAPGKGLEW
VALISDDGMRKYHSDSMWGRVTISRDNSKNTLYLQFSSLKVEDTAMFFC
AREAGGPIWHDDVKYYDFNDGYYNYHYMDVWGKGTTVTVSSASTKGPS
VFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCP
APELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHY
TQKSLSLSPGK

1480_I08 gamma heavy chain variable region amino acid sequence: (Kabat CDRs
underlined, Chothia CDRs in bold italics)

(SEQ ID NO: 31)

QEQLVESGGGVVQPGGSLRLSCLAS*GFTFHK*YGMHWVRQAPGKGLEWVA*L*
*ISDDGMRKY*HSDSMWGRVTISRDNSKNTLYLQFSSLKVEDTAMFFCAR*EAG*
*GPIWHDDVKYYDFNDGYYNYHYMDV*WGKGTTVTVSS

1480_I08 gamma heavy chain Kabat CDRs:

(SEQ ID NO: 88)

CDR 1: KYGMH (SEQ ID NO: 89)

CDR 2: LISDDGMRKYHSDSMWG (SEQ ID NO: 6)

CDR 3: EAGGPIWHDDVKYYDFNDGYYNYHYMDV

1480_I08 gamma heavy chain Chothia CDRs:

(SEQ ID NO: 266)

CDR 1: GFTFHK (SEQ ID NO: 267)

CDR 2: LISDDGMRKY (SEQ ID NO: 6)

CDR 3: EAGGPIWHDDVKYYDFNDGYYNYHYMDV

1480_I08 lambda light chain nucleotide sequence: 1480_108 λ2 coding sequence
(variable region in bold)

(SEQ ID NO: 67)

ATGGCCTGGGCTCTGCTATTCGTCACCCTCCTCACTCAGGGCACAGGGTCC
TGGGGCCAGTCTGCCCTGACTCAGCCTGCCTCCGTGTCTGGGTCTCCT
GGACAGACGATCACCATCTCCTGCAATGGAACCAGCAGTGACGTTGG
TGGATTTGACTCTGTCTCCTGGTATCAACAATCCCCAGGGAAAGCCC
CCAAAGTCATGGTTTTTGATGTCAGTCATCGGCCCTCAGGTATCTCTA
ATCGCTTCTCTGGCTCCAAGTCCGGCAACACGGCCTCCCTGACCATC
TCTGGGCTCCACATTGAGGACGAGGGCGATTATTTCTGCTCTTCACT
GACAGACAGAAGCCATCGCATATTCGGCGGCGGGACCAAGGTGACC
GTTCTAGGTCAGCCCAAGGCTGCCCCCTCGGTCACTCTGTTCCCGCCCTC
CTCTGAGGAGCTTCAAGCCAACAAGGCCACACTGGTGTGTCTCATAAGTG
ACTTCTACCCGGGAGCCGTGACAGTGGCCTGGAAGGCAGATAGCAGCCCC
GTCAAGGCGGGAGTGGAGACCACCACACCCTCCAAACAAAGCAACAACA
AGTACGCGGCCAGCAGCTACCTGAGCCTGACGCCTGAGCAGTGGAAGTCC
CACAAAAGCTACAGCTGCCAGGTCACGCATGAAGGGAGCACCGTGGAGA
AGACAGTGGCCCCTACAGAATGTTCATAG

1480_I08 lambda light chain variable region nucleotide sequence:

(SEQ ID NO: 137)

CAGTCTGCCCTGACTCAGCCTGCCTCCGTGTCTGGGTCTCCTGGACAGACG
ATCACCATCTCCTGCAATGGAACCAGCAGTGACGTTGGTGGATTTGACTC
TGTCTCCTGGTATCAACAATCCCCAGGGAAAGCCCCCAAAGTCATGGTTT
TTGATGTCAGTCATCGGCCCTCAGGTATCTCTAATCGCTTCTCTGGCTCCA
AGTCCGGCAACACGGCCTCCCTGACCATCTCTGGGCTCCACATTGAGGAC
GAGGGCGATTATTTCTGCTCTTCACTGACAGACAGAAGCCATCGCATATT
CGGCGGCGGGACCAAGGTGACCGTTCTA

1480_I08 lambda light chain amino acid sequence: expressed protein with variable
region in bold.

(SEQ ID NO: 14)

QSALTQPASVSGSPGQTITISCNGTSSDVGGFDSVSWYQQSPGKAPKVMV
FDVSHRPSGISNRFSGSKSGNTASLTISGLHIEDEGDYFCSSLTDRSHRIFG
GGTKVTVLGQPKAAPSVTLFPPSSEELQANKATLVCLISDFYPGAVTVAWK

```
                                            -continued
ADSSPVKAGVETTTPSKQSNNKYAASSYLSLTPEQWKSHKSYSCQVTHEGST
VEKTVAPTECS 1480_I08 lambda light chain variable region amino acid sequence: (Kabat CDRs
underlined, Chothia CDRs in bold italics)
                                                                  (SEQ ID NO: 32)
QSALTQPASVSGSPGQTITISCNGTSSDVGGFDSVSWYQQSPGKAPKVMVFD
VSHRPSGISNRFSGSKSGNTASLTISGLHIEDEGDYFCSSLTDRSHRIFGGGTK
VTVL 1480_I08 lambda light chain Kabat CDRs:
                                                                  (SEQ ID NO: 97)
CDR 1: NGTSSDVGGFDSVS (SEQ ID NO: 95)
CDR 2: DVSHRPS (SEQ ID NO: 41)
CDR 3: SSLTDRSHRI 1480_I08 lambda light chain Chothia CDRs:
                                                                  (SEQ ID NO: 97)
CDR 1: NGTSSDVGGFDSVS (SEQ ID NO: 95)
CDR 2: DVSHRPS (SEQ ID NO: 41)
CDR 3: SSLTDRSHRI
```

The 1469_M23 (PG16) antibody includes a heavy chain variable region (SEQ ID NO: 139), encoded by the nucleic acid sequence shown in SEQ ID NO: 128, and a light chain variable region (SEQ ID NO: 142) encoded by the nucleic acid sequence shown in SEQ ID NO: 129.

The heavy chain CDRs of the 1469_M23 (PG16) antibody have the following sequences per Kabat and Chothia definitions: KYGMH (SEQ ID NO: 88), LIS-DDGMRKYHSDSMWG (SEQ ID NO: 89), and EAGG-PIWHDDVKYYDFNDGYYNYHYMDV (SEQ ID NO: 6). The light chain CDRs of the 1469 M23 (PG16) antibody have the following sequences per Kabat and Chothia definitions: NGTRSDVGGFDSVS (SEQ ID NO: 92), DVSHRPS (SEQ ID NO: 95), and SSLTDRSHRI (SEQ ID NO: 41).

The 1456_A12 (PG16) antibody includes a heavy chain variable region (SEQ ID NO: 47), encoded by the nucleic acid sequence shown in SEQ ID NO: 130, and a light chain variable region (SEQ ID NO: 50) encoded by the nucleic acid sequence shown in SEQ ID NO: 131.

The heavy chain CDRs of the 1456_A12 (PG16) antibody have the following sequences per Kabat and Chothia definitions: KYGMH (SEQ ID NO: 88), LIS-DDGMRKYHSDSMWG (SEQ ID NO: 89), and EAGG-PIWHDDVKYYDFNDGYYNYHYMDV (SEQ ID NO: 6). The light chain CDRs of the 1456 A12 (PG16) antibody have the following sequences per Kabat and Chothia definitions: NGTSRDVGGFDSVS (SEQ ID NO: 93), DVSHRPS (SEQ ID NO: 95), and SSLTDRSHRI (SEQ ID NO: 41).

The 1503_H05 (PG16) antibody includes a heavy chain variable region (SEQ ID NO: 53), encoded by the nucleic acid sequence shown in SEQ ID NO: 132, and a light chain variable region (SEQ ID NO: 56) encoded by the nucleic acid sequence shown in SEQ ID NO: 133.

The heavy chain CDRs of the 1503_H05 (PG16) antibody have the following sequences per Kabat and Chothia definitions: KYGMH (SEQ ID NO: 88), LIS-DDGMRKYHSDSMWG (SEQ ID NO: 89), and EAGG-PIWHDDVKYYDFNDGYYNYHYMDV (SEQ ID NO: 6). The light chain CDRs of the 1503_H05 (PG16) antibody have the following sequences per Kabat and Chothia definitions: NGTRSDVGGFDSVS (SEQ ID NO: 92), DVSHRPS (SEQ ID NO: 95), and SSLTDRSHRI (SEQ ID NO: 41).

The 1489_I13 (PG16) antibody includes a heavy chain variable region (SEQ ID NO: 59), encoded by the nucleic acid sequence shown in SEQ ID NO: 134, and a light chain variable region (SEQ ID NO: 14) encoded by the nucleic acid sequence shown in SEQ ID NO: 135.

The heavy chain CDRs of the 1489_I13 (PG16) antibody have the following sequences per Kabat and Chothia definitions: KYGMH (SEQ ID NO: 88), LIS-DDGMRKYHSNSMWG (SEQ ID NO: 98), and EAGG-PIWHDDVKYYDFNDGYYNYHYMDV (SEQ ID NO: 6). The light chain CDRs of the 1489_I13 (PG16) antibody have the following sequences per Kabat and Chothia definitions: NGTSSDVGGFDSVS (SEQ ID NO: 97), DVSHRPS (SEQ ID NO: 95), and SSLTDRSHRI (SEQ ID NO: 41).

The 1480_I08 (PG16) antibody includes a heavy chain variable region (SEQ ID NO: 65), encoded by the nucleic acid sequence shown in SEQ ID NO: 136, and a light chain variable region (SEQ ID NO: 14) encoded by the nucleic acid sequence shown in SEQ ID NO: 137.

The heavy chain CDRs of the 1480_I08 (PG16) antibody have the following sequences per Kabat and Chothia definitions: KYGMH (SEQ ID NO: 88), LIS-DDGMRKYHSDSMWG (SEQ ID NO: 89), and EAGG-PIWHDDVKYYDFNDGYYNYHYMDV (SEQ ID NO: 6). The light chain CDRs of the 1480_I08 (PG16) antibody have the following sequences per Kabat and Chothia definitions: NGTSSDVGGFDSVS (SEQ ID NO: 97), DVSHRPS (SEQ ID NO: 95), and SSLTDRSHRI (SEQ ID NO: 41).

The sequences of additional human monoclonal antibodies were determined, including the sequences of the variable regions of the Gamma heavy and Kappa or Lambda light chains. In addition, the sequence of each of the polynucleotides encoding the antibody sequences was determined. Shown below are the polypeptide and polynucleotide sequences of the gamma heavy chains and kappa light chains, with the signal peptides at the N-terminus (or 5' end) and the constant regions at the C-terminus (or 3' end) of the variable regions, which are shown in bolded text.

4838_L06 (PGT-121) gamma heavy chain nucleotide sequence: coding sequence
(variable region in bold)

(SEQ ID NO: 62)

ATGAAACACCTGTGGTTCTTCCTTCTCCTGGTGGCAGCTCCCAGATGGGTC
CTGTCA**CAGATGCAGTTACAGGAGTCGGGCCCCGGACTGGTGAAGCC
TTCGGAAACCCTGTCCCTCACGTGCAGTGTGTCTGGTGCCTCCATAA
GTGACAGTTACTGGAGCTGGATCCGGCGGTCCCCAGGGAAGGGACTT
GAGTGGATTGGGTATGTCCACAAAAGCGGCGACACAAATTACAGCCC
CTCCCTCAAGAGTCGAGTCAACTTGTCGTTAGACACGTCCAAAAATC
AGGTGTCCCTGAGCCTTGTGGCCGCGACCGCTGCGGACTCGGGCAAA
TATTATTGCGCGAGAACACTGCACGGGAGGAGAATTTATGGAATCGT
TGCCTTCAATGAGTGGTTCACCTACTTCTACATGGACGTCTGGGGCA
ATGGGACTCAGGTCACCGTCTCCTCA**GCCTCCACCAAGGGCCCATCGG
TCTTCCCCCTGGCACCCTCCTCCAAGAGCACCTCTGGGGGCACAGCGGCC
CTGGGCTGCCTGGTCAAGGACTACTTCCCCGAACCGGTGACGGTGTCGTG
GAACTCAGGCGCCCTGACCAGCGGCGTGCACACCTTCCCGGCTGTCCTAC
AGTCCTCAGGACTCTACTCCCTCAGCAGCGTGGTGACCGTGCCCTCCAGC
AGCTTGGGCACCCAGACCTACATCTGCAACGTGAATCACAAGCCCAGCAA
CACCAAGGTGGACAAGAGAGTTGAGCCCAAATCTTGTGACAAAACTCAC
ACATGCCCACCGTGCCCAGCACCTGAACTCCTGGGGGGACCGTCAGTCTT
CCTCTTCCCCCCAAAACCCAAGGACACCCTCATGATCTCCCGGACCCCTG
AGGTCACATGCGTGGTGGTGGACGTGAGCCACGAAGACCCTGAGGTCAA
GTTCAACTGGTACGTGGACGGCGTGGAGGTGCATAATGCCAAGACAAAG
CCGCGGGAGGAGCAGTACAACAGCACGTACCGTGTGGTCAGCGTCCTCAC
CGTCCTGCACCAGGACTGGCTGAATGGCAAGGAGTACAAGTGCAAGGTCT
CCAACAAAGCCCTCCCAGCCCCCATCGAGAAAACCATCTCCAAAGCCAAA
GGGCAGCCCCGAGAACCACAGGTGTACACCCTGCCCCCATCCCGGGAGG
AGATGACCAAGAACCAGGTCAGCCTGACCTGCCTGGTCAAAGGCTTCTAT
CCCAGCGACATCGCCGTGGAGTGGGAGAGCAATGGGCAGCCGGAGAACA
ACTACAAGACCACGCCTCCCGTGCTGGACTCCGACGGCTCCTTCTTCCTCT
ATAGCAAGCTCACCGTGGACAAGAGCAGGTGGCAGCAGGGGAACGTCTT
CTCATGCTCCGTGATGCATGAGGCTCTGCACAACCACTACACGCAGAAGA
GCCTCTCCCTGTCTCCGGGTAAATGA

4838_L06 (PGT-121) gamma heavy chain variable region nucleotide sequence:

(SEQ ID NO: 63)

CAGATGCAGTTACAGGAGTCGGGCCCCGGACTGGTGAAGCCTTCGGAAA
CCCTGTCCCTCACGTGCAGTGTGTCTGGTGCCTCCATAAGTGACAGTTACT
GGAGCTGGATCCGGCGGTCCCCAGGGAAGGGACTTGAGTGGATTGGGTAT
GTCCACAAAAGCGGCGACACAAATTACAGCCCCTCCCTCAAGAGTCGAGT
CAACTTGTCGTTAGACACGTCCAAAAATCAGGTGTCCCTGAGCCTTGTGG
CCGCGACCGCTGCGGACTCGGGCAAATATTATTGCGCGAGAACACTGCAC
GGGAGGAGAATTTATGGAATCGTTGCCTTCAATGAGTGGTTCACCTACTT
CTACATGGACGTCTGGGGCAATGGGACTCAGGTCACCGTCTCCTCA

4838_L06 (PGT-121) gamma heavy chain amino acid sequence: expressed protein
with variable region in bold.

(SEQ ID NO: 66)

**QMQLQESGPGLVKPSETLSLTCSVSGASISDSYWSWIRRSPGKGLEWIGY
VHKSGDTNYSPSLKSRVNLSLDTSKNQVSLSLVAATAADSGKYYCARTLH
GRRIYGIVAFNEWFTYFYMDVWGNGTQVTVSS**ASTKGPSVFPLAPSSKSTS
GGTAALGCLVKDYFPEPVTVSWNSGALTSGVHTFPAVLQSSGLYSLSSVVTV
PSSSLGTQTYICNVNHKPSNTKVDKRVEPKSCDKTHTCPPCPAPELLGGPSVF
LFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPGK

4838_L06 (PGT-121) gamma heavy chain variable region amino acid sequence: (Kabat
CDRs underlined, Chothia CDRs in bold italics)

(SEQ ID NO: 79)

QMQLQESGPGLVKPSETLSLTCSVS*GASISD*SYWSWIRRSPGKGLEWIG<u>YVHK
SGDT</u>NYSPSLKSRVNLSLDTSKNQVSLSLVAATAADSGKYYCAR<u>***TLHGRRIY
GIVAFNEWFTYFYMDV***</u>WGNGTQVTVSS

4838_L06 (PGT-121) gamma heavy chain Kabat CDRs:

(SEQ ID NO: 90)

CDR 1: DSYWS (SEQ ID NO: 265)

CDR 2: YVHKSGDTNYSPSLKS (SEQ ID NO: 143)

CDR 3: TLHGRRIYGIVAFNEWFTYFYMDV

4838_L06 (PGT-121) gamma heavy chain Chothia CDRs:

(SEQ ID NO: 144)

CDR 1: GASISD (SEQ ID NO: 145)

CDR 2: YVHKSGDTN

```
                                                           (SEQ ID NO: 143)
CDR 3: TLHGRRIYGIVAFNEWFTYFYMDV

4838_L06 (PGT-121) lambda light chain nucleotide sequence: coding sequence
(variable region in bold)
                                                           (SEQ ID NO: 146)
ATGGCCTGGACCTTTCTCCTCCTCGGCCTCCTCTCTCACTGCACAGCCTCT
GTGACCTCCGATATATCTGTGGCCCCAGGAGAGACGGCCAGGATTTC
CTGTGGGGAAAAGAGCCTTGGAAGTAGAGCTGTACAATGGTATCAAC
ACAGGGCCGGCCAGGCCCCCTCTTTAATCATATATAATAATCAGGAC
CGGCCCTCAGGGATCCCTGAGCGATTCTCTGGCTCCCCTGACTCCCC
TTTTGGGACCACGGCCACCCTGACCATCACCAGTGTCGAAGCCGGGG
ATGAGGCCGACTATTACTGTCATATATGGGATAGTAGAGTTCCCACC
AAATGGGTCTTCGGCGGAGGGACCACGCTGACCGTGTTAGGTCAGCC
CAAGGCTGCCCCCTCGGTCACTCTGTTCCCGCCCTCCTCTGAGGAGCTTCA
AGCCAACAAGGCCACACTGGTGTGTCTCATAAGTGACTTCTACCCGGGAG
CCGTGACAGTGGCCTGGAAGGCAGATAGCAGCCCCGTCAAGGCGGGAGT
GGAGACCACCACACCCTCCAAACAAAGCAACAACAAGTACGCGGCCAGC
AGCTACCTGAGCCTGACGCCTGAGCAGTGGAAGTCCCACAAAAGCTACA
GCTGCCAGGTCACGCATGAAGGGAGCACCGTGGAGAAGACAGTGGCCCC
TACAGAATGTTCATAG 4838_L06 (PGT-121) lambda light chain variable region nucleotide sequence:
                                                           (SEQ ID NO: 147)
TCCGATATATCTGTGGCCCCAGGAGAGACGGCCAGGATTTCCTGTGGGGA
AAAGAGCCTTGGAAGTAGAGCTGTACAATGGTATCAACACAGGGCCGGC
CAGGCCCCCTCTTTAATCATATATAATAATCAGGACCGGCCCTCAGGGAT
CCCTGAGCGATTCTCTGGCTCCCCTGACTCCCCTTTTGGGACCACGGCCAC
CCTGACCATCACCAGTGTCGAAGCCGGGGATGAGGCCGACTATTACTGTC
ATATATGGGATAGTAGAGTTCCCACCAAATGGGTCTTCGGCGGAGGGACC
ACGCTGACCGTGTTA 4838_L06 (PGT-121) lambda light chain amino acid sequence: expressed protein with
variable region in bold.
                                                           (SEQ ID NO: 148)
SDISVAPGETARISCGEKSLGSRAVQWYQHRAGQAPSLIIYNNQDRPSGIP
ERFSGSPDSPFGTTATLTITSVEAGDEADYYCHIWDSRVPTKWVFGGGTT
LTVLGQPKAAPSVTLFPPSSEELQANKATLVCLISDFYPGAVTVAWKADSSP
VKAGVETTTPSKQSNNKYAASSYLSLTPEQWKSHKSYSCQVTHEGSTVEKTV
APTECS 4838_L06 (PGT-121) lambda light chain variable region amino acid sequence: (Kabat
CDRs underlined, Chothia CDRs in bold italics)
                                                           (SEQ ID NO: 149)
SDISVAPGETARISC*GEKSLGSRAVQ*WYQHRAGQAPSLIIY*NNQDRPS*GIPERF
SGSPDSPFGTTATLTITSVEAGDEADYYC*HIWDSRVPTKWV*FGGGTTLTVL 4838_L06 (PGT-121) lambda light chain Kabat CDRs:
                                                           (SEQ ID NO: 150)
CDR 1: GEKSLGSRAVQ (SEQ ID NO: 151)
CDR 2: NNQDRPS (SEQ ID NO: 152)
CDR 3: HIWDSRVPTKWV 4838_L06 (PGT-121) lambda light chain Chothia CDRs:
                                                           (SEQ ID NO: 150)
CDR 1: GEKSLGSRAVQ (SEQ ID NO: 151)
CDR 2: NNQDRPS (SEQ ID NO: 152)
CDR 3: HIWDSRVPTKWV 4873_E03 (PGT-121) gamma heavy chain nucleotide sequence: coding sequence
(variable region in bold)
                                                           (SEQ ID NO: 62)
ATGAAACACCTGTGGTTCTTCCTTCTCCTGGTGGCAGCTCCCAGATGGGTC
CTGTCCCAGATGCAGTTACAGGAGTCGGGCCCCGGACTGGTGAAGCCT
TCGGAAACCCTGTCCCTCACGTGCAGTGTGTCTGGTGCCTCCATAAG
TGACAGTTACTGGAGCTGGATCCGGCGGTCCCCAGGGAAGGGACTTG
AGTGGATTGGGTATGTCCACAAAAGCGGCGACACAAATTACATCCCC
TCCCTCAAGAGTCGAGTCAACTTGTCGTTAGACACGTCCAAAAATCA
GGTGTCCCTGAGCCTTGTGGCCGCGACCGCTGCGGACTCGGGCAAAT
ATTATTGCGCGAGAACACTGCACGGGAGGAGAATTTATGGAATCGTT
GCCTTCAATGAGTGGTTCACCTACTTCTACATGGACGTCTGGGGCAA
TGGGACTCAGGTCACCGTCTCCTCAGCCTCCACCAAGGGCCCATCGGTC
```

-continued
TTCCCCCTGGCACCCTCCTCCAAGAGCACCTCTGGGGGCACAGCGGCCCT
GGGCTGCCTGGTCAAGGACTACTTCCCCGAACCGGTGACGGTGTCGTGGA
ACTCAGGCGCCCTGACCAGCGGCGTGCACACCTTCCCGGCTGTCCTACAG
TCCTCAGGACTCTACTCCCTCAGCAGCGTGGTGACCGTGCCCTCCAGCAG
CTTGGGCACCCAGACCTACATCTGCAACGTGAATCACAAGCCCAGCAACA
CCAAGGTGGACAAGAGAGTTGAGCCCAAATCTTGTGACAAAACTCACAC
ATGCCCACCGTGCCCAGCACCTGAACTCCTGGGGGGACCGTCAGTCTTCC
TCTTCCCCCCAAAACCCAAGGACACCCTCATGATCTCCCGGACCCCTGAG
GTCACATGCGTGGTGGTGGACGTGAGCCACGAAGACCCTGAGGTCAAGTT
CAACTGGTACGTGGACGGCGTGGAGGTGCATAATGCCAAGACAAAGCCG
CGGGAGGAGCAGTACAACAGCACGTACCGTGTGGTCAGCGTCCTCACCGT
CCTGCACCAGGACTGGCTGAATGGCAAGGAGTACAAGTGCAAGGTCTCC
AACAAAGCCCTCCCAGCCCCCATCGAGAAAACCATCTCCAAAGCCAAAG
GGCAGCCCCGAGAACCACAGGTGTACACCCTGCCCCCATCCCGGGAGGA
GATGACCAAGAACCAGGTCAGCCTGACCTGCCTGGTCAAAGGCTTCTATC
CCAGCGACATCGCCGTGGAGTGGGAGAGCAATGGGCAGCCGGAGAACAA
CTACAAGACCACGCCTCCCGTGCTGGACTCCGACGGCTCCTTCTTCCTCTA
TAGCAAGCTCACCGTGGACAAGAGCAGGTGGCAGCAGGGGAACGTCTTC
TCATGCTCCGTGATGCATGAGGCTCTGCACAACCACTACACGCAGAAGAG
CCTCTCCCTGTCTCCGGGTAAATGA 4873_E03 (PGT-121) gamma heavy chain variable region nucleotide sequence:
(SEQ ID NO: 63)
CAGATGCAGTTACAGGAGTCGGGCCCCGGACTGGTGAAGCCTTCGGAAA
CCCTGTCCCTCACGTGCAGTGTGTCTGGTGCCTCCATAAGTGACAGTTACT
GGAGCTGGATCCGGCGGTCCCCAGGGAAGGGACTTGAGTGGATTGGGTAT
GTCCACAAAAGCGGCGACACAAATTACAGCCCCTCCCTCAAGAGTCGAGT
CAACTTGTCGTTAGACACGTCCAAAAATCAGGTGTCCCTGAGCCTTGTGG
CCGCGACCGCTGCGGACTCGGGCAAATATTATTGCGCGAGAACACTGCAC
GGGAGGAGAATTTATGGAATCGTTGCCTTCAATGAGTGGTTCACCTACTT
CTACATGGACGTCTGGGGCAATGGGACTCAGGTCACCGTCTCCTCA 4873_E03 (PGT-121) gamma heavy chain amino acid sequence: expressed protein
with variable region in bold.
(SEQ ID NO: 66)
**MKHLWFFLLLVAAPRWVLSQMQLQESGPGLVKPSETLSLTCSVSGASIS
DSYWSWIRRSPGKGLEWIGYVHKSGDTNYIPSLKSRVNLSLDTSKNQVSL
SLVAATAADSGKYYCARTLHGRRIYGIVAFNEWFTYFYMDVWGNGTQV
TVSS**ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKRVEPKS
CDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVKGFYP
SDIAVEWESNGQPENNYKTTPPVLDSDGSFFLYSKLTVDKSRWQQGNVFSCS
VMHEALHNHYTQKSLSLSPGK 4873_E03 (PGT-121) gamma heavy chain variable region amino acid sequence: (Kabat
CDRs underlined, Chothia CDRs in bold italics)
(SEQ ID NO: 79)
QMQLQESGPGLVKPSETLSLTCSVS*GASIS**D*SYWSWIRRSPGKGLEWIG<u>YVHK
SGDT</u>NYSPSLKSRVNLSLDTSKNQVSLSLVAATAADSGKYYCAR<u>***TLHGRRIY
GIVAFNEWFTYFYMDV***</u>WGNGTQVTVSS 4873_E03 (PGT-121) gamma heavy chain Kabat CDRs:
(SEQ ID NO: 90)
CDR 1: DSYWS (SEQ ID NO: 265)
CDR 2: YVHKSGDTNYSPSLKS (SEQ ID NO: 143)
CDR 3: TLHGRRIYGIVAFNEWFTYFYMDV 4873_E03 (PGT-121) gamma heavy chain Chothia CDRs:
(SEQ ID NO: 144)
CDR 1: GASISD (SEQ ID NO: 145)
CDR 2: YVHKSGDTN (SEQ ID NO: 143)
CDR 3: TLHGRRIYGIVAFNEWFTYFYMDV 4873_E03 (PGT-121) lambda light chain nucleotide sequence: coding sequence
(variable region in bold)
(SEQ ID NO: 146)
ATGGCCTGGACCTTTCTCCTCCTCGGCCTCCTCTCTCACTGCACAGCCTCT
GTGACC**TCCGATATATCTGTGGCCCCAGGAGAGACGGCCAGGATTTC
CTGTGGGGAAAAGAGCCTTGGAAGTAGAGCTGTACAATGGTATCAAC
ACAGGGCCGGCCAGGCCCCCTCTTTAATCATATATAATAATCAGGAC
CGGCCCTCAGGGATCCCTGAGCGATTCTCTGGCTCCCCTGACTCCCC**

-continued
**TTTTGGGACCACGGCCACCCTGACCATCACCAGTGTCGAAGCCGGGG
ATGAGGCCGACTATTACTGTCATATATGGGATAGTAGAGTTCCCACC
AAATGGGTCTTCGGCGGAGGGACCACGCTGACCGTGTT**AGGTCAGCC
CAAGGCTGCCCCCTCGGTCACTCTGTTCCCGCCCTCCTCTGAGGAGCTTCA
AGCCAACAAGGCCACACTGGTGTGTCTCATAAGTGACTTCTACCCGGGAG
CCGTGACAGTGGCCTGGAAGGCAGATAGCAGCCCCGTCAAGGCGGGAGT
GGGAGACCACCACACCCTCCAAACAAAGCAACAACAAGTACGCGGCCAGC
AGCTACCTGAGCCTGACGCCTGAGCAGTGGAAGTCCCACAAAAGCTACA
GCTGCCAGGTCACGCATGAAGGGAGCACCGTGGAGAAGACAGTGGCCCC
TACAGAATGTTCATAG 4873_E03 (PGT-121) lambda light chain variable region nucleotide sequence:
(SEQ ID NO: 147)
TCCGATATATCTGTGGCCCCAGGAGAGACGGCCAGGATTTCCTGTGGGGA
AAAGAGCCTTGGAAGTAGAGCTGTACAATGGTATCAACACAGGGCCGGC
CAGGCCCCCTCTTTAATCATATATAATAATCAGGACCGGCCCTCAGGGAT
CCCCTGAGCGATTCTCTGGCTCCCCTGACTCCCCTTTTGGGACCACGGCCAC
CCTGACCATCACCAGTGTCGAAGCCGGGGATGAGGCCGACTATTACTGTC
ATATATGGGATAGTAGAGTTCCCACCAAATGGGTCTTCGGCGGAGGGACC
ACGCTGACCGTGTTA 4873_E03 (PGT-121) lambda light chain amino acid sequence: expressed protein with variable region in bold.
(SEQ ID NO: 148)
**MAWTFLLLGLLSHCTASVTSDISVAPGETARISCGEKSLGSRAVQWYQH
RAGQAPSLIIYNNQDRPSGIPERFSGSPDSPFGTTATLTITSVEAGDEADYY
CHIWDSRVPTKWVFGGGTTLTVL**GQPKAAPSVTLFPPSSEELQANKATLVC
LISDFYPGAVTVAWKADSSPVKAGVETTTPSKQSNNKYAASSYLSLTPEQWK
SHKSYSCQVTHEGSTVEKTVAPTECS 4873_E03 (PGT-121) lambda light chain variable region amino acid sequence: (Kabat CDRs underlined, Chothia CDRs in bold italics)
(SEQ ID NO: 149)
SDISVAPGETARISC*GEKSLGSRAVQ*WYQHRAGQAPSLIIY*NNQDRPS*GIPERF
SGSPDSPFGTTATLTITSVEAGDEADYYC*HIWDSRVPTKWV*FGGGTTLTVL 4873_E03 (PGT-121) lambda light chain Kabat CDRs:
(SEQ ID NO: 150)
CDR 1: GEKSLGSRAVQ (SEQ ID NO: 151)
CDR 2: NNQDRPS (SEQ ID NO: 152)
CDR 3: HIWDSRVPTKWV 4873_E03 (PGT-121) lambda light chain Chothia CDRs:
(SEQ ID NO: 150)
CDR 1: GEKSLGSRAVQ (SEQ ID NO: 151)
CDR 2: NNQDRPS (SEQ ID NO: 152)
CDR 3: HIWDSRVPTKWV 4877_D15 (PGT-122) gamma heavy chain nucleotide sequence: coding sequence (variable region in bold)
(SEQ ID NO: 153)
ATGAAACACCTGTGGTTCTTCCTTCTCCTGGTGGCAGCTCCCAGATGGGTC
CTGTCC**CAGGTTCATCTGCAGGAGTCGGGCCCCGGACTGGTGAAGCC
TTCGGAGACCCTGTCCCTCACGTGCAATGTGTCTGGGACCCTCGTGC
GTGATAACTACTGGAGCTGGATCAGACAACCCCTCGGGAAGCAACCT
GAGTGGATTGGCTATGTCCATGACAGCGGGGACACGAATTACAACCC
CTCCCTGAAGAGTCGAGTCCACTTATCGTTGGACAAGTCCAAAAACC
TGGTGTCCCTGAGGCTGACCGGCGTGACCGCCGCGGACTCGGCCATA
TATTATTGCGCGACAACAAAACACGGGAGGAGGATTTATGGCGTCGT
TGCCTTCAAAGAGTGGTTCACCTATTTCTACATGGACGTCTGGGGCA
AAGGGACTTCGGTCACCGTCTCCTCAG**CCTCCACCAAGGGCCCATCGG
TCTTCCCCCTGGCACCCTCCTCCAAGAGCACCTCTGGGGGCACAGCGGCC
CTGGGCTGCCTGGTCAAGGACTACTTCCCCGAACCGGTGACGGTGTCGTG
GAACTCAGGCGCCCTGACCAGCGGCGTGCACACCTTCCCGGCTGTCCTAC
AGTCCTCAGGACTCTACTCCCTCAGCAGCGTGGTGACCGTGCCCTCCAGC
AGCTTGGGCACCCAGACCTACATCTGCAACGTGAATCACAAGCCCAGCAA
CACCAAGGTGGACAAGAGAGTTGAGCCCAAATCTTGTGACAAAACTCAC
ACATGCCCACCGTGCCCAGCACCTGAACTCCTGGGGGGACCGTCAGTCTT
CCTCTTCCCCCCAAAACCCAAGGACACCCTCATGATCTCCCGGACCCCTG
AGGTCACATGCGTGGTGGTGGACGTGAGCCACGAAGACCCTGAGGTCAA
GTTCAACTGGTACGTGGACGGCGTGGAGGTGCATAATGCCAAGACAAAG
CCGCGGGAGGAGCAGTACAACAGCACGTACCGTGTGGTCAGCGTCCTCAC
CGTCCTGCACCAGGACTGGCTGAATGGCAAGGAGTACAAGTGCAAGGTCT

```
CCAACAAAGCCCTCCCAGCCCCCATCGAGAAAACCATCTCCAAAGCCAAA
GGGCAGCCCCGAGAACCACAGGTGTACACCCTGCCCCCATCCCGGGAGG
AGATGACCAAGAACCAGGTCAGCCTGACCTGCCTGGTCAAAGGCTTCTAT
CCCAGCGACATCGCCGTGGAGTGGGAGAGCAATGGGCAGCCGGAGAACA
ACTACAAGACCACGCCTCCCGTGCTGGACTCCGACGGCTCCTTCTTCCTCT
ATAGCAAGCTCACCGTGGACAAGAGCAGGTGGCAGCAGGGGAACGTCTT
CTCATGCTCCGTGATGCATGAGGCTCTGCACAACCACTACACGCAGAAGA
GCCTCTCCCTGTCTCCGGGTAAATGA
```

4877_D15 (PGT-122) gamma heavy chain variable region nucleotide sequence:
(SEQ ID NO: 154)
```
CAGGTTCATCTGCAGGAGTCGGGCCCCGGACTGGTGAAGCCTTCGGAGAC
CCTGTCCCTCACGTGCAATGTGTCTGGGACCCTCGTGCGTGATAACTACTG
GAGCTGGATCAGACAACCCCTCGGGAAGCAACCTGAGTGGATTGGCTATG
TCCATGACAGCGGGGACACGAATTACAACCCCTCCCTGAAGAGTCGAGTC
CACTTATCGTTGGACAAGTCCAAAAACCTGGTGTCCCTGAGGCTGACCGG
CGTGACCGCCGCGGACTCGGCCATATATTATTGCGCGACAACAAAACACG
GGAGGAGGATTTATGGCGTCGTTGCCTTCAAAGAGTGGTTCACCTATTTCT
ACATGGACGTCTGGGGCAAAGGGACTTCGGTCACCGTCTCCTCA
```

4877_D15 (PGT-122) gamma heavy chain amino acid sequence: expressed protein with variable region in bold.
(SEQ ID NO: 155)
**MKHLWFFLLLVAAPRWVLSQVHLQESGPGLVKPSETLSLTCNVSGTLVR
DNYWSWIRQPLGKQPEWIGYVHDSGDTNYNPSLKSRVHLSLDKSKNLVS
LRLTGVTAADSAIYYCATTKHGRRIYGVVAFKEWFTYFYMDVWGKGTS
VTVSS**ASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKRVEPK
SCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVKGFYP
SDIAVEWESNGQPENNYKTTPPVLDSDGSFFLYSKLTVDKSRWQQGNVFSCS
VMHEALHNHYTQKSLSLSPGK 4877_D15 (PGT-122) gamma heavy chain variable region amino acid sequence:
(Kabat CDRs underlined, Chothia CDRs in bold italics)
(SEQ ID NO: 156)
QVHLQESGPGLVKPSETLSLTCNVS*GTLVRD*NYWSWIRQPLGKQPEWIG***YVH
DSGDTN*YNPSLKSRVHLSLDKSKNLVSLRLTGVTAADSAIYYCAT*TKHGRRI
YGVVAFKEWFTYFYMDV***WGKGTSVTVSS 4877_D15 (PGT-122) gamma heavy chain Kabat CDRs:

(SEQ ID NO: 261)
CDR 1: DNYWS (SEQ ID NO: 157)
CDR 2: YVHDSGDTNYNPSLKS (SEQ ID NO: 262)
CDR 3: TKHGRRIYGVVAFKEWFTYFYMDV

4877_D15 (PGT-122) gamma heavy chain Chothia CDRs:

(SEQ ID NO: 263)
CDR 1: GTLVRD (SEQ ID NO: 264)
CDR 2: YVHDSGDTN (SEQ ID NO: 262)
CDR 3: TKHGRRIYGVVAFKEWFTYFYMDV

4877_D15 (PGT-122) lambda light chain nucleotide sequence: coding sequence (variable region in bold)
(SEQ ID NO: 158)
ATGGCCTGGACCGTTCTCCTCCTCGGCCTCCTCTCTCACTGCACAGGCGCG
GTGTCT**ACCTTTGTGTCAGTGGCCCCAGGACAGACGGCCAGGATTACT
TGTGGGGAAGAGAGCCTTGGAAGTAGATCTGTTATTTGGTATCAACA
GAGGCCAGGCCAGGCCCCTTCATTAATCATCTATAATAATAATGACC
GGCCCTCAGGGATTCCTGACCGATTTTCTGGGTCCCCTGGCTCCACT
TTTGGGACCACGGCCACCCTGACCATCACCAGTGTCGAAGCCGGGGA
TGAGGCCGACTATTATTGTCATATCTGGGATAGTAGACGACCAACCA
ATTGGGTCTTCGGCGAAGGGACCACACTGATCGTGTT**AGGTCAGCCCA
AGGCTGCCCCCTCGGTCACTCTGTTCCCGCCCTCCTCTGAGGAGCTTCAAG
CCAACAAGGCCACACTGGTGTGTCTCATAAGTGACTTCTACCCGGGAGCC
GTGACAGTGGCCTGGAAGGCAGATAGCAGCCCCGTCAAGGCGGGAGTGG
AGACCACCACACCCTCCAAACAAAGCAACAACAAGTACGCGGCCAGCAG
CTACCTGAGCCTGACGCCTGAGCAGTGGAAGTCCCACAAAAGCTACAGCT
GCCAGGTCACGCATGAAGGGAGCACCGTGGAGAAGACAGTGGCCCCTAC
AGAATGTTCATAG
```

-continued

4877_D15 (PGT-122) lambda light chain variable region nucleotide sequence:
(SEQ ID NO: 159)
```
ACCTTTGTGTCAGTGGCCCCAGGACAGACGGCCAGGATTACTTGTGGGGA
AGAGAGCCTTGGAAGTAGATCTGTTATTTGGTATCAACAGAGGCCAGGCC
AGGCCCCTTCATTAATCATCTATAATAATAATGACCGGCCCTCAGGGATTC
CTGACCGATTTTCTGGGTCCCCTGGCTCCACTTTTGGGACCACGGCCACCC
TGACCATCACCAGTGTCGAAGCCGGGGATGAGGCCGACTATTATTGTCAT
ATCTGGGATAGTAGACGACCAACCAATTGGGTCTTCGGCGAAGGGACCAC
ACTGATCGTGTTA
```

4877_D15 (PGT-122) lambda light chain amino acid sequence: expressed protein with variable region in bold.
(SEQ ID NO: 160)
MAWTVLLLGLLSHCTGAVSTFVSVAPGQTARITCGEESLGSRSVIWYQQ
RPGQAPSLIIYNNNDRPSGIPDRFSGSPGSTFGTTATLTITSVEAGDEADYY
CHIWDSRRPTNWVFGEGTTLIVLGQPKAAPSVTLFPPSSEELQANKATLVC
LISDFYPGAVTVAWKADSSPVKAGVETTTPSKQSNNKYAASSYLSLTPEQWK
SHKSYSCQVTHEGSTVEKTVAPTECS 4877_D15 (PGT-122) lambda light chain variable region amino acid sequence: (Kabat CDRs underlined, Chothia CDRs in bold italics)
(SEQ ID NO: 161)
TFVSVAPGQTARITC*GEESLGSRSVI*WYQQRPGQAPSLIIY*NNNDRPS*GIPDRF
SGSPGSTFGTTATLTITSVEAGDEADYYC*HIWDSRRPTNWV*FGEGTTLIVL 4877_D15 (PGT-122) lambda light chain Kabat CDRs:
(SEQ ID NO: 162)
CDR 1: GEESLGSRSVI (SEQ ID NO: 163)
CDR 2: NNNDRPS (SEQ ID NO: 164)
CDR 3: HIWDSRRPTNWV 4877_D15 (PGT-122) lambda light chain Chothia CDRs:
(SEQ ID NO: 162)
CDR 1: GEESLGSRSVI (SEQ ID NO: 163)
CDR 2: NNNDRPS (SEQ ID NO: 164)
CDR 3: HIWDSRRPTNWV 4858_P08 (PGT-123) gamma heavy chain nucleotide sequence: coding sequence (variable region in bold)
(SEQ ID NO: 165)
```
ATGAAACACCTGTGGATCTTCCTTCTCCTGGTGGCAACTCCCAGATGGGTC
GAGTCCCAGCTGCACCTGCAGGAGTCGGGCCCAGGGCTGGTGAAGCC
TTCCGGAGACCCTGTCCCTCACGTGTAGTGTGTCTGGCGCCTCCATCA
ATGATGCCTATTGGAGTTGGATTCGGCAGTCCCCAGGGAAGCGGCCT
GAGTGGGTTGGATATGTCCATCACAGCGGTGACACAAATTATAATCC
CTCACTCAAGAGGCGCGTCACGTTTTCATTAGACACGGCCAAGAATG
AAGTGTCCCTGAAATTAGTAGACCTGACCGCTGCGGACTCGGCCACA
TATTTTTGTGCGCGAGCACTTCACGGGAAGAGGATTTATGGGATAGT
TGCCCTCGGAGAGTTGTTCACCTACTTCTACATGGACGTCTGGGGCA
AGGGGACTGCGGTCACCGTCTCCTCAGCCTCCACCAAGGGCCCATCGG
TCTTCCCCCTGGCACCCTCCTCCAAGAGCACCTCTGGGGGCACAGCGGCC
CTGGGCTGCCTGGTCAAGGACTACTTCCCCGAACCGGTGACGGTGTCGTG
GAACTCAGGCGCCCTGACCAGCGGCGTGCACACCTTCCCGGCTGTCCTAC
AGTCCTCAGGACTCTACTCCCTCAGCAGCGTGGTGACCGTGCCCTCCAGC
AGCTTGGGCACCCAGACCTACATCTGCAACGTGAATCACAAGCCCAGCAA
CACCAAGGTGGACAAGAGAGTTGAGCCCAAATCTTGTGACAAAACTCAC
ACATGCCCACCGTGCCCAGCACCTGAACTCCTGGGGGGACCGTCAGTCTT
CCTCTTCCCCCCAAAACCCAAGGACACCCTCATGATCTCCCGGACCCCTG
AGGTCACATGCGTGGTGGTGGACGTGAGCCACGAAGACCCTGAGGTCAA
GTTCAACTGGTACGTGGACGGCGTGGAGGTGCATAATGCCAAGACAAAG
CCGCGGGAGGAGCAGTACAACAGCACGTACCGTGTGGTCAGCGTCCTCAC
CGTCCTGCACCAGGACTGGCTGAATGGCAAGGAGTACAAGTGCAAGGTCT
CCAACAAAGCCCTCCCAGCCCCCATCGAGAAAACCATCTCCAAAGCCAAA
GGGCAGCCCCGAGAACCACAGGTGTACACCCTGCCCCCATCCCGGGAGG
AGATGACCAAGAACCAGGTCAGCCTGACCTGCCTGGTCAAAGGCTTCTAT
CCCAGCGACATCGCCGTGGAGTGGGAGAGCAATGGGCAGCCGGAGAACA
ACTACAAGACCACGCCTCCCGTGCTGGACTCCGACGGCTCCTTCTTCCTCT
ATAGCAAGCTCACCGTGGACAAGAGCAGGTGGCAGCAGGGGAACGTCTT
CTCATGCTCCGTGATGCATGAGGCTCTGCACAACCACTACACGCAGAAGA
GCCTCTCCCTGTCTCCGGGTAAATGA
```

4858_P08 (PGT-123) gamma heavy chain variable region nucleotide sequence:
(SEQ ID NO: 166)

```
CAGCTGCACCTGCAGGAGTCGGGCCCAGGGCTGGTGAAGCCTCCGGAGA
CCCTGTCCCTCACGTGTAGTGTGTCTGGCGCCTCCATCAATGATGCCTATT
GGAGTTGGATTCGGCAGTCCCCAGGGAAGCGGCCTGAGTGGGTTGGATAT
GTCCATCACAGCGGTGACACAAATTATAATCCCTCACTCAAGAGGCGCGT
CACGTTTTCATTAGACACGGCCAAGAATGAAGTGTCCCTGAAATTAGTAG
ACCTGACCGCTGCGGACTCGGCCACATATTTTTGTGCGCGAGCACTTCAC
GGGAAGAGGATTTATGGGATAGTTGCCCTCGGAGAGTTGTTCACCTACTT
CTACATGGACGTCTGGGGCAAGGGGACTGCGGTCACCGTCTCCTCA
```

4858_P08 (PGT-123) gamma heavy chain amino acid sequence: expressed protein with variable region in bold.
(SEQ ID NO: 167)

**MKHLWIFLLLVATPRWVESQLHLQESGPGLVKPPETLSLTCSVSGASIND
AYWSWIRQSPGKRPEWVGYVHHSGDTNYNPSLKRRVTFSLDTAKNEVS
LKLVDLTAADSATYFCARALHGKRIYGIVALGELFTYFYMDVWGKGTA
VTVSS**ASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKRVEPK
SCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVKGFYP
SDIAVEWESNGQPENNYKTTPPVLDSDGSFFLYSKLTVDKSRWQQGNVFSCS
VMHEALHNHYTQKSLSLSPGK

4858_P08 (PGT-123) gamma heavy chain variable region amino acid sequence: (Kabat CDRs underlined, Chothia CDRs in bold italics)
(SEQ ID NO: 168)

QLHLQESGPGLVKPPETLSLTCSVS*GASIND*AYWSWIRQSPGKRPEWVG***YVH
HSGDTN*YNPSLKRRVTFSLDTAKNEVSLKLVDLTAADSATYFCAR*ALHGKRI
YGIVALGELFTYFYMDV***WGKGTAVTVSS

4858_P08 (PGT-123) gamma heavy chain Kabat CDRs:
(SEQ ID NO: 169)
CDR 1: DAYWS (SEQ ID NO: 170)
CDR 2: YVHHSGDTNYNPSLKR (SEQ ID NO: 171)
CDR 3: ALHGKRIYGIVALGELFTYFYMDV 4858_P08 (PGT-123) gamma heavy chain Chothia CDRs:
(SEQ ID NO: 172)
CDR 1: GASIND (SEQ ID NO: 173)
CDR 2: YVHHSGDTN (SEQ ID NO: 171)
CDR 3: ALHGKRIYGIVALGELFTYFYMDV 4858_P08 (PGT-123) lambda light chain nucleotide sequence: coding sequence (variable region in bold)
(SEQ ID NO: 174)

ATGGCCTGGACCGTTCTCCTCCTCGGCCTCCTCTCTCACTGCACAGGCTCT
CTGGCC**TCCTCTATGTCCGTGTCCCCGGGGGAGACGGCCAAGATCTC
CTGTGGAAAAGAGAGCATTGGTAGCAGAGCTGTGCAATGGTATCAGC
AGAAGCCAGGCCAGCCCCCCTCATTGATTATCTATAATAATCAGGAC
CGCCCCGCAGGGGTCCCTGAGCGATTCTCTGCCTCCCCTGACTTCCG
TCCTGGGACCACGGCCACCCTGACCATCACCAATGTCGACGCCGAGG
ATGAGGCCGACTATTACTGTCATATATATGATGCTAGAGGTGGCACC
AATTGGGTCTTCGACAGAGGGACCACACTGACCGTCTTA**GGTCAGCCC
AAGGCTGCCCCCTCGGTCACTCTGTTCCCGCCCTCCTCTGAGGAGCTTCAA
GCCAACAAGGCCACACTGGTGTGTCTCATAAGTGACTTCTACCCGGGAGC
CGTGACAGTGGCCTGGAAGGCAGATAGCAGCCCCGTCAAGGCGGGAGTG
GAGACCACCACACCCTCCAAACAAAGCAACAACAAGTACGCGGCCAGCA
GCTACCTGAGCCTGACGCCTGAGCAGTGGAAGTCCCACAAAAGCTACAGC
TGCCAGGTCACGCATGAAGGGAGCACCGTGGAGAAGACAGTGGCCCCTA
CAGAATGTTCATAG

4858_P08 (PGT-123) lambda light chain variable region nucleotide sequence:
(SEQ ID NO: 175)

```
TCCTCTATGTCCGTGTCCCCGGGGGAGACGGCCAAGATCTCCTGTGGAAA
AGAGAGCATTGGTAGCAGAGCTGTGCAATGGTATCAGCAGAAGCCAGGC
CAGCCCCCCTCATTGATTATCTATAATAATCAGGACCGCCCCGCAGGGGT
CCCTGAGCGATTCTCTGCCTCCCCTGACTTCCGTCCTGGGACCACGGCCAC
CCTGACCATCACCAATGTCGACGCCGAGGATGAGGCCGACTATTACTGTC
ATATATATGATGCTAGAGGTGGCACCAATTGGGTCTTCGACAGAGGGACC
ACACTGACCGTCTTA
```

-continued

4858_P08 (PGT-123) lambda light chain amino acid sequence: expressed protein with variable region in bold.
(SEQ ID NO: 176)

MAWTVLLLGLLSHCTGSLASSMSVSPGETAKISCGKESIGSRAVQWYQQ
KPGQPPSLIIYNNQDRPAGVPERFSASPDFRPGTTATLTITNVDAEDEADY
YCHIYDARGGTNWVFDRGTTLTVLGQPKAAPSVTLFPPSSEELQANKATLV
CLISDFYPGAVTVAWKADSSPVKAGVETTTPSKQSNNKYAASSYLSLTPEQW
KSHKSYSCQVTHEGSTVEKTVAPTECS

4858_P08 (PGT-123) lambda light chain variable region amino acid sequence: (Kabat CDRs underlined, Chothia CDRs in bold italics)
(SEQ ID NO: 177)

SSMSVSPGETAKISC<u>*GKESIGSRAVQ*</u>WYQQKPGQPPSLIIY<u>*NNQDRPA*</u>GVPER
FSASPDFRPGTTATLTITNVDAEDEADYYC<u>*HIYDARGGTNWV*</u>FDRGTTLTVL

4858_P08 (PGT-123) lambda light chain Kabat CDRs:
(SEQ ID NO: 178)
CDR 1: GKESIGSRAVQ (SEQ ID NO: 179)
CDR 2: NNQDRPA (SEQ ID NO: 180)
CDR 3: HIYDARGGTNWV 4858_P08 (PGT-123) lambda light chain Chothia CDRs:
(SEQ ID NO: 178)
CDR 1: GKESIGSRAVQ (SEQ ID NO: 179)
CDR 2: NNQDRPA (SEQ ID NO: 180)
CDR 3: HIYDARGGTNWV 5123_A06 (PGT-125) gamma heavy chain nucleotide sequence: coding sequence (variable region in bold)
(SEQ ID NO: 181)

ATGAAACACCTGTGGTTCTTCTTCCTGCTGGTGGCGGCTCCCAGATGCGTC
CTGTCCCAGTCGCAGCTGCAGGAGTCGGGCCCACGACTGGTGGAGGC
CTCGGAGACCCTGTCACTCACGTGCAATGTGTCCGGCGAGTCCACTG
GTGCCTGTACTTATTTCTGGGGCTGGGTCCGGCAGGCCCCAGGGAAG
GGGCTGGAGTGGATCGGGAGTTTGTCCCATTGTCAGAGTTTCTGGGG
TTCCGGTTGGACCTTCCACAACCCGTCTCTCAAGAGTCGACTCACGA
TTTCACTCGACACGCCCAAGAATCAGGTCTTCCTCAAGCTCACTTCTC
TGACTGCCGCGGACACGGCCACTTACTACTGTGCGCGATTCGACGGC
GAAGTCTTGGTCTATAATCATTGGCCAAAGCCGGCCTGGGTGGACCT
CTGGGGCCGCGGAATACCGGTCACCGTCTCCTCAGCCTCCACCAAGGG
CCCATCGGTCTTCCCCCTGGCACCCTCCTCCAAGAGCACCTCTGGGGGCA
CAGCGGCCCTGGGCTGCCTGGTCAAGGACTACTTCCCCGAACCGGTGACG
GTGTCGTGGAACTCAGGCGCCCTGACCAGCGGCGTGCACACCTTCCCGGC
TGTCCTACAGTCCTCAGGACTCTACTCCCTCAGCAGCGTGGTGACCGTGCC
CTCCAGCAGCTTGGGCACCCAGACCTACATCTGCAACGTGAATCACAAGC
CCAGCAACACCAAGGTGGACAAGAGAGTTGAGCCCAAATCTTGTGACAA
AACTCACACATGCCCACCGTGCCCAGCACCTGAACTCCTGGGGGGACCGT
CAGTCTTCCTCTTCCCCCCAAAACCCAAGGACACCCTCATGATCTCCCGGA
CCCCTGAGGTCACATGCGTGGTGGTGGACGTGAGCCACGAAGACCCTGAG
GTCAAGTTCAACTGGTACGTGGACGGCGTGGAGGTGCATAATGCCAAGAC
AAAGCCGCGGGAGGAGCAGTACAACAGCACGTACCGTGTGGTCAGCGTC
CTCACCGTCCTGCACCAGGACTGGCTGAATGGCAAGGAGTACAAGTGCAA
GGTCTCCAACAAAGCCCTCCCAGCCCCCATCGAGAAAACCATCTCCAAAG
CCAAAGGGCAGCCCCGAGAACCACAGGTGTACACCCTGCCCCCATCCCGG
GAGGAGATGACCAAGAACCAGGTCAGCCTGACCTGCCTGGTCAAAGGCT
TCTATCCCAGCGACATCGCCGTGGAGTGGGAGAGCAATGGGCAGCCGGA
GAACAACTACAAGACCACGCCTCCCGTGCTGGACTCCGACGGCTCCTTCT
TCCTCTATAGCAAGCTCACCGTGGACAAGAGCAGGTGGCAGCAGGGGAA
CGTCTTCTCATGCTCCGTGATGCATGAGGCTCTGCACAACCACTACACGC
AGAAGAGCCTCTCCCTGTCTCCGGGTAAATGA

5123_A06 (PGT-125) gamma heavy chain variable region nucleotide sequence:
(SEQ ID NO: 182)
CAGTCGCAGCTGCAGGAGTCGGGCCCACGACTGGTGGAGGCCTCGGAGA
CCCTGTCACTCACGTGCAATGTGTCCGGCGAGTCCACTGGTGCCTGTACTT
ATTTCTGGGGCTGGGTCCGGCAGGCCCCAGGGAAGGGGCTGGAGTGGATC
GGGAGTTTGTCCCATTGTCAGAGTTTCTGGGGTTCCGGTTGGACCTTCCAC
AACCCGTCTCTCAAGAGTCGACTCACGATTTCACTCGACACGCCCAAGAA
TCAGGTCTTCCTCAAGCTCACTTCTCTGACTGCCGCGGACACGGCCACTTA
CTACTGTGCGCGATTCGACGGCGAAGTCTTGGTCTATAATCATTGGCCAA
AGCCGGCCTGGGTGGACCTCTGGGGCCGCGGAATACCGGTCACCGTCTCC
TCA 5123_A06 (PGT-125) gamma heavy chain amino acid sequence: expressed protein with variable region in bold.

(SEQ ID NO: 183)

**MKHLWFFFLLVAAPRCVLSQSQLQESGPRLVEASETLSLTCNVSGESTG
ACTYFWGWVRQAPGKGLEWIGSLSHCQSFWGSGWTFHNPSLKSRLTIS
LDTPKNQVFLKLTSLTAADTATYYCARFDGEVLVYNHWPKPAWVDLW
GRGIPVTVSS**ASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDK
RVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQGNV
FSCSVMHEALHNHYTQKSLSLSPGK

5123_A06 (PGT-125) gamma heavy chain variable region amino acid sequence: (Kabat CDRs underlined, Chothia CDRs in bold italics)

(SEQ ID NO: 184)

QSQLQESGPRLVEASETLSLTCNVS*GESTGACT*YFWGWVRQAPGKGLEWIGS
LSHCQSFWGSGWTFHNPSLKSRLTISLDTPKNQVFLKLTSLTAADTATYYCA
R*FDGEVLVYNHWPKPAWVDL*WGRGIPVTVSS

5123_A06 (PGT-125) gamma heavy chain Kabat CDRs:

(SEQ ID NO: 185)

CDR 1: ACTYFWG (SEQ ID NO: 186)

CDR 2: SLSHCQSFWGSGWTFHNPSLKS (SEQ ID NO: 187)

CDR 3: FDGEVLVYNHWPKPAWVDL

5123_A06 (PGT-125) gamma heavy chain Chothia CDRs:

(SEQ ID NO: 188)

CDR 1: GESTGACT (SEQ ID NO: 189)

CDR 2: SLSHCQSFWGSGWTF (SEQ ID NO: 187)

CDR 3: FDGEVLVYNHWPKPAWVDL

5123_A06 (PGT-125) lambda light chain nucleotide sequence: coding sequence (variable region in bold)

(SEQ ID NO: 190)

ATGGCCTGGGCTCTGCTCCTCCTCACCCTCCTCACTCAGGGCACAGGGGC
CTGGGCC**CAGTCTGCCCTGACTCAGCCTCCCTCCGCGTCCGGGTCTCC
TGGACAGTCAATCACCATCTCCTGCAATGGAACCGCCACTAACTTTGT
CTCCTGGTACCAACAATTCCCAGACAAGGCCCCCAAACTCATCATTTTT
TGGGGTCGATAAGCGCCCCCCCGGTGTCCCCGATCGTTTCTCTGGCT
CCCGGTCTGGCACGACGGCCTCCCTTACCGTCTCCCGACTCCAGACT
GACGATGAGGCTGTCTATTATTGCGGTTCACTTGTCGGCAACTGGGA
TGTGATTTTCGGCGGAGGGACCACCTTGACCGTCCTA**GGTCAGCCCAA
GGCTGCCCCCTCGGTCACTCTGTTCCCGCCCTCCTCTGAGGAGCTTCAAGC
CAACAAGGCCACACTGGTGTGTCTCATAAGTGACTTCTACCCGGGAGCCG
TGACAGTGGCCTGGAAGGCAGATAGCAGCCCCGTCAAGGCGGGAGTGGA
GACCACCACACCCTCCAAACAAAGCAACAACAAGTACGCGGCCAGCAGC
TACCTGAGCCTGACGCCTGAGCAGTGGAAGTCCCACAAAAGCTACAGCTG
CCAGGTCACGCATGAAGGGAGCACCGTGGAGAAGACAGTGGCCCCTACA
GAATGTTCATAG

5123_A06 (PGT-125) lambda light chain variable region nucleotide sequence:

(SEQ ID NO: 191)

CAGTCTGCCCTGACTCAGCCTCCCTCCGCGTCCGGGTCTCCTGGACAGTCA
ATCACCATCTCCTGCAATGGAACCGCCACTAACTTTGTCTCCTGGTACCAA
CAATTCCCAGACAAGGCCCCCAAACTCATCATTTTTGGGGTCGATAAGCG
CCCCCCCGGTGTCCCCGATCGTTTCTCTGGCTCCCGGTCTGGCACGACGGC
CTCCCTTACCGTCTCCCGACTCCAGACTGACGATGAGGCTGTCTATTATTG
CGGTTCACTTGTCGGCAACTGGGATGTGATTTTCGGCGGAGGGACCACCT
TGACCGTCCTA

5123_A06 (PGT-125) lambda light chain amino acid sequence: expressed protein with variable region in bold.

(SEQ ID NO: 192)

MAWALLLLTLLTQGTGAWA**QSALTQPPSASGSPGQSITISCNGTATNFVS
WYQQFPDKAPKLIIFGVDKRPPGVPDRFSGSRSGTTASLTVSRLQTDDEA
VYYCGSLVGNWDVIFGGGTTLTVL**GQPKAAPSVTLFPPSSEELQANKATLV
CLISDFYPGAVTVAWKADSSPVKAGVETTTPSKQSNNKYAASSYLSLTPEQW
KSHKSYSCQVTHEGSTVEKTVAPTECS

-continued

5123_A06 (PGT-125) lambda light chain variable region amino acid sequence: (Kabat CDRs underlined, Chothia CDRs in bold italics)

(SEQ ID NO: 193)

QSALTQPPSASGSPGQSITISC*NGTATNFVS*WYQQFPDKAPKLIIF*GVDKRPP*G
VPDRFSGSRSGTTASLTVSRLQTDDEAVYYC*GSLVGNWDVI*FGGGTTLTVL

5123_A06 (PGT-125) lambda light chain Kabat CDRs:

(SEQ ID NO: 194)
CDR 1: NGTATNFVS (SEQ ID NO: 195)
CDR 2: GVDKRPP (SEQ ID NO: 196)
CDR 3: GSLVGNWDVI

5123_A06 (PGT-125) lambda light chain Chothia CDRs:

(SEQ ID NO: 194)
CDR 1: NGTATNFVS (SEQ ID NO: 195)
CDR 2: GVDKRPP (SEQ ID NO: 196)
CDR 3: GSLVGNWDVI

5141_B17 (PGT-126) gamma heavy chain nucleotide sequence: coding sequence (variable region in bold)

(SEQ ID NO: 197)

ATGAAACACCTGTGGTTCTTCCTCCTGCTGGTGGCGGCTCCCAGATGGGTC
CTGTCC**CAGCCGCAGCTGCAGGAGTCGGGGCCAGGACTGGTGGAGGC
TTCGGAGACCCTGTCCCTCACCTGCACTGTGTCCGGCGACTCCACTG
CTGCTTGTGACTATTTCTGGGGCTGGGTCCGGCAGCCCCAGGGAAG
GGCCTGGAGTGGATTGGGGGTTTGTCACATTGTGCAGGTTACTACAA
TACTGGCTGGACCTACCACAACCCGTCTCTCAAGAGTCGGCTCACGA
TTTCACTCGACACCCCCAAGAATCAGGTCTTCCTGAAGTTAAATTCTG
TGACCGCCGCGGACACGGCCATTTACTACTGTGCGCGATTCGACGGC
GAAGTTTTGGTGTACCACGATTGGCCAAAGCCGGCCTGGGTCGACCT
CTGGGGCCGGGGAACTTTGGTCACCGTCTCCTCAG**CCTCCACCAAGGG
CCCATCGGTCTTCCCCCTGGCACCCTCCTCCAAGAGCACCTCTGGGGGCA
CAGCGGCCCTGGGCTGCCTGGTCAAGGACTACTTCCCCGAACCGGTGACG
GTGTCGTGGAACTCAGGCGCCCTGACCAGCGGCGTGCACACCTTCCCGGC
TGTCCTACAGTCCTCAGGACTCTACTCCCTCAGCAGCGTGGTGACCGTGCC
CTCCAGCAGCTTGGGCACCCAGACCTACATCTGCAACGTGAATCACAAGC
CCAGCAACACCAAGGTGGACAAGAGAGTTGAGCCCAAATCTTGTGACAA
AACTCACACATGCCCACCGTGCCCAGCACCTGAACTCCTGGGGGGACCGT
CAGTCTTCCTCTTCCCCCCAAAACCCAAGGACACCCTCATGATCTCCCGGA
CCCCTGAGGTCACATGCGTGGTGGTGGACGTGAGCCACGAAGACCCTGAG
GTCAAGTTCAACTGGTACGTGGACGGCGTGGAGGTGCATAATGCCAAGAC
AAAGCCGCGGGAGGAGCAGTACAACAGCACGTACCGTGTGGTCAGCGTC
CTCACCGTCCTGCACCAGGACTGGCTGAATGGCAAGGAGTACAAGTGCAA
GGTCTCCAACAAAGCCCTCCCAGCCCCCATCGAGAAAACCATCTCCAAAG
CCAAAGGGCAGCCCCGAGAACCACAGGTGTACACCCTGCCCCCATCCCGG
GAGGAGATGACCAAGAACCAGGTCAGCCTGACCTGCCTGGTCAAAGGCT
TCTATCCCAGCGACATCGCCGTGGAGTGGGAGAGCAATGGGCAGCCGGA
GAACAACTACAAGACCACGCCTCCCGTGCTGGACTCCGACGGCTCCTTCT
TCCTCTATAGCAAGCTCACCGTGGACAAGAGCAGGTGGCAGCAGGGGAA
CGTCTTCTCATGCTCCGTGATGCATGAGGCTCTGCACAACCACTACACGC
AGAAGAGCCTCTCCCTGTCTCCGGGTAAATGA

5141_B17 (PGT-126) gamma heavy chain variable region nucleotide sequence:

(SEQ ID NO: 198)

CAGCCGCAGCTGCAGGAGTCGGGGCCAGGACTGGTGGAGGCTTCGGAGA
CCCTGTCCCTCACCTGCACTGTGTCCGGCGACTCCACTGCTGCTTGTGACT
ATTTCTGGGGCTGGGTCCGGCAGCCCCCAGGGAAGGGCCTGGAGTGGATT
GGGGGTTTGTCACATTGTGCAGGTTACTACAATACTGGCTGGACCTACCA
CAACCCGTCTCTCAAGAGTCGGCTCACGATTTCACTCGACACCCCCAAGA
ATCAGGTCTTCCTGAAGTTAAATTCTGTGACCGCCGCGGACACGGCCATTT
ACTACTGTGCGCGATTCGACGGCGAAGTTTTGGTGTACCACGATTGGCCA
AAGCCGGCCTGGGTCGACCTCTGGGGCCGGGGAACTTTGGTCACCGTCTC
CTCA

5141_B17 (PGT-126) gamma heavy chain amino acid sequence: expressed protein with variable region in bold.

(SEQ ID NO: 199)

MKHLWFFLLLVAAPRWVLS**QPQLQESGPGLVEASETLSLTCTVSGDSTA
ACDYFWGWVRQPPGKGLEWIGGLSHCAGYYNTGWTYHNPSLKSRLTIS
LDTPKNQVFLKLNSVTAADTAIYYCARFDGEVLVYHDWPKPAWVDLWG
RGTLVTVSS**ASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDK
RVEPKSCDKTHTCPPCPAPELLGGPSVFLFPPKPKDTLMISRTPEVTCVVVDVS

```
HEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQGNV
FSCSVMHEALHNHYTQKSLSLSPGK
```

5141_B17 (PGT-126) gamma heavy chain variable region amino acid sequence:
(Kabat CDRs underlined, Chothia CDRs in bold italics)

(SEQ ID NO: 200)
```
QPQLQESGPGLVEASETLSLTCTVSGDSTAACDYFWGWVRQPPGKGLEWIG**G
LSHCAGYYNTGWTY**HNPSLKSRLTISLDTPKNQVFLKLNSVTAADTAIYYCAR
FDGEVLVYHDWPKPAWVDLNGRGTLVTVSS
```

5141_B17 (PGT-126) gamma heavy chain Kabat CDRs:

(SEQ ID NO: 201)
CDR 1: ACDYFWG (SEQ ID NO: 202)
CDR 2: GLSHCAGYYNTGWTYHNPSLKS (SEQ ID NO: 203)
CDR 3: FDGEVLVYHDWPKPAWVDL

5141_B17 (PGT-126) gamma heavy chain Chothia CDRs:

(SEQ ID NO: 204)
CDR 1: GDSTAACD (SEQ ID NO: 205)
CDR 2: GLSHCAGYYNTGWTY (SEQ ID NO: 203)
CDR 3: FDGEVLVYHDWPKPAWVDL

5141_B17 (PGT-126) lambda light chain nucleotide sequence: coding sequence
(variable region in bold)

(SEQ ID NO: 206)
```
ATGGCCTGGGCTCTGCTCCTCCTCACCCTCCTCACTCAGGGCACAGGGGC
CTGGGCC**CAGTCTGCCCTGACTCAGCCTCCCTCCGCGTCCGGGTCTCC
TGGACAGTCAATCTCCATCTCCTGCACTGGAACCAGCAATAGGTTTG
TCTCCTGGTACCAGCAACACCCAGGCAAGGCCCCCAAACTCGTCATT
TATGGGGTCAATAAGCGCCCCTCAGGTGTCCCTGATCGTTTTTCTGG
CTCCAAGTCTGGCAACACGGCCTCCCTGACCGTCTCTGGGCTCCAGA
CTGACGATGAGGCTGTCTATTACTGCAGCTCACTTGTAGGCAACTGG
GATGTGATTTTCGGCGGAGGGACCAAGTTGACCGTCCTGGGTCAGCC**
CAAGGCTGCCCCCTCGGTCACTCTGTTCCCGCCCTCCTCTGAGGAGCTTCA
AGCCAACAAGGCCACACTGGTGTGTCTCATAAGTGACTTCTACCCGGGAG
CCGTGACAGTGGCCTGGAAGGCAGATAGCAGCCCCGTCAAGGCGGGAGT
GGAGACCACCACACCCTCCAAACAAAGCAACAACAAGTACGCGGCCAGC
AGCTACCTGAGCCTGACGCCTGAGCAGTGGAAGTCCCACAAAAGCTACA
GCTGCCAGGTCACGCATGAAGGGAGCACCGTGGAGAAGACAGTGGCCCC
TACAGAATGTTCATAG
```

5141_B17 (PGT-126) lambda light chain variable region nucleotide sequence:

(SEQ ID NO: 207)
```
CAGTCTGCCCTGACTCAGCCTCCCTCCGCGTCCGGGTCTCCTGGACAGTCA
ATCTCCATCTCCTGCACTGGAACCAGCAATAGGTTTGTCTCCTGGTACCAG
CAACACCCAGGCAAGGCCCCCAAACTCGTCATTTATGGGGTCAATAAGCG
CCCCTCAGGTGTCCCTGATCGTTTTTCTGGCTCCAAGTCTGGCAACACGGC
CTCCCTGACCGTCTCTGGGCTCCAGACTGACGATGAGGCTGTCTATTACTG
CAGCTCACTTGTAGGCAACTGGGATGTGATTTTCGGCGGAGGGACCAAGT
TGACCGTCCTG
```

5141_B17 (PGT-126) lambda light chain amino acid sequence: expressed protein with
variable region in bold.

(SEQ ID NO: 208)
```
MAWALLLLTLLTQGTGAWA**QSALTQPPSASGSPGQSISISCTGTSNRFVS
WYQQHPGKAPKLVIYGVNKRPSGVPDRFSGSKSGNTASLTVSGLQTDDE
AVYYCSSLVGNWDVIFGGGTKLTVL**GQPKAAPSVTLFPPSSEELQANKATL
VCLISDFYPGAVTVAWKADSSPVKAGVETTTPSKQSNNKYAASSYLSLTPEQ
WKSHKSYSCQVTHEGSTVEKTVAPTECS
```

5141_B17 (PGT-126) lambda light chain variable region amino acid sequence: (Kabat
CDRs underlined, Chothia CDRs in bold italics)

(SEQ ID NO: 209)
```
QSALTQPPSASGSPGQSISISCTGTSNRFVSWYQQHPGKAPKLVIYGVNKRPS
GVPDRFSGSKSGNTASLTVSGLQTDDEAVYYCSSLVGNWDVIFGGGTKLTVL
```

5141_B17 (PGT-126) lambda light chain Kabat CDRs:

CDR 1: TGTSNRFVS (SEQ ID NO: 210)

CDR 2: GVNKRPS (SEQ ID NO: 211)

CDR 3: SSLVGNWDVI (SEQ ID NO: 212)

5141_B17 (PGT-126) lambda light chain Chothia CDRs:

CDR 1: TGTSNRFVS (SEQ ID NO: 210)

CDR 2: GVNKRPS (SEQ ID NO: 211)

CDR 3: SSLVGNWDVI (SEQ ID NO: 212)

5147_N06 (PGT-130) gamma heavy chain nucleotide sequence: coding sequence (variable region in bold)

(SEQ ID NO: 213)

ATGAAACACCTGTGGTTCTTCCTCCTGCTGGTGGCGGCTCCCAGATGGGTC
CTGTCC**CAGGTGCAGCTGCAGGAGTCGGGCCCAGGACTGGTGAAGCC
TGCGGAGACCCTGTCCCTCACCTGCAGTGTCTCTGGAGAATCTATCA
ATACTGGTCATTACTACTGGGGCTGGGTCCGTCAGGTCCCAGGGAAG
GGACTTGAGTGGATAGGTCATATCCATTATACGACGGCTGTCCTGCA
CAACCCGTCCCTCAAGAGTCGACTCACCATCAAAATTTACACGTTGA
GAAACCAGATTACCCTGAGGCTCAGTAATGTGACGGCCGCGGACACG
GCCGTCTATCACTGCGTACGATCCGGCGGCGACATCTTATATTATTAT
GAGTGGCAAAAGCCGCACTGGTTCTCTCCCTGGGGCCCGGGAATCCA
CGTCACCGTCTCGAGC**GCCTCCACCAAGGGCCCATCGGTCTTCCCCCTG
GCACCCTCCTCCAAGAGCACCTCTGGGGGCACAGCGGCCCTGGGCTGCCT
GGTCAAGGACTACTTCCCCGAACCGGTGACGGTGTCGTGGAACTCAGGCG
CCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCAC
CCAGACCTACATCTGCAACGTGAATCACAAGCCCAGCAACACCAAGGTG
GACAAGAGAGTTGAGCCCAAATCTTGTGACAAAACTCACACATGCCCACC
GTGCCCAGCACCTGAACTCCTGGGGGGACCGTCAGTCTTCCTCTTCCCCCC
AAAACCCAAGGACACCCTCATGATCTCCCGGACCCCTGAGGTCACATGCG
TGGTGGTGGACGTGAGCCACGAAGACCCTGAGGTCAAGTTCAACTGGTAC
GTGGACGGCGTGGAGGTGCATAATGCCAAGACAAAGCCGCGGGAGGAGC
AGTACAACAGCACGTACCGTGTGGTCAGCGTCCTCACCGTCCTGCACCAG
GACTGGCTGAATGGCAAGGAGTACAAGTGCAAGGTCTCCAACAAAGCCC
TCCCAGCCCCCATCGAGAAAACCATCTCCAAAGCCAAAGGGCAGCCCCG
AGAACCACAGGTGTACACCCTGCCCCCATCCCGGGAGGAGATGACCAAG
AACCAGGTCAGCCTGACCTGCCTGGTCAAAGGCTTCTATCCCAGCGACAT
CGCCGTGGAGTGGGAGAGCAATGGGCAGCCGGAGAACAACTACAAGACC
ACGCCTCCCGTGCTGGACTCCGACGGCTCCTTCTTCCTCTATAGCAAGCTC
ACCGTGGACAAGAGCAGGTGGCAGCAGGGGAACGTCTTCTCATGCTCCGT
GATGCATGAGGCTCTGCACAACCACTACACGCAGAAGAGCCTCTCCCTGT
CTCCGGGTAAATGA

5147_N06 (PGT-130) gamma heavy chain variable region nucleotide sequence:

(SEQ ID NO: 214)

CAGGTGCAGCTGCAGGAGTCGGGCCCAGGACTGGTGAAGCCTGCGGAGA
CCCTGTCCCTCACCTGCAGTGTCTCTGGAGAATCTATCAATACTGGTCATT
ACTACTGGGGCTGGGTCCGTCAGGTCCCAGGGAAGGGACTTGAGTGGATA
GGTCATATCCATTATACGACGGCTGTCCTGCACAACCCGTCCCTCAAGAG
TCGACTCACCATCAAAATTTACACGTTGAGAAACCAGATTACCCTGAGGC
TCAGTAATGTGACGGCCGCGGACACGGCCGTCTATCACTGCGTACGATCC
GGCGGCGACATCTTATATTATTATGAGTGGCAAAAGCCGCACTGGTTCTC
TCCCTGGGGCCCGGGAATCCACGTCACCGTCTCGAGC

5147 N06 (PGT-130) gamma heavy chain amino acid sequence: expressed protein with variable region in bold.

(SEQ ID NO: 215)

**MKHLWFFLLLVAAPRWVLSQVQLQESGPGLVKPAETLSLTCSVSGESIN
TGHYYWGWVRQVPGKGLEWIGHIHYTTAVLHNPSLKSRLTIKIYTLRN
QITLRLSNVTAADTAVYHCVRSGGDILYYYEWQKPHWFSPWGPGIHVTV
SS**ASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKRVEPKSCD
KTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVM
HEALHNHYTQKSLSLSPGK

5147_N06 (PGT-130) gamma heavy chain variable region amino acid sequence:
(Kabat CDRs underlined, Chothia CDRs in bold italics)

(SEQ ID NO: 216)
QVQLQESGPGLVKPAETLSLTCSVS*GESINTGH*YYWGWVRQVPGKGLEWIG
*HIHYTTAVL*HNPSLKSRLTIKIYTLRNQITLRLSNVTAADTAVYHCVR***SGGDIL
YYYEWQKPHWFSP***WGPGIHVTVSS

5147_N06 (PGT-130) gamma heavy chain Kabat CDRs:

(SEQ ID NO: 217)
CDR 1: TGHYYWG (SEQ ID NO: 218)
CDR 2: HIHYTTAVLHNPSLKS (SEQ ID NO: 219)
CDR 3: SGGDILYYYEWQKPHWFSP

5147_N06 (PGT-130) gamma heavy chain Chothia CDRs:

(SEQ ID NO: 220)
CDR 1: GESINTGH (SEQ ID NO: 221)
CDR 2: HIHYTTAVL (SEQ ID NO: 219)
CDR 3: SGGDILYYYEWQKPHWFSP

5147_N06 (PGT-130) lambda light chain nucleotide sequence: coding sequence
(variable region in bold)

(SEQ ID NO: 222)
ATGGCCTGGGCTCTGCTCCTCCTCACCCTCCTCACTCAGGGCACAGGGTCC
TGGGCC**AGTCTGCCCTGACTCAGCCTCCCTCCGCGTCCGGGTCTCTT
GGACAGTCAGTCACCATCTCCTGCAATGGAACCAGCAGTGACATTGG
CGGTTGGAATTTTGTCTCCTGGTATCAACAGTTCCCGGGCAGAGCCC
CCAGACTCATTATTTTTGAGGTCAATAAGCGGCCCTCAGGGGTCCCT
GGTCGCTTCTCTGGCTCCAAGTCGGGCAATTCGGCCTCCCTGACCGT
CTCTGGGCTCCAGTCTGACGATGAGGGTCAATATTTCTGCAGTTCAC
TTTTCGGCAGGTGGGATGTTGTTTTTGGCGGGGGGACCAAGCTGACC
GTCCTA**GGTCAGCCCAAGGCTGCCCCCTCGGTCACTCTGTTCCCGCCCTC
CTCTGAGGAGCTTCAAGCCAACAAGGCCACACTGGTGTGTCTCATAAGTG
ACTTCTACCCGGGAGCCGTGACAGTGGCCTGGAAGGCAGATAGCAGCCCC
GTCAAGGCGGGAGTGGAGACCACCACACCCTCCAAACAAAGCAACAACA
AGTACGCGGCCAGCAGCTACCTGAGCCTGACGCCTGAGCAGTGGAAGTCC
CACAAAAGCTACAGCTGCCAGGTCACGCATGAAGGGAGCACCGTGGAGA
AGACAGTGGCCCCTACAGAATGTTCATAG

5147_N06 (PGT-130) lambda light chain variable region nucleotide sequence:
(SEQ ID NO: 223)
CAGTCTGCCCTGACTCAGCCTCCCTCCGCGTCCGGGTCTCTTGGACAGTCA
GTCACCATCTCCTGCAATGGAACCAGCAGTGACATTGGCGGTTGGAATTT
TGTCTCCTGGTATCAACAGTTCCCGGGCAGAGCCCCCAGACTCATTATTTT
TGAGGTCAATAAGCGGCCCTCAGGGGTCCCTGGTCGCTTCTCTGGCTCCA
AGTCGGGCAATTCGGCCTCCCTGACCGTCTCTGGGCTCCAGTCTGACGAT
GAGGGTCAATATTTCTGCAGTTCACTTTTCGGCAGGTGGGATGTTGTTTTT
GGCGGGGGGACCAAGCTGACCGTCCTA 5147_N06 (PGT-130) lambda light chain amino acid sequence: expressed protein with
variable region in bold.

(SEQ ID NO: 224)
MAWALLLLTLLTQGTGSWAQ**SALTQPPSASGSLGQSVTISCNGTSSDIGG
WNFVSWYQQFPGRAPRLIIFEVNKRPSGVPGRFSGSKSGNSASLTVSGLQ
SDDEGQYFCSSLFGRWDVVFGGGTKLTVL**GQPKAAPSVTLFPPSSEELQAN
KATLVCLISDFYPGAVTVAWKADSSPVKAGVETTTPSKQSNNKYAASSYLSL
TPEQWKSHKSYSCQVTHEGSTVEKTVAPTECS

5147_N06 (PGT-130) lambda light chain variable region amino acid sequence: (Kabat
CDRs underlined, Chothia CDRs in bold italics)

(SEQ ID NO: 225)
QSALTQPPSASGSLGQSVTISC*NGTSSDIGGWNFVS*WYQQFPGRAPRLIIF***EVN
KRPS*GVPGRFSGSKSGNSASLTVSGLQSDDEGQYFC*SSLFGRWDVV***FGGGTK
LTVL

5147_N06 (PGT-130) lambda light chain Kabat CDRs:

(SEQ ID NO: 226)
CDR 1: NGTSSDIGGWNFVS (SEQ ID NO: 227)
CDR 2: EVNKRPS (SEQ ID NO: 228)
CDR 3: SSLFGRWDVV

5147_N06 (PGT-130) lambda light chain Chothia CDRs:

(SEQ ID NO: 226)
CDR 1: NGTSSDIGGWNFVS (SEQ ID NO: 227)
CDR 2: EVNKRPS (SEQ ID NO: 228)
CDR 3: SSLFGRWDVV

5343_B08 (PGT-135) gamma heavy chain nucleotide sequence: coding sequence (variable region in bold)

(SEQ ID NO: 229)
ATGAAACACCTGTGGTTCTTCCTCTTGCTGGTGGCGGCTCCCAGATGGGTC
CTGTCC**CAGTTGCAGATGCAGGAGTCGGGCCCAGGACTGGTGAAGCC
TTCGGAGACCCTGTCTCTGAGTTGCACTGTCTCTGGTGACTCCATAA
GGGGTGGCGAGTGGGGCGATAAAGATTATCATTGGGGCTGGGTCCG
CCACTCAGCAGGAAAGGGCCTGGAGTGGATTGGGAGTATCCATTGGA
GGGGGACCACCCACTACAAAGAGTCCCTCAGGAGAAGAGTGAGTATG
TCGATCGACACGTCCAGGAATTGGTTCTCCCTGAGGCTGGCCTCTGT
GACCGCCGCGGACACGGCCGTCTACTTTTGTGCGAGACACCGACATC
ATGATGTTTTCATGTTGGTCCCTATTGCGGGCTGGTTCGACGTCTGG
GGCCCGGGAGTCCAGGTCACCGTCTCGAGC**GCCTCCACCAAGGGCCCA
TCGGTCTTCCCCCTGGCACCCTCCTCCAAGAGCACCTCTGGGGGCACAGC
GGCCCTGGGCTGCCTGGTCAAGGACTACTTCCCCGAACCGGTGACGGTGT
CGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCC
AGCAGCTTGGGCACCCAGACCTACATCTGCAACGTGAATCACAAGCCCAG
CAACACCAAGGTGGACAAGAGAGTTGAGCCCAAATCTTGTGACAAAACT
CACACATGCCCACCGTGCCCAGCACCTGAACTCCTGGGGGGACCGTCAGT
CTTCCTCTTCCCCCCAAAACCCAAGGACACCCTCATGATCTCCCGGACCCC
TGAGGTCACATGCGTGGTGGTGGACGTGAGCCACGAAGACCCTGAGGTCA
AGTTCAACTGGTACGTGGACGGCGTGGAGGTGCATAATGCCAAGACAAA
GCCGCGGGAGGAGCAGTACAACAGCACGTACCGTGTGGTCAGCGTCCTC
ACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCC
AAAGGGCAGCCCCGAGAACCACAGGTGTACACCCTGCCCCCATCCCGGG
AGGAGATGACCAAGAACCAGGTCAGCCTGACCTGCCTGGTCAAAGGCTTC
TATCCCAGCGACATCGCCGTGGAGTGGGAGAGCAATGGGCAGCCGGAGA
ACAACTACAAGACCACGCCTCCCGTGCTGGACTCCGACGGCTCCTTCTTC
CTCTATAGCAAGCTCACCGTGGACAAGAGCAGGTGGCAGCAGGGGAACG
TCTTCTCATGCTCCGTGATGCATGAGGCTCTGCACAACCACTACACGCAG
AAGAGCCTCTCCCTGTCTCCGGGTAAATGA

5343_B08 (PGT-135) gamma heavy chain variable region nucleotide sequence:

(SEQ ID NO: 230)
CAGTTGCAGATGCAGGAGTCGGGCCCAGGACTGGTGAAGCCTTCGGAGA
CCCTGTCTCTGAGTTGCACTGTCTCTGGTGACTCCATAAGGGGTGGCGAGT
GGGGCGATAAAGATTATCATTGGGGCTGGGTCCGCCACTCAGCAGGAAA
GGGCCTGGAGTGGATTGGGAGTATCCATTGGAGGGGGGACCACCCACTACA
AAGAGTCCCTCAGGAGAAGAGTGAGTATGTCGATCGACACGTCCAGGAA
TTGGTTCTCCCTGAGGCTGGCCTCTGTGACCGCCGCGGACACGGCCGTCT
ACTTTTGTGCGAGACACCGACATCATGATGTTTTCATGTTGGTCCCTATTG
CGGGCTGGTTCGACGTCTGGGGCCCGGGAGTCCAGGTCACCGTCTCGAGC

5343_B08 (PGT-135) gamma heavy chain amino acid sequence: expressed protein with variable region in bold.

(SEQ ID NO: 231)
**MKHLWFFLLLVAAPRWVLSQLQMQESGPGLVKPSETLSLSCTVSGDSIR
GGEWGDKDYHWGWVRHSAGKGLEWIGSIHWRGTTHYKESLRRRVSM
SIDTSRNWFSLRLASVTAADTAVYFCARHRHHDVFMLVPIAGWFDVWGP
GVQVTVSS**ASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKR
VEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQGNV
FSCSVMHEALHNHYTQKSLSLSPGK

5343_B08 (PGT-135) gamma heavy chain variable region amino acid sequence: (Kabat CDRs underlined, Chothia CDRs in bold italics)

(SEQ ID NO: 232)
QLQMQESGPGLVKPSETLSLSCTVS*GDSIR*<u>*GGEWGDKD*</u>YHWGWVRHSAGK
GLEWIG<u>*SIHWRGTTH*</u>YKESLRRRVSMSIDTSRNWFSLRLASVTAADTAVYFC
AR<u>*HRHHDVFMLVPIAGWFDV*</u>WGPGVQVTVSS

-continued

5343_B08 (PGT-135) gamma heavy chain Kabat CDRs:

(SEQ ID NO: 233)
CDR 1: GGEWGDKDYHWG (SEQ ID NO: 234)
CDR 2: SIHWRGTTHYKESLRR (SEQ ID NO: 235)
CDR 3: HRHHDVFMLVPIAGWFDV

5343_B08 (PGT-135) gamma heavy chain Chothia CDRs:

(SEQ ID NO: 236)
CDR 1: GDSIRGGEWGDKD (SEQ ID NO: 237)
CDR 2: SIHWRGTTH (SEQ ID NO: 235)
CDR 3: HRHHDVFMLVPIAGWFDV

5343_B08 (PGT-135) kappa light chain nucleotide sequence: coding sequence (variable region in bold)

(SEQ ID NO: 238)

ATGGAAACCCCAGCTCAGCTTCTCTTCCTCCTGCTACTCTGGCTCCCAGAT
ACCACTGGAGAAATTGTGATGACGCAGTCTCCCGACACCCTGTCTGTC
TCTCCAGGGGAGACAGTCACACTCTCCTGCAGGGCCAGTCAGAATAT
TAACAAGAATTTAGCCTGGTACCAATACAAACCTGGCCAGTCTCCCA
GGCTCGTAATTTTTGAAACATATAGCAAGATCGCTGCTTTCCCTGCCA
GGTTCGTTGCCAGTGGTTCTGGGACAGAGTTCACTCTCACCATCAAC
AACATGCAGTCTGAAGATGTTGCAGTTTATTACTGTCAACAATATGAA
GAGTGGCCTCGGACGTTCGGGCAAGGGACCAAGGTGGATATCAAACG
TACGGTGGCTGCACCATCTGTCTTCATCTTCCCGCCATCTGATGAGCAGTT
GAAATCTGGAACTGCCTCTGTTGTGTGCCTGCTGAATAACTTCTATCCCAG
AGAGGCCAAAGTACAGTGGAAGGTGGATAACGCCCTCCAATCGGGTAAC
TCCCAGGAGAGTGTCACAGAGCAGGACAGCAAGGACAGCACCTACAGCC
TCAGCAGCACCCTGACGCTGAGCAAAGCAGACTACGAGAAACACAAAGT
CTACGCCTGCGAAGTCACCCATCAGGGCCTGAGCTCGCCCGTCACAAAGA
GCTTCAACAGGGGAGAGTGTTAG

5343_B08 (PGT-135) kappa light chain variable region nucleotide sequence:

(SEQ ID NO: 239)

GAAATTGTGATGACGCAGTCTCCCGACACCCTGTCTGTCTCTCCAGGGGA
GACAGTCACACTCTCCTGCAGGGCCAGTCAGAATATTAACAAGAATTTAG
CCTGGTACCAATACAAACCTGGCCAGTCTCCCAGGCTCGTAATTTTTGAA
ACATATAGCAAGATCGCTGCTTTCCCTGCCAGGTTCGTTGCCAGTGGTTCT
GGGACAGAGTTCACTCTCACCATCAACAACATGCAGTCTGAAGATGTTGC
AGTTTATTACTGTCAACAATATGAAGAGTGGCCTCGGACGTTCGGGCAAG
GGACCAAGGTGGATATCAAA

5343_B08 (PGT-135) kappa light chain amino acid sequence: expressed protein with variable region in bold.

(SEQ ID NO: 240)

METPAQLLFLLLLWLPDTTGEIVMTQSPDTLSVSPGETVTLSCRASQNIN
KNLAWYQYKPGQSPRLVIFETYSKIAAFPARFVASGSGTEFTLTINNMQS
EDVAVYYCQQYEEWPRTFGQGTKVDIKRTVAAPSVFIFPPSDEQLKSGTAS
VVCLLNNFYPREAKVQWKVDNALQSGNSQESVTEQDSKDSTYSLSSTLTLSK
ADYEKHKVYACEVTHQGLSSPVTKSFNRGEC

5343_B08 (PGT-135) kappa light chain variable region amino acid sequence: (Kabat CDRs underlined, Chothia CDRs in bold italics)

(SEQ ID NO: 242)

EIVMTQSPDTLSVSPGETVTLSC<u>*RASQNINKNLA*</u>WYQYKPGQSPRLVIF<u>*ETYS*</u>
<u>*KIA*</u>AFPARFVASGSGTEFTLTINNMQSEDVAVYYC<u>*QQYEEWPRT*</u>FGQGTKVD
IK

5343_B08 (PGT-135) kappa light chain Kabat CDRs:

(SEQ ID NO: 243)
CDR 1: RASQNINKNLA (SEQ ID NO: 244)
CDR 2: ETYSKIA (SEQ ID NO: 245)
CDR 3: QQYEEWPRT

-continued

5343_B08 (PGT-135) kappa light chain Chothia CDRs:

CDR 1: RASQNINKNLA
(SEQ ID NO: 243)

CDR 2: ETYSKIA
(SEQ ID NO: 244)

CDR 3: QQYEEWPRT
(SEQ ID NO: 245)

5344_E16 (PGT-135) gamma heavy chain nucleotide sequence: coding sequence (variable region in bold)
(SEQ ID NO: 229)

ATGAAACACCTGTGGTTCTTCCTCTTGCTGGTGGCGGCTCCCAGATGGGTC
CTGTCC**CAGTTGCAGATGCAGGAGTCGGGCCCAGGACTGGTGAAGCC
TTCGGAGACCCTGTCTCTGAGTTGCACTGTCTCTGGTGACTCCATAA
GGGGTGGCGAGTGGGGCGATAAAGATTATCATTGGGGCTGGGTCCG
CCACTCAGCAGGAAAGGGCCTGGAGTGGATTGGGAGTATCCATTGGA
GGGGGACCACCCACTACAAAGAGTCCCTCAGGAGAAGAGTGAGTATG
TCGATCGACACGTCCAGGAATTGGTTCTCCCTGAGGCTGGCCTCTGT
GACCGCCGCGGACACGGCCGTCTACTTTTGTGCGAGACACCGACATC
ATGATGTTTTCATGTTGGTCCCTATTGCGGGCTGGTTCGACGTCTGG
GGCCCGGGAGTCCAGGTCACCGTCTCGAGC**GCCTCCACCAAGGGCCCA
TCGGTCTTCCCCCTGGCACCCTCCTCCAAGAGCACCTCTGGGGGCACAGC
GGCCCTGGGCTGCCTGGTCAAGGACTACTTCCCCGAACCGGTGACGGTGT
CGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCC
AGCAGCTTGGGCACCCAGACCTACATCTGCAACGTGAATCACAAGCCCAG
CAACACCAAGGTGGACAAGAGAGTTGAGCCCAAATCTTGTGACAAAACT
CACACATGCCCACCGTGCCCAGCACCTGAACTCCTGGGGGACCGTCAGT
CTTCCTCTTCCCCCCAAAACCCAAGGACACCCTCATGATCTCCCGGACCCC
TGAGGTCACATGCGTGGTGGTGGACGTGAGCCACGAAGACCCTGAGGTCA
AGTTCAACTGGTACGTGGACGGCGTGGAGGTGCATAATGCCAAGACAAA
GCCGCGGGAGGAGCAGTACAACAGCACGTACCGTGTGGTCAGCGTCCTC
ACCGTCCTGCACCAGGACTGGCTGAATGGCAAGGAGTACAAGTGCAAGG
TCTCCAACAAAGCCCTCCCAGCCCCCATCGAGAAACCATCTCCAAAGCC
AAAGGGCAGCCCCGAGAACCACAGGTGTACACCCTGCCCCCATCCCGGG
AGGAGATGACCAAGAACCAGGTCAGCCTGACCTGCCTGGTCAAAGGCTTC
TATCCCAGCGACATCGCCGTGGAGTGGGAGAGCAATGGGCAGCCGGAGA
ACAACTACAAGACCACGCCTCCCGTGCTGGACTCCGACGGCTCCTTCTTC
CTCTATAGCAAGCTCACCGTGGACAAGAGCAGGTGGCAGCAGGGGAACG
TCTTCTCATGCTCCGTGATGCATGAGGCTCTGCACAACCACTACACGCAG
AAGAGCCTCTCCCTGTCTCCGGGTAAATGA

5344_E16 (PGT-135) gamma heavy chain variable region nucleotide sequence:
(SEQ ID NO: 230)

CAGTTGCAGATGCAGGAGTCGGGCCCAGGACTGGTGAAGCCTTCGGAGA
CCCTGTCTCTGAGTTGCACTGTCTCTGGTGACTCCATAAGGGGTGGCGAGT
GGGGCGATAAAGATTATCATTGGGGCTGGGTCCGCCACTCAGCAGGAAA
GGGCCTGGAGTGGATTGGGAGTATCCATTGGAGGGGGACCACCCACTACA
AAGAGTCCCTCAGGAAGAGTGAGTATGTCGATCGACACGTCCAGGAA
TTGGTTCTCCCTGAGGCTGGCCTCTGTGACCGCCGCGGACACGGCCGTCT
ACTTTTGTGCGAGACACCGACATCATGATGTTTTCATGTTGGTCCCTATTG
CGGGCTGGTTCGACGTCTGGGGCCCGGGAGTCCAGGTCACCGTCTCGAGC

5344_E16 (PGT-135) gamma heavy chain amino acid sequence: expressed protein with variable region in bold.
(SEQ ID NO: 231)

**MKHLWFFLLLVAAPRWVLSQLQMQESGPGLVKPSETLSLSCTVSGDSIR
GGEWGDKDYHWGWVRHSAGKGLEWIGSIHWRGTTHYKESLRRRVSM
SIDTSRNWFSLRLASVTAADTAVYFCARHRHHDVFMLVPIAGWFDVWGP
GVQVTVSS**ASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKR
VEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQGNV
FSCSVMHEALHNHYTQKSLSLSPGK

5344_E16 (PGT-135) gamma heavy chain variable region amino acid sequence: (Kabat CDRs underlined, Chothia CDRs in bold italics)
(SEQ ID NO: 232)

QLQMQESGPGLVKPSETLSLSCTVS*GDSIR*<u>*GGEWGDKD*</u>YHWGWVRHSAGK
GLEWIG<u>*SIHWRGTTH*</u>YKESLRRRVSMSIDTSRNWFSLRLASVTAADTAVYFC
AR<u>*HRHHDVFMLVPIAGWFDV*</u>WGPGVQVTVSS

-continued

5344_E16 (PGT-135) gamma heavy chain Kabat CDRs:

(SEQ ID NO: 233)
CDR 1: GGEWGDKDYHWG (SEQ ID NO: 234)
CDR 2: SIHWRGTTHYKESLRR (SEQ ID NO: 235)
CDR 3: HRHHDVFMLVPIAGWFDV

5344_E16 (PGT-135) gamma heavy chain Chothia CDRs:

(SEQ ID NO: 236)
CDR 1: GDSIRGGEWGDKD (SEQ ID NO: 237)
CDR 2: SIHWRGTTH (SEQ ID NO: 235)
CDR 3: HRHHDVFMLVPIAGWFDV

5344_E16 (PGT-135) kappa light chain nucleotide sequence: coding sequence (variable region in bold)

(SEQ ID NO: 238)
ATGGAAACCCCAGCTCAGCTTCTCTTCCTCCTGCTACTCTGGCTCCCAGAT
ACCACTGGA**GAAATTGTGATGACGCAGTCTCCCGACACCCTGTCTGTC
TCTCCAGGGGAGACAGTCACACTCTCCTGCAGGGCCAGTCAGAATAT
TAACAAGAATTTAGCCTGGTACCAATACAAACCTGGCCAGTCTCCCA
GGCTCGTAATTTTTGAAACATATAGCAAGATCGCTGCTTTCCCTGCCA
GGTTCGTTGCCAGTGGTTCTGGGACAGAGTTCACTCTCACCATCAAC
AACATGCAGTCTGAAGATGTTGCAGTTTATTACTGTCAACAATATGAA
GAGTGGCCTCGGACGTTCGGGCAAGGGACCAAGGTGGATATCAAA**CG
TACGGTGGCTGCACCATCTGTCTTCATCTTCCCGCCATCTGATGAGCAGTT
GAAATCTGGAACTGCCTCTGTTGTGTGCCTGCTGAATAACTTCTATCCCAG
AGAGGCCAAAGTACAGTGGAAGGTGGATAACGCCCTCCAATCGGGTAAC
TCCCAGGAGAGTGTCACAGAGCAGGACAGCAAGGACAGCACCTACAGCC
TCAGCAGCACCCTGACGCTGAGCAAAGCAGACTACGAGAAACACAAAGT
CTACGCCTGCGAAGTCACCCATCAGGGCCTGAGCTCGCCCGTCACAAAGA
GCTTCAACAGGGGAGAGTGTTAG

5344_E16 (PGT-135) kappa light chain variable region nucleotide sequence:

(SEQ ID NO: 239)
GAAATTGTGATGACGCAGTCTCCCGACACCCTGTCTGTCTCTCCAGGGGA
GACAGTCACACTCTCCTGCAGGGCCAGTCAGAATATTAACAAGAATTTAG
CCTGGTACCAATACAAACCTGGCCAGTCTCCCAGGCTCGTAATTTTTGAA
ACATATAGCAAGATCGCTGCTTTCCCTGCCAGGTTCGTTGCCAGTGGTTCT
GGGACAGAGTTCACTCTCACCATCAACAACATGCAGTCTGAAGATGTTGC
AGTTTATTACTGTCAACAATATGAAGAGTGGCCTCGGACGTTCGGGCAAG
GGACCAAGGTGGATATCAAA

5344_E16 (PGT-135) kappa light chain amino acid sequence: expressed protein with variable region in bold.

(SEQ ID NO: 240)
**METPAQLLFLLLLWLPDTTGEIVMTQSPDTLSVSPGETVTLSCRASQNIN
KNLAWYQYKPGQSPRLVIFETYSKIAAFPARFVASGSGTEFTLTINNMQS
EDVAVYYCQQYEEWPRTFGQGTKVDIK**RTVAAPSVFIFPPSDEQLKSGTAS
VVCLLNNFYPREAKVQWKVDNALQSGNSQESVTEQDSKDSTYSLSSTLTLSK
ADYEKHKVYACEVTHQGLSSPVTKSFNRGEC

5344_E16 (PGT-135) kappa light chain variable region amino acid sequence: (Kabat CDRs underlined, Chothia CDRs in bold italics)

(SEQ ID NO: 242)
EIVMTQSPDTLSVSPGETVTLSC<u>*RASQNINKNLA*</u>WYQYKPGQSPRLVIF<u>***ETYS
KIA*</u>AFPARFVASGSGTEFTLTINNMQSEDVAVYYC<u>*QQYEEWPRT***</u>FGQGTKVD
IK

5344_E16 (PGT-135) kappa light chain Kabat CDRs:

(SEQ ID NO: 243)
CDR 1: RASQNINKNLA (SEQ ID NO: 244)
CDR 2: ETYSKIA (SEQ ID NO: 245)
CDR 3: QQYEEWPRT

5344_E16 (PGT-135) kappa light chain Chothia CDRs:

(SEQ ID NO: 243)
CDR 1: RASQNINKNLA (SEQ ID NO: 244)
CDR 2: ETYSKIA (SEQ ID NO: 245)
CDR 3: QQYEEWPRT

5329_C19 (PGT-136) gamma heavy chain nucleotide sequence: coding sequence (variable region in bold)

(SEQ ID NO: 246)

ATGAAACACCTGTGGTTCTTCCTCCTGCTAGTGGCGGCTCCCAGATGGGTC
CTGTCG**CAGCTGCAGTTGCAGGAATCGGGCCCAGGACTGGTGAAGCC
TTCGGAGACCCTGTCCCTGACTTGCACAGTTTCTGGTGGCTCCATGA
GGGGCACCGACTGGGGCGAGAATGACTTCCACTACGGCTGGATCCG
CCAGTCCTCCGCAAAGGGGCTGGAGTGGATTGGGAGCATCCATTGGA
GGGGGAGGACCACCCACTACAAGACGTCCTTCAGGAGTCGGGCCAC
CTTGTCGATAGACACGTCCAATAATCGCTTCTCCCTGACGTTTAGTTT
TGTGACCGCCGCGGACACGGCCGTCTACTATTGTGCGAGACATAAAT
ATCATGATATTTTCAGGGTGGTCCCTGTTGCGGGCTGGTTCGACCCC
TGGGGCCAGGGATTACTGGTCACCGTCTCGAG**CGCCTCCACCAAGGGC
CCATCGGTCTTCCCCCTGGCACCCTCCTCCAAGAGCACCTCTGGGGCAC
AGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCT
GTCCTACAGTCCTCAGGACTCTACTCCCTCAGCAGCGTGGTGACCGTGCC
CTCCAGCAGCTTGGGCACCCAGACCTACATCTGCAACGTGAATCACAAGC
CCAGCAACACCAAGGTGGACAAGAGAGTTGAGCCCAAATCTTGTGACAA
AACTCACACATGCCCACCGTGCCCAGCACCTGAACTCCTGGGGGGACCGT
CAGTCTTCCTCTTCCCCCCAAAACCCAAGGACACCCTCATGATCTCCCGGA
CCCCTGAGGTCACATGCGTGGTGGTGGACGTGAGCCACGAAGACCCTGAG
GTCAAGTTCAACTGGTACGTGGACGGCGTGGAGGTGCATAATGCCAAGAC
AAAGCCGCGGGAGGAGCAGTACAACAGCACGTACCGTGTGGTCAGCGTC
CTCACCGTCCTGCACCAGGACTGGCTGAATGGCAAGGAGTACAAGTGCAA
GGTCTCCAACAAAGCCCTCCCAGCCCCCATCGAGAAAACCATCTCCAAAG
CCAAAGGGCAGCCCCGAGAACCACAGGTGTACACCCTGCCCCCATCCCGG
GAGGAGATGACCAAGAACCAGGTCAGCCTGACCTGCCTGGTCAAAGGCT
TCTATCCCAGCGACATCGCCGTGGAGTGGGAGAGCAATGGGCAGCCGGA
GAACAACTACAAGACCACGCCTCCCGTGCTGGACTCCGACGGCTCCTTCT
TCCTCTATAGCAAGCTCACCGTGGACAAGAGCAGGTGGCAGCAGGGGAA
CGTCTTCTCATGCTCCGTGATGCATGAGGCTCTGCACAACCACTACACGC
AGAAGAGCCTCTCCCTGTCTCCGGGTAAATGA

5329_C19 (PGT-136) gamma heavy chain variable region nucleotide sequence:

(SEQ ID NO: 247)

CAGCTGCAGTTGCAGGAATCGGGCCCAGGACTGGTGAAGCCTTCGGAGA
CCCTGTCCCTGACTTGCACAGTTTCTGGTGGCTCCATGAGGGGCACCGACT
GGGGCGAGAATGACTTCCACTACGGCTGGATCCGCCAGTCCTCCGCAAAG
GGGCTGGAGTGGATTGGGAGCATCCATTGGAGGGGGAGGACCACCCACT
ACAAGACGTCCTTCAGGAGTCGGGCCACCTTGTCGATAGACACGTCCAAT
AATCGCTTCTCCCTGACGTTTAGTTTTGTGACCGCCGCGGACACGGCCGTC
TACTATTGTGCGAGACATAAATATCATGATATTTTCAGGGTGGTCCCTGTT
GCGGGCTGGTTCGACCCCTGGGGCCAGGGATTACTGGTCACCGTCTCGAG
C

5329_C19 (PGT-136) gamma heavy chain amino acid sequence: expressed protein with variable region in bold.

(SEQ ID NO: 248)

**MKHLWFFLLLVAAPRWVLSQLQLQESGPGLVKPSETLSLTCTVSGGSM
RGTDWGENDFHYGWIRQSSAKGLEWIGSIHWRGRTTHYKTSFRSRATLS
IDTSNNRFSLTFSFVTAADTAVYYCARHKYHDIFRVVPVAGWFDPWGQG
LLVTVSS**ASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVE
PKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNVFS
CSVMHEALHNHYTQKSLSLSPGK

5329_C19 (PGT-136) gamma heavy chain variable region amino acid sequence: (Kabat CDRs underlined, Chothia CDRs in bold italics)

(SEQ ID NO: 249)

QLQLQESGPGLVKPSETLSLTCTVS*GGSM<u>RGTDWGEND</u>*FHYGWIRQSSAKG
LEWIG*<u>SIHWRGRTTH</u>*YKTSFRSRATLSIDTSNNRFSLTFSFVTAADTAVYYCA
R*<u>HKYHDIFRVVPVAGWFDP</u>*WGQGLLVTVSS

-continued

5329_C19 (PGT-136) gamma heavy chain Kabat CDRs:

(SEQ ID NO: 250)
CDR 1: GTDWGENDFHYG (SEQ ID NO: 251)
CDR 2: SIHWRGRTTHYKTSFRS (SEQ ID NO: 252)
CDR 3: HKYHDIFRVVPVAGWFDP

5329_C19 (PGT-136) gamma heavy chain Chothia CDRs:

(SEQ ID NO: 253)
CDR 1: GGSMRGTDWGEND (SEQ ID NO: 254)
CDR 2: SIHWRGRTTH (SEQ ID NO: 252)
CDR 3: HKYHDIFRVVPVAGWFDP

5329_C19 (PGT-136) kappa light chain nucleotide sequence: coding sequence
(variable region in bold)

(SEQ ID NO: 255)
ATGGAAACCCCAGCTCAGCTTCTCTTCCTCCTGCTACTCTGGCTCCCAGAT
AGCACTGGA**GAAATAGTGATGACGCAGTCTCCACCCACCCTGTCTGTG
TCTCCAGGGGAAACAGCCACACTCTCCTGTAGGGCCAGTCAGAATGT
TAAGAATAATTTAGCCTGGTACCAGCTGAAACCTGGCCAGGCTCCCA
GGCTCCTCATCTTTGATGCGTCCAGCAGGGCCGGTGGTATTCCTGAC
AGGTTCAGTGGCAGCGGTTATGGGACAGACTTCACTCTCACCGTCAA
CAGTGTGCAGTCCGAAGATTTTGGAGATTATTTTTGTCAGCAATATGA
AGAGTGGCCTCGGACGTTCGGCCAAGGGACCAAGGTGGATATCAAA**C
GTACGGTGGCTGCACCATCTGTCTTCATCTTCCCGCCATCTGATGAGCAGT
TGAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAAG
AGCTTCAACAGGGGAGAGTGTTAG

5329_C19 (PGT-136) kappa light chain variable region nucleotide sequence:

(SEQ ID NO: 256)
GAAATAGTGATGACGCAGTCTCCACCCACCCTGTCTGTGTCTCCAGGGGA
AACAGCCACACTCTCCTGTAGGGCCAGTCAGAATGTTAAGAATAATTTAG
CCTGGTACCAGCTGAAACCTGGCCAGGCTCCCAGGCTCCTCATCTTTGAT
GCGTCCAGCAGGGCCGGTGGTATTCCTGACAGGTTCAGTGGCAGCGGTTA
TGGGACAGACTTCACTCTCACCGTCAACAGTGTGCAGTCCGAAGATTTTG
GAGATTATTTTTGTCAGCAATATGAAGAGTGGCCTCGGACGTTCGGCCAA
GGGACCAAGGTGGATATCAAA

5329_C19 (PGT-136) kappa light chain amino acid sequence: expressed protein with
variable region in bold.

(SEQ ID NO: 257)
**METPAQLLFLLLLWLPDSTGEIVMTQSPPTLSVSPGETATLSCRASQNVK
NNLAWYQLKPGQAPRLLIFDASSRAGGIPDRFSGSGYGTDFTLTVNSVQS
EDFGDYFCQQYEEWPRTFGQGTKVDIK**RTVAAPSVFIFPPSDEQLKSGTAS
VVCLLNNFYPREAKVQWKVDNALQSGNSQESVTEQDSKDSTYSLSSTLTLSK
ADYEKHKVYACEVTHQGLSSPVTKSFNRGEC

5329_C19 (PGT-136) kappa light chain variable region amino acid sequence: (Kabat
CDRs underlined, Chothia CDRs in bold italics)

(SEQ ID NO: 258)
EIVMTQSPPTLSVSPGETATLSC<u>*RASQNVKNNLA*</u>WYQLKPGQAPRLLIF<u>***DASS
RAG*</u>GIPDRFSGSGYGTDFTLTVNSVQSEDFGDYFC<u>*QQYEEWPRT***</u>FGQGTKVD
IK

5329_C19 (PGT-136) kappa light chain Kabat CDRs:

(SEQ ID NO: 259)
CDR 1: RASQNVKNNLA (SEQ ID NO: 260)
CDR 2: DASSRAG (SEQ ID NO: 245)
CDR 3: QQYEEWPRT

5329_C19 (PGT-136) kappa light chain Chothia CDRs:

(SEQ ID NO: 259)
CDR 1: RASQNVKNNLA (SEQ ID NO: 260)
CDR 2: DASSRAG (SEQ ID NO: 245)
CDR 3: QQYEEWPRT

5366_P21 (PGT-136) gamma heavy chain nucleotide sequence: coding sequence (variable region in bold)

(SEQ ID NO: 246)

ATGAAACACCTGTGGTTCTTCCTCCTGCTAGTGGCGGCTCCCAGATGGGTC
CTGTCG**CAGCTGCAGTTGCAGGAATCGGGCCCAGGACTGGTGAAGCC
TTCGGAGACCCTGTCCCTGACTTGCACAGTTTCTGGTGGCTCCATGA
GGGGCACCGACTGGGGCGAGAATGACTTCCACTACGGCTGGATCCG
CCAGTCCTCCGCAAAGGGGCTGGAGTGGATTGGGAGCATCCATTGGA
GGGGGAGGACCACCCACTACAAGACGTCCTTCAGGAGTCGGGCCAC
CTTGTCGATAGACACGTCCAATAATCGCTTCTCCCTGACGTTTAGTTT
TGTGACCGCCGCGGACACGGCCGTCTACTATTGTGCGAGACATAAAT
ATCATGATATTTTCAGGGTGGTCCCTGTTGCGGGCTGGTTCGACCCC
TGGGGCCAGGGATTACTGGTCACCGTCTCGAG**CGCCTCCACCAAGGGC
CCATCGGTCTTCCCCCTGGCACCCTCCTCAAGAGCACCTCTGGGGCAC
AGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCT
GTCCTACAGTCCTCAGGACTCTACTCCCTCAGCAGCGTGGTGACCGTGCC
CTCCAGCAGCTTGGGCACCCAGACCTACATCTGCAACGTGAATCACAAGC
CCAGCAACACCAAGGTGGACAAGAGAGTTGAGCCCAAATCTTGTGACAA
AACTCACACATGCCCACCGTGCCCAGCACCTGAACTCCTGGGGGGACCGT
CAGTCTTCCTCTTCCCCCCAAAACCCAAGGACACCCTCATGATCTCCCGGA
CCCCTGAGGTCACATGCGTGGTGGTGGACGTGAGCCACGAAGACCCTGAG
GTCAAGTTCAACTGGTACGTGGACGGCGTGGAGGTGCATAATGCCAAGAC
AAAGCCGCGGGAGGAGCAGTACAACAGCACGTACCGTGTGGTCAGCGTC
CTCACCGTCCTGCACCAGGACTGGCTGAATGGCAAGGAGTACAAGTGCAA
GGTCTCCAACAAAGCCCTCCCAGCCCCCATCGAGAAAACCATCTCCAAAG
CCAAAGGGCAGCCCCGAGAACCACAGGTGTACACCCTGCCCCCATCCCGG
GAGGAGATGACCAAGAACCAGGTCAGCCTGACCTGCCTGGTCAAAGGCT
TCTATCCCAGCGACATCGCCGTGGAGTGGGAGAGCAATGGGCAGCCGGA
GAACAACTACAAGACCACGCCTCCCGTGCTGGACTCCGACGGCTCCTTCT
TCCTCTATAGCAAGCTCACCGTGGACAAGAGCAGGTGGCAGCAGGGGAA
CGTCTTCTCATGCTCCGTGATGCATGAGGCTCTGCACAACCACTACACGC
AGAAGAGCCTCTCCCTGTCTCCGGGTAAATGA

5366_P21 (PGT-136) gamma heavy chain variable region nucleotide sequence:

(SEQ ID NO: 247)
CAGCTGCAGTTGCAGGAATCGGGCCCAGGACTGGTGAAGCCTTCGGAGA
CCCTGTCCCTGACTTGCACAGTTTCTGGTGGCTCCATGAGGGGCACCGACT
GGGGCGAGAATGACTTCCACTACGGCTGGATCCGCCAGTCCTCCGCAAAG
GGGCTGGAGTGGATTGGGAGCATCCATTGGAGGGGGAGGACCACCCACT
ACAAGACGTCCTTCAGGAGTCGGGCCACCTTGTCGATAGACACGTCCAAT
AATCGCTTCTCCCTGACGTTTAGTTTTGTGACCGCCGCGGACACGGCCGTC
TACTATTGTGCGAGACATAAATATCATGATATTTTCAGGGTGGTCCCTGTT
GCGGGCTGGTTCGACCCCTGGGGCCAGGGATTACTGGTCACCGTCTCGAG
C

5366_P21 (PGT-136) gamma heavy chain amino acid sequence: expressed protein with variable region in bold.

(SEQ ID NO: 248)
**MKHLWFFLLLVAAPRWVLSQLQLQESGPGLVKPSETLSLTCTVSGGSM
RGTDWGENDFHYGWIRQSSAKGLEWIGSIHWRGRTTHYKTSFRSRATLS
IDTSNNRFSLTFSFVTAADTAVYYCARHKYHDIFRVVPVAGWFDPWGQG
LLVTVSS**ASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVE
PKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNVFS
CSVMHEALHNHYTQKSLSLSPGK

5366_P21 (PGT-136) gamma heavy chain variable region amino acid sequence: (Kabat CDRs underlined, Chothia CDRs in bold italics)

(SEQ ID NO: 249)
QLQLQESGPGLVKPSETLSLTCTVS*GGSM**RGTDWGEND*FHYGWIRQSSAKG
LEWIG*SIHWRGRTTH*YKTSFRSRATLSIDTSNNRFSLTFSFVTAADTAVYYCA
R*HKYHDIFRVVPVAGWFDP*WGQGLLVTVSS

-continued

5366_P21 (PGT-136) gamma heavy chain Kabat CDRs:

(SEQ ID NO: 250)
CDR 1: GTDWGENDFHYG (SEQ ID NO: 251)
CDR 2: SIHWRGRTTHYKTSFRS (SEQ ID NO: 252)
CDR 3: HKYHDIFRVVPVAGWFDP

5366_P21 (PGT-136) gamma heavy chain Chothia CDRs:

(SEQ ID NO: 253)
CDR 1: GGSMRGTDWGEND (SEQ ID NO: 254)
CDR 2: SIHWRGRTTH (SEQ ID NO: 252)
CDR 3: HKYHDIFRVVPVAGWFDP

5366_P21 (PGT-136) kappa light chain nucleotide sequence: coding sequence
(variable region in bold)

(SEQ ID NO: 255)
ATGGAAACCCCAGCTCAGCTTCTCTTCCTCCTGCTACTCTGGCTCCCAGAT
AGCACTGGAGAAATAGTGATGACGCAGTCTCCACCCACCCTGTCTGTG
TCTCCAGGGGAAACAGCCACACTCTCCTGTAGGGCCAGTCAGAATGT
TAAGAATAATTTAGCCTGGTACCAGCTGAAACCTGGCCAGGCTCCCA
GGCTCCTCATCTTTGATGCGTCCAGCAGGGCCGGTGGTATTCCTGAC
AGGTTCAGTGGCAGCGGTTATGGGACAGACTTCACTCTCACCGTCAA
CAGTGTGCAGTCCGAAGATTTTGGAGATTATTTTTGTCAGCAATATGA
AGAGTGGCCTCGGACGTTCGGCCAAGGGACCAAGGTGGATATCAAAC
GTACGGTGGCTGCACCATCTGTCTTCATCTTCCCGCCATCTGATGAGCAGT
TGAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAAG
AGCTTCAACAGGGGAGAGTGTTAG

5366_P21 (PGT-136) kappa light chain variable region nucleotide sequence:

(SEQ ID NO: 256)
GAAATAGTGATGACGCAGTCTCCACCCACCCTGTCTGTGTCTCCAGGGGA
AACAGCCACACTCTCCTGTAGGGCCAGTCAGAATGTTAAGAATAATTTAG
CCTGGTACCAGCTGAAACCTGGCCAGGCTCCCAGGCTCCTCATCTTTGAT
GCGTCCAGCAGGGCCGGTGGTATTCCTGACAGGTTCAGTGGCAGCGGTTA
TGGGACAGACTTCACTCTCACCGTCAACAGTGTGCAGTCCGAAGATTTTG
GAGATTATTTTTGTCAGCAATATGAAGAGTGGCCTCGGACGTTCGGCCAA
GGGACCAAGGTGGATATCAAA

5366_P21 (PGT-136) kappa light chain amino acid sequence: expressed protein with
variable region in bold.

(SEQ ID NO: 257)
METPAQLLFLLLLWLPDSTGEIVMTQSPPTLSVSPGETATLSCRASQNVK
NNLAWYQLKPGQAPRLLIFDASSRAGGIPDRFSGSGYGTDFTLTVNSVQS
EDFGDYFCQQYEEWPRTFGQGTKVDIKRTVAAPSVFIFPPSDEQLKSGTAS
VVCLLNNFYPREAKVQWKVDNALQSGNSQESVTEQDSKDSTYSLSSTLTLSK
ADYEKHKVYACEVTHQGLSSPVTKSFNRGEC

5366_P21 (PGT-136) kappa light chain variable region amino acid sequence: (Kabat
CDRs underlined, Chothia CDRs in bold italics)

(SEQ ID NO: 258)
EIVMTQSPPTLSVSPGETATLSC<u>*RASQNVKNNLA*</u>WYQLKPGQAPRLLIF*<u>DASS</u>*
*<u>RAG</u>*GIPDRFSGSGYGTDFTLTVNSVQSEDFGDYFC*<u>QQYEEWPRT</u>*FGQGTKVD
IK

5366_P21 (PGT-136) kappa light chain Kabat CDRs:

(SEQ ID NO: 259)
CDR 1: RASQNVKNNLA (SEQ ID NO: 260)
CDR 2: DASSRAG (SEQ ID NO: 245)
CDR 3: QQYEEWPRT

-continued

5366_P21 (PGT-136) kappa light chain Chothia CDRs:

(SEQ ID NO: 259)
CDR 1: RASQNVKNNLA (SEQ ID NO: 260)
CDR 2: DASSRAG (SEQ ID NO: 245)
CDR 3: QQYEEWPRT

4964_G22 (PGT-141) gamma heavy chain nucleotide sequence: coding sequence (variable region in bold)

(SEQ ID NO: 273)
ATGGACTGGATTTGGAGGATCCTCTTCTTGGTGGCAGCAGTTGCAAGTGC
CCACTCG**CAGGTGCAGCTGGTGCAGTCTGGGCCGGAGGTGAAGAAGC
CTGGGTCCTCAGTGAAGGTCTCCTGCAAGGCCTCTGGAAACACCTTC
AGTAAATATGATGTCCACTGGGTACGACAGGCCACTGGACAGGGGCT
TGAATGGGTGGGATGGATGAGTCATGAGGGTGATAAGACAGAATCTG
CACAGAGATTTAAGGGCCGAGTCACCTTCACGAGGGACACTTCCGCA
AGCACAGCCTACATGGAACTGCGCGGCCTGACATCTGACGACACGGC
CATCTATTATTGTACGAGAGGCTCAAAACATCGTTTGCGAGACTACGT
TCTCTACGATGACTACGGCTTAATTAATTATCAAGAGTGGAATGACTA
CCTTGAATTTTTGGACGTCTGGGGCCATGGAACCGCGGTCACCGTCT
CCTCA**GCCTCCACCAAGGGCCCATCGGTCTTCCCCCTGGCACCCTCCTCC
AAGAGCACCTCTGGGGGCACAGCGGCCCTGGGCTGCCTGGTCAAGGACT
ACTTCCCCGAACCGGTGACGGTGTCGTGGAACTCAGGCGCCCTGACCAGC
GGCGTGCACACCTTCCCGGCTGTCCTACAGTCCTCAGGACTCTACTCCCTC
AGCAGCGTGGTGACCGTGCCCTCCAGCAGCTTGGGCACCCAGACCTACAT
CTGCAACGTGAATCACAAGCCCAGCAACACCAAGGTGGACAAGAGAGTT
GAGCCCAAATCTTGTGACAAAACTCACACATGCCCACCGTGCCCAGCACC
TGAACTCCTGGGGGGACCGTCAGTCTTCCTCTTCCCCCCAAAACCCAAGG
ACACCCTCATGATCTCCCGGACCCCTGAGGTCACATGCGTGGTGGTGGAC
GTGAGCCACGAAGACCCTGAGGTCAAGTTCAACTGGTACGTGGACGGCGT
GGAGGTGCATAATGCCAAGACAAAGCCGCGGGAGGAGCAGTACAACAGC
ACGTACCGTGTGGTCAGCGTCCTCACCGTCCTGCACCAGGACTGGCTGAA
TGGCAAGGAGTACAAGTGCAAGGTCTCCAACAAAGCCCTCCCAGCCCCCA
TCGAGAAAACCATCTCCAAAGCCAAAGGGCAGCCCCGAGAACCACAGGT
GTACACCCTGCCCCCATCCCGGGAGGAGATGACCAAGAACCAGGTCAGC
CTGACCTGCCTGGTCAAAGGCTTCTATCCCAGCGACATCGCCGTGGAGTG
GGAGAGCAATGGGCAGCCGGAGAACAACTACAAGACCACGCCTCCCGTG
CTGGACTCCGACGGCTCCTTCTTCCTCTATAGCAAGCTCACCGTGGACAA
GAGCAGGTGGCAGCAGGGGAACGTCTTCTCATGCTCCGTGATGCATGAGG
CTCTGCACAACCACTACACGCAGAAGAGCCTCTCCCTGTCTCCGGGTAAA
TGA

4964_G22 (PGT-141) gamma heavy chain variable region nucleotide sequence:

(SEQ ID NO: 274)
**CAGGTGCAGCTGGTGCAGTCTGGGCCGGAGGTGAAGAAGCCTGGGT
CCTCAGTGAAGGTCTCCTGCAAGGCCTCTGGAAACACCTTCAGTAAA
TATGATGTCCACTGGGTACGACAGGCCACTGGACAGGGGCTTAATG
GGTGGGATGGATGAGTCATGAGGGTGATAAGACAGAATCTGCACAGA
GATTTAAGGGCCGAGTCACCTTCACGAGGGACACTTCCGAAGCACA
GCCTACATGGAACTGCGCGGCCTGACATCTGACGACACGGCCATCTA
TTATTGTACGAGAGGCTCAAAACATCGTTTGCGAGACTACGTTCTCTA
CGATGACTACGGCTTAATTAATTATCAAGAGTGGAATGACTACCTTGA
ATTTTTGGACGTCTGGGGCCATGGAACCGCGGTCACCGTCTCCTCA**

4964_G22 (PGT-141) gamma heavy chain amino acid sequence: expressed protein with leader sequence in italics and variable region in bold.

(SEQ ID NO: 275)
*MDWIWRILFLVAAVASAHS***QVQLVQSGPEVKKPGSSVKVSCKASGNTFSKY
DVHWVRQATGQGLEWVGWMSHEGDKTESAQRFKGRVTFTRDTSASTA
YMELRGLTSDDTAIYYCTRGSKHRLRDYVLYDDYGLINYQEWNDYLEFL
DVWGHGTAVTVSS**ASTKGPSVFPLAPSSKSTSGGTAALGCLVKDYFPEPVTV
SWNSGALTSGVHTFPAVLQSSGLYSLSSVVTVPSSSLGTQTYICNVNHKPSNT
KVDKRVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVS
LTCLVKGFYPSDIAVEWESNGQPENNYKTTPPVLDSDGSFFLYSKLTVDKSR
WQQGNVFSCSVMHEALHNHYTQKSLSLSPGK

4964_G22 (PGT-141) gamma heavy chain variable region amino acid sequence: (Kabat CDRs underlined, Chothia CDRs in bold italics)

(SEQ ID NO: 276)
QVQLVQSGPEVKKPGSSVKVSCKAS*GNTFSK*YDVHWVRQATGQGLEWVG
*WMSHEGDKTE*SAQRFKGRVTFTRDTSASTAYMELRGLTSDDTAIYYCTR***GS
KHRLRDYVLYDDYGLINYQEWNDYLEFLDV***WGHGTAVTVSS

-continued

4964_G22 (PGT-141) gamma heavy chain Kabat CDRs:

(SEQ ID NO: 277)
CDR 1: KYDVH (SEQ ID NO: 278)
CDR 2: WMSHEGDKTESAQRFKG (SEQ ID NO: 279)
CDR 3: GSKHRLRDYVLYDDYGLINYQEWNDYLEFLDV

4964_G22 (PGT-141) gamma heavy chain Chothia CDRs:

(SEQ ID NO: 280)
CDR 1: GNTFSK (SEQ ID NO: 281)
CDR 2: WMSHEGDKTE (SEQ ID NO: 279)
CDR 3: GSKHRLRDYVLYDDYGLINYQEWNDYLEFLDV

4964_G22 (PGT-141) kappa light chain nucleotide sequence: coding sequence (variable region in bold)

(SEQ ID NO: 282)
ATGAGGCTCCCTGCTCAGCTCCTGGGGCTGCTAATGCTCTGGGTCTCTGGA
TCCAGTGCG**GATACTGTCGTGACTCAGTCTCCACTCTCCCTGCCCGTC
ACCCCTGGAGAGGCGGCCTCCATGTCCTGTTCGTCGACTCAGAGCCT
CCGGCATAGTAATGGAGCCAACTATTTGGCTTGGTATCAGCACAAAC
CGGGGCAGTCTCCACGACTCCTAATCCGTTTAGGTTCTCAACGGGGCC
TCCGGGGTCCCTGACAGATTCAGTGGCAGTGGATCAGGCACTCATTT
TACACTGAAAATCAGTAGAGTGGAGGCTGAAGATGCTGCAATTTATT
ATTGCATGCAAGGTCTGAACCGTCCCTGGACGTTCGGCAAGGGGACC
AAGTTGGAAATCAAA**CGTACGGTGGCTGCACCATCTGTCTTCATCTTCCC
GCCATCTGATGAGCAGTTGAAATCTGGAACTGCCTCTGTTGTGTGCCTGCT
GAATAACTTCTATCCCAGAGAGGCCAAAGTACAGTGGAAGGTGGATAAC
GCCCTCCAATCGGGTAACTCCCAGGAGAGTGTCACAGAGCAGGACAGCA
AGGACAGCACCTACAGCCTCAGCAGCACCCTGACGCTGAGCAAAGCAGA
CTACGAGAAACACAAAGTCTACGCCTGCGAAGTCACCCATCAGGGCCTGA
GCTCGCCCGTCACAAAGAGCTTCAACAGGGGAGAGTGTTAG

4964_G22 (PGT-141) kappa light chain variable region nucleotide sequence:

(SEQ ID NO: 283)
**GATACTGTCGTGACTCAGTCTCCACTCTCCCTGCCCGTCACCCCTGG
AGAGGCGGCCTCCATGTCCTGTTCGTCGACTCAGAGCCTCCGGCATA
GTAATGGAGCCAACTATTTGGCTTGGTATCAGCACAAACCGGGGCAG
TCTCCACGACTCCTAATCCGTTTAGGTTCTCAACGGGCCTCCGGGGT
CCCTGACAGATTCAGTGGCAGTGGATCAGGCACTCATTTTACACTGA
AAATCAGTAGAGTGGAGGCTGAAGATGCTGCAATTTATTATTGCATG
CAAGGTCTGAACCGTCCCTGGACGTTCGGCAAGGGGACCAAGTTGGA
AATCAAA**

4964_G22 (PGT-141) kappa light chain amino acid sequence: expressed protein with leader sequence in italics and variable region in bold.

(SEQ ID NO: 284)
*MRLPAQLLGLLMLWVSGSSA***DTVVTQSPLSLPVTPGEAASMSCSSTQSLRHS
NGANYLAWYQHKPGQSPRLLIRLGSQRASGVPDRFSGSGSGTHFTLKISR
VEAEDAAIYYCMQGLNRPWTFGKGTKLEIK**RTVAAPSVFIFPPSDEQLKSG
TASVVCLLNNFYPREAKVQWKVDNALQSGNSQESVTEQDSKDSTYSLSSTLT
LSKADYEKHKVYACEVTHQGLSSPVTKSFNRGEC

4964_G22 (PGT-141) kappa light chain variable region amino acid sequence: (Kabat CDRs underlined, Chothia CDRs in bold italics)

(SEQ ID NO: 285)
DTVVTQSPLSLPVTPGEAASMSC<u>*SSTQSLRHSNGANYLA*</u>WYQHKPGQSPRLLI
R<u>*LGSQRAS*</u>GVPDRFSGSGSGTHFTLKISRVEAEDAAIYYC<u>*MQGLNRPWT*</u>FGK
GTKLEIK

4964_G22 (PGT-141) kappa light chain Kabat CDRs:

(SEQ ID NO: 286)
CDR 1: SSTQSLRHSNGANYLA (SEQ ID NO: 287)
CDR 2: LGSQRAS (SEQ ID NO: 288)
CDR 3: MQGLNRPWT

-continued

4964_G22 (PGT-141) kappa light chain Chothia CDRs:

(SEQ ID NO: 286)
CDR 1: SSTQSLRHSNGANYLA (SEQ ID NO: 287)
CDR 2: LGSQRAS (SEQ ID NO: 288)
CDR 3: MQGLNRPWT

4993_K13 (PGT-141) gamma heavy chain nucleotide sequence: coding sequence (variable region in bold)

(SEQ ID NO: 289)

ATGGACTGGATTTGGAGGATCCTCTTCTTGGTGGCAGCAGTTGCAAGTGC
CCACTCG**CAGGTGCAGCTGGTGCAGTCTGGGCCTGAGGTGAAGAAGC
CTGGGTCCTCAGTGAAGGTCTCCTGCAAGGCCTCTGGAAACACCTTC
AGTAAATATGATGTCCACTGGGTACGGCAGGCCACTGGACAGGGGCT
TGAATGGGTGGGATGGATGAGTCATGAGGGTGATAAGACAGAATCTG
CACAGAGATTTAAGGGCCGAGTCACCTTCACGAGGGACACTTCCGCA
AGCACAGCCTACATGGAACTGCGCGGCCTGACATCTGACGACACGGC
CATTTATTATTGTACGAGAGGCTCAAAACATCGCTTGCGAGACTATGT
TCTCTACGATGACTACGGCTTAATTAATTATCAAGAGTGGAATGACTA
CCTTGAATTTTTGGACGTCTGGGGCCATGGAACCGCGGTCACCGTCT
CCTCA**GCCTCCACCAAGGGCCCATCGGTCTTCCCCCTGGCACCCTCCTCC
AAGAGCACCTCTGGGGGCACAGCGGCCCTGGGCTGCCTGGTCAAGGACT
ACTTCCCCGAACCGGTGACGGTGTCGTGGAACTCAGGCGCCCTGACCAGC
GGCGTGCACACCTTCCCGGCTGTCCTACAGTCCTCAGGACTCTACTCCCTC
AGCAGCGTGGTGACCGTGCCCTCCAGCAGCTTGGGCACCCAGACCTACAT
CTGCAACGTGAATCACAAGCCCAGCAACACCAAGGTGGACAAGAGAGTT
GAGCCCAAATCTTGTGACAAAACTCACACATGCCCACCGTGCCCAGCACC
TGAACTCCTGGGGGGACCGTCAGTCTTCCTCTTCCCCCCAAAACCCAAGG
ACACCCTCATGATCTCCCGGACCCCTGAGGTCACATGCGTGGTGGTGGAC
GTGAGCCACGAAGACCCTGAGGTCAAGTTCAACTGGTACGTGGACGGCGT
GGAGGTGCATAATGCCAAGACAAAGCCGCGGGAGGAGCAGTACAACAGC
ACGTACCGTGTGGTCAGCGTCCTCACCGTCCTGCACCAGGACTGGCTGAA
TGGCAAGGAGTACAAGTGCAAGGTCTCCAACAAAGCCCTCCCAGCCCCCA
TCGAGAAAACCATCTCCAAAGCCAAAGGGCAGCCCCGAGAACCACAGGT
GTACACCCTGCCCCCATCCCGGGAGGAGATGACCAAGAACCAGGTCAGC
CTGACCTGCCTGGTCAAAGGCTTCTATCCCAGCGACATCGCCGTGGAGTG
GGAGAGCAATGGGCAGCCGGAGAACAACTACAAGACCACGCCTCCCGTG
CTGGACTCCGACGGCTCCTTCTTCCTCTATAGCAAGCTCACCGTGGACAA
GAGCAGGTGGCAGCAGGGGAACGTCTTCTCATGCTCCGTGATGCATGAGG
CTCTGCACAACCACTACACGCAGAAGAGCCTCTCCCTGTCTCCGGGTAAA
TGA

4993_K13 (PGT-141) gamma heavy chain variable region nucleotide sequence:

(SEQ ID NO: 290)

**CAGGTGCAGCTGGTGCAGTCTGGGCCTGAGGTGAAGAAGCCTGGGT
CCTCAGTGAAGGTCTCCTGCAAGGCCTCTGGAAACACCTTCAGTAAA
TATGATGTCCACTGGGTACGGCAGGCCACTGGACAGGGGCTTGAATG
GGTGGGATGGATGAGTCATGAGGGTGATAAGACAGAATCTGCACAGA
GATTTAAGGGCCGAGTCACCTTCACGAGGGACACTTCCGCAAGCACA
GCCTACATGGAACTGCGCGGCCTGACATCTGACGACACGGCCATTTA
TTATTGTACGAGAGGCTCAAAACATCGCTTGCGAGACTATGTTCTCTA
CGATGACTACGGCTTAATTAATTATCAAGAGTGGAATGACTACCTTGA
ATTTTTGGACGTCTGGGGCCATGGAACCGCGGTCACCGTCTCCTCA**

4993 K13 (PGT-141) gamma heavy chain amino acid sequence: expressed protein with leader sequence in italics and variable region in bold.

(SEQ ID NO: 275)

*MDWIWRILFLVAAVASAHS***QVQLVQSGPEVKKPGSSVKVSCKASGNTFSKY
DVHWVRQATGQGLEWVGWMSHEGDKTESAQRFKGRVTFTRDTSASTA
YMELRGLTSDDTAIYYCTRGSKHRLRDYVLYDDYGLINYQEWNDYLEFL
DVWGHGTAVTVSS**ASTKGPSVFPLAPSSKSTSGGTAALGCLVKDYFPEPVTV
SWNSGALTSGVHTFPAVLQSSGLYSLSSVVTVPSSSLGTQTYICNVNHKPSNT
KVDKRVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVS
LTCLVKGFYPSDIAVEWESNGQPENNYKTTPPVLDSDGSFFLYSKLTVDKSR
WQQGNVFSCSVMHEALHNHYTQKSLSLSPGK

4993_K13 (PGT-141) gamma heavy chain variable region amino acid sequence: (Kabat CDRs underlined, Chothia CDRs in bold italics)

(SEQ ID NO: 276)

QVQLVQSGPEVKKPGSSVKVSCKAS*GNTFSK*YDVHWVRQATGQGLEWVG
*WMSHEGDKTE*SAQRFKGRVTFTRDTSASTAYMELRGLTSDDTAIYYCTR<u>*GS*</u>
<u>*KHRLRDYVLYDDYGLINYQEWNDYLEFLDV*</u>WGHGTAVTVSS

-continued

4993_K13 (PGT-141) gamma heavy chain Kabat CDRs:

(SEQ ID NO: 277)
CDR 1: KYDVH (SEQ ID NO: 278)
CDR 2: WMSHEGDKTESAQRFKG (SEQ ID NO: 279)
CDR 3: GSKHRLRDYVLYDDYGLINYQEWNDYLEFLDV

4993_K13 (PGT-141) gamma heavy chain Chothia CDRs:

(SEQ ID NO: 280)
CDR 1: GNTFSK (SEQ ID NO: 281)
CDR 2: WMSHEGDKTE (SEQ ID NO: 279)
CDR 3: GSKHRLRDYVLYDDYGLINYQEWNDYLEFLDV

4993_K13 (PGT-141) kappa light chain nucleotide sequence: coding sequence (variable region in bold)

(SEQ ID NO: 282)
ATGAGGCTCCCTGCTCAGCTCCTGGGGCTGCTAATGCTCTGGGTCTCTGGA
TCCAGTGCGGATACTGTCGTGACTCAGTCTCCACTCTCCCTGCCCGTC
ACCCCTGGAGAGGCGGCCTCCATGTCCTGTTCGTCGACTCAGAGCCT
CCGGCATAGTAATGGAGCCAACTATTTGGCTTGGTATCAGCACAAAC
CGGGGCAGTCTCCACGACTCCTAATCCGTTTAGGTTCTCAACGGGGCC
TCCGGGGTCCCTGACAGATTCAGTGGCAGTGGATCAGGCACTCATTT
TACACTGAAAATCAGTAGAGTGGAGGCTGAAGATGCTGCAATTTATT
ATTGCATGCAAGGTCTGAACCGTCCCTGGACGTTCGGCAAGGGGACC
AAGTTGGAAATCAAACGTACGGTGGCTGCACCATCTGTCTTCATCTTCCC
GCCATCTGATGAGCAGTTGAAATCTGGAACTGCCTCTGTTGTGTGCCTGCT
GAATAACTTCTATCCCAGAGAGGCCAAAGTACAGTGGAAGGTGGATAAC
GCCCTCCAATCGGGTAACTCCCAGGAGAGTGTCACAGAGCAGGACAGCA
AGGACAGCACCTACAGCCTCAGCAGCACCCTGACGCTGAGCAAAGCAGA
CTACGAGAAACACAAAGTCTACGCCTGCGAAGTCACCCATCAGGGCCTGA
GCTCGCCCGTCACAAAGAGCTTCAACAGGGGAGAGTGTTAG

4993_K13 (PGT-141) kappa light chain variable region nucleotide sequence:

(SEQ ID NO: 283)
GATACTGTCGTGACTCAGTCTCCACTCTCCCTGCCCGTCACCCCTGG
AGAGGCGGCCTCCATGTCCTGTTCGTCGACTCAGAGCCTCCGGCATA
GTAATGGAGCCAACTATTTGGCTTGGTATCAGCACAAACCGGGGCAG
TCTCCACGACTCCTAATCCGTTTAGGTTCTCAACGGGCCTCCGGGGT
CCCTGACAGATTCAGTGGCAGTGGATCAGGCACTCATTTTACACTGA
AAATCAGTAGAGTGGAGGCTGAAGATGCTGCAATTTATTATTGCATG
CAAGGTCTGAACCGTCCCTGGACGTTCGGCAAGGGGACCAAGTTGGA
AATCAAA

4993_K13 (PGT-141) kappa light chain amino acid sequence: expressed protein with leader sequence in italics and variable region in bold.

(SEQ ID NO: 284)
*MRLPAQLLGLLMLWVSGSSA*DTVVTQSPLSLPVTPGEAASMSCSSTQSLRHS
NGANYLAWYQHKPGQSPRLLIRLGSQRASGVPDRFSGSGSGTHFTLKISR
VEAEDAAIYYCMQGLNRPWTFGKGTKLEIKRTVAAPSVFIFPPSDEQLKSG
TASVVCLLNNFYPREAKVQWKVDNALQSGNSQESVTEQDSKDSTYSLSSTLT
LSKADYEKHKVYACEVTHQGLSSPVTKSFNRGEC

4993_K13 (PGT-141) kappa light chain variable region amino acid sequence: (Kabat CDRs underlined, Chothia CDRs in bold italics)

(SEQ ID NO: 285)
DTVVTQSPLSLPVTPGEAASMSC<u>*SSTQSLRHSNGANYLA*</u>WYQHKPGQSPRLLI
R<u>*LGSQRAS*</u>GVPDRFSGSGSGTHFTLKISRVEAEDAAIYYC<u>*MQGLNRPWT*</u>FGK
GTKLEIK

4993 K13 (PGT-141) kappa light chain Kabat CDRs:

(SEQ ID NO: 286)
CDR 1: SSTQSLRHSNGANYLA (SEQ ID NO: 287)
CDR 2: LGSQRAS (SEQ ID NO: 288)
CDR 3: MQGLNRPWT

-continued

4993_K13 (PGT-141) kappa light chain Chothia CDRs:
(SEQ ID NO: 286)
CDR 1: SSTQSLRHSNGANYLA (SEQ ID NO: 287)
CDR 2: LGSQRAS (SEQ ID NO: 288)
CDR 3: MQGLNRPWT 4995_E20 (PGT-142) gamma heavy chain nucleotide sequence: coding sequence (variable region in bold)
(SEQ ID NO: 314)

ATGGACTGGATTTGGAGGATCCTCTTCTTGGTGGCAGCAGTTGCAAGTGC
CCACTCG**CAGGTGCAGCTGGTGCAGTCTGGGCCTGAGGTGAAGAAGC
CTGGGTCCTCAGTGAAGGTCTCCTGCAAGGCCTCTGGAAACACCTTC
AGTAAATATGATGTCCACTGGGTACGACAGGCCACTGGACAGGGGCT
TGAATGGGTGGGATGGATTAGTCATGAGCGTGATAAGACAGAATCTG
CACAGAGATTTAAGGGCCGAGTCACCTTCACGAGGGACACTTCCGCA
ACCACAGCCTACATGGAACTGCGCGGCCTGACATCTGACGACACGGC
CATTTATTATTGTACGAGAGGCTCAAAACATCGCTTGCGAGACTACGT
TCTCTACGATGACTACGGCTTAATTAATTATCAAGAGTGAATGACTA
CCTTGAATTTTTGGACGTCTGGGGCCATGGAACCGCGGTCACCGTCT
CCTCA**GCCTCCACCAAGGGCCCATCGGTCTTCCCCCTGGCACCCTCCTCC
AAGAGCACCTCTGGGGGCACAGCGGCCCTGGGCTGCCTGGTCAAGGACT
ACTTCCCCGAACCGGTGACGGTGTCGTGGAACTCAGGCGCCCTGACCAGC
GGCGTGCACACCTTCCCGGCTGTCCTACAGTCCTCAGGACTCTACTCCCTC
AGCAGCGTGGTGACCGTGCCCTCCAGCAGCTTGGGCACCCAGACCTACAT
CTGCAACGTGAATCACAAGCCCAGCAACACCAAGGTGGACAAGAGAGTT
GAGCCCAAATCTTGTGACAAAACTCACACATGCCCACCGTGCCCAGCACC
TGAACTCCTGGGGGGACCGTCAGTCTTCCTCTTCCCCCCAAAACCCAAGG
ACACCCTCATGATCTCCCGGACCCCTGAGGTCACATGCGTGGTGGTGGAC
GTGAGCCACGAAGACCCTGAGGTCAAGTTCAACTGGTACGTGGACGGCGT
GGAGGTGCATAATGCCAAGACAAAGCCGCGGGAGGAGCAGTACAACAGC
ACGTACCGTGTGGTCAGCGTCCTCACCGTCCTGCACCAGGACTGGCTGAA
TGGCAAGGAGTACAAGTGCAAGGTCTCCAACAAAGCCCTCCCAGCCCCCA
TCGAGAAAACCATCTCCAAAGCCAAAGGGCAGCCCCGAGAACCACAGGT
GTACACCCTGCCCCCATCCCGGGAGGAGATGACCAAGAACCAGGTCAGC
CTGACCTGCCTGGTCAAAGGCTTCTATCCCAGCGACATCGCCGTGGAGTG
GGAGAGCAATGGGCAGCCGGAGAACAACTACAAGACCACGCCTCCCGTG
CTGGACTCCGACGGCTCCTTCTTCCTCTATAGCAAGCTCACCGTGGACAA
GAGCAGGTGGCAGCAGGGGAACGTCTTCTCATGCTCCGTGATGCATGAGG
CTCTGCACAACCACTACACGCAGAAGAGCCTCTCCCTGTCTCCGGGTAAA
TGA

4995_E20 (PGT-142) gamma heavy chain variable region nucleotide sequence:
(SEQ ID NO: 315)

**CAGGTGCAGCTGGTGCAGTCTGGGCCTGAGGTGAAGAAGCCTGGGT
CCTCAGTGAAGGTCTCCTGCAAGGCCTCTGGAAACACCTTCAGTAAA
TATGATGTCCACTGGGTACGACAGGCCACTGGACAGGGGCTTGAATG
GGTGGGATGGATTAGTCATGAGCGTGATAAGACAGAATCTGCACAGA
GATTTAAGGGCCGAGTCACCTTCACGAGGGACACTTCCGCAACCACA
GCCTACATGGAACTGCGCGGCCTGACATCTGACGACACGGCCATTTA
TTATTGTACGAGAGGCTCAAAACATCGCTTGCGAGACTACGTTCTCTA
CGATGACTACGGCTTAATTAATTATCAAGAGTGGAATGACTACCTTGA
ATTTTTGGACGTCTGGGGCCATGGAACCGCGGTCACCGTCTCCTCA**

4995_E20 (PGT-142) gamma heavy chain amino acid sequence: expressed protein with leader sequence in italics and variable region in bold.
(SEQ ID NO: 291)

*MDWIWRILFLVAAVASAHS***QVQLVQSGPEVKKPGSSVKVSCKASGNTFSKY
DVHWVRQATGQGLEWVGWISHERDKTESAQRFKGRVTFTRDTSATTAY
MELRGLTSDDTAIYYCTRGSKHRLRDYVLYDDYGLINYQEWNDYLEFLD
VWGHGTAVTVSS**ASTKGPSVFPLAPSSKSTSGGTAALGCLVKDYFPEPVTVS
WNSGALTSGVHTFPAVLQSSGLYSLSSVVTVPSSSLGTQTYICNVNHKPSNTK
VDKRVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSRWQ
QGNVFSCSVMHEALHNHYTQKSLSLSPGK

4995_E20 (PGT-142) gamma heavy chain variable region amino acid sequence: (Kabat CDRs underlined, Chothia CDRs in bold italics)
(SEQ ID NO: 292)

QVQLVQSGPEVKKPGSSVKVSCKAS*GNTFSK*YDVHWVRQATGQGLEWVG
*WISHERDKTE*SAQRFKGRVTFTRDTSATTAYMELRGLTSDDTAIYYCTR<u>*GSK*
*HRLRDYVLYDDYGLINYQEWNDYLEFLDV*</u>WGHGTAVTVSS

-continued

4995_E20 (PGT-142) gamma heavy chain Kabat CDRs:

(SEQ ID NO: 277)
CDR 1: KYDVH (SEQ ID NO: 293)
CDR 2: WISHERDKTESAQRFKG (SEQ ID NO: 279)
CDR 3: GSKHRLRDYVLYDDYGLINYQEWNDYLEFLDV

4995_E20 (PGT-142) gamma heavy chain Chothia CDRs:

(SEQ ID NO: 280)
CDR 1: GNTFSK (SEQ ID NO: 294)
CDR 2: WISHERDKTE (SEQ ID NO: 279)
CDR 3: GSKHRLRDYVLYDDYGLINYQEWNDYLEFLDV

4995_E20 (PGT-142) kappa light chain nucleotide sequence: coding sequence
(variable region in bold)

(SEQ ID NO: 282)
ATGAGGCTCCCTGCTCAGCTCCTGGGGCTGCTAATGCTCTGGGTCTCTGGA
TCCAGTGCGGATACTGTCGTGACTCAGTCTCCACTCTCCCTGCCCGTC
ACCCCTGGAGAGGCGGCCTCCATGTCCTGTTCGTCGACTCAGAGCCT
CCGGCATAGTAATGGAGCCAACTATTTGGCTTGGTATCAGCACAAAC
CGGGGCAGTCTCCACGACTCCTAATCCGTTTAGGTTCTCAACGGGGCC
TCCGGGGTCCCTGACAGATTCAGTGGCAGTGGATCAGGCACTCATTT
TACACTGAAAATCAGTAGAGTGGAGGCTGAAGATGCTGCAATTTATT
ATTGCATGCAAGGTCTGAACCGTCCCTGGACGTTCGGCAAGGGGACC
AAGTTGGAAATCAAACGTACGGTGGCTGCACCATCTGTCTTCATCTTCCC
GCCATCTGATGAGCAGTTGAAATCTGGAACTGCCTCTGTTGTGCCTGCT
GAATAACTTCTATCCCAGAGAGGCCAAAGTACAGTGGAAGGTGGATAAC
GCCCTCCAATCGGGTAACTCCCAGGAGAGTGTCACAGAGCAGGACAGCA
AGGACAGCACCTACAGCCTCAGCAGCACCCTGACGCTGAGCAAAGCAGA
CTACGAGAAACACAAAGTCTACGCCTGCGAAGTCACCCATCAGGGCCTGA
GCTCGCCCGTCACAAAGAGCTTCAACAGGGGAGAGTGTTAG

4995_E20 (PGT-142) kappa light chain variable region nucleotide sequence:

(SEQ ID NO: 283)
GATACTGTCGTGACTCAGTCTCCACTCTCCCTGCCCGTCACCCCTGG
AGAGGCGGCCTCCATGTCCTGTTCGTCGACTCAGAGCCTCCGGCATA
GTAATGGAGCCAACTATTTGGCTTGGTATCAGCACAAACCGGGGCAG
TCTCCACGACTCCTAATCCGTTTAGGTTCTCAACGGGCCTCCGGGGT
CCCTGACAGATTCAGTGGCAGTGGATCAGGCACTCATTTTACACTGA
AAATCAGTAGAGTGGAGGCTGAAGATGCTGCAATTTATTATTGCATG
CAAGGTCTGAACCGTCCCTGGACGTTCGGCAAGGGGACCAAGTTGGA
AATCAAA

4995_E20 (PGT-142) kappa light chain amino acid sequence: expressed protein with
leader sequence in italics and variable region in bold.

(SEQ ID NO: 284)
*MRLPAQLLGLLMLWVSGSSA*DTVVTQSPLSLPVTPGEAASMSCSSTQSLRHS
NGANYLAWYQHKPGQSPRLLIRLGSQRASGVPDRFSGSGSGTHFTLKISR
VEAEDAAIYYCMQGLNRPWTFGKGTKLEIKRTVAAPSVFIFPPSDEQLKSG
TASVVCLLNNFYPREAKVQWKVDNALQSGNSQESVTEQDSKDSTYSLSSTLT
LSKADYEKHKVYACEVTHQGLSSPVTKSFNRGEC

4995_E20 (PGT-142) kappa light chain variable region amino acid sequence: (Kabat
CDRs underlined, Chothia CDRs in bold italics)

(SEQ ID NO: 285)
DTVVTQSPLSLPVTPGEAASMSC*SSTQSLRHSNGANYLA*WYQHKPGQSPRLLI
R*LGSQRAS*GVPDRFSGSGSGTHFTLKISRVEAEDAAIYYC*MQGLNRPWT*FGK
GTKLEIK

4995_E20 (PGT-142) kappa light chain Kabat CDRs:

(SEQ ID NO: 286)
CDR 1: SSTQSLRHSNGANYLA (SEQ ID NO: 287)
CDR 2: LGSQRAS (SEQ ID NO: 288)
CDR 3: MQGLNRPWT

-continued

4995_E20 (PGT-142) kappa light chain Chothia CDRs:

(SEQ ID NO: 286)
CDR 1: SSTQSLRHSNGANYLA (SEQ ID NO: 287)
CDR 2: LGSQRAS (SEQ ID NO: 288)
CDR 3: MQGLNRPWT

4980_N08 (PGT-143) gamma heavy chain nucleotide sequence: coding sequence (variable region in bold)

(SEQ ID NO: 295)
ATGGACTGGATTTGGAGGATCCTCTTCTTGGTGGCAGCAGTTGCAAGTGC
CCACGCG**CAGGTGCAGCTGGAGCAGTCTGGGGCTGAGGTGAAGAAGC
CTGGGTCCTCAGTGAAGGTCTCCTGCAAGGCCTCTGGAAACACCTTC
AGTAAATATGATGTCCACTGGGTACGACAGGCCACTGGACAGGGGCT
TGAATGGGTGGGATGGATGAGTCATGAGGGTGATAAGACAGAATCTG
CACAGAGATTTAAGGGGCGAGTCACCTTCACGAGGGACACTTCCGCA
AGCACAGCCTACATGGAACTGCGCGGCCTGACATCTGACGACACGGC
CATTTATTATTGTACGAGAGGTTCAAAACATCGCTTGCGAGACTACGT
TCTCTACGATGACTACGGCTTAATTAATTATCAAGAGTGAATGACTA
CCTTGAATTTTTGGACGTCTGGGGCCATGGAACCGCGGTCACCGTCT
CCTCA**GCCTCCACCAAGGGCCCATCGGTCTTCCCCCTGGCACCCTCCTCC
AAGAGCACCTCTGGGGGCACAGCGGCCCTGGGCTGCCTGGTCAAGGACT
ACTTCCCCGAACCGGTGACGGTGTCGTGGAACTCAGGCGCCCTGACCAGC
GGCGTGCACACCTTCCCGGCTGTCCTACAGTCCTCAGGACTCTACTCCCTC
AGCAGCGTGGTGACCGTGCCCTCCAGCAGCTTGGGCACCCAGACCTACAT
CTGCAACGTGAATCACAAGCCCAGCAACACCAAGGTGGACAAGAGAGTT
GAGCCCAAATCTTGTGACAAAACTCACACATGCCCACCGTGCCCAGCACC
TGAACTCCTGGGGGGACCGTCAGTCTTCCTCTTCCCCCCAAAACCCAAGG
ACACCCTCATGATCTCCCGGACCCCTGAGGTCACATGCGTGGTGGTGGAC
GTGAGCCACGAAGACCCTGAGGTCAAGTTCAACTGGTACGTGGACGGCGT
GGAGGTGCATAATGCCAAGACAAAGCCGCGGGAGGAGCAGTACAACAGC
ACGTACCGTGTGGTCAGCGTCCTCACCGTCCTGCACCAGGACTGGCTGAA
TGGCAAGGAGTACAAGTGCAAGGTCTCCAACAAAGCCCTCCCAGCCCCCA
TCGAGAAAACCATCTCCAAAGCCAAAGGGCAGCCCCGAGAACCACAGGT
GTACACCCTGCCCCCATCCCGGGAGGAGATGACCAAGAACCAGGTCAGC
CTGACCTGCCTGGTCAAAGGCTTCTATCCCAGCGACATCGCCGTGGAGTG
GGAGAGCAATGGGCAGCCGGAGAACAACTACAAGACCACGCCTCCCGTG
CTGGACTCCGACGGCTCCTTCTTCCTCTATAGCAAGCTCACCGTGGACAA
GAGCAGGTGGCAGCAGGGGAACGTCTTCTCATGCTCCGTGATGCATGAGG
CTCTGCACAACCACTACACGCAGAAGAGCCTCTCCCTGTCTCCGGGTAAA
TGA

4980_N08 (PGT-143) gamma heavy chain variable region nucleotide sequence:

(SEQ ID NO: 296)
**CAGGTGCAGCTGGAGCAGTCTGGGGCTGAGGTGAAGAAGCCTGGGT
CCTCAGTGAAGGTCTCCTGCAAGGCCTCTGGAAACACCTTCAGTAAA
TATGATGTCCACTGGGTACGACAGGCCACTGGACAGGGGCTTGAATG
GGTGGGATGGATGAGTCATGAGGGTGATAAGACAGAATCTGCACAGA
GATTTAAGGGGCGAGTCACCTTCACGAGGGACACTTCCGCAAGCACA
GCCTACATGGAACTGCGCGGCCTGACATCTGACGACACGGCCATTTA
TTATTGTACGAGAGGTTCAAAACATCGCTTGCGAGACTACGTTCTCTA
CGATGACTACGGCTTAATTAATTATCAAGAGTGGAATGACTACCTTGA
ATTTTTGGACGTCTGGGGCCATGGAACCGCGGTCACCGTCTCCTCA**

4980_N08 (PGT-143) gamma heavy chain amino acid sequence: expressed protein with leader sequence in italics and variable region in bold.

(SEQ ID NO: 297)
*MDWIWRILFLVAAVASAHA***QVQLEQSGAEVKKPGSSVKVSCKASGNTFSKY
DVHWVRQATGQGLEWVGWMSHEGDKTESAQRFKGRVTFTRDTSASTA
YMELRGLTSDDTAIYYCTRGSKHRLRDYVLYDDYGLINYQEWNDYLEFL
DV**WGHGTAVTVSSASTKGPSVFPLAPSSKSTSGGTAALGCLVKDYFPEPVTV
SWNSGALTSGVHTFPAVLQSSGLYSLSSVVTVPSSSLGTQTYICNVNHKPSNT
KVDKRVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVS
LTCLVKGFYPSDIAVEWESNGQPENNYKTTPPVLDSDGSFFLYSKLTVDKSR
WQQGNVFSCSVMHEALHNHYTQKSLSLSPGK

4980_N08 (PGT-143) gamma heavy chain variable region amino acid sequence: (Kabat CDRs underlined, Chothia CDRs in bold italics)

(SEQ ID NO: 298)
QVQLEQSGAEVKKPGSSVKVSCKAS*GNTFSK*YDVHWVRQATGQGLEWVG
*WMSHEGDKTE*SAQRFKGRVTFTRDTSASTAYMELRGLTSDDTAIYYCTR<u>***GS
KHRLRDYVLYDDYGLINYQEWNDYLEFLDV***</u>WGHGTAVTVSS

-continued

4980_N08 (PGT-143) gamma heavy chain Kabat CDRs:

(SEQ ID NO: 277)
CDR 1: KYDVH (SEQ ID NO: 278)
CDR 2: WMSHEGDKTESAQRFKG (SEQ ID NO: 279)
CDR 3: GSKHRLRDYVLYDDYGLINYQEWNDYLEFLDV

4980_N08 (PGT-143) gamma heavy chain Chothia CDRs:

(SEQ ID NO: 280)
CDR 1: GNTFSK (SEQ ID NO: 281)
CDR 2: WMSHEGDKTE (SEQ ID NO: 279)
CDR 3: GSKHRLRDYVLYDDYGLINYQEWNDYLEFLDV

4980_N08 (PGT-143) kappa light chain nucleotide sequence: coding sequence
(variable region in bold)

(SEQ ID NO: 299)
ATGAGGCTCCCTGCTCAGCTCCTGGGGCTGCTAATGCTCTGGGTCTCTGGA
TCCAGTGCG**GATACTGTCGTGACTCAGTCTCCACTCTCCCTGCCCGTC
ACCCCTGGAGAGGCGGCCTCCATGTCCTGTACGTCGACTCAGAGCCT
CCGTCATAGTAATGGAGCCAACTATTTGGCTTGGTACCAGCACAAAC
CAGGGCAGTCTCCACGACTCCTAATCCGTTTAGGTTCTCAACGGGGCC
TCCGGGGTCCCTGACAGATTCAGTGGCAGTGGATCAGGCACTCATTT
TACACTGAAAATCAGTCGAGTGGAGCCTGAAGATGCTGCAATTTATT
ATTGCATGCAAGGTCTGAACCGTCCCTGGACGTTCGGCAAGGGGACC
AAGTTGGAAATCAAA**CGTACGGTGGCTGCACCATCTGTCTTCATCTTCCC
GCCATCTGATGAGCAGTTGAAATCTGGAACTGCCTCTGTTGTGTGCCTGCT
GAATAACTTCTATCCCAGAGAGGCCAAAGTACAGTGGAAGGTGGATAAC
GCCCTCCAATCGGGTAACTCCCAGGAGAGTGTCACAGAGCAGGACAGCA
AGGACAGCACCTACAGCCTCAGCAGCACCCTGACGCTGAGCAAAGCAGA
CTACGAGAAACACAAAGTCTACGCCTGCGAAGTCACCCATCAGGGCCTGA
GCTCGCCCGTCACAAAGAGCTTCAACAGGGGAGAGTGTTAG

4980_N08 (PGT-143) kappa light chain variable region nucleotide sequence:

(SEQ ID NO: 300)
**GATACTGTCGTGACTCAGTCTCCACTCTCCCTGCCCGTCACCCCTGG
AGAGGCGGCCTCCATGTCCTGTACGTCGACTCAGAGCCTCCGTCATA
GTAATGGAGCCAACTATTTGGCTTGGTACCAGCACAAACCAGGGCAG
TCTCCACGACTCCTAATCCGTTTAGGTTCTCAACGGGCCTCCGGGGT
CCCTGACAGATTCAGTGGCAGTGGATCAGGCACTCATTTTACACTGA
AAATCAGTCGAGTGGAGCCTGAAGATGCTGCAATTTATTATTGCATG
CAAGGTCTGAACCGTCCCTGGACGTTCGGCAAGGGGACCAAGTTGGA
AATCAAA**

4980_N08 (PGT-143) kappa light chain amino acid sequence: expressed protein with
leader sequence in italics and variable region in bold.

(SEQ ID NO: 301)
*MRLPAQLLGLLMLWVSGSSA***DTVVTQSPLSLPVTPGEAASMSCTSTQSLRHS
NGANYLAWYQHKPGQSPRLLIRLGSQRASGVPDRFSGSGSGTHFTLKISR
VEPEDAAIYYCMQGLNRPWTFGKGTKLEIK**RTVAAPSVFIFPPSDEQLKSG
TASVVCLLNNFYPREAKVQWKVDNALQSGNSQESVTEQDSKDSTYSLSSTLT
LSKADYEKHKVYACEVTHQGLSSPVTKSFNRGEC

4980_N08 (PGT-143) kappa light chain variable region amino acid sequence: (Kabat
CDRs underlined, Chothia CDRs in bold italics)

(SEQ ID NO: 302)
DTVVTQSPLSLPVTPGEAASMSC<u>*TSTQSLRHSNGANYLA*</u>WYQHKPGQSPRLLI
R<u>*LGSQRAS*</u>GVPDRFSGSGSGTHFTLKISRVEPEDAAIYYC<u>*MQGLNRPWT*</u>FGK
GTKLEIK

4980_N08 (PGT-143) kappa light chain Kabat CDRs:

(SEQ ID NO: 303)
CDR 1: TSTQSLRHSNGANYLA (SEQ ID NO: 287)
CDR 2: LGSQRAS (SEQ ID NO: 288)
CDR 3: MQGLNRPWT

4980_N08 (PGT-143) kappa light chain Chothia CDRs:

(SEQ ID NO: 303)
CDR 1: TSTQSLRHSNGANYLA (SEQ ID NO: 287)
CDR 2: LGSQRAS (SEQ ID NO: 288)
CDR 3: MQGLNRPWT

4970_K22 (PGT-144) gamma heavy chain nucleotide sequence: coding sequence (variable region in bold)

(SEQ ID NO: 304)
ATGGACTGGATTTGGAGGATCCTCTTCTTGGTGGCAGCAGTTGCAAGTGC
CCACTCG**CAGGTGCAGCTGGTGCAGTCTGGGGCTGAGGTGAAGAAGC
CTGGGTCCTCAGTGAAGGTCTCCTGCAAGGCCTCTGGAAACACCTTC
AGGAAATATGATGTCCACTGGGTACGACAGGCCACTGGACAGGGGCT
TGAATGGGTGGGATGGATGAGTCATGAGGGTGATAAGACAGAATCTG
CACAGAGATTTAAGGGCCGAGTCTCTTTCACGAGGGACAATTCCGCA
AGCACAGCCTACATTGAACTGCGCGGCCTGACATCTGACGACACGGC
CATTTATTATTGTACCGGAGGCTCAAAACATCGCTTGCGAGACTACGT
TCTCTACGATGATTACGGCCTAATAAATCAGCAAGAGTGGAATGACT
ACCTTGAATTTTTGGACGTCTGGGGCCATGGAACCGCGGTCACCGTC
TCCTCA**GCCTCCACCAAGGGCCCATCGGTCTTCCCCCTGGCACCCTCCTC
CAAGAGCACCTCTGGGGGCACAGCGGCCCTGGGCTGCCTGGTCAAGGACT
ACTTCCCCGAACCGGTGACGGTGTCGTGGAACTCAGGCGCCCTGACCAGC
GGCGTGCACACCTTCCCGGCTGTCCTACAGTCCTCAGGACTCTACTCCCTC
AGCAGCGTGGTGACCGTGCCCTCCAGCAGCTTGGGCACCCAGACCTACAT
CTGCAACGTGAATCACAAGCCCAGCAACACCAAGGTGGACAAGAGAGTT
GAGCCCAAATCTTGTGACAAAACTCACACATGCCCACCGTGCCCAGCACC
TGAACTCCTGGGGGGACCGTCAGTCTTCCTCTTCCCCCCAAAACCCAAGG
ACACCCTCATGATCTCCCGGACCCCTGAGGTCACATGCGTGGTGGTGGAC
GTGAGCCACGAAGACCCTGAGGTCAAGTTCAACTGGTACGTGGACGGCGT
GGAGGTGCATAATGCCAAGACAAAGCCGCGGGAGGAGCAGTACAACAGC
ACGTACCGTGTGGTCAGCGTCCTCACCGTCCTGCACCAGGACTGGCTGAA
TGGCAAGGAGTACAAGTGCAAGGTCTCCAACAAAGCCCTCCCAGCCCCA
TCGAGAAAACCATCTCCAAAGCCAAAGGGCAGCCCCGAGAACCACAGGT
GTACACCCTGCCCCCATCCCGGGAGGAGATGACCAAGAACCAGGTCAGC
CTGACCTGCCTGGTCAAAGGCTTCTATCCCAGCGACATCGCCGTGGAGTG
GGAGAGCAATGGGCAGCCGGAGAACAACTACAAGACCACGCCTCCCGTG
CTGGACTCCGACGGCTCCTTCTTCCTCTATAGCAAGCTCACCGTGGACAA
GAGCAGGTGGCAGCAGGGGAACGTCTTCTCATGCTCCGTGATGCATGAGG
CTCTGCACAACCACTACACGCAGAAGAGCCTCTCCCTGTCTCCGGGTAAA
TGA

4970_K22 (PGT-144) gamma heavy chain variable region nucleotide sequence:

(SEQ ID NO: 305)
**CAGGTGCAGCTGGTGCAGTCTGGGGCTGAGGTGAAGAAGCCTGGGT
CCTCAGTGAAGGTCTCCTGCAAGGCCTCTGGAAACACCTTCAGGAAA
TATGATGTCCACTGGGTACGACAGGCCACTGGACAGGGGCTTGAATG
GGTGGGATGGATGAGTCATGAGGGTGATAAGACAGAATCTGCACAGA
GATTTAAGGGCCGAGTCTCTTTCACGAGGGACAATTCCGCAAGCACA
GCCTACATTGAACTGCGCGGCCTGACATCTGACGACACGGCCATTTA
TTATTGTACCGGAGGCTCAAAACATCGCTTGCGAGACTACGTTCTCTA
CGATGATTACGGCCTAATAAATCAGCAAGAGTGGAATGACTACCTTG
AATTTTTGGACGTCTGGGGCCATGGAACCGCGGTCACCGTCTCCTCA**

4970_K22 (PGT-144) gamma heavy chain amino acid sequence: expressed protein with leader sequence in italics and variable region in bold.

(SEQ ID NO: 306)
*MDWIWRILFLVAAVASAHS***QVQLVQSGAEVKKPGSSVKVSCKASGNTFRKY
DVHWVRQATGQGLEWVGWMSHEGDKTESAQRFKGRVSFTRDNSASTA
YIELRGLTSDDTAIYYCTGGSKHRLRDYVLYDDYGLINQQEWNDYLEFL
DVWGHGTAVTVSS**ASTKGPSVFPLAPSSKSTSGGTAALGCLVKDYFPEPVTV
SWNSGALTSGVHTFPAVLQSSGLYSLSSVVTVPSSSLGTQTYICNVNHKPSNT
KVDKRVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVS
LTCLVKGFYPSDIAVEWESNGQPENNYKTTPPVLDSDGSFFLYSKLTVDKSR
WQQGNVFSCSVMHEALHNHYTQKSLSLSPGK

4970_K22 (PGT-144) gamma heavy chain variable region amino acid sequence: (Kabat CDRs underlined, Chothia CDRs in bold italics)

(SEQ ID NO: 307)
QVQLVQSGAEVKKPGSSVKVSCKAS*GNTFRK*YDVHWVRQATGQGLEWVG
*WMSHEGDKTE*SAQRFKGRVSFTRDNSASTAYIELRGLTSDDTAIYYCTG***GSK
HRLRDYVLYDDYGLINQQEWNDYLEFLDV***WGHGTAVTVSS

-continued

4970_K22 (PGT-144) gamma heavy chain Kabat CDRs:

(SEQ ID NO: 277)
CDR 1: KYDVH (SEQ ID NO: 278)
CDR 2: WMSHEGDKTESAQRFKG (SEQ ID NO: 308)
CDR 3: GSKHRLRDYVLYDDYGLINQQEWNDYLEFLDV

4970_K22 (PGT-144) gamma heavy chain Chothia CDRs:

(SEQ ID NO: 309)
CDR 1: GNTFRK (SEQ ID NO: 281)
CDR 2: WMSHEGDKTE (SEQ ID NO: 308)
CDR 3: GSKHRLRDYVLYDDYGLINQQEWNDYLEFLDV

4970_K22 (PGT-144) kappa light chain nucleotide sequence: coding sequence
(variable region in bold)

(SEQ ID NO: 310)
ATGAGGCTCCCTGCTCAGCTCCTGGGGCTGCTAATGCTCTGGGTCTCTGGA
TCCAGTGCGGATACTGTCGTGACTCAGTCTCCACTCTCCCTGTCCGTC
ACCCCTGGAGAGGCGGCCTCCATGTCCTGTACGTCGACTCAGAGCCT
CCGGCATAGTAATGGAGCCAACTATTTGGCTTGGTACCAGCACAAAC
CAGGGCAGTCTCCACGACTCCTAATCCGTTTAGGTTCTCAACGGGGCC
TCCGGGGTCCCTGACAGATTCAGTGGCAGTGGATCAGGCACTCATTT
TACACTGAAAATCAGTAGAGTGGAGGCTGACGATGCTGCAATTTATT
ATTGCATGCAAGGTCTGAACCGTCCCTGGACGTTCGGCAAGGGGACC
AAGTTGGAGATCAAACGTACGGTGGCTGCACCATCTGTCTTCATCTTCCC
GCCATCTGATGAGCAGTTGAAATCTGGAACTGCCTCTGTTGTGCCTGCT
GAATAACTTCTATCCCAGAGAGGCCAAAGTACAGTGGAAGGTGGATAAC
GCCCTCCAATCGGGTAACTCCCAGGAGAGTGTCACAGAGCAGGACAGCA
AGGACAGCACCTACAGCCTCAGCAGCACCCTGACGCTGAGCAAAGCAGA
CTACGAGAAACACAAAGTCTACGCCTGCGAAGTCACCCATCAGGGCCTGA
GCTCGCCCGTCACAAAGAGCTTCAACAGGGGAGAGTGTTAG

4970_K22 (PGT-144) kappa light chain variable region nucleotide sequence:

(SEQ ID NO: 311)
GATACTGTCGTGACTCAGTCTCCACTCTCCCTGTCCGTCACCCCTGGA
GAGGCGGCCTCCATGTCCTGTACGTCGACTCAGAGCCTCCGGCATAG
TAATGGAGCCAACTATTTGGCTTGGTACCAGCACAAACCAGGGCAGT
CTCCACGACTCCTAATCCGTTTAGGTTCTCAACGGGCCTCCGGGGTC
CCTGACAGATTCAGTGGCAGTGGATCAGGCACTCATTTTACACTGAA
AATCAGTAGAGTGGAGGCTGACGATGCTGCAATTTATTATTGCATGC
AAGGTCTGAACCGTCCCTGGACGTTCGGCAAGGGGACCAAGTTGGAG
ATCAAA

4970_K22 (PGT-144) kappa light chain amino acid sequence: expressed protein with
leader sequence in italics and variable region in bold.

(SEQ ID NO: 312)
*MRLPAQLLGLLMLWVSGSSA*DTVVTQSPLSLSVTPGEAASMSCTSTQSLRHS
NGANYLAWYQHKPGQSPRLLIRLGSQRASGVPDRFSGSGSGTHFTLKISR
VEADDAAIYYCMQGLNRPWTFGKGTKLEIKRTVAAPSVFIFPPSDEQLKSG
TASVVCLLNNFYPREAKVQWKVDNALQSGNSQESVTEQDSKDSTYSLSSTLT
LSKADYEKHKVYACEVTHQGLSSPVTKSFNRGEC

4970_K22 (PGT-144) kappa light chain variable region amino acid sequence: (Kabat
CDRs underlined, Chothia CDRs in bold italics)

(SEQ ID NO: 313)
DTVVTQSPLSLSVTPGEAASMSC*TSTQSLRHSNGANYLA*WYQHKPGQSPRLLI
R*LGSQRAS*GVPDRFSGSGSGTHFTLKISRVEADDAAIYYC*MQGLNRPWT*FGK
GTKLEIK

4970_K22 (PGT-144) kappa light chain Kabat CDRs:

(SEQ ID NO: 303)
CDR 1: TSTQSLRHSNGANYLA (SEQ ID NO: 287)
CDR 2: LGSQRAS (SEQ ID NO: 288)
CDR 3: MQGLNRPWT

```
4970_K22 (PGT-144) kappa light chain Chothia CDRs:
                                                             (SEQ ID NO: 303)
CDR 1: TSTQSLRHSNGANYLA (SEQ ID NO: 287)
CDR 2: LGSQRAS (SEQ ID NO: 288)
CDR 3: MQGLNRPWT
```

The 4838_L06 (PGT-121) antibody includes a heavy chain variable region (SEQ ID NO: 79), encoded by the nucleic acid sequence shown in SEQ ID NO: 63, and a light chain variable region (SEQ ID NO: 149) encoded by the nucleic acid sequence shown in SEQ ID NO: 147.

The heavy chain CDRs of the 4838_L06 (PGT-121) antibody have the following sequences per Kabat definition: DSYWS (SEQ ID NO: 90), YVHKSGDTNYSPSLKS (SEQ ID NO: 265), and TLHGRRIYGIVAFNEWFTYFYMDV (SEQ ID NO: 143). The light chain CDRs of the 4838_L06 (PGT-121) antibody have the following sequences per Kabat definition: GEKSLGSRAVQ (SEQ ID NO: 150), NNQDRPS (SEQ ID NO: 151), and HIWDSRVPTKWV (SEQ ID NO: 152).

The heavy chain CDRs of the 4838_L06 (PGT-121) antibody have the following sequences per Chothia definition: GASISD (SEQ ID NO: 144), YVHKSGDTN (SEQ ID NO: 145), and TLHGRRIYGIVAFNEWFTYFYMDV (SEQ ID NO: 143). The light chain CDRs of the 4838_L06 (PGT-121) antibody have the following sequences per Chothia definition: GEKSLGSRAVQ (SEQ ID NO: 150), NNQDRPS (SEQ ID NO: 151), and HIWDSRVPTKWV (SEQ ID NO: 152).

The 4873_E03 (PGT-121) antibody includes a heavy chain variable region (SEQ ID NO: 79), encoded by the nucleic acid sequence shown in SEQ ID NO: 63, and a light chain variable region (SEQ ID NO: 149) encoded by the nucleic acid sequence shown in SEQ ID NO: 147.

The heavy chain CDRs of the 4873_E03 (PGT-121) antibody have the following sequences per Kabat definition: DSYWS (SEQ ID NO: 90), YVHKSGDTNYSPSLKS (SEQ ID NO: 265), and TLHGRRIYGIVAFNEWFTYFYMDV (SEQ ID NO: 143). The light chain CDRs of the 4873_E03 (PGT-121) antibody have the following sequences per Kabat definition: GEKSLGSRAVQ (SEQ ID NO: 150), NNQDRPS (SEQ ID NO: 151), and HIWDSRVPTKWV (SEQ ID NO: 152).

The heavy chain CDRs of the 4873_E03 (PGT-121) antibody have the following sequences per Chothia definition: GASISD (SEQ ID NO: 144), YVHKSGDTN (SEQ ID NO: 145), and TLHGRRIYGIVAFNEWFTYFYMDV (SEQ ID NO: 143). The light chain CDRs of the 4873_E03 (PGT-121) antibody have the following sequences per Chothia definition: GEKSLGSRAVQ (SEQ ID NO: 150), NNQDRPS (SEQ ID NO: 151), and HIWDSRVPTKWV (SEQ ID NO: 152).

The 4877_D15 (PGT-122) antibody includes a heavy chain variable region (SEQ ID NO: 156), encoded by the nucleic acid sequence shown in SEQ ID NO: 154, and a light chain variable region (SEQ ID NO: 161) encoded by the nucleic acid sequence shown in SEQ ID NO: 159.

The heavy chain CDRs of the 4877_D15 (PGT-122) antibody have the following sequences per Kabat definition: DNYWS (SEQ ID NO: 261), YVHDSGDTNYNPSLKS (SEQ ID NO: 157), and TKHGRRIYGVVAFKEWFTYFYMDV (SEQ ID NO: 262). The light chain CDRs of the 4877_D15 (PGT-122) antibody have the following sequences per Kabat definition: GEESLGSRSVI (SEQ ID NO: 162), NNNDRPS (SEQ ID NO: 163), and HIWDSRRPTNWV (SEQ ID NO: 164).

The heavy chain CDRs of the 4877_D15 (PGT-122) antibody have the following sequences per Chothia definition: GTLVRD (SEQ ID NO: 263), YVHDSGDTN (SEQ ID NO: 264), and TKHGRRIYGVVAFKEWFTYFYMDV (SEQ ID NO: 262). The light chain CDRs of the 4877_D15 (PGT-122) antibody have the following sequences per Chothia definition: GEESLGSRSVI (SEQ ID NO: 162), NNNDRPS (SEQ ID NO: 163), and HIWDSRRPTNWV (SEQ ID NO: 164).

The 4858_P08 (PGT-123) antibody includes a heavy chain variable region (SEQ ID NO: 168), encoded by the nucleic acid sequence shown in SEQ ID NO: 166, and a light chain variable region (SEQ ID NO: 177) encoded by the nucleic acid sequence shown in SEQ ID NO: 175.

The heavy chain CDRs of the 4858_P08 (PGT-123) antibody have the following sequences per Kabat definition: DAYWS (SEQ ID NO: 169), YVHHSGDTNYNPSLKR (SEQ ID NO: 170), ALHGKRIYGIVALGELFTYFYMDV (SEQ ID NO: 171). The light chain CDRs of the 4858_P08 (PGT-123) antibody have the following sequences per Kabat definition: GKESIGSRAVQ (SEQ ID NO: 178), NNQDRPA (SEQ ID NO: 179), and HIYDARGGTNWV (SEQ ID NO: 180).

The heavy chain CDRs of the 4858_P08 (PGT-123) antibody have the following sequences per Chothia definition: GASIND (SEQ ID NO: 172), YVHHSGDTN (SEQ ID NO: 173), ALHGKRIYGIVALGELFTYFYMDV (SEQ ID NO: 171). The light chain CDRs of the 4858_P08 (PGT-123) antibody have the following sequences per Chothia definition: GKESIGSRAVQ (SEQ ID NO: 178), NNQDRPA (SEQ ID NO: 179), HIYDARGGTNWV (SEQ ID NO: 180).

The 5123_A06 (PGT-125) antibody includes a heavy chain variable region (SEQ ID NO: 164), encoded by the nucleic acid sequence shown in SEQ ID NO: 182, and a light chain variable region (SEQ ID NO: 193) encoded by the nucleic acid sequence shown in SEQ ID NO: 191.

The heavy chain CDRs of the 5123_A06 (PGT-125) antibody have the following sequences per Kabat definition: ACTYFWG (SEQ ID NO: 185), SLSHCQSFWGSGWTFHNPSLKS (SEQ ID NO: 186), and FDGEVLVYNHWPKPAWVDL (SEQ ID NO: 187). The light chain CDRs of the 5123_A06 (PGT-125) antibody have the following sequences per Kabat definition: NGTATNFVS (SEQ ID NO: 194), GVDKRPP (SEQ ID NO: 195), and GSLVGNWDVI (SEQ ID NO: 196).

The heavy chain CDRs of the 5123_A06 (PGT-125) antibody have the following sequences per Chothia definition: GESTGACT (SEQ ID NO: 188), SLSHCQSFWGSGWTF (SEQ ID NO: 189), and FDGEVLVYNHWPKPAWVDL (SEQ ID NO: 187). The light chain CDRs of the 5123_A06 (PGT-125) antibody have the following sequences per Chothia definition:

NGTATNFVS (SEQ ID NO: 194), GVDKRPP (SEQ ID NO: 195), and GSLVGNWDVI (SEQ ID NO: 196).

The 5141_B17 (PGT-126) antibody includes a heavy chain variable region (SEQ ID NO: 200), encoded by the nucleic acid sequence shown in SEQ ID NO: 198, and a light chain variable region (SEQ ID NO: 209) encoded by the nucleic acid sequence shown in SEQ ID NO: 207.

The heavy chain CDRs of the 5141_B17 (PGT-126) antibody have the following sequences per Kabat definition: ACDYFWG (SEQ ID NO: 201), GLSHCAGYYNTGWT-YHNPSLKS (SEQ ID NO: 202), and FDGEVLVYHDWPKPAWVDL (SEQ ID NO: 203). The light chain CDRs of the 5141_B17 (PGT-126) antibody have the following sequences per Kabat definition: TGTSNRFVS (SEQ ID NO: 210), GVNKRPS (SEQ ID NO: 211), and SSLVGNWDVI (SEQ ID NO: 212).

The heavy chain CDRs of the 5141_B17 (PGT-126) antibody have the following sequences per Chothia definition: GDSTAACD (SEQ ID NO: 204), GLSHCAGYYN-TGWTY (SEQ ID NO: 205), and FDGEVLVYHDWPKPAWVDL (SEQ ID NO: 203). The light chain CDRs of the 5141_B17 (PGT-126) antibody have the following sequences per Chothia definition: TGTSNRFVS (SEQ ID NO: 210), GVNKRPS (SEQ ID NO: 211), and SSLVGNWDVI (SEQ ID NO: 212).

The 5147_N06 (PGT-130) antibody includes a heavy chain variable region (SEQ ID NO: 216), encoded by the nucleic acid sequence shown in SEQ ID NO: 214, and a light chain variable region (SEQ ID NO: 225) encoded by the nucleic acid sequence shown in SEQ ID NO: 223.

The heavy chain CDRs of the 5147_N06 (PGT-130) antibody have the following sequences per Kabat definition: TGHYYWG (SEQ ID NO: 217), HIHYTTAVLHNPSLKS (SEQ ID NO: 218), and SGGDILYYYEWQKPHWFSP (SEQ ID NO: 219). The light chain CDRs of the 5147_N06 (PGT-130) antibody have the following sequences per Kabat definition: NGTSSDIGGWNFVS (SEQ ID NO: 226), EVNKRPS (SEQ ID NO: 227), and SSLFGRWDVV (SEQ ID NO: 228).

The heavy chain CDRs of the 5147_N06 (PGT-130) antibody have the following sequences per Chothia definition: GESINTGH (SEQ ID NO: 220), HIHYTTAVL (SEQ ID NO: 221), and SGGDILYYYEWQKPHWFSP (SEQ ID NO: 219). The light chain CDRs of the 5147_N06 (PGT-130) antibody have the following sequences per Chothia definition: NGTSSDIGGWNFVS (SEQ ID NO: 226), EVNKRPS (SEQ ID NO: 227), and SSLFGRWDVV (SEQ ID NO: 228).

The 5343_B08 (PGT-135) antibody includes a heavy chain variable region (SEQ ID NO: 232), encoded by the nucleic acid sequence shown in SEQ ID NO: 230, and a light chain variable region (SEQ ID NO: 242) encoded by the nucleic acid sequence shown in SEQ ID NO: 239.

The heavy chain CDRs of the 5343_B08 (PGT-135) antibody have the following sequences per Kabat definition: GGEWGDKDYHWG (SEQ ID NO: 233), SIHWRGTTHYKESLRR (SEQ ID NO: 234), and HRHHDVFMLVPIAGWFDV (SEQ ID NO: 235). The light chain CDRs of the 5343_B08 (PGT-135) antibody have the following sequences per Kabat definition: RASQNINKNLA (SEQ ID NO: 243), ETYSKIA (SEQ ID NO: 244), and QQYEEWPRT (SEQ ID NO: 245).

The heavy chain CDRs of the 5343_B08 (PGT-135) antibody have the following sequences per Chothia definition: GDSIRGGEWGDKD (SEQ ID NO: 236), SIHWRGTTH (SEQ ID NO: 237), and HRHEIDVFMLV-PIAGWFDV (SEQ ID NO: 235). The light chain CDRs of the 5343_B08 (PGT-135) antibody have the following sequences per Chothia definition: RASQNINKNLA (SEQ ID NO: 243), ETYSKIA (SEQ ID NO: 244), and QQYEEWPRT (SEQ ID NO: 245).

The 5344_E16 (PGT-135) antibody includes a heavy chain variable region (SEQ ID NO: 232), encoded by the nucleic acid sequence shown in SEQ ID NO: 230, and a light chain variable region (SEQ ID NO: 242) encoded by the nucleic acid sequence shown in SEQ ID NO: 239.

The heavy chain CDRs of the 5344_E16 (PGT-135) antibody have the following sequences per Kabat definition: GGEWGDKDYHWG (SEQ ID NO: 233), SIHWRGTTHYKESLRR (SEQ ID NO: 234), and HRHHDVFMLVPIAGWFDV (SEQ ID NO: 235). The light chain CDRs of the 5344_E16 (PGT-135) antibody have the following sequences per Kabat definition: RASQNINKNLA (SEQ ID NO: 243), ETYSKIA (SEQ ID NO: 244), and QQYEEWPRT (SEQ ID NO: 245).

The heavy chain CDRs of the 5344 E16 (PGT-135) antibody have the following sequences per Chothia definition: GDSIRGGEWGDKD (SEQ ID NO: 236), SIHWRGTTH (SEQ ID NO: 237), and HRHEIDVFMLV-PIAGWFDV (SEQ ID NO: 235). The light chain CDRs of the 5344 E16 (PGT-135) antibody have the following sequences per Chothia definition: RASQNINKNLA (SEQ ID NO: 243), ETYSKIA (SEQ ID NO: 244), and QQYEEWPRT (SEQ ID NO: 245).

The 5329_C19 (PGT-136) antibody includes a heavy chain variable region (SEQ ID NO: 249), encoded by the nucleic acid sequence shown in SEQ ID NO: 247, and a light chain variable region (SEQ ID NO: 258) encoded by the nucleic acid sequence shown in SEQ ID NO: 256.

The heavy chain CDRs of the 5329_C19 (PGT-136) antibody have the following sequences per Kabat definition: GTDWGENDFHYG (SEQ ID NO: 250), SIHWR-GRTTHYKTSFRS (SEQ ID NO: 251), and HKYHDI-FRVVPVAGWFDP (SEQ ID NO: 252). The light chain CDRs of the 5329_C19 (PGT-136) antibody have the following sequences per Kabat definition: RASQNVKNNLA (SEQ ID NO: 259), DASSRAG (SEQ ID NO: 260), and QQYEEWPRT (SEQ ID NO: 245).

The heavy chain CDRs of the 5329_C19 (PGT-136) antibody have the following sequences per Chothia definition: GGSMRGTDWGEND (SEQ ID NO: 253), SIHWR-GRTTH (SEQ ID NO: 254), and HKYHDI-FRVVPVAGWFDP (SEQ ID NO: 252). The light chain CDRs of the 5329_C19 (PGT-136) antibody have the following sequences per Chothia definition: RASQNVKNNLA (SEQ ID NO: 259), DASSRAG (SEQ ID NO: 260), and QQYEEWPRT (SEQ ID NO: 245).

The 5366_P21 (PGT-136) antibody includes a heavy chain variable region (SEQ ID NO: 249), encoded by the nucleic acid sequence shown in SEQ ID NO: 247, and a light chain variable region (SEQ ID NO: 258) encoded by the nucleic acid sequence shown in SEQ ID NO: 256.

The heavy chain CDRs of the 5366_P21 (PGT-136) antibody have the following sequences per Kabat definition: GTDWGENDFHYG (SEQ ID NO: 250), SIHWR-GRTTHYKTSFRS (SEQ ID NO: 251), and HKYHDI-FRVVPVAGWFDP (SEQ ID NO: 252). The light chain CDRs of the 5366_P21 (PGT-136) antibody have the following sequences per Kabat definition: RASQNVKNNLA (SEQ ID NO: 259), DASSRAG (SEQ ID NO: 260), and QQYEEWPRT (SEQ ID NO: 245).

The heavy chain CDRs of the 5366_P21 (PGT-136) antibody have the following sequences per Chothia definition: GGSMRGTDWGEND (SEQ ID NO: 253), SIHWR- GRTTH (SEQ ID NO: 254), and HKYHDI-FRVVPVAGWFDP (SEQ ID NO: 252). The light chain CDRs of the 5366 P21 (PGT-136) antibody have the following sequences per Chothia definition: RASQNVKNNLA (SEQ ID NO: 259), DASSRAG (SEQ ID NO: 260), and QQYEEWPRT (SEQ ID NO: 245).

The 5964_G22 (PGT-141) antibody includes a heavy chain variable region (SEQ ID NO: 276), encoded by the nucleic acid sequence shown in SEQ ID NO: 274, and a light chain variable region (SEQ ID NO: 285) encoded by the nucleic acid sequence shown in SEQ ID NO: 283.

The heavy chain CDRs of the 5964_G22 (PGT-141) antibody have the following sequences per Kabat definition: KYDVH (SEQ ID NO: 277), WMSHEGDKTESAQRFKG (SEQ ID NO: 278), and GSKHRLRDYVLYDD-YGLINYQEWNDYLEFLDV (SEQ ID NO: 279). The light chain CDRs of the 5964_G22 (PGT-141) antibody have the following sequences per Kabat definition: SSTQSLRHSN-GANYLA (SEQ ID NO: 286), LGSQRAS (SEQ ID NO: 287), and MQGLNRPWT (SEQ ID NO: 288).

The heavy chain CDRs of the 5964_G22 (PGT-141) antibody have the following sequences per Chothia definition: GNTFSK (SEQ ID NO: 280), WMSHEGDKTE (SEQ ID NO: 281), and GSKHRLRDYVLYDDYGLINYQEWN-DYLEFLDV (SEQ ID NO: 279). The light chain CDRs of the 5964_G22 (PGT-141) antibody have the following sequences per Chothia definition: SSTQSLRHSNGANYLA (SEQ ID NO: 286), LGSQRAS (SEQ ID NO: 287), and MQGLNRPWT (SEQ ID NO: 288).

The 4993_K13 (PGT-141) antibody includes a heavy chain variable region (SEQ ID NO: 276), encoded by the nucleic acid sequence shown in SEQ ID NO: 290, and a light chain variable region (SEQ ID NO: 285) encoded by the nucleic acid sequence shown in SEQ ID NO: 283.

The heavy chain CDRs of the 4993_K13 (PGT-141) antibody have the following sequences per Kabat definition: KYDVH (SEQ ID NO: 277), WMSHEGDKTESAQRFKG (SEQ ID NO: 278), and GSKHRLRDYVLYDD-YGLINYQEWNDYLEFLDV (SEQ ID NO: 279). The light chain CDRs of the 4993 K13 (PGT-141) antibody have the following sequences per Kabat definition: SSTQSLRHSN-GANYLA (SEQ ID NO: 286), LGSQRAS (SEQ ID NO: 287), and MQGLNRPWT (SEQ ID NO: 288).

The heavy chain CDRs of the 4993_K13 (PGT-141) antibody have the following sequences per Chothia definition: GNTFSK (SEQ ID NO: 280), WMSHEGDKTE (SEQ ID NO: 281), and GSKHRLRDYVLYDDYGLINYQEWN-DYLEFLDV (SEQ ID NO: 279). The light chain CDRs of the 4993 K13 (PGT-141) antibody have the following sequences per Chothia definition: SSTQSLRHSNGANYLA (SEQ ID NO: 286), LGSQRAS (SEQ ID NO: 287), and MQGLNRPWT (SEQ ID NO: 288).

The 4995 E20 (PGT-142) antibody includes a heavy chain variable region (SEQ ID NO: 292), encoded by the nucleic acid sequence shown in SEQ ID NO: 315, and a light chain variable region (SEQ ID NO: 285) encoded by the nucleic acid sequence shown in SEQ ID NO: 283.

The heavy chain CDRs of the 4995 E20 (PGT-142) antibody have the following sequences per Kabat definition: KYDVH (SEQ ID NO: 277), WISHERDKTESAQRFKG (SEQ ID NO: 293), and GSKHRLRDYVLYDD-YGLINYQEWNDYLEFLDV (SEQ ID NO: 279). The light chain CDRs of the 4995 E20 (PGT-142) antibody have the following sequences per Kabat definition: SSTQSLRHSN-GANYLA (SEQ ID NO: 286), LGSQRAS (SEQ ID NO: 287), and MQGLNRPWT (SEQ ID NO: 288).

The heavy chain CDRs of the 4995 E20 (PGT-142) antibody have the following sequences per Chothia definition: GNTFSK (SEQ ID NO: 280), WISHERDKTE (SEQ ID NO: 294), and GSKHRLRDYVLYDDYGLINYQEWN-DYLEFLDV (SEQ ID NO: 279). The light chain CDRs of the 4995 E20 (PGT-142) antibody have the following sequences per Chothia definition: SSTQSLRHSNGANYLA (SEQ ID NO: 286), LGSQRAS (SEQ ID NO: 287), and MQGLNRPWT (SEQ ID NO: 288).

The 4980_N08 (PGT-143) antibody includes a heavy chain variable region (SEQ ID NO: 298), encoded by the nucleic acid sequence shown in SEQ ID NO: 296, and a light chain variable region (SEQ ID NO: 302) encoded by the nucleic acid sequence shown in SEQ ID NO: 300.

The heavy chain CDRs of the 4980_N08 (PGT-143) antibody have the following sequences per Kabat definition: KYDVH (SEQ ID NO: 277), WMSHEGDKTESAQRFKG (SEQ ID NO: 278), and GSKHRLRDYVLYDD-YGLINYQEWNDYLEFLDV (SEQ ID NO: 279). The light chain CDRs of the 4980_N08 (PGT-143) antibody have the following sequences per Kabat definition: TSTQSLRHSN-GANYLA (SEQ ID NO: 303), LGSQRAS (SEQ ID NO: 287), and MQGLNRPWT (SEQ ID NO: 288).

The heavy chain CDRs of the 4980_N08 (PGT-143) antibody have the following sequences per Chothia definition: GNTFSK (SEQ ID NO: 280), WMSHEGDKTE (SEQ ID NO: 281), and GSKHRLRDYVLYDDYGLINYQEWN-DYLEFLDV (SEQ ID NO: 279). The light chain CDRs of the 4980_N08 (PGT-143) antibody have the following sequences per Chothia definition: TSTQSLRHSNGANYLA (SEQ ID NO: 303), LGSQRAS (SEQ ID NO: 287), and MQGLNRPWT (SEQ ID NO: 288).

The 4970_K22 (PGT-144) antibody includes a heavy chain variable region (SEQ ID NO: 307), encoded by the nucleic acid sequence shown in SEQ ID NO: 305, and a light chain variable region (SEQ ID NO: 313) encoded by the nucleic acid sequence shown in SEQ ID NO: 311.

The heavy chain CDRs of the 4970 K22 (PGT-144) antibody have the following sequences per Kabat definition: KYDVH (SEQ ID NO: 277), WMSHEGDKTESAQRFKG (SEQ ID NO: 278), and GSKHRLRDYVLYDDYG-LINQQEWNDYLEFLDV (SEQ ID NO: 308). The light chain CDRs of the 4970_K22 (PGT-144) antibody have the following sequences per Kabat definition: TSTQSLRHSN-GANYLA (SEQ ID NO: 303), LGSQRAS (SEQ ID NO: 287), and MQGLNRPWT (SEQ ID NO: 288).

The heavy chain CDRs of the 4970_K22 (PGT-144) antibody have the following sequences per Chothia definition: GNTFRK (SEQ ID NO: 309), WMSHEGDKTE (SEQ ID NO: 281), and GSKHRLRDYVLYDDYGLINQQEWN-DYLEFLDV (SEQ ID NO: 308). The light chain CDRs of the 4970 K22 (PGT-144) antibody have the following sequences per Chothia definition: TSTQSLRHSNGANYLA (SEQ ID NO: 303), LGSQRAS (SEQ ID NO: 287), and MQGLNRPWT (SEQ ID NO: 288).

The sequences of additional human monoclonal antibodies were determined, including the sequences of the variable regions of the Gamma heavy and Kappa or Lambda light chains. In addition, the sequence of each of the polynucleotides encoding the antibody sequences was determined. Shown below are the polypeptide and polynucleotide sequences of the gamma heavy chains and kappa light chains, with the signal peptides at the N-terminus (or 5' end) and the constant regions at the C-terminus (or 3' end) of the variable regions, which are shown in bolded text.

5145_B14 (PGT-127) gamma heavy chain nucleotide sequence:
coding sequence (variable region in bold)

(SEQ ID NO: 316)

ATGAAACACCTGTGGTTCTTCCTCCTGCTGGTGGCGGCTCCCAGATGGGTC

CTGTCCAGCCGCAGCTGCAGGAGTCGGGCCCAGGACTGGTGGAGGC

TTCGGAGACCCTGTCCCTCACGTGCACTGTGTCCGGCGACTCCACTG

GTCGTTGTAATTATTTCTGGGGCTGGGTCCGGCAGCCCCCAGGGAAG

GGGCTGGAGTGGATTGGGAGTTTGTCCCACTGTAGAAGTTACTACAA

TACTGACTGGACCTACCACAACCCGTCTCTCAAGAGTCGACTCACTAT

TTCACTCGACACGCCCAAGAATCAGGTCTTCCTGAGATTGACCTCTGT

GACCGCCGCGGACACGGCCACTTATTACTGTGCGCGATTCGGCGGCG

AAGTTCTAGTGTACAGAGATTGGCCAAAGCCGGCCTGGGTCGACCTC

TGGGGCCGGGGAACGCTGGTCGTCACCGTCTCGAGCGCCTCCACCAA

GGGCCCATCGGTCTTCCCCCTGGCACCCTCCTCCAAGAGCACCTCTGGGG

GCACAGCGGCCCTGGGCTGCCTGGTCAAGGACTACTTCCCCGAACCGGTG

ACGGTGTCGTGGAACTCAGGCGCCCTGACCAGCGGCGTGCACACCTTCCC

GGCTGTCCTACAGTCCTCAGGACTCTACTCCCTCAGCAGCGTGGTGACCG

TGCCCTCCAGCAGCTTGGGCACCCAGACCTACATCTGCAACGTGAATCAC

AAGCCCAGCAACACCAAGGTGGACAAGAGAGTTGAGCCCAAATCTTGTG

ACAAAACTCACACATGCCCACCGTGCCCAGCACCTGAACTCCTGGGGGGA

CCGTCAGTCTTCCTCTTCCCCCCAAAACCCAAGGACACCCTCATGATCTCC

CGGACCCCTGAGGTCACATGCGTGGTGGTGGACGTGAGCCACGAAGACC

CTGAGGTCAAGTTCAACTGGTACGTGGACGGCGTGGAGGTGCATAATGCC

AAGACAAAGCCGCGGGAGGAGCAGTACAACAGCACGTACCGTGTGGTCA

GCGTCCTCACCGTCCTGCACCAGGACTGGCTGAATGGCAAGGAGTACAAG

TGCAAGGTCTCCAACAAAGCCCTCCCAGCCCCCATCGAGAAAACCATCTC

CAAAGCCAAAGGGCAGCCCCGAGAACCACAGGTGTACACCCTGCCCCCA

TCCCGGGAGGAGATGACCAAGAACCAGGTCAGCCTGACCTGCCTGGTCA

AAGGCTTCTATCCCAGCGACATCGCCGTGGAGTGGGAGAGCAATGGGCA

GCCGGAGAACAACTACAAGACCACGCCTCCCGTGCTGGACTCCGACGGCT

CCTTCTTCCTCTATAGCAAGCTCACCGTGGACAAGAGCAGGTGGCAGCAG

GGGAACGTCTTCTCATGCTCCGTGATGCATGAGGCTCTGCACAACCACTA

CACGCAGAAGAGCCTCTCCCTGTCTCCGGGTAAATGA

5145_B14 (PGT-127) gamma heavy chain variable region nucleotide
sequence:

(SEQ ID NO: 317)

CAGCCGCAGCTGCAGGAGTCGGGCCCAGGACTGGTGGAGGCTTCGGAGA

CCCTGTCCCTCACGTGCACTGTGTCCGGCGACTCCACTGGTCGTTGTAATT

ATTTCTGGGGCTGGGTCCGGCAGCCCCCAGGGAAGGGGCTGGAGTGGATT

GGGAGTTTGTCCCACTGTAGAAGTTACTACAATACTGACTGGACCTACCA

CAACCCGTCTCTCAAGAGTCGACTCACTATTTCACTCGACACGCCCAAGA

ATCAGGTCTTCCTGAGATTGACCTCTGTGACCGCCGCGGACACGGCCACT

-continued

```
TATTACTGTGCGCGATTCGGCGGCGAAGTTCTAGTGTACAGAGATTGGCC

AAAGCCGGCCTGGGTCGACCTCTGGGGCCGGGGAACGCTGGTCGTCACCG

TCTCGAGC
```

5145_B14 (PGT-127) gamma heavy chain amino acid sequence:
expressed protein with leader sequence in italics and variable
region in bold.
(SEQ ID NO: 318)

*MKHLWFFLLLVAAPRWVLS*QPQLQESGPGLVEASETLSLTCTVSGDSTGRC

NYFWGWVRQPPGKGLEWIGSLSHCRSYYNTDWTYHNPSLKSRLTISLDT

PKNQVFLRLTSVTAADTATYYCARFGGEVLVYRDWPKPAWVDLWGRG

TLVVTVSSASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKVDKR

VEPKSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQGNV

FSCSVMHEALHNHYTQKSLSLSPGK

5145_B14 (PGT-127) gamma heavy chain variable region amino acid
sequence: (Kabat CDRs underlined, Chothia CDRs in bold italics)
(SEQ ID NO: 319)

QPQLQESGPGLVEASETLSLTCTVS*GDSTGRCN*YFWGWVRQPPGKGLEWIG*S*

*LSHCRSYYNTDWTY*HNPSLKSRLTISLDTPKNQVFLRLTSVTAADTATYYCAR

*FGGEVLVYRDWPKPAWVDL*WGRGTLVVTVSS

5145_B14 (PGT-127) gamma heavy chain Kabat CDRs:
(SEQ ID NO: 320)
CDR 1: RCNYFWG (SEQ ID NO: 321)
CDR 2: SLSHCRSYYNTDWTYHNPSLKS (SEQ ID NO: 322)
CDR 3: FGGEVLVYRDWPKPAWVDL 5145_B14 (PGT-127) gamma heavy chain Chothia CDRs:
(SEQ ID NO: 323)
CDR 1: GDSTGRCN (SEQ ID NO: 324)
CDR 2: SLSHCRSYYNTDWTY (SEQ ID NO: 322)
CDR 3: FGGEVLVYRDWPKPAWVDL 5145_B14 (PGT-127) lambda light chain nucleotide sequence:
coding sequence (variable region in bold)
(SEQ ID NO: 327)
ATGGCCTGGGCTCTGCTCCTCCTCACCCTCCTCACTCAGGGCACAGGGGC

CTGGGCCCAGTCTGCCCTGACTCAGCCTCCCTCCGCGTCCGGGTCTCC

TGGACAGTCAATCACCATCTCCTGCACTGGAACCAGCAATAACTTTGT

CTCCTGGTACCAACAATACCCAGGCAAGGCCCCCAAACTCGTCATTT

ATGAGGTCAATAAGCGCCCCTCAGGTGTCCCTGATCGTTTCTCTGGC

TCCAAGTCTGGCAGCACGGCCTCCCTGACCGTCTCTGGACTCCAGGC

TGACGATGAGGGTGTCTATTATTGTAGTTCACTTGTAGGCAACTGGG

ATGTGATTTTCGGCGGAGGGACCAAGTTGACCGTCCTAGGTCAGCCCA

AGGCTGCCCCCTCGGTCACTCTGTTCCCGCCCTCCTCTGAGGAGCTTCAAG

CCAACAAGGCCACACTGGTGTGTCTCATAAGTGACTTCTACCCGGGAGCC

GTGACAGTGGCCTGGAAGGCAGATAGCAGCCCCGTCAAGGCGGGAGTGG

AGACCACCACACCCTCCAAACAAAGCAACAACAAGTACGCGGCCAGCAG

CTATCTGAGCCTGACGCCTGAGCAGTGGAAGTCCCACAGAAGCTACAGCT

GCCAGGTCACGCATGAAGGGAGCACCGTGGAGAAGACAGTGGCCCCTAC

AGAATGTTCATAG

5145_B14 (PGT-127) lambda light chain variable region nucleotide
sequence:
(SEQ ID NO: 328)
CAGTCTGCCCTGACTCAGCCTCCCTCCGCGTCCGGGTCTCCTGGACAGTCA

ATCACCATCTCCTGCACTGGAACCAGCAATAACTTTGTCTCCTGGTACCAA

CAATACCCAGGCAAGGCCCCCAAACTCGTCATTTATGAGGTCAATAAGCG

CCCCTCAGGTGTCCCTGATCGTTTCTCTGGCTCCAAGTCTGGCAGCACGGC

CTCCCTGACCGTCTCTGGACTCCAGGCTGACGATGAGGGTGTCTATTATTG

TAGTTCACTTGTAGGCAACTGGGATGTGATTTTCGGCGGAGGGACCAAGT

TGACCGTCCTA

5145_B14 (PGT-127) lambda light chain amino acid sequence:
expressed protein with leader sequence in italics and variable
region in bold.
(SEQ ID NO: 329)
*MAWALLLLTLLTQGTGAWA*QSALTQPPSASGSPGQSITISCTGTSNNFVSWY

QQYPGKAPKLVIYEVNKRPSGVPDRFSGSKSGSTASLTVSGLQADDEGVY

YCSSLVGNWDVIFGGGTKLTVLGQPKAAPSVTLFPPSSEELQANKATLVCLI

SDFYPGAVTVAWKADSSPVKAGVETTTPSKQSNNKYAASSYLSLTPEQWKS

HRSYSCQVTHEGSTVEKTVAPTECS

5145_B14 (PGT-127) lambda light chain variable region amino
acid sequence: (Kabat CDRs underlined, Chothia CDRs in bold
italics)
(SEQ ID NO: 330)
QSALTQPPSASGSPGQSITISC*TGTSNNFVS*WYQQYPGKAPKLVIY*EVNKRPS*

GVPDRFSGSKSGSTASLTVSGLQADDEGVYYC*SSLVGNWDVI*FGGGTKLTVL

5145_B14 (PGT-127) lambda light chain Kabat CDRs:
(SEQ ID NO: 325)
CDR 1: TGTSNNFVS (SEQ ID NO: 227)
CDR 2: EVNKRPS (SEQ ID NO: 212)
CDR 3: SSLVGNWDVI 5145_B14 (PGT-127) lambda light chain Chothia CDRs:
(SEQ ID NO: 325)
CDR 1: TGTSNNFVS (SEQ ID NO: 227)
CDR 2: EVNKRPS (SEQ ID NO: 212)
CDR 3: SSLVGNWDVI 5114_A19 (PGT-128) gamma heavy chain nucleotide sequence:
coding sequence (variable region in bold)
(SEQ ID NO: 331)
ATGAAACACCTGTGGTTCTTCCTCCTGCTGGTGGCGGCTCCCAGATGGGTC

CTGTCCCAGCCGCAGCTGCAGGAGTCGGGCCCAACACTGGTGGAGGC

TTCGGAGACTCTGTCCCTCACCTGCGCTGTGTCCGGCGACTCCACTG

CTGCATGTAATTCTTTCTGGGGCTGGGTCCGGCAGCCCCCAGGGAAG

-continued
GGGCTGGAGTGGGTTGGGAGTTTGTCCCATTGTGCAAGCTATTGGAA

TCGTGGGTGGACCTACCACAACCCGTCTCTCAAGAGTCGGCTCACGC

TTGCTCTCGACACACCCAAGAATCTGGTCTTCCTCAAATTAAATTCTG

TGACTGCCGCGGACACGGCCACTTACTACTGTGCGCGATTCGGCGGC

GAAGTTTTACGCTACACGGATTGGCCAAAGCCGGCCTGGGTCGACCT

CTGGGGCCGGGAACGCTGGTCACCGTCTCGAGCGCCTCCACCAAGG

GCCCATCGGTCTTCCCCCTGGCACCCTCCTCCAAGAGCACCTCTGGGGGC

ACAGCGGCCCTGGGCTGCCTGGTCAAGGACTACTTCCCCGAACCGGTGAC

GGTGTCGTGGAACTCAGGCGCCCTGACCAGCGGCGTGCACACCTTCCCGG

CTGTCCTACAGTCCTCAGGACTCTACTCCCTCAGCAGCGTGGTGACCGTGC

CCTCCAGCAGCTTGGGCACCCAGACCTACATCTGCAACGTGAATCACAAG

CCCAGCAACACCAAGGTGGACAAGAGAGTTGAGCCCAAATCTTGTGACA

AAACTCACACATGCCCACCGTGCCCAGCACCTGAACTCCTGGGGGGACCG

TCAGTCTTCCTCTTCCCCCCAAAACCCAAGGACACCCTCATGATCTCCCGG

ACCCCTGAGGTCACATGCGTGGTGGTGGACGTGAGCCACGAAGACCCTGA

GGTCAAGTTCAACTGGTACGTGGACGGCGTGGAGGTGCATAATGCCAAGA

CAAAGCCGCGGGAGGAGCAGTACAACAGCACGTACCGTGTGGTCAGCGT

CCTCACCGTCCTGCACCAGGACTGGCTGAATGGCAAGGAGTACAAGTGCA

AGGTCTCCAACAAAGCCCTCCCAGCCCCCATCGAGAAAACCATCTCCAAA

GCCAAAGGGCAGCCCCGAGAACCACAGGTGTACACCCTGCCCCCATCCCG

GGAGGAGATGACCAAGAACCAGGTCAGCCTGACCTGCCTGGTCAAAGGC

TTCTATCCCAGCGACATCGCCGTGGAGTGGGAGAGCAATGGGCAGCCGG

AGAACAACTACAAGACCACGCCTCCCGTGCTGGACTCCGACGGCTCCTTC

TTCCTCTATAGCAAGCTCACCGTGGACAAGAGCAGGTGGCAGCAGGGGA

ACGTCTTCTCATGCTCCGTGATGCATGAGGCTCTGCACAACCACTACACG

CAGAAGAGCCTCTCCCTGTCTCCGGGTAAATGA

5114_A19 (PGT-128) gamma heavy chain variable region nucleotide
sequence:
(SEQ ID NO: 332)
CAGCCGCAGCTGCAGGAGTCGGGCCCAACACTGGTGGAGGCTTCGGAGA

CTCTGTCCCTCACCTGCGCTGTGTCCGGCGACTCCACTGCTGCATGTAATT

CTTTCTGGGGCTGGGTCCGGCAGCCCCCAGGGAAGGGGCTGGAGTGGGTT

GGGAGTTTGTCCCATTGTGCAAGCTATTGGAATCGTGGGTGGACCTACCA

CAACCCGTCTCTCAAGAGTCGGCTCACGCTTGCTCTCGACACACCCAAGA

ATCTGGTCTTCCTCAAATTAAATTCTGTGACTGCCGCGGACACGGCCACTT

ACTACTGTGCGCGATTCGGCGGCGAAGTTTTACGCTACACGGATTGGCCA

AAGCCGGCCTGGGTCGACCTCTGGGGCCGGGAACGCTGGTCACCGTCTC

GAGC

5114_A19 (PGT-128) gamma heavy chain amino acid sequence:
expressed protein with leader sequence in italics and variable
region in bold.
(SEQ ID NO: 333)
*MKHLWFFLLLVAAPRWVLS*QPQLQESGPTLVEASETLSLTCAVSGDSTAAC

NSFWGWVRQPPGKGLEWVGSLSHCASYWNRGWTYHNPSLKSRLTLAL

DTPKNLVFLKLNSVTAADTATYYCARFGGEVLRYTDWPKPAWVDLWG

RGTLVTVSSASTKGPSVFPLAPSSKSTSGGTAALGCLVKDYFPEPVTVSWNS

GALTSGVHTFPAVLQSSGLYSLSSVVTVPSSSLGTQTYICNVNHKPSNTKVDK

RVEPKSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQGNV

FSCSVMHEALHNHYTQKSLSLSPGK

5114_A19 (PGT-128) gamma heavy chain variable region amino acid sequence: (Kabat CDRs underlined, Chothia CDRs in bold italics)
(SEQ ID NO: 334)
QPQLQESGPTLVEASETLSLTCAVS*GDSTAACN*SFWGWVRQPPGKGLEWVG

*SLSHCASYWNRGWTY*HNPSLKSRLTLALDTPKNLVFLKLNSVTAADTATYYC

AR*FGGEVLRYTDWPKPAWVDL*WGRGTLVTVSS

5114_A19 (PGT-128) gamma heavy chain Kabat CDRs:
(SEQ ID NO: 326)
CDR 1: ACNSFWG (SEQ ID NO: 335)
CDR 2: SLSHCASYWNRGWTYHNPSLKS (SEQ ID NO: 336)
CDR 3: FGGEVLRYTDWPKPAWVDL 5114_A19 (PGT-128) gamma heavy chain Chothia CDRs:
(SEQ ID NO: 337)
CDR 1: GDSTAACN (SEQ ID NO: 338)
CDR 2: SLSHCASYWNRGWTY (SEQ ID NO: 336)
CDR 3: FGGEVLRYTDWPKPAWVDL 5114_A19 (PGT-128) lambda light chain nucleotide sequence: coding sequence (variable region in bold)
(SEQ ID NO: 390)
ATGGCCTGGGCTCTGCTCCTCCTCACCCTCCTCACTCAGGGCACAGGGGC

CTGGGCCCAGTCTGCCCTGACTCAGCCTCCCTCCGCGTCCGGGTCTCC

TGGACAGTCAATCACCATCTCCTGCACTGGAACCAGCAATAACTTTGT

CTCCTGGTACCAGCAACACGCAGGCAAGGCCCCCAAGCTCGTCATTT

ATGACGTCAATAAGCGCCCCTCAGGTGTCCCTGATCGTTTCTCTGGC

TCCAAGTCTGGCAACACGGCCTCCCTGACCGTCTCTGGACTCCAGAC

TGACGATGAGGCTGTCTATTACTGCGGCTCACTTGTAGGCAACTGGG

ATGTGATTTTCGGCGGAGGGACCAAGTTGACCGTCCTAGGTCAGCCCA

AGGCTGCCCCCTCGGTCACTCTGTTCCCGCCCTCCTCTGAGGAGCTTCAAG

CCAACAAGGCCACACTGGTGTGTCTCATAAGTGACTTCTACCCGGGAGCC

GTGACAGTGGCCTGGAAGGCAGATAGCAGCCCCGTCAAGGCGGGAGTGG

AGACCACCACACCCTCCAAACAAAGCAACAACAAGTACGCGGCCAGCAG

CTATCTGAGCCTGACGCCTGAGCAGTGGAAGTCCCACAGAAGCTACAGCT

GCCAGGTCACGCATGAAGGGAGCACCGTGGAGAAGACAGTGGCCCCTAC

AGAATGTTCATAG

5114_A19 (PGT-128) lambda light chain variable region nucleotide sequence:

(SEQ ID NO: 391)
CAGTCTGCCCTGACTCAGCCTCCCTCCGCGTCCGGGTCTCCTGGACAGTCA

ATCACCATCTCCTGCACTGGAACCAGCAATAACTTTGTCTCCTGGTACCAG

CAACACGCAGGCAAGGCCCCCAAGCTCGTCATTTATGACGTCAATAAGCG

CCCCTCAGGTGTCCCTGATCGTTTCTCTGGCTCCAAGTCTGGCAACACGGC

CTCCCTGACCGTCTCTGGACTCCAGACTGACGATGAGGCTGTCTATTACTG

CGGCTCACTTGTAGGCAACTGGGATGTGATTTTCGGCGGAGGGACCAAGT

TGACCGTCCTA

5114_A19 (PGT-128) lambda light chain amino acid sequence: expressed protein with leader sequence in italics and variable region in bold.

(SEQ ID NO: 392)
*MAWALLLLTLLTQGTGAWAQ*SALTQPPSASGSPGQSITISCTGTSNNFVSWY

QQHAGKAPKLVIYDVNKRPSGVPDRFSGSKSGNTASLTVSGLQTDDEAV

YYCGSLVGNWDVIFGGGTKLTVLGQPKAAPSVTLFPPSSEELQANKATLVC

LISDFYPGAVTVAWKADSSPVKAGVETTTPSKQSNNKYAASSYLSLTPEQWK

SHRSYSCQVTHEGSTVEKTVAPTECS (SEQ ID NO: 393)
5114_A19 (PGT-128) lambda light chain variable region amino acid sequence: (Kabat CDRs underlined, Chothia CDRs in bold italics)
QSALTQPPSASGSPGQSITISC*TGTSNNFVS*WYQQHAGKAPKLVIY*DVNKRPS*

GVPDRFSGSKSGNTASLTVSGLQTDDEAVYYC*GSLVGNWDVI*FGGGTKLTVL

5114_A19 (PGT-128) lambda light chain Kabat CDRs:

(SEQ ID NO: 325)
CDR 1: TGTSNNFVS (SEQ ID NO: 343)
CDR 2: DVNKRPS (SEQ ID NO: 196)
CDR 3: GSLVGNWDVI

5114_A19 (PGT-128) lambda light chain Chothia CDRs:

(SEQ ID NO: 325)
CDR 1: TGTSNNFVS (SEQ ID NO: 343)
CDR 2: DVNKRPS (SEQ ID NO: 196)
CDR 3: GSLVGNWDVI

5136_H01 (PGT-131) gamma heavy chain nucleotide sequence: coding sequence (variable region in bold)

(SEQ ID NO: 344)
ATGAAACACCTGTGGTTCTTCCTCCTGCTGGTGGCGGCTCCCAGATGGGTC

CTTTCCCAGGTGCAACTACAGGAGTCGGGCCCAGGACTGGTGAAGCC

TTCGGAGACCCTTTCCCTCACCTGCACTGTCTCTGGTGACTCCATCAA

CACTGGTCATCACTACTGGGGCTGGGTCCGTCAGGTCCCAGGGAAGG

GACCGGAATGGATTGCTCACATCCACTATAATACGGCTGTCTTACAC

AATCCGGCCCTCAAGAGTCGAGTCACCATTTCGATTTTCACCCTGAA

GAATCTGATTACCCTGAGCCTCAGTAATGTGACCGCCGCGGACACGG

CCGTCTATTTCTGCGTTCGATCCGGCGGCGACATTTTATACTATATTG

AGTGGCAAAAACCCCACTGGTTCTATCCCTGGGGCCCGGGAATTTTG

GTCACCGTCTCGAGCGCCTCCACCAAGGGCCCATCGGTCTTCCCCCTGG

-continued

```
CACCCTCCTCCAAGAGCACCTCTGGGGGCACAGCGGCCCTGGGCTGCCTG

GTCAAGGACTACTTCCCCGAACCGGTGACGGTGTCGTGGAACTCAGGCGC

CCTGACCAGCGGCGTGCACACCTTCCCGGCTGTCCTACAGTCCTCAGGAC

TCTACTCCCTCAGCAGCGTGGTGACCGTGCCCTCCAGCAGCTTGGGCACC

CAGACCTACATCTGCAACGTGAATCACAAGCCCAGCAACACCAAGGTGG

ACAAGAGAGTTGAGCCCAAATCTTGTGACAAAACTCACACATGCCCACCG

TGCCCAGCACCTGAACTCCTGGGGGGACCGTCAGTCTTCCTCTTCCCCCCA

AAACCCAAGGACACCCTCATGATCTCCCGGACCCCTGAGGTCACATGCGT

GGTGGTGGACGTGAGCCACGAAGACCCTGAGGTCAAGTTCAACTGGTACG

TGGACGGCGTGGAGGTGCATAATGCCAAGACAAAGCCGCGGGAGGAGCA

GTACAACAGCACGTACCGTGTGGTCAGCGTCCTCACCGTCCTGCACCAGG

ACTGGCTGAATGGCAAGGAGTACAAGTGCAAGGTCTCCAACAAAGCCCT

CCCAGCCCCCATCGAGAAAACCATCTCCAAAGCCAAAGGGCAGCCCCGA

GAACCACAGGTGTACACCCTGCCCCCATCCCGGGAGGAGATGACCAAGA

ACCAGGTCAGCCTGACCTGCCTGGTCAAAGGCTTCTATCCCAGCGACATC

GCCGTGGAGTGGGAGAGCAATGGGCAGCCGGAGAACAACTACAAGACCA

CGCCTCCCGTGCTGGACTCCGACGGCTCCTTCTTCCTCTATAGCAAGCTCA

CCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTC

TCCGGGTAAATGA
```

5136_H01 (PGT-131) gamma heavy chain variable region nucleotide sequence:
(SEQ ID NO: 345)

```
CAGGTGCAACTACAGGAGTCGGGCCCAGGACTGGTGAAGCCTTCGGAGA

CCCTTTCCCTCACCTGCACTGTCTCTGGTGACTCCATCAACACTGGTCATC

ACTACTGGGGCTGGGTCCGTCAGGTCCCAGGGAAGGGACCGGAATGGATT

GCTCACATCCACTATAATACGGCTGTCTTACACAATCCGGCCCTCAAGAG

TCGAGTCACCATTTCGATTTTCACCCTGAAGAATCTGATTACCCTGAGCCT

CAGTAATGTGACCGCCGCGGACACGGCCGTCTATTTCTGCGTTCGATCCG

GCGGCGACATTTTATACTATATTGAGTGGCAAAAACCCCACTGGTTCTATC

CCTGGGGCCCGGGAATTTTGGTCACCGTCTCGAGC
```

5136_H01 (PGT-131) gamma heavy chain amino acid sequence: expressed protein with leader sequence in italics and variable region in bold.
(SEQ ID NO: 346)

*MKHLWFFLLLVAAPRWVLS*QVQLQESGPGLVKPSETLSLTCTVSGDSINTGH

HYWGWVRQVPGKGPEWIAHIHYNTAVLENPALKSRVTISIFTLKNLITLS

LSNVTAADTAVYFCVRSGGDILYYIEWQKPHWFYPWGPGILVTVSSASTK

GPSVFPLAPSSKSTSGGTAALGCLVKDYFPEPVTVSWNSGALTSGVHTFPAVL

QSSGLYSLSSVVTVPSSSLGTQTYICNVNHKPSNTKVDKRVEPKSCDKTHTCP

PCPAPELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

-continued
PIEKTISKAKGQPREPQVYTLPPSREEMTKNQVSLTCLVKGFYPSDIAVEWES

NGQPENNYKTTPPVLDSDGSFFLYSKLTVDKSRWQQGNVFSCSVMHEALHN

HYTQKSLSLSPGK

5136_H01 (PGT-131) gamma heavy chain variable region amino acid
sequence: (Kabat CDRs underlined, Chothia CDRs in bold italics)

(SEQ ID NO: 347)
QVQLQESGPGLVKPSETLSLTCTVS*GDSINTGH*HYWGWVRQVPGKGPEWIA

*HIHYNTAVL*HNPALKSRVTISIFTLKNLITLSLSNVTAADTAVYFCVR*SGGDIL*

*YYIEWQKPHWFYP*WGPGILVTVSS

5136_H01 (PGT-131) gamma heavy chain Kabat CDRs:

(SEQ ID NO: 348)
CDR 1: TGHHYWG (SEQ ID NO: 349)
CDR 2: HIHYNTAVLHNPALKS (SEQ ID NO: 350)
CDR 3: SGGDILYYIEWQKPHWFYP

5136_H01 (PGT-131) gamma heavy chain Chothia CDRs:

(SEQ ID NO: 351)
CDR 1: GDSINTGH (SEQ ID NO: 352)
CDR 2: HIHYNTAVL (SEQ ID NO: 350)
CDR 3: SGGDILYYIEWQKPHWFYP

5136 H01 (PGT-131) lambda light chain nucleotide sequence:
coding sequence (variable region in bold)

(SEQ ID NO: 353)
ATGGCCTGGGCTCTGCTCCTCCTCACCCTCCTCACTCAGGGCACAGGGTCC

TGGGCCCAGTCTGCCCTGACTCAGCCTCCCTCCGCGTCCGGGTCTCTT

GGACAGTCACTCACCATCTCCTGCAGTGGAACCGGCAGTGACATTGG

CAGTTGGAATTTTGTCTCCTGGTATCAACAATTCCCAGGCAGAGCCC

CCAACCTCATTATTTTTGAGGTCAATAGGCGGCGATCAGGGGTCCCT

GATCGCTTCTCTGGTTCCAAGTCGGGCAATACGGCCTCCCTGACCGT

CTCTGGGCTCCGGTCTGAGGATGAGGCTGAATATTTTTGCAGTTCCC

TTTCAGGCAGGTGGGACATTGTTTTTGGCGGAGGGACCAAGGTGACC

GTCCTAGGTCAGCCCAAGGCTGCCCCCTCGGTCACTCTGTTCCCGCCCTC

CTCTGAGGAGCTTCAAGCCAACAAGGCCACACTGGTGTGTCTCATAAGTG

ACTTCTACCCGGGAGCCGTGACAGTGGCCTGGAAGGCAGATAGCAGCCCC

GTCAAGGCGGGAGTGGAGACCACCACACCCTCCAAACAAAGCAACAACA

AGTACGCGGCCAGCAGCTATCTGAGCCTGACGCCTGAGCAGTGGAAGTCC

CACAGAAGCTACAGCTGCCAGGTCACGCATGAAGGGAGCACCGTGGAGA

AGACAGTGGCCCCTACAGAATGTTCATAG

5136_H01 (PGT-131) lambda light chain variable region
nucleotide sequence:

(SEQ ID NO: 354)
CAGTCTGCCCTGACTCAGCCTCCCTCCGCGTCCGGGTCTCTTGGACAGTCA

CTCACCATCTCCTGCAGTGGAACCGGCAGTGACATTGGCAGTTGGAATTT

TGTCTCCTGGTATCAACAATTCCCAGGCAGAGCCCCCAACCTCATTATTTT

TGAGGTCAATAGGCGGCGATCAGGGGTCCCTGATCGCTTCTCTGGTTCCA

AGTCGGGCAATACGGCCTCCCTGACCGTCTCTGGGCTCCGGTCTGAGGAT

```
GAGGCTGAATATTTTTGCAGTTCCCTTTCAGGCAGGTGGGACATTGTTTTT

GGCGGAGGGACCAAGGTGACCGTCCTA
```

5136_H01 (PGT-131) lambda light chain amino acid sequence:
expressed protein with leader sequence in italics and
variable region in bold.

(SEQ ID NO: 355)

```
MAWALLLLTLLTQGTGSWAQSALTQPPSASGSLGQSLTISCSGTGSDIGSWNF

VSWYQQFPGRAPNLIIFEVNRRRSGVPDRFSGSKSGNTASLTVSGLRSEDE

AEYFCSSLSGRWDIVFGGGTKVTVLGQPKAAPSVTLFPPSSEELQANKATL

VCLISDFYPGAVTVAWKADSSPVKAGVETTTPSKQSNNKYAASSYLSLTPEQ

WKSHRSYSCQVTHEGSTVEKTVAPTECS
```

5136_H01 (PGT-131) lambda light chain variable region amino acid
sequence: (Kabat CDRs underlined, Chothia CDRs in bold italics)

(SEQ ID NO: 356)

```
QSALTQPPSASGSLGQSLTISC*SGTGSDIGSWNFVS*WYQQFPGRAPNLIIF*EVN

RRRS*GVPDRFSGSKSGNTASLTVSGLRSEDEAEYFC*SSLSGRWDIV*FGGGTKV

TVL
```

5136_H01 (PGT-131) lambda light chain Kabat CDRs:

(SEQ ID NO: 357)
CDR 1: SGTGSDIGSWNFVS (SEQ ID NO: 358)
CDR 2: EVNRRRS (SEQ ID NO: 359)
CDR 3: SSLSGRWDIV

5136_H01 (PGT-131) lambda light chain Chothia CDRs:

(SEQ ID NO: 357)
CDR 1: SGTGSDIGSWNFVS (SEQ ID NO: 358)
CDR 2: EVNRRRS (SEQ ID NO: 359)
CDR 3: SSLSGRWDIV

5345_I01 (PGT-137) gamma heavy chain nucleotide sequence: coding
sequence (variable region in bold)

(SEQ ID NO: 360)
```
ATGAAACACCTGTGGTTCTTCCTCCTGCTGGTTGCGGCTCCCAGATGTGTC

CTGTCT**GAGGTGCATCTGGAGGAGTCGGGCCCAGGACTGGTGAGGCC

CTCGGAGACCTTGTCCCTGACTTGCACGGCCTCTGGTGGCTCCATAA

GGGGGGGGAGTGGGGCGATAGTGACTACCACTGGGGCTGGGTCCG

CCACTCTCCCGAAAAGGGACTGGAATGGATTGGAAGTATTCATTGGC

GGGGGACCACCCACTACAACGCGCCCTTCCGGGGGCGAGGCAGATT

GTCGATAGACCTCTCCCGGAATCAATTCTCCCTGCGCCTGACGTCTG

TGACCGCCGAAGACACTGCCGTCTATTATTGTGTGAAGCACAAATAT

CATGACATTGTCATGGTGGTCCCCATTGCGGGCTGGTTCGACCCCTG

GGGCCAGGGACTCCAGGTCACCGTCTCGAGC**GCCTCCACCAAGGGCCC

ATCGGTCTTCCCCCTGGCACCCTCCTCCAAGAGCACCTCTGGGGGCACAG

CGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGT

CCTACAGTCCTCAGGACTCTACTCCCTCAGCAGCGTGGTGACCGTGCCCTC

CAGCAGCTTGGGCACCCAGACCTACATCTGCAACGTGAATCACAAGCCCA

GCAACACCAAGGTGGACAAGAGAGTTGAGCCCAAATCTTGTGACAAAAC
```

```
TCACACATGCCCACCGTGCCCAGCACCTGAACTCCTGGGGGACCGTCAG

TCTTCCTCTTCCCCCCAAAACCCAAGGACACCCTCATGATCTCCCGGACCC

CTGAGGTCACATGCGTGGTGGTGGACGTGAGCCACGAAGACCCTGAGGTC

AAGTTCAACTGGTACGTGGACGGCGTGGAGGTGCATAATGCCAAGACAA

AGCCGCGGGAGGAGCAGTACAACAGCACGTACCGTGTGGTCAGCGTCCT

CACCGTCCTGCACCAGGACTGGCTGAATGGCAAGGAGTACAAGTGCAAG

GTCTCCAACAAAGCCCTCCCAGCCCCCATCGAGAAAACCATCTCCAAAGC

CAAAGGGCAGCCCCGAGAACCACAGGTGTACACCCTGCCCCCATCCCGG

GAGGAGATGACCAAGAACCAGGTCAGCCTGACCTGCCTGGTCAAAGGCT

TCTATCCCAGCGACATCGCCGTGGAGTGGGAGAGCAATGGGCAGCCGGA

GAACAACTACAAGACCACGCCTCCCGTGCTGGACTCCGACGGCTCCTTCT

TCCTCTATAGCAAGCTCACCGTGGACAAGAGCAGGTGGCAGCAGGGGAA

CGTCTTCTCATGCTCCGTGATGCATGAGGCTCTGCACAACCACTACACGC

AGAAGAGCCTCTCCCTGTCTCCGGGTAAATGA
```

5345_I01 (PGT-137) gamma heavy chain variable region nucleotide sequence:
(SEQ ID NO: 361)
```
GAGGTGCATCTGGAGGAGTCGGGCCCAGGACTGGTGAGGCCCTCGGAGA

CCTTGTCCCTGACTTGCACGGCCTCTGGTGGCTCCATAAGGGGGGCGAG

TGGGGCGATAGTGACTACCACTGGGGCTGGGTCCGCCACTCTCCCGAAAA

GGGACTGGAATGGATTGGAAGTATTCATTGGCGGGGGACCACCCACTACA

ACGCGCCCTTCCGGGGGCGAGGCAGATTGTCGATAGACCTCTCCCGGAAT

CAATTCTCCCTGCGCCTGACGTCTGTGACCGCCGAAGACACTGCCGTCTAT

TATTGTGTGAAGCACAAATATCATGACATTGTCATGGTGGTCCCCATTGCG

GGCTGGTTCGACCCCTGGGGCCAGGGACTCCAGGTCACCGTCTCGAGC
```

5345_I01 (PGT-137) gamma heavy chain amino acid sequence: expressed protein with leader sequence in italics and variable region in bold.
(SEQ ID NO: 362)

*MKHLWFFLLLVAAPRCVLS*EVHLEESGPGLVRPSETLSLTCTASGGSIRGGE

WGDSDYHWGWVRHSPEKGLEWIGSIHWRGTTHYNAPFRGRGRLSIDLS

RNQFSLRLTSVTAEDTAVYYCVKHKYHDIVMVVPIAGWFDPWGQGLQV

TVSSASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKR VEPKS

CDKTHTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKGFYP

SDIA VEWESNGQPENNYKTTPPVLDSDGSFFLYSKLTVDKSRWQQGNVFSCS

VMHEALHNHYTQKSLSLSPGK

-continued

5345_I01 (PGT-137) gamma heavy chain variable region amino acid
sequence: (Kabat CDRs underlined, Chothia CDRs in bold italics)
(SEQ ID NO: 363)
EVHLEESGPGLVRPSETLSLTCTAS*GGSIRGGEWGDSD*YHWGWVRHSPEKGL

EWIG*SIHWRGTTH*YNAPFRGRGRLSIDLSRNQFSLRLTSVTAEDTAVYYCVK

*HKYHDIVMVVPIAGWEDP*WGQGLQVTVSS

5345_I01 (PGT-137) gamma heavy chain Kabat CDRs:
(SEQ ID NO: 364)
CDR 1: GGEWGDSDYHWG (SEQ ID NO: 365)
CDR 2: SIHWRGTTHYNAPFRG (SEQ ID NO: 366)
CDR 3: HKYHDIVMVVPIAGWFDP 5345_I01 (PGT-137) gamma heavy chain Chothia CDRs:
(SEQ ID NO: 367)
CDR 1: GGSIRGGEWGDSD (SEQ ID NO: 237)
CDR 2: SIHWRGTTH (SEQ ID NO: 366)
CDR 3: HKYHDIVMVVPIAGWFDP 5345_I01 (PGT-137) kappa light chain nucleotide sequence: coding
sequence (variable region in bold)
(SEQ ID NO: 394)
ATGGAAACCCCAGCTCAGCTTCTCTTCCTCCTGCTACTCTGGCTCCCAGAT

ACTACTGGAGAAATAATGATGACGCAGTCTCCAGCCATCCTGTCTGTG

TCTCCAGGAGACAGAGCCACACTCTCCTGCAGGGCCAGTCAGAGTGT

GAAGAATAATTTAGCCTGGTACCAGAAGAGACCTGGCCAGGCTCCCA

GACTCCTCATCTTTGATACATCCAGCAGGGCCTCTGGTATCCCTGCCA

GGTTCAGTGGCGGTGGTTCTGGGACAGAGTTCACTCTCACCGTCAAC

AGCATGCAGTCTGAAGACTTTGCGACTTATTACTGTCAGCAATATGAA

GAGTGGCCTCGGACGTTCGGCCAGGGGACCAAGGTGGAAATCAAAC

GTACGGTGGCTGCACCATCTGTCTTCATCTTCCCGCCATCTGATGAGCAGT

TGAAATCTGGAACTGCCTCTGTTGTGTGCCTGCTGAATAACTTCTATCCCA

GAGAGGCCAAAGTACAGTGGAAGGTGGATAACGCCCTCCAATCGGGTAA

CTCCCAGGAGAGTGTCACAGAGCAGGACAGCAAGGACAGCACCTACAGC

CTCAGCAGCACCCTGACGCTGAGCAAAGCAGACTACGAGAAACACAAAG

TCTACGCCTGCGAAGTCACCCATCAGGGCCTGAGCTCGCCCGTCACAAAG

AGCTTCAACAGGGGAGAGTGTTAG

5345_I01 (PGT-137) kappa light chain variable region nucleotide
sequence:
(SEQ ID NO: 395)
GAAATAATGATGACGCAGTCTCCAGCCATCCTGTCTGTGTCTCCAGGAGA

CAGAGCCACACTCTCCTGCAGGGCCAGTCAGAGTGTGAAGAATAATTTAG

CCTGGTACCAGAAGAGACCTGGCCAGGCTCCCAGACTCCTCATCTTTGAT

ACATCCAGCAGGGCCTCTGGTATCCCTGCCAGGTTCAGTGGCGGTGGTTC

TGGGACAGAGTTCACTCTCACCGTCAACAGCATGCAGTCTGAAGACTTTG

CGACTTATTACTGTCAGCAATATGAAGAGTGGCCTCGGACGTTCGGCCAG

GGGACCAAGGTGGAAATCAAA

-continued

5345_I01 (PGT-137) kappa light chain amino acid sequence:
expressed protein with leader sequence in italics and variable
region in bold.
(SEQ ID NO: 396)
*METPAQLLFLLLLWLPDTTG*EIMMTQSPAILSVSPGDRATLSCRASQSVKNN

LAWYQKRPGQAPRLLIFDTSSRASGIPARFSGGGSGTEFTLTVNSMQSED

FATYYCQQYEEWPRTFGQGTKVEIKRTVAAPSVFIFPPSDEQLKSGTASVV

CLLNNFYPREAKVQWKVDNALQSGNSQESVTEQDSKDSTYSLSSTLTLSKAD

YEKHKVYACEVTHQGLSSPVTKSFNRGEC

5345_I01 (PGT-137) kappa light chain variable region amino acid
sequence: (Kabat CDRs underlined, Chothia CDRs in bold italics)
(SEQ ID NO: 397)
EIMMTQSPAILSVSPGDRATLSC*RASQSVKNNLA*WYQKRPGQAPRLLIF*DTSS*

*RAS*GIPARFSGGGSGTEFTLTVNSMQSEDFATYYC*QQYEEWPRT*FGQGTKVEI

K

5345_I01 (PGT-137) kappa light chain Kabat CDRs:
(SEQ ID NO: 372)
CDR 1: RASQSVKNNLA (SEQ ID NO: 373)
CDR 2: DTSSRAS (SEQ ID NO: 245)
CDR 3: QQYEEWPRT 5345_I01 (PGT-137) kappa light chain Chothia CDRs:
(SEQ ID NO: 372)
CDR 1: RASQSVKNNLA (SEQ ID NO: 373)
CDR 2: DTSSRAS (SEQ ID NO: 245)
CDR 3: QQYEEWPRT 4995_P16 (PGT-145) gamma heavy chain nucleotide sequence: coding
sequence (variable region in bold)
(SEQ ID NO: 398)
ATGGACTGGATTTGGAGGATCCTCTTCTTGGTGGCAGCAGCTACAAGTGC

CCACTCCCAGGTGCAGTTGGTGCAGTCTGGGGCTGAAGTGAAGAAGC

CTGGGTCCTCAGTGAAGGTCTCCTGCAAGGCCTCTGGAAACAGTTTC

AGTAATCATGATGTCCACTGGGTACGACAGGCCACTGGACAGGGGCT

TGAATGGATGGGATGGATGAGTCATGAGGGTGATAAGACAGGCTTGG

CACAAAAGTTTCAGGGCAGAGTCACCATCACGAGGGACAGTGGCGCA

AGTACAGTCTACATGGAGTTGCGCGGCCTGACAGCTGACGACACGGC

CATTTATTATTGTTTGACCGGCTCAAAACATCGCCTGCGAGATTATTT

TCTGTACAATGAATATGGCCCCAATTATGAAGAGTGGGGTGACTACC

TTGCGACTTTGGACGTCTGGGGCCATGGGACCGCGGTCACCGTCTCG

AGCGCCTCCACCAAGGGCCCATCGGTCTTCCCCCTGGCACCCTCCTCCAA

GAGCACCTCTGGGGGCACAGCGGCCCTGGGCTGCCTGGTCAAGGACTACT

TCCCCGAACCGGTGACGGTGTCGTGGAACTCAGGCGCCCTGACCAGCGGC

GTGCACACCTTCCCGGCTGTCCTACAGTCCTCAGGACTCTACTCCCTCAGC

AGCGTGGTGACCGTGCCCTCCAGCAGCTTGGGCACCCAGACCTACATCTG

CAACGTGAATCACAAGCCCAGCAACACCAAGGTGGACAAGAGAGTTGAG

CCCAAATCTTGTGACAAAACTCACACATGCCCACCGTGCCCAGCACCTGA

ACTCCTGGGGGGACCGTCAGTCTTCCTCTTCCCCCCAAAACCCAAGGACA

```
CCCTCATGATCTCCCGGACCCCTGAGGTCACATGCGTGGTGGTGGACGTG

AGCCACGAAGACCCTGAGGTCAAGTTCAACTGGTACGTGGACGGCGTGG

AGGTGCATAATGCCAAGACAAAGCCGCGGGAGGAGCAGTACAACAGCAC

GTACCGTGTGGTCAGCGTCCTCACCGTCCTGCACCAGGACTGGCTGAATG

GCAAGGAGTACAAGTGCAAGGTCTCCAACAAAGCCCTCCCAGCCCCCATC

GAGAAAACCATCTCCAAAGCCAAGGGCAGCCCCGAGAACCACAGGTGT

ACACCCTGCCCCCATCCCGGGAGGAGATGACCAAGAACCAGGTCAGCCT

GACCTGCCTGGTCAAAGGCTTCTATCCCAGCGACATCGCCGTGGAGTGGG

AGAGCAATGGGCAGCCGGAGAACAACTACAAGACCACGCCTCCCGTGCT

GGACTCCGACGGCTCCTTCTTCCTCTATAGCAAGCTCACCGTGGACAAGA

GCAGGTGGCAGCAGGGGAACGTCTTCTCATGCTCCGTGATGCATGAGGCT

CTGCACAACCACTACACGCAGAAGAGCCTCTCCCTGTCTCCGGGTAAATG

A
```

4995_P16 (PGT-145) gamma heavy chain variable region nucleotide sequence:
(SEQ ID NO: 399)

```
CAGGTGCAGTTGGTGCAGTCTGGGGCTGAAGTGAAGAAGCCTGGGTCCTC

AGTGAAGGTCTCCTGCAAGGCCTCTGGAAACAGTTTCAGTAATCATGATG

TCCACTGGGTACGACAGGCCACTGGACAGGGGCTTGAATGGATGGGATG

GATGAGTCATGAGGGTGATAAGACAGGCTTGGCACAAAAGTTTCAGGGC

AGAGTCACCATCACGAGGGACAGTGGCGCAAGTACAGTCTACATGGAGTT

GCGCGGCCTGACAGCTGACGACACGGCCATTTATTATTGTTTGACCGGCT

CAAAACATCGCCTGCGAGATTATTTTCTGTACAATGAATATGGCCCCAATT

ATGAAGAGTGGGGTGACTACCTTGCGACTTTGGACGTCTGGGGCCATGGG

ACCGCGGTCACCGTCTCGAGC
```

4995_P16 (PGT-145) gamma heavy chain amino acid sequence: expressed protein with leader sequence in italics and variable region in bold.
(SEQ ID NO: 400)

*MDWIWRILFLVAAATSAHS*QVQLVQSGAEVKKPGSSVKVSCKASGNSFSNH

DVHWVRQATGQGLEWMGWMSHEGDKTGLAQKFQGRVTITRDSGAST

VYMELRGLTADDTAIYYCLTGSKHRLRDYFLYNEYGPNYEEWGDYLAT

LDVWGHGTAVTVSSASTKGPSVFPLAPSSKSTSGGTAALGCLVKDYFPEPVT

VSWNSGALTSGVHTFPAVLQSSGLYSLSSVVTVPSSSLGTQTYICNVNHKPSN

TKVDKRVEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSREEMTKNQV

SLTCLVKGFYPSDIA VEWESNGQPENNYKTTPPVLDSDGSFFLYSKLTVDKSR

WQQGNVFSCSVMHEALHNHYTQKSLSLSPGK

-continued

4995_P16 (PGT-145) gamma heavy chain variable region amino acid sequence: (Kabat CDRs underlined, Chothia CDRs in bold italics)
(SEQ ID NO: 401)
QVQLVQSGAEVKKPGSSVKVSCKAS*GNSFSN*HDVHWVRQATGQGLEWMG

*WMSHEGDKTG*LAQKFQGRVTITRDSGASTVYMELRGLTADDTAIYYCLT*GS*

*KHRLRDYFLYNEYGPNYEEWGDYLATLDV*WGHGTAVTVSS

4995_P16 (PGT-145) gamma heavy chain Kabat CDRs:
(SEQ ID NO: 378)
CDR 1: NHDVH (SEQ ID NO: 379)
CDR 2: WMSHEGDKTGLAQKFQG (SEQ ID NO: 380)
CDR 3: GSKHRLRDYFLYNEYGPNYEEWGDYLATLDV 4995_P16 (PGT-145) gamma heavy chain Chothia CDRs:
(SEQ ID NO: 381)
CDR 1: GNSFSN (SEQ ID NO: 382)
CDR 2: WMSHEGDKTG (SEQ ID NO: 380)
CDR 3: GSKHRLRDYFLYNEYGPNYEEWGDYLATLDV 4995_P16 (PGT-145) kappa light chain nucleotide sequence: coding sequence (variable region in bold)
(SEQ ID NO: 383)
ATGAGGCTCCCTGCTCAGCTCCTGGGGCTGCTAATGCTCTGGGTCTCTGGA

TCCGGTGCGGAGGTTGTCATAACTCAGTCTCCACTCTTCCTGCCCGTC

ACCCCTGGAGAGGCGGCCTCCTTGTCTTGCAAGTGCAGCCACAGCCT

CCAACATTCAACTGGAGCCAACTATTTGGCTTGGTACCTGCAGAGAC

CAGGGCAAACTCCACGCCTGTTGATCCATTTGGCCACTCATCGGGCC

TCCGGGGTCCCTGACAGATTCAGTGGCAGTGGATCAGGCACAGATTT

TACACTTAAAATCAGTCGAGTGGAGTCTGACGATGTTGGAACTTATTA

TTGCATGCAGGGTCTGCACAGTCCCTGGACGTTCGGCCAAGGGACCA

AGGTGGAGATCAAACGTACGGTGGCTGCACCATCTGTCTTCATCTTCCCG

CCATCTGATGAGCAGTTGAAATCTGGAACTGCCTCTGTTGTGTGCCTGCTG

AATAACTTCTATCCCAGAGAGGCCAAAGTACAGTGGAAGGTGGATAACG

CCCTCCAATCGGGTAACTCCCAGGAGAGTGTCACAGAGCAGGACAGCAA

GGACAGCACCTACAGCCTCAGCAGCACCCTGACGCTGAGCAAAGCAGAC

TACGAGAAACACAAAGTCTACGCCTGCGAAGTCACCCATCAGGGCCTGA

GCTCGCCCGTCACAAAGAGCTTCAACAGGGGAGAGTGTTAG

4995_P16 (PGT-145) kappa light chain variable region nucleotide sequence:
(SEQ ID NO: 384)
GAGGTTGTCATAACTCAGTCTCCACTCTTCCTGCCCGTCACCCCTGGAGAG

GCGGCCTCCTTGTCTTGCAAGTGCAGCCACAGCCTCCAACATTCAACTGG

AGCCAACTATTTGGCTTGGTACCTGCAGAGACCAGGGCAAACTCCACGCC

TGTTGATCCATTTGGCCACTCATCGGGCCTCCGGGGTCCCTGACAGATTCA

GTGGCAGTGGATCAGGCACAGATTTTACACTTAAAATCAGTCGAGTGGAG

TCTGACGATGTTGGAACTTATTATTGCATGCAGGGTCTGCACAGTCCCTGG

ACGTTCGGCCAAGGGACCAAGGTGGAGATCAAA

-continued

4995_P16 (PGT-145) kappa light chain amino acid sequence:
expressed protein with leader sequence in italics and variable
region in bold.
(SEQ ID NO: 385)
*MRLPAQLLGLLMLWVSGSGA*EVVITQSPLFLPVTPGEAASLSCKCSHSLQHS

TGANYLAWYLQRPGQTPRLLIHLATHRASGVPDRFSGSGSGTDFTLKISR

VESDDVGTYYCMQGLHSPWTFGQGTKVEIKRTVAAPSVFIFPPSDEQLKS

GTASVVCLLNNFYPREAKVQWKVDNALQSGNSQESVTEQDSKDSTYSLSST

LTLSKADYEKHKVYACEVTHQGLSSPVTKSFNRGEC

4995_P16 (PGT-145) kappa light chain variable region amino acid
sequence: (Kabat CDRs underlined, Chothia CDRs in bold italics)
(SEQ ID NO: 386)
EVVITQSPLFLPVTPGEAASLSC*KCSHSLQHSTGANYLA*WYLQRPGQTPRLLI H<u>LATHRAS</u>GVPDRFSGSGSGTDFTLKISR VESDDVGTYYC*MQGLHSPWT*FGQ

GTKVEIK

4995_P16 (PGT-145) kappa lambda light chain Kabat CDRs:
(SEQ ID NO: 387)
CDR 1: KCSHSLQHSTGANYLA (SEQ ID NO: 388)
CDR 2: LATHRAS (SEQ ID NO: 389)
CDR 3: MQGLHSPWT 4995_P16 (PGT-145) kappa light chain Chothia CDRs:
(SEQ ID NO: 387)
CDR 1: KCSHSLQHSTGANYLA (SEQ ID NO: 388)
CDR 2: LATHRAS (SEQ ID NO: 389)
CDR 3: MQGLHSPWT The 5145_B14 (PGT-127) antibody includes a heavy chain variable region (SEQ ID NO: 319), encoded by the nucleic acid sequence shown in SEQ ID NO: 317, and a light chain variable region (SEQ ID NO: 330) encoded by the nucleic acid sequence shown in SEQ ID NO: 328.

The heavy chain CDRs of the 5145_B14 (PGT-127) antibody have the following sequences per Kabat definition: RCNYFWG (SEQ ID NO: 320), SLSHCRSYYNTDWT-YHNPSLKS (SEQ ID NO: 321), and FGGEVLVYRDWPKPAWVDL (SEQ ID NO: 322). The light chain CDRs of the 5145_B14 (PGT-127) antibody have the following sequences per Kabat definition: TGTSNNFVS (SEQ ID NO: 325), EVNKRPS (SEQ ID NO: 227), and SSLVGNWDVI (SEQ ID NO: 212).

The heavy chain CDRs of the 5145_B14 (PGT-127) antibody have the following sequences per Chothia definition: GDSTGRCN (SEQ ID NO: 323), SLSHCRSYYN-TDWTY (SEQ ID NO: 324), and FGGEVLVYRDWPKPAWVDL (SEQ ID NO: 322). The light chain CDRs of the 5145_B14 (PGT-127) antibody have the following sequences per Chothia definition: TGTSNNFVS (SEQ ID NO: 325), EVNKRPS (SEQ ID NO: 227), and SSLVGNWDVI (SEQ ID NO: 212).

The 5114_A19 (PGT-128) antibody includes a heavy chain variable region (SEQ ID NO: 334), encoded by the nucleic acid sequence shown in SEQ ID NO: 332, and a light chain variable region (SEQ ID NO: 393) encoded by the nucleic acid sequence shown in SEQ ID NO: 391.

The heavy chain CDRs of the 5114_A19 (PGT-128) antibody have the following sequences per Kabat definition: ACNSFWG (SEQ ID NO: 326), SLSHCASYWNRGWT-YHNPSLKS (SEQ ID NO: 335), and FGGEVL-RYTDWPKPAWVDL (SEQ ID NO: 336). The light chain CDRs of the 5114_A19 (PGT-128) antibody have the following sequences per Kabat definition: TGTSNNFVS (SEQ ID NO: 325), DVNKRPS (SEQ ID NO: 343), GSLVGNWDVI (SEQ ID NO: 196).

The heavy chain CDRs of the 5114_A19 (PGT-128) antibody have the following sequences per Chothia definition: GDSTAACN (SEQ ID NO: 337), SLSHCASYWNRGWTY (SEQ ID NO: 338), FGGEVL-RYTDWPKPAWVDL (SEQ ID NO: 336)

The light chain CDRs of the 5114_A19 (PGT-128) antibody have the following sequences per Chothia definition: TGTSNNFVS (SEQ ID NO: 325), DVNKRPS (SEQ ID NO: 343), GSLVGNWDVI (SEQ ID NO: 196).

The 5136_H01 (PGT-131) antibody includes a heavy chain variable region (SEQ ID NO: 347), encoded by the nucleic acid sequence shown in SEQ ID NO: 345, and a light chain variable region (SEQ ID NO: 356) encoded by the nucleic acid sequence shown in SEQ ID NO: 354.

The heavy chain CDRs of the 5136_H01 (PGT-131) antibody have the following sequences per Kabat definition: TGHHYWG (SEQ ID NO: 348), HIHYNTAVLHNPALKS (SEQ ID NO: 349), and SGGDILYYIEWQKPHWFYP (SEQ ID NO: 350). The light chain CDRs of the 5136 HO1 (PGT-131) antibody have the following sequences per Kabat definition: SGTGSDIGSWNFVS (SEQ ID NO: 357), EVNRRRS (SEQ ID NO: 358), and SSLSGRWDIV (SEQ ID NO: 359).

The heavy chain CDRs of the 5136_H01 (PGT-131) antibody have the following sequences per Chothia definition: GDSINTGH (SEQ ID NO: 351), HIHYNTAVL (SEQ ID NO: 352), and SGGDILYYIEWQKPHWFYP (SEQ ID NO: 350). The light chain CDRs of the 5136 HO1 (PGT-131) antibody have the following sequences per Chothia definition: SGTGSDIGSWNFVS (SEQ ID NO: 357), EVNRRRS (SEQ ID NO: 358), and SSLSGRWDIV (SEQ ID NO: 359).

The 5345 I01 (PGT-137) antibody includes a heavy chain variable region (SEQ ID NO: 363), encoded by the nucleic acid sequence shown in SEQ ID NO: 361, and a light chain variable region (SEQ ID NO: 397) encoded by the nucleic acid sequence shown in SEQ ID NO: 395.

The heavy chain CDRs of the 5345 I01 (PGT-137) antibody have the following sequences per Kabat definition: GGEWGDSDYHWG (SEQ ID NO: 364), SIHWRGTTHYNAPFRG (SEQ ID NO: 365), and HKYHDIVMVVPIAGWFDP (SEQ ID NO: 366). The light chain CDRs of the 5345_101 (PGT-137) antibody have the following sequences per Kabat definition: RASQSVKNNLA (SEQ ID NO: 372), DTSSRAS (SEQ ID NO: 373), and QQYEEWPRT (SEQ ID NO: 245).

The heavy chain CDRs of the 5345_101 (PGT-137) antibody have the following sequences per Chothia definition: GGSIRGGEWGDSD (SEQ ID NO: 367), SIHWRGTTH (SEQ ID NO: 237), and HKYHDIVMVV-PIAGWFDP (SEQ ID NO: 366). The light chain CDRs of the 5345 I01 (PGT-137) antibody have the following sequences per Chothia definition: RASQSVKNNLA (SEQ ID NO: 372), DTSSRAS (SEQ ID NO: 373), and QQYEEWPRT (SEQ ID NO: 245).

The 4995_P16 (PGT-145) antibody includes a heavy chain variable region (SEQ ID NO: 401), encoded by the nucleic acid sequence shown in SEQ ID NO: 399, and a light chain variable region (SEQ ID NO: 386) encoded by the nucleic acid sequence shown in SEQ ID NO: 384.

The heavy chain CDRs of the 4995_P16 (PGT-145) antibody have the following sequences per Kabat definition: NHDVH (SEQ ID NO: 378), WMSHEGDKTGLAQKFQG (SEQ ID NO: 379), and GSKHRLRDYFLYNEYGPNYEE-WGDYLATLDV (SEQ ID NO: 380). The light chain CDRs of the 4995_P16 (PGT-145) antibody have the following sequences per Kabat definition: KCSHSLQHSTGANYLA (SEQ ID NO: 387), LATHRAS (SEQ ID NO: 388), and MQGLHSPWT (SEQ ID NO: 389).

The heavy chain CDRs of the 4995 P16 (PGT-145) antibody have the following sequences per Chothia definition: GNSFSN (SEQ ID NO: 381), WMSHEGDKTG (SEQ ID NO: 382), and GSKHRLRDYFLYNEYGPNYEE-WGDYLATLDV (SEQ ID NO: 380). The light chain CDRs of the 4995 P16 (PGT-145) antibody have the following sequences per Chothia definition: KCSHSLQHSTGA-NYLA (SEQ ID NO: 387), LATHRAS (SEQ ID NO: 388), and MQGLHSPWT (SEQ ID NO: 389).

The sequences of additional human monoclonal antibodies were determined, including the sequences of the variable regions of the Gamma heavy and Kappa or Lambda light chains. In addition, the sequence of each of the polynucleotides encoding the antibody sequences was determined. Shown below are the polypeptide and polynucleotide sequences of the gamma heavy chains and kappa light chains, with the signal peptides at the N-terminus (or 5' end) and the constant regions at the C-terminus (or 3' end) of the variable regions, which are shown in bolded text.

```
4835_F12 (PGT-124) gamma heavy chain nucleotide sequence: coding sequence
(leader sequence in italics, variable region in bold)
                                                               (SEQ ID NO: 402)
ATGAAACACCTGTGGTTCTTCCTCCTGCTGGTGGCAGCTCCCAGATGGGTCCT
ATCCCAGGTGCAGCTGCAGGAGTCGGGCCCAGGACTGGTGAGACCTT
CGGAGACCCTGTCCGTCACCTGCATCGTCTCTGGGGGCTCCATCAGC
AATTACTACTGGACTTGGATCCGACAGTCCCCAGGAAAGGGACTGGA
GTGGATAGGCTATATTTCTGACAGAGAAACAACGACTTACAATCCCT
CCCTCAACAGTCGAGCCGTCATATCACGAGACACGTCGAAAAACCAA
TTGTCCCTACAATTACGTTCCGTCACCACTGCGGACACGGCCATCTAT
TTCTGTGCGACAGCGCGCCGAGGACAGAGGATTTATGGAGTGGTTTC
ATTTGGAGAGTTCTTCTACTACTACTACATGGACGTCTGGGGCAAAG
GGACTGCGGTCACCGTCTCCTCAGCGTCGACCAAGGGCCCATCGGTCTT
CCCTCTGGCACCATCATCCAAGTCGACCTCTGGGGGCACAGCGGCCCTGG
GCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTC
CTCAGGACTCTACTCCCTCAGCAGCGTGGTGACCGTGCCCTCCAGCAGCT
TGGGCACCCAGACCTACATCTGCAACGTGAATCACAAGCCCAGCAACACC
AAGGTGGACAAGAGAGTTGAGCCCAAATCTTGTGACAAAACTCACACAT
GCCCACCGTGCCCAGCACCTGAACTCCTGGGGGGACCGTCAGTCTTCCTC
TTCCCCCCAAAACCCAAGGACACCCTCATGATCTCCCGGACCCCTGAGGT
CACATGCGTGGTGGTGGACGTGAGCCACGAAGACCCTGAGGTCAAGTTCA
ACTGGTACGTGGACGGCGTGGAGGTGCATAATGCCAAGACAAAGCCGCG
GGAGGAGCAGTACAACAGCACGTACCGTGTGGTCAGCGTCCTCACCGTCC
TGCACCAGGACTGGCTGAATGGCAAGGAGTACAAGTGCAAGGTCTCCAA
CAAAGCCCTCCCAGCCCCCATCGAGAAAACCATCTCCAAAGCCAAAGGG
CAGCCCCGAGAACCACAGGTGTACACCCTGCCCCCATCCCGGGAGGAGAT
GACCAAGAACCAGGTCAGCCTGACCTGCCTGGTCAAAGGCTTCTATCCCA
GCGACATCGCCGTGGAGTGGGAGAGCAATGGGCAGCCGGAGAACAACTA
CAAGACCACGCCTCCCGTGCTGGACTCCGACGGCTCCTTCTTCCTCTATAG
CAAGCTCACCGTGGACAAGAGCAGGTGGCAGCAGGGGAACGTCTTCTCA
TGCTCCGTGATGCATGAGGCTCTGCACAACCACTACACGCAGAAGAGCCT
CTCCCTGTCTCCGGGTAAATGA 4835_F12 (PGT-124) gamma heavy chain variable region nucleotide sequence:
                                                               (SEQ ID NO: 403)
CAGGTGCAGCTGCAGGAGTCGGGCCCAGGACTGGTGAGACCTTCGG
AGACCCTGTCCGTCACCTGCATCGTCTCTGGGGGCTCCATCAGCAAT
TACTACTGGACTTGGATCCGACAGTCCCCAGGAAAGGGACTGGAGTG
```

```
GATAGGCTATATTTCTGACAGAGAAACAACGACTTACAATCCCTCCCT
CAACAGTCGAGCCGTCATATCACGAGACACGTCGAAAAACCAATTGT
CCCTACAATTACGTTCCGTCACCACTGCGGACACGGCCATCTATTTCT
GTGCGACAGCGCGCCGAGGACAGAGGATTTATGGAGTGGTTTCATTT
GGAGAGTTCTTCTACTACTACATGGACGTCTGGGGCAAAGGGAC
TGCGGTCACCGTCTCCTCA
```

4835_F12 (PGT-124) gamma heavy chain amino acid sequence: expressed protein with leader sequence in italics and variable region in bold.

(SEQ ID NO: 404)

*MKHLWFFLLLVAAPRWVLS***QVQLQESGPGLVRPSETLSVTCIVSGGSISNYY
WTWIRQSPGKGLEWIGYISDRETTTYNPSLNSRAVISRDTSKNQLSLQLR
SVTTADTAIYFCATARRGQRIYGVVSFGEFFYYYYMDVWGKGTAVTVSS**
ASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKRVEPKSCDKT
HTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSN
KALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMH
EALHNHYTQKSLSLSPGK

4835_F12 (PGT-124) gamma heavy chain variable region amino acid sequence: (Kabat CDRs underlined, Chothia CDRs in bold italics)

(SEQ ID NO: 405)

QVQLQESGPGLVRPSETLSVTCIVS*GGSIS*<u>NYYWT</u>WIRQSPGKGLEWIG<u>***YISD
RETTT*YNPSLNS</u>RAVISRDTSKNQLSLQLRSVTTADTAIYFCAT<u>*ARRGQRIYG
VVSFGEFFYYYYMDV***</u>WGKGTAVTVSS

4835_F12 (PGT-124) gamma heavy chain Kabat CDRs:

(SEQ ID NO: 406)

CDR 1: NYYWT (SEQ ID NO: 407)

CDR 2: YISDRETTTYNPSLNS (SEQ ID NO: 408)

CDR 3: ARRGQRIYGVVSFGEFFYYYYMDV

4835_F12 (PGT-124) gamma heavy chain Chothia CDRs:

(SEQ ID NO: 409)

CDR 1: GGSISN (SEQ ID NO: 410)

CDR 2: YISDRETTT (SEQ ID NO: 408)

CDR 3: ARRGQRIYGVVSFGEFFYYYYMDV

4835_F12 (PGT-124) light chain nucleotide sequence: coding sequence (variable region in bold)

(SEQ ID NO: 411)

*ATGGCCTGGATCCCTCTCCTCCTCGGCCTCCTCTCTCACTGCACAGGGTCTGT
GACG***TCCTATGTGAGCCCACTGTCAGTGGCCCTGGGGGAGACGGCCA
GGATTTCCTGTGGACGACAGGCCCTTGGAAGTAGAGCTGTGCAGTGG
TATCAACATAAGCCAGGCCAGGCCCCTATTTTGCTCATCTATAATAAT
CAAGACCGGCCCTCAGGGATCCCTGAGCGGTTCTCTGGCACCCCTGA
TATTAATTTTGGGACCACGGCCACCCTGACTATCAGCGGGGTCGAAG
TCGGGGATGAAGCCGACTATTACTGTCACATGTGGGACTCTAGAAGT
GGTTTCAGTTGGTCTTTCGGCGGGGCGACCAGGCTGACCGTCCTAGG**
TCAGCCCAAGGCTGCCCCCTCGGTCACTCTGTTCCCGCCCTCCTCTGAGGA
GCTTCAAGCCAACAAGGCCACACTGGTGTGTCTCATAAGTGACTTCTACC
CGGGAGCCGTGACAGTGGCCTGGAAGGCAGATAGCAGCCCCGTCAAGGC
GGGAGTGGAGACCACCACACCCTCCAAACAAAGCAACAACAAGTACGCG
GCCAGCAGCTATCTGAGCCTGACGCCTGAGCAGTGGAAGTCCCACAAAA
GCTACAGCTGCCAGGTCACGCATGAAGGGAGCACCGTGGAGAAGACAGT
GGCCCCTACAGAATGTTCATAG

4835_F12 (PGT-124) light chain variable region nucleotide sequence:

(SEQ ID NO: 412)

**TCCTATGTGAGCCCACTGTCAGTGGCCCTGGGGGAGACGGCCAGGAT
TTCCTGTGGACGACAGGCCCTTGGAAGTAGAGCTGTGCAGTGGTATC
AACATAAGCCAGGCCAGGCCCCTATTTTGCTCATCTATAATAATCAAG
ACCGGCCCTCAGGGATCCCTGAGCGGTTCTCTGGCACCCCTGATATT
AATTTTGGGACCACGGCCACCCTGACTATCAGCGGGGTCGAAGTCGG
GGATGAAGCCGACTATTACTGTCACATGTGGGACTCTAGAAGTGGTT
TCAGTTGGTCTTTCGGCGGGGCGACCAGGCTGACCGTCCTA**

-continued

4835_F12 (PGT-124) light chain amino acid sequence: expressed protein with leader sequence in italics and variable region in bold.

(SEQ ID NO: 413)

*MAWIPLLLGLLSHCTGSVT*SYVSPLSVALGETARISCGRQALGSRAVQWYQ HKPGQAPILLIYNNQDRPSGIPERFSGTPDINFGTTATLTISGVEVGDEAD YYCHMWDSRSGFSWSFGGATRLTVLGQPKAAPSVTLFPPSSEELQANKAT LVCLISDFYPGAVTVAWKADSSPVKAGVETTTPSKQSNNKYAASSYLSLTPE QWKSHKSYSCQVTHEGSTVEKTVAPTECS

4835_F12 (PGT-124) light chain variable region amino acid sequence: (Kabat CDRs underlined, Chothia CDRs in bold italics)

(SEQ ID NO: 414)

SYVSPLSVALGETARISC*GRQALGSRAVQ*WYQHKPGQAPILLIY*NNQDRPS*GI PERFSGTPDINFGTTATLTISGVEVGDEADYYC*HMWDSRSGFSWS*FGGATRL TVL

4835_F12 (PGT-124) light chain Kabat CDRs:

(SEQ ID NO: 415)

CDR 1: GRQALGSRAVQ (SEQ ID NO: 151)

CDR 2: NNQDRPS (SEQ ID NO: 416)

CDR 3: HMWDSRSGFSWS

4835_F12 (PGT-124) light chain Chothia CDRs:

(SEQ ID NO: 415)

CDR 1: GRQALGSRAVQ (SEQ ID NO: 151)

CDR 2: NNQDRPS (SEQ ID NO: 416)

CDR 3: HMWDSRSGFSWS

4869_K15 (PGT-133) gamma heavy chain nucleotide sequence: coding sequence (variable region in bold)

(SEQ ID NO: 417)

*ATGAAACACCTGTGGTTCTTCCTTCTCCTGGTGGCAGCTCCCAGATGGGTCGT GTCCC*AGGTGCATCTGCAAGAGTCGGGGCCAGGACTGGTGACGCCTT CGGAAACCCTGTCCCTCACTTGCACTGTGTCGAATGGCTCCGTCAGT GGTCGCTTCTGGAGCTGGATCCGGCAGTCCCCAGGGAGAGGACTGG AATGGATCGGTTATTTTTCTGACACTGACAGGTCTGAATATAATCCTT CTCTCAGGAGTCGACTCACCTTATCAGTAGATAGATCTAAGAACCAG TTGTCCCTGAGATTGAAGTCCGTGACCGCTGCGGATTCGCCACTTA TTACTGTGCGAGAGCACAGCAGGGGAAGAGGATCTATGGAATAGTGT CTTTCGGAGAGTTCTTCTATTATTATTACATGGACGCCTGGGGCAAAG GGACTCCGGTCACCGTCTCCTCAGCGTCGACCAAGGGCCCATCGGTCTT CCCTCTGGCACCATCATCCAAGTCGACCTCTGGGGGCACAGCGGCCCTGG GCTGCCTGGTCAAGGACTACTTCCCCGAACCGGTGACGGTGTCGTGGAAC TCAGGCGCCCTGACCAGCGGCGTGCACACCTTCCCGGCTGTCCTACAGTC CTCAGGACTCTACTCCCTCAGCAGCGTGGTGACCGTGCCCTCCAGCAGCT TGGGCACCCAGACCTACATCTGCAACGTGAATCACAAGCCCAGCAACACC AAGGTGGACAAGAGAGTTGAGCCCAAATCTTGTGACAAAACTCACACAT GCCCACCGTGCCCAGCACCTGAACTCCTGGGGGGACCGTCAGTCTTCCTC TTCCCCCCAAAACCCAAGGACACCCTCATGATCTCCCGGACCCCTGAGGT CACATGCGTGGTGGTGGACGTGAGCCACGAAGACCCTGAGGTCAAGTTCA ACTGGTACGTGGACGGCGTGGAGGTGCATAATGCCAAGACAAAGCCGCG GGAGGAGCAGTACAACAGCACGTACCGTGTGGTCAGCGTCCTCACCGTCC TGCACCAGGACTGGCTGAATGGCAAGGAGTACAAGTGCAAGGTCTCCAA CAAAGCCCTCCCAGCCCCCATCGAGAAAACCATCTCCAAAGCCAAAGGG CAGCCCCGAGAACCACAGGTGTACACCCTGCCCCCATCCCGGGAGGAGAT GACCAAGAACCAGGTCAGCCTGACCTGCCTGGTCAAAGGCTTCTATCCCA GCGACATCGCCGTGGAGTGGGAGAGCAATGGGCAGCCGGAGAACAACTA CAAGACCACGCCTCCCGTGCTGGACTCCGACGGCTCCTTCTTCCTCTATAG CAAGCTCACCGTGGACAAGAGCAGGTGGCAGCAGGGGAACGTCTTCTCA TGCTCCGTGATGCATGAGGCTCTGCACAACCACTACACGCAGAAGAGCCT CTCCCTGTCTCCGGGTAAATGA

4869_K15 (PGT-133) gamma heavy chain variable region nucleotide sequence:

(SEQ ID NO: 418)

CAGGTGCATCTGCAAGAGTCGGGGCCAGGACTGGTGACGCCTTCGG AAACCCTGTCCCTCACTTGCACTGTGTCGAATGGCTCCGTCAGTGGT CGCTTCTGGAGCTGGATCCGGCAGTCCCCAGGGAGAGGACTGGAAT GGATCGGTTATTTTTCTGACACTGACAGGTCTGAATATAATCCTTCTC TCAGGAGTCGACTCACCTTATCAGTAGATAGATCTAAGAACCAGTTG TCCCTGAGATTGAAGTCCGTGACCGCTGCGGATTCGCCACTTATTA CTGTGCGAGAGCACAGCAGGGGAAGAGGATCTATGGAATAGTGTCTT TCGGAGAGTTCTTCTATTATTATTACATGGACGCCTGGGGCAAAGGG ACTCCGGTCACCGTCTCCTCA

4869_K15 (PGT-133) gamma heavy chain amino acid sequence: expressed protein with leader sequence in italics and variable region in bold.

(SEQ ID NO: 419)

*MKHLWFFLLLVAAPRWVVS***QVHLQESGPGLVTPSETLSLTCTVSNGSVSGRF
WSWIRQSPGRGLEWIGYFSDTDRSEYNPSLRSRLTLSVDRSKNQLSLRLK
SVTAADSATYYCARAQQGKRIYGIVSFGEFFYYYYMDAWGKGTPVTVSS**
ASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKRVEPKSCDKT
HTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSN
KALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMH
EALHNHYTQKSLSLSPGK

4869_K15 (PGT-133) gamma heavy chain variable region amino acid sequence: (Kabat CDRs underlined, Chothia CDRs in bold italics)

(SEQ ID NO: 420)

QVHLQESGPGLVTPSETLSLTCTVS*NGSVSG*RFWSWIRQSPGRGLEWIG***YFSD
TDRSE*YNPSLRSRLTLSVDRSKNQLSLRLKSVTAADSATYYCAR*AQQGKRIY
GIVSFGEFFYYYYMDA***WGKGTPVTVSS

4869_K15 (PGT-133) gamma heavy chain Kabat CDRs:

(SEQ ID NO: 421)

CDR 1: GRFWS (SEQ ID NO: 422)

CDR 2: YFSDTDRSEYNPSLRS (SEQ ID NO: 423)

CDR 3: AQQGKRIYGIVSFGEFFYYYYMDA

4869_K15 (PGT-133) gamma heavy chain Chothia CDRs:

(SEQ ID NO: 424)

CDR 1: NGSVSG (SEQ ID NO: 425)

CDR 2: YFSDTDRSE (SEQ ID NO: 423)

CDR 3: AQQGKRIYGIVSFGEFFYYYYMDA

4869_K15 (PGT-133) light chain nucleotide sequence: coding sequence (variable region in bold)

(SEQ ID NO: 426)

*ATGGCCTGGATCCCTCTCCTCCTCGGCCTCCTCTCTCACTGCACAGGTTCTGA
CACT***TCGTTAAACCCACTGTCGCTGGCCCCAGGAGCGACGGCCAAAA
TTCCCTGCGGAGAAAGGAGCCGTGGAAGTAGGGCTGTCCAGTGGTAT
CAGCAGAAGCCAGGCCAGGCCCCCACATTGATCATTTATAATAATCA
AGACCGGCCCGCAGGGGTCTCTGAACGATTTTCTGGCAATCCTGACG
TCGCTATTGGGGTGACGGCCACCCTGACCATCAGTCGGGTCGAAGTC
GGGGATGAGGCCGACTATTATTGTCACTATTGGGACAGTAGAAGTCC
CATCAGCTGGATTTTCGGCGGAGGGACCCAGCTGACCGTCCTGGGTC**
AGCCCAAGGCTGCCCCCTCGGTCACTCTGTTCCCGCCCTCCTCTGAGGAGC
TTCAAGCCAACAAGGCCACACTGGTGTGTCTCATAAGTGACTTCTACCCG
GGAGCCGTGACAGTGGCCTGGAAGGCAGATAGCAGCCCCGTCAAGGCGG
GAGTGGAGACCACCACACCCTCCAAACAAAGCAACAACAAGTACGCGGC
CAGCAGCTATCTGAGCCTGACGCCTGAGCAGTGGAAGTCCCACAAAAGCT
ACAGCTGCCAGGTCACGCATGAAGGGAGCACCGTGGAGAAGACAGTGGC
CCCTACAGAATGTTCATAG

4869_K15 (PGT-133) light chain variable region nucleotide sequence:

(SEQ ID NO: 427)

TCGTTAAACCCACTGTCGCTGGCCCCAGGAGCGACGGCCAAAATTCC
CTGCGGAGAAAGGAGCCGTGGAAGTAGGGCTGTCCAGTGGTATCAG
CAGAAGCCAGGCCAGGCCCCCACATTGATCATTTATAATAATCAAGA
CCGGCCCGCAGGGGTCTCTGAACGATTTTCTGGCAATCCTGACGTCG
CTATTGGGGTGACGGCCACCCTGACCATCAGTCGGGTCGAAGTCGGG
GATGAGGCCGACTATTATTGTCACTATTGGGACAGTAGAAGTCCCAT
CAGCTGGATTTTCGGCGGAGGGACCCAGCTGACCGTCCTG

4869_K15 (PGT-133) light chain amino acid sequence: expressed protein with leader sequence in italics and variable region in bold.

(SEQ ID NO: 428)

*MAWIPLLLGLLSHCTGSDT***SLNPLSLAPGATAKIPCGERSRGSRAVQWYQQ
KPGQAPTLIIYNNQDRPAGVSERFSGNPDVAIGVTATLTISRVEVGDEADY
YCHYWDSRSPISWIFGGGTQLTVL**GQPKAAPSVTLFPPSSEELQANKATLV
CLISDFYPGAVTVAWKADSSPVKAGVETTTPSKQSNNKYAASSYLSLTPEQW
KSHKSYSCQVTHEGSTVEKTVAPTECS

-continued

4869_K15 (PGT-133) light chain variable region amino acid sequence: (Kabat CDRs underlined, Chothia CDRs in bold italics)
(SEQ ID NO: 429)
SLNPLSLAPGATAKIPC*GERSRGSRAVQ*WYQQKPGQAPTLIIY*NNQDRPA*GVS
ERFSGNPDVAIGVTATLTISRVEVGDEADYYC*HYWDSRSPISWI*FGGGTQLTV
L 4869_K15 (PGT-133) light chain Kabat CDRs:
(SEQ ID NO: 430)
CDR 1: GERSRGSRAVQ (SEQ ID NO: 179)
CDR 2: NNQDRPA (SEQ ID NO: 431)
CDR 3: HYWDSRSPISWI 4869_K15 (PGT-133) light chain Chothia CDRs:
(SEQ ID NO: 430)
CDR 1: GERSRGSRAVQ (SEQ ID NO: 179)
CDR 2: NNQDRPA (SEQ ID NO: 431)
CDR 3: HYWDSRSPISWI 4876_M06 (PGT-134) gamma heavy chain nucleotide sequence: coding sequence (variable region in bold)
(SEQ ID NO: 432)
*ATGAAACACCTGTGGTTCTTCCTCCTGCTGGTGGCAGCTCCCAGATGGGTCGT*
*GTCCC*AGGTGCATCTGCAAGAGTCGGGGCCAGGACTGGTGACGCCTT
CGGAAACCCTGTCCCTCACTTGCACTGTGTCGAATGGCTCCGTCAGT
GGTCGCTTCTGGAGCTGGATCCGGCAGTCCCCAGGGAGAGGACTGG
AATGGATCGGTTATTTTTCTGACACTGACAGGTCTGAATATAATCCTT
CTCTCAGGAGTCGACTCACCTTATCAGTCGATAGATCCAAGAACCAG
TTGTCCCTAAAATTGAAGTCCGTGACCGCTGCGGATTCGGCCACTTA
TTACTGTGCGAGAGCACAACAGGGGAAGAGGATCTATGGAATAGTGT
CTTTCGGAGAGTTGTTCTATTATTATTACATGGACGCCTGGGGCAAA
GGGACTCCGGTCACCGTCTCCTCAGCGTCGACCAAGGGCCCATCGGTC
TTCCCTCTGGCACCATCATCCAAGTCGACCTCTGGGGGCACAGCGGCCCT
GGGCTGCCTGGTCAAGGACTACTTCCCCGAACCGGTGACGGTGTCGTGGA
ACTCAGGCGCCCTGACCAGCGGCGTGCACACCTTCCCGGCTGTCCTACAG
TCCTCAGGACTCTACTCCCTCAGCAGCGTGGTGACCGTGCCCTCCAGCAG
CTTGGGCACCCAGACCTACATCTGCAACGTGAATCACAAGCCCAGCAACA
CCAAGGTGGACAAGAGAGTTGAGCCCAAATCTTGTGACAAAACTCACAC
ATGCCCACCGTGCCCAGCACCTGAACTCCTGGGGGGACCGTCAGTCTTCC
TCTTCCCCCCAAAACCCAAGGACACCCTCATGATCTCCCGGACCCCTGAG
GTCACATGCGTGGTGGTGGACGTGAGCCACGAAGACCCTGAGGTCAAGTT
CAACTGGTACGTGGACGGCGTGGAGGTGCATAATGCCAAGACAAAGCCG
CGGGAGGAGCAGTACAACAGCACGTACCGTGTGGTCAGCGTCCTCACCGT
CCTGCACCAGGACTGGCTGAATGGCAAGGAGTACAAGTGCAAGGTCTCC
AACAAAGCCCTCCCAGCCCCCATCGAGAAAACCATCTCCAAAGCCAAAG
GGCAGCCCCGAGAACCACAGGTGTACACCCTGCCCCCATCCCGGGAGGA
GATGACCAAGAACCAGGTCAGCCTGACCTGCCTGGTCAAAGGCTTCTATC
CCAGCGACATCGCCGTGGAGTGGGAGAGCAATGGGCAGCCGGAGAACAA
CTACAAGACCACGCCTCCCGTGCTGGACTCCGACGGCTCCTTCTTCCTCTA
TAGCAAGCTCACCGTGGACAAGAGCAGGTGGCAGCAGGGGAACGTCTTC
TCATGCTCCGTGATGCATGAGGCTCTGCACAACCACTACACGCAGAAGAG
CCTCTCCCTGTCTCCGGGTAAATGA 4876_M06 (PGT-134) gamma heavy chain variable region nucleotide sequence:
(SEQ ID NO: 433)
CAGGTGCATCTGCAAGAGTCGGGGCCAGGACTGGTGACGCCTTCGG
AAACCCTGTCCCTCACTTGCACTGTGTCGAATGGCTCCGTCAGTGGT
CGCTTCTGGAGCTGGATCCGGCAGTCCCCAGGGAGAGGACTGGAAT
GGATCGGTTATTTTTCTGACACTGACAGGTCTGAATATAATCCTTCTC
TCAGGAGTCGACTCACCTTATCAGTCGATAGATCCAAGAACCAGTTG
TCCCTAAAATTGAAGTCCGTGACCGCTGCGGATTCGGCCACTTATTA
CTGTGCGAGAGCACAACAGGGGAAGAGGATCTATGGAATAGTGTCTT
TCGGAGAGTTGTTCTATTATTATTACATGGACGCCTGGGGCAAAGGG
ACTCCGGTCACCGTCTCCTCA

4876_M06 (PGT-134) gamma heavy chain amino acid sequence: expressed protein with leader sequence in italics and variable region in bold.
(SEQ ID NO: 434)
*MKHLWFFLLLVAAPRWVVS*QVHLQESGPGLVTPSETLSLTCTVSNGSVSGRF
WSWIRQSPGRGLEWIGYFSDTDRSEYNPSLRSRLTLSVDRSKNQLSLKLK
SVTAADSATYYCARAQQGKRIYGIVSFGELFYYYMDAWGKGTPVTVSS
ASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKRVEPKSCDKT

```
HTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSN
KALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMH
EALHNHYTQKSLSLSPGK
```

4876_M06 (PGT-134) gamma heavy chain variable region amino acid sequence:
(Kabat CDRs underlined, Chothia CDRs in bold italics)

(SEQ ID NO: 435)

```
QVHLQESGPGLVTPSETLSLTCTVSNGSVSGRFWSWIRQSPGRGLEWIGYFSD
TDRSEYNPSLRSRLTLSVDRSKNQLSLKLKSVTAADSATYYCARAQQGKRIY
GIVSFGELFYYYMDAWGKGTPVTVSS
```

4876_M06 (PGT-134) gamma heavy chain Kabat CDRs:

(SEQ ID NO: 421)
CDR 1: GRFWS (SEQ ID NO: 422)
CDR 2: YFSDTDRSEYNPSLRS (SEQ ID NO: 436)
CDR 3: AQQGKRIYGIVSFGELFYYYMDA

4876_M06 (PGT-134) gamma heavy chain Chothia CDRs:

(SEQ ID NO: 424)
CDR 1: NGSVSG (SEQ ID NO: 425)
CDR 2: YFSDTDRSE (SEQ ID NO: 436)
CDR 3: AQQGKRIYGIVSFGELFYYYMDA

4876_M06 (PGT-134) light chain nucleotide sequence: coding sequence (variable region in bold)

(SEQ ID NO: 437)

```
ATGGCCTGGATCCCTCTCCTCCTCGGCCTCCTCTCTCACTGCACAGGTTCTGA
CACTTCGTTAAACCCACTGTCGCTGGCCCCGGGAGCGACGGCCAAAA
TTCCCTGCGGAGAAAGGAGCCGTGGAAGTAGGGCTGTCCAGTGGTAT
CAGCAGAAGCCAGGCCAGGCCCCCACATTGATCATTTATAATAATCA
AGACCGGCCCGCAGGGGTCTCTGAACGATTTTCTGGCAATCCTGACG
TCGCTATTGGGGTGACGGCCACCCTGACCATCAGTCGGGTCGAAGTC
GGGGATGAGGGCGACTATTATTGTCACTATTGGGACAGTAGAAGTCC
CATCAGCTGGATTTTCGCCGGAGGGACCCAGTTGACCGTCCTGGGTC
AGCCCAAGGCTGCCCCCTCGGTCACTCTGTTCCCGCCCTCCTCTGAGGAGC
TTCAAGCCAACAAGGCCACACTGGTGTGTCTCATAAGTGACTTCTACCCG
GGAGCCGTGACAGTGGCCTGGAAGGCAGATAGCAGCCCCGTCAAGGCGG
GAGTGGAGACCACCACACCCTCCAAACAAAGCAACAACAAGTACGCGGC
CAGCAGCTATCTGAGCCTGACGCCTGAGCAGTGGAAGTCCCACAAAAGCT
ACAGCTGCCAGGTCACGCATGAAGGGAGCACCGTGGAGAAGACAGTGGC
CCCTACAGAATGTTCATAG
```

4876_M06 (PGT-134) light chain variable region nucleotide sequence:

(SEQ ID NO: 438)

```
TCGTTAAACCCACTGTCGCTGGCCCCGGGAGCGACGGCCAAAATTCC
CTGCGGAGAAAGGAGCCGTGGAAGTAGGGCTGTCCAGTGGTATCAG
CAGAAGCCAGGCCAGGCCCCCACATTGATCATTTATAATAATCAAGA
CCGGCCCGCAGGGGTCTCTGAACGATTTTCTGGCAATCCTGACGTCG
CTATTGGGGTGACGGCCACCCTGACCATCAGTCGGGTCGAAGTCGGG
GATGAGGGCGACTATTATTGTCACTATTGGGACAGTAGAAGTCCCAT
CAGCTGGATTTTCGCCGGAGGGACCCAGTTGACCGTCCTG
```

4876_M06 (PGT-134) light chain amino acid sequence: expressed protein with leader sequence in italics and variable region in bold.

(SEQ ID NO: 439)

```
MAWIPLLLGLLSHCTGSDTSLNPLSLAPGATAKIPCGERSRGSRAVQWYQQ
KPGQAPTLIIYNNQDRPAGVSERFSGNPDVAIGVTATLTISRVEVGDEGDY
YCHYWDSRSPISWIFAGGTQLTVLGQPKAAPSVTLFPPSSEELQANKATLV
CLISDFYPGAVTVAWKADSSPVKAGVETTTPSKQSNNKYAASSYLSLTPEQW
KSHKSYSCQVTHEGSTVEKTVAPTECS
```

4876_M06 (PGT-134) light chain variable region amino acid sequence: (Kabat CDRs underlined, Chothia CDRs in bold italics)

(SEQ ID NO: 440)

```
SLNPLSLAPGATAKIPCGERSRGSRAVQWYQQKPGQAPTLIIYNNQDRPAGVS
ERFSGNPDVAIGVTATLTISRVEVGDEGDYYCHYWDSRSPISWIFAGGTQLTV
L
```

4876_M06 (PGT-134) light chain Kabat CDRs:
(SEQ ID NO: 430)
CDR 1: GERSRGSRAVQ (SEQ ID NO: 179)
CDR 2: NNQDRPA (SEQ ID NO: 431)
CDR 3: HYWDSRSPISWI 4876_M06 (PGT-134) light chain Chothia CDRs:
(SEQ ID NO: 430)
CDR 1: GERSRGSRAVQ (SEQ ID NO: 179)
CDR 2: NNQDRPA (SEQ ID NO: 431)
CDR 3: HYWDSRSPISWI 5131_A17 (PGT-132) gamma heavy chain nucleotide sequence: coding sequence (variable region in bold)
(SEQ ID NO: 441)

*ATGAAACACCTGTGGTTCTTCCTCCTGCTGGTGGCAGCTCCCAGATGGGTCCT*
*TTCCC*AGGTGCAACTACAGGAGTCGGGCCCAGGACTGGTGAAGCCTT
CGGAGACCCTTTCCCTCACCTGCACTGTCTCTGGTGACTCCATCAACA
CTGGTCATCACTACTGGGGCTGGGTCCGTCAGGTCCCAGGGAAGGGA
CCGGAATGGATTGCTCACATCCACTATAATACGGCTGTCTTGCACAAT
CCGGCCCTCAAGAGTCGAGTCACCATTTCGATTTTCACCCTGAAGAA
TCTGATTACCCTGAGGCTCAGTAATATGACCGCCGCGGACACGGCCG
TCTATTTCTGCGTTCGATCCGGCGGCGACATTTTATACTATAATGAGT
GGCAAAAACCCCACTGGTTCTATCCCTGGGGCCCGGGAATTTTGGTC
ACCGTCTCGAGCGCCTCCACCAAGGGCCCATCGGTCTTCCCCCTGGCACC
CTCCTCCAAGAGCACCTCTGGGGGCACAGCGGCCCTGGGCTGCCTGGTCA
AGGACTACTTCCCCGAACCGGTGACGGTGTCGTGGAACTCAGGCGCCCTG
ACCAGCGGCGTGCACACCTTCCCGGCTGTCCTACAGTCCTCAGGACTCTA
CTCCCTCAGCAGCGTGGTGACCGTGCCCTCCAGCAGCTTGGGCACCCAGA
CCTACATCTGCAACGTGAATCACAAGCCCAGCAACACCAAGGTGGACAA
GAGAGTTGAGCCCAAATCTTGTGACAAAACTCACACATGCCCACCGTGC
CAGCACCTGAACTCCTGGGGGGACCGTCAGTCTTCCTCTTCCCCCCAAAA
CCCAAGGACACCCTCATGATCTCCCGGACCCCTGAGGTCACATGCGTGGT
GGTGGACGTGAGCCACGAAGACCCTGAGGTCAAGTTCAACTGGTACGTGG
ACGGCGTGGAGGTGCATAATGCCAAGACAAAGCCGCGGGAGGAGCAGTA
CAACAGCACGTACCGTGTGGTCAGCGTCCTCACCGTCCTGCACCAGGACT
GGCTGAATGGCAAGGAGTACAAGTGCAAGGTCTCCAACAAAGCCCTCCC
AGCCCCCATCGAGAAAACCATCTCCAAAGCCAAAGGGCAGCCCCGAGAA
CCACAGGTGTACACCCTGCCCCCATCCCGGGAGGAGATGACCAAGAACC
AGGTCAGCCTGACCTGCCTGGTCAAAGGCTTCTATCCCAGCGACATCGCC
GTGGAGTGGGAGAGCAATGGGCAGCCGGAGAACAACTACAAGACCACGC
CTCCCGTGCTGGACTCCGACGGCTCCTTCTTCCTCTATAGCAAGCTCACCG
TGGACAAGAGCAGGTGGCAGCAGGGGAACGTCTTCTCATGCTCCGTGATG
CATGAGGCTCTGCACAACCACTACACGCAGAAGAGCCTCTCCCTGTCTCC
GGGTAAATGA

5131_A17 (PGT-132) gamma heavy chain variable region nucleotide sequence:
(SEQ ID NO: 442)

CAGGTGCAACTACAGGAGTCGGGCCCAGGACTGGTGAAGCCTTCGG
AGACCCTTTCCCTCACCTGCACTGTCTCTGGTGACTCCATCAACACTG
GTCATCACTACTGGGGCTGGGTCCGTCAGGTCCCAGGGAAGGGACC
GGAATGGATTGCTCACATCCACTATAATACGGCTGTCTTGCACAATCC
GGCCCTCAAGAGTCGAGTCACCATTTCGATTTTCACCCTGAAGAATCT
GATTACCCTGAGGCTCAGTAATATGACCGCCGCGGACACGGCCGTCT
ATTTCTGCGTTCGATCCGGCGGCGACATTTTATACTATAATGAGTGGC
AAAAACCCCACTGGTTCTATCCCTGGGGCCCGGGAATTTTGGTCACC
GTCTCGAGC

5131_A17 (PGT-132) gamma heavy chain amino acid sequence: expressed protein with leader sequence in italics and variable region in bold.
(SEQ ID NO: 443)

*MKHLWFFLLLVAAPRWVLS*QVQLQESGPGLVKPSETLSLTCTVSGDSINTGH
HYWGWVRQVPGKGPEWIAHIHYNTAVLENPALKSRVTISIFTLKNLITL
RLSNMTAADTAVYFCVRSGGDILYYNEWQKPHWFYPWGPGILVTVSSAS
TKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKRVEPKSCDKTHT
CPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEAL
HNHYTQKSLSLSPGK

5131_A17 (PGT-132) gamma heavy chain variable region amino acid sequence:
(Kabat CDRs underlined, Chothia CDRs in bold italics)
(SEQ ID NO: 444)
QVQLQESGPGLVKPSETLSLTCTVS*GDSINTGH*HYWGVRQVPGKGPEWIA
*HIHYNTAVL*HNPALKSRVTISIFTLKNLITLRLSNMTAADTAVYFCVR*SGGDIL*
*YYNEWQKPHWFYP*WGPGILVTVSS 5131_A17 (PGT-132) gamma heavy chain Kabat CDRs:
(SEQ ID NO: 348)
CDR 1: TGHHYWG (SEQ ID NO: 349)
CDR 2: HIHYNTAVLHNPALKS (SEQ ID NO: 445)
CDR 3: SGGDILYYNEWQKPHWFYP 5131_A17 (PGT-132) gamma heavy chain Chothia CDRs:
(SEQ ID NO: 351)
CDR 1: GDSINTGH (SEQ ID NO: 352)
CDR 2: HIHYNTAVL (SEQ ID NO: 445)
CDR 3: SGGDILYYNEWQKPHWFYP 5131_A17 (PGT-132) light chain nucleotide sequence: coding sequence (variable region in bold)
(SEQ ID NO: 446)
ATGGCCTGGGCTCTGCTCCTCCTCACCCTCCTCACTCAGGGCACAGGGTCCTG
GGCCCAGTCTGCCCTGACTCAGCCTCCCTCCGCGTCCGGGTCTCTTG
GACAGTCACTCACCATCTCCTGCAGTGGAACCGCCAGTGACATTGGC
AGTTGGAATTTTGTCTCCTGGTATCAACAATTCCCAGGCAGAGCCCC
CAACCTCATTATTTTTGAGGTCAATAGGCGGCGATCAGGGGTCCCTG
ATCGCTTCTCTGGTTCCAAGTCGGGCAATACGGCCTCCCTGACCGTC
TCTGGGCTCCGGTCTGAGGATGAGGCTGAATATTTTTGCAGTTCCCT
TTCAGGCAGGTGGGACATTGTTTTTGGCGGAGGGACCAAGGTGACCG
TCCTAGGTCAGCCCAAGGCTGCCCCCTCGGTCACTCTGTTCCCGCCCTCCT
CTGAGGAGCTTCAAGCCAACAAGGCCACACTGGTGTGTCTCATAAGTGAC
TTCTACCCGGGAGCCGTGACAGTGGCCTGGAAGGCAGATAGCAGCCCCGT
CAAGGCGGGAGTGGAGACCACCACACCCTCCAAACAAAGCAACAACAAG
TACGCGGCCAGCAGCTACCTGAGCCTGACGCCTGAGCAGTGGAAGTCCCA
CAAAAGCTACAGCTGCCAGGTCACGCATGAAGGGAGCACCGTGGAGAAG
ACAGTGGCCCCTACAGAATGTTCATAG 5131_A17 (PGT-132) light chain variable region nucleotide sequence:
(SEQ ID NO: 447)
CAGTCTGCCCTGACTCAGCCTCCCTCCGCGTCCGGGTCTCTTGGACA
GTCACTCACCATCTCCTGCAGTGGAACCGCCAGTGACATTGGCAGTT
GGAATTTTGTCTCCTGGTATCAACAATTCCCAGGCAGAGCCCCCAAC
CTCATTATTTTTGAGGTCAATAGGCGGCGATCAGGGGTCCCTGATCG
CTTCTCTGGTTCCAAGTCGGGCAATACGGCCTCCCTGACCGTCTCTG
GGCTCCGGTCTGAGGATGAGGCTGAATATTTTTGCAGTTCCCTTTCA
GGCAGGTGGGACATTGTTTTTGGCGGAGGGACCAAGGTGACCGTCCT
A

5131_A17 (PGT-132) light chain amino acid sequence: expressed protein with leader sequence in italics and variable region in bold.
(SEQ ID NO: 448)
*MAWALLLLTLLTQGTGSWA*QSALTQPPSASGSLGQSLTISCSGTASDIGSWNF
VSWYQQFPGRAPNLIIFEVNRRRSGVPDRFSGSKSGNTASLTVSGLRSEDE
AEYFCSSLSGRWDIVFGGGTKVTVLGQPKAAPSVTLFPPSSEELQANKATL
VCLISDFYPGAVTVAWKADSSPVKAGVETTTPSKQSNNKYAASSYLSLTPEQ
WKSHKSYSCQVTHEGSTVEKTVAPTECS 5131_A17 (PGT-132) light chain variable region amino acid sequence: (Kabat CDRs underlined, Chothia CDRs in bold italics)
(SEQ ID NO: 449)
QSALTQPPSASGSLGQSLTISC*SGTASDIGSWNFVS*NYQQFPGRAPNLIIF*EVN*
*RRRS*GVPDRFSGSKSGNTASLTVSGLRSEDEAEYFC*SSLSGRWDIV*FGGGTKV
TVL -continued 5131_A17 (PGT-132) light chain Kabat CDRs:

(SEQ ID NO: 450)
CDR 1: SGTASDIGSWNFVS (SEQ ID NO: 358)
CDR 2: EVNRRRS (SEQ ID NO: 359)
CDR 3: SSLSGRWDIV

5131_A17 (PGT-132) light chain Chothia CDRs:

(SEQ ID NO: 450)
CDR 1: SGTASDIGSWNFVS (SEQ ID NO: 358)
CDR 2: EVNRRRS (SEQ ID NO: 359)
CDR 3: SSLSGRWDIV

5138_G07 (PGT-138) gamma heavy chain nucleotide sequence: coding sequence (variable region in bold)

(SEQ ID NO: 451)

*ATGAAACACCTGTGGTTCTTCCTCCTGCTGGTGGCAGCTCCCAGATGGGTCCT*
*GTCCC*CAGCCGCAGCTGCAGGAGTCGGGGCCAGGACTGGTGGAGGCTT
CGGAGACCCTGTCCCTCACCTGCACTGTGTCCGGCGACTCCACTGCT
GCTTGTGACTATTTCTGGGGCTGGGTCCGGCAGCCCCAGGGAAGGG
GCTGGAGTGGATTGGAAGTTTGTCACATTGTGCAGGTTACTACAATA
GTGGCTGGACCTACCACAACCCGTCTCTCAAGAGTCGACTCACGATT
TCACTCGACACGCCCAAGAATCAGGTCTTCCTGAAGTTAAATTCTGTG
ACCGCCGCGGACACGGCCATTTACTACTGTGCGCGATTCGGTGGCGA
CGTTTTGGTGTACCACGATTGGCCAAAGCCGGCCTGGGTCGACCTCT
GGGGCCGGGGAGTTTTGGTCACCGTCTCGAGCGCCTCCACCAAGGGC
CCATCGGTCTTCCCCCTGGCACCCTCCTCCAAGAGCACCTCTGGGGGCAC
AGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCT
GTCCTACAGTCCTCAGGACTCTACTCCCTCAGCAGCGTGGTGACCGTGCC
CTCCAGCAGCTTGGGCACCCAGACCTACATCTGCAACGTGAATCACAAGC
CCAGCAACACCAAGGTGGACAAGAGAGTTGAGCCCAAATCTTGTGACAA
AACTCACACATGCCCACCGTGCCCAGCACCTGAACTCCTGGGGGGACCGT
CAGTCTTCCTCTTCCCCCCAAAACCCAAGGACACCCTCATGATCTCCCGGA
CCCCTGAGGTCACATGCGTGGTGGTGGACGTGAGCCACGAAGACCCTGAG
GTCAAGTTCAACTGGTACGTGGACGGCGTGGAGGTGCATAATGCCAAGAC
AAAGCCGCGGGAGGAGCAGTACAACAGCACGTACCGTGTGGTCAGCGTC
CTCACCGTCCTGCACCAGGACTGGCTGAATGGCAAGGAGTACAAGTGCAA
GGTCTCCAACAAAGCCCTCCCAGCCCCCATCGAGAAAACCATCTCCAAAG
CCAAAGGGCAGCCCCGAGAACCACAGGTGTACACCCTGCCCCCATCCCGG
GAGGAGATGACCAAGAACCAGGTCAGCCTGACCTGCCTGGTCAAAGGCT
TCTATCCCAGCGACATCGCCGTGGAGTGGGAGAGCAATGGGCAGCCGGA
GAACAACTACAAGACCACGCCTCCCGTGCTGGACTCCGACGGCTCCTTCT
TCCTCTATAGCAAGCTCACCGTGGACAAGAGCAGGTGGCAGCAGGGGAA
CGTCTTCTCATGCTCCGTGATGCATGAGGCTCTGCACAACCACTACACGC
AGAAGAGCCTCTCCCTGTCTCCGGGTAAATGA

5138_G07 (PGT-138) gamma heavy chain variable region nucleotide sequence:

(SEQ ID NO: 452)

CAGCCGCAGCTGCAGGAGTCGGGGCCAGGACTGGTGGAGGCTTCGG
AGACCCTGTCCCTCACCTGCACTGTGTCCGGCGACTCCACTGCTGCT
TGTGACTATTTCTGGGGCTGGGTCCGGCAGCCCCAGGGAAGGGGCT
GGAGTGGATTGGAAGTTTGTCACATTGTGCAGGTTACTACAATAGTG
GCTGGACCTACCACAACCCGTCTCTCAAGAGTCGACTCACGATTTCA
CTCGACACGCCCAAGAATCAGGTCTTCCTGAAGTTAAATTCTGTGAC
CGCCGCGGACACGGCCATTTACTACTGTGCGCGATTCGGTGGCGACG
TTTTGGTGTACCACGATTGGCCAAAGCCGGCCTGGGTCGACCTCTGG
GGCCGGGGAGTTTTGGTCACCGTCTCGAGC

5138_G07 (PGT-138) gamma heavy chain amino acid sequence: expressed protein with leader sequence in italics and variable region in bold.

(SEQ ID NO: 453)

*MKHLWFFLLLVAAPRWVLS***QPQLQESGPGLVEASETLSLTCTVSGDSTAAC
DYFWGWVRQPPGKGLEWIGSLSHCAGYYNSGWTYHNPSLKSRLTISLD
TPKNQVFLKLNSVTAADTAIYYCARFGGDVLVYHDWPKPAWVDLWGR
GVLVTVSS**ASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKR
VEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQGNV
FSCSVMHEALHNHYTQKSLSLSPGK

-continued

5138_G07 (PGT-138) gamma heavy chain variable region amino acid sequence:
(Kabat CDRs underlined, Chothia CDRs in bold italics)

(SEQ ID NO: 454)
QPQLQESGPGLVEASETLSLTCTVS*GDSTAACD**YFWGWVRQPPGKGLEWIGS
LSHCAGYYNSGWTY**HNPSLKSRLTISLDTPKNQVFLKLNSVTAADTAIYYCAR
FGGDVLVYHDWPKPAWVDLWGRGVLVTVSS

5138_G07 (PGT-138) gamma heavy chain Kabat CDRs:

(SEQ ID NO: 201)
CDR 1: ACDYFWG (SEQ ID NO: 455)
CDR 2: SLSHCAGYYNSGWTYHNPSLKS (SEQ ID NO: 456)
CDR 3: FGGDVLVYHDWPKPAWVDL

5138_G07 (PGT-138) gamma heavy chain Chothia CDRs:

(SEQ ID NO: 204)
CDR 1: GDSTAACD (SEQ ID NO: 457)
CDR 2: SLSHCAGYYNSGWTY (SEQ ID NO: 456)
CDR 3: FGGDVLVYHDWPKPAWVDL

5138_G07 (PGT-138) light chain nucleotide sequence: coding sequence (variable region in bold)

(SEQ ID NO: 581)
*ATGGCCTGGGCTCTGCTCCTCCTCACCCTCCTCACTCAGGGCACAGGGGCCT
GGGCC*CAGTCTGCCCTGACTCAGCCTCCCTCCGCGTCCGGGTCTCCT
GGACAGTCAATCACCATCTCCTGCACTGGAAATATCAATAACTTTGTC
TCCTGGTACCAACAACACCCTGGCAAGGCCCCCAAACTCGTCATTTA
TGGGGTCAATAAGCGCCCCTCAGGTGTCCCTGATCGTTTTTCTGGCT
CCAAGTCTGGCAACGCGGCCTCCCTGACCGTCTCTGGACTCCAGACT
GACGATGAGGCTGTCTATTACTGCGGCTCACTTGCAGGCAACTGGGA
TGTGGTTTTCGGCGGAGGGACCAAGTTGACTGTCCTGGGTCAGCCCAT
GGCTGCCCCCTCGGTCACTCTGTTCCCGCCCTCCTCTGAGGAGCTTCAAGC
CAACAAGGCCACACTGGTGTGTCTCATAAGTGACTTCTACCCGGGAGCCG
TGACAGTGGCCTGGAAGGCAGATAGCAGCCCCGTCAAGGCGGGAGTGGA
GACCACCACACCCTCCAAACAAAGCAACAACAAGTACGCGGCCAGCAGC
TACCTGAGCCTGACGCCTGAGCAGTGGAAGTCCCACAAAAGCTACAGCTG
CCAGGTCACGCATGAAGGGAGCACCGTGGAGAAGACAGTGGCCCCTACA
GAATGTTCATAG

5138_G07 (PGT-138) light chain variable region nucleotide sequence:

(SEQ ID NO: 582)
**CAGTCTGCCCTGACTCAGCCTCCCTCCGCGTCCGGGTCTCCTGGACA
GTCAATCACCATCTCCTGCACTGGAAATATCAATAACTTTGTCTCCTG
GTACCAACAACACCCTGGCAAGGCCCCCAAACTCGTCATTTATGGGG
TCAATAAGCGCCCCTCAGGTGTCCCTGATCGTTTTTCTGGCTCCAAGT
CTGGCAACGCGGCCTCCCTGACCGTCTCTGGACTCCAGACTGACGAT
GAGGCTGTCTATTACTGCGGCTCACTTGCAGGCAACTGGGATGTGGT
TTTCGGCGGAGGGACCAAGTTGACTGTCCTG**

5138_G07 (PGT-138) light chain amino acid sequence: expressed protein with leader sequence in italics and variable region in bold.
(SEQ ID NO: 583)
*MAWALLLLTLLTQGTGAWA***QSALTQPPSASGSPGQSITISCTGNINNFVSWY
QQHPGKAPKLVIYGVNKRPSGVPDRFSGSKSGNAASLTVSGLQTDDEAV
YYCGSLAGNWDVVFGGGTKLTVL**GQPMAAPSVTLFPPSSEELQANKATLV
CLISDFYPGAVTVAWKADSSPVKAGVETTTPSKQSNNKYAASSYLSLTPEQW
KSHKSYSCQVTHEGSTVEKTVAPTECS 5138_G07 (PGT-138) light chain variable region amino acid sequence: (Kabat CDRs underlined, Chothia CDRs in bold italics)

(SEQ ID NO: 584)
QSALTQPPSASGSPGQSITISC*TGNINNFVS*WYQQHPGKAPKLVIY*GVNKRPS*
GVPDRFSGSKSGNAASLTVSGLQTDDEAVYYC*GSLAGNWDVV*FGGGTKLTV
L

5138_G07 (PGT-138) light chain Kabat CDRs:

(SEQ ID NO: 458)
CDR 1: TGNINNFVS (SEQ ID NO: 211)
CDR 2: GVNKRPS (SEQ ID NO: 459)
CDR 3: GSLAGNWDVV

5138_G07 (PGT-138) light chain Chothia CDRs:

(SEQ ID NO: 458)
CDR 1: TGNINNFVS (SEQ ID NO: 211)
CDR 2: GVNKRPS (SEQ ID NO: 459)
CDR 3: GSLAGNWDVV

5120_N10 (PGT-139) gamma heavy chain nucleotide sequence: coding sequence (variable region in bold)
(SEQ ID NO: 460)

ATGAAACACCTGTGGTTCTTCCTCCTGCTGGTGGCAGCTCCCAGATGGGTCCT
GTCCCAGCCGCAGCTGCAGGAGTCGGGGCCAGGACTGGTGGAGGCTT
CGGAGACCCTGTCCCTCACCTGCACTGTGTCCGGCGACTCCACTGCT
GGTTGTGACTATTTCTGGGGCTGGGTCCGGCAGCCCCAGGGAAGG
GGCTGGAGTGGATTGGGGGTTTGTCACATTGTGCAGGTTACTACAAT
ACTGGCTGGACCTACCACAACCCGTCTCTCAAGAGTCGACTCACGAT
TTCACTCGACACGCCCAAGAATCAGGTCTTCCTGAAGTTAAATTCTGT
GACCGCCGCGGACACGGCCATTTACTACTGTGCGCGATTCGACGGCG
AAGTTTTGGTGTACAACGATTGGCCAAAGCCGGCCTGGGTCGACCTC
TGGGGCCGGGGAACTTTGGTCACCGTCTCGAGCGCCTCCACCAAGGG
CCCATCGGTCTTCCCCCTGGCACCCTCCTCCAAGAGCACCTCTGGGGGCA
CAGCGGCCCTGGGCTGCCTGGTCAAGGACTACTTCCCCGAACCGGTGACG
GTGTCGTGGAACTCAGGCGCCCTGACCAGCGGCGTGCACACCTTCCCGGC
TGTCCTACAGTCCTCAGGACTCTACTCCCTCAGCAGCGTGGTGACCGTGCC
CTCCAGCAGCTTGGGCACCCAGACCTACATCTGCAACGTGAATCACAAGC
CCAGCAACACCAAGGTGGACAAGAGAGTTGAGCCCAAATCTTGTGACAA
AACTCACACATGCCCACCGTGCCCAGCACCTGAACTCCTGGGGGGACCGT
CAGTCTTCCTCTTCCCCCCAAAACCCAAGGACACCCTCATGATCTCCCGGA
CCCCTGAGGTCACATGCGTGGTGGTGGACGTGAGCCACGAAGACCCTGAG
GTCAAGTTCAACTGGTACGTGGACGGCGTGGAGGTGCATAATGCCAAGAC
AAAGCCGCGGGAGGAGCAGTACAACAGCACGTACCGTGTGGTCAGCGTC
CTCACCGTCCTGCACCAGGACTGGCTGAATGGCAAGGAGTACAAGTGCAA
GGTCTCCAACAAAGCCCTCCCAGCCCCCATCGAGAAAACCATCTCCAAAG
CCAAAGGGCAGCCCCGAGAACCACAGGTGTACACCCTGCCCCCATCCCGG
GAGGAGATGACCAAGAACCAGGTCAGCCTGACCTGCCTGGTCAAAGGCT
TCTATCCCAGCGACATCGCCGTGGAGTGGGAGAGCAATGGGCAGCCGGA
GAACAACTACAAGACCACGCCTCCCGTGCTGGACTCCGACGGCTCCTTCT
TCCTCTATAGCAAGCTCACCGTGGACAAGAGCAGGTGGCAGCAGGGGAA
CGTCTTCTCATGCTCCGTGATGCATGAGGCTCTGCACAACCACTACACGC
AGAAGAGCCTCTCCCTGTCTCCGGGTAAATGA

5120_N10 (PGT-139) gamma heavy chain variable region nucleotide sequence:
(SEQ ID NO: 461)
CAGCCGCAGCTGCAGGAGTCGGGGCCAGGACTGGTGGAGGCTTCGG
AGACCCTGTCCCTCACCTGCACTGTGTCCGGCGACTCCACTGCTGGT
TGTGACTATTTCTGGGGCTGGGTCCGGCAGCCCCAGGGAAGGGGCT
GGAGTGGATTGGGGGTTTGTCACATTGTGCAGGTTACTACAATACTG
GCTGGACCTACCACAACCCGTCTCTCAAGAGTCGACTCACGATTTCA
CTCGACACGCCCAAGAATCAGGTCTTCCTGAAGTTAAATTCTGTGAC
CGCCGCGGACACGGCCATTTACTACTGTGCGCGATTCGACGGCGAAG
TTTTGGTGTACAACGATTGGCCAAAGCCGGCCTGGGTCGACCTCTGG
GGCCGGGGAACTTTGGTCACCGTCTCGAGC 5120_N10 (PGT-139) gamma heavy chain amino acid sequence: expressed protein with leader sequence in italics and variable region in bold.
(SEQ ID NO: 462)
*MKHLWFFLLLVAAPRWVLS*QPQLQESGPGLVEASETLSLTCTVSGDSTAGC
DYFWGWVRQPPGKGLEWIGGLSHCAGYYNTGWTYHNPSLKSRLTISLD
TPKNQVFLKLNSVTAADTAIYYCARFDGEVLVYNDWPKPAWVDLWGRG
TLVTVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVE
PKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNVFS
CSVMHEALHNHYTQKSLSLSPGK -continued 5120_N10 (PGT-139) gamma heavy chain variable region amino acid sequence:
(Kabat CDRs underlined, Chothia CDRs in bold italics)

(SEQ ID NO: 463)
QPQLQESGPGLVEASETLSLTCTVS*GDSTAGCD*YFWGWVRQPPGKGLEWIG
*GLSHCAGYYNTGWTY*HNPSLKSRLTISLDTPKNQVFLKLNSVTAADTAIYYC
AR*FDGEVLVYNDWPKPAWVDL*WGRGTLVTVSS

5120_N10 (PGT-139) gamma heavy chain Kabat CDRs:

(SEQ ID NO: 464)
CDR 1: GCDYFWG (SEQ ID NO: 202)
CDR 2: GLSHCAGYYNTGWTYHNPSLKS (SEQ ID NO: 465)
CDR 3: FDGEVLVYNDWPKPAWVDL

5120_N10 (PGT-139) gamma heavy chain Chothia CDRs:

(SEQ ID NO: 466)
CDR 1: GDSTAGCD (SEQ ID NO: 205)
CDR 2: GLSHCAGYYNTGWTY (SEQ ID NO: 465)
CDR 3: FDGEVLVYNDWPKPAWVDL

5120_N10 (PGT-139) light chain nucleotide sequence: coding sequence (variable region in bold)

(SEQ ID NO: 467)
ATGGCCTGGGCTCTGCTCCTCCTCACCCTCCTCACTCAGGGCACAGGGGCCT
GGGCCCAGTCTGCCCTGACTCAGCCTCCCTCCGCGTCCGGGTCTCCT
GGACAGTCAATCACCATCTCCTGCACTGGAACCAGCAATAACTTTGT
CTCCTGGTACCAGCAACACCCAGCCAAGGCCCCCAAACTCGTCATTT
ATGGGGTCAATAAGCGCCCCTCAGGTGTCCCTGATCGTTTTTCTGGC
TCCAAGTCTGGCAACACGGCCTCCCTGACCGTCTCTGGACTCCAGAC
TGACGATGAGGCTGTCTATTACTGCGGCTCACTTGTAGGCAACTGGG
ATGTGATTTTCGGCGGAGGGACCAAGTTGACCGTCCTGGGTCAGCCC
ATGGCTGCCCCCTCGGTCACTCTGTTCCCGCCCTCCTCTGAGGAGCTTCAA
GCCAACAAGGCCACACTGGTGTGTCTCATAAGTGACTTCTACCCGGGAGC
CGTGACAGTGGCCTGGAAGGCAGATAGCAGCCCCGTCAAGGCGGGAGTG
GAGACCACCACACCCTCCAAACAAAGCAACAACAAGTACGCGGCCAGCA
GCTACCTGAGCCTGACGCCTGAGCAGTGGAAGTCCCACAAAAGCTACAGC
TGCCAGGTCACGCATGAAGGGAGCACCGTGGAGAAGACAGTGGCCCCTA
CAGAATGTTCATAG

5120_N10 (PGT-139) light chain variable region nucleotide sequence:

(SEQ ID NO: 468)
CAGTCTGCCCTGACTCAGCCTCCCTCCGCGTCCGGGTCTCCTGGACA
GTCAATCACCATCTCCTGCACTGGAACCAGCAATAACTTTGTCTCCTG
GTACCAGCAACACCCAGCCAAGGCCCCCAAACTCGTCATTTATGGGG
TCAATAAGCGCCCCTCAGGTGTCCCTGATCGTTTTTCTGGCTCCAAGT
CTGGCAACACGGCCTCCCTGACCGTCTCTGGACTCCAGACTGACGAT
GAGGCTGTCTATTACTGCGGCTCACTTGTAGGCAACTGGGATGTGAT
TTTCGGCGGAGGGACCAAGTTGACCGTCCTG

5120_N10 (PGT-139) light chain amino acid sequence: expressed protein with leader sequence in italics and variable region in bold.

(SEQ ID NO: 469)
*MAWALLLLTLLTQGTGAWA***QSALTQPPSASGSPGQSITISCTGTSNNFVSWY
QQHPAKAPKLVIYGVNKRPSGVPDRFSGSKSGNTASLTVSGLQTDDEAV
YYCGSLVGNWDVIFGGGTKLTVL**GQPMAAPSVTLFPPSSEELQANKATLV
CLISDFYPGAVTVAWKADSSPVKAGVETTTPSKQSNNKYAASSYLSLTPEQW
KSHKSYSCQVTHEGSTVEKTVAPTECS

5120_N10 (PGT-139) light chain variable region amino acid sequence: (Kabat CDRs underlined, Chothia CDRs in bold italics)

(SEQ ID NO: 470)
QSALTQPPSASGSPGQSITISC*TGTSNNFVS*WYQQHPAKAPKLVIY*GVNKRPS*
GVPDRFSGSKSGNTASLTVSGLQTDDEAVYYC*GSLVGNWDVI*FGGGTKLTVL

5120_N10 (PGT-139) light chain Kabat CDRs:

(SEQ ID NO: 325)
CDR 1: TGTSNNFVS (SEQ ID NO: 211)
CDR 2: GVNKRPS (SEQ ID NO: 196)
CDR 3: GSLVGNWDVI

5120_N10 (PGT-139) light chain Chothia CDRs:

CDR 1: TGTSNNFVS
(SEQ ID NO: 325)

CDR 2: GVNKRPS
(SEQ ID NO: 211)

CDR 3: GSLVGNWDVI
(SEQ ID NO: 196)

The 4835_F12 (PGT-124) antibody includes a heavy chain variable region (SEQ ID NO: 405), encoded by the nucleic acid sequence shown in SEQ ID NO: 403, and a light chain variable region (SEQ ID NO: 414) encoded by the nucleic acid sequence shown in SEQ ID NO: 412.

The heavy chain CDRs of the 4835 F12 (PGT-124) antibody have the following sequences per Kabat definition: NYYWT (SEQ ID NO: 406), YISDRETTTYNPSLNS (SEQ ID NO: 407), and ARRGQRIYGVVSFGEF-FYYYYMDV (SEQ ID NO: 408). The light chain CDRs of the 4835 F12 (PGT-124) antibody have the following sequences per Kabat definition: GRQALGSRAVQ (SEQ ID NO: 415), NNQDRPS (SEQ ID NO: 151), and HMWDSRSGFSWS (SEQ ID NO: 416).

The heavy chain CDRs of the 4835_F12 (PGT-124) antibody have the following sequences per Chothia definition: GGSISN (SEQ ID NO: 409), YISDRETTT (SEQ ID NO: 410), and ARRGQRIYGVVSFGEFFYYYYMDV (SEQ ID NO: 408). The light chain CDRs of the 4835 F12 (PGT-124) antibody have the following sequences per Chothia definition: GRQALGSRAVQ (SEQ ID NO: 415), NNQDRPS (SEQ ID NO: 151), and HMWDSRSGFSWS (SEQ ID NO: 416).

The 4869_K15 (PGT-133) antibody includes a heavy chain variable region (SEQ ID NO: 420), encoded by the nucleic acid sequence shown in SEQ ID NO: 418, and a light chain variable region (SEQ ID NO: 429) encoded by the nucleic acid sequence shown in SEQ ID NO: 427.

The heavy chain CDRs of the 4869_K15 (PGT-133) antibody have the following sequences per Kabat definition: GRFWS (SEQ ID NO: 421), YFSDTDRSEYNPSLRS (SEQ ID NO: 422), and AQQGKRIYGIVSFGEF-FYYYYMDA (SEQ ID NO: 423). The light chain CDRs of the 4869 K15 (PGT-133) antibody have the following sequences per Kabat definition: GERSRGSRAVQ (SEQ ID NO: 430), NNQDRPA (SEQ ID NO: 179), and HYWDSR-SPISWI (SEQ ID NO: 431).

The heavy chain CDRs of the 4869_K15 (PGT-133) antibody have the following sequences per Chothia definition: NGSVSG (SEQ ID NO: 424), YFSDTDRSE (SEQ ID NO: 425), and AQQGKRIYGIVSFGEFFYYYYMDA (SEQ ID NO: 423). The light chain CDRs of the 4869 K15 (PGT-133) antibody have the following sequences per Chothia definition: GERSRGSRAVQ (SEQ ID NO: 430), NNQDRPA (SEQ ID NO: 179), and HYWDSRSPISWI (SEQ ID NO: 431).

The 4876 M06 (PGT-134) antibody includes a heavy chain variable region (SEQ ID NO: 435), encoded by the nucleic acid sequence shown in SEQ ID NO: 433, and a light chain variable region (SEQ ID NO: 440) encoded by the nucleic acid sequence shown in SEQ ID NO: 438.

The heavy chain CDRs of the 4876_M06 (PGT-134) antibody have the following sequences per Kabat definition: GRFWS (SEQ ID NO: 421), YFSDTDRSEYNPSLRS (SEQ ID NO: 422), and AQQGKRIYGIVSFGEL-FYYYYMDA (SEQ ID NO: 436). The light chain CDRs of the 4876 M06 (PGT-134) antibody have the following sequences per Kabat definition: GERSRGSRAVQ (SEQ ID NO: 430), NNQDRPA (SEQ ID NO: 179), and HYWDSR-SPISWI (SEQ ID NO: 431).

The heavy chain CDRs of the 4876 M06 (PGT-134) antibody have the following sequences per Chothia definition: NGSVSG (SEQ ID NO: 424), YFSDTDRSE (SEQ ID NO: 425), and AQQGKRIYGIVSFGELFYYYYMDA (SEQ ID NO: 436). The light chain CDRs of the 4876 M06 (PGT-134) antibody have the following sequences per Chothia definition: GERSRGSRAVQ (SEQ ID NO: 430), NNQDRPA (SEQ ID NO: 179), and HYWDSRSPISWI (SEQ ID NO: 431).

The 5131_A17 (PGT-132) antibody includes a heavy chain variable region (SEQ ID NO: 444), encoded by the nucleic acid sequence shown in SEQ ID NO: 442, and a light chain variable region (SEQ ID NO: 449) encoded by the nucleic acid sequence shown in SEQ ID NO: 447.

The heavy chain CDRs of the 5131_A17 (PGT-132) antibody have the following sequences per Kabat definition: TGHHYWG (SEQ ID NO: 348), HIHYNTAVLHNPALKS (SEQ ID NO: 349), and SGGDILYYNEWQKPHWFYP (SEQ ID NO: 445). The light chain CDRs of the 5131 A17 (PGT-132) antibody have the following sequences per Kabat definition: SGTASDIGSWNFVS (SEQ ID NO: 450), EVNRRRS (SEQ ID NO: 358), and SSLSGRWDIV (SEQ ID NO: 359).

The heavy chain CDRs of the 5131 A17 (PGT-132) antibody have the following sequences per Chothia definition: GDSINTGH (SEQ ID NO: 351), HIHYNTAVL (SEQ ID NO: 352), and SGGDILYYNEWQKPHWFYP (SEQ ID NO: 445). The light chain CDRs of the 5131 A17 (PGT-132) antibody have the following sequences per Chothia definition: SGTASDIGSWNFVS (SEQ ID NO: 450), EVNRRRS (SEQ ID NO: 358), and SSLSGRWDIV (SEQ ID NO: 359).

The 5138_G07 (PGT-138) antibody includes a heavy chain variable region (SEQ ID NO: 454), encoded by the nucleic acid sequence shown in SEQ ID NO: 452, and a light chain variable region (SEQ ID NO: 461) encoded by the nucleic acid sequence shown in SEQ ID NO: 459.

The heavy chain CDRs of the 5138_G07 (PGT-138) antibody have the following sequences per Kabat definition: ACDYFWG (SEQ ID NO: 201), SLSHCAGYYNSGWT-YHNPSLKS (SEQ ID NO: 455), and FGGDVLVYHDWPKPAWVDL (SEQ ID NO: 456). The light chain CDRs of the 5138_G07 (PGT-138) antibody have the following sequences per Kabat definition: TGNINNFVS (SEQ ID NO: 458), GVNKRPS (SEQ ID NO: 211), and GSLAGNWDVV (SEQ ID NO: 459).

The heavy chain CDRs of the 5138_G07 (PGT-138) antibody have the following sequences per Chothia definition: GDSTAACD (SEQ ID NO: 204), SLSH-CAGYYNSGWTY (SEQ ID NO: 457), and FGGDVLVYHDWPKPAWVDL (SEQ ID NO: 456). The light chain CDRs of the 5138_G07 (PGT-138) antibody have the following sequences per Chothia definition: TGNINNFVS (SEQ ID NO: 458), GVNKRPS (SEQ ID NO: 211), and GSLAGNWDVV (SEQ ID NO: 459).

The 5120_N10 (PGT-139) antibody includes a heavy chain variable region (SEQ ID NO: 463), encoded by the nucleic acid sequence shown in SEQ ID NO: 461, and a light chain variable region (SEQ ID NO: 470) encoded by the nucleic acid sequence shown in SEQ ID NO: 468.

The heavy chain CDRs of the 5120_N10 (PGT-139) antibody have the following sequences per Kabat definition: GCDYFWG (SEQ ID NO: 464), GLSHCAGYYNTGWTYHNPSLKS (SEQ ID NO: 202), and FDGEVLVYNDWPKPAWVDL (SEQ ID NO: 465). The light chain CDRs of the 5120_N10 (PGT-139) antibody have the following sequences per Kabat definition: TGTSNNFVS (SEQ ID NO: 325), GVNKRPS (SEQ ID NO: 211), and GSLVGNWDVI (SEQ ID NO: 196).

The heavy chain CDRs of the 5120_N10 (PGT-139) antibody have the following sequences per Chothia definition: GDSTAGCD (SEQ ID NO: 466), GLSHCAGYYNTGWTY (SEQ ID NO: 205), and FDGEVLVYNDWPKPAWVDL (SEQ ID NO: 465). The light chain CDRs of the 5120_N10 (PGT-139) antibody have the following sequences per Chothia definition: TGTSNNFVS (SEQ ID NO: 325), GVNKRPS (SEQ ID NO: 211), and GSLVGNWDVI (SEQ ID NO: 196).

The sequences of additional human monoclonal antibodies were determined, including the sequences of the variable regions of the Gamma heavy and Kappa or Lambda light chains. In addition, the sequence of each of the polynucleotides encoding the antibody sequences was determined. Shown below are the polypeptide and polynucleotide sequences of the gamma heavy chains and kappa light chains, with the signal peptides at the N-terminus (or 5' end) and the constant regions at the C-terminus (or 3' end) of the variable regions, which are shown in bolded text.

```
6831_A21 (PGT-151) gamma heavy chain nucleotide sequence: coding sequence
(leader sequence in italics, variable region in bold)
                                                        (SEQ ID NO: 471)
ATGGAATTGGGGCTGAGCTGGGTTTTCCTCGTTGGTCTCTTAAGAGGTGTCCA
GTGTCGGGTGCAGTTGGTGGAGTCGGGGGGAGGCGTGGTCCAGCCTG
GGAAGTCCGTGAGACTTTCCTGTGTAGTCTCCGATTTCCCCTTCAGCA
AGTATCCTATGTATTGGGTTCGCCAGGCTCCAGGCAAGGGGCTGGAG
TGGGTGGCAGCCATCTCCGGTGATGCCTGGCATGTGGTCTACTCAAA
TTCCGTGCAGGGCCGATTTCTCGTCTCCAGGGACAATGTCAAGAACA
CTCTATATTTAGAAATGAACAGCCTGAAAATTGAGGATACGGCCGTA
TATCGCTGCGCGAGAATGTTCCAGGAGTCTGGTCCACCACGTTTGGA
TCGTTGGAGCGGTCGAAATTATTACTATTATTCTGGTATGGACGTCTG
GGGCCAAGGGACCACGGTCACCGTCTCGAGCGCCTCCACCAAGGGCC
CATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGT
GTCGTGGAACTCAGGCGCCCTGACCAGCGGCGTGCACACCTTCCCGGCTG
TCCTACAGTCCTCAGGACTCTACTCCCTCAGCAGCGTGGTGACCGTGCCCT
CCAGCAGCTTGGGCACCCAGACCTACATCTGCAACGTGAATCACAAGCCC
AGCAACACCAAGGTGGACAAGAGAGTTGAGCCCAAATCTTGTGACAAAA
CTCACACATGCCCACCGTGCCCAGCACCTGAACTCCTGGGGGGACCGTCA
GTCTTCCTCTTCCCCCCAAAACCCAAGGACACCCTCATGATCTCCCGGACC
CCTGAGGTCACATGCGTGGTGGTGGACGTGAGCCACGAAGACCCTGAGGT
CAAGTTCAACTGGTACGTGGACGGCGTGGAGGTGCATAATGCCAAGACA
AAGCCGCGGGAGGAGCAGTACAACAGCACGTACCGTGTGGTCAGCGTCC
TCACCGTCCTGCACCAGGACTGGCTGAATGGCAAGGAGTACAAGTGCAA
GGTCTCCAACAAAGCCCTCCCAGCCCCCATCGAGAAAACCATCTCCAAAG
CCAAAGGGCAGCCCCGAGAACCACAGGTGTACACCCTGCCCCCATCCCGG
GAGGAGATGACCAAGAACCAGGTCAGCCTGACCTGCCTGGTCAAAGGCT
TCTATCCCAGCGACATCGCCGTGGAGTGGGAGAGCAATGGGCAGCCGGA
GAACAACTACAAGACCACGCCTCCCGTGCTGGACTCCGACGGCTCCTTCT
TCCTCTATAGCAAGCTCACCGTGGACAAGAGCAGGTGGCAGCAGGGGAA
CGTCTTCTCATGCTCCGTGATGCATGAGGCTCTGCACAACCACTACACGC
AGAAGAGCCTCTCCCTGTCTCCGGGTAAATGA 6831_A21 (PGT-151) gamma heavy chain variable region nucleotide sequence:
                                                        (SEQ ID NO: 472)
CGGGTGCAGTTGGTGGAGTCGGGGGGAGGCGTGGTCCAGCCTGGGA
AGTCCGTGAGACTTTCCTGTGTAGTCTCCGATTTCCCCTTCAGCAAGT
ATCCTATGTATTGGGTTCGCCAGGCTCCAGGCAAGGGGCTGGAGTGG
GTGGCAGCCATCTCCGGTGATGCCTGGCATGTGGTCTACTCAAATTC
CGTGCAGGGCCGATTTCTCGTCTCCAGGGACAATGTCAAGAACACTC
TATATTTAGAAATGAACAGCCTGAAAATTGAGGATACGGCCGTATAT
CGCTGCGCGAGAATGTTCCAGGAGTCTGGTCCACCACGTTTGGATCG
TTGGAGCGGTCGAAATTATTACTATTATTCTGGTATGGACGTCTGGG
GCCAAGGGACCACGGTCACCGTCTCGAGC 6831_A21 (PGT-151) gamma heavy chain amino acid sequence: expressed protein
with leader sequence in italics and variable region in bold.
                                                        (SEQ ID NO: 473)
MELGLSWVFLVGLLRGVQCRVQLVESGGGVVQPGKSVRLSCVVSDFPFSKY
PMYWVRQAPGKGLEWVAAISGDAWHVVYSNSVQGRFLVSRDNVKNTL
YLEMNSLKIEDTAVYRCARMFQESGPPRLDRWSGRNYYYSGMDVWG
QGTTVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDK
RVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQGNV
FSCSVMHEALHNHYTQKSLSLSPGK
```

6831_A21 (PGT-151) gamma heavy chain variable region amino acid sequence:
(Kabat CDRs underlined, Chothia CDRs in bold italics)

(SEQ ID NO: 474)

RVQLVESGGGVVQPGKSVRLSCVVS*DFPFSK*YPMYWVRQAPGKGLEWVA*A*
*ISGDAWHVV*YSNSVQGRFLVSRDNVKNTLYLEMNSLKIEDTAVYRCAR*MFQ*
*ESGPPRLDRWSGRNYYYYSGMDV*WGQGTTVTVSS

6831_A21 (PGT-151) gamma heavy chain Kabat CDRs:

(SEQ ID NO: 475)

CDR 1: KYPMY (SEQ ID NO: 476)

CDR 2: AISGDAWHVVYSNSVQG (SEQ ID NO: 477)

CDR 3: MFQESGPPRLDRWSGRNYYYYSGMDV

6831_A21 (PGT-151) gamma heavy chain Chothia CDRs:

(SEQ ID NO: 478)

CDR 1: DFPFSK (SEQ ID NO: 479)

CDR 2: AISGDAWHVV (SEQ ID NO: 477)

CDR 3: MFQESGPPRLDRWSGRNYYYYSGMDV

6831_A21 (PGT-151) light chain nucleotide sequence: coding sequence (variable region in bold)

(SEQ ID NO: 480)

*ATGAGGCTCCCTGCTCAGCTCCTGGGGCTGCTAATGCTCTGGATACCTGAATT*
*CACTGCA*GACATTGTGATGACCCAGACTCCTCTCTCTTTGTCCGTCAC
CCCTGGACAGCCGGCCTCCATCTCCTGCAAGTCCAGTGAGAGCCTCC
GACAAAGTAATGGAAAGACCTCTTTGTATTGGTATCGGCAGAAGCCA
GGCCAGTCTCCACAACTCCTAGTGTTTGAAGTTTCTAATCGATTCTCT
GGCGTGTCGGATAGGTTTGTTGGCAGCGGGTCAGGGACAGACTTCAC
ACTGAGAATCAGCCGGGTAGAGGCTGAGGATGTTGGATTTTATTACT
GCATGCAAAGTAAAGACTTCCCACTTACATTTGGCGGCGGGACCAAG
GTGGATCTCAAACGTACGGTGGCTGCACCATCTGTCTTCATCTTCCCGCC
ATCTGATGAGCAGTTGAAATCTGGAACTGCCTCTGTTGTGTGCCTGCTGAA
TAACTTCTATCCCAGAGAGGCCAAAGTACAGTGGAAGGTGGATAACGCCC
TCCAATCGGGTAACTCCCAGGAGAGTGTCACAGAGCAGGACAGCAAGGA
CAGCACCTACAGCCTCAGCAGCACCCTGACGCTGAGCAAAGCAGACTAC
GAGAAACACAAAGTCTACGCCTGCGAAGTCACCCATCAGGGCCTGAGCTC
GCCCGTCACAAAGAGCTTCAACAGGGGAGAGTGTTAG

6831_A21 (PGT-151) light chain variable region nucleotide sequence:

(SEQ ID NO: 481)

GACATTGTGATGACCCAGACTCCTCTCTCTTTGTCCGTCACCCCTGGA
CAGCCGGCCTCCATCTCCTGCAAGTCCAGTGAGAGCCTCCGACAAAG
TAATGGAAAGACCTCTTTGTATTGGTATCGGCAGAAGCCAGGCCAGT
CTCCACAACTCCTAGTGTTTGAAGTTTCTAATCGATTCTCTGGCGTGT
CGGATAGGTTTGTTGGCAGCGGGTCAGGGACAGACTTCACACTGAGA
ATCAGCCGGGTAGAGGCTGAGGATGTTGGATTTTATTACTGCATGCA
AAGTAAAGACTTCCCACTTACATTTGGCGGCGGGACCAAGGTGGATC
TCAAA

6831_A21 (PGT-151) light chain amino acid sequence: expressed protein with leader sequence in italics and variable region in bold.

(SEQ ID NO: 482)

*MRLPAQLLGLLMLWIPEFTA*DIVMTQTPLSLSVTPGQPASISCKSSESLRQSN
GKTSLYWYRQKPGQSPQLLVFEVSNRFSGVSDRFVGSGSGTDFTLRISRV
EAEDVGFYYCMQSKDFPLTFGGGTKVDLKRTVAAPSVFIFPPSDEQLKSGT
ASVVCLLNNFYPREAKVQWKVDNALQSGNSQESVTEQDSKDSTYSLSSTLTL
SKADYEKHKVYACEVTHQGLSSPVTKSFNRGEC

6831_A21 (PGT-151) light chain variable region amino acid sequence: (Kabat CDRs underlined, Chothia CDRs in bold italics)

(SEQ ID NO: 483)

DIVMTQTPLSLSVTPGQPASISC*KSSESLRQSNGKTSLY*WYRQKPGQSPQLLVF
*EVSNRFS*GVSDRFVGSGSGTDFTLRISRVEAEDVGFYYC*MQSKDFPLT*FGGG
TKVDLK

6831_A21 (PGT-151) light chain Kabat CDRs:

(SEQ ID NO: 484)
CDR 1: KSSESLRQSNGKTSLY (SEQ ID NO: 485)
CDR 2: EVSNRFS (SEQ ID NO: 486)
CDR 3: MQSKDFPLT

6831_A21 (PGT-151) light chain Chothia CDRs:

(SEQ ID NO: 484)
CDR 1: KSSESLRQSNGKTSLY (SEQ ID NO: 485)
CDR 2: EVSNRFS (SEQ ID NO: 486)
CDR 3: MQSKDFPLT

6889_117 (PGT-152) gamma heavy chain nucleotide sequence: coding sequence (variable region in bold)

(SEQ ID NO: 487)

*ATGGAATTGGGGCTGAGCTGGGTTTTCCTCGTTGGTCTCTTAAGAGGTGTCCA*
*CTGT*CGGGTGCAGTTGGTGGAGTCGGGGGGAGGCGTGGTCCAGCCTG
GGAAGTCCGTGAGACTTTCCTGTGTAGTCTCTGATTTCCCCTTCAGCA
AGTATCCTATGTATTGGGTTCGCCAGGCTCCAGGCAAGGGGCTGGAG
TGGGTGGCAGCCATCTCCGCTGATGCCTGGCATGTGGTCTACTCAGG
CTCCGTGCAGGGCCGATTTCTCGTCTCCAGGGACAACTCCAAGAACA
TTCTGTATTTGGAAATGAACACCCTGAAAATTGAGGACACGGCCGTA
TATCGCTGCGCGAGAATGTTCCAGGAGTCTGGTCCACCACGTTTCGA
TTCTTGGAGCGGTCGAAATTACTACTATTACTCTGGTATGGACGTCTG
GGGCCAAGGGACCACGGTCACCGTCTCGAGCGCCTCCACCAAGGGCC
CATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGT
GTCGTGGAACTCAGGCGCCCTGACCAGCGGCGTGCACACCTTCCCGGCTG
TCCTACAGTCCTCAGGACTCTACTCCCTCAGCAGCGTGGTGACCGTGCCCT
CCAGCAGCTTGGGCACCCAGACCTACATCTGCAACGTGAATCACAAGCCC
AGCAACACCAAGGTGGACAAGAGAGTTGAGCCCAAATCTTGTGACAAAA
CTCACACATGCCCACCGTGCCCAGCACCTGAACTCCTGGGGGGACCGTCA
GTCTTCCTCTTCCCCCCAAAACCCAAGGACACCCTCATGATCTCCCGGACC
CCTGAGGTCACATGCGTGGTGGTGGACGTGAGCCACGAAGACCCTGAGGT
CAAGTTCAACTGGTACGTGGACGGCGTGGAGGTGCATAATGCCAAGACA
AAGCCGCGGGAGGAGCAGTACAACAGCACGTACCGTGTGGTCAGCGTCC
TCACCGTCCTGCACCAGGACTGGCTGAATGGCAAGGAGTACAAGTGCAA
GGTCTCCAACAAAGCCCTCCCAGCCCCCATCGAGAAAACCATCTCCAAAG
CCAAAGGGCAGCCCCGAGAACCACAGGTGTACACCCTGCCCCCATCCCGG
GAGGAGATGACCAAGAACCAGGTCAGCCTGACCTGCCTGGTCAAAGGCT
TCTATCCCAGCGACATCGCCGTGGAGTGGGAGAGCAATGGGCAGCCGGA
GAACAACTACAAGACCACGCCTCCCGTGCTGGACTCCGACGGCTCCTTCT
TCCTCTATAGCAAGCTCACCGTGGACAAGAGCAGGTGGCAGCAGGGGAA
CGTCTTCTCATGCTCCGTGATGCATGAGGCTCTGCACAACCACTACACGC
AGAAGAGCCTCTCCCTGTCTCCGGGTAAATGA

6889_117 (PGT-152) gamma heavy chain variable region nucleotide sequence:

(SEQ ID NO: 488)

CGGGTGCAGTTGGTGGAGTCGGGGGGAGGCGTGGTCCAGCCTGGGA
AGTCCGTGAGACTTTCCTGTGTAGTCTCTGATTTCCCCTTCAGCAAGT
ATCCTATGTATTGGGTTCGCCAGGCTCCAGGCAAGGGGCTGGAGTGG
GTGGCAGCCATCTCCGCTGATGCCTGGCATGTGGTCTACTCAGGCTC
CGTGCAGGGCCGATTTCTCGTCTCCAGGGACAACTCCAAGAACATTC
TGTATTTGGAAATGAACACCCTGAAAATTGAGGACACGGCCGTATAT
CGCTGCGCGAGAATGTTCCAGGAGTCTGGTCCACCACGTTTCGATTC
TTGGAGCGGTCGAAATTACTACTATTACTCTGGTATGGACGTCTGGG
GCCAAGGGACCACGGTCACCGTCTCGAGC

6889_117 (PGT-152) gamma heavy chain amino acid sequence: expressed protein with leader sequence in italics and variable region in bold.

(SEQ ID NO: 489)

*MELGLSWVFLVGLLRGVHC*RVQLVESGGGVVQPGKSVRLSCVVSDFPFSKY
PMYWVRQAPGKGLEWVAAISADAWHVVYSGSVQGRFLVSRDNSKNILY
LEMNTLKIEDTAVYRCARMFQESGPPRFDSWSGRNYYYYSGMDVWGQ
GTTVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKR
VEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQGNV
FSCSVMHEALHNHYTQKSLSLSPGK

-continued

6889_I17 (PGT-152) gamma heavy chain variable region amino acid sequence: (Kabat CDRs underlined, Chothia CDRs in bold italics)

(SEQ ID NO: 490)

RVQLVESGGGVVQPGKSVRLSCVVS*DFPFS*KYPMYWVRQAPGKGLEWVA**A
ISADAWHVVYSGSVQGRFLVSRDNSKNILYLEMNTLKIEDTAVYRCAR*MFQ*
*ESGPPRFDSWSGRNYYYYSGMDV*WGQGTTVTVSS

6889_I17 (PGT-152) gamma heavy chain Kabat CDRs:

(SEQ ID NO: 475)

CDR 1: KYPMY (SEQ ID NO: 491)

CDR 2: AISADAWHVVYSGSVQG (SEQ ID NO: 492)

CDR 3: MFQESGPPRFDSWSGRNYYYYSGMDV

6889_I17 (PGT-152) gamma heavy chain Chothia CDRs:

(SEQ ID NO: 478)

CDR 1: DFPFSK (SEQ ID NO: 493)

CDR 2: AISADAWHVV (SEQ ID NO: 492)

CDR 3: MFQESGPPRFDSWSGRNYYYYSGMDV

6889_I17 (PGT-152) light chain nucleotide sequence: coding sequence (variable region in bold)

(SEQ ID NO: 494)

ATGAGGCTCCCTGCTCAGCTCCTGGGGCTGCTAATGCTCTGGATACCTGAATT
TATTGCC**GACATTGTGATGACCCAGACTCCTCTCTCTTTGTCCGTCGAC
CCTGGACAGCCGGCCTCCATCTCCTGCAAGTCCAGTCAGAGCCTCCG
ACAAAGTAATGGAAAGACCTCTTTGTATTGGTATCAGCAGAAGCCAG
GCCAGTCTCCACAACTCCTAATATTTGAAGTTTCTAATCGATTCTCTG
GCGTGTCGGATAGGTTTGTTGGCAGCGGGTCAGGGACAGACTTCACA
CTGAGAATCAGCCGGGTAGAGGCTGAGGATGTTGGATTTTATTACTG
CATGCAAAGTAAAGACTTCCCACTCACCTTTGGCGGCGGGACCAAGG
TGGATCTCAAC**CGTACGGTGGCTGCACCATCTGTCTTCATCTTCCCGCCA
TCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCT
CCAATCGGGTAACTCCCAGGAGAGTGTCACAGAGCAGGACAGCAAGGAC
AGCACCTACAGCCTCAGCAGCACCCTGACGCTGAGCAAAGCAGACTACG
AGAAACACAAAGTCTACGCCTGCGAAGTCACCCATCAGGGCCTGAGCTCG
CCCGTCACAAAGAGCTTCAACAGGGGAGAGTGTTAG

6889_I17 (PGT-152) light chain variable region nucleotide sequence:

(SEQ ID NO: 495)

**GACATTGTGATGACCCAGACTCCTCTCTCTTTGTCCGTCGACCCTGGA
CAGCCGGCCTCCATCTCCTGCAAGTCCAGTCAGAGCCTCCGACAAAG
TAATGGAAAGACCTCTTTGTATTGGTATCAGCAGAAGCCAGGCCAGT
CTCCACAACTCCTAATATTTGAAGTTTCTAATCGATTCTCTGGCGTGT
CGGATAGGTTTGTTGGCAGCGGGTCAGGGACAGACTTCACACTGAGA
ATCAGCCGGGTAGAGGCTGAGGATGTTGGATTTTATTACTGCATGCA
AAGTAAAGACTTCCCACTCACCTTTGGCGGCGGGACCAAGGTGGATC
TCAAC**

6889_I17 (PGT-152) light chain amino acid sequence: expressed protein with leader sequence in italics and variable region in bold.

(SEQ ID NO: 496)

*MRLPAQLLGLLMLWIPEFIA***DIVMTQTPLSLSVDPGQPASISCKSSQSLRQSN
GKTSLYWYQQKPGQSPQLLIFEVSNRFSGVSDRFVGSGSTDFTLRISRV
EAEDVGFYYCMQSKDFPLTFGGGTKVDLN**RTVAAPSVFIFPPSDEQLKSGT
ASVVCLLNNFYPREAKVQWKVDNALQSGNSQESVTEQDSKDSTYSLSSTLTL
SKADYEKHKVYACEVTHQGLSSPVTKSFNRGEC

6889_I17 (PGT-152) light chain variable region amino acid sequence: (Kabat CDRs underlined, Chothia CDRs in bold italics)

(SEQ ID NO: 497)

DIVMTQTPLSLSVDPGQPASISC*KSSQSLRQSNGKTSLY*WYQQKPGQSPQLLIF
*EVSNRFS*GVSDRFVGSGSTDFTLRISRVEAEDVGFYYC*MQSKDFPLT*FGGG
TKVDLN

6889_117 (PGT-152) light chain Kabat CDRs:
(SEQ ID NO: 498)
CDR 1: KSSQSLRQSNGKTSLY (SEQ ID NO: 485)
CDR 2: EVSNRFS (SEQ ID NO: 486)
CDR 3: MQSKDFPLT 6889_117 (PGT-152) light chain Chothia CDRs:
(SEQ ID NO: 498)
CDR 1: KSSQSLRQSNGKTSLY (SEQ ID NO: 485)
CDR 2: EVSNRFS (SEQ ID NO: 486)
CDR 3: MQSKDFPLT 6891_F06 (PGT-153) gamma heavy chain nucleotide sequence: coding sequence
(leader sequence in italics, variable region in bold)
(SEQ ID NO: 499)
*ATGGAATTGGGGCTGAGCTGGGTTTTCCTCGTTGCTCTCTTAAGAGGTGTCCA*
*GTGT*CAGGTGCAGTTGGTGGAGTCGGGCGGAGGCGTGGTCCAGCCTG
GGAAGTCCCTGAGACTCTCCTGTGTAGTCTCTAATTTTCTCTTCAATA
AACGTCACATGCACTGGGTCCGCCAGGCTCCAGGCAAGGGACTAGAG
TGGATAGCAGTCATTTCCTCTGATGCCATTCACGTAGACTACGCAAGT
TCCGTGCGGGGCCGATCCCTCATCTCCAGAGACAATTCCAAAAATAG
TTTATATCTAGACATGAATAACCTGAAAATTGAGGACACGGCCACATA
TTATTGTGCAAGAGATAGAGACGGATATGGTCCACCACAGATCCAGA
CTTGGAGCGGTCGATACCTCCACCTTTATTCTGGAATAGACGCCTGG
GGCCTAGGGACCACGGTCACCGTCTCGAGCGCCTCCACCAAGGGCCCA
TCGGTCTTCCCCCTGGCACCCTCCTCCAAGAGCACCTCTGGGGGCACAGC
GGCCCTGGGCTGCCTGGTCAAGGACTACTTCCCCGAACCGGTGACGGTGT
CGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCC
AGCAGCTTGGGCACCCAGACCTACATCTGCAACGTGAATCACAAGCCCAG
CAACACCAAGGTGGACAAGAGAGTTGAGCCCAAATCTTGTGACAAAACT
CACACATGCCCACCGTGCCCAGCACCTGAACTCCTGGGGGGACCGTCAGT
CTTCCTCTTCCCCCCAAAACCCAAGGACACCCTCATGATCTCCCGGACCCC
TGAGGTCACATGCGTGGTGGTGGACGTGAGCCACGAAGACCCTGAGGTCA
AGTTCAACTGGTACGTGGACGGCGTGGAGGTGCATAATGCCAAGACAAA
GCCGCGGGAGGAGCAGTACAACAGCACGTACCGTGTGGTCAGCGTCCTC
ACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCC
AAAGGGCAGCCCCGAGAACCACAGGTGTACACCCTGCCCCCATCCCGGG
AGGAGATGACCAAGAACCAGGTCAGCCTGACCTGCCTGGTCAAAGGCTTC
TATCCCAGCGACATCGCCGTGGAGTGGGAGAGCAATGGGCAGCCGGAGA
ACAACTACAAGACCACGCCTCCCGTGCTGGACTCCGACGGCTCCTTCTTC
CTCTATAGCAAGCTCACCGTGGACAAGAGCAGGTGGCAGCAGGGGAACG
TCTTCTCATGCTCCGTGATGCATGAGGCTCTGCACAACCACTACACGCAG
AAGAGCCTCTCCCTGTCTCCGGGTAAATGA 6891_F06 (PGT-153) gamma heavy chain variable region nucleotide sequence:
(SEQ ID NO: 500)
CAGGTGCAGTTGGTGGAGTCGGGCGGAGGCGTGGTCCAGCCTGGGA
AGTCCCTGAGACTCTCCTGTGTAGTCTCTAATTTTCTCTTCAATAAAC
GTCACATGCACTGGGTCCGCCAGGCTCCAGGCAAGGGACTAGAGTG
GATAGCAGTCATTTCCTCTGATGCCATTCACGTAGACTACGCAAGTTC
CGTGCGGGGCCGATCCCTCATCTCCAGAGACAATTCCAAAAATAGTT
TATATCTAGACATGAATAACCTGAAAATTGAGGACACGGCCACATATT
ATTGTGCAAGAGATAGAGACGGATATGGTCCACCACAGATCCAGACT
TGGAGCGGTCGATACCTCCACCTTTATTCTGGAATAGACGCCTGGGG
CCTAGGGACCACGGTCACCGTCTCGAGC

6891_F06 (PGT-153) gamma heavy chain amino acid sequence: expressed protein with
leader sequence in italics and variable region in bold.
(SEQ ID NO: 501)
*MELGLSWVFLVALLRGVQC*QVQLVESGGGVVQPGKSLRLSCVVSNFLFNKR
HMHWVRQAPGKGLEWIAVISSDAIHVDYASSVRGRSLISRDNSKNSLYLD
MNNLKIEDTATYYCARDRDGYGPPQIQTWSGRYLHLYSGIDAWGLGTT
VTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKRVEPK
SCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVKGFYP
SDIAVEWESNGQPENNYKTTPPVLDSDGSFFLYSKLTVDKSRWQQGNVFSCS
VMHEALHNHYTQKSLSLSPGK 6891_F06 (PGT-153) gamma heavy chain variable region amino acid sequence: (Kabat CDRs underlined, Chothia CDRs in bold italics)

(SEQ ID NO: 502)

QVQLVESGGGVVQPGKSLRLSCVVS*NFLFNK*RHMHWVRQAPGKGLEWIA<u>*V*</u>
<u>*ISSDAIHVD*Y</u>ASSVRGRSLISRDNSKNSLYLDMNNLKIEDTATYYCAR<u>*DRDGY*</u>
<u>*GPPQIQTWSGRYLHLYSGIDA*</u>WGLGTTVTVSS

6891_F06 (PGT-153) gamma heavy chain Kabat CDRs:

(SEQ ID NO: 503)

CDR 1: KRHMH (SEQ ID NO: 504)

CDR 2: VISSDAIHVDYASSVRG (SEQ ID NO: 505)

CDR 3: DRDGYGPPQIQTWSGRYLHLYSGIDA

6891_F06 (PGT-153) gamma heavy chain Chothia CDRs:

(SEQ ID NO: 506)

CDR 1: NFLFNK (SEQ ID NO: 507)

CDR 2: VISSDAIHVD (SEQ ID NO: 505)

CDR 3: DRDGYGPPQIQTWSGRYLHLYSGIDA

6891_F06 (PGT-153) light chain nucleotide sequence: coding sequence (variable region in bold)

(SEQ ID NO: 508)

*ATGAGGCTCCCTGCTCAGCTCCTGGGGCTGCTAATGCTCTGGATACCTGAATT*
*CACTGCC*GACATTGTGCTGACCCAGAGCCCCCTCTTTCTGTCCGTCAG
TCCTGGACAGCCGGCCTCCATCTCCTGTAAGTCTAGTCAGAGCCTCC
GACAAAGTAATGGAAAGACATATTTGTATTGGTACGTACAAAAGTCC
GGCCAGTCTCCACAACCCCTGATCCAGGAAGTTTCCATTCGCTTCTCT
GGAGTGCCAGGTAGATTCGCTGGCAGCGGATCAGGGACAGACTTCAC
ACTGAAAATCAGCCGGGTGGAGGCTGAAGATGTTGGAGTTTATTTCT
GCATGCAAAGTAAAGACTTTCCACTCACTTTTGGCGGAGGGACCAAG
GTGGACCTCAATCGTACGGTGGCTGCACCATCTGTCTTCATCTTCCCGCC
ATCTGATGAGCAGTTGAAATCTGGAACTGCCTCTGTTGTGTGCCTGCTGAA
TAACTTCTATCCCAGAGAGGCCAAAGTACAGTGGAAGGTGGATAACGCCC
TCCAATCGGGTAACTCCCAGGAGAGTGTCACAGAGCAGGACAGCAAGGA
CAGCACCTACAGCCTCAGCAGCACCCTGACGCTGAGCAAAGCAGACTAC
GAGAAACACAAAGTCTACGCCTGCGAAGTCACCCATCAGGGCCTGAGCTC
GCCCGTCACAAAGAGCTTCAACAGGGGAGAGTGTTAG

6891_F06 (PGT-153) light chain variable region nucleotide sequence:

(SEQ ID NO: 509)

GACATTGTGCTGACCCAGAGCCCCCTCTTTCTGTCCGTCAGTCCTGG
ACAGCCGGCCTCCATCTCCTGTAAGTCTAGTCAGAGCCTCCGACAAA
GTAATGGAAAGACATATTTGTATTGGTACGTACAAAAGTCCGGCCAG
TCTCCACAACCCCTGATCCAGGAAGTTTCCATTCGCTTCTCTGGAGTG
CCAGGTAGATTCGCTGGCAGCGGATCAGGGACAGACTTCACACTGAA
AATCAGCCGGGTGGAGGCTGAAGATGTTGGAGTTTATTTCTGCATGC
AAAGTAAAGACTTTCCACTCACTTTTGGCGGAGGGACCAAGGTGGAC
CTCAAT

6891_F06 (PGT-153) light chain amino acid sequence: expressed protein with leader sequence in italics and variable region in bold.

(SEQ ID NO: 510)

*MRLPAQLLGLLMLWIPEFTA*DIVLTQSPLFLSVSPGQPASISCKSSQSLRQSN
GKTYLYWYVQKSGQSPQPLIQEVSIRFSGVPGRFAGSGSGTDFTLKISRV
EAEDVGVYFCMQSKDFPLTFGGGTKVDLNRTVAAPSVFIFPPSDEQLKSGT
ASVVCLLNNFYPREAKVQWKVDNALQSGNSQESVTEQDSKDSTYSLSSTLTL
SKADYEKHKVYACEVTHQGLSSPVTKSFNRGEC

6891_F06 (PGT-153) light chain variable region amino acid sequence: (Kabat CDRs underlined, Chothia CDRs in bold italics)

(SEQ ID NO: 511)

DIVLTQSPLFLSVSPGQPASISC<u>*KSSQSLRQSNGKTYLY*</u>WYVQKSGQSPQPLIQ
<u>*EVSIRFS*</u>GVPGRFAGSGSGTDFTLKISRVEAEDVGVYFC<u>*MQSKDFPLT*</u>FGGGT
KVDLN

-continued

6891_F06 (PGT-153) light chain Kabat CDRs:

(SEQ ID NO: 512)
CDR 1: KSSQSLRQSNGKTYLY (SEQ ID NO: 513)
CDR 2: EVSIRFS (SEQ ID NO: 486)
CDR 3: MQSKDFPLT

6891_F06 (PGT-153) light chain Chothia CDRs:

(SEQ ID NO: 512)
CDR 1: KSSQSLRQSNGKTYLY (SEQ ID NO: 513)
CDR 2: EVSIRFS (SEQ ID NO: 486)
CDR 3: MQSKDFPLT

6843_G20 (PGT-154) gamma heavy chain nucleotide sequence: coding sequence
(variable region in bold)

(SEQ ID NO: 514)

*ATGGAATTGGGGCTGAGCTGGGTTTTCCTCGTTGCTCTCTTAAGAGGTGTCCA
GTGT***CAGGTGCAGCTGGTGGAATCGGGAGGAGGCGTGGTCCAGCCTG
GAAAGTCCCTCAGACTCTCATGTGTCGTCTCTAATTTCATCTTTAATA
AATATCCTATGTATTGGGTCCGCCAGGCTCCAGGCAAGGGGCTGGAG
TGGGTGGCAGCCATCTCCGCTGATGCCTGGCATGTAGACTACGCAGC
CTCCGTGAAGGACCGATTTCTCATCTCCAGAGACAATTCCAAGAATG
CTCTATATTTGGAAATGAACACCCTGAGAGTTGAAGACACGGGTATC
TACTACTGTGCGAGAAATATAGAGGAGTTTAGTGTTCCACAGTTCGA
TTCTTGGAGCGGTCGAAGCTACTACCACTATTTTGGGATGGACGTCT
GGGGCCAAGGGACCACGGTCACCGTCTCGAGC**GCCTCCACCAAGGGC
CCATCGGTCTTCCCCCTGGCACCCTCCTCCAAGAGCACCTCTGGGGGCAC
AGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCT
GTCCTACAGTCCTCAGGACTCTACTCCCTCAGCAGCGTGGTGACCGTGCC
CTCCAGCAGCTTGGGCACCCAGACCTACATCTGCAACGTGAATCACAAGC
CCAGCAACACCAAGGTGGACAAGAGAGTTGAGCCCAAATCTTGTGACAA
AACTCACACATGCCCACCGTGCCCAGCACCTGAACTCCTGGGGGGACCGT
CAGTCTTCCTCTTCCCCCCAAAACCCAAGGACACCCTCATGATCTCCCGGA
CCCCTGAGGTCACATGCGTGGTGGTGGACGTGAGCCACGAAGACCCTGAG
GTCAAGTTCAACTGGTACGTGGACGGCGTGGAGGTGCATAATGCCAAGAC
AAAGCCGCGGGAGGAGCAGTACAACAGCACGTACCGTGTGGTCAGCGTC
CTCACCGTCCTGCACCAGGACTGGCTGAATGGCAAGGAGTACAAGTGCAA
GGTCTCCAACAAAGCCCTCCCAGCCCCCATCGAGAAAACCATCTCCAAAG
CCAAAGGGCAGCCCCGAGAACCACAGGTGTACACCCTGCCCCCATCCCGG
GAGGAGATGACCAAGAACCAGGTCAGCCTGACCTGCCTGGTCAAAGGCT
TCTATCCCAGCGACATCGCCGTGGAGTGGGAGAGCAATGGGCAGCCGGA
GAACAACTACAAGACCACGCCTCCCGTGCTGGACTCCGACGGCTCCTTCT
TCCTCTATAGCAAGCTCACCGTGGACAAGAGCAGGTGGCAGCAGGGGAA
CGTCTTCTCATGCTCCGTGATGCATGAGGCTCTGCACAACCACTACACGC
AGAAGAGCCTCTCCCTGTCTCCGGGTAAATGA

6843_G20 (PGT-154) gamma heavy chain variable region nucleotide sequence:

(SEQ ID NO: 515)

**CAGGTGCAGCTGGTGGAATCGGGAGGAGGCGTGGTCCAGCCTGGAA
AGTCCCTCAGACTCTCATGTGTCGTCTCTAATTTCATCTTTAATAAAT
ATCCTATGTATTGGGTCCGCCAGGCTCCAGGCAAGGGGCTGGAGTGG
GTGGCAGCCATCTCCGCTGATGCCTGGCATGTAGACTACGCAGCCTC
CGTGAAGGACCGATTTCTCATCTCCAGAGACAATTCCAAGAATGCTC
TATATTTGGAAATGAACACCCTGAGAGTTGAAGACACGGGTATCTAC
TACTGTGCGAGAAATATAGAGGAGTTTAGTGTTCCACAGTTCGATTCT
TGGAGCGGTCGAAGCTACTACCACTATTTTGGGATGGACGTCTGGGG
CCAAGGGACCACGGTCACCGTCTCGAGC**

6843_G20 (PGT-154) gamma heavy chain amino acid sequence: expressed protein
with leader sequence in italics and variable region in bold.

(SEQ ID NO: 516)

*MELGLSWVFLVALLRGVQC***QVQLVESGGGVVQPGKSLRLSCVVSNFIFNKY
PMYWVRQAPGKGLEWVAAISADAWHVDYAASVKDRFLISRDNSKNALY
LEMNTLRVEDTGIYYCARNIEEFSVPQFDSWSGRSYYHYFGMDVWGQG
TTVTVSS**ASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVE
PKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNVFS
CSVMHEALHNHYTQKSLSLSPGK

6843_G20 (PGT-154) gamma heavy chain variable region amino acid sequence:
(Kabat CDRs underlined, Chothia CDRs in bold italics)

(SEQ ID NO: 517)
QVQLVESGGGVVQPGKSLRLSCVVS*NFIFNK*<u>YPMY</u>WVRQAPGKGLEWVA<u>A
ISADAWHVDY</u>AASVKDRFLISRDNSKNALYLEMNTLRVEDTGIYYCAR<u>*NIEE*
*FSVPQFDSWSGRSYYHYFGMDV*</u>WGQGTTVTVSS

6843_G20 (PGT-154) gamma heavy chain Kabat CDRs:

(SEQ ID NO: 475)
CDR 1: KYPMY (SEQ ID NO: 518)
CDR 2: AISADAWHVDYAASVKD (SEQ ID NO: 519)
CDR 3: NIEEFSVPQFDSWSGRSYYHYFGMDV

6843_G20 (PGT-154) gamma heavy chain Chothia CDRs:

(SEQ ID NO: 520)
CDR 1: NFIFNK (SEQ ID NO: 521)
CDR 2: AISADAWHVD (SEQ ID NO: 519)
CDR 3: NIEEFSVPQFDSWSGRSYYHYFGMDV

6843_G20 (PGT-154) light chain nucleotide sequence: coding sequence (variable region in bold)

(SEQ ID NO: 522)
*ATGAGGCTCCCTGCTCAGCTCCTGGGGCTGCTAATGCTCTGGATACCTGAGTT*
*CGCTGCA*GACATTGTGATGACTCAGACTCCTGTCTCTCTGTCCGTCAG
TCTTGGACAGGCGGCCTCCATCTCCTGCAGCTCCAGTGAGAGTCTCG
GACGTGGTGATGGAAGGACCTATTTGCATTGGTACCGACAGAAGCCA
GGCCAGACTCCACAATTACTCATGTATGAAGTTTCTACTCGATTCTCT
GGAGTGTCCGACAGGTTCGCTGGCAGCGGGTCACGTACACAATTCAC
ATTGAAAATTAGTCGGGTGGAGGCTGAAGATGTTGGCGTTTATTACT
GCATGCAAAGTAGAGACTTCCCAATCACTTTTGGCGGAGGGACCAGG
GTGGATCTCAAACGTACGGTGGCTGCACCATCTGTCTTCATCTTCCCGCC
ATCTGATGAGCAGTTGAAATCTGGAACTGCCTCTGTTGTGTGCCTGCTGAA
TAACTTCTATCCCAGAGAGGCCAAAGTACAGTGGAAGGTGGATAACGCCC
TCCAATCGGGTAACTCCCAGGAGAGTGTCACAGAGCAGGACAGCAAGGA
CAGCACCTACAGCCTCAGCAGCACCCTGACGCTGAGCAAAGCAGACTAC
GAGAAACACAAAGTCTACGCCTGCGAAGTCACCCATCAGGGCCTGAGCTC
GCCCGTCACAAAGAGCTTCAACAGGGGAGAGTGTTAG

6843_G20 (PGT-154) light chain variable region nucleotide sequence:

(SEQ ID NO: 523)
GACATTGTGATGACTCAGACTCCTGTCTCTCTGTCCGTCAGTCTTGGA
CAGGCGGCCTCCATCTCCTGCAGCTCCAGTGAGAGTCTCGGACGTGG
TGATGGAAGGACCTATTTGCATTGGTACCGACAGAAGCCAGGCCAGA
CTCCACAATTACTCATGTATGAAGTTTCTACTCGATTCTCTGGAGTGT
CCGACAGGTTCGCTGGCAGCGGGTCACGTACACAATTCACATTGAAA
ATTAGTCGGGTGGAGGCTGAAGATGTTGGCGTTTATTACTGCATGCA
AAGTAGAGACTTCCCAATCACTTTTGGCGGAGGGACCAGGGTGGATC
TCAAA

6843_G20 (PGT-154) light chain amino acid sequence: expressed protein with leader sequence in italics and variable region in bold.

(SEQ ID NO: 524)
*MRLPAQLLGLLMLWIPEFAA*DIVMTQTPVSLSVSLGQAASISCSSSESLGRGD
GRTYLHWYRQKPGQTPQLLMYEVSTRFSGVSDRFAGSGSRTQFTLKISR
VEAEDVGVYYCMQSRDFPITFGGGTRVDLKRTVAAPSVFIFPPSDEQLKSG
TASVVCLLNNFYPREAKVQWKVDNALQSGNSQESVTEQDSKDSTYSLSSTLT
LSKADYEKHKVYACEVTHQGLSSPVTKSFNRGEC

6843_G20 (PGT-154) light chain variable region amino acid sequence: (Kabat CDRs underlined, Chothia CDRs in bold italics)

(SEQ ID NO: 525)
DIVMTQTPVSLSVSLGQAASISC<u>*SSSESLGRGDGRTYLH*</u>WYRQKPGQTPQLL
MY<u>*EVSTRFS*</u>GVSDRFAGSGSRTQFTLKISRVEAEDVGVYYC<u>*MQSRDFPIT*</u>FG
GGTRVDLK

-continued

6843_G20 (PGT-154) light chain Kabat CDRs:
(SEQ ID NO: 526)
CDR 1: SSSESLGRGDGRTYLH (SEQ ID NO: 527)
CDR 2: EVSTRFS (SEQ ID NO: 528)
CDR 3: MQSRDFPIT 6843_G20 (PGT-154) light chain Chothia CDRs:
(SEQ ID NO: 526)
CDR 1: SSSESLGRGDGRTYLH (SEQ ID NO: 527)
CDR 2: EVSTRFS (SEQ ID NO: 528)
CDR 3: MQSRDFPIT 6892_D19 (PGT-155) gamma heavy chain nucleotide sequence: coding sequence
(leader sequence in italics, variable region in bold)
(SEQ ID NO: 529)

*ATGGAATTGGGGCTGAGCTGGGTTTTCCTCGTCGTTCTCCTAAGAGGTGTCCA
CTGT***CAGGTGCATCTGGTGGAGTCGGGGGGAGGCGTGGTCCAACCTG
GGAAGTCCCTAAGACTCTCCTGTGAAACCTCTGGCTTCATCTTCAACG
AATATCCCATGTATTGGATCCGCCAGGCTCCAGGCAAGGGACCGGAG
TGGGTGGCCGCCATCTCCGCTGACGCCTGGCATGTGGACTACGCAGG
CTCCGTGCGGGGCCGATTTACCGTCTCCAGAGACAATTCTAAGAATT
CTCTATATTTAGACATGAAGAGTCTGAAAGTTGAAGACACGCTATATT
ATTTCTGTGCGAAAGATGGGGAGGAACACAAGGTACCACAATTGCAT
TCCTGGAGCGGACGAAACTTATATCACTACACTGGTTTTGACGTCTG
GGGCCCAGGGACCACGGTCACCGTCTCGAGC**GCCTCCACCAAGGGCC
CATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGT
GTCGTGGAACTCAGGCGCCCTGACCAGCGGCGTGCACACCTTCCCGGCTG
TCCTACAGTCCTCAGGACTCTACTCCCTCAGCAGCGTGGTGACCGTGCCCT
CCAGCAGCTTGGGCACCCAGACCTACATCTGCAACGTGAATCACAAGCCC
AGCAACACCAAGGTGGACAAGAGAGTTGAGCCCAAATCTTGTGACAAAA
CTCACACATGCCCACCGTGCCCAGCACCTGAACTCCTGGGGGGACCGTCA
GTCTTCCTCTTCCCCCCAAAACCCAAGGACACCCTCATGATCTCCCGGACC
CCTGAGGTCACATGCGTGGTGGTGGACGTGAGCCACGAAGACCCTGAGGT
CAAGTTCAACTGGTACGTGGACGGCGTGGAGGTGCATAATGCCAAGACA
AAGCCGCGGGAGGAGCAGTACAACAGCACGTACCGTGTGGTCAGCGTCC
TCACCGTCCTGCACCAGGACTGGCTGAATGGCAAGGAGTACAAGTGCAA
GGTCTCCAACAAAGCCCTCCCAGCCCCCATCGAGAAAACCATCTCCAAAG
CCAAAGGGCAGCCCCGAGAACCACAGGTGTACACCCTGCCCCCATCCCGG
GAGGAGATGACCAAGAACCAGGTCAGCCTGACCTGCCTGGTCAAAGGCT
TCTATCCCAGCGACATCGCCGTGGAGTGGGAGAGCAATGGGCAGCCGGA
GAACAACTACAAGACCACGCCTCCCGTGCTGGACTCCGACGGCTCCTTCT
TCCTCTATAGCAAGCTCACCGTGGACAAGAGCAGGTGGCAGCAGGGGAA
CGTCTTCTCATGCTCCGTGATGCATGAGGCTCTGCACAACCACTACACGC
AGAAGAGCCTCTCCCTGTCTCCGGGTAAATGA

6892_D19 (PGT-155) gamma heavy chain variable region nucleotide sequence:
(SEQ ID NO: 530)
**CAGGTGCATCTGGTGGAGTCGGGGGGAGGCGTGGTCCAACCTGGGA
AGTCCCTAAGACTCTCCTGTGAAACCTCTGGCTTCATCTTCAACGAAT
ATCCCATGTATTGGATCCGCCAGGCTCCAGGCAAGGGACCGGAGTGG
GTGGCCGCCATCTCCGCTGACGCCTGGCATGTGGACTACGCAGGCTC
CGTGCGGGGCCGATTTACCGTCTCCAGAGACAATTCTAAGAATTCTC
TATATTTAGACATGAAGAGTCTGAAAGTTGAAGACACGGCTATATATT
TCTGTGCGAAAGATGGGGAGGAACACAAGGTACCACAATTGCATTCC
TGGAGCGGACGAAACTTATATCACTACACTGGTTTTGACGTCTGGGG
CCCAGGGACCACGGTCACCGTCTCGAGC**

6892_D19 (PGT-155) gamma heavy chain amino acid sequence: expressed protein
with leader sequence in italics and variable region in bold.
(SEQ ID NO: 531)
*MELGLSWVFLVVLLRGVHC***QVHLVESGGGVVQPGKSLRLSCETSGFIFNEY
PMYWIRQAPGKGPEWVAAISADAWHVDYAGSVRGRFTVSRDNKNSLY
LDMKSLKVEDTAIYFCAKDGEEHKVPQLHSWSGRNLYHYTGFDVWGPG
TTVTVSS**ASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVE
PKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNVFS
CSVMHEALHNHYTQKSLSLSPGK 6892_D19 (PGT-155) gamma heavy chain variable region amino acid sequence: (Kabat CDRs underlined, Chothia CDRs in bold italics)

(SEQ ID NO: 532)

QVHLVESGGGVVQPGKSLRLSCETS*GFIFNE*<u>YPMY</u>WIRQAPGKPEWVA<u>*AIS*</u>
<u>*ADAWHVD*</u>YAGSVRGRFTVSRDNSKNSLYLDMKSLKVEDTAIYFCAK<u>*DGEE*</u>
<u>*HKVPQLHSWSGRNLYHYTGFDV*</u>WGPGTTVTVSS

6892_D19 (PGT-155) gamma heavy chain Kabat CDRs:

(SEQ ID NO: 533)
CDR 1: EYPMY (SEQ ID NO: 534)
CDR 2: AISADAWHVDYAGSVRG (SEQ ID NO: 535)
CDR 3: DGEEHKVPQLHSWSGRNLYHYTGFDV

6892_D19 (PGT-155) gamma heavy chain Chothia CDRs:

(SEQ ID NO: 536)
CDR 1: GFIFNE (SEQ ID NO: 521)
CDR 2: AISADAWHVD (SEQ ID NO: 535)
CDR 3: DGEEHKVPQLHSWSGRNLYHYTGFDV

6892_D19 (PGT-155) light chain nucleotide sequence: coding sequence (variable region in bold)

(SEQ ID NO: 537)

ATGAGGCTCCCTGCTCAGCTCCTGGGGCTGCTAATGCTCTGGATACCTGAACT
TGCTGCAGACATTGTGATGACCCAGTCTCCTGTCTCTCTGTCCGTCAC
CCTCGGACAGCCGGCCTCCATGTCCTGCAAGTCCAGTCAGAGTGTCC
GACAGAGTGATGGCAAGACTTTCTTATATTGGTATCGACAGAAGCCA
GGCCAGTCTCCACAACTGTTAATATATGAGGGTTCGAGTCGATTCTCT
GGAGTGTCAGATAGGATCTCTGGCAGCGGGTCAGGGACAGACTTCAC
ACTGAGGATCAGTCGAGTGGAGGCTGAGGATGCTGGCGTTTACTTCT
GCTTGCAAACTAAAGACTTCCCCCTCACTTTTGGCGGAGGGACCAGG
GTGGATCTCAAACGTACGGTGGCTGCACCATCTGTCTTCATCTTCCCGCC
ATCTGATGAGCAGTTGAAATCTGGAACTGCCTCTGTTGTGTGCCTGCTGAA
TAACTTCTATCCCAGAGAGGCCAAAGTACAGTGGAAGGTGGATAACGCCC
TCCAATCGGGTAACTCCCAGGAGAGTGTCACAGAGCAGGACAGCAAGGA
CAGCACCTACAGCCTCAGCAGCACCCTGACGCTGAGCAAAGCAGACTAC
GAGAAACACAAAGTCTACGCCTGCGAAGTCACCCATCAGGGCCTGAGCTC
GCCCGTCACAAAGAGCTTCAACAGGGGAGAGTGTTAG

6892_D19 (PGT-155) light chain variable region nucleotide sequence:

(SEQ ID NO: 538)

GACATTGTGATGACCCAGTCTCCTGTCTCTCTGTCCGTCACCCTCGGA
CAGCCGGCCTCCATGTCCTGCAAGTCCAGTCAGAGTGTCCGACAGAG
TGATGGCAAGACTTTCTTATATTGGTATCGACAGAAGCCAGGCCAGT
CTCCACAACTGTTAATATATGAGGGTTCGAGTCGATTCTCTGGAGTGT
CAGATAGGATCTCTGGCAGCGGGTCAGGGACAGACTTCACACTGAGG
ATCAGTCGAGTGGAGGCTGAGGATGCTGGCGTTTACTTCTGCTTGCA
AACTAAAGACTTCCCCCTCACTTTTGGCGGAGGGACCAGGGTGGATC
TCAAA

6892_D19 (PGT-155) light chain amino acid sequence: expressed protein with leader sequence in italics and variable region in bold.

(SEQ ID NO: 539)

*MRLPAQLLGLLMLWIPELAA*DIVMTQSPVSLSVTLGQPASMSCKSSQSVRQS
DGKTFLYWYRQKPGQSPQLLIYEGSSRFSGVSDRISGSGSGTDFTLRISRV
EAEDAGVYFCLQTKDFPLTFGGGTRVDLKRTVAAPSVFIFPPSDEQLKSGT
ASVVCLLNNFYPREAKVQWKVDNALQSGNSQESVTEQDSKDSTYSLSSTLTL
SKADYEKHKVYACEVTHQGLSSPVTKSFNRGEC

6892_D19 (PGT-155) light chain variable region amino acid sequence: (Kabat CDRs underlined, Chothia CDRs in bold italics)

(SEQ ID NO: 540)

DIVMTQSPVSLSVTLGQPASMSC<u>*KSSQSVRQSDGKTFLY*</u>WYRQKPGQSPQLLI
Y<u>*EGSSRFS*</u>GVSDRISGSGSGTDFTLRISRVEAEDAGVYFC<u>*LQTKDFPLT*</u>FGGG
TRVDLK

-continued

6892_D19 (PGT-155) light chain Kabat CDRs:

(SEQ ID NO: 541)
CDR 1: KSSQSVRQSDGKTFLY (SEQ ID NO: 542)
CDR 2: EGSSRFS (SEQ ID NO: 543)
CDR 3: LQTKDFPLT

6892_D19 (PGT-155) light chain Chothia CDRs:

(SEQ ID NO: 541)
CDR 1: KSSQSVRQSDGKTFLY (SEQ ID NO: 542)
CDR 2: EGSSRFS (SEQ ID NO: 543)
CDR 3: LQTKDFPLT

6808_B09 (PGT-156) gamma heavy chain nucleotide sequence: coding sequence (variable region in bold)

(SEQ ID NO: 544)
*ATGGAATTGGGGCTGAGCTGGGTTTTCCTCGTCGTTCTCCTAAGAGGTGTCCA*
*CTGT*CAGGTGCATCTGGTGGAGTCGGGGGGAGGCGTTGTCCAACCTG
GAAAGTCCCTAAGACTCTCCTGTGAAACCTCTGGCTTCATCTTCAATC
AATATCCCATGTATTGGGTCCGCCAGGCTCCAGGCAAGGGACCGGAG
TGGGTGGCCGCCATCTCCGCTGATGCCTGGCATGTGGACTACCCAGG
CTCCGTGCGGGGCCGATTTACCGTCTCCAGAGACAATTCCAAGAGTT
CTCTATATTTAGACATGAAGAGTCTGAAAGTTGAAGACACGGCTATAT
ATTTCTGTGCGAAAGATGGGGAGGAACACAAGGTACCACAATTGCAT
TCCTGGAGCGGACGAAACTTATATCACTACACTGGTTTTGACGTCTG
GGGCCCAGGGACCACGGTCACCGTCTCGAGCGCCTCCACCAAGGGCC
CATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGT
GTCGTGGAACTCAGGCGCCCTGACCAGCGGCGTGCACACCTTCCCGGCTG
TCCTACAGTCCTCAGGACTCTACTCCCTCAGCAGCGTGGTGACCGTGCCCT
CCAGCAGCTTGGGCACCCAGACCTACATCTGCAACGTGAATCACAAGCCC
AGCAACACCAAGGTGGACAAGAGAGTTGAGCCCAAATCTTGTGACAAAA
CTCACACATGCCCACCGTGCCCAGCACCTGAACTCCTGGGGGGACCGTCA
GTCTTCCTCTTCCCCCCAAAACCCAAGGACACCCTCATGATCTCCCGGACC
CCTGAGGTCACATGCGTGGTGGTGGACGTGAGCCACGAAGACCCTGAGGT
CAAGTTCAACTGGTACGTGGACGGCGTGGAGGTGCATAATGCCAAGACA
AAGCCGCGGGAGGAGCAGTACAACAGCACGTACCGTGTGGTCAGCGTCC
TCACCGTCCTGCACCAGGACTGGCTGAATGGCAAGGAGTACAAGTGCAA
GGTCTCCAACAAAGCCCTCCCAGCCCCCATCGAGAAAACCATCTCCAAAG
CCAAAGGGCAGCCCCGAGAACCACAGGTGTACACCCTGCCCCCATCCCGG
GAGGAGATGACCAAGAACCAGGTCAGCCTGACCTGCCTGGTCAAAGGCT
TCTATCCCAGCGACATCGCCGTGGAGTGGGAGAGCAATGGGCAGCCGGA
GAACAACTACAAGACCACGCCTCCCGTGCTGGACTCCGACGGCTCCTTCT
TCCTCTATAGCAAGCTCACCGTGGACAAGAGCAGGTGGCAGCAGGGGAA
CGTCTTCTCATGCTCCGTGATGCATGAGGCTCTGCACAACCACTACACGC
AGAAGAGCCTCTCCCTGTCTCCGGGTAAATGA

6808_B09 (PGT-156) gamma heavy chain variable region nucleotide sequence:

(SEQ ID NO: 545)
CAGGTGCATCTGGTGGAGTCGGGGGGAGGCGTTGTCCAACCTGGAA
AGTCCCTAAGACTCTCCTGTGAAACCTCTGGCTTCATCTTCAATCAAT
ATCCCATGTATTGGGTCCGCCAGGCTCCAGGCAAGGGACCGGAGTGG
GTGGCCGCCATCTCCGCTGATGCCTGGCATGTGGACTACCCAGGCTC
CGTGCGGGGCCGATTTACCGTCTCCAGAGACAATTCCAAGAGTTCTC
TATATTTAGACATGAAGAGTCTGAAAGTTGAAGACACGGCTATATATT
TCTGTGCGAAAGATGGGGAGGAACACAAGGTACCACAATTGCATTCC
TGGAGCGGACGAAACTTATATCACTACACTGGTTTTGACGTCTGGGG
CCCAGGGACCACGGTCACCGTCTCGAGC

6808_B09 (PGT-156) gamma heavy chain amino acid sequence: expressed protein with leader sequence in italics and variable region in bold.

(SEQ ID NO: 546)
*MELGLSWVFLVVLLRGVHC*QVHLVESGGGVVQPGKSLRLSCETSGFIFNQY
PMYWVRQAPGKGPEWVAAISADAWHVDYPGSVRGRFTVSRDNSKSSLY
LDMKSLKVEDTAIYFCAKDGEEHKVPQLHSWSGRNLYHYTGFDVWGPG
TTVTVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVE
PKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNVFS
CSVMHEALHNHYTQKSLSLSPGK

-continued

6808_B09 (PGT-156) gamma heavy chain variable region amino acid sequence: (Kabat CDRs underlined, Chothia CDRs in bold italics)

(SEQ ID NO: 547)

QVHLVESGGGVVQPGKSLRLSCETS*GFIFNQ*YPMYWVRQAPGKGPEWVAAI SADAWHVDYPGSVRGRFTVSRDNSKSSLYLDMKSLKVEDTAIYFCAK*DGEE HKVPQLHSWSGRNLYHYTGFDV*WGPGTTVTVSS

6808_B09 (PGT-156) gamma heavy chain Kabat CDRs:

(SEQ ID NO: 548)
CDR 1: QYPMY (SEQ ID NO: 549)
CDR 2: AISADAWHVDYPGSVRG (SEQ ID NO: 535)
CDR 3: DGEEHKVPQLHSWSGRNLYHYTGFDV

6808_B09 (PGT-156) gamma heavy chain Chothia CDRs:

(SEQ ID NO: 550)
CDR 1: GFIFNQ (SEQ ID NO: 521)
CDR 2: AISADAWHVD (SEQ ID NO: 535)
CDR 3: DGEEHKVPQLHSWSGRNLYHYTGFDV

6808_B09 (PGT-156) light chain nucleotide sequence: coding sequence (variable region in bold)

(SEQ ID NO: 551)

*ATGAGGCTCCCTGCTCAGCTCCTGGGGCTGCTAATGCTCTGGATACCTGAACT TGCTGCA*GACATTGTGATGACCCAGTCTCCTGTCTCTCTGTCCGTCAC CCTCGGACAGCCGGCCTCCATGTCCTGCAAGTCCAGTCAGACTGTCC GACAGAGTGATGGCAAGACTTTCTTATATTGGTATCGACAGAAGGCA GGCCAGTCTCCACAACTGTTAATATATGAGGGTTCGAATCGATTCTCT GGAGTGTCAGATAGGATCTCTGGCAGCGGGTCGGGGACAGATTTCAC ACTGAGAATCAGTCGAGTGGAGGCTGAGGATGTTGGCGTTTATTTCT GCCTGCAAACTAAAGACTTCCCCCTCACTTTTGGCGGAGGGACCAGG GTGGATATCAAACGTACGGTGGCTGCACCATCTGTCTTCATCTTCCCGCC ATCTGATGAGCAGTTGAAATCTGGAACTGCCTCTGTTGTGTGCCTGCTGAA TAACTTCTATCCCAGAGAGGCCAAAGTACAGTGGAAGGTGGATAACGCCC TCCAATCGGGTAACTCCCAGGAGAGTGTCACAGAGCAGGACAGCAAGGA CAGCACCTACAGCCTCAGCAGCACCCTGACGCTGAGCAAAGCAGACTAC GAGAAACACAAAGTCTACGCCTGCGAAGTCACCCATCAGGGCCTGAGCTC GCCCGTCACAAAGAGCTTCAACAGGGGAGAGTGTTAG

6808_B09 (PGT-156) light chain variable region nucleotide sequence:

(SEQ ID NO: 552)

GACATTGTGATGACCCAGTCTCCTGTCTCTCTGTCCGTCACCCTCGGA CAGCCGGCCTCCATGTCCTGCAAGTCCAGTCAGACTGTCCGACAGAG TGATGGCAAGACTTTCTTATATTGGTATCGACAGAAGGCAGGCCAGT CTCCACAACTGTTAATATATGAGGGTTCGAATCGATTCTCTGGAGTGT CAGATAGGATCTCTGGCAGCGGGTCGGGGACAGATTTCACACTGAGA ATCAGTCGAGTGGAGGCTGAGGATGTTGGCGTTTATTTCTGCCTGCA AACTAAAGACTTCCCCCTCACTTTTGGCGGAGGGACCAGGGTGGATA TCAAA

6808_B09 (PGT-156) light chain amino acid sequence: expressed protein with leader sequence in italics and variable region in bold.

(SEQ ID NO: 553)

*MRLPAQLLGLLMLWIPELAA*DIVMTQSPVSLSVTLGQPASMSCKSSQTVRQS DGKTFLYWYRQKAGQSPQLLIYEGSNRFSGVSDRISGSGSGTDFTLRISR VEAEDVGVYFCLQTKDFPLTFGGGTRVDIKRTVAAPSVFIFPPSDEQLKSG TASVVCLLNNFYPREAKVQWKVDNALQSGNSQESVTEQDSKDSTYSLSSTLT LSKADYEKHKVYACEVTHQGLSSPVTKSFNRGEC

6808_B09 (PGT-156) light chain variable region amino acid sequence: (Kabat CDRs underlined, Chothia CDRs in bold italics)

(SEQ ID NO: 554)

DIVMTQSPVSLSVTLGQPASMSC*KSSQTVRQSDGKTFLY*WYRQKAGQSPQLL IY*EGSNRFS*GVSDRISGSGSGTDFTLRISRVEAEDVGVYFC*LQTKDFPLT*FGG GTRVDIK

-continued

6808_B09 (PGT-156) light chain Kabat CDRs:

(SEQ ID NO: 555)
CDR 1: KSSQTVRQSDGKTFLY (SEQ ID NO: 556)
CDR 2: EGSNRFS (SEQ ID NO: 543)
CDR 3: LQTKDFPLT

6808_B09 (PGT-156) light chain Chothia CDRs:

(SEQ ID NO: 555)
CDR 1: KSSQTVRQSDGKTFLY (SEQ ID NO: 556)
CDR 2: EGSNRFS (SEQ ID NO: 543)
CDR 3: LQTKDFPLT

6892_C23 (PGT-157) gamma heavy chain nucleotide sequence: coding sequence
(leader sequence in italics, variable region in bold)

(SEQ ID NO: 557)

*ATGGAATTGGGGCTGAGCTGGGTTTTCCTCGTCGCTCTCCTAAGAGGTGTCCA*
*CTGT*GAAGTGCATCTGGTGGAGTCGGGGGGAGGCGTGGTCCAACCTG
GAAAGTCCCTCAGACTCTCCTGTGTAACTTCTGGCTTCATCTTCAAAC
AATATCCTATGTATTGGATCCGCCAGGCTCCAGGCAAGGGGCTGGAG
TGGGTGGCCGCCATCTCCGCTGATGCCTGGCATGTGGACTACGCAGG
CTCCGTGCGGGGCCGATTTACCGTCTCCAGAGACAACTCCAAGAATT
CTCTATATTTAGACATGAACAGTCTGACAGTTGAAGACACGCTATAT
ATTTCTGTGCGAAAGATGGGGAAGAACACGAAGTACCACAGTTGCAC
TCCTGGAGCGGACGAAATTTATATCACTACACTGGTGTGGACATCTG
GGGCCCAGGGACCACGGTCACCGTCTCGAGCGCCTCCACCAAGGGCC
CATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGT
GTCGTGGAACTCAGGCGCCCTGACCAGCGGCGTGCACACCTTCCCGGCTG
TCCTACAGTCCTCAGGACTCTACTCCCTCAGCAGCGTGGTGACCGTGCCCT
CCAGCAGCTTGGGCACCCAGACCTACATCTGCAACGTGAATCACAAGCCC
AGCAACACCAAGGTGGACAAGAGAGTTGAGCCCAAATCTTGTGACAAAA
CTCACACATGCCCACCGTGCCCAGCACCTGAACTCCTGGGGGGACCGTCA
GTCTTCCTCTTCCCCCCAAAACCCAAGGACACCCTCATGATCTCCCGGACC
CCTGAGGTCACATGCGTGGTGGTGGACGTGAGCCACGAAGACCCTGAGGT
CAAGTTCAACTGGTACGTGGACGGCGTGGAGGTGCATAATGCCAAGACA
AAGCCGCGGGAGGAGCAGTACAACAGCACGTACCGTGTGGTCAGCGTCC
TCACCGTCCTGCACCAGGACTGGCTGAATGGCAAGGAGTACAAGTGCAA
GGTCTCCAACAAAGCCCTCCCAGCCCCCATCGAGAAAACCATCTCCAAAG
CCAAAGGGCAGCCCCGAGAACCACAGGTGTACACCCTGCCCCCATCCCGG
GAGGAGATGACCAAGAACCAGGTCAGCCTGACCTGCCTGGTCAAAGGCT
TCTATCCCAGCGACATCGCCGTGGAGTGGGAGAGCAATGGGCAGCCGGA
GAACAACTACAAGACCACGCCTCCCGTGCTGGACTCCGACGGCTCCTTCT
TCCTCTATAGCAAGCTCACCGTGGACAAGAGCAGGTGGCAGCAGGGGAA
CGTCTTCTCATGCTCCGTGATGCATGAGGCTCTGCACAACCACTACACGC
AGAAGAGCCTCTCCCTGTCTCCGGGTAAATGA

6892_C23 (PGT-157) gamma heavy chain variable region nucleotide sequence:

(SEQ ID NO: 558)

GAAGTGCATCTGGTGGAGTCGGGGGGAGGCGTGGTCCAACCTGGAA
AGTCCCTCAGACTCTCCTGTGTAACTTCTGGCTTCATCTTCAAACAAT
ATCCTATGTATTGGATCCGCCAGGCTCCAGGCAAGGGGCTGGAGTGG
GTGGCCGCCATCTCCGCTGATGCCTGGCATGTGGACTACGCAGGCTC
CGTGCGGGGCCGATTTACCGTCTCCAGAGACAACTCCAAGAATTCTC
TATATTTAGACATGAACAGTCTGACAGTTGAAGACACGGCTATATATT
TCTGTGCGAAAGATGGGGAAGAACACGAAGTACCACAGTTGCACTCC
TGGAGCGGACGAAATTTATATCACTACACTGGTGTGGACATCTGGGG
CCCAGGGACCACGGTCACCGTCTCGAGC

6892_C23 (PGT-157) gamma heavy chain amino acid sequence: expressed protein
with leader sequence in italics and variable region in bold.

(SEQ ID NO: 559)

*MELGLSWVFLVALLRGVHC*EVHLVESGGGVVQPGKSLRLSCVTSGFIFKQY
PMYWIRQAPGKGLEWVAAISADAWHVDYAGSVRGRFTVSRDNSKNSLY
LDMNSLTVEDTAIYFCAKDGEEHEVPQLHSWSGRNLYHYTGVDIWPG
TTVTVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVE
PKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNVFS
CSVMHEALHNHYTQKSLSLSPGK

-continued

6892_C23 (PGT-157) gamma heavy chain variable region amino acid sequence:
(Kabat CDRs underlined, Chothia CDRs in bold italics)

(SEQ ID NO: 560)

EVHLVESGGGVVQPGKSLRLSCVTS*GFIFKQ*<u>YPMY</u>WIRQAPGKGLEWVA<u>*AI*</u>
<u>*SADAWHVD*YAGSVRG</u>RFTVSRDNSKNSLYLDMNSLTVEDTAIYFCAK<u>*DGEE*</u>
<u>*HEVPQLHSWSGRNLYHYTGVDI*</u>WGPGTTVTVSS

6892_C23 (PGT-157) gamma heavy chain Kabat CDRs:

(SEQ ID NO: 548)
CDR 1: QYPMY (SEQ ID NO: 534)
CDR 2: AISADAWHVDYAGSVRG (SEQ ID NO: 561)
CDR 3: DGEEHEVPQLHSWSGRNLYHYTGVDI

6892_C23 (PGT-157) gamma heavy chain Chothia CDRs:

(SEQ ID NO: 562)
CDR 1: GFIFKQ (SEQ ID NO: 521)
CDR 2: AISADAWHVD (SEQ ID NO: 561)
CDR 3: DGEEHEVPQLHSWSGRNLYHYTGVDI

6892_C23 (PGT-157) light chain nucleotide sequence: coding sequence (variable region in bold)

(SEQ ID NO: 563)

ATGAGGCTCCCTGCTCAGCTCCTGGGGCTGCTAATGCTCTGGATACCTGAACT
TACTGCAGACATTGTGATGACCCAGACTCCTGTCTCTCTGTCCGTCAC
CCTCGGACAGCCGGCCTCCATGTCCTGTAAGTCCAGTCAGAGCCTCC
GACAAAGTGATGGCAAGACTTTCTTGTATTGGTATCGACAGAAGGCA
GGCCAGTCTCCACAACTCCTAATATCTGAGGCTTCGAATCGATTCTCT
GGAGTGTCAGATAGGTTCTCTGGCAGCGGTTCAGGGACAGACTTCAC
ACTGAAAATCAGTCGGGTGGAGGCTGAGGATGTTGGCATTTATTTCT
GCATGCAAACTAAAGACTTCCCCCTCACTTTTGGCGGAGGGACCAAG
GTGGATCTCAAACGTACGGTGGCTGCACCATCTGTCTTCATCTTCCCGCC
ATCTGATGAGCAGTTGAAATCTGGAACTGCCTCTGTTGTGTGCCTGCTGAA
TAACTTCTATCCCAGAGAGGCCAAAGTACAGTGGAAGGTGGATAACGCCC
TCCAATCGGGTAACTCCCAGGAGAGTGTCACAGAGCAGGACAGCAAGGA
CAGCACCTACAGCCTCAGCAGCACCCTGACGCTGAGCAAAGCAGACTAC
GAGAAACACAAAGTCTACGCCTGCGAAGTCACCCATCAGGGCCTGAGCTC
GCCCGTCACAAAGAGCTTCAACAGGGGAGAGTGTTAG

6892_C23 (PGT-157) light chain variable region nucleotide sequence:

(SEQ ID NO: 564)

GACATTGTGATGACCCAGACTCCTGTCTCTCTGTCCGTCACCCTCGG
ACAGCCGGCCTCCATGTCCTGTAAGTCCAGTCAGAGCCTCCGACAAA
GTGATGGCAAGACTTTCTTGTATTGGTATCGACAGAAGGCAGGCCAG
TCTCCACAACTCCTAATATCTGAGGCTTCGAATCGATTCTCTGGAGTG
TCAGATAGGTTCTCTGGCAGCGGTTCAGGGACAGACTTCACACTGAA
AATCAGTCGGGTGGAGGCTGAGGATGTTGGCATTTATTTCTGCATGC
AAACTAAAGACTTCCCCCTCACTTTTGGCGGAGGGACCAAGGTGGAT
CTCAAA

6892_C23 (PGT-157) light chain amino acid sequence: expressed protein with leader sequence in italics and variable region in bold.

(SEQ ID NO: 565)

*MRLPAQLLGLLMLWIPELTA*DIVMTQTPVSLSVTLGQPASMSCKSSQSLRQS
DGKTFLYWYRQKAGQSPQLLISEASNRFSGVSDRFSGSGSGTDFTLKISR
VEAEDVGIYFCMQTKDFPLTFGGGTKVDLKRTVAAPSVFIFPPSDEQLKSG
TASVVCLLNNFYPREAKVQWKVDNALQSGNSQESVTEQDSKDSTYSLSSTLT
LSKADYEKHKVYACEVTHQGLSSPVTKSFNRGEC

6892_C23 (PGT-157) light chain variable region amino acid sequence: (Kabat CDRs underlined, Chothia CDRs in bold italics)

(SEQ ID NO: 566)

DIVMTQTPVSLSVTLGQPASMSC<u>*KSSQSLRQSDGKTFLY*</u>WYRQKAGQSPQLL
IS<u>*EASNRFS*</u>GVSDRFSGSGSGTDFTLKISRVEAEDVGIYFC<u>*MQTKDFPLT*</u>FGG
GTKVDLK

-continued

6892_C23 (PGT-157) light chain Kabat CDRs:

(SEQ ID NO: 567)
CDR 1: KSSQSLRQSDGKTFLY (SEQ ID NO: 568)
CDR 2: EASNRFS (SEQ ID NO: 569)
CDR 3: MQTKDFPLT

6892_C23 (PGT-157) light chain Chothia CDRs:

(SEQ ID NO: 567)
CDR 1: KSSQSLRQSDGKTFLY (SEQ ID NO: 568)
CDR 2: EASNRFS (SEQ ID NO: 569)
CDR 3: MQTKDFPLT

6881_N05 (PGT-158) gamma heavy chain nucleotide sequence: coding sequence (variable region in bold)

(SEQ ID NO: 570)

*ATGGAATTGGGGCTGAGCTGGGTTTTCCTCGTCGCTCTCCTAAGAGGTGTCCA*
*CTGT*GAGGTGCGTCTGATGGAGTCGGGGGGAGGCGTGGTCCAGCCTG
GGAAGTCCCTCAGACTCTCCTGTGTAACCTCTGGCTTCATCTTCAAAA
AATATCCTATGTACTGGATCCGCCAGGCTCCAGGCAAGGGGCTGGAG
TGGGTGGCCGCCATCTCCGCTGATGCCTGGCATGTGGACTACCCAGG
CTCCGTGCGGGGCCGATTTACCGTCTCAAGAGACAACTCCAAGAATT
CTCTATATTTAGACATGAATAGTCTGACAGTAGAAGACACGCTATAT
ATTTTTGTGCGAAAGATGGGGAGGAACACGAAGTCCCACAACTGCAC
TCCTGGAGCGGACGAAATTTATATCACTACACTGGTGTAGACGTCTG
GGGCCCAGGGACCACGGTCACCGTCTCGAGCGCCTCCACCAAGGGCC
CATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGT
GTCGTGGAACTCAGGCGCCCTGACCAGCGGCGTGCACACCTTCCCGGCTG
TCCTACAGTCCTCAGGACTCTACTCCCTCAGCAGCGTGGTGACCGTGCCCT
CCAGCAGCTTGGGCACCCAGACCTACATCTGCAACGTGAATCACAAGCCC
AGCAACACCAAGGTGGACAAGAGAGTTGAGCCCAAATCTTGTGACAAAA
CTCACACATGCCCACCGTGCCCAGCACCTGAACTCCTGGGGGGACCGTCA
GTCTTCCTCTTCCCCCCAAAACCCAAGGACACCCTCATGATCTCCCGGACC
CCTGAGGTCACATGCGTGGTGGTGGACGTGAGCCACGAAGACCCTGAGGT
CAAGTTCAACTGGTACGTGGACGGCGTGGAGGTGCATAATGCCAAGACA
AAGCCGCGGGAGGAGCAGTACAACAGCACGTACCGTGTGGTCAGCGTCC
TCACCGTCCTGCACCAGGACTGGCTGAATGGCAAGGAGTACAAGTGCAA
GGTCTCCAACAAAGCCCTCCCAGCCCCCATCGAGAAAACCATCTCCAAAG
CCAAAGGGCAGCCCCGAGAACCACAGGTGTACACCCTGCCCCCATCCCGG
GAGGAGATGACCAAGAACCAGGTCAGCCTGACCTGCCTGGTCAAAGGCT
TCTATCCCAGCGACATCGCCGTGGAGTGGGAGAGCAATGGGCAGCCGGA
GAACAACTACAAGACCACGCCTCCCGTGCTGGACTCCGACGGCTCCTTCT
TCCTCTATAGCAAGCTCACCGTGGACAAGAGCAGGTGGCAGCAGGGGAA
CGTCTTCTCATGCTCCGTGATGCATGAGGCTCTGCACAACCACTACACGC
AGAAGAGCCTCTCCCTGTCTCGGGTAAATGA

6881_N05 (PGT-158) gamma heavy chain variable region nucleotide sequence:

(SEQ ID NO: 571)

GAGGTGCGTCTGATGGAGTCGGGGGGAGGCGTGGTCCAGCCTGGGA
AGTCCCTCAGACTCTCCTGTGTAACCTCTGGCTTCATCTTCAAAAAAT
ATCCTATGTACTGGATCCGCCAGGCTCCAGGCAAGGGGCTGGAGTGG
GTGGCCGCCATCTCCGCTGATGCCTGGCATGTGGACTACCCAGGCTC
CGTGCGGGGCCGATTTACCGTCTCAAGAGACAACTCCAAGAATTCTC
TATATTTAGACATGAATAGTCTGACAGTAGAAGACACGGCTATATATT
TTTGTGCGAAAGATGGGGAGGAACACGAAGTCCCACAACTGCACTCC
TGGAGCGGACGAAATTTATATCACTACACTGGTGTAGACGTCTGGGG
CCCAGGGACCACGGTCACCGTCTCGAGC

6881_N05 (PGT-158) gamma heavy chain amino acid sequence: expressed protein with leader sequence in italics and variable region in bold.

(SEQ ID NO: 572)

*MELGLSWVFLVALLRGVHC*EVRLMESGGGVVQPGKSLRLSCVTSGFIFKKY
PMYWIRQAPGKGLEWVAAISADAWHVDYPGSVRGRFTVSRDNSKNSLY
LDMNSLTVEDTAIYFCAKDGEEHEVPQLHSWSGRNLYHYTGVDVWGPG
TTVTVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVE
PKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNVFS
CSVMHEALHNHYTQKSLSLSPGK

-continued

6881_N05 (PGT-158) gamma heavy chain variable region amino acid sequence:
(Kabat CDRs underlined, Chothia CDRs in bold italics)

(SEQ ID NO: 573)

EVRLMESGGGVVQPGKSLRLSCVTS*GFIFKK*KYPMYWIRQAPGKGLEWVA*AI*
*SADAWHVD*YPGSVRGRFTVSRDNSKNSLYLDMNSLTVEDTAIYFCAK*DGEE*
*HEVPQLHSWSGRNLYHYTGVDV*WGPGTTVTVSS

6881_N05 (PGT-158) gamma heavy chain Kabat CDRs:

(SEQ ID NO: 475)

CDR 1: KYPMY (SEQ ID NO: 549)

CDR 2: AISADAWHVDYPGSVRG (SEQ ID NO: 574)

CDR 3: DGEEHEVPQLHSWSGRNLYHYTGVDV

6881_N05 (PGT-158) gamma heavy chain Chothia CDRs:

(SEQ ID NO: 575)

CDR 1: GFIFKK (SEQ ID NO: 521)

CDR 2: AISADAWHVD (SEQ ID NO: 574)

CDR 3: DGEEHEVPQLHSWSGRNLYHYTGVDV

6881_N05 (PGT-158) light chain nucleotide sequence: coding sequence (variable region in bold)

(SEQ ID NO: 576)

ATGAGGCTCCCTGCTCAGCTCCTGGGGCTGCTAATGCTCTGGATACCTGAAGT
GACTGCAGACATTGTGATGACCCAGACTCCTGTCTCTGTGTCCGTCAC
CCTCGGACAGCCGGCCTCCATGTCCTGCAAGTCCAGTCAGAGCGTCC
GACAAAGTGATGGCAAGACTTTTTTATATTGGTATCGACAGAAGGCA
GGCCAGTCTCCACAACTCTTAATATATGAGGCTTCGAAGCGATTCTCT
GGAGTGTCAGATAGGTTCTCTGGCAGCGGGTCAGGGACAGACTTCAC
ACTGAAAATCAGTCGGGTGGGGGCTGAGGATGTTGGCGTTTATTTCT
GCATGCAAACTAAAGACTTCCCCCTTACTTTTGGCGGAGGGACCAAG
GTGGATCTCAAACGTACGGTGGCTGCACCATCTGTCTTCATCTTCCCGCC
ATCTGATGAGCAGTTGAAATCTGGAACTGCCTCTGTTGTGTGCCTGCTGAA
TAACTTCTATCCCAGAGAGGCCAAAGTACAGTGGAAGGTGGATAACGCCC
TCCAATCGGGTAACTCCCAGGAGAGTGTCACAGAGCAGGACAGCAAGGA
CAGCACCTACAGCCTCAGCAGCACCCTGACGCTGAGCAAAGCAGACTAC
GAGAAACACAAAGTCTACGCCTGCGAAGTCACCCATCAGGGCCTGAGCTC
GCCCGTCACAAAGAGCTTCAACAGGGGAGAGTGTTAG

6881_N05 (PGT-158) light chain variable region nucleotide sequence:

(SEQ ID NO: 577)

GACATTGTGATGACCCAGACTCCTGTCTCTGTGTCCGTCACCCTCGG
ACAGCCGGCCTCCATGTCCTGCAAGTCCAGTCAGAGCGTCCGACAAA
GTGATGGCAAGACTTTTTTATATTGGTATCGACAGAAGGCAGGCCAG
TCTCCACAACTCTTAATATATGAGGCTTCGAAGCGATTCTCTGGAGTG
TCAGATAGGTTCTCTGGCAGCGGGTCAGGGACAGACTTCACACTGAA
AATCAGTCGGGTGGGGGCTGAGGATGTTGGCGTTTATTTCTGCATGC
AAACTAAAGACTTCCCCCTTACTTTTGGCGGAGGGACCAAGGTGGAT
CTCAAA

6881_N05 (PGT-158) light chain amino acid sequence: expressed protein with leader sequence in italics and variable region in bold.

(SEQ ID NO: 578)

*MRLPAQLLGLLMLWIPEVTA*DIVMTQTPVSVSVTLGQPASMSCKSSQSVRQS
DGKTFLYWYRQKAGQSPQLLIYEASKRFSGVSDRFSGSGSGTDFTLKISR
VGAEDVGVYFCMQTKDFPLTFGGGTKVDLKRTVAAPSVFIFPPSDEQLKS
GTASVVCLLNNFYPREAKVQWKVDNALQSGNSQESVTEQDSKDSTYSLSST
LTLSKADYEKHKVYACEVTHQGLSSPVTKSFNRGEC

6881_N05 (PGT-158) light chain variable region amino acid sequence: (Kabat CDRs underlined, Chothia CDRs in bold italics)

(SEQ ID NO: 579)

DIVMTQTPVSVSVTLGQPASMSC*KSSQSVRQSDGKTFLY*WYRQKAGQSPQLL
IY*EASKRFS*GVSDRFSGSGSGTDFTLKISRVGAEDVGVYFC*MQTKDFPLT*FGG
GTKVDLK

-continued

6881_N05 (PGT-158) light chain Kabat CDRs:

CDR 1: KSSQSVRQSDGKTFLY
(SEQ ID NO: 541)

CDR 2: EASKRFS
(SEQ ID NO: 580)

CDR 3: MQTKDFPLT
(SEQ ID NO: 569)

6881_N05 (PGT-158) light chain Chothia CDRs:

CDR 1: KSSQSVRQSDGKTFLY
(SEQ ID NO: 541)

CDR 2: EASKRFS
(SEQ ID NO: 580)

CDR 3: MQTKDFPLT
(SEQ ID NO: 569)

The 6831 A21 (PGT-151) antibody includes a heavy chain variable region (SEQ ID NO: 474), encoded by the nucleic acid sequence shown in SEQ ID NO: 472, and a light chain variable region (SEQ ID NO: 483) encoded by the nucleic acid sequence shown in SEQ ID NO: 481.

The heavy chain CDRs of the 6831 A21 (PGT-151) antibody have the following sequences per Kabat definition: KYPMY (SEQ ID NO: 475), AISGDAWHVVYSNSVQG (SEQ ID NO: 476), and MFQESGPPRLDRWS-GRNYYYYSGMDV (SEQ ID NO: 477). The light chain CDRs of the 6831 A21 (PGT-151) antibody have the following sequences per Kabat definition: KSS-ESLRQSNGKTSLY (SEQ ID NO: 484), EVSNRFS (SEQ ID NO: 485), and MQSKDFPLT (SEQ ID NO: 486).

The heavy chain CDRs of the 6831_A21 (PGT-151) antibody have the following sequences per Chothia definition: DFPFSK (SEQ ID NO: 478), AISGDAWHVV (SEQ ID NO: 479), and MFQESGPPRLDRWS-GRNYYYYSGMDV (SEQ ID NO: 477). The light chain CDRs of the 6831_A21 (PGT-151) antibody have the following sequences per Chothia definition: KSS-ESLRQSNGKTSLY (SEQ ID NO: 484), EVSNRFS (SEQ ID NO: 485), and MQSKDFPLT (SEQ ID NO: 486).

The 6889_I17 (PGT-152) antibody includes a heavy chain variable region (SEQ ID NO: 490), encoded by the nucleic acid sequence shown in SEQ ID NO: 488, and a light chain variable region (SEQ ID NO: 497) encoded by the nucleic acid sequence shown in SEQ ID NO: 495.

The heavy chain CDRs of the 6889_I17 (PGT-152) antibody have the following sequences per Kabat definition: KYPMY (SEQ ID NO: 475), AISADAWHVVYSGSVQG (SEQ ID NO: 491), and MFQESGPPRFDSWS-GRNYYYYSGMDV (SEQ ID NO: 492). The light chain CDRs of the 6889_I17 (PGT-152) antibody have the following sequences per Kabat definition: KSSQSLRQSNGKTSLY (SEQ ID NO: 498), EVSNRFS (SEQ ID NO: 485), and MQSKDFPLT (SEQ ID NO: 486).

The heavy chain CDRs of the 6889_I17 (PGT-152) antibody have the following sequences per Chothia definition: DFPFSK (SEQ ID NO: 478), AISADAWHVV (SEQ ID NO: 493), and MFQESGPPRFDSWSGRNYYYYSGMDV (SEQ ID NO: 492). The light chain CDRs of the 6889_I17 (PGT-152) antibody have the following sequences per Chothia definition: KSSQSLRQSNGKTSLY (SEQ ID NO: 498), EVSNRFS (SEQ ID NO: 485), and MQSKDFPLT (SEQ ID NO: 486).

The 6891_F06 (PGT-153) antibody includes a heavy chain variable region (SEQ ID NO: 502), encoded by the nucleic acid sequence shown in SEQ ID NO: 500, and a light chain variable region (SEQ ID NO: 511) encoded by the nucleic acid sequence shown in SEQ ID NO: 509.

The heavy chain CDRs of the 6891_F06 (PGT-153) antibody have the following sequences per Kabat definition: KRHMH (SEQ ID NO: 503), VISSDAIHVDYASSVRG (SEQ ID NO: 504), and DRDGYGPPQIQTWSGRYLH-LYSGIDA (SEQ ID NO: 505). The light chain CDRs of the 6891_F06 (PGT-153) antibody have the following sequences per Kabat definition: KSSQSLRQSNGKTYLY (SEQ ID NO: 512), EVSIRFS (SEQ ID NO: 513), and MQSKDFPLT (SEQ ID NO: 486).

The heavy chain CDRs of the 6891_F06 (PGT-153) antibody have the following sequences per Chothia definition: NFLFNK (SEQ ID NO: 506), VISSDAIHVD (SEQ ID NO: 507), and DRDGYGPPQIQTWSGRYLHLYSGIDA (SEQ ID NO: 505). The light chain CDRs of the 6891_F06 (PGT-153) antibody have the following sequences per Chothia definition: KSSQSLRQSNGKTYLY (SEQ ID NO: 512), EVSIRFS (SEQ ID NO: 513), and MQSKDFPLT (SEQ ID NO: 486).

The 6843_G20 (PGT-154) antibody includes a heavy chain variable region (SEQ ID NO: 517), encoded by the nucleic acid sequence shown in SEQ ID NO: 515, and a light chain variable region (SEQ ID NO: 525) encoded by the nucleic acid sequence shown in SEQ ID NO: 523.

The heavy chain CDRs of the 6843_G20 (PGT-154) antibody have the following sequences per Kabat definition: KYPMY (SEQ ID NO: 475), AISADAWHVDYAASVKD (SEQ ID NO: 518), and NIEEFSVPQFDSWSGRSYY-HYFGMDV (SEQ ID NO: 519). The light chain CDRs of the 6843_G20 (PGT-154) antibody have the following sequences per Kabat definition: SSSESLGRGDGRTYLH (SEQ ID NO: 526), EVSTRFS (SEQ ID NO: 527), and MQSRDFPIT (SEQ ID NO: 528).

The heavy chain CDRs of the 6843_G20 (PGT-154) antibody have the following sequences per Chothia definition: NFIFNK (SEQ ID NO: 520), AISADAWHVD (SEQ ID NO: 521), and NIEEFSVPQFDSWSGRSYY-HYFGMDV (SEQ ID NO: 519). The light chain CDRs of the 6843_G20 (PGT-154) antibody have the following sequences per Chothia definition: SSSESLGRGDGRTYLH (SEQ ID NO: 526), EVSTRFS (SEQ ID NO: 527), and MQSRDFPIT (SEQ ID NO: 528).

The 6892_D19 (PGT-155) antibody includes a heavy chain variable region (SEQ ID NO: 532), encoded by the nucleic acid sequence shown in SEQ ID NO: 530, and a light chain variable region (SEQ ID NO: 540) encoded by the nucleic acid sequence shown in SEQ ID NO: 538.

The heavy chain CDRs of the 6892_D19 (PGT-155) antibody have the following sequences per Kabat definition: EYPMY (SEQ ID NO: 533), AISADAWHVDYAGSVRG (SEQ ID NO: 534), and DGEEHKVPQLHSWSGRNLY-HYTGFDV (SEQ ID NO: 535). The light chain CDRs of the 6892_D19 (PGT-155) antibody have the following sequences per Kabat definition: KSSQSVRQSDGKTFLY (SEQ ID NO: 541), EGSSRFS (SEQ ID NO: 542), and LQTKDFPLT (SEQ ID NO: 543).

The heavy chain CDRs of the 6892_D19 (PGT-155) antibody have the following sequences per Chothia definition: GFIFNE (SEQ ID NO: 536), AISADAWHVD (SEQ ID NO: 521), and DGEEHKVPQLHSWSGRNLY-HYTGFDV (SEQ ID NO: 535). The light chain CDRs of the 6892_D19 (PGT-155) antibody have the following sequences per Chothia definition: KSSQSVRQSDGKTFLY (SEQ ID NO: 541), EGSSRFS (SEQ ID NO: 542), and LQTKDFPLT (SEQ ID NO: 543).

The 6808_B09 (PGT-156) antibody includes a heavy chain variable region (SEQ ID NO: 547), encoded by the nucleic acid sequence shown in SEQ ID NO: 545, and a light chain variable region (SEQ ID NO: 554) encoded by the nucleic acid sequence shown in SEQ ID NO: 552.

The heavy chain CDRs of the 6808_B09 (PGT-156) antibody have the following sequences per Kabat definition: QYPMY (SEQ ID NO: 548), AISADAWHVDYPGSVRG (SEQ ID NO: 549), and DGEEHKVPQLHSWSGRNLY-HYTGFDV (SEQ ID NO: 535). The light chain CDRs of the 6808_B09 (PGT-156) antibody have the following sequences per Kabat definition: KSSQTVRQSDGKTFLY (SEQ ID NO: 555), EGSNRFS (SEQ ID NO: 556), and LQTKDFPLT (SEQ ID NO: 543).

The heavy chain CDRs of the 6808_B09 (PGT-156) antibody have the following sequences per Chothia definition: GFIFNQ (SEQ ID NO: 550), AISADAWHVD (SEQ ID NO: 521), and DGEEHKVPQLHSWSGRNLY-HYTGFDV (SEQ ID NO: 535). The light chain CDRs of the 6808_B09 (PGT-156) antibody have the following sequences per Chothia definition: KSSQTVRQSDGKTFLY (SEQ ID NO: 555), EGSNRFS (SEQ ID NO: 556), and LQTKDFPLT (SEQ ID NO: 543).

The 6892_C23 (PGT-157) antibody includes a heavy chain variable region (SEQ ID NO: 560), encoded by the nucleic acid sequence shown in SEQ ID NO: 558, and a light chain variable region (SEQ ID NO: 566) encoded by the nucleic acid sequence shown in SEQ ID NO: 564.

The heavy chain CDRs of the 6892_C23 (PGT-157) antibody have the following sequences per Kabat definition: QYPMY (SEQ ID NO: 548), AISADAWHVDYAGSVRG (SEQ ID NO: 534), and DGEEHEVPQLHSWSGRNLY-HYTGVDI (SEQ ID NO: 561). The light chain CDRs of the 6892_C23 (PGT-157) antibody have the following sequences per Kabat definition: KSSQSLRQSDGKTFLY (SEQ ID NO: 567), EASNRFS (SEQ ID NO: 568), and MQTKDFPLT (SEQ ID NO: 569).

The heavy chain CDRs of the 6892_C23 (PGT-157) antibody have the following sequences per Chothia definition: GFIFKQ (SEQ ID NO: 562), AISADAWHVD (SEQ ID NO: 521), and DGEEHEVPQLHSWSGRNLY-HYTGVDI (SEQ ID NO: 561). The light chain CDRs of the 6892_C23 (PGT-157) antibody have the following sequences per Chothia definition: KSSQSLRQSDGKTFLY (SEQ ID NO: 567), EASNRFS (SEQ ID NO: 568), and MQTKDFPLT (SEQ ID NO: 569).

The 6881_N05 (PGT-158) antibody includes a heavy chain variable region (SEQ ID NO: 573), encoded by the nucleic acid sequence shown in SEQ ID NO: 571, and a light chain variable region (SEQ ID NO: 579) encoded by the nucleic acid sequence shown in SEQ ID NO: 577.

The heavy chain CDRs of the 6881_N05 (PGT-158) antibody have the following sequences per Kabat definition: KYPMY (SEQ ID NO: 475), AISADAWHVDYPGSVRG (SEQ ID NO: 549), and DGEEHEVPQLHSWSGRNLY-HYTGVDV (SEQ ID NO: 574). The light chain CDRs of the 6881_N05 (PGT-158) antibody have the following sequences per Kabat definition: KSSQSVRQSDGKTFLY (SEQ ID NO: 541), EASKRFS (SEQ ID NO: 580), and MQTKDFPLT (SEQ ID NO: 569).

The heavy chain CDRs of the 6881_N05 (PGT-158) antibody have the following sequences per Chothia definition: GFIFKK (SEQ ID NO: 575), AISADAWHVD (SEQ ID NO: 521), and DGEEHEVPQLHSWSGRNLY-HYTGVDV (SEQ ID NO: 574). The light chain CDRs of the 6881_N05 (PGT-158) antibody have the following sequences per Chothia definition: KSSQSVRQSDGKTFLY (SEQ ID NO: 541), EASKRFS (SEQ ID NO: 580), and MQTKDFPLT (SEQ ID NO: 569).

In one aspect, an antibody according to the invention contains a heavy chain having the amino acid sequence of SEQ ID NOs: 12, 16, 20, 24, 28, 139, 47, 53, 59, 65, 62, 153, 165, 181, 197, 213, 229, 246, 275, 291, 297, 306, 318, 333, 346, 362, 400, 404, 419, 434, 443, 453, 462, 473, 489, 501, 516, 531, 546, 559, or 572, and a light chain having the amino acid sequence of SEQ ID NOs: 14, 18, 22, 26, 30, 142, 50, 56, 148, 158, 174, 190, 206, 222, 238, 255, 284, 301, 312, 329, 392, 355, 396, 385, 413, 428, 439, 448, 583, 469, 482, 496, 510, 524, 539, 553, 565, or 578. Alternatively, an antibody according to the invention contains a heavy chain variable region having the amino acid sequence of SEQ ID NOs: 31, 33, 35, 37, 39, 140, 48, 54, 60, 79, 156, 168, 184, 200, 216, 232, 149, 276, 292, 298, 307, 319, 334, 347, 363, 401, 405, 420, 435, 444, 454, 463, 474, 490, 502, 517, 532, 547, 560, or 573, and a light chain variable region having the amino acid sequence of SEQ ID NOs: 32, 34, 36, 38, 40, 96, 51, 57, 149, 161, 177, 193, 209, 225, 242, 258, 285, 302, 313, 330, 393, 356, 397, 386, 414, 429, 440, 449, 584, 470, 483, 497, 511, 525, 540, 554, 566, or 579.

In another aspect, an antibody according to the invention contains a heavy chain having the amino acid sequence encoded by the nucleic acid sequence of SEQ ID NOs: 11, 15, 19, 23, 27, 138, 46, 52, 58, 64, 66, 166, 167, 183, 199, 215, 231, 248, 273, 289, 295, 304, 314, 316, 331, 344, 360, 398, 402, 417, 432, 441, 451, 460, 471, 487, 499, 514, 529, 544, 557, or 570, and a light chain having the amino acid sequence encoded by the nucleic acid sequence of SEQ ID NOs: 13, 17, 21, 25, 29, 141, 49, 55, 61, 67, 146, 160, 176, 192, 208, 224, 240, 257, 282, 299, 310, 327, 390, 353, 394, 383, 411, 426, 437, 446, 581, 467, 480, 494, 508, 522, 537, 551, 563, or 576. Alternatively, an antibody according to the invention contains a heavy chain variable region having the amino acid sequence encoded by the nucleic acid sequence of SEQ ID NOs: 99, 101, 109, 115, 122, 128, 130, 132, 134, 136, 63, 154, 166, 182, 198, 214, 230, 247, 274, 290, 296, 305, 315, 317, 332, 345, 361, 399, 403, 418, 433, 442, 452, 461, 472, 488, 500, 515, 530, 545, 558, or 571, and a light chain variable region having the amino acid sequence encoded by the nucleic acid sequence of SEQ ID NOs: 100, 106, 112, 119, 125, 129, 131, 133, 135, 137, 147, 159, 175, 191, 207, 223, 239, 256, 283, 300, 311, 328, 391, 354, 395, 384, 412, 427, 438, 447, 582, 468, 481, 495, 509, 523, 538, 552, 564, or 577. Furthermore, an antibody according to the invention contains a heavy chain having the amino acid sequence encoded by a nucleic acid sequence of SEQ ID NOs: 11, 15, 19, 23, 27, 138, 46, 52, 58, 64, 66, 166, 167, 183, 199, 215, 231, 248, 273, 289, 295, 304, 314, 316, 331, 344, 360, 398, 402, 417, 432, 441, 451, 460, 471, 487, 499, 514, 529, 544, 557, or 570, which contains a silent or degenerate mutation, and a light chain having the amino acid sequence encoded by the nucleic acid sequence of SEQ ID NOs: 13, 17, 21, 25, 29, 141, 49, 55, 61, 67, 146, 160, 176, 192, 208, 224, 240, 257, 282, 299, 310, 327, 390, 353, 394, 383, 411, 426, 437, 446, 581, 467, 480, 494, 508, 522, 537, 551, 563, or 576, which contains a silent or degenerate mutation. Silent and degenerate mutations alter the nucleic acid sequence, but do not alter the resultant amino acid sequence.

Preferably the three heavy chain CDRs include an amino acid sequence of at least 90%, 92%, 95%, 97%, 98%, 99%, or more identical to the amino acid sequence of KYGMH (SEQ ID NO: 88), LISDDGMRKYHSDSMWG (SEQ ID NO: 89), EAGGPIWHDDVKYYDFNDGYYNYHYMDV (SEQ ID NO: 6), SYAFT (SEQ ID NO: 104), MVTPIFGEAKYSQRFEG (SEQ ID NO: 105), DRRAVPIATDNWLDP (SEQ ID NO: 9), SYAFS (SEQ ID NO: 110), MITPVFGETKYAPRFQG (SEQ ID NO: 111), DRRVVPMATDNWLDP (SEQ ID NO: 8), DYYLH (SEQ ID NO: 116), LIDPENGEARYAEKFQG (SEQ ID NO: 117), GAVGADSGSWFDP (SEQ ID NO: 10), RQGMH (SEQ ID NO: 123), FIKYDGSEKYHADSVWG (SEQ ID NO: 124), EAGGPDYRNGYNYYDFYDGYYNYHYMDV (SEQ ID NO: 7), LISDDGMRKYHSNSMWG (SEQ ID NO: 98), DSYWS (SEQ ID NO: 90), YVHKSGDTNYSPSLKS (SEQ ID NO: 265), TLHGRRIYGIVAFNEWFTYFYMDV (SEQ ID NO: 143), DNYWS (SEQ ID NO: 261), YVHDSGDTNYNPSLKS (SEQ ID NO: 157), TKHGRRIYGVVAFKEWFTYFYMDV (SEQ ID NO: 262), DAYWS (SEQ ID NO: 169), YVHHSGDTNYNPSLKR (SEQ ID NO: 170), ALHGKRIYGIVALGELFTYFYMDV (SEQ ID NO: 171), ACTYFWG (SEQ ID NO: 185), SLSHCQSFWGSGWTFHNPSLKS (SEQ ID NO: 186), FDGEVLVYNHWPKPAWVDL (SEQ ID NO: 187), ACDYFWG (SEQ ID NO: 201), GLSHCAGYYNTGWTYHNPSLKS (SEQ ID NO: 202), FDGEVLVYHDWPKPAWVDL (SEQ ID NO: 203), TGHYYWG (SEQ ID NO: 217), HIHYTTAVLHNPSLKS (SEQ ID NO: 218), SGGDILYYYEWQKPHWFSP (SEQ ID NO: 219), GGEWGDKDYHWG (SEQ ID NO: 233), SIHWRGTTHYKESLRR (SEQ ID NO: 234), HRHHDVFMLVPIAGWFDV (SEQ ID NO: 235), GTDWGENDFHYG (SEQ ID NO: 250), SIHWRGRTTHYKTSFRS (SEQ ID NO: 251), HKYHDIFRVVPVAGWFDP (SEQ ID NO: 252), KYDVH (SEQ ID NO: 277), WMSHEGDKTESAQRFKG (SEQ ID NO: 278), GSKHRLRDYVLYDDYGLINYQEWNDYLEFLDV (SEQ ID NO: 279), WISHERDKTESAQRFKG (SEQ ID NO: 293), GSKHRLRDYVLYDDYGLINQQEWNDYLEFLDV (SEQ ID NO: 308), RCNYFWG (SEQ ID NO: 320), SLSHCRSYYNTDWTYHNPSLKS (SEQ ID NO: 321), FGGEVLVYRDWPKPAWVDL (SEQ ID NO: 322), ACNSFWG (SEQ ID NO: 326), SLSHCASYWNRGWTYHNPSLKS (SEQ ID NO: 335), FGGEVLRYTDWPKPAWVDL (SEQ ID NO: 336), TGHHYWG (SEQ ID NO: 348), HIHYNTAVLHNPALKS (SEQ ID NO: 349), SGGDILYYIEWQKPHWFYP (SEQ ID NO: 350), GGEWGDSDYHWG (SEQ ID NO: 364), SIHWRGTTHYNAPFRG (SEQ ID NO: 365), HKYHDIVMVVPIAGWFDP (SEQ ID NO: 366), NHDVH (SEQ ID NO: 378), WMSHEGDKTGLAQKFQG (SEQ ID NO: 379), GSKHRLRDYFLYNEYGPNYEEWGDYLATLDV (SEQ ID NO: 380), NYYWT (SEQ ID NO: 406), YISDRETTTYNPSLNS (SEQ ID NO: 407), ARRGQRIYGVVSFGEFFYYYYMDV (SEQ ID NO: 408), GRFWS (SEQ ID NO: 421), YFSDTDRSEYNPSLRS (SEQ ID NO: 422), AQQGKRIYGIVSFGEFFYYYYMDA (SEQ ID NO: 423), AQQGKRIYGIVSFGELFYYYYMDA (SEQ ID NO: 436), SGGDILYYNEWQKPHWFYP (SEQ ID NO: 445), SLSHCAGYYNSGWTYHNPSLKS (SEQ ID NO: 455), FGGDVLVYHDWPKPAWVDL (SEQ ID NO: 456), GCDYFWG (SEQ ID NO: 464), FDGEVLVYNDWPKPAWVDL (SEQ ID NO: 465), KYPMY (SEQ ID NO: 475), AISGDAWHVVYSNSVQG (SEQ ID NO: 476), MFQESGPPRLDRWSGRNYYYYSGMDV (SEQ ID NO: 477), AISADAWHVVYSGSVQG (SEQ ID NO: 491), MFQESGPPRFDSWSGRNYYYYSGMDV (SEQ ID NO: 492), KRHMH (SEQ ID NO: 503), VISSDAIHVDYASSVRG (SEQ ID NO: 504), DRDGYGPPQIQTWSGRYLHLYSGIDA (SEQ ID NO: 505), AISADAWHVDYAASVKD (SEQ ID NO: 518), NIEEFSVPQFDSWSGRSYYHYFGMDV (SEQ ID NO: 519), EYPMY (SEQ ID NO: 533), AISADAWHVDYAGSVRG (SEQ ID NO: 534), DGEEHKVPQLHSWSGRNLYHYTGFDV (SEQ ID NO: 535), QYPMY (SEQ ID NO: 548), AISADAWHVDYPGSVRG (SEQ ID NO: 549), DGEEHEVPQLHSWSGRNLYHYTGVDI (SEQ ID NO: 561), DGEEHEVPQLHSWSGRNLYHYTGVDV (SEQ ID NO: 574), (as determined by the Kabat method) or GFTFHK (SEQ ID NO: 266), LISDDGMRKY (SEQ ID NO: 267), EAGGPIWHDDVKYYDFNDGYYNYHYMDV (SEQ ID NO: 6), GGTFSS (SEQ ID NO: 268), MVTPIFGEAK (SEQ ID NO: 269), DRRAVPIATDNWLDP (SEQ ID NO: 9), GGAFSS (SEQ ID NO: 270), MITPVFGETK (SEQ ID NO: 271), DRRVVPMATDNWLDP (SEQ ID NO: 8), GYSFID (SEQ ID NO: 102), LIDPENGEAR (SEQ ID NO: 103), GAVGADSGSWFDP (SEQ ID NO: 10), GFDFSR (SEQ ID NO: 118), FIKYDGSEKY (SEQ ID NO: 272), EAGGPDYRNGYNYYDFYDGYYNYHYMDV (SEQ ID NO: 7), GASISD (SEQ ID NO: 144), YVHKSGDTN (SEQ ID NO: 145), TLHGRRIYGIVAFNEWFTYFYMDV (SEQ ID NO: 143), GTLVRD (SEQ ID NO: 263), YVHDSGDTN (SEQ ID NO: 264), TKHGRRIYGVVAFKEWFTYFYMDV (SEQ ID NO: 262), GASIND (SEQ ID NO: 172), YVHHSGDTN (SEQ ID NO: 173), ALHGKRIYGIVALGELFTYFYMDV (SEQ ID NO: 171), GESTGACT (SEQ ID NO: 188), SLSHCQSFWGSGWTF (SEQ ID NO: 189), FDGEVLVYNHWPKPAWVDL (SEQ ID NO: 187), GDSTAACD (SEQ ID NO: 204), GLSHCAGYYNTGWTY (SEQ ID NO: 205), FDGEVLVYHDWPKPAWVDL (SEQ ID NO: 203), GESINTGH (SEQ ID NO: 220), HIHYTTAVL (SEQ ID NO: 221), SGGDILYYYEWQKPHWFSP (SEQ ID NO: 219), GDSIRGGEWGDKD (SEQ ID NO: 236), SIHWRGTTH (SEQ ID NO: 237), HRHHDVFMLVPIAGWFDV (SEQ ID NO: 235), GGSMRGTDWGEND (SEQ ID NO: 253), SIHWRGRTTH (SEQ ID NO: 254), HKYHDIFRVVPVAGWFDP (SEQ ID NO: 252), GNTFSK (SEQ ID NO: 280), WMSHEGDKTE (SEQ ID NO: 281), GSKHRLRDYVLYDDYGLINYQEWNDYLEFLDV (SEQ ID NO: 279), WISHERDKTE (SEQ ID NO: 294), GSKHRLRDYVLYDDYGLINQQEWNDYLEFLDV (SEQ ID NO: 308), or GNTFRK (SEQ ID NO: 309), GDSTGRCN (SEQ ID NO: 323), SLSHCRSYYNTDWTY (SEQ ID NO: 324), FGGEVLVYRDWPKPAWVDL (SEQ ID NO: 322), GDSTAACN (SEQ ID NO: 337), SLSHCASYWNRGWTY (SEQ ID NO: 338), FGGEVLRYTDWPKPAWVDL (SEQ ID NO: 336), GDSINTGH (SEQ ID NO: 351), HIHYNTAVL (SEQ ID NO: 352), SGGDILYYIEWQKPHWFYP (SEQ ID NO: 350), GGSIRGGEWGDSD (SEQ ID NO: 367), SIHWRGTTH (SEQ ID NO: 237), HKYHDIVMVVPIAGWFDP (SEQ ID NO: 366), GNSFSN (SEQ ID NO: 381), WMSHEGDKTG (SEQ ID NO: 382), GSKHRLRDYFLYNEYGPNYEEWGDYLATLDV (SEQ ID NO: 380), GGSISN (SEQ ID NO: 409), YISDRETTT (SEQ ID NO: 410), ARRGQRIYGVVSFGEFFYYYYMDV (SEQ ID NO: 408), NGSVSG (SEQ ID NO: 424), YFSDTDRSE (SEQ ID NO: 425), AQQGKRIYGIVSFGEFFYYYYMDA (SEQ ID NO: 423), AQQGKRIYGIVSFGELFYYYYMDA (SEQ ID NO: 436), SGGDILYYNEWQKPHWFYP (SEQ ID NO: 445), SLSHCAGYYNSGWTY (SEQ ID NO: 457), FGGDVLVYHDWPKPAWVDL (SEQ ID NO: 456), GDSTAGCD (SEQ ID NO: 466), FDGEVLVYNDWPKPAWVDL (SEQ ID NO: 465), DFPFSK (SEQ ID NO: 478), AISGDAWHVV (SEQ ID NO: 479), MFQESGPPRLDRWSGRNYYYYSGMDV (SEQ ID NO: 477), AISADAWHVV (SEQ ID NO: 493), MFQESGPPRFDSWSGRNYYYYSGMDV (SEQ ID NO: 492), NFLFNK (SEQ ID NO: 506), VISSDAIHVD (SEQ ID NO: 507), DRDGYGPPQIQTWSGRYLHLYSGIDA (SEQ ID NO: 505), NFIFNK (SEQ ID NO: 520), AISADAWHVD (SEQ ID NO: 521), NIEEFSVPQFDSWSGRSYYHYFGMDV (SEQ ID NO: 519), GFIFNE (SEQ ID NO: 536), DGEEHKVPQLHSWSGRNLYHYTGFDV (SEQ ID NO: 535), GFIFNQ (SEQ ID NO: 550), GFIFKQ (SEQ ID NO: 562), DGEEHEVPQLHSWSGRNLYHYTGVDI (SEQ ID NO: 561), GFIFKK (SEQ ID NO: 575), DGEEHEVPQLHSWSGRNLYHYTGVDV (SEQ ID NO: 574), (as determined by the Chothia method), and a light chain with three CDRs that include an amino acid sequence of at least 90%, 92%, 95%, 97%, 98%, 99%, or more identical to the amino acid sequence of NGTSSDVGGFDSVS (SEQ ID NO: 97), DVSHRPS (SEQ ID NO: 95), SSLTDRSHRI (SEQ ID NO: 41), RASQTINNYLN (SEQ ID NO: 107), GASNLQN (SEQ ID NO: 108), QQSFSTPRT (SEQ ID NO: 42), RASQTIHTYLN (SEQ ID NO: 113), GASTLQS (SEQ ID NO: 114), QQSYSTPRT (SEQ ID NO: 43), SGSKLGDKYVS (SEQ ID NO: 120), ENDRRPS (SEQ ID NO: 121), QAWETTTTTFVF (SEQ ID NO: 44), NGTSNDVGGYESVS (SEQ ID NO: 126), DVSKRPS (SEQ ID NO: 127), KSLTSTRRRV (SEQ ID NO: 45), NGTRSDVGGFDSVS (SEQ ID NO: 92), NGTSRDVGGFDSVS (SEQ ID NO: 93), GEKSLGSRAVQ (SEQ ID NO: 150), NNQDRPS (SEQ ID NO: 151), HIWDSRVPTKWV (SEQ ID NO: 152), GEESLGSRSVI (SEQ ID NO: 162), NNNDRPS (SEQ ID NO: 163), HIWDSRRPTNWV (SEQ ID NO: 164), GKESIGSRAVQ (SEQ ID NO: 178), NNQDRPA (SEQ ID NO: 179), HIYDARGGTNWV (SEQ ID NO: 180), NGTATNFVS (SEQ ID NO: 194), GVDKRPP (SEQ ID NO: 195), GSLVGNWDVI (SEQ ID NO: 196), TGTSNRFVS (SEQ ID NO: 210), GVNKRPS (SEQ ID NO: 211), SSLVGNWDVI (SEQ ID NO: 212), NGTSSDIGGWNFVS (SEQ ID NO: 226), EVNKRPS (SEQ ID NO: 227), SSLFGRWDVV (SEQ ID NO: 228), RASQNINKNLA (SEQ ID NO: 243), ETYSKIA (SEQ ID NO: 244), QQYEEWPRT (SEQ ID NO: 245), RASQNVKNNLA (SEQ ID NO: 259), DASSRAG (SEQ ID NO: 260), SSTQSLRHSNGANYLA (SEQ ID NO: 286), LGSQRAS (SEQ ID NO: 287), MQGLNRPWT (SEQ ID NO: 288), or TSTQSLRHSNGANYLA (SEQ ID NO: 303), TGTSNNFVS (SEQ ID NO: 325), DVNKRPS (SEQ ID NO: 343), GSLVGNWDVI (SEQ ID NO: 196), SGTGSDIGWNFVS (SEQ ID NO: 357), EVNRRRS (SEQ ID NO: 358), SSLSGRWDIV (SEQ ID NO: 359), RASQSVKNNLA (SEQ ID NO: 372), DTSSRAS (SEQ ID NO: 373), KCSHSLQHSTGANYLA (SEQ ID NO: 387), LATHRAS (SEQ ID NO: 388), MQGLHSPWT (SEQ ID NO: 389), GRQALGSRAVQ (SEQ ID NO: 415), HMWDSRSGFSWS (SEQ ID NO: 416), GERSRGSRAVQ (SEQ ID NO: 430), HYWDSRSPISWI (SEQ ID NO: 431), SGTASDIGSWNFVS (SEQ ID NO: 450), TGNINNFVS (SEQ ID NO: 458), GSLAGNWDVV (SEQ ID NO: 459), KSSESLRQSNGKTSLY (SEQ ID NO: 484), EVSNRFS (SEQ ID NO: 485), MQSKDFPLT (SEQ ID NO: 486), KSSQSLRQSNGKTSLY (SEQ ID NO: 498), KSSQSLRQSNGKTYLY (SEQ ID NO: 512), EVSIRFS (SEQ ID NO: 513), SSSESLRGDGRTYLH (SEQ ID NO: 526), EVSTRFS (SEQ ID NO: 527), MQSRDFPIT (SEQ ID NO: 528), KSSQSVRQSDGKTFLY (SEQ ID NO: 541), EGSSRFS (SEQ ID NO: 542), LQTKDFPLT (SEQ ID NO: 543), KSSQTVRQSDGKTFLY (SEQ ID NO: 555), EGSNRFS (SEQ ID NO: 556), KSSQSLRQSDGKTFLY (SEQ ID NO: 567), EASNRFS (SEQ ID NO: 568), MQTKDFPLT (SEQ ID NO: 569), EASKRFS (SEQ ID NO: 580), (as determined by the Kabat method), or NGTSSDVGGFDSVS (SEQ ID NO: 97), DVSHRPS (SEQ ID NO: 95), SSLTDRSHRI (SEQ ID NO: 41), RASQTINNYLN (SEQ ID NO: 107), GASNLQN (SEQ ID NO: 108), QQSFSTPRT (SEQ ID NO: 42), RASQTIHTYLN (SEQ ID NO: 113), GASTLQS (SEQ ID NO: 114), QQSYSTPRT (SEQ ID NO: 43), SGSKLGDKYVS (SEQ ID NO: 120), ENDRRPS (SEQ ID NO: 121), QAWETTTTTFVF (SEQ ID NO: 44), NGTSNDVGGYESVS (SEQ ID NO: 126), DVSKRPS (SEQ ID NO: 127), KSLTSTRRRV (SEQ ID NO: 45), NGTRSDVGGFDSVS (SEQ ID NO: 92), NGTSRDVGGFDSVS (SEQ ID NO: 93) GEKSLGSRAVQ (SEQ ID NO: 150), NNQDRPS (SEQ ID NO: 151), HIWDSRVPTKWV (SEQ ID NO: 152), GEESLGSRSVI (SEQ ID NO: 162), NNNDRPS (SEQ ID NO: 163), HIWDSRRPTNWV (SEQ ID NO: 164), GKESIGSRAVQ (SEQ ID NO: 178), NNQDRPA (SEQ ID NO: 179), HIYDARGGTNWV (SEQ ID NO: 180), NGTATNFVS (SEQ ID NO: 194), GVDKRPP (SEQ ID NO: 195), GSLVGNWDVI (SEQ ID NO: 196), TGTSNRFVS (SEQ ID NO: 210), GVNKRPS (SEQ ID NO: 211), SSLVGNWDVI (SEQ ID NO: 212), NGTSSDIGGWNFVS (SEQ ID NO: 226), EVNKRPS (SEQ ID NO: 227), SSLFGRWDVV (SEQ ID NO: 228), RASQNINKNLA (SEQ ID NO: 243), ETYSKIA (SEQ ID NO: 244), QQYEEWPRT (SEQ ID NO: 245), RASQNVKNNLA (SEQ ID NO: 259), DASSRAG (SEQ ID NO: 260), SSTQSLRHSNGANYLA (SEQ ID NO: 286), LGSQRAS (SEQ ID NO: 287), MQGLNRPWT (SEQ ID NO: 288), TSTQSLRHSNGANYLA (SEQ ID NO: 303), TGTSNNFVS (SEQ ID NO: 325), DVNKRPS (SEQ ID NO: 343), GSLVGNWDVI (SEQ ID NO: 196), SGTGSDIGWNFVS (SEQ ID NO: 357), EVNRRRS (SEQ ID NO: 358), SSLSGRWDIV (SEQ ID NO: 359), RASQSVKNNLA (SEQ ID NO: 372), DTSSRAS (SEQ ID NO: 373), KCSHSLQHSTGANYLA (SEQ ID NO: 387), LATHRAS (SEQ ID NO: 388), MQGLHSPWT (SEQ ID NO: 389), GRQALGSRAVQ (SEQ ID NO: 415), HMWDSRSGFSWS (SEQ ID NO: 416), GERSRGSRAVQ (SEQ ID NO: 430), HYWDSRSPISWI (SEQ ID NO: 431), SGTASDIGSWNFVS (SEQ ID NO: 450), TGNINNFVS (SEQ ID NO: 458), GSLAGNWDVV (SEQ ID NO: 459), KSSESLRQSNGKTSLY (SEQ ID NO: 484), EVSNRFS (SEQ ID NO: 485), MQSKDFPLT (SEQ ID NO: 486), KS SQSLRQSNGKTSLY (SEQ ID NO: 498), KS SQSLRQSNGKTYLY (SEQ ID NO: 512), EVSIRFS (SEQ ID NO: 513), SSSESLGRGDGRTYLH (SEQ ID NO: 526), EVSTRFS (SEQ ID NO: 527), MQSRDFPIT (SEQ ID NO: 528), KSSQSVRQSDGKTFLY (SEQ ID NO: 541), EGSSRFS (SEQ ID NO: 542), LQTKDFPLT (SEQ ID NO: 543), KSSQTVRQSDGKTFLY (SEQ ID NO: 555), EGSNRFS (SEQ ID NO: 556), KSSQSLRQSDGKTFLY (SEQ ID NO: 567), EASNRFS (SEQ ID NO: 568), MQTKDFPLT (SEQ ID NO: 569), EASKRFS (SEQ ID NO: 580), (as determined by the Chothia method).

The heavy chain of the anti-HIV monoclonal antibody is derived from a germ line variable (V) gene such as, for example, the IGHV1, IGHV3, or IGHV4 germline gene or an allele thereof.

The anti-HIV antibodies of the invention include a variable heavy chain ($V_H$) region encoded by a human IGHV1, IGHV3, or IGHV4 germline gene sequence or an allele thereof. Antibodies of the invention are derived from the IGHV1-2, IGHV1-8, or IGHV1-46 genes, or an allele thereof. Exemplary alleles of the IGHV1 germline gene include, but are not limited to, IGHV1-2*02, IGHV1-2*04, IGHV1-8*01, IGHV1-46*01, IGHV1-46*02, or IGHV1-46*03. IGHV1 germline gene sequences are shown, e.g., in Accession numbers L22582, X27506, X92340, M83132, X67905, L22583, Z29978, Z14309, Z14307, Z14300, Z14296, and Z14301. IGHV3 germline gene sequences are shown, e.g., in Accession numbers AB019439, M99665, M77305, M77335, and M77334. Antibodies of the invention are derived from the IGHV4-59, IGHV4-64, IGHV4-b, IGHV4-39, or IGHV4-28 genes, or an allele thereof. Exemplary alleles of the IGHV4 germline gene include, but are not limited to, IGHV4-59*01, IGHV4-59*07, IGHV4-59*02, IGHV4-59*03, IGHV4-59*04, IGHV4-61*08, IGHV4-b*02, IGHV4-b*01, IGHV4-39*07, IGHV4-39*03, IGHV4-39*06, IGHV4-39*01, IGHV4-39*02, or IGHV4-28*05. IGHV4 germline gene sequences are shown, e.g., in Accession numbers AB019439, L10094, X05715, X92259, X92297, M95116, Z14236, AM940222, X54447, X56362, Z14075, Z75352, AB019438, M29812, M95114, M95117, M95118, M95119, X56360, X87091, Z75359, Z14243, L10088, U03896, X56355, X56359, X92248, X92296, Z12371, M29811, L10097, X92230, X92250, X56356, Z75347, Z75348, AB019437, M95111, X92249, X92251, Z12366, Z75346, Z75361, Z12367, X56365, and X92289. The anti-HIV antibodies of the invention include a $V_H$ region that is encoded by a nucleic acid sequence that is at least 80% homologous to the IGHV1, IGHV3, or IGHV4 germline gene sequence or an allele thereof. Preferably, the nucleic acid sequence is at least 90%, 95%, 96%, 97% homologous to the IGHV1, IGHV3, or IGHV4 germline gene sequence, and more preferably, at least 98%, 99% homologous to the IGHV1, IGHV3, or IGHV4 germline gene sequence or an allele thereof. The $V_H$ region of the anti-HIV antibody is at least 80% homologous to the amino acid sequence of the $V_H$ region encoded by the IGHV1, IGHV3, or IGHV4 germline gene sequence or an allele thereof. Preferably, the amino acid sequence of $V_H$ region of the anti-HIV antibody is at least 90%, 95%, 96%, 97% homologous to the amino acid sequence encoded by the IGHV1, IGHV3, or IGHV4 germline gene sequence or an allele thereof, and more preferably, at least 98%, 99% homologous to the sequence encoded by the IGHV1, IGHV3, or IGHV4 germline gene sequence or an allele thereof.

The light chain of the anti-HIV monoclonal antibody is derived from a germ line variable (V) gene such as, for example, the IGLV2, IGLV3, IGKV1, IGKV2, IGKV2D, or IGKV3 germline gene or an allele thereof.

The anti-HIV antibodies of the invention also include a variable light chain ($V_L$) region encoded by a human IGLV2, IGLV3, IGKV1, IGKV2, IGKV2D, IGKV3, or IGKV3D germline gene or an allele thereof. A human IGLV2 $V_L$ germline gene sequence is shown, e.g., Accession numbers Z73664, L27822, Y12412, and Y12413. A human IGLV3 $V_L$ germline gene sequence is shown, e.g., Accession number X57826. Antibodies of the invention are derived from the IGLV2-8 germline gene, or an allele thereof.

Exemplary alleles of the IGLV2-8 germline gene include, but are not limited to, IGLV2-8*01 and IGLV2-8*02. Antibodies of the invention are derived from the IGLV3-21 germline gene, or an allele thereof. Exemplary alleles of the IGLV3-21 germline gene include, but are not limited to, IGLV3-21*01, IGLV3-21*02, and IGLV3-21*03. Antibodies of the invention are derived from the IGKV2-28 and IGKV2D-28 germline genes, or an allele thereof. Exemplary alleles of the IGKV2-28 and IGKV2D-28 germline genes include, but are not limited to, IGKV2-28*01 and IGKV2D-28*01. Antibodies of the invention are derived from the IGKV3-15 and IGKV3D-15 germline genes, or an allele thereof. Exemplary alleles of the IGKV3-15 and IGKV3D-15 germline genes include, but are not limited to, IGKV3-15*01, IGKV3D-15*01, and IGKV3D-15*02(P).

A human IGLV2 $V_L$ germline gene sequence is shown, e.g., Accession numbers Z73657, Z73664, Z73642, X14616, X97466, Z73643, D87013, Z73641, X97462, D87021, Y12417, L27695, and Z22209. A human IGLV3 $V_L$ germline gene sequence is shown, e.g., Accession numbers X57826, X97464, Z73658, X97463, D87015, X97471, X97472, X56178, X97468, X71966, D87007, M94115, Z73666, Z71968, X97474, X97467, D86994, Z73644, Z73646, X97469, Z73645, D87024, X97465, X97470, and X97473. A human IGKV1 $V_L$ germline gene sequence is shown, e.g., Accession numbers AF306358, AF490911, L12062, L12064, L12065, L12066, L12068, L12072, L12075, L12076, L12079, L12080, L12081, L12082, L12083, L12084, L12085, L12086, :12088, L12091, L12093, L12101, L12106, L12108, L12110, L12112, M95721, M95722, M95723, X73855, X73860, X98972, X98973, Z15073, Z15074, Z15075, Z15077, Z15079, Z15081. A human IGKV3 $V_L$ germline gene sequence is shown, e.g., Accession numbers X01668, M23090, X12686, X06583, X71883, X71891, X02725, L37728, L37727, L37730, L19271, L19272, X17264, X72815, X12687, X71886, X71896, X71895, X72820.

Alternatively, the anti-HIV antibodies include a $V_L$ region that is encoded by a nucleic acid sequence that is at least 80% homologous to the IGLV2, IGLV3, IGKV1, IGKV2, IGKV2D, IGKV3, or IGKV3D germline gene or an allele thereof. Preferably, the nucleic acid sequence is at least 90%, 95%, 96%, 97% homologous to the IGLV2, IGLV3, IGKV1, IGKV2, IGKV2D, IGKV3, or IGKV3D germline gene or an allele thereof, and more preferably, at least 98%, 99% homologous to the IGLV2, IGLV3, IGKV1, IGKV2, IGKV2D, IGKV3, or IGKV3D germline gene or an allele thereof. The $V_L$ region of the anti-HIV antibody is at least 80% homologous to the amino acid sequence of the $V_L$ region encoded the IGLV2, IGLV3, IGKV1, IGKV2, IGKV2D, IGKV3, or IGKV3D germline gene or an allele thereof. Preferably, the amino acid sequence of $V_L$ region of the anti-HIV antibody is at least 90%, 95%, 96%, 97% homologous to the amino acid sequence encoded by the IGLV2, IGLV3, IGKV1, IGKV2, IGKV2D, IGKV3, or IGKV3D germline gene or an allele thereof, and more preferably, at least 98%, 99% homologous to the sequence encoded by the IGLV2, IGLV3, IGKV1, IGKV2, IGKV2D, IGKV3, or IGKV3D germline gene or an allele thereof.

TABLE 11

Consensus nucleotide sequences of Kabat CDRs of heavy chains of 1443 PG16 sister clones.

| CDR1 (kabat): | |
|---|---|
| 1443 C16 | AAATATGGCATGCAC (SEQ ID NO: 68) |
| 1469 M23 | AAATATGGCATGCAC (SEQ ID NO: 68) |
| 1456 A12 | AAATATGGCATGCAC (SEQ ID NO: 68) |
| 1503 H05 | AAATATGGCATGCAC (SEQ ID NO: 68) |
| 1489 I13 | AAATATGGCATGCAC (SEQ ID NO: 68) |
| 1480 I08 | AAATATGGCATGCAC (SEQ ID NO: 68) |
| Consensus | AAATATGGCATGCAC (SEQ ID NO: 68) |

| CDR1 (chothia): | |
|---|---|
| 1443 C16 | TCTGGATTCACGTTTCACAAA (SEQ ID NO: 69) |
| 1469 M23 | TCTGGATTCACCTTTCACAAA (SEQ ID NO: 70) |
| 1456 A12 | TCTGGATTCACGTTTCACAAA (SEQ ID NO: 69) |
| 1503 H05 | TCTGGATTCACCTTTCACAAA (SEQ ID NO: 70) |
| 1489 I13 | TCTGGATTCACGTTTCACAAA (SEQ ID NO: 69) |
| 1480 I08 | TCTGGATTCACGTTTCACAAA (SEQ ID NO: 69) |
| Consensus* | TCTGGATTCACXTTTCACAAA (SEQ ID NO: 71) |
| Variation1 | TCTGGATTCACGTTTCACAAA (SEQ ID NO: 69) |
| Variation2 | TCTGGATTCACCTTTCACAAA (SEQ ID NO: 70) |

*Wherein X is C or G.

| CDR2: | |
|---|---|
| 1443 C16 | CTCATCTCAGATGACGGAATGAGGAAATATCATTCAGACTCCATGTGGGGC (SEQ ID NO: 72) |
| 1469 M23 | CTCATCTCAGATGACGGAATGAGGAAATATCATTCAGACTCCATGTGGGGC (SEQ ID NO: 72) |
| 1456 A12 | CTCATCTCAGATGACGGAATGAGGAAATATCATTCAGACTCCATGTGGGGC (SEQ ID NO: 72) |
| 1503 H05 | CTCATCTCAGATGACGGAATGAGGAAATATCATTCAGACTCCATGTGGGGC (SEQ ID NO: 72) |
| 1489 I13 | CTCATCTCAGATGACGGAATGAGGAAATATCATTCAAACTCCATGTGGGGC (SEQ ID NO: 73) |
| 1480 I08 | CTCATCTCAGATGACGGAATGAGGAAATATCATTCAGACTCCATGTGGGGC (SEQ ID NO: 72) |
| Consensus* | CTCATCTCAGATGACGGAATGAGGAAATATCATTCAXACTCCATGTGGGGC (SEQ ID NO: 74) |
| Variation1 | CTCATCTCAGATGACGGAATGAGGAAATATCATTCAGACTCCATGTGGGGC (SEQ ID NO: 72) |
| Variation2 | CTCATCTCAGATGACGGAATGAGGAAATATCATTCAAACTCCATGTGGGGC (SEQ ID NO: 73) |

*Wherein X is A or G.

CDR3:

1443 C16 (SEQ ID NO: 75)
GAGGCTGGTGGGCCAATCTGGCATGACGACGTCAAATATTACGATTTTAATGACGGCTACTACAACTACCACTACATGGACGTC

1469 M23 (SEQ ID NO: 75)
GAGGCTGGTGGGCCAATCTGGCATGACGACGTCAAATATTACGATTTTAATGACGGCTACTACAACTACCACTACATGGACGTC

TABLE 11-continued

Consensus nucleotide sequences of Kabat CDRs of heavy chains of 1443 PG16 sister clones.

1456 A12 (SEQ ID NO: 77)
GAGGCCGGTGGGCCAATCTGGCATGACGACGTCAAATATTACGATTTTAATGACG
GCTACTACAACTATCACTACATGGACGTC

1503 H05 (SEQ ID NO: 79)
GAGGCTGGTGGGCCAATCTGGCATGACGACGTCAAATATTACGATTTTAATGACG
GCTACTACAATTACCACTACATGGACGTC

1489 I13 (SEQ ID NO: 75)
GAGGCTGGTGGGCCAATCTGGCATGACGACGTCAAATATTACGATTTTAATGACG
GCTACTACAACTACCACTACATGGACGTC

1480 I08 (SEQ ID NO: 75)
GAGGCTGGTGGGCCAATCTGGCATGACGACGTCAAATATTACGATTTTAATGACG
GCTACTACAACTACCACTACATGGACGTC

Consensus (SEQ ID NO: 76)
GAGGCXGGTGGGCCAATCTGGCATGACGACGTCAAATATTACGATTTTAATGACG
GCTACTACAACTATCACTACATGGACGTC Variation1 (SEQ ID NO: 78)
GAGGCGGGTGGGCCAATCTGGCATGACGACGTCAAATATTACGATTTTAATGACG
GCTACTACAACTATCACTACATGGACGTC Variation2 (SEQ ID NO: 77)
GAGGCCGGTGGGCCAATCTGGCATGACGACGTCAAATATTACGATTTTAATGACG
GCTACTACAACTATCACTACATGGACGTC
*Wherein X is T, C or G.

TABLE 12

Consensus nucleotide sequences of Kabat CDRs of light chains of 1443 PG16 sister clones.

CDR1:

| | |
|---|---|
| 1443 C16 | AATGGAACCAGCAGTGACGTTGGTGGATTTGACTCTGTCTCC (SEQ ID NO: 80) |
| 1469 M23 | AATGGAACCAGAAGTGACGTTGGTGGATTTGACTCTGTCTCC (SEQ ID NO: 82) |
| 1456 A12 | AATGGAACCAGCCGTGACGTTGGTGGATTTGACTCTGTCTCC (SEQ ID NO: 83) |
| 1503 H05 | AATGGAACCAGAAGTGACGTTGGTGGATTTGACTCTGTCTCC (SEQ ID NO: 82) |
| 1489 I13 | AATGGAACCAGCAGTGACGTTGGTGGATTTGACTCTGTCTCC (SEQ ID NO: 80) |
| 1480 I08 | AATGGAACCAGCAGTGACGTTGGTGGATTTGACTCTGTCTCC (SEQ ID NO: 80) |
| Consensus* | AATGGAACCAG$X_1 X_2$GTGACGTTGGTGGATTTGACTCTGTCTCC (SEQ ID NO: 81) |
| Variation1 | AATGGAACCAGCAGTGACGTTGGTGGATTTGACTCTGTCTCC (SEQ ID NO: 80) |
| Variation2 | AATGGAACCAGAAGTGACGTTGGTGGATTTGACTCTGTCTCC (SEQ ID NO: 82) |
| Variation2 | AATGGAACCAGCCGTGACGTTGGTGGATTTGACTCTGTCTCC (SEQ ID NO: 83) |

*Wherein $X_1$ is C or A. Wherein $X_2$ is C or A.

CDR2:

| | |
|---|---|
| 1443 C16 | GATGTCAGTCATCGGCCCTCA (SEQ ID NO: 84) |
| 1469 M23 | GATGTCAGTCATCGGCCCTCA (SEQ ID NO: 84) |
| 1456 A12 | GATGTCAGTCATCGGCCCTCA (SEQ ID NO: 84) |

TABLE 12-continued

Consensus nucleotide sequences of Kabat CDRs of light chains of 1443 PG16 sister clones.

| | |
|---|---|
| 1503 H05 | GATGTCAGTCATCGGCCCTCA (SEQ ID NO: 84) |
| 1489 I13 | GATGTCAGTCATCGGCCCTCA (SEQ ID NO: 84) |
| 1480 I08 | GATGTCAGTCATCGGCCCTCA (SEQ ID NO: 84) |
| Consensus | GATGTCAGTCATCGGCCCTCA (SEQ ID NO: 84) |

CDR3:

| | |
|---|---|
| 1443 C16 | TCTTCACTGACAGACAGAAGCCATCGCATA (SEQ ID NO: 85) |
| 1469 M23 | TCTTCACTGACAGACAGAAGCCATCGCATA (SEQ ID NO: 85) |
| 1456 A12 | TCTTCATTGACAGACAGAAGCCATCGCATA (SEQ ID NO: 86) |
| 1503 H05 | TCTTCACTGACAGACAGAAGCCATCGCATA (SEQ ID NO: 85) |
| 1489 I13 | TCTTCACTGACAGACAGAAGCCATCGCATA (SEQ ID NO: 85) |
| 1480 I08 | TCTTCACTGACAGACAGAAGCCATCGCATA (SEQ ID NO: 85) |
| Consensus* | TCTTCAXTGACAGACAGAAGCCATCGCATA (SEQ ID NO: 87) |
| Variation1 | TCTTCACTGACAGACAGAAGCCATCGCATA (SEQ ID NO: 85) |
| Variation2 | TCTTCATTGACAGACAGAAGCCATCGCATA (SEQ ID NO: 86) |

*Wherein $X_1$ is C or T and wherein $X_2$ is C or T.

TABLE 13

Consensus protein sequences of Kabat CDRs of Heavy chains of 1443 PG16 sister clones.

CDR1:

| | |
|---|---|
| 1443 C16 | KYGMH (SEQ ID NO: 88) |
| 1469 M23 | KYGMH (SEQ ID NO: 88) |
| 1456 A12 | KYGMH (SEQ ID NO: 88) |
| 1503 H05 | KYGMH (SEQ ID NO: 88) |
| 1489 I13 | KYGMH (SEQ ID NO: 88) |
| 1480 I08 | KYGMH (SEQ ID NO: 88) |
| Consensus | KYGMH (SEQ ID NO: 88) |

CDR2:

| | |
|---|---|
| 1443 C16 | LISDDGMRKYHSDSMWG (SEQ ID NO: 89) |
| 1469 M23 | LISDDGMRKYHSDSMWG (SEQ ID NO: 89) |
| 1456 A12 | LISDDGMRKYHSDSMWG (SEQ ID NO: 89) |
| 1503 H05 | LISDDGMRKYHSDSMWG (SEQ ID NO: 89) |
| 1489 I13 | LISDDGMRKYHSNSMWG (SEQ ID NO: 98) |
| 1480 I08 | LISDDGMRKYHSDSMWG (SEQ ID NO: 89) |
| Consensus* | LISDDGMRKYHSXSMWG (SEQ ID NO: 91) |
| Variation1 | LISDDGMRKYHSDSMWG (SEQ ID NO: 89) |
| Variation2 | LISDDGMRKYHSNSMWG (SEQ ID NO: 98) |

TABLE 13-continued

Consensus protein sequences of Kabat CDRs of Heavy chains of 1443 PG16 sister clones.

*Wherein X is D or N, or wherein X is an amino acid with similar physical properties to either D or N.

CDR3:

| | | |
|---|---|---|
| 1443 C16 | EAGGPIWHDDVKYYDFNDGYYNYHYMDV | (SEQ ID NO: 6) |
| 1469 M23 | EAGGPIWHDDVKYYDFNDGYYNYHYMDV | (SEQ ID NO: 6) |
| 1456 A12 | EAGGPIWHDDVKYYDFNDGYYNYHYMDV | (SEQ ID NO: 6) |
| 1503 H05 | EAGGPIWHDDVKYYDFNDGYYNYHYMDV | (SEQ ID NO: 6) |
| 1489 I13 | EAGGPIWHDDVKYYDFNDGYYNYHYMDV | (SEQ ID NO: 6) |
| 1480 I08 | EAGGPIWHDDVKYYDFNDGYYNYHYMDV | (SEQ ID NO: 6) |
| Consensus | EAGGPIWHDDVKYYDFNDGYYNYHYMDV | (SEQ ID NO: 6) |

TABLE 14

Consensus protein sequences of Kabat CDRs of light chains of 1443 PG16 sister clones.

CDR1:

| | | |
|---|---|---|
| 1443 C16 | NGTSSDVGGFDSVS | (SEQ ID NO: 97) |
| 1469 M23 | NGTRSDVGGFDSVS | (SEQ ID NO: 92) |
| 1456 A12 | NGTSRDVGGFDSVS | (SEQ ID NO: 93) |
| 1503 H05 | NGTRSDVGGFDSVS | (SEQ ID NO: 92) |
| 1489 I13 | NGTSSDVGGFDSVS | (SEQ ID NO: 97) |
| 1480 I08 | NGTSSDVGGFDSVS | (SEQ ID NO: 97) |
| Consensus* | NGT$X_1X_2$DVGGFDSVS | (SEQ ID NO: 94) |
| Variation1 | NGTSSDVGGFDSVS | (SEQ ID NO: 97) |
| Variation2 | NGTRSDVGGFDSVS | (SEQ ID NO: 92) |
| Variation3 | NGTSRDVGGFDSVS | (SEQ ID NO: 93) |

*Wherein $X_1$ is S or R, or wherein $X_1$ is an amino acid with similar physical properties to either S or R. Wherein $X_2$ is S or R, or wherein $X_2$ is an amino acid with similar physical properties to either S or R.

CDR2:

| | | |
|---|---|---|
| 1443 C16 | DVSHRPS | (SEQ ID NO: 95) |
| 1469 M23 | DVSHRPS | (SEQ ID NO: 95) |
| 1456 A12 | DVSHRPS | (SEQ ID NO: 95) |
| 1503 H05 | DVSHRPS | (SEQ ID NO: 95) |
| 1489 I13 | DVSHRPS | (SEQ ID NO: 95) |
| 1408 I08 | DVSHRPS | (SEQ ID NO: 95) |
| Consensus | DVSHRPS | (SEQ ID NO: 95) |

CDR3:

| | | |
|---|---|---|
| 1443 C16 | SSLTDRSHRI | (SEQ ID NO: 41) |
| 1469 M23 | SSLTDRSHRI | (SEQ ID NO: 41) |
| 1456 A12 | SSLTDRSHRI | (SEQ ID NO: 41) |
| 1503 H05 | SSLTDRSHRI | (SEQ ID NO: 41) |

TABLE 14-continued

Consensus protein sequences of Kabat CDRs of light chains of 1443 PG16 sister clones.

| | |
|---|---|
| 1489 I13 | SSLTDRSHRI (SEQ ID NO: 41) |
| 1480 I08 | SSLTDRSHRI (SEQ ID NO: 41) |
| Consensus | SSLTDRSHRI (SEQ ID NO: 41) |

Monoclonal and recombinant antibodies are particularly useful in identification and purification of the individual polypeptides or other antigens against which they are directed. The antibodies of the invention have additional utility in that they may be employed as reagents in immunoassays, radioimmunoassays (MA) or enzyme-linked immunosorbent assays (ELISA). In these applications, the antibodies can be labeled with an analytically-detectable reagent such as a radioisotope, a fluorescent molecule or an enzyme. The antibodies may also be used for the molecular identification and characterization (epitope mapping) of antigens.

As mentioned above, the antibodies of the invention can be used to map the epitopes to which they bind. Applicants have discovered that the antibodies 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456 P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_101 (PGT-137), 4993_K13 (PGT-141), 4995_E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and/or 6881_N05 (PGT-158) neutralize HIV. Although the Applicant does not wish to be bound by this theory, it is postulated that the antibodies 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_101 (PGT-137), 4993_K13 (PGT-141), 4995_E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and/or 6881_N05 (PGT-158) bind to one or more conformational epitopes formed by HIV1-encoded proteins.

Neutralization activity of human monoclonal antibodies was tested against HIV-1 strains SF162 and JR-CSF. HIV-1 strains SF162 and JR-CSF both belong to HIV Glade B. Each clonal monoclonal antibody was screened for neutralization activity and for anti-gp120, anti-gp41 and total IgG in quantitative ELISA. For the monoclonal antibodies 1456_P20, 1495_C14, and 1460_G14 anti-gp120 antigen-specific binding was detected. Neutralizing activity against SF162, but not JR-CSF was detected for 1456 P20 (PG20), 1495_C14 (PGC14), and 1460_G14 (PGG14). For the two monoclonal antibody preparations that did not show binding to gp120 in the ELISA assay, 1443_C16 (PG16) and 1496_C09 (PG9), high quantities of human IgG were determined to be present in the assay. However, 1443_C16 (PG16) and 1496_C09 (PG9) both were found to exhibit neutralizing activity against HIV-1 strain JR-CSF, but not against strain SF162. 1443_C16 (PG16) and 1496_C09 (PG9) also were found to lack gp41 binding activity in the ELISA assay.

The epitopes recognized by these antibodies may have a number of uses. The epitopes and mimotopes in purified or synthetic form can be used to raise immune responses (i.e. as a vaccine, or for the production of antibodies for other uses) or for screening patient serum for antibodies that immunoreact with the epitopes or mimotopes. Preferably, such an epitope or mimotope, or antigen comprising such an epitope or mimotope is used as a vaccine for raising an immune response. The antibodies of the invention can also be used in a method to monitor the quality of vaccines in particular to check that the antigen in a vaccine contains the correct immunogenic epitope in the correct conformation.

The epitopes may also be useful in screening for ligands that bind to said epitopes. Such ligands preferably block the epitopes and thus prevent infection. Such ligands are encompassed within the scope of the invention.

Standard techniques of molecular biology may be used to prepare DNA sequences coding for the antibodies or fragments of the antibodies of the present invention. Desired DNA sequences may be synthesized completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example E. coli, and other microbial systems may be used, in part, for expression of antibody fragments such as Fab and F(ab')2 fragments, and especially Fv fragments and single chain antibody fragments, for example, single chain Fvs. Eukaryotic, e.g. mammalian, host cell expression systems may be used for production of larger antibody molecules, including complete antibody molecules. Suitable mammalian host cells include CHO, HEK293T, PER.C6, myeloma or hybridoma cells.

The present invention also provides a process for the production of an antibody molecule according to the present invention comprising culturing a host cell comprising a vector of the present invention under conditions suitable for leading to expression of protein from DNA encoding the antibody molecule of the present invention, and isolating the antibody molecule. The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Alternatively, antibodies according to the invention may be produced by i) expressing a nucleic acid sequence according to the invention in a cell, and ii) isolating the expressed antibody product. Additionally, the method may include iii) purifying the antibody. Transformed B cells are screened for those producing antibodies of the desired antigen specificity, and individual B cell clones can then be produced from the positive cells. The screening step may be carried out by ELISA, by staining of tissues or cells (including transfected cells), a neutralization assay or one of a number of other methods known in the art for identifying desired antigen specificity. The assay may select on the basis of simple antigen recognition, or may select on the additional basis of a desired function e.g. to select neutralizing antibodies rather than just antigen-binding antibodies, to select antibodies that can change characteristics of targeted cells, such as their signaling cascades, their shape, their growth rate, their capability of influencing other cells, their response to the influence by other cells or by other reagents or by a change in conditions, their differentiation status, etc.

The cloning step for separating individual clones from the mixture of positive cells may be carried out using limiting dilution, micromanipulation, single cell deposition by cell sorting or another method known in the art. Preferably the cloning is carried out using limiting dilution.

The immortalized B cell clones of the invention can be used in various ways e.g. as a source of monoclonal antibodies, as a source of nucleic acid (DNA or mRNA) encoding a monoclonal antibody of interest, for research, etc.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following definitions are useful in understanding the present invention: The term "antibody" (Ab) as used herein includes monoclonal antibodies, polyclonal antibodies, multispecific antibodies (e.g., bispecific antibodies), and antibody fragments, as long as they exhibit the desired biological activity. The term "immunoglobulin" (Ig) is used interchangeably with "antibody" herein.

A "neutralizing antibody" may inhibit the entry of HIV-1 virus for example SF162 and/or JR-CSF with a neutralization index>1.5 or >2.0. (Kostrikis L G et al. J Virol. 1996; 70(1): 445-458.) By "broad and potent neutralizing antibodies" are meant antibodies that neutralize more than one HIV-1 virus species (from diverse clades and different strains within a Glade) in a neutralization assay. A broad neutralizing antibody may neutralize at least 2, 3, 4, 5, 6, 7, 8, 9 or more different strains of HIV-1, the strains belonging to the same or different clades. A broad neutralizing antibody may neutralize multiple HIV-1 species belonging to at least 2, 3, 4, 5, or 6 different clades. The inhibitory concentration of the monoclonal antibody may be less than about 25 mg/ml to neutralize about 50% of the input virus in the neutralization assay.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SD S-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the α and γ chains and four $C_H$ domains for μ and ε isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa (κ) and lambda (λ), based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha (α), delta (δ), epsilon (ε), gamma (γ) and mu (μ), respectively. The γ and α classes are further divided into subclasses on the basis of relatively minor differences in $C_H$ sequence and function, e.g., humans express the following subclasses: $IgG_1$, $IgG_2$, $IgG_3$, $IgG_4$, $IgA_1$, and $IgA_2$.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. e al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

In some aspects, the alternative EBV immortalization method described in WO2004/076677 is used. Using this method, B-cells producing the antibody of the invention can be transformed with EBV in the presence of a polyclonal B cell activator. Transformation with EBV is a standard technique and can easily be adapted to include polyclonal B cell activators. Additional stimulants of cellular growth and differentiation may be added during the transformation step to further enhance the efficiency. These stimulants may be cytokines such as IL-2 and IL-15. In a particularly preferred aspect, IL-2 is added during the immortalization step to further improve the efficiency of immortalization, but its use is not essential.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). The present invention provides variable region antigen-binding sequences derived from human antibodies. Accordingly, chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable region antigen binding sequence of one antibody class or subclass and another sequence, e.g., FR or C region sequence, derived from another antibody class or subclass. Chimeric antibodies of interest herein also include those containing variable region antigen-binding sequences related to those described herein or derived from a different species, such as a non-human primate (e.g., Old World Monkey, Ape, etc.). Chimeric antibodies also include primatized and humanized antibodies.

Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332: 323-329 (1988); and Presta, Curr. Op. Struct. Biol. 2:593-596 (1992).

A "humanized antibody" is generally considered to be a human antibody that has one or more amino acid residues introduced into it from a source that is non-human. These non-human amino acid residues are often referred to as "import" residues, which are typically taken from an "import" variable region. Humanization is traditionally performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting import hypervariable region sequences for the corresponding sequences of a human antibody. Accordingly, such "humanized" antibodies are chimeric antibodies (U.S. Pat. No. 4,816,567), wherein substantially less than an intact human variable region has been substituted by the corresponding sequence from a non-human species.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance.

An "intact" antibody is one that comprises an antigen-binding site as well as a $C_L$ and at least heavy chain constant domains, $C_H1$, $C_H2$ and $C_H3$. The constant domains may be native sequence constant domains (e.g., human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, Fc $_\epsilon$RI.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')2 fragment that roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable region (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

Domain antibodies (dAbs), which can be produced in fully human form, are the smallest known antigen-binding fragments of antibodies, ranging from 11 kDa to 15 kDa. dAbs are the robust variable regions of the heavy and light chains of immunoglobulins ($V_H$ and $V_L$ respectively). They are highly expressed in microbial cell culture, show favourable biophysical properties including solubility and temperature stability, and are well suited to selection and affinity maturation by in vitro selection systems such as phage display. dAbs are bioactive as monomers and, owing to their small size and inherent stability, can be formatted into larger molecules to create drugs with prolonged serum half-lives or other pharmacological activities. Examples of this technology have been described in WO9425591 for antibodies derived from Camelidae heavy chain Ig, as well in US20030130496 describing the isolation of single domain fully human antibodies from phage libraries.

As used herein, an antibody that "internalizes" is one that is taken up by (i.e., enters) the cell upon binding to an antigen on a mammalian cell (e.g., a cell surface polypeptide or receptor). The internalizing antibody will of course include antibody fragments, human or chimeric antibody, and antibody conjugates. For certain therapeutic applications, internalization in vivo is contemplated. The number of antibody molecules internalized will be sufficient or adequate to kill a cell or inhibit its growth, especially an infected cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the infected cell.

As used herein, an antibody is said to be "immunospecific," "specific for" or to "specifically bind" an antigen if it reacts at a detectable level with the antigen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. Affinity of an antibody for its cognate antigen is also commonly expressed as a dissociation constant $K_D$, and in certain embodiments, HIV1 antibody specifically binds to an HIV1 polypeptide if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of antibodies can be readily determined using conventional techniques, for example, those described by Scatchard et al. (*Ann. N.Y. Acad. Sci. USA* 51:660 (1949)).

Binding properties of an antibody to antigens, cells or tissues thereof may generally be determined and assessed using immunodetection methods including, for example, immunofluorescence-based assays, such as immuno-histo-chemistry (IHC) and/or fluorescence-activated cell sorting (FACS).

An antibody having a "biological characteristic" of a designated antibody is one that possesses one or more of the biological characteristics of that antibody which distinguish it from other antibodies. For example, in certain embodiments, an antibody with a biological characteristic of a designated antibody will bind the same epitope as that bound by the designated antibody and/or have a common effector function as the designated antibody.

The term "antagonist" antibody is used in the broadest sense, and includes an antibody that partially or fully blocks, inhibits, or neutralizes a biological activity of an epitope, polypeptide, or cell that it specifically binds. Methods for identifying antagonist antibodies may comprise contacting a polypeptide or cell specifically bound by a candidate antagonist antibody with the candidate antagonist antibody and measuring a detectable change in one or more biological activities normally associated with the polypeptide or cell.

An "antibody that inhibits the growth of infected cells" or a "growth inhibitory" antibody is one that binds to and results in measurable growth inhibition of infected cells expressing or capable of expressing an HIV1 epitope bound by an antibody. Preferred growth inhibitory antibodies inhibit growth of infected cells by greater than 20%, preferably from about 20% to about 50%, and even more preferably, by greater than 50% (e.g., from about 50% to about 100%) as compared to the appropriate control, the control typically being infected cells not treated with the antibody being tested. Growth inhibition can be measured at an antibody concentration of about 0.1 to 30 μg/ml or about 0.5 nM to 200 nM in cell culture, where the growth inhibition is determined 1-10 days after exposure of the infected cells to the antibody. Growth inhibition of infected cells in vivo can be determined in various ways known in the art.

The antibody is growth inhibitory in vivo if administration of the antibody at about 1 μg/kg to about 100 mg/kg body weight results in reduction the percent of infected cells or total number of infected cells within about 5 days to 3 months from the first administration of the antibody, preferably within about 5 to 30 days.

An antibody that "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Preferably the cell is an infected cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody that induces apoptosis is one that results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in Table 4 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells.

Alternatively, or additionally, ADCC activity of the molecule of interest may be assessed in vivo, e.g., in a animal model such as that disclosed in Clynes et al., *Proc. Natl. Acad. Sci.* (USA) 95:652-656 (1998).

"Fc receptor" or "FcR" describes a receptor that binds to the Fc region of an antibody. In certain embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FCγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include PBMC, NK cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al., J. Immunol. Methods 202:163 (1996), may be performed.

A "mammal" for purposes of treating an infection, refers to any mammal, including humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to "treat" a disease or disorder in a subject or mammal. See preceding definition of "treating."

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (polysorbate), polyethylene glycol (PEG), and PLURONICS® (poloxamer).

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $y^{90}$, $Re^{186}$, $Re^{188}$, $Sm^{153}$, $Bi^{212}$, $P^{32}$ and radioactive isotopes of Lu), chemotherapeutic agents e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below.

A "growth inhibitory agent" when used herein refers to a compound or composition which inhibits growth of a cell, either in vitro or in vivo. Examples of growth inhibitory agents include agents that block cell cycle progression, such as agents that induce G1 arrest and M-phase arrest. Classical M-phase blockers include the *vinca* alkaloids (vincristine, vinorelbine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (W B Saunders: Philadelphia, 1995), especially p. 13. The taxanes (paclitaxel and docetaxel) are anticancer drugs both derived from the yew tree. Docetaxel (TAXOTERE™, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Label" as used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable.

The term "epitope tagged" as used herein refers to a chimeric polypeptide comprising a polypeptide fused to a "tag polypeptide." The tag polypeptide has enough residues to provide an epitope against which an antibody can be made, yet is short enough such that it does not interfere with activity of the polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The terms "nucleic acid" and "polynucleotide" are used interchangeably herein to refer to single- or double-stranded RNA, DNA, or mixed polymers. Polynucleotides may include genomic sequences, extra-genomic and plasmid sequences, and smaller engineered gene segments that express, or may be adapted to express polypeptides.

An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising CDRs and being capable of binding an antigen or HIV-infected cell.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "native sequence" polynucleotide is one that has the same nucleotide sequence as a polynucleotide derived from nature. A "native sequence" polypeptide is one that has the same amino acid sequence as a polypeptide (e.g., antibody) derived from nature (e.g., from any species). Such native sequence polynucleotides and polypeptides can be isolated from nature or can be produced by recombinant or synthetic means.

A polynucleotide "variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the invention and evaluating one or more biological activities of the encoded polypeptide as described herein and/or using any of a number of techniques well known in the art.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art.

Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, it's underlying DNA coding sequence, and nevertheless obtain a protein with like properties. It is thus contemplated that various changes may be made in the peptide sequences of the disclosed compositions, or corresponding DNA sequences that encode said peptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, WI), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, CA; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, CA; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, WI), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

"Homology" refers to the percentage of residues in the polynucleotide or polypeptide sequence variant that are identical to the non-variant sequence after aligning the sequences and introducing gaps, if necessary, to achieve the maximum percent homology. In particular embodiments, polynucleotide and polypeptide variants have at least 70%, at least 75%, at least 80%, at least 90%, at least 95%, at least 98%, or at least 99% polynucleotide or polypeptide homology with a polynucleotide or polypeptide described herein.

"Vector" includes shuttle and expression vectors. Typically, the plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells. Suitable vectors are disclosed below. As used in this specification and the appended claims, the singular forms "a," "an" and "the" include plural references unless the content clearly dictates otherwise.

The invention also includes nucleic acid sequences encoding part or all of the light and heavy chains and CDRs of the present invention. Due to redundancy of the genetic code, variants of these sequences will exist that encode the same amino acid sequences.

Variant antibodies are also included within the scope of the invention. Thus, variants of the sequences recited in the application are also included within the scope of the invention. Further variants of the antibody sequences having improved affinity may be obtained using methods known in the art and are included within the scope of the invention. For example, amino acid substitutions may be used to obtain antibodies with further improved affinity. Alternatively, codon optimization of the nucleotide sequence may be used to improve the efficiency of translation in expression systems for the production of the antibody.

Preferably, such variant antibody sequences will share 70% or more (i.e. 80, 85, 90, 95, 97, 98, 99% or more) sequence identity with the sequences recited in the application. Preferably such sequence identity is calculated with regard to the full length of the reference sequence (i.e. the sequence recited in the application). Preferably, percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1].

Further included within the scope of the invention are vectors such as expression vectors, comprising a nucleic acid sequence according to the invention. Cells transformed with such vectors are also included within the scope of the invention.

As will be understood by the skilled artisan, general description of antibodies herein and methods of preparing and using the same also apply to individual antibody polypeptide constituents and antibody fragments.

The antibodies of the present invention may be polyclonal or monoclonal antibodies. However, in preferred embodiments, they are monoclonal. In particular embodiments, antibodies of the present invention are human antibodies. Methods of producing polyclonal and monoclonal antibodies are known in the art and described generally, e.g., in U.S. Pat. No. 6,824,780.

Typically, the antibodies of the present invention are produced recombinantly, using vectors and methods available in the art, as described further below. Human antibodies may also be generated by in vitro activated B cells (see U.S. Pat. Nos. 5,567,610 and 5,229,275).

Human antibodies may also be produced in transgenic animals (e.g., mice) that are capable of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice results in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; and WO 97/17852. Such animals may be genetically engineered to produce human antibodies comprising a polypeptide of the present invention.

In certain embodiments, antibodies of the present invention are chimeric antibodies that comprise sequences derived from both human and non-human sources. In particular embodiments, these chimeric antibodies are humanized or Primatized™. In practice, humanized antibodies are typically human antibodies in which some hypervariable region residues and possibly some FR residues are substituted by residues from analogous sites in rodent antibodies.

In the context of the present invention, chimeric antibodies also include human antibodies wherein the human hypervariable region or one or more CDRs are retained, but one or more other regions of sequence have been replaced by corresponding sequences from a non-human animal.

The choice of non-human sequences, both light and heavy, to be used in making the chimeric antibodies is important to reduce antigenicity and human anti-non-human antibody responses when the antibody is intended for human therapeutic use. It is further important that chimeric antibodies retain high binding affinity for the antigen and other favorable biological properties. To achieve this goal, according to a preferred method, chimeric antibodies are prepared by a process of analysis of the parental sequences and various conceptual chimeric products using three-dimensional models of the parental human and non-human sequences. Three-dimensional immunoglobulin models are commonly available and are familiar to those skilled in the art. Computer programs are available which illustrate and display probable three-dimensional conformational structures of selected candidate immunoglobulin sequences.

Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

As noted above, antibodies (or immunoglobulins) can be divided into five different classes, based on differences in the amino acid sequences in the constant region of the heavy chains. All immunoglobulins within a given class have very similar heavy chain constant regions. These differences can be detected by sequence studies or more commonly by serological means (i.e. by the use of antibodies directed to these differences). Antibodies, or fragments thereof, of the present invention may be any class, and may, therefore, have a gamma, mu, alpha, delta, or epsilon heavy chain. A gamma chain may be gamma 1, gamma 2, gamma 3, or gamma 4; and an alpha chain may be alpha 1 or alpha 2.

In a preferred embodiment, an antibody of the present invention, or fragment thereof, is an IgG. IgG is considered the most versatile immunoglobulin, because it is capable of carrying out all of the functions of immunoglobulin molecules. IgG is the major Ig in serum, and the only class of Ig that crosses the placenta. IgG also fixes complement, although the $IgG_4$ subclass does not. Macrophages, monocytes, PMN's and some lymphocytes have Fc receptors for the Fc region of IgG. Not all subclasses bind equally well: $IgG_2$ and $IgG_4$ do not bind to Fc receptors. A consequence of binding to the Fc receptors on PMN's, monocytes and macrophages is that the cell can now internalize the antigen better. IgG is an opsonin that enhances phagocytosis. Binding of IgG to Fc receptors on other types of cells results in the activation of other functions. Antibodies of the present invention may be of any IgG subclass.

In another preferred embodiment, an antibody, or fragment thereof, of the present invention is an IgE. IgE is the least common serum Ig since it binds very tightly to Fc receptors on basophils and mast cells even before interacting with antigen. As a consequence of its binding to basophils and mast cells, IgE is involved in allergic reactions. Binding of the allergen to the IgE on the cells results in the release of various pharmacological mediators that result in allergic symptoms. IgE also plays a role in parasitic helminth diseases. Eosinophils have Fc receptors for IgE and binding of eosinophils to IgE-coated helminths results in killing of the parasite. IgE does not fix complement.

In various embodiments, antibodies of the present invention, and fragments thereof, comprise a variable light chain that is either kappa or lambda. The lamba chain may be any of subtype, including, e.g., lambda 1, lambda 2, lambda 3, and lambda 4.

As noted above, the present invention further provides antibody fragments comprising a polypeptide of the present invention. In certain circumstances there are advantages of using antibody fragments, rather than whole antibodies. For example, the smaller size of the fragments allows for rapid clearance, and may lead to improved access to certain tissues, such as solid tumors. Examples of antibody fragments include: Fab, Fab', F(ab')2 and Fv fragments; diabodies; linear antibodies; single-chain antibodies; and multispecific antibodies formed from antibody fragments.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Fab'-SH fragments can be directly recovered from *E. coli* and chemically coupled to form F(ab')2 fragments (Carter et al., Bio/Technology 10:163-167 (1992)). According to another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046. Other techniques for the production of antibody fragments will be apparent to the skilled practitioner.

In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions. Thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

In certain embodiments, antibodies of the present invention are bispecific or multispecific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-HIV1 arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and FcγRIII (CD16), so as to focus and localize cellular defense mechanisms to the infected cell. Bispecific antibodies may also be used to localize cytotoxic agents to infected cells. These antibodies possess an HIV1-binding arm and an arm that binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')2 bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a humanized bispecific antibody F(ab')2 molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al., J. Immunol. 147: 60 (1991). A multivalent antibody may be internalized (and/or catabolized) faster than a bivalent antibody by a cell expressing an antigen to which the antibodies bind. The antibodies of the present invention can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-(X1)$_n$-VD2-(X2)$_n$-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a $C_L$ domain.

Antibodies of the invention further include single chain antibodies. In particular embodiments, antibodies of the invention are internalizing antibodies.

Amino acid sequence modification(s) of the antibodies described herein are contemplated. For example, it may be desirable to improve the binding affinity and/or other biological properties of the antibody. Amino acid sequence variants of the antibody may be prepared by introducing appropriate nucleotide changes into a polynucleotide that encodes the antibody, or a chain thereof, or by peptide synthesis. Such modifications include, for example, deletions from, and/or insertions into and/or substitutions of, residues within the amino acid sequences of the antibody. Any combination of deletion, insertion, and substitution may be made to arrive at the final antibody, provided that the final construct possesses the desired characteristics. The amino acid changes also may alter post-translational processes of the antibody, such as changing the number or position of glycosylation sites. Any of the variations and modifications described above for polypeptides of the present invention may be included in antibodies of the present invention.

A useful method for identification of certain residues or regions of an antibody that are preferred locations for mutagenesis is called "alanine scanning mutagenesis" as described by Cunningham and Wells in Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with PSCA antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of an antibody include the fusion to the N- or C-terminus of the antibody to an enzyme (e.g., for ADEPT) or a polypeptide that increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative and non-conservative substitutions are contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

One type of substitutional variant involves substituting one or more hypervariable region residues of a parent antibody. Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and an antigen or infected cell. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The antibody of the invention is modified with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-infection activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-230 (1989). To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Antibodies of the present invention may also be modified to include an epitope tag or label, e.g., for use in purification or diagnostic applications. The invention also pertains to therapy with immunoconjugates comprising an antibody conjugated to an anti-cancer agent such as a cytotoxic agent or a growth inhibitory agent. Chemotherapeutic agents useful in the generation of such immunoconjugates have been described above.

Conjugates of an antibody and one or more small molecule toxins, such as a calicheamicin, maytansinoids, a trichothene, and CC1065, and the derivatives of these toxins that have toxin activity, are also contemplated herein.

In one preferred embodiment, an antibody (full length or fragments) of the invention is conjugated to one or more maytansinoid molecules. Maytansinoids are mitototic inhibitors that act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235_B1. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody conjugates, including, for example, those disclosed in U.S. Pat. No. 5,208,020 or EP Patent 0 425 235_B1, and Chari et al., Cancer Research 52: 127-131 (1992). The linking groups include disufide groups, thioether groups, acid labile groups, photolabile groups, peptidase labile groups, or esterase labile groups, as disclosed in the above-identified patents, disulfide and thioether groups being preferred.

Immunoconjugates may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 [1978]) and N-succinimidyl-4-(2-pyridylthio) pentanoate (SPP) to provide for a disulfide linkage. For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, Cancer Research 52: 127-131 (1992); U.S. Pat. No. 5,208,020) may be used.

Another immunoconjugate of interest comprises an antibody conjugated to one or more calicheamicin molecules. The calicheamicin family of antibiotics is capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Another drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Examples of other agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof that can be used include, e.g., diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232.

The present invention further includes an immunoconjugate formed between an antibody and a compound with nucleolytic activity (e.g., a ribonuclease or a DNA endonuclease such as a deoxyribonuclease; DNase).

For selective destruction of infected cells, the antibody includes a highly radioactive atom. A variety of radioactive isotopes are available for the production of radioconjugated anti-PSCA antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other label is incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al. (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Alternatively, a fusion protein comprising the antibody and cytotoxic agent is made, e.g., by recombinant techniques or peptide synthesis. The length of DNA may comprise respective regions encoding the two portions of the conjugate either adjacent one another or separated by a region encoding a linker peptide which does not destroy the desired properties of the conjugate. The antibodies of the present invention are also used in antibody dependent enzyme mediated prodrug therapy (ADET) by conjugating the antibody to a prodrug-activating enzyme which converts a prodrug (e.g., a peptidyl chemotherapeutic agent, see WO81/01145) to an active anti-cancer drug (see, e.g., WO 88/07378 and U.S. Pat. No. 4,975,278).

The enzyme component of +the immunoconjugate useful for ADEPT includes any enzyme capable of acting on a prodrug in such a way so as to convert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a infected cell population.

The enzymes of this invention can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The antibodies disclosed herein are also formulated as immunoliposomes. A "liposome" is a small vesicle composed of various types of lipids, phospholipids and/or surfactant that is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82:3688 (1985); Hwang et al., Proc. Natl Acad. Sci. USA, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired a diameter. Fab' fragments of the antibody of the present invention can be conjugated to the liposomes as described in Martin et al., J. Biol. Chem. 257: 286-288 (1982) via a disulfide interchange reaction. A chemotherapeutic agent is optionally contained within the liposome. See Gabizon et al., J. National Cancer Inst. 81(19)1484 (1989). Antibodies of the present invention, or fragments thereof, may possess any of a variety of biological or functional characteristics. In certain embodiments, these antibodies are HIV1 protein specific antibodies, indicating that they specifically bind to or preferentially bind to HIV1 as compared to a normal control cell.

In particular embodiments, an antibody of the present invention is an antagonist antibody, which partially or fully blocks or inhibits a biological activity of a polypeptide or cell to which it specifically or preferentially binds. In other embodiments, an antibody of the present invention is a growth inhibitory antibody, which partially or fully blocks or inhibits the growth of an infected cell to which it binds. In another embodiment, an antibody of the present invention induces apoptosis. In yet another embodiment, an antibody of the present invention induces or promotes antibody-dependent cell-mediated cytotoxicity or complement dependent cytotoxicity.

HIV1-expressing cells or virus described above are used to screen the biological sample obtained from a patient infected with HIV1 for the presence of antibodies that preferentially bind to the cell expressing HIV1 polypeptides using standard biological techniques. For example, in certain embodiments, the antibodies may be labeled, and the presence of label associated with the cell detected, e.g., using FMAT or FACs analysis. In particular embodiments, the biological sample is blood, serum, plasma, bronchial lavage, or saliva. Methods of the present invention may be practiced using high throughput techniques.

Identified human antibodies may then be characterized further. For example the particular conformational epitopes with in the HIV1 polypeptides that are necessary or sufficient for binding of the antibody may be determined, e.g., using site-directed mutagenesis of expressed HIV1 polypeptides. These methods may be readily adapted to identify human antibodies that bind any protein expressed on a cell surface. Furthermore, these methods may be adapted to determine binding of the antibody to the virus itself, as opposed to a cell expressing recombinant HIV1 or infected with the virus.

Polynucleotide sequences encoding the antibodies, variable regions thereof, or antigen-binding fragments thereof may be subcloned into expression vectors for the recombinant production of human anti-HIV1 antibodies. In one embodiment, this is accomplished by obtaining mononuclear cells from the patient from the serum containing the identified HIV1 antibody was obtained; producing B cell clones from the mononuclear cells; inducing the B cells to become antibody-producing plasma cells; and screening the supernatants produced by the plasma cells to determine if it contains the HIV1 antibody. Once a B cell clone that produces an HIV1 antibody is identified, reverse-transcription polymerase chain reaction (RT-PCR) is performed to clone the DNAs encoding the variable regions or portions thereof of the HIV1 antibody. These sequences are then subcloned into expression vectors suitable for the recombinant production of human HIV1 antibodies. The binding specificity may be confirmed by determining the recombinant antibody's ability to bind cells expressing HIV1 polypeptide.

In particular embodiments of the methods described herein, B cells isolated from peripheral blood or lymph nodes are sorted, e.g., based on their being CD19 positive, and plated, e.g., as low as a single cell specificity per well, e.g., in 96, 384, or 1536 well configurations. The cells are induced to differentiate into antibody-producing cells, e.g., plasma cells, and the culture supernatants are harvested and tested for binding to cells expressing the infectious agent polypeptide on their surface using, e.g., FMAT or FACS analysis. Positive wells are then subjected to whole well RT-PCR to amplify heavy and light chain variable regions of the IgG molecule expressed by the clonal daughter plasma cells. The resulting PCR products encoding the heavy and light chain variable regions, or portions thereof, are subcloned into human antibody expression vectors for recombinant expression. The resulting recombinant antibodies are then tested to confirm their original binding specificity and may be further tested for pan-specificity across various strains of isolates of the infectious agent.

Thus, in one embodiment, a method of identifying HIV1 antibodies is practiced as follows. First, full length or approximately full length HIV1 cDNAs are transfected into a cell line for expression of HIV1 polypeptides. Secondly, individual human plasma or sera samples are tested for antibodies that bind the cell-expressed HIV1 polypeptides. And lastly, MAbs derived from plasma- or serum-positive individuals are characterized for binding to the same cell-expressed HIV1 polypeptides. Further definition of the fine specificities of the MAbs can be performed at this point.

Polynucleotides that encode the HIV1 antibodies or portions thereof of the present invention may be isolated from cells expressing HIV1 antibodies, according to methods available in the art and described herein, including amplification by polymerase chain reaction using primers specific for conserved regions of human antibody polypeptides. For example, light chain and heavy chain variable regions may be cloned from the B cell according to molecular biology techniques described in WO 92/02551; U.S. Pat. No. 5,627,052; or Babcook et al., Proc. Natl. Acad. Sci. USA 93:7843-48 (1996). In certain embodiments, polynucleotides encoding all or a region of both the heavy and light chain variable regions of the IgG molecule expressed by the clonal daughter plasma cells expressing the HIV1 antibody are subcloned and sequenced. The sequence of the encoded polypeptide may be readily determined from the polynucleotide sequence.

Isolated polynucleotides encoding a polypeptide of the present invention may be subcloned into an expression vector to recombinantly produce antibodies and polypeptides of the present invention, using procedures known in the art and described herein.

Binding properties of an antibody (or fragment thereof) to HIV1 polypeptides or HIv1infected cells or tissues may generally be determined and assessed using immunodetection methods including, for example, immunofluorescence-based assays, such as immuno-histochemistry (IHC) and/or fluorescence-activated cell sorting (FACS). Immunoassay methods may include controls and procedures to determine whether antibodies bind specifically to HIV1 polypeptides from one or more specific clades or strains of HIV, and do not recognize or cross-react with normal control cells.

Following pre-screening of serum to identify patients that produce antibodies to an infectious agent or polypeptide thereof, e.g., HIV1, the methods of the present invention typically include the isolation or purification of B cells from a biological sample previously obtained from a patient or subject. The patient or subject may be currently or previously diagnosed with or suspect or having a particular disease or infection, or the patient or subject may be considered free or a particular disease or infection. Typically, the patient or subject is a mammal and, in particular embodiments, a human. The biological sample may be any sample that contains B cells, including but not limited to, lymph node or lymph node tissue, pleural effusions, peripheral blood, ascites, tumor tissue, or cerebrospinal fluid (CSF). In various embodiments, B cells are isolated from different types of biological samples, such as a biological sample affected by a particular disease or infection. However, it is understood that any biological sample comprising B cells may be used for any of the embodiments of the present invention.

Once isolated, the B cells are induced to produce antibodies, e.g., by culturing the B cells under conditions that support B cell proliferation or development into a plasmacyte, plasmablast, or plasma cell. The antibodies are then screened, typically using high throughput techniques, to identify an antibody that specifically binds to a target antigen, e.g., a particular tissue, cell, infectious agent, or polypeptide. In certain embodiments, the specific antigen, e.g., cell surface polypeptide bound by the antibody is not known, while in other embodiments, the antigen specifically bound by the antibody is known.

According to the present invention, B cells may be isolated from a biological sample, e.g., a tumor, tissue, peripheral blood or lymph node sample, by any means known and available in the art. B cells are typically sorted by FACS based on the presence on their surface of a B cell-specific marker, e.g., CD19, CD138, and/or surface IgG. However, other methods known in the art may be employed, such as, e.g., column purification using CD19 magnetic beads or IgG-specific magnetic beads, followed by elution from the column. However, magnetic isolation of B cells utilizing any marker may result in loss of certain B cells. Therefore, in certain embodiments, the isolated cells are not sorted but, instead, phicol-purified mononuclear cells isolated from tumor are directly plated to the appropriate or desired number of specificities per well.

In order to identify B cells that produce an infectious agent-specific antibody, the B cells are typically plated at low density (e.g., a single cell specificity per well, 1-10 cells per well, 10-100 cells per well, 1-100 cells per well, less than 10 cells per well, or less than 100 cells per well) in multi-well or microtiter plates, e.g., in 96, 384, or 1536 well configurations. When the B cells are initially plated at a density greater than one cell per well, then the methods of the present invention may include the step of subsequently diluting cells in a well identified as producing an antigen-specific antibody, until a single cell specificity per well is achieved, thereby facilitating the identification of the B cell that produces the antigen-specific antibody. Cell supernatants or a portion thereof and/or cells may be frozen and stored for future testing and later recovery of antibody polynucleotides.

In certain embodiments, the B cells are cultured under conditions that favor the production of antibodies by the B cells. For example, the B cells may be cultured under conditions favorable for B cell proliferation and differentiation to yield antibody-producing plasmablast, plasmacytes, or plasma cells. In particular embodiments, the B cells are cultured in the presence of a B cell mitogen, such as lipopolysaccharide (LPS) or CD40 ligand. In one specific embodiment, B cells are differentiated to antibody-producing cells by culturing them with feed cells and/or other B cell activators, such as CD40 ligand.

Cell culture supernatants or antibodies obtained therefrom may be tested for their ability to bind to a target antigen, using routine methods available in the art, including those described herein. In particular embodiments, culture supernatants are tested for the presence of antibodies that bind to a target antigen using high-throughput methods. For example, B cells may be cultured in multi-well microtiter dishes, such that robotic plate handlers may be used to simultaneously sample multiple cell supernatants and test for the presence of antibodies that bind to a target antigen. In particular embodiments, antigens are bound to beads, e.g., paramagnetic or latex beads) to facilitate the capture of antibody/antigen complexes. In other embodiments, antigens and antibodies are fluorescently labeled (with different labels) and FACS analysis is performed to identify the presence of antibodies that bind to target antigen. In one embodiment, antibody binding is determined using FMAT™ analysis and instrumentation (Applied Biosystems, Foster City, CA). FMAT™ is a fluorescence macro-confocal platform for high-throughput screening, which mix-and-read, non-radioactive assays using live cells or beads.

In the context of comparing the binding of an antibody to a particular target antigen (e.g., a biological sample such as infected tissue or cells, or infectious agents) as compared to a control sample (e.g., a biological sample such as uninfected cells, or a different infectious agent), in various embodiments, the antibody is considered to preferentially bind a particular target antigen if at least two-fold, at least three-fold, at least five-fold, or at least ten-fold more antibody binds to the particular target antigen as compared to the amount that binds a control sample.

Polynucleotides encoding antibody chains, variable regions thereof, or fragments thereof, may be isolated from cells utilizing any means available in the art. In one embodiment, polynucleotides are isolated using polymerase chain reaction (PCR), e.g., reverse transcription-PCR (RT-PCR) using oligonucleotide primers that specifically bind to heavy or light chain encoding polynucleotide sequences or complements thereof using routine procedures available in the art. In one embodiment, positive wells are subjected to whole well RT-PCR to amplify the heavy and light chain variable regions of the IgG molecule expressed by the clonal daughter plasma cells. These PCR products may be sequenced.

The resulting PCR products encoding the heavy and light chain variable regions or portions thereof are then subcloned into human antibody expression vectors and recombinantly expressed according to routine procedures in the art (see, e.g., U.S. Pat. No. 7,112,439). The nucleic acid molecules encoding a tumor-specific antibody or fragment thereof, as described herein, may be propagated and expressed according to any of a variety of well-known procedures for nucleic acid excision, ligation, transformation, and transfection. Thus, in certain embodiments expression of an antibody fragment may be preferred in a prokaryotic host cell, such as *Escherichia coli* (see, e.g., Pluckthun et al., *Methods Enzymol.* 178:497-515 (1989)). In certain other embodiments, expression of the antibody or an antigen-binding fragment thereof may be preferred in a eukaryotic host cell, including yeast (e.g., *Saccharomyces cerevisiae, Schizosaccharomyces pombe*, and *Pichia pastoris*); animal cells (including mammalian cells); or plant cells. Examples of suitable animal cells include, but are not limited to, myeloma, COS, CHO, or hybridoma cells. Examples of plant cells include tobacco, corn, soybean, and rice cells. By methods known to those having ordinary skill in the art and based on the present disclosure, a nucleic acid vector may be designed for expressing foreign sequences in a particular host system, and then polynucleotide sequences encoding the tumor-specific antibody (or fragment thereof) may be inserted. The regulatory elements will vary according to the particular host.

One or more replicable expression vectors containing a polynucleotide encoding a variable and/or constant region may be prepared and used to transform an appropriate cell line, for example, a non-producing myeloma cell line, such as a mouse NSO line or a bacterium, such as *E. coli*, in which production of the antibody will occur. In order to obtain efficient transcription and translation, the polynucleotide sequence in each vector should include appropriate regulatory sequences, particularly a promoter and leader sequence operatively linked to the variable region sequence. Particular methods for producing antibodies in this way are generally well known and routinely used. For example, molecular biology procedures are described by Sambrook et al. (*Molecular Cloning, A Laboratory Manual*, 2nd ed., Cold Spring Harbor Laboratory, New York, 1989; see also Sambrook et al., 3rd ed., Cold Spring Harbor Laboratory, New York, (2001)). While not required, in certain embodiments, regions of polynucleotides encoding the recombinant antibodies may be sequenced. DNA sequencing can be performed as described in Sanger et al. (*Proc. Natl. Acad. Sci. USA* 74:5463 (1977)) and the Amersham International plc sequencing handbook and including improvements thereto.

In particular embodiments, the resulting recombinant antibodies or fragments thereof are then tested to confirm their original specificity and may be further tested for pan-specificity, e.g., with related infectious agents. In particular embodiments, an antibody identified or produced according to methods described herein is tested for cell killing via antibody dependent cellular cytotoxicity (ADCC) or apoptosis, and/or well as its ability to internalize.

The present invention, in other aspects, provides polynucleotide compositions. In preferred embodiments, these polynucleotides encode a polypeptide of the invention, e.g., a region of a variable chain of an antibody that binds to HIV1. Polynucleotides of the invention are single-stranded (coding or antisense) or double-stranded DNA (genomic, cDNA or synthetic) or RNA molecules. RNA molecules include, but are not limited to, HnRNA molecules, which contain introns and correspond to a DNA molecule in a one-to-one manner, and mRNA molecules, which do not contain introns. Alternatively, or in addition, coding or non-coding sequences are present within a polynucleotide of the present invention. Also alternatively, or in addition, a polynucleotide is linked to other molecules and/or support materials of the invention. Polynucleotides of the invention are used, e.g., in hybridization assays to detect the presence of an HIV1 antibody in a biological sample, and in the recombinant production of polypeptides of the invention. Further, the invention includes all polynucleotides that encode any polypeptide of the present invention.

In other related embodiments, the invention provides polynucleotide variants having substantial identity to the sequences of 1443_C16 (PG16) (TCN-116), 1503_H05 (PG16) (TCN-119), 1456 A12 (PG16) (TCN-117), 1469 M23 (PG16) (TCN-118), 1489_I13 (PG16) (TCN-120), 1480_I08 (PG16), 1456_P20 (PG20), 1460_G14 (PGG14), 1495_C14 (PGC14), 1496_C09 (PG9) (TCN-109), 4838_L06 (PGT-121), 4873 E03 (PGT-121), 4877_D15 (PGT-122), 4858_P08 (PGT-123), 6123 A06 (PGT-125), 5141_B17 (PGT-126), 5145_B14 (PGT-127), 5114_A19 (PGT-128), 5147_N06 (PGT-130), 5136_H01 (PGT-131), 5343_B08 (PGT-135), 5344_E16 (PGT-135), 5329_C19 (PGT-136), 5366_P21 (PGT-136), 4964_G22 (PGT-141), 5345_101 (PGT-137), 4993_K13 (PGT-141), 4995 E20 (PGT-142), 4980_N08 (PGT-143), 4970_K22 (PGT-144), 4995_P16 (PGT-145), 4835_F12 (PGT-124), 4869-K15 (PGT-133), 4876_M06 (PGT-134), 5131_A17 (PGT-132), 5138_G07 (PGT-138), 5120_N10 (PGT-139), 6831_A21 (PGT-151), 6889_I17 (PGT-152), 6891_F06 (PGT-153), 6843_G20 (PGT-154), 6892_D19 (PGT-155), 6808_B09 (PGT-156), 6892_C23 (PGT-157), and/or 6881_N05 (PGT-158), for example those comprising at least 70% sequence identity, preferably at least 75%, 80%, 85%, 90%, 95%, 96%, 97%, 98%, or 99% or higher, sequence identity compared to a polynucleotide sequence of this invention, as determined using the methods described herein, (e.g., BLAST analysis using standard parameters). One skilled in this art will recognize that these values can be appropriately adjusted to determine corresponding identity of proteins encoded by two nucleotide sequences by taking into account codon degeneracy, amino acid similarity, reading frame positioning, and the like.

Typically, polynucleotide variants contain one or more substitutions, additions, deletions and/or insertions, preferably such that the immunogenic binding properties of the polypeptide encoded by the variant polynucleotide is not substantially diminished relative to a polypeptide encoded by a polynucleotide sequence specifically set forth herein.

In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. As used herein, the term "intermediate lengths" is meant to describe any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In preferred embodiments, the polypeptide encoded by the polynucleotide variant or fragment has the same binding specificity (i.e., specifically or preferentially binds to the same epitope or HIV strain) as the polypeptide encoded by the native polynucleotide. In certain preferred embodiments, the polynucleotides described above, e.g., polynucleotide variants, fragments and hybridizing sequences, encode polypeptides that have a level of binding activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. A nucleic acid fragment of almost any length is employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are included in many implementations of this invention.

It will be appreciated by those of ordinary skill in the art that, as a result of the degeneracy of the genetic code, there are multiple nucleotide sequences that encode a polypeptide as described herein. Some of these polynucleotides bear minimal homology to the nucleotide sequence of any native gene. Nonetheless, polynucleotides that encode a polypeptide of the present invention but which vary due to differences in codon usage are specifically contemplated by the invention. Further, alleles of the genes including the polynucleotide sequences provided herein are within the scope of the invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

In certain embodiments of the present invention, mutagenesis of the disclosed polynucleotide sequences is performed in order to alter one or more properties of the encoded polypeptide, such as its binding specificity or binding strength. Techniques for mutagenesis are well-known in the art, and are widely used to create variants of both polypeptides and polynucleotides. A mutagenesis approach, such as site-specific mutagenesis, is employed for the preparation of variants and/or derivatives of the polypeptides described herein. By this approach, specific modifications in a polypeptide sequence are made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences include the nucleotide sequence of the desired mutation, as well as a sufficient number of adjacent nucleotides, to provide a primer sequence of sufficient size and sequence complexity to form a stable duplex on both sides of the deletion junction being traversed. Mutations are employed in a selected polynucleotide sequence to improve, alter, decrease, modify, or otherwise change the properties of the polynucleotide itself, and/or alter the properties, activity, composition, stability, or primary sequence of the encoded polypeptide.

In other embodiments of the present invention, the polynucleotide sequences provided herein are used as probes or primers for nucleic acid hybridization, e.g., as PCR primers. The ability of such nucleic acid probes to specifically hybridize to a sequence of interest enables them to detect the presence of complementary sequences in a given sample. However, other uses are also encompassed by the invention, such as the use of the sequence information for the preparation of mutant species primers, or primers for use in preparing other genetic constructions. As such, nucleic acid segments of the invention that include a sequence region of at least about a 15-nucleotide long contiguous sequence that has the same sequence as, or is complementary to, a 15 nucleotide long contiguous sequence disclosed herein is particularly useful. Longer contiguous identical or complementary sequences, e.g., those of about 20, 30, 40, 50, 100, 200, 500, 1000 (including all intermediate lengths) including full length sequences, and all lengths in between, are also used in certain embodiments.

Polynucleotide molecules having sequence regions consisting of contiguous nucleotide stretches of 10-14, 15-20, 30, 50, or even of 100-200 nucleotides or so (including intermediate lengths as well), identical or complementary to a polynucleotide sequence disclosed herein, are particularly contemplated as hybridization probes for use in, e.g., Southern and Northern blotting, and/or primers for use in, e.g., polymerase chain reaction (PCR). The total size of fragment, as well as the size of the complementary stretch (es), ultimately depends on the intended use or application of the particular nucleic acid segment. Smaller fragments are generally used in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15-25 nucleotides in length allows the formation of a duplex molecule that is both stable and selective. Molecules having contiguous complementary sequences over stretches greater than 12 bases in length are generally preferred, though, in order to increase stability and selectivity of the hybrid, and thereby improve the quality and degree of specific hybrid molecules obtained. Nucleic acid molecules having gene-complementary stretches of 15 to 25 contiguous nucleotides, or even longer where desired, are generally preferred.

Hybridization probes are selected from any portion of any of the sequences disclosed herein. All that is required is to review the sequences set forth herein, or to any continuous portion of the sequences, from about 15-25 nucleotides in length up to and including the full length sequence, that one wishes to utilize as a probe or primer. The choice of probe and primer sequences is governed by various factors. For example, one may wish to employ primers from towards the termini of the total sequence.

Polynucleotide of the present invention, or fragments or variants thereof, are readily prepared by, for example, directly synthesizing the fragment by chemical means, as is commonly practiced using an automated oligonucleotide synthesizer. Also, fragments are obtained by application of nucleic acid reproduction technology, such as the PCR™ technology of U.S. Pat. No. 4,683,202, by introducing selected sequences into recombinant vectors for recombinant production, and by other recombinant DNA techniques generally known to those of skill in the art of molecular biology.

The invention provides vectors and host cells comprising a nucleic acid of the present invention, as well as recombinant techniques for the production of a polypeptide of the present invention. Vectors of the invention include those capable of replication in any type of cell or organism, including, e.g., plasmids, phage, cosmids, and mini chromosomes. In various embodiments, vectors comprising a polynucleotide of the present invention are vectors suitable for propagation or replication of the polynucleotide, or vectors suitable for expressing a polypeptide of the present invention. Such vectors are known in the art and commercially available.

Polynucleotides of the present invention are synthesized, whole or in parts that are then combined, and inserted into a vector using routine molecular and cell biology techniques, including, e.g., subcloning the polynucleotide into a linearized vector using appropriate restriction sites and restriction enzymes. Polynucleotides of the present invention are amplified by polymerase chain reaction using oligonucleotide primers complementary to each strand of the polynucleotide. These primers also include restriction enzyme cleavage sites to facilitate subcloning into a vector. The replicable vector components generally include, but are not limited to, one or more of the following: a signal sequence, an origin of replication, and one or more marker or selectable genes.

In order to express a polypeptide of the present invention, the nucleotide sequences encoding the polypeptide, or functional equivalents, are inserted into an appropriate expression vector, i.e., a vector that contains the necessary elements for the transcription and translation of the inserted coding sequence. Methods well known to those skilled in the art are used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J., et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems are utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

Within one embodiment, the variable regions of a gene expressing a monoclonal antibody of interest are amplified from a hybridoma cell using nucleotide primers. These primers are synthesized by one of ordinary skill in the art, or may be purchased from commercially available sources (see, e.g., Stratagene (La Jolla, California), which sells primers for amplifying mouse and human variable regions. The primers are used to amplify heavy or light chain variable regions, which are then inserted into vectors such as ImmunoZAP™ H or ImmunoZAP™ L (Stratagene), respectively. These vectors are then introduced into E. coli, yeast, or mammalian-based systems for expression. Large amounts of a single-chain protein containing a fusion of the V H and V L domains are produced using these methods (see Bird et al., Science 242:423-426 (1988)).

The "control elements" or "regulatory sequences" present in an expression vector are those non-translated regions of the vector, e.g., enhancers, promoters, 5' and 3' untranslated regions, that interact with host cellular proteins to carry out transcription and translation. Such elements may vary in their strength and specificity. Depending on the vector system and host utilized, any number of suitable transcription and translation elements, including constitutive and inducible promoters, are used.

Examples of promoters suitable for use with prokaryotic hosts include the phoa promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also usually contain a Shine-Dalgarno sequence operably linked to the DNA encoding the polypeptide. Inducible promoters such as the hybrid lacZ promoter of the PBLUESCRIPT phagemid (Stratagene, La Jolla, Calif.) or PSPORT1 plasmid (Gibco BRL, Gaithersburg, MD) and the like are used.

A variety of promoter sequences are known for eukaryotes and any are used according to the present invention.

Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

In mammalian cell systems, promoters from mammalian genes or from mammalian viruses are generally preferred. Polypeptide expression from vectors in mammalian host cells are controlled, for example, by promoters obtained from the genomes of viruses such as polyoma virus, fowlpox virus, adenovirus (e.g., Adenovirus 2), bovine papilloma virus, avian sarcoma virus, cytomegalovirus (CMV), a retrovirus, hepatitis-B virus and most preferably Simian Virus 40 (SV40), from heterologous mammalian promoters, e.g., the actin promoter or an immunoglobulin promoter, and from heat-shock promoters, provided such promoters are compatible with the host cell systems. If it is necessary to generate a cell line that contains multiple copies of the sequence encoding a polypeptide, vectors based on SV40 or EBV may be advantageously used with an appropriate selectable marker. One example of a suitable expression vector is pcDNA-3.1 (Invitrogen, Carlsbad, CA), which includes a CMV promoter.

A number of viral-based expression systems are available for mammalian expression of polypeptides. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus that is capable of expressing the polypeptide in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

In bacterial systems, any of a number of expression vectors are selected depending upon the use intended for the expressed polypeptide. For example, when large quantities are desired, vectors that direct high level expression of fusion proteins that are readily purified are used. Such vectors include, but are not limited to, the multifunctional E. coli cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase, so that a hybrid protein is produced; pIN vectors (Van Heeke, G. and S. M. Schuster (1989) J. Biol. Chem. 264:5503-5509); and the like. pGEX Vectors (Promega, Madison, WI) are also used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH are used. Examples of other suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. For reviews, see Ausubel et al. (supra) and Grant et al. (1987) Methods Enzymol. 153:516-544. Other yeast promoters that are inducible promoters having the additional advantage of transcription controlled by growth conditions include the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

In cases where plant expression vectors are used, the expression of sequences encoding polypeptides are driven by any of a number of promoters. For example, viral promoters such as the 35S and 19S promoters of CaMV are used alone or in combination with the omega leader sequence from TMV (Takamatsu, N. (1987) EMBO J. 6:307-311. Alternatively, plant promoters such as the small subunit of RUBISCO or heat shock promoters are used (Coruzzi, G. et al. (1984) EMBO J. 3:1671-1680; Broglie, R. et al. (1984) Science 224:838-843; and Winter, J., et al. (1991) Results Probl. Cell Differ. 17:85-105). These constructs can be introduced into plant cells by direct DNA transformation or pathogen-mediated transfection. Such techniques are described in a number of generally available reviews (see, e.g., Hobbs, S. or Murry, L. E. in McGraw Hill Yearbook of Science and Technology (1992) McGraw Hill, New York, N.Y.; pp. 191-196).

An insect system is also used to express a polypeptide of interest. For example, in one such system, Autographa californica nuclear polyhedrosis virus (AcNPV) is used as a vector to express foreign genes in Spodoptera frupperda cells or in Trichoplusia larvae. The sequences encoding the polypeptide are cloned into a non-essential region of the virus, such as the polyhedrin gene, and placed under control of the polyhedrin promoter. Successful insertion of the polypeptide-encoding sequence renders the polyhedrin gene inactive and produce recombinant virus lacking coat protein. The recombinant viruses are then used to infect, for example, S. frugiperda cells or Trichoplusia larvae, in which the polypeptide of interest is expressed (Engelhard, E. K. et al. (1994) Proc. Natl. Acad. Sci. 91:3224-3227).

Specific initiation signals are also used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon are provided. Furthermore, the initiation codon is in the correct reading frame to ensure correct translation of the inserted polynucleotide. Exogenous translational elements and initiation codons are of various origins, both natural and synthetic.

Transcription of a DNA encoding a polypeptide of the invention is often increased by inserting an enhancer sequence into the vector. Many enhancer sequences are known, including, e.g., those identified in genes encoding globin, elastase, albumin, a-fetoprotein, and insulin. Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer is spliced into the vector at a position 5' or 3' to the polypeptide-encoding sequence, but is preferably located at a site 5' from the promoter.

Expression vectors used in eukaryotic host cells (yeast, fungi, insect, plant, animal, human, or nucleated cells from other multicellular organisms) typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-PSCA antibody. One useful transcription termination component is the bovine growth hormone polyadenylation region. See WO94/11026 and the expression vector disclosed therein.

Suitable host cells for cloning or expressing the DNA in the vectors herein are the prokaryote, yeast, plant or higher eukaryote cells described above. Examples of suitable prokaryotes for this purpose include eubacteria, such as Gram-negative or Gram-positive organisms, for example, Enterobacteriaceae such as *Escherichia*, e.g., *E. coli, Enterobacter, Envinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli*_B, *E. coli* X1776 (ATCC 31,537), and *E. coli* W3110 (ATCC 27,325) are suitable. These examples are illustrative rather than limiting.

*Saccharomyces cerevisiae*, or common baker's yeast, is the most commonly used among lower eukaryotic host microorganisms. However, a number of other genera, species, and strains are commonly available and used herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waitii* (ATCC 56,500), *K. drosophilarum* (ATCC 36,906), *K. thermotolerans*, and *K. marxianus; yarrowia* (EP 402, 226); *Pichia pastoris*. (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

In certain embodiments, a host cell strain is chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing that cleaves a "prepro" form of the protein is also used to facilitate correct insertion, folding and/or function. Different host cells such as CHO, COS, HeLa, MDCK, HEK293, and WI38, which have specific cellular machinery and characteristic mechanisms for such post-translational activities, are chosen to ensure the correct modification and processing of the foreign protein.

Methods and reagents specifically adapted for the expression of antibodies or fragments thereof are also known and available in the art, including those described, e.g., in U.S. Pat. Nos. 4,816,567 and 6,331,415. In various embodiments, antibody heavy and light chains, or fragments thereof, are expressed from the same or separate expression vectors. In one embodiment, both chains are expressed in the same cell, thereby facilitating the formation of a functional antibody or fragment thereof.

Full length antibody, antibody fragments, and antibody fusion proteins are produced in bacteria, in particular when glycosylation and Fc effector function are not needed, such as when the therapeutic antibody is conjugated to a cytotoxic agent (e.g., a toxin) and the immunoconjugate by itself shows effectiveness in infected cell destruction. For expression of antibody fragments and polypeptides in bacteria, see, e.g., U.S. Pat. Nos. 5,648,237, 5,789,199, and 5,840,523, which describes translation initiation region (TIR) and signal sequences for optimizing expression and secretion. After expression, the antibody is isolated from the *E. coli* cell paste in a soluble fraction and can be purified through, e.g., a protein A or G column depending on the isotype. Final purification can be carried out using a process similar to that used for purifying antibody expressed e.g., in CHO cells.

Suitable host cells for the expression of glycosylated polypeptides and antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopicius* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses are used as the virus herein according to the present invention, particularly for transfection of *Spodoptera frugiperda* cells. Plant cell cultures of cotton, corn, potato, soybean, *petunia*, tomato, and tobacco are also utilized as hosts.

Methods of propagation of antibody polypeptides and fragments thereof in vertebrate cells in culture (tissue culture) are encompassed by the invention. Examples of mammalian host cell lines used in the methods of the invention are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for polypeptide production and cultured in conventional nutrient media modified as appropriate for inducing promoters, selecting transformants, or amplifying the genes encoding the desired sequences.

For long-term, high-yield production of recombinant proteins, stable expression is generally preferred. For example, cell lines that stably express a polynucleotide of interest are transformed using expression vectors that contain viral origins of replication and/or endogenous expression elements and a selectable marker gene on the same or on a separate vector. Following the introduction of the vector, cells are allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells are proliferated using tissue culture techniques appropriate to the cell type.

A plurality of selection systems are used to recover transformed cell lines. These include, but are not limited to, the herpes simplex virus thymidine kinase (Wigler, M. et al. (1977) Cell 11:223-32) and adenine phosphoribosyltransferase (Lowy, I. et al. (1990) Cell 22:817-23) genes that are employed in tk⁻ or aprt⁻ cells, respectively. Also, antimetabolite, antibiotic or herbicide resistance is used as the basis for selection; for example, dhfr, which confers resistance to methotrexate (Wigler, M. et al. (1980) *Proc. Natl. Acad. Sci.* 77:3567-70); npt, which confers resistance to the aminoglycosides, neomycin and G-418 (Colbere-Garapin, F. et al. (1981) *J Mol. Biol.* 150:1-14); and als or pat, which confer resistance to chlorsulfuron and phosphinotricin acetyltransferase, respectively (Murry, supra). Additional selectable genes have been described. For example, trpB allows cells to utilize indole in place of tryptophan, and hisD allows cells to utilize histinol in place of histidine (Hartman, S. C. and R. C. Mulligan (1988) *Proc. Natl. Acad. Sci.* 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121-131).

Although the presence/absence of marker gene expression suggests that the gene of interest is also present, its presence and expression is confirmed. For example, if the sequence encoding a polypeptide is inserted within a marker gene sequence, recombinant cells containing sequences are identified by the absence of marker gene function. Alternatively, a marker gene is placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence are identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Nonlimiting examples include enzyme-linked immunosorbent assay (ELISA), radioimmunoassay (MA), and fluorescence activated cell sorting (FACS). A two-site, monoclonal-based immunoassay utilizing monoclonal antibodies reactive to two non-interfering epitopes on a given polypeptide is preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; J. Exp. Med. 158:1211-1216).

Various labels and conjugation techniques are known by those skilled in the art and are used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof are cloned into a vector for the production of an mRNA probe. Such vectors are known in the art, are commercially available, and are used to synthesize RNA probes in vitro by addition of an appropriate RNA polymerase such as T7, T3, or SP6 and labeled nucleotides. These procedures are conducted using a variety of commercially available kits. Suitable reporter molecules or labels, which are used include, but are not limited to, radionucleotides, enzymes, fluorescent, chemiluminescent, or chromogenic agents as well as substrates, cofactors, inhibitors, magnetic particles, and the like.

The polypeptide produced by a recombinant cell is secreted or contained intracellularly depending on the sequence and/or the vector used. Expression vectors containing polynucleotides of the invention are designed to contain signal sequences that direct secretion of the encoded polypeptide through a prokaryotic or eukaryotic cell membrane.

In certain embodiments, a polypeptide of the invention is produced as a fusion polypeptide further including a polypeptide domain that facilitates purification of soluble proteins. Such purification-facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Amgen, Seattle, WA). The inclusion of cleavable linker sequences such as those specific for Factor XA or enterokinase (Invitrogen. San Diego, CA) between the purification domain and the encoded polypeptide are used to facilitate purification. An exemplary expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3:263-281) while the enterokinase cleavage site provides a means for purifying the desired polypeptide from the fusion protein. A discussion of vectors used for producing fusion proteins is provided in Kroll, D. J. et al. (1993; DNA Cell Biol. /2:441-453).

In certain embodiments, a polypeptide of the present invention is fused with a heterologous polypeptide, which may be a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells, the signal sequence is selected, for example, from the group of the alkaline phosphatase, penicillinase, lpp, or heat-stable enterotoxin II leaders. For yeast secretion, the signal sequence is selected from, e.g., the yeast invertase leader, a factor leader (including *Saccharomyces* and *Kluyveromyces* factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

When using recombinant techniques, the polypeptide or antibody is produced intracellularly, in the periplasmic space, or directly secreted into the medium. If the polypeptide or antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies that are secreted to the periplasmic space of E. coli. Briefly, cell paste is thawed in the presence of sodium acetate (pH 3.5), EDTA, and phenylmethylsulfonylfluoride (PMSF) over about 30 min. Cell debris is removed by centrifugation. Where the polypeptide or antibody is secreted into the medium, supernatants from such expression systems are generally first concentrated using a commercially available protein concentration filter, for example, an Amicon or Millipore Pellicon ultrafiltration unit. Optionally, a protease inhibitor such as PMSF is included in any of the foregoing steps to inhibit proteolysis and antibiotics are included to prevent the growth of adventitious contaminants.

The polypeptide or antibody composition prepared from the cells are purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the polypeptide or antibody. Protein A is used to purify antibodies or fragments thereof that are based on human $\gamma_1$, $\gamma_2$, or $\gamma_4$ heavy chains (Lindmark et al., J. Immunol. Meth. 62:1-13 (1983)). Protein G is recommended for all mouse isotypes and for human $\gamma_3$ (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the polypeptide or antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the polypeptide or antibody to be recovered.

Following any preliminary purification step(s), the mixture comprising the polypeptide or antibody of interest and contaminants are subjected to low pH hydrophobic interaction chromatography using an elution buffer at a pH between about 2.5-4.5, preferably performed at low salt concentrations (e.g., from about 0-0.25M salt).

The invention further includes pharmaceutical formulations including a polypeptide, antibody, or modulator of the present invention, at a desired degree of purity, and a pharmaceutically acceptable carrier, excipient, or stabilizer (Remington's Pharmaceutical Sciences 16th edition, Osol, A. Ed. (1980)). In certain embodiments, pharmaceutical formulations are prepared to enhance the stability of the polypeptide or antibody during storage, e.g., in the form of lyophilized formulations or aqueous solutions.

Acceptable carriers, excipients, or stabilizers are nontoxic to recipients at the dosages and concentrations employed, and include, e.g., buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN® (polysorbate), PLURONICS® (poloxamer), or polyethylene glycol (PEG). In certain embodiments, the therapeutic formulation preferably comprises the polypeptide or antibody at a concentration of between 5-200 mg/ml, preferably between 10-100 mg/ml.

The formulations herein also contain one or more additional therapeutic agents suitable for the treatment of the particular indication, e.g., infection being treated, or to prevent undesired side-effects. Preferably, the additional therapeutic agent has an activity complementary to the polypeptide or antibody of the resent invention, and the two do not adversely affect each other. For example, in addition to the polypeptide or antibody of the invention, an additional or second antibody, anti-viral agent, anti-infective agent and/or cardioprotectant is added to the formulation. Such molecules are suitably present in the pharmaceutical formulation in amounts that are effective for the purpose intended.

The active ingredients, e.g., polypeptides and antibodies of the invention and other therapeutic agents, are also entrapped in microcapsules prepared, for example, by coacervation techniques or by interfacial polymerization, for example, hydroxymethylcellulose or gelatin-microcapsules and polymethylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations are prepared. Suitable examples of sustained-release preparations include, but are not limited to, semi-permeable matrices of solid hydrophobic polymers containing the antibody, which matrices are in the form of shaped articles, e.g., films, or microcapsules. Nonlimiting examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

Formulations to be used for in vivo administration are preferably sterile. This is readily accomplished by filtration through sterile filtration membranes.

Antibodies of the invention can be coupled to a drug for delivery to a treatment site or coupled to a detectable label to facilitate imaging of a site comprising cells of interest, such as cells infected with HIV. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody of the invention and an epitope of interest (an HIV epitope) can be facilitated by attaching a detectable substance to the antibody. Suitable detection means include the use of labels such as radionucleotides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, B-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include $^{125}I$, $^{131}I$, $^{35}S$, or $^3H$. Such labeled reagents may be used in a variety of well-known assays, such as radioimmunoassays, enzyme immunoassays, e.g., ELISA, fluorescent immunoassays, and the like.

The antibodies are tagged with such labels by known methods. For instance, coupling agents such as aldehydes, carbodiimides, dimaleimide, imidates, succinimides, biddiazotized benzadine and the like are used to tag the antibodies with the above-described fluorescent, chemiluminescent, and enzyme labels. An enzyme is typically combined with an antibody using bridging molecules such as carbodiimides, periodate, diisocyanates, glutaraldehyde and the like. Various labeling techniques are described in Morrison, Methods in Enzymology 32b, 103 (1974), Syvanen et al., J. Biol. Chem. 284, 3762 (1973) and Bolton and Hunter, Biochem J. 133, 529(1973).

An antibody according to the invention may be conjugated to a therapeutic moiety such as a cytotoxin, a therapeutic agent, or a radioactive metal ion or radioisotope. Examples of radioisotopes include, but are not limited to, 1-131, 1-123, 1-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin.

Techniques for conjugating such therapeutic moiety to antibodies are well known. See, for example, Arnon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-256; ed. Hellstrom et al. (1987) "Antibodies for Drug Delivery," in Controlled Drug Delivery, ed. Robinson et al. (2d ed; Marcel Dekker, Inc.), pp. 623-653; Thorpe (1985) "Antibody Carriers of Cytotoxic Agents in Cancer Therapy: A Review," in Monoclonal Antibodies '84: Biological and Clinical Applications, ed. Pinchera et al. pp. 475-506 (Editrice Kurtis, Milano, Italy, 1985); "Analysis, Results, and Future Prospective of the Therapeutic Use of Radiolabeled Antibody in Cancer Therapy," in Monoclonal Antibodies for Cancer Detection and Therapy, ed. Baldwin et al. (Academic Press, New York, 1985), pp. 303-316; and Thorpe et al. (1982) Immunol. Rev. 62:119-158.

Diagnostic methods generally involve contacting a biological sample obtained from a patient, such as, e.g., blood, serum, saliva, urine, sputum, a cell swab sample, or a tissue biopsy, with an HIV1 antibody and determining whether the antibody preferentially binds to the sample as compared to a control sample or predetermined cut-off value, thereby indicating the presence of infected cells. In particular embodiments, at least two-fold, three-fold, or five-fold more HIV1 antibody binds to an infected cell as compared to an appropriate control normal cell or tissue sample. A predetermined cut-off value is determined, e.g., by averaging the amount of HIV1 antibody that binds to several different appropriate control samples under the same conditions used to perform the diagnostic assay of the biological sample being tested.

Bound antibody is detected using procedures described herein and known in the art. In certain embodiments, diagnostic methods of the invention are practiced using HIV1 antibodies that are conjugated to a detectable label, e.g., a fluorophore, to facilitate detection of bound antibody. However, they are also practiced using methods of secondary detection of the HIV1 antibody. These include, for example, MA, ELISA, precipitation, agglutination, complement fixation and immunofluorescence.

HIV1 antibodies of the present invention are capable of differentiating between patients with and patients without an HIV infection, and determining whether or not a patient has an infection, using the representative assays provided herein. According to one method, a biological sample is obtained from a patient suspected of having or known to have HIV1 infection. In preferred embodiments, the biological sample includes cells from the patient. The sample is contacted with an HIV1 antibody, e.g., for a time and under conditions sufficient to allow the HIV1 antibody to bind to infected cells present in the sample. For instance, the sample is contacted with an HIV1 antibody for 10 seconds, 30 seconds, 1 minute, 5 minutes, 10 minutes, 30 minutes, 1 hour, 6 hours, 12 hours, 24 hours, 3 days or any point in between. The amount of bound HIV1 antibody is determined and compared to a control value, which may be, e.g., a predetermined value or a value determined from normal tissue sample. An increased amount of antibody bound to the patient sample as compared to the control sample is indicative of the presence of infected cells in the patient sample.

In a related method, a biological sample obtained from a patient is contacted with an HIV1 antibody for a time and under conditions sufficient to allow the antibody to bind to infected cells. Bound antibody is then detected, and the presence of bound antibody indicates that the sample contains infected cells. This embodiment is particularly useful when the HIV1 antibody does not bind normal cells at a detectable level.

Different HIV1 antibodies possess different binding and specificity characteristics. Depending upon these characteristics, particular HIV1 antibodies are used to detect the presence of one or more strains of HIV1. For example, certain antibodies bind specifically to only one or several strains of HIV1, whereas others bind to all or a majority of different strains of HIV1. Antibodies specific for only one strain of HIV1 are used to identify the strain of an infection.

In certain embodiments, antibodies that bind to an infected cell preferably generate a signal indicating the presence of an infection in at least about 20% of patients with the infection being detected, more preferably at least about 30% of patients. Alternatively, or in addition, the antibody generates a negative signal indicating the absence of the infection in at least about 90% of individuals without the infection being detected. Each antibody satisfies the above criteria; however, antibodies of the present invention are used in combination to improve sensitivity.

The present invention also includes kits useful in performing diagnostic and prognostic assays using the antibodies of the present invention. Kits of the invention include a suitable container comprising an HIV1 antibody of the invention in either labeled or unlabeled form. In addition, when the antibody is supplied in a labeled form suitable for an indirect binding assay, the kit further includes reagents for performing the appropriate indirect assay. For example, the kit includes one or more suitable containers including enzyme substrates or derivatizing agents, depending on the nature of the label. Control samples and/or instructions are also included.

Passive immunization has proven to be an effective and safe strategy for the prevention and treatment of viral diseases. (See Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999), each of which are incorporated herein by reference)). Passive immunization using human monoclonal antibodies, provide an immediate treatment strategy for emergency prophylaxis and treatment of HIV1.

HIV1 antibodies and fragments thereof, and therapeutic compositions, of the invention specifically bind or preferentially bind to infected cells, as compared to normal control uninfected cells and tissue. Thus, these HIV1 antibodies are used to selectively target infected cells or tissues in a patient, biological sample, or cell population. In light of the infection-specific binding properties of these antibodies, the present invention provides methods of regulating (e.g., inhibiting) the growth of infected cells, methods of killing infected cells, and methods of inducing apoptosis of infected cells. These methods include contacting an infected cell with an HIV1 antibody of the invention. These methods are practiced in vitro, ex vivo, and in vivo.

In various embodiments, antibodies of the invention are intrinsically therapeutically active. Alternatively, or in addition, antibodies of the invention are conjugated to a cytotoxic agent or growth inhibitory agent, e.g., a radioisotope or toxin that is used in treating infected cells bound or contacted by the antibody.

Subjects at risk for HIV1-related diseases or disorders include patients who have come into contact with an infected person or who have been exposed to HIV1 in some other way. Administration of a prophylactic agent can occur prior to the manifestation of symptoms characteristic of HIV1-related disease or disorder, such that a disease or disorder is prevented or, alternatively, delayed in its progression.

Methods for preventing an increase in HIV1 virus titer, virus replication, virus proliferation or an amount of an HIV1 viral protein in a subject are further provided. In one embodiment, a method includes administering to the subject an amount of an HIV1 antibody effective to prevent an increase in HIV1 titer, virus replication or an amount of an HIV1 protein of one or more HIV strains or isolates in the subject.

For in vivo treatment of human and non-human patients, the patient is usually administered or provided a pharmaceutical formulation including an HIV1 antibody of the invention. When used for in vivo therapy, the antibodies of the invention are administered to the patient in therapeutically effective amounts (i.e., amounts that eliminate or reduce the patient's viral burden). The antibodies are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The antibodies may be administered parenterally, when possible, at the target cell site, or intravenously. Intravenous or subcutaneous administration of the antibody is preferred in certain embodiments. Therapeutic compositions of the invention are administered to a patient or subject systemically, parenterally, or locally.

For parenteral administration, the antibodies are formulated in a unit dosage injectable form (solution, suspension, emulsion) in association with a pharmaceutically acceptable, parenteral vehicle. Examples of such vehicles are water, saline, Ringer's solution, dextrose solution, and 5% human serum albumin. Nonaqueous vehicles such as fixed oils and ethyl oleate are also used. Liposomes are used as carriers. The vehicle contains minor amounts of additives such as substances that enhance isotonicity and chemical stability, e.g., buffers and preservatives. The antibodies are typically formulated in such vehicles at concentrations of about 1 mg/ml to 10 mg/ml.

The dose and dosage regimen depends upon a variety of factors readily determined by a physician, such as the nature of the infection and the characteristics of the particular cytotoxic agent or growth inhibitory agent conjugated to the antibody (when used), e.g., its therapeutic index, the patient, and the patient's history. Generally, a therapeutically effective amount of an antibody is administered to a patient. In particular embodiments, the amount of antibody administered is in the range of about 0.1 mg/kg to about 50 mg/kg of patient body weight. Depending on the type and severity of the infection, about 0.1 mg/kg to about 50 mg/kg body weight (e.g., about 0.1-15 mg/kg/dose) of antibody is an initial candidate dosage for administration to the patient, whether, for example, by one or more separate administrations, or by continuous infusion. The progress of this therapy is readily monitored by conventional methods and assays and based on criteria known to the physician or other persons of skill in the art.

In one particular embodiment, an immunoconjugate including the antibody conjugated with a cytotoxic agent is administered to the patient. Preferably, the immunoconjugate is internalized by the cell, resulting in increased therapeutic efficacy of the immunoconjugate in killing the cell to which it binds. In one embodiment, the cytotoxic agent targets or interferes with the nucleic acid in the infected cell. Examples of such cytotoxic agents are described above and include, but are not limited to, maytansinoids, calicheamicins, ribonucleases and DNA endonucleases.

Other therapeutic regimens are combined with the administration of the HIV1 antibody of the present invention. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

In certain embodiments, it is desirable to combine administration of an antibody of the invention with another antibody directed against another antigen associated with the infectious agent.

Aside from administration of the antibody protein to the patient, the invention provides methods of administration of the antibody by gene therapy. Such administration of nucleic acid encoding the antibody is encompassed by the expression "administering a therapeutically effective amount of an antibody". See, for example, PCT Patent Application Publication WO96/07321 concerning the use of gene therapy to generate intracellular antibodies.

In another embodiment, anti-HIV1 antibodies of the invention are used to determine the structure of bound antigen, e.g., conformational epitopes, the structure of which is then used to develop a vaccine having or mimicking this structure, e.g., through chemical modeling and SAR methods. Such a vaccine could then be used to prevent HIV1 infection.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Selection of Patient Sample

Serum from approximately 1,800 HIV-1 infected donors from Asia, Australia, Europe, North America and sub-Saharan African countries were screened for neutralization activity and donors who exhibit among the broadest and most potent neutralizing serum activity observed to date were identified. (Simek, M. D., *J Virol* (2009)). Monoclonal antibodies were generated from these donors using different approaches.

A patient was selected based upon the patient's eligibility for enrollment, which was defined as: male or female at least 18 years of age with documented HIV infection for at least three years, clinically asymptomatic at the time of enrollment, and not currently receiving antiretroviral therapy. (Simek, M. D., *J Virol* (2009 July) 83(14):7337-48). Selection of individuals for monoclonal antibody generation was based on a rank-order high throughput analytical screening algorithm. The volunteer was identified as an individual with broad neutralizing serum based on broad and potent neutralizing activity against a cross-Glade pseudovirus panel.

A novel high-throughput strategy was used to screen IgG-containing culture supernatants from approximately 30,000 activated memory B cells from a Glade A infected donor for recombinant, monomeric $gp120_{JR-CSF}$ and $gp41_{HxB2}$ (Env) binding as well as neutralization activity against $HIV-1_{JR-CSF}$ and $HIV-1_{SF162}$ as shown in Table 1. The memory B cells were cultured at near clonal density such that the authentic antibody heavy and light chain pair could be reconstituted from each culture well.

Example 2: Generation of Monoclonal Antibodies

The human monoclonal antibody discovery platform utilized a short term B cell culture system to interrogate the memory B cell repertoire. 30,300 $CD19^+$ and surface IgG-expressing memory B cells were isolated from ten million peripheral blood mononuclear cells (PBMC) of the HIV-1 infected donor. $CD19^+/sIgG^+$ B cells were then seeded in 384-well microtiter plates at an average of 1.3 cells/well under conditions that promoted B cell activation, proliferation, terminal differentiation and antibody secretion. Culture supernatants were screened in a high throughput format for binding reactivity to recombinant gp120 and gp41 indirectly and directly immobilized on ELISA plates, respectively. In parallel, the culture supernatants were also screened for neutralization activity in a high throughput micro-neutralization assay.

Heavy and light variable regions were isolated from lysates of selected neutralizing hits by RT-PCR amplification using family-specific primer sets. From positive family-specific PCR reactions, pools of the $V_H$ or $V_L$-region clones were cloned into an expression vector upstream to human $IgG_1$ constant domain sequence. Minipreps (QIAGEN, Valencia, CA) of these DNA pools, derived from suspension bacterial cultures, were combined in all possible heavy and light chain family-specific pairs and used to transiently transfect 293 cells. All transfectant supernatants containing secreted recombinant antibodies were screened in ELISA and neutralization assays. For B-cell wells that contained more than one B cell clone per culture well, multiple $V_H$ and $V_L$ domain sequences were isolated. ELISA (for B-cell wells positive for ELISA) and neutralization screens identified the heavy and light chain combination pools that reconstituted the binding and neutralizing activity as observed for the B-cell well. DNA sequences of the heavy and light chain variable regions for all neutralizing mAbs were confirmed by multiple sequencing reactions using purified DNA from maxipreps (QIAGEN).

Example 3: Screening of Monoclonal Antibodies for Binding to Recombinant Gp120 and Gp41 by ELISA Assay Recombinant gp120 with sequence derived from gp120 of primary HIV-1 isolate JR-CSF and expressed in insect cells was obtained from IAVI NAC repository. Recombinant gp41 generated with sequences derived from HxB2 clone of HIV-1 and expressed in *Pichia pastoris* was manufactured by Vybion, Inc., obtained from IAVI NAC repository Sheep anti-gp120 antibodies used as capturing agent to indirectly immobilize gp120 on ELISA plates was purchased from Aalto Bio Reagents (Dublin, Ireland). All ELISA assays were conducted at 25 µL/well on Maxi Sorp plates from Nunc.

In anti-gp120 ELISA, recombinant gp120 (0.5 µg/ml) was captured on 384 well ELISA plates pre-coated (at 4° C. overnight) with goat anti-gp120 (5 µg/ml) in BSA-containing assay buffer (PBS with 0.05% TWEEN® 20 (polysorbate 20)) for 1 hr at room temperature. After excess gp120 was removed and plates were washed thrice with assay buffer, B cell culture supernatants diluted 5-fold was added to incubate for 1 hr at room temperature. Following three washes in assay buffer, secondary HRP-conjugated goat anti-human Ig Fc in BSA-containing assay buffer was added and incubated for about 1 hr at room temperature. 3,3',5,5'-tetramethylbenzidine (TMB) substrate was used to develop the colorimetric readouts after washing the ELISA plates 3 times.

For anti-gp41 ELISA, recombinant gp41 was directly immobilized on 384 well ELISA plates by adding 1 µg/ml and incubating at 4° C. overnight, followed by blocking with BSA-containing assay buffer. The rest of the assay protocol was similar to that for anti-gp120 ELISA.

Hits from the ELISA assay were identified in a singlet screen based on optical density (OD) values above 3x assay background. A serial titration standard curve of control antibody was included on each plate.

Example 4: Neutralization Assay for Screening Antibodies against Pseudotyped HIV Viruses The neutralization assay approach has been described previously (Binley J M, et al., (2004). Comprehensive Cross-Clade Neutralization Analysis of a Panel of Anti-Human Immunodeficiency Virus Type 1 Monoclonal Antibodies. *J. Virol.* 78: 13232-13252) and was modified and standardized for implementation in 384-well format.

Neutralization by monoclonal antibodies and patient sera was performed using a single round of replication pseudovirus assay. (Richman, D. D., et al. *Proc Natl Acad Sci USA* 100, 4144-4149 (2003)). Pseudovirus neutralization assays were performed using HIV-1JR-csF alanine mutants as described in Pantophlet, R., et al. *J Virol* 77, 642-658 (2003). Neutralization activity was measured as a reduction in viral infectivity compared to an antibody-free control using a TZM-BL assay. (Li, M., et al., *J Virol* 79, 10108-10125 (2005)). Monoclonal antibody neutralization assays using phytohaemgglutinin-activated peripheral blood mononuclear cells (PBMC) isolated from three healthy human donors as target cells were performed as described in Scarlatti, G. et al, (1993) J. Infect. Dis. 168:207-210; Polonis, V. et al, (2001) AIDS Res. Hum. Retroviruses 17:69-79. Memory B cell supernatants were screened in a microneutralization assay against HIV-ISF162, HIV-1$_{JR\text{-}CSF}$, and SIV$_{mac239}$ (negative control). This assay was based on the 96-well pseudotyped HIV-1 neutralization assay (Monogram Biosciences) and was modified for screening 15 μl B cell culture supernatants in a 384-well format.

Pseudotyped virus from SF162 and JR-CSF isolates of HIV-1 and SIV mac239 (control virus) were generated by co-transfecting Human Embryonic Kidney 293 cells (293 cells) with 2 plasmids encoding the Envelope cDNA sequence and the rest of the HIV genome separately. In the HIV genome encoding vector, the Env gene was replaced by the firefly luciferase gene. Transfectant supernatants containing pseudotyped virus were co-incubated overnight (18 hours) with B cell supernatants derived from activation of an infected donor's primary peripheral blood mononuclear cells (PBMCs). U87 cells stably transfected with and expressing CD4 plus the CCR5 and CXCR4 coreceptors were added to the mixture and incubated for 3 days at 37° C. Infected cells were quantified by luminometry. SIVmac239 was used as the negative control virus.

The neutralization index was expressed as the ratio of normalized relative luminescence units (RLU) of the test viral strain to that of the control virus SIVmac239 derived from the same test B cell culture supernatant. The cut-off values used to distinguish neutralizing hits were determined by the neutralization index of a large number of "negative control wells" containing B cell culture supernatants derived from healthy donors. The false positive rate using the cut-off value of 1.5 was very low (1-3%; FIG. 5A), and it was reduced to zero if the cut-off value of 2.0 was used (FIG. 5B).

FIG. 5 summarizes the screening results from which B cell cultures were selected for antibody rescue and the monoclonal antibodies 1496_C09 (PG9), 1443_C16 (PG16), 1456_P20 (PG20), 1460_G14 (PGG14), and 1495_C14 (PGC14) were derived. The results reveal that the majority of neutralizing B cell culture supernatants did not have binding reactivity to soluble recombinant gp120 or gp41 proteins.

Table 15 shows the screening results of the monoclonal antibodies 1496_C09 (PG9), 1443_C16 (PG16), 1456_P20 (PG20), 1460_G14 (PGG14), and 1495_C14 (PGC14) during the course of their identification in the method described in this invention. The neutralization activity of each antibody and its corresponding binding reactivity to soluble recombinant gp120 or gp41, in the context of B cell culture supernatant and recombinant transfectant supernatants are illustrated.

TABLE 15

| B Cell Culture Hit Priority | Sample ID by B Cell Culture | | Primary B Cell Culture Screening | | | |
|---|---|---|---|---|---|---|
| | | | Neutralization Index | | ELISA OD | |
| Rank | Plate | Well | JRSCF | SF162 | gp120 | gp41 |
| 1 | 1456 | P20 | 42.77 | 1.63 | 3.78 | Neg |
| 1 | 1456 | P20 | 42.77 | 1.63 | 3.78 | Neg |
| 1 | 1456 | P20 | 42.77 | 1.63 | 3.78 | Neg |
| 1 | 1456 | P20 | 42.77 | 1.63 | 3.78 | Neg |
| 2 | 1477 | B12 | 18.52 | 0.81 | Neg | 2.02 |
| 2 | 1477 | B12 | 18.52 | 0.81 | Neg | 2.02 |
| 4 | 1443 | C16 | 179.12 | 1.11 | Neg | Neg |
| 4 | 1443 | C16 | 179.12 | 1.11 | Neg | Neg |
| 4 | 1443 | C16 | 179.12 | 1.11 | Neg | Neg |
| 5 | 1496 | C9 | 166.09 | 1.34 | Neg | Neg |
| 5 | 1496 | C9 | 166.09 | 1.34 | Neg | Neg |
| 5 | 1496 | C9 | 166.09 | 1.34 | Neg | Neg |
| 5 | 1496 | C9 | 166.09 | 1.34 | Neg | Neg |
| 6 | 1495 | C14 | 1.42 | 87.13 | 3.76 | Neg |
| 6 | 1495 | C14 | 1.42 | 87.13 | 3.76 | Neg |
| 6 | 1495 | C14 | 1.42 | 87.13 | 3.76 | Neg |
| 6 | 1495 | C14 | 1.42 | 87.13 | 3.76 | Neg |
| 6 | 1495 | C14 | 1.42 | 87.13 | 3.76 | Neg |
| 6 | 1495 | C14 | 1.42 | 87.13 | 3.76 | Neg |
| 6 | 1495 | C14 | 1.42 | 87.13 | 3.76 | Neg |
| 6 | 1495 | C14 | 1.42 | 87.13 | 3.76 | Neg |
| 6 | 1495 | C14 | 1.42 | 87.13 | 3.76 | Neg |

TABLE 15-continued

| | | | | | | |
|---|---|---|---|---|---|---|
| 6 | 1495 | C14 | 1.42 | 87.13 | 3.76 | Neg |
| 6 | 1495 | C14 | 1.42 | 87.13 | 3.76 | Neg |
| 6 | 1495 | C14 | 1.42 | 87.13 | 3.76 | Neg |
| 6 | 1495 | C14 | 1.42 | 87.13 | 3.76 | Neg |
| 10 | 1460 | G14 | 1.62 | 1.57 | 3.49 | Neg |
| 10 | 1460 | G14 | 1.62 | 1.57 | 3.49 | Neg |

Transfectant Screening for Recombinant Antibodies

| H & L Combinations | | Transfectant Quantitative ELISA | | Neutralization Index | |
|---|---|---|---|---|---|
| | | Average anti-gp-120 or anti-gp41 Conc* | Average total IgG Conc | | |
| Heavy Chain Family | Light Chain Family | (μg/ml) | (μg/ml) | JRCSF | SF162 |
| 1456 P20 γ1 | 1456 P20 kl | 4.03 | 4.62 | 0.80 | 9.57 |
| 1456 P20 γ1 | 1456 P20 kl | 4.03 | 4.62 | 0.80 | 9.57 |
| 1456 P20 γ1 | 1456 P20 kl | 4.03 | 4.62 | 0.80 | 9.57 |
| 1456 P20 γ1 | 1456 P20 kl | 4.03 | 4.62 | 0.80 | 9.57 |
| 1477 B12 γ3 | 1477 B12 λ2 | 0.04 | 3.23 | 13.25 | 1.20 |
| 1477 B12 γ3 | 1477 B12 λ2 | 0.04 | 3.23 | 13.25 | 1.20 |
| 1443 C16 γ1 | 1443 C16 λ2 | N/A | 0.63 | 2.96 | 0.86 |
| 1443 C16 γ1 | 1443 C16 λ2 | N/A | 1.63 | 2.96 | 0.86 |
| 1443 C16 γ3 | 1443 C16 λ2 | N/A | 3.50 | 115.86 | 0.88 |
| 1496 C09 γ3 | 1496 C09 λ2 | N/A | 5.61 | 111.45 | 0.58 |
| 1496 C09 γ3 | 1496 C09 λ3 | N/A | 5.73 | 115.76 | 0.63 |
| 1496 C09 γ3 | 1496 C09 λ5 | N/A | 4.22 | 86.86 | 0.67 |
| 1496 C09 γ3 | 1496 C09 λ7 | N/A | 0.92 | 261.00 | 1.14 |
| 1495 C14 γ1 | 1495 C14 λ1 | 160 | 2.66 | 1.67 | 56.48 |
| 1495 C14 γ1 | 1495 C14 λ3 | 2.20 | 3.34 | 1.67 | 84.87 |
| 1495 C14 γ1 | 1495 C14 λ3 | 2.20 | 3.34 | 0.80 | 84.87 |
| 1495 C14 γ1 | 1495 C14 λ3 | 2.20 | 3.34 | 0.80 | 84.87 |
| 1495 C14 γ1 | 1495 C14 λ3 | 2.20 | 3.34 | 0.80 | 84.87 |
| 1495 C14 γ1 | 1495 C14 λ3 | 2.20 | 3.34 | 0.80 | 84.87 |
| 1495 C14 γ1 | 1495 C14 λ3 | 2.20 | 3.34 | 0.80 | 84.87 |
| 1495 C14 γ1 | 1495 C14 λ3 | 2.20 | 3.34 | 0.80 | 84.87 |
| 1495 C14 γ1 | 1495 C14 λ3 | 2.20 | 3.34 | 0.80 | 84.87 |
| 1503 C14 γ1 | 1503 C14 λ5 | 0.39 | 0.64 | 0.58 | 18.95 |
| 1503 C14 γ1 | 1503 C14 λ5 | 0.39 | 0.64 | 0.58 | 18.95 |
| 1503 C14 γ1 | 1503 C14 λ5 | 0.39 | 0.64 | 0.58 | 18.95 |
| 1460 G14 k1 | 1460 G14 k1 | 13.41 | 16.25 | 0.61 | 17.07 |
| 1460 G14 k2 | 1460 G14 k2 | 12.49 | 14.61 | 0.81 | 15.37 |

Transfectant Screening for Recombinant Monoclonal Antibodies

| Clonal H & L Combinations | | Transfectant Quantitative ELISA | | Neutralization Index | |
|---|---|---|---|---|---|
| | | Average anti-gp-120 or anti-gp41 Conc* | Average total IgG Conc | | |
| Heavy Chain Clone | Light Chain Clone | (μg/ml) | (μg/ml) | JRCSF | SF162 |
| 1456 P20 γ1 018 | 1456 P20 kl 021 | 0.07 | 8.01 | 0.66 | 0.66 |
| 1456 P20 γ1 018 | 1456 P20 kl 024 | 0.01 | 6.81 | 0.88 | 0.78 |
| 1456 P20 γ1 023 | 1456 P20 kl 021 | 9.45 | 6.99 | 0.89 | 10.72 |
| 1456 P20 γ1 023 | 1456 P20 kl 024 | 12.49 | 7.76 | 1.39 | 20.83 |
| 1477 B12 γ3 017 | 1477 B12 λ2 022 | 0.00 | 5.98 | 0.72 | 0.83 |
| 1477 B12 γ3 023 | 1477 B12 λ2 022 | 10.96 | 6.02 | 0.90 | 0.94 |
| 1443 C16 γ1 018 | 1443 C16 λ2 019 | 0.00 | 0.25 | 1.00 | 1.07 |
| 1443 C16 γ1 021 | 1443 C16 λ2 019 | 0.00 | 1.51 | 0.97 | 1.20 |
| 1443 C16 γ3 023 | 1443 C16 λ2 019 | 0.00 | 6.38 | 55.62 | 0.67 |
| 1496 C09 γ3 017 | 1496 C09 λ2 017 | 0.00 | 8.60 | 282.47 | 1.10 |
| 1496 C09 γ3 017 | 1496 C09 λ3 024 | 0.00 | 12.31 | 227.65 | 0.94 |
| 1496 C09 γ3 017 | 1496 C09 λ5 023 | 0.00 | 0.00 | 1.21 | 0.86 |
| ND | ND | ND | ND | ND | ND |
| ND | ND | ND | ND | ND | ND |
| 1495 C14 γ1 017 | 1495 C14 λ3 017 | 0.00 | 0.00 | 0.89 | 0.97 |
| 1495 C14 γ1 017 | 1495 C14 λ3 018 | 0.20 | 1.43 | 0.91 | 7.97 |
| 1495 C14 γ1 017 | 1495 C14 λ3 022 | 0.22 | 1.65 | 0.89 | 9.90 |
| 1495 C14 γ1 020 | 1495 C14 λ3 017 | 0.00 | 0.00 | 0.86 | 0.81 |
| 1495 C14 γ1 020 | 1495 C14 λ3 018 | 12.61 | 3.76 | 1.26 | 95.15 |
| 1495 C14 γ1 020 | 1495 C14 λ3 022 | 13.03 | 3.95 | 0.91 | 105.92 |
| 1495 C14 γ1 022 | 1495 C14 λ3 017 | 0.00 | 0.00 | 1.07 | 0.79 |
| 1495 C14 γ1 022 | 1495 C14 λ3 018 | 4.65 | 2.30 | 1.13 | 60.60 |
| 1495 C14 γ1 022 | 1495 C14 λ3 022 | 5.91 | 3.18 | 0.89 | 39.65 |
| 1503 C14 γ1 017 | 1503 C14 λ5 020 | 0.00 | 0.00 | 0.84 | 0.69 |

TABLE 15-continued

| | | | | | |
|---|---|---|---|---|---|
| 1503 C14 γ1 020 | 1503 C14 λ5 020 | 0.00 | 0.00 | 0.95 | 0.65 |
| 1503 C14 γ1 022 | 1503 C14 λ5 020 | 0.00 | 0.00 | 0.99 | 0.87 |
| 1460 G14 γ1 023 | 1460 G14 λ1 017 | 17.37 | 12.44 | 1.64 | 39.43 |
| ND | ND | ND | ND | ND | ND |

Lightest grey: suggested H&L pair for monoclonal antibody per priority well.
Medium grey with black lettering: Denotes clones derived from same recombinant H or L chain pool of the priority well with identical sequences.
Bolded: 1496 C09 λ3 clone 024 is likely a cross-contaminant in the recombinant DNA pool as it is identical to 1443 C16 λ2 019 in sequence. 1496 C09 λ2 017 sequence represents 21/22 clones in the pool.
*Anti-gp120 and anti-gp41 concentrations were extrapolated from b12 and 2F5 standard curves in quantitative ELISA, respectively.
N/A = not applicable because these hits were neither gp-120 nor gp-41 positive in B cell culture.
ND = not done.

The purified monoclonal antibodies 1496_C09 (PG9), 1443_C16 (PG16), 1456_P20 (PG20), 1460_G14 (PGG14), and 1495_C14 (PGC14) were tested for neutralization of 6 additional HIV strains from clades A (94UG103), B (92BR020, JR-CSF), C (93IN905, IAVI C22), and CRF01_AE (92TH021) (Table 16). The antibodies 1496_C09 (PG9), 1443_C16 (PG16) and 1495_C14 (PGC14) showed neutralization profile similar to that obtained with the donor sera neutralization profile. The pseudoviruses were preincubated with each monoclonal antibody for 1 hour or 18 hours prior to the infection of target cells. $IC_{50}$ values derived from 1 or 18 hours preincubation were similar. Therefore, in further neutralization assays testing purified monoclonal antibodies, 1 hour of preincubation was used.

Table 17A shows the neutralization profiles for the 5 monoclonal antibodies 1496_C09 (PG9), 1443_C16 (PG16), 1456_P20 (PG20), 1460_G14 (PGG14), and 1495_C14 (PGC14) in $IC_{50}$ values on an extended panel of 16 pseudoviruses, together with known cross-clade neutralizing antibodies b12, 2G12, 2F5 and 4E10.

Table 17B shows the IC90 of two monoclonal antibodies, 1443_C16 (PG16) and 1496_C09 (PG9) on the same expanded diverse panel of 16 HIV pseudoviruses from different clades, together with known cross-clade neutralizing antibodies b12, 2G12, 2F5 and 4E10. FIG. 4 shows neutralization activity of monoclonal antibodies 1443_C16 (PG16) and 1496_C09 (PG9) to 3 other pseudoviruses not included in Table 16.

TABLE 16

Neutralizing Antibody Assay: IC50 Summary

IC50 (ug/mL) Except Where Noted

| Virus/Ab Incubation | | SF162 | 94UG103 | 92BR020 | 93IN905 | IAVI_C22 | 92TH021 | JRCSF | NL43 | aMLV |
|---|---|---|---|---|---|---|---|---|---|---|
| 1 hour | 1443C16 | >50 | 0.0211 | >50 | 0.3302**** | 0.1143* | 0.1362* | <0.0025 | <0.0025 | >50 |
| 18 hour | 1443C16 | >50 | 0.0085 | >50 | 0.2553* | 0.1064* | 0.0435 | <0.0025 | 4.9874 | >50 |
| 1 hour | 1456P20 | 0.1946 | >50 | >50 | >50 | >50 | >50 | >50 | 0.20 | >50 |
| 18 hour | 1456P20 | 0.0661 | >50 | >50 | 3.8384* | >50 | >50 | >50 | 0.05 | >50 |
| 1 hour | 1460G14 | 0.1789 | >50 | >50 | >50 | >50 | >50 | >50 | 0.17 | >50 |
| 18 hour | 1460G14 | 0.0573 | >50 | >50 | 3.1738* | >50 | >50 | >50 | 0.05 | >50 |
| 1 hour | 1495C14 | 0.0069 | >50 | 1.1697 | >50 | >50 | >50 | >50 | 0.35 | >50 |
| 18 hour | 1495C14 | <0.0025 | >50 | 0.2442 | 0.1456* | 13.3798 | >50 | >50 | 0.15 | >50 |
| 1 hour | 1496C09 | >50 | 0.3336 | >50 | 0.1444 | 24.8611 | 0.0612 | <0.0025 | 0.2944* | >50 |
| 18 hour | 1496C09 | >50 | 0.0942 | >50 | 0.0619 | 2.1073 | 0.0571 | <0.0025 | 38.03 | >50 |
| 1 hour | Z23 (1/dil'n) | 13521 | 188 | 616 | 369 | 340 | 175 | 438 | 4793 | <100 |
| 18 hour | Z23 (1/dil'n) | 66074 | 262 | 1292 | 1396 | 614 | 336 | 1054 | 9472 | <100 |

*plateau
**flat inhibition curve - probably <0.0025 with plateau
***very long, shallow slope
****plateau with very long, shallow slope to curve

TABLE 17A

Neutralization Profile on a Diverse Panel of Viruses: $IC_{50}$ Values

| | | PG9 | PG16 | PGC14 | PGG14 | PG20 | b12 | 2G12 | 2F5 | 4E10 |
|---|---|---|---|---|---|---|---|---|---|---|
| Clade A | 94UG103 | 0.1731 | 0.0080 | >50 | >50 | >50 | 3.54 | >50 | 3.79 | 9.7 |
| | 92RW020 | 0.0637 | 0.0040**** | 28.5960 | >50 | >50 | >50 | 0.56 | 3.37 | 3.38 |
| | 93UG077 | >50 | >50 | >50 | >50 | >50 | 41.12 | >50 | 4.45 | 11.15 |
| Clade B | 92BR020 | >50 | >50 | 0.6366 | >50 | >50 | 27.5 | 2.26 | >50 | 41.44 |
| | APV-13 | >50 | >50 | >50 | >50 | >50 | >25 | 23.9 | 2.8 | 3.8 |
| | APV-17 | 26.4465 | >50 | >50 | >50 | >50 | >25 | >50 | 2 | 5.1 |
| | APV-6 | 0.0869 | 0.08**** | 7.4062 | >50 | 25.7798 | >25 | 5.3 | 0.1 | 0.4 |
| | JRCSF | <0.0025 | <0.0025 | >50 | >50 | >50 | 0.16 | 0.66 | 3.36 | 6 |

TABLE 17A-continued

Neutralization Profile on a Diverse Panel of Viruses: $IC_{50}$ Values

|  |  | PG9 | PG16 | PGC14 | PGG14 | PG20 | b12 | 2G12 | 2F5 | 4E10 |
|---|---|---|---|---|---|---|---|---|---|---|
| Clade C | 93IN905 | 0.1400 | 0.1016*** | >50 | >50 | >50 | 34.15 | >50 | >50 | 1.55 |
|  | IAVI-C18 | 0.0535 | 0.0067 | >50 | >50 | >50 | >50 | >50 | >50 | >50 |
|  | IAVI-C22 | 24.8600 | 0.0687* | 9.4999 | >50 | >50 | 3.6042 | >50 | >50 | 1.0229 |
|  | IAVI-C3 | 12.9103 | 14.8372 | >50 | >50 | >50 | 5.0000 | >50 | >50 | 5.0000 |
| Clade D | 92UG024 | 10.9552 | >50 | >50 | >50 | >50 | 49.06 | 0.59 | 1.27 | 1.32 |
|  | 92UG005 | >50 | >50 | >50 | >50 | >50 | >50 | >50 | 11.75 | 8.86 |
| CRF01_AE | 92TH021 | 0.1105 | 0.1273*** | >50 | >50 | >50 | 9.99 | >50 | 1.51 | 1.9 |
|  | CMU02 | >50 | >50 | >50 | >50 | >50 | 4.25 | >50 | 0.38 | 0.59 |
| Pos C | NL43 | N/A | <0.0025** | 0.3727 | 0.1717 | 0.1880 | 0.06 | 0.75 | 2.41 | 4.95 |
| Neg C | aMLV | >50 | >50 | >50 | >50 | >50 | >50 | >50 | >50 | >50 |

NA Not Applicable
$IC_{50}$: Inhibitory concentration to inhibit 50% of the virus

TABLE 17B

Neutralization Profile on a Diverse Panel of Viruses: $IC_{90}$ Values for mAbs PG9 and PG16

|  |  | PG9 | PG16 | b12 | 2G12 | 2F5 | 4E10 |
|---|---|---|---|---|---|---|---|
| Clade A | 94UG103 | 3.3736 | 1.5915 | 47.29 | >50 | 46.63 | >50 |
|  | 92RW020 | 6.5462 | >50 | >50 | 6.23 | 27.74 | 36.11 |
|  | 93UG077 | >50 | >50 | >50 | >50 | 33.44 | >50 |
| Clade B | 92BR020 | >50 | >50 | >50 | 24.09 | >50 | >50 |
|  | APV-13 | >50 | >50 | >50 | N/A | N/A | N/A |
|  | APV-17 | >50 | >50 | >50 | N/A | N/A | N/A |
|  | APV-6 | 1.9591 | 44.2600 | >50 | N/A | N/A | N/A |
|  | JRCSF | <0.0025 | 0.0130 | 1.17 | 5.38 | 25.31 | 44.07 |
| Clade C | 93IN905 | 1.8945 | >50 | >50 | >50 | >50 | 12.82 |
|  | IAVI-C18 | 0.8659 | 0.2074 | >50 | >50 | N/A | >50 |
|  | IAVI-C22 | >50 | >50 | 29.6187 | >50 | >50 | 16.405 |
|  | IAVI-C3 | >50 | >50 |  | >50 | N/A | N/A |
| Clade D | 92UG024 | >50 | >50 | >50 | 7.57 | 34.44 | 23.71 |
|  | 92UG005 | >50 | >50 | >50 | >50 | >50 | >50 |
| CRF01_AE | 92TH021 | 1.9871 | 23.4110 | >50 | >50 | 18.78 | 23.52 |
|  | CMU02 | >50 | >50 | 34.2 | >50 | 12.25 | 13.4 |
| Pos C | NL43 | N/A | >50 | 0.28 | 15.75 | 19.32 | 29.56 |
| Neg C | aMLV | >50 | >50 | >50 | >50 | >50 | >50 |

NA—Not Applicable
$IC_{90}$: Inhibitory concentration to inhibit 90% of the virus
***Plateau effect Example 5: Binding Specificity of Monoclonal Antibodies for HIV Gp120 by ELISA Assay The purified anti-gp120 monoclonal antibodies, 1456_P20 (PG20), 1460_G14 (PGG14), and 1495_C14 (PGC14), were confirmed for binding reactivity to gp120 in ELISA assays. When titrated in serial dilutions, all three antibodies exhibited similar binding profiles that suggest significantly higher relative avidity than control anti-gp120 (b12). MAb b12 is directed against an epitope overlapping the CD4 binding site. (Burton D R et al. 1994. Efficient neutralization of primary isolates of HIV-1 by a recombinant human monoclonal antibody. Science 266:1024-1027).

FIG. 5 shows dose response curves of 1456_P20 (PG20), 1460_G14 (PGG14), and 1495_C14 (PGC14) binding to recombinant gp120 in ELISA as compared to control anti-gp120 (b12). Data shown represented average OD values of triplicate ELISA wells obtained on the same plate.

The monoclonal antibodies 1443_C16 (PG16) and 1496_C09 (PG9) were tested for binding to soluble recombinant envelope proteins derived from several HIV strains in ELISA assay. ELISA assays were performed as described in Pantophlet, R., et al. *J Virol* 77, 642-658 (2003). For antigen binding ELISAs, serial dilutions of PG9 were added to antigen coated wells and binding was probed with alkaline phosphatase-conjugated goat anti-human immunoglobulin G (IgG) F(ab')2 Ab (Pierce). For competition ELISAs, competitor mAbs were added to ELISA wells and incubated for 15 min prior to adding 15 μg/mL biotinylated PG9 to each well. Biotinylated PG9 was detected using alkaline phosphatase conjugated streptavidin (Pierce) and visualized using p-nitrophenol phosphate substrate (Sigma). HIV-HXB2 gp120 was used for competition ELISA assays.

FIG. 6 shows results from ELISA binding assays of monoclonal antibodies 1443_C16 (PG16) and 1496_C09 (PG9) to HIV-1 YU2 gp140, JR-CSFgp120, membrane-proximal external regions (MPER) peptide of gp41 and V3 polypeptide. Specificity of the monoclonal antibodies 1443_C16 (PG16) and 1496_C09 (PG9) for gp120 was then confirmed, but it was noted that the binding to soluble envelope glycoprotein was weak.

Example 6: Binding Reactivity of Monoclonal Antibodies 1443_C16 (PG16) and 1496_C09 (PG9) to Envelope Proteins Expressed on Transfected Cell Surface and Competition by Soluble CD4 (sCD4)

MAb cell binding assays were performed as described in Pancera, M. & Wyatt, R. *Virology* 332, 145-156 (2005). Titrating amounts of PG9 and PG16 were added to HIV-1 Env transfected 293T cells, incubated for 1 hr at 4° C., washed with FACS buffer, and stained with goat anti-human IgG F(ab') 2 conjugated to phycoerythin. For competition assays, competitor antibodies were added to the cells 15 min prior to adding 0.1 µg/mL biotinylated PG9 or PG16. For sCD4 inhibition assays, 40 µg/mL sCD4 was added to the cells and incubated for 1 h at 4° C. prior to adding titrating amounts of antibodies. Binding was analyzed using flow cytometry, and binding curves were generated by plotting the mean fluorescence intensity of antigen binding as a function of antibody concentration.

Ninety-six-well ELISA plates were coated overnight at 4° C. with 50 µL PBS containing 100 ng gp120 or gp140 per well. The wells were washed four times with PBS containing 0.025% TWEEN® 20 (polysorbate 20) and blocked with 3% BSA at room temperature for 1 h. Serial dilutions of PG9 were added to antigen coated wells, incubated for 1 h at room temperature, and washed 4× with PBS supplemented with 0.025% TWEEN® 20 (polysorbate 20). Binding was probed with alkaline phosphatase-conjugated goat anti-human immunoglobulin G (IgG) F(ab')2 Ab (Pierce) diluted 1:1000 in PBS containing 1% BSA and 0.025% TWEEN® 20 (polysorbate 20). The plate was incubated at room temperature for 1 h, washed four times, and the plate was developed by adding 50 µL of alkaline phosphatase substrate (Sigma) to 5 mL alkaline phosphatase staining buffer (pH 9.8), according to the manufacturer's instructions. The optical density at 405 nm was read on a microplate reader (Molecular Devices). For competition ELISAs, competitor mAbs were added to gp120Hx132 or gp140Yu2 coated ELISA wells and incubated for 15 min prior to adding 15 µg/mL biotinylated PG9 to each well. Biotinylated PG9 was detected using alkaline phosphatase conjugated streptavidin (Pierce) and visualized using p-nitrophenol phosphate substrate (Sigma). For sCD4 inhibition ELISAs, 5 µg/mL sCD4 was added to antigen-coated wells and incubated for 15 min at room temperature prior to adding titrating amounts of PG9. A FACSArray™ plate reader (BD Biosciences, San Jose, CA) was used for flow cytometric analysis and FlowJo™ software was used for data interpretation.

HIV gp160 derived from YU2 was transfected in 293 cells. Binding of monoclonal antibodies 1443_C16 (PG16) and 1496_C09 (PG9) were detected in transfected cells (FIG. 7). The preincubation of transfected cells with soluble CD4 (sCD4) partially inhibited binding of monoclonal antibody for 1496_C09 (PG9), and for 1443_C16 (PG16) suggesting that antibody binding is effected by the presence of sCD4. Binding is inhibited by at least 15%, at least 20%, at least 25%, or at least 30%. Binding of monoclonal antibodies 1443_C16 (PG16) and 1496_C09 (PG9) to 293 cells transfected with gp160 derived from JR-CSF and ADA strains was also detected (FIG. 8). The binding of both monoclonal antibodies 1443_C16 (PG16) and 1496_C09 (PG9) to JR-CSF transfected cells was blocked by sCD4. Results further confirm that binding activities of monoclonal antibodies 1443_C16 (PG16) and 1496_C09 (PG9) are affected by the presence of sCD4.

Example 7: Binding Reactivity of Monoclonal Antibodies 1443_C16 (PG16) and 1496_C09 (PG9) to Pseudoviruses In vitro virus capture assay was used to test if monoclonal antibodies 1443_C16 (PG16) and 1496_C09 (PG9) bind to intact entry competent pseudoviruses. The monoclonal antibodies 1443_C16 (PG16) and 1496_C09 (PG9) were coated at the bottom of 96-well plate via anti-human Fc. JR-CSF pseudovirus was added and captured by the monoclonal antibody 1443_C16 (PG16) or 1496_C09 (PG9) in a dose dependent manner. Target cells were added to initiate infection. Infection measured in RLU then represented the binding and capture activity of monoclonal antibodies 1443_C16 (PG16) and 1496_C09 (PG9). FIG. 9 shows the binding and capture of JR-CSF pseudovirus by both monoclonal antibodies 1443_C16 (PG16) and 1496_C09 (PG9) in a dose dependent manner, which is similar or better than another known broad and potent neutralizing antibody 2G12.

Example 8: Monoclonal Antibodies 1443_C16 (PG16) and 1496_C09 (PG9) Cross-Compete with Each Other and with sCD4 in Binding to JR-CSF Pseudovirus In a competition version of virus capture assay where JR-CSF pseudovirus was captured by monoclonal antibodies 1443_C16 (PG16), competition of the capture by either monoclonal antibodies 1443_C16 (PG16), 1496_C09 (PG9) and sCD4 was measured. FIG. 10B shows that binding of monoclonal antibody 1443_C16 (PG16) to JR-CSF pseudovirus was blocked by itself, monoclonal antibody 1496_C09 (PG9) and sCD4 in a dose dependent manner. In a corresponding manner, FIG. 10B shows that binding of monoclonal antibody 1496_C09 (PG9) to JR-CSF pseudovirus was blocked by itself, monoclonal antibody 1443_C16 (PG16) and sCD4 in a dose dependent manner. Results indicated that the monoclonal antibodies 1443_C16 (PG16) and 1496_C09 (PG9) bind to closely related epitopes on gp120 and their binding is affected by the presence of sCD4 presumably due to conformational changes induced on HIV-1 envelope by sCD4.

Example 9: Antigen Binding Properties of PG9 and PG16

Figure 11A:
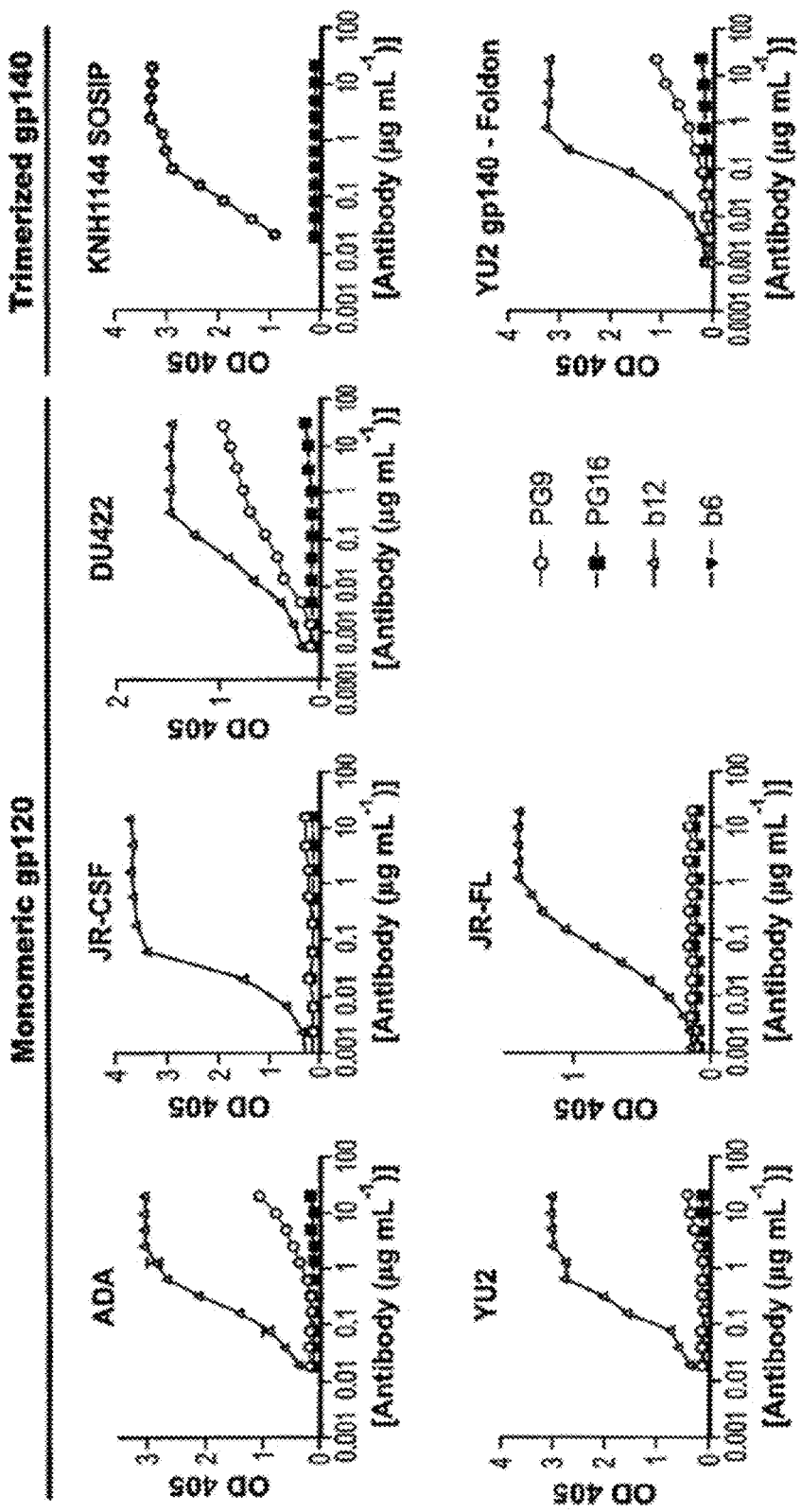
FIG. 11A is a series of graphs depicting the results of a binding assay using PG9 and PG16. The data show that PG9 and PG16 bind to monomeric gp120 and artificially trimerized gp140 constructs as determined by ELISA. IgG b12 was used as a control for ELISA assays.
Figure 11B:
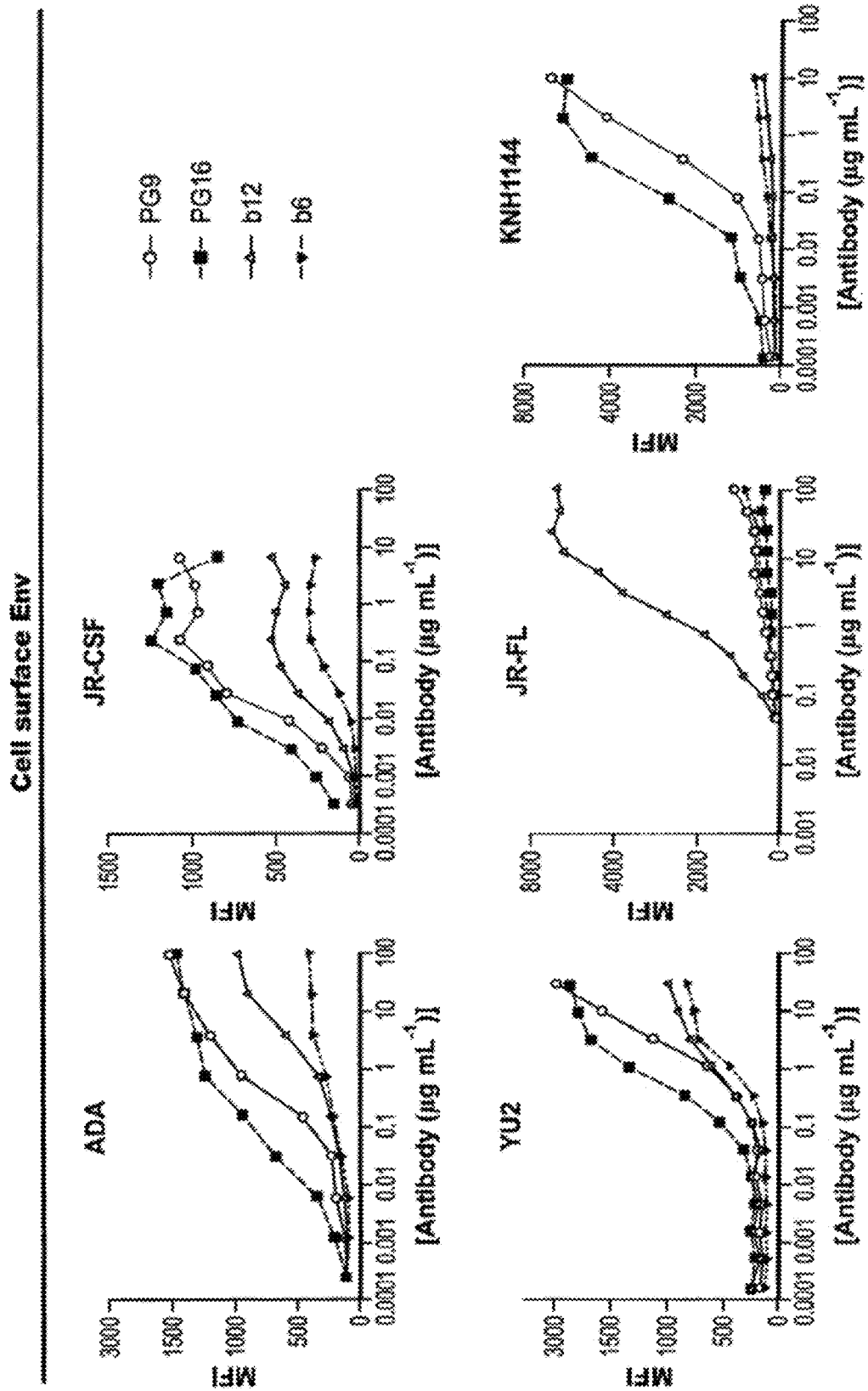
FIG. 11B is a series of graphs depicting the results of a binding assay using PG9 and PG16. The data show that PG9 and PG16 bind to Env expressed on the surface of 293T cells as determined by flow cytometry. The bNAb b12 and the non-neutralizing antibody b6 are included in the cell surface binding assays to show the expected percentages of cleaved and uncleaved Env expressed on the cell surface.
Figure 12:
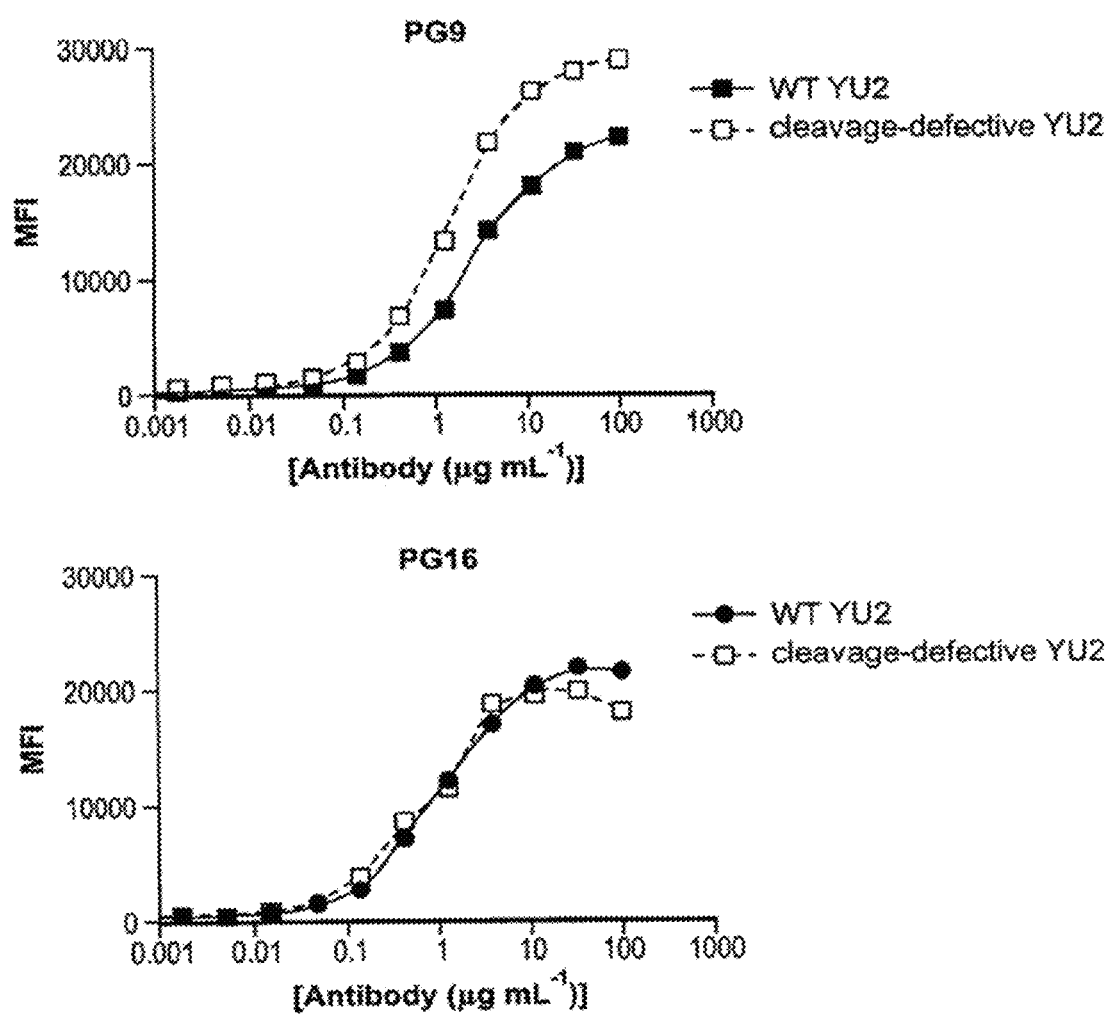
FIG. 12 is a series of graphs depicting the results of a binding assay using PG9 and PG16 and cleavage-defective HIV-1YU2 trimers. PG9 and PG16 bind with high affinity to cleavage-defective HIV-1YU2 trimers as determined by flow cytometry. Binding curves were generated by plotting the MFI of antigen binding as a function of antibody concentration.

Antigen binding properties of PG9 and PG16 were determined by ELISA assays as shown in FIG. 11A-B. Binding of PG9 and PG16 to monomeric gp120 and artificially trimerized gp140 constructs were determined (FIG. 11A). Binding of PG9 and PG16 to Env expressed on the surface of 293T cells as determined by flow cytometry. (FIG. 11B). b12 was used as a control for ELISA assays. The bNAb b12 and the non-neutralizing antibody b6 were included in the cell surface binding assays to show the expected percentages of cleaved and uncleaved Env expressed on the cell surface.

Example 10: Binding of PG9 and PG16 to Cleavage-Defective HIV-1$_{YU2}$ Trimers

Binding of PG9 and PG16 to cleavage-defective HIV-1$_{YU2}$ trimers was determined by flow cytometry. PG9 and PG16 bind with high affinity to cleavage-defective HIV-1$_{YU2}$ trimers as shown in FIG. 12. Binding curves were generated by plotting the mean fluorescence intensity (MFI) of antigen binding as a function of antibody concentration.

Example 11: Mapping the PG9 and PG16 Epitopes

Mapping the epitopes of PG9 and PG16 epitopes was performed by a competitive binding assay as shown in FIG. 13. PG9 and PG16 competed with each other for cell surface Env binding and neither antibody competed with the CD4bs antibody b12 for Env binding. Competitor antibody is indicated at the top of each graph. (FIG. 13A). Ligation of cell surface Env with sCD4 diminished binding of PG9 and PG16. 2G12 was included to control for CD4-induced shedding of gp120. (FIG. 13B). sCD4 inhibited binding of PG9 to artificially trimerized gp140$_{JR\text{-}CSF}$ as determined by ELISA. (FIG. 13C). PG9 competed with 10/76b (anti-V2), F425/b4e8 (anti-V3) and X5 (CD4i) for gp120 binding in competition ELISA assays. (FIG. 13D). PG9 and PG16 failed to bind variable loop deleted HIV-1$_{JR\text{-}CSF}$ variants expressed on the surface of 293T cells. 2G12 was included to control for cell surface Env expression. (FIG. 13E).

Example 12: Competition ELISA Assays Using PG9

When competition ELISA assays using PG9 were performed, PG9 competed with c108g (anti-V2) and partially competed with 17b (CD4i). No competition was observed with A32 (anti-C1/C2/C4/CD4i), C11 (C1), 2G12 (glycan shield), b6 (CD4bs), b3 (CD4bs) or 23b (C1/C5) for gp120Dxs2 binding as shown in FIG. 14.

Example 13: Binding of PG9 and PG16 to HIV-1$_{JR\_FL}$ E168K

Figure 15:
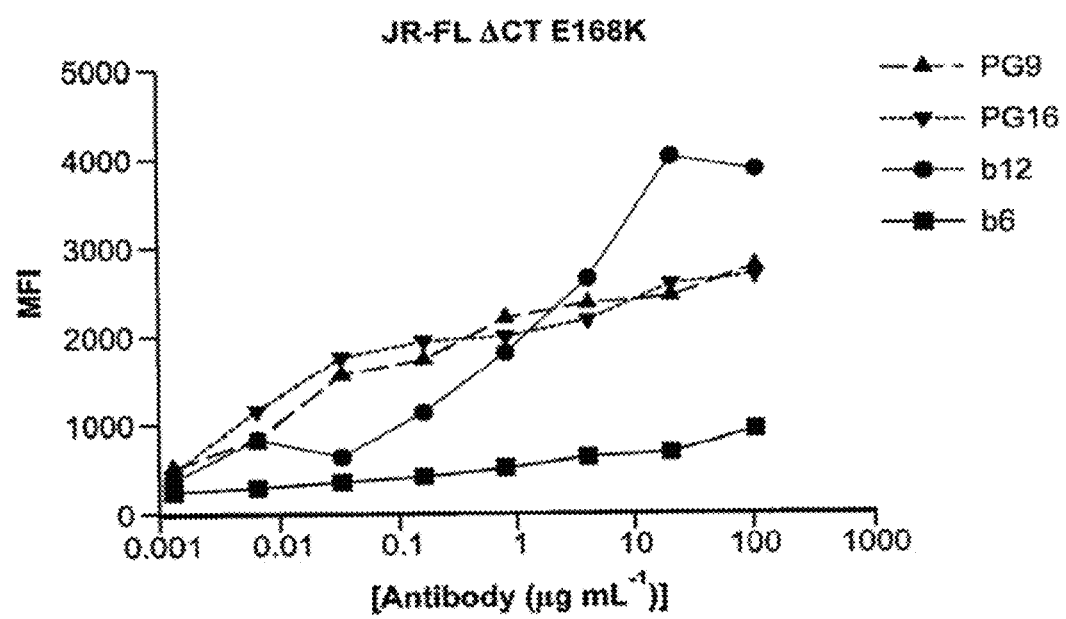
FIG. 15 is a graph depicting monoclonal antibody binding, PG9 or PG16, to HIV-1JR-FLACT E168K Env expressed on the surface of 293T cells as determined by flow cytometry.

Antibody binding to HIV-1JR-FLACT E168K Env expressed on the surface of 293T cells as determined by flow cytometry is shown in FIG. 15. A cytoplasmic tail deleted construct was used to increase cell surface expression. The bNAb b12 and the non-neutralizing antibody b6 were included in the cell surface binding assays to show the expected percentages of cleaved and uncleaved Env expressed on the cell surface. (Pancera M., et al. Virology 332:145 (2005). HIV-1JR-FL E168K was generated by site-directed mutagenesis. Binding curves were generated by plotting the MFI of antigen binding as a function of antibody concentration.

Figure 16:
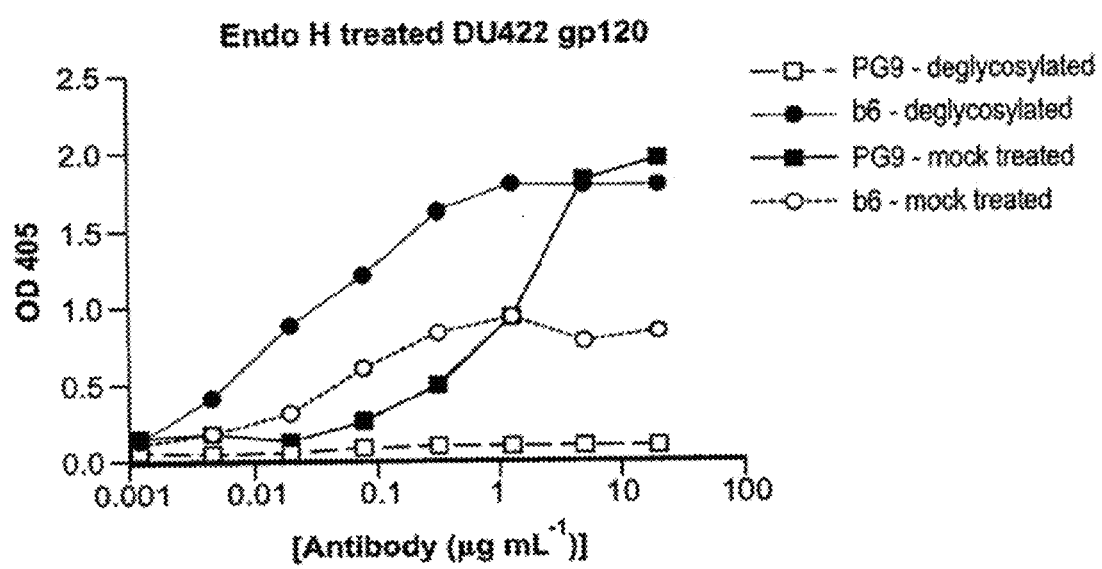
FIG. 16 is a graph depicting monoclonal antibody PG9 binding to deglycosylated gp120.

Example 14: PG9 binding to deglycosylated gp120 gp120$_{DU422}$ was treated with 40 mU/μg Endoglycosidase H (Endo H, New England Biolabs) in sodium acetate buffer for 24 hr at 37° C. Mock treated gp120 was treated under same conditions, but the enzyme was omitted from the reaction. Binding of PG9 and b6 to EndoH treated and mock treated gp120 was determined by ELISA as shown in FIG. 16.

Example 15: Neutralization Activity Against HIV-1$_{SF162}$K160N

Neutralization activity of PG9 and PG16 against HIV-1 SF162 and HIV-1 SF162K160N was determined using a single-round replication luciferase reporter assay of pseudotyped virus. HIV-1 SF162 K160N was generated by site-directed mutagenesis as shown in FIG. 17.

Example 16: Binding of PG9 and PG16 to Mixed Trimers

Alanine substitutions at positions 160 and 299 were introduced into HIV-1$_{YU2}$ Env to abolish binding of PG9 and PG16. An alanine substitution at position 295 was also introduced into the same construct to abrogate binding of 2G12. Co-transfection of 293T cells with WT and mutant plasmids in a 1:2 ratio resulted in the expression of 29% mutant homotrimers, 44% heterotrimers with two mutant subunits, 23% heterotrimers with one mutant subunit, and 4% wild-type homotrimers. These proportions were calculated using the formula described in Yang, X., Kurteva, S., Lee, S., and J. Sodroski, J Virol 79(6):3500-3508 (March 2005), and assumes that mutant and wild-type gp120s mix randomly to form trimers. Binding of mAbs to Env trimers was determined by flow cytometry as shown in FIG. 18. b12 was included as control for Env cell surface expression.

Example 17: PG9 or PG16 Neutralization Activity on HIV with Alanine Mutations within Gp120

Alanine mutations within gp120 of HIV decrease PG9 or PG16 neutralization activity as shown in Table 21. In the table, amino acid numbering is based on the sequence of HIV-1HxB2. Boxes are color coded as follows: white, the amino acid is identical among 0 to 49% of all HIV-1 isolates; light grey, the amino acid is identical among 50 to 90% of isolates; dark grey, the amino acid is identical among 90 to 100% of isolates. Amino acid identity was determined based on a sequence alignment of HIV-1 isolates listed in the HIV sequence database at hiv-web.lanl.gov/content/hiv-db/main-page.html. C refers to constant domains and V refers to variable loops. Neutralization activity is reported as fold increase in IC$_{50}$ value relative to WT JR-CSF and was calculated using the equation (IC$_{50}$ mutant/IC$_{50}$ WT). Boxes are color coded as follows: white, substitutions which had a negative effect on neutralization activity; light grey, 4-9 fold IC$_{50}$ increase; medium grey, 10-100 fold IC$_{50}$ increase; dark grey, >100 fold IC$_{50}$ increase. Experiments were performed in triplicate and values represent an average of at least three independent experiments.

TABLE 18A

| Clade | Virus | b12 | 2G12 | 2F5 | 4E10 | PG9 | PG16 | PGC14 | IC50 (1/Dil'n)[b] Donor Serum |
|---|---|---|---|---|---|---|---|---|---|
| | | | | IC50 (μg/ml)[a] | | | | | |
| A | MGRM-A-001 | >50 | >50 | >50 | 15.08 | >50 | >50 | >50 | <100 |
| | MGRM-A-002 | >50 | >50 | >50 | 6.45 | 0.02 | 0.004 | >50 | 804 |
| | MGRM-A-003 | >50 | >50 | 7.37 | 5.94 | 0.65 | 2.65 | >50 | <100 |
| | MGRM-A-004 | >50 | >50 | 7.49 | 3.14 | 0.02 | 0.04 | >50 | 523 |
| | MGRM-A-005 | 3.64 | >50 | 5.70 | 4.09 | 0.28 | 0.09 | >50 | 175 |
| | MGRM-A-006 | 13.62 | 13.75 | 15.73 | 9.87 | >50 | >50 | >50 | 131 |
| | MGRM-A-007 | >50 | >50 | 16.33 | 1.82 | 0.37 | 5.91 | >50 | 142 |
| | MGRM-A-008 | >50 | >50 | >50 | 7.59 | >50 | >50 | >50 | 142 |
| | MGRM-A-009 | 4.34 | 7.47 | 9.40 | 12.01 | 0.03 | 0.01 | >50 | 941 |
| | MGRM-A-010 | >50 | 17.01 | 20.75 | 14.44 | 0.02 | 0.004 | >50 | 1430 |
| | MGRM-A-011 | 4.01 | >50 | >50 | 2.88 | 0.02 | 0.24 | >50 | 404 |
| | MGRM-A-012 | >50 | >50 | 2.36 | 4.27 | 11.18 | 20.72 | >50 | <100 |
| | MGRM-A-013 | 7.04 | >50 | 0.66 | 1.46 | 0.16 | 0.09 | >50 | 350 |
| | MGRM-A-014 | >50 | >50 | 1.43 | 1.74 | 0.62 | 20.33 | >50 | 158 |

TABLE 18A-continued

| Clade | Virus | IC50 (µg/ml)[a] | | | | | | | IC50 (1/Dil'n)[b] Donor Serum |
|---|---|---|---|---|---|---|---|---|---|
| | | b12 | 2G12 | 2F5 | 4E10 | PG9 | PG16 | PGC14 | |
| | 94UG103 | 6.92 | 48.12 | 1.92 | 4.97 | 0.24 | 0.04 | >50 | 350 |
| | 92RW020 | >50 | 0.48 | 3.36 | 4.54 | 0.08 | 0.28 | 46 | 282 |
| | 93UG077 | 46.95 | >50 | 3.30 | 10.60 | >50 | >50 | >50 | 206 |
| | 94KE105 | >50 | 7.22 | >50 | 7.63 | 29.56 | 6.13 | >50 | <100 |
| | 93RW029 | >50 | >50 | >50 | 15.52 | 1.19 | 3.83 | 42 | 256 |
| | 92RW009 | >50 | 26.14 | 39.08 | >50 | 0.03 | 0.11 | >50 | 254 |
| | 92UG031 | >50 | >50 | 3.81 | 4.94 | 3.08 | 0.43 | >50 | 259 |
| | 92RW026 | >50 | 17.20 | 8.63 | 12.88 | 0.27 | 0.03 | >50 | 361 |
| | 92UG037 | >50 | 45.24 | 3.24 | 8.84 | 0.02 | 0.01 | >50 | 1252 |
| | 92RW008 | 9.46 | 22.47 | 10.41 | 14.53 | 0.01 | 0.002 | 37 | 4067 |
| | 92RW021* | >50 | >50 | 4.16 | 4.87 | 0.05 | 0.11 | >50 | 316 |
| | VLGCA1 | >50 | >50 | 3.90 | 4.58 | 0.07 | 0.18 | >50 | 197 |
| | 92RW024 | >50 | >50 | 8.22 | 8.88 | 0.18 | 0.08 | >50 | 241 |

TABLE 18B

| Clade | Virus | IC50 (µg/ml)[a] | | | | | | | IC50 (1/Dil'n)[b] Donor Serum |
|---|---|---|---|---|---|---|---|---|---|
| | | b12 | 2G12 | 2F5 | 4E10 | PG9 | PG16 | PGC14 | |
| B | 6535.3 (Acute) | 1.93 | 3.85 | 2.76 | 1.23 | 0.22 | 36.88 | 35 | 387 |
| | QH0692.42 (Acute) | 0.73 | 4.39 | 5.42 | 12.67 | >50 | >50 | >50 | <100 |
| | SC422661.8 (Acute) | 6.11 | 0.84 | >50 | 6.35 | 0.79 | 1.13 | >50 | 182 |
| | PVO.4 (Acute) | >50 | 0.80 | >50 | 18.32 | 4.01 | 5.43 | >50 | 171 |
| | TRO.11 (Acute) | >50 | 0.29 | >50 | 1.39 | 5.43 | 0.22 | >50 | 222 |
| | CAAN.A2 (Acute) | >50 | >50 | 23.05 | 17.89 | 5.67 | 8.83 | >50 | <100 |
| | TRJ0.58 (Acute) | >50 | >50 | >50 | 11.94 | 0.43 | 1.16 | >50 | 171 |
| | THR0.18 (Acute) | 3.62 | >50 | >50 | 4.68 | 12.39 | 1.34 | >50 | <100 |
| | 92BR020 | >50 | 4.84 | >50 | >50 | >50 | >50 | 4 | <100 |
| | APV_13 | >50 | 9.24 | 3.81 | 7.33 | >50 | >50 | >50 | <100 |
| | APV_17 | >50 | >50 | 4.61 | 10.53 | 14.59 | 24.78 | >50 | <100 |
| | APV_6 | >50 | 1.90 | 0.25 | 1.10 | 0.12 | 0.29 | 23 | 394 |
| | 93TH305 | 4.17 | 0.55 | 7.61 | 12.33 | 2.08 | 19.34 | 6 | 133 |
| | VLGCB3 | 0.15 | 7.90 | >50 | 5.76 | 0.02 | 0.40 | 21 | 244 |
| | JRCSF | 0.21 | 0.37 | 1.85 | 3.30 | 0.003 | 0.001 | 15 | 8425 |
| | NL43 | 0.17 | 0.49 | 2.02 | 4.67 | 0.32 | 0.02 | 40 | 1488 |
| | MGRM-Chronic-B-001 | 0.75 | 0.08 | 0.55 | 1.46 | >50 | >50 | >50 | <100 |
| | MGRM-Chronic-B-002 | 0.86 | >50 | 1.25 | 2.19 | 1.41 | 3.06 | >50 | 220 |
| | MGRM-Chronic-B-003 | >50 | 0.06 | 1.00 | 3.50 | 50.00 | 0.19 | >50 | 280 |
| | MGRM-Chronic-B-004 | 0.26 | 8.65 | 2.41 | 3.70 | 0.11 | 0.01 | >50 | 1316 |
| | MGRM-Chronic-B-008 | 2.82 | 0.55 | >50 | 16.70 | 6.66 | 0.73 | >50 | 140 |
| | MGRM-Chronic-B-010 | >50 | 1.50 | 0.96 | 1.69 | 0.004 | 0.01 | 27 | 1640 |
| | MGRM-Chronic-B-011 | 2.11 | >50 | 0.81 | 1.07 | >50 | >50 | >50 | 249 |
| | MGRM-Chronic-B-012 | >50 | 0.22 | 17.65 | 48.05 | 0.91 | 3.74 | >50 | 304 |

TABLE 18B-continued

| Clade | Virus | IC50 (μg/ml)[a] | | | | | | | IC50 (1/Dil'n)[b] Donor Serum |
|---|---|---|---|---|---|---|---|---|---|
| | | b12 | 2G12 | 2F5 | 4E10 | PG9 | PG16 | PGC14 | |
| | MGRM-Chronic-B-017 | 2.59 | >50 | >50 | 2.77 | 0.32 | 0.02 | >50 | 644 |
| | MGRM-Chronic-B-018 | 0.66 | >50 | 10.80 | 23.19 | 0.16 | 0.70 | >50 | 180 |
| | MGRM-Chronic-B-020 | 6.16 | 0.20 | 0.78 | 2.45 | >50 | >50 | >50 | <100 |
| | MGRM-Chronic-B-023 | >50 | 0.16 | 0.10 | 27.92 | 0.04 | 0.13 | >50 | 286 |
| | MGRM-Chronic-B-024 | >50 | >50 | >50 | 9.19 | 0.18 | 0.01 | >50 | 884 |
| | JRFL | 0.02 | 1.45 | 3.54 | 18.91 | >50 | >50 | >50 | <100 |
| | SF162 | 0.02 | 1.67 | 2.52 | 4.28 | >50 | >50 | <0.0025 | 9777 |

TABLE 18C

| Clade | Virus | IC50 (μg/ml)[a] | | | | | | | IC50 (1/Dil'n)[b] Donor Serum |
|---|---|---|---|---|---|---|---|---|---|
| | | b12 | 2G12 | 2F5 | 4E10 | PG9 | PG16 | PGC14 | |
| C | MGRM-C-001 | >50 | 2.93 | >50 | 5.66 | >50 | 16.79 | >50 | 175 |
| | MGRM-C-002 | >50 | >50 | 44.68 | 18.19 | >50 | 28.30 | >50 | <100 |
| | MGRM-C-004 | 5.46 | >50 | >50 | 24.24 | 1.18 | 5.09 | >50 | 183 |
| | MGRM-C-005 | 2.66 | >50 | >50 | 16.41 | 2.98 | 2.55 | >50 | 306 |
| | MGRM-C-006 | >50 | >50 | >50 | 4.94 | 0.23 | 2.62 | >50 | 224 |
| | MGRM-C-007 | >50 | >50 | >50 | 5.84 | 0.09 | 0.05 | >50 | 598 |
| | MGRM-C-008 | 1.51 | >50 | >50 | 2.97 | >50 | >50 | >50 | 160 |
| | MGRM-C-009 | >50 | >50 | >50 | 0.56 | >50 | >50 | >50 | <100 |
| | MGRM-C-010 | >50 | >50 | >50 | 10.96 | 12.45 | >50 | >50 | <100 |
| | MGRM-C-012 | >50 | >50 | >50 | 0.44 | 0.24 | 0.48 | >50 | 432 |
| | MGRM-C-013 | >50 | >50 | 18.35 | 2.10 | >50 | >50 | >50 | 105 |
| | MGRM-C-014 | >50 | >50 | >50 | 2.48 | 0.64 | >50 | >50 | 124 |
| | MGRM-C-015 | 13.30 | 1.75 | >50 | 2.52 | 0.50 | 0.26 | >50 | 365 |
| | MGRM-C-017 | >50 | >50 | >50 | 1.47 | 1.52 | 1.80 | >50 | 190 |
| | MGRM-C-019 | >50 | >50 | >50 | 3.49 | 0.01 | 0.002 | 12 | 6894 |
| | MGRM-C-020 | >50 | 18.58 | >50 | 2.80 | >50 | >50 | >50 | <100 |
| | MGRM-C-022 | >50 | >50 | >50 | 5.71 | 0.19 | 0.25 | >50 | 126 |
| | MGRM-C-023 | 13.88 | >50 | >50 | 1.95 | 0.51 | 0.09 | >50 | 220 |
| | MGRM-C-024 | >50 | >50 | >50 | 22.61 | 0.22 | 0.04 | >50 | 494 |
| | MGRM-C-025 | >50 | >50 | >50 | 5.58 | 0.17 | 0.04 | >50 | 434 |
| | 93IN905 | 21.38 | >50 | >50 | 1.26 | 0.03 | 0.25 | 19 | 647 |
| | LAVIC_18 | >50 | >50 | >50 | >50 | 0.10 | 0.02 | >50 | 577 |
| | LAVI_C22 | 7.64 | >50 | >50 | 2.02 | 0.14 | 0.02 | 25 | 1002 |
| | LAVI_C3 | 0.94 | >50 | >50 | 2.85 | 1.45 | 9.55 | 12 | 443 |
| | 98IN022 | 0.42 | >50 | >50 | 0.53 | 0.006 | 0.003 | 9 | 2708 |
| | 93MW959 | >50 | >50 | >50 | 4.55 | 0.04 | 0.007 | >50 | 976 |
| | 97ZA012 | >50 | >50 | >50 | 4.70 | 1.27 | 2.55 | >50 | 188 |
| CRF08 BC | 98CN006 | >50 | >50 | >50 | 1.91 | >50 | >50 | >50 | 397 |
| CRF07 BC | 98CN009 | 1.52 | >50 | >50 | 2.46 | 1.07 | 5.76 | 43 | 289 |

TABLE 18D

| Clade | Virus | IC50 (μg/ml)[a] | | | | | | | IC50 (1/Dil'n)[b] Donor Serum |
|---|---|---|---|---|---|---|---|---|---|
| | | b12 | 2G12 | 2F5 | 4E10 | PG9 | PG16 | PGC14 | |
| D | MGRM-D-001 | >50 | >50 | 0.63 | 1.84 | >50 | >50 | >50 | <100 |
| | MGRM-D-002 | >50 | >50 | 24.64 | 9.44 | 0.027 | 0.01 | 29 | 515 |
| | MGRM-D-003 | >50 | >50 | >50 | 2.49 | 0.02 | 0.01 | >50 | 363 |
| | MGRM-D-004 | >50 | >50 | 2.30 | 1.58 | 0.03 | 0.01 | >50 | 616 |
| | MGRM-D-005 | >50 | 25.66 | >50 | 35.16 | 0.59 | 19.66 | >50 | <100 |
| | MGRM-D-008 | >50 | >50 | >50 | 42.90 | 6.86 | >50 | >50 | <100 |
| | MGRM-D-011 | 7.75 | 1.50 | >50 | 0.91 | 0.06 | 0.01 | >50 | 298 |
| | MGRM-D-012 | 0.13 | >50 | 1.70 | 1.13 | 9.31 | 0.35 | >50 | <100 |
| | MGRM-D-013 | >50 | >50 | 2.12 | 5.38 | 0.06 | 0.11 | >50 | <100 |
| | MGRM-D-014 | >50 | >50 | 2.22 | 3.24 | 0.02 | 0.003 | 48 | 5127 |
| | MGRM-D-016 | 1.12 | >50 | 9.85 | 15.45 | 0.10 | 0.02 | >50 | 364 |
| | MGRM-D-018 | 1.39 | 0.12 | 4.05 | 3.90 | 0.02 | 0.004 | >50 | 883 |
| | MGRM-D-019 | >50 | >50 | 0.14 | 0.04 | 0.03 | 0.01 | >50 | 497 |
| | MGRM-D-020 | >50 | >50 | >50 | >50 | 2.03 | 16.27 | >50 | <100 |
| | MGRM-D-021 | 5.23 | 22.98 | >50 | 13.26 | >50 | >50 | >50 | <100 |
| | MGRM-D-022 | 17.63 | >50 | 8.45 | 16.92 | >50 | >50 | >50 | <100 |
| | MGRM-D-024 | 5.92 | >50 | >50 | 3.60 | 0.03 | 0.02 | >50 | 239 |
| | MGRM-D-026 | 1.55 | >50 | 4.37 | 2.95 | 17.51 | >50 | >50 | <100 |
| | MGRM-D-028 | 0.78 | >50 | >50 | 1.28 | 4.39 | >50 | >50 | <100 |
| | MGRM-D-029 | >50 | >50 | >50 | 5.30 | >50 | >50 | >50 | <100 |
| | 92UG024 | 45.64 | 0.42 | 0.95 | 2.17 | 1.91 | 23.98 | >50 | 112 |
| | 92UG005 | >50 | >50 | 8.61 | 7.46 | >50 | >50 | >50 | <100 |
| | 92UG046 | 0.07 | >50 | >50 | 12.15 | 0.64 | 1.42 | >50 | 114 |
| | 92UG001 | 1.01 | >50 | 12.98 | 13.58 | 41.79 | >50 | >50 | <100 |
| | 94UG114 | >50 | 13.92 | >50 | 9.72 | >50 | >50 | >50 | <100 |

TABLE 18E

| Clade | Virus | IC50 (μg/ml)[a] | | | | | | | IC50 (1/Dil'n)[b] Donor Serum |
|---|---|---|---|---|---|---|---|---|---|
| | | b12 | 2G12 | 2F5 | 4E10 | PG9 | PG16 | PGC14 | |
| CRF01_AE | MGRM-AE-001 | 25.95 | >50 | 0.29 | 0.85 | 2.97 | 4.33 | >50 | <100 |
| | MGRM-AE-002 | 17.10 | >50 | 0.31 | 0.55 | 0.04 | 0.01 | >50 | 653 |
| | MGRM-AE-003 | >50 | >50 | 0.24 | 0.34 | 0.02 | 0.03 | >50 | 211 |
| | MGRM-AE-004 | >50 | >50 | 0.98 | 1.27 | 0.01 | 0.002 | >50 | 1773 |
| | MGRM-AE-005 | 0.63 | >50 | 0.14 | 0.47 | 0.16 | 0.02 | >50 | 233 |
| | MGRM-AE-006 | >50 | >50 | 0.18 | 0.23 | 0.05 | 0.03 | >50 | 151 |
| | MGRM-AE-007 | >50 | >50 | 0.07 | 0.45 | 0.11 | 0.04 | >50 | 176 |
| | MGRM-AE-008 | >50 | >50 | >50 | 0.94 | 10.58 | 3.25 | >50 | 141 |
| | 92TH021 | N/A | >50 | N/A | 1.17 | 0.09 | 0.10 | >50 | 192 |
| | CMU02 | 29.32 | >50 | 0.60 | 0.72 | 7.69 | 43.63 | >50 | 142 |
| CRF_AG | MGRM-AG-001 | 11.87 | 0.69 | 0.75 | 1.12 | 8.83 | 0.03 | >50 | 388 |
| | MGRM-AG-002 | 0.89 | 0.54 | 0.54 | 0.80 | 0.04 | 0.03 | >50 | 147 |
| | MGRM-AG-003 | >50 | >50 | 0.14 | 0.64 | 9.71 | >50 | >50 | <100 |
| | MGRM-AG-005 | >50 | >50 | >50 | 2.13 | 29.67 | >50 | >50 | 150 |
| | MGRM-AG-006 | >50 | 3.92 | 0.85 | 1.76 | >50 | >50 | >50 | <100 |
| | MGRM-AG-008 | >50 | >50 | 0.54 | 1.48 | 0.02 | 0.002 | 45 | 1518 |
| | MGRM-AG-009 | >50 | >50 | 24.80 | 31.39 | >50 | >50 | >50 | <100 |
| | MGRM-AG-011 | >50 | >50 | >50 | 1.36 | 0.01 | 0.002 | >50 | 1427 |
| | MGRM-AG-012 | 10.40 | 1.94 | 0.33 | 0.86 | 1.37 | 25.13 | >50 | <100 |
| | MGRM-AG-013 | >50 | 0.95 | 1.79 | 2.61 | 0.23 | 0.31 | >50 | <100 |
| G | MGRM-G-001 | >50 | >50 | 4.1 | 2.04 | 0.16 | 0.15 | >50 | <100 |
| | MGRM-G-004 | >50 | >50 | >50 | 1.47 | >50 | >50 | >50 | <100 |
| | MGRM-G-006 | >50 | >50 | 1.33 | 1.23 | 0.51 | 2.42 | >50 | 116 |
| | MGRM-G-009 | >50 | >50 | 7.21 | 1.34 | 4.90 | >50 | >50 | <100 |
| | MGRM-G-011 | >50 | >50 | 1.16 | 1.44 | 0.19 | 0.04 | >50 | 150 |
| | MGRM-G-013 | >50 | >50 | 0.59 | 1.15 | >50 | >50 | >50 | <100 |
| | MGRM-G-014 | >50 | >50 | 9.65 | 13.67 | 6.32 | 6.98 | >50 | <100 |
| | MGRM-G-015 | >50 | >50 | 0.43 | 1.07 | 1.51 | 5.33 | >50 | <100 |
| | MGRM-G-016 | >50 | >50 | 16.82 | 1.02 | 0.40 | 11.35 | >50 | <100 |
| | MGRM-G-017 | >50 | >50 | 0.60 | 1.14 | 0.03 | 0.02 | >50 | 453 |
| | MGRM-G-019 | 3.77 | 31.03 | >50 | 6.53 | 0.67 | 1.21 | >50 | <100 |
| | MGRM-G-024 | 2.38 | >50 | 1.07 | 1.57 | 0.07 | 0.01 | >50 | 236 |
| | MGRM-G-025 | >50 | 31.94 | >50 | 1.70 | >50 | >50 | >50 | <100 |
| | MGRM-G-027 | >50 | >50 | 0.28 | 1.19 | 0.01 | 0.01 | >50 | 351 |
| | MGRM-G-028 | >50 | 28.25 | 2.24 | 6.32 | 0.13 | 3.09 | >50 | <100 |

TABLE 18F

| Clade | Virus | IC50 (µg/ml)[a] | | | | | | | IC50 (1/Dil'n)[b] Donor Serum |
|---|---|---|---|---|---|---|---|---|---|
| | | b12 | 2G12 | 2F5 | 4E10 | PG9 | PG16 | PGC14 | |
| F | MGRM-F1-004 | >50 | >50 | 4.31 | 2.74 | 0.11 | 0.43 | >50 | 104 |
| | MGRM-F1-006 | >50 | >50 | 1.10 | 1.01 | 1.45 | 0.27 | >50 | <100 |
| | MGRM-F1-008 | >50 | >50 | 1.61 | 2.75 | >50 | >50 | >50 | <100 |
| | MGRM-F1-010 | >50 | N/A | 14.56 | 3.69 | 0.03 | 0.01 | >50 | 634 |
| | MGRM-F1-012 | >50 | 1.81 | >50 | 0.37 | 0.01 | 0.003 | >50 | 866 |
| | MGRM-F1-013 | >50 | >50 | 4.57 | N/A | 0.56 | N/A | 6 | 142 |
| | MGRM-F1-014 | >50 | >50 | 15.13 | 7.36 | 0.01 | 0.01 | >50 | 437 |
| | MGRM-F1-015 | >50 | >50 | 0.10 | 0.53 | >50 | >50 | >50 | <100 |
| | MGRM-F1-016 | >50 | >50 | 21.47 | 7.61 | 0.58 | 1.12 | >50 | <100 |
| | MGRM-F1-017 | >50 | >50 | >50 | 4.92 | >50 | >50 | >50 | <100 |
| | MGRM-F1-018 | >50 | >50 | 3.91 | 3.60 | 0.03 | 0.01 | >50 | 432 |
| | MGRM-F1-020 | >50 | >50 | 0.59 | 0.66 | 4.55 | 4.35 | >50 | <100 |
| | MGRM-F1-021 | >50 | 14.09 | 1.37 | 1.87 | >50 | >50 | 46 | <100 |
| | MGRM-F1-022 | >50 | >50 | 1.26 | 1.01 | 0.06 | 0.08 | >50 | 246 |
| | MGRM-F1-023 | >50 | 9.23 | 1.78 | 0.44 | >50 | >50 | >50 | 101 |
| neg. control | aMLV | >50 | >50 | >50 | >50 | >50 | >50 | >50 | <100 |

TABLE 19A

Neutralization Potency.

Median $IC_{90}$ (µg/mL) against viruses neutralized with an $IC_{90}$ <50 µg/ml

| Clade[a] | # viruses | b12 | 2G12 | 2F5 | 4E10 | PG9 | PG16 | PGC14 |
|---|---|---|---|---|---|---|---|---|
| A | 27 | 48.45 | 17.77 | 28.82 | 40.62 | 0.99 | 0.81 | >50 |
| B | 31 | 2.30 | 4.65 | 25.85 | 32.38 | 0.11 | 0.01 | 9.45 |
| C | 27 | 28.41 | 28.67 | >50 | 23.37 | 2.94 | 5.10 | >50 |
| D | 25 | 12.68 | 8.76 | 9.02 | 23.45 | 0.34 | 0.44 | >50 |
| CRF01_AE | 10 | 12.68 | >50 | 8.14 | 12.95 | 0.36 | 1.51 | >50 |
| CRF_AG | 10 | 16.97 | 7.04 | 13.49 | 15.78 | 0.28 | 1.86 | >50 |
| G | 15 | 23.62 | >50 | 17.54 | 16.67 | 1.91 | 1.96 | >50 |
| F | 15 | >50 | 21.49 | 17.77 | 7.64 | 0.25 | 0.55 | >50 |
| total | 162 | 20.30 | 13.27 | 17.54 | 23.37 | 0.36 | 1.16 | 9.45 |

* White boxes indicate a medium potency of >50 µg/mL, darkest grey between 20 and 50 µg/mL, lightest grey between 2 and 20 µg/mL, medium grey between 0.2 and 2 µg/mL, and darker grey <0.2 µg/mL.
CRF_07BC and CRF_08BC viruses not included in the clade analysis because there was only one virus tested from each of these clades.

TABLE 19B

Neutralization Breadth.

| Clade[a] | # viruses | % viruses neutralized with an $IC_{90}$ <50 µg/ml | | | | | | |
|---|---|---|---|---|---|---|---|---|
| | | b12 | 2G12 | 2F5 | 4E10 | PG9 | PG16 | PGC14 |
| A | 27 | 4 | 4 | 33 | 22 | 74 | 41 | 0 |
| B | 31 | 45 | 52 | 45 | 23 | 42 | 26 | 6 |
| C | 27 | 15 | 4 | 0 | 41 | 52 | 41 | 0 |
| D | 25 | 28 | 12 | 12 | 20 | 44 | 36 | 0 |
| CRF01_AE | 10 | 11 | 0 | 67 | 70 | 60 | 60 | 0 |
| CRF_AG | 10 | 10 | 30 | 70 | 60 | 40 | 40 | 0 |
| G | 15 | 13 | 0 | 53 | 53 | 47 | 27 | 0 |
| F | 15 | 0 | 7 | 47 | 43 | 47 | 29 | 0 |
| total | 162 | 19 | 15 | 33 | 36 | 51 | 35 | 4 |

TABLE 19B-continued

Neutralization Breadth.

| Clade [a] | # viruses | % viruses neutralized with an $IC_{90}$ <1.0 µg/ml | | | | | | |
|---|---|---|---|---|---|---|---|---|
| | | b12 | 2G12 | 2F5 | 4E10 | PG9 | PG16 | PGC14 |
| A | 27 | 0 | 0 | 0 | 0 | 36 | 27 | 0 |
| B | 31 | 10 | 6 | 0 | 0 | 13 | 19 | 3 |
| C | 27 | 0 | 0 | 0 | 0 | 15 | 15 | 0 |
| D | 25 | 0 | 4 | 0 | 0 | 32 | 20 | 0 |
| CRF_01AE | 10 | 0 | 0 | 0 | 0 | 40 | 30 | 0 |
| CRF_AG | 10 | 0 | 0 | 0 | 0 | 30 | 10 | 0 |
| G | 15 | 0 | 0 | 0 | 0 | 13 | 7 | 0 |
| F | 15 | 0 | 0 | 0 | 0 | 33 | 21 | 0 |
| total | 162 | 2 | 2 | 0 | 0 | 25 | 18 | <1 |

* White boxes indicate that no viruses were neutralized, darkest grey indicate 1 to 30% of viruses were neutralized, lightest grey indicate 30 to 60% of viruses were neutralized, medium grey indicate 60 to 90% of viruses were neutralized, and darker grey indicate 90 to 100% of viruses were neutralized.
CRF_07BC and CRF_08BC viruses not included in the clade analysis because there was only one virus tested from each of these clades.

TABLE 20

Neutralization activity of PG9 and PG16 against JR-CSF pseudovirus containing alanine point mutations.

| Mutation[a,b] | gp120 domain[c] | Fold $IC_{50}$ increase relative to wild-type[d] | | Mutation[a,b] | gp120 domain[c] | Fold $IC_{50}$ increase relative to wild-type[d] | |
|---|---|---|---|---|---|---|---|
| | | PG9 | PG16 | | | PG9 | PG16 |
| W112A | C1 | 1 | 1 | P299A | V3 (base) | 200 | 1400 |
| V120A | C1 | 2 | 1 | N301A | V3 (base) | 9 | 3 |
| K121A | C1 (V1/V2 stem) | 1 | 1 | N302A | V3 (stem) | 1 | 1 |
| L122A | C1 (V1/V2 stem) | 2 | 1 | R304A | V3 (stem) | 2 | 3 |
| L125A | C1 (V1/V2 stem) | 1 | 1 | K305A | V3 (stem) | 50 | 2800 |
| V127A | C1 (V1/V2 stem) | 30 | 57 | S306A | V3 (tip) | 1 | 1 |
| N134A | V1 | 5 | 23 | I307A | V3 (tip) | 10 | 3000 |
| N156A | C1 | 280 | 1500 | H308A | V3 (tip) | 3 | 1 |
| S158A | C1 (V1/V2 stem) | >2000 | >2000 | I309A | V3 (tip) | 9 | 150 |
| F159A | C1 (V1/V2 stem) | >2000 | >2500 | P313A | V3 (tip) | 1 | 1 |
| N160k | V2 | >2000 | >2500 | R315A | V3 (tip) | 1 | 1 |
| T162A | V2 | >2000 | >2500 | F317A | V3 (tip) | 3 | 1400 |
| I165A | V2 | 1 | 1 | Y318A | V3 (tip) | 2 | 1000 |
| R166A | V2 | 2 | 1 | T319A | V3 (tip) | 1 | 1 |
| D167A | V2 | 5 | 30 | T320A | V3 (tip) | 2 | 1 |
| K168A | V2 | 1 | 3 | E322A | V3 (stem) | 2 | 3 |
| K171A | V2 | 1 | 1 | D325A | V3 (stem) | 1 | 1 |
| E172A | V2 | 1 | 1 | H330A | V3 (base) | 1 | 1 |
| Y173A | V2 | 1400 | 1000 | N332A | V3 (base) | 1 | 1 |
| F176A | V2 | ≥5000 | ≥7000 | Q337A | C3 | 1 | 1 |
| Y177A | V2 | 1 | 5 | N339A | C3 | 1 | 1 |
| L179A | V2 | 1 | 3 | K343A | C3 | 1 | 1 |
| D180A | V2 | 1 | 4 | R350A | C3 | 1 | 1 |
| V181A | V2 | 200 | 250 | N355A | C3 | 9 | 3 |
| V182A | V2 | 1 | 3 | S365A | C3 | 2 | 3 |
| I184A | V2 | 1 | 1 | N386A | C3 | 1 | 1 |
| D185A | V2 | 1 | 1 | T388A | C3 | 1 | 1 |
| N188A | V2 | 3 | 3 | N392A | V4 | 7 | 23 |
| T190A | V2 | 2 | 4 | W395A | V4 | 1 | 1 |
| N197K | C2 (V1/V2 stem) | 1 | 1 | R419A | C4 | 3 | 3 |
| T198A | C2 (V1/V2 stem) | 2 | 1 | I420A | C4 | 9 | 11 |
| S199A | C2 (V1/V2 stem) | 2 | 1 | K421A | C4 | 1 | 1 |
| T202A | C2 (V1/V2 stem) | 1 | 1 | Q422A | C4 | 9 | 5 |
| F210A | C2 | 3 | 1 | I423A | C4 | 40 | 14 |
| I213A | C2 | 1 | 1 | I424A | C4 | 10 | 9 |
| N241A | C2 | 4 | 3 | I439A | C4 | 2 | 3 |
| N262A | C2 | 1 | 1 | T450A | C4 | 1 | 1 |

TABLE 20-continued

Neutralization activity of PG9 and PG16 against JR-CSF pseudovirus containing alanine point mutations.

| Mutation[a,b] | gp120 domain[c] | Fold IC$_{50}$ increase relative to wild-type[d] | | Mutation[a,b] | gp120 domain[c] | Fold IC$_{50}$ increase relative to wild-type[d] | |
|---|---|---|---|---|---|---|---|
| | | PG9 | PG16 | | | PG9 | PG16 |
| N276A | C2 | 1 | 1 | L452A | C4 | 1 | 1 |
| N295A | C2 | 2 | 1 | P470A | V5 | 1 | 1 |
| T297A | V3 (base) | 1 | 1 | | | | |

[a]Amino acid number is based on the sequence of HIV-1$_{HxB2}$.
[b]White boxes indicate that the amino acid is identical among 0 to 49% of all HIV isolates, light gray boxes indicate that the amino acid is identical among 50-90% of all HIV isolates, and dark gray boxes indicate that the amino acid is identical among 90-100% of all HIV isolates. Amino acid identity was determined based upon a sequence alignment of HIV-1 isolates listed in the HIV sequence database http://hiv-gov/content/hiv-db/mainpage.html.
[c]C refers to constant domains and V refers to variable loops.
[d]Neutralization activity is reported as fold increase in IC50 value relative to WT JR-CSF and was calculated using the equation (IC50 mutant/IC50 WT). White: substitutions which had a negligible effect on neutralization activity, lightest grey: 4-9 fold IC50 increase, dark grey: 10-100 fold IC50 increase, darkest grey: >100 fold IC50 increase. Experiments were performed in triplicate and values represent an average of at least three independent experiments.

TABLE 21

Alanine mutations that decrease PG9 and PG16 neutralization activity.

| Mutation[a,b] | gp120 domain[c] | Fold IC$_{50}$ increase relative to wild-type[d] | |
|---|---|---|---|
| | | PG9 | PG16 |
| V127A | C1 (V1/V2 stem) | 30 | 57 |
| N134A | V1 | 5 | 23 |
| N156A | C1 (V1/V2 stem) | 280 | 1500 |
| S158A | C1 (V1/V2 stem) | >2000 | >2000 |
| F159A | C1 (V1/V2 stem) | >2000 | >2500 |
| N160K | V2 | >2000 | >2500 |
| T162A | V2 | >2000 | >2500 |
| D167A | V2 | 5 | 30 |
| Y173A | V2 | 1400 | 1000 |
| F176A | V2 | >5000 | >7000 |
| V181A | V2 | 200 | 250 |
| P299A | V3 (base) | 200 | 1400 |
| K305A | V3 (stem) | 50 | 2800 |
| I307A | V3 (tip) | 10 | 3000 |
| I309A | V3 (tip) | 9 | 150 |
| F317A | V3 (tip) | 3 | 1400 |
| Y318A | V3 (tip) | 2 | 1000 |
| N392A | V4 | 7 | 23 |
| I420A | C4 | 9 | 11 |
| I423A | C4 | 40 | 14 |
| I424A | C4 | 10 | 9 |

[a]Amino acid numbering is based on the sequence of HIV-1$_{HxB2}$.
[b]Boxes are color coded as follows: white, the amino acid is identical among 0 to 49% of all HIV-1 isolates; light grey, the amino acid is identical among 50 to 90% of isolates; dark grey, the amino acid is identical among 90 to 100% of isolates. Amino acid identity was determined based on a sequence alignment of HIV-1 isolates listed in the HIV sequence database at http://hiv-weblanl.gov/content/hiv-db/mainpage.html
[c]C refers to constant domains and V refers to variable loops.
[d]Neutralization activity is reported as fold increase in IC$_{50}$ value relative to WT JR-CSF and was calculated using the equation (IC$_{50}$ mutant/IC$_{50}$ WT). Boxes are color coded as follows: white, substitutions which had a negative effect on neutralization activity; light grey, 4-9 fold IC$_{50}$ increase; medium grey, 10-100 fold IC$_{50}$ increase; dark grey, >100 fold IC$_{50}$ increase. Experiments were performed in triplicate and values represent an average of at least three independent experiments.

Example 18: Identification of 14443_C16 (PG16) Sister Clones

1443_C16 sister clones were identified by screening clonal transfection of rescued variable region genes for JR-CSR neutralization. Thus, antibodies that were identified as sister clones of 1443_C16 (PG16) have the similar HIV neutralization profiles as the human monoclonal 1443_C16 (PG16). Moreover, the nucleic acid or amino acid sequences of the sister clone antibodies are at least 50%, 55%, 60%, 70%, 75%, 80%, 85%, 90%, 95%, 99%, 100% or any percentage point in between, identical to those of 1443_C16 (PG16).

TABLE 22

| 1443 C16 Sister mAbs | Gamma Chain Clone | Light Chain Clone | Antibody concentration (μg/ml) | JRCSF Neutralization Index |
|---|---|---|---|---|
| 1456 A12 | 1456_A12_G3_01_002 | 1456_A12_L2_01_023 | 0.006 | 0.90 |
| | | 1456_A12_L2_01_036 | 0.012 | 0.82 |
| | | 1456_A12_L2_01_040 | 0.016 | 2.79 |
| | 1456_A12_G3_01_004 | 1456_A12_L2_01_023 | <0.005 | 1.00 |
| | | 1456_A12_L2_01_036 | <0.005 | 1.02 |
| | | 1456_A12_L2_01_040 | 0.005 | 6.95 |
| 1469 M23 | 1469_M23_G3_01_005 | 1469_M23_L2_01_001 | 2.624 | 215.74 |
| | 1469_M23_G3_01_006 | | 0.000 | 10.05 |
| 1480 I08 | 1480_I08_G3_01_012 | 1480_I08_L2_01_005 | <0.005 | 10.34 |
| | 1480_I08_G3_01_016 | | 10 | 223.14 |
| | 1480_I08_G3_01 021 | | <0.005 | 2.98 |

TABLE 22-continued

| 1443 C16 Sister mAbs | Gamma Chain Clone | Light Chain Clone | Antibody concentration (µg/ml) | JRCSF Neutralization Index |
|---|---|---|---|---|
| | 1480_I08_G3_01_032 | | <0.005 | 3.83 |
| | 1480_I08_G3_01_037 | | 34 | 1.36 |
| | 1480_I08_G3_01_055 | | <0.005 | 1.16 |
| 1489 I13 | 1489_I13_G3_01_003 | 1489_I13_L2_01_007 | 0.0000 | 2.02 |
| | 1489_I13_G3_01_004 | | 0.0009 | 22.86 |
| | 1489_I13_G3_01_007 | | 1.455 | 139.35 |
| 1503 H05 | 1503_H05_G1_01_001 | 1503_H05_L2_01_021 | 0.013 | 0.96 |
| | 1503_H05_G1_01_006 | | 0.000 | 3.75 |
| | 1503_H05_G3_01_005 | | 1.108 | 91.41 |
| | 1503_H05_G3_01_007 | | 0.567 | 155.54 |

Note
that the constant region of the 1456_A12 heavy chain clones used in transfection contains an error generated during the cloning process that lead to no full-length IgG production.

Example 19: 1443_C16 (PG16) Antibody Sister Clones and the 1443_C16 (PG16) Antibody Exhibit Similar Neutralization Specificity Antibodies 1456 A12, 1503_H05, 1489_I13 and 1469 M23 were tested for neutralization activity against several pseudoviruses containing distinct mutations that map the reactivity epitope of 1443_C16 (PG16) on gp120 in a standard TZM-bl assay (Table 23). Like 1443_C16 (PG16), which does not bind or neutralize wild-type JR-FL, but instead, neutralizes JR-FL with the E168K mutation, all 1443_C16 (PG16) sister clones neutralize JR-FL(E168K) with low IC50 values. Similarly, all 1443_C16 (PG16) sister clones do not neutralize the Y318A mutants and 1309A mutants of JR-CSF, where the part of the putative binding epitope is mapped on the V3 tip.

TABLE 23

Neutralization specificity of 1443 C16 (PG16) sister clones as shown with specific mutations on gp120.

| | IC50 (ug/ml) | | | | | |
|---|---|---|---|---|---|---|
| mAb | JR-CSF | JR-CSF (Y318A) | JR-CSF (I309A) | JR-FL (E168K) | ADA | 92RW020 |
| 1503 H05 | 0.001 | >1.0 | >1.0 | 0.002 | 0.003 | 0.020 |
| 1456 A12 | 0.001 | >1.0 | >1.0 | 0.003 | 0.005 | 0.050 |
| 1469 M23 | 0.002 | >1.0 | >1.0 | 0.005 | 0.005 | 0.050 |
| 1489 I13 | 0.002 | >1.0 | >1.0 | 0.005 | 0.008 | 0.030 |
| 1443 C16 | 0.001 | >1.0 | >1.0 | 0.006 | 0.004 | 0.090 |
| 1496 C09 | 0.006 | 0.001 | 0.001 | 0.020 | 0.200 | 0.100 |

Example 20: 1443_C16 (PG16) Sister Clones Exhibit Similar Neutralization Breadth and Potency as 1443_C16 (PG16) for Clade B and Clade C Viruses The antibodies 1456 A12, 1503_H05, 1489_I13 and 1469 M23 exhibit neutralization activity against a panel of Glade B and Glade C pseudoviruses with similar breadth as does 1443 C16 (PG16) in a standard TZM-bl assay (Table 24). The neutralization potency of each sister clone for each pseudovirus is comparable to that for 1443_C16 (PG16). When the IC50 value is determined, the value for the sister clone is within a 0.5 log range from that for 1443_C16 (PG16).

TABLE 24

Neutralization breadth and potency of 1443 C16 (PG16) sister clones.

| | | IC50 (ug/ml) | | | | |
|---|---|---|---|---|---|---|
| | Virus | 1443 C16 | 1456 A12 | 1469 M23 | 1503 H05 | 1489 I13 |
| Clade B | CAAN | 6.37 | 10.61 | 17.72 | 13.46 | 24.87 |
| | REJ04541 | <0.01 | <0.01 | 0.39 | 0.22 | 0.34 |
| | THRO.18 | 2.19 | 2.08 | 7.01 | 4.12 | 7.41 |
| | PVO.4 | 12.3 | 10.42 | 21.25 | 11.01 | 20.57 |
| | TR0.11 | 3.61 | 3.05 | 7.52 | 4.30 | 10.94 |
| | AC10 | <0.01 | <0.01 | <0.01 | <0.01 | <0.01 |
| Clade C | DU156 | <0.01 | <0.01 | <0.01 | <0.01 | <0.01 |
| | DU422 | 0.59 | 0.36 | 0.97 | 0.71 | 1.87 |
| | Du172 | <0.01 | <0.01 | <0.01 | <0.01 | <0.01 |
| | ZM214 | >25 | >25 | >25 | >25 | >25 |
| | ZM233 | <0.01 | <0.01 | <0.01 | <0.01 | <0.01 |
| | CAP45 | <0.01 | <0.01 | <0.01 | <0.01 | <0.01 |
| | ZM249 | <0.01 | <0.01 | <0.01 | <0.01 | <0.01 |
| Control | MuLV | >25 | >25 | >25 | >25 | >25 |

Example 21: Primary and Confirmatory Screening Results for Selected Antibodies Isolated from B-Cell Cultures Established from Human Donors The screening strategy used in the isolation of the monoclonal antibodies PGT-121 (corresponding to clones 4838_L06 and 4873 E03), PGT-122 (corresponding to clone 4877_D15), PGT-123 (corresponding to clone 4858_P08), PGT-125 (corresponding to clone 5123 A06), PGT-126 (corresponding to clone 5141_B17), PGT-130 (corresponding to clone 5147_N06), PGT-135 (corresponding to clones 5343_B08 and 5344_E16), and PGT-136 (corresponding to clones 5329_C19 and 5366_P21) is the same as the PG9 and PG16 mAbs, except that functional neutralization was the only primary screening assay used (i.e. no ELISA was used to screen these antibodies).

Moreover, the strategy use to identify these mAbs following reverse transcription polymerase chain reaction (RT-PCR) rescue differs from previous protocols. Specifically, in addition to performing a primary neutralization screening step, a confirmatory screening step was performed for some of the positive hits identified from the primary screening step (Tables 25-27). The confirmatory screening step was performed using the same assay as the primary screening step. Following functional screening, the B cell culture lysates were subjected to variable gene family-specific RT-PCR, as performed previously to identify the PG9 and PG16 mAbs. However, instead of directly cloning into $IgG_1$ expression vector, the PCR products representing the rescued heavy and light chains were subjected to deep sequencing, which is also known as "next-generation sequencing", "454 sequencing" or "pyrosequencing."

In the process of deep sequencing, a B cell well location-specific sequence tag was built into the second round of PCR to enable the identification of B cell well origin of each sequence determined in the subsequent pooled sequencing reaction. One or more consensus variable gene sequences were generated from each B cell culture well by an informatics algorithm. The consensus sequences from an individual B cell well were then compared among all consensus sequences generated from other B cell culture wells. Similar heavy chains or light chain sequences were "clustered" because similar mAbs may be derived from the same precursor B cell. Selected variable genes were then cloned into an IgG$_1$ expression vector to produce and purify monoclonal antibodies. Unlike the previous rescue strategy, polyclonal transfection was not performed to screen for neutralization activity to identify potential variable genes from the PCR product pool prior to proceeding to monoclonal transfection.

The similarity among variable genes that were "clustered" is apparent in the alignment of nucleotide and amino acid sequence alignments (Tables 28-31). For instance, all three mAbs from donor 517, i.e. PGT-121, PGT-122 and PGT-123 are in the same cluster. Donor 196 provided two distantly related clusters of mAbs, with one cluster including PGT-125 and PGT-126, and another including PGT-130. Donor 039 provided two distantly related clusters of mAbs, each including PGT-135 or PGT-136.

TABLE 25

Donor 517

| mAb ID | B Cell Culture Well ID | Primary Neutralization Index | | | | Confirmatory Neutralization Index Range |
|---|---|---|---|---|---|---|
| | | 92BR020 | 94UG103 | JRCSF | MGRM-C-26 | MGRM-C-026 |
| PGT-121 | 4838_L06 | 4.9 | 1.4 | 3.2 | 996.3 | high >50 |
| | 4873_E03 | 3.6 | 0.8 | 2.2 | 371.4 | high >50 |
| N/A | 4869_K15 | 3.9 | 1.5 | 2.1 | 103.9 | high >50 |
| PGT-122 | 4877_D15 | 5.4 | 1.3 | 2.3 | 37.5 | moderate 10-50 |
| PGT-123 | 4858_P8 | 2.8 | 1.1 | 1.6 | 33.8 | moderate 10-50 |
| N/A | 4834_C11 | 2.5 | 1.1 | 2.0 | 28.3 | moderate 10-50 |

TABLE 26

Donor 196

| mAb ID | B Cell Culture Well ID | Primary Neutralization Index | | | Confirmatory Neutralization | | Polyclonal Transfectant Neutralization Index | | |
|---|---|---|---|---|---|---|---|---|---|
| | | 92TH021 | JRCSF | MGRM-C-26 | Virus | Index Range | 92TH021 | JRCSF | MGRM-C-026 |
| PGT-125 | 5123_A6 | 133.0 | 1727.6 | 511.5 | JRCSF | high >50 | 50.65 | 118.60 | 88.31 |
| PGT-126 | 5141_B17 | 2.3 | 1410.1 | 653.9 | JRCSF | high >50 | 2.74 | 101.51 | 102.41 |
| PGT-127 | 5145_B14 | 1.0 | 31.1 | 86.9 | MGRM-C-026 | high >50 | 0.94 | 1.61 | 2.62 |
| PGT-128 | 5114_A19 | 6.6 | 77.5 | 17.1 | JRCSF | high >50 | 10.02 | 136.49 | 32.19 |
| PGT-130 | 5147_N6 | 538.2 | 19.3 | 3.0 | 92TH021 | high >50 | 4.20 | 1.24 | 1.05 |
| PGT-131 | 5136_H1 | 354.0 | 6.2 | 1.2 | 92TH021 | high >50 | | | |
| PGT-132 | 5113_D22 | 51.0 | 3.0 | 6.0 | 92TH021 | high >50 | | | |
| PGT-133 | 5117_E22 | 42.5 | 3.6 | 3.4 | 92TH021 | high >50 | | | |

TABLE 27

Donor 039

| mAb ID | B Cell Culture Well ID | Primary Neutralization Index | | | Confirmatory Neutralization Index | |
|---|---|---|---|---|---|---|
| | | 93IN905 | JRCSF | MGRM-C-26 | Virus | Index Range |
| PGT-135 | 5343_B8 | 43.0 | 1.8 | 6.5 | 93IN905 | moderate 10-50 |
| PGT-137 | 5345_I1 | 3.3 | 1.1 | 11.3 | MGRM-C-026 | moderate 10-50 |
| PGT-136 | 5366_P21 | 5.5 | 1.1 | 6.2 | MGRM-C-026 | mod low 5-10 |
| | 5329_C19 | 5.6 | 0.9 | 6.0 | MGRM-C-026 | mod low 5-10 |
| PGT-135 | 5344_E16 | 2.3 | 1.5 | 3.6 | MGRM-C-026 | low 1.5-5 |

Example 22: Neutralization Values (IC50, IC80, IC90, and IC95) Against 23 HIV Viruses for Selected Antibodies Isolated from B-Cell Cultures Established from Human Donors Table 32 shows neutralization profiles (IC50 values) of monoclonal antibodies PGT 121, PGT 122, PGT 123, PGT 125, PGT 126, PGT 130, PGT 135, PGT 136, and PG9 on a diverse panel of 23 HIV viruses from different clades (A, B, C, D, AE, and AG). PGT 121, PGT 122, PGT 123, PGT 125, PGT 126, PGT 130, PGT 135, and PGT 136 all neutralize virus in clades A, B, C, and D. Moreover, PGT 121, PGT 122, and PGT 123 also neutralize virus in Glade AG. PGT 125 neutralizes clades A, B, C, D, AE, whereas PGT 126 and PGT 130 neutralize all clades, i.e. A, B, C, D, AE, and AG.

Table 33 shows $IC_{50}$, $IC_{50}$, $IC_{90}$, and $IC_{95}$ values of the PGT 121 monoclonal antibody on the same panel of viruses shown in Table 32. The results shown on this table recapitulate those shown on Table 32 for the PGT 121 monoclonal antibody. This table further demonstrates that the PGT 121 monoclonal antibody neutralizes HIV virus from clades A, B, C, and D strongly, as evidenced by low $IC_{95}$ values shown for these clades.

Table 34 shows $IC_{50}$, $IC_{50}$, $IC_{90}$, and $IC_{95}$ values of the PGT 122 monoclonal antibody on the same panel of viruses shown in Table 32. The results shown on this table recapitulate those shown on Table 32 for the PGT 122 monoclonal antibody. This table further demonstrates that the PGT 122 monoclonal antibody neutralizes HIV virus from clades A, B, C, and D strongly, as evidenced by low $IC_{95}$ values shown for these clades.

Table 35 shows $IC_{50}$, $IC_{50}$, $IC_{90}$, and $IC_{95}$ values of the PGT 123 monoclonal antibody on the same panel of viruses shown in Table 32. The results shown on this table recapitulate those shown on Table 32 for the PGT 123 monoclonal antibody. This table further demonstrates that the PGT 123 monoclonal antibody neutralizes HIV virus from clades A, B, C, and D strongly, as evidenced by low $IC_{95}$ values shown for these clades.

Table 36 shows $IC_{50}$, $IC_{50}$, $IC_{90}$, and $IC_{95}$ values of the PGT 125 monoclonal antibody on the same panel of viruses shown in Table 32. The results shown on this table recapitulate those shown on Table 32 for the PGT 125 monoclonal antibody. This table further demonstrates that the PGT 125 monoclonal antibody neutralizes HIV virus from clades A, B, C, D, and AE strongly, as evidenced by low $IC_{95}$ values shown for these clades.

Table 37 shows $IC_{50}$, $IC_{50}$, $IC_{90}$, and $IC_{95}$ values of the PGT 126 monoclonal antibody on the same panel of viruses shown in Table 32. The results shown on this table recapitulate those shown on Table 32 for the PGT 126 monoclonal antibody. This table further demonstrates that the PGT 126 monoclonal antibody neutralizes HIV virus from clades A, B, C, and D strongly, as evidenced by low $IC_{95}$ values shown for these clades.

Table 38 shows $IC_{50}$, $IC_{80}$, $IC_{90}$, and $IC_{95}$ values of the PGT 130 monoclonal antibody on the same panel of viruses shown in Table 32. The results shown on this table recapitulate those shown on Table 32 for the PGT 130 monoclonal antibody. This table further demonstrates that the PGT 130 monoclonal antibody neutralizes HIV virus from clades A, B, C, and AE strongly, as evidenced by low $IC_{95}$ values shown for these clades.

Table 39 shows $IC_{50}$, $IC_{80}$, $IC_{90}$, and $IC_{95}$ values of the PGT 135 monoclonal antibody on the same panel of viruses shown in Table 32. The results shown on this table recapitulate those shown on Table 32 for the PGT 135 monoclonal antibody. This table further demonstrates that the PGT 135 monoclonal antibody neutralizes HIV virus from clades B, C, and D strongly, as evidenced by low $IC_{95}$ values shown for these clades.

Table 40 shows $IC_{50}$, $IC_{80}$, $IC_{90}$, and $IC_{95}$ values of the PGT 136 monoclonal antibody on the same panel of viruses shown in Table 32. The results shown on this table recapitulate those shown on Table 32 for the PGT 136 monoclonal antibody. This table further demonstrates that the PGT 136 monoclonal antibody neutralizes HIV virus from clades C and D strongly, as evidenced by low $IC_{95}$ values shown for these clades.

Table 41 shows $IC_{50}$, $IC_{80}$, $IC_{90}$, and $IC_{95}$ values of the PG9 monoclonal antibody on the same panel of viruses shown in Table 32. The results shown on this table recapitulate those shown on Table 32 for the PG9 monoclonal antibody. This table further demonstrates that the PG9 monoclonal antibody neutralizes HIV virus from clades A, B, C, D, and AE strongly, as evidenced by low $IC_{95}$ values shown for these clades.

For Tables 32-41, the following color-coding scheme applies regarding the concentration of the appropriate antibody:

| |
|---|
| 10 ng/ml |
| 100 ng/ml |
| 1000 ng/ml |
| 1000-10,000 ng/ml |
| Negative = >10 |

TABLE 32

$IC_{50}$ Neutralization Values for PGT-121, PGT-122, PGT-123, PGT-125, PGT-126, PGT-130, PGT-135, and PGT-136.

| | | IC50 (ug/mL) | | | | | | | | | IC50 (Reciprocal of dilution) Reference Serum | | |
|---|---|---|---|---|---|---|---|---|---|---|---|---|---|
| | | Donor 517 | | | Donor 196 | | | Donor 039 | | Donor 064 | | | |
| Clade | Virus | PGT-121 | PGT-122 | PGT-123 | PGT-125 | PGT-126 | PGT-130 | PGT-135 | PGT-136 | PG9 | Z23-6X | Z23 | Z23 |
| A | 92RW020 | 0.0063 | 0.0072 | 0.0038 | 0.0028 | 0.0046 | 0.0140 | 0.1573 | 0.7383 | 0.1614 | 219 | 327 | 322 |
| | 93UG077 | 0.0459 | 0.1913 | 0.0303 | 0.0262 | 0.0256 | >10* | >10 | >10 | >10 | 336 | 392 | 365 |
| | 94UG103 | 1.3778 | 1.4643 | 0.8461 | 0.0124 | 0.0091 | 0.6355 | >10 | >10 | 0.3098 | 179 | 238 | 235 |
| | MGRM-A-010 | 2.6078 | 1.6836 | 0.4921 | 0.0055 | 0.0033 | 0.0054 | >10 | >10 | 0.0375 | 236 | 258 | 308 |
| B | 92BR020 | 0.0177 | 0.0337 | 0.0130 | 0.0214 | 0.0163 | 1.1242 | 0.1043 | >10 | >10 | 308 | 364 | 336 |
| | APV13 | 0.3157 | 0.9923 | 0.2215 | 0.0128 | 0.0120 | 0.0345 | 0.5452 | >10 | >10 | 217 | 297 | 232 |
| | APV17 | 0.0950 | 0.5220 | 0.1798 | 7.3065 | 0.5013 | >10 | >10 | >10 | >10 | 297 | 283 | 273 |

TABLE 32-continued IC$_{50}$ Neutralization Values for PGT-121, PGT-122, PGT-123, PGT-125, PGT-126, PGT-130, PGT-135, and PGT-136.

| | | IC50 (ug/mL) | | | | | | | | IC50 (Reciprocal of dilution) Reference Serum | | |
|---|---|---|---|---|---|---|---|---|---|---|---|---|
| | | Donor 517 | | | Donor 196 | | | Donor 039 | | Donor 064 | | |
| Clade | Virus | PGT-121 | PGT-122 | PGT-123 | PGT-125 | PGT-126 | PGT-130 | PGT-135 | PGT-136 | PG9 | Z23-6X | Z23 | Z23 |
| | APV6 | 0.0423 | 0.0851 | 0.0328 | 0.0359 | 0.0249 | >10 | >10 | >10 | 0.2139 | 396 | 458 | 682 |
| | JRFL | 0.0276 | 0.0471 | 0.0283 | 0.0156 | 0.0140 | 0.0346 | >10 | >10 | >10 | 533 | 608 | 612 |
| | JRCSF | 0.0343 | 0.0727 | 0.0423 | 0.0060 | 0.0061 | 0.0089 | 0.1131 | >10 | 0.0048 | 425 | 401 | 472 |
| | NL43 | >10 | >10 | >10 | >10 | >10 | >10 | 6.7910 | >10 | 0.6871 | 3905 | 3823 | 3577 |
| C | 93IN905 | 0.0082 | 0.0138 | 0.0071 | 0.0137 | 0.0194 | 0.0182 | 0.0183 | 0.0135 | 0.0480 | 366 | 405 | 395 |
| | MGRM-C-026 | 0.0034 | 0.0089 | 0.0031 | 0.0106 | 0.0076 | 0.0173 | 0.0123 | 0.0065 | 0.1130 | 426 | 299 | 298 |
| | MGRM-C-027 | 0.0094 | 0.0388 | 0.0169 | >10 | 1.1404 | 0.0052 | >10 | >10 | 2.4538 | 355 | 340 | 472 |
| | MGRM-C-028 | 1.1929 | 2.0600 | 0.4433 | 5.7772 | 0.2827 | >10 | 2.1608 | >10 | 0.1211 | 168 | 145 | 195 |
| D | 92UG005 | >10 | >10 | 2.4924 | >10 | 0.0181 | 0.4741 | >10 | >10 | >10 | 350 | 361 | 379 |
| | 92UG024 | >10 | >10 | >10 | >10 | >10 | >10 | 0.0139 | 0.0915 | 1.9142 | 343 | 338 | 433 |
| | MGRM-D-001 | 0.7442 | 0.8673 | 0.2154 | 2.3116 | 0.0639 | >10 | >10 | >10 | >10 | <100 | 114 | 150 |
| | MGRM-D-018 | 0.0086 | 0.0115 | 0.0047 | 0.0382 | 0.0093 | 0.0378 | 0.0433 | >10 | 0.0444 | 414 | 367 | 329 |
| AE | 92TH021 | >10 | >10 | >10 | 0.0066 | 0.1147 | 0.0082 | >10 | >10 | 0.1026 | 287 | 290 | 304 |
| | CMU02 | >10 | >10 | >10 | >10 | >10 | >10 | >10 | >10 | >10 | 309 | 308 | 277 |
| AG | MGRM-AG-005 | 1.1719 | >10 | 0.1036 | >10 | 1.3488 | 0.9466 | >10 | >10 | >10 | 134 | 197 | 209 |
| | aMLV | >10 | >10 | >10 | >10 | >10 | >10 | >10 | >10 | >10 | <100 | <100 | <100 |

TABLE 33

Neutralization Values for PGT-121.
Neutralization by PGT-121 (ug/ml)

| Clade | Virus | IC50 | IC80 | IC90 | IC95 | Overall |
|---|---|---|---|---|---|---|
| A | 92RW020 | 0.0063 | 0.0188 | 0.0361 | 0.0671 | P |
| | 93UG077 | 0.0459 | 0.1716 | 0.3691 | 0.7402 | P |
| | 94UG103 | 1.3778 | 8.8543 | >10.0000 | >10.0000 | P |
| | MGRM-A-010 | 2.6078 | >10.0000 | >10.0000 | >10.0000 | P |
| B | 92BR020 | 0.0177 | 0.0532 | 0.1011 | 0.1828 | P |
| | APV13 | 0.3157 | 1.3067 | 2.7989 | 5.1522 | P |
| | APV17 | 0.0950 | 0.3707 | 0.7991 | 1.5541 | P |
| | APV6 | 0.0423 | 0.1447 | 0.2960 | 0.5688 | P |
| | JRFL | 0.0276 | 0.0806 | 0.1506 | 0.2674 | P |
| | JRCSF | 0.0343 | 0.1119 | 0.2226 | 0.4169 | P |
| | NL43 | >10.0000 | >10.0000 | >10.0000 | >10.0000 | N |
| C | 93IN905 | 0.0082 | 0.0302 | 0.0645 | 0.1298 | P |
| | MGRM-C-026 | 0.0034 | 0.0140 | 0.0320 | 0.0687 | P |
| | MGRM-C-027 | 0.0094 | 0.0829 | 0.3739 | 3.1434 | P |
| | MGRM-C-028 | 1.1929 | 4.9098 | >10.0000 | >10.0000 | P |
| D | 92UG005 | >10.0000 | >10.0000 | >10.0000 | >10.0000 | N |
| | 92UG024 | >10.0000 | >10.0000 | >10.0000 | >10.0000 | N |
| | MGRM-D-001 | 0.7442 | 3.2881 | 6.2560 | 9.3894 | P |
| | MGRM-D-018 | 0.0086 | 0.0231 | 0.0414 | 0.0715 | P |
| AE | 92TH021 | >10.0000 | >10.0000 | >10.0000 | >10.0000 | N |
| | CMU02 | >10.0000 | >10.0000 | >10.0000 | >10.0000 | N |
| AG | MGRM-AG-005 | 1.1719 | >10.0000 | >10.0000 | >10.0000 | P |
| | aMLV | >10.0000 | >10.0000 | >10.0000 | >10.0000 | N |

TABLE 34

Neutralization Values for PGT-122.
Neutralization by PGT-122 (ug/ml)

| Clade | Virus | IC50 | IC80 | IC90 | IC95 | Overall |
|---|---|---|---|---|---|---|
| A | 92RW020 | 0.0072 | 0.0407 | 0.1127 | 0.2891 | P |
| | 93UG077 | 0.1913 | 0.9312 | 2.0994 | 3.8823 | P |
| | 94UG103 | 1.4643 | 6.5793 | >10.0000 | >10.0000 | P |
| | MGRM-A-010 | 1.6836 | >10.0000 | >10.0000 | >10.0000 | P |
| B | 92BR020 | 0.0337 | 0.0929 | 0.1680 | 0.2895 | P |
| | APV13 | 0.9923 | 4.1434 | 8.6010 | >10.0000 | P |
| | APV17 | 0.5220 | 1.7580 | 3.5831 | 6.9228 | P |
| | APV6 | 0.0851 | 0.3508 | 0.7787 | 1.5492 | P |
| | JRFL | 0.0471 | 0.1655 | 0.3422 | 0.6590 | P |
| | JRCSF | 0.0727 | 0.2455 | 0.4945 | 0.9261 | P |
| | NL43 | >10.0000 | >10.0000 | >10.0000 | >10.0000 | N |
| C | 93IN905 | 0.0138 | 0.0505 | 0.1080 | 0.2172 | P |
| | MGRM-C-026 | 0.0089 | 0.0370 | 0.0849 | 0.1811 | P |
| | MGRM-C-027 | 0.0388 | 0.4995 | >10.0000 | >10.0000 | P |
| | MGRM-C-028 | 2.0600 | >10.0000 | >10.0000 | >10.0000 | P |
| D | 92UG005 | >10.0000 | >10.0000 | >10.0000 | >10.0000 | N |
| | 92UG024 | >10.0000 | >10.0000 | >10.0000 | >10.0000 | N |
| | MGRM-D-001 | 0.8673 | 4.4756 | >10.0000 | >10.0000 | P |
| | MGRM-D-018 | 0.0115 | 0.0350 | 0.0674 | 0.1247 | P |
| AE | 92TH021 | >10.0000 | >10.0000 | >10.0000 | >10.0000 | N |
| | CMU02 | >10.0000 | >10.0000 | >10.0000 | >10.0000 | N |
| AG | MGRM-AG-005 | >10.0000 | >10.0000 | >10.0000 | >10.0000 | N |
| | aMLV | >10.0000 | >10.0000 | >10.0000 | >10.0000 | N |

TABLE 35

Neutralization Values for PGT-123.
Neutralization by PGT-123 (ug/mll)

| Clade | Virus | IC50 | IC80 | IC90 | IC95 | Overall |
|---|---|---|---|---|---|---|
| A | 92RW020 | 0.0038 | 0.0106 | 0.0194 | 0.0343 | P |
|   | 93UG077 | 0.0303 | 0.1433 | 0.3504 | 0.7798 | P |
|   | 94UG103 | 0.8461 | 3.2922 | 8.5552 | >10.0000 | P |
|   | MGRM-A-010 | 0.4921 | 2.7917 | 6.4406 | >10.0000 | P |
| B | 92BR020 | 0.0130 | 0.0390 | 0.0741 | 0.1339 | P |
|   | APV13 | 0.2215 | 0.8787 | 1.8718 | 3.5039 | P |
|   | APV17 | 0.1798 | 0.5389 | 1.0082 | 1.7530 | P |
|   | APV6 | 0.0328 | 0.1447 | 0.3394 | 0.7264 | P |
|   | JRFL | 0.0283 | 0.0904 | 0.1782 | 0.3318 | P |
|   | JRCSF | 0.0423 | 0.1428 | 0.2890 | 0.5467 | P |
|   | NL43 | >10.0000 | >10.0000 | >10.0000 | >10.0000 | N |
| C | 93IN905 | 0.0071 | 0.0281 | 0.0625 | 0.1306 | P |
|   | MGRM-C-026 | 0.0031 | 0.0094 | 0.0183 | 0.0338 | P |
|   | MGRM-C-027 | 0.0169 | 0.1495 | >10.0000 | >10.0000 | P |
|   | MGRM-C-028 | 0.4433 | 2.8001 | 7.1057 | >10.0000 | P |
| D | 92UG005 | 2.4924 | >10.0000 | >10.0000 | >10.0000 | P |
|   | 92UG024 | >10.0000 | >10.0000 | >10.0000 | >10.0000 | N |
|   | MGRM-D-001 | 0.2154 | 0.6779 | 1.3056 | 2.3279 | P |
|   | MGRM-D-018 | 0.0047 | 0.0175 | 0.0381 | 0.0791 | P |
| AE | 92TH021 | >10.0000 | >10.0000 | >10.0000 | >10.0000 | N |
|   | CMU02 | >10.0000 | >10.0000 | >10.0000 | >10.0000 | N |
| AG | MGRM-AG-005 | 0.1036 | 1.2780 | 6.3844 | >10.0000 | P |
|   | aMLV | >10.0000 | >10.0000 | >10.0000 | >10.0000 | N |

TABLE 36

Neutralization Values for PGT-125.
Neutralization by PGT-125 (ug/ml)

| Clade | Virus | IC50 | IC80 | IC90 | IC95 | Overall |
|---|---|---|---|---|---|---|
| A | 92RW020 | 0.0028 | 0.0110 | 0.0248 | 0.0526 | P |
|   | 93UG077 | 0.0262 | 0.0926 | 0.2057 | 0.4866 | P |
|   | 94UG103 | 0.0124 | 0.0373 | 0.0710 | 0.1287 | P |
|   | MGRM-A-010 | 0.0055 | 0.0240 | 0.0575 | 0.1313 | P |
| B | 92BR020 | 0.0214 | 0.0738 | 0.1557 | 0.3228 | P |
|   | APV13 | 0.0128 | 0.0414 | 0.0821 | 0.1543 | P |
|   | APV17 | 7.3065 | >10.0000 | >10.0000 | >10.0000 | P |
|   | APV6 | 0.0359 | 0.1330 | 0.2885 | 0.5974 | P |
|   | JRFL | 0.0156 | 0.0462 | 0.0873 | 0.1571 | P |
|   | JRCSF | 0.0060 | 0.0196 | 0.0392 | 0.0741 | P |
|   | NL43 | >10.0000 | >10.0000 | >10.0000 | >10.0000 | N |
| C | 93IN905 | 0.0137 | 0.0494 | 0.1056 | 0.2165 | P |
|   | MGRM-C-026 | 0.0106 | 0.0350 | 0.0705 | 0.1342 | P |
|   | MGRM-C-027 | >10.0000 | >10.0000 | >10.0000 | >10.0000 | N |
|   | MGRM-C-028 | 5.7772 | >10.0000 | >10.0000 | >10.0000 | P |
| D | 92UG005 | >10.0000 | >10.0000 | >10.0000 | >10.0000 | N |
|   | 92UG024 | >10.0000 | >10.0000 | >10.0000 | >10.0000 | N |
|   | MGRM-D-001 | 2.3116 | >10.0000 | >10.0000 | >10.0000 | P |
|   | MGRM-D-018 | 0.0382 | 0.1440 | 0.3389 | 0.8924 | P |
| AE | 92TH021 | 0.0066 | 0.0292 | 0.0701 | 0.1572 | P |
|   | CMU02 | >10.0000 | >10.0000 | >10.0000 | >10.0000 | N |
| AG | MGRM-AG-005 | >10.0000 | >10.0000 | >10.0000 | >10.0000 | N |
|   | aMLV | >10.0000 | >10.0000 | >10.0000 | >10.0000 | N |

TABLE 37

Neutralization Values for PGT-126.
Neutralization by PGT-126 (ug/ml)

| Clade | Virus | IC50 | IC80 | IC90 | IC95 | Overall |
|---|---|---|---|---|---|---|
| A | 92RW020 | 0.0046 | 0.0168 | 0.0359 | 0.0728 | P |
|   | 93UG077 | 0.0256 | 0.1015 | 0.2385 | 0.5771 | P |
|   | 94UG103 | 0.0091 | 0.0316 | 0.0655 | 0.1280 | P |
|   | MGRM-A-010 | 0.0033 | 0.0137 | 0.0316 | 0.0687 | P |
| B | 92BR020 | 0.0163 | 0.0457 | 0.0846 | 0.1521 | P |
|   | APV13 | 0.0120 | 0.0411 | 0.0840 | 0.1621 | P |
|   | APV17 | 0.5013 | 4.4290 | >10.0000 | >10.0000 | P |
|   | APV6 | 0.0249 | 0.0681 | 0.1230 | 0.2134 | P |
|   | JRFL | 0.0140 | 0.0454 | 0.0900 | 0.1688 | P |
|   | JRCSF | 0.0061 | 0.0180 | 0.0339 | 0.0608 | P |
|   | NL43 | >10.0000 | >10.0000 | >10.0000 | >10.0000 | N |
| C | 93IN905 | 0.0194 | 0.0676 | 0.1404 | 0.2751 | P |
|   | MGRM-C-026 | 0.0076 | 0.0345 | 0.0831 | 0.1849 | P |
|   | MGRM-C-027 | 1.1404 | >10.0000 | >10.0000 | >10.0000 | P |
|   | MGRM-C-028 | 0.2827 | 2.6247 | >10.0000 | >10.0000 | P |
|   | 92UG005 | 0.0181 | 0.1455 | 0.5529 | 2.4508 | P |
| D | 92UG024 | >10.0000 | >10.0000 | >10.0000 | >10.0000 | N |
|   | MGRM-D-001 | 0.0639 | 0.3334 | 0.8321 | 1.7951 | P |
|   | MGRM-D-018 | 0.0093 | 0.0391 | 0.0918 | 0.2053 | P |
| AE | 92TH021 | 0.1147 | 1.6162 | 6.9070 | >10.0000 | P |
|   | CMU02 | >10.0000 | >10.0000 | >10.0000 | >10.0000 | N |
| AG | MGRM-AG-005 | 1.3488 | >10.0000 | >10.0000 | >10.0000 | P |
|   | aMLV | >10.0000 | >10.0000 | >10.0000 | >10.0000 | N |

TABLE 38

Neutralization Values for PGT-130.
Neutralization by PGT-130 (ug/ml)

| Clade | Virus | IC50 | IC80 | IC90 | IC95 | Overall |
|---|---|---|---|---|---|---|
| A | 92RW020 | 0.0140 | 0.5079 | 3.6823 | >10.0000 | P |
| | 93UG077 | >10.0000 | >10.0000 | >10.0000 | >10.0000 | N |
| | 94UG103 | 0.6355 | >10.0000 | >10.0000 | >10.0000 | P |
| | MGRM-A-010 | 0.0054 | 0.0251 | 0.0643 | 0.1642 | P |
| B | 92BR020 | 1.1242 | >10.0000 | >10.0000 | >10.0000 | P |
| | APV13 | 0.0345 | 0.5731 | 2.8823 | >10.0000 | P |
| | APV17 | >10.0000 | >10.0000 | >10.0000 | >10.0000 | N |
| | APV6 | >10.0000 | >10.0000 | >10.0000 | >10.0000 | N |
| | JRFL | 0.0346 | 0.7510 | 5.7157 | >10.0000 | P |
| | JRCSF | 0.0089 | 0.0317 | 0.0669 | 0.1341 | P |
| | NL43 | >10.0000 | >10.0000 | >10.0000 | >10.0000 | N |
| C | 93IN905 | 0.0182 | 0.2716 | 1.3069 | 5.4770 | P |
| | MGRM-C-026 | 0.0173 | 0.2629 | 1.3244 | 6.1260 | P |
| | MGRM-C-027 | 0.0052 | 0.0318 | 0.1061 | 0.4638 | P |
| | MGRM-C-028 | >10.0000 | >10.0000 | >10.0000 | >10.0000 | N |
| D | 92UG005 | 0.4741 | >10.0000 | >10.0000 | >10.0000 | P |
| | 92UG024 | >10.0000 | >10.0000 | >10.0000 | >10.0000 | N |
| | MGRM-D-001 | >10.0000 | >10.0000 | >10.0000 | >10.0000 | N |
| | MGRM-D-018 | 0.0378 | 0.2892 | 2.3096 | >10.0000 | P |
| AE | 92TH021 | 0.0082 | 0.0261 | 0.0513 | 0.0963 | P |
| | CMU02 | >10.0000 | >10.0000 | >10.0000 | >10.0000 | N |
| AG | MGRM-AG-005 | 0.9466 | >10.0000 | >10.0000 | >10.0000 | P |
| | aMLV | >10.0000 | >10.0000 | >10.0000 | >10.0000 | N |

TABLE 39

Neutralization Values for PGT-135.
Neutralization by PGT-135 (ug/ml)

| Clade | Virus | IC50 | IC80 | IC90 | IC95 | Overall |
|---|---|---|---|---|---|---|
| A | 92RW020 | 0.1573 | 3.4582 | >10.0000 | >10.0000 | P |
| | 93UG077 | >10.0000 | >10.0000 | >10.0000 | >10.0000 | N |
| | 94UG103 | >10.0000 | >10.0000 | >10.0000 | >10.0000 | N |
| | MGRM-A-010 | >10.0000 | >10.0000 | >10.0000 | >10.0000 | N |
| B | 92BR020 | 0.1043 | 0.2526 | 0.4298 | 0.7203 | P |
| | APV13 | 0.5452 | >10.0000 | >10.0000 | >10.0000 | P |
| | APV17 | >10.0000 | >10.0000 | >10.0000 | >10.0000 | N |
| | APV6 | >10.0000 | >10.0000 | >10.0000 | >10.0000 | N |
| | JRFL | >10.0000 | >10.0000 | >10.0000 | >10.0000 | N |
| | JRCSF | 0.1131 | 0.5033 | 1.4664 | 8.2996 | P |
| | NL43 | 6.7910 | >10.0000 | >10.0000 | >10.0000 | P |
| C | 93IN905 | 0.0183 | 0.0648 | 0.1356 | 0.2677 | P |
| | MGRM-C-026 | 0.0123 | 0.0562 | 0.1390 | 0.3312 | P |
| | MGRM-C-027 | >10.0000 | >10.0000 | >10.0000 | >10.0000 | N |
| | MGRM-C-028 | 2.1608 | >10.0000 | >10.0000 | >10.0000 | P |
| D | 92UG005 | >10.0000 | >10.0000 | >10.0000 | >10.0000 | N |
| | 92UG024 | 0.0139 | 0.0540 | 0.1220 | 0.2673 | P |
| | MGRM-D-001 | >10.0000 | >10.0000 | >10.0000 | >10.0000 | N |
| | MGRM-D-018 | 0.0433 | 0.1999 | >10.0000 | >10.0000 | P |
| AE | 92TH021 | >10.0000 | >10.0000 | >10.0000 | >10.0000 | N |
| | CMU02 | >10.0000 | >10.0000 | >10.0000 | >10.0000 | N |
| AG | MGRM-AG-005 | >10.0000 | >10.0000 | >10.0000 | >10.0000 | N |
| | aMLV | >10.0000 | >10.0000 | >10.0000 | >10.0000 | N |

TABLE 40

Neutralization Values for PGT-136.
Neutralization by PGT-136 (ug/ml)

| Clade | Virus | IC50 | IC80 | IC90 | IC95 | Overall |
|---|---|---|---|---|---|---|
| A | 92RW020 | 0.7383 | >10.0000 | >10.0000 | >10.0000 | P |
|  | 93UG077 | >10.0000 | >10.0000 | >10.0000 | >10.0000 | N |
|  | 94UG103 | >10.0000 | >10.0000 | >10.0000 | >10.0000 | N |
|  | MGRM-A-010 | >10.0000 | >10.0000 | >10.0000 | >10.0000 | N |
| B | 92BR020 | >10.0000 | >10.0000 | >10.0000 | >10.0000 | N |
|  | APV13 | >10.0000 | >10.0000 | >10.0000 | >10.0000 | N |
|  | APV17 | >10.0000 | >10.0000 | >10.0000 | >10.0000 | N |
|  | APV6 | >10.0000 | >10.0000 | >10.0000 | >10.0000 | N |
|  | JRFL | >10.0000 | >10.0000 | >10.0000 | >10.0000 | N |
|  | JRCSF | >10.0000 | >10.0000 | >10.0000 | >10.0000 | N |
|  | NL43 | >10.0000 | >10.0000 | >10.0000 | >10.0000 | N |
| C | 93IN905 | 0.0135 | 0.0623 | 0.1562 | 0.3791 | P |
|  | MGRM-C-026 | 0.0065 | 0.0285 | 0.0687 | 0.1590 | P |
|  | MGRM-C-027 | >10.0000 | >10.0000 | >10.0000 | >10.0000 | N |
|  | MGRM-C-028 | >10.0000 | >10.0000 | >10.0000 | >10.0000 | N |
| D | 92UG005 | >10.0000 | >10.0000 | >10.0000 | >10.0000 | N |
|  | 92UG024 | 0.0915 | 0.6193 | 1.9558 | 5.9700 | P |
|  | MGRM-D-001 | >10.0000 | >10.0000 | >10.0000 | >10.0000 | N |
|  | MGRM-D-018 | >10.0000 | >10.0000 | >10.0000 | >10.0000 | N |
| AE | 92TH021 | >10.0000 | >10.0000 | >10.0000 | >10.0000 | N |
|  | CMU02 | >10.0000 | >10.0000 | >10.0000 | >10.0000 | N |
| AG | MGRM-AG-005 | >10.0000 | >10.0000 | >10.0000 | >10.0000 | N |
|  | aMLV | >10.0000 | >10.0000 | >10.0000 | >10.0000 | N |

TABLE 41

Neutralization Values for PG9.
Neutralization by PG9 (ug/ml)

| Clade | Virus | IC50 | IC80 | IC90 | IC95 | Overall |
|---|---|---|---|---|---|---|
| A | 92RW020 | 0.1614 | 1.0383 | 3.4024 | >10.0000 | P |
|  | 93UG077 | >10.0000 | >10.0000 | >10.0000 | >10.0000 | N |
|  | 94UG103 | 0.3098 | 1.9524 | 5.5354 | >10.0000 | P |
|  | MGRM-A-010 | 0.0375 | 0.1215 | 0.2418 | 0.4561 | P |
| B | 92BR020 | >10.0000 | >10.0000 | >10.0000 | >10.0000 | N |
|  | APV13 | >10.0000 | >10.0000 | >10.0000 | >10.0000 | N |
|  | APV17 | >10.0000 | >10.0000 | >10.0000 | >10.0000 | N |
|  | APV6 | 0.2139 | 1.1316 | 3.2130 | 9.6532 | P |
|  | JRFL | >10.0000 | >10.0000 | >10.0000 | >10.0000 | N |
|  | JRCSF | 0.0048 | 0.0181 | 0.0391 | 0.0798 | P |
|  | NL43 | 0.6871 | >10.0000 | >10.0000 | >10.0000 | P |
| C | 93IN905 | 0.0480 | 0.3077 | 0.9807 | 3.3063 | P |
|  | MGRM-C-026 | 0.1130 | >10.0000 | >10.0000 | >10.0000 | P |
|  | MGRM-C-027 | 2.4538 | >10.0000 | >10.0000 | >10.0000 | P |
|  | MGRM-C-028 | 0.1211 | 0.6455 | 1.6522 | 3.7075 | P |
| D | 92UG005 | >10.0000 | >10.0000 | >10.0000 | >10.0000 | N |
|  | 92UG024 | 1.9142 | >10.0000 | >10.0000 | >10.0000 | P |
|  | MGRM-D-001 | >10.0000 | >10.0000 | >10.0000 | >10.0000 | N |
|  | MGRM-D-018 | 0.0444 | 0.1805 | 0.4300 | 1.0466 | P |
| AE | 92TH021 | 0.1026 | 0.4475 | 1.0694 | 2.4256 | P |
|  | CMU02 | >10.0000 | >10.0000 | >10.0000 | >10.0000 | N |
| AG | MGRM-AG-005 | >10.0000 | >10.0000 | >10.0000 | >10.0000 | N |
|  | aMLV | >10.0000 | >10.0000 | >10.0000 | >10.0000 | N |

Example 23: Heavy and Light Chain Usage for Selected Antibodies Isolated from B-Cell Cultures Established from Human Donors Monoclonal antibodies PGT-121 (corresponding to clones 4838_L06 and 4873 E03), PGT-122 (corresponding to clone 4877_D15), PGT-123 (corresponding to clone 4858_P08), PGT-125 (corresponding to clone 5123 A06), PGT-126 (corresponding to clone 5141_B17), PGT-130 (corresponding to clone 5147_N06), PGT-135 (corresponding to clones 5343_B08 and 5344_E16), and PGT-136 (corresponding to clones 5329_C19 and 5366_P21) are derived from related germline genes.

The similarity of the variable genes is apparent based on the gene usage (Tables 42 and 43). Although the exact gene alleles used may not be definitive, the alleles that are most likely used are provided with the percentage identity to the germline gene noted.

TABLE 42

Heavy Chain Germline Gene Usage for PGT-121, PGT-122, PGT-123, PGT-125, PGT-126, PGT-130, PGT-135, and PGT-136.

| mAb Clone | Germline V-gene allele | Identity to V-gene | Germline J-gene allele | Identity to J-gene | Heavy chain CDR3 |
|---|---|---|---|---|---|
| PGT-121 | IGHV4-59*01 or IGHV4-59*07 | 80.35% (229/285 nt) | IGHJ6*03 | 82.26% (51/62 nt) | TLHGRRIYGIVAFNEW FTYFYMDV (SEQ ID NO: 143) |
| | IGHV4-59*02 or IGHV4-59*03 or IGHV4-61*08 | 80.00% (228/285 nt) | | | |
| PGT-122 | IGHV4-61*08 | 80.35% (229/285 nt) | IGHJ6*03 | 83.87% (52/62 nt) | TKHGRRIYGVVAFKE WFTYFYMDV (SEQ ID NO: 262) |
| | IGHV4-59*02 | 80.00% (228/285 nt) | | | |
| | IGHV4-59*01 | 79.65% (227/285 nt) | | | |
| PGT-123 | IGHV4-59*03 | 77.54% (221/285 nt) | IGHJ6*03 | 83.87% (52/62 nt) | ALHGKRIYGIVALGEL FTYFYMDV (SEQ ID NO: 171) |
| | IGHV4-59*01 | 77.19% (220/285 nt) | | | |
| | IGHV4-59*02 or IGHV4-59*07 or IGHV4-61*08 | 76.84% (219/285 nt) | | | |
| PGT-125 | IGHV4-b*02 | 80.21% (231/288 nt) | IGHJ5*02 | 66.67% (34/51 nt) | FDGEVLVYNHWPKPA WVDL (SEQ ID NO: 187) |
| | IGHV4-b*01 | 79.86% (230/288 nt) | IGHJ5*01 | 64.71% (33/51 nt) | |
| | IGHV4-39*07 | 79.38% (231/291 nt) | IGHJ4*03 | 62.50% (30/48 nt) | |
| PGT-126 | IGHV4-b*02 | 82.29% (237/288 nt) | IGHJ5*02 | 72.55% (37/51 nt) | FDGEVLVYHDWPKPA WVDL (SEQ ID NO: 203) |
| | IGHV4-39*07 | 81.79% (238/291 nt) | IGHJ5*01 | 68.63% (35/51 nt) | |
| | IGHV4-b*01 | 81.94% (236/288 nt) | IGHJ4*03 | 64.58% (31/48 nt) | |
| PGT-130 | IGHV4-39*07 | 79.38% (231/291 nt) | IGHJ5*02 | 72.55% (37/51 nt) | SGGDILYYYEWQKPH WFSP (SEQ ID NO: 219) |
| | IGHV4-59*04 | 80.00% (228/285 nt) | IGHJ5*01 | 68.63% (35/51 nt) | |
| PGT-135 | IGHV4-39*07 | 82.46% (235/285 nt) | IGHJ5*02 | 72.55% (37/51 nt) | HRHHDVFMLVPIAGW FDV (SEQ ID NO: 235) |
| | IGHV4-39*03 | 82.04% (233/284 nt) | IGHJ5*01 | 70.59% (36/51 nt) | |
| PGT-136 | IGHV4-39*07 | 83.86% (239/285 nt) | IGHJ5*02 | 78.43% (40/51 nt) | HKYHDIFRVVPVAGW FDP (SEQ ID NO: 252) |
| | IGHV4-39*03 | 83.45% (237/284 nt) | IGHJ5*01 | 74.51% (38/51 nt) | |

TABLE 43

Light Chain Germline Gene Usage for PGT-121, PGT-122, PGT-123, PGT-125, PGT-126, PGT-130, PGT-135, and PGT-136.

| mAb Clone | Germline V-gene allele | Identity to V-gene | Germline J-gene allele | Identity to J-gene | Light chain CDR3 |
|---|---|---|---|---|---|
| PGT-121 | IGLV3-21*01 or IGLV3-21*02 or IGLV3-21*03 | 81.01% (209/258 nt) | IGLJ3*02 | 86.49% (32/37 nt) | HIWDSRVPTKWV (SEQ ID NO: 152) |
| PGT-122 | IGLV3-21*02 | 82.56% (213/258 nt) | IGLJ3*02 | 81.08% (30/37 nt) | HIWDSRRPTNWV (SEQ ID NO: 164) |
| | IGLV3-21*01 or IGLV3-21*03 | 82.17% (212/258 nt) | | | |

TABLE 43-continued

Light Chain Germline Gene Usage for PGT-121, PGT-122, PGT-123, PGT-125, PGT-126, PGT-130, PGT-135, and PGT-136.

| mAb Clone | Germline V-gene allele | Identity to V-gene | Germline J-gene allele | Identity to J-gene | Light chain CDR3 |
|---|---|---|---|---|---|
| PGT-123 | IGLV3-21*01 or IGLV3-21*02 or IGLV3-21*03 | 76.74% (198/258 nt) | IGLJ3*02 | 83.78% (31/37 nt) | HIYDARGGTNWV (SEQ ID NO: 180) |
| PGT-125 | IGLV2-8*01 IGLJ2*01 or IGLV2-8*02 | 84.62% (231/273 nt) 84.25% (230/273 nt) | IGLJ3*01 | 86.49% (32/37 nt) | GSLVGNWDVI (SEQ ID NO: 196) |
| PGT-126 | IGLV2-8*01 IGLV2-8*02 | 91.21% (249/273 nt) 90.84% (248/273 nt) | IGLJ2*01 or IGLJ3*01 | 89.19% (33/37 nt) | SSLVGNWDVI (SEQ ID NO: 212) |
| PGT-130 | IGLV2-8*01 IGLV2-8*02 | 88.19% 87.85% (253/288 nt) | IGLJ2*01 or IGLJ3*01 | 89.19% (33/37 nt) | SSLFGRWDVV (SEQ ID NO: 228) |
| PGT-135 | IGKV3-15*01 IGKV3D-15*01 | 82.44% (230/279 nt) 82.08% (229/279 nt) | IGKJ1*01 | 94.44% (34/36 nt) | QQYEEWPRT (SEQ ID NO: 245) |
| PGT-136 | IGKV3-15*01 IGKV3D-15*01 | 86.38% (241/279 nt) 86.02% (240/279 nt) | IGKJ1*01 | 97.22% (35/36 nt) | QQYEEWPRT (SEQ ID NO: 245) |

Example 24: Heavy and Light Chain Usage for Selected Antibodies Isolated from B-Cell Cultures Established from Human Donors Monoclonal antibodies PGT-141 (corresponding to clones 4964_G22 and 4993_K13), PGT-142 (corresponding to clone 4995_E20), PGT-143 (corresponding to clone 4980_N08), and PGT-144 (corresponding to clone 4970_K22) are derived from related germline genes.

The similarity of the variable genes is apparent based on the gene usage (Tables 44 and 45). Although the exact gene alleles used may not be definitive, the alleles that are most likely used are provided with the percentage identity to the germline gene noted.

TABLE 44

Heavy Chain Germline Gene Usage for PGT-141, PGT-142, PGT-143, and PGT-144.

| mAb Clone | Germline V-gene allele | Identity to V-gene | Germline J-gene allele | Identity to J-gene | Heavy chain CDR3 |
|---|---|---|---|---|---|
| PGT-141 (4964_G22; 4993_K13) | IGHV1-8*01 IGHV1-2*02 or IGHV1-2*04 | 84.03% (242/288 nt) 81.60% (235/288 nt) | IGHJ6*02 IGHJ6*01 or IGHJ6*03 or IGHJ6*04 | 74.19% (46/62 nt) 72.58% (45/62 nt) | GSKHRLRDYVLYDDYGLINYQEWND YLEFLDV (SEQ ID NO: 279) |
| PGT-142 (4995_E20) | IGHV1-8*01 IGHV1-2*02 or IGHV1-2*04 | 83.68% (241/288 nt) 81.60% (235/288 nt) | IGHJ6*02 IGHJ6*01 or IGHJ6*03 or IGHJ6*04 | 74.19% (46/62 nt) 72.58% (45/62 nt) | GSKHRLRDYVLYDDYGLINYQEWND YLEFLDV (SEQ ID NO: 279) |
| PGT-143 (4980_N08) | IGHV1-8*01 IGHV1-2*02 or IGHV1-2*04 | 84.03% (242/288 nt) 81.60% (235/288 nt) | IGHJ6*02 IGHJ6*01 or IGHJ6*03 or IGHJ6*04 | 74.19% (46/62 nt) 72.58% (45/62 nt) | GSKHRLRDYVLYDDYGLINYQEWND YLEFLDV (SEQ ID NO: 279) |

TABLE 44-continued

Heavy Chain Germline Gene Usage for PGT-141, PGT-142, PGT-143, and PGT-144.

| mAb Clone | Germline V-gene allele | Identity to V-gene | Germline J-gene allele | Identity to J-gene | Heavy chain CDR3 |
|---|---|---|---|---|---|
| PGT-144 (4970_K22) | IGHV1-8*01 IGHV1-2*02 or IGHV1-2*04 | 83.33% (240/288 nt) 80.90% (233/288 nt) | IGHJ6*02 or IGHJ6*01 or IGHJ6*03 or IGHJ6*04 | 74.19% (46/62 nt) 72.58% (45/62 nt) | GSKHRLRDYVLYDDYGLINQQEWND YLEFLDV (SEQ ID NO: 308) |

TABLE 45

Light Chain Germline Gene Usage for PGT-141, PGT-142, PGT-143, and PGT-144.

| mAb Clone | Germline V-gene allele | Identity to V-gene | Germline J-gene allele | Identity to J-gene | Light chain CDR3 |
|---|---|---|---|---|---|
| PGT-141 (4964_G22; 4993_K13) | IGKV2-28*01 or IGKV2D-28*01 | 86.05% (253/294 nt) | IGKJ1*01 | 89.19% (33/37 nt) | MQGLNRPWT (SEQ ID NO: 288) |
| PGT-142 (4995_E20) | IGKV2-28*01 or IGKV2D-28*01 | 86.05% (253/294 nt) | IGKJ1*01 | 89.19% (33/37 nt) | MQGLNRPWT (SEQ ID NO: 288) |
| PGT-143 (4980_N08) | IGKV2-28*01 or IGKV2D-28*01 | 86.05% (253/294 nt) | IGKJ1*01 | 89.19% (33/37 nt) | MQGLNRPWT (SEQ ID NO: 288) |
| PGT-144 (4970_K22) | IGKV2-28*01 or IGKV2D-28*01 | 86.73% (255/294 nt) | IGKJ1*01 | 86.49% (32/37 nt) | MQGLNRPWT (SEQ ID NO: 288) |

Example 25: Heavy and Light Chain Alignments for Selected Antibodies (PGT-141, PGT-142, PGT-143, and PGT-144)

Alignments of the genes (nucleic acid sequences) and proteins (amino acid sequence) for variable regions of both the heavy and light chains of the PGT-141, PGT-142, PGT-143, and PGT-144 antibodies are provided in Tables 46-49.

Figure 25:
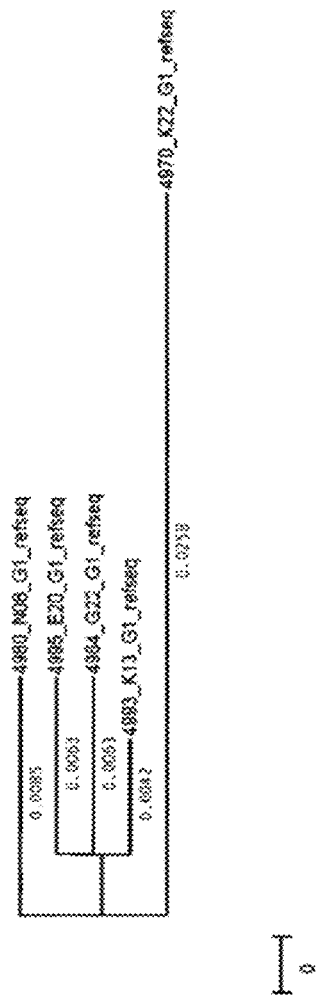
FIG. 25 is a tree diagram illustrating the relationships between the heavy chain variable gene sequences of antibodies PGT-141, PGT-142, and PGT-143. Scale bar=0.04. A value of zero demonstrates that an identical antibody was produced by two separate B-cell clones. Antibodies are less closely-related as the provided values increase.
Figure 26:
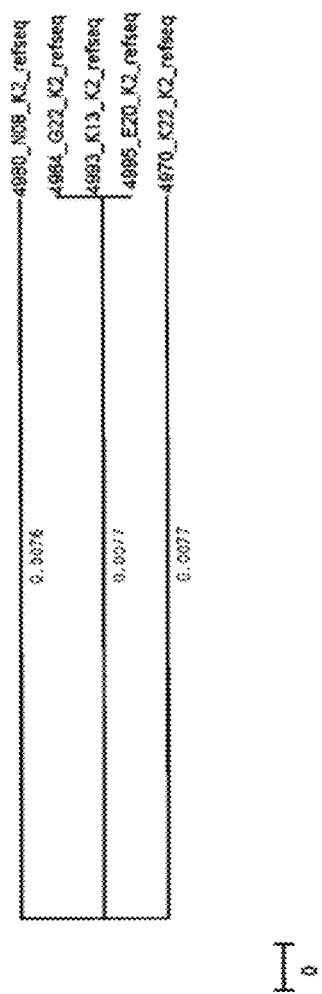
FIG. 26 is a tree diagram illustrating the relationships between the light chain variable gene sequences of antibodies PGT-141, PGT-142, and PGT-143. Scale bar=0.04. A value of zero demonstrates that an identical antibody was produced by two separate B-cell clones. Antibodies are less closely-related as the provided values increase.
Figure 27:
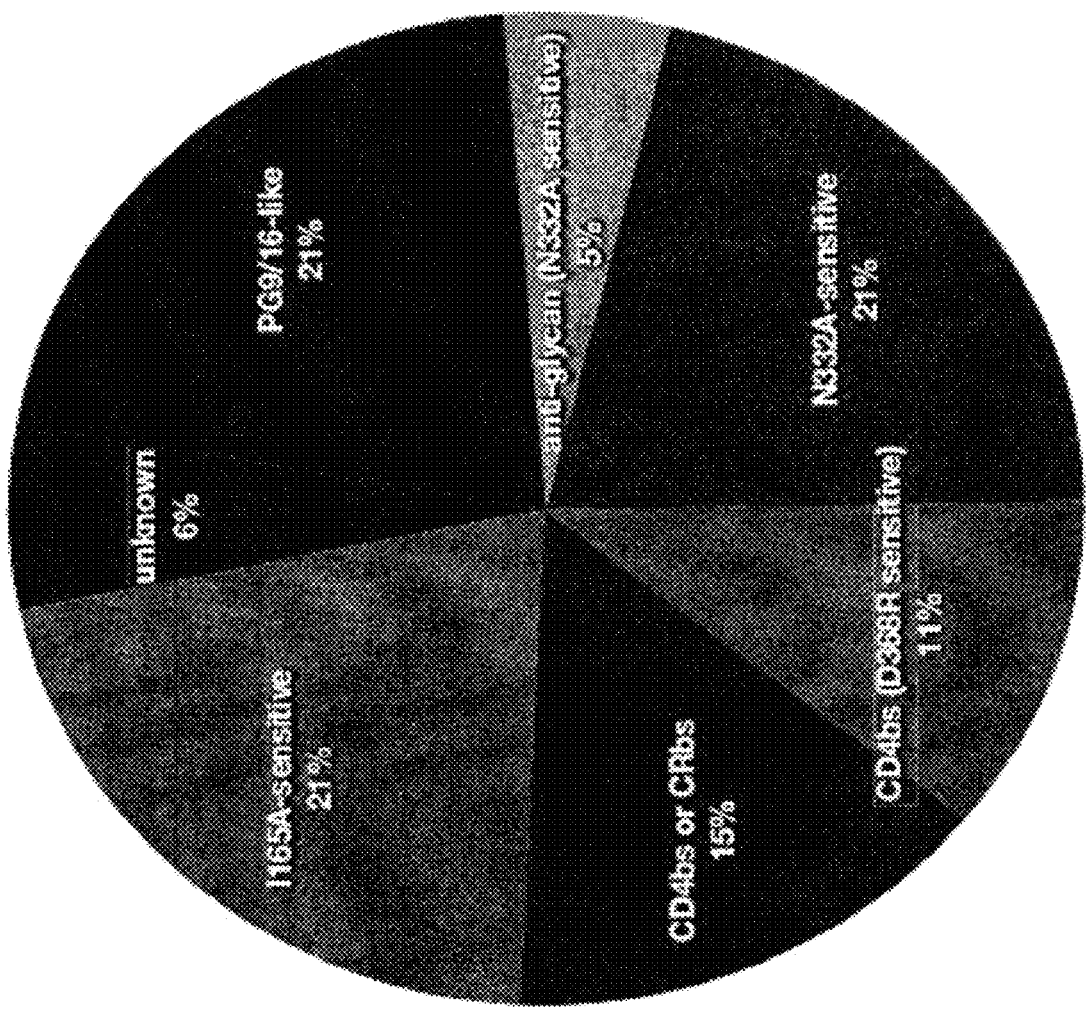
FIG. 27 is a pie chart showing that a limited number of antibody specificities mediate broad and potent serum neutralization in elite neutralizers (Walker L M, et al. PLOS Pathogen, 2010).

Moreover, gene relationship trees that depict the relatedness of either the heavy or light chains of these antibodies to one another are provided in FIGS. 25 and 26, respectively.

Figure 28:
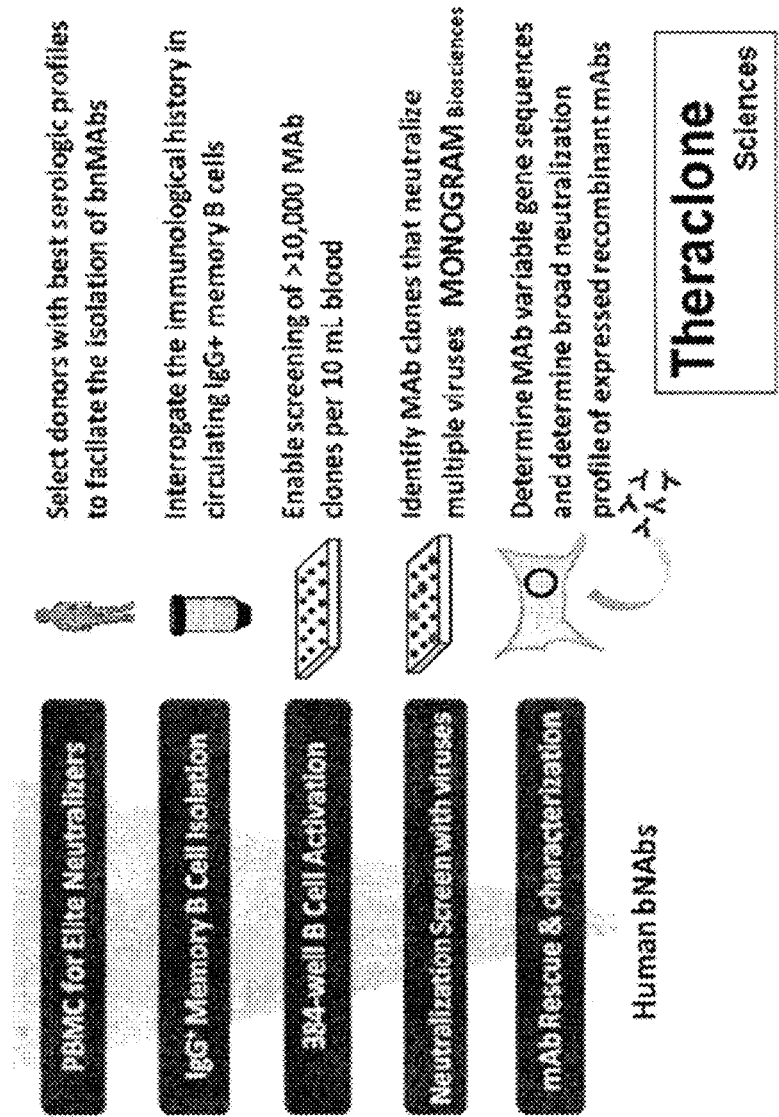
FIG. 28 is a schematic diagram depicting the I-Star™ Human bNAb (broadly Neutralizing Antibody) Discovery Platform developed by Theraclone Sciences.
Figure 29:
FIG. 29 is a schematic diagram depicting the method of bNMab (broadly Neutralizing Monoclonal Antibody) isolation form IgG-positive (IgG+) Memory B Cells developed by Theraclone Sciences.
Figure 30:
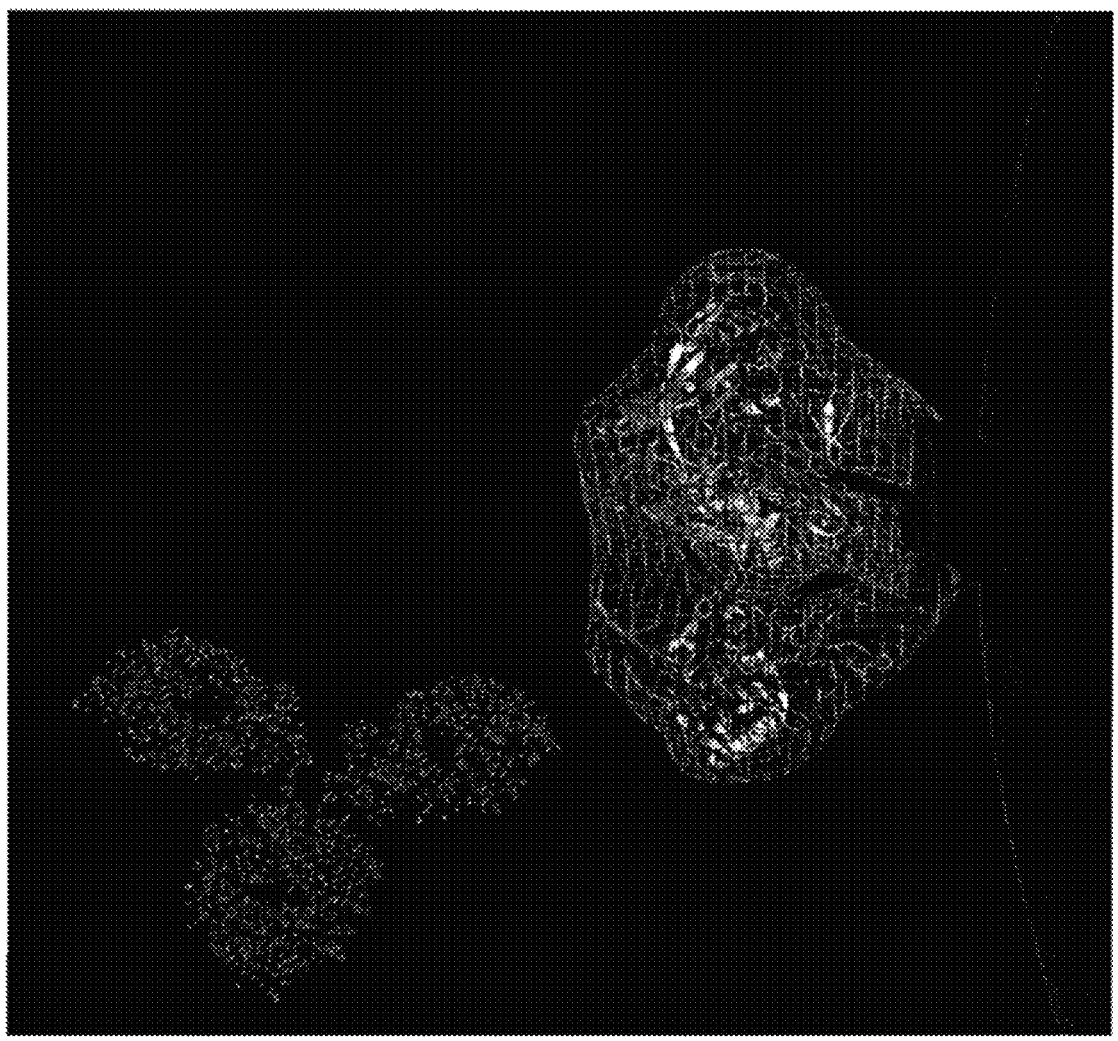
FIG. 30 is a computer-generated three-dimensional depiction of trimer-specific PG9 and PG16 antibodies in close proximity of conserved regions of V2 and V3, where they bind.
Figure 31:
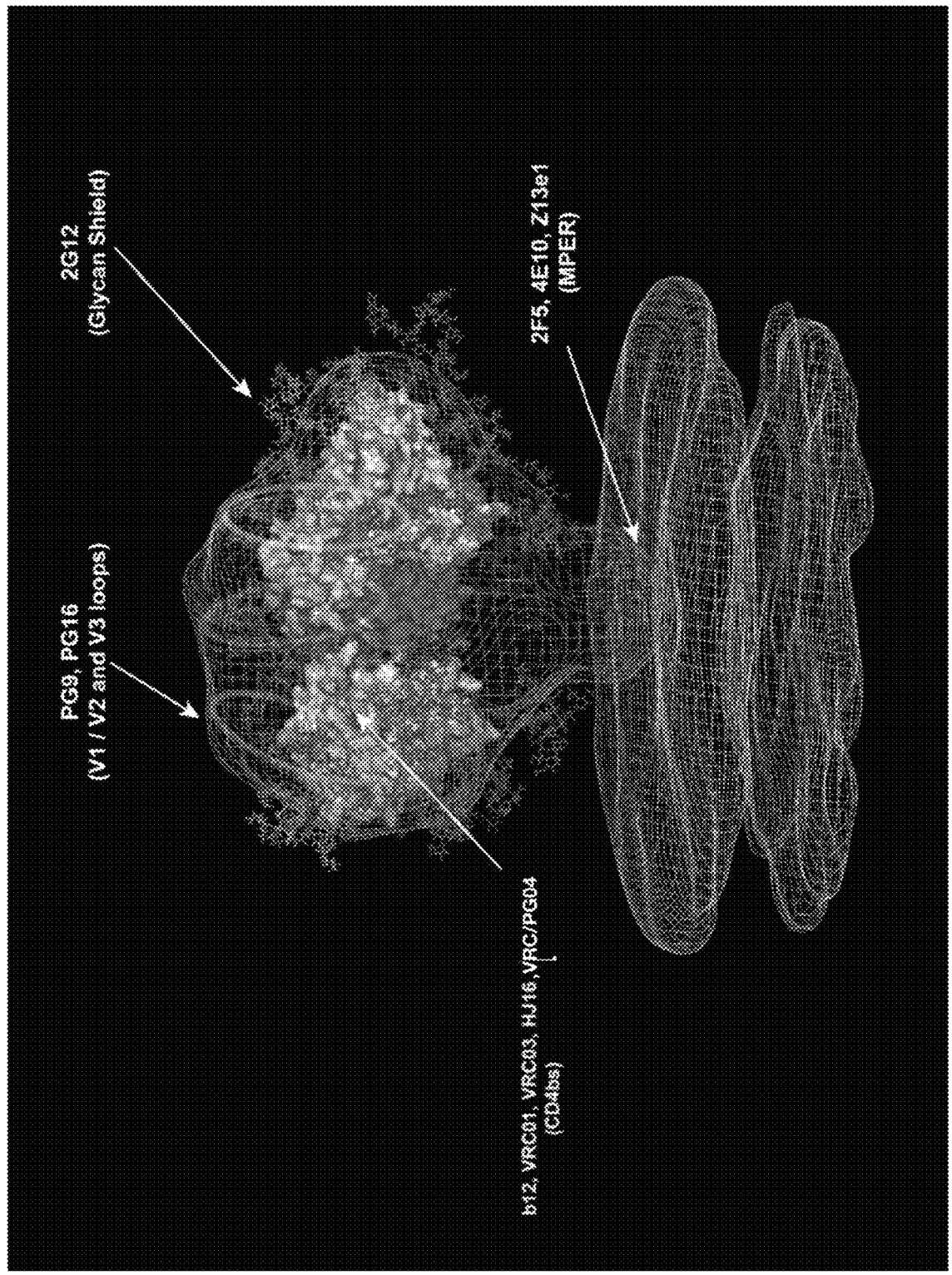
FIG. 31 is a computer-generated three-dimensional depiction of highly conserved epitopes on the HIV spike, including the V1/V2 and V3 loops to which PG9 and PG16 bind and the epitopes to which PGT-121, PGT-122, PGT-123, PGT-125, PGT-126, PGT-130, PGT-135, PGT-136, PGT-141, PGT-142, PGT-143, and PGT-144.

Example 26: High Through put Functional Screening of Activated B Cells From 4 African Elite Neutralizers Yields a Panel of Novel Broadly Neutralizing Antibodies Antibodies PGT-121, PGT-122, PGT-123, PGT-125, PGT-126, PGT-130, PGT-135, PGT-136, PGT-141, PGT-142, PGT-143, and PGT-144 were generated according to the I-STAR™ Human bNAb (broadly Neutralizing Antibody) Discovery Platform depicted in FIG. 28. The isolation process involves identifying multiple neutralizing hits from IgG Memory B cells (as shown in FIG. 29). Once the recombinant monoclonal antibody is generated, then the neutralizing ability of the monoclonal antibody is confirmed. As a consequence of these methods, the recombinant antibodies of the invention are highly related (as shown in Examples 21-24). Moreover, these methods identify clusters of related sequences with increased neutralization activity. Furthermore, the antibodies of the invention bind to highly conserved regions of the HIV viral spike (FIGS. 30 and 31).

Thirteen new monoclonal antibodies were isolated from 4 Protocol G elite neutralizers. Table 50 provides information regarding characteristics of each antibody.

Preliminary mapping indicates that the antibodies from donors 17, 36 and 39 provided in Table 50 define a collection of overlapping and highly conserved epitopes at the viral spike. Evidence of the overlapping nature of these epitopes is provided by, for instance, the results of competition studies (Table 54). As an example, PGT-121 and PGT-125 demonstrate strong competition for binding to the spatially overlapping epitopes.

TABLE 50

| Donor | Cluster | Mabs | HCDR3 Length | Identity to V-gene |
|---|---|---|---|---|
| 17 | #1 | 3 (PGT-121-3) | 24 | 77-80% |
| 36 | #1 | 2 (PGT-125-6) | 19 | 79-82% |
|  | #2 | 2 (PGT-130-1) | 19 | 80% |
| 39 | #1 | 1 (PGT-135) | 18 | 82% |
|  | #2 | 1 (PGT-136) | 18 | 83% |
| 84 | #1 | 4 (PGT-141-4) | 32 | 83-84% |

TABLE 51

| | | | Clade A | Clade B | | Clade C | | CRF01_AE |
|---|---|---|---|---|---|---|---|---|
| Rank | Score | Country | 94UG103 | 92BR020 | JRCSF | IAVI C22 | 93IN905 | 92TI1021 |
| 1 | 3.67 | Ivory Coast | 900 | 900 | 2700 | 2700 | 2700 | 2700 |
| 2 | 3 | Zambia | 300 | 300 | 2700 | 300 | 2700 | 2700 |
| 5 | 2.83 | Ivory Coast | 300 | 300 | 900 | 300 | 2700 | 2700 |
| 5 | 2.83 | Ivory Coast | 300 | 900 | 2700 | 900 | 2700 | 100 |
| 5 | 2.83 | Kenya | 300 | 900 | 900 | 900 | 2700 | 300 |
| 5 | 2.83 | South Africa | 300 | 900 | 900 | 2700 | 2700 | 100 |
| 5 | 2.83 | Rwanda | 300 | 2700 | 900 | 2700 | 2700 | <100 |
| 8 | 2.69 | Zambia | 345 | 345 | 1190 | 1190 | 1190 | 345 |
| 10 | 2.67 | UK | 300 | 900 | 900 | 2700 | 900 | 100 |
| 10 | 2.67 | Zambia | 900 | 900 | 900 | 300 | 2700 | 100 |
| 10 | 2.67 | Uganda | 900 | 900 | 900 | 2700 | 900 | <100 |
| 15 | 2.5 | Ivory Coast | 300 | 900 | 300 | 900 | 900 | 300 |
| 15 | 2.5 | South Africa | 100 | 300 | 300 | 2700 | 900 | 900 |
| 15 | 2.5 | South Africa | 300 | 300 | 300 | 2700 | 2700 | 100 |
| 15 | 2.5 | UK | 300 | 900 | 300 | 900 | 900 | 300 |
| 15 | 2.5 | South Africa | 2700 | 100 | 300 | 2700 | 2700 | <100 |
| 15 | 2.5 | Uganda | 900 | 900 | 900 | 900 | 900 | <100 |
| 15 | 2.5 | Zambia | 300 | <100 | 900 | 300 | 2700 | 2700 |

Table 52 provides quantitative values for the neutralizing activity of each monoclonal antibody isolated from the 4 protocol G elite neutralizers.

TABLE 52

| | 1050 (ug/ml) | | | | | | |
|---|---|---|---|---|---|---|---|
| | | Donor 17 | | | Donor 36 | | |
| | PG9 | PGT121 | PGT122 | PGT123 | PGT125 | PGT126 | PGT130 |
| 92BR020 | >10 | 0.0177 | 0.0337 | 0.0130 | 0.0214 | 0.0163 | 1.1242 |
| 92RW020 | 0.1614 | 0.0063 | 0.0072 | 0.0038 | 0.0028 | 0.0046 | 0.0140 |
| 92TH021 | 0.1026 | >10 | >10 | >10 | 0.0066 | 0.1147 | 0.0082 |
| 92UG005 | >10 | >10 | >10 | 2.4924 | >10 | 0.0181 | 0.4741 |
| 92UG024 | 1.9142 | >10 | >10 | >10 | >10 | >10 | >10 |
| 93IN905 | 0.0480 | 0.0082 | 0.0138 | 0.0071 | 0.0137 | 0.0194 | 0.0182 |
| 93UG077 | >10 | 0.0459 | 0.1913 | 0.0303 | 0.0262 | 0.0256 | >10* |
| 94UG103 | 0.3098 | 1.3778 | 1.4643 | 0.8461 | 0.0124 | 0.0091 | 0.6355 |
| CMU02 | >10 | >10 | >10 | >10 | >10 | >10 | >10 |
| MGRM-C-026 | 0.1130 | 0.0034 | 0.0089 | 0.0031 | 0.0106 | 0.0076 | 0.0173 |
| APV13 | >10 | 0.3157 | 0.9923 | 0.2215 | 0.0128 | 0.0120 | 0.0345 |
| APV17 | >10 | 0.0950 | 0.5220 | 0.1798 | 7.3065 | 0.5013 | >10 |
| APV6 | 0.2139 | 0.0423 | 0.0851 | 0.0327 | 0.0359 | 0.0249 | >10 |
| JRFL | >10 | 0.0276 | 0.0471 | 0.0283 | 0.0156 | 0.0140 | 0.0346 |
| MGRM-A-010 | 0.0375 | 2.6078 | 1.6836 | 0.4921 | 0.0025 | 0.0033 | 0.0054 |
| MGRM-AG-005 | >10 | 1.1719 | >10 | 0.1036 | >10 | 1.3488 | 0.9466 |
| MGRM-C-027 | 2.4538 | 0.0094 | 0.0388 | 0.0169 | >10 | 1.1404 | 0.0052 |
| MGRM-C-028 | 0.1211 | 1.1929 | 2.0600 | 0.4433 | 5.7772 | 0.2827 | >10 |
| MGRM-D-001 | >10 | 0.7442 | 0.8673 | 0.2154 | 2.3116 | 0.0639 | >10 |
| MGRM-D-018 | 2.0444 | 0.0086 | 0.0115 | 0.0047 | 0.0382 | 0.0093 | 0.0378 |
| JRCSF | 0.0048 | 0.0343 | 0.0727 | 0.0423 | 0.0060 | 0.0061 | 0.0089 |
| NL43 | 0.6871 | >10 | >10 | >10 | >10 | >10 | >10 |
| aMLV | >10 | >10 | >10 | >10 | >10 | >10 | >10 |
| median IC50 | 0.12 | 0.04 | 0.08 | 0.04 | 0.01 | 0.02 | 0.03 |
| % neutralized | 59 | 77 | 73 | 82 | 73 | 86 | 64 |

| | 1050 (ug/ml) | | | | | |
|---|---|---|---|---|---|---|
| | Donor 39 | | Donor 84 | | | |
| | PGT135 | PGT136 | PGT141 | PGT142 | PGT143 | PGT144 |
| 92BR020 | 0.1043 | >10 | >10 | >10 | >10 | >10 |
| 92RW020 | 0.1573 | 0.7383 | >10 | >10 | >10 | >10 |
| 92TH021 | >10 | >10 | 0.0019 | 0.0022 | 0.0028 | 0.0934 |
| 92UG005 | >10 | >10 | >10 | >10 | >10 | >10 |
| 92UG024 | 0.0139 | 0.0915 | >10 | >10 | >10 | >10 |
| 93IN905 | 0.0183 | 0.0135 | 0.0016 | 0.0017 | 0.0021 | 0.1581 |

TABLE 52-continued

| | | | | | | |
|---|---|---|---|---|---|---|
| 93UG077 | >10 | >10 | >10 | >10 | >10 | >10 |
| 94UG103 | >10 | >10 | >10 | >10 | >10 | >10 |
| CMU02 | >10 | >10 | >10 | >10 | >10 | >10 |
| MGRM-C-026 | 0.0123 | 0.0065 | >10 | >10 | >10 | >10 |
| APV13 | 0.5452 | >10 | >10 | >10 | >10 | >10 |
| APV17 | >10 | >10 | 0.6159 | 0.3929 | 0.6179 | 5.1207 |
| APV6 | >10 | >10 | 5.0838 | 5.4170 | 4.4341 | >10 |
| JRFL | >10 | >10 | >10 | >10 | >10 | >10 |
| MGRM-A-010 | >10 | >10 | 0.0563 | 0.0578 | 0.0657 | 4.0160 |
| MGRM-AG-005 | >10 | >10 | 0.3915 | 0.2196 | 0.2441 | >10 |
| MGRM-C-027 | >10 | >10 | 0.8219 | 0.2722 | 0.5049 | >10 |
| MGRM-C-028 | 2.1608 | >10 | 2.3504 | 1.2264 | 1.8230 | >10 |
| MGRM-D-001 | >10 | >10 | >10 | >10 | >10 | >10 |
| MGRM-D-018 | 0.0433 | >10 | >10 | >10 | >10 | >10 |
| JRCSF | 0.1131 | >10 | 0.0047 | 0.0085 | 0.0064 | 0.1279 |
| NL43 | 6.7910 | >10 | 0.8562 | 0.7123 | 0.5849 | >10 |
| aMLV | >10 | >10 | >10 | >10 | >10 | >10 |
| median IC50 | 0.11 | 0.05 | 0.50 | 0.25 | 0.37 | 0.16 |
| % neutralized | 54 | 18 | 45 | 45 | 45 | 23 |

TABLE 53

Preliminary mapping of Mabs isolated from donors 17, 36, and 39: Cross competition (1)

| Donor | Cluster | mAB ID | sCD4 | b12 | 2G12 | F425/b4e8 | X5 | PG9 |
|---|---|---|---|---|---|---|---|---|
| 17 | 1 | 121 | ++ | − | +++ | +++ | + | +++ |
| | | 122 | + | − | +++ | ++ | − | +++ |
| | | 123 | + | − | +++ | +++ | − | +++ |
| 36 | 2 | 125 | ++ | − | +++ | ++ | − | + |
| | | 126 | + | − | +++ | ++ | − | + |
| | 3 | 130 | +++ | − | +++ | +++ | − | + |
| 39 | 4 | 135 | − | − | +++ | enhanced | − | − |
| | 5 | 136 | − | − | +++ | enhanced | − | − |

+++ Strong competition;
++ Moderate competition,
+ Weak Competition;
− none

TABLE 54

| | Competitor Antibody | | | | | | | | |
|---|---|---|---|---|---|---|---|---|---|
| mAb | sCD4 | b12 | 2G12 | F425 | X5 | PG9 | 121 | 125 | 130 | 135 |
| 121 | + | − | +++ | ++ | + | +++ | +++ | +++ | + | ++ |
| 122 | − | − | ++ | + | − | +++ | +++ | ++ | + | +++ |
| 123 | + | − | +++ | +++ | − | +++ | +++ | +++ | ++ | +++ |
| 125 | ++ | − | +++ | ++ | − | + | +++ | +++ | + | + |
| 126 | + | − | +++ | + | − | + | +++ | ++ | + | +++ |
| 127 | + | − | +++ | ++ | − | + | +++ | +++ | + | +++ |
| 128 | − | − | +++ | + | − | + | ++ | + | + | ++ |
| 130 | ++ | − | ++ | +++ | − | + | + | +++ | +++ | − |
| 131 | +++ | − | +++ | +++ | + | + | +++ | +++ | +++ | + |
| 135 | − | ++ | +++ | − | − | − | ++ | ++ | − | +++ |
| 136 | − | ++ | +++ | − | − | − | ++ | ++ | − | +++ |
| 137 | − | + | +++ | − | − | − | − | − | − | +++ |

Example 27: PGT Monoclonal Anti HIV Antibody Potency

Figure 32:
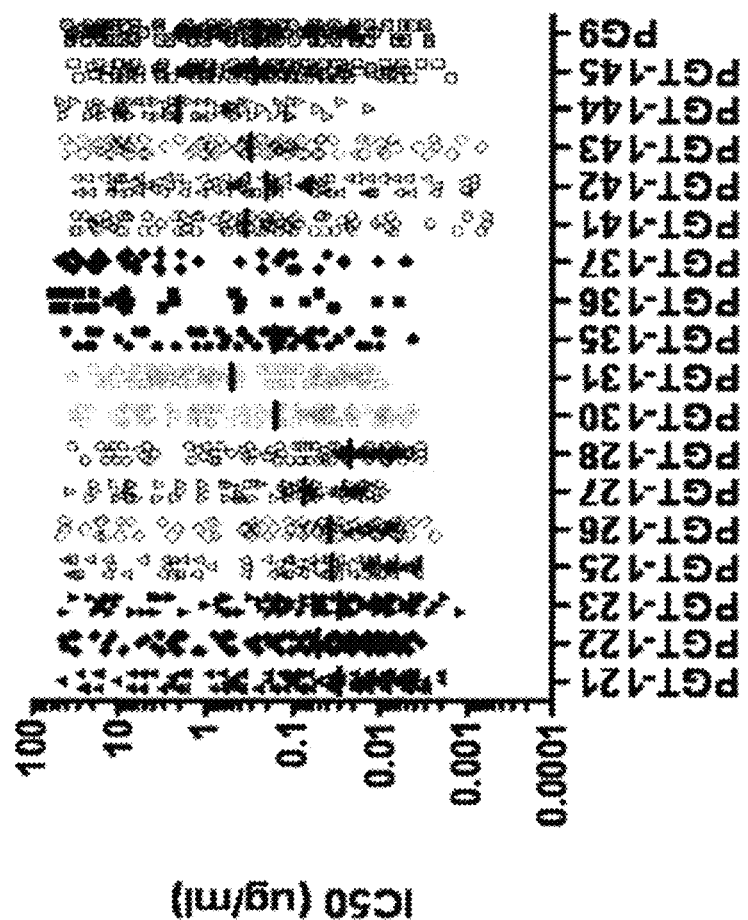
FIG. 32 is a graph depicting the potency of monoclonal anti-HIV antibodies PGT-121, PGT-122, PGT-123, PGT-125, PGT-126, PGT-127, PGT-128, PGT-130, PGT-131, PGT-135, PGT-136, PGT-137, PGT-141, PGT-142, PGT-143, PGT-144, PGT-145, and PG9, expressed as the half-maximal inhibitory concentration, or $IC_{50}$ (µg/ml). The bar for each antibody represents the median $IC_{50}$ value.

The potency of monoclonal anti-HIV antibodies PGT-121, PGT-122, PGT-123, PGT-125, PGT-126, PGT-127, PGT-128, PGT-130, PGT-131, PGT-135, PGT-136, PGT-137, PGT-141, PGT-142, PGT-143, PGT-144, PGT-145, and PG9 was determined against a 162 virus panel. FIG. 32 shows that the median concentration required to inhibit the activity, or neutralize, half of the virus in each panel (i.e., the half maximal inhibitory concentration ($IC_{50}$), expressed in µg/ml, the mean depicted by the black bar in each column) for each antibody of the PGT group is either comparable or superior to the PG9 control.

Example 28: Isolation of Anti-HIV Antibodies PGT-127, PGT-128, PGT-131, PGT-137, and PGT-145

Antibodies of the invention may be isolated from memory B cells in circulation as described in Walker L. M. et al, 2009, Science 326: 285-9. Specifically, surface IgG B cells seeded at near clonal density in 384-well microplates were activated in short-term culture. Supernatants were screened for neutralization activity against 2-4 pseudotyped viruses for which neutralization activity was detected at higher titers in the donor serum. Heavy and light chain variable regions were isolated from B cell lysates of selected neutralizing hits by reverse transcription from RNA followed by multiplex PCR amplification using family-specific V-gene primer sets. Amplicons from each lysate were uniquely tagged with multiplex identifier (MID) sequences and 454 sequencing regions (Roche). A normalized pooling of gamma, kappa and lambda chains was performed based on agarose gel image quantitation and the pool was analyzed by 454 Titanium® sequencing. Consensus sequences of the $V_H$ and $V_L$ chains were generated using the Amplicon Variant Analyzer (Roche) and assigned to specific B cell culture wells by decoding the MID tags. Clonally related sequences were identified by Clustal analysis. Selected $V_H$ and $V_L$ chains were synthesized and cloned in expression vectors with the appropriate $IgG_1$, IgK or IgL constant domain. Monoclonal antibodies were reconstituted by transient transfection in HEK293 cells followed by purification from serum-free culture supernatants.

Table 55 provides the gene usage data for the heavy chains of monoclonal anti-HIV antibodies PGT-127, PGT-128, PGT-131, PGT-137, and PGT-145.

TABLE 55

| Donor | mAb Clone | Germline V-gene allele | Identity to V-gene | Germline J-gene allele | Identity to J-gene | Heavy chain CDR3 |
|---|---|---|---|---|---|---|
| 196 | PGT-127 (5145_B14) | IGHV4-39*07 | 84.19% (245/291 nt) | IGHJ5*02 | 68.63% (35/51 nt) | FGGEVLVYRDW PKPAWVDL (SEQ ID NO: 322) |
|  |  | IGHV4-39*03 | 83.45% (242/290 nt) |  |  |  |
|  |  | IGHV4-39*06 | 83.51% (243/291 nt) | IGHJ5*01 | 64.71% (33/51 nt) |  |
|  |  | IGHV4-b*02 | 83.68% (241/288 nt) |  |  |  |
|  | PGT-128 (5114_A19) | IGHV4-39*07 | 79.73% (232/291 nt) | IGHJ5*02 | 74.51% (38/51 nt) | FGGEVLRYTDW PKPAWVDL (SEQ ID NO: 336) |
|  |  | IGHV4-b*01 | 79.86% (230/288 nt) |  |  |  |
|  |  | IGHv4-39*03 | 79.31% (230/290 nt) | IGHJ5*01 | 70.59% (36/51 nt) |  |
|  |  | IGHV4-b*02 | 79.51% (229/288 nt) |  |  |  |
|  | PGT-131 (5136_H01) | IGHV4-39*07 | 78.69% (229/291 nt) | IGHJ5*02 | 76.47% (39/51 nt) | SGGDILYYIEWQ KPHWFYP (SEQ ID NO: 350) |
|  |  | IGHV4-28*05 | 78.69% (229/291 nt) |  |  |  |
|  |  | IGHV4-39*03 | 78.62% (228/290 nt) | GHJ5*01 | 72.55% (37/51 nt) |  |
|  |  | IGHV4-39*06 | 78.35% (228/291 nt) |  |  |  |
|  |  | IGHV4-59*04 | 78.95% (225/285 nt) |  |  |  |
| 039 | PGT-137 (5345_I01) | IGHV4-39*03 | 77.46% (220/284 nt) | IGHJ5*02 | 78.00% (39/50 nt) | HKYHDIVMVVPI AGWFDP (SEQ ID NO: 366) |
|  |  | IGHV4-39*01 or IGHV4-39*02 or IGHV4-39*07 | 77.19% (220/285 nt) | GHJ5*01 | 74.00% (37/50 nt) |  |
| 584 | PGT-145 (4995_P16) | IGHV1-8*01 | 83.33% (240/288 nt) | IGHJ3*01 | 73.47% (36/49 nt) | GSKHRLRDYFL YNEYGPNYEEW GDYLATLDV (SEQ ID NO: 380) |
|  |  |  |  | IGHJ6*02 | 66.13% (41/62 nt) |  |
|  |  | IGHV1-46*01 or IGHV1-46*02 or IGHV1-46*03 | 80.21% (231/288 nt) | IGHJ3*02 | 71.43% (35/49 nt) |  |
|  |  |  |  | IGHJ6*01 or IGHJ6*04 | 64.52% (40/62 nt) |  |

Example 29: Broad Neutralization Coverage of HIV by Multiple High Potent Antibodies Broadly cross-reactive neutralizing antibodies (bnMAbs) against highly variable viral pathogens are much sought-after to treat or protect against global circulating viruses. The neutralizing antibody repertoires of four HIV-infected donors with remarkably broad and potent neutralizing responses were probed and 17 new monoclonal antibodies (mAbs) were rescued that neutralize broadly across clades. Many of these new monoclonal anti-HIV antibodies are almost 10-fold more potent than the PG9, PG16, and VRC01 bnMAbs and 100-fold more potent than the original prototype bnMAbs (Wu, X., et al. Science 329, 856-861 (2010); Walker, L. M., et al. Science 326, 285-289 (2009); Binley, J. M., et al. J Virol 78, 13232-13252 (2004)). The MAbs largely recapitulate the neutralization breadth and potency found in the corresponding donor serum and many recognize previously undescribed epitopes on envelope (Env) glycoprotein gp120, illuminating new targets for vaccine design. Analysis of neutralization by the full complement of anti-HIV bnMAbs now available reveals that certain combinations of antibodies provide significantly more favorable coverage of the enormous diversity of global circulating viruses than others and these combinations might be sought in active or passive immunization regimes. Overall, the isolation of multiple HIV bnMAbs, from several donors, that, in aggregate, provide broad coverage at low concentrations is a highly positive indicator for the eventual design of an effective antibody-based HIV vaccine.

Most successful anti-viral vaccines elicit neutralizing antibodies as a correlate of protection (Amanna, I. J., et al. Hum Vaccin 4, 316-319 (2008); Plotkin, S. A. Pediatr Infect Dis J 20, 63-75 (2001)). For highly variable viruses, such as HIV, HCV and, to a lesser extent influenza, vaccine design efforts have been hampered by the difficulties associated with eliciting neutralizing antibodies that are effective against the enormous diversity of global circulating isolates (i.e. broadly neutralizing antibodies, also referred to as bnAbs) (Barouch, D. H. Nature 455, 613-619 (2008); Karlsson Hedestam, G. B., et al. Nat Rev Microbiol 6, 143-155 (2008)). However, for HIV for example, 10-30% of infected individuals do, in fact, develop broadly neutralizing sera, and protective bnMAbs have been isolated from infected donors (Wu, X., et al. Science 329, 856-861 (2010); Walker, L. M., et al. Science 326, 285-289 (2009); Stamatatos, L., et al. Nat Med 15, 866-870 (2009); Trkola, A., et al. J Virol 69, 6609-6617 (1995); Stiegler, G., et al. AIDS Res Hum Retroviruses 17, 1757-1765 (2001); Burton, D. R., et al. Science 266, 1024-1027 (1994); Kwong, P. D. & Wilson, I. A. Nat Immunol 10, 573-578 (2009)). It has been suggested that, given the appropriate immunogen, it should be possible to elicit these types of responses by vaccination (Schief, W. R., et al. Curr Opin HIV AIDS 4, 431-440 (2009)) and understanding the properties of bnMAbs has become a major thrust in research on highly variable viruses.

Sera from approximately 1,800 HIV-1 infected donors was previously screened for neutralization breadth and potency, designating the top 1% as "elite neutralizers", based on a score incorporating both breadth and potency (Simek, M. D., et al. J Virol 83, 7337-7348 (2009)). In this study, bnMAbs were isolated from the top four elite neutralizers (Tables 56) by screening antibody-containing memory B cell supernatants for broad neutralizing activity using a recently described high-throughput functional approach (Walker, L. M., et al. Science 326, 285-289 (2009)). Antibody variable genes were rescued from B cell cultures that displayed cross-clade neutralizing activity and expressed as full-length IgGs. Analysis of the sequences revealed that all of the mAbs isolated from each individual donor belong to a distant, but clonally related cluster of antibodies (FIG. 49). Since it has been proposed that antibodies from HIV-1 infected patients are often polyreactive (Haynes, B. F., et al. Science 308, 1906-1908 (2005).; Mouquet, H., et al. Nature 467, 591-595 (2010)), the new mAbs were tested for binding to a panel of antigens and showed that they were not polyreactive (FIG. 36).

TABLE 56

Serum neutralizing activity of selected donors.

| Donor | presumed clade | Score | Clade A 94UG103 | Clade B 92BR020 | Clade B JRCSF | Clade C MGRM-C26 | Clade C 93IN905 | CRF01_AE 92TH021 |
|---|---|---|---|---|---|---|---|---|
| #36 | CRF02_AG | 3.67 | 900 | 900 | ≥2700 | ≥2700 | ≥2700 | ≥2700 |
| #84 | A or D | 3.00 | 300 | 300 | ≥2700 | 300 | ≥2700 | ≥2700 |
| #17 | A | 2.83 | 300 | ≥2700 | 900 | ≥2700 | ≥2700 | <100 |
| #39 | C | 2.83 | 300 | 900 | 900 | ≥2700 | ≥2700 | 100 |

TABLE 61

Neutralization activity of the newly identified PGT antibodies.

| | Median $IC_{50}$ (µg/ml) | Percent viruses neutralized $IC_{50} < 50$ µg/ml | Percent viruses neutralized $IC_{50} < 1$ µg/ml | Percent viruses neutralized $IC_{50} < 0.1$ µg/ml |
|---|---|---|---|---|
| PGT121 | 0.03 | 70 | 57 | 44 |
| PGT122 | 0.05 | 65 | 48 | 36 |
| PGT123 | 0.03 | 67 | 54 | 40 |
| PGT125 | 0.04 | 52 | 40 | 32 |
| PGT126 | 0.04 | 60 | 50 | 40 |
| PGT127 | 0.08 | 50 | 37 | 27 |
| PGT128 | 0.02 | 72 | 60 | 50 |
| PGT130 | 0.16 | 52 | 35 | 23 |
| PGT131 | 0.52 | 40 | 23 | 13 |
| PGT135 | 0.17 | 33 | 23 | 13 |
| PGT136 | 7.81 | 16 | 6 | 3 |
| PGT137 | 3.46 | 22 | 8 | 4 |
| PGT141 | 0.35 | 56 | 36 | 15 |
| PGT142 | 0.21 | 57 | 40 | 23 |
| PGT143 | 0.31 | 56 | 37 | 17 |
| PGT144 | 2.06 | 38 | 16 | 3 |
| PGT145 | 0.29 | 78 | 52 | 27 |
| PG9 | 0.23 | 77 | 54 | 29 |
| VRC01 | 0.32 | 93 | 74 | 20 |
| PGV04 | 0.20 | 88 | 65 | 25 |
| b12 | 2.82 | 34 | 10 | 2 |
| 2G12 | 2.38 | 32 | 11 | 1 |
| 4E10 | 3.41 | 96 | 13 | 1 |

Median neutralization potency against viruses neutralized with an $IC_{50} < 50$ µg/ml is color-coded as follows: green, 20-50 µg/ml; yellow, 2-20 µg/ml; orange, 0.2-2 µg/ml; red, <0.2 µg/ml. Neutralization breadth is color-coded as follows: green, 1% to 30%; yellow, 30% to 60%; orange, 60% to 90%; red, >90%.

The potency and breadth of the mAbs were next assessed on a 162-pseudovirus panel representing all major circulating HIV-1 subtypes (Table 58A-E and Table 61) (Walker, L. M., et al. Science 326, 285-289 (2009)). All of the mAbs exhibited cross-Glade neutralizing activity, but more strikingly, several displayed exceptional potency. The median $IC_{50}$s and $IC_{90}$s of PGTs 121-123 and 125-128 were almost 10-fold lower (i.e. more potent) than the recently described PG9, PG16, VRC01, and PGV04 bnMAbs (Wu, X., et al. Science 329, 856-861 (2010); Walker, L. M., et al. Science 326, 285-289 (2009)) and approximately 100-fold lower than other bnMAbs described earlier (Table 61). At concentrations less than 0.1 µg/ml, these mAbs still neutralized 27% to 50% of viruses in the panel (Table 61 and FIG. 33b). Although PGTs 135, 136, and 137 displayed a lesser degree of overall neutralization breadth relative to the other mAbs, they all still neutralized over 30% of the Glade C viruses on the panel (FIG. 36 and Table 58A). These results are significant considering that HIV-1_Glade C predominates in sub-Saharan Africa and accounts for more than 50% of all HIV-1 infections worldwide.

TABLE 58A

Neutralizing activity of PGT mAbs against a cross-clade 162-pseudovirus panel.

A) Median IC$_{50}$ (μg/ml) against viruses neutralized with an IC$_{50}$ <50 μg/ml$^3$

| Clade | n | PGT121 | PGT122 | PGT123 | PGT125 | PGT126 | PGT127 | PGT128 | PGT130 | PGT131 | PGT135 | PGT136 |
|---|---|---|---|---|---|---|---|---|---|---|---|---|
| A | 26 | 0.02 | 0.07 | 0.02 | 0.01 | 0.01 | 0.02 | 0.01 | 0.09 | 0.09 | 0.64 | 2.34 |
| B | 31 | 0.02 | 0.02 | 0.02 | 0.02 | 0.02 | 0.06 | 0.01 | 0.09 | 0.07 | 0.15 | 13.19 |
| C | 27 | 0.02 | 0.03 | 0.01 | 1.83 | 0.18 | 0.55 | 0.04 | 0.15 | 0.78 | 0.05 | 7.52 |
| D | 25 | 0.01 | 0.02 | 0.02 | 0.09 | 0.04 | 0.49 | 0.02 | 0.65 | 0.85 | 1.09 | 0.05 |
| F | 15 | 0.13 | 0.43 | 0.09 | 0.04 | 0.05 | 0.65 | 0.52 | 0.07 | 0.55 | 0.21 | 4.75 |
| G | 15 | 0.02 | 0.05 | 0.04 | 0.02 | 0.18 | 0.22 | 0.04 | 4.14 | 3.54 | 0.14 | 18.95 |
| AE | 10 | na | na | na | 0.03 | 1.77 | n a | 0.05 | 0.17 | 0.08 | na | na |
| AG | 10 | 0.49 | 2.75 | 0.61 | 0.01 | 0.03 | 0.04 | 0.67 | 0.04 | 0.18 | 27.37 | 29.11 |
| All | 162 | 0.03 | 0.05 | 0.03 | 0.04 | 0.04 | 0.08 | 0.07 | 0.18 | 0.52 | 0.17 | 7.81 |

| Clade | PGT137 | PGT141 | PGT142 | PGT143 | PGT144 | PGT145 | PG9 | VRC01 | PGV04 | b12 | 2G12 | 4E10 |
|---|---|---|---|---|---|---|---|---|---|---|---|---|
| A | 0.72 | 0.22 | 0.25 | 0.27 | 2.81 | 0.40 | 0.12 | 0.26 | 0.14 | 6.98 | 17.20 | 5.50 |
| B | 8.55 | 0.48 | 0.40 | 0.39 | 3.37 | 0.09 | 0.43 | 0.24 | 0.17 | 0.80 | 0.82 | 5.79 |
| C | 0.23 | 0.33 | 0.09 | 0.17 | 0.85 | 0.14 | 0.23 | 0.48 | 0.79 | 5.46 | 2.50 | 3.98 |
| D | 6.30 | 0.37 | 0.19 | 0.28 | 2.13 | 1.07 | 0.10 | 0.44 | 0.44 | 1.47 | 4.57 | 4.54 |
| F | 6.23 | 0.24 | 0.22 | 0.36 | 0.51 | 0.87 | 0.09 | 0.39 | 0.18 | na | 9.23 | 2.26 |
| G | 0.23 | 0.30 | 0.21 | 0.21 | 3.84 | 0.11 | 0.27 | 0.10 | 0.06 | 2.99 | 31.03 | 1.44 |
| AE | na | 0.01 | 0.01 | 0.02 | 0.10 | 0.97 | 0.10 | 0.36 | 1.24 | 21.07 | na | 0.63 |
| AG | 28.30 | 0.50 | 2.16 | 1.11 | 18.02 | 0.16 | 0.36 | 0.12 | 0.10 | 10.40 | 0.95 | 1.42 |
| All | 3.48 | 0.35 | 0.21 | 0.31 | 2.06 | 0.29 | 0.23 | 0.32 | 0.20 | 2.82 | 2.38 | 3.41 |

B) Percent viruses neutralized with an IC$_{50}$ <50 μg/ml$^3$

| Clade | n | PGT121 | PGT122 | PGT123 | PGT125 | PGT126 | PGT127 | PGT128 | PGT130 | PGT131 | PGT135 | PGT136 |
|---|---|---|---|---|---|---|---|---|---|---|---|---|
| A | 26 | 62 | 58 | 58 | 65 | 50 | 50 | 50 | 50 | 38 | 19 | 4 |
| B | 31 | 84 | 84 | 81 | 74 | 81 | 81 | 81 | 65 | 45 | 39 | 19 |
| C | 27 | 85 | 81 | 85 | 56 | 74 | 52 | 78 | 48 | 41 | 37 | 33 |
| D | 25 | 48 | 40 | 48 | 40 | 52 | 48 | 60 | 44 | 36 | 24 | 4 |
| F | 15 | 80 | 80 | 80 | 20 | 33 | 27 | 80 | 33 | 13 | 60 | 13 |
| G | 15 | 80 | 80 | 80 | 27 | 33 | 40 | 67 | 47 | 40 | 40 | 27 |
| AE | 10 | 0 | 0 | 0 | 60 | 40 | 0 | 60 | 80 | 60 | 0 | 0 |
| AG | 10 | 70 | 60 | 60 | 30 | 50 | 40 | 90 | 50 | 40 | 20 | 10 |
| All | 162 | 70 | 65 | 87 | 52 | 60 | 50 | 72 | 52 | 40 | 33 | 18 |

| Clade | PGT137 | PGT141 | PGT142 | PGT143 | PGT144 | PGT145 | PG9 | VRC01 | PGV04 | b12 | 2012 | 4E10 |
|---|---|---|---|---|---|---|---|---|---|---|---|---|
| A | 23 | 66 | 69 | 65 | 46 | 81 | 85 | 92 | 10 | 31 | 35 | 96 |
| B | 19 | 52 | 52 | 52 | 39 | 77 | 74 | 100 | 94 | 58 | 71 | 97 |
| C | 33 | 70 | 70 | 70 | 52 | 70 | 67 | 89 | 70 | 26 | 11 | 89 |
| D | 12 | 28 | 28 | 28 | 16 | 72 | 76 | 84 | 76 | 48 | 24 | 96 |
| F | 20 | 67 | 67 | 67 | 33 | 100 | 67 | 100 | 93 | 0 | 20 | 93 |
| G | 33 | 67 | 67 | 67 | 33 | 80 | 80 | 93 | 87 | 13 | 20 | 100 |
| AE | 0 | 40 | 40 | 40 | 30 | 90 | 100 | 100 | 90 | 40 | 0 | 100 |
| AG | 10 | 50 | 60 | 50 | 20 | 70 | 80 | 90 | 100 | 30 | 50 | 100 |
| All | 22 | 56 | 57 | 58 | 38 | 78 | 77 | 90 | 88 | 34 | 32 | 96 |

C) Median IC$_{50}$ (μg/ml) against all viruses$^3$

| Clade | n | PGT121 | PGT122 | PGT123 | PGT125 | PGT126 | PGT127 | PGT028 | PGT130 | PGT131 | PGT135 | PGT136 |
|---|---|---|---|---|---|---|---|---|---|---|---|---|
| A | 26 | 0.87 | 3.69 | 0.69 | 0.16 | 2.62 | 21.71 | 0.35 | 41.39 | 50.00 | 50.00 | 50.00 |
| B | 31 | 0.03 | 0.05 | 0.04 | 0.06 | 0.04 | 0.12 | 0.02 | 5.17 | 50.00 | 50.00 | 50.00 |
| C | 27 | 0.02 | 0.04 | 0.02 | 37.48 | 0.79 | 19.19 | 0.08 | 50.00 | 50.00 | 50.00 | 50.00 |
| D | 25 | 50.00 | 50.00 | 50.00 | 50.00 | 43.14 | 50.00 | 0.14 | 50.00 | 50.00 | 50.00 | 50.00 |
| F | 15 | 0.17 | 1.29 | 0.31 | 50.00 | 50.00 | 50.00 | 1.21 | 50.00 | 50.00 | 7.79 | 50.00 |
| G | 15 | 0.06 | 0.51 | 0.18 | 50.00 | 48.85 | 50.00 | 0.32 | 50.00 | 50.00 | 50.00 | 50.00 |
| AE | 10 | 50.00 | 50.00 | 50.00 | 1.61 | 50.00 | 50.00 | 0.31 | 0.58 | 2.60 | 50.00 | 50.00 |
| AG | 10 | 0.60 | 38.45 | 8.04 | 50.00 | 11.07 | 50.00 | 1.62 | 21.75 | 50.00 | 50.00 | 50.00 |
| All | 162 | 0.31 | 2.02 | 0.35 | 34.07 | 1.08 | 42.83 | 0.10 | 22.08 | 50.00 | 50.00 | 50.00 |

| Clade | PGT137 | PGT141 | PGT142 | PGT143 | PGT144 | PGT145 | PG9 | VRC01 | PGV04 | b12 | 2G12 | 4E10 |
|---|---|---|---|---|---|---|---|---|---|---|---|---|
| A | 50.00 | 1.92 | 2.21 | 6.34 | 50.00 | 1.16 | 0.21 | 0.28 | 0.14 | 50.00 | 50.00 | 6.79 |
| B | 50.00 | 33.21 | 15.15 | 25.89 | 50.00 | 0.34 | 2.08 | 0.24 | 0.25 | 4.17 | 1.90 | 5.76 |
| C | 50.00 | 3.28 | 0.79 | 0.80 | 48.89 | 0.49 | 0.57 | 0.71 | 2.76 | 50.00 | 50.00 | 3.98 |
| D | 50.00 | 50.00 | 50.00 | 50.00 | 50.00 | 10.00 | 1.91 | 0.58 | 1.01 | 50.00 | 50.00 | 5.30 |
| F | 50.00 | 1.15 | 0.82 | 0.98 | 29.56 | 0.82 | 0.58 | 0.39 | 0.18 | 50.00 | 50.00 | 2.26 |
| G | 50.00 | 4.69 | 5.95 | 4.77 | 50.00 | 0.21 | 0.51 | 0.12 | 0.13 | 50.00 | 50.00 | 1.44 |
| AE | 50.00 | 50.00 | 50.00 | 50.00 | 50.00 | 1.17 | 0.13 | 0.56 | 1.26 | 50.00 | 50.00 | 0.63 |
| AG | 50.00 | 31.02 | 16.43 | 41.24 | 50.00 | 1.27 | 3.47 | 0.16 | 0.10 | 50.00 | 14.00 | 1.42 |
| All | 50.00 | 18.01 | 9.46 | 13.76 | 50.00 | 0.88 | 0.82 | 0.34 | 0.30 | 50.00 | 50.00 | 3.50 |

TABLE 58A-continued

Neutralizing activity of PGT mAbs against a cross-clade 162-pseudovirus panel.

D) Median IC$_{50}$ (µg/ml) against viruses neutralized with an IC$_{50}$ <50 µg/ml[3]

| Clade | n | PGT121 | PGT122 | PGT123 | PGT125 | PGT126 | PGT127 | PGT128 | PGT130 | PGT131 | PGT135 | PGT136 |
|---|---|---|---|---|---|---|---|---|---|---|---|---|
| A | 26 | 0.20 | 0.33 | 0.18 | 0.07 | 0.06 | 0.16 | 0.04 | 4.99 | 0.73 | 1.01 | na |
| B | 31 | 0.11 | 0.15 | 0.14 | 0.13 | 0.17 | 0.36 | 0.07 | 0.77 | 0.50 | 2.87 | 2.09 |
| C | 27 | 0.12 | 0.17 | 0.08 | 0.18 | 0.96 | 7.99 | 0.17 | 2.67 | 15.80 | 0.28 | 0.28 |
| D | 25 | 0.12 | 0.11 | 0.13 | 0.87 | 0.33 | 0.18 | 0.12 | 3.18 | 2.67 | 1.13 | 2.10 |
| F | 15 | 0.17 | 5.53 | 0.74 | 0.37 | 1.00 | 0.86 | 1.17 | 4.84 | 1.92 | 1.26 | na |
| G | 15 | 0.22 | 0.65 | 0.19 | 0.05 | 0.17 | 0.67 | 0.12 | 28.06 | na | 1.01 | 7.54 |
| AE | 10 | na | na | na | 0.22 | 19.58 | na | 1.47 | 0.08 | 0.21 | na | na |
| AG | 10 | 0.56 | 0.97 | 2.27 | 0.05 | 0.06 | 0.24 | 0.13 | 0.07 | 0.16 | na | na |
| All | 162 | 0.13 | 0.26 | 0.18 | 0.78 | 0.17 | 0.46 | 0.32 | 1.88 | 0.54 | 1.13 | 2.00 |

| Clade | PGT137 | PGT141 | PGT142 | PGT143 | PGT144 | PGT145 | PG9 | VRC01 | PGV04 | b12 | 2G12 | 4E10 |
|---|---|---|---|---|---|---|---|---|---|---|---|---|
| A | 2.54 | 2.88 | 2.37 | 1.57 | 4.31 | 4.30 | 2.24 | 2.20 | 1.45 | 48.45 | 17.77 | 40.61 |
| B | na | 4.62 | 9.52 | 2.84 | 7.06 | 0.54 | 2.00 | 2.05 | 1.06 | 5.96 | 4.52 | 30.31 |
| C | 1.32 | 3.83 | 1.69 | 2.02 | 12.43 | 1.76 | 7.00 | 6.18 | 3.83 | 27.42 | 28.67 | 21.21 |
| D | 16.10 | 25.10 | 9.75 | 8.36 | 19.06 | 5.27 | 0.80 | 5.72 | 3.23 | 12.08 | 3.77 | 23.46 |
| F | 21.09 | 4.55 | 3.45 | 6.08 | 7.79 | 9.74 | 0.52 | 2.72 | 2.34 | na | 21.50 | 7.63 |
| G | 1.45 | 1.58 | 1.99 | 1.85 | 7.57 | 2.18 | 6.35 | 1.44 | 1.74 | 22.81 | na | 16.57 |
| AE | na | 0.03 | 0.03 | 0.05 | 3.41 | 11.09 | 1.02 | 4.08 | 8.18 | 12.08 | na | 12.96 |
| AG | na | 3.66 | 5.15 | 4.97 | na | 0.87 | 0.36 | 1.17 | 1.97 | 16.96 | 7.04 | 15.36 |
| All | 2.10 | 3.80 | 3.75 | 2.60 | 8.37 | 2.10 | 1.22 | 2.70 | 2.00 | 18.01 | 8.06 | 22.37 |

E) Percent viruses neutralized with an IC$_{50}$ <50 µg/ml[3]

| Clade | n | PGT121 | PGT122 | PGT123 | PGT125 | PGT126 | PGT127 | PGT128 | PGT130 | PGT131 | PGT135 | PGT136 |
|---|---|---|---|---|---|---|---|---|---|---|---|---|
| A | 26 | 50 | 50 | 50 | 54 | 50 | 46 | 50 | 31 | 13 | 4 | 0 |
| B | 31 | 81 | 77 | 77 | 58 | 74 | 05 | 77 | 42 | 29 | 23 | 3 |
| C | 27 | 67 | 59 | 63 | 26 | 48 | 38 | 67 | 26 | 21 | 33 | 13 |
| D | 25 | 36 | 32 | 32 | 28 | 36 | 28 | 48 | 16 | 8 | 8 | 4 |
| F | 15 | 00 | 73 | 53 | 20 | 27 | 13 | 53 | 20 | 7 | 33 | 0 |
| G | 15 | 00 | 00 | 47 | 7 | 20 | 20 | 47 | 7 | 0 | 20 | 7 |
| AE | 10 | 0 | 0 | 0 | 40 | 20 | 0 | 50 | 50 | 40 | 0 | 0 |
| AG | 10 | 30 | 30 | 40 | 30 | 30 | 30 | 50 | 30 | 20 | 0 | 0 |
| All | 162 | 56 | 54 | 52 | 37 | 46 | 36 | 57 | 28 | 10 | 17 | 5 |

| Clade | PGT137 | PGT141 | PGT142 | PGT143 | PGT144 | PGT145 | PG9 | VRC01 | PGV04 | b12 | 2G12 | 4E10 |
|---|---|---|---|---|---|---|---|---|---|---|---|---|
| A | 12 | 38 | 46 | 35 | 4 | 46 | 69 | 88 | 88 | 4 | 4 | 23 |
| B | 0 | 32 | 39 | 29 | 13 | 61 | 29 | 100 | 84 | 45 | 52 | 16 |
| C | 21 | 48 | 58 | 50 | 29 | 58 | 48 | 81 | 48 | 17 | 4 | 42 |
| D | 4 | 20 | 20 | 16 | 8 | 36 | 40 | 72 | 56 | 28 | 12 | 20 |
| F | 7 | 47 | 53 | 47 | 27 | 67 | 40 | 100 | 93 | 0 | 7 | 40 |
| G | 13 | 33 | 47 | 40 | 7 | 67 | 40 | 93 | 87 | 13 | 0 | 53 |
| AE | 00 | 30 | 30 | 30 | 20 | 60 | 70 | 100 | 80 | 10 | 0 | 70 |
| AG | 0 | 20 | 30 | 20 | 0 | 50 | 40 | 90 | 100 | 10 | 30 | 60 |
| All | 7 | 36 | 40 | 33 | 14 | 53 | 48 | 80 | 77 | 10 | 15 | 34 |

F) Median IC$_{50}$ (µg/ml) against all viruses[3]

| Clade | n | PGT121 | PGT122 | PGT123 | PGT125 | PGT126 | PGT127 | PGT128 | PGT130 | PGT131 | PGT135 | PGT136 |
|---|---|---|---|---|---|---|---|---|---|---|---|---|
| A | 26 | 47.89 | 48.07 | 23.26 | 26.63 | 6.27 | 50.00 | 9.38 | 50:00 | 50.00 | 50.00 | 50.00 |
| B | 31 | 0.23 | 0.41 | 0.42 | 0.49 | 0.29 | 1.17 | 0.12 | 50.00 | 50.00 | 50.00 | 50.00 |
| C | 27 | 0.47 | 7.99 | 7.29 | 50.00 | 50.00 | 50.00 | 2.54 | 50.00 | 50.00 | 50.00 | 50.00 |
| D | 25 | 50.00 | 50.00 | 50.00 | 50.00 | 50.00 | 50.00 | 50.00 | 50.00 | 50.00 | 50.00 | 50.00 |
| F | 15 | 1.86 | 23.47 | 5.05 | 50.00 | 50.00 | 50.00 | 38.14 | 50.00 | 50.00 | 50.00 | 50.00 |
| G | 15 | 2.10 | 26.35 | 50.00 | 50.00 | 50.00 | 50.00 | 50.00 | 50.00 | 50.00. | 50.00 | 50.00 |
| AE | 10 | 50.00 | 50.00 | 50.00 | 50.00 | 50.00 | 50.00 | 29.21 | 50.00 | 50.00 | 50.00 | 50.00 |
| AG | 10 | 50.00 | 50.00 | 50.00 | 50.00 | 50.00 | 50.00 | 42.87 | 50.00 | 50.00 | 50.00 | 50.00 |
| All | 162 | 10.40 | 38.11 | 18.25 | 50.00 | 50.00 | 50.00 | 3.73 | 50.00 | 5000 | 50.00 | 50.00 |

| Clade | PGT137 | PGT141 | PGT142 | PGT143 | PGT144 | PGT145 | PG9 | VRC01 | PGV04 | b12 | 2G12 | 4E10 |
|---|---|---|---|---|---|---|---|---|---|---|---|---|
| A | 50.00 | 50.00 | 50.00 | 50.00 | 50.00 | 50.00 | 2.71 | 2.38 | 1.62 | 50.00 | 50.00 | 50.00 |
| B | 50.00 | 50.00 | 50.00 | 50.00 | 50.00 | 6.51 | 50.00 | 2.05 | 2.05 | 50.00 | 44.23 | 50.00 |
| C | 50.00 | 50.00 | 43.11 | 50.00 | 50.00 | 30.57 | 22.11 | 6.71 | 50.00 | 50.00 | 50.00 | 50.00 |
| D | 50.00 | 50.00 | 50.00 | 50.00 | 50.00 | 50.00 | 50.00 | 8.77 | 7.58 | 50.00 | 50.00 | 50.00 |
| F | 50.00 | 50.00 | 34.51 | 50.00 | 50.00 | 16.34 | 50.00 | 2.72 | 2.52 | 50.00 | 50.00 | 50.00 |

TABLE 58A-continued

Neutralizing activity of PGT mAbs against a cross-clade 162-pseudovirus panel.

| G | 50.00 | 50.00 | 50.00 | 50.00 | 50.00 | 9.93 | 50.00 | 1.69 | 2.07 | 50.00 | 50.00 | 29.65 |
| AE | 50.00 | 50.00 | 50.00 | 50.00 | 50.00 | 39.37 | 0.78 | 4.08 | 11.00 | 50.00 | 50.00 | 19.49 |
| AG | 50.00 | 50.00 | 50.00 | 50.00 | 50.00 | 35.44 | 50.00 | 1.40 | 1.97 | 50.00 | 50.00 | 26.15 |
| All | 50.00 | 50.00 | 50.00 | 50.00 | 50.00. | 31.20 | 46.50 | 3.31 | 4.11 | 50.00 | 50.00 | 50.00 | a) Neutralization potency is color-coded as follows: white, median potency >50 μg/ml; green, median potency between 20 and 50 ug/ml; yellow, median potency between 2 and 20 μg/ml; orange, median potency between 0.2 and 2 μg/ml; red, median potency <0.2 μg/ml.
b) Neutralization breadth is color-coded as follows: white, no virus neutralized; green, 1% to 30% of viruses neutralized; yellow, 30% to 60% of viruses neutralized; orange, 60% to 90% of viruses neutralized; red, >90% of viruses neutralized.

TABLE 58B

| Isolate | Subtype | IC$_{50}$ (μg/mL)$^a$ | | | | | |
| --- | --- | --- | --- | --- | --- | --- | --- |
| | | PGT-121 | PGT-122 | PGT-123 | PGT-125 | PGT-126 | PGT-127 |
| 92RW008 | A | 0.003 | 0.003 | 0.003 | 0.004 | 0.008 | 0.012 |
| 92WR009 | | 1.739 | 42.406 | 15.680 | 0.144 | >50 | >50 |
| 92WR020 | | 0.004 | 0.009 | 0.002 | 0.004 | 0.006 | 0.010 |
| 92WR021 | | 0.009 | 0.021 | 0.005 | 0.005 | 0.006 | 0.011 |
| 92WR024 | | >50 | >50 | >50 | 35.530 | 41.995 | >50 |
| 92WR026 | | 0.014 | 0.036 | 0.012 | 0.007 | 0.008 | 0.024 |
| 92UG031 | | >50 | >50 | >50 | >50 | >50 | >50 |
| 92UG037 | | 0.031 | 0.068 | 0.023 | 0.005 | 0.011 | 0.014 |
| 93WR029 | | >50 | >50 | >50 | >50 | >50 | >50 |
| 93UG077 | | 0.019 | 0.084 | 0.028 | 0.012 | 0.020 | 0.055 |
| 94UG103 | | 2.518 | 2.041 | 0.678 | 0.008 | 0.008 | 0.017 |
| MG RM-A-001 | | >50 | >50 | >50 | 12.392 | >50 | >50 |
| MG RM-A-002 | | 0.013 | 0.017 | 0.011 | 0.013 | 0.015 | 9.422 |
| MG RM-A-003 | | 0.435 | 3.794 | 0.495 | >50 | >50 | >50 |
| MG RM-A-004 | | >50 | >50 | >50 | >50 | >50 | >50 |
| MG RM-A-005 | | >50 | >50 | >50 | >50 | >50 | >50 |
| MG RM-A-006 | | 0.396 | >50 | >50 | >50 | >50 | >50 |
| MG RM-A-007 | | >50 | >50 | >50 | >50 | >50 | >50 |
| MG RM-A-008 | | >50 | >50 | >50 | >50 | >50 | >50 |
| MG RM-A-009 | | 0.006 | 0.012 | 0.004 | 0.009 | 0.004 | 0.013 |
| MG RM-A-010 | | 2.444 | 2.509 | 0.705 | 0.004 | 0.002 | 0.017 |
| MG RM-A-011 | | >50 | >50 | >50 | >50 | >50 | >50 |
| MG RM-A-012 | | 0.092 | 0.257 | 0.192 | 0.177 | 0.097 | 0.105 |
| MG RM-A-013 | | 0.387 | 2.474 | 0.565 | 0.014 | 0.006 | 0.029 |
| MG RM-A-014 | | 0.003 | 0.007 | 0.003 | 13.913 | 0.010 | 0.040 |
| VLGCA1 | | >50 | >50 | >50 | 0.078 | >50 | >50 |
| 94 KE 105 | AC | 0.029 | 0.056 | 0.024 | 0.004 | 0.006 | 0.023 |
| 92TH021 | AE | >50 | >50 | >50 | 0.006 | 0.197 | >50 |
| CMU02 | | >50 | >50 | >50 | >50 | >50 | >50 |
| MGRM-AE-001 | | >50 | >50 | >50 | 2.948 | 9.684 | >50 |
| MGRM-AE-002 | | >50 | >50 | >50 | >50 | >50 | >50 |
| MGRM-AE-003 | | >50 | >50 | >50 | 0.092 | >50 | >50 |
| MGRM-AE-004 | | >50 | >50 | >50 | >50 | >50 | >50 |
| MGRM-AE-005 | | >50 | >50 | >50 | 0.010 | 0.324 | >50 |
| MGRM-AE-006 | | >50 | >50 | >50 | 0.009 | 17.253 | >50 |
| MGRM-AE-007 | | >50 | >50 | >50 | 0.876 | >50 | >50 |
| MGRM-AE-008 | | >50 | >50 | >50 | >50 | >50 | >50 |
| MG RM-AG-001 | AG | 2.096 | 14.472 | 2.509 | >50 | >50 | >50 |
| MG RM-AG-002 | | >50 | >50 | >50 | >50 | >50 | >50 |
| MG RM-AG-003 | | 0.465 | 43.663 | >50 | >50 | >50 | >50 |
| MG RM-AG-005 | | 0.649 | 33.861 | 0.149 | >50 | 1.207 | >50 |
| MG RM-AG-006 | | 0.014 | 0.028 | 0.014 | 0.008 | 0.010 | 0.021 |
| MG RM-AG-008 | | 0.494 | >50 | 19.162 | >50 | >50 | >50 |
| MG RM-AG-009 | | 0.080 | 0.128 | 0.073 | 0.026 | 0.030 | 0.059 |
| MG RM-AG-011 | | >50 | >50 | >50 | >50 | 24.51 | >50 |
| MG RM-AG-012 | | >50 | >50 | >50 | >50 | >50 | >50 |
| MG RM-AG-013 | | 0.557 | 0.521 | 3.371 | 0.004 | 0.008 | 0.018 |

| Isolate | Subtype | IC$_{50}$ (μg/mL)$^a$ | | | | | |
| --- | --- | --- | --- | --- | --- | --- | --- |
| | | PGT-128 | PGT-130 | PGT-131 | PGT-135 | PGT-136 | PGT-137 |
| 92RW008 | A | 0.003 | 0.039 | 1.011 | 1.417 | >50 | 0.148 |
| 92WR009 | | 0.812 | 1.274 | 3.115 | >50 | >50 | >50 |
| 92WR020 | | 0.005 | 0.039 | 0.168 | 0.067 | 2.335 | 0.005 |
| 92WR021 | | 0.005 | 0.004 | 0.012 | >50 | >50 | 3.516 |
| 92WR024 | | >50 | >50 | >50 | >50 | >50 | >50 |
| 92WR026 | | 0.010 | 0.037 | 0.041 | 0.068 | >50 | 0.092 |
| 92UG031 | | >50 | >50 | >50 | >50 | >50 | >50 |
| 92UG037 | | 0.006 | 0.061 | 0.048 | 3.672 | >50 | >50 |
| 93WR029 | | >50 | 34.264 | >50 | >50 | >50 | >50 |

TABLE 58B-continued

| Isolate | Subtype | | | | | | |
|---|---|---|---|---|---|---|---|
| 93UG077 | | 0.014 | 21.392 | >50 | >50 | >50 | >50 |
| 94UG103 | | 0.011 | 1.402 | 1.097 | >50 | >50 | >50 |
| MG RM-A-001 | | >50 | >50 | >50 | >50 | >50 | >50 |
| MG RM-A-002 | | 0.149 | 0.010 | >50 | >50 | >50 | >50 |
| MG RM-A-003 | | >50 | >50 | >50 | >50 | >50 | >50 |
| MG RM-A-004 | | >50 | >50 | >50 | >50 | >50 | >50 |
| MG RM-A-005 | | >50 | >50 | >50 | >50 | >50 | >50 |
| MG RM-A-006 | | >50 | >50 | >50 | >50 | >50 | >50 |
| MG RM-A-007 | | >50 | >50 | >50 | >50 | >50 | >50 |
| MG RM-A-008 | | >50 | >50 | >50 | >50 | >50 | >50 |
| MG RM-A-009 | | 0.005 | 0.308 | 0.035 | >50 | >50 | >50 |
| MG RM-A-010 | | 0.005 | 0.005 | 0.010 | >50 | >50 | >50 |
| MG RM-A-011 | | >50 | >50 | >50 | >50 | >50 | >50 |
| MG RM-A-012 | | 0.025 | >50 | >50 | >50 | >50 | >50 |
| MG RM-A-013 | | 0.008 | >50 | >50 | >50 | >50 | 49.188 |
| MG RM-A-014 | | 0.007 | 0.161 | 15.444 | 0.636 | >50 | 18.576 |
| VLGCA1 | | 0.838 | >50 | >50 | >50 | >50 | >50 |
| 94 KE 105 | AC | 0.007 | 0.004 | 0.013 | 0.063 | >50 | 18.548 |
| 92TH021 | AE | 0.010 | 0.009 | 0.014 | >50 | >50 | >50 |
| CMU02 | | >50 | >50 | >50 | >50 | >50 | >50 |
| MGRM-AE-001 | | 0.069 | 1.005 | 4.805 | >50 | >50 | >50 |
| MGRM-AE-002 | | 0.522 | 1.534 | >50 | >50 | >50 | >50 |
| MGRM-AE-003 | | 0.180 | 0.337 | 1.407 | >50 | >50 | >50 |
| MGRM-AE-004 | | >50 | 2.429 | >50 | >50 | >50 | >50 |
| MGRM-AE-005 | | 0.032 | 0.006 | 0.017 | >50 | >50 | >50 |
| MGRM-AE-006 | | 0.044 | 0.009 | 0.026 | >50 | >50 | >50 |
| MGRM-AE-007 | | >50 | 0.083 | 0.026 | >50 | >50 | >50 |
| MGRM-AE-008 | | >50 | >50 | >50 | >50 | >50 | >50 |
| MG RM-AG-001 | AG | 4.730 | >50 | >50 | >50 | >50 | >50 |
| MG RM-AG-002 | | 4.987 | >50 | >50 | >50 | >50 | >50 |
| MG RM-AG-003 | | 34.787 | 0.041 | 2.917 | >50 | >50 | >50 |
| MG RM-AG-005 | | 0.037 | 0.540 | 1.041 | >50 | >50 | >50 |
| MG RM-AG-006 | | 0.009 | 0.009 | 0.019 | 17.890 | 29.108 | 28.298 |
| MG RM-AG-008 | | 0.668 | >50 | >50 | >50 | >50 | >50 |
| MG RM-AG-009 | | 0.021 | 9.461 | >50 | >50 | >50 | >50 |
| MG RM-AG-011 | | 3.931 | >50 | >50 | >50 | >50 | >50 |
| MG RM-AG-012 | | >50 | >50 | >50 | 41.885 | >50 | >50 |
| MG RM-AG-013 | | 0.004 | 0.010 | 0.030 | >50 | >50 | >50 |

| | | IC$_{50}$ (μg/mL)$^a$ | | | | | |
|---|---|---|---|---|---|---|---|
| Isolate | Subtype | PGT-141 | PGT-142 | PGT-143 | PGT-144 | PGT-145 | VRC01 |
| 92RW008 | A | 0.579 | 0.447 | 0.385 | >50 | 0.400 | 0.037 |
| 92WR009 | | 0.022 | 0.006 | 0.010 | 0.893 | 0.026 | 0.187 |
| 92WR020 | | >50 | 31.523 | >50 | >50 | 0.997 | 0.130 |
| 92WR021 | | >50 | >50 | >50 | >50 | 1.620 | 0.066 |
| 92WR024 | | 0.175 | 0.069 | 0.122 | 16.346 | 0.069 | 0.327 |
| 92WR026 | | 1.781 | 1.780 | 5.364 | 32.691 | 1.453 | N/A |
| 92UG031 | | 0.093 | 0.050 | 0.095 | 2.175 | 3.220 | 0.469 |
| 92UG037 | | 1.276 | 0.557 | 0.854 | 8.241 | 3.148 | 0.245 |
| 93WR029 | | 0.019 | 0.014 | 0.053 | 4.391 | >50 | 1.570 |
| 93UG077 | | >50 | >50 | >50 | >50 | >50 | 0.097 |
| 94UG103 | | >50 | >50 | >50 | >50 | 0.331 | 0.285 |
| MG RM-A-001 | | 0.209 | 0.169 | 0.274 | 1.111 | 0.062 | >50 |
| MG RM-A-002 | | 0.217 | 0.007 | 0.016 | 0.085 | 0.019 | N/A |
| MG RM-A-003 | | 7.961 | 9.239 | 11.154 | >50 | 3.315 | 0.422 |
| MG RM-A-004 | | 0.007 | 0.002 | 0.007 | 0.855 | 0.068 | 0.064 |
| MG RM-A-005 | | 11.112 | 9.695 | 7.483 | 18.590 | 0.128 | 0.095 |
| MG RM-A-006 | | >50 | >50 | >50 | >50 | >50 | 0.521 |
| MG RM-A-007 | | >50 | >50 | >50 | >50 | >50 | 12.584 |
| MG RM-A-008 | | >50 | >50 | >50 | >50 | >50 | 0.303 |
| MG RM-A-009 | | 0.029 | 0.058 | 0.050 | 2.834 | 0.235 | 0.118 |
| MG RM-A-010 | | 0.022 | 0.015 | 0.019 | 2.791 | 0.028 | 0.325 |
| MG RM-A-011 | | >50 | >50 | >50 | >50 | 0.484 | 0.273 |
| MG RM-A-012 | | >50 | >50 | >50 | >50 | 0.230 | >50 |
| MG RM-A-013 | | 9.856 | 3.775 | 9.241 | >50 | 1.761 | 0.152 |
| MG RM-A-014 | | 0.628 | 0.367 | 1.071 | >50 | 1.357 | 0.135 |
| VLGCA1 | | 2.067 | 2.754 | 17.389 | >50 | 8.009 | 0.163 |
| 94 KE 105 | AC | 0.204 | 0.190 | 0.368 | 0.290 | 1.317 | 0.499 |
| 92TH021 | AE | 0.001 | 0.002 | 0.003 | 0.052 | 0.013 | 0.616 |
| CMU02 | | >50 | >50 | >50 | >50 | 1.425 | 0.515 |
| MGRM-AE-001 | | >50 | >50 | >50 | >50 | 20.916 | 0.167 |
| MGRM-AE-002 | | >50 | >50 | >50 | >50 | 1.868 | 0.217 |
| MGRM-AE-003 | | >50 | >50 | >50 | >50 | 0.552 | 0.685 |
| MGRM-AE-004 | | >50 | 0.001 | 0.002 | 0.104 | 0.006 | 0.187 |
| MGRM-AE-005 | | >50 | >50 | >50 | >50 | 0.967 | 0.029 |
| MGRM-AE-006 | | >50 | >50 | >50 | >50 | >50 | 4.648 |
| MGRM-AE-007 | | 33.133 | 6.697 | 13.558 | >50 | 0.181 | 0.835 |
| MGRM-AE-008 | | 0.101 | 0.080 | 0.135 | 3.553 | 1.464 | 1.715 |

TABLE 58B-continued

| | | | | | | | |
|---|---|---|---|---|---|---|---|
| MG RM-AG-001 | AG | 18.030 | 12.423 | 18.933 | >50 | 0.164 | 0.228 |
| MG RM-AG-002 | | 0.049 | 0.044 | 0.076 | 7.780 | 0.056 | 0.950 |
| MG RM-AG-003 | | >50 | >50 | >50 | >50 | >50 | 0.043 |
| MG RM-AG-005 | | 0.497 | 0.383 | 1.114 | >50 | 0.045 | 0.091 |
| MG RM-AG-006 | | >50 | >50 | >50 | >50 | 6.603 | 0.344 |
| MG RM-AG-008 | | 19.242 | 12.125 | 34.009 | >50 | 0.244 | 0.124 |
| MG RM-AG-009 | | >50 | >50 | >50 | >50 | >50 | >50 |
| MG RM-AG-011 | | 0.118 | 0.081 | 0.156 | 44.563 | 0.003 | 0.084 |
| MG RM-AG-012 | | >50 | >50 | >50 | >50 | >50 | 0.031 |
| MG RM-AG-013 | | >50 | 21.719 | >50 | >40 | 14.387 | 0.197 |

| | | IC$_{50}$ (µg/mL)$^a$ | | IC$_{50}$ (l/dil'n)$^b$ | | | |
|---|---|---|---|---|---|---|---|
| Isolate | Subtype | PGV04 | PG9 | #17 | #84 | #36 | #39 |
| 92RW008 | A | 0.014 | 0.006 | 6500.7 | 9301.5 | 2084.1 | 644.0 |
| 92WR009 | | 0.108 | 0.050 | 463.6 | 1247.6 | 241.0 | <100 |
| 92WR020 | | 0.055 | 0.141 | 5671.1 | 428.3 | 2617.1 | 2730.0 |
| 92WR021 | | 0.038 | 0.027 | 2343.6 | 1092.1 | 4204.8 | 428.0 |
| 92WR024 | | 0.310 | 0.258 | <100 | 507.7 | 149.7 | 178.0 |
| 92WR026 | | 0.140 | 0.164 | 1561.0 | 717.3 | 2183.4 | 1046.0 |
| 92UG031 | | 4.463 | 3.605 | <100 | 282.5 | 422.2 | 459.0 |
| 92UG037 | | 0.145 | 0.014 | 1120.4 | 501.8 | 1431.8 | 410.0 |
| 93WR029 | | 0.540 | 0.690 | <100 | 589.2 | <100 | 270.0 |
| 93UG077 | | 0.083 | >50 | 1082.8 | 326.4 | 707.2 | 436.0 |
| 94UG103 | | 0.202 | 0.340 | 193.4 | 208.3 | 1138.4 | 568.0 |
| MG RM-A-001 | | 6.781 | >50 | <100 | 231.7 | <100 | 149.0 |
| MG RM-A-002 | | 0.093 | 0.020 | 839.3 | 533.0 | 2782.2 | 264.0 |
| MG RM-A-003 | | 0.128 | 1.942 | <100 | 612.2 | <100 | 375.0 |
| MG RM-A-004 | | 0.175 | 0.020 | <100 | 4567.2 | <100 | 319.0 |
| MG RM-A-005 | | 0.134 | 0.750 | <100 | 151.2 | <100 | 282.0 |
| MG RM-A-006 | | 0.244 | <50 | 260.6 | 646.5 | 120.0 | 564.0 |
| MG RM-A-007 | | 7.213 | 1.061 | <100 | <100 | <100 | 556.0 |
| MG RM-A-008 | | 0.555 | <50 | <100 | <100 | <100 | 196.0 |
| MG RM-A-009 | | 0.033 | 0.023 | 4535.8 | 2228.7 | 1611.4 | 286.0 |
| MG RM-A-010 | | 0.205 | 0.022 | 271.3 | 1704.2 | 2779.2 | 279.0 |
| MG RM-A-011 | | 0.090 | 0.033 | <100 | 242.3 | <100 | 169.0 |
| MG RM-A-012 | | 0.225 | 19.294 | 229.9 | <100 | 770.6 | 215.0 |
| MG RM-A-013 | | 0.086 | 0.122 | 892.0 | 162.8 | 835.9 | 776.0 |
| MG RM-A-014 | | 0.172 | 1.248 | 7222.6 | 412.6 | 705.2 | 681.0 |
| VLGCA1 | | 0.024 | 0.069 | <100 | 311.2 | 203.2 | <100 |
| 94 KE 105 | AC | 2.981 | 37.875 | 955.0 | 1035.2 | 4540.1 | 1633.0 |
| 92TH021 | AE | 1.289 | 0.059 | <100 | 5298.1 | 3301.2 | 212.0 |
| CMU02 | | 1.238 | >50 | <100 | 101.3 | <100 | 312.0 |
| MGRM-AE-001 | | 0.063 | 20.586 | <100 | <100 | 222.6 | 223.0 |
| MGRM-AE-002 | | 0.569 | 0.040 | <100 | 169.1 | 254.0 | 249.0 |
| MGRM-AE-003 | | 6.401 | 0.044 | <100 | 150.0 | <100 | 181.0 |
| MGRM-AE-004 | | 0.183 | 0.009 | <100 | 6926.5 | 131.7 | 123.0 |
| MGRM-AE-005 | | 0.051 | 0.282 | <100 | 208.2 | 2772.2 | 265.0 |
| MGRM-AE-006 | | >50 | 0.063 | <100 | 117.5 | 1352.7 | 194.0 |
| MGRM-AE-007 | | 5.753 | 0.180 | <100 | 270.9 | 444.5 | 184.0 |
| MGRM-AE-008 | | 1.513 | 31.482 | <100 | 611.7 | <100 | 341.0 |
| MG RM-AG-001 | AG | 0.218 | 17.125 | 174.8 | 292.1 | 302.2 | 499.0 |
| MG RM-AG-002 | | 0.879 | 0.076 | 125.5 | 748.0 | 139.4 | 206.0 |
| MG RM-AG-003 | | 0.058 | >50 | <100 | 505.3 | <100 | 121.0 |
| MG RM-AG-005 | | 0.027 | >50 | 517.3 | 775.6 | 865.9 | 708.0 |
| MG RM-AG-006 | | 1.230 | >50 | 1105.3 | 321.1 | 4106.0 | 536.0 |
| MG RM-AG-008 | | 2.484 | 0.013 | 125.1 | 827.8 | <100 | 692.0 |
| MG RM-AG-009 | | 0.148 | >50 | 525.2 | 101.4 | 220.2 | 128.0 |
| MG RM-AG-011 | | 0.071 | 0.007 | <100 | 2785.8 | 228.1 | 274.0 |
| MG RM-AG-012 | | 0.040 | 22.845 | 104.9 | <100 | 136.6 | 235.0 |
| MG RM-AG-013 | | 0.030 | 0.259 | 321.2 | 319.1 | 2055.6 | 303.0 |

TABLE 58C

| | | IC$_{50}$ (µg/mL)$^a$ | | | | | |
|---|---|---|---|---|---|---|---|
| Isolate | Subtype | PGT-121 | PGT-122 | PGT-123 | PGT-125 | PGT-126 | PGT-127 |
| 6535.3 | B | 0.005 | 0.006 | 0.004 | 0.010 | 0.022 | 0.020 |
| 92 BR 020 | | 0.014 | 0.021 | 0.008 | 0.016 | 0.015 | 0.059 |
| 93TH305 | | 0.007 | 0.013 | 0.008 | 0.008 | 0.013 | 0.017 |
| APV 13 | | 0.251 | 0.778 | 0.138 | 0.007 | 0.012 | 0.026 |
| APV_17 | | 0.066 | 0.250 | 0.114 | 8.063 | 0.353 | 10.378 |
| APV 6 | | 0.018 | 0.019 | 0.023 | 0.021 | 0.007 | 0.040 |
| CAAN.A2 | | 0.011 | 0.011 | 0.015 | 5.467 | 0.273 | 0.371 |
| JRFL | | 0.021 | 0.026 | 0.014 | 0.009 | 0.014 | 0.029 |

TABLE 58C-continued

| Isolate | Subtype | | | | | |
|---|---|---|---|---|---|---|
| MGRM-Chronic-B-001 | | 0.102 | 0.138 | 0.150 | >50 | >50 | >50 |
| MGRM-Chronic-B-002 | | 0.386 | 1.801 | 0.234 | 0.064 | 0.078 | 0.279 |
| MGRM-Chronic-B-003 | | 0.011 | 0.008 | 0.008 | 0.157 | 0.041 | 0.120 |
| MGRM-Chronic-B-004 | | 0.009 | 0.008 | 0.008 | 0.007 | 0.010 | 0.018 |
| MGRM-Chronic-B-008 | | 0.007 | 0.017 | 0.010 | >50 | 5.890 | 21.515 |
| MGRM-Chronic-B-010 | | 0.014 | 0.018 | 0.009 | 0.006 | 0.005 | 0.019 |
| MGRM-Chronic-B-011 | | >50 | >50 | >50 | 3.228 | 0.108 | 0.297 |
| MGRM-Chronic-B-012 | | 0.036 | 0.066 | 0.227 | 0.036 | 0.027 | 0.075 |
| MGRM-Chronic-B-017 | | >50 | 5.664 | >50 | >50 | >50 | >50 |
| MGRM-Chronic-B-018 | | >50 | >50 | >50 | >50 | 0.052 | 1.896 |
| MGRM-Chronic-B-020 | | 0.004 | 0.005 | 0.005 | 0.087 | 0.021 | 0.050 |
| MGRM-Chronic-B-023 | | 0.005 | 0.010 | 0.055 | >50 | >50 | >50 |
| MGRM-Chronic-B-024 | | 0.195 | 2.308 | >50 | >50 | >50 | >50 |
| PVO.4 | | 0.137 | 0.689 | 0.105 | 0.042 | 0.017 | 0.164 |
| QH0692.42 | | 0.823 | 0.493 | 0.158 | 0.048 | 0.048 | 0.129 |
| SC422661.8 | | 0.098 | 0.103 | 0.039 | 30.138 | 0.119 | 36.688 |
| SF162 | | 0.005 | 0.009 | 0.005 | 0.004 | 0.003 | 0.019 |
| THR0.18 | | >50 | >50 | >50 | >50 | >50 | >50 |
| TRJ04551.58 | | 7.095 | >50 | 16.913 | 0.019 | 0.025 | 0.063 |
| TRO.11 | | 0.008 | 0.011 | 0.008 | 0.111 | 0.041 | 0.079 |
| VLGCB3 | | 0.005 | 0.008 | 0.004 | 0.015 | 0.007 | 0.022 |
| NL43 | | >50 | >50 | >50 | >50 | >50 | >50 |
| JRCSF | | 0.027 | 0.057 | 0.046 | 0.004 | 0.008 | 0.018 |
| 93IN905 | C | 0.005 | 0.013 | 0.004 | 0.009 | 0.015 | 0.024 |
| 93MW959 | | 0.013 | 0.016 | 0.011 | 37.481 | 9.441 | 6.951 |
| 97ZA012 | | 0.002 | 0.004 | 0.002 | 2.465 | 0.042 | >50 |
| 98IN022 | | 0.007 | 0.032 | 0.011 | 22.057 | 0.279 | 19.189 |
| MG RM-C-001 | | 17.482 | 19.103 | 42.406 | >50 | >50 | >50 |
| MG RM-C-002 | | 0.019 | 0.022 | 0.010 | 0.008 | 0.011 | 0.057 |
| MG RM-C-004 | | 0.011 | 0.020 | 0.009 | 1.825 | 0.033 | 0.532 |
| MG RM-C-005 | | 0.015 | 0.027 | 0.012 | 2.087 | 0.298 | 0.570 |
| MG RM-C-006 | | 0.017 | 0.018 | 0.021 | 0.015 | 0.014 | 0.319 |
| MG RM-C-007 | | 0.196 | 3.348 | 0.547 | >50 | 25.298 | >50 |
| MG RM-C-008 | | 0.012 | 0.028 | 0.011 | >50 | 2.118 | >50 |
| MG RM-C-009 | | >50 | >50 | >50 | >50 | >50 | >50 |
| MG RM-C-010 | | >50 | >50 | >50 | >50 | >50 | >50 |
| MG RM-C-012 | | 0.123 | 2.002 | 0.605 | >50 | 0.111 | 1.073 |
| MG RM-C-013 | | 7.228 | 32.575 | 14.879 | >50 | >50 | >50 |
| MG RM-C-014 | | 26.941 | >50 | 1.003 | >50 | >50 | >50 |
| MG RM-C-015 | | 25.071 | >50 | 13.141 | >50 | 3.140 | >50 |
| MG RM-C-017 | | 0.009 | 0.015 | 0.010 | 2.358 | 0.170 | 3.397 |
| MG RM-C-019 | | >50 | 0>50 | >50 | 0.130 | 0.005 | 0.017 |
| MG RM-C-020 | | >50 | 13.955 | >50 | >50 | >50 | >50 |
| MG RM-C-022 | | 0.015 | 0.012 | 0.010 | 1.233 | 0.960 | 0.410 |
| MG RM-C-023 | | 0.017 | 0.027 | 0.011 | 1.314 | 0.065 | 1.082 |
| MG RM-C-024 | | 0.052 | 0.102 | 0.195 | >50 | >50 | >50 |
| MG RM-C-025 | | 46.753 | 8.691 | 13.304 | 42.541 | 0.786 | >50 |
| MG RM-C-026 | | 0.002 | 0.006 | 0.001 | 0.005 | 0.007 | 0.014 |
| MG RM-C-027 | | 0.011 | 0.039 | 0.020 | >50 | 15.557 | >50 |
| MG RM-C-028 | | 0.472 | 2.216 | 0.402 | 14.023 | 0.196 | 7.567 |

| | | IC$_{50}$ (µg/mL)$^a$ | | | | | |
|---|---|---|---|---|---|---|---|
| Isolate | Subtype | PGT-128 | PGT130 | PGT-131 | PG1-135 | PGT-136 | PGT-137 |
| 6535.3 | B | 0.011 | 0.031 | 0.056 | >50 | >50 | >50 |
| 92 BR 020 | | 0.009 | 1.395 | 6.157 | 0.073 | 8.608 | 7.811 |
| 93TH305 | | 0.006 | 0.021 | 0.016 | >50 | 20.214 | >50 |
| APV 13 | | 0.008 | 0.052 | 0.189 | 0.716 | >50 | >50 |
| APV_17 | | 0.016 | 10.661 | >50 | >50 | >50 | >50 |
| APV 6 | | 0.007 | >50 | >50 | >50 | >50 | >50 |
| CAAN.A2 | | 1.482 | >50 | >50 | 5.154 | >50 | >50 |
| JRFL | | 0.007 | 0.046 | 0.454 | >50 | >50 | >50 |
| MGRM-Chronic-B-001 | | >50 | >50 | >50 | >50 | >50 | >50 |
| MGRM-Chronic-B-002 | | 0.036 | >50 | >50 | >50 | >50 | >50 |
| MGRM-Chronic-B-003 | | 0.007 | >50 | >50 | >50 | >50 | >50 |
| MGRM-Chronic-B-004 | | 0.009 | 0.010 | 0.040 | >50 | >50 | >50 |
| MGRM-Chronic-B-008 | | 0.143 | 5.183 | >50 | >50 | >50 | >50 |
| MGRM-Chronic-B-010 | | 0.004 | 0.006 | 0.016 | >50 | >50 | >50 |
| MGRM-Chronic-B-011 | | 0.020 | 0.153 | 6.468 | >50 | >50 | >50 |
| MGRM-Chronic-B-012 | | 0.026 | 0.373 | 15.708 | 0.166 | 43.142 | >50 |
| MGRM-Chronic-B-017 | | >50 | >50 | >50 | >50 | >50 | >50 |
| MGRM-Chronic-B-018 | | 0.020 | 31.873 | >50 | >50 | >50 | >50 |
| MGRM-Chronic-B-020 | | 0.007 | 0.014 | 0.053 | 0.057 | >50 | 32.851 |
| MGRM-Chronic-B-023 | | >50 | >50 | >50 | >50 | 0.329 | >50 |
| MGRM-Chronic-B-024 | | >50 | 5.776 | >50 | >50 | >50 | >50 |
| PVO.4 | | 0.005 | 5.171 | >50 | >50 | >50 | |
| QH0692.42 | | 0.029 | >50 | >50 | >50 | >50 | >50 |
| SC422661.8 | | 1.578 | >50 | >50 | 21.751 | >50 | >50 |
| SF162 | | 0.007 | 0.007 | 0.025 | 0.023 | 0.482 | 3.407 |

TABLE 58C-continued

| Isolate | | | | | | |
|---|---|---|---|---|---|---|
| THR0.18 | >50 | >50 | >50 | >50 | >50 | >50 |
| TRJ04551.58 | 0.019 | 0.023 | 0.088 | >50 | >50 | >50 |
| TRO.11 | 0.018 | 0.257 | 1.913 | 0.030 | 0.073 | 9.349 |
| VLGCB3 | 0.012 | 4.596 | >50 | 0.142 | >50 | 3.361 |
| NL43 | >50 | >50 | >50 | 8.034 | 27.695 | 17.444 |
| JRCSF | 0.003 | 0.010 | 0.029 | 0.131 | >50 | >50 |
| 93IN905 C | 0.009 | 0.020 | 0.177 | 0.011 | 0.011 | 0.042 |
| 93MW959 | 0.045 | 8.548 | >50 | >50 | >50 | >50 |
| 97ZA012 | 0.019 | 1.318 | 1.814 | >50 | >50 | >50 |
| 98IN022 | 0.014 | >50 | >50 | 0.014 | 13.622 | 0.408 |
| MG RM-C-001 | >50 | >50 | >50 | 10.121 | 7.518 | 21.503 |
| MG RM-C-002 | 0.019 | >50 | >50 | >50 | >50 | 8.034 |
| MG RM-C-004 | 0.025 | 2.756 | 3.714 | 0.046 | 0.034 | 0.026 |
| MG RM-C-005 | 0.030 | 0.935 | 1.356 | >50 | >50 | >50 |
| MG RM-C-006 | 0.014 | 0.095 | 0.611 | >50 | >50 | >50 |
| MG RM-C-007 | 0.111 | >50 | >50 | >50 | >50 | >50 |
| MG RM-C-008 | 0.373 | 7.277 | >50 | >50 | >50 | >50 |
| MG RM-C-009 | >50 | >50 | >50 | >50 | >50 | >50 |
| MG RM-C-010 | >50 | >50 | >50 | >50 | >50 | >50 |
| MG RM-C-012 | 0.058 | >50 | >50 | 0.017 | >50 | 0.102 |
| MG RM-C-013 | >50 | >50 | >50 | >50 | >50 | >50 |
| MG RM-C-014 | >50 | >50 | >50 | >50 | >50 | >50 |
| MG RM-C-015 | 0.196 | 0.344 | 1.015 | 0.104 | 11.066 | 1.983 |
| MG RM-C-017 | 1.065 | >50 | >50 | >50 | >50 | >50 |
| MG RM-C-019 | 0.010 | 0.010 | 0.021 | 0.264 | 20.100 | >50 |
| MG RM-C-020 | 5.846 | >50 | >50 | >50 | >50 | >50 |
| MG RM-C-022 | 0.042 | 0.127 | 0.780 | >50 | >50 | >50 |
| MG RM-C-023 | 0.026 | 0.151 | 0.143 | 0.051 | 3.198 | 0.230 |
| MG RM-C-024 | >50 | >50 | >50 | >50 | >50 | >50 |
| MG RM-C-025 | 10.489 | >50 | >50 | >50 | >50 | >50 |
| MG RM-C-026 | 0.007 | 0.036 | 1.674 | 0.004 | 0.006 | 0.011 |
| MG RM-C-027 | 0.081 | 0.008 | 0.065 | >50 | >50 | >50 |
| MG RM-C-028 | 14.423 | >50 | >50 | 1.474 | 33.676 | >50 |

| | | IC$_{50}$ (μg/mL)$^a$ | | | | | |
|---|---|---|---|---|---|---|---|
| Isolate | Subtype | PGT-141 | PGT-142 | PGT-143 | PGT-144 | PGT-145 | VRC01 |
| 6535.3 | B | >50 | >50 | >50 | >50 | >50 | 1.755 |
| 92 BR 020 | | 20.299 | 15.146 | 25.892 | 44.036 | 1.051 | 0.290 |
| 93TH305 | | >50 | 5.856 | 17.270 | >50 | 0.032 | 0.243 |
| APV 13 | | >50 | >50 | >50 | >50 | 0.337 | 0.657 |
| APV_17 | | 0.590 | 0.628 | 1.108 | 10.298 | 0.488 | 0.477 |
| APV 6 | | 14.216 | 4.725 | 13.968 | >50 | 0.104 | 1.812 |
| CAAN.A2 | | >50 | >50 | >50 | >50 | 7.085 | 0.722 |
| JRFL | | >50 | >50 | >50 | >50 | 30.401 | 0.034 |
| MGRM-Chronic-B-001 | | >50 | >50 | >50 | >50 | 3.223 | 0.066 |
| MGRM-Chronic-B-002 | | >50 | >50 | >50 | >50 | 3.672 | 0.117 |
| MGRM-Chronic-B-003 | | 0.400 | 0.484 | 0.854 | 7.408 | 0.045 | 0.100 |
| MGRM-Chronic-B-004 | | 0.586 | 0.172 | 0.395 | 9.415 | 0.023 | 0.055 |
| MGRM-Chronic-B-008 | | >50 | >50 | >50 | >50 | 1.903 | 0.155 |
| MGRM-Chronic-B-010 | | >50 | >50 | >50 | >50 | >50 | 0.156 |
| MGRM-Chronic-B-011 | | 2.241 | 0.994 | 1.557 | 5.637 | 0.206 | 0.587 |
| MGRM-Chronic-B-012 | | >50 | >50 | >50 | >50 | 9.662 | 1.033 |
| MGRM-Chronic-B-017 | | 0.147 | 0.076 | 0.145 | 0.712 | 0.054 | 0.141 |
| MGRM-Chronic-B-018 | | 0.572 | 0.323 | 0.377 | 2.397 | 0.013 | 0.328 |
| MGRM-Chronic-B-020 | | >50 | >50 | >50 | >50 | >50 | 0.424 |
| MGRM-Chronic-B-023 | | 0.318 | 0.486 | 0.236 | >50 | 0.009 | 0.275 |
| MGRM-Chronic-B-024 | | 0.011 | 0.005 | 0.010 | 0.040 | 0.018 | 0.377 |
| PVO.4 | | 0.113 | 0.066 | 0.162 | 0.535 | 0.299 | 0.218 |
| QH0692.42 | | >50 | >50 | >50 | >50 | >50 | 1.194 |
| SC422661.8 | | 1.656 | 3.153 | 2.017 | >50 | 0.079 | 0.179 |
| SF162 | | >50 | >50 | >50 | >50 | >50 | 0.421 |
| THR0.18 | | 0.007 | 0.012 | 0.016 | 0.029 | 0.013 | 2.461 |
| TRJ04551.58 | | >50 | >50 | >50 | >50 | >50 | 0.060 |
| TRO.11 | | 0.383 | 0.270 | 0.219 | 4.728 | 0.044 | 0.186 |
| VLGCB3 | | >50 | >50 | >50 | >50 | >50 | 0.108 |
| NL43 | | >50 | >50 | >50 | >50 | 0.006 | 0.100 |
| JRCSF | | 0.009 | 0.010 | 0.007 | 0.149 | 0.002 | 0.164 |
| 93IN905 | C | 0.001 | 0.001 | 0.002 | 0.132 | 0.002 | 0.138 |
| 93MW959 | | 0.003 | 0.001 | 0.002 | 0.332 | 1.203 | 0.053 |
| 97ZA012 | | >50 | >50 | >50 | >50 | 0.915 | 0.088 |
| 98IN022 | | 0.001 | 0.001 | 0.001 | 0.171 | 0.005 | 0.342 |
| MG RM-C-001 | | >50 | >50 | >50 | >50 | >50 | 1.369 |
| MG RM-C-002 | | 7.834 | 10.535 | 6.766 | >50 | 0.008 | 0.577 |
| MG RM-C-004 | | >50 | >50 | >50 | >50 | >50 | 1.077 |
| MG RM-C-005 | | 8.332 | 1.854 | 9.192 | >50 | >50 | 5.417 |
| MG RM-C-006 | | 0.330 | 0.478 | 0.369 | 48.894 | 0.010 | 2.202 |
| MG RM-C-007 | | >50 | >50 | >50 | >50 | >50 | >50 |
| MG RM-C-008 | | >50 | >50 | >50 | >50 | >50 | 1.445 |

TABLE 58C-continued

| | | | | | | |
|---|---|---|---|---|---|---|
| MG RM-C-009 | | 0.143 | 0.061 | 0.121 | 0.561 | 0.193 | 0.261 |
| MG RM-C-010 | | 0.411 | 0.070 | 0.171 | 7.616 | 0.141 | 0.085 |
| MG RM-C-012 | | >50 | >50 | >50 | >50 | 6.984 | 0.073 |
| MG RM-C-013 | | >50 | >50 | >50 | >50 | >50 | >50 |
| MG RM-C-014 | | 11.807 | 6.024 | 8.811 | >50 | 5.816 | >50 |
| MG RM-C-015 | | 0.033 | 0.038 | 0.085 | 0.236 | 0.120 | 1.569 |
| MG RM-C-017 | | 4.018 | 1.111 | 5.170 | 23.035 | >50 | 0.366 |
| MG RM-C-019 | | 0.008 | 0.003 | 0.004 | 0.513 | 0.005 | 1.126 |
| MG RM-C-020 | | 1.336 | 0.446 | 0.797 | 1.288 | 0.712 | 0.396 |
| MG RM-C-022 | | 0.381 | 0.086 | 0.103 | 2.578 | 0.492 | 12.989 |
| MG RM-C-023 | | 0.153 | 0.087 | 0.148 | 0.380 | 0.201 | 0.077 |
| MG RM-C-024 | | 0.101 | 0.030 | 0.050 | 2.064 | 0.174 | 3.395 |
| MG RM-C-025 | | 0.247 | 0.183 | 0.336 | 17.550 | 0.044 | 2.364 |
| MG RM-C-026 | | >50 | >50 | >50 | >50 | >50 | 0.707 |
| MG RM-C-027 | | 3.275 | 0.792 | 0.598 | >50 | 0.095 | 0.125 |
| MG RM-C-028 | | 13.771 | 2.117 | 12.367 | >50 | 0.099 | 0.319 |

| | | IC$_{50}$ (µg/mL)$^a$ | | IC$_{50}$ (l/dil'n)$^b$ | | | |
|---|---|---|---|---|---|---|---|
| Isolate | Subtype | PGV04 | PG9 | #17 | #84 | #36 | #39 |
| 6535.3 | B | 0.757 | 1.053 | 3712.0 | 477.8 | 848.0 | 387.0 |
| 92 BR 020 | | 0.250 | >50 | 1623.7 | 262.2 | 741.3 | 421.0 |
| 93TH305 | | 0.255 | 8.124 | 3675.2 | 828.0 | 1520.7 | 306.0 |
| APV 13 | | 1.227 | >50 | 177.8 | 211.6 | 1460.1 | 173.0 |
| APV_17 | | 0.309 | 34.778 | 470.0 | 161.5 | 279.4 | 482.0 |
| APV 6 | | 24.187 | 0.181 | 914.6 | 253.2 | 512.9 | 706.0 |
| CAAN.A2 | | 2.262 | 19.267 | 1743.1 | 173.1 | 148.8 | 222.0 |
| JRFL | | 0.032 | >50 | 1291.5 | 348.5 | 858.2 | 471.0 |
| MGRM-Chronic-B-001 | | 0.048 | >50 | 330.1 | 160.6 | 246.0 | 390.0 |
| MGRM-Chronic-B-002 | | 0.142 | 3.439 | 200.1 | <100 | 344.4 | 320.0 |
| MGRM-Chronic-B-003 | | 0.258 | >50 | 3664.9 | 307.2 | 370.4 | 103.0 |
| MGRM-Chronic-B-004 | | 0.047 | 0.533 | 1874.9 | 796.5 | 1463.1 | 304.0 |
| MGRM-Chronic-B-008 | | 0.166 | 8.784 | 2805.1 | 251.8 | 260.2 | 685.0 |
| MGRM-Chronic-B-010 | | 0.744 | 0.004 | 1145.5 | 443.0 | 3234.8 | 383.0 |
| MGRM-Chronic-B-011 | | 0.497 | >50 | 130.8 | 458.4 | 1030.2 | 759.0 |
| MGRM-Chronic-B-012 | | >50 | 0.200 | 903.5 | 480.6 | 634.2 | 664.0 |
| MGRM-Chronic-B-017 | | 0.129 | 0.688 | 132.7 | 317.6 | <100 | 383.0 |
| MGRM-Chronic-B-018 | | 0.164 | 0.216 | <100 | 612.7 | 289.3 | 375.0 |
| MGRM-Chronic-B-020 | | 1.262 | >50 | 4132.2 | 390.1 | 858.8 | 305.0 |
| MGRM-Chronic-B-023 | | 0.139 | 0.027 | 2216.5 | 950.0 | 196.7 | 523.0 |
| MGRM-Chronic-B-024 | | 2.517 | 0.222 | 157.1 | 1060.2 | 104.4 | 110.0 |
| PVO.4 | | 0.454 | 24.752 | 212.9 | 239.4 | 420.8 | 123.0 |
| QH0692.42 | | 1.904 | >50 | 175.1 | <100 | 227.6 | 359.0 |
| SC422661.8 | | 0.110 | 1.477 | 367.3 | 228.7 | <100 | 220.0 |
| SF162 | | 0.0028 | >50 | 5329.3 | 2049.0 | 5103.0 | 3043.0 |
| THR0.18 | | >50 | 26.379 | <100 | 1036.0 | 107.7 | 126.0 |
| TRJ04551.58 | | 0.028 | 0.858 | 152.5 | 400.2 | 1416.1 | 617.0 |
| TRO.11 | | 0.121 | 16.865 | 2706.9 | 861.3 | 454.5 | 2740.0 |
| VLGCB3 | | 0.045 | 0.022 | 2961.7 | 238.5 | 1333.0 | 754.0 |
| NL43 | | 0.028 | >50 | 418.2 | 3308.8 | 3033.8 | 1184.0 |
| JRCSF | | 0.078 | 0.003 | 863.0 | 6255.4 | 2371.1 | 433.0 |
| 93IN905 | C | 0.332 | 0.035 | 4396.9 | 14817.0 | 1313.8 | 3667.0 |
| 93MW959 | | >50 | 0.054 | 1602.2 | 6171.8 | 176.1 | 506.0 |
| 97ZA012 | | 0.041 | 3.400 | 8150.0 | 1083.1 | 433.0 | 594.0 |
| 98IN022 | | 5.693 | 0.003 | 3711.8 | 15197.1 | 729.6 | 1918.0 |
| MG RM-C-001 | | >50 | >50 | <100 | 117.0 | <100 | 174.0 |
| MG RM-C-002 | | >50 | >50 | 1799.2 | 733.6 | 704.1 | 556.0 |
| MG RM-C-004 | | 0.899 | 2.011 | 2177.9 | 234.5 | 327.9 | 2064.0 |
| MG RM-C-005 | | 23.898 | 8.742 | 1323.5 | 405.1 | 383.0 | 600.0 |
| MG RM-C-006 | | >50 | 0.427 | 1681.6 | 1231.3 | 532.3 | 564.0 |
| MG RM-C-007 | | >50 | 0.064 | 330.7 | 244.2 | <100 | 442.0 |
| MG RM-C-008 | | 0.791 | >50 | 1742.3 | 223.3 | <100 | 903.0 |
| MG RM-C-009 | | 1.042 | >50 | <100 | 460.9 | <100 | 224.0 |
| MG RM-C-010 | | 0.299 | >50 | <100 | 836.6 | <100 | 316.0 |
| MG RM-C-012 | | 0.025 | 0.610 | 716.3 | 521.6 | 169.8 | 2150.0 |
| MG RM-C-013 | | >50 | >50 | <100 | <100 | <100 | 453.0 |
| MG RM-C-014 | | 21.190 | 1.099 | <100 | 702.6 | <100 | <100 |
| MG RM-C-015 | | 0.983 | 0.427 | 141.6 | 544.2 | 253.4 | 1095.0 |
| MG RM-C-017 | | 0.383 | 2.688 | 3154.6 | 225.7 | 266.4 | 1587.0 |
| MG RM-C-019 | | 9.632 | 0.005 | <100 | 4576.4 | 1383.6 | 424.0 |
| MG RM-C-020 | | 0.112 | >50 | 110.9 | 245.6 | 115.3 | <100 |
| MG RM-C-022 | | 18.283 | 0.346 | 1972.8 | 921.3 | 725.8 | 658.0 |
| MG RM-C-023 | | 0.128 | 0.614 | 1046.6 | 354.6 | 285.3 | 1358.0 |
| MG RM-C-024 | | >50 | 0.227 | 718.0 | 607.2 | <100 | 170.0 |
| MG RM-C-025 | | >50 | 0.148 | 228.2 | 886.0 | 129.6 | 651.0 |
| MG RM-C-026 | | 0.303 | 0.060 | 12635.8 | 2201.2 | 2438.1 | 9554.0 |
| MG RM-C-027 | | 2.762 | 5.358 | 2368.0 | 859.3 | 1636.4 | 869.0 |
| MG RM-C-028 | | 0.149 | 0.067 | 115.0 | 363.0 | <100 | 502.0 |

TABLE 58D

| | | IC$_{50}$ (µg/mL)$^a$ | | | | | |
|---|---|---|---|---|---|---|---|
| Isolate | Subtype | PGT-121 | PGT-122 | PGT-123 | PGT-125 | PGT-126 | PGT-127 |
| 98CN009 | CRF07_BC | 0.009 | 0.013 | 0.007 | 0.030 | 0.019 | 0.090 |
| 98CN006 | CRF08_BC | 0.010 | 0.021 | 0.008 | 0.201 | 0.046 | 0.067 |
| 92UG001 | D | >50 | >50 | >50 | >50 | >50 | >50 |
| 92UG005 | | 18.292 | >50 | 9.794 | >50 | 0.037 | 1.107 |
| 92UG024 | | >50 | >50 | >50 | >50 | >50 | >50 |
| 92UG046 | | >50 | >50 | >50 | >50 | >50 | >50 |
| 92UG114 | | 0.004 | 0.011 | 0.005 | 0.349 | 0.038 | 7.091 |
| MG RM-D-001 | | 0.615 | 1.130 | 0.147 | 2.837 | 0.084 | 2.234 |
| MG RM-D-002 | | 0.006 | 0.005 | 0.012 | 0.118 | 0.039 | 0.600 |
| MG RM-D-003 | | 10.685 | >50 | 3.736 | 0.065 | 0.021 | 0.029 |
| MG RM-D-004 | | >50 | >50 | >50 | 0.371 | >50 | >50 |
| MG RM-D-005 | | >50 | >50 | >50 | >50 | 0.792 | 6.024 |
| MG RM-D-008 | | >50 | >50 | >50 | >50 | 43.139 | >50 |
| MG RM-D-011 | | 0.018 | 0.019 | 0.012 | 0.008 | 0.009 | 0.015 |
| MG RM-D-012 | | >50 | >50 | >50 | >50 | >50 | >50 |
| MG RM-D-013 | | >50 | >50 | >50 | >50 | >50 | >50 |
| MG RM-D-014 | | 0.009 | 0.012 | 0.009 | >50 | 0.030 | 0.393 |
| MG RM-D-016 | | >50 | >50 | >50 | 0.120 | >50 | >50 |
| MG RM-D-018 | | 0.005 | 0.007 | 0.007 | >50 | 0.009 | 0.021 |
| MG RM-D-019 | | >50 | >50 | >50 | 0.049 | >50 | >50 |
| MG RM-D-020 | | 0.010 | 0.007 | 0.018 | >50 | 0.023 | 0.015 |
| MG RM-D-021 | | 5.334 | 11.735 | 11.120 | 0.015 | 0.047 | 0.056 |
| MG RM-D-022 | | >50 | >50 | >50 | 0.040 | >50 | >50 |
| MG RM-D-024 | | 0.038 | 0.185 | 0.023 | >50 | 0.376 | 1.945 |
| MG RM-D-026 | | >50 | >50 | >50 | >50 | >50 | >50 |
| MG RM-D-028 | | 0.009 | 3.338 | 0.132 | >50 | >50 | >50 |
| MG RM-D-029 | | >50 | >50 | >50 | >50 | >50 | >50 |
| MGRM-F1-004 | F | 1.665 | 1.291 | 1.783 | >50 | 0.063 | 0.068 |
| MGRM-F1-006 | | 5.328 | 3.266 | 6.894 | 0.035 | 0.078 | 7.172 |
| MGRM-F1-008 | | >50 | >50 | >50 | 0.361 | >50 | >50 |
| MGRM-F1-010 | | 0.016 | 0.024 | 0.016 | >50 | >50 | >50 |
| MGRM-F1-012 | | 1.907 | >50 | 22.222 | >50 | 0.300 | >50 |
| MGRM-F1-013 | | 0.083 | 0.152 | 0.080 | >50 | >50 | >50 |
| MGRM-F1-014 | | 0.082 | 0.195 | 0.111 | >50 | >50 | >50 |
| MGRM-F1-015 | | 28.359 | 31.437 | >50 | >50 | >50 | >50 |
| MGRM-F1-016 | | 0.931 | 4.808 | 4.948 | >50 | >50 | >50 |
| MGRM-F1-017 | | 16.891 | >50 | >50 | >50 | >50 | >50 |
| MGRM-F1-018 | | 0.040 | 0.563 | 0.054 | >50 | 14.941 | 3.586 |
| MGRM-F1-020 | | 0.167 | 0.321 | 0.051 | >50 | >50 | >50 |
| MGRM-F1-021 | | 0.099 | 2.301 | 0.307 | >50 | >50 | >50 |
| MGRM-F1-022 | | 0.104 | 0.277 | 0.075 | >50 | >50 | >50 |
| MGRM-F1-023 | | 0.097 | 0.154 | 0.053 | 0.12 | 0.009 | 0.119 |

| | | IC$_{50}$ (µg/mL)$^a$ | | | | | |
|---|---|---|---|---|---|---|---|
| Isolate | Subtype | PGT-128 | PGT-130 | PGT-131 | PGT-135 | PGT-136 | PGT-137 |
| 98CN009 | CRF07_BC | 0.025 | 0.136 | 4.051 | 0.071 | 0.428 | 5.059 |
| 98CN006 | CRF08_BC | 0.015 | 0.258 | 35.286 | 0.429 | 0.406 | 1.217 |
| 92UG001 | D | >50 | >50 | >50 | >50 | >50 | >50 |
| 92UG005 | | 0.018 | 0.959 | 0.854 | >50 | >50 | >50 |
| 92UG024 | | >50 | >50 | >50 | 0.010 | 0.052 | 0.106 |
| 92UG046 | | >50 | >50 | >50 | >50 | >50 | >50 |
| 92UG114 | | 0.083 | >50 | >50 | 1.289 | >5>50 | >50 |
| MG RM-D-001 | | 0.138 | >50 | >50 | >50 | >50 | >50 |
| MG RM-D-002 | | 0.011 | 0.869 | 11.150 | >50 | >50 | >50 |
| MG RM-D-003 | | 0.019 | 0.651 | 19.624 | >50 | >50 | >50 |
| MG RM-D-004 | | 24.887 | 1.208 | 2.007 | >50 | >50 | >50 |
| MG RM-D-005 | | 0.051 | >50 | >50 | >50 | >50 | >50 |
| MG RM-D-008 | | 0.033 | >50 | >50 | >50 | >50 | >50 |
| MG RM-D-011 | | 0.007 | 0.019 | 0.756 | 23.478 | >50 | 6.297 |
| MG RM-D-012 | | >50 | >50 | >50 | >50 | >50 | >50 |
| MG RM-D-013 | | 8.847 | 0.429 | 4.141 | >50 | >50 | >50 |
| MG RM-D-014 | | 0.013 | 0.061 | 0.516 | 2.209 | >50 | >50 |
| MG RM-D-016 | | >50 | >50 | >50 | >50 | >50 | >50 |
| MG RM-D-018 | | 0.008 | 0.049 | 0.148 | 0.039 | >50 | 15.100 |
| MG RM-D-019 | | >50 | >50 | >50 | >50 | >50 | >50 |
| MG RM-D-020 | | 0.011 | 24.677 | >50 | >50 | >50 | >50 |
| MG RM-D-021 | | 0.014 | 0.156 | 0.106 | >50 | >50 | >50 |
| MG RM-D-022 | | >50 | >50 | >50 | >50 | >50 | >50 |
| MG RM-D-024 | | 0.067 | >50 | >50 | >50 | >50 | >50 |
| MG RM-D-026 | | >50 | >50 | >50 | >50 | >50 | >50 |
| MG RM-D-028 | | >50 | 0.825 | >50 | >50 | >50 | >50 |
| MG RM-D-029 | | >50 | >50 | >50 | 30.849 | >50 | >50 |
| MGRM-F1-004 | F | 0.027 | 0.023 | 0.114 | 0.211 | >50 | 40.343 |
| MGRM-F1-006 | | 0.763 | >50 | >50 | >50 | >50 | >50 |

TABLE 58D-continued

| | | | | | | |
|---|---|---|---|---|---|---|
| MGRM-F1-008 | >50 | 0.065 | 2.742 | >50 | >50 | >50 |
| MGRM-F1-010 | 16.663 | >50 | >50 | >50 | >50 | >50 |
| MGRM-F1-012 | 0.007 | >50 | >50 | 0.010 | >50 | >50 |
| MGRM-F1-013 | 12.723 | >50 | >50 | 21.080 | >50 | >50 |
| MGRM-F1-014 | 0.277 | 11.795 | >50 | >50 | >50 | >50 |
| MGRM-F1-015 | >50 | >50 | >50 | 1.114 | >50 | >50 |
| MGRM-F1-016 | 1.209 | >50 | >50 | >50 | >50 | >50 |
| MGRM-F1-017 | 11.659 | >50 | >50 | 7.788 | >50 | >50 |
| MGRM-F1-018 | 0.023 | >50 | >50 | >50 | >50 | >50 |
| MGRM-F1-020 | 0.355 | 9.728 | >50 | 0.168 | 9.311 | 1.931 |
| MGRM-F1-021 | >50 | >50 | >50 | 0.065 | >50 | >50 |
| MGRM-F1-022 | 4.545 | >50 | >50 | 0.964 | 2.418 | 6.231 |
| MGRM-F1-023 | 0.007 | 0.050 | >50 | 0.088 | >50 | >50 |

| | | IC$_{50}$ (µg/mL)$^a$ | | | | |
|---|---|---|---|---|---|---|
| Isolate | Subtype | PGT-141 | PGT-142 | PGT-143 | PGT-144 | PGT-145 | VRC01 |
| 98CN009 | CRF07_BC | 1.277 | 3.999 | 10.206 | >50 | 0.136 | 0.346 |
| 98CN006 | CRF08_BC | >50 | >50 | >50 | >50 | >50 | 0.644 |
| 92UG001 | D | >50 | >50 | >50 | >50 | >50 | 1.159 |
| 92UG005 | | >5.0 | >50 | >50 | >50 | >50 | 0.576 |
| 92UG024 | | >50 | >50 | >50 | >50 | 1.600 | 0.576 |
| 92UG046 | | >50 | >50 | >50 | >50 | >50 | 12.687 |
| 92UG114 | | >50 | >50 | >50 | >50 | 20.113 | 0.330 |
| MG RM-D-001 | | >50 | >50 | >50 | >50 | 0.560 | >50 |
| MG RM-D-002 | | >50 | >50 | >50 | >50 | >50 | 0.252 |
| MG RM-D-003 | | >50 | >50 | >50 | >50 | 0.006 | 2.064 |
| MG RM-D-004 | | >50 | >50 | >50 | >50 | 10.881 | 1.250 |
| MG RM-D-005 | | 5.154 | 1.153 | 1.414 | 14.807 | 10.398 | >50 |
| MG RM-D-008 | | 0.371 | 0.174 | 0.153 | 9.849 | 0.025 | 0.854 |
| MG RM-D-011 | | >50 | >50 | >50 | >50 | 14.655 | 0.075 |
| MG RM-D-012 | | >50 | >50 | >50 | >50 | >50 | 0.216 |
| MG RM-D-013 | | 0.179 | 0.221 | 0.386 | >50 | 3.480 | 0.087 |
| MG RM-D-014 | | 0.010 | 0.005 | 0.009 | 0.113 | 2.511 | 0.332 |
| MG RM-D-016 | | >50 | >50 | >50 | >50 | >50 | 0.452 |
| MG RM-D-018 | | >50 | >50 | >50 | >50 | 0.065 | >50 |
| MG RM-D-019 | | 1.655 | 0.155 | 0.277 | >50 | 0.111 | 0.119 |
| MG RM-D-020 | | >50 | >50 | >50 | >50 | 10.003 | 0.192 |
| MG RM-D-021 | | >50 | >50 | >50 | >50 | >50 | 33.445 |
| MG RM-D-022 | | >50 | >50 | >50 | >50 | 34.305 | >50 |
| MG RM-D-024 | | >50 | >50 | >50 | >50 | 0.224 | 0.366 |
| MG RM-D-026 | | 32.480 | 12.512 | 44.566 | >50 | 0.410 | 0.435 |
| MG RM-D-028 | | <50 | >50 | >50 | >50 | 0.721 | 0.377 |
| MG RM-D-029 | | 0.057 | 0.192 | 0.200 | 0.459 | 0.030 | 3.224 |
| MGRM-F1-004 | F | 0.021 | 0.013 | 0.036 | 0.105 | 0.361 | 0.305 |
| MGRM-F1-006 | | 8.993 | 12.874 | 12.341 | 20.563 | 13.642 | 2.856 |
| MGRM-F1-008 | | 0.193 | 0.124 | 0.189 | 0.507 | 0.228 | 1.114 |
| MGRM-F1-010 | | >50 | >50 | >50 | >50 | 3.321 | 0.097 |
| MGRM-F1-012 | | >50 | >50 | >50 | >50 | 0.113 | 0.488 |
| MGRM-F1-013 | | 0.043 | 0.023 | 0.013 | 0.509 | 0.402 | 0.170 |
| MGRM-F1-014 | | 0.001 | 0.001 | 0.001 | 0.014 | 0.009 | 0.056 |
| MGRM-F1-015 | | >50 | >50 | >50 | >50 | 1.764 | 0.387 |
| MGRM-F1-016 | | >50 | >50 | >50 | >50 | 17.531 | 0.517 |
| MGRM-F1-017 | | 30.829 | 23.465 | 26.279 | >50 | 0.286 | 1.077 |
| MGRM-F1-018 | | 0.785 | 0.404 | 0.701 | >50 | 1.020 | 0.032 |
| MGRM-F1-020 | | 1.152 | 0.824 | 0.980 | 8.929 | 0.816 | 1.890 |
| MGRM-F1-021 | | >50 | >50 | >50 | >50 | 8.038 | 0.039 |
| MGRM-F1-022 | | 0.114 | 0.040 | 0.082 | 0.382 | 0.009 | 0.055 |
| MGRM-F1-023 | | 0.307 | 0.602 | 0.972 | 1.163 | 5.879 | 0.392 |

| | | IC$_{50}$ (µg/mL)$^a$ | | IC$_{50}$ (l/dil'n)$^b$ | | | |
|---|---|---|---|---|---|---|---|
| Isolate | Subtype | PGV04 | PG9 | #17 | #84 | #36 | #39 |
| 98CN009 | CRF07_BC | 0.0125 | 0.371 | 2551.0 | 1469.5 | 756.3 | 1430.0 |
| 98CN006 | CRF08_BC | 1.320 | >50 | 1908.7 | 365.2 | 367.0 | 980.0 |
| 92UG001 | D | 0.553 | >50 | <100 | <100 | <100 | 260.0 |
| 92UG005 | | 0.440 | >50 | 265.5 | <100 | 590.3 | 480.0 |
| 92UG024 | | 0.201 | 1.861 | <100 | 202.0 | 138.1 | 1930.0 |
| 92UG046 | | 22.362 | 1.861 | <100 | 200.5 | <100 | 137.0 |
| 92UG114 | | 0.461 | 40.608 | 5390.2 | <100 | 292.1 | 548.0 |
| MG RM-D-001 | | >50 | >50 | <100 | <100 | 112.8 | <100 |
| MG RM-D-002 | | 0.322 | 0.021 | 5960.5 | <100 | 726.4 | 442.0 |
| MG RM-D-003 | | >50 | 0.033 | 183.1 | 695.8 | 414.7 | 176.0 |
| MG RM-D-004 | | 43.200 | 0.060 | <100 | 125.9 | 108.5 | 397.0 |
| MG RM-D-005 | | >50 | 1.802 | <100 | 235.9 | 109.3 | 249.0 |
| MG RM-D-008 | | 3.564 | 11.454 | <100 | 348.8 | <100 | 356.0 |
| MG RM-D-011 | | 0.025 | 0.071 | 1037.5 | 123.2 | 769.0 | 498.0 |
| MG RM-D-012 | | 0.125 | 16.182 | <100 | 109.0 | 109.1 | 261.0 |

TABLE 58D-continued

| | | | | | | |
|---|---|---|---|---|---|---|
| MG RM-D-013 | | 0.088 | 0.021 | <100 | 745.4 | 422.8 | 377.0 |
| MG RM-D-014 | | 0.194 | 0.023 | 2249.9 | 1526.5 | 428.0 | 322.0 |
| MG RM-D-016 | | 0.201 | 0.098 | <100 | 282.7 | 203.4 | 253.0 |
| MG RM-D-018 | | 17.528 | 0.025 | 6632.6 | 259.2 | 1730.4 | 642.0 |
| MG RM-D-019 | | 0.350 | 0.038 | <100 | 296.7 | 260.0 | 467.0 |
| MG RM-D-020 | | 0.097 | 1.665 | 2488.0 | <100 | 393.5 | 190.0 |
| MG RM-D-021 | | >50 | >50 | <100 | <100 | 457.5 | 148.0 |
| MG RM-D-022 | | >50 | >50 | <100 | <100 | <100 | <100 |
| MG RM-D-024 | | >50 | 0.038 | 355.3 | 144.4 | 124.7 | 399.0 |
| MG RM-D-026 | | 1.761 | 23.664 | <100 | 401.4 | 103.2 | <100 |
| MG RM-D-028 | | 1.008 | 20.234 | 2028.2 | 259.0 | <000 | 563.0 |
| MG RM-D-029 | | 1.557 | >50 | <100 | 291.4 | <100 | 387.0 |
| MGRM-F1-004 | F | 0.580 | 0.175 | 260.7 | 874.0 | 687.6 | 366.0 |
| MGRM-F1-006 | | >50 | 7.249 | <100 | 147.3 | 110.8 | 487.0 |
| MGRM-F1-008 | | 1.031 | >50 | <100 | 242.1 | <100 | 308.0 |
| MGRM-F1-010 | | 0.184 | 0.012 | 825.3 | 420.4 | <100 | 564.0 |
| MGRM-F1-012 | | 0.250 | 0.023 | 573.3 | 332.3 | 299.8 | 1366.0 |
| MGRM-F1-013 | | 0.084 | 1.253 | 283.9 | 2403.4 | 377.4 | 625.0 |
| MGRM-F1-014 | | 0.020 | 0.020 | 314.2 | 6934.5 | <100 | 538.0 |
| MGRM-F1-015 | | 0.179 | >50 | <100 | 145.7 | <100 | 234.0 |
| MGRM-F1-016 | | 0.268 | 0.518 | 110.3 | 103.0 | <100 | 407.0 |
| MGRM-F1-017 | | 2.383 | >50 | <100 | 279.4 | <100 | 832.0 |
| MGRM-F1-018 | | 0.027 | 0.019 | 770.0 | 518.6 | 151.2 | 391.0 |
| MGRM-F1-020 | | 5.987 | 6.396 | 305.4 | 220.8 | <100 | 306.0 |
| MGRM-F1-021 | | 0.031 | >50 | 227.6 | 505.7 | 218.7 | 919.0 |
| MGRM-F1-022 | | 0.072 | 0.028 | 350.0 | 1296.4 | 221.3 | 638.0 |
| MGRM-F1-023 | | 0.171 | >50 | 362.3 | 337.3 | 674.5 | 2177.0 |

TABLE 58E

| | | IC$_{50}$ (µg/mL)$^a$ | | | | | |
|---|---|---|---|---|---|---|---|
| Isolate | Subtype | PGT-121 | PGT-122 | PGT-123 | PGT-125 | PGT-126 | PGT-127 |
| MGRM-G-001 | G | 0.004 | 0.005 | 0.009 | 0.033 | 0.038 | 0.113 |
| MGRM-G-004 | | 0.115 | 2.146 | 0.181 | >50 | >50 | >50 |
| MGRM-G-006 | | >50 | >50 | >50 | >50 | >50 | >50 |
| MGRM-G-009 | | 0.020 | 0.514 | 33.546 | >50 | >50 | >50 |
| MGRM-G-011 | | 3.167 | 31.299 | 14.900 | >50 | 7.318 | >50 |
| MGRM-G-013 | | 3.991 | 3.448 | 3.969 | >50 | 48.845 | 7.699 |
| MGRM-G-014 | | 0.009 | 0.008 | 0.005 | 0.007 | 0.009 | 0.009 |
| MGRM-G-015 | | >50 | >50 | >50 | >50 | >50 | >50 |
| MGRM-G-016 | | >50 | >50 | >50 | >50 | >50 | >50 |
| MGRM-G-017 | | 0.004 | 0.032 | 0.026 | >50 | >50 | >50 |
| MGRM-G-019 | | 0.011 | 0.016 | 0.008 | >50 | 0.018 | 0.429 |
| MGRM-G-024 | | 0.014 | 0.033 | 0.032 | >50 | >50 | >50 |
| MGRM-G-025 | | 0.063 | 0.079 | 0.046 | >50 | 17.054 | 19.279 |
| MGRM-G-027 | | 0.124 | 0.606 | 0.182 | 34.414 | 0.875 | >50 |
| MGRM-G-028 | | 0.014 | 0.010 | 0.008 | 0.012 | 0.012 | 0.032 |
| aMLV | negative | >50 | >50 | >50 | >50 | >50 | >50 |

| | | IC$_{50}$ (µg/mL)$^a$ | | | | | |
|---|---|---|---|---|---|---|---|
| Isolate | Subtype | PGT-128 | PGT-130 | PGT-131 | PGT-135 | PGT-136 | PGT-137 |
| MGRM-G-001 | G | 0.019 | 0.0198 | 0.404 | 0.393 | 8.113 | 41.703 |
| MGRM-G-004 | | >50 | >50 | >50 | >50 | >50 | >50 |
| MGRM-G-006 | | >50 | >50 | >50 | >50 | >50 | >50 |
| MGRM-G-009 | | >50 | >50 | >50 | >50 | >50 | >50 |
| MGRM-G-011 | | 8.212 | >50 | >50 | >50 | >50 | >50 |
| MGRM-G-013 | | 0.995 | >50 | >50 | >50 | >50 | >50 |
| MGRM-G-014 | | 0.004 | 2.226 | 4.313 | >50 | >50 | >50 |
| MGRM-G-015 | | >50 | >50 | >50 | >50 | >50 | >50 |
| MGRM-G-016 | | >50 | >50 | >50 | >50 | >50 | >50 |
| MGRM-G-017 | | 0.319 | >50 | >50 | 0.137 | >50 | 34.905 |
| MGRM-G-019 | | 0.010 | 27.938 | >50 | 0.145 | 44.285 | 0.126 |
| MGRM-G-024 | | 0.095 | 5.838 | 10.730 | 0.062 | 0.152 | 0.051 |
| MGRM-G-025 | | 0.017 | 8.452 | 7.750 | 0.592 | >50 | >50 |
| MGRM-G-027 | | 0.313 | 4.137 | 2.904 | 0.062 | 45.222 | 0.228 |
| MGRM-G-028 | | 0.008 | 0.074 | 0.466 | >50 | >50 | >50 |
| aMLV | negative | >50 | >50 | >50 | >50 | >50 | >50 |

TABLE 58E-continued

| | | IC$_{50}$ (µg/mL)$^a$ | | | | | |
|---|---|---|---|---|---|---|---|
| Isolate | Subtype | PGT-141 | PGT-142 | PGT-143 | PGT-144 | PGT-145 | VRC01 |
| MGRM-G-001 | G | 0.392 | 0.362 | 0.423 | >50 | 0.028 | 0.0371 |
| MGRM-G-004 | | >50 | >50 | >50 | >50 | >50 | >50 |
| MGRM-G-006 | | 0.043 | 0.019 | 0.031 | 3.843 | 0.286 | 0.055 |
| MGRM-G-009 | | 1.890 | 2.811 | 2.968 | >50 | 0.982 | 0.073 |
| MGRM-G-011 | | 0.086 | 0.046 | 0.074 | 1.577 | 0.028 | 0.065 |
| MGRM-G-013 | | >50 | >50 | >50 | >50 | >50 | 0.553 |
| MGRM-G-014 | | 0.222 | 0.076 | 0.107 | 0.562 | 0.144 | 0.056 |
| MGRM-G-015 | | >50 | >50 | >50 | >50 | 10.465 | 0.548 |
| MGRM-G-016 | | 4.690 | 8.170 | 7.600 | >50 | 0.081 | 0.063 |
| MGRM-G-017 | | 0.164 | 0.125 | 0.107 | 9.972 | 0.205 | 0.124 |
| MGRM-G-019 | | 20.310 | 5.949 | 4.773 | >50 | 0.041 | 0.060 |
| MGRM-G-024 | | 0.051 | 0.054 | 0.048 | 7.923 | 0.060 | 0.025 |
| MGRM-G-025 | | >50 | >50 | >50 | >50 | >50 | 0.292 |
| MGRM-G-027 | | >50 | >50 | >50 | >50 | 0.433 | 0.360 |
| MGRM-G-028 | | 24.888 | 30.309 | 42.988 | >50 | 0.046 | 0.164 |
| aMLV | negative | >50 | >50 | >50 | >50 | >50 | >50 |

| | | IC$_{50}$ (µg/mL)$^a$ | | IC$_{50}$ (1/dil'n)$^b$ | | | |
|---|---|---|---|---|---|---|---|
| Isolate | Subtype | PGV04 | PG9 | #17 | #84 | #36 | #39 |
| MGRM-G-001 | G | >50 | 0.166 | 5296.0 | 557.6 | 635.9 | 169.0 |
| MGRM-G-004 | | >50 | >50 | 600.5 | 157.8 | 107.3 | 574.0 |
| MGRM-G-006 | | 0.083 | 1.983 | <100 | 548.1 | <100 | <100 |
| MGRM-G-009 | | 0.043 | 10.704 | 160.3 | 336.3 | <100 | 345.0 |
| MGRM-G-011 | | 0.780 | 0.335 | <100 | 641.1 | <100 | 891.0 |
| MGRM-G-013 | | 0.168 | >50 | 100.5 | 561.4 | 480.3 | 629.0 |
| MGRM-G-014 | | 0.056 | 16.478 | 3593.6 | 389.5 | 1058.0 | 295.0 |
| MGRM-G-015 | | 0.333 | 6.599 | <100 | <100 | <100 | 266.0 |
| MGRM-G-016 | | 0.019 | 1.363 | <100 | 681.8 | 106.0 | 440.0 |
| MGRM-G-017 | | 0.065 | 0.104 | 1582.3 | 701.7 | 282.9 | 420.0 |
| MGRM-G-019 | | 0.027 | 14.559 | 1416.7 | 253.3 | 354.8 | 524.0 |
| MGRM-G-024 | | 0.033 | 0.163 | 1077.4 | 388.2 | 131.5 | 516.0 |
| MGRM-G-025 | | 1.608 | >50 | 396.1 | 129.5 | 164.2 | 213.0 |
| MGRM-G-027 | | 0.125 | 0.007 | 289.0 | 140.8 | 143.4 | 676.0 |
| MGRM-G-028 | | 0.352 | 0.891 | 2769.4 | 522.4 | 1201.4 | 621.0 |
| aMLV | negative | >50 | >50 | <100 | <100 | <100 | <100 |

$^a$White squares indicate an IC$_{50}$ of >50 Pg/mL, green squares indicate 50 Pg/mL >IC$_{50}$ >10 Pg/mL, yellow squares indicate 10 Pg/mL >IC$_{50}$ >1 Pg/mL, orange squares indicate 1 Pg/mL >IC$_{50}$ >0.1 Pg/mL, and red squares indicate IC$_{50}$ <0.1 Pg/mL.
$^b$White squares indicate an IC$_{50}$ of <1:100 dilution, green squares indicate 1:100 >IC$_{50}$ >1:150, yellow squares indicate 1:150 >IC$_{50}$ >1:500, orange squares indicate 1:500 >IC$_{50}$ >1:1000, and red squares indicate IC$_{50}$ >1:1000 dilution.

TABLE 59

Binding activity PGT mAbs.

| | | EC$_{50}$ (µg/ml)$^a$ | | | |
|---|---|---|---|---|---|
| Donor | mAb | WT JR-FL gp120 | JR-FL gp120 Δ V1/ΔV2 | JR-FL GP120 ΔV3 | Endo H treated JR-FL gP120 |
| #17 | 121 | 0.2 | 0.2 | >10 | >10 |
| | 122 | 0.3 | 0.3 | >10 | >10 |
| | 123 | 0.2 | 0.3 | >10 | >10 |
| #36 | 125 | 0.2 | 0.6 | >10 | >10 |
| | 126 | 0.1 | 0.3 | >10 | >10 |
| | 127 | 0.1 | 0.7 | >10 | >10 |
| | 128 | 0.1 | 0.3 | 7.8 | >10 |
| | 130 | 0.2 | >10 | >10 | >10 |
| | 131 | 0.4 | >10 | >10 | >10 |
| #39 | 135 | 0.1 | 0.1 | 0.2 | >10 |
| | 136 | 0.2 | 0.3 | 0.1 | >10 |
| | 137 | 0.1 | 0.2 | 0.1 | >10 |

$^a$Binding was evaluated by ELISA. EC$_{50}$ values were derived by nonlinear regression analysis. Boxes are color coded as follows: red, EC$_{50}$ < 1.0 µg/ml; yellow, 1.0 µg/ml < EC$_{50}$ < 10 µg/ml; gray, EC$_{50}$ > 10 µg/ml. Experiments were performed in duplicate, and data represent an average of at least two independent experiments.

Figure 33A:
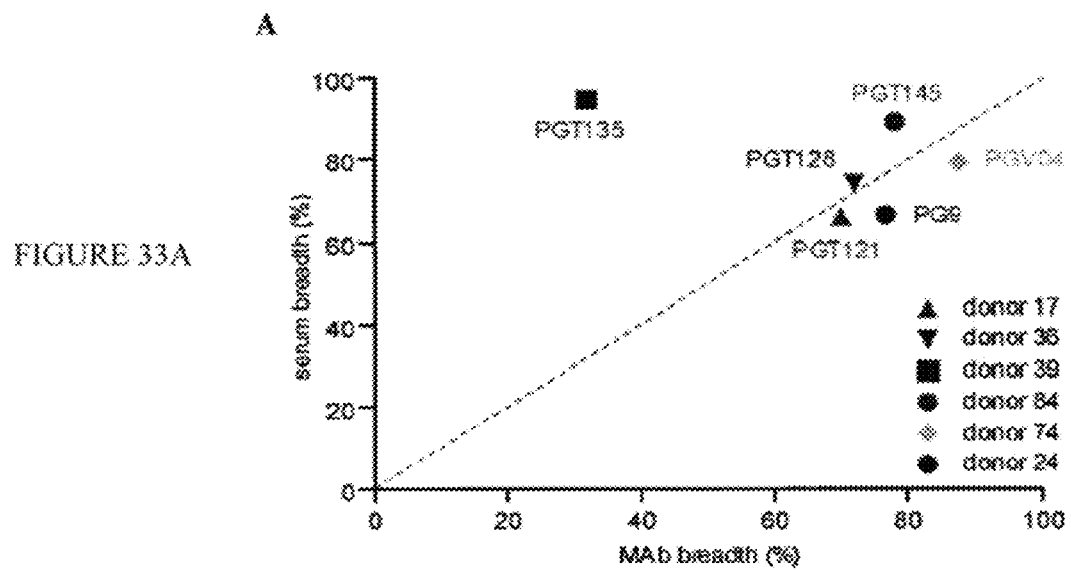
FIG. 33A-33D is a series of graphs depicting the newly identified PGT antibodies redefine broad and potent neutralisation of HIV. A, Key MAbs fully recapitulate serum neutralization by the corresponding donor serum. Serum breadth was correlated with the breadth of the broadest MAb for each donor (% viruses neutralized at $NT_{50}>100$ or $IC_{50}<50$ µg/ml, respectively). Of note, MAbs isolated from donor 39 could not completely recapitulate the serum neutralization breadth. B-D. Certain antibodies or antibody combinations are able to cover a broad range of HIV isolates at low, vaccine achievable, concentrations. B, Cumulative frequency distribution of $IC_{50}$ values of broadly neutralizing MAbs tested against a 162-virus panel. The y-axis shows the cumulative frequency of $IC_{50}$ values up to the concentration shown on the x-axis and can therefore also be interpreted as the breadth at a specific $IC_{50}$ cut-off. C-D, Percent viruses covered by single MAbs (solid lines) or by at least one of the MAbs in dual combinations (dashed black lines) dependent on individual concentrations. The grey area in both panels is the coverage of 26 MAbs tested on the 162-virus panel (PGT121-123, PGT125-128, PGT130-131, PGT135-137, PGT141-145, PG9, PG16, PGC14, VRC01, PGV04, b12, 2G12, 4E10, 2F5) and depicts the theoretical maximal achievable coverage known to date.

Many of the clonally related mAbs exhibited differing degrees of overall neutralization potency. For example, the median IC$_{50}$s of PGTs 131, 136, 137, and 144 were approximately 10- to 50-fold higher than those of their somatically-related sister clones (Table 61). Also, in some cases, the somatically-related mAbs exhibited similar neutralization potency, but differing degrees of neutralization breadth, against the panel of viruses tested (Tables 58A-E and Table 61). For example, PGT-128 neutralized with comparable overall potency but significantly greater neutralization breadth than the clonally related PGT-125, -126, and -127 mAbs (Tables 58A-E and Table 61). Overall, these observations suggest that serum neutralization breadth may develop from the successive selection of somatic mutants that bind to a modified epitope or a slightly different envelope (Env) conformation expressed on virus escape variants. Additionally, these results indicate that the full serum neutralization breadth and potency may be mediated by a small number of sequentially selected mAbs that bind to distinct, but overlapping, epitopes differentially expressed on various isolates. In this respect, antibody somatic variants could in effect "slide" around the Env spike surface. Comparison of the neutralization profiles of the mAbs isolated from a given donor with the profiles from the sera revealed that the mAbs isolated could largely recapitulate the corresponding serum neutralization breadth and potency (FIGS. 33a and 37).

Figure 38A:
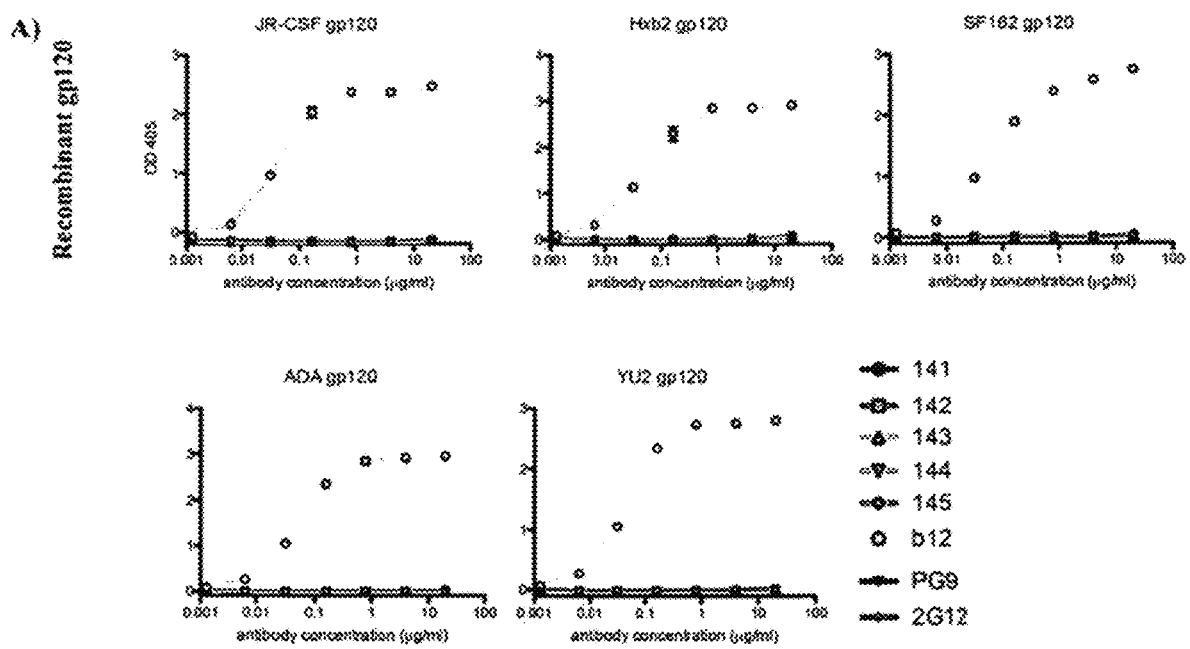
FIG. 38A-38C is a series of graphs showing that PGT 141-145 bind preferentially to cell-surface expressed trimers. A) Binding of PGTs 141-145 to monomeric gp120 and artificially trimerized gp140 constructs as determined by ELISA. The bNAbs b12 and PG9 are included for comparison. OD, optical density (absorbance at 450 nm). B) Binding of PGTs 141-145 to Env expressed on the surface of 293T cells as determined by flow cytometry. The bNAbs 2G12 and PG9 are included for comparison.
Figure 38B:
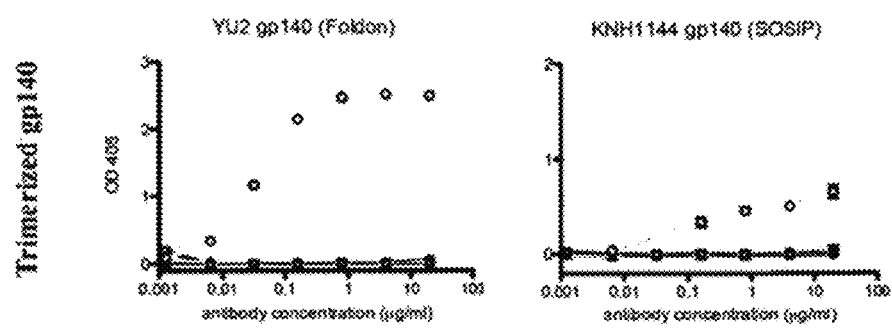
Figure 38C:
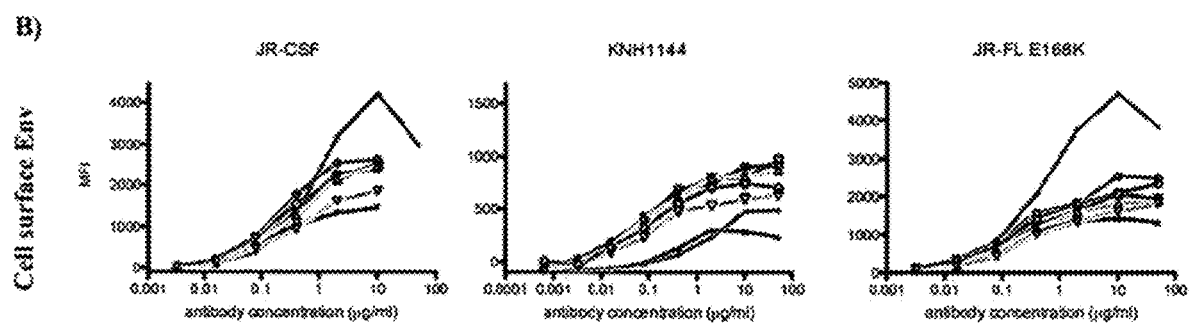
Figure 39A:
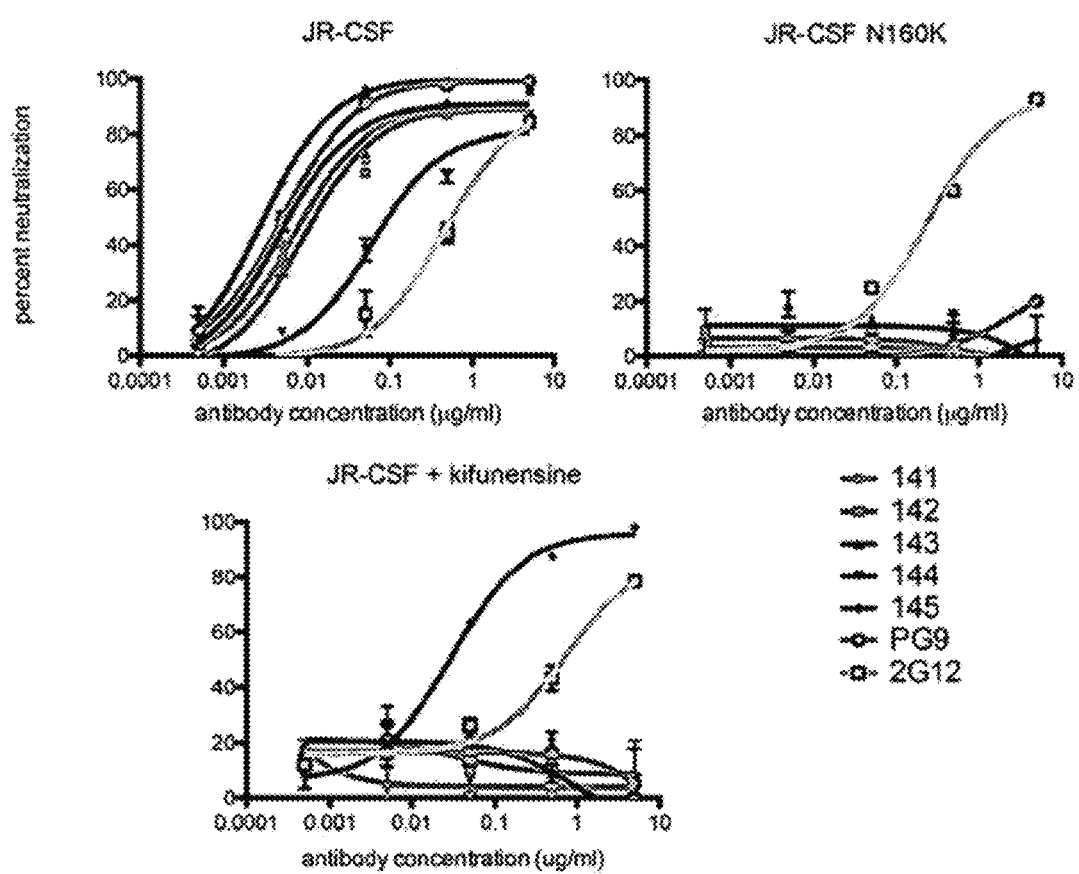
FIG. 39A-39B is a series of graphs showing that PGT mAbs 141-145 bind to epitopes overlapping those of PG9 and PG16. A) PGTs 141-145 are sensitive to the N160K mutation and PGTs 141-144 fail to neutralize pseudoviruses produced in the presence of kifunensine. The bNAb 2G12 was also included for comparison. B) PG9 competes with PGTs 141-145 for binding to cell-surface trimers. The bNAb 2G12 was included as a negative control.
Figure 39B:
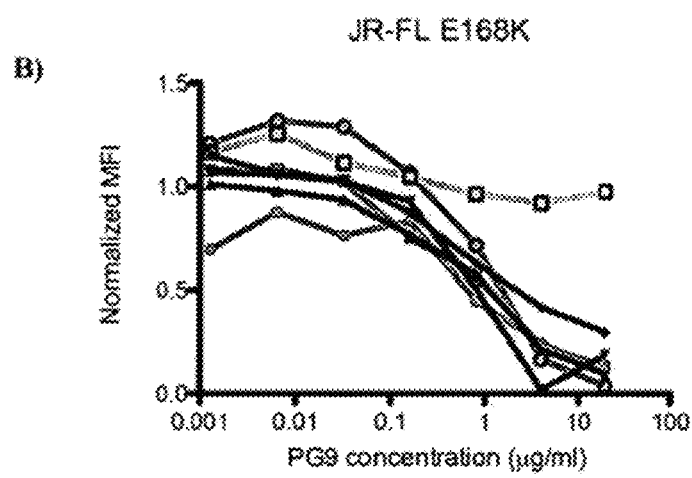

The epitopes recognized by the newly isolated bnMAbs were determined. ELISA binding assays indicated that PGTs 121-123, 125-128, 130, 131, and 135-137 bound to monomeric gp120 (Table 59). In contrast, the PGT 141-145 bnMAbs exhibited a strong preference for membrane-bound, trimeric HIV-1 Env (FIG. 38). Based on this result, it was postulated that these bnMAbs bound to quaternary epitopes similar to those of the recently described PG9 and PG16 bnMAbs (Walker, L. M., et al. Science 326, 285-289 (2009)). Indeed, this hypothesis was confirmed by competition studies, N160K sensitivity, and, for PGTs 141-144, an inability to neutralize JR-CSF pseudoviruses expressing homogenous $Man_9GlcNAc_2$ glycans (Walker, L. M., et al. PLoS Pathog 6(2010)) (FIG. 39).

Figure 34A:
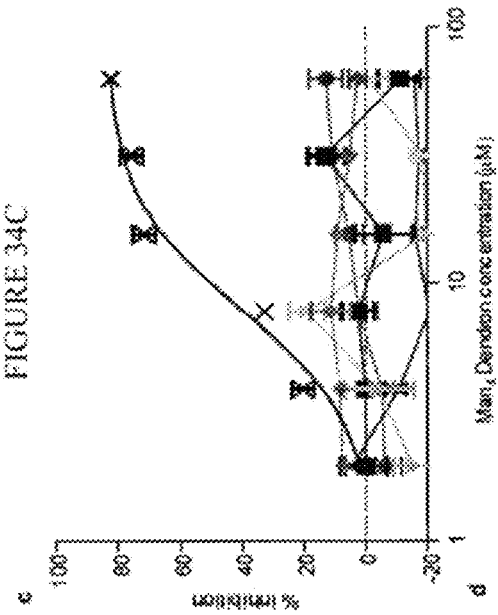
FIG. 34A is a table depicting the competition of PGT MAbs with sCD4 (soluble CD4), b12 (anti-CD4bs), 2G12 (anti-glycan), F425/b4e8 (anti-V3), X5 (CD4i), PG9 (anti-V1/V2 and V3, quaternary) and each other. Competition assays were performed by ELISA using gp120$_{Bal}$ or gp120$_{JR-FL}$, except for the PG9 competition assay, which was performed on the surface of JR-FL$_{E168K}$ or JR-CSF transfected cells. Boxes are color coded as follows: red, 75-100% competition; orange, 50-75% competition; yellow, 25-50% competition; gray, <25% competition. Experiments were performed in duplicate, and data represent an average of at least two independent experiments.
Figure 34B:
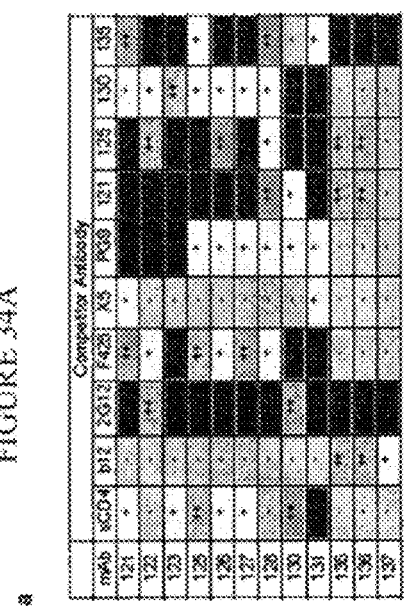
FIG. 34B-34D is a series of graphs depicting the epitope mapping of PGT antibodies. b, Glycan microarray analysis (Consortium for Functional Glycomics, CFG, v 5.0) reveals that PGT MAbs 125, 126, 127, 128, and 130 contact Man$_8$ (313), Man$_8$GlcNAc$_2$ (193), Man$_9$ (314) and Man$_9$GlcNAc$_2$ (194) glycans directly. Only glycans structures with RFU (relative fluorescent units)>3000 are shown. PGT-131 showed no detectable binding to the CFG glycan array but bound to Man$_9$-oligodendrons[30] (data not shown). Error bars represent standard deviation. c, d, Binding of PGT MAbs 125, 126, 127, 128 and 130 to gp120 is competed by Man$_9$ oligodendrons but not Man$_4$ oligodendrons. Binding of 131 to immobilized gp120 was too low to measure any competition.
Figure 34C:
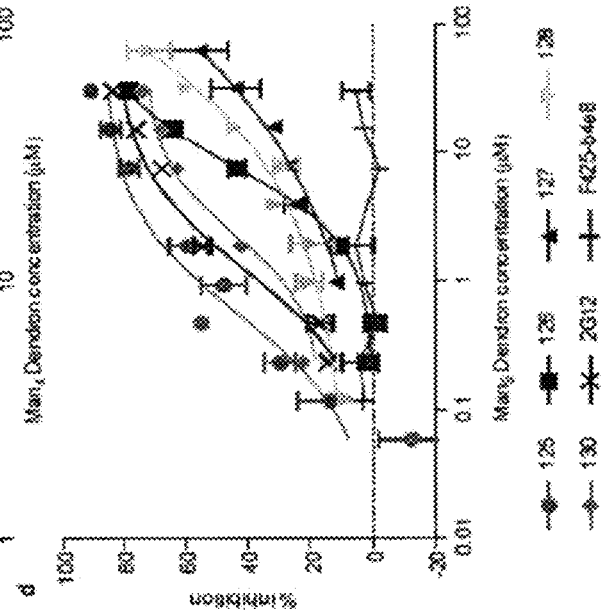
Figure 34D:
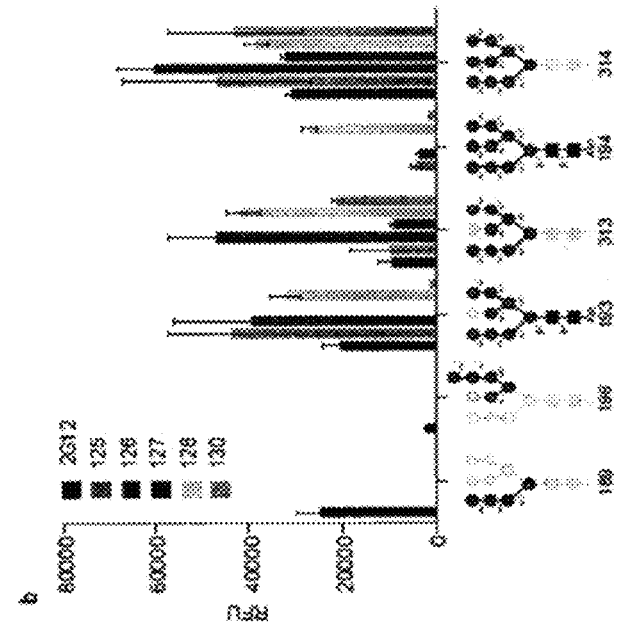
Figure 35A:
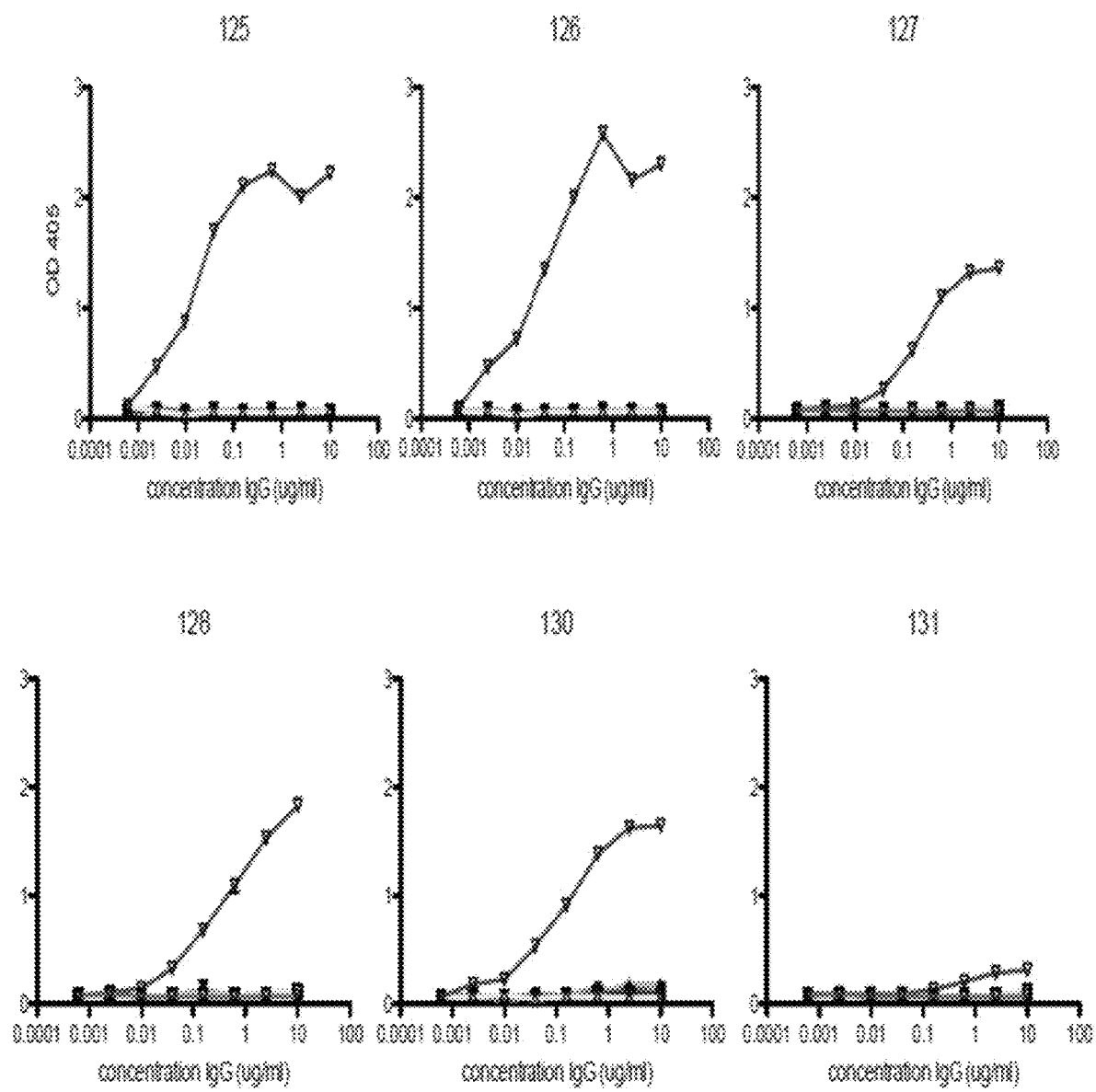
FIG. 35A-35D is a series of graphs depicting the lack of polyreactivity of PGT monoclonal antibodies (mAbs) in ELISA assay. PGT mAbs were tested for ELISA reactivity against a panel of antigens. The bNAbs b12 and 4E10 were also included for comparison. d.s, double-stranded; s.s, single-stranded.
Figure 35B:
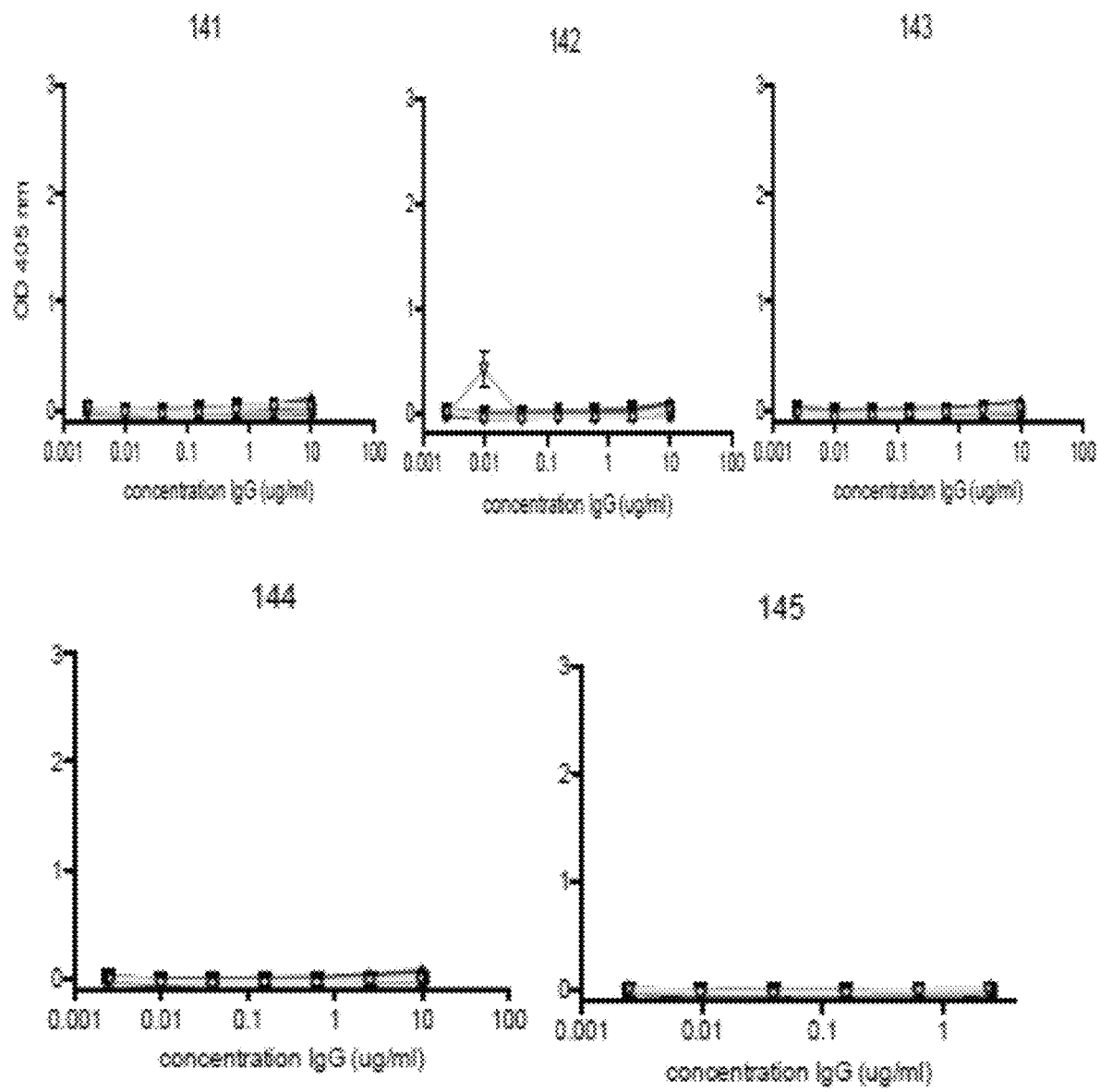
Figure 35C:
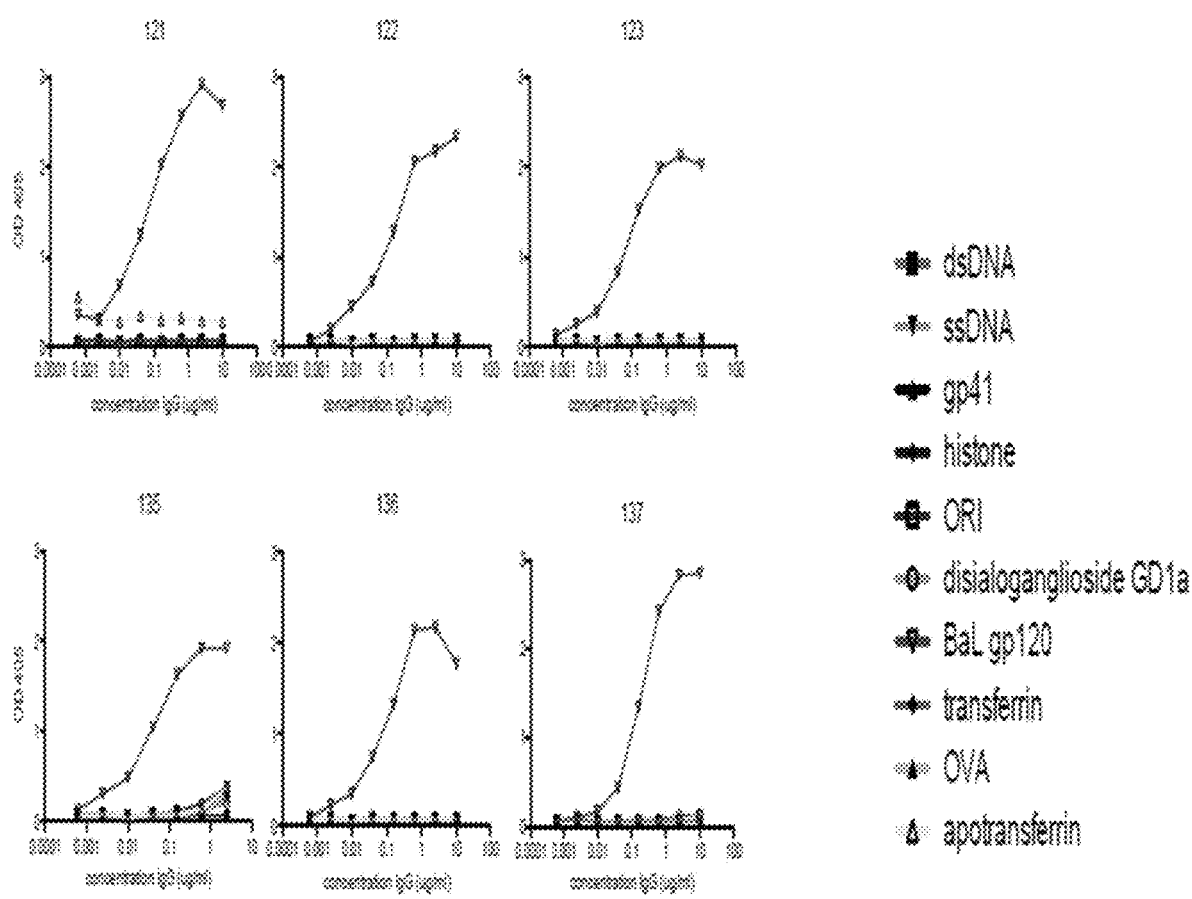
Figure 35D:
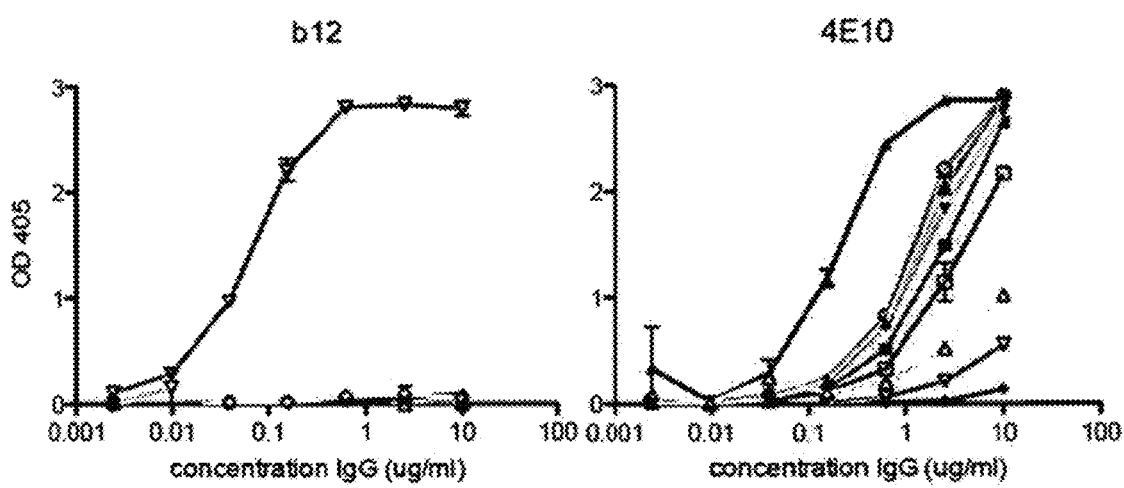
Figure 36A:
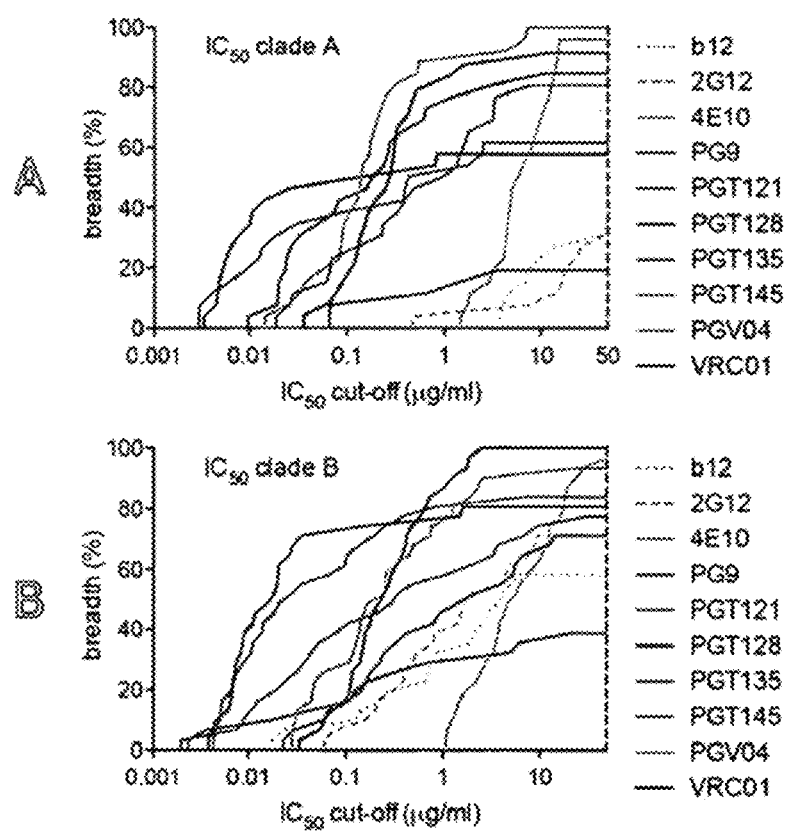
FIG. 36A-36D is a series of graphs depicting the results of an analysis of neutralization activity by virus clades. Cumulative frequency distribution of IC50 values of broadly neutralizing Mabs tested against a 162 virus panel separated by clades A, B, C, D, F, G, AE and AG. VRC01 was tested on a different virus panel (n=190, ref 6).
Figure 36B:
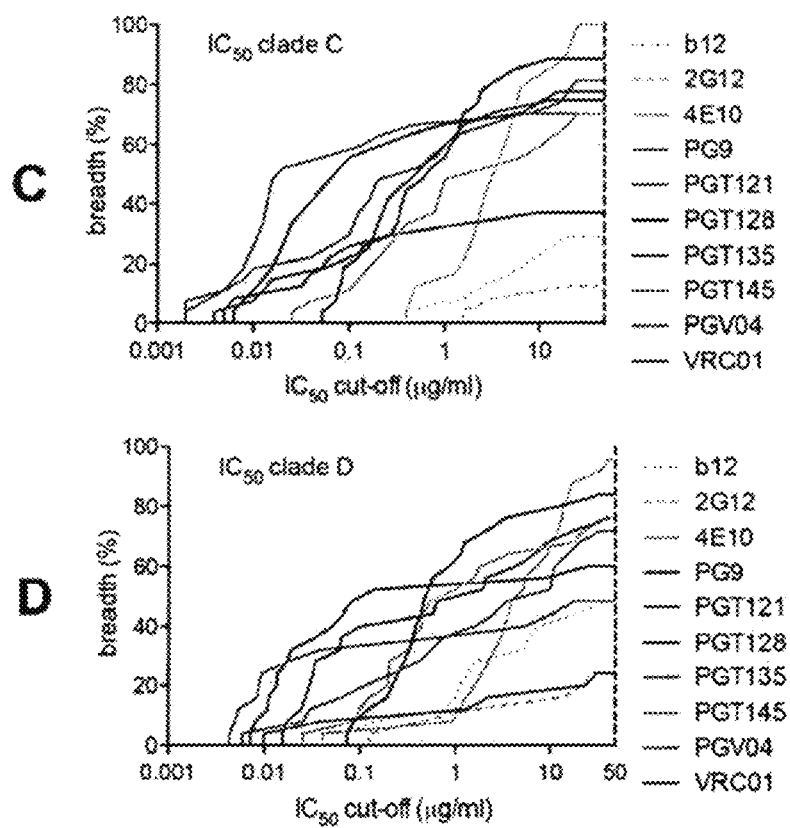
Figure 36C:
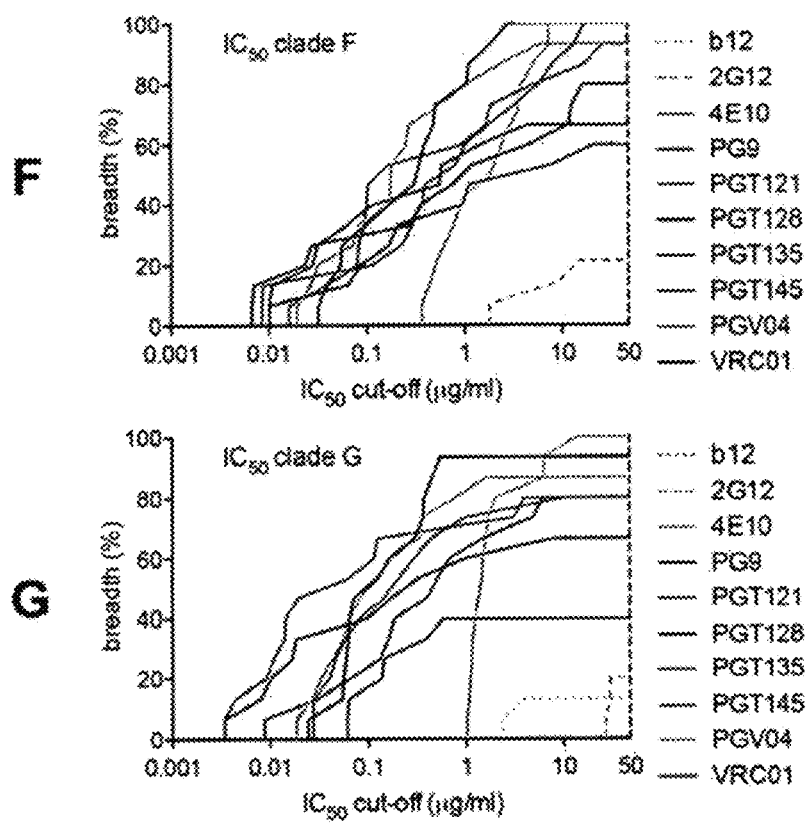
Figure 36D:
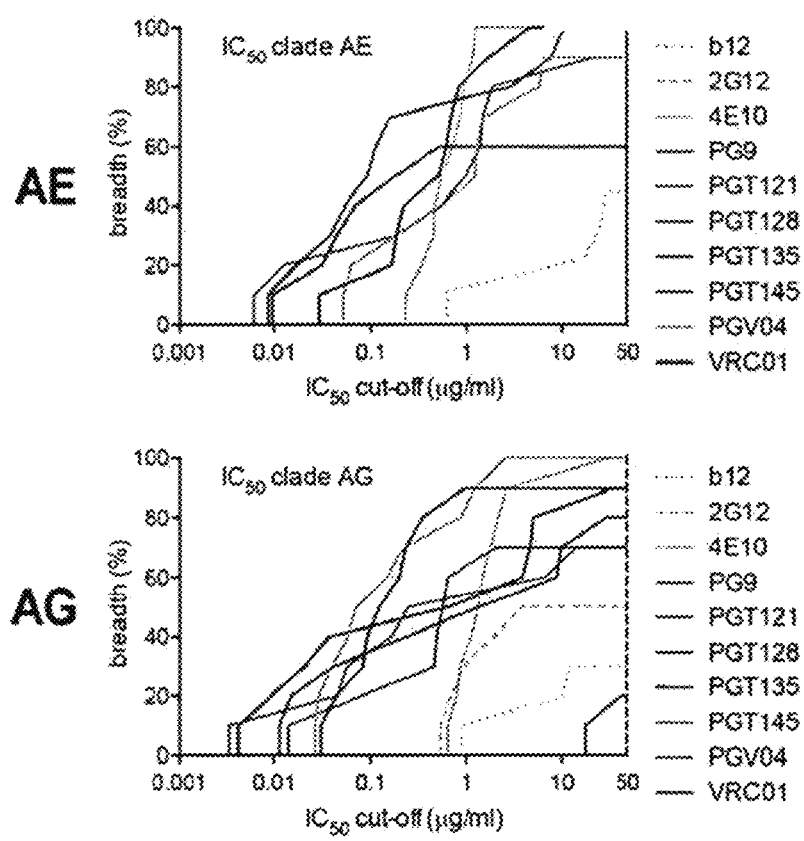
Figure 37A:
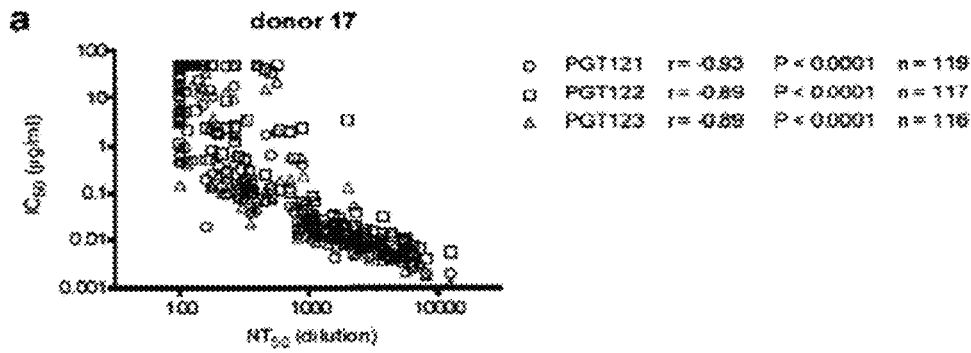
FIG. 37A-37D is a series of graphs showing that MAb neutralization correlates strongly with serum neutralization. Correlation of $IC_{50}$s of the MAbs and serum $NT_{50}$s of the corresponding donors 17 (a), 36 (b), 39 (c) and 84 (d) is shown. Spearman correlation was used for statistical analyses. Only viruses neutralized by either the MAb (IC50<50 µg/ml) or the serum ($NT_{50}$>100) were included.
Figure 37B:
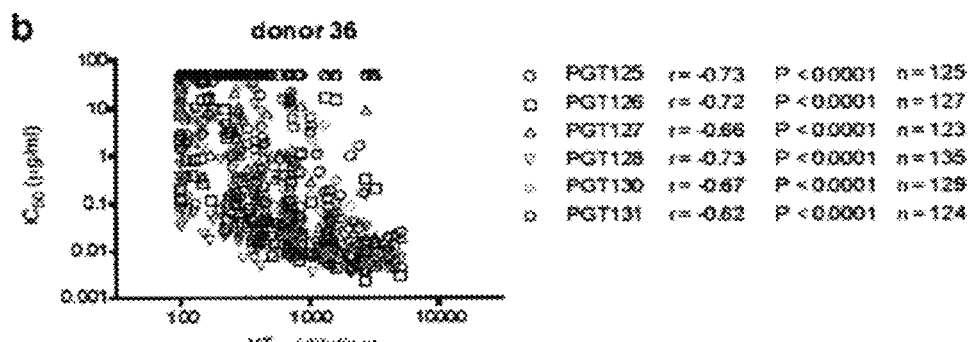
Figure 37C:
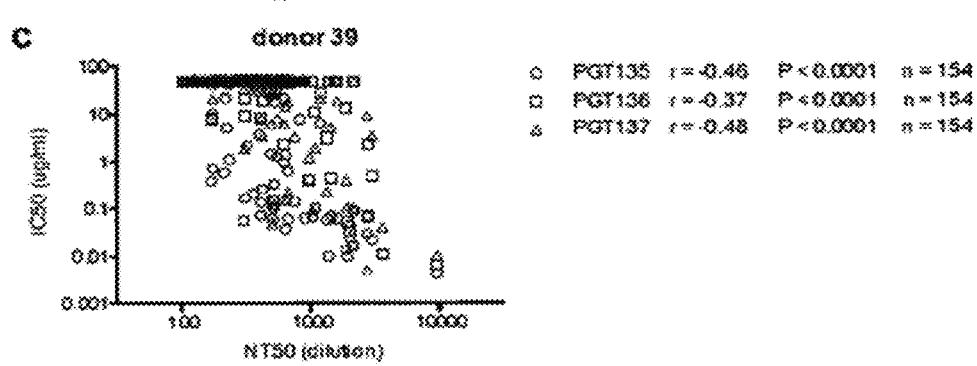
Figure 37D:
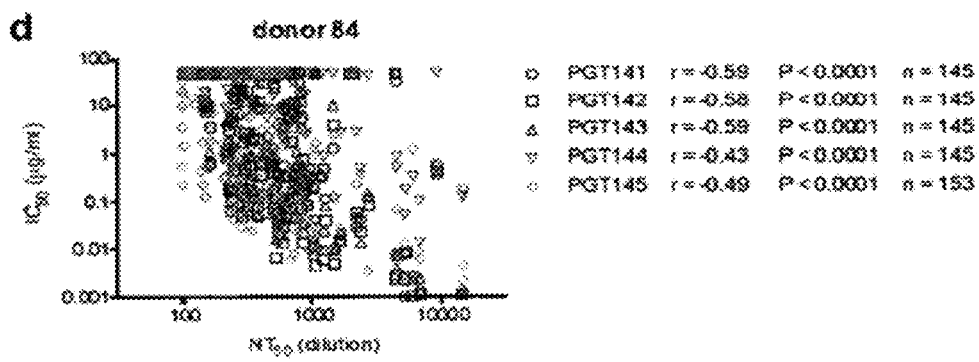
Figure 41:
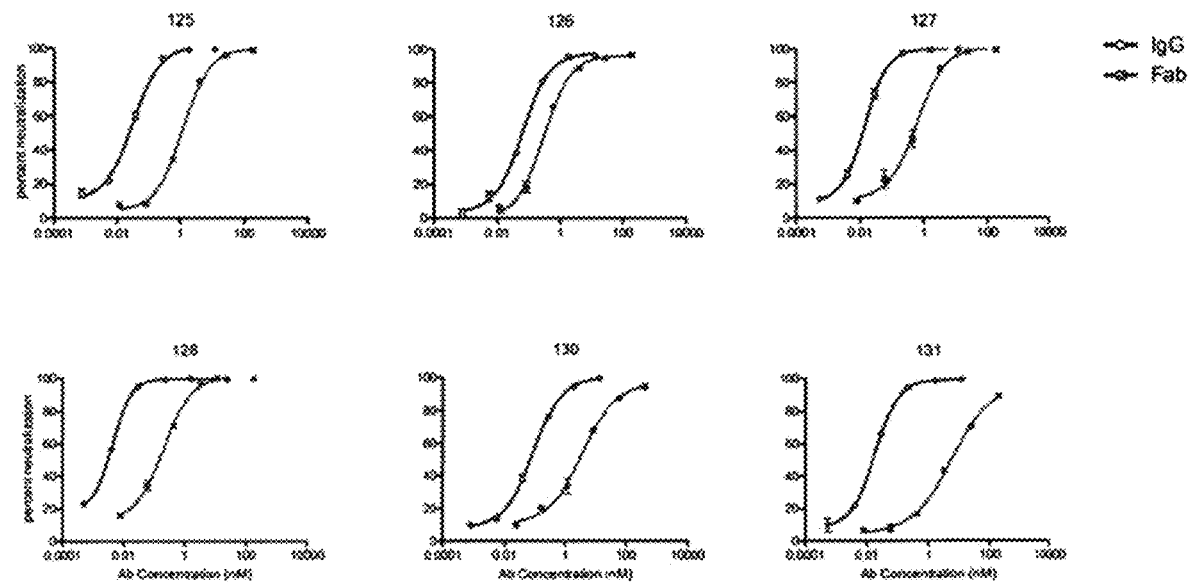
FIG. 41 is a series of graphs showing the neutralization activity of Fab fragments. Fab fragments of PGTs-125, 126, 127, 128, 130 and 131 were generated by Lys-C digestion and the neutralizing activity tested against HIV-1 JR-CSF using a single round of replication pseudovirus assay.
Figures 42A, 42B:
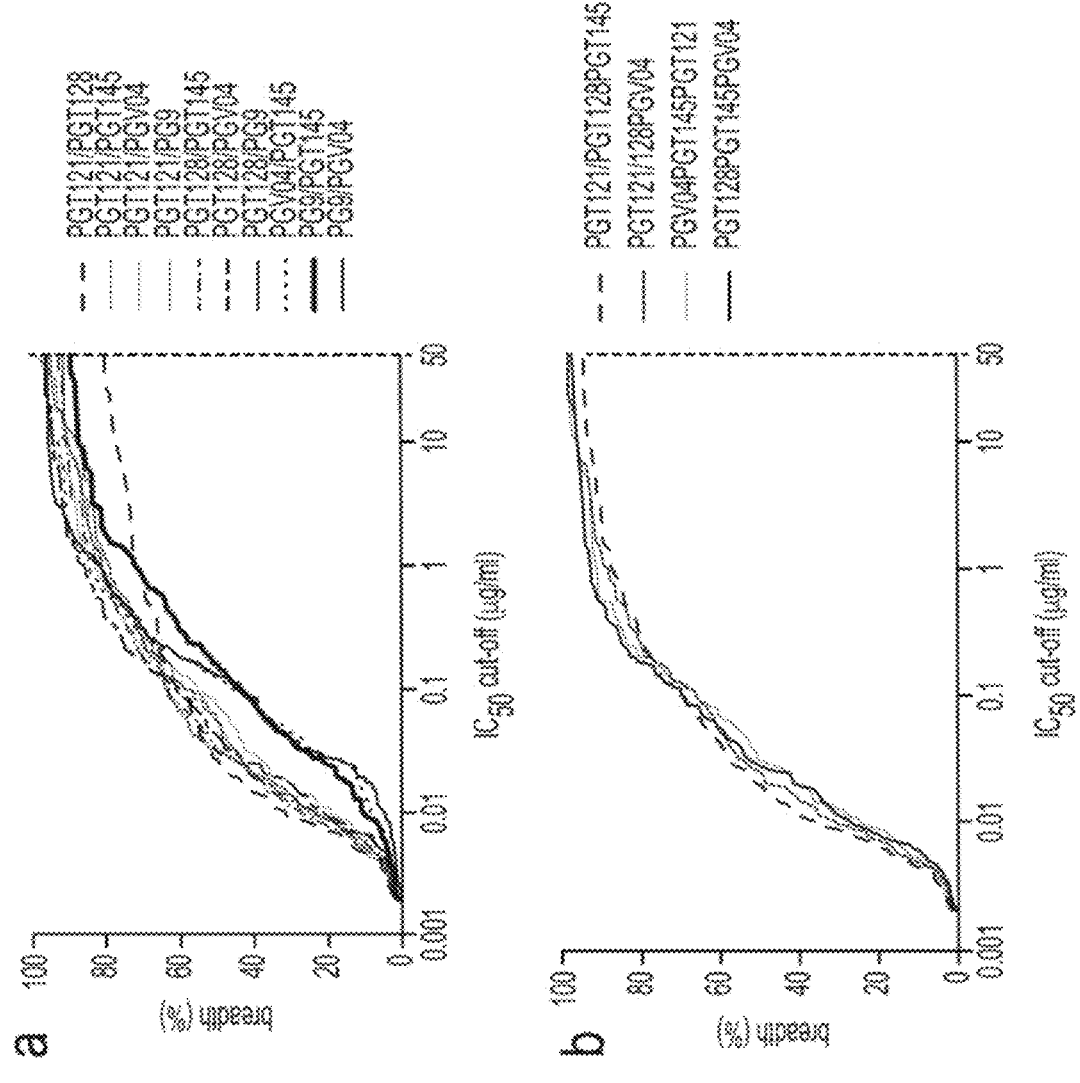
FIG. 42A-42B is a series of graphs showing that the combination of two or three antibody specificities is sufficient to cover a broad range of HIV isolates at vaccine achievable concentration. Cumulative frequency distribution of IC50 values of double (a) and triple (b) combinations of neutralization activities (overall lowest IC50 against each isolate). The grey area depicts the theoretical maximal achievable neutralization activity known to date.
Figure 43A:
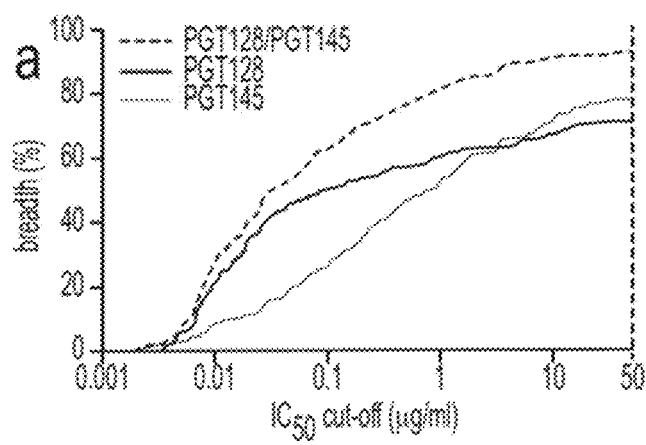
FIG. 43A-43C is a series of graphs showing that combinations of two or three antibody specificities are sufficient to cover a broad range of HIV isolates at vaccine achievable concentrations. A-C Cumulative frequency distribution of $IC_{50}$ values of single MAbs (solid lines) and combined neutralisation activity (overall lowest $IC_{50}$ against each isolate) of two or three MAbs (dashed lines). The grey area is the combined neutralisation activity of 25 MAbs tested on the 162-virus panel (b12, 2G12, 4E10, 2F5, PG9, PG16, PGC14, PGV04, PGTs 121-123, PGTs 125-128, PGTs 130-131, PGTs 135-137, PGTs 141-145) and depicts the theoretical maximal achievable neutralisation activity known to date. VRC01 and PGV04 in panel c are measured on a different virus panel (n=97).
Figure 43B:
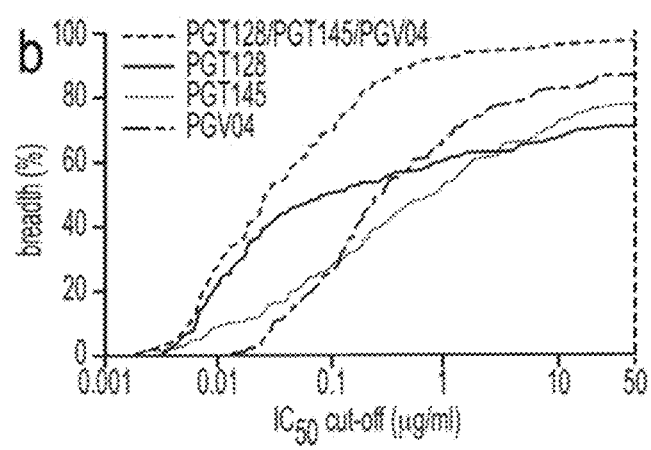
Figure 43C:
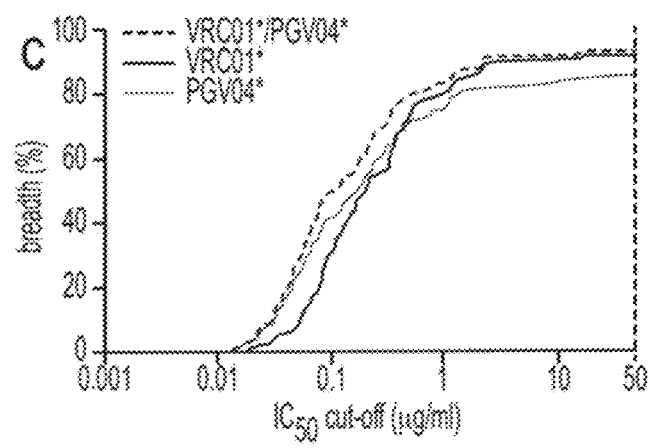
Figure 44G:
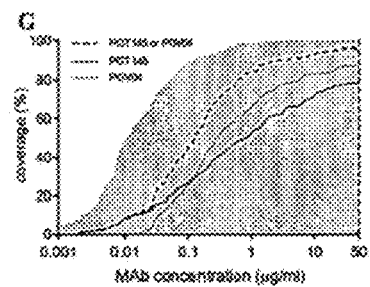
Figure 44H:
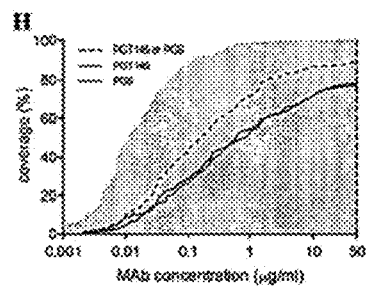
Figure 44I:
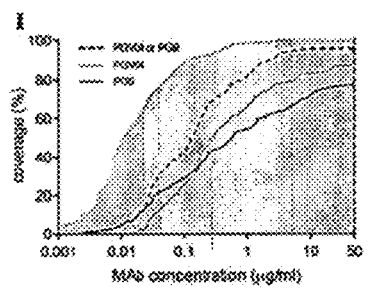
Figure 44J:
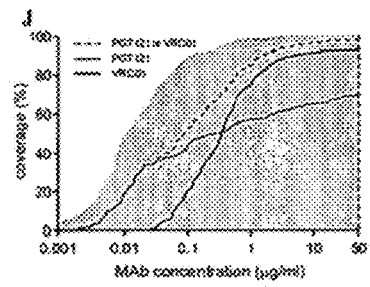
Figure 44K:
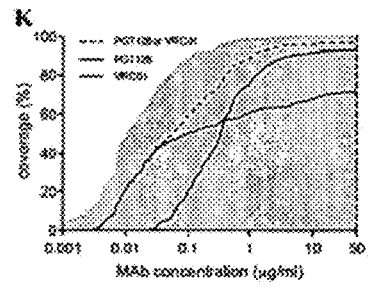
Figure 44L:
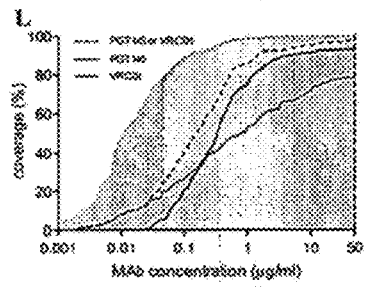
Figure 44M:
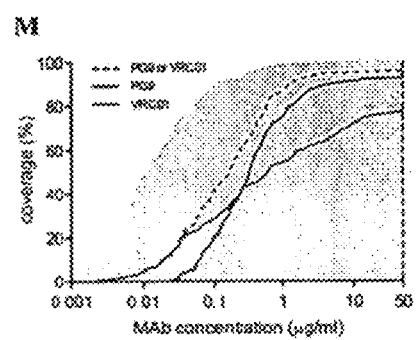
Figure 45:
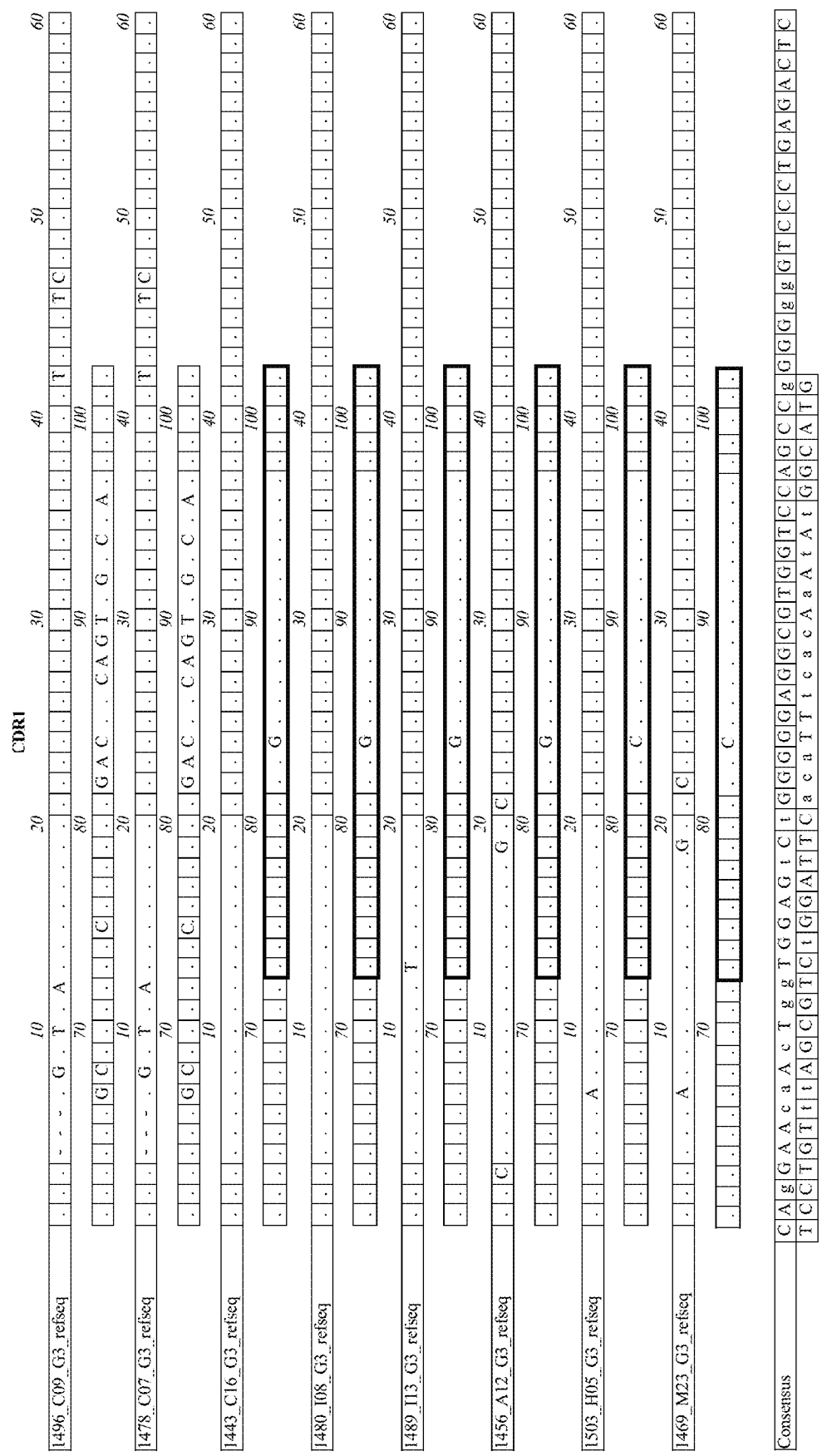
FIG. 45 is an alignment of heavy chain coding sequences of the variable domain of 1443_C16 sister clones to 1443_C16 and 1496_C09 (SEQ ID NO: 652-653).
Figure 45:
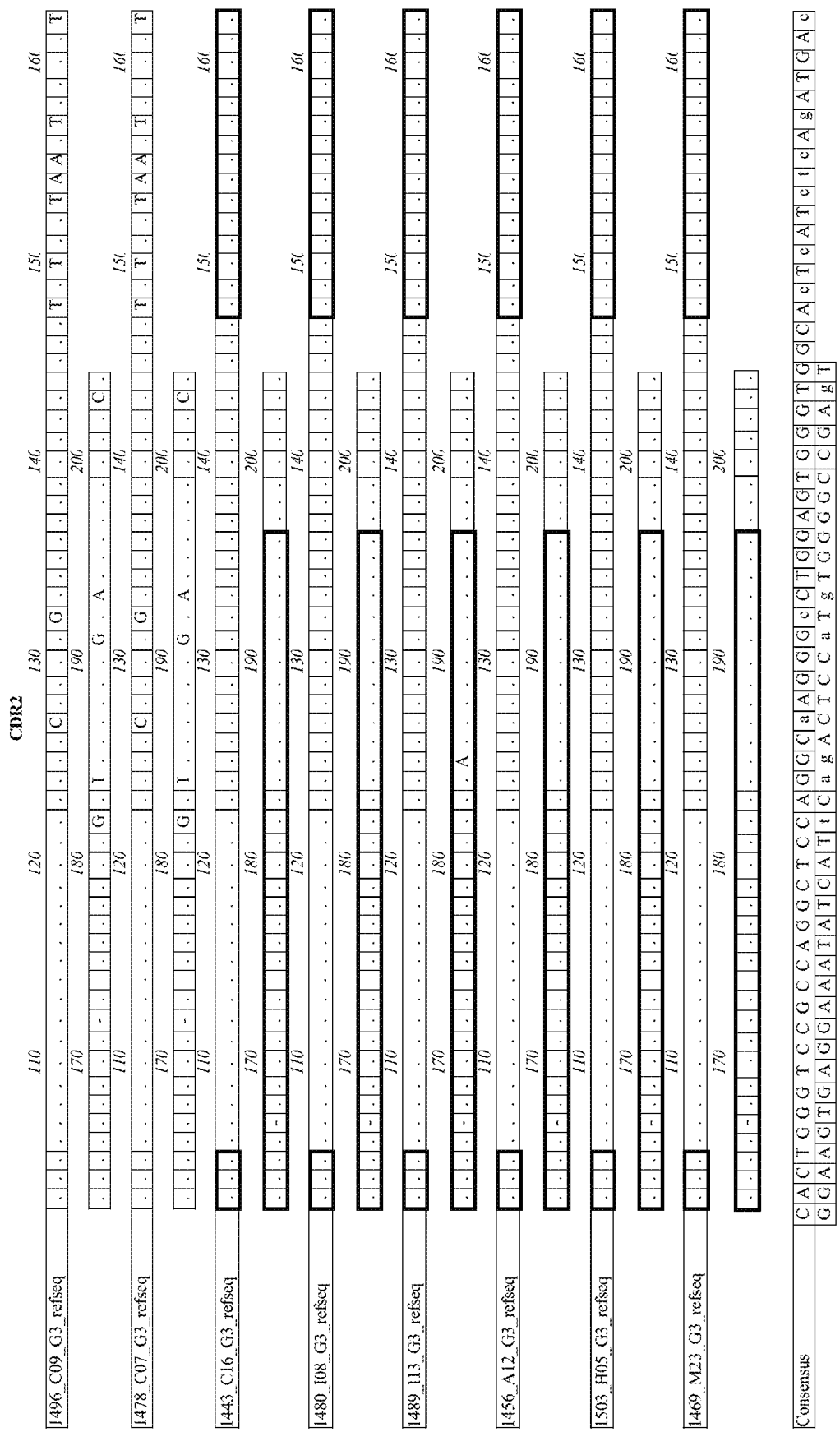
Figure 45:
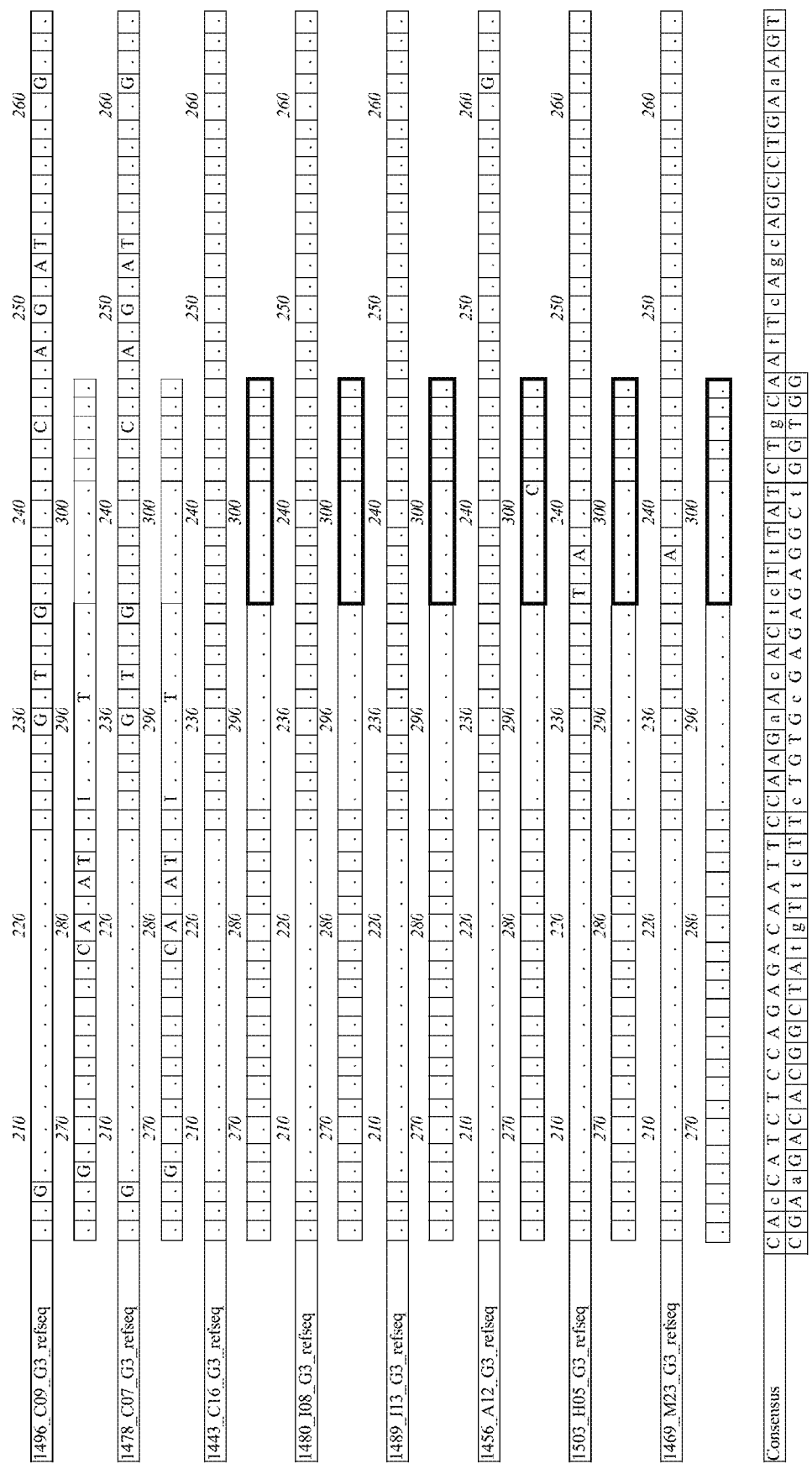
Figure 45:
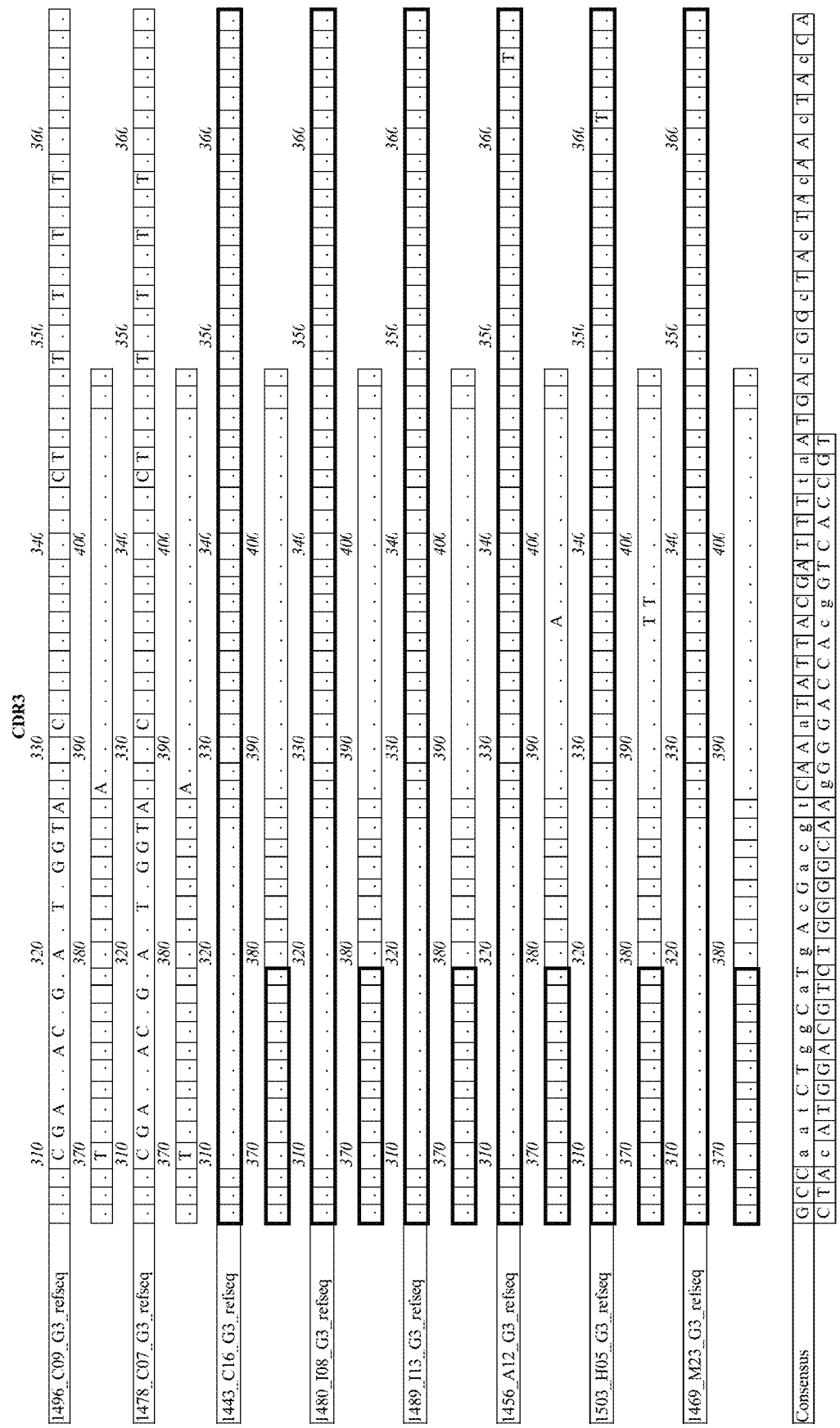
Figure 46:
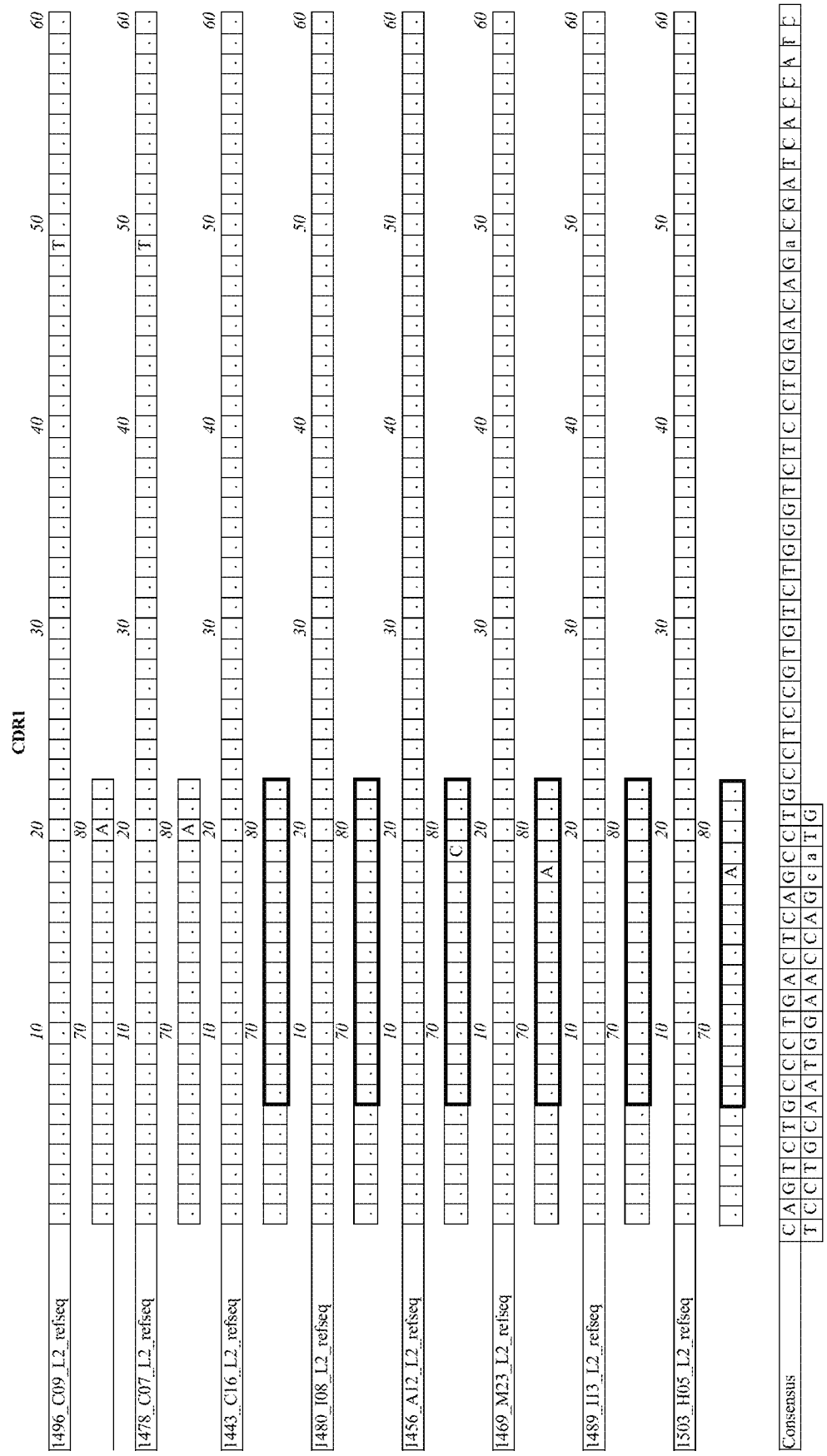
FIG. 46 is an alignment of light chain coding sequences of the variable domain of 1443_C16 sister clones to 1443_C16 and 1496_C09 (SEQ ID NO: 654-655).
Figure 46:
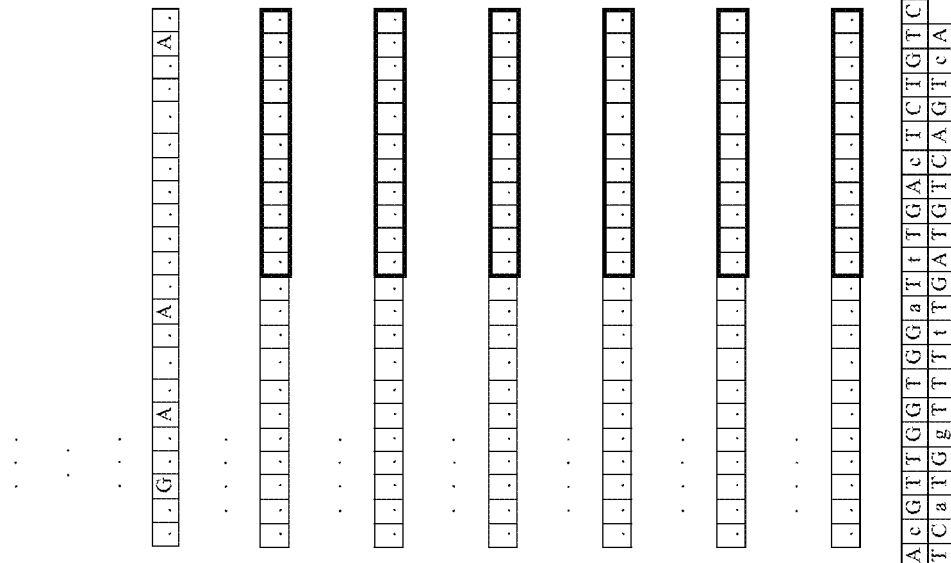
Figure 46:
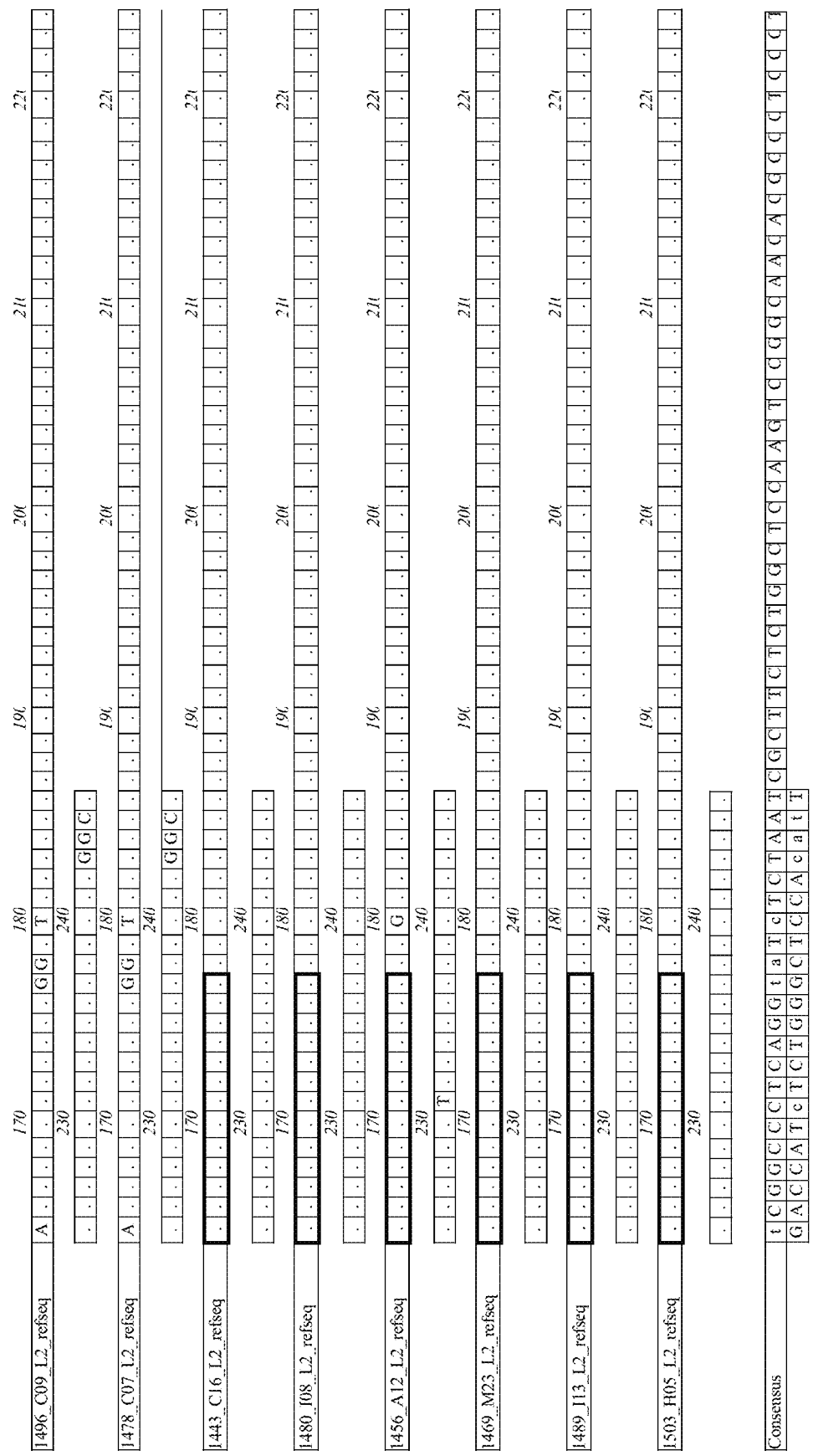
Figure 46:
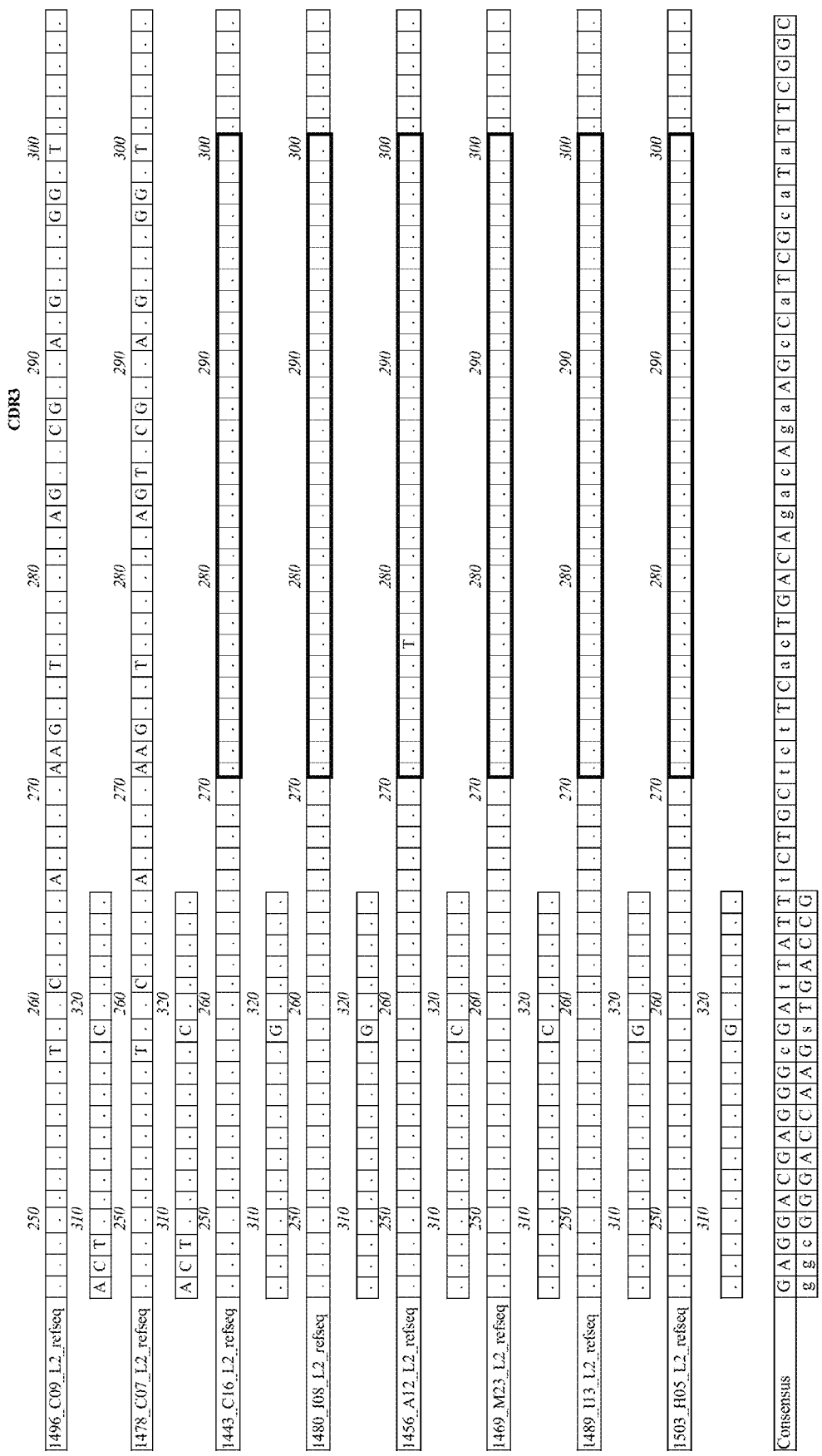
Figure 50:
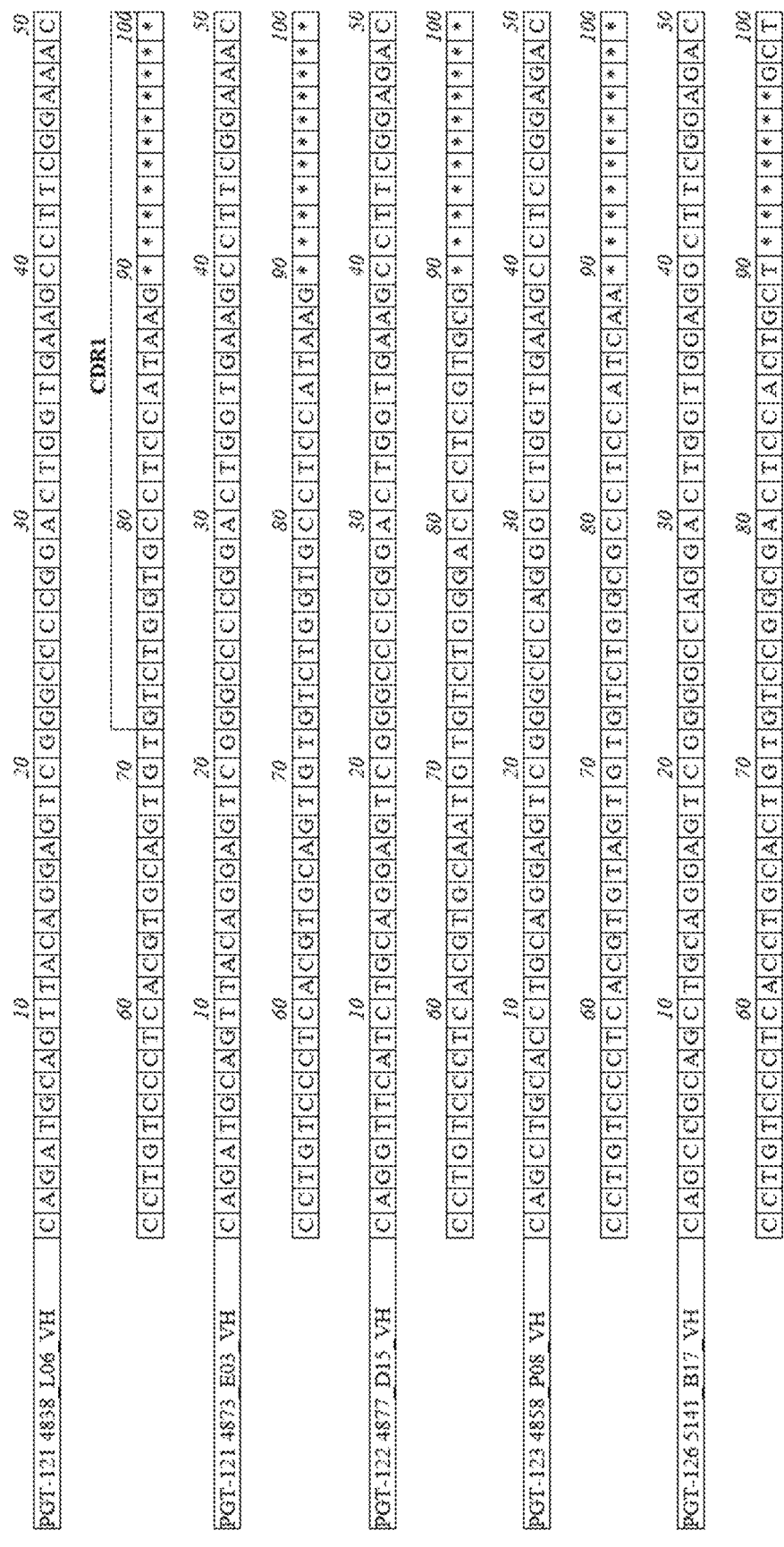
FIG. 50 is a table showing heavy chain variable gene alignment for PGT-121, PGT-122, PGT-123, PGT-125, PGT-126, PGT-130, PGT 135, and PGT-136 (SEQ ID NO: 662-673 from top to bottom).
Figure 50:
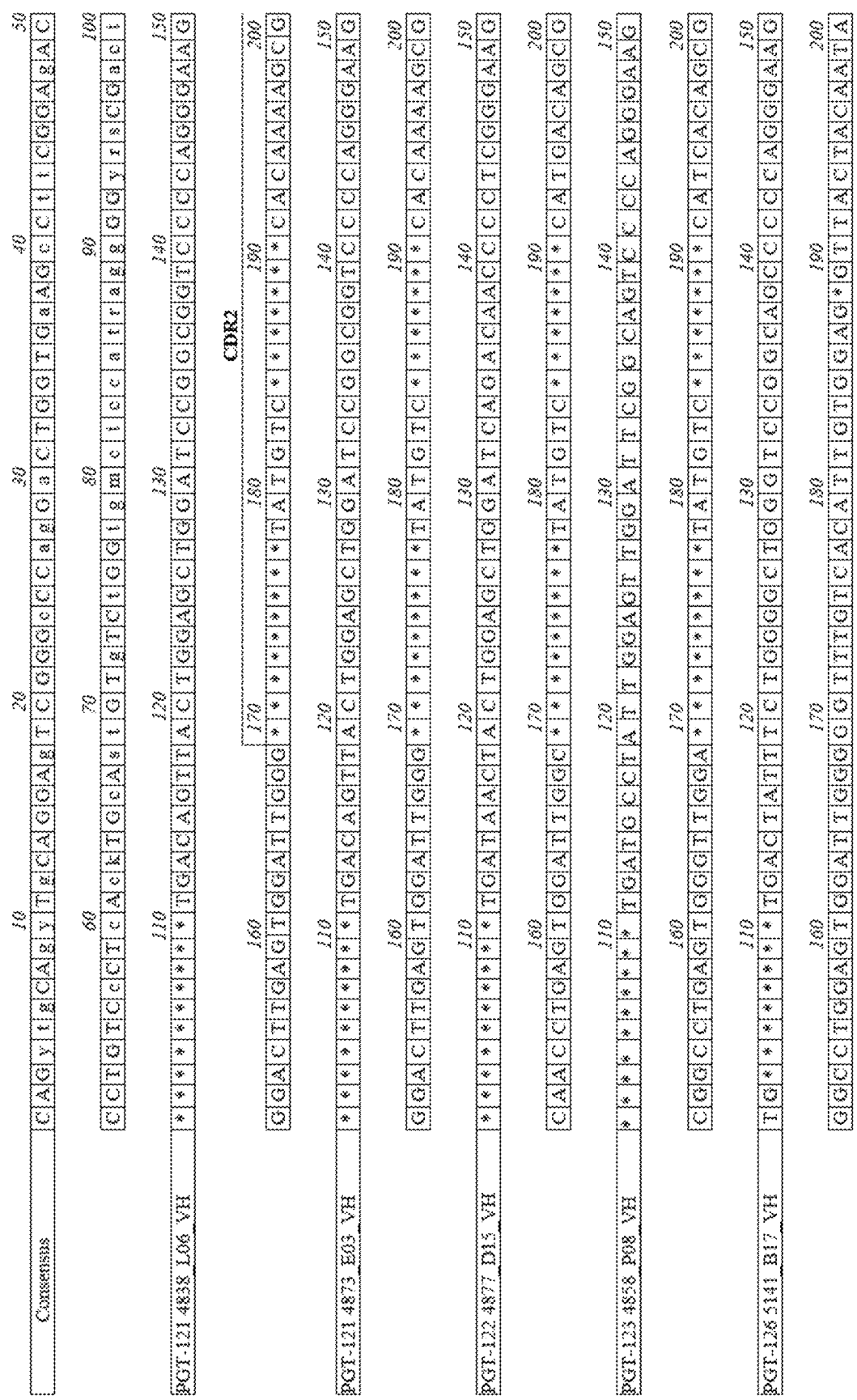
Figure 50:
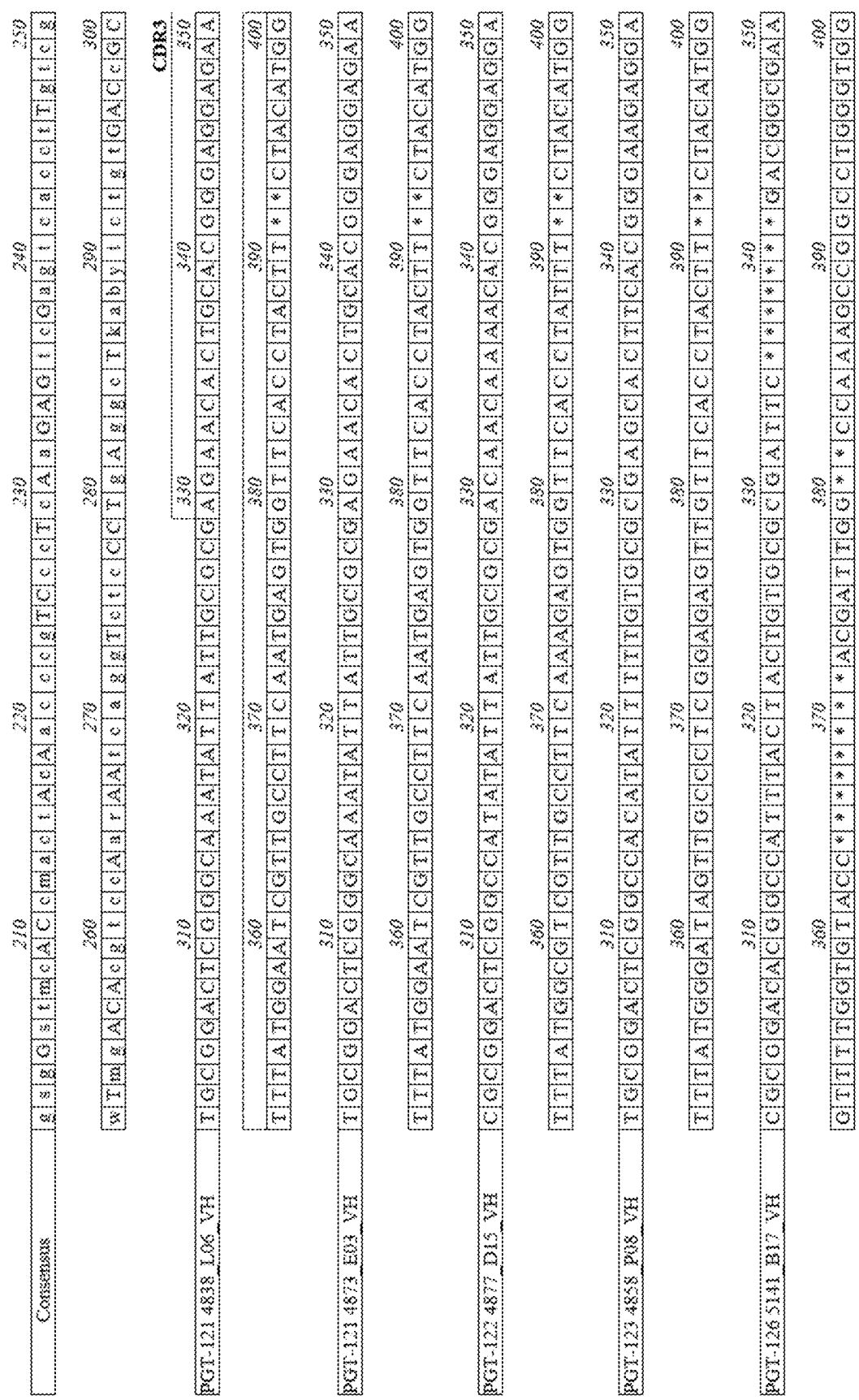
Figure 50:
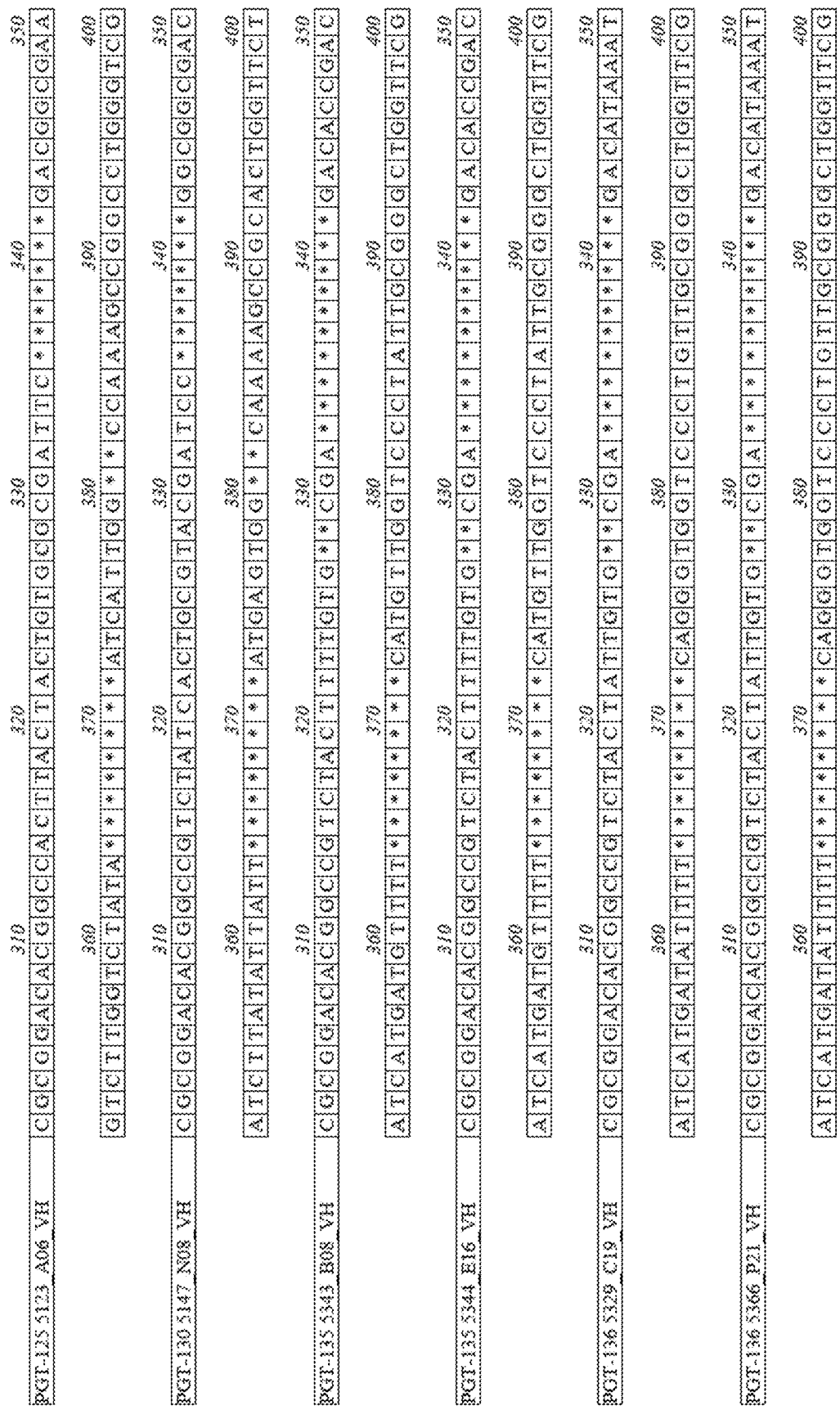
Figure 50:
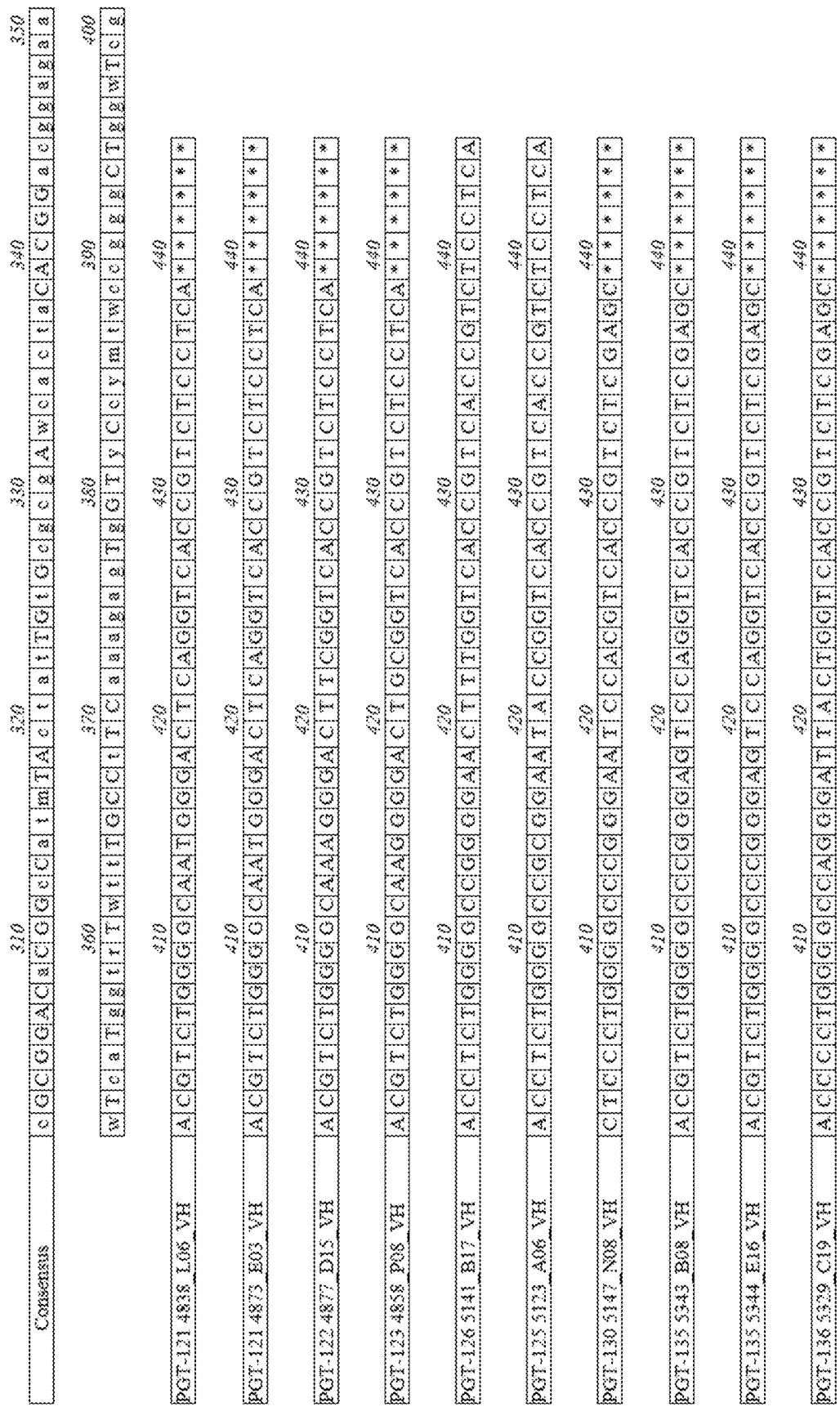
Figure 51:
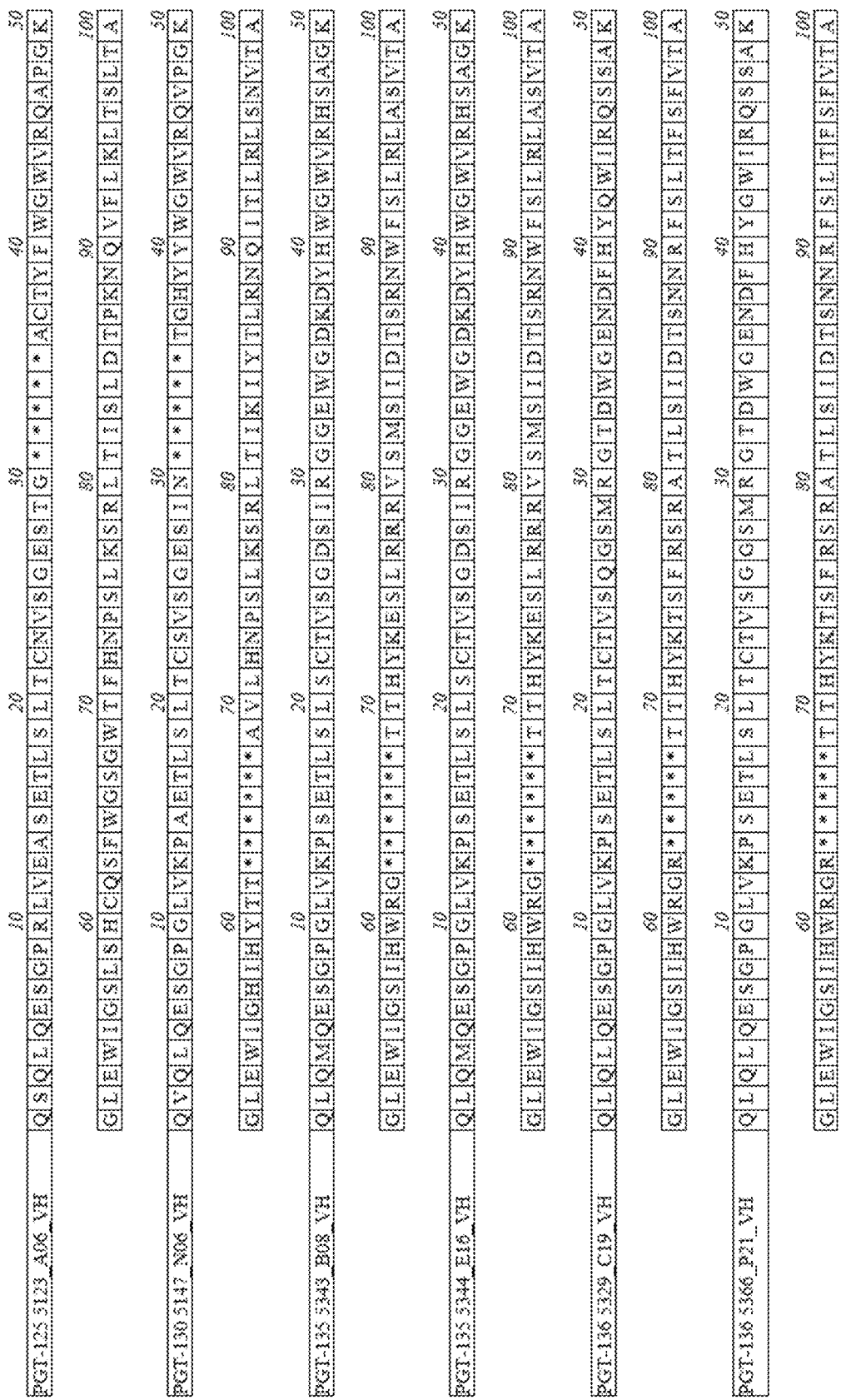
FIG. 51 is a table showing heavy chain variable protein alignment for PGT-121, PGT-122, PGT-123, PGT-125, PGT-126, PGT-130, PGT 135, and PGT-136 (SEQ ID NO: 674-684 from top to bottom).
Figure 51:
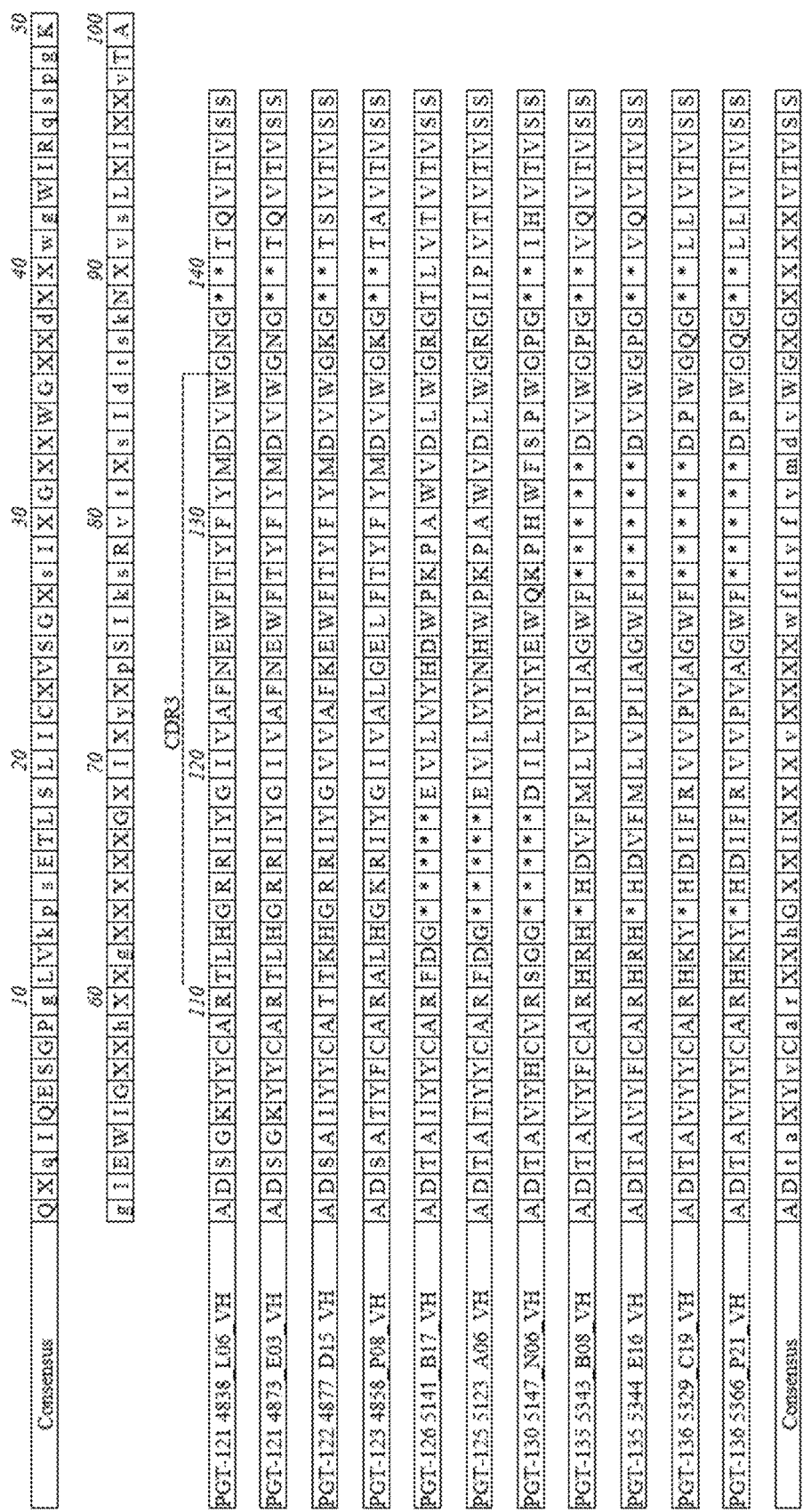
Figure 52:
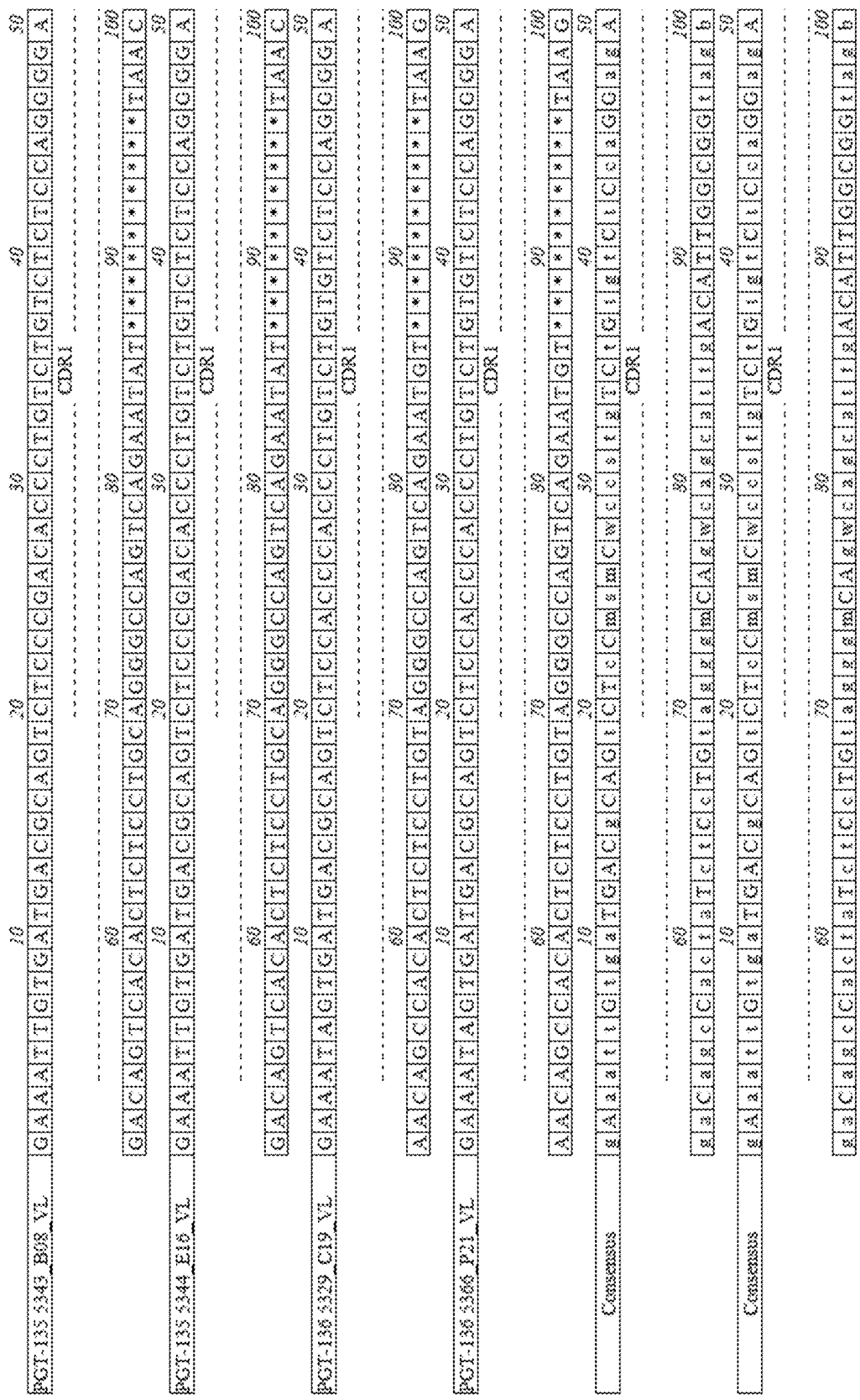
FIG. 52 is a table showing light chain variable gene alignment for PGT-121, PGT-122, PGT-123, PGT-125, PGT-126, PGT-130, PGT-135, and PGT-136 (SEQ ID NO: 685-697 from top to bottom).
Figure 52:
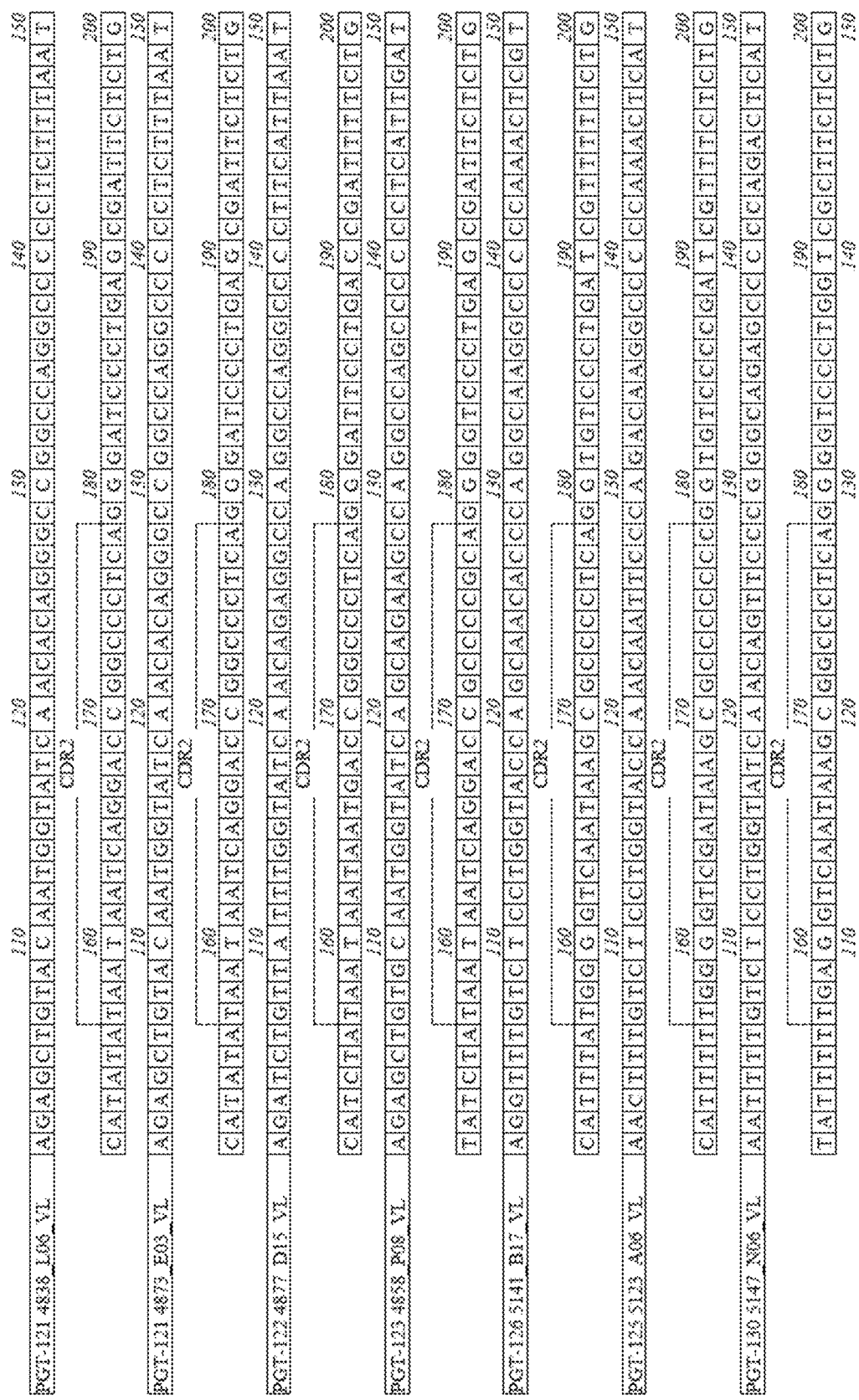
Figure 52:
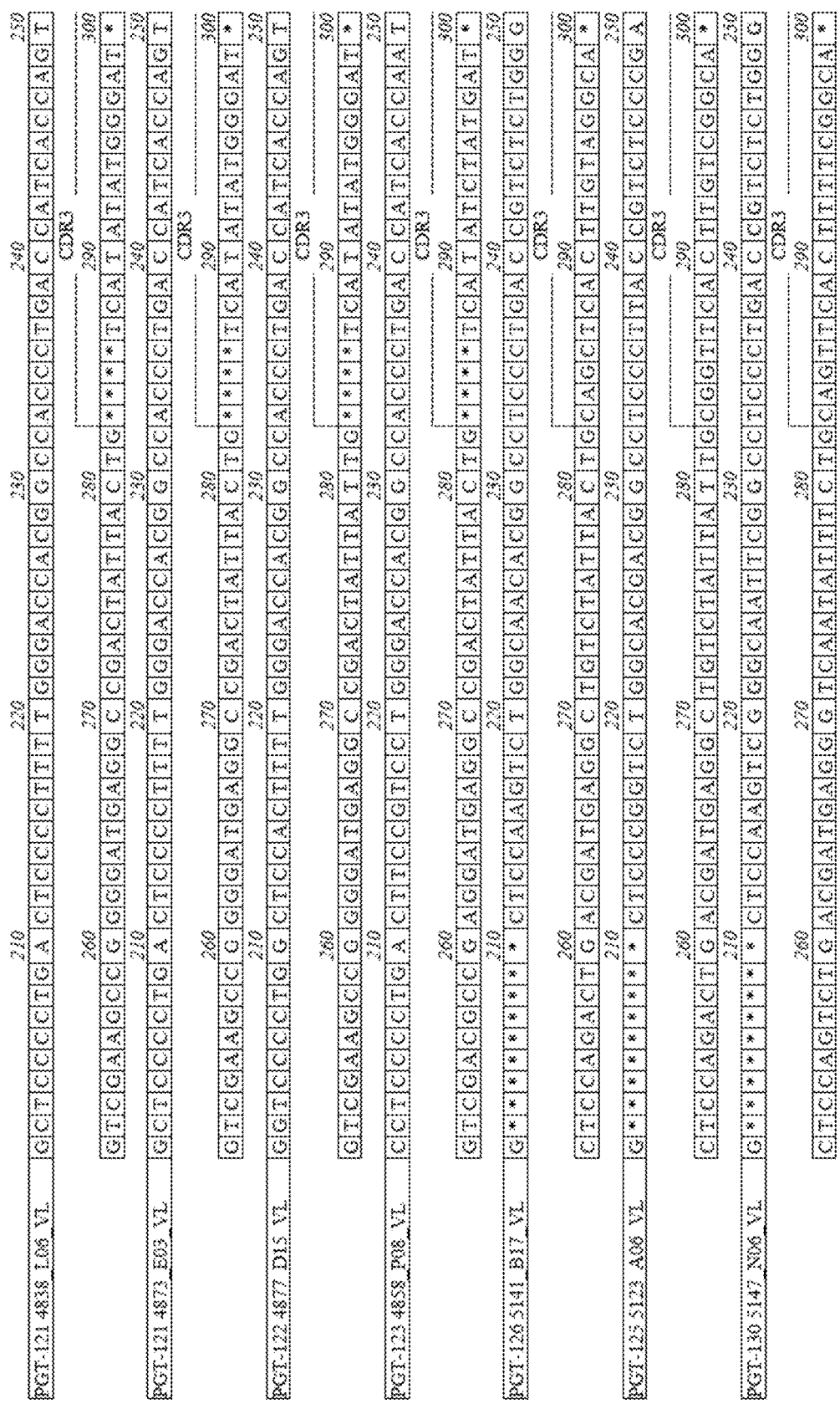
Figure 52:
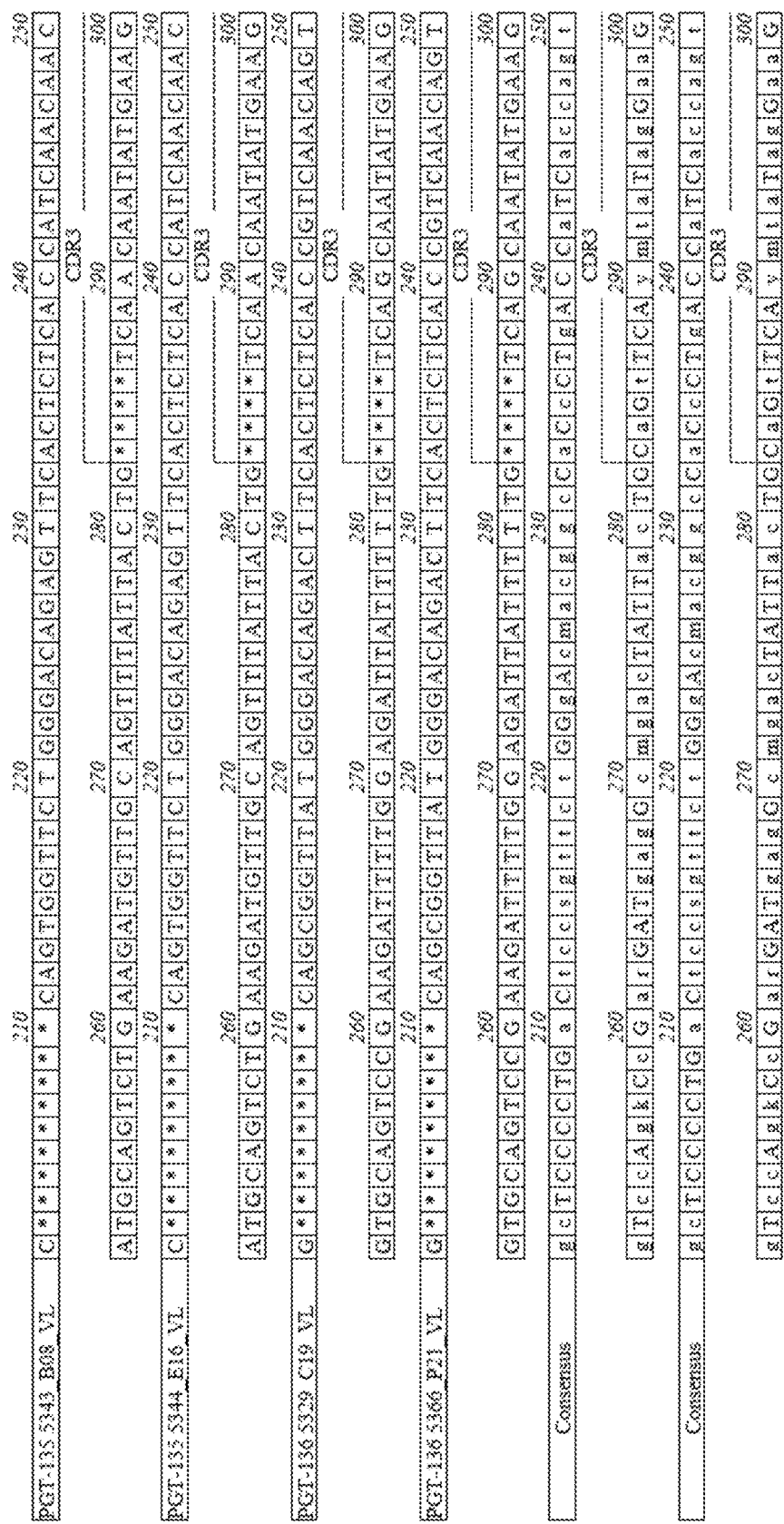
Figure 52:
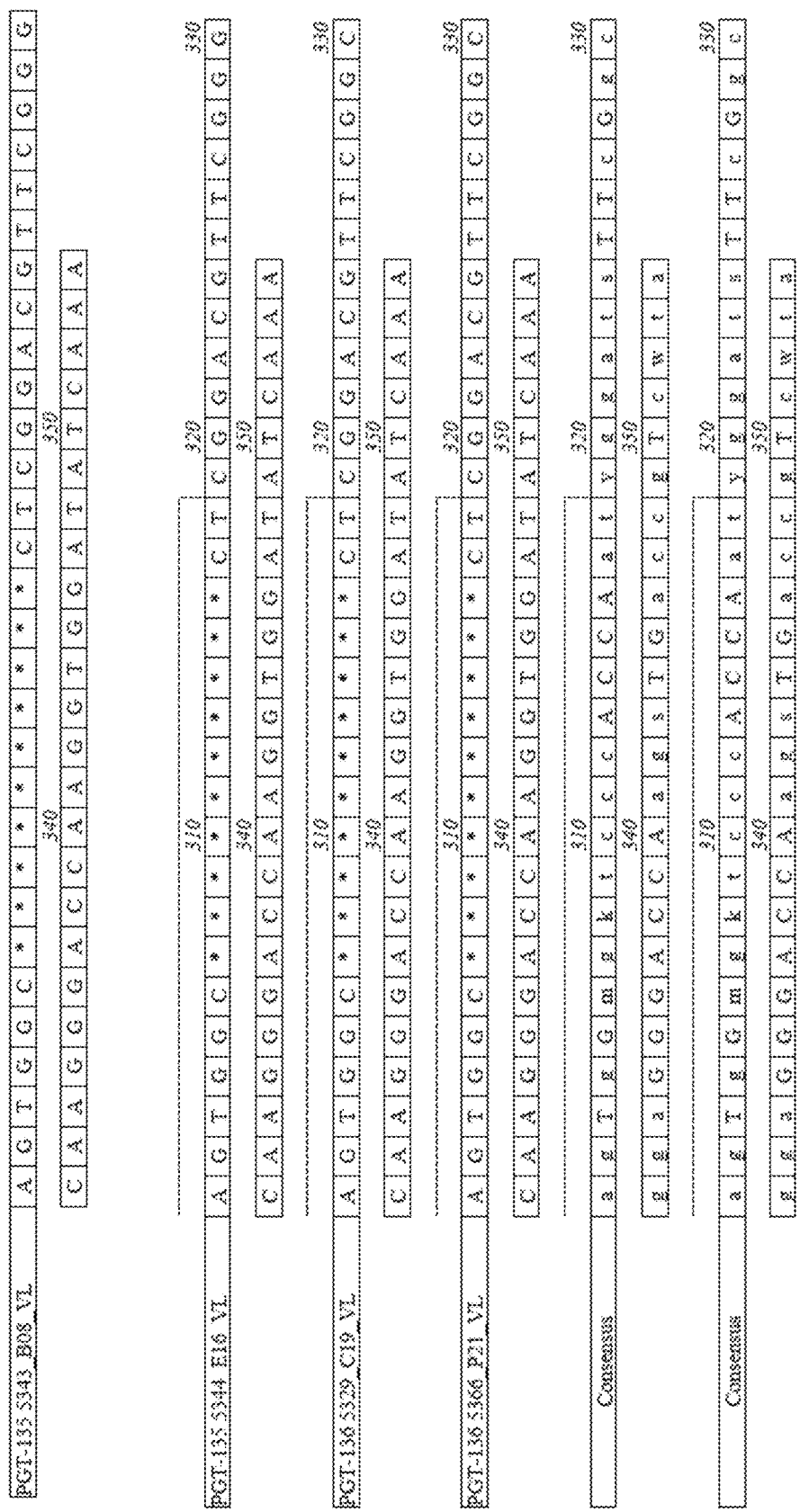
Figure 53:
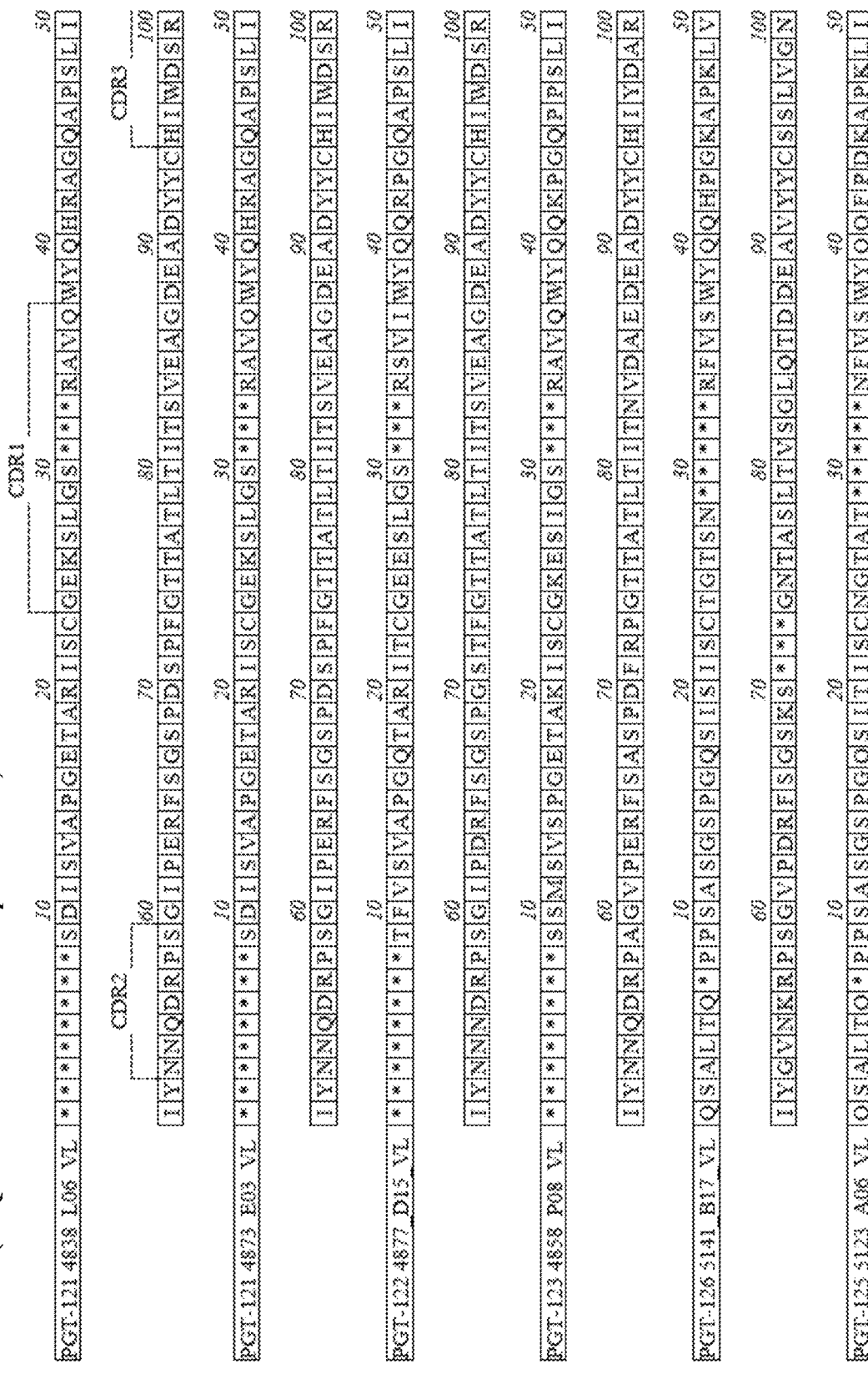
FIG. 53 is a table showing light chain variable protein alignment for PGT-121, PGT-122, PGT-123, PGT-125, PGT-126, PGT-130, PGT-135, and PGT-136 (SEQ ID NO: 698-706 from top to bottom).
Figure 53:
Figure 54:
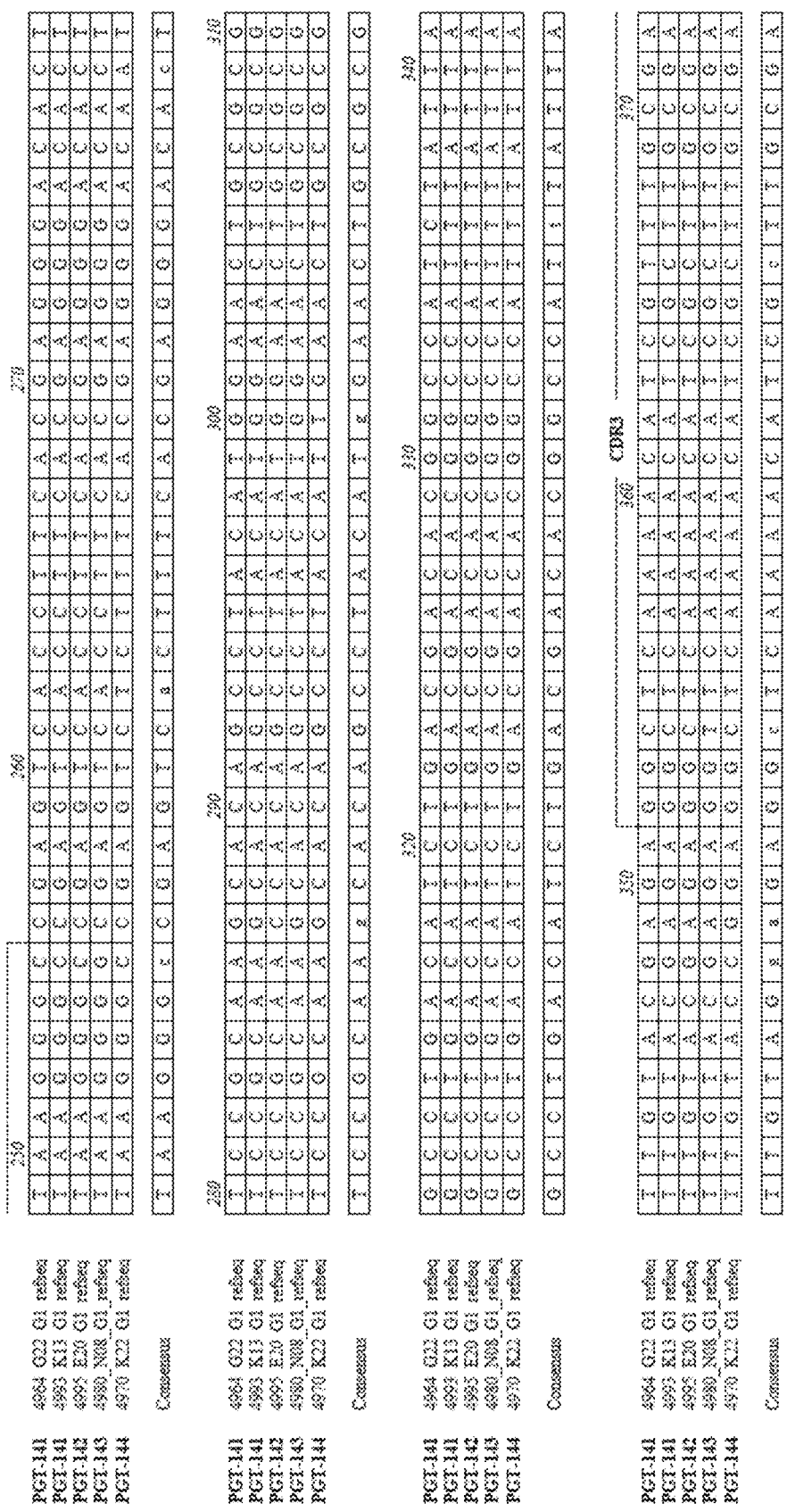
FIG. 54 is a table showing heavy chain variable gene alignment for PGT-141, PGT-142, PGT-143, and PGT-144 (SEQ ID NO: 707-712 from top to bottom).

To define the epitopes recognized by the remaining PGT antibodies, competition ELISA assays were carried out with a panel of well-characterized neutralizing and non-neutralizing antibodies (FIG. 34a). Unexpectedly, all of the remaining antibodies (PGTs 121-123, 125-128, 130, 131, 135-137) competed with the glycan-specific bnMAb 2G12. This result was surprising given that 2G12 had previously formed its own unique competition group. All of the mAbs except for PGTs 135, 136 and 137 also competed with a V3 loop-specific mAb and failed to bind to gp120 ΔV3, suggesting their epitopes were in proximity to or contiguous with the V3 loop (FIG. 34a and Table 59). Deglycosylation of gp120 with Endo H abolished binding by all the mAbs, indicating that certain oligomannose glycans were important for epitope recognition (Table 59). Competition of these mAbs with 2G12 and lack of binding to deglycosylated gp120 prompted us to investigate whether these antibodies contacted glycans directly. Glycan array analysis revealed that PGTs 125-128, and 130 bound specifically to both $Man_8GlcNAc_2$ and $Man_9GlcNAc_2$, whereas the remaining antibodies showed no detectable binding to high-mannose glycans (FIG. 34b). Interestingly, the binding of PGTs 125-128, 130 to gp120 was competed by $Man_9$ but, unlike 2G12, was not competed by monomeric mannose or $Man_4$ (D1 arm of $Man_9GlcNAc_2$) (FIGS. 34c and 34d), suggesting a different mode of glycan recognition. Furthermore, in contrast to 2G12, no evidence was found for domain exchange and monomeric Fab fragments exhibited potent neutralizing activity (FIG. 41).

Figure 40A:
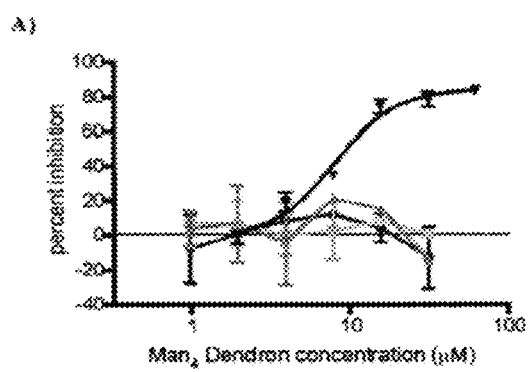
FIG. 40A-40B is a series of graphs showing PGTs 121, 122 and 123 in competition with oligodendrons. Unlike PGTs 125, 126, 127, 128 and 130, the binding of PGTs 121, 122 and 123 to gp120 could not be competed by A) $Man_4$ or B) $Man_9$ dendrons.
Figure 40B:
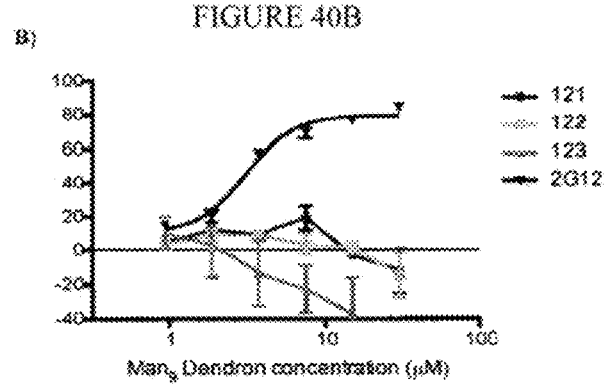

To further define the epitopes recognized by the mAbs, neutralizing activity against a large panel of $HIV-1_{JR-CSF}$ variants incorporating single alanine substitutions was assessed using a single round of replication pseudovirus assay (Table 60). In the panel of mutants, the N-linked glycans at positions 332 and/or 301 were important for neutralization by PGTs 125-128, 130, and 131 suggesting their direct involvement in epitope formation. The apparent dependency on so few glycans suggests that, although PGTs 125-128, 130, and 131 contact $Man_{8-9}G1cNAc2$ glycans directly, their arrangement in the context of gp120 is critical for high affinity glycan recognition and neutralization potency. This is further highlighted by the inability of PGT Mabs to neutralize SIVmac239, HIV-2 or HCV, which display a high level of glycosylation. Although PGTs 121-123 failed to exhibit detectable binding to high-mannose glycans and be competed by mannose sugars (FIG. 40), the only substitutions that completely abolished neutralization by these mAbs were those that resulted in removal of the glycan at position 332. Although structural studies will be required to fully define the epitopes recognized by these antibodies, the above result suggests either that the PGT 121-123 mabs bind to a protein epitope along the gp120 polypeptide backbone that is conformationally dependent on the N332 glycan or that the glycan contributes more strongly to binding in the context of the intact protein.

TABLE 60A

Neutralizing activity of PGT mAbs against a panel of JR-CSF alanine mutants.

| Mutation[a] | gp120 domain[b] | Fold $IC_{50}$ increase relative to wild-type[c] | | | | | | | | | |
|---|---|---|---|---|---|---|---|---|---|---|---|
| | | PGT-121 | PGT-122 | PGT-123 | PGT-125 | PGT-126 | PGT-127 | PGT-128 | PGT-130 | PGT-131 | PGT-135 |
| D113A | C1 | 1.2 | 1.0 | 1.1 | 1.1 | 1.2 | 0.3 | 0.5 | 0.8 | ND | 0.8 |
| V120A | | 0.8 | 1.2 | 1.1 | 0.5 | 0.7 | 1.5 | 1.4 | 0.8 | 0.7 | 1.4 |
| L125A | | 0.9 | 2.4 | 2.5 | 1.6 | 1.2 | 1.4 | 2.9 | 2.5 | 2.5 | 0.9 |
| V127A | | 0.7 | 1.0 | 1.2 | 0.9 | 1.3 | 2.5 | 1.1 | 0.8 | 0.6 | 1.4 |
| N134A | V1 | 0.2 | 0.3 | 0.4 | 0.5 | 0.6 | 1.0 | 1.2 | 0.6 | 0.5 | 0.2 |
| N156A | V2 | 0.9 | 1.1 | 6.2 | 3.6 | 1.8 | 1.6 | 0.4 | 1.5 | 1.0 | 0.3 |
| N160K | | 1.1 | 1.1 | 1.0 | 0.5 | 0.5 | 0.8 | 1.0 | 3.4 | 0.4 | 7.7 |
| T162A | | 0.3 | 0.6 | 0.7 | 0.5 | 0.6 | 1.1 | 1.1 | 0.6 | 0.6 | 0.9 |
| I165A | | 3.3 | 3.0 | 2.2 | 2.3 | 2.5 | 1.7 | 2.1 | 3.2 | 2.4 | 4.0 |
| R166A | | 1.4 | 0.9 | 0.9 | 1.5 | 1.0 | 1.6 | 2.7 | 1.2 | 1.6 | 0.9 |
| D167A | | 1.0 | 1.1 | 1.2 | 1.7 | 1.6 | 1.6 | 0.3 | 1.2 | 1.2 | 0.7 |
| K168A | | 1.5 | 0.8 | 0.8 | 0.9 | 0.7 | 1.9 | 1.1 | 1.2 | 1.7 | 0.4 |
| E172A | | 1.4 | 1.0 | 1.1 | 1.8 | 0.7 | 2.1 | 2.5 | 1.4 | ND | 1.3 |
| Y177A | | 1.4 | 2.4 | 2.4 | 1.1 | 0.9 | 2.9 | 1.4 | 3.6 | 5.3 | 0.3 |
| L179A | | 1.9 | 1.1 | 1.2 | 1.3 | 2.6 | 2.5 | 2.8 | 2.4 | 4.8 | 1.2 |
| V182A | | 2.1 | 2.2 | 2.8 | 1.3 | 1.4 | 1.6 | 1.2 | 1.2 | 1.1 | 1.5 |
| D185A | | 1.0 | 1.8 | 1.9 | 0.6 | 1.0 | 2.0 | 1.5 | 0.9 | 0.7 | 1.3 |
| N188A | | 0.8 | 1.0 | 1.1 | 0.7 | 0.8 | 0.8 | 1.3 | 1.0 | 0.9 | 0.4 |
| N197A | C2 | 1.1 | 1.4 | 1.4 | 1.0 | 1.1 | 0.6 | 1.0 | 1.2 | 1.1 | 0.3 |
| S199A | (V1/V2 stem) | 0.8 | 1.0 | 1.1 | 0.7 | 0.8 | 3.0 | 1.0 | 0.9 | 1.6 | 0.3 |
| T202A | | 1.2 | 1.5 | 1.2 | 0.8 | 0.8 | 1.8 | 1.1 | 1.2 | 2.7 | 1.8 |
| F210A | C2 | 1.5 | 2.6 | 2.8 | 1.4 | 1.5 | 0.8 | 0.8 | 1.7 | 1.0 | 1.3 |
| N241A | | 0.5 | 1.4 | 0.8 | 0.5 | 0.6 | 0.6 | 0.7 | 0.6 | 0.7 | 0.1 |
| N262A | | 1.1 | 1.1 | 0.5 | 0.9 | 1.0 | 1.4 | 1.6 | 0.7 | 0.4 | 2.1 |
| N276A | | 0.8 | 1.4 | 1.1 | 0.9 | 0.9 | 1.6 | 0.6 | 1.0 | 0.8 | 2.5 |

TABLE 60B

| Mutation[a] | gp120 domain[b] | Fold IC$_{50}$ Increase relative to wild-type[c] | | | | | | | | | |
|---|---|---|---|---|---|---|---|---|---|---|---|
| | | PGT-121 | PGT-122 | PGT-123 | PGT-125 | PGT-126 | PGT-127 | PGT-128 | PGT-130 | PGT-131 | PGT-135 |
| V292A | | 2.7 | 1.3 | 1.7 | 3.3 | 5.0 | 0.9 | 2.1 | 0.9 | 1.4 | 2.0 |
| N295A | V3 | 0.6 | 0.7 | 1.2 | 0.8 | 0.9 | 2.3 | 1.0 | 0.7 | 2.1 | >18 |
| T297A | | 0.7 | 0.6 | 0.3 | 0.9 | 0.8 | 1.7 | 1.1 | 0.9 | 1.2 | >30 |
| P299A | | 0.2 | 0.5 | 0.7 | 0.2 | 0.2 | 0.2 | 1.2 | 0.8 | 2.0 | 0.36 |
| N301A | | 0.4 | 0.4 | 1.0 | 213 | 314 | >250 | 10.7 | >1000 | >170 | 0.5 |
| N302A | | 0.7 | 1.1 | 1.3 | 0.7 | 0.9 | 3.0 | 1.5 | 1.1 | 1.0 | 0.8 |
| T303A | | 0.7 | 2.5 | 1.1 | >250 | >250 | >500 | >500 | >250 | >170 | 0.3 |
| R304A | | 1.7 | 0.7 | 0.7 | 1.9 | 1.8 | 0.4 | 0.7 | 2.5 | 1.5 | 0.7 |
| K305A | | 1.9 | 3.0 | 1.9 | 1.9 | 1.0 | 2.6 | 1.8 | 6.9 | ND | 0.2 |
| S306A | | 0.7 | 0.5 | 0.5 | 1.2 | 0.7 | 0.6 | 1.1 | 1.5 | 0.7 | 0.4 |
| I307A | | 3.7 | 3.8 | 5.9 | 5.0 | 1.8 | 10.2 | 3.7 | 1000.0 | >170 | 0.3 |
| I309A | | 1.1 | 2.1 | 1.6 | 1.0 | 1.2 | 6.0 | 2.8 | >77.9 | 8.8 | 0.3 |
| P313A | | 0.5 | 0.4 | 0.2 | 0.3 | 0.4 | 1.3 | 1.0 | 0.3 | 0.52 | 0.5 |
| R315A | | 0.9 | 0.5 | 0.7 | 0.9 | 1.0 | 0.3 | 0.4 | 0.6 | 0.7 | 1.8 |
| F317A | | 1.7 | 3.4 | 3.1 | 1.8 | 1.0 | 0.2 | 0.8 | 17.0 | 96 | 0.5 |
| T319A | | 1.3 | 0.5 | 0.4 | 1.1 | 0.8 | 1.0 | 0.5 | 1.6 | 0.9 | 0.4 |
| T320A | | 1.2 | 0.7 | 0.7 | 0.8 | 0.6 | 1.8 | 1.0 | 0.9 | 4.5 | 0.5 |
| E321aA | | 0.3 | 0.4 | 0.6 | 1.0 | 0.6 | 1.9 | 1.3 | 1.7 | 1.8 | 0.8 |
| I323A | | 1.9 | 2.2 | 1.0 | 0.9 | 0.9 | 4.0 | 3.0 | 0.8 | 38.0 | 1.5 |
| G324A | | 16.6 | 12.5 | 14.5 | 1.7 | 3.3 | ND | ND | >50 | ND | 0.4 |
| D325A | | 2.0 | 44.0 | 64.0 | 0.4 | 0.5 | 0.93 | 0.5 | >1000 | >170 | 0.5 |
| I326A | | 0.7 | 0.6 | 0.4 | 0.9 | 0.8 | 3.5 | 1.6 | 1.3 | 1.7 | 1.2 |
| R327A | | 2.5 | 1.7 | 1.7 | 2.1 | 2.2 | 1.8 | 2.5 | 2.4 | 19.0 | 0.67 |
| H330A | | 0.8 | 0.5 | 0.3 | 0.7 | 0.5 | 0.5 | 0.3 | 0.9 | 0.5 | >250 |
| N332A | | >200 | >200 | >200 | 2.0 | 181 | >100 | 1.4 | 0.6 | 0.5 | >250 |
| S334A | | >50 | >50 | >50 | 0.8 | >30 | >500 | 1.4 | 0.5 | 0.4 | >30 |
| Q337A | C3 | 1.0 | 0.5 | 0.5 | 0.8 | 0.4 | 0.5 | 0.7 | 1.0 | 1.3 | 2.1 |
| N339A | | 0.5 | 0.4 | 0.8 | 0.9 | 0.6 | 1.1 | 0.8 | 0.2 | 1.0 | 1.2 |
| T341A | | 0.5 | 0.3 | 0.3 | 1.1 | 0.5 | 1.7 | 1.3 | 0.8 | 1.3 | 0.6 |
| K343A | | 0.6 | 0.3 | 0.3 | 0.7 | 1.2 | 1.0 | 1.0 | 1.1 | 1.1 | 1.1 |
| R350A | | 0.8 | 0.6 | 0.5 | 0.6 | 0.7 | 1.1 | 1.0 | 0.5 | 1.3 | 0.9 |
| N355A | | 1.4 | 0.8 | 0.5 | 1.2 | 0.2 | 1.4 | 0.7 | 1.3 | 2.3 | 0.8 |
| N386A | | 1.3 | 1.2 | 1.4 | 0.8 | 0.9 | 0.6 | 1.1 | 0.1 | 1.1 | 0.3 |
| S387A | | 0.5 | 0.9 | 0.9 | 0.6 | 0.6 | 1.0 | 1.2 | 0.7 | 1.1 | 0.6 |
| T388A | | 0.9 | 0.3 | 0.2 | 0.6 | 0.6 | 0.5 | 1.0 | 1.0 | 0.6 | 0.1 |

TABLE 60C

| Mutation[a] | gp120 domain[b] | Fold IC$_{50}$ increase relative to wild-type[c] | | | | | | | | | |
|---|---|---|---|---|---|---|---|---|---|---|---|
| | | PGT-121 | PGT-122 | PGT-123 | PGT-125 | PGT-126 | PGT-127 | PGT-128 | PGT-130 | PGT-131 | PGT-135 |
| N392Q | V4 | 0.9 | 1.0 | 1.0 | 1.2 | 1.6 | 1.1 | 0.9 | 1.2 | 0.4 | >250 |
| S393A | | 0.6 | 0.5 | 0.6 | 0.5 | 0.5 | 1.2 | 1.4 | 0.7 | 1.1 | 0.9 |
| T394A | | 0.2 | 0.6 | 0.4 | 0.6 | 0.6 | 1.6 | 3.0 | 1.2 | 0.9 | >75 |
| W395A | | 0.5 | 0.4 | 0.4 | 0.9 | 0.6 | 1.6 | 0.8 | 0.6 | 0.5 | 0.6 |
| N396A | | 1.3 | 1.1 | 1.2 | 1.6 | 1.7 | 2.4 | 0.9 | 1.0 | 0.9 | 1 |
| N411A | | 0.4 | 0.7 | 0.5 | 0.5 | 0.7 | 0.8 | 0.7 | 0.6 | 0.6 | 0.2 |
| T413A | | 0.5 | 0.8 | 0.4 | 0.5 | 0.7 | 0.8 | 1.0 | 0.6 | 0.6 | 0.3 |
| I414A | | 0.5 | 0.5 | 0.3 | 0.3 | 0.4 | 2.2 | 1.4 | 0.7 | 1.0 | 1.2 |
| I415A | | 0.6 | 0.4 | 0.4 | 0.3 | 0.3 | 2.1 | 0.7 | 0.6 | 0.6 | 5 |
| L416A | | 0.6 | 1.0 | 0.9 | 0.8 | 0.8 | 1.0 | 1.1 | 1.0 | 1.0 | 1.2 |
| D417A | | 0.7 | 0.5 | 0.7 | 0.5 | 1.0 | 0.4 | 0.5 | 1.0 | 1.0 | 5.0 |
| R419A | C4 | 1.8 | 0.8 | 0.7 | 1.0 | 1.2 | 2.5 | 0.5 | 2.6 | 1.7 | 3.9 |
| I420A | | 3.3 | 3.5 | 3.2 | 1.1 | 0.6 | 1.8 | 0.8 | 9.8 | 153 | 1.4 |
| K421A | | 1.3 | 1.2 | 0.9 | 1.2 | 0.7 | 1.5 | 2.0 | 2.9 | 11.0 | 0.3 |
| Q422A | | 1.2 | 1.1 | 0.8 | 1.2 | 1.1 | 0.1 | 0.2 | 1.0 | 1.9 | 0.8 |
| I4234 | | 3.3 | 2.8 | 1.5 | 5.0 | 1.1 | 0.5 | 2.6 | >1000 | >80 | 0.1 |
| I424A | | 0.9 | 0.8 | 0.5 | 0.7 | 0.4 | 2.0 | 1.3 | 3.9 | 4.8 | 0.1 |
| E466A | V5 | 1.2 | 0.9 | 0.60 | 1.6 | 1.4 | 0.9 | 0.6 | 1.7 | 1.7 | 0.5 |
| F468A | | 0.8 | 1.0 | 0.50 | 1.0 | 0.7 | 3.0 | 0.5 | 0.4 | 1.6 | 1.1 |
| P470A | | 0.9 | 2.1 | 0.8 | 1.6 | 2.7 | 1.0 | 0.6 | 2.4 | 1.0 | 0.8 |
| G471A | | 0.8 | 1.8 | 1.3 | 1.0 | 1.2 | 1.2 | 0.9 | 0.8 | 1.2 | 3 |
| D474A | | 1.3 | 1.8 | 1.1 | 1.4 | 3.3 | 1.5 | 0.8 | 2.0 | 1.6 | 1.2 |
| R476A | | 1.1 | 0.9 | 2.0 | 1.9 | 1.5 | 1.2 | 0.7 | 1.3 | 1.0 | 0.8 |

TABLE 60C-continued

| | | Fold IC$_{50}$ increase relative to wild-type[c] | | | | | | | | |
|---|---|---|---|---|---|---|---|---|---|---|
| Mutation[a] | gp120 domain[b] | PGT-121 | PGT-122 | PGT-123 | PGT-125 | PGT-126 | PGT-127 | PGT-128 | PGT-130 | PGT-131 | PGT-135 |
| D477A | | 1.9 | 0.9 | 2.3 | 3.4 | 1.1 | 1.7 | 0.7 | 1.1 | 1.0 | 1.5 |
| N478A | | 0.8 | 0.9 | 0.6 | 1.5 | 1.0 | 1.2 | 0.8 | 0.8 | 1.0 | 0.7 |
| R480A | | 0.8 | 1.4 | 1.7 | 2.1 | 1.9 | 0.2 | 0.1 | 1.0 | 1.5 | 1.4 |

[a]Amino acid numbering is based on the sequence of HIV-1$_{HxB2}$
[b]C refers to constant domains and V refers to variable loops.
cNeutralization activity is reported as fold increase in IC$_{50}$ value relative to WT JR-CSF and was calculated using the equation (IC$_{50}$mutant/IC$_{50}$WT). Gray: substitutions which had a negligible effect on neutralization activity, yellow: 10-40 fold IC$_{50}$ increase, red: >40 fold IC$_{50}$ increase. Experiments were performed in duplicate and values represent an average of at least two independent experiments.

Vaccines against pathogens with low antigenic diversity, such as hepatitis B virus (HBV) or measles, commonly achieve 90-95% efficacy (Plotkin. Vaccines (Elsevier Health Sciences, Philadelphia, 2008)). Similarly, the influenza vaccine achieves 85-90% efficacy in years when the vaccine and circulating strain are well-matched (Bridges, C. B., et al. JAMA 284, 1655-1663 (2000); Herrera, G. A., et al. Vaccine 25, 154-160 (2007)). However, efficacy drops severely in years when there is a mismatch between the vaccine and circulating strain. In the case of HIV, the global diversity of circulating viruses is such that the match between the prophylactic antibodies and the circulating viruses, i.e. the antibody viral coverage, will be crucial for the degree of efficacy of active or passive prophylaxis approaches. To date, although the recent RV144 trail has led to speculation that some degree of protection against HIV may be achieved through extra-neutralizing activities of antibodies, such as antibody-dependent cell-mediated cytotoxicity or phagocytosis, the strongest evidence for protection is for neutralizing antibodies in non-human primate models using simian-human immunodeficiency virus (SHIV) challenge (Parren, P. W., et al. J Virol 75, 8340-8347 (2001); Nishimura, Y., et al. J Virol 76, 2123-2130 (2002); Hessell, A. J., et al. Nat Med 15, 951-954 (2009); Hessell, A. J., et al. PLoS Pathog 5, e1000433 (2009); Willey, R., et al. AIDS Res Hum Retroviruses 26, 89-98 (2010)).

Figure 33B:
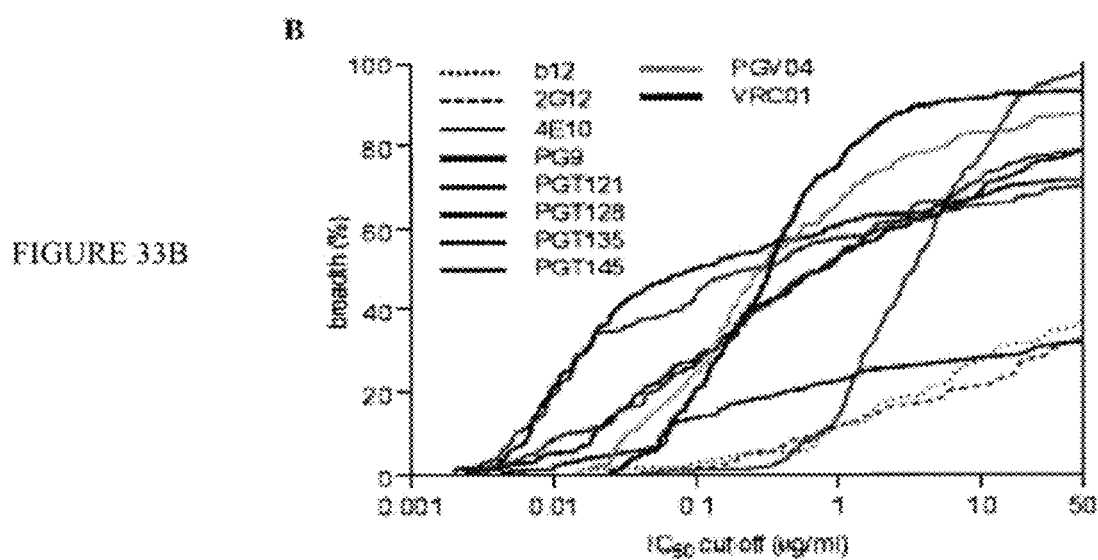
Figure 33C:
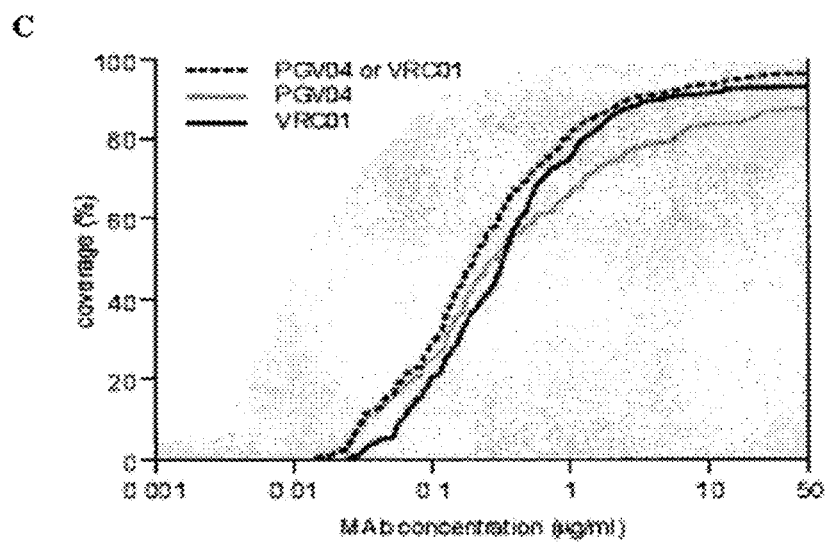
Figure 33D:
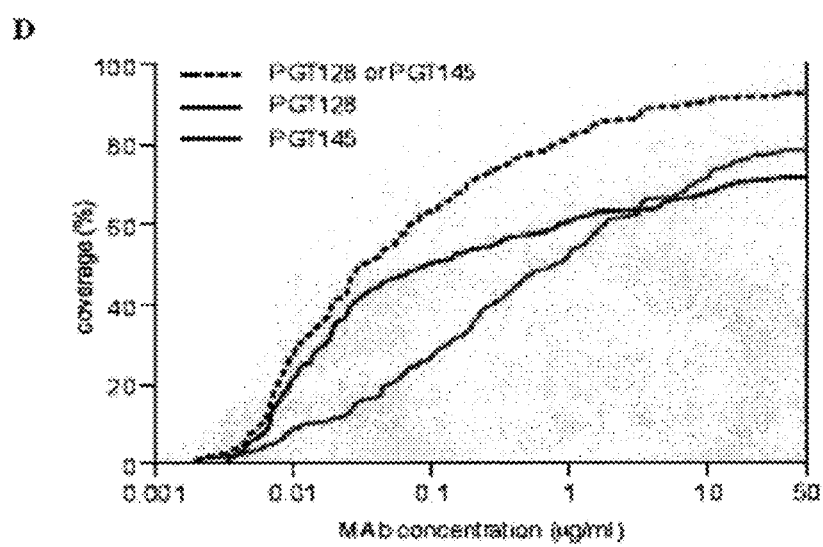

Passive administration of neutralizing antibodies in animal models suggest that a serum titer of approximately or greater than 100 times the IC$_{50}$ is often required to achieve a meaningful level of protection (Parren, P. W., et al. J Virol 75, 8340-8347 (2001); Nishimura, Y., et al. J Virol 76, 2123-2130 (2002); Hessell, A. J., et al. Nat Med 15, 951-954 (2009); Hessell, A. J., et al. PLoS Pathog 5, e1000433 (2009); Willey, R., et al. AIDS Res Hum Retroviruses 26, 89-98 (2010)). Therefore, if a vaccine elicits a serum bNAb concentration on the order of 10 µg/ml, and if an IC$_{50}$: protective serum ratio of 1:100 is assumed, then protection would be then be achieved by bNAb IC$_{50}$ is lower than 0.1 µg/ml. As a second conservative scenario, for an IC$_{50}$: protective serum ratio of 1:500, protection would be achieved against viruses for which the bNAb IC$_{50}$ is lower than 0.02 µg/ml. As shown in FIG. 33b-d, although various bnMAbs display breadth at high concentrations, viral coverage often drops sharply at lower concentrations. Therefore, if elicited or delivered singly, only the most potent Abs, such as 121 and 128, would be able to achieve a meaningful level of viral coverage, in particular at concentrations corresponding to the more conservative scenario given above. As bnMAbs display different and in some cases complementary breadth, we further looked at the coverage achieved by antibody combinations. For the two IC$_{50}$: protective serum concentration ratios above, a combination of PGV04 and VRC01, the two most potent CD4bs bnMAbs, would provide protection against 50% and 3% of viruses, respectively (FIG. 33c). In contrast, for a vaccine eliciting antibodies with high potency and favorable non-overlapping breadth, such as 128 and 145, coverage would be achieved against 70% and 40% of viruses for the two scenarios (FIG. 33d). Several combinations of two bnMAbs, including those directed to overlapping epitopes, can yield this degree of coverage (FIG. 44). In addition, a combination of all of the bnMAbs would cover 89% and 62% of viruses, correspondingly. Coverage against such a large proportion of viruses would likely have an important impact on the pandemic.

In summary, an effective vaccine against HIV-1 may require the elicitation of a combination of complementary potent neutralizing antibodies. The demonstration that large numbers of potent and diverse bNAbs can be isolated from several different individuals provides grounds for renewed optimism that an antibody-based vaccine is achievable. Critically, the instant invention provides the required large number of potent and diverse bNAbs that comprise an antibody-based vaccine.

Methods Summary

Activated memory B cell supernatants were screened in a high throughput format for neutralization activity using a micro-neutralization assay, as described (Walker, L. M., et al. Science 326, 285-289 (2009)). Heavy and light chain variable regions were isolated from B cell lysates of selected neutralizing hits by reverse transcription from RNA followed by multiplex PCR amplification using family-specific V-gene primer sets. For some antibodies, traditional cloning methods were used for antibody isolation, as described (Walker, L. M., et al. Science 326, 285-289 (2009)). For other antibodies, amplicons from each lysate were uniquely tagged with multiplex identifier (MID) sequences and 454 sequencing regions (Roche). Single round of replication pseudovirus neutralization assays and cell surface binding assays were performed as described previously (Walker, L. M., et al. Science 326, 285-289 (2009); Pantophlet, R., et al. J Virol 77, 642-658 (2003); Li, M., et al. J Virol 79, 10108-10125 (2005)). Glycan reactivities were profiled on a printed glycan microarray (version 5.0 from the Consortium for Functional Glycomics (CFG)) as described previously (Blixt, O., et al. Proc Natl Acad Sci USA 101, 17033-17038 (2004)).

Antibodies and Antigens

The following antibodies and reagents were procured by the IAVI Neutralizing Antibody Consortium: antibody 2G12 (Polymun Scientific, Vienna, Austria), antibody F425/b4E8 (provided by Lisa Cavacini, Beth Israel Deaconess Medical Center, Boston, MA), soluble CD4 (Progenics, Tarrytown, NY), HxB2 gp120, SF162 gp120, BaL gp120, JR-FL gp120, JR-CSF gp120 and YU2 gp120 (provided by Guillaume Stewart-Jones, Oxford University). Purified ADA gp120 was produced in the laboratory of Robert Doms, University of Pennsylvania. Fab X5 was expressed in E. coli and purified using an anti-human Fab specific affinity column. Deglycosylated gp120 JRFL was expressed in HEK 293S GnT$^{-/-}$ cells and treated with Endo H (Roche).

Donors

The donors identified for this study were selected from the IAVI sponsored study, Protocol G (Simek, M. D., et al. J Virol 83, 7337-7348 (2009)). Eligibility for enrolment into Protocol G was defined as: male or female at least 18 years of age with documented HIV infection for at least three years, clinically asymptomatic at the time of enrolment, and not currently receiving antiretroviral therapy. Selection of individuals for monoclonal antibody generation was based on a rank-order high throughput screening and analytical algorithm (Simek, M. D., et al. J Virol 83, 7337-7348 (2009)). Volunteers were identified as elite neutralizers based on broad and potent neutralizing activity against a cross-clade pseudovirus panel (Simek, M. D., et al. J Virol 83, 7337-7348 (2009)).

Isolation of MAbs

The method for isolating human MAbs from memory B cells in circulation has previously been described (Walker, L. M., et al. Science 326, 285-289 (2009)). Surface IgG B cells seeded at near clonal density in 384-well microplates were activated in short-term culture. Supernatants were screened for neutralization activity against 2-4 pseudotyped viruses for which neutralization activity was detected at high titers in the donor serum. Heavy and light chain variable regions were isolated from B cell lysates of selected neutralizing hits by reverse transcription from RNA followed by multiplex PCR amplification using family-specific V-gene primer sets. Amplicons from each lysate were uniquely tagged with multiplex identifier (MID) sequences and 454 sequencing regions (Roche, Indianapolis, IN). A normalized pooling of gamma, kappa and lambda chains was performed based on agarose gel image quantitation and the pool was analysed by 454 Titanium® sequencing. Consensus sequences of the $V_H$ and $V_L$ chains were generated using the Amplicon Variant Analyzer (Roche) and assigned to specific B cell culture wells by decoding the MID tags. Selected $V_H$ and $V_L$ chains were synthesized and cloned in expression vectors with the appropriate $IgG_1$, $IgG_3$ or $IgG_4$ constant domain. Monoclonal antibodies were reconstituted by transient transfection in HEK293 cells followed by purification from serum-free culture supernatants.

TABLE 62

| Donor | Antibody | Chain | Primer | Sequence (Direction is 5'-3' for forward/sense or reverse/antisense primers) | SEQ ID NO: |
|---|---|---|---|---|---|
| 584 | PGT-141 | Heavy | Forward-VH1 | ACTATGGACTGGATTTGGAGGATC | 585 |
| 584 | PGT-142 | Heavy | Forward-VH1 | ACTATGGACTGGATTTGGAGGATC | 585 |
| 584 | PGT-143 | Heavy | Forward-VH1 | ACTATGGACTGGATTTGGAGGATC | 585 |
| 584 | PGT-144 | Heavy | Forward-VH1 | ACTATGGACTGGATTTGGAGGATC | 585 |
| 584 | PGT-145 | Heavy | Forward-VH1 | ACTATGGACTGGATTTGGAGGATC | 585 |
| 517 | PGT-121 | Heavy | Forward-VH4 | AACATGAAACACCTGTGGTTCTTCCT | 586 |
| 517 | PGT-122 | Heavy | Forward-VH4 | AACATGAAACACCTGTGGTTCTTCCT | 586 |
| 517 | PGT-123 | Heavy | Forward-VH4 | AACATGAAACACCTGTGGTTCTTCCT | 586 |
| 517 | PGT-124 | Heavy | Forward-VH4 | AACATGAAACACCTGTGGTTCTTCCT | 586 |
| 517 | PGT-133 | Heavy | Forward-VH4 | AACATGAAACACCTGTGGTTCTTCCT | 586 |
| 517 | PGT-134 | Heavy | Forward-VH4 | AACATGAAACACCTGTGGTTCTTCCT | 586 |
| 196 | PGT-125 | Heavy | Forward-VH4 | AACATGAAACACCTGTGGTTCTTCCT | 586 |
| 196 | PGT-126 | Heavy | Forward-VH4 | AACATGAAACACCTGTGGTTCTTCCT | 586 |
| 196 | PGT-127 | Heavy | Forward-VH4 | AACATGAAACACCTGTGGTTCTTCCT | 586 |
| 196 | PGT-128 | Heavy | Forward-VH4 | AACATGAAACACCTGTGGTTCTTCCT | 586 |
| 196 | PGT-130 | Heavy | Forward-VH4 | AACATGAAACACCTGTGGTTCTTCCT | 586 |
| 196 | PGT-131 | Heavy | Forward-VH4 | AACATGAAACACCTGTGGTTCTTCCT | 586 |
| 196 | PGT-132 | Heavy | Forward-VH4 | AACATGAAACACCTGTGGTTCTTCCT | 586 |
| 196 | PGT-135 | Heavy | Forward-VH4 | AACATGAAACACCTGTGGTTCTTCCT | 586 |
| 196 | PGT-138 | Heavy | Forward-VH4 | AACATGAAACACCTGTGGTTCTTCCT | 586 |
| 196 | PGT-139 | Heavy | Forward-VH4 | AACATGAAACACCTGTGGTTCTTCCT | 586 |
| 039 | PGT-135 | Heavy | Forward-VH4 | AACATGAAACACCTGTGGTTCTTCCT | 586 |
| 039 | PGT-136 | Heavy | Forward-VH4 | AACATGAAACACCTGTGGTTCTTCCT | 586 |
| 039 | PGT-137 | Heavy | Forward-VH4 | AACATGAAACACCTGTGGTTCTTCCT | 586 |

TABLE 62-continued

| Donor | Antibody | Chain | Primer | Sequence (Direction is 5'-3' for forward/sense or reverse/antisense primers) | SEQ ID NO: |
|---|---|---|---|---|---|
| 584 | PGT-141 | Heavy | Reverse | GGAAGTAGTCCTTGACCAGGCAGC | 587 |
| 584 | PGT-142 | Heavy | Reverse | GGAAGTAGTCCTTGACCAGGCAGC | 587 |
| 584 | PGT-143 | Heavy | Reverse | GGAAGTAGTCCTTGACCAGGCAGC | 587 |
| 584 | PGT-144 | Heavy | Reverse | GGAAGTAGTCCTTGACCAGGCAGC | 587 |
| 584 | PGT-145 | Heavy | Reverse | GGAAGTAGTCCTTGACCAGGCAGC | 587 |
| 517 | PGT-121 | Heavy | Reverse | GGAAGTAGTCCTTGACCAGGCAGC | 587 |
| 517 | PGT-122 | Heavy | Reverse | GGAAGTAGTCCTTGACCAGGCAGC | 587 |
| 517 | PGT-123 | Heavy | Reverse | GGAAGTAGTCCTTGACCAGGCAGC | 587 |
| 517 | PGT-124 | Heavy | Reverse | GGAAGTAGTCCTTGACCAGGCAGC | 587 |
| 517 | PGT-133 | Heavy | Reverse | GGAAGTAGTCCTTGACCAGGCAGC | 587 |
| 517 | PGT-134 | Heavy | Reverse | GGAAGTAGTCCTTGACCAGGCAGC | 587 |
| 196 | PGT-125 | Heavy | Reverse | GGAAGTAGTCCTTGACCAGGCAGC | 587 |
| 196 | PGT-126 | Heavy | Reverse | GGAAGTAGTCCTTGACCAGGCAGC | 587 |
| 196 | PGT-127 | Heavy | Reverse | GGAAGTAGTCCTTGACCAGGCAGC | 587 |
| 196 | PGT-128 | Heavy | Reverse | GGAAGTAGTCCTTGACCAGGCAGC | 587 |
| 196 | PGT-130 | Heavy | Reverse | GGAAGTAGTCCTTGACCAGGCAGC | 587 |
| 196 | PGT-131 | Heavy | Reverse | GGAAGTAGTCCTTGACCAGGCAGC | 587 |
| 196 | PGT-132 | Heavy | Reverse | GGAAGTAGTCCTTGACCAGGCAGC | 587 |
| 196 | PGT-135 | Heavy | Reverse | GGAAGTAGTCCTTGACCAGGCAGC | 587 |
| 196 | PGT-138 | Heavy | Reverse | GGAAGTAGTCCTTGACCAGGCAGC | 587 |
| 196 | PGT-139 | Heavy | Reverse | GGAAGTAGTCCTTGACCAGGCAGC | 587 |
| 039 | PGT-135 | Heavy | Reverse | GGAAGTAGTCCTTGACCAGGCAGC | 587 |
| 039 | PGT-136 | Heavy | Reverse | GGAAGTAGTCCTTGACCAGGCAGC | 587 |
| 039 | PGT-137 | Heavy | Reverse | GGAAGTAGTCCTTGACCAGGCAGC | 587 |
| 584 | PGT-141 | Light | Forward-VK2 | ATGAGGCTCCCTGCTCAGCT | 588 |
| 584 | PGT-142 | Light | Forward-VK2 | ATGAGGCTCCCTGCTCAGCT | 588 |
| 584 | PGT-143 | Light | Forward-VK2 | ATGAGGCTCCCTGCTCAGCT | 588 |
| 584 | PGT-144 | Light | Forward-VK2 | ATGAGGCTCCCTGCTCAGCT | 588 |
| 584 | PGT-145 | Light | Forward-VK2 | ATGAGGCTCCCTGCTCAGCT | 588 |
| 039 | PGT-135 | Light | Forward-VK3 | CCCCAGCTCAGCTTCTCTTCC | 589 |
| 039 | PGT-136 | Light | Forward-VK3 | CCCCAGCTCAGCTTCTCTTCC | 589 |
| 039 | PGT-137 | Light | Forward-VK3 | CCCCAGCTCAGCTTCTCTTCC | 589 |
| 584 | PGT-141 | Light | Reverse | CCTTGGATAGAAGTTATTCAGC | 590 |
| 584 | PGT-142 | Light | Reverse | CCTTGGATAGAAGTTATTCAGC | 590 |
| 584 | PGT-143 | Light | Reverse | CCTTGGATAGAAGTTATTCAGC | 590 |
| 584 | PGT-144 | Light | Reverse | CCTTGGATAGAAGTTATTCAGC | 590 |
| 584 | PGT-145 | Light | Reverse | CCTTGGATAGAAGTTATTCAGC | 590 |
| 039 | PGT-135 | Light | Reverse | CCTTGGATAGAAGTTATTCAGC | 590 |

TABLE 62-continued

| Donor | Antibody | Chain | Primer | Sequence (Direction is 5'-3' for forward/sense or reverse/antisense primers) | SEQ ID NO: |
|---|---|---|---|---|---|
| 039 | PGT-136 | Light | Reverse | CCTTGGATAGAAGTTATTCAGC | 590 |
| 039 | PGT-137 | Light | Reverse | CCTTGGATAGAAGTTATTCAGC | 590 |
| 196 | PGT-125 | Light | Forward-VL2 | CATGGCCTGGGCTCTGCT | 591 |
| 196 | PGT-126 | Light | Forward-VL2 | CATGGCCTGGGCTCTGCT | 591 |
| 196 | PGT-127 | Light | Forward-VL2 | CATGGCCTGGGCTCTGCT | 591 |
| 196 | PGT-128 | Light | Forward-VL2 | CATGGCCTGGGCTCTGCT | 591 |
| 196 | PGT-130 | Light | Forward-VL2 | CATGGCCTGGGCTCTGCT | 591 |
| 196 | PGT-131 | Light | Forward-VL2 | CATGGCCTGGGCTCTGCT | 591 |
| 196 | PGT-132 | Light | Forward-VL2 | CATGGCCTGGGCTCTGCT | 591 |
| 196 | PGT-135 | Light | Forward-VL2 | CATGGCCTGGGCTCTGCT | 591 |
| 196 | PGT-138 | Light | Forward-VL2 | CATGGCCTGGGCTCTGCT | 591 |
| 196 | PGT-139 | Light | Forward-VL2 | CATGGCCTGGGCTCTGCT | 591 |
| 517 | PGT-121 | Light | Forward-VL3 | CCATGGCCTGGATCCCTCT | 592 |
| 517 | PGT-122 | Light | Forward-VL3 | CCATGGCCTGGATCCCTCT | 592 |
| 517 | PGT-123 | Light | Forward-VL3 | CCATGGCCTGGATCCCTCT | 592 |
| 517 | PGT-124 | Light | Forward-VL3 | CCATGGCCTGGATCCCTCT | 592 |
| 517 | PGT-133 | Light | Forward-VL3 | CCATGGCCTGGATCCCTCT | 592 |
| 517 | PGT-134 | Light | Forward-VL3 | CCATGGCCTGGATCCCTCT | 592 |
| 196 | PGT-125 | Light | Reverse | CCTTCATGCGTGACCTGGCAGC | 593 |
| 196 | PGT-126 | Light | Reverse | CCTTCATGCGTGACCTGGCAGC | 593 |
| 196 | PGT-127 | Light | Reverse | CCTTCATGCGTGACCTGGCAGC | 593 |
| 196 | PGT-128 | Light | Reverse | CCTTCATGCGTGACCTGGCAGC | 593 |
| 196 | PGT-130 | Light | Reverse | CCTTCATGCGTGACCTGGCAGC | 593 |
| 196 | PGT-131 | Light | Reverse | CCTTCATGCGTGACCTGGCAGC | 593 |
| 196 | PGT-132 | Light | Reverse | CCTTCATGCGTGACCTGGCAGC | 593 |
| 196 | PGT-135 | Light | Reverse | CCTTCATGCGTGACCTGGCAGC | 593 |
| 196 | PGT-138 | Light | Reverse | CCTTCATGCGTGACCTGGCAGC | 593 |
| 196 | PGT-139 | Light | Reverse | CCTTCATGCGTGACCTGGCAGC | 593 |
| 517 | PGT-121 | Light | Reverse | CCTTCATGCGTGACCTGGCAGC | 593 |
| 517 | PGT-122 | Light | Reverse | CCTTCATGCGTGACCTGGCAGC | 593 |
| 517 | PGT-123 | Light | Reverse | CCTTCATGCGTGACCTGGCAGC | 593 |
| 517 | PGT-124 | Light | Reverse | CCTTCATGCGTGACCTGGCAGC | 593 |
| 517 | PGT-133 | Light | Reverse | CCTTCATGCGTGACCTGGCAGC | 593 |
| 517 | PGT-134 | Light | Reverse | CCTTCATGCGTGACCTGGCAGC | 593 |

PGT Antibody Expression and Purification

Antibody genes were cloned into an expression vector and transiently expressed with the FreeStyle 293 Expression System (Invitrogen, Carlsbad, CA). Antibodies were purified using affinity chromatography (Protein A Sepharose Fast Flow, GE Healthcare, UK). Purity and integrity were checked with SDS-PAGE.

Neutralization Assays

Neutralization by monoclonal antibodies and donor sera was performed by Monogram Biosciences using a single round of replication pseudovirus assay as previously described (Richman, D. D., et al. Proc Natl Acad Sci USA 100, 4144-4149 (2003)). Briefly, pseudoviruses capable of a single round of infection were produced by co-transfection of HEK293 cells with a subgenomic plasmid, pHIV-1lucu3, that incorporates a firefly luciferase indicator gene and a second plasmid, pCXAS that expressed HIV-1 Env libraries or clones. Following transfection, pseudoviruses were harvested and used to infect U87 cell lines expressing co-receptors CCR5 or CXCR4. Pseudovirus neutralization assays using HIV-1JR-csF alanine mutants are fully described elsewhere (Walker, L. M., et al. Science 326, 285-289 (2009)). Neutralization activity of MAbs against HIV-1JR-csF alanine mutants was measured using a TZM-BL assay, as described (Walker, L. M., et al. Science 326, 285-289 (2009)). Kifunensine-treated pseudoviruses were produced by treating 293T cells with 25 µM kifunensine on the day of transfection. Memory B cell supernatants were screened in a micro-neutralization assay against a cross-clade panel of HIV-1 isolates and SIVmac239 (negative control). This assay was based on the 96-well pseudotyped HIV-1 neutralization assay (Monogram Biosciences) and was modified for screening 15 µl of B cell culture supernatants in a 384-well format.

Cell Surface Binding Assays

Titrating amounts of antibodies were added to HIV-1 Env transfected 293T cells, incubated for 1 hr at 37° C., washed with FACS buffer, and stained with goat anti-human IgG F(ab')2 conjugated to phycoerythin (Jackson ImmunoResearch, West Grove, PA). Binding was analyzed using flow cytometry, and binding curves were generated by plotting the mean fluorescence intensity of antigen binding as a function of antibody concentration. For competition assays, titrating amounts of competitor antibodies were added to the cells 30 min prior to adding biotinylated PGT MAbs at a concentration required to give $EC_{50}$.

ELISA Assays

For antigen-binding ELISAs, serial dilutions of MAbs were added to antigen-coated wells and binding was probed with alkaline phosphatase-conjugated goat anti-human immunoglobulin G (IgG) F(ab')2 Ab (Pierce, Rockford, IL). For competition ELISAs, titrating amounts of competitor MAbs were added to gp120-coated ELISA wells and incubated for 30 min prior to adding biotinylated PGT MAbs at a concentration required to give $IC_{70}$. Biotinylated PGT MAbs were detected using alkaline phosphatase conjugated streptavidin (Pierce) and visualized using p-nitrophenol phosphate substrate (Sigma, St. Louis, MO).

Glycan Microarray Analysis

Monoclonal antibodies were screened on a printed glycan microarray version 5.0 from the Consortium for Functional Glycomics (CFG) as described previously (Blixt, O., et al. Proc Natl Acad Sci USA 101, 17033-17038 (2004)). Antibodies were used at a concentration of 30 µg/ml and were precomplexed with 15 µg/ml secondary antibody (goat-anti-human-Fc-rPE, Jackson Immunoresearch) before addition to the slide. Complete glycan array data sets for all antibodies may be found at www.functionalglycomics.org in the CFG data archive under "cfg_rRequest_2250".

Oligomannose Dendron Synthesis

The oligomannose dendrons ($Man_4D$ and $Man_9D$) were synthesized by Cu(I) catalyzed alkyne-azide cycloaddition between azido oligomannose and the second generation of AB3 type alkynyl dendron. Detailed procedures and characterization were previously reported (Wang, S. K., et al. Proc Natl Acad Sci USA 105, 3690-3695 (2008)).

Fabrication of Gp120 Microarray

NETS-activated glass slides (Nexterion slide H, Schott North American) were printed with robotic pin (Arrayit 946) to deposit gp120 JRFL at concentrations of 750 or 250 µg/ml in printing buffer (120 mM phosphate, pH 8.5; containing 5% glycerol and 0.01% TWEEN® 20 (polysorbate 20)). 12 replicates were used for each concentration. The printed slides were incubated in relative humidity 75% chamber overnight and treated with blocking solution (superblock blocking buffer in PBS, Thermo) at room temperature for 1 h. The slides were then rinsed with PBS-T (0.05% Tween 20) and PBS buffer, and centrifuged at 200 g to remove residual solution from slide surface.

Oligomannose Dendron-Gp120 Competition Assay with MAbs

Serial diluted oligomannose dendrons were mixed with MAb (40 µg/ml) in PBS-BT buffer (1% BSA and 0.05% TWEEN® 20 (polysorbate 20) in PBS). The mixtures were applied directly to each sub-array on slide. After incubation in a humidified chamber for 1 h at RT, the slides were rinsed sequentially with PBS-T and PBS buffer, and then centrifuged at 200 g. Each sub-array was then stained with Cy3 labeled goat anti-human Fc IgG (7.5 m/ml in PBSBT) for 1 h in a humidified chamber. The slides were then rinsed sequentially with PBS-T and demonized water and centrifuged at 200 g. The fluorescence of the final arrays was imaged at 10 µm resolution (Ex: 540 nm; Em: 595 nm) with an ArrayWorx microarray reader (Applied Precision).

Sequence Analysis

Germ line genes were predicted using the immunoglobulin sequence alignment tools IMGT/V-QUEST (Brochet, X., et al. Nucleic Acids Res 36, W503-508 (2008)) and SoDA2 (Munshaw, S. & Kepler, T. B. Bioinformatics 26, 867-872 (2010)). Clonally-related sequences were identified by common germ line V-genes and long stretches of identical N-nucleotides.

Statistical Analysis

Statistical analyses were done with Prism 5.0 for Mac (GraphPad, La Jolla, CA). Viruses that are not neutralized at an $IC_{50}$ or $IC_{90}$<50 µg/ml were given a value of 50 µg/ml for median calculations. For combinations of antibodies, a virus was counted as covered if at least one of the MAbs was neutralized depending on individual concentrations ($IC_{50}$). This approach does not take additivity into account and therefore underestimates the neutralization potency of antibody combinations.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

SEQUENCE LISTING

```
Sequence total quantity: 724
SEQ ID NO: 1            moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 1
SSLTDRSHRI F                                                                    11

SEQ ID NO: 2            moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 2
KSLTSTRRRV F                                                                    11

SEQ ID NO: 3            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 3
SYSTPRTF                                                                        8

SEQ ID NO: 4            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 4
SFSTPRTF                                                                        8

SEQ ID NO: 5            moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 5
AWETTTTTFV FF                                                                   12

SEQ ID NO: 6            moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 6
EAGGPIWHDD VKYYDFNDGY YNYHYMDV                                                  28

SEQ ID NO: 7            moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 7
EAGGPDYRNG YNYYDFYDGY YNYHYMDV                                                  28

SEQ ID NO: 8            moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
```

```
SEQUENCE: 8
DRRVVPMATD NWLDP                                                           15

SEQ ID NO: 9             moltype = AA   length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 9
DRRAVPIATD NWLDP                                                           15

SEQ ID NO: 10            moltype = AA   length = 13
FEATURE                  Location/Qualifiers
REGION                   1..13
                         note = Description of Artificial Sequence: Synthetic peptide
source                   1..13
                         mol_type = protein
                         organism = synthetic construct
SEQUENCE: 10
GAVGADSGSW FDP                                                             13

SEQ ID NO: 11            moltype = DNA   length = 1461
FEATURE                  Location/Qualifiers
misc_feature             1..1461
                         note = Description of Artificial Sequence: Synthetic
                          polynucleotide
source                   1..1461
                         mol_type = other DNA
                         organism = synthetic construct
SEQUENCE: 11
atggagtttg ggctgagctg gttttcctc gcaactctgt taagagttgt gaagtgtcag            60
gaacaactgg tggagtctgg ggggaggcgtg gtccagccgg ggggtctcct gagactctca         120
tgtttagcgt ctggattcac gtttcacaaa tatggcatgc actgggtccg ccaggctcca         180
ggcaagggcc tggagtgggt ggcactcatc tcagatgacg gaatgaggaa atatcattca         240
gactccatgt ggggccgagt caccatctcc agagacaatt ccaagaacac tctttatctg         300
caattcagca gcctgaaagt cgaagacacg gctatgttct ctgtgcgaga gaggctggt          360
gggccaatct ggcatgacga cgtcaaatat tacgatttta atgacggcta ctacaactac         420
cactacatgg acgtctgggg caaggggacc acggtcaccg tctcgagcgc ctccaccaag         480
ggcccatcgg tcttccccct ggcaccctcc tccaagagca cctctggggg cacagcggcc         540
ctgggctgcc tggtcaagga ctacttcccc gaaccggtga cggtgtcgtg aactcaggc          600
gccctgacca gcggcgtgca caccttcccg gctgtcctac agtcctcagg actctactcc         660
ctcagcagcg tggtgaccgt gccctccagc agcttgggca cccagaccta catctgcaac         720
gtgaatcaca agcccagcaa caccaaggtg gacaagagag ttgagcccaa atcttgtgac         780
aaaactcaca catgcccacc gtgcccagca cctgaactcc tggggggacc gtcagtcttc         840
ctcttccccc caaaacccaa ggacaccctc atgatctccc ggaccccctga ggtcacatgc         900
gtggtggtgg acgtgagcca cgaagaccct gaggtcaagt tcaactggta cgtggacggc         960
gtggaggtgc ataatgccaa gacaaagccg cgggaggagc agtacaacag cacgtaccgt        1020
gtggtcagcg tcctcaccgt cctgcaccag gactggctga atggcaagga gtacaagtgc        1080
aaggtctcca acaaagccct cccagccccc atcgagaaaa ccatctccaa agccaaaggg        1140
cagccccgag aaccacaggt gtacaccctg cccccatccc gggaggagat gaccaagaac        1200
caggtcagcc tgacctgcct ggtcaaaggc ttctatccca gcgacatcgc cgtggagtgg        1260
gagagcaatg ggcagccgga gaacaactac aagaccacgc tcccgtgct ggactccgac        1320
ggctccttct tcctctatag caagctcacc gtggacaaga gcaggtggca gcaggggaac        1380
gtcttctcat gctccgtgat gcatgaggct ctgcacaacc actacacgca gaagagcctc        1440
tccctgtctc cgggtaaatg a                                                  1461

SEQ ID NO: 12            moltype = AA   length = 467
FEATURE                  Location/Qualifiers
REGION                   1..467
                         note = Description of Artificial Sequence: Synthetic
                          polypeptide
source                   1..467
                         mol_type = protein
                         organism = synthetic construct
SEQUENCE: 12
QEQLVESGGG VVQPGGSLRL SCLASGFTFH KYGMHWVRQA PGKGLEWVAL ISDDGMRKYH           60
SDSMWGRVTI SRDNSKNTLY LQFSSLKVED TAMFFCAREA GGPIWHDDVK YYDFNDGYYN         120
YHYMDVWGKG TTVTVSSAST KGPSVFPLAP SSKSTSGGTA ALGCLVKDYF PEPVTVSWNS         180
GALTSGVHTF PAVLQSSGLY SLSSVVTVPS SSLGTQTYIC NVNHKPSNTK VDKRVEPKSC         240
DKTHTCPPCP APELLGGPSV FLFPPKPKDT LMISRTPEVT CVVVDVSHED PEVKFNWYVD         300
GVEVHNAKTK PREEQYNSTY RVVSVLTVLH QDWLNGKEYK CKVSNKALPA PIEKTISKAK         360
GQPREPQVYT LPPSREEMTK NQVSLTCLVK GFYPSDIAVE WESNGQPENN YKTTPPVLDS         420
DGSFFLYSKL TVDKSRWQQG NVFSCSVMHE ALHNHYTQKS LSLSPGK                      467

SEQ ID NO: 13            moltype = DNA   length = 708
FEATURE                  Location/Qualifiers
misc_feature             1..708
```

```
                        note = Description of Artificial Sequence: Synthetic
                          polynucleotide
source                  1..708
                        mol_type = other DNA
                        organism = synthetic construct
SEQUENCE: 13
atggcctggg ctctgctatt cctcaccctc ttcactcagg gcacagggtc ctggggccag    60
tctgccctga ctcagcctgc ctccgtgtct gggtctcctg gacagacgat caccatctcc   120
tgcaatggaa ccagcagtga cgttggtgga tttgactgtc tctcctggta ccaacaatcc   180
ccagggaaag cccccaaagt catggttttt gatgtcagtc atccggccctc aggtatctct   240
aatcgcttct ctggctccaa gtccggcaac acggcctccc tgaccatctc tgggctccac   300
attgaggacg agggcgatta tttctgctct tcactgacag acagaagcca tcgcatattc   360
ggcggcggga ccaaggtgac cgttctaggt cagcccaagg ctgccccctc ggtcactctg   420
ttcccgccct cctctgagga gcttcaagcc aacaagtaca cactggtgtg tctcataagt   480
gacttctacc cgggagccgt gacagtggcc tggaaggcag atagcagccc cgtcaaggcg   540
ggagtggaga ccaccacacc ctccaaacaa agcaacaaca gtacgcggc cagcagctac    600
ctgagcctga cgcctgagca gtggaagtcc cacaaaagct acagctgcca ggtcacgcat   660
gaaggggagca ccgtggagaa gacagtggcc cctacagaat gttcatag                708

SEQ ID NO: 14           moltype = AA  length = 216
FEATURE                 Location/Qualifiers
REGION                  1..216
                        note = Description of Artificial Sequence: Synthetic
                          polypeptide
source                  1..216
                        mol_type = protein
                        organism = synthetic construct
SEQUENCE: 14
QSALTQPASV SGSPGQTITI SCNGTSSDVG GFDSVSWYQQ SPGKAPKVMV FDVSHRPSGI    60
SNRFSGSKSG NTASLTISGL HIEDEGDYFC SSLTDRSHRI FGGGTKVTVL GQPKAAPSVT   120
LFPPSSEELQ ANKATLVCLI SDFYPGAVTV AWKADSSPVK AGVETTTPSK QSNNKYAASS   180
YLSLTPEQWK SHKSYSCQVT HEGSTVEKTV APTECS                             216

SEQ ID NO: 15           moltype = DNA  length = 1422
FEATURE                 Location/Qualifiers
misc_feature            1..1422
                        note = Description of Artificial Sequence: Synthetic
                          polynucleotide
source                  1..1422
                        mol_type = other DNA
                        organism = synthetic construct
SEQUENCE: 15
atggactgga tttggaggtt cctctttgtg gtggcagcag ctacaggtgt ccagtcccag    60
gtccgcctgg tacagtctgg gcctgaggtg aagaagcctg gtcctcggt gacggtctcc    120
tgccaggctt ctgaggcac cttcagcagt tatgctttca cctgggtgcg ccaggccccc   180
ggacaaggtc ttgagtggtt gggcatggtc accccaatct ttggtgaggc caagtactca   240
caaagattcg agggcagagt caccatcacc gcggacgaat ccagcaccac aacctccata   300
gaattgagag gcctgacatc cgaagacacg gccatttatt actgtgcgcg agatcggcgc   360
gcggttccaa ttgccacgga caactggtta gaccccctggg gccaggggac cctggtcacc   420
gtctcgagcc cctccaccaa gggcccatcg gtcttccccc tggcaccctc ctccaagagc   480
acctctgggg gcacagcggc cctgggctgc ctggtcaagg actacttccc cgaaccggtg   540
acggtgtcgt ggaactcagg cgccctgacc agcggcgtgc acaccttccc ggctgtccta   600
cagtcctcag gactctactc cctcagcagc gtggtgaccg tgccctccag cagcttgggc   660
acccagacct acatctgcaa cgtgaatcac aagcccagca acaccaaggt ggacaagaga   720
gttgagccca aatcttgtga caaaactcac acatgcccac cgtgcccagc acctgaactc   780
ctggggggac cgtcagtctt cctcttcccc ccaaaaccca aggacaccct catgatctcc   840
cggacccctg aggtcacatg cgtggtggtg gacgtgagcc acgaagaccc tgaggtcaag   900
ttcaactggt acgtggacgg cgtggaggtg cataatgcca agacaaagcc gcgggaggag   960
cagtacaaca gcacgtaccg tgtggtcagc gtcctcaccg tcctgcacca ggactggctg  1020
aatggcaagg agtacaagtg caaggtctcc aacaaagccc tcccagcccc catcgagaaa  1080
accatctcca aagccaaagg gcagccccga gaaccacagg tgtacaccct gcccccatcc  1140
cgggaggaga tgaccaagaa ccaggtcagc ctgacctgcc tggtcaaagg cttctatccc  1200
agcgacatcg ccgtggagtg ggagagcaat gggcagccgg agaacaacta caagaccacg  1260
cctcccgtgc tggactccga cggctccttc ttcctctaca gcaagctcac cgtggacaag  1320
agcaggtggc agcaggggaa cgtcttctca tgctccgtga tgcatgaggc tctgcacaac  1380
cactacacgc agaagagcct ctccctgtct ccgggtaaat ga                      1422

SEQ ID NO: 16           moltype = AA  length = 454
FEATURE                 Location/Qualifiers
REGION                  1..454
                        note = Description of Artificial Sequence: Synthetic
                          polypeptide
source                  1..454
                        mol_type = protein
                        organism = synthetic construct
SEQUENCE: 16
QVRLVQSGPE VKKPGSSVTV SCQASGGTFS SYAFTWVRQA PGQGLEWLGM VTPIFGEAKY    60
SQRFEGRVTI TADESTSTTS IELRGLTSED TAIYYCARDR RAVPIATDNW LDPWGQGTLV   120
TVSSASTKGP SVFPLAPSSK STSGGTAALG CLVKDYFPEP VTVSWNSGAL TSGVHTFPAV   180
```

```
LQSSGLYSLS SVVTVPSSSL GTQTYICNVN HKPSNTKVDK RVEPKSCDKT HTCPPCPAPE    240
LLGGPSVFLF PPKPKDTLMI SRTPEVTCVV VDVSHEDPEV KFNWYVDGVE VHNAKTKPRE    300
EQYNSTYRVV SVLTVLHQDW LNGKEYKCKV SNKALPAPIE KTISKAKGQP REPQVYTLPP    360
SREEMTKNQV SLTCLVKGFY PSDIAVEWES NGQPENNYKT TPPVLDSDGS FFLYSKLTVD    420
KSRWQQGNVF SCSVMHEALH NHYTQKSLSL SPGK                               454

SEQ ID NO: 17              moltype = DNA   length = 711
FEATURE                    Location/Qualifiers
misc_feature               1..711
                           note = Description of Artificial Sequence: Synthetic
                           polynucleotide
source                     1..711
                           mol_type = other DNA
                           organism = synthetic construct
SEQUENCE: 17
atggacatga gggtccccgc tcagctcctg gggctcctgc tactctggct ccgaggtgcc    60
agatgtgaca tccagttgac ccagtctcca tcctccctgt ctgcatctgt tggcgacaga   120
gtctccatca cttgccgggc gagtcagacc attaacaact acttaaattg gtatcaacag   180
acacccggga agcccctaa actcctgatc tatggtgcct ccaatttgca aaatggggtc    240
ccatcaaggt tcagcggcag tggatctggg acagacttca ctctcaccat cagcagtctg   300
caacctgagg attttgcaac ttactactgt caacagagtt tcagtactcc gaggaccttc   360
ggccaaggga cacgactgga tattaaacgt acggtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata cgccctcca atcgggtaac    540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgtta g            711

SEQ ID NO: 18              moltype = AA   length = 214
FEATURE                    Location/Qualifiers
REGION                     1..214
                           note = Description of Artificial Sequence: Synthetic
                           polypeptide
source                     1..214
                           mol_type = protein
                           organism = synthetic construct
SEQUENCE: 18
DIQLTQSPSS LSASVGDRVS ITCRASQTIN NYLNWYQQTP GKAPKLLIYG ASNLQNGVPS    60
RFSGSGSGTD FTLTISSLQP EDFATYYCQQ SFSTPRTFGQ GTRLDIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 19              moltype = DNA   length = 1422
FEATURE                    Location/Qualifiers
misc_feature               1..1422
                           note = Description of Artificial Sequence: Synthetic
                           polynucleotide
source                     1..1422
                           mol_type = other DNA
                           organism = synthetic construct
SEQUENCE: 19
atggactgga tttggaggtt cctcttggtg gtggcagcag ctacaggtgt ccagtcccag    60
gtcctgctgg tgcagtctgg gactgaggtg aagaagcctg gtcctcggt gaaggtctcc    120
tgtcaggctt ctggaggcgc cttcagtagt tatgctttca ctgggtgcg acaggcccct    180
ggacaggggc ttgaatggat gggcatgatc acccctgtct ttggtgagac taaatatgca   240
ccgaggttcc agggcagact cacacttacc gcggaagaat ccttgagcac cacctacatg   300
gaattgagaa gcctgacatc tgatgacacg gccttttatt attgtacgag agatcggcgc   360
gtagttccaa tggccacaga caactggtta gaccccctgg gccaggggac gctggtcacc   420
gtctcgagcg cctccaccaa gggcccatcg gtcttcccc tggcaccctc ctccaagagc    480
acctctgggg gcacagcggc cctgggctgc ctggtcaagg actacttccc cgaaccggtg   540
acggtgtcgt ggaactcagg cgccctgacc agcggcgtgc acaccttccc ggctgtccta   600
cagtcctcag gactctactc cctcagcagc gtggtgaccg tgccctccag cagcttgggc   660
acccagacct acatctgcaa cgtgaatcac aagcccagca acaccaaggt ggacaagaga   720
gttgagccca aatcttgtga caaaactcac acatgcccac cgtgcccagc acctgaactc   780
ctgggggggac cgtcagtctt cctcttcccc ccaaaaccca aggacaccct catgatctcc   840
cggacccctg aggtcacatg cgtggtggtg gacgtgagcc acgaagaccc tgaggtcaag   900
ttcaactggt acgtggacgg cgtggaggtg cataatgcca agacaaagcc gcggaggag    960
cagtacaaca gcacgtaccg tgtggtcagc gtcctcaccg tcctgcacca ggactggctg   1020
aatggcaagg agtacaagtg caaggtctcc aacaaagcc tcccagcccc catcgagaaa   1080
accatctccca aagccaaagg gcagccccga gaaccacagg tgtacaccct gcccccatcc   1140
cgggaggaga tgaccaagaa ccaggtcagc ctgacctgcc tggtcaaagg cttctatccc   1200
agcgacatcg ccgtggagtg ggagagcaat gggcagccgg agaacaacta caagaccacg   1260
cctcccgtgc tggactccga cggctccttc ttcctctata gcaagctcac cgtggacaag   1320
agcaggtggc agcaggggaa cgtcttctca tgctccgtga tgcatgaggc tctgcacaac   1380
cactacacgc agaagagcct ctccctgtct ccgggtaaat ga                     1422

SEQ ID NO: 20              moltype = AA   length = 453
FEATURE                    Location/Qualifiers
REGION                     1..453
```

```
                        note = Description of Artificial Sequence: Synthetic
                         polypeptide
source                  1..453
                        mol_type = protein
                        organism = synthetic construct
SEQUENCE: 20
QVLLVQSGTE VKKPGSSVKV SCQASGGAFS SYAFSWVRQA PGQGLEWMGM ITPVFGETKY    60
APRFQGRLTL TAEESLSTTY MELRSLTSDD TAFYYCTRDR RVVPMATDNW LDPWGQGTLV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK RVEPKSCDKT HTCPPCPAPE   240
LLGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SREEMTKNQV SLTCLVKGFY PSDIAVEWES NGQPENNYKT TPPVLDSDGS FFLYSKLTVD   420
KSRWQQGNVF SCSVMHEALH NHYTQKSLSL SPG                                453

SEQ ID NO: 21           moltype = DNA   length = 711
FEATURE                 Location/Qualifiers
misc_feature            1..711
                        note = Description of Artificial Sequence: Synthetic
                         polynucleotide
source                  1..711
                        mol_type = other DNA
                        organism = synthetic construct
SEQUENCE: 21
atggacatga gggtccccgc tcagctcctg gggctcctgc tcctctggct ccgaggtgcc    60
acatgtgaca tccagttgac ccagtctcca tcctccctgt ctgcatctgt aggagacagg   120
gtcaccgtca cttgccgggc gagtcagacc atacacacct atttaaattg gtatcagcaa   180
attccaggaa aagcccctaa gctcctgatc tatggtgcct ccaccttgca aagtggggtc   240
ccgtcaaggt tcagtggcag tggatctggg acagatttca ctctcaccat caacagtctc   300
caacctgagg actttgcaac ttactactgt caacagagta acagtacccc aaggacctc    360
ggccaaggga cacgactgga tattaaacgt acggtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacagg gagagtgtta g             711

SEQ ID NO: 22           moltype = AA   length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 22
DIQLTQSPSS LSASVGDRVT VTCRASQTIH TYLNWYQQIP GKAPKLLIYG ASTLQSGVPS    60
RFSGSGSGTD FTLTINSLQP EDFATYYCQQ SYSTPRTFGQ GTRLDIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214

SEQ ID NO: 23           moltype = DNA   length = 1416
FEATURE                 Location/Qualifiers
misc_feature            1..1416
                        note = Description of Artificial Sequence: Synthetic
                         polynucleotide
source                  1..1416
                        mol_type = other DNA
                        organism = synthetic construct
SEQUENCE: 23
atggactgga tttggaggat cctcctcttg gtggcagcag ctacaggcac cctcgccgac    60
ggccacctgg ttcagtctgg ggttgaggtg aagaagactg ggctacagt caaaatctcc    120
tgcaaggttt ctggatacag cttcatcgac tactacttc attgggtgca acgggccct    180
ggaaaaggcc ttgagtgggt gggacttatt gatcctgaaa atggtgaggc tcgatatgca   240
gagaagttcc agggcagagt caccataatc gcggacacgt ctatagatac aggctacatg   300
gaaatgagga gcctgaaatc tgaggacacg gccgtgtatt tctgtgcagc aggtgccgtg   360
ggggctgatt ccgggagctg gttcgacccc tggggccagg gaactctggt caccgtctcg   420
agcgcctcca caagggccc atcggtcttc ccctggcac cctcctcaa gagcacctct   480
gggggcacag cggcctgg ctgcctggtc aaggactact tccccgaacc ggtgacggtg   540
tcgtggaact caggcgccct gaccagcggc gtgcacacct tcccggctgt cctacagtcc   600
tcaggactct actccctcag cagcgtggtg accgtgccct ccagcagctt gggcacccag   660
acctacatct gcaacgtgaa tcacaagccc agcaacacca aggtggacaa gagagttgag   720
cccaaatctt gtgacaaaac tcacacatgc ccaccgtgcc cagcacctga actcctgggg   780
ggaccgtcag tcttcctctt ccccccaaaa cccaaggaca cctcatgat ctcccggacc   840
cctgaggtca catgcgtggt ggtggacgtg agccacgaag accctgaggt caagttcaac   900
tggtacgtgg acggcgtgga ggtgcataat gccaagacaa agccgcggga ggagcagtac   960
aacagcacgt accgtgtggt cagcgtcctc accgtcctgc accaggactg gctgaatggc  1020
aaggagtaca agtgcaaggt ctccaacaaa gccctcccag cccccatcga gaaaaccatc  1080
tccaaagcca aagggcagcc ccgagaacca caggtgtaca ccctgccccc atcccgggag  1140
```

```
gagatgacca agaaccaggt cagcctgacc tgcctggtca aaggcttcta tcccagcgac  1200
atcgccgtgg agtgggagag caatgggcag ccggagaaca actacaagac cacgcctccc  1260
gtgctggact ccgacggctc cttcttcctc tatagcaagc tcaccgtgga caagagcagg  1320
tggcagcagg ggaacgtctt ctcatgctcc gtgatgcatg aggctctgca caaccactac  1380
acgcagaaga gcctctccct gtctccgggt aaatga                            1416

SEQ ID NO: 24           moltype = AA   length = 452
FEATURE                 Location/Qualifiers
REGION                  1..452
                        note = Description of Artificial Sequence: Synthetic
                         polypeptide
source                  1..452
                        mol_type = protein
                        organism = synthetic construct
SEQUENCE: 24
DGHLVQSGVE VKKTGATVKI SCKVSGYSFI DYYLHWVQRA PGKGLEWVGL IDPENGEARY   60
AEKFQGRVTI IADTSIDTGY MEMRSLKSED TAVYFCAAGA VGADSGSWFD PWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 25           moltype = DNA   length = 705
FEATURE                 Location/Qualifiers
misc_feature            1..705
                        note = Description of Artificial Sequence: Synthetic
                         polynucleotide
source                  1..705
                        mol_type = other DNA
                        organism = synthetic construct
SEQUENCE: 25
atggcctgga tccctctctt cctcggcgtc cttgcttact gcacagattc cgtagtctcc   60
tatgaactga ctcagccacc tcagtgtcc gtgtcccag acagacagc cagcatcacc  120
tgttctggat ctaaattggg ggataaatat gtttcctggt atcaactgag gccaggccag  180
tccccccatac tggtcatgta tgaaaatgac aggcggccct ccgggatccc tgagcgattc  240
tccggttcca attctggcga cactgccact ctgaccatca gcgggaccca ggcttttgat  300
gaggctgact tctactgtca ggcgtggag accaccacca ccactttgt tttcttcggg  360
ggagggaccc agctgaccgt tctaggtcag cccaaggctg cccctcggt cactctgttc  420
ccgccctcct ctgaggagct tcaagccaac aaggccacac tggtgtgtct cataagtgac  480
ttctaccgg gagccgtgac agtggcctgg aaggcagata gcagcccgt caaggcggga  540
gtggagacca ccacccctc caaacaaagc aacaacaagt acgcggccag cagctacctg  600
agcctgacgc ctgagcagtg gaagtccac aaaaagctaca gctgccaggt cacgcatgaa  660
gggagcaccg tggagaagac agtggcccct acagaatgtt catag                  705

SEQ ID NO: 26           moltype = AA   length = 215
FEATURE                 Location/Qualifiers
REGION                  1..215
                        note = Description of Artificial Sequence: Synthetic
                         polypeptide
source                  1..215
                        mol_type = protein
                        organism = synthetic construct
SEQUENCE: 26
SYELTQPPSV SVSPGQTASI TCSGSKLGDK YVSWYQLRPG QSPILVMYEN DRRPSGIPER   60
FSGSNSGDTA TLTISGTQAL DEADFYCQAW ETTTTTFVFF GGGTQLTVLG QPKAAPSVTL  120
FPPSSEELQA NKATLVCLIS DFYPGAVTVA WKADSSPVKA GVETTTPSKQ SNNKYAASSY  180
LSLTPEQWKS HKSYSCQVTH EGSTVEKTVA PTECS                             215

SEQ ID NO: 27           moltype = DNA   length = 1458
FEATURE                 Location/Qualifiers
misc_feature            1..1458
                        note = Description of Artificial Sequence: Synthetic
                         polynucleotide
source                  1..1458
                        mol_type = other DNA
                        organism = synthetic construct
SEQUENCE: 27
atggagtttg ggctgagctg gttttcctc gttgctttct taagaggtgt ccagtgtcag   60
cgattagtgg agtctggggg aggcgtggtc cagcctgggt cgtccctgag actctcctgt  120
gcagcgtccg gattcgactt cagtagacaa ggcatgcact gggtccgcca ggctccaggc  180
caggggctgg agtgggtggc atttattaaa tatgatggaa gtgagaaata tcatgctgac  240
tccgtatggg gccgactcag catctccaga gacaattcca aggatacgct ttatctccaa  300
atgaatagcc tgagagtcga ggacacggct acatatttt gtgtgagaga ggctggtggg  360
cccgactacc gtaatgggta caactattac gatttctatg atggttatta taactaccac  420
tatatggacg tctggggcaa agggaccacg gtcaccgtct cgagcgcctc caccaagggc  480
ccatcggtct tccccctggc accctcctcc aagagcacct ctgggggcac agcggccctg  540
ggctgcctgg tcaaggacta cttccccgaa ccggtgacgg tgtcgtggaa ctcaggcgcc  600
```

```
ctgaccagcg gcgtgcacac cttcccggct gtcctacagt ccctcaggact ctactccctc  660
agcagcgtgg tgaccgtgcc ctccagcagc ttgggcaccc agacctacat ctgcaacgtg  720
aatcacaagc ccagcaacac caaggtggac aagagagttg agcccaaatc ttgtgacaaa  780
actcacacat gcccaccgtg cccagcacct gaactcctgg ggggaccgtc agtcttcctc  840
ttcccccaa aacccaagga caccctcatg atctcccgga cccctgaggt cacatgcgtg  900
gtggtggacg tgagccacga agaccctgag gtcaagttca actggtacgt ggacggcgtg  960
gaggtgcata atgccaagac aaagccgcgg gaggagcagt acaacagcac gtaccgtgtg 1020
gtcagcgtcc tcaccgtcct gcaccaggac tggctgaatg gcaaggagta caagtgcaag 1080
gtctccaaca aagccctccc agcccccatc gagaaaacca tctccaaagc caaagggcag 1140
ccccgagaac cacaggtgta caccctgccc ccatcccggg aggagatgac caagaaccag 1200
gtcagcctga cctgcctggt caaaggcttc tatcccagcg acatcgccgt ggagtgggag 1260
agcaatgggc agccggagaa caactacaag accacgcctc ccgtgctgga ctccgacggc 1320
tccttcttcc tctatagcaa gctcaccgtg gacaagagca ggtggcagca ggggaacgtc 1380
ttctcatgct ccgtgatgca tgaggctctg cacaaccact acacgcagaa gagcctctcc 1440
ctgtctccgg gtaaatga                                                1458

SEQ ID NO: 28              moltype = AA   length = 466
FEATURE                    Location/Qualifiers
REGION                     1..466
                           note = Description of Artificial Sequence: Synthetic
                           polypeptide
source                     1..466
                           mol_type = protein
                           organism = synthetic construct
SEQUENCE: 28
QRLVESGGGV VQPGSSLRLS CAASGFDFSR QGMHWVRQAP GQGLEWVAFI KYDGSEKYHA  60
DSVWGRLSIS RDNSKDTLYL QMNSLRVEDT ATYFCVREAG GPDYRNGYNY YDFYDGYYNY 120
HYMDVWGKGT TVTVSSASTK GPSVFPLAPS SKSTSGGTAA LGCLVKDYFP EPVTVSWNSG 180
ALTSGVHTFP AVLQSSGLYS LSSVVTVPSS SLGTQTYICN VNHKPSNTKV DKRVEPKSCD 240
KTHTCPPCPA PELLGGPSVF LFPPKPKDTL MISRTPEVTC VVVDVSHEDP EVKFNWYVDG 300
VEVHNAKTKP REEQYNSTYR VVSVLTVLHQ DWLNGKEYKC KVSNKALPAP IEKTISKAKG 360
QPREPQVYTL PPSREEMTKN QVSLTCLVKG FYPSDIAVEW ESNGQPENNY KTTPPVLDSD 420
GSFFLYSKLT VDKSRWQQGN VFSCSVMHEA LHNHYTQKSL SLSPGK                466

SEQ ID NO: 29              moltype = DNA   length = 708
FEATURE                    Location/Qualifiers
misc_feature               1..708
                           note = Description of Artificial Sequence: Synthetic
                           polynucleotide
source                     1..708
                           mol_type = other DNA
                           organism = synthetic construct
SEQUENCE: 29
atggcctggg ctctgctttt cctcaccctc ctcactcagg gcacagggtc ctgggcccag  60
tctgccctga ctcagcctgc ctccgtgtct gggtctcctg gacagtcgat caccatctcc 120
tgcaatggaa ccagcaatga tgttggtggc tatgaatctg tctcctggta ccaacaacat 180
cccggcaaag cccccaaagt cgtgatttat gatgtcagta acaggccctc agggggtttct 240
aatcgcttct ctggctccaa gtccggcaac acggcctccc tgaccatctc tgggctccag 300
gctgaggacg agggtgacta ttactgcaag tctctgacaa gcacgagacg tcgggtttct 360
ggcactggga ccaagctgac cgttctaggt cagcccaagg ctgccccctc ggtcactctg 420
ttcccgccct cctctgagga gcttcaagcc aacaaggcca cactggtgtg tctcataagt 480
gacttctacc cggagccgt gacagtggcc tggaaggcag atagcagccc cgtcaaggcg 540
ggagtggaga ccaccacacc ctccaaacaa agcaacaaca gtacgcggc agcagctac 600
ctgagcctga cgcctgagca gtggaagtcc cacaaaagct acagctgcca ggtcacgcat 660
gaagggagca ccgtggagaa gacagtggcc cctacagaat gttcatag              708

SEQ ID NO: 30              moltype = AA   length = 216
FEATURE                    Location/Qualifiers
REGION                     1..216
                           note = Description of Artificial Sequence: Synthetic
                           polypeptide
source                     1..216
                           mol_type = protein
                           organism = synthetic construct
SEQUENCE: 30
QSALTQPASV SGSPGQSITI SCNGTSNDVG GYESVSWYQQ HPGKAPKVVI YDVSKRPSGV  60
SNRFSGSKSG NTASLTISGL QAEDEGDYYC KSLTSTRRRV FGTGTKLTVL GQPKAAPSVT 120
LFPPSSEELQ ANKATLVCLI SDFYPGAVTV AWKADSSPVK AGVETTTPSK QSNNKYAASS 180
YLSLTPEQWK SHKSYSCQVT HEGSTVEKTV APTECS                           216

SEQ ID NO: 31              moltype = AA   length = 137
FEATURE                    Location/Qualifiers
REGION                     1..137
                           note = Description of Artificial Sequence: Synthetic
                           polypeptide
source                     1..137
                           mol_type = protein
                           organism = synthetic construct
SEQUENCE: 31
```

```
QEQLVESGGG VVQPGGSLRL SCLASGFTFH KYGMHWVRQA PGKGLEWVAL ISDDGMRKYH    60
SDSMWGRVTI SRDNSKNTLY LQFSSLKVED TAMFFCAREA GGPIWHDDVK YYDFNDGYYN   120
YHYMDVWGKG TTVTVSS                                                  137

SEQ ID NO: 32           moltype = AA  length = 110
FEATURE                 Location/Qualifiers
REGION                  1..110
                        note = Description of Artificial Sequence: Synthetic
                        polypeptide
source                  1..110
                        mol_type = protein
                        organism = synthetic construct
SEQUENCE: 32
QSALTQPASV SGSPGQTITI SCNGTSSDVG GFDSVSWYQQ SPGKAPKVMV FDVSHRPSGI    60
SNRFSGSKSG NTASLTISGL HIEDEGDYFC SSLTDRSHRI FGGGTKVTVL              110

SEQ ID NO: 33           moltype = AA  length = 124
FEATURE                 Location/Qualifiers
REGION                  1..124
                        note = Description of Artificial Sequence: Synthetic
                        polypeptide
source                  1..124
                        mol_type = protein
                        organism = synthetic construct
SEQUENCE: 33
QVRLVQSGPE VKKPGSSVTV SCQASGGTFS SYAFTWVRQA PGQGLEWLGM VTPIFGEAKY    60
SQRFEGRVTI TADESTSTTS IELRGLTSED TAIYYCARDR RAVPIATDNW LDPWGQGTLV   120
TVSS                                                                124

SEQ ID NO: 34           moltype = AA  length = 107
FEATURE                 Location/Qualifiers
REGION                  1..107
                        note = Description of Artificial Sequence: Synthetic
                        polypeptide
source                  1..107
                        mol_type = protein
                        organism = synthetic construct
SEQUENCE: 34
DIQLTQSPSS LSASVGDRVS ITCRASQTIN NYLNWYQQTP GKAPKLLIYG ASNLQNGVPS    60
RFSGSGSGTD FTLTISSLQP EDFATYYCQQ SFSTPRTFGQ GTRLDIK                 107

SEQ ID NO: 35           moltype = AA  length = 124
FEATURE                 Location/Qualifiers
REGION                  1..124
                        note = Description of Artificial Sequence: Synthetic
                        polypeptide
source                  1..124
                        mol_type = protein
                        organism = synthetic construct
SEQUENCE: 35
QVLLVQSGTE VKKPGSSVKV SCQASGGAFS SYAFSWVRQA PGQGLEWMGM ITPVFGETKY    60
APRFQGRLTL TAEESLSTTY MELRSLTSDD TAFYYCTRDR RVVPMATDNW LDPWGQGTLV   120
TVSS                                                                124

SEQ ID NO: 36           moltype = AA  length = 107
FEATURE                 Location/Qualifiers
REGION                  1..107
                        note = Description of Artificial Sequence: Synthetic
                        polypeptide
source                  1..107
                        mol_type = protein
                        organism = synthetic construct
SEQUENCE: 36
DIQLTQSPSS LSASVGDRVT VTCRASQTIH TYLNWYQQIP GKAPKLLIYG ASTLQSGVPS    60
RFSGSGSGTD FTLTINSLQP EDFATYYCQQ SYSTPRTFGQ GTRLDIK                 107

SEQ ID NO: 37           moltype = AA  length = 122
FEATURE                 Location/Qualifiers
REGION                  1..122
                        note = Description of Artificial Sequence: Synthetic
                        polypeptide
source                  1..122
                        mol_type = protein
                        organism = synthetic construct
SEQUENCE: 37
DGHLVQSGVE VKKTGATVKI SCKVSGYSFI DYYLHWVQRA PGKGLEWVGL IDPENGEARY    60
AEKFQGRVTI IADTSIDTGY MEMRSLKSED TAVYFCAAGA VGADSGSWFD PWGQGTLVTV   120
SS                                                                  122
```

```
SEQ ID NO: 38            moltype = AA   length = 109
FEATURE                  Location/Qualifiers
REGION                   1..109
                         note = Description of Artificial Sequence: Synthetic
                         polypeptide
source                   1..109
                         mol_type = protein
                         organism = synthetic construct
SEQUENCE: 38
SYELTQPPSV SVSPGQTASI TCSGSKLGDK YVSWYQLRPG QSPILVMYEN DRRPSGIPER    60
FSGSNSGDTA TLTISGTQAL DEADFYCQAW ETTTTTFVFF GGGTQLTVL               109

SEQ ID NO: 39            moltype = AA   length = 136
FEATURE                  Location/Qualifiers
REGION                   1..136
                         note = Description of Artificial Sequence: Synthetic
                         polypeptide
source                   1..136
                         mol_type = protein
                         organism = synthetic construct
SEQUENCE: 39
QRLVESGGGV VQPGSSLRLS CAASGFDFSR QGMHWVRQAP GQGLEWVAFI KYDGSEKYHA    60
DSVWGRLSIS RDNSKDTLYL QMNSLRVEDT ATYFCVREAG GPDYRNGYNY YDFYDGYYNY   120
HYMDVWGKGT TVTVSS                                                   136

SEQ ID NO: 40            moltype = AA   length = 110
FEATURE                  Location/Qualifiers
REGION                   1..110
                         note = Description of Artificial Sequence: Synthetic
                         polypeptide
source                   1..110
                         mol_type = protein
                         organism = synthetic construct
SEQUENCE: 40
QSALTQPASV SGSPGQSITI SCNGTSNDVG GYESVSWYQQ HPGKAPKVVI YDVSKRPSGV    60
SNRFSGSKSG NTASLTISGL QAEDEGDYYC KSLTSTRRRV FGTGTKLTVL              110

SEQ ID NO: 41            moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 41
SSLTDRSHRI                                                           10

SEQ ID NO: 42            moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 42
QQSFSTPRT                                                             9

SEQ ID NO: 43            moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 43
QQSYSTPRT                                                             9

SEQ ID NO: 44            moltype = AA   length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 44
QAWETTTTTF VF                                                        12

SEQ ID NO: 45            moltype = AA   length = 10
FEATURE                  Location/Qualifiers
```

```
REGION                    1..10
                          note = Description of Artificial Sequence: Synthetic peptide
source                    1..10
                          mol_type = protein
                          organism = synthetic construct
SEQUENCE: 45
KSLTSTRRRV                                                                          10

SEQ ID NO: 46             moltype = DNA  length = 1461
FEATURE                   Location/Qualifiers
misc_feature              1..1461
                          note = Description of Artificial Sequence: Synthetic
                           polynucleotide
source                    1..1461
                          mol_type = other DNA
                          organism = synthetic construct
SEQUENCE: 46
atggagtttg ggctgagctg ggttttcctc gcaactctgt taagagttgt gaagtgtcac     60
gaacaactgg tggaggccgg gggaggcgtg gtccagccgg gggggtccct gagactctcc    120
tgtttagcgt ctggattcac gtttcacaaa tatggcatgc actgggtccg ccaggctcca    180
ggcaagggcc tggagtgggt ggcactcatc tcagatgacg gaatgaggaa atatcattca    240
gactccatgt ggggccgagt caccatctcc agagacaatt ccaagaacac tctttatctg    300
caattcagca gcctgagagt cgaagacacg gctatgttct tctgtgcgag agaggccggt    360
gggccaatct ggcatgacga cgtcaaatat tacgattta atgacggcta ctacaactat    420
cactacatgg acgtctgggg caaggggacc aaggtcaccg tctcctcagc gtcgaccaag    480
ggcccatcgg tcttccctct ggcaccatca tccaagtgca cctctggggg cacagcggcc    540
ctgggctgcc tggtcaagga ctacttccc gaaccggtga cggtgtcgtg gaactcaggc    600
gccctgacca gcggcgtgca caccttcccg gctgtcctac agtcctcagg actctactcc    660
ctcagcagcg tggtgaccgt gccctccagc agcttgggca cccagaccta catctgcaac    720
gtgaatcaca agcccagcaa caccaaggtg gacaagagag ttgagcccaa atcttgtgac    780
aaaactcaca catgcccacc gtgcccagca cctgaactcc tggggggacc gtcagtcttc    840
ctcttccccc caaaacccaa ggacaccctc atgatctccc ggacccctga ggtcacatgc    900
gtggtggtgg acgtgagcca cgaagaccct gaggtcaagt tcaactggta cgtggacggc    960
gtggaggtgc ataatgccaa gacaaagccg cgggaggagc agtacaacag cacgtaccgt   1020
gtggtcagcg tcctcaccgt cctgcaccag gactggctga atggcaagga gtacaagtgc   1080
aaggtctcca acaaagccct cccagccccc atcgagaaaa ccatctccaa agccaaaggg   1140
cagccccgag aaccacaggt gtacaccctg cccccatccc gggaggagat gaccaagaac   1200
caggtcagcc tgacctgcct ggtcaaaggc ttctatccca gcgacatcgc cgtggagtgg   1260
gagagcaatg ggcagccgga gaacaactac aagaccacgc ctcccgtgct ggactccgac   1320
ggctccttct cctctatag caagctcacc gtggacaaga gcaggtggca gcaggggaac   1380
gtcttctcat gctccgtgat gcatgaggct ctgcacaacc actacacgca gaagagcctc   1440
tccctgtctc cgggtaaatg a                                              1461

SEQ ID NO: 47             moltype = AA  length = 467
FEATURE                   Location/Qualifiers
REGION                    1..467
                          note = Description of Artificial Sequence: Synthetic
                           polypeptide
source                    1..467
                          mol_type = protein
                          organism = synthetic construct
SEQUENCE: 47
HEQLVEAGGG VVQPGGSLRL SCLASGFTFH KYGMHWVRQA PGKGLEWVAL ISDDGMRKYH      60
SDSMWGRVTI SRDNSKNTLY LQFSSLRVED TAMFFCAREA GGPIWHDDVK YYDFNDGYYN     120
YHYMDVWGKG TKVTVSSAST KGPSVFPLAP SSKSTSGGTA ALGCLVKDYF PEPVTVSWNS     180
GALTSGVHTF PAVLQSSGLY SLSSVVTVPS SSLGTQTYIC NVNHKPSNTK VDKRVEPKSC     240
DKTHTCPPCP APELLGGPSV FLFPPKPKDT LMISRTPEVT CVVVDVSHED PEVKFNWYVD     300
GVEVHNAKTK PREEQYNSTY RVVSVLTVLH QDWLNGKEYK CKVSNKALPA PIEKTISKAK     360
GQPREPQVYT LPPSREEMTK NQVSLTCLVK GFYPSDIAVE WESNGQPENN YKTTPPVLDS     420
DGSFFLYSKL TVDKSRWQQG NVFSCSVMHE ALHNHYTQKS LSLSPGK                   467

SEQ ID NO: 48             moltype = AA  length = 137
FEATURE                   Location/Qualifiers
REGION                    1..137
                          note = Description of Artificial Sequence: Synthetic
                           polypeptide
source                    1..137
                          mol_type = protein
                          organism = synthetic construct
SEQUENCE: 48
HEQLVEAGGG VVQPGGSLRL SCLASGFTFH KYGMHWVRQA PGKGLEWVAL ISDDGMRKYH      60
SDSMWGRVTI SRDNSKNTLY LQFSSLRVED TAMFFCAREA GGPIWHDDVK YYDFNDGYYN     120
YHYMDVWGKG TKVTVSS                                                   137

SEQ ID NO: 49             moltype = DNA  length = 707
FEATURE                   Location/Qualifiers
misc_feature              1..707
                          note = Description of Artificial Sequence: Synthetic
                           polynucleotide
```

```
source                  1..707
                        mol_type = other DNA
                        organism = synthetic construct
SEQUENCE: 49
atggcctggg cttgctattc ctcaccctct tcactcaggg cacagggtcc tggggccagt    60
ctgccctgac tcagcctgcc tccgtgtctg ggtctcctgg acagacgatc accatctcct   120
gcaatggaac cagccgtgac gttggtggat ttgactctgt ctcctggtat caacaatccc   180
cagggaaagc ccccaaagtc atggtttttg atgtcagtca tcggccctca ggtatgtcta   240
atcgcttctc tggctccaag tccggcaaca cggcctccct gaccatttct gggctccaca   300
ttgaggacga gggcgattat ttctgctctt cattgacaga cagaagccat cgcatattcg   360
gcggcgggac caagctgacc gttctaggtc agcccaaggc tgcccctcg gtcactctgt    420
tcccgccctc ctctgaggag cttcaagcca acaaggccac actggtgtgt ctcataagtg   480
acttctaccc gggagccgtg acagtggcct ggaaggcaga tagcagcccc gtcaaggcgg   540
gagtggagac caccacaccc tccaaacaaa gcaacaacaa gtacgcggcc agcagctacc   600
tgagcctgac gcctgagcag tggaagtccc acaaaagcta cagctgccag gtcacgcatg   660
aagggagcac cgtggagaag acagtggccc ctacagaatg ttcatag                707

SEQ ID NO: 50          moltype = AA   length = 216
FEATURE                Location/Qualifiers
REGION                 1..216
                       note = Description of Artificial Sequence: Synthetic
                        polypeptide
source                 1..216
                       mol_type = protein
                       organism = synthetic construct
SEQUENCE: 50
QSALTQPASV SGSPGQTITI SCNGTSRDVG GFDSVSWYQQ SPGKAPKVMV FDVSHRPSGM    60
SNRFSGSKSG NTASLTISGL HIEDEGDYFC SSLTDRSHRI FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHKSYSCQVT HEGSTVEKTV APTECS                            216

SEQ ID NO: 51          moltype = AA   length = 110
FEATURE                Location/Qualifiers
REGION                 1..110
                       note = Description of Artificial Sequence: Synthetic
                        polypeptide
source                 1..110
                       mol_type = protein
                       organism = synthetic construct
SEQUENCE: 51
QSALTQPASV SGSPGQTITI SCNGTSRDVG GFDSVSWYQQ SPGKAPKVMV FDVSHRPSGM    60
SNRFSGSKSG NTASLTISGL HIEDEGDYFC SSLTDRSHRI FGGGTKLTVL              110

SEQ ID NO: 52          moltype = DNA   length = 1460
FEATURE                Location/Qualifiers
misc_feature           1..1460
                       note = Description of Artificial Sequence: Synthetic
                        polynucleotide
source                 1..1460
                       mol_type = other DNA
                       organism = synthetic construct
SEQUENCE: 52
atggagtttg gctgagctgg gttttcctcg caactctgtt aagagttgtg aagtgtcagg    60
aaaaactggt ggagtctggg ggaggcgtgg tccagccggg ggggtccctg agactctcct   120
gtttagcgtc tggattcacc tttcacaaat atggcatgca ctgggtccgc caggctccag   180
gcaaggggcct ggagtgggtg gcactcatct cagatgacgg aatgaggaaa tatcattcag  240
actccatgtg gggccgagtc accatctcca gagacaattc caagaacact ttatatctgc   300
aattcagcag cctgaaagtc gaagacacgg ctatgttctt ctgtgcgaga gaggctggtg   360
ggccaatctg gcatgacgac gtcaaatatt acgattttaa tgacggctac tacaattacc   420
actacatgga cgtctggggc aaggggacca ttgtcaccgt ctcccagcg tcgaccaagg    480
gcccatcggt cttccctctg gcaccatcat ccaagtcgac ctctggggc acagcggccc    540
tgggctgcct ggtcaaggac tacttccccg aaccggtgac ggtgtcgtgg aactcaggcg   600
ccctgaccag cggcgtgcac accttcccgg ctgtcctaca gtcctcagga ctctactccc   660
tcagcagcgt ggtgaccgtg ccctccagca gcttgggcac ccagacctac atctgcaacg   720
tgaatcacaa gcccagcaac accaaggtgg acaagagagt tgagcccaaa tcttgtgaca   780
aaactcacac atgcccaccg tgcccagcac ctgaactcct ggggggaccg tcagtcttcc   840
tcttcccccc aaaacccaag gacaccctca tgatctcccg gaccctgag gtcacatgcg    900
tggtggtgga cgtgagccac gaagacctg aggtcaagtt caactggtac gtggacggcg    960
tggaggtgca taatgccaag acaaagccgc gggaggagca gtacaacagc acgtaccgtg  1020
tggtcagcgt cctcaccgtc ctgcaccagg actggctgaa tggcaaggag tacaagtgca  1080
aggtctccaa caaagccctc ccagccccca tcgagaaaac catctccaaa gccaagggc   1140
agccccgaga accacaggtg tacaccctgc cccatcccg ggaggagatg accaagaacc   1200
aggtcagcct gacctgcctg gtcaaaggct tctatcccag cgacatcgcc gtggagtggg  1260
agagcaatgg gcagccggag aacaactaca agaccacgcc tcccgtgctg gactccgacg  1320
gctccttctt cctctatagc aagctcaccg tggacaagag caggtggcag caggggaacg  1380
tcttctcatg ctccgtgatg catgaggctc tgcacaacca ctacacgcag aagagcctct  1440
ccctgtctcc gggtaaatga                                             1460

SEQ ID NO: 53          moltype = AA   length = 467
```

| | | |
|---|---|---|
| FEATURE | Location/Qualifiers | |
| REGION | 1..467<br>note = Description of Artificial Sequence: Synthetic polypeptide | |
| source | 1..467<br>mol_type = protein<br>organism = synthetic construct | |
| SEQUENCE: 53 | | |

```
QEKLVESGGG VVQPGGSLRL SCLASGFTFH KYGMHWVRQA PGKGLEWVAL ISDDGMRKYH    60
SDSMWGRVTI SRDNSKNTLY LQFSSLKVED TAMFFCAREA GGPIWHDDVK YYDFNDGYYN   120
YHYMDVWGKG TIVTVSSAST KGPSVFPLAP SSKSTSGGTA ALGCLVKDYF PEPVTVSWNS   180
GALTSGVHTF PAVLQSSGLY SLSSVVTVPS SSLGTQTYIC NVNHKPSNTK VDKRVEPKSC   240
DKTHTCPPCP APELLGGPSV FLFPPKPKDT LMISRTPEVT CVVVDVSHED PEVKFNWYVD   300
GVEVHNAKTK PREEQYNSTY RVVSVLTVLH QDWLNGKEYK CKVSNKALPA PIEKTISKAK   360
GQPREPQVYT LPPSREEMTK NQVSLTCLVK GFYPSDIAVE WESNGQPENN YKTTPPVLDS   420
DGSFFLYSKL TVDKSRWQQG NVFSCSVMHE ALHNHYTQKS LSLSPGK                 467
```

| | | |
|---|---|---|
| SEQ ID NO: 54 | moltype = AA length = 137 | |
| FEATURE | Location/Qualifiers | |
| REGION | 1..137<br>note = Description of Artificial Sequence: Synthetic polypeptide | |
| source | 1..137<br>mol_type = protein<br>organism = synthetic construct | |
| SEQUENCE: 54 | | |

```
QEKLVESGGG VVQPGGSLRL SCLASGFTFH KYGMHWVRQA PGKGLEWVAL ISDDGMRKYH    60
SDSMWGRVTI SRDNSKNTLY LQFSSLKVED TAMFFCAREA GGPIWHDDVK YYDFNDGYYN   120
YHYMDVWGKG TIVTVSS                                                  137
```

| | | |
|---|---|---|
| SEQ ID NO: 55 | moltype = DNA length = 707 | |
| FEATURE | Location/Qualifiers | |
| misc_feature | 1..707<br>note = Description of Artificial Sequence: Synthetic polynucleotide | |
| source | 1..707<br>mol_type = other DNA<br>organism = synthetic construct | |
| SEQUENCE: 55 | | |

```
atggcctggg cttgctattc ctcaccctct tcactcaggg cacagggtcc tggggccagt    60
ctgcccctga ctcagcctgc ctccgtgtct ggtctcctgg acagacgatc accatctcct   120
gcaatggaac cagaagtgac gttggtggat ttgactctgt tcctggtac caacaatccc    180
cagggaaagc ccccaaagtc atggttttg tgtcagtca tcggccctca ggtatctcta    240
atcgcttctc tggctccaag tccggcaaca cggcctccct gaccatctct gggctccaca   300
ttgaggacga gggcgattat ttctgctctt cactgacaga cagaagccat cgcatattcg   360
gcggcgggac caaggtgacc gttctaggtc agcccaaggc tgcccctcg gtcactctgt    420
tcccgccctc ctctgaggag cttcaagcca caaggccaca ctggtgtgtc tcataagtg    480
acttctaccc gggagccgtg acagtggcct ggaaggcaga tagcagcccc gtcaaggcgg   540
gagtggagac caccacaccc tccaaacaaa gcaacaacaa gtacgcggcc agcagctacc   600
tgagcctgac gcctgagcag tggaagtccc acaaaagcta cagctgccag gtcacgcatg   660
aagggagcac cgtggagaag acagtggccc ctacagaatg ttcatag                 707
```

| | | |
|---|---|---|
| SEQ ID NO: 56 | moltype = AA length = 216 | |
| FEATURE | Location/Qualifiers | |
| REGION | 1..216<br>note = Description of Artificial Sequence: Synthetic polypeptide | |
| source | 1..216<br>mol_type = protein<br>organism = synthetic construct | |
| SEQUENCE: 56 | | |

```
QSALTQPASV SGSPGQTITI SCNGTRSDVG GFDSVSWYQQ SPGKAPKVMV FDVSHRPSGI    60
SNRFSGSKSG NTASLTISGL HIEDEGDYFC SSLTDRSHRI FGGGTKVTVL GQPKAAPSVT   120
LFPPSSEELQ ANKATLVCLI SDFYPGAVTV AWKADSSPVK AGVETTTPSK QSNNKYAASS   180
YLSLTPEQWK SHKSYSCQVT HEGSTVEKTV APTECS                             216
```

| | | |
|---|---|---|
| SEQ ID NO: 57 | moltype = AA length = 110 | |
| FEATURE | Location/Qualifiers | |
| REGION | 1..110<br>note = Description of Artificial Sequence: Synthetic polypeptide | |
| source | 1..110<br>mol_type = protein<br>organism = synthetic construct | |
| SEQUENCE: 57 | | |

```
QSALTQPASV SGSPGQTITI SCNGTRSDVG GFDSVSWYQQ SPGKAPKVMV FDVSHRPSGI    60
SNRFSGSKSG NTASLTISGL HIEDEGDYFC SSLTDRSHRI FGGGTKVTVL               110
```

| | | |
|---|---|---|
| SEQ ID NO: 58 | moltype = DNA length = 1461 | |

| FEATURE | Location/Qualifiers |
|---|---|
| misc_feature | 1..1461 |
| | note = Description of Artificial Sequence: Synthetic polynucleotide |
| source | 1..1461 |
| | mol_type = other DNA |
| | organism = synthetic construct |

SEQUENCE: 58

```
atggagtttg ggctgagctg ggttttcctc gcaactctgt taagagttgt gaagtgtcag   60
gaacaactgt tggagtctgg ggggaggcgtg gtccagccgg gggggtccct gagactctcc  120
tgtttagcgt ctggattcac gtttcacaaa tatggcatgc actgggtccg ccaggctcca  180
ggcaagggcc tggagtgggt ggcactcatc tcagatgacg gaatgaggaa atatcattca  240
aactccatgt ggggccgagt caccatctcc agagacaatt ccaagaacac tctttatctg  300
caattcagca gcctgaaagt cgaagacacg gctatgttct tctgtgcgag agaggctggt  360
gggccaatct ggcatgacga cgtcaaatat tacgatttta atgacggcta ctacaactac  420
cactacatgg acgtctgggg caaggggacc acggtcaccg tctcctcagc gtcgaccaag  480
ggcccatcgg tcttccctct ggcaccatca tccaagtcga cctctggggg cacagcggcc  540
ctgggctgcc tggtcaagga ctacttcccc gaaccggtga cggtgtcgtg gaactcaggc  600
gccctgacca gcggcgtgca caccttcccg gctgtcctac agtcctcagg actctactcc  660
ctcagcagcg tggtgaccgt gccctccagc agcttgggca cccagaccta catctgcaac  720
gtgaatcaca agcccagcaa caccaaggtg gacaagagag ttgagcccaa atcttgtgac  780
aaaactcaca catgcccacc gtgcccagca cctgaactcc tggggggacc gtcagtcttc  840
ctcttccccc caaaacccaa ggacaccctc atgatctccc ggaccccctga ggtcacatgc  900
gtggtggtgg acgtgagcca cgaagaccct gaggtcaagt tcaactggta cgtggacggc  960
gtggaggtgc ataatgccaa gacaaagccg cgggaggagc agtacaacag cacgtaccgt 1020
gtggtcagcg tcctcaccgt cctgcaccag gactggctga atggcaagga gtacaagtgc 1080
aaggtctcca acaaagccct cccagccccc atcgagaaaa ccatctccaa agccaaaggg 1140
cagccccgag aaccacaggt gtacaccctg cccccatccc gggaggagat gaccaagaac 1200
caggtcagcc tgacctgcct ggtcaaaggc ttctatccca gcgacatcgc cgtggagtgg 1260
gagagcaatg ggcagccgga gaacaactac aagaccacgc ctcccgtgct ggactccgac 1320
ggctccttct tcctctatag caagctcacc gtggacaaga gcaggtggca gcaggggaac 1380
gtcttctcat gctccgtgat gcatgaggct ctgcacaacc actacacgca gaagagcctc 1440
tccctgtctc cgggtaaatg a                                            1461
```

| SEQ ID NO: 59 | moltype = AA  length = 467 |
|---|---|
| FEATURE | Location/Qualifiers |
| REGION | 1..467 |
| | note = Description of Artificial Sequence: Synthetic polypeptide |
| source | 1..467 |
| | mol_type = protein |
| | organism = synthetic construct |

SEQUENCE: 59

```
QEQLLESGGG VVQPGGSLRL SCLASGFTFH KYGMHWVRQA PGKGLEWVAL ISDDGMRKYH   60
SNSMWGRVTI SRDNSKNTLY LQFSSLKVED TAMFFCAREA GGPIWHDDVK YYDFNDGYYN  120
YHYMDVWGKG TTVTVSSAST KGPSVFPLAP SSKSTSGGTA ALGCLVKDYF PEPVTVSWNS  180
GALTSGVHTF PAVLQSSGLY SLSSVVTVPS SSLGTQTYIC NVNHKPSNTK VDKRVEPKSC  240
DKTHTCPPCP APELLGGPSV FLFPPKPKDT LMISRTPEVT CVVVDVSHED PEVKFNWYVD  300
GVEVHNAKTK PREEQYNSTY RVVSVLTVLH QDWLNGKEYK CKVSNKALPA PIEKTISKAK  360
GQPREPQVYT LPPSREEMTK NQVSLTCLVK GFYPSDIAVE WESNGQPENN YKTTPPVLDS  420
DGSFFLYSKL TVDKSRWQQG NVFSCSVMHE ALHNHYTQKS LSLSPGK              467
```

| SEQ ID NO: 60 | moltype = AA  length = 137 |
|---|---|
| FEATURE | Location/Qualifiers |
| REGION | 1..137 |
| | note = Description of Artificial Sequence: Synthetic polypeptide |
| source | 1..137 |
| | mol_type = protein |
| | organism = synthetic construct |

SEQUENCE: 60

```
QEQLLESGGG VVQPGGSLRL SCLASGFTFH KYGMHWVRQA PGKGLEWVAL ISDDGMRKYH   60
SNSMWGRVTI SRDNSKNTLY LQFSSLKVED TAMFFCAREA GGPIWHDDVK YYDFNDGYYN  120
YHYMDVWGKG TTVTVSS                                                137
```

| SEQ ID NO: 61 | moltype = DNA  length = 708 |
|---|---|
| FEATURE | Location/Qualifiers |
| misc_feature | 1..708 |
| | note = Description of Artificial Sequence: Synthetic polynucleotide |
| source | 1..708 |
| | mol_type = other DNA |
| | organism = synthetic construct |

SEQUENCE: 61

```
atggcctggg ctctgctatt cctcaccctc ttcactcagg gcacagggtc ccggggccag   60
tctgccctga ctcagcctgc ctccgtgtct gggtctcctg gacagacgat caccatctcc  120
tgcaatggaa ccagcagtga cgttggtgga tttgactctg tctcctggta tcaacaatcc  180
ccagggaaag ccccccaaagt catggtttt gatgtcagtc atcggccctc aggtatctct  240
aatcgcttct ctggctccaa gtccggcaac acggcctccc tgaccatctc tgggctccac  300
```

```
attgaggacg agggcgatta tttctgctct tcactgacag acagaagcca tcgcatattc   360
ggcggcggga ccaaggtgac cgttctaggt cagcccaagg ctgcccccctc ggtcactctg  420
ttccccgccct cctctgagga gcttcaagcc aacaaggcca cactggtgtg tctcataagt  480
gacttctacc cggagccgt gacagtggcc tggaaggcag atagcagccc cgtcaaggcg   540
ggagtggaga ccaccacacc ctccaaacaa agcaacaaca agtacgcggc cagcagctac  600
ctgagcctga cgcctgagca gtggaagtcc cacaaaagct acagctgcca ggtcacgcat  660
gaagggagca ccgtggagaa gacagtggcc cctacagaat gttcatag                708

SEQ ID NO: 62          moltype = DNA  length = 1446
FEATURE                Location/Qualifiers
misc_feature           1..1446
                       note = Description of Artificial Sequence: Synthetic
                        polynucleotide
source                 1..1446
                       mol_type = other DNA
                       organism = synthetic construct
SEQUENCE: 62
atgaaacacc tgtggttctt ccttctcctg gtggcagctc ccagatgggt cctgtcacag   60
atgcagttac aggagtcggg ccccggactg gtgaagcctt cggaaaccct gtccctcacg  120
tgcagtgtgt ctggtgcctc cataagtgac agttactgga gctggatccg gcggtcccca  180
gggaaggac ttgagtggat tgggtatgtc cacaaaagcg gcgacacaaa ttacagcccc   240
tccctcaaga gtcgagtcaa cttgtcgtta gacacgtcca aaatcaggt gtccctgagc  300
cttgtggccg cgaccgctgc ggactcgggc aaatattatt gcgcgagaac actgcacggg  360
aggagaattt atggaatcgt tgccttcaat gagtggttca cctacttcta catggacgtc  420
tggggcaatg ggactcaggt caccgtctcc tcagcctcca ccaagggccc atcggtcttc  480
cccctggcac cctcctccaa gagcacctct gggggcacag cggccctggc ctgcctggtc  540
aaggactact tccccgaacc ggtgacggtg tcgtggaact caggcgccct gaccagcggc  600
gtgcacacct tcccggctgt cctacagtcc tcaggactct actccctcag cagcgtggtg  660
accgtgccct ccagcagctt gggcacccag acctacatct gcaacgtgaa tcacaagccc  720
agcaacacca aggtggacaa gagagttgag cccaaatctt gtgacaaaac tcacacatgc  780
ccaccgtgcc cagcacctga actcctgggg ggaccgtcag tcttcctctt cccccccaaaa  840
cccaaggaca ccctcatgat ctccggacc cctgaggtca catgcgtggt ggtggacgtg   900
agccacgaag accctgaggt caagttcaac tggtacgtgg acggcgtgga ggtgcataat  960
gccaagacaa agccgcggga ggagcagtac aacagcacgt accgtgtggt cagcgtcctc  1020
accgtcctgc accaggactg gctgaatggc aaggagtaca agtgcaaggt ctccaacaaa  1080
gccctcccag cccccatcga gaaaaccatc tccaaagcca aagggcagcc ccgagaacca  1140
caggtgtaca ccctgccccc atcccgggag gagatgacca agaaccaggt cagcctgacc  1200
tgcctggtca aaggcttcta tcccagcgac atcgccgtgg agtgggagag caatgggcag  1260
ccggagaaca actacaagac cacgcctccc gtgctggact ccgacggctc cttcttcctc  1320
tatagcaagc tcaccgtgga caagagcagg tggcagcagg ggaacgtctt ctcatgctcc  1380
gtgatgcatg aggctctgca caaccactac acgcagaaga gcctctccct gtctccgggt  1440
aaatga                                                             1446

SEQ ID NO: 63          moltype = DNA  length = 396
FEATURE                Location/Qualifiers
misc_feature           1..396
                       note = Description of Artificial Sequence: Synthetic
                        polynucleotide
source                 1..396
                       mol_type = other DNA
                       organism = synthetic construct
SEQUENCE: 63
cagatgcagt tacaggagtc ggggcccgga ctggtgaagc cttcggaaac cctgtccctc   60
acgtgcagtg tgtctggtgc ctccataagt gacagttact ggagctggat ccggcggtcc  120
ccagggaagg gacttgagtg gattgggtat gtccacaaaa gcggcgacac aaattacagc  180
ccctccctca agagtcgagt caacttgtcg ttagacacgt ccaaaaatca ggtgtccctg  240
agccttgtgg ccgcgaccgc tgcggactcg ggcaaatatt attgcgcgag aacactgcac  300
gggaggagaa tttatggaat cgttgccttc aatgagtggt tcacctactt ctacatggac  360
gtctggggca atgggactca ggtcaccgtc tcctca                             396

SEQ ID NO: 64          moltype = DNA  length = 1460
FEATURE                Location/Qualifiers
misc_feature           1..1460
                       note = Description of Artificial Sequence: Synthetic
                        polynucleotide
source                 1..1460
                       mol_type = other DNA
                       organism = synthetic construct
SEQUENCE: 64
atggagtttg gctgagctgg gttttcctcg caactctgtt aagagttgtg aagtgtcagg  60
aacaactggt ggagtctggg ggaggcgtgg tccagccggg ggggtccctg agactctcct  120
gtttagcgtc tggattcacg tttcacaaat atggcatgca ctgggtccgc caggctccag  180
gcaagggcct ggagtgggtg gcactcatct cagatgacgg aatgaggaaa tatcattcag  240
actccatgtg gggccgagtc accatctcca gagacaattcc caagaacact ctttatctgc  300
aattcagcag cctgaaagtc gaagacacgc tatgttctt ctgtgcgaga gaggctggtg  360
ggccaatctg gcatgacgac gtcaaatatt acgatttaa tgacggctac tacaactacc  420
actacatgga cgtctggggc aaggggacca cggtcaccgt ctcctcagcg tcgaccaagg  480
gcccatcggt cttccctctg gcaccatcat ccaagtcgac ctctggggc acagcggccc  540
tgggctgcct ggtcaaggac tacttccccg aaccggtgac ggtgtcgtgg aactcaggcg  600
```

```
                                     -continued
ccctgaccag cggcgtgcac accttcccgg ctgtcctaca gtcctcagga ctctactccc   660
tcagcagcgt ggtgaccgtg ccctccagca gcttgggcac ccagacctac atctgcaacg   720
tgaatcacaa gcccagcaac accaaggtgg acaagagagt tgagcccaaa tcttgtgaca   780
aaactcacac atgcccaccg tgcccagcac ctgaactcct gggggaccg tcagtcttcc    840
tcttcccccc aaaacccaag gacaccctca tgatctccg gacccctgag gtcacatgc    900
tggtggtgga cgtgagccac gaagaccctg aggtcaagtt caactggtac gtggacggcg   960
tggaggtgca taatgccaag acaaagccgc gggaggagca gtacaacagc acgtaccgtg  1020
tggtcagcgt cctcaccgtc ctgcaccagg actggctgaa tggcaaggag tacaagtgca  1080
aggtctccaa caaagccctc ccagcccca tcgagaaaac catctccaaa gccaaagggc   1140
agccccgaga accacaggtg tacaccctgc cccatcccg ggaggagatg accaagaacc   1200
aggtcagcct gacctgcctg gtcaaaggct tctatcccag cgacatcgcc gtggagtggg  1260
agagcaatgg gcagccggag aacaactaca agaccacgcc tcccgtgctg gactccgacg  1320
gctccttctt cctctatagc aagctcaccg tggacaagag caggtggcag caggggaacg  1380
tcttctcatg ctccgtgatg catgaggctc tgcacaacca ctacacgcag aagagcctct  1440
ccctgtctcc gggtaaatga                                              1460

SEQ ID NO: 65           moltype = AA  length = 467
FEATURE                 Location/Qualifiers
REGION                  1..467
                        note = Description of Artificial Sequence: Synthetic
                        polypeptide
source                  1..467
                        mol_type = protein
                        organism = synthetic construct
SEQUENCE: 65
QEQLVESGGG VVQPGGSLRL SCLASGFTFH KYGMHWVRQA PGKGLEWVAL ISDDGMRKYH   60
SDSMWGRVTI SRDNSKNTLY LQFSSLKVED TAMFFCAREA GGPIWHDDVK YYDFNDGYYN  120
YHYMDVWGKG TTVTVSSAST KGPSVFPLAP SSKSTSGGTA ALGCLVKDYF PEPVTVSWNS  180
GALTSGVHTF PAVLQSSGLY SLSSVVTVPS SSLGTQTYIC NVNHKPSNTK VDKRVEPKSC  240
DKTHTCPPCP APELLGGPSV FLFPPKPKDT LMISRTPEVT CVVVDVSHED PEVKFNWYVD  300
GVEVHNAKTK PREEQYNSTY RVVSVLTVLH QDWLNGKEYK CKVSNKALPA PIEKTISKAK  360
GQPREPQVYT LPPSREEMTK NQVSLTCLVK GFYPSDIAVE WESNGQPENN YKTTPPVLDS  420
DGSFFLYSKL TVDKSRWQQG NVFSCSVMHE ALHNHYTQKS LSLSPGK                467

SEQ ID NO: 66           moltype = AA  length = 462
FEATURE                 Location/Qualifiers
REGION                  1..462
                        note = Description of Artificial Sequence: Synthetic
                        polypeptide
source                  1..462
                        mol_type = protein
                        organism = synthetic construct
SEQUENCE: 66
QMQLQESGPG LVKPSETLSL TCSVSGASIS DSYWSWIRRS PGKGLEWIGY VHKSGDTNYS   60
PSLKSRVNLS LDTSKNQVSL SLVAATAADS GKYYCARTLH GRRIYGIVAF NEWFTYFYMD  120
VWGNGTQVTV SSASTKGPSV FPLAPSSKST SGGTAALGCL VKDYFPEPVT VSWNSGALTS  180
GVHTFPAVLQ SSGLYSLSSV VTVPSSSLGT QTYICNVNHK PSNTKVDKRV EPKSCDKTHT  240
CPPCPAPELL GGPSVFLFPP KPKDTLMISR TPEVTCVVVD VSHEDPEVKF NWYVDGVEVH  300
NAKTKPREEQ YNSTYRVVSV LTVLHQDWLN GKEYKCKVSN KALPAPIEKT ISKAKGQPRE  360
PQVYTLPPSR EEMTKNQVSL TCLVKGFYPS DIAVEWESNG QPENNYKTTP PVLDSDGSFF  420
LYSKLTVDKS RWQQGNVFSC SVMHEALHNH YTQKSLSLSP GK                     462

SEQ ID NO: 67           moltype = DNA  length = 708
FEATURE                 Location/Qualifiers
misc_feature            1..708
                        note = Description of Artificial Sequence: Synthetic
                        polynucleotide
source                  1..708
                        mol_type = other DNA
                        organism = synthetic construct
SEQUENCE: 67
atggcctggg ctctgctatt cgtcaccctc tcactcagg gcacagggtc ctggggccag    60
tctgccctga ctcagcctgc ctccgtgtct gggtctcctg gacagacgat caccatctcc  120
tgcaatgaa ccagcagtga cgttggtgga tttgaactct tctcctggta tcaacaatcc   180
ccagggaaag cccccaaagt catggttttt gatgtcagtc atcggccctc aggtatctct  240
aatcgcttct ctggctccaa gtccggcaac acggcctccc tgaccatctc tgggctccac  300
attgaggacg agggcgatta tttctgctct tcactgacag acagaagcca tcgcatattc  360
ggcggcggga ccaaggtgac cgttctaggt cagcccaagg ctgccccctc ggtcactctg  420
ttcccgccct cctctgagga gcttcaagcc aacaaggcca cactggtgtg tctcataagt  480
gacttctacc cgggagccgt gacagtggcc tggaaggcag atagcagccc cgtcaaggcg  540
ggagtggaga ccaccacacc ctccaaacaa agcaacaaca gtacgcggc cagcagctac  600
ctgagcctga cgcctgagca gtggaagtcc cacaaaagct acagctgcca ggtcacgcat  660
gaagggagca ccgtggagaa gacagtggcc cctacagaat gttcatag               708

SEQ ID NO: 68           moltype = DNA  length = 15
FEATURE                 Location/Qualifiers
misc_feature            1..15
                        note = Description of Artificial Sequence: Synthetic
                        oligonucleotide
```

```
source                   1..15
                         mol_type = other DNA
                         organism = synthetic construct
SEQUENCE: 68
aaatatggca tgcac                                                      15

SEQ ID NO: 69            moltype = DNA   length = 21
FEATURE                  Location/Qualifiers
misc_feature             1..21
                         note = Description of Artificial Sequence: Synthetic
                         oligonucleotide
source                   1..21
                         mol_type = other DNA
                         organism = synthetic construct
SEQUENCE: 69
tctggattca cgtttcacaa a                                               21

SEQ ID NO: 70            moltype = DNA   length = 21
FEATURE                  Location/Qualifiers
misc_feature             1..21
                         note = Description of Artificial Sequence: Synthetic
                         oligonucleotide
source                   1..21
                         mol_type = other DNA
                         organism = synthetic construct
SEQUENCE: 70
tctggattca cctttcacaa a                                               21

SEQ ID NO: 71            moltype = DNA   length = 21
FEATURE                  Location/Qualifiers
misc_feature             1..21
                         note = Description of Artificial Sequence: Synthetic
                         oligonucleotide
source                   1..21
                         mol_type = other DNA
                         organism = synthetic construct
SEQUENCE: 71
tctggattca cstttcacaa a                                               21

SEQ ID NO: 72            moltype = DNA   length = 51
FEATURE                  Location/Qualifiers
misc_feature             1..51
                         note = Description of Artificial Sequence: Synthetic
                         oligonucleotide
source                   1..51
                         mol_type = other DNA
                         organism = synthetic construct
SEQUENCE: 72
ctcatctcag atgacggaat gaggaaatat cattcagact ccatgtgggg c              51

SEQ ID NO: 73            moltype = DNA   length = 51
FEATURE                  Location/Qualifiers
misc_feature             1..51
                         note = Description of Artificial Sequence: Synthetic
                         oligonucleotide
source                   1..51
                         mol_type = other DNA
                         organism = synthetic construct
SEQUENCE: 73
ctcatctcag atgacggaat gaggaaatat cattcaaact ccatgtgggg c              51

SEQ ID NO: 74            moltype = DNA   length = 51
FEATURE                  Location/Qualifiers
misc_feature             1..51
                         note = Description of Artificial Sequence: Synthetic
                         oligonucleotide
source                   1..51
                         mol_type = other DNA
                         organism = synthetic construct
SEQUENCE: 74
ctcatctcag atgacggaat gaggaaatat cattcaract ccatgtgggg c              51

SEQ ID NO: 75            moltype = DNA   length = 84
FEATURE                  Location/Qualifiers
misc_feature             1..84
                         note = Description of Artificial Sequence: Synthetic
                         oligonucleotide
source                   1..84
                         mol_type = other DNA
```

```
                          organism = synthetic construct
SEQUENCE: 75
gaggctggtg ggccaatctg gcatgacgac gtcaaatatt acgattttaa tgacggctac    60
tacaactacc actacatgga cgtc                                           84

SEQ ID NO: 76             moltype = DNA   length = 84
FEATURE                   Location/Qualifiers
misc_feature              1..84
                          note = Description of Artificial Sequence: Synthetic
                            oligonucleotide
source                    1..84
                          mol_type = other DNA
                          organism = synthetic construct
SEQUENCE: 76
gaggcbggtg ggccaatctg gcatgacgac gtcaaatatt acgattttaa tgacggctac    60
tacaactatc actacatgga cgtc                                           84

SEQ ID NO: 77             moltype = DNA   length = 84
FEATURE                   Location/Qualifiers
misc_feature              1..84
                          note = Description of Artificial Sequence: Synthetic
                            oligonucleotide
source                    1..84
                          mol_type = other DNA
                          organism = synthetic construct
SEQUENCE: 77
gaggccggtg ggccaatctg gcatgacgac gtcaaatatt acgattttaa tgacggctac    60
tacaactatc actacatgga cgtc                                           84

SEQ ID NO: 78             moltype = DNA   length = 84
FEATURE                   Location/Qualifiers
misc_feature              1..84
                          note = Description of Artificial Sequence: Synthetic
                            oligonucleotide
source                    1..84
                          mol_type = other DNA
                          organism = synthetic construct
SEQUENCE: 78
gaggcgggtg ggccaatctg gcatgacgac gtcaaatatt acgattttaa tgacggctac    60
tacaactatc actacatgga cgtc                                           84

SEQ ID NO: 79             moltype = AA    length = 132
FEATURE                   Location/Qualifiers
REGION                    1..132
                          note = Description of Artificial Sequence: Synthetic
                            polypeptide
source                    1..132
                          mol_type = protein
                          organism = synthetic construct
SEQUENCE: 79
QMQLQESGPG LVKPSETLSL TCSVSGASIS DSYWSWIRRS PGKGLEWIGY VHKSGDTNYS    60
PSLKSRVNLS LDTSKNQVSL SLVAATAADS GKYYCARTLH GRRIYGIVAF NEWFTYFYMD   120
VWGNGTQVTV SS                                                       132

SEQ ID NO: 80             moltype = DNA   length = 42
FEATURE                   Location/Qualifiers
misc_feature              1..42
                          note = Description of Artificial Sequence: Synthetic
                            oligonucleotide
source                    1..42
                          mol_type = other DNA
                          organism = synthetic construct
SEQUENCE: 80
aatggaacca gcagtgacgt tggtggattt gactctgtct cc                       42

SEQ ID NO: 81             moltype = DNA   length = 42
FEATURE                   Location/Qualifiers
misc_feature              1..42
                          note = Description of Artificial Sequence: Synthetic
                            oligonucleotide
source                    1..42
                          mol_type = other DNA
                          organism = synthetic construct
SEQUENCE: 81
aatggaacca gmmgtgacgt tggtggattt gactctgtct cc                       42

SEQ ID NO: 82             moltype = DNA   length = 42
FEATURE                   Location/Qualifiers
misc_feature              1..42
```

```
                    note = Description of Artificial Sequence: Synthetic
                        oligonucleotide
source              1..42
                    mol_type = other DNA
                    organism = synthetic construct
SEQUENCE: 82
aatggaacca gaagtgacgt tggtggattt gactctgtct cc                              42

SEQ ID NO: 83       moltype = DNA   length = 42
FEATURE             Location/Qualifiers
misc_feature        1..42
                    note = Description of Artificial Sequence: Synthetic
                        oligonucleotide
source              1..42
                    mol_type = other DNA
                    organism = synthetic construct
SEQUENCE: 83
aatggaacca gccgtgacgt tggtggattt gactctgtct cc                              42

SEQ ID NO: 84       moltype = DNA   length = 21
FEATURE             Location/Qualifiers
misc_feature        1..21
                    note = Description of Artificial Sequence: Synthetic
                        oligonucleotide
source              1..21
                    mol_type = other DNA
                    organism = synthetic construct
SEQUENCE: 84
gatgtcagtc atcggccctc a                                                     21

SEQ ID NO: 85       moltype = DNA   length = 30
FEATURE             Location/Qualifiers
misc_feature        1..30
                    note = Description of Artificial Sequence: Synthetic
                        oligonucleotide
source              1..30
                    mol_type = other DNA
                    organism = synthetic construct
SEQUENCE: 85
tcttcactga cagacagaag ccatcgcata                                            30

SEQ ID NO: 86       moltype = DNA   length = 30
FEATURE             Location/Qualifiers
misc_feature        1..30
                    note = Description of Artificial Sequence: Synthetic
                        oligonucleotide
source              1..30
                    mol_type = other DNA
                    organism = synthetic construct
SEQUENCE: 86
tcttcattga cagacagaag ccatcgcata                                            30

SEQ ID NO: 87       moltype = DNA   length = 30
FEATURE             Location/Qualifiers
misc_feature        1..30
                    note = Description of Artificial Sequence: Synthetic
                        oligonucleotide
source              1..30
                    mol_type = other DNA
                    organism = synthetic construct
SEQUENCE: 87
tcttcaytga cagacagaag ccatcgcata                                            30

SEQ ID NO: 88       moltype = AA    length = 5
FEATURE             Location/Qualifiers
REGION              1..5
                    note = Description of Artificial Sequence: Synthetic peptide
source              1..5
                    mol_type = protein
                    organism = synthetic construct
SEQUENCE: 88
KYGMH                                                                       5

SEQ ID NO: 89       moltype = AA    length = 17
FEATURE             Location/Qualifiers
REGION              1..17
                    note = Description of Artificial Sequence: Synthetic peptide
source              1..17
                    mol_type = protein
```

```
                        organism = synthetic construct
SEQUENCE: 89
LISDDGMRKY HSDSMWG                                                      17

SEQ ID NO: 90           moltype = AA   length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 90
DSYWS                                                                    5

SEQ ID NO: 91           moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
VARIANT                 13
                        note = X Can be D,N or an amino acid with similar physical
                         properties to either D or N
SEQUENCE: 91
LISDDGMRKY HSXSMWG                                                      17

SEQ ID NO: 92           moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 92
NGTRSDVGGF DSVS                                                         14

SEQ ID NO: 93           moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 93
NGTSRDVGGF DSVS                                                         14

SEQ ID NO: 94           moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
VARIANT                 4..5
                        note = X can be S or R an amino acid with similar physical
                         properties to either S or R
SEQUENCE: 94
NGTXXDVGGF DSVS                                                         14

SEQ ID NO: 95           moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 95
DVSHRPS                                                                  7

SEQ ID NO: 96           moltype = AA   length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 96
```

QSALTQPASV SGSPGQTITI SCNGTRSDVG GFDSVSWYQQ SPGRAPKVMV FDVSHRPSGI    60
SNRFSGSKSG NTASLTISGL HIEDEGDYFC SSLTDRSHRI FGGGTKLTVL              110

SEQ ID NO: 97          moltype = AA   length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 97
NGTSSDVGGF DSVS                                                     14

SEQ ID NO: 98          moltype = AA   length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 98
LISDDGMRKY HSNSMWG                                                  17

SEQ ID NO: 99          moltype = DNA   length = 411
FEATURE                Location/Qualifiers
misc_feature           1..411
                       note = Description of Artificial Sequence: Synthetic
                         polynucleotide
source                 1..411
                       mol_type = other DNA
                       organism = synthetic construct
SEQUENCE: 99
caggaacaac tggtggagtc tggggaggc gtggtccagc cggggggtc cctgagactc     60
tcctgtttag cgtctggatt cacgtttcac aaatatggca tgcctgggt ccgccaggct   120
ccaggcaagg gcctggagtg ggtggcactc atctcagatg acggaatgag gaaatatcat  180
tcagactcca gtggggccg agtcaccatc tccagagaca attccaagaa cactctttat   240
ctgcaattca gcagcctgaa agtcgaagac acggctatgt tcttctgtgc gagagaggct  300
ggtgggccaa tctggcatga cgacgtcaaa tattacgatt ttaatgacgg ctactacaac  360
taccactaca tggacgtctg gggcaagggg accacggtca ccgtctcgag c           411

SEQ ID NO: 100         moltype = DNA   length = 330
FEATURE                Location/Qualifiers
misc_feature           1..330
                       note = Description of Artificial Sequence: Synthetic
                         polynucleotide
source                 1..330
                       mol_type = other DNA
                       organism = synthetic construct
SEQUENCE: 100
cagtctgccc tgactcagcc tgcctccgtg tctgggtctc ctggacagac gatcaccatc    60
tcctgcaatg gaaccagcag tgacgttggt ggatttgact ctgtctcctg gtaccaacaa  120
tccccaggga aagcccccaa agtcatggtt tttgatgtca gtcatcggcc ctcaggtatc  180
tctaatcgct tctctggctc caagtccggc aacacggcct ccctgaccat ctctgggctc  240
cacattgagg acgagggcga ttatttctgc tcttcactga cagacagaag ccatcgcata  300
ttcggcggcg ggaccaaggt gaccgttcta                                   330

SEQ ID NO: 101         moltype = DNA   length = 372
FEATURE                Location/Qualifiers
misc_feature           1..372
                       note = Description of Artificial Sequence: Synthetic
                         polynucleotide
source                 1..372
                       mol_type = other DNA
                       organism = synthetic construct
SEQUENCE: 101
caggtccgcc tggtacagtc tgggcctgag gtgaagaagc ctgggtcctc ggtgacggtc    60
tcctgccagg cttctggagg caccttcagc agttatgctt tcacctgggt gcgcaggcc   120
cccggacaag gtcttgagtg gttgggcatg gtcaccccaa tctttggtga ggcaagtac   180
tcacaaagat tcgagggcag agtcaccatc accgcgacg aatccacgag cacaacctcc   240
atagaattga gaggcctgac atccgaagac acggccattt attactgtgc gcagatcgg   300
cgcgcggttc caattgccac ggacaactgg ttagacccct ggggccaggg accctggtc   360
accgtctcga gc                                                      372

SEQ ID NO: 102         moltype = AA   length = 6
FEATURE                Location/Qualifiers
REGION                 1..6
                       note = Description of Artificial Sequence: Synthetic peptide
source                 1..6
                       mol_type = protein

```
                        organism = synthetic construct
SEQUENCE: 102
GYSFID                                                                     6

SEQ ID NO: 103          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 103
LIDPENGEAR                                                                10

SEQ ID NO: 104          moltype = AA   length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 104
SYAFT                                                                      5

SEQ ID NO: 105          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 105
MVTPIFGEAK YSQRFEG                                                        17

SEQ ID NO: 106          moltype = DNA   length = 321
FEATURE                 Location/Qualifiers
misc_feature            1..321
                        note = Description of Artificial Sequence: Synthetic
                         polynucleotide
source                  1..321
                        mol_type = other DNA
                        organism = synthetic construct
SEQUENCE: 106
gacatccagt tgacccagtc tccatcctcc ctgtctgcat ctgttggcga cagagtctcc         60
atcacttgcc gggcgagtca gaccattaac aactacttaa attggtatca acagacaccc        120
gggaaagccc ctaaactcct gatctatggt gcctccaatt tgcaaaatgg ggtcccatca        180
aggttcagcg gcagtggctc tgggacagac ttcactctca ccatcagcag tctgcaacct        240
gaggattttg caacttacta ctgtcaacag agtttcagta ctccgaggac cttcggccaa        300
gggacacgac tggatattaa a                                                  321

SEQ ID NO: 107          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 107
RASQTINNYL N                                                              11

SEQ ID NO: 108          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 108
GASNLQN                                                                    7

SEQ ID NO: 109          moltype = DNA   length = 372
FEATURE                 Location/Qualifiers
misc_feature            1..372
                        note = Description of Artificial Sequence: Synthetic
                         polynucleotide
source                  1..372
                        mol_type = other DNA
                        organism = synthetic construct
SEQUENCE: 109
```

```
caggtcctgc tggtgcagtc tgggactgag gtgaagaagc ctgggtcctc ggtgaaggtc   60
tcctgtcagg cttctggagg cgccttcagt agttatgctt tcagctgggt gcgacaggcc  120
cctggacagg ggcttaatgg gatgggcatg atcaccctg tctttggtga gactaaatat  180
gcaccgaggt tccagggcag actcacactt accgcggaaa atccttgag caccacctac  240
atggaattga aagcctgac atctgatgac acggcctttt attattgtac gagagatcgg  300
cgcgtagttc aatggccac agacaactgg ttagaccct ggggcaggg gacgctggtc  360
accgtctcga gc                                                      372

SEQ ID NO: 110         moltype = AA   length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 110
SYAFS                                                                5

SEQ ID NO: 111         moltype = AA   length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 111
MITPVFGETK YAPRFQG                                                  17

SEQ ID NO: 112         moltype = DNA   length = 321
FEATURE                Location/Qualifiers
misc_feature           1..321
                       note = Description of Artificial Sequence: Synthetic
                       polynucleotide
source                 1..321
                       mol_type = other DNA
                       organism = synthetic construct
SEQUENCE: 112
gacatccagt tgacccagtc tccatcctcc ctgtctgcat ctgtaggaga cagggtcacc   60
gtcacttgcc gggcgagtca gaccatacac acctatttaa attggtatca gcaaattcca  120
ggaaaagccc ctaagctcct gatctatggt gcctccacct tgcaaagtgg ggtcccgtca  180
aggttcagtg gcagtggatc tgggacagat ttcactctca ccatcaacag tctccaacct  240
gaggactttg caacttacta ctgtcaacag agttacagta ccccaaggac cttcggccaa  300
gggacacgac tggatattaa a                                             321

SEQ ID NO: 113         moltype = AA   length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 113
RASQTIHTYL N                                                        11

SEQ ID NO: 114         moltype = AA   length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 114
GASTLQS                                                              7

SEQ ID NO: 115         moltype = DNA   length = 366
FEATURE                Location/Qualifiers
misc_feature           1..366
                       note = Description of Artificial Sequence: Synthetic
                       polynucleotide
source                 1..366
                       mol_type = other DNA
                       organism = synthetic construct
SEQUENCE: 115
gacggccacc tggttcagtc tgggggttgag gtgaagaaga ctggggctac agtcaaaatc   60
tcctgcaagg tttctggata cagcttcatc gactactacc ttcattggt gcaacgggcc   120
cctggaaaag gccttgagtg ggtgggactt attgatcctg aaaatggtga ggctcgatat  180
gcagagaagt tccagggcag agtcaccata atcgcggaca cgtctataga tacaggctac  240
atggaaatga ggagcctgaa atctgaggac acggccgtgt atttctgtgc agcaggtgcc  300
gtgggggctg attccgggag ctggttcgac ccctggggcc aggaactct ggtcaccgtc  360
```

```
tcgagc                                                                        366

SEQ ID NO: 116          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 116
DYYLH                                                                         5

SEQ ID NO: 117          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 117
LIDPENGEAR YAEKFQG                                                            17

SEQ ID NO: 118          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 118
GFDFSR                                                                        6

SEQ ID NO: 119          moltype = DNA  length = 327
FEATURE                 Location/Qualifiers
misc_feature            1..327
                        note = Description of Artificial Sequence: Synthetic
                        polynucleotide
source                  1..327
                        mol_type = other DNA
                        organism = synthetic construct
SEQUENCE: 119
tcctatgaac tgactcagcc accctcagtg tccgtgtccc caggacagac agccagcatc             60
acctgttctg gatctaaatt gggggataaa tatgtttcct ggtatcaact gaggccaggc             120
cagtccccca tactggtcat gtatgaaaat gacaggcggc cctccgggat ccctgagcga             180
ttctccggtt ccaattctgg cgacactgcc actctgacca tcagcgggac ccaggctttg             240
gatgaggctg acttctactg tcaggcgtgg gagaccacca ccaccacttt tgttttcttc             300
ggcggaggga cccagctgac cgttcta                                                 327

SEQ ID NO: 120          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 120
SGSKLGDKYV S                                                                  11

SEQ ID NO: 121          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 121
ENDRRPS                                                                       7

SEQ ID NO: 122          moltype = DNA  length = 408
FEATURE                 Location/Qualifiers
misc_feature            1..408
                        note = Description of Artificial Sequence: Synthetic
                        polynucleotide
source                  1..408
                        mol_type = other DNA
                        organism = synthetic construct
SEQUENCE: 122
cagcgattag tggagtctgg gggaggcgtg gtccagcctg gtcgtccct gagactctcc              60
tgtgcagcgt ccggattcga cttcagtaga caaggcatgc actgggtccg ccaggctcca             120
```

```
ggccagggc   tggagtgggt   ggcatttatt   aaatatgatg   gaagtgagaa   atatcatgct    180
gactccgtat  ggggccgact   cagcatctcc   agagacaatt   ccaaggatac   gctttatctc    240
caaatgaata  gcctgagagt   cgaggacacg   gctacatatt   tttgtgtgag   agaggctggt    300
gggcccgact  accgtaatgg   gtacaactat   tacgatttct   atgatggtta   ttataactac    360
cactatatgg  acgtctgggg   caaagggacc   acggtcaccg   tctcgagc                   408
```

SEQ ID NO: 123           moltype = AA   length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 123
RQGMH                                                                         5

SEQ ID NO: 124           moltype = AA   length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 124
FIKYDGSEKY HADSVWG                                                            17

SEQ ID NO: 125           moltype = DNA   length = 330
FEATURE                  Location/Qualifiers
misc_feature             1..330
                         note = Description of Artificial Sequence: Synthetic
                         polynucleotide
source                   1..330
                         mol_type = other DNA
                         organism = synthetic construct
SEQUENCE: 125
```
cagtctgccc  tgactcagcc   tgcctccgtg   tctgggtctc   ctggacagtc   gatcaccatc    60
tcctgcaatg  gaaccagcaa   tgatgttggt   ggctatgaat   ctgtctcctg   gtaccaacaa    120
catcccggca  aagcccccaa   agtcgtgatt   tatgatgtca   gtaaacggcc   ctcagggggtt   180
tctaatcgct  tctctggctc   caagtccggc   aacacggcct   ccctgaccat   ctctgggctc    240
caggctgagg  acgagggtga   ctattactgc   aagtctctga   caagcacgag   acgtcgggtt    300
ttcggcactg  ggaccaagct   gaccgttcta                                           330
```

SEQ ID NO: 126           moltype = AA   length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 126
NGTSNDVGGY ESVS                                                               14

SEQ ID NO: 127           moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 127
DVSKRPS                                                                       7

SEQ ID NO: 128           moltype = DNA   length = 411
FEATURE                  Location/Qualifiers
misc_feature             1..411
                         note = Description of Artificial Sequence: Synthetic
                         polynucleotide
source                   1..411
                         mol_type = other DNA
                         organism = synthetic construct
SEQUENCE: 128
```
caggaaaaac  tggtggagtc   tgggggaggc   gtggtccagc   cggggggtc    cctgagactc    60
tcctgtttag  cgtctggatt   caccttcac    aaatatggca   tgcactgggt   ccgcaggct     120
ccaggcaagg  gcctggagtg   ggtggcactc   atctcagatg   acggaatgag   gaaatatcat    180
tcagactcca  tgtggggccg   agtcaccatc   tccagagaca   attccaagaa   cactctatat    240
ctgcaattca  gcagcctgaa   agtcgaagac   acggctatgt   tcttctgtgc   gagagaggct    300
ggtgggccaa  tctggcatga   cgacgtcaaa   tattacgatt   ttaatgacgg   ctactacaac    360
taccactaca  tggacgtctg   gggcaagggg   accacggtca   ccgtctcctc   a             411
```

```
SEQ ID NO: 129           moltype = DNA   length = 330
FEATURE                  Location/Qualifiers
misc_feature             1..330
                         note = Description of Artificial Sequence: Synthetic
                         polynucleotide
source                   1..330
                         mol_type = other DNA
                         organism = synthetic construct
SEQUENCE: 129
cagtctgccc tgactcagcc tgcctccgtg tctgggtctc ctggacagac gatcaccatc   60
tcctgcaatg gaaccagaag tgacgttggt ggatttgact ctgtctcctg gtaccaacaa  120
tccccaggga gagcccccaa agtcatggtt tttgatgtca gtcatcggcc ctcaggtatc  180
tctaatcgct tctctggctc caagtccggc aacacggcct ccctgaccat ctctgggctc  240
cacattgagg acgagggcga ttatttctgc tcttcactga cagacagaag ccatcgcata  300
ttcggcggcg ggaccaagct gaccgttcta                                   330

SEQ ID NO: 130           moltype = DNA   length = 411
FEATURE                  Location/Qualifiers
misc_feature             1..411
                         note = Description of Artificial Sequence: Synthetic
                         polynucleotide
source                   1..411
                         mol_type = other DNA
                         organism = synthetic construct
SEQUENCE: 130
cacgaacaac tggtggaggc cggggaggc gtggtccagc cggggggtc cctgagactc     60
tcctgtttag cgtctggatt cacgtttcac aaatatggca tgcactgggt ccgccaggct  120
ccaggcaagg gcctggagtg ggtggcactc atctcagatg acggaatgag gaaatatcat  180
tcagactcca tgtggggccg agtcaccatc tccagagaca attccaagaa cactctttat  240
ctgcaattca gcagcctgag agtcgaagac acggctatgt tcttctgtgc gagagaggcc  300
ggtgggccaa tctggcatga cgacgtcaaa tattacgatt ttaatgacgg ctactacaac  360
tatcactaca tggacgtctg ggcaaggggg accaaggtca ccgtctcctc a           411

SEQ ID NO: 131           moltype = DNA   length = 330
FEATURE                  Location/Qualifiers
misc_feature             1..330
                         note = Description of Artificial Sequence: Synthetic
                         polynucleotide
source                   1..330
                         mol_type = other DNA
                         organism = synthetic construct
SEQUENCE: 131
cagtctgccc tgactcagcc tgcctccgtg tctgggtctc ctggacagac gatcaccatc   60
tcctgcaatg gaaccagccg tgacgttggt ggatttgact ctgtctcctg gtatcaacaa  120
tccccaggga aagcccccaa agtcatggtt tttgatgtca gtcatcggcc ctcaggtatg  180
tctaatcgct tctctggctc caagtccggc aacacggcct ccctgaccat ttctgggctc  240
cacattgagg acgagggcga ttatttctgc tcttcattga cagacagaag ccatcgcata  300
ttcggcggcg ggaccaagct gaccgttcta                                   330

SEQ ID NO: 132           moltype = DNA   length = 411
FEATURE                  Location/Qualifiers
misc_feature             1..411
                         note = Description of Artificial Sequence: Synthetic
                         polynucleotide
source                   1..411
                         mol_type = other DNA
                         organism = synthetic construct
SEQUENCE: 132
caggaaaaac tggtggagtc tgggggaggc gtggtccagc cggggggtc cctgagactc     60
tcctgtttag cgtctggatt caccttcac aaatatggca tgcactgggt ccgccaggct  120
ccaggcaagg gcctggagtg ggtggcactc atctcagatg acggaatgag gaaatatcat  180
tcagactcca tgtggggccg agtcaccatc tccagagaca attccaagaa cactttat  240
ctgcaattca gcagcctgaa agtcgaagac acggctatgt tcttctgtgc gagagaggct  300
ggtgggccaa tctggcatga cgacgtcaaa tattacgatt ttaatgcgg ctactacaat  360
taccactaca tggacgtctg ggcaagggg accattgtca ccgtctcctc a            411

SEQ ID NO: 133           moltype = DNA   length = 330
FEATURE                  Location/Qualifiers
misc_feature             1..330
                         note = Description of Artificial Sequence: Synthetic
                         polynucleotide
source                   1..330
                         mol_type = other DNA
                         organism = synthetic construct
SEQUENCE: 133
cagtctgccc tgactcagcc tgcctccgtg tctgggtctc ctggacagac gatcaccatc   60
tcctgcaatg gaaccagaag tgacgttggt ggatttgact ctgtctcctg gtaccaacaa  120
tccccaggga aagcccccaa agtcatggtt tttgatgtca gtcatcggcc ctcaggtatc  180
tctaatcgct tctctggctc caagtccggc aacacggcct ccctgaccat ctctgggctc  240
```

```
cacattgagg acgagggcga ttatttctgc tcttcactga cagacagaag ccatcgcata   300
ttcggcggcg ggaccaaggt gaccgttcta                                    330

SEQ ID NO: 134          moltype = DNA  length = 411
FEATURE                 Location/Qualifiers
misc_feature            1..411
                        note = Description of Artificial Sequence: Synthetic
                         polynucleotide
source                  1..411
                        mol_type = other DNA
                        organism = synthetic construct
SEQUENCE: 134
caggaacaac tgttggagtc tgggggaggc gtggtccagc cggggggtc cctgagactc    60
tcctgtttag cgtctggatt cacgtttcac aaatatggca tgcactgggt ccgccaggct  120
ccaggcaagg gcctggagtg ggtggcactc atctcagatg acggaatgag gaaatatcat  180
tcaaactcca tgtggggccg agtcaccatc tccagagaca attccaagaa cactctttat  240
ctgcaattca gcagcctgaa agtcgaagac acggctatgt tcttctgtgc gagagaggct  300
ggtgggccaa tctggcatga cgacgtcaaa tattacgatt ttaatgacgg ctactacaac  360
taccactaca tggacgtctg gggcaagggg accacggtca ccgtctcctc a           411

SEQ ID NO: 135          moltype = DNA  length = 330
FEATURE                 Location/Qualifiers
misc_feature            1..330
                        note = Description of Artificial Sequence: Synthetic
                         polynucleotide
source                  1..330
                        mol_type = other DNA
                        organism = synthetic construct
SEQUENCE: 135
cagtctgccc tgactcagcc tgcctccgtg tctgggtctc ctggacagac gatcaccatc   60
tcctgcaatg gaaccagcag tgacgttggt ggatttgact ctgtctcctg gtatcaacaa  120
tccccaggga aagcccccaa agtcatggtt tttgatgtca gtcatcggcc ctcaggtatc  180
tctaatcgct tctctggctc caagtccggc aacacggcct ccctgaccat ctctgggctc  240
cacattgagg acgagggcga ttatttctgc tcttcactga cagacagaag ccatcgcata  300
ttcggcggcg ggaccaaggt gaccgttcta                                   330

SEQ ID NO: 136          moltype = DNA  length = 411
FEATURE                 Location/Qualifiers
misc_feature            1..411
                        note = Description of Artificial Sequence: Synthetic
                         polynucleotide
source                  1..411
                        mol_type = other DNA
                        organism = synthetic construct
SEQUENCE: 136
caggaacaac tggtggagtc tgggggaggc gtggtccagc cggggggtc cctgagactc    60
tcctgtttag cgtctggatt cacgtttcac aaatatggca tgcactgggt ccgccaggct  120
ccaggcaagg gcctggagtg ggtggcactc atctcagatg acggaatgag gaaatatcat  180
tcagactcca tgtggggccg agtcaccatc tccagagaca attccaagaa cactctttat  240
ctgcaattca gcagcctgaa agtcgaagac acggctatgt tcttctgtgc gagagaggct  300
ggtgggccaa tctggcatga cgacgtcaaa tattacgatt ttaatgacgg ctactacaac  360
taccactaca tggacgtctg gggcaagggg accacggtca ccgtctcctc a           411

SEQ ID NO: 137          moltype = DNA  length = 330
FEATURE                 Location/Qualifiers
misc_feature            1..330
                        note = Description of Artificial Sequence: Synthetic
                         polynucleotide
source                  1..330
                        mol_type = other DNA
                        organism = synthetic construct
SEQUENCE: 137
cagtctgccc tgactcagcc tgcctccgtg tctgggtctc ctggacagac gatcaccatc   60
tcctgcaatg gaaccagcag tgacgttggt ggatttgact ctgtctcctg gtatcaacaa  120
tccccaggga aagcccccaa agtcatggtt tttgatgtca gtcatcggcc ctcaggtatc  180
tctaatcgct tctctggctc caagtccggc aacacggcct ccctgaccat ctctgggctc  240
cacattgagg acgagggcga ttatttctgc tcttcactga cagacagaag ccatcgcata  300
ttcggcggcg ggaccaaggt gaccgttcta                                   330

SEQ ID NO: 138          moltype = DNA  length = 1461
FEATURE                 Location/Qualifiers
misc_feature            1..1461
                        note = Description of Artificial Sequence: Synthetic
                         polynucleotide
source                  1..1461
                        mol_type = other DNA
                        organism = synthetic construct
SEQUENCE: 138
atggagtttg ggctgagctg ggttttcctc gcaactctgt taagagttgt gaagtgtcag   60
```

```
gaaaaactgg tggagtctgg gggaggcgtg gtccagccgg ggggtcccct gagactctcc    120
tgtttagcgt ctggattcac ctttcacaaa tatggcatgc actgggtccg ccaggctcca    180
ggcaagggcc tggagtgggt ggcactcatc tcagatgacg gaatgaggaa atatcattca    240
gactccatgt ggggccgagt caccatctcc agagacaatt ccaagaacac tctatatctg    300
caattcagca gcctgaaagt cgaagacacg gctatgttct tctgtgcgag agaggctggt    360
gggccaatct ggcatgacga cgtcaaatat tacgatttta atgacggcta ctacaactac    420
cactacatgg acgtctgggg caaggggacc acggtcaccg tctcctcagc gtcgaccaag    480
ggcccatcgg tcttccctct ggcaccatca tccaagtcga cctctggggg cacagcggcc    540
ctgggctgcc tggtcaagga ctacttcccc gaaccggtga cggtgtcgtg gaactcaggc    600
gccctgacca gcggcgtgca caccttcccg gctgtcctac agtcctcagg actctactcc    660
ctcagcagcg tggtgaccgt gccctccagc agcttgggca cccagaccta catctgcaac    720
gtgaatcaca agcccagcaa caccaaggtg gacaagagag ttgagcccaa atcttgtgac    780
aaaactcaca catgcccacc gtgcccagca cctgaactcc tggggggacc gtcagtcttc    840
ctcttccccc caaaacccaa ggacaccctc atgatctccc ggacccctga ggtcacatgc    900
gtggtggtgg acgtgagcca cgaagaccct gaggtcaagt tcaactggta cgtggacggc    960
gtggaggtgc ataatgccaa gacaaagccg cgggaggagc agtacaacag cacgtaccgt   1020
gtggtcagcg tcctcaccgt cctgcaccag gactggctga atggcaagga gtacaagtgc   1080
aaggtctcca acaaagccct cccagccccc atcgagaaaa ccatctccaa agccaaaggg   1140
cagccccgag aaccacaggt gtacaccctg cccccatccc gggaggagat gaccaagaac   1200
caggtcagcc tgacctgcct ggtcaaaggc ttctatccca gcgacatcgc cgtggagtgg   1260
gagagcaatg ggcagccgga gaacaactac aagaccacgc tcccgtgct ggactccgac    1320
ggctccttct tcctctatag caagctcacc gtggacaaga gcaggtggca gcaggggaac   1380
gtcttctcat gctccgtgat gcatgaggct ctgcacaacc actacacgca gaagagcctc   1440
tccctgtctc cgggtaaatg a                                              1461

SEQ ID NO: 139          moltype = AA   length = 467
FEATURE                 Location/Qualifiers
REGION                  1..467
                        note = Description of Artificial Sequence: Synthetic
                         polypeptide
source                  1..467
                        mol_type = protein
                        organism = synthetic construct
SEQUENCE: 139
QEKLVESGGG VVQPGGSLRL SCLASGFTFH KYGMHWVRQA PGKGLEWVAL ISDDGMRKYH     60
SDSMWGRVTI SRDNSKNTLY LQFSSLKVED TAMFFCAREA GGPIWHDDVK YYDFNDGYYN    120
YHYMDVWGKG TTVTVSSAST KGPSVFPLAP SSKSTSGGTA ALGCLVKDYF PEPVTVSWNS    180
GALTSGVHTF PAVLQSSGLY SLSSVVTVPS SSLGTQTYIC NVNHKPSNTK VDKRVEPKSC    240
DKTHTCPPCP APELLGGPSV FLFPPKPKDT LMISRTPEVT CVVVDVSHED PEVKFNWYVD    300
GVEVHNAKTK PREEQYNSTY RVVSVLTVLH QDWLNGKEYK CKVSNKALPA PIEKTISKAK    360
GQPREPQVYT LPPSREEMTK NQVSLTCLVK GFYPSDIAVE WESNGQPENN YKTTPPVLDS    420
DGSFFLYSKL TVDKSRWQQG NVFSCSVMHE ALHNHYTQKS LSLSPGK                  467

SEQ ID NO: 140          moltype = AA   length = 137
FEATURE                 Location/Qualifiers
REGION                  1..137
                        note = Description of Artificial Sequence: Synthetic
                         polypeptide
source                  1..137
                        mol_type = protein
                        organism = synthetic construct
SEQUENCE: 140
QEKLVESGGG VVQPGGSLRL SCLASGFTFH KYGMHWVRQA PGKGLEWVAL ISDDGMRKYH     60
SDSMWGRVTI SRDNSKNTLY LQFSSLKVED TAMFFCAREA GGPIWHDDVK YYDFNDGYYN    120
YHYMDVWGKG TTVTVSS                                                   137

SEQ ID NO: 141          moltype = DNA   length = 708
FEATURE                 Location/Qualifiers
misc_feature            1..708
                        note = Description of Artificial Sequence: Synthetic
                         polynucleotide
source                  1..708
                        mol_type = other DNA
                        organism = synthetic construct
SEQUENCE: 141
atggcctggg ctctgctatt cctcaccctc ttcactcagg gcacagggtc ctggggccag     60
tctgccctga ctcagcctgc ctccgtgtct gggtctcctg gacagacgat caccatctcc    120
tgcaatggaa ccagaaagtg acgttggtgga tttgactctg tctcctggta ccaacaatcc    180
ccaggaagag cccccaaagt catggttttt gatgtcagtc atcggccctc aggtatctct    240
aatcgcttct ctggctccaa gtccggcaac acggcctccc tgaccatctc tgggctccac    300
attgaggacg aggcgattta tttctgctct cactgacag acagaagcca tcgcatattc    360
ggcggcggga ccaagctgac cgttctaggt cagcccaagg ctgcccctc ggtcactctg    420
ttcccgcccc cctctgagga gcttcaagcc aacaaggcca cactggtgtg tctcataagt    480
gacttctacc cgggagccgt gacagtggcc tggaaggcag atagcagccc gtcaaggcg    540
ggagtggaga ccaccacacc ctccaaacaa agcaacaaca gtacgcggc cagcagctac    600
ctgagcctga cgcctgagca gtggaagtcc cacaaaagct acagctgcca ggtcacgcat    660
gaagggagca ccgtggagaa gacagtggcc cctacagaat gttcatag                 708

SEQ ID NO: 142          moltype = AA   length = 216
```

```
                                       -continued
FEATURE                    Location/Qualifiers
REGION                     1..216
                           note = Description of Artificial Sequence: Synthetic
                            polypeptide
source                     1..216
                           mol_type = protein
                           organism = synthetic construct
SEQUENCE: 142
QSALTQPASV SGSPGQTITI SCNGTRSDVG GFDSVSWYQQ SPGRAPKVMV FDVSHRPSGI    60
SNRFSGSKSG NTASLTISGL HIEDEGDYFC SSLTDRSHRI FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHKSYSCQVT HEGSTVEKTV APTECS                            216

SEQ ID NO: 143             moltype = AA  length = 24
FEATURE                    Location/Qualifiers
REGION                     1..24
                           note = Description of Artificial Sequence: Synthetic peptide
source                     1..24
                           mol_type = protein
                           organism = synthetic construct
SEQUENCE: 143
TLHGRRIYGI VAFNEWFTYF YMDV                                          24

SEQ ID NO: 144             moltype = AA  length = 6
FEATURE                    Location/Qualifiers
REGION                     1..6
                           note = Description of Artificial Sequence: Synthetic peptide
source                     1..6
                           mol_type = protein
                           organism = synthetic construct
SEQUENCE: 144
GASISD                                                               6

SEQ ID NO: 145             moltype = AA  length = 9
FEATURE                    Location/Qualifiers
REGION                     1..9
                           note = Description of Artificial Sequence: Synthetic peptide
source                     1..9
                           mol_type = protein
                           organism = synthetic construct
SEQUENCE: 145
YVHKSGDTN                                                            9

SEQ ID NO: 146             moltype = DNA  length = 693
FEATURE                    Location/Qualifiers
misc_feature               1..693
                           note = Description of Artificial Sequence: Synthetic
                            polynucleotide
source                     1..693
                           mol_type = other DNA
                           organism = synthetic construct
SEQUENCE: 146
atggcctgga cctttctcct cctcggcctc ctctctcact gcacagcctc tgtgacctcc    60
gatatatctg tgggcccagg agagacggcc aggatttcct gtggggaaaa gagccttgga   120
agtagagctg tacaatggta tcaacacagg gccggccagg cccctctttt aatcatatat   180
aataatcagg accggccctc agggatccct gagcgattct ctggctcccc tgactcccct   240
tttgggacca cggccaccct gaccatcacc agtgtcgaag ccggggatga ggccgactat   300
tactgtcata tatgggatag tagagttccc accaaatggg tcttcggcgg agggaccacg   360
ctgaccgtgt taggtcagcc caaggctgcc cctcggtca ctctgttccc gccctcctct    420
gaggagcttc aagccaacaa ggccacactg gtgtgtctca taagtgactt ctacccggga   480
gccgtgacag tggcctggaa ggcagatagc agccccgtca aggcgggagt ggagaccacc   540
acaccctcca acaaagcaa caacaagtac gcggccagca gctacctgag cctgacgcct   600
gagcagtgga agtcccacaa aagctacagc tgccaggtca cgcatgaagg gagcaccgtg   660
gagaagacag tggccccta cagaatgttca tag                                693

SEQ ID NO: 147             moltype = DNA  length = 315
FEATURE                    Location/Qualifiers
misc_feature               1..315
                           note = Description of Artificial Sequence: Synthetic
                            polynucleotide
source                     1..315
                           mol_type = other DNA
                           organism = synthetic construct
SEQUENCE: 147
tccgatatat ctgtggcccc aggagagacg gccaggattt cctgtgggga aagagccttt    60
ggaagtagag ctgtacaatg gtatcaacac agggccggcc aggccccctc tttaatcata   120
taataatc aggaccggcc ctcagggatc cctgagcgat tctctggctc ccctgactcc     180
ccttttggga ccacgccac cctgaccatc accagtgtcg aagccgggga tgaggccgac    240
tattactgtc atatatggga tagtagagtt cccaccaaat gggtcttcgg cggagggacc   300
```
acgctgaccg tgtta                                                            315

SEQ ID NO: 148          moltype = AA   length = 211
FEATURE                 Location/Qualifiers
REGION                  1..211
                        note = Description of Artificial Sequence: Synthetic
                        polypeptide
source                  1..211
                        mol_type = protein
                        organism = synthetic construct
SEQUENCE: 148
SDISVAPGET ARISCGEKSL GSRAVQWYQH RAGQAPSLII YNNQDRPSGI PERFSGSPDS   60
PFGTTATLTI TSVEAGDEAD YYCHIWDSRV PTKWVFGGGT TLTVLGQPKA APSVTLFPPS  120
SEELQANKAT LVCLISDFYP GAVTVAWKAD SSPVKAGVET TTPSKQSNNK YAASSYLSLT  180
PEQWKSHKSY SCQVTHEGST VEKTVAPTEC S                                 211

SEQ ID NO: 149          moltype = AA   length = 105
FEATURE                 Location/Qualifiers
REGION                  1..105
                        note = Description of Artificial Sequence: Synthetic
                        polypeptide
source                  1..105
                        mol_type = protein
                        organism = synthetic construct
SEQUENCE: 149
SDISVAPGET ARISCGEKSL GSRAVQWYQH RAGQAPSLII YNNQDRPSGI PERFSGSPDS   60
PFGTTATLTI TSVEAGDEAD YYCHIWDSRV PTKWVFGGGT TLTVL                  105

SEQ ID NO: 150          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 150
GEKSLGSRAV Q                                                        11

SEQ ID NO: 151          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 151
NNQDRPS                                                             7

SEQ ID NO: 152          moltype = AA   length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 152
HIWDSRVPTK WV                                                       12

SEQ ID NO: 153          moltype = DNA  length = 1446
FEATURE                 Location/Qualifiers
misc_feature            1..1446
                        note = Description of Artificial Sequence: Synthetic
                        polynucleotide
source                  1..1446
                        mol_type = other DNA
                        organism = synthetic construct
SEQUENCE: 153
atgaaacacc tgtggttctt ccttctcctg gtggcagctc ccagatgggt cctgtcccag   60
gttcatctgc aggagtcggg ccccggactg gtgaagcctt cggagaccct gtccctcacg  120
tgcaatgtgt ctgggaccct cgtgcgtgat aactactgga gctggatcag acaacccctc  180
gggaagcaac tgagtggat tggctatgtc catgacagcg ggacacgaa ttacaacccc    240
tccctgaaga gtcgagtcca cttatcgttg acaagtcca aaaacctggt gtccctgagg   300
ctgaccggcg tgaccgccgc ggactcggcc atatattatt gcgcgacaac aaaacacggg  360
aggaggattt atggcgttcg tgccttcaaa gagtggttca cctatttcta catggacgtc  420
tggggcaaag ggacttcggt caccgtctcc tcagctcca ccaagggccc atcggtcttc   480
cccctgcac cctcctccaa gagcacctct ggggcacag cggccctggg ctgcctggtc   540
aaggactact cccccgaacc ggtgacggtg tcgtggaact caggcgccct gaccagcggc  600
gtgcacacct tcccggctgt cctacagtcc tcaggactac actccctcag cagcgtggtg  660
accgtgccct ccagcagctt gggcacccag acctacatct gcaacgtgaa tcacaagccc  720

```
agcaacacca aggtggacaa gagagttgag cccaaatctt gtgacaaaac tcacacatgc  780
ccaccgtgcc cagcacctga actcctgggg ggaccgtcag tcttcctctt cccccccaaaa  840
cccaaggaca ccctcatgat ctcccggacc cctgaggtca catgcgtggt ggtggacgtg  900
agccacgaag accctgaggt caagttcaac tggtacgtgg acggcgtgga ggtgcataat  960
gccaagacaa agccgcggga ggagcagtac aacagcacgt accgtgtgt cagcgtcctc 1020
accgtcctgc accaggactg gctgaatggc aaggagtaca agtgcaaggt ctccaacaaa 1080
gccctcccag cccccatcga gaaaaccatc tccaaagcca agggcagcc ccgagaacca 1140
caggtgtaca ccctgccccc atcccggag gagatgacca gaaccaggt cagcctgacc 1200
tgcctggtca aaggcttcta tcccagcgac atcgccgtgg agtgggagag caatgggcag 1260
ccggagaaca actacaagac cacgcctcc gtgctgact ccgacggctc cttcttcctc 1320
tatagcaagc tcaccgtgga caagagcagg tggcagcagg ggaacgtctt ctcatgctcc 1380
gtgatgcatg aggctctgca caaccactac acgcagaaga gcctctccct gtctccgggt 1440
aaatga                                                             1446

SEQ ID NO: 154           moltype = DNA  length = 396
FEATURE                  Location/Qualifiers
misc_feature             1..396
                         note = Description of Artificial Sequence: Synthetic
                         polynucleotide
source                   1..396
                         mol_type = other DNA
                         organism = synthetic construct
SEQUENCE: 154
caggttcatc tgcaggagtc gggccccgga ctggtgaagc cttcggagac cctgtccctc  60
acgtgcaatg tgtctgggac cctgtgcgt gataactact ggagctggat cagacaaccc 120
ctcggaagc aacctgagtg gattggctat gtccatgaca gcggggacac gaattacaac 180
ccctccctga agagtcgagt ccacttatcg ttggacaagt ccaaaaacct ggtgtccctg 240
aggctgaccg cgtgaccgc cgcggactcg gccatatatt attgcgcgac aacaaaaac 300
gggaggagga tttatggcgt cgttgccttc aaagagtggt tcacctattt ctacatggac 360
gtctggggca aagggacttc ggtcaccgtc tcctca                            396

SEQ ID NO: 155           moltype = AA  length = 481
FEATURE                  Location/Qualifiers
REGION                   1..481
                         note = Description of Artificial Sequence: Synthetic
                         polypeptide
source                   1..481
                         mol_type = protein
                         organism = synthetic construct
SEQUENCE: 155
MKHLWFFLLL VAAPRWVLSQ VHLQESGPGL VKPSETLSLT CNVSGTLVRD NYWSWIRQPL  60
GKQPEWIGYV HDSGDTNYNP SLKSRVHLSL DKSKNLVSLR LTGVTAADSA IYYCATTKHG 120
RRIYGVVAFK EWFTYFYMDV WGKGTSVTVS SASTKGPSVF PLAPSSKSTS GGTAALGCLV 180
KDYFPEPVTV SWNSGALTSG VHTFPAVLQS SGLYSLSSVV TVPSSSLGTQ TYICNVNHKP 240
SNTKVDKRVE PKSCDKTHTC PPCPAPELLG GPSVFLFPPK PKDTLMISRT PEVTCVVVDV 300
SHEDPEVKFN WYVDGVEVHN AKTKPREEQY NSTYRVVSVL TVLHQDWLNG KEYKCKVSNK 360
ALPAPIEKTI SKAKGQPREP QVYTLPPSRE EMTKNQVSLT CLVKGFYPSD IAVEWESNGQ 420
PENNYKTTPP VLDSDGSFFL YSKLTVDKSR WQQGNVFSCS VMHEALHNHY TQKSLSLSPG 480
K                                                                  481

SEQ ID NO: 156           moltype = AA  length = 132
FEATURE                  Location/Qualifiers
REGION                   1..132
                         note = Description of Artificial Sequence: Synthetic
                         polypeptide
source                   1..132
                         mol_type = protein
                         organism = synthetic construct
SEQUENCE: 156
QVHLQESGPG LVKPSETLSL TCNVSGTLVR DNYWSWIRQP LGKQPEWIGY VHDSGDTNYN  60
PSLKSRVHLS LDKSKNLVSL RLTGVTAADS AIYYCATTKH GRRIYGVVAF KEWFTYFYMD 120
VWGKGTSVTV SS                                                      132

SEQ ID NO: 157           moltype = AA  length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 157
YVHDSGDTNY NPSLKS                                                   16

SEQ ID NO: 158           moltype = DNA  length = 693
FEATURE                  Location/Qualifiers
misc_feature             1..693
                         note = Description of Artificial Sequence: Synthetic
                         polynucleotide
source                   1..693
```

```
                        mol_type = other DNA
                        organism = synthetic construct
SEQUENCE: 158
atggcctgga ccgttctcct cctcggcctc ctctctcact gcacaggcgc ggtgtctacc    60
tttgtgtcag tggccccagg acagacggcc aggattactt gtggggaaga gagcctttga   120
agtagatctg ttatttggta tcaacagagg ccaggccagg ccccttcatt aatcatctat   180
aataataatg accggccctc agggattcct gaccgatttt ctgggtcccc tggctccact   240
tttgggacca cggccaccct gaccatcacc agtgtcgaag ccggggatga ggccgactat   300
tattgtcata tctgggatag tagacgacca accaattggg tcttcggcga agggaccaca   360
ctgatcgtgt taggtcagcc caaggctgcc ccctcggtca ctctgttccc gccctcctct   420
gaggagcttc aagccaacaa ggccacactg gtgtgtctca agtgacttc taccccggga   480
gccgtgacga tggcctggaa ggcagatagc agccccgtca aggcgggagt ggagaccacc   540
acaccctcca acaaagcaa caacaagtac gcggccagca gctacctgag cctgacgcct   600
gagcagtgga agtcccacaa aagctacagc tgccaggtca cgcatgaagg gagcaccgtg   660
gagaagacag tggcccctac agaatgttca tag                                693

SEQ ID NO: 159          moltype = DNA  length = 315
FEATURE                 Location/Qualifiers
misc_feature            1..315
                        note = Description of Artificial Sequence: Synthetic
                         polynucleotide
source                  1..315
                        mol_type = other DNA
                        organism = synthetic construct
SEQUENCE: 159
acctttgtgt cagtggcccc aggacagacg gccaggatta cttgtgggga agagagcctt    60
ggaagtagat ctgttatttg gtatcaacag aggccaggcc aggccccttc attaatcatc   120
tataataata atgaccggcc ctcagggatt cctgaccgat tttctgggtc ccctggctcc   180
acttttggga ccacggccac cctgaccatc accagtgtcg aagccgggga tgaggccgac   240
tattattgtc atatctggga tagtagacga ccaaccaatt gggtcttcgg cgaagggacc   300
acactgatcg tgtta                                                   315

SEQ ID NO: 160          moltype = AA  length = 230
FEATURE                 Location/Qualifiers
REGION                  1..230
                        note = Description of Artificial Sequence: Synthetic
                         polypeptide
source                  1..230
                        mol_type = protein
                        organism = synthetic construct
SEQUENCE: 160
MAWTVLLLGL LSHCTGAVST FVSVAPGQTA RITCGEESLG SRSVIWYQQR PGQAPSLIIY    60
NNNDRPSGIP DRFSGSPGST FGTTATLTIT SVEAGDEADY YCHIWDSRRP TNWVFGEGTT   120
LIVLGQPKAA PSVTLFPPSS EELQANKATL VCLISDFYPG AVTVAWKADS SPVKAGVETT   180
TPSKQSNNKY AASSYLSLTP EQWKSHKSYS CQVTHEGSTV EKTVAPTECS              230

SEQ ID NO: 161          moltype = AA  length = 105
FEATURE                 Location/Qualifiers
REGION                  1..105
                        note = Description of Artificial Sequence: Synthetic
                         polypeptide
source                  1..105
                        mol_type = protein
                        organism = synthetic construct
SEQUENCE: 161
TFVSVAPGQT ARITCGEESL GSRSVIWYQQ RPGQAPSLII YNNNDRPSGI PDRFSGSPGS    60
TFGTTATLTI TSVEAGDEAD YYCHIWDSRR PTNWVFGEGT TLIVL                   105

SEQ ID NO: 162          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 162
GEESLGSRSV I                                                        11

SEQ ID NO: 163          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 163
NNNDRPS                                                             7

SEQ ID NO: 164          moltype = AA  length = 12
```

```
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 164
HIWDSRRPTN WV                                                          12

SEQ ID NO: 165          moltype = DNA  length = 1446
FEATURE                 Location/Qualifiers
misc_feature            1..1446
                        note = Description of Artificial Sequence: Synthetic
                         polynucleotide
source                  1..1446
                        mol_type = other DNA
                        organism = synthetic construct
SEQUENCE: 165
atgaaacacc tgtggatctt ccttctcctg gtggcaactc ccagatgggg cgagtcccag    60
ctgcacctgc aggagtcggg cccagggctg gtgaagcctc cggagaccct gtccctcacg   120
tgtagtgtgt ctggcgcctc catcaatgat gcctattgga gttggattcg gcagtcccca   180
gggaagcggc ctgagtgggt tggatatgtc catcacaggt gtgacacaaa ttataatccc   240
tcactcaaga ggcgcgtcac gttttcatta gacacggcca agaatgaagt gtccctgaaa   300
ttagtagacc tgaccgctgc ggactcggcc acatattttt gtgcgcgagc acttcacggg   360
aagaggattt atgggatagt tgccctcgga gagttgttca cctacttcta catggacgtc   420
tggggcagag ggactgcggt caccgtctcc tcagcctcca ccaagggccc atcggtcttc   480
cccctggcac cctcctccaa gagcacctct gggggcacag cggccctggg ctgcctggtc   540
aaggactact ccccgaaccc ggtgacggtg tcgtggaact caggcgccct gaccagcggc   600
gtgcacacct tcccggctgt cctacagtcc tcaggactct actccctcag cagcgtggtg   660
accgtgccct ccagcagctt gggcacccag acctacatct gcaacgtgaa tcacaagccc   720
agcaacacca aggtggacaa gagagttgag cccaaatctt gtgacaaaac tcacacatgc   780
ccaccgtgcc cagcacctga actcctgggg ggaccgtcag tcttcctctt ccccccaaaa   840
cccaaggaca cctctcatga tctcccggac ccctgaggtca catgcgtggt ggtggacgtg   900
agccacgaag accctgaggt caagttcaac tggtacgtgg acggcgtgga ggtgcataat   960
gccaagacaa agccgcggga ggagcagtac aacagcacgt accgtgtggt cagcgtcctc  1020
accgtcctgc accaggactg gctgaatggc aaggagtaca agtgcaaggt ctccaacaaa  1080
gccctcccag cccccatcga gaaaaccatc tccaaagcca agggcagccc cgagaaccac  1140
caggtgtaca ccctgccccc atcccgggag gagatgacca agaaccaggt cagcctgacc  1200
tgcctggtca aaggcttcta tcccagcgac atcgccgtgg agtgggagag caatgggcag  1260
ccggagaaca actacaagac cacgcctccc gtgctggact ccgacggctc cttcttcctc  1320
tatagcaagc tcaccgtgga caagagcagg tggcagcagg ggaacgtctt ctcatgctcc  1380
gtgatgcatg aggctctgca caaccactac acgcagaaga gcctctccct gtctccgggt  1440
aaatga                                                              1446

SEQ ID NO: 166          moltype = DNA  length = 396
FEATURE                 Location/Qualifiers
misc_feature            1..396
                        note = Description of Artificial Sequence: Synthetic
                         polynucleotide
source                  1..396
                        mol_type = other DNA
                        organism = synthetic construct
SEQUENCE: 166
cagctgcacc tgcaggagtc gggcccaggg ctggtgaagc ctccggagac cctgtccctc    60
acgtgtagtg tgtctggcgc ctccatcaat gatgcctatt ggagttggat tcggcagtcc   120
ccagggaagc ggcctgagtg ggttggatat gtccatcaca ggtgtgacac aaattataat   180
ccctcactca agaggcgcgt cacgttttca ttagacacgg ccaagaatga agtgtccctg   240
aaattagtag acctgaccgc tgcggactcg gccacatatt tttgtgcgcg agcacttcac   300
gggaagagga tttatgggat agttgccctc ggagagttgt tcacctactt ctacatggac   360
gtctggggca gggggactgc ggtcaccgtc tcctca                             396

SEQ ID NO: 167          moltype = AA  length = 481
FEATURE                 Location/Qualifiers
REGION                  1..481
                        note = Description of Artificial Sequence: Synthetic
                         polypeptide
source                  1..481
                        mol_type = protein
                        organism = synthetic construct
SEQUENCE: 167
MKHLWIFLLL VATPRWVESQ LHLQESGPGL VKPPETLSLT CSVSGASIND AYWSWIRQSP    60
GKRPEWVGYV HHSGDTNYNP SLKRRVTFSL DTAKNEVSLK LVDLTAADSA TYFCARALHG   120
KRIYGIVALG ELFTYFYMDV WGKGTAVTVS SASTKGPSVF PLAPSSKSTS GGTAALGCLV   180
KDYFPEPVTV SWNSGALTSG VHTFPAVLQS SGLYSLSSVV TVPSSSLGTQ TYICNVNHKP   240
SNTKVDKRVE PKSCDKTHTC PPCPAPELLG GPSVFLFPPK PKDTLMISRT PEVTCVVVDV   300
SHEDPEVKFN WYVDGVEVHN AKTKPREEQY NSTYRVVSVL TVLHQDWLNG KEYKCKVSNK   360
ALPAPIEKTI SKAKGQPREP QVYTLPPSRE EMTKNQVSLT CLVKGFYPSD IAVEWESNGQ   420
PENNYKTTPP VLDSDGSFFL YSKLTVDKSR WQQGNVFSCS VMHEALHNHY TQKSLSLSPG   480
K                                                                  481
```

```
SEQ ID NO: 168            moltype = AA   length = 132
FEATURE                   Location/Qualifiers
REGION                    1..132
                          note = Description of Artificial Sequence: Synthetic
                           polypeptide
source                    1..132
                          mol_type = protein
                          organism = synthetic construct
SEQUENCE: 168
QLHLQESGPG LVKPPETLSL TCSVSGASIN DAYWSWIRQS PGKRPEWVGY VHHSGDTNYN    60
PSLKRRVTFS LDTAKNEVSL KLVDLTAADS ATYFCARALH GKRIYGIVAL GELFTYFYMD   120
VWGKGTAVTV SS                                                      132

SEQ ID NO: 169            moltype = AA   length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 169
DAYWS                                                                5

SEQ ID NO: 170            moltype = AA   length = 16
FEATURE                   Location/Qualifiers
REGION                    1..16
                          note = Description of Artificial Sequence: Synthetic peptide
source                    1..16
                          mol_type = protein
                          organism = synthetic construct
SEQUENCE: 170
YVHHSGDTNY NPSLKR                                                   16

SEQ ID NO: 171            moltype = AA   length = 24
FEATURE                   Location/Qualifiers
REGION                    1..24
                          note = Description of Artificial Sequence: Synthetic peptide
source                    1..24
                          mol_type = protein
                          organism = synthetic construct
SEQUENCE: 171
ALHGKRIYGI VALGELFTYF YMDV                                          24

SEQ ID NO: 172            moltype = AA   length = 6
FEATURE                   Location/Qualifiers
REGION                    1..6
                          note = Description of Artificial Sequence: Synthetic peptide
source                    1..6
                          mol_type = protein
                          organism = synthetic construct
SEQUENCE: 172
GASIND                                                               6

SEQ ID NO: 173            moltype = AA   length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 173
YVHHSGDTN                                                            9

SEQ ID NO: 174            moltype = DNA   length = 693
FEATURE                   Location/Qualifiers
misc_feature              1..693
                          note = Description of Artificial Sequence: Synthetic
                           polynucleotide
source                    1..693
                          mol_type = other DNA
                          organism = synthetic construct
SEQUENCE: 174
atggcctgga ccgttctcct cctcggcctc ctctctcact gcacaggctc tctggcctcc    60
tctatgtccg tgtccccggg ggagacggcc aagatctcct gtggaaaaga gagcattggt   120
agcagagctg tgcaatggta tcagcagaag ccaggccagc cccccatt gattatctat    180
aataatcagg accgccccgc aggggtccct gagcgattct ctgcctcccc tgacttccgt   240
cctgggacca cggccaccct gaccatcacc aatgtcgacg ccgaggatga ggccgactat   300
tactgtcata tatatgatgc tagaggtggc accaattggg tcttcgacag aggaccaca   360
```

```
ctgaccgtct taggtcagcc caaggctgcc cctcggtca ctctgttccc gccctcctct   420
gaggagcttc aagccaacaa ggccacactg tgtgtctca taagtgactt ctacccggga   480
gccgtgacag tggcctggaa ggcagatagc agcccgtca aggcgggagt ggagaccacc   540
acaccctcca acaaagcaa caacaagtac gcggccagca gctacctgag cctgacgcct   600
gagcagtgga agtcccacaa aagctacagc tgccaggtca cgcatgaagg gagcaccgtg   660
gagaagacag tggcccctac agaatgttca tag                                693

SEQ ID NO: 175          moltype = DNA  length = 315
FEATURE                 Location/Qualifiers
misc_feature            1..315
                        note = Description of Artificial Sequence: Synthetic
                         polynucleotide
source                  1..315
                        mol_type = other DNA
                        organism = synthetic construct
SEQUENCE: 175
tcctctatgt ccgtgtcccc gggggagacg gccaagatct cctgtggaaa agagagcatt   60
ggtagcagag ctgtgcaatg gtatcagcag aagccaggcc agcccccctc attgattatc   120
tataataatc aggaccgccc cgcaggggtc cctgagcgat tctctgcctc ccctgacttc   180
cgtcctggga ccacggccac cctgaccatc accaatgtcg acgccgagga tgaggccgac   240
tattactgtc atatatatga tgctagaggt ggcaccaatt gggtcttcga cagagggacc   300
acactgaccg tctta                                                    315

SEQ ID NO: 176          moltype = AA  length = 230
FEATURE                 Location/Qualifiers
REGION                  1..230
                        note = Description of Artificial Sequence: Synthetic
                         polypeptide
source                  1..230
                        mol_type = protein
                        organism = synthetic construct
SEQUENCE: 176
MAWTVLLLGL LSHCTGSLAS SMSVSPGETA KISCGKESIG SRAVQWYQQK PGQPPSLIIY    60
NNQDRPAGVP ERFSASPDFR PGTTATLTIT NVDAEDEADY YCHIYDARGG TNWVFDRGTT   120
LTVLGQPKAA PSVTLFPPSS EELQANKATL VCLISDFYPG AVTVAWKADS SPVKAGVETT   180
TPSKQSNNKY AASSYLSLTP EQWKSHKSYS CQVTHEGSTV EKTVAPTECS              230

SEQ ID NO: 177          moltype = AA  length = 105
FEATURE                 Location/Qualifiers
REGION                  1..105
                        note = Description of Artificial Sequence: Synthetic
                         polypeptide
source                  1..105
                        mol_type = protein
                        organism = synthetic construct
SEQUENCE: 177
SSMSVSPGET AKISCGKESI GSRAVQWYQQ KPGQPPSLII YNNQDRPAGV PERFSASPDF    60
RPGTTATLTI TNVDAEDEAD YYCHIYDARG GTNWVFDRGT TLTVL                   105

SEQ ID NO: 178          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 178
GKESIGSRAV Q                                                         11

SEQ ID NO: 179          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 179
NNQDRPA                                                              7

SEQ ID NO: 180          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 180
HIYDARGGTN WV                                                        12
```

| SEQ ID NO: 181 | moltype = DNA length = 1455 |
| --- | --- |
| FEATURE | Location/Qualifiers |
| misc_feature | 1..1455 |
| | note = Description of Artificial Sequence: Synthetic polynucleotide |
| source | 1..1455 |
| | mol_type = other DNA |
| | organism = synthetic construct |

SEQUENCE: 181

```
atgaaacacc tgtggttctt cttcctgctg gtggcggctc ccagatgcgt cctgtcccag   60
tcgcagctgc aggagtcggg cccacgactg gtggaggcct cggagaccct gtcactcacg  120
tgcaatgtgt ccggcgagtc cactggtgcc tgtacttatt tctggggctg ggtccggcag  180
gccccaggga aggggctgga gtggatcggg agtttgtccc attgtcagag tttctggggt  240
tccggtttgga ccttccacaa cccgtctctc aagagtcgac tcacgatttc actcgacacg  300
cccaagaatc aggtcttcct caagctcact tctctgactg ccgcggacac ggccacttac  360
tactgtgcgc gattcgacgg cgaagtcttg gtctataatc attggccaaa gccggcctgg  420
gtggaccctc ggggccgcgg aataccggtc accgtctcct cagcctccac caagggccca  480
tcggtcttcc ccctggcacc ctcctccaag agcacctctg ggggcacagc ggccctgggc  540
tgcctggtca aggactactt ccccgaaccg gtgacggtgt cgtggaactc aggcgccctg  600
accagcggcg tgcacacctt cccggctgtc ctacagtcct caggactcta ctccctcagc  660
agcgtggtga ccgtgccctc cagcagcttg gcacccagac ctacatctg caacgtgaat  720
cacaagccca gcaacaccaa ggtggacaag agagttgcag ccaaatcttg tgacaaaact  780
cacacatgcc caccgtgccc agcacctgaa ctcctggggg gaccgtcagt cttcctcttc  840
cccccaaaac ccaaggacac cctcatgatc tcccggaccc ctgaggtcac atgcgtggtg  900
gtggacgtga gccacgaaga ccctgaggtc aagttcaact ggtacgtgga cggcgtggag  960
gtgcataatg ccaagacaaa gccgcgggag gagcagtaca acagcacgta ccgtgtggtc 1020
agcgtcctca ccgtcctgca ccaggactgg ctgaatggca aggagtacaa gtgcaaggtc 1080
tccaacaaag cctccccagc ccccatcgag aaaaccatct ccaaagccaa agggcagccc 1140
cgagaaccac aggtgtacac cctgccccca tcccgggagg agatgaccaa gaaccaggtc 1200
agcctgacct gcctggtcaa aggcttctat cccagcgaca tcgccgtgga gtgggagagc 1260
aatgggcagc cggagaacaa ctacaagacc acgcctcccg tgctggactc cgacggctcc 1320
ttcttcctct atagcaagct caccgtggac aagagcaggt ggcagcaggg gaacgtcttc 1380
tcatgctccg tgatgcatga ggctctgcac aaccactaca cgcagaagag cctctccctg 1440
tctccgggta aatga                                                  1455
```

| SEQ ID NO: 182 | moltype = DNA length = 405 |
| --- | --- |
| FEATURE | Location/Qualifiers |
| misc_feature | 1..405 |
| | note = Description of Artificial Sequence: Synthetic polynucleotide |
| source | 1..405 |
| | mol_type = other DNA |
| | organism = synthetic construct |

SEQUENCE: 182

```
cagtcgcagc tgcaggagtc gggcccacga ctggtggagg cctcggagac cctgtcactc   60
acgtgcaatg tgtccggcga gtccactggt gcctgtactt atttctgggg ctgggtccgg  120
caggccccag ggaaggggct ggagtggatc gggagtttgt ccattgtcag agtttctggg  180
gttccggttt ggaccttcca caacccgtct ctcaagagtc gactcacgat ttcactcgac  240
acgcccaaga tcaggtcttt cctcaagctc acttctctga ctgccgcgga cacggccact  300
tactactgtg cgcgattcga cggcgaagtc ttggtctata tcattggcc aaagccggcc  360
tggggtggacc tctggggccg cggaataccg gtcaccgtct cctca                 405
```

| SEQ ID NO: 183 | moltype = AA length = 484 |
| --- | --- |
| FEATURE | Location/Qualifiers |
| REGION | 1..484 |
| | note = Description of Artificial Sequence: Synthetic polypeptide |
| source | 1..484 |
| | mol_type = protein |
| | organism = synthetic construct |

SEQUENCE: 183

```
MKHLWFFFLL VAAPRCVLSQ SQLQESGPRL VEASETLSLT CNVSGESTGA CTYFWGWVRQ   60
APGKGLEWIG SLSHCQSFWG SGWTFHNPSL KSRLTISLDT PKNQVFLKLT SLTAADTATY  120
YCARFDGEVL VYNHWPKPAW VDLWGRGIPV TVSSASTKGP SVFPLAPSSK STSGGTAALG  180
CLVKDYFPEP VTVSWNSGAL TSGVHTFPAV LQSSGLYSLS SVVTVPSSSL GTQTYICNVN  240
HKPSNTKVDK RVEPKSCDKT HTCPPCPAPE LLGGPSVFLF PPKPKDTLMI SRTPEVTCVV  300
VDVSHEDPEV KFNWYVDGVE VHNAKTKPRE EQYNSTYRVV SVLTVLHQDW LNGKEYKCKV  360
SNKALPAPIE KTISKAKGQP REPQVYTLPP SREEMTKNQV SLTCLVKGFY PSDIAVEWES  420
NGQPENNYKT TPPVLDSDGS FFLYSKLTVD KSRWQQGNVF SCSVMHEALH NHYTQKSLSL  480
SPGK                                                              484
```

| SEQ ID NO: 184 | moltype = AA length = 135 |
| --- | --- |
| FEATURE | Location/Qualifiers |
| REGION | 1..135 |
| | note = Description of Artificial Sequence: Synthetic polypeptide |
| source | 1..135 |
| | mol_type = protein |
| | organism = synthetic construct |

```
SEQUENCE: 184
QSQLQESGPR LVEASETLSL TCNVSGESTG ACTYFWGWVR QAPGKGLEWI GSLSHCQSFW   60
GSGWTFHNPS LKSRLTISLD TPKNQVFLKL TSLTAADTAT YYCARFDGEV LVYNHWPKPA  120
WVDLWGRGIP VTVSS                                                  135

SEQ ID NO: 185          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 185
ACTYFWG                                                             7

SEQ ID NO: 186          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 186
SLSHCQSFWG SGWTFHNPSL KS                                           22

SEQ ID NO: 187          moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 187
FDGEVLVYNH WPKPAWVDL                                               19

SEQ ID NO: 188          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 188
GESTGACT                                                            8

SEQ ID NO: 189          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 189
SLSHCQSFWG SGWTF                                                   15

SEQ ID NO: 190          moltype = DNA  length = 693
FEATURE                 Location/Qualifiers
misc_feature            1..693
                        note = Description of Artificial Sequence: Synthetic
                         polynucleotide
source                  1..693
                        mol_type = other DNA
                        organism = synthetic construct
SEQUENCE: 190
atggcctggg ctctgctcct cctcaccctc ctcactcagg cacaggggc ctggcccag     60
tctgccctga tcagcctcc ctccgcgtcc gggtctcctg acagtcaat caccatctcc   120
tgcaatggaa ccgccactaa cttttgtctcc tggtaccaac aattcccaga caaggccccc  180
aaactcatca ttttttgggt cgataagcgc ccccccggtg tccccgatcg ttttctctggc 240
tcccggtctg gcacgacggc ctcccttacc gtctcccgac tccagactga cgatgaggct  300
gtctattatt gcggttcact tgtcggcaac tgggatgtga ttttcggcgg agggaccacc  360
ttgaccgtcc taggtcagcc caaggctgcc cctcggtca ctctgttccc gccctcctct   420
gaggagcttc aagccaacaa ggccacactg gtgtgtctca agtgactt ctaccccgga    480
gccgtgacag tggcctggaa ggcagatagc agccccgtca aggcgggagt ggagaccacc  540
acaccctcca aacaaagcaa caacaagtac cggccagca gctacctgag cctgacgcct   600
gagcagtgga agtcccacaa aagctacagc tgccaggtca cgcatgaagg gagcaccgtg   660
gagaagacag tggcccctac agaatgttca tag                                693

SEQ ID NO: 191          moltype = DNA  length = 315
FEATURE                 Location/Qualifiers
```

```
misc_feature           1..315
                       note = Description of Artificial Sequence: Synthetic
                         polynucleotide
source                 1..315
                       mol_type = other DNA
                       organism = synthetic construct
SEQUENCE: 191
cagtctgccc tgactcagcc tccctccgcg tccgggtctc ctggacagtc aatcaccatc    60
tcctgcaatg gaaccgccac taactttgtc tcctggtacc aacaattccc agacaaggcc   120
cccaaactca tcatttttgg ggtcgataag cgccccccg gtgtcccga tcgtttctct    180
ggctcccggt ctggcacgac ggcctcctt accgtctccc gactccagac tgacgatgag   240
gctgtctatt attgcggttc acttgtcggc aactgggatg tgattttcgg cggagggacc   300
accttgaccg tccta                                                    315

SEQ ID NO: 192         moltype = AA  length = 230
FEATURE                Location/Qualifiers
REGION                 1..230
                       note = Description of Artificial Sequence: Synthetic
                         polypeptide
source                 1..230
                       mol_type = protein
                       organism = synthetic construct
SEQUENCE: 192
MAWALLLLTL LTQGTGAWAQ SALTQPPSAS GSPGQSITIS CNGTATNFVS WYQQFPDKAP    60
KLIIFGVDKR PPGVPDRFSG SRSGTTASLT VSRLQTDDEA VYYCGSLVGN WDVIFGGGTT   120
LTVLGQPKAA PSVTLFPPSS EELQANKATL VCLISDFYPG AVTVAWKADS SPVKAGVETT   180
TPSKQSNNKY AASSYLSLTP EQWKSHKSYS CQVTHEGSTV EKTVAPTECS              230

SEQ ID NO: 193         moltype = AA  length = 105
FEATURE                Location/Qualifiers
REGION                 1..105
                       note = Description of Artificial Sequence: Synthetic
                         polypeptide
source                 1..105
                       mol_type = protein
                       organism = synthetic construct
SEQUENCE: 193
QSALTQPPSA SGSPGQSITI SCNGTATNFV SWYQQFPDKA PKLIIFGVDK RPPGVPDRFS    60
GSRSGTTASL TVSRLQTDDE AVYYCGSLVG NWDVIFGGGT TLTVL                   105

SEQ ID NO: 194         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 194
NGTATNFVS                                                             9

SEQ ID NO: 195         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 195
GVDKRPP                                                               7

SEQ ID NO: 196         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 196
GSLVGNWDVI                                                           10

SEQ ID NO: 197         moltype = DNA  length = 1455
FEATURE                Location/Qualifiers
misc_feature           1..1455
                       note = Description of Artificial Sequence: Synthetic
                         polynucleotide
source                 1..1455
                       mol_type = other DNA
                       organism = synthetic construct
SEQUENCE: 197
```

```
atgaaacacc tgtggttctt cctcctgctg gtggcggctc ccagatgggt cctgtcccag    60
ccgcagctgc aggagtcggg gccaggactg gtggaggctt cggagaccct gtccctcacc   120
tgcactgtgt ccggcgactc cactgctgct tgtgactatt tctggggctg gtccggcag   180
cccccaggga agggcctgga gtggattggg ggtttgtcac attgtgcagg ttactacaat   240
actggctgga cctaccacaa cccgtctctc aagagtcggc tcacgatttc actcgacacc   300
cccaagaatc aggtcttcct gaagttaaat tctgtgaccg ccgcggacac ggccatttac   360
tactgtgcgc gattcgacgg cgaagttttg tgtaccacg attggccaaa gccggcctgg   420
gtcgacctct ggggccgggg aactttggtc accgtctcct cagcctccac caagggccca   480
tcggtcttcc ccctggcacc ctcctccaag agcacctctg gggcacagc ggcctgggc   540
tgcctggtca aggactactt ccccgaaccg gtgacggtgt cgtggaactc aggcgccctg   600
accagcggcg tgcacacctt cccggctgtc ctacagtcct caggactcta ctccctcagc   660
agcgtggtga ccgtgccctc cagcagcttg ggcacccaga cctacatctg caacgtgaat   720
cacaagccca gcaacaccaa ggtggacaag agagttgagc ccaaatcttg tgacaaaact   780
cacacatgcc caccgtgccc agcacctgaa ctcctggggg gaccgtcagt cttcctcttc   840
cccccaaaac ccaaggacac cctcatgatc tcccggaccc ctgaggtcac atgcgtggtg   900
gtggacgtga gccacgaaga ccctgaggtc aagttcaact ggtacgtgga cggcgtggag   960
gtgcataatg ccaagacaaa gccgcgggag gagcagtaca acagcacgta ccgtgtggtc  1020
agcgtcctca ccgtcctgca ccaggactgg ctgaatgcaa aggagtacaa gtgcaaggtc  1080
tccaacaaag ccctcccagc ccccatcgag aaaaccatct ccaaagccaa agggcagccc  1140
cgagaaccac aggtgtacac cctgcccca tcccgggagg agatgaccaa gaaccaggtc  1200
agcctgacct gcctggtcaa aggcttctat cccagcgaca tcgccgtgga gtgggagagc  1260
aatgggcagc cggagaacaa ctacaagacc acgcctcccg tgctggactc cgacggctcc  1320
ttcttcctct atagcaagct caccgtggac aagagcaggt ggcagcaggg gaacgtcttc  1380
tcatgctccg tgatgcatga ggctctgcac aaccactaca cgcagaagag cctctccctg  1440
tctccgggta aatga                                                   1455

SEQ ID NO: 198          moltype = DNA   length = 405
FEATURE                 Location/Qualifiers
misc_feature            1..405
                        note = Description of Artificial Sequence: Synthetic
                         polynucleotide
source                  1..405
                        mol_type = other DNA
                        organism = synthetic construct
SEQUENCE: 198
cagccgcagc tgcaggagtc ggggccagga ctggtggagg cttcggagac cctgtccctc    60
acctgcactg tgtccggcga ctccactgct gcttgtgact attctgggg ctgggtccgg   120
cagccccag ggaagggcct ggagtggatt ggggtttgt cacattgtgc aggttactac   180
aatactggct ggacctacca caacccgtct ctcaagagtc ggctcacgat ttcactcgac   240
acccccaaga atcaggtctt cctgaagtta aattctgtga ccgccgcgga cacggccatt   300
tactactgtg cgcgattcga cggcgaagtt ttggtgtacc acgattggcc aaagccggcc   360
tgggtcgacc tctggggccg gggaactttg gtcaccgtct cctca                  405

SEQ ID NO: 199          moltype = AA   length = 484
FEATURE                 Location/Qualifiers
REGION                  1..484
                        note = Description of Artificial Sequence: Synthetic
                         polypeptide
source                  1..484
                        mol_type = protein
                        organism = synthetic construct
SEQUENCE: 199
MKHLWFFLLL  VAAPRWVLSQ  PQLQESGPGL  VEASETLSLT  CTVSGDSTAA  CDYFWGWVRQ   60
PPGKGLEWIG  GLSHCAGYYN  TGWTYHNPSL  KSRLTISLDT  PKNVFLKLN  SVTAADTAIY   120
YCARFDGEVL  VYHDWPKPAW  VDLWGRGTLV  TVSSASTKGP  SVFPLAPSSK  STSGGTAALG  180
CLVKDYFPEP  VTVSWNSGAL  TSGVHTFPAV  LQSSGLYSLS  SVVTVPSSSL  GTQTYICNVN  240
HKPSNTKVDK  RVEPKSCDKT  HTCPPCPAPE  LLGGPSVFLF  PPKPKDTLMI  SRTPEVTCVV  300
VDVSHEDPEV  KFNWYVDGVE  VHNAKTKPRE  EQYNSTYRVV  SVLTVLHQDW  LNGKEYKCKV  360
SNKALPAPIE  KTISKAKGQP  REPQVYTLPP  SREEMTKNQV  SLTCLVKGFY  PSDIAVEWES  420
NGQPENNYKT  TPPVLDSDGS  FFLYSKLTVD  KSRWQQGNVF  SCSVMHEALH  NHYTQKSLSL  480
SPGK                                                                  484

SEQ ID NO: 200          moltype = AA   length = 135
FEATURE                 Location/Qualifiers
REGION                  1..135
                        note = Description of Artificial Sequence: Synthetic
                         polypeptide
source                  1..135
                        mol_type = protein
                        organism = synthetic construct
SEQUENCE: 200
QPQLQESGPG  LVEASETLSL  TCTVSGDSTA  ACDYFWGWVR  QPPGKGLEWI  GGLSHCAGYY   60
NTGWTYHNPS  LKSRLTISLD  TPKNVFLKL  NSVTAADTAI  YYCARFDGEV  LVYHDWPKPA  120
WVDLWGRGTL  VTVSS                                                     135

SEQ ID NO: 201          moltype = AA   length = 7
FEATURE                 Location/Qualifiers
REGION                  1..7
                        note = Description of Artificial Sequence: Synthetic peptide
```

| | | |
|---|---|---|
| source | 1..7<br>mol_type = protein<br>organism = synthetic construct | |
| SEQUENCE: 201<br>ACDYFWG | | 7 |
| SEQ ID NO: 202<br>FEATURE<br>REGION | moltype = AA   length = 22<br>Location/Qualifiers<br>1..22<br>note = Description of Artificial Sequence: Synthetic peptide | |
| source | 1..22<br>mol_type = protein<br>organism = synthetic construct | |
| SEQUENCE: 202<br>GLSHCAGYYN TGWTYHNPSL KS | | 22 |
| SEQ ID NO: 203<br>FEATURE<br>REGION | moltype = AA   length = 19<br>Location/Qualifiers<br>1..19<br>note = Description of Artificial Sequence: Synthetic peptide | |
| source | 1..19<br>mol_type = protein<br>organism = synthetic construct | |
| SEQUENCE: 203<br>FDGEVLVYHD WPKPAWVDL | | 19 |
| SEQ ID NO: 204<br>FEATURE<br>REGION | moltype = AA   length = 8<br>Location/Qualifiers<br>1..8<br>note = Description of Artificial Sequence: Synthetic peptide | |
| source | 1..8<br>mol_type = protein<br>organism = synthetic construct | |
| SEQUENCE: 204<br>GDSTAACD | | 8 |
| SEQ ID NO: 205<br>FEATURE<br>REGION | moltype = AA   length = 15<br>Location/Qualifiers<br>1..15<br>note = Description of Artificial Sequence: Synthetic peptide | |
| source | 1..15<br>mol_type = protein<br>organism = synthetic construct | |
| SEQUENCE: 205<br>GLSHCAGYYN TGWTY | | 15 |
| SEQ ID NO: 206<br>FEATURE<br>misc_feature | moltype = DNA   length = 693<br>Location/Qualifiers<br>1..693<br>note = Description of Artificial Sequence: Synthetic<br>polynucleotide | |
| source | 1..693<br>mol_type = other DNA<br>organism = synthetic construct | |

SEQUENCE: 206
```
atggcctggg ctctgctcct cctcaccctc ctcactcagg gcacaggggc ctgggcccag   60
tctgccctga ctcagcctcc ctccgcgtcc gggtctcctg gacagtcaat ctccatctcc  120
tgcactggaa ccagcaatag gtttgtctcc tggtaccagc aacacccagg caaggccccc  180
aaactcgtca tttatggggt caataagcgc ccctcaggtg tccctgatcg tttttctggc  240
tccaagtctg gcaacacggc ctccctgacc gtctctgggc tccagactga cgatgaggct  300
gtctattact gcagctcact tgtaggcaac tgggatgtga ttttcggcgg agggaccaag  360
ttgaccgtcc tgggtcagcc caaggctgcc cctcggtca ctctgttccc gccctcctct  420
gaggagcttc aagccaacaa ggccacactg gtgtgtctca taagtgactt ctacccggga  480
gccgtgacag tggcctggaa ggcagatagc agccccgtca aggggagt ggagaccacc  540
acacccttcca aacaaagcaa caacaagtac gcggccagca gctacctgag cctgacgcct  600
gagcagtgga gtcccacaaa agctacagc tgccaggtca cgcatgaagg gagcaccgtg  660
gagaagacag tggcccctac agaatgttca tag                              693
```

| | | |
|---|---|---|
| SEQ ID NO: 207<br>FEATURE<br>misc_feature | moltype = DNA   length = 315<br>Location/Qualifiers<br>1..315<br>note = Description of Artificial Sequence: Synthetic<br>polynucleotide | |
| source | 1..315<br>mol_type = other DNA<br>organism = synthetic construct | |

SEQUENCE: 207
```
cagtctgccc tgactcagcc tcctccgcg tccgggtctc ctggacagtc aatctccatc   60
tcctgcactg gaaccagcaa taggtttgtc tcctggtacc agcaacaccc aggcaaggcc  120
```

```
cccaaaactcg tcatttatgg ggtcaataag cgcccctcag gtgtccctga tcgttttttct    180
ggctccaagt ctggcaacac ggcctccctg accgtctctg ggctccagac tgacgatgag    240
gctgtctatt actgcagctc acttgtaggc aactgggatg tgattttcgg cggagggacc    300
aagttgaccg tcctg                                                      315

SEQ ID NO: 208           moltype = AA  length = 230
FEATURE                  Location/Qualifiers
REGION                   1..230
                         note = Description of Artificial Sequence: Synthetic
                           polypeptide
source                   1..230
                         mol_type = protein
                         organism = synthetic construct
SEQUENCE: 208
MAWALLLLTL LTQGTGAWAQ SALTQPPSAS GSPGQSISIS CTGTSNRFVS WYQQHPGKAP    60
KLVIYGVNKR PSGVPDRFSG SKSGNTASLT VSGLQTDDEA VYYCSSLVGN WDVIFGGGTK    120
LTVLGQPKAA PSVTLFPPSS EELQANKATL VCLISDFYPG AVTVAWKADS SPVKAGVETT    180
TPSKQSNNKY AASSYLSLTP EQWKSHKSYS CQVTHEGSTV EKTVAPTECS              230

SEQ ID NO: 209           moltype = AA  length = 105
FEATURE                  Location/Qualifiers
REGION                   1..105
                         note = Description of Artificial Sequence: Synthetic
                           polypeptide
source                   1..105
                         mol_type = protein
                         organism = synthetic construct
SEQUENCE: 209
QSALTQPPSA SGSPGQSISI SCTGTSNRFV SWYQQHPGKA PKLVIYGVNK RPSGVPDRFS    60
GSKSGNTASL TVSGLQTDDE AVYYCSSLVG NWDVIFGGGT KLTVL                  105

SEQ ID NO: 210           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 210
TGTSNRFVS                                                              9

SEQ ID NO: 211           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 211
GVNKRPS                                                                7

SEQ ID NO: 212           moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 212
SSLVGNWDVI                                                            10

SEQ ID NO: 213           moltype = DNA  length = 1437
FEATURE                  Location/Qualifiers
misc_feature             1..1437
                         note = Description of Artificial Sequence: Synthetic
                           polynucleotide
source                   1..1437
                         mol_type = other DNA
                         organism = synthetic construct
SEQUENCE: 213
atgaaacacc tgtggttctt cctcctgctg gtggcggctc ccagatgggt cctgtcccag    60
gtgcagctgc aggagtcggg cccaggactg gtgaagcctg cggagaccct gtccctcacc    120
tgcagtgtct ctggagaatc tatcaatact ggtcattact actggggctg ggtccgtcag    180
gtcccaggga agggactgga gtggataggt catatccatt atacgacggc tgtcctgcac    240
aacccgtccc tcaagagtcg actcaccatc aaaatttaca cgttgagaaa ccagattacc    300
ctgaggctca gtaatgtgac ggccgcggac acggccgtct atcactgcgt acgatccggc    360
ggcgacatct tatattatta tgagtggcaa aagccgcact ggttctctcc ctggggcccg    420
ggaatccacg tcaccgtctc gagcgcctcc accaagggcc catcggtctt ccccctggca    480
ccctcctcca agagcacctc tgggggcaca gcggccctgg gctgcctggt caaggactac    540
```

```
ttccccgaac cggtgacggt gtcgtggaac tcaggcgccc tgaccagcgg cgtgcacacc    600
ttccggctg  tcctacagtc ctcaggactc tactccctca gcagcgtggt gaccgtgccc    660
tccagcagct tgggcaccca gacctacatc tgcaacgtga atcacaagcc cagcaacacc    720
aaggtggaca gagagttga  gcccaaatct tgtgacaaaa ctcacacatg cccaccgtgc    780
ccagcacctg aactcctggg gggaccgtca gtcttcctct ccccccaaa  acccaaggac    840
accctcatga tctcccggac ccctgaggtc acatgcgtgg tggtggacgt gagccacgaa    900
gaccctgagg tcaagttcaa ctggtacgtg gacggcgtgg aggtgcataa tgccaagaca    960
aagccgcggg aggagcagta caacagcacg taccgtgtgg tcagcgtcct caccgtcctg   1020
caccaggact ggctgaatgg caaggagtac aagtgcaagg tctccaacaa agccctccca   1080
gcccccatcg agaaaaccat ctccaaagcc aaagggcagc cccgagaacc acaggtgtac   1140
accctgcccc catcccggga ggagatgacc aagaaccagg tcagcctgac ctgcctggtc   1200
aaaggcttct atcccagcga catcgccgtg gagtgggaga gcaatgggca gccggagaac   1260
aactacaaga ccacgcctcc cgtgctggac tccgacggct ccttcttcct ctatagcaag   1320
ctcaccgtgg acaagagcag gtggcagcag gggaacgtct tctcatgctc cgtgatgcat   1380
gaggctctgc acaaccacta cacgcagaag agcctctccc tgtctccggg taaatga     1437

SEQ ID NO: 214          moltype = DNA  length = 387
FEATURE                 Location/Qualifiers
misc_feature            1..387
                        note = Description of Artificial Sequence: Synthetic
                         polynucleotide
source                  1..387
                        mol_type = other DNA
                        organism = synthetic construct
SEQUENCE: 214
caggtgcagc tgcaggagtc gggcccagga ctggtgaagc ctgcggagac cctgtccctc    60
acctgcagtg tctctggaga atctatcaat actggtcatt actactgggg ctgggtccgt   120
caggtcccag ggaagggact tgagtggata ggtcatatcc attatacgac ggctgtcctg   180
cacaacccgt ccctcaagag tcgactcacc atcaaaattt acacgttgag aaaccagatt   240
accctgaggc tcagtaatgt gacggccgcg gacacggccg tctatcactg cgtacgatcc   300
ggcggcgaca tcttatatta ttatgagtgg caaaagccgc actggttctc tccctggggc   360
ccgggaatcc acgtcaccgt ctcgagc                                        387

SEQ ID NO: 215          moltype = AA   length = 478
FEATURE                 Location/Qualifiers
REGION                  1..478
                        note = Description of Artificial Sequence: Synthetic
                         polypeptide
source                  1..478
                        mol_type = protein
                        organism = synthetic construct
SEQUENCE: 215
MKHLWFFLLL VAAPRWVLSQ VQLQESGPGL VKPAETLSLT CSVSGESINT GHYYWGWVRQ    60
VPGKGLEWIG HIHYTTAVLH NPSLKSRLTI KIYTLRNQIT LRLSNVTAAD TAVYHCVRSG   120
GDILYYYEWQ KPHWFSPWGP GIHVTVSSAS TKGPSVFPLA PSSKSTSGGT AALGCLVKDY   180
FPEPVTVSWN SGALTSGVHT FPAVLQSSGL YSLSSVVTVP SSSLGTQTYI CNVNHKPSNT   240
KVDKRVEPKS CDKTHTCPPC PAPELLGGPS VFLFPPKPKD TLMISRTPEV TCVVVDVSHE   300
DPEVKFNWYV DGVEVHNAKT KPREEQYNST YRVVSVLTVL HQDWLNGKEY KCKVSNKALP   360
APIEKTISKA KGQPREPQVY TLPPSREEMT KNQVSLTCLV KGFYPSDIAV EWESNGQPEN   420
NYKTTPPVLD SDGSFFLYSK LTVDKSRWQQ GNVFSCSVMH EALHNHYTQK SLSLSPGK     478

SEQ ID NO: 216          moltype = AA   length = 129
FEATURE                 Location/Qualifiers
REGION                  1..129
                        note = Description of Artificial Sequence: Synthetic
                         polypeptide
source                  1..129
                        mol_type = protein
                        organism = synthetic construct
SEQUENCE: 216
QVQLQESGPG LVKPAETLSL TCSVSGESIN TGHYYWGWVR QVPGKGLEWI GHIHYTTAVL    60
HNPSLKSRLT IKIYTLRNQI TLRLSNVTAA DTAVYHCVRS GGDILYYYEW QKPHWFSPWG   120
PGIHVTVSS                                                            129

SEQ ID NO: 217          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 217
TGHYYWG                                                                7

SEQ ID NO: 218          moltype = AA   length = 16
FEATURE                 Location/Qualifiers
REGION                  1..16
                        note = Description of Artificial Sequence: Synthetic peptide
source                  1..16
```

```
                        mol_type = protein
                        organism = synthetic construct
SEQUENCE: 218
HIHYTTAVLH NPSLKS                                                    16

SEQ ID NO: 219          moltype = AA   length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 219
SGGDILYYYE WQKPHWFSP                                                 19

SEQ ID NO: 220          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 220
GESINTGH                                                             8

SEQ ID NO: 221          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 221
HIHYTTAVL                                                            9

SEQ ID NO: 222          moltype = DNA   length = 708
FEATURE                 Location/Qualifiers
misc_feature            1..708
                        note = Description of Artificial Sequence: Synthetic
                         polynucleotide
source                  1..708
                        mol_type = other DNA
                        organism = synthetic construct
SEQUENCE: 222
atggcctggg ctctgctcct cctcaccctc ctcactcagg gcacagggtc ctgggcccag    60
tctgccctga ctcagcctcc ctccgcgtcc gggtctcttg gacagtcagt caccatctcc   120
tgcaatgaa ccagcagtga cattggcggt tggaatttg tctcctggta tcaacagttc    180
ccgggcagag ccccagact cattatttt gaggtcaata agcggcctc aggggtccct     240
ggtcgcttct ctggctccaa gtcgggcaat tcggcctccc tgaccgtctc tgggctccag   300
tctgacgatg agggtcaata tttctgcagt tcacttttcg gcaggtggga tgttgttttt   360
ggcgggggga ccaagctgac cgtcctaggt cagcccaagg ctgcccctc ggtcactctg    420
ttcccgccct cctctgagga gcttcaagcc aacaaggcca cactggtgtg tctcataagt   480
gacttctacc cgggagccgt gacagtggcc tggaaggcag atagcagccc cgtcaaggcg   540
ggagtggaga ccaccacacc ctccaaacaa agcaacaaca gtacgcggc cagcagctac    600
ctgagcctga cgcctgagca gtggaagtcc cacaaaagct acagctgcca ggtcacgcat   660
gaagggagca ccgtggagaa gacagtggcc cctacagaat gttcatag                708

SEQ ID NO: 223          moltype = DNA   length = 330
FEATURE                 Location/Qualifiers
misc_feature            1..330
                        note = Description of Artificial Sequence: Synthetic
                         polynucleotide
source                  1..330
                        mol_type = other DNA
                        organism = synthetic construct
SEQUENCE: 223
cagtctgccc tgactcagcc tccctccgcg tccgggtctc ttggacagtc agtcaccatc    60
tcctgcaatg gaaccagcag tgacattggc ggttggaatt ttgtctcctg gtatcaacag   120
ttcccgggca gagcccccag actcattatt tttgaggtca ataagcggcc ctcaggggtc   180
cctggtcgct ctctggctc caagtcgggc aattcggcct ccctgaccgt ctctgggctc    240
cagtctgacg atgagggtca atatttctgc agttcacttt tcggcaggtg ggatgttgtt   300
tttggcgggg gaccaagct gaccgtccta                                     330

SEQ ID NO: 224          moltype = AA   length = 235
FEATURE                 Location/Qualifiers
REGION                  1..235
                        note = Description of Artificial Sequence: Synthetic
                         polypeptide
source                  1..235
```

```
                        mol_type = protein
                        organism = synthetic construct
SEQUENCE: 224
MAWALLLLTL LTQGTGSWAQ SALTQPPSAS GSLGQSVTIS CNGTSSDIGG WNFVSWYQQF    60
PGRAPRLIIF EVNKRPSGVP GRFSGSKSGN SASLTVSGLQ SDDEGQYFCS SLFGRWDVVF   120
GGGTKLTVLG QPKAAPSVTL FPPSSEELQA NKATLVCLIS DFYPGAVTVA WKADSSPVKA   180
GVETTTPSKQ SNNKYAASSY LSLTPEQWKS HKSYSCQVTH EGSTVEKTVA PTECS        235

SEQ ID NO: 225          moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 225
QSALTQPPSA SGSLGQSVTI SCNGTSSDIG GWNFVSWYQQ FPGRAPRLII FEVNKRPSGV    60
PGRFSGSKSG NSASLTVSGL QSDDEGQYFC SSLFGRWDVV FGGGTKLTVL              110

SEQ ID NO: 226          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 226
NGTSSDIGGW NFVS                                                      14

SEQ ID NO: 227          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 227
EVNKRPS                                                               7

SEQ ID NO: 228          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 228
SSLFGRWDVV                                                           10

SEQ ID NO: 229          moltype = DNA  length = 1449
FEATURE                 Location/Qualifiers
misc_feature            1..1449
                        note = Description of Artificial Sequence: Synthetic
                         polynucleotide
source                  1..1449
                        mol_type = other DNA
                        organism = synthetic construct
SEQUENCE: 229
atgaaacacc tgtggttctt cctcttgctg gtggcggctc ccagatgggg cctgtcccag    60
ttgcagatgc aggagtcggg cccaggactg tgaagccttt cggagaccct gtctctgagt   120
tgcactgtct ctggtgactc cataaggggt ggcgagtggg gcgataaaga ttatcattgg   180
ggctgggtcc gccactcagc aggaaagggc ctggagtgga ttgggagtat ccattggagg   240
gggaccaccc actacaaaga gtccctcagg agaagagtga gtatgtcgat cgacacgtcc   300
aggaattggt tctccctgag gctggcctct gtgaccgccg cggacacggc cgtctacttt   360
tgtgcgagac accgacatca tgatgttttc atgttggtcc ctattgcggg ctggttcgac   420
gtctggggcc cggagtccag ggtcaccgtc tcgagcgcct ccaccaaggg cccatcggtc   480
ttccccctgg cacccctcct caagagcacc tctgggggca cagcggccct gggctgcctg   540
gtcaaggact acttcccga accggtgacg gtgtcgtgga actcaggcgc cctgaccagc   600
ggcgtgcaca ccttcccggc tgtcctacag tcctcaggac tctactccct cagcagcgtg   660
gtgaccgtgc cctccagcag cttgggcacc cagacctaca tctgcaacgt gaatcacaag   720
cccagcaaca ccaaggtgga caagagagtt gagcccaaat cttgtgacaa aactcacaca   780
tgcccaccgt gcccagcacc tgaactcctg ggggaccgt cagtcttcct cttccccca    840
aaacccaagg acaccctcat gatctcccgg acccctgagg tcacatgcgt ggtggtggac   900
gtgagccacg aagaccctga ggtcaagttc aactggtacg tggacggcgt ggaggtgcat   960
aatgccaaga caaagccgcg ggaggagcag tacaacagca cgtaccgtgt ggtcagcgtc  1020
ctcaccgtcc tgcaccagga ctggctgaat ggcaaggagt acaagtgcaa ggtctccaac  1080
aaagccctcc cagcccccat cgagaaaacc atctccaaag ccaaagggca gccccgagaa  1140
ccacaggtgt acaccctgcc cccatcccgg gaggagatga ccaagaacca ggtcagcctg  1200
```

```
acctgcctgg tcaaaggctt ctatcccagc gacatcgccg tggagtggga gagcaatggg   1260
cagccggaga acaactacaa gaccacgcct cccgtgctgg actccgacgg ctccttcttc   1320
ctctatagca agctcaccgt ggacaagagc aggtggcagc aggggaacgt cttctcatgc   1380
tccgtgatgc atgaggctct gcacaaccac tacacgcaga agagcctctc cctgtctccg   1440
ggtaaatga                                                           1449
```

| | | |
|---|---|---|
| SEQ ID NO: 230 | moltype = DNA length = 399 | |
| FEATURE | Location/Qualifiers | |
| misc_feature | 1..399 | |
| | note = Description of Artificial Sequence: Synthetic polynucleotide | |
| source | 1..399 | |
| | mol_type = other DNA | |
| | organism = synthetic construct | |

SEQUENCE: 230
```
cagttgcaga tgcaggagtc gggcccagga ctggtgaagc cttcggagac cctgtctctg    60
agttgcactg tctctggtga ctccataagg ggtggcgagt ggggcgataa agattatcat   120
tggggctggg tccgccactc agcaggaaag ggcctggagt ggattgggag tatccattgg   180
aggggggacca cccactacaa agagtccctc aggagaagag tgagtatgtc gatcgacacg   240
tccaggaatt ggttctccct gaggctggcc tctgtgaccg ccgcggacac ggccgtctac   300
ttttgtgcga gacaccgaca tcatgatgtt ttcatgttgg tccctattgc gggctggttc   360
gacgtctggg gcccgggagt ccaggtcacc gtctcgagc                          399
```

| | | |
|---|---|---|
| SEQ ID NO: 231 | moltype = AA length = 482 | |
| FEATURE | Location/Qualifiers | |
| REGION | 1..482 | |
| | note = Description of Artificial Sequence: Synthetic polypeptide | |
| source | 1..482 | |
| | mol_type = protein | |
| | organism = synthetic construct | |

SEQUENCE: 231
```
MKHLWFFLLL VAAPRWVLSQ LQMQESGPGL VKPSETLSLS CTVSGDSIRG GEWGDKDYHW    60
GWVRHSAGKG LEWIGSIHWR GTTHYKESLR RRVSMSIDTS RNWFSLRLAS VTAADTAVYF   120
CARHRHHDVF MLVPIAGWFD VWGPGVQVTV SSASTKGPSV FPLAPSSKST SGGTAALGCL   180
VKDYFPEPVT VSWNSGALTS GVHTFPAVLQ SSGLYSLSSV VTVPSSSLGT QTYICNVNHK   240
PSNTKVDKRV EPKSCDKTHT CPPCPAPELL GGPSVFLFPP KPKDTLMISR TPEVTCVVVD   300
VSHEDPEVKF NWYVDGVEVH NAKTKPREEQ YNSTYRVVSV LTVLHQDWLN GKEYKCKVSN   360
KALPAPIEKT ISKAKGQPRE PQVYTLPPSR EEMTKNQVSL TCLVKGFYPS DIAVEWESNG   420
QPENNYKTTP PVLDSDGSFF LYSKLTVDKS RWQQGNVFSC SVMHEALHNH YTQKSLSLSP   480
GK                                                                 482
```

| | | |
|---|---|---|
| SEQ ID NO: 232 | moltype = AA length = 133 | |
| FEATURE | Location/Qualifiers | |
| REGION | 1..133 | |
| | note = Description of Artificial Sequence: Synthetic polypeptide | |
| source | 1..133 | |
| | mol_type = protein | |
| | organism = synthetic construct | |

SEQUENCE: 232
```
QLQMQESGPG LVKPSETLSL SCTVSGDSIR GGEWGDKDYH WGWVRHSAGK GLEWIGSIHW    60
RGTTHYKESL RRRVSMSIDT SRNWFSLRLA SVTAADTAVY FCARHRHHDV FMLVPIAGWF   120
DVWGPGVQVT VSS                                                     133
```

| | | |
|---|---|---|
| SEQ ID NO: 233 | moltype = AA length = 12 | |
| FEATURE | Location/Qualifiers | |
| REGION | 1..12 | |
| | note = Description of Artificial Sequence: Synthetic peptide | |
| source | 1..12 | |
| | mol_type = protein | |
| | organism = synthetic construct | |

SEQUENCE: 233
```
GGEWGDKDYH WG                                                       12
```

| | | |
|---|---|---|
| SEQ ID NO: 234 | moltype = AA length = 16 | |
| FEATURE | Location/Qualifiers | |
| REGION | 1..16 | |
| | note = Description of Artificial Sequence: Synthetic peptide | |
| source | 1..16 | |
| | mol_type = protein | |
| | organism = synthetic construct | |

SEQUENCE: 234
```
SIHWRGTTHY KESLRR                                                   16
```

| | | |
|---|---|---|
| SEQ ID NO: 235 | moltype = AA length = 18 | |
| FEATURE | Location/Qualifiers | |
| REGION | 1..18 | |
| | note = Description of Artificial Sequence: Synthetic peptide | |

```
source                  1..18
                        mol_type = protein
                        organism = synthetic construct
SEQUENCE: 235
HRHHDVFMLV PIAGWFDV                                                  18

SEQ ID NO: 236          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 236
GDSIRGGEWG DKD                                                       13

SEQ ID NO: 237          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 237
SIHWRGTTH                                                             9

SEQ ID NO: 238          moltype = DNA  length = 705
FEATURE                 Location/Qualifiers
misc_feature            1..705
                        note = Description of Artificial Sequence: Synthetic
                        polynucleotide
source                  1..705
                        mol_type = other DNA
                        organism = synthetic construct
SEQUENCE: 238
atggaaaccc cagctcagct tctcttcctc ctgctactct ggctcccaga taccactgga   60
gaaattgtga tgacgcagtc tcccgacacc ctgtctgtct ctccagggga gacagtcaca  120
ctctcctgca gggccagtca gaatattaac aagaatttag cctggtacca atacaaacct  180
ggccagtctc ccaggctcgt aatttttgaa acatatagca agatcgctgc tttccctgcc  240
aggttcgttg ccagtggttc tgggacagag ttcactctca ccatcaacaa catgcagtct  300
gaagatgttg cagtttatta ctgtcaacaa tatgaagagt ggcctcggac gttcgggcaa  360
gggaccaagg tggatatcaa acgtacggtg gctgcaccat ctgtcttcat cttccctgcc  420
tctgatgagc agttgaaatc tggaactgcc tctgttgtgt gcctgctgaa taacttctat  480
cccagagagg ccaaagtaca gtggaaggtg gataacgccc tccaatcggg taactcccag  540
gagagtgtca cagagcagga cagcaaggac agcacctaca gcctcagcag caccctgacg  600
ctgagcaaag cagactacga gaaacacaaa gtctacgcct gcgaagtcac ccatcagggc  660
ctgagctcgc ccgtcacaaa gagcttcaac aggggagagt gttag                  705

SEQ ID NO: 239          moltype = DNA  length = 321
FEATURE                 Location/Qualifiers
misc_feature            1..321
                        note = Description of Artificial Sequence: Synthetic
                        polynucleotide
source                  1..321
                        mol_type = other DNA
                        organism = synthetic construct
SEQUENCE: 239
gaaattgtga tgacgcagtc tcccgacacc ctgtctgtct ctccagggga gacagtcaca   60
ctctcctgca gggccagtca gaatattaac aagaatttag cctggtacca atacaaacct  120
ggccagtctc ccaggctcgt aatttttgaa acatatagca agatcgctgc tttccctgcc  180
aggttcgttg ccagtggttc tgggacagag ttcactctca ccatcaacaa catgcagtct  240
gaagatgttg cagtttatta ctgtcaacaa tatgaagagt ggcctcggac gttcgggcaa  300
gggaccaagg tggatatcaa a                                            321

SEQ ID NO: 240          moltype = AA  length = 234
FEATURE                 Location/Qualifiers
REGION                  1..234
                        note = Description of Artificial Sequence: Synthetic
                        polypeptide
source                  1..234
                        mol_type = protein
                        organism = synthetic construct
SEQUENCE: 240
METPAQLLFL LLLWLPDTTG EIVMTQSPDT LSVSPGETVT LSCRASQNIN KNLAWYQYKP   60
GQSPRLVIFE TYSKIAAFPA RFVASGSGTE FTLTINNMQS EDVAVYYCQQ YEEWPRTFGQ  120
GTKVDIKRTV AAPSVIFPP  SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 241          moltype =     length =
```

```
SEQUENCE: 241
000

SEQ ID NO: 242           moltype = AA  length = 107
FEATURE                  Location/Qualifiers
REGION                   1..107
                         note = Description of Artificial Sequence: Synthetic
                         polypeptide
source                   1..107
                         mol_type = protein
                         organism = synthetic construct
SEQUENCE: 242
EIVMTQSPDT LSVSPGETVT LSCRASQNIN KNLAWYQYKP GQSPRLVIFE TYSKIAAFPA    60
RFVASGSGTE FTLTINNMQS EDVAVYYCQQ YEEWPRTFGQ GTKVDIK                 107

SEQ ID NO: 243           moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 243
RASQNINKNL A                                                        11

SEQ ID NO: 244           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 244
ETYSKIA                                                             7

SEQ ID NO: 245           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 245
QQYEEWPRT                                                           9

SEQ ID NO: 246           moltype = DNA  length = 1452
FEATURE                  Location/Qualifiers
misc_feature             1..1452
                         note = Description of Artificial Sequence: Synthetic
                         polynucleotide
source                   1..1452
                         mol_type = other DNA
                         organism = synthetic construct
SEQUENCE: 246
atgaaacacc tgtggttctt cctcctgcta gtggcggctc ccagatgggt cctgtcgcag    60
ctgcagttgc aggaatcggg cccaggactg tgaagccttt cggagaccct gtccctgact   120
tgcacagttt ctggtggctc atgaggggc accgactggg gcgagaatga cttccactac   180
ggctggatcc gccagtcctc cgcaaagggg ctggagtgga ttgggagcat ccattggagg   240
gggaggacca cccactacaa gacgtccttc ccaccttgtc gatagacacg               300
tccaataatc gcttctccct gacgtttagt tttgtgaccg ccgcggacac ggccgtctac   360
tattgtgcga gacataaata tcatgatatt ttcaggtgg tccctgttgc gggctggttc   420
gaccctgg gccaggatt actggtcacc gtctcgagcg cctccaccaa gggcccatcg    480
gtcttccccc tggcaccctc ctccaagagc acctctgggg cacagcggc cctgggctgc   540
ctggtcaagg actacttccc cgaaccggtg acggtgtcgt ggaactcagg cgccctgacc   600
agcggcgtgc acaccttccc ggctgtccta cagtcctcag gactctactc cctcagcagc   660
gtggtgaccg tgccctccag cagcttgggc acccagacct acatctgcaa cgtgaatcac   720
aagcccagca caccaaggt ggacaagaga gttgagccca atcttgtga caaaactcac    780
acatgcccac cgtgcccagc acctgaactc ctggggggac cgtcagtctt cctcttcccc   840
ccaaaaccca aggacaccct catgatctcc cggacccctg aggtcacatg cgtggtggtg   900
gacgtgagcc acgaagaccc tgaggtcaag ttcaactggt acgtggacgg cgtggaggtg   960
cataatgcca agacaaagcc gcgggaggag cagtacaaca gcacgtaccg tgtggtcagc  1020
gtcctcaccg tcctgcacca ggactggctg aatggcaagg agtacaagtg caaggtctcc  1080
aacaaagccc tcccagcccc catcgagaaa accatctcca aagccaaagg cagccccga   1140
gaaccacagg tgtacaccct gcccccatcc cgggaggaga tgaccaagaa ccaggtcagc  1200
ctgacctgcc tggtcaaagg cttctatccc agcgacatcg ccgtggagtg ggagagcaat  1260
gggcagccgg agaacaacta caagaccacg cctcccgtgc tggactccga cggctccttc  1320
ttcctctata gcaagctcac cgtggacaag agcaggtggc agcagggaa cgtcttctca  1380
tgctccgtga tgcatgaggc tctgcacaac cactacacgc agaagagcct ctccctgtct  1440
ccgggtaaat ga                                                     1452
```

```
SEQ ID NO: 247          moltype = DNA  length = 402
FEATURE                 Location/Qualifiers
misc_feature            1..402
                        note = Description of Artificial Sequence: Synthetic
                         polynucleotide
source                  1..402
                        mol_type = other DNA
                        organism = synthetic construct
SEQUENCE: 247
cagctgcagt tgcaggaatc gggcccagga ctggtgaagc cttcggagac cctgtccctg    60
acttgcacag tttctggtgg ctccatgagg ggcaccgact ggggcgagaa tgacttccac   120
tacggctgga tccgccagtc ctccgcaaag gggctgagtg ggattgggag catccattgg   180
agggggagga ccacccacta caagacgtcc ttcaggagtc gggccaccttgtcgatagac   240
acgtccaata atcgcttctc cctgacgttt agttttgtga ccgccgcgga cacggccgtc   300
tactattgtg cgagacataa atatcatgat attttcaggg tggtcccctgt tgcgggctgg   360
ttcgacccct ggggccaggg attactggtc accgtctcga gc                     402

SEQ ID NO: 248          moltype = AA  length = 483
FEATURE                 Location/Qualifiers
REGION                  1..483
                        note = Description of Artificial Sequence: Synthetic
                         polypeptide
source                  1..483
                        mol_type = protein
                        organism = synthetic construct
SEQUENCE: 248
MKHLWFLLL  VAAPRWVLSQ  LQLQESGPGL  VKPSETLSLT  CTVSGGSMRG  TDWGENDFHY    60
GWIRQSSAKG LEWIGSIHWR  GRTTHYKTSF  RSRATLSIDT  SNNRFSLTFS  FVTAADTAVY   120
YCARHKYHDI FRVVPVAGWF  DPWGQGLLVT  VSSASTKGPS  VFPLAPSSKS  TSGGTAALGC   180
LVKDYFPEPV TVSWNSGALT  SGVHTFPAVL  QSSGLYSLSS  VVTVPSSSLG  TQTYICNVNH   240
KPSNTKVDKR VEPKSCDKTH  TCPPCPAPEL  LGGPSVFLFP  PKPKDTLMIS  RTPEVTCVVV   300
DVSHEDPEVK FNWYVDGVEV  HNAKTKPREE  QYNSTYRVVS  VLTVLHQDWL  NGKEYKCKVS   360
NKALPAPIEK TISKAKGQPR  EPQVYTLPPS  REEMTKNQVS  LTCLVKGFYP  SDIAVEWESN   420
GQPENNYKTT PPVLDSDGSF  FLYSKLTVDK  SRWQQGNVFS  CSVMHEALHN  HYTQKSLSLS   480
PGK                                                                    483

SEQ ID NO: 249          moltype = AA  length = 134
FEATURE                 Location/Qualifiers
REGION                  1..134
                        note = Description of Artificial Sequence: Synthetic
                         polypeptide
source                  1..134
                        mol_type = protein
                        organism = synthetic construct
SEQUENCE: 249
QLQLQESGPG LVKPSETLSL TCTVSGGSMR GTDWGENDFH YGWIRQSSAK GLEWIGSIHW       60
RGRTTHYKTS FRSRATLSID TSNNRFSLTF SFVTAADTAV YYCARHKYHD IFRVVPVAGW      120
FDPWGQGLLV TVSS                                                       134

SEQ ID NO: 250          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 250
GTDWGENDFH YG                                                          12

SEQ ID NO: 251          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 251
SIHWRGRTTH YKTSFRS                                                     17

SEQ ID NO: 252          moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 252
HKYHDIFRVV PVAGWFDP                                                    18
```

```
SEQ ID NO: 253          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 253
GGSMRGTDWG END                                                              13

SEQ ID NO: 254          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 254
SIHWRGRTTH                                                                  10

SEQ ID NO: 255          moltype = DNA  length = 705
FEATURE                 Location/Qualifiers
misc_feature            1..705
                        note = Description of Artificial Sequence: Synthetic
                         polynucleotide
source                  1..705
                        mol_type = other DNA
                        organism = synthetic construct
SEQUENCE: 255
atggaaaccc cagctcagct tctcttcctc ctgctactct ggctcccaga tagcactgga       60
gaaatagtga tgacgcagtc tccacccacc ctgtctgtgt ctccagggga aacagccaca      120
ctctcctgta gggccagtca gaatgttaag aataatttag cctggtacca gctgaaacct      180
ggccaggctc ccaggctcct catctttgat gcgtccagca gggccggtgg tattcctgac      240
aggttcagtg gcagcggtta tgggacagac ttcactctca ccgtcaacag tgtgcagtcc      300
gaagattttg gagattattt ttgtcagcaa tatgaagagt ggcctcggac gttcggccaa      360
gggaccaagg tggatatcaa acgtacggtg gctgcaccat ctgtcttcat cttcccgcca      420
tctgatgagc agttgaaatc tggaactgcc tctgttgtgt gcctgctgaa taacttctat      480
cccagagagg ccaaagtaca gtggaaggtg gataacgccc tccaatcggg taactcccag      540
gagagtgtca cagagcagga cagcaaggac agcacctaca gcctcagcag caccctgacg      600
ctgagcaaag cagactacga aaacacaaa gtctacgcct gcgaagtcac ccatcagggc      660
ctgagctcgc ccgtcacaaa gagcttcaac aggggagagt gttag                      705

SEQ ID NO: 256          moltype = DNA  length = 321
FEATURE                 Location/Qualifiers
misc_feature            1..321
                        note = Description of Artificial Sequence: Synthetic
                         polynucleotide
source                  1..321
                        mol_type = other DNA
                        organism = synthetic construct
SEQUENCE: 256
gaaatagtga tgacgcagtc tccacccacc ctgtctgtgt ctccagggga aacagccaca       60
ctctcctgta gggccagtca gaatgttaag aataatttag cctggtacca gctgaaacct      120
ggccaggctc ccaggctcct catctttgat gcgtccagca gggccggtgg tattcctgac      180
aggttcagtg gcagcggtta tgggacagac ttcactctca ccgtcaacag tgtgcagtcc      240
gaagattttg gagattattt ttgtcagcaa tatgaagagt ggcctcggac gttcggccaa      300
gggaccaagg tggatatcaa a                                                 321

SEQ ID NO: 257          moltype = AA  length = 234
FEATURE                 Location/Qualifiers
REGION                  1..234
                        note = Description of Artificial Sequence: Synthetic
                         polypeptide
source                  1..234
                        mol_type = protein
                        organism = synthetic construct
SEQUENCE: 257
METPAQLLFL LLLWLPDSTG EIVMTQSPPT LSVSPGETAT LSCRASQNVK NNLAWYQLKP        60
GQAPRLLIFD ASSRAGGIPD RFSGSGYGTD FTLTVNSVQS EDFGDYFCQQ YEEWPRTFGQ      120
GTKVDIKRTV AAPSVFIFPP SDEQLKSGTA SVVCLLNNFY PREAKVQWKV DNALQSGNSQ      180
ESVTEQDSKD STYSLSSTLT LSKADYEKHK VYACEVTHQG LSSPVTKSFN RGEC            234

SEQ ID NO: 258          moltype = AA  length = 107
FEATURE                 Location/Qualifiers
REGION                  1..107
                        note = Description of Artificial Sequence: Synthetic
                         polypeptide
source                  1..107
```

```
                              mol_type = protein
                              organism = synthetic construct
SEQUENCE: 258
EIVMTQSPPT LSVSPGETAT LSCRASQNVK NNLAWYQLKP GQAPRLLIFD ASSRAGGIPD    60
RFSGSGYGTD FTLTVNSVQS EDFGDYFCQQ YEEWPRTFGQ GTKVDIK                 107

SEQ ID NO: 259                moltype = AA   length = 11
FEATURE                       Location/Qualifiers
REGION                        1..11
                              note = Description of Artificial Sequence: Synthetic peptide
source                        1..11
                              mol_type = protein
                              organism = synthetic construct
SEQUENCE: 259
RASQNVKNNL A                                                         11

SEQ ID NO: 260                moltype = AA   length = 7
FEATURE                       Location/Qualifiers
REGION                        1..7
                              note = Description of Artificial Sequence: Synthetic peptide
source                        1..7
                              mol_type = protein
                              organism = synthetic construct
SEQUENCE: 260
DASSRAG                                                               7

SEQ ID NO: 261                moltype = AA   length = 5
FEATURE                       Location/Qualifiers
REGION                        1..5
                              note = Description of Artificial Sequence: Synthetic peptide
source                        1..5
                              mol_type = protein
                              organism = synthetic construct
SEQUENCE: 261
DNYWS                                                                 5

SEQ ID NO: 262                moltype = AA   length = 24
FEATURE                       Location/Qualifiers
REGION                        1..24
                              note = Description of Artificial Sequence: Synthetic peptide
source                        1..24
                              mol_type = protein
                              organism = synthetic construct
SEQUENCE: 262
TKHGRRIYGV VAFKEWFTYF YMDV                                           24

SEQ ID NO: 263                moltype = AA   length = 6
FEATURE                       Location/Qualifiers
REGION                        1..6
                              note = Description of Artificial Sequence: Synthetic peptide
source                        1..6
                              mol_type = protein
                              organism = synthetic construct
SEQUENCE: 263
GTLVRD                                                                6

SEQ ID NO: 264                moltype = AA   length = 9
FEATURE                       Location/Qualifiers
REGION                        1..9
                              note = Description of Artificial Sequence: Synthetic peptide
source                        1..9
                              mol_type = protein
                              organism = synthetic construct
SEQUENCE: 264
YVHDSGDTN                                                             9

SEQ ID NO: 265                moltype = AA   length = 16
FEATURE                       Location/Qualifiers
REGION                        1..16
                              note = Description of Artificial Sequence: Synthetic peptide
source                        1..16
                              mol_type = protein
                              organism = synthetic construct
SEQUENCE: 265
YVHKSGDTNY SPSLKS                                                    16

SEQ ID NO: 266                moltype = AA   length = 6
FEATURE                       Location/Qualifiers
REGION                        1..6
```

```
                        note = Description of Artificial Sequence: Synthetic peptide
source                  1..6
                        mol_type = protein
                        organism = synthetic construct
SEQUENCE: 266
GFTFHK                                                                          6

SEQ ID NO: 267          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 267
LISDDGMRKY                                                                     10

SEQ ID NO: 268          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 268
GGTFSS                                                                          6

SEQ ID NO: 269          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 269
MVTPIFGEAK                                                                     10

SEQ ID NO: 270          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 270
GGAFSS                                                                          6

SEQ ID NO: 271          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 271
MITPVFGETK                                                                     10

SEQ ID NO: 272          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 272
FIKYDGSEKY                                                                     10

SEQ ID NO: 273          moltype = DNA   length = 1473
FEATURE                 Location/Qualifiers
misc_feature            1..1473
                        note = Description of Artificial Sequence: Synthetic
                        polynucleotide
source                  1..1473
                        mol_type = other DNA
                        organism = synthetic construct
SEQUENCE: 273
atggactgga tttggaggat cctcttcttg gtggcagcag ttgcaagtgc ccactcgcag    60
gtgcagctgg tgcagtctgg gccggaggtg aagaagcctg gtcctcagt gaaggtctcc    120
tgcaaggcct ggaaaacac cttcagtaaa tatgatgtcc actgggtacg acaggccact    180
```

```
ggacagggc  ttgaatgggt  gggatggatg  agtcatgagg  gtgataagac  agaatctgca   240
cagagattta  agggccgagt  caccttcacg  agggacactt  ccgcaagcac  agcctacatg   300
gaactgcgcg  gcctgacatc  tgacgacacg  gccatctatt  attgtacgag  aggctcaaaa   360
catcgtttgc  gagactacgt  tctctacgat  gactacggct  taattaatta  tcaagagtgg   420
aatgactacc  ttgaattttt  ggacgtctgg  ggccatgaa   ccgcggtcac  cgtctcctca   480
gcctccacca  agggcccatc  ggtcttcccc  ctggcaccct  cctccaagag  cacctctggg   540
ggcacagcgg  ccctgggctg  cctggtcaag  gactacttcc  ccgaaccggt  gacggtgtcg   600
tggaactcag  gcgccctgac  cagcggcgtg  cacaccttcc  cggctgtcct  acagtcctca   660
ggactctact  ccctcagcag  cgtggtgacc  gtgccctcca  gcagcttggg  cacccagacc   720
tacatctgca  acgtgaatca  caagcccagc  aacaccaagg  tggacaagag  agttgagccc   780
aaatcttgtg  acaaaactca  cacatgccca  ccgtgcccag  cacctgaact  cctgggggga   840
ccgtcagtct  tcctcttccc  cccaaaaccc  aaggacaccc  tcatgatctc  ccggacccct   900
gaggtcacat  gcgtggtggt  ggacgtgagc  cacgaagacc  ctgaggtcaa  gttcaactgg   960
tacgtggacg  gcgtggaggt  gcataatgcc  aagacaaagc  cgcgggagga  gcagtacaac  1020
agcacgtacc  gtgtggtcag  cgtcctcacc  gtcctgcacc  aggactggct  gaatggcaag  1080
gagtacaagt  gcaaggtctc  caacaaagcc  ctcccagccc  ccatcgagaa  aaccatctcc  1140
aaagccaaag  ggcagccccg  agaaccacag  gtgtacaccc  tgcccccatc  ccgggaggag  1200
atgaccaaga  accaggtcag  cctgacctgc  ctggtcaaag  gcttctatcc  cagcgacatc  1260
gccgtggagt  gggagagcaa  tgggcagccg  gagaacaact  acaagaccac  gcctcccgtg  1320
ctggactccg  acggctcctt  cttcctctat  agcaagctca  ccgtggacaa  gagcaggtgg  1380
cagcagggga  acgtcttctc  atgctccgtg  atgcatgagg  ctctgcacaa  ccactacacg  1440
cagaagagcc  tctccctgtc  tccgggtaaa  tga                                1473

SEQ ID NO: 274          moltype = DNA  length = 423
FEATURE                 Location/Qualifiers
misc_feature            1..423
                        note = Description of Artificial Sequence: Synthetic
                          polynucleotide
source                  1..423
                        mol_type = other DNA
                        organism = synthetic construct
SEQUENCE: 274
caggtgcagc  tggtgcagtc  tgggccggag  gtgaagaagc  ctgggtcctc  agtgaaggtc    60
tcctgcaagg  cctctggaaa  caccttcagt  aaatatgatg  tccactgggt  acgacaggcc   120
actggacagg  ggcttgaatg  ggtgggatgg  atgagtcatg  agggtgataa  gacagaatct   180
gcacagagat  taagggccg   agtcaccttc  acgagggaca  cttccgcaag  cacagcctac   240
atggaactgc  gcgccctgac  atctgacgac  acggccatct  attattgtac  gagaggctca   300
aaacatcgtt  tgcgagacta  cgttctctac  gatgactacg  gcttaattaa  ttatcaagag   360
tggaatgact  accttgaatt  tttggacgtc  tggggccatg  gaaccgcggt  caccgtctcc   420
tca                                                                     423

SEQ ID NO: 275          moltype = AA  length = 490
FEATURE                 Location/Qualifiers
REGION                  1..490
                        note = Description of Artificial Sequence: Synthetic
                          polypeptide
source                  1..490
                        mol_type = protein
                        organism = synthetic construct
SEQUENCE: 275
MDWIWRILFL VAAVASAHSQ VQLVQSGPEV KKPGSSVKVS CKASGNTFSK YDVHWVRQAT    60
GQGLEWVGWM SHEGDKTESA QRFKGRVTFT RDTSASTAYM ELRGLTSDDT AIYYCTRGSK   120
HRLRDYVLYD DYGLINYQEW NDYLEFLDVW GHGTAVTVSS ASTKGPSVFP LAPSSKSTSG   180
GTAALGCLVK DYFPEPVTVS WNSGALTSGV HTFPAVLQSS GLYSLSSVVT VPSSSLGTQT   240
YICNVNHKPS NTKVDKRVEP KSCDKTHTCP PCPAPELLGG PSVFLFPPKP KDTLMISRTP   300
EVTCVVVDVS HEDPEVKFNW YVDGVEVHNA KTKPREEQYN STYRVVSVLT VLHQDWLNGK   360
EYKCKVSNKA LPAPIEKTIS KAKGQPREPQ VYTLPPSREE MTKNQVSLTC LVKGFYPSDI   420
AVEWESNGQP ENNYKTTPPV LDSDGSFFLY SKLTVDKSRW QQGNVFSCSV MHEALHNHYT   480
QKSLSLSPGK                                                          490

SEQ ID NO: 276          moltype = AA  length = 141
FEATURE                 Location/Qualifiers
REGION                  1..141
                        note = Description of Artificial Sequence: Synthetic
                          polypeptide
source                  1..141
                        mol_type = protein
                        organism = synthetic construct
SEQUENCE: 276
QVQLVQSGPE VKKPGSSVKV SCKASGNTFS KYDVHWVRQA TGQGLEWVGW MSHEGDKTES    60
AQRFKGRVTF TRDTSASTAY MELRGLTSDD TAIYYCTRGS KHRLRDYVLY DDYGLINYQE   120
WNDYLEFLDV WGHGTAVTVS S                                             141

SEQ ID NO: 277          moltype = AA  length = 5
FEATURE                 Location/Qualifiers
REGION                  1..5
                        note = Description of Artificial Sequence: Synthetic peptide
source                  1..5
                        mol_type = protein
```

```
                            organism = synthetic construct
SEQUENCE: 277
KYDVH                                                                       5

SEQ ID NO: 278          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 278
WMSHEGDKTE SAQRFKG                                                         17

SEQ ID NO: 279          moltype = AA   length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 279
GSKHRLRDYV LYDDYGLINY QEWNDYLEFL DV                                        32

SEQ ID NO: 280          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 280
GNTFSK                                                                      6

SEQ ID NO: 281          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 281
WMSHEGDKTE                                                                 10

SEQ ID NO: 282          moltype = DNA   length = 720
FEATURE                 Location/Qualifiers
misc_feature            1..720
                        note = Description of Artificial Sequence: Synthetic
                         polynucleotide
source                  1..720
                        mol_type = other DNA
                        organism = synthetic construct
SEQUENCE: 282
atgaggctcc ctgctcagct cctggggctg ctaatgctct gggtctctgg atccagtgcg           60
gatactgtcg tgactcagtc tccactctcc ctgcccgtca cccctggaga ggcggcctcc          120
atgtcctgtt cgtcgactca gagcctccgg catagtaatg gagccaacta tttggcttgg          180
tatcagcaca aaccggggca gtctccacga ctcctaatcc gtttaggttc tcaacgggcc          240
tccgggtgtcc ctgacagatt cagtggcagt ggatcaggca ctcattttac actgaaaatc         300
agtagagtgg aggctgaaga tgctgcaatt tattattgca tgcaaggtct gaaccgtccc          360
tggacgttcg gcaaggggac caagttggaa atcaaacgta cggtggctgc accatctgtc          420
ttcatcttcc cgccatctga tgagcagttg aaatctggaa ctgcctctgt tgtgtgcctg          480
ctgaataact tctatcccag agaggccaaa gtacagtgga aggtggataa cgccctccaa          540
tcgggtaact cccaggagag tgtcacagag caggacagca aggacagcac ctacagcctc          600
agcagcaccc tgacgctgag caaagcagac tacgagaaac acaaagtcta cgcctgcgaa          660
gtcacccatc agggcctgag ctcgcccgtc acaaagagct tcaacagggg agagtgttag          720

SEQ ID NO: 283          moltype = DNA   length = 336
FEATURE                 Location/Qualifiers
misc_feature            1..336
                        note = Description of Artificial Sequence: Synthetic
                         polynucleotide
source                  1..336
                        mol_type = other DNA
                        organism = synthetic construct
SEQUENCE: 283
gatactgtcg tgactcagtc tccactctcc ctgcccgtca cccctggaga ggcggcctcc           60
atgtcctgtt cgtcgactca gagcctccgg catagtaatg gagccaacta tttggcttgg         120
tatcagcaca aaccggggca gtctccacga ctcctaatcc gtttaggttc tcaacgggcc         180
```

```
tccggggtcc ctgacagatt cagtggcagt ggatcaggca ctcattttac actgaaaatc   240
agtagagtgg aggctgaaga tgctgcaatt tattattgca tgcaaggtct gaaccgtccc   300
tggacgttcg gcaagggac caagttggaa atcaaa                              336
```

```
SEQ ID NO: 284              moltype = AA   length = 239
FEATURE                     Location/Qualifiers
REGION                      1..239
                            note = Description of Artificial Sequence: Synthetic
                             polypeptide
source                      1..239
                            mol_type = protein
                            organism = synthetic construct
SEQUENCE: 284
MRLPAQLLGL LMLWVSGSSA DTVVTQSPLS LPVTPGEAAS MSCSSTQSLR HSNGANYLAW   60
YQHKPGQSPR LLIRLGSQRA SGVPDRFSGS GSGTHFTLKI SRVEAEDAAI YYCMQGLNRP   120
WTFGKGTKLE IKRTVAAPSV FIFPPSDEQL KSGTASVVCL LNNFYPREAK VQWKVDNALQ   180
SGNSQESVTE QDSKDSTYSL SSTLTLSKAD YEKHKVYACE VTHQGLSSPV TKSFNRGEC    239
```

```
SEQ ID NO: 285              moltype = AA   length = 112
FEATURE                     Location/Qualifiers
REGION                      1..112
                            note = Description of Artificial Sequence: Synthetic
                             polypeptide
source                      1..112
                            mol_type = protein
                            organism = synthetic construct
SEQUENCE: 285
DTVVTQSPLS LPVTPGEAAS MSCSSTQSLR HSNGANYLAW YQHKPGQSPR LLIRLGSQRA   60
SGVPDRFSGS GSGTHFTLKI SRVEAEDAAI YYCMQGLNRP WTFGKGTKLE IK           112
```

```
SEQ ID NO: 286              moltype = AA   length = 16
FEATURE                     Location/Qualifiers
REGION                      1..16
                            note = Description of Artificial Sequence: Synthetic peptide
source                      1..16
                            mol_type = protein
                            organism = synthetic construct
SEQUENCE: 286
SSTQSLRHSN GANYLA                                                   16
```

```
SEQ ID NO: 287              moltype = AA   length = 7
FEATURE                     Location/Qualifiers
REGION                      1..7
                            note = Description of Artificial Sequence: Synthetic peptide
source                      1..7
                            mol_type = protein
                            organism = synthetic construct
SEQUENCE: 287
LGSQRAS                                                             7
```

```
SEQ ID NO: 288              moltype = AA   length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 288
MQGLNRPWT                                                           9
```

```
SEQ ID NO: 289              moltype = DNA   length = 1473
FEATURE                     Location/Qualifiers
misc_feature                1..1473
                            note = Description of Artificial Sequence: Synthetic
                             polynucleotide
source                      1..1473
                            mol_type = other DNA
                            organism = synthetic construct
SEQUENCE: 289
atggactgga tttggaggat cctcttcttg gtggcagcag ttgcaagtgc ccactcgcag   60
gtgcagctgg tgcagtctgg gcctgaggtg aagaagcctg gtcctcagt gaaggtctcc    120
tgcaaggcct ctggaaacac cttcagtaaa tatgatgtcc actgggtacg gcaggccact   180
ggacagggc ttgaatgggt gggatggatg agtcatgagg tgataagac agaatctgca    240
cagagattta agggccgagt caccttcacg agggacactt ccgcaagcac agcctacatg   300
gaactgcgcg gcctgacatc tgacgacacg gccatttatt attgtacgag aggctcaaaa   360
catcgcttgc gagactatgt tctctacgat gactacggct taattaatta tcaagagtgg   420
aatgactacc ttgaattttt ggacgtctgg ggccatggaa ccgcggtcac cgtctcctca   480
gcctccacca agggcccatc ggtcttcccc ctggcaccct cctccaagag cacctctggg   540
ggcacagcgg ccctgggctg cctggtcaag gactacttcc ccgaaccggt gacggtgtcg   600
```

```
tggaactcag gcgccctgac cagcggcgtg cacaccttcc cggctgtcct acagtcctca    660
ggactctact ccctcagcag cgtggtgacc gtgccctcca gcagcttggg cacccagacc    720
tacatctgca acgtgaatca caagcccagc aacaccaagg tggacaagag agttgagccc    780
aaatcttgtg acaaaactca cacatgccca ccgtgcccag cacctgaact cctgggggga    840
ccgtcagtct tcctcttccc cccaaaaccc aaggacaccc tcatgatctc ccggacccct    900
gaggtcacat gcgtggtggt ggacgtgagc cacgaagacc ctgaggtcaa gttcaactgg    960
tacgtggacg gcgtggaggt gcataatgcc aagacaaagc cgcgggagga gcagtacaac   1020
agcacgtacc gtgtggtcag cgtcctcacc gtcctgcacc aggactggct gaatggcaag   1080
gagtacaagt gcaaggtctc caacaaagcc ctcccagccc ccatcgagaa aaccatctcc   1140
aaagccaaag ggcagccccg agaaccacag gtgtacaccc tgcccccatc ccgggaggag   1200
atgaccaaga accaggtcag cctgacctgc ctggtcaaag gcttctatcc cagcgacatc   1260
gccgtggagt gggagagcaa tgggcagccg gagaacaact acaagaccac gcctcccgtg   1320
ctggactccg acggctcctt cttcctctat agcaagctca ccgtggacaa gagcaggtgg   1380
cagcagggga acgtcttctc atgctccgtg atgcatgagg ctctgcacaa ccactacacg   1440
cagaagagcc tctccctgtc tccgggtaaa tga                                1473

SEQ ID NO: 290          moltype = DNA  length = 423
FEATURE                 Location/Qualifiers
misc_feature            1..423
                        note = Description of Artificial Sequence: Synthetic
                         polynucleotide
source                  1..423
                        mol_type = other DNA
                        organism = synthetic construct
SEQUENCE: 290
caggtgcagc tggtgcagtc tgggcctgag gtgaagaagc ctgggtcctc agtgaaggtc     60
tcctgcaagg cctctggaaa caccttcagt aaatatgatg tccactgggt acggcaggcc    120
actggacagg ggcttgaatg ggtgggatgg atgagtcatg agggtgataa gacagaatct    180
gcacagagat ttaagggccg agtcaccttc acgagggaca cttccgcaag cacagcctac    240
atggaactgc gcgggctgac atctgacgac acggccattt attattgtac gagaggctca    300
aaacatcgct tgcgagacta tgttctctac gatgactacg gcttaattaa ttatcaagag    360
tggaatgact accttgaatt tttggacgtc tggggccatg gaaccgcggt caccgtctcc    420
tca                                                                  423

SEQ ID NO: 291          moltype = AA  length = 490
FEATURE                 Location/Qualifiers
REGION                  1..490
                        note = Description of Artificial Sequence: Synthetic
                         polypeptide
source                  1..490
                        mol_type = protein
                        organism = synthetic construct
SEQUENCE: 291
MDWIWRILFL VAAVASAHSQ VQLVQSGPEV KKPGSSVKVS CKASGNTFSK YDVHWVRQAT     60
GQGLEWVGWI SHERDKTESA QRFKGRVTFT RDTSATTAYM ELRGLTSDDT AIYYCTRGSK    120
HRLRDYVLYD DYGLINYQEW NDYLEFLDVW GHGTAVTVSS ASTKGPSVFP LAPSSKSTSG    180
GTAALGCLVK DYFPEPVTVS WNSGALTSGV HTFPAVLQSS GLYSLSSVVT VPSSSLGTQT    240
YICNVNHKPS NTKVDKRVEP KSCDKTHTCP PCPAPELLGG PSVFLFPPKP KDTLMISRTP    300
EVTCVVVDVS HEDPEVKFNW YVDGVEVHNA KTKPREEQYN STYRVVSVLT VLHQDWLNGK    360
EYKCKVSNKA LPAPIEKTIS KAKGQPREPQ VYTLPPSREE MTKNQVSLTC LVKGFYPSDI    420
AVEWESNGQP ENNYKTTPPV LDSDGSFFLY SKLTVDKSRW QQGNVFSCSV MHEALHNHYT    480
QKSLSLSPGK                                                           490

SEQ ID NO: 292          moltype = AA  length = 141
FEATURE                 Location/Qualifiers
REGION                  1..141
                        note = Description of Artificial Sequence: Synthetic
                         polypeptide
source                  1..141
                        mol_type = protein
                        organism = synthetic construct
SEQUENCE: 292
QVQLVQSGPE VKKPGSSVKV SCKASGNTFS KYDVHWVRQA TGQGLEWVGW ISHERDKTES     60
AQRFKGRVTF TRDTSATTAY MELRGLTSDD TAIYYCTRGS KHRLRDYVLY DDYGLINYQE    120
WNDYLEFLDV WGHGTAVTVS S                                              141

SEQ ID NO: 293          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 293
WISHERDKTE SAQRFKG                                                    17

SEQ ID NO: 294          moltype = AA  length = 10
FEATURE                 Location/Qualifiers
REGION                  1..10
```

```
                        note = Description of Artificial Sequence: Synthetic peptide
source                  1..10
                        mol_type = protein
                        organism = synthetic construct
SEQUENCE: 294
WISHERDKTE                                                                       10

SEQ ID NO: 295          moltype = DNA  length = 1473
FEATURE                 Location/Qualifiers
misc_feature            1..1473
                        note = Description of Artificial Sequence: Synthetic
                        polynucleotide
source                  1..1473
                        mol_type = other DNA
                        organism = synthetic construct
SEQUENCE: 295
atggactgga tttggaggat cctcttcttg gtggcagcag ttgcaagtgc ccacgcgcag    60
gtgcagctgg agcagtctgg ggctgaggtg aagaagcctg gtcctcagt gaaggtctcc   120
tgcaaggcct ctggaaacac cttcagtaaa tatgatgtcc actgggtacg acaggccact   180
ggacaggggc ttgaatgggt gggatggatg agtcatgagg gtgataagac agaatctgca   240
cagagattta aggggcgagt caccttcacg agggacactt ccgcaagcac agcctacatg   300
gaactgcgcg gcctgacatc tgacgacacg gccatttatt attgtacgag aggttcaaaa   360
catcgcttgc gagactacgt tctctacgat gactacggct taattaatta tcaagagtgg   420
aatgactacc ttgaattttt ggacgtctgg ggccatggaa ccgcggtcac cgtctcctca   480
gcctccacca agggcccatc ggtcttcccc ctggcaccct cctccaagag cacctctggg   540
ggcacagcgg ccctgggctg cctggtcaag gactacttcc ccgaaccggt gacggtgtcg   600
tggaactcag gcgccctgac cagcggcgtg cacaccttcc cggctgtcct acagtcctca   660
ggactctact ccctcagcag cgtggtgacc gtgccctcca gcagcttggg cacccagacc   720
tacatctgca acgtgaatca caagcccagc aacaccaagg tggacaagag agttgagccc   780
aaatcttgtg acaaaactca cacatgccca cgtgcccac cacctgaact cctgggggga   840
ccgtcagtct tcctcttccc cccaaaaccc aaggacaccc tcatgatctc ccggacccct   900
gaggtcacat gcgtggtggt ggacgtgagc cacgaagacc ctgaggtcaa gttcaactgg   960
tacgtggacg gcgtggaggt gcataatgcc aagacaaagc cgcggggagga gcagtacaac  1020
agcacgtacc gtgtggtcag cgtcctcacc gtcctgcacc aggactggct gaatggcaag  1080
gagtacaagt gcaaggtctc caacaaagcc ctcccagccc ccatcgagaa aaccatctcc  1140
aaagccaaag ggcagccccg agaaccacag gtgtacaccc tgcccccatc ccgggaggag  1200
atgaccaaga accaggtcag cctgacctgc ctggtcaaag gcttctatcc cagcgacatc  1260
gccgtggagt gggagagcaa tgggcagccg gagaacaact acaagaccac gcctcccgtg  1320
ctggactccg acggctcctt cttcctctat agcaagctca ccgtggacaa gagcaggtgg  1380
cagcagggga acgtcttctc atgctccgtg atgcatgagg ctctgcacaa ccactacacg  1440
cagaagagcc tctccctgtc tccgggtaaa tga                              1473

SEQ ID NO: 296          moltype = DNA  length = 423
FEATURE                 Location/Qualifiers
misc_feature            1..423
                        note = Description of Artificial Sequence: Synthetic
                        polynucleotide
source                  1..423
                        mol_type = other DNA
                        organism = synthetic construct
SEQUENCE: 296
caggtgcagc tggagcagtc tggggctgag gtgaagaagc ctgggtcctc agtgaaggtc    60
tcctgcaagg cctctggaaa caccttcagt aaatatgatg tccactgggt acgacaggcc   120
actggacagg ggcttgaatg ggtgggatgg atgagtcatg agggtgataa gacagaatct   180
gcacagagat ttaaggggcg agtcaccttc acgagggaca cttccgcaag cacagcctac   240
atggaactgc gcggcctgac atctgacgac acggccattt attattgtac gagaggttca   300
aaacatcgct tgcgagacta cgttctctac gatgactacg gcttaattaa ttatcaagag   360
tggaatgact accttgaatt tttggacgtc tggggccatg gaaccgcggt caccgtctcc   420
tca                                                               423

SEQ ID NO: 297          moltype = AA  length = 490
FEATURE                 Location/Qualifiers
REGION                  1..490
                        note = Description of Artificial Sequence: Synthetic
                        polypeptide
source                  1..490
                        mol_type = protein
                        organism = synthetic construct
SEQUENCE: 297
MDWIWRILFL VAAVASAHAQ VQLEQSGAEV KKPGSSVKVS CKASGNTFSK YDVHWVRQAT    60
GQGLEWVGWM SHEGDKTESA QRFKGRVTFT RDTSASTAYM ELRGLTSDDT AIYYCTRGSK   120
HRLRDYVLYD DYGLINYQEW NDYLEFLDVW GHGTAVTVSS ASTKGPSVFP LAPSSKSTSG   180
GTAALGCLVK DYFPEPVTVS WNSGALTSGV HTFPAVLQSS GLYSLSSVVT VPSSSLGTQT   240
YICNVNHKPS NTKVDKRVEP KSCDKTHTCP PCPAPELLGG PSVFLFPPKP KDTLMISRTP   300
EVTCVVVDVS HEDPEVKFNW YVDGVEVHNA KTKPREEQYN STYRVVSVLT VLHQDWLNGK   360
EYKCKVSNKA LPAPIEKTIS KAKGQPREPQ VYTLPPSREE MTKNQVSLTC LVKGFYPSDI   420
AVEWESNGQP ENNYKTTPPV LDSDGSFFLY SKLTVDKSRW QQGNVFSCSV MHEALHNHYT   480
QKSLSLSPGK                                                        490
```

```
SEQ ID NO: 298             moltype = AA   length = 141
FEATURE                    Location/Qualifiers
REGION                     1..141
                           note = Description of Artificial Sequence: Synthetic
                           polypeptide
source                     1..141
                           mol_type = protein
                           organism = synthetic construct
SEQUENCE: 298
QVQLEQSGAE VKKPGSSVKV SCKASGNTFS KYDVHWVRQA TGQGLEWVGW MSHEGDKTES   60
AQRFKGRVTF TRDTSASTAY MELRGLTSDD TAIYYCTRGS KHRLRDYVLY DDYGLINYQE  120
WNDYLEFLDV WGHGTAVTVS S                                            141

SEQ ID NO: 299             moltype = DNA   length = 720
FEATURE                    Location/Qualifiers
misc_feature               1..720
                           note = Description of Artificial Sequence: Synthetic
                           polynucleotide
source                     1..720
                           mol_type = other DNA
                           organism = synthetic construct
SEQUENCE: 299
atgaggctcc ctgctcagct cctggggctg ctaatgctct gggtctctgg atccagtgcg   60
gatactgtcg tgactcagtc tccactctcc ctgcccgtca ccctggaga ggcggcctcc  120
atgtcctgta cgtcgactca gagcctccgt catagtaatg gagccaacta tttggcttgg  180
taccagcaca aaccagggca gtctccacga ctcctaatcc gtttaggttc tcaacgggcc  240
tccggggtcc ctgacagatt cagtggcagt ggatcaggca ctcattttac actgaaaatc  300
agtcgagtgg agcctgaaga tgctgcaatt tattattgca tgcaaggtct gaaccgtccc  360
tggacgttcg gcaaggggac caagttggaa atcaaacgta cggtggctgc accatctgtc  420
ttcatcttcc cgccatctga tgagcagttg aaatctggaa ctgcctctgt tgtgtgcctg  480
ctgaataact tctatcccag agaggccaaa gtacagtgga aggtggataa cgccctccaa  540
tcgggtaact cccaggagag tgtcacagag caggacagca aggacagcac ctacagcctc  600
agcagcaccc tgacgctgag caaagcagac tacgagaaac acaaagtcta cgcctgcgaa  660
gtcacccatc agggcctgag ctcgcccgtc acaaagagct caacagggg agagtgttag   720

SEQ ID NO: 300             moltype = DNA   length = 336
FEATURE                    Location/Qualifiers
misc_feature               1..336
                           note = Description of Artificial Sequence: Synthetic
                           polynucleotide
source                     1..336
                           mol_type = other DNA
                           organism = synthetic construct
SEQUENCE: 300
gatactgtcg tgactcagtc tccactctcc ctgcccgtca ccctggaga ggcggcctcc   60
atgtcctgta cgtcgactca gagcctccgt catagtaatg gagccaacta tttggcttgg  120
taccagcaca aaccagggca gtctccacga ctcctaatcc gtttaggttc tcaacgggcc  180
tccggggtcc ctgacagatt cagtggcagt ggatcaggca ctcattttac actgaaaatc  240
agtcgagtgg agcctgaaga tgctgcaatt tattattgca tgcaaggtct gaaccgtccc  300
tggacgttcg gcaaggggac caagttggaa atcaaa                            336

SEQ ID NO: 301             moltype = AA   length = 239
FEATURE                    Location/Qualifiers
REGION                     1..239
                           note = Description of Artificial Sequence: Synthetic
                           polypeptide
source                     1..239
                           mol_type = protein
                           organism = synthetic construct
SEQUENCE: 301
MRLPAQLLGL LMLWVSGSSA DTVVTQSPLS LPVTPGEAAS MSCTSTQSLR HSNGANYLAW   60
YQHKPGQSPR LLIRLGSQRA SGVPDRFSGS GSGTHFTLKI SRVEPEDAAI YYCMQGLNRP  120
WTFGKGTKLE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 302             moltype = AA   length = 112
FEATURE                    Location/Qualifiers
REGION                     1..112
                           note = Description of Artificial Sequence: Synthetic
                           polypeptide
source                     1..112
                           mol_type = protein
                           organism = synthetic construct
SEQUENCE: 302
DTVVTQSPLS LPVTPGEAAS MSCTSTQSLR HSNGANYLAW YQHKPGQSPR LLIRLGSQRA   60
SGVPDRFSGS GSGTHFTLKI SRVEPEDAAI YYCMQGLNRP WTFGKGTKLE IK          112

SEQ ID NO: 303             moltype = AA   length = 16
FEATURE                    Location/Qualifiers
```

| REGION | 1..16 |
| --- | --- |
| | note = Description of Artificial Sequence: Synthetic peptide |
| source | 1..16 |
| | mol_type = protein |
| | organism = synthetic construct |

SEQUENCE: 303
TSTQSLRHSN GANYLA                                                          16

| SEQ ID NO: 304 | moltype = DNA  length = 1473 |
| --- | --- |
| FEATURE | Location/Qualifiers |
| misc_feature | 1..1473 |
| | note = Description of Artificial Sequence: Synthetic |
| | polynucleotide |
| source | 1..1473 |
| | mol_type = other DNA |
| | organism = synthetic construct |

SEQUENCE: 304
```
atggactgga tttggaggat cctcttcttg gtggcagcag ttgcaagtgc ccactcgcag    60
gtgcagctgg tgcagtctgg ggctgaggtg aagaagcctg gtcctcagt gaaggtctcc    120
tgcaaggcct ctggaaacac cttcaggaaa tatgatgtcc actgggtacg acaggccact   180
ggacagggc ttgaatgggt gggatggatg agtcatgagg gtgataagac agaatctgca    240
cagagattta agggccgagt ctctttcacg agggacacac ccgcaagcac agcctacatt   300
gaactgcgcg gcctgacatc tgacgacacg gccatttatt attgtaccgg aggctcaaaa   360
catcgcttgc gagactacgt tctctacgat gattacggcc taataaatca gcaagagtgg   420
aatgactacc ttgaatttt ggacgtctgg ggccatggaa ccgcggtcac cgtctcctca    480
gcctccacca agggccccatc ggtcttcccc ctggcaccct cctccaagag cacctctggg   540
ggcacagcgg ccctgggctg cctggtcaag gactacttcc ccgaaccggt gacggtgtcg    600
tggaactcag gcgccctgac cagcggcgtg cacaccttcc cggctgtcct acagtcctca    660
ggactctact ccctcagcag cgtggtgacc gtgcccctcca gcagcttggg cacccagacc   720
tacatctgca acgtgaatca caagcccagc aacaccaagg tggacaagaa agttgagccc    780
aaatcttgtg acaaaactca cacatgccca ccgtgcccca cctgaact cctgggggga   840
ccgtcagtct tcctcttccc cccaaaaccc aaggacaccc tcatgatctc ccggaccct    900
gaggtcacat gcgtggtggt ggacgtgagc cacgaagacc ctgaggtcaa gttcaactgg   960
tacgtggacg gcgtggaggt gcataatgcc aagacaaagc cgcgggagga gcagtacaac   1020
agcacgtacc gtgtggtcag cgtcctcacc gtcctgcacc aggactggct gaatggcaag   1080
gagtacaagt gcaaggtctc caacaaagcc ctcccagccc ccatcgagaa aaccatctcc   1140
aaagccaaag ggcagccccg agaaccacag gtgtacaccc tgccccatc ccgggaggag    1200
atgaccaaga accaggtcag cctgacctgc ctggtcaaag gcttctatcc cagcgacatc   1260
gccgtggagt gggagagcaa tgggcagccg gagaacaact acaagaccac gcctcccgtg   1320
ctggactccg acggctcctt cttcctctat agcaagctca ccgtggacaa gagcaggtgg   1380
cagcagggga acgtcttctc atgctccgtg atgcatgagg ctctgcacaa ccactacacg   1440
cagaagagcc tctccctgtc tccgggtaaa tga                                  1473
```

| SEQ ID NO: 305 | moltype = DNA  length = 423 |
| --- | --- |
| FEATURE | Location/Qualifiers |
| misc_feature | 1..423 |
| | note = Description of Artificial Sequence: Synthetic |
| | polynucleotide |
| source | 1..423 |
| | mol_type = other DNA |
| | organism = synthetic construct |

SEQUENCE: 305
```
caggtgcagc tggtgcagtc tggggctgag gtgaagaagc ctgggtcctc agtgaaggtc    60
tcctgcaagg cctctggaaa caccttcagg aaatatgatg tccactgggt acgacaggcc   120
actgggacag ggcttgaatg ggtgggatgg atgagtcatg agggtgataa gacagaatct   180
gcacagagat ttaagggccg agtctctttc acgagggaca caattccgcaag cacagcctac   240
attgaactgc gcggcctgac atctgacgac acggccattt attattgtac cggaggctca    300
aaacatcgct tgcgagacta cgttctctac gatgattacg gcctaataaa tcagcaagag   360
tggaatgact accttgaatt tttggacgtc tggggccatg gaaccgcggt caccgtctcc   420
tca                                                                   423
```

| SEQ ID NO: 306 | moltype = AA  length = 490 |
| --- | --- |
| FEATURE | Location/Qualifiers |
| REGION | 1..490 |
| | note = Description of Artificial Sequence: Synthetic |
| | polypeptide |
| source | 1..490 |
| | mol_type = protein |
| | organism = synthetic construct |

SEQUENCE: 306
```
MDWIWRILFL VAAVASAHSQ VQLVQSGAEV KKPGSSVKVS CKASGNTFRK YDVHWVRQAT     60
GQGLEWVGWM SHEGDKTESA QRFKGRVSFT RDNSASTAYI ELRGLTSDDT AIYYCTGGSK   120
HRLRDYVLYD DYGLINQQEW NDYLEFLDVW GHGTAVTVSS ASTKGPSVFP LAPSSKSTSG   180
GTAALGCLVK DYFPEPVTVS WNSGALTSGV HTFPAVLQSS GLYSLSSVVT VPSSSLGTQT   240
YICNVNHKPS NTKVDKRVEP KSCDKTHTCP PCPAPELLGG PSVFLFPPKP KDTLMISRTP   300
EVTCVVVDVS HEDPEVKFNW YVDGVEVHNA KTKPREEQYN STYRVVSVLT VLHQDWLNGK   360
EYKCKVSNKA LPAPIEKTIS KAKGQPREPQ VYTLPPSREE MTKNQVSLTC LVKGFYPSDI   420
AVEWESNGQP ENNYKTTPPV LDSDGSFFLY SKLTVDKSRW QQGNVFSCSV MHEALHNHYT   480
QKSLSLSPGK                                                            490
```

| SEQ ID NO: 307 | moltype = AA   length = 141 |
| --- | --- |
| FEATURE | Location/Qualifiers |
| REGION | 1..141 |
| | note = Description of Artificial Sequence: Synthetic polypeptide |
| source | 1..141 |
| | mol_type = protein |
| | organism = synthetic construct |

SEQUENCE: 307
```
QVQLVQSGAE VKKPGSSVKV SCKASGNTFR KYDVHWVRQA TGQGLEWVGW MSHEGDKTES   60
AQRFKGRVSF TRDNSASTAY IELRGLTSDD TAIYYCTGGS KHRLRDYVLY DDYGLINQQE  120
WNDYLEFLDV WGHGTAVTVS S                                            141
```

| SEQ ID NO: 308 | moltype = AA   length = 32 |
| --- | --- |
| FEATURE | Location/Qualifiers |
| REGION | 1..32 |
| | note = Description of Artificial Sequence: Synthetic polypeptide |
| source | 1..32 |
| | mol_type = protein |
| | organism = synthetic construct |

SEQUENCE: 308
```
GSKHRLRDYV LYDDYGLINQ QEWNDYLEFL DV                                 32
```

| SEQ ID NO: 309 | moltype = AA   length = 6 |
| --- | --- |
| FEATURE | Location/Qualifiers |
| REGION | 1..6 |
| | note = Description of Artificial Sequence: Synthetic peptide |
| source | 1..6 |
| | mol_type = protein |
| | organism = synthetic construct |

SEQUENCE: 309
```
GNTFRK                                                              6
```

| SEQ ID NO: 310 | moltype = DNA   length = 720 |
| --- | --- |
| FEATURE | Location/Qualifiers |
| misc_feature | 1..720 |
| | note = Description of Artificial Sequence: Synthetic polynucleotide |
| source | 1..720 |
| | mol_type = other DNA |
| | organism = synthetic construct |

SEQUENCE: 310
```
atgaggctcc ctgctcagct cctggggctg ctaatgctct gggtctctgg atccagtgcg   60
gatactgtcg tgactcagtc tccactctcc ctgtccgtca ccctggaga ggcggcctcc  120
atgtcctgta cgtcgactca gagcctccgg catagtaatg gagccaacta tttggcttgg  180
taccagcaca aaccagggca gtctccacga ctcctaatcc gtttaggttc tcaacgggcc  240
tccggggtcc ctgacagatt cagtggcagt ggatcaggca ctcattttac actgaaaatc  300
agtagagtgg aggctgacga tgctgcaatt tattattgca tgcaaggtct gaaccgtccc  360
tggacgttcg gcaaggggac caagttggag atcaaacgta cggtggctgc accatctgtc  420
ttcatcttcc cgccatctga tgagcagttg aaatctggaa ctgcctctgt tgtgtgcctg  480
ctgaataact tctatcccag agaggccaaa gtacagtgga aggtggataa cgccctccaa  540
tcgggtaact cccaggagag tgtcacagag caggacagca aggacagcac ctacagcctc  600
agcagcaccc tgacgctgag caaagcagac tacgagaaac acaaagtcta cgcctgcgaa  660
gtcacccatc agggcctgag ctcgcccgtc acaaagagct tcaacagggg agagtgttag  720
```

| SEQ ID NO: 311 | moltype = DNA   length = 336 |
| --- | --- |
| FEATURE | Location/Qualifiers |
| misc_feature | 1..336 |
| | note = Description of Artificial Sequence: Synthetic polynucleotide |
| source | 1..336 |
| | mol_type = other DNA |
| | organism = synthetic construct |

SEQUENCE: 311
```
gatactgtcg tgactcagtc tccactctcc ctgtccgtca ccctggaga ggcggcctcc   60
atgtcctgta cgtcgactca gagcctccgg catagtaatg gagccaacta tttggcttgg  120
taccagcaca aaccagggca gtctccacga ctcctaatcc gtttaggttc tcaacgggca  180
tccggggtcc ctgacagatt cagtggcagt ggatcaggca ctcattttac actgaaaatc  240
agtagagtgg aggctgacga tgctgcaatt tattattgca tgcaaggtct gaaccgtccc  300
tggacgttcg gcaaggggac caagttggag atcaaa                            336
```

| SEQ ID NO: 312 | moltype = AA   length = 239 |
| --- | --- |
| FEATURE | Location/Qualifiers |
| REGION | 1..239 |
| | note = Description of Artificial Sequence: Synthetic polypeptide |
| source | 1..239 |

```
                            mol_type = protein
                            organism = synthetic construct
SEQUENCE: 312
MRLPAQLLGL LMLWVSGSSA DTVVTQSPLS LSVTPGEAAS MSCTSTQSLR HSNGANYLAW    60
YQHKPGQSPR LLIRLGSQRA SGVPDRFSGS GSGTHFTLKI SRVEADDAAI YYCMQGLNRP   120
WTFGKGTKLE IKRTVAAPSV FIFPPSDEQL KSGTASVVCL LNNFYPREAK VQWKVDNALQ   180
SGNSQESVTE QDSKDSTYSL SSTLTLSKAD YEKHKVYACE VTHQGLSSPV TKSFNRGEC    239

SEQ ID NO: 313              moltype = AA   length = 112
FEATURE                     Location/Qualifiers
REGION                      1..112
                            note = Description of Artificial Sequence: Synthetic
                             polypeptide
source                      1..112
                            mol_type = protein
                            organism = synthetic construct
SEQUENCE: 313
DTVVTQSPLS LSVTPGEAAS MSCTSTQSLR HSNGANYLAW YQHKPGQSPR LLIRLGSQRA    60
SGVPDRFSGS GSGTHFTLKI SRVEADDAAI YYCMQGLNRP WTFGKGTKLE IK           112

SEQ ID NO: 314              moltype = DNA   length = 1473
FEATURE                     Location/Qualifiers
misc_feature                1..1473
                            note = Description of Artificial Sequence: Synthetic
                             polynucleotide
source                      1..1473
                            mol_type = other DNA
                            organism = synthetic construct
SEQUENCE: 314
atggactgga tttggaggat cctcttcttg gtggcagcag ttgcaagtgc ccactcgcag    60
gtgcagctgg tgcagtctgg gcctgaggtg aagaagcctg ggtcctcagt gaaggtctcc   120
tgcaaggcct ctggaaacac cttcagtaaa tatgatgtcc actgggtacg acaggccact   180
ggacaggggc ttgaatgggt gggatggatt agtcatgagc gtgataagac agaatctgca   240
cagagattta agggccgagt caccttcacg agggacactt ccgcaaccac agcctacatg   300
gaactgcgcg gcctgacatc tgacgacacg gccatttatt attgtacgag aggctcaaaa   360
catcgcttgc gagactacgt tctctacgat gactacggct taattaatta tcaagagtgg   420
aatgactacc ttgaattttt ggacgtctgg ggccatggaa ccgcggtcac cgtctcctca   480
gcctccacca agggcccatc ggtcttcccc ctggcacccc cctccaagag cacctctggg   540
ggcacagcgg ccctgggctg cctggtcaag gactacttcc ccgaaccggt gacggtgtcg   600
tggaactcag gcgccctgac cagcggcgtg cacaccttcc cggctgtcct acagtcctca   660
ggactctact ccctcagcag cgtggtgacc gtgccctcca gcagcttggg cacccagacc   720
tacatctgca acgtgaatca caagcccagc aacaccaagg tggacaagag agttgagccc   780
aaatcttgtg acaaaactca cacatgccca ccgtgcccag cacctgaact cctggggggga   840
ccgtcagtct tcctcttccc cccaaaaccc aaggacaccc tcatgatctc ccggacccct   900
gaggtcacat gcgtggtggt ggacgtgagc cacgaagacc ctgaggtcaa gttcaactgg   960
tacgtggacg gcgtggaggt gcataatgcc aagacaaagc cgcgggagga gcagtacaac  1020
agcacgtacc gtgtggtcag cgtcctcacc gtcctgcacc aggactggct gaatggcaag  1080
gagtacaagt gcaaggtctc caacaaagcc ctcccagccc ccatcgagaa aaccatctcc  1140
aaagccaaag gcagccccg agaaccacag gtgtacaccc tgcccccatc ccgggaggag  1200
atgaccaaga accaggtcag cctgacctgc ctggtcaaag gcttctatcc cagcgacatc  1260
gccgtggagt gggagagcaa tgggcagccg gagaacaact acaagaccac gcctcccgtg  1320
ctggactccg acggctcctt cttcctctat agcaagctca ccgtggacaa gagcaggtgg  1380
cagcagggga acgtcttctc atgctccgtg atgcatgagg ctctgcacaa ccactacacg  1440
cagaagagcc tctccctgtc tccgggtaaa tga                               1473

SEQ ID NO: 315              moltype = DNA   length = 423
FEATURE                     Location/Qualifiers
misc_feature                1..423
                            note = Description of Artificial Sequence: Synthetic
                             polynucleotide
source                      1..423
                            mol_type = other DNA
                            organism = synthetic construct
SEQUENCE: 315
caggtgcagc tggtgcagtc tgggcctgag gtgaagaagc tgggtcctc agtgaaggtc    60
tcctgcaagg cctctggaaa caccttcagt aaatatgatg tccactgggt acgacaggcc   120
actggacagg ggcttgaatg ggtgggatgg attagtcatg agcgtgataa gacagaatct   180
gcacagagat ttaagggccg agtcaccttc acgagggaca cttccgcaac cacagcctac   240
atggaactgc gcggcctgac atctgacgac acggccattt attattgtac gagaggctac   300
aaacatcgct tgcgagacta cgttctctac gatgactacg gcttaattaa ttatcaagag   360
tggaatgact accttgaatt tttggacgtc tggggccatg gaaccgcggt caccgtctcc   420
tca                                                                423

SEQ ID NO: 316              moltype = DNA   length = 1458
FEATURE                     Location/Qualifiers
misc_feature                1..1458
                            note = Description of Artificial Sequence: Synthetic
                             polynucleotide
source                      1..1458
```

```
                        mol_type = other DNA
                        organism = synthetic construct
SEQUENCE: 316
atgaaacacc tgtggttctt cctcctgctg gtggcggctc ccagatgggt cctgtcccag   60
ccgcagctgc aggagtcggg cccaggactg gtggaggctt cggagaccct gtccctcacg  120
tgcactgtgt ccggcgactc cactggtcgt tgtaattatt tctggggctg ggtccggcag  180
cccccaggga aggggctgga gtggattggg agtttgtccc actgtagaag ttactacaat  240
actgactgga cctaccacaa cccgtctctc aagagtcgac tcactatttc actcgacacg  300
cccaagaatc aggtcttcct gagattgacc tctgtgaccg ccgcggacac ggccacttat  360
tactgtgcgc gattcggcgg cgaagttcta gtgtacagag attggccaaa gccggcctgg  420
gtcgacctct ggggccgggg aacgctggtc gtcaccgtct cgagcgcctc caccaagggc  480
ccatcggtct tccccctggc accctcctcc aagagcacct ctgggggcac agcggccctg  540
ggctgcctgg tcaaggacta cttccccgaa ccggtgacgg tgtcgtggaa ctcaggcgcc  600
ctgaccagcg gcgtgcacac cttcccggct gtcctacagt cctcaggact ctactccctc  660
agcagcgtgg tgaccgtgcc ctccagcagc ttgggcaccc agacctacat ctgcaacgtg  720
aatcacaagc ccagcaacac caaggtggac aagagagttg agcccaaatc ttgtgacaaa  780
actcacacat gcccaccgtg cccagcacct gaactcctgg ggggaccgtc agtcttcctc  840
ttccccccaa aacccaagga caccctcatg atctcccgga cccctgaggt cacatgcgtg  900
gtggtggacg tgagccacga agaccctgag gtcaagttca actggtacgt ggacggcgtg  960
gaggtgcata atgccaagac aaagccgcgg gaggagcagt acaacagcac gtaccgtgtg 1020
gtcagcgtcc tcaccgtcct gcaccaggac tggctgaatg gcaaggagta caagtgcaag 1080
gtctccaaca agccctccag ccccccatcg agaaaaacca tctccaaagc caaagggcag 1140
ccccgagaac cacaggtgta caccctgccc ccatcccggg aggagatgac caagaaccag 1200
gtcagcctga cctgcctggt caaaggcttc tatcccagcg acatcgccgt ggagtgggag 1260
agcaatgggc agccggagaa caactacaag accacgcctc ccgtgctgga ctccgacggc 1320
tccttcttcc tctatagcaa gctcaccgtg gacaagagca ggtggcagca ggggaacgtc 1380
ttctcatgct ccgtgatgca tgaggctctg cacaaccact acacgcagaa gagcctctcc 1440
ctgtctccgg gtaaatga                                                1458

SEQ ID NO: 317          moltype = DNA  length = 408
FEATURE                 Location/Qualifiers
misc_feature            1..408
                        note = Description of Artificial Sequence: Synthetic
                         polynucleotide
source                  1..408
                        mol_type = other DNA
                        organism = synthetic construct
SEQUENCE: 317
cagccgcagc tgcaggagtc gggcccagga ctggtggagg cttcggagac cctgtccctc   60
acgtgcactg tgtccggcga ctccactggt cgttgtaatt atttctgggg ctgggtccgg  120
cagcccccag ggaaggggct ggagtggatt gggagtttgt cccactgtag aagttactac  180
aatactgact ggacctacca caacccgtct ctcaagagtc gactcactat ttcactcgac  240
acgcccaaga atcaggtctt cctgagattg acctctgtga ccgccgcgga cacggccact  300
tattactgtg cgcgattcgg cggcgaagtt ctagtgtaca gagattggcc aaagccggcc  360
tgggtcgacc tctggggccg gggaacgctg gtcgtcaccg tctcgagc              408

SEQ ID NO: 318          moltype = AA  length = 485
FEATURE                 Location/Qualifiers
REGION                  1..485
                        note = Description of Artificial Sequence: Synthetic
                         polypeptide
source                  1..485
                        mol_type = protein
                        organism = synthetic construct
SEQUENCE: 318
MKHLWFFLLL VAAPRWVLSQ PQLQESGPGL VEASETLSLT CTVSGDSTGR CNYFWGWVRQ   60
PPGKGLEWIG SLSHCRSYYN TDWTYHNPSL KSRLTISLDT PKNQVFLRLT SVTAADTATY  120
YCARFGGEVL VYRDWPKPAW VDLWGRGTLV VTVSSASTKG PSVFPLAPSS KSTSGGTAAL  180
GCLVKDYFPE PVTVSWNSGA LTSGVHTFPA VLQSSGLYSL SSVVTVPSSS LGTQTYICNV  240
NHKPSNTKVD KRVEPKSCDK THTCPPCPAP ELLGGPSVFL FPPKPKDTLM ISRTPEVTCV  300
VVDVSHEDPE VKFNWYVDGV EVHNAKTKPR EEQYNSTYRV VSVLTVLHQD WLNGKEYKCK  360
VSNKALPAPI EKTISKAKGQ PREPQVYTLP PSREEMTKNQ VSLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                              485

SEQ ID NO: 319          moltype = AA  length = 136
FEATURE                 Location/Qualifiers
REGION                  1..136
                        note = Description of Artificial Sequence: Synthetic
                         polypeptide
source                  1..136
                        mol_type = protein
                        organism = synthetic construct
SEQUENCE: 319
QPQLQESGPG LVEASETLSL TCTVSGDSTG RCNYFWGWVR QPPGKGLEWI GSLSHCRSYY   60
NTDWTYHNPS LKSRLTISLD TPKNQVFLRL TSVTAADTAT YYCARFGGEV LVYRDWPKPA  120
WVDLWGRGTL VVTVSS                                                  136

SEQ ID NO: 320          moltype = AA  length = 7
```

| | | |
|---|---|---|
| FEATURE | Location/Qualifiers | |
| REGION | 1..7 | |
| | note = Description of Artificial Sequence: Synthetic peptide | |
| source | 1..7 | |
| | mol_type = protein | |
| | organism = synthetic construct | |
| SEQUENCE: 320 | | |
| RCNYFWG | | 7 |
| | | |
| SEQ ID NO: 321 | moltype = AA length = 22 | |
| FEATURE | Location/Qualifiers | |
| REGION | 1..22 | |
| | note = Description of Artificial Sequence: Synthetic peptide | |
| source | 1..22 | |
| | mol_type = protein | |
| | organism = synthetic construct | |
| SEQUENCE: 321 | | |
| SLSHCRSYYN TDWTYHNPSL KS | | 22 |
| | | |
| SEQ ID NO: 322 | moltype = AA length = 19 | |
| FEATURE | Location/Qualifiers | |
| REGION | 1..19 | |
| | note = Description of Artificial Sequence: Synthetic peptide | |
| source | 1..19 | |
| | mol_type = protein | |
| | organism = synthetic construct | |
| SEQUENCE: 322 | | |
| FGGEVLVYRD WPKPAWVDL | | 19 |
| | | |
| SEQ ID NO: 323 | moltype = AA length = 8 | |
| FEATURE | Location/Qualifiers | |
| REGION | 1..8 | |
| | note = Description of Artificial Sequence: Synthetic peptide | |
| source | 1..8 | |
| | mol_type = protein | |
| | organism = synthetic construct | |
| SEQUENCE: 323 | | |
| GDSTGRCN | | 8 |
| | | |
| SEQ ID NO: 324 | moltype = AA length = 15 | |
| FEATURE | Location/Qualifiers | |
| REGION | 1..15 | |
| | note = Description of Artificial Sequence: Synthetic peptide | |
| source | 1..15 | |
| | mol_type = protein | |
| | organism = synthetic construct | |
| SEQUENCE: 324 | | |
| SLSHCRSYYN TDWTY | | 15 |
| | | |
| SEQ ID NO: 325 | moltype = AA length = 9 | |
| FEATURE | Location/Qualifiers | |
| REGION | 1..9 | |
| | note = Description of Artificial Sequence: Synthetic peptide | |
| source | 1..9 | |
| | mol_type = protein | |
| | organism = synthetic construct | |
| SEQUENCE: 325 | | |
| TGTSNNFVS | | 9 |
| | | |
| SEQ ID NO: 326 | moltype = AA length = 7 | |
| FEATURE | Location/Qualifiers | |
| REGION | 1..7 | |
| | note = Description of Artificial Sequence: Synthetic peptide | |
| source | 1..7 | |
| | mol_type = protein | |
| | organism = synthetic construct | |
| SEQUENCE: 326 | | |
| ACNSFWG | | 7 |
| | | |
| SEQ ID NO: 327 | moltype = DNA length = 693 | |
| FEATURE | Location/Qualifiers | |
| misc_feature | 1..693 | |
| | note = Description of Artificial Sequence: Synthetic polynucleotide | |
| source | 1..693 | |
| | mol_type = other DNA | |
| | organism = synthetic construct | |
| SEQUENCE: 327 | | |
| atggcctggg ctctgctcct cctcaccctc ctcactcagg gcacaggggc ctgggcccag | | 60 |

```
tctgccctga ctcagcctcc ctccgcgtcc gggtctcctg acagtcaat caccatctcc    120
tgcactggaa ccagcaataa ctttgtctct tggtaccaac aatacccagg caaggccccc    180
aaactcgtca tttatgaggt caataagcgc ccctcaggtg tccctgatcg tttctctggc    240
tccaagtctg gcagcacggc ctccctgacc gtctctggac tccaggctga cgatgagggt    300
gtctattatt gtagttcact tgtaggcaac tgggatgtga ttttcggcgg agggaccaag    360
ttgaccgtcc taggtcagcc caaggctgcc ccctcggtca ctctgttccc gccctcctct    420
gaggagcttc aagccaacaa ggccacactg gtgtgtctca taagtgactt ctacccggga    480
gccgtgacag tggcctggaa ggcagatagc agccccgtca aggcgggagt ggagaccacc    540
acaccctcca aacaaagcaa caacaagtac gcggccagca gctatctgag cctgacgcct    600
gagcagtgga gtcccacag aagctacag tgccagtca cgcatgaagg gagcaccgtg    660
gagaagacag tggcccctac agaatgttca tag                                693
```

| SEQ ID NO: 328 | moltype = DNA length = 315 |
|---|---|
| FEATURE | Location/Qualifiers |
| misc_feature | 1..315 |
| | note = Description of Artificial Sequence: Synthetic polynucleotide |
| source | 1..315 |
| | mol_type = other DNA |
| | organism = synthetic construct |

```
SEQUENCE: 328
cagtctgccc tgactcagcc tccctccgcg tccgggtctc ctggacagtc aatcaccatc     60
tcctgcactg gaaccagcaa taactttgtc tcctggtacc aacaataccc aggcaaggcc    120
cccaaactcg tcatttatga ggtcaataag cgccctcag gtgtccctga tcgtttctct    180
ggctccaagt ctggcagcac ggcctccctg accgtctctg gactccaggc tgacgatgag    240
ggtgtctatt attgtagttc acttgtaggc aactgggatg tgattttcgg cggagggacc    300
aagttgaccg tccta                                                     315
```

| SEQ ID NO: 329 | moltype = AA length = 230 |
|---|---|
| FEATURE | Location/Qualifiers |
| REGION | 1..230 |
| | note = Description of Artificial Sequence: Synthetic polypeptide |
| source | 1..230 |
| | mol_type = protein |
| | organism = synthetic construct |

```
SEQUENCE: 329
MAWALLLLTL LTQGTGAWAQ SALTQPPSAS GSPGQSITIS CTGTSNNFVS WYQQYPGKAP     60
KLVIYEVNKR PSGVPDRFSG SKSGSTASLT VSGLQADDEG VYYCSSLVGN WDVIFGGGTK    120
LTVLGQPKAA PSVTLFPPSS EELQANKATL VCLISDFYPG AVTVAWKADS SPVKAGVETT    180
TPSKQSNNKY AASSYLSLTP EQWKSHRSYS CQVTHEGSTV EKTVAPTECS              230
```

| SEQ ID NO: 330 | moltype = AA length = 105 |
|---|---|
| FEATURE | Location/Qualifiers |
| REGION | 1..105 |
| | note = Description of Artificial Sequence: Synthetic polypeptide |
| source | 1..105 |
| | mol_type = protein |
| | organism = synthetic construct |

```
SEQUENCE: 330
QSALTQPPSA SGSPGQSITI SCTGTSNNFV SWYQQYPGKA PKLVIYEVNK RPSGVPDRFS     60
GSKSGSTASL TVSGLQADDE GVYYCSSLVG NWDVIFGGGT KLTVL                   105
```

| SEQ ID NO: 331 | moltype = DNA length = 1455 |
|---|---|
| FEATURE | Location/Qualifiers |
| misc_feature | 1..1455 |
| | note = Description of Artificial Sequence: Synthetic polynucleotide |
| source | 1..1455 |
| | mol_type = other DNA |
| | organism = synthetic construct |

```
SEQUENCE: 331
atgaaacacc tgtggttctt cctcctgctg gtggcgggct ccagatgggg cctgtcccag     60
ccgcagctgc aggagtcggg cccaacactg tggaggcttc ggagactct gtccctcacc    120
tgcgctgtgt ccgcgactc cactgctgca tgtaattctt tctggggctg gtccggcag    180
cccccaggga aggggctgga gtggttggga gtttgtccc attgtgcaag ctattggaat    240
cgtgggtgga cctaccacaa cccgtctctc aagagtcggc tcacgcttgc tctcgacaca    300
tccaagaatc tggtcttcct caaattaat tctgtgactc ccgcggacac ggccacttac    360
tactgtgcgc gattcggcgg cgaagtttta cgctacacgg attggccaaa gccggcctgg    420
gtcgacctct ggggccgggg aacgctggtc accgtctcga gcgcctccac caagggccca    480
tcggtcttcc ccctggcacc ctcctccaag agcacctctg gggcacagc ggccctggc    540
tgcctggtca aggactactt ccccgaaccg gtgacggtgt cgtggaactc aggcgccctg    600
accagcggcg tgcacacctt cccggctgtc ctacagtcct caggactcta ctccctcagc    660
agcgtggtga ccgtgccctc agcagcttg gcacccaga cctacatctg caacgtgaat    720
cacaagccca gcaacaccaa ggtggacaag agagttgagc ccaaatcttg tgacaaaact    780
cacacatgcc caccgtgccc agcacctgaa ctcctggggg gaccgtcagt cttcctcttc    840
ccccaaaac ccaaggacac cctcatgatc tcccggaccc ctgaggtcac atgcgtggtg    900
gtggacgtga gccacgaaga ccctgaggtc aagttcaact ggtacgtgga cggcgtggag    960
```

```
gtgcataatg ccaagacaaa gccgcgggag gagcagtaca acagcacgta ccgtgtggtc   1020
agcgtcctca ccgtcctgca ccaggactgg ctgaatggca aggagtacaa gtgcaaggtc   1080
tccaacaaag ccctcccagc ccccatcgag aaaaccatct ccaaagccaa agggcagccc   1140
cgagaaccac aggtgtacac cctgccccca tcccgggagg agatgaccaa gaaccaggtc   1200
agcctgacct gcctggtcaa aggcttctat cccagcgaca tcgccgtgga gtgggagagc   1260
aatgggcagc cggagaacaa ctacaagacc acgcctcccg tgctggactc cgacggctcc   1320
ttcttcctct atagcaagct caccgtggac aagagcaggt ggcagcaggg gaacgtcttc   1380
tcatgctccg tgatgcatga ggctctgcac aaccactaca cgcagaagag cctctccctg   1440
tctccgggta aatga                                                    1455

SEQ ID NO: 332          moltype = DNA  length = 405
FEATURE                 Location/Qualifiers
misc_feature            1..405
                        note = Description of Artificial Sequence: Synthetic
                        polynucleotide
source                  1..405
                        mol_type = other DNA
                        organism = synthetic construct
SEQUENCE: 332
cagccgcagc tgcaggagtc gggcccaaca ctggtggagg cttcggagac tctgtccctc   60
acctgcgctg tgtccggcga ctccactgct gcatgtaatt ctttctgggg ctgggtccgg   120
cagccccag ggaagggct ggagtgggtt gggagtttgt cccattgtgc aagctattgg    180
aatcgtgggt ggacctacca caacccgtct ctcaagagtc ggctcacgct tgctctcgac   240
acacccaaga atctggtctt cctcaaatta aattctgtga ctgccgcgga cacggccact   300
tactactgtg cgcgattcgg cggcgaagtt ttacgctaca cggattggcc aaagccggcc   360
tgggtcgacc tctggggccg gggaacgctg gtcaccgtct cgagc                   405

SEQ ID NO: 333          moltype = AA  length = 484
FEATURE                 Location/Qualifiers
REGION                  1..484
                        note = Description of Artificial Sequence: Synthetic
                        polypeptide
source                  1..484
                        mol_type = protein
                        organism = synthetic construct
SEQUENCE: 333
MKHLWFFLLL VAAPRWVLSQ PQLQESGPTL VEASETLSLT CAVSGDSTAA CNSFWGWVRQ   60
PPGKGLEWVG SLSHCASYWN RGWTYHNPSL KSRLTLALDT PKNLVFLKLN SVTAADTATY   120
YCARFGGEVL RYTDWPKPAW VDLWGRGTLV TVSSASTKGP SVFPLAPSSK STSGGTAALG   180
CLVKDYFPEP VTVSWNSGAL TSGVHTFPAV LQSSGLYSLS SVVTVPSSSL GTQTYICNVN   240
HKPSNTKVDK RVEPKSCDKT HTCPPCPAPE LLGGPSVFLF PPKPKDTLMI SRTPEVTCVV   300
VDVSHEDPEV KFNWYVDGVE VHNAKTKPRE EQYNSTYRVV SVLTVLHQDW LNGKEYKCKV   360
SNKALPAPIE KTISKAKGQP REPQVYTLPP SREEMTKNQV SLTCLVKGFY PSDIAVEWES   420
NGQPENNYKT TPPVLDSDGS FFLYSKLTVD KSRWQQGNVF SCSVMHEALH NHYTQKSLSL   480
SPGK                                                                484

SEQ ID NO: 334          moltype = AA  length = 135
FEATURE                 Location/Qualifiers
REGION                  1..135
                        note = Description of Artificial Sequence: Synthetic
                        polypeptide
source                  1..135
                        mol_type = protein
                        organism = synthetic construct
SEQUENCE: 334
QPQLQESGPT LVEASETLSL TCAVSGDSTA ACNSFWGWVR QPPGKGLEWV GSLSHCASYW   60
NRGWTYHNPS LKSRLTLALD TPKNLVFLKL NSVTAADTAT YYCARFGGEV LRYTDWPKPA   120
WVDLWGRGTL VTVSS                                                    135

SEQ ID NO: 335          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 335
SLSHCASYWN RGWTYHNPSL KS                                            22

SEQ ID NO: 336          moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 336
FGGEVLRYTD WPKPAWVDL                                                19
```

| SEQ ID NO: 337 | moltype = AA length = 8 |
| --- | --- |
| FEATURE | Location/Qualifiers |
| REGION | 1..8 |
| | note = Description of Artificial Sequence: Synthetic peptide |
| source | 1..8 |
| | mol_type = protein |
| | organism = synthetic construct |
| SEQUENCE: 337 | |
| GDSTAACN | 8 |

| SEQ ID NO: 338 | moltype = AA length = 15 |
| --- | --- |
| FEATURE | Location/Qualifiers |
| REGION | 1..15 |
| | note = Description of Artificial Sequence: Synthetic peptide |
| source | 1..15 |
| | mol_type = protein |
| | organism = synthetic construct |
| SEQUENCE: 338 | |
| SLSHCASYWN RGWTY | 15 |

| SEQ ID NO: 339 | moltype = length = |
| --- | --- |
| SEQUENCE: 339 | |
| 000 | |

| SEQ ID NO: 340 | moltype = length = |
| --- | --- |
| SEQUENCE: 340 | |
| 000 | |

| SEQ ID NO: 341 | moltype = length = |
| --- | --- |
| SEQUENCE: 341 | |
| 000 | |

| SEQ ID NO: 342 | moltype = length = |
| --- | --- |
| SEQUENCE: 342 | |
| 000 | |

| SEQ ID NO: 343 | moltype = AA length = 7 |
| --- | --- |
| FEATURE | Location/Qualifiers |
| REGION | 1..7 |
| | note = Description of Artificial Sequence: Synthetic peptide |
| source | 1..7 |
| | mol_type = protein |
| | organism = synthetic construct |
| SEQUENCE: 343 | |
| DVNKRPS | 7 |

| SEQ ID NO: 344 | moltype = DNA length = 1437 |
| --- | --- |
| FEATURE | Location/Qualifiers |
| misc_feature | 1..1437 |
| | note = Description of Artificial Sequence: Synthetic polynucleotide |
| source | 1..1437 |
| | mol_type = other DNA |
| | organism = synthetic construct |
| SEQUENCE: 344 | |

```
atgaaacacc tgtggttctt cctcctgctg gtggcggctc ccagatgggt cctttcccag   60
gtgcaactac aggagtcggg cccaggactg gtgaagcctt cggagaccct ttccctcacc  120
tgcactgtct ctggtgactc catcaacact ggtcatcact actggggctg ggtccgtcag  180
gtcccaggga agggaccgga atggattgct cacatccact ataatacggc tgtcttacac  240
aatccggccc tcaagagtcg agtcaccatt tcgattttca ccctgaagaa tctgattacc  300
ctgagcctca gtaatgtgac cgccgcggac acggccgtct attttgcgt tcgatccggc  360
ggcgacattt tatactatat tgagtggcaa aaacccact ggttctatcc ctggggcccg  420
ggaattttgg tcaccgtctc gagcgcctcc accaagggcc catcggtctt ccccctggca  480
ccctcctcca agagcacctc tgggggcaca gcggccctgg gctgcctgt caaggactac  540
ttccccgaac cggtgacggt gtcgtggaac tcaggcgccc tgaccagcgg cgtgcacacc  600
ttcccggctg tcctacagtc ctcaggactc tactccctca gcagcgtggt gaccgtgccc  660
tccagcagct gggcacccca gacctacatc tgcaacgtga atcacaagcc cagcaacacc  720
aaggtggaca gagagttga gcccaaatct tgtgacaaaa ctcacacatg ccaccgtgc  780
ccagcacctg aactcctggg ggaccgtca gtcttcctct tccccccaaa acccaaggac  840
accctcatga tctcccggac ccctgaggtc acatgcgtgg tggtggacgt gagccacgaa  900
gaccctgagg tcaagttcaa ctggtacgtg gacggcgtgg aggtgcataa tgccaagaca  960
aagccgcgg aggagcagta caacagcacg taccgtgtgg tcagcgtcct caccgtcctg 1020
caccaggact ggctgaatgg caaggagtac aagtgcaagg tctccaacaa agccctccca 1080
gccccatcg agaaaaccat ctccaaagcc aaagggcagc ccgagaacc acaggtgtac 1140
accctgcccc catcccggga ggagatgacc aagaaccagg tcagcctgac ctgcctggtc 1200
aaaggcttct atcccagcga catcgccgtg gagtgggaga gcaatgggca gccggagaac 1260
aactacaaga ccacgcctcc cgtgctggac tccgacggct ccttcttcct ctatagcaag 1320
ctcaccgtgg acaagagcag gtggcagcag gggaacgtct tctcatgctc cgtgatgcat 1380
gaggctctgc acaaccacta cacgcagaag agcctctccc tgtctccggg taaatga     1437
```

```
SEQ ID NO: 345            moltype = DNA   length = 387
FEATURE                   Location/Qualifiers
misc_feature              1..387
                          note = Description of Artificial Sequence: Synthetic
                           polynucleotide
source                    1..387
                          mol_type = other DNA
                          organism = synthetic construct
SEQUENCE: 345
caggtgcaac tacaggagtc gggcccagga ctggtgaagc cttcggagac cctttccctc    60
acctgcactg tctctggtga ctccatcaac actggtcatc actactgggg ctgggtccgt   120
caggtcccag ggaagggacc ggaatggatt gctcacatcc actataatac ggctgtctta   180
cacaatccgg ccctcaagag tcgagtcacc atttcgattt tcaccctgaa gaatctgatt   240
accctgagcc tcagtaatgt gaccgccgcg gacacggccg tctatttctg cgttcgatcc   300
ggcggcgaca ttttatacta tattgagtgg caaaaacccc actggttcta tccctggggc   360
ccgggaattt tggtcaccgt ctcgagc                                       387

SEQ ID NO: 346            moltype = AA  length = 478
FEATURE                   Location/Qualifiers
REGION                    1..478
                          note = Description of Artificial Sequence: Synthetic
                           polypeptide
source                    1..478
                          mol_type = protein
                          organism = synthetic construct
SEQUENCE: 346
MKHLWFFLLL VAAPRWVLSQ VQLQESGPGL VKPSETLSLT CTVSGDSINT GHHYWGWVRQ    60
VPGKGPEWIA HIHYNTAVLH NPALKSRVTI SIFTLKNLIT LSLSNVTAAD TAVYFCVRSG   120
GDILYYIEWQ KPHWFYPWGP GILVTVSSAS TKGPSVFPLA PSSKSTSGGT AALGCLVKDY   180
FPEPVTVSWN SGALTSGVHT FPAVLQSSGL YSLSSVVTVP SSSLGTQTYI CNVNHKPSNT   240
KVDKRVEPKS CDKTHTCPPC PAPELLGGPS VFLFPPKPKD TLMISRTPEV TCVVVDVSHE   300
DPEVKFNWYV DGVEVHNAKT KPREEQYNST YRVVSVLTVL HQDWLNGKEY KCKVSNKALP   360
APIEKTISKA KGQPREPQVY TLPPSREEMT KNQVSLTCLV KGFYPSDIAV EWESNGQPEN   420
NYKTTPPVLD SDGSFFLYSK LTVDKSRWQQ GNVFSCSVMH EALHNHYTQK SLSLSPGK     478

SEQ ID NO: 347            moltype = AA  length = 129
FEATURE                   Location/Qualifiers
REGION                    1..129
                          note = Description of Artificial Sequence: Synthetic
                           polypeptide
source                    1..129
                          mol_type = protein
                          organism = synthetic construct
SEQUENCE: 347
QVQLQESGPG LVKPSETLSL TCTVSGDSIN TGHHYWGWVR QVPGKGPEWI AHIHYNTAVL    60
HNPALKSRVT ISIFTLKNLI TLSLSNVTAA DTAVYFCVRS GGDILYYIEW QKPHWFYPWG   120
PGILVTVSS                                                           129

SEQ ID NO: 348            moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 348
TGHHYWG                                                               7

SEQ ID NO: 349            moltype = AA  length = 16
FEATURE                   Location/Qualifiers
REGION                    1..16
                          note = Description of Artificial Sequence: Synthetic peptide
source                    1..16
                          mol_type = protein
                          organism = synthetic construct
SEQUENCE: 349
HIHYNTAVLH NPALKS                                                    16

SEQ ID NO: 350            moltype = AA  length = 19
FEATURE                   Location/Qualifiers
REGION                    1..19
                          note = Description of Artificial Sequence: Synthetic peptide
source                    1..19
                          mol_type = protein
                          organism = synthetic construct
SEQUENCE: 350
SGGDILYYIE WQKPHWFYP                                                 19
```

```
SEQ ID NO: 351           moltype = AA   length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 351
GDSINTGH                                                                  8

SEQ ID NO: 352           moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 352
HIHYNTAVL                                                                 9

SEQ ID NO: 353           moltype = DNA   length = 708
FEATURE                  Location/Qualifiers
misc_feature             1..708
                         note = Description of Artificial Sequence: Synthetic
                          polynucleotide
source                   1..708
                         mol_type = other DNA
                         organism = synthetic construct
SEQUENCE: 353
atggcctggg ctctgctcct cctcaccctc ctcactcagg gcacagggtc ctgggcccag     60
tctgccctga ctcagcctcc ctccgcgtcc gggtctcttg gacagtcact caccatctcc    120
tgcagtggaa ccggcagtga cattggcagt tggaattttg tctcctggta tcaacaattc    180
ccaggcagag cccccaacct cattattttt gaggtcaata ggcggcgatc aggggtccct    240
gatcgcttct ctggttccaa gtcgggcaat acggcctccc tgaccgtctc tgggctccgg    300
tctgaggatg aggctgaata ttttgcagt tccctttcag gcaggtggga cattgttttt    360
ggcggaggga ccaaggtgac cgtcctaggt cagcccaagg ctgccccctc ggtcactctg    420
ttcccgccct cctctgagga gcttcaagcc aacaaggcca cactggtgtg tctcataagt    480
gacttctacc cgggagccgt gacagtggcc tggaaggcag atagcagccc cgtcaaggcg    540
ggagtggaga ccaccacacc ctccaaacaa agcaacaaca gtacgcggc cagcagctat    600
ctgagcctga cgcctgagca gtggaagtcc cacagaagct acagctgcca ggtcacgcat    660
gaagggagca ccgtggagaa gacagtggcc cctacagaat gttcatag               708

SEQ ID NO: 354           moltype = DNA   length = 330
FEATURE                  Location/Qualifiers
misc_feature             1..330
                         note = Description of Artificial Sequence: Synthetic
                          polynucleotide
source                   1..330
                         mol_type = other DNA
                         organism = synthetic construct
SEQUENCE: 354
cagtctgccc tgactcagcc tccctccgcg tccgggtctc ttggacagtc actcaccatc     60
tcctgcagtg gaaccggcag tgacattggc agttggaatt ttgtctcctg gtatcaacaa    120
ttcccaggca gagcccccaa cctcattatt tttgaggtca ataggcggcg atcaggggtc    180
cctgatcgct tctctggttc caagtcgggc aatacggcct ccctgaccgt ctctgggctc    240
cggtctgagg atgaggctga atattttgc agttccctt caggcaggtg ggacattgtt    300
tttggcggag ggaccaaggt gaccgtccta                                    330

SEQ ID NO: 355           moltype = AA   length = 235
FEATURE                  Location/Qualifiers
REGION                   1..235
                         note = Description of Artificial Sequence: Synthetic
                          polypeptide
source                   1..235
                         mol_type = protein
                         organism = synthetic construct
SEQUENCE: 355
MAWALLLLTL LTQGTGSWAQ SALTQPPSAS GSLGQSLTIS CSGTGSDIGS WNFVSWYQQF     60
PGRAPNLIIF EVNRRRSGVP DRFSGSKSGN TASLTVSGLR SEDEAEYFCS SLSGRWDIVF    120
GGGTKVTVLG QPKAAPSVTL FPPSSEELQA NKATLVCLIS DFYPGAVTVA WKADSSPVKA    180
GVETTTPSKQ SNNKYAASSY LSLTPEQWKS HRSYSCQVTH EGSTVEKTVA PTECS         235

SEQ ID NO: 356           moltype = AA   length = 110
FEATURE                  Location/Qualifiers
REGION                   1..110
                         note = Description of Artificial Sequence: Synthetic
                          polypeptide
source                   1..110
                         mol_type = protein
```

```
                        organism = synthetic construct
SEQUENCE: 356
QSALTQPPSA SGSLGQSLTI SCSGTGSDIG SWNFVSWYQQ FPGRAPNLII FEVNRRRSGV      60
PDRFSGSKSG NTASLTVSGL RSEDEAEYFC SSLSGRWDIV FGGGTKVTVL                110

SEQ ID NO: 357          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 357
SGTGSDIGSW NFVS                                                        14

SEQ ID NO: 358          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 358
EVNRRRS                                                                 7

SEQ ID NO: 359          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 359
SSLSGRWDIV                                                             10

SEQ ID NO: 360          moltype = DNA   length = 1449
FEATURE                 Location/Qualifiers
misc_feature            1..1449
                        note = Description of Artificial Sequence: Synthetic
                         polynucleotide
source                  1..1449
                        mol_type = other DNA
                        organism = synthetic construct
SEQUENCE: 360
atgaaacacc tgtggttctt cctcctgctg gttgcggctc ccagatgtgt cctgtctgag      60
gtgcatctgg aggagtcggg cccaggactg gtgaggccct cggagacctt gtccctgact     120
tgcacggcct ctggtggctc cataaggggg ggcgagtggg gcgatagtga ctaccactgg     180
ggctgggtcc gccactctcc cgaaaaggga ctgaatggga ttggaagtat tcattggcgg     240
gggaccaccc actacaacgc gcccttccgg gggcgaggca gattgtcgat agacctctcc     300
cggaatcaat tctccctgcg cctgacgtct gtgaccgccg aagacactgc cgtctattat     360
tgtgtgaagc acaaatatca tgacattgtc atggtggtcc ccattgcggg ctggttcgac     420
ccctggggcc aggactcca ggtcaccgtc tcgagcgcct ccaccaaggg cccatcggtc      480
ttccccctgg caccctcctc aagagcacc tctgggggca gcggccct gggctgcctg        540
gtcaaggact acttccccga accggtgacg gtgtcgtgga actcaggcgc cctgaccagc     600
ggcgtgcaca ccttccccgg ctgtcctaca tcctcaggac tctactccct cagcagcgtg     660
gtgaccgtgc cctccagcag cttgggcacc cagacctaca tctgcaacgt gaatcacaag     720
cccagcaaca ccaaggtgga caagagagtt gagcccaaat cttgtgacaa aactcacaca     780
tgcccaccgt gcccagcacc tgaactcctg gggggaccgt cagtcttcct cttcccccca     840
aaacccaagg acaccctcat gatctccgg accctgagg tcacatgcgt ggtggtggac      900
gtgagccacg aagaccctga ggtcaagttc aactggtacg tggacggcgt ggaggtgcat     960
aatgccaaga caaagccgcg ggaggagcag tacaacagca cgtaccgtgt ggtcagcgtc    1020
ctcaccgtcc tgcaccagga ctggctgaat ggcaaggagt acaagtgcaa ggtctccaac    1080
aaagccctcc cagcccccat cgagaaaacc atctccaaag ccaaagggca gccccgagaa    1140
ccacaggtgt acaccctgcc cccatcccgg gaggagatga ccaagaacca ggtcagcctg    1200
acctgcctgg tcaaaggctt ctatcccagc gacatcgccg tggagtggga gagcaatggg    1260
cagccggaga caactacaa gaccacgcct cccgtgctgg actccgacgg ctccttcttc     1320
ctctatagca agctcaccgt ggacaagagc aggtggcagc aggggaacgt cttctcatgc    1380
tccgtgatgc atgaggctct gcacaaccac tacacgcaga agagcctctc cctgtctccg    1440
ggtaaatga                                                            1449

SEQ ID NO: 361          moltype = DNA   length = 399
FEATURE                 Location/Qualifiers
misc_feature            1..399
                        note = Description of Artificial Sequence: Synthetic
                         polynucleotide
source                  1..399
                        mol_type = other DNA
                        organism = synthetic construct
SEQUENCE: 361
```

```
gaggtgcatc tggaggagtc gggcccagga ctggtgaggc cctcggagac cttgtccctg   60
acttgcacgg cctctggtgg ctccataagg gggggcgagt ggggcgatag tgactaccac  120
tggggctggg tccgccactc tcccgaaaag ggactggaat ggattggaag tattcattgg  180
cgggggacca cccactacaa cgcgcccttc cgggggcgag gcagattgtc gatagacctc  240
tcccggaatc aattctccct gcgcctgacg tctgtgaccg ccgaagacac tgccgtctat  300
tattgtgtga agcacaaata tcatgacatt gtcatggttg tccccattgc gggctggttc  360
gaccctgggg gccagggact ccaggtcacc gtctcgagc                         399
```

```
SEQ ID NO: 362              moltype = AA  length = 482
FEATURE                     Location/Qualifiers
REGION                      1..482
                            note = Description of Artificial Sequence: Synthetic
                             polypeptide
source                      1..482
                            mol_type = protein
                            organism = synthetic construct
SEQUENCE: 362
MKHLWFFLLL VAAPRCVLSE VHLEESGPGL VRPSETLSLT CTASGGSIRG GEWGDSDYHW   60
GWVRHSPEKG LEWIGSIHWR GTTHYNAPFR GRGRLSIDLS RNQFSLRLTS VTAEDTAVYY  120
CVKHKYHDIV MVVPIAGWFD PWGQGLQVTV SSASTKGPSV FPLAPSSKST SGGTAALGCL  180
VKDYFPEPVT VSWNSGALTS GVHTFPAVLQ SSGLYSLSSV VTVPSSSLGT QTYICNVNHK  240
PSNTKVDKRV EPKSCDKTHT CPPCPAPELL GGPSVFLFPP KPKDTLMISR TPEVTCVVVD  300
VSHEDPEVKF NWYVDGVEVH NAKTKPREEQ YNSTYRVVSV LTVLHQDWLN GKEYKCKVSN  360
KALPAPIEKT ISKAKGQPRE PQVYTLPPSR EEMTKNQVSL TCLVKGFYPS DIAVEWESNG  420
QPENNYKTTP PVLDSDGSFF LYSKLTVDKS RWQQGNVFSC SVMHEALHNH YTQKSLSLSP  480
GK                                                                 482

SEQ ID NO: 363              moltype = AA  length = 133
FEATURE                     Location/Qualifiers
REGION                      1..133
                            note = Description of Artificial Sequence: Synthetic
                             polypeptide
source                      1..133
                            mol_type = protein
                            organism = synthetic construct
SEQUENCE: 363
EVHLEESGPG LVRPSETLSL TCTASGGSIR GGEWGDSDYH WGWVRHSPEK GLEWIGSIHW   60
RGTTHYNAPF RGRGRLSIDL SRNQFSLRLT SVTAEDTAVY YCVKHKYHDI VMVVPIAGWF  120
DPWGQGLQVT VSS                                                     133

SEQ ID NO: 364              moltype = AA  length = 12
FEATURE                     Location/Qualifiers
REGION                      1..12
                            note = Description of Artificial Sequence: Synthetic peptide
source                      1..12
                            mol_type = protein
                            organism = synthetic construct
SEQUENCE: 364
GGEWGDSDYH WG                                                       12

SEQ ID NO: 365              moltype = AA  length = 16
FEATURE                     Location/Qualifiers
REGION                      1..16
                            note = Description of Artificial Sequence: Synthetic peptide
source                      1..16
                            mol_type = protein
                            organism = synthetic construct
SEQUENCE: 365
SIHWRGTTHY NAPFRG                                                   16

SEQ ID NO: 366              moltype = AA  length = 18
FEATURE                     Location/Qualifiers
REGION                      1..18
                            note = Description of Artificial Sequence: Synthetic peptide
source                      1..18
                            mol_type = protein
                            organism = synthetic construct
SEQUENCE: 366
HKYHDIVMVV PIAGWFDP                                                 18

SEQ ID NO: 367              moltype = AA  length = 13
FEATURE                     Location/Qualifiers
REGION                      1..13
                            note = Description of Artificial Sequence: Synthetic peptide
source                      1..13
                            mol_type = protein
                            organism = synthetic construct
SEQUENCE: 367
GGSIRGGEWG DSD                                                      13
```

```
SEQ ID NO: 368          moltype =     length =
SEQUENCE: 368
000

SEQ ID NO: 369          moltype =     length =
SEQUENCE: 369
000

SEQ ID NO: 370          moltype =     length =
SEQUENCE: 370
000

SEQ ID NO: 371          moltype =     length =
SEQUENCE: 371
000

SEQ ID NO: 372          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 372
RASQSVKNNL A                                                                   11

SEQ ID NO: 373          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 373
DTSSRAS                                                                         7

SEQ ID NO: 374          moltype =     length =
SEQUENCE: 374
000

SEQ ID NO: 375          moltype =     length =
SEQUENCE: 375
000

SEQ ID NO: 376          moltype =     length =
SEQUENCE: 376
000

SEQ ID NO: 377          moltype =     length =
SEQUENCE: 377
000

SEQ ID NO: 378          moltype = AA   length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 378
NHDVH                                                                           5

SEQ ID NO: 379          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 379
WMSHEGDKTG LAQKFQG                                                             17

SEQ ID NO: 380          moltype = AA   length = 31
FEATURE                 Location/Qualifiers
REGION                  1..31
                        note = Description of Artificial Sequence: Synthetic
                         polypeptide
source                  1..31
```

```
                        mol_type = protein
                        organism = synthetic construct
SEQUENCE: 380
GSKHRLRDYF LYNEYGPNYE EWGDYLATLD V                                      31

SEQ ID NO: 381          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 381
GNSFSN                                                                   6

SEQ ID NO: 382          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 382
WMSHEGDKTG                                                              10

SEQ ID NO: 383          moltype = DNA   length = 720
FEATURE                 Location/Qualifiers
misc_feature            1..720
                        note = Description of Artificial Sequence: Synthetic
                         polynucleotide
source                  1..720
                        mol_type = other DNA
                        organism = synthetic construct
SEQUENCE: 383
atgaggctcc ctgctcagct cctggggctg ctaatgctct gggtctctgg atccggtgcg       60
gaggttgtca taactcagtc tccactcttc ctgcccgtca ccctggaga ggcggcctcc       120
ttgtcttgca gtgcagcca cagcctccaa cattcaactg gagccaacta tttggcttgg       180
tacctgcaga gaccagggca aactccacgc ctgttgatcc atttggccac tcatcgggcc     240
tccggggtcc ctgacagatt cagtggcagt ggatcaggca cagattttac acttaaaatc     300
agtcgagtgg agtctgacga tgttggaact tattattgca tgcagggtct gcacagtccc     360
tggacgttcg gccaagggac caaggtggag atcaaacgta cggtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct tcaacagggg agagtgttag     720

SEQ ID NO: 384          moltype = DNA   length = 336
FEATURE                 Location/Qualifiers
misc_feature            1..336
                        note = Description of Artificial Sequence: Synthetic
                         polynucleotide
source                  1..336
                        mol_type = other DNA
                        organism = synthetic construct
SEQUENCE: 384
gaggttgtca taactcagtc tccactcttc ctgcccgtca ccctggaga ggcggcctcc        60
ttgtcttgca gtgcagcca cagcctccaa cattcaactg gagccaacta tttggcttgg      120
tacctgcaga gaccagggca aactccacgc ctgttgatcc atttggccac tcatcgggcc     180
tccggggtcc ctgacagatt cagtggcagt ggatcaggca cagattttac acttaaaatc    240
agtcgagtgg agtctgacga tgttggaact tattattgca tgcagggtct gcacagtccc    300
tggacgttcg gccaagggac caaggtggag atcaaa                              336

SEQ ID NO: 385          moltype = AA   length = 239
FEATURE                 Location/Qualifiers
REGION                  1..239
                        note = Description of Artificial Sequence: Synthetic
                         polypeptide
source                  1..239
                        mol_type = protein
                        organism = synthetic construct
SEQUENCE: 385
MRLPAQLLGL LMLWVSGSGA EVVITQSPLF LPVTPGEAAS LSCKCSHSLQ HSTGANYLAW       60
YLQRPGQTPR LLIHLATHRA SGVPDRFSGS GSGTDFTLKI SRVESDDVGT YYCMQGLHSP      120
WTFGQGTKVE IKRTVAAPSV FIFPPSDEQL KSGTASVVCL LNNFYPREAK VQWKVDNALQ      180
SGNSQESVTE QDSKDSTYSL SSTLTLSKAD YEKHKVYACE VTHQGLSSPV TKSFNRGEC       239

SEQ ID NO: 386          moltype = AA   length = 112
FEATURE                 Location/Qualifiers
```

```
REGION                  1..112
                        note = Description of Artificial Sequence: Synthetic
                        polypeptide
source                  1..112
                        mol_type = protein
                        organism = synthetic construct
SEQUENCE: 386
EVVITQSPLF LPVTPGEAAS LSCKCSHSLQ HSTGANYLAW YLQRPGQTPR LLIHLATHRA    60
SGVPDRFSGS GSGTDFTLKI SRVESDDVGT YYCMQGLHSP WTFGQGTKVE IK           112

SEQ ID NO: 387          moltype = AA   length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 387
KCSHSLQHST GANYLA                                                    16

SEQ ID NO: 388          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 388
LATHRAS                                                               7

SEQ ID NO: 389          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 389
MQGLHSPWT                                                             9

SEQ ID NO: 390          moltype = DNA   length = 693
FEATURE                 Location/Qualifiers
misc_feature            1..693
                        note = Description of Artificial Sequence: Synthetic
                        polynucleotide
source                  1..693
                        mol_type = other DNA
                        organism = synthetic construct
SEQUENCE: 390
atggcctggg ctctgctcct cctcaccctc ctcactcagg gcacaggggc ctgggcccag    60
tctgccctga ctcagcctcc ctccgcgtcc gggtctcctg gacagtcaat caccatctcc   120
tgcactggaa ccagcaataa ctttgtctcc tggtaccagc aacacgcagg caaggccccc   180
aagctcgtca tttatgacgt caataagcgc ccctcaggtg tccctgatcg tttctctggc   240
tccaagtctg gcaacaccgg ctccctgacc gtctctggac tccagactga cgatgaggct   300
gtctattact gcggctcact tgtaggcaac tgggatgtga ttttcggcgg agggaccaag   360
ttgaccgtcc taggtcagcc caaggctgcc ccctcggtca ctctgttccc gccctcctct   420
gaggagcttc aagccaacaa ggccacactg gtgtgtctca taagtgactt ctacccggga   480
gccgtgacga tggcctggaa ggcagatagc agccccgtca aggcgggagt ggagaccacc   540
acaccctcca aacaaagcaa caacaagtac gcggccagca gctatctgag cctgacgcct   600
gagcagtgga gtcccacag aagctacagc tgccaggtca cgcatgaagg gagcaccgtg   660
gagaagacag tggcccctac agaatgttca tag                                693

SEQ ID NO: 391          moltype = DNA   length = 315
FEATURE                 Location/Qualifiers
misc_feature            1..315
                        note = Description of Artificial Sequence: Synthetic
                        polynucleotide
source                  1..315
                        mol_type = other DNA
                        organism = synthetic construct
SEQUENCE: 391
cagtctgccc tgactcagcc tcctccgcg tccgggtctc ctggacagtc aatcaccatc    60
tcctgcactg gaaccagcaa taactttgtc tcctggtacc agcaacacgc aggcaaggcc   120
cccaagctcg tcatttatga cgtcaataag cgcccctcag gtgtccctga tcgtttctct   180
ggctccaagt ctggcaacac cggctccctg accgtctctg gactccagac tgacgatgag   240
gctgtctatt actgcggctc acttgtaggc aactgggatg tgattttcgg cggagggacc   300
aagttgaccg tccta                                                    315

SEQ ID NO: 392          moltype = AA   length = 230
```

```
FEATURE                 Location/Qualifiers
REGION                  1..230
                        note = Description of Artificial Sequence: Synthetic
                         polypeptide
source                  1..230
                        mol_type = protein
                        organism = synthetic construct
SEQUENCE: 392
MAWALLLLTL LTQGTGAWAQ SALTQPPSAS GSPGQSITIS CTGTSNNFVS WYQQHAGKAP    60
KLVIYDVNKR PSGVPDRFSG SKSGNTASLT VSGLQTDDEA VYYCGSLVGN WDVIFGGGTK   120
LTVLGQPKAA PSVTLFPPSS EELQANKATL VCLISDFYPG AVTVAWKADS SPVKAGVETT   180
TPSKQSNNKY AASSYLSLTP EQWKSHRSYS CQVTHEGSTV EKTVAPTECS              230

SEQ ID NO: 393          moltype = AA   length = 105
FEATURE                 Location/Qualifiers
REGION                  1..105
                        note = Description of Artificial Sequence: Synthetic
                         polypeptide
source                  1..105
                        mol_type = protein
                        organism = synthetic construct
SEQUENCE: 393
QSALTQPPSA SGSPGQSITI SCTGTSNNFV SWYQQHAGKA PKLVIYDVNK RPSGVPDRFS    60
GSKSGNTASL TVSGLQTDDE AVYYCGSLVG NWDVIFGGGT KLTVL                   105

SEQ ID NO: 394          moltype = DNA   length = 705
FEATURE                 Location/Qualifiers
misc_feature            1..705
                        note = Description of Artificial Sequence: Synthetic
                         polynucleotide
source                  1..705
                        mol_type = other DNA
                        organism = synthetic construct
SEQUENCE: 394
atggaaaccc cagctcagct tctcttcctc ctgctactct ggctcccaga tactactgga    60
gaaataatga tgacgcagtc tccagccatc ctgtctgtgt ctccaggaga cagagccaca   120
ctctcctgca gggccagtca gagtgtgaag aataatttag cctggtacca aaagagacct   180
ggccaggctc ccagactcct catctttgat acatccagca gggcctctgg tatccctgcc   240
aggttcagtg gcggtggttc tgggacagag ttcactctca ccgtcaacag catgcagtct   300
gaagactttg cgacttatta ctgtcagcaa tatgaagagt ggcctcggac gttcggccag   360
gggaccaagg tggaaatcaa acgtacggtg gctgcaccat ctgtcttcat cttcccgcca   420
tctgatgagc agttgaaatc tggaactgcc tctgttgtgt gcctgctgaa taacttctat   480
cccagagtaca ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga gaaacacaaa gtctacgcct gcgaagtcac ccatcagggc   660
ctgagctcgc ccgtcacaaa gagcttcaac aggggagagt gttag                   705

SEQ ID NO: 395          moltype = DNA   length = 321
FEATURE                 Location/Qualifiers
misc_feature            1..321
                        note = Description of Artificial Sequence: Synthetic
                         polynucleotide
source                  1..321
                        mol_type = other DNA
                        organism = synthetic construct
SEQUENCE: 395
gaaataatga tgacgcagtc tccagccatc ctgtctgtgt ctccaggaga cagagccaca    60
ctctcctgca gggccagtca gagtgtgaag aataatttag cctggtacca aaagagacct   120
ggccaggctc ccagactcct catctttgat acatccagca gggcctctgg tatccctgcc   180
aggttcagtg gcggtggttc tgggacagag ttcactctca ccgtcaacag catgcagtct   240
gaagactttg cgacttatta ctgtcagcaa tatgaagagt ggcctcggac gttcggccag   300
gggaccaagg tggaaatcaa a                                             321

SEQ ID NO: 396          moltype = AA   length = 234
FEATURE                 Location/Qualifiers
REGION                  1..234
                        note = Description of Artificial Sequence: Synthetic
                         polypeptide
source                  1..234
                        mol_type = protein
                        organism = synthetic construct
SEQUENCE: 396
METPAQLLFL LLLWLPDTTG EIMMTQSPAI LSVSPGDRAT LSCRASQSVK NNLAWYQKRP    60
GQAPRLLIFD TSSRASGIPA RFSGGGSGTE FTLTVNSMQS EDFATYYCQQ YEEWPRTFGQ   120
GTKVEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234

SEQ ID NO: 397          moltype = AA   length = 107
FEATURE                 Location/Qualifiers
```

```
REGION                    1..107
                          note = Description of Artificial Sequence: Synthetic
                             polypeptide
source                    1..107
                          mol_type = protein
                          organism = synthetic construct
SEQUENCE: 397
EIMMTQSPAI LSVSPGDRAT LSCRASQSVK NNLAWYQKRP GQAPRLLIFD TSSRASGIPA    60
RFSGGGSGTE FTLTVNSMQS EDFATYYCQQ YEEWPRTFGQ GTKVEIK                 107

SEQ ID NO: 398            moltype = DNA  length = 1470
FEATURE                   Location/Qualifiers
misc_feature              1..1470
                          note = Description of Artificial Sequence: Synthetic
                             polynucleotide
source                    1..1470
                          mol_type = other DNA
                          organism = synthetic construct
SEQUENCE: 398
atggactgga tttggaggat cctcttcttg gtggcagcag ctacaagtgc ccactcccag     60
gtgcagttga tgcagtctgg ggctgaagtg aagaagcctg gtcctcagt gaaggtctcc    120
tgcaaggcct ctggaaacag tttcagtaat catgatgtc actgggtacg acaggccact    180
ggacaggggc ttgaatggat gggatggatg agtcatgagg gtgataagac aggcttggca   240
caaaagtttc agggcagagt caccatcacg agggacagtg cgcaagtac agtctacatg    300
gagttgcgcg gcctgacagc tgacgacacg gccatttatt attgtttgac cggctcaaaa   360
catcgcctgc gagattattt tctgtacaat gaatatgcc caattatga agagtgggt     420
gactaccttg cgactttgga cgtctggggc catgggaccg cggtcaccgt ctcgagcgcc   480
tccaccaagg gcccatcggt cttccccctg gcaccctcct ccaagagcac ctctgggggc   540
acagcggccc tgggctgcct ggtcaaggac tacttccccg aaccggtgac ggtgtcgtgg   600
aactcaggcg ccctgaccag cggcgtgcac accttcccgg ctgtcctaca gtcctcagga   660
ctctactccc tcagcagcgt ggtgaccgtg ccctccagca gcttgggcac ccagacctac   720
atctgcaacg tgaatcacaa gcccagcaac accaaggtgg acaagagagt tgagcccaaa   780
tcttgtgaca aaactcacac atgcccaccg tgcccagcac ctgaactcct ggggggaccg   840
tcagtcttcc tcttcccccc aaaacccaag gacaccctca tgatctcccg gacccctgag   900
gtcacatgcg tggtggtgga cgtgagccac gaagaccctg aggtcaagtt caactggtac   960
gtggacggcg tggaggtgca taatgccaag acaaagccgc gggaggagca gtacaacagc  1020
acgtaccgtg tggtcagcgt cctcaccgtc ctgcaccagg actggctgaa tggcaaggag  1080
tacaagtgca aggtctccaa caaagccctc ccagccccca tcgagaaaac catctccaaa  1140
gccaaaggtc agccccgaga accacaggtg tacaccctgc cccatcccg ggaggagatg   1200
accaagaacc aggtcagcct gacctgcctg gtcaaaggct tctatcccag cgacatcgcc  1260
gtggagtggg agagcaatgg gcagccggag aacaactaca agaccacgcc tcccgtgctg  1320
gactccgacg gctccttctt cctctatagc aagctcaccg tggacaagag caggtggcag  1380
caggggaacg tcttctcatg ctccgtgatg catgaggctc tgcacaacca ctacacgcag  1440
aagagcctct ccctgtctcc gggtaaatga                                   1470

SEQ ID NO: 399            moltype = DNA  length = 420
FEATURE                   Location/Qualifiers
misc_feature              1..420
                          note = Description of Artificial Sequence: Synthetic
                             polynucleotide
source                    1..420
                          mol_type = other DNA
                          organism = synthetic construct
SEQUENCE: 399
caggtgcagt tggtgcagtc tggggctgaa gtgaagaagc ctgggtcctc agtgaaggtc    60
tcctgcaagg cctctggaaa cagtttcagt aatcatgatg tccactgggt acgacaggcc   120
actggacagg gcttgaatg gatgggatgg atgagtcatg agggtgataa gacaggcttg    180
gcacaaaagt ttcagggcag agtcaccatc acgagggaca gtggcgcaag tacagtctac   240
atggagttgc gcggcctgac agctgacgac acggccattt attattgttt gaccggctca   300
aaacatcgcc tgcgagatta ttttctgtac aatgaatatg gccccaatta tgaagagtgg   360
ggtgactacc ttgcgacttt ggacgtctgg ggccatggga ccgcggtcac cgtctcgagc   420

SEQ ID NO: 400            moltype = AA  length = 489
FEATURE                   Location/Qualifiers
REGION                    1..489
                          note = Description of Artificial Sequence: Synthetic
                             polypeptide
source                    1..489
                          mol_type = protein
                          organism = synthetic construct
SEQUENCE: 400
MDWIWRILFL VAAATSAHSQ VQLVQSGAEV KKPGSSVKVS CKASGNSFSN HDVHWVRQAT    60
GQGLEWMGWM SHEGDKTGLA QKFQGRVTIT RDSGASTVYM ELRGLTADDT AIYYCLTGSK   120
HRLRDYFLYN EYGPNYEEWG DYLATLDVWG HGTAVTVSSA STKGPSVFPL APSSKSTSGG   180
TAALGCLVKD YFPEPVTVSW NSGALTSGVH TFPAVLQSSG LYSLSSVVTV PSSSLGTQTY   240
ICNVNHKPSN TKVDKRVEPK SCDKTHTCPP CPAPELLGGP SVFLFPPKPK DTLMISRTPE   300
VTCVVVDVSH EDPEVKFNWY VDGVEVHNAK TKPREEQYNS TYRVVSVLTV LHQDWLNGKE   360
YKCKVSNKAL PAPIEKTISK AKGQPREPQV YTLPPSREEM TKNQVSLTCL VKGFYPSDIA   420
VEWESNGQPE NNYKTTPPVL DSDGSFFLYS KLTVDKSRWQ QGNVFSCSVM HEALHNHYTQ   480
```

KSLSLSPGK                                                                         489

SEQ ID NO: 401           moltype = AA   length = 140
FEATURE                  Location/Qualifiers
REGION                   1..140
                         note = Description of Artificial Sequence: Synthetic
                           polypeptide
source                   1..140
                         mol_type = protein
                         organism = synthetic construct
SEQUENCE: 401
QVQLVQSGAE VKKPGSSVKV SCKASGNSFS NHDVHWVRQA TGQGLEWMGW MSHEGDKTGL  60
AQKFQGRVTI TRDSGASTVY MELRGLTADD TAIYYCLTGS KHRLRDYFLY NEYGPNYEEW  120
GDYLATLDVW GHGTAVTVSS                                              140

SEQ ID NO: 402           moltype = DNA   length = 1446
FEATURE                  Location/Qualifiers
misc_feature             1..1446
                         note = Description of Artificial Sequence: Synthetic
                           polynucleotide
source                   1..1446
                         mol_type = other DNA
                         organism = synthetic construct
SEQUENCE: 402
atgaaacacc tgtggttctt cctcctgctg gtggcagctc ccagatgggt cctatcccag  60
gtgcagctgc aggagtcggg cccaggactg gtgagacctt cggagaccct gtccgtcacc  120
tgcatcgtct ctgggggctc catcagcaat tactactgga cttggatccg acagtcccca  180
ggaaagggac tggagtggat aggctatatt tctgacagag aaacaacgac ttacaatccc  240
tccctcaaca gtcgagccgt catatcacga gacacgtcga aaaaccaatt gtccctacaa  300
ttacgttccg tcaccactgc ggacacggcc atctatttct gtgcgacacg gcgccgagga  360
cagaggattt atggagtggt ttcatttgga gagttcttct actactacta catggacgtc  420
tggggcaaag ggactgcggt caccgtctcc tcagcgtcga ccaagggccc atcggtcttc  480
cctctggcac catcatccaa gtcgacctct ggggcacag cggccctggg ctgcctggtc  540
aaggactact cccccgaacc ggtgacggtg tcgtggaact caggcgccct gaccagcggc  600
gtgcacacct tcccggctgt cctacagtcc tcaggactct actccctcag cagcgtggtg  660
accgtgccct ccagcagctt gggcacccag acctacatct gcaacgtgaa tcacaagccc  720
agcaacacca aggtggacaa gagagttgag cccaaatctt gtgacaaaac tcacacatgc  780
ccaccgtgcc cagcacctga actcctgggg ggaccgtcag tcttcctctt ccccccaaaa  840
cccaaggaca cccctcatga tctcccggac cctgaggtca catgcgtggt ggtggacgtg  900
agccacgaag accctgaggt caagttcaac tggtacgtgg acggcgtgga ggtgcataat  960
gccaagacaa agccgcggga ggagcagtac aacagcacgt accgtgtggt cagcgtcctc  1020
accgtcctgc accaggactg gctgaatggc aaggagtaca agtgcaaggt ctccaacaaa  1080
gccctcccag cccccatcga gaaaaccatc tccaaagcca aagggcagcc ccgagaacca  1140
caggtgtaca ccctgccccc atcccgggag gagatgacca agaaccaggt cagcctgacc  1200
tgcctggtca aaggcttcta tcccagcgac atcgccgtgg agtgggagag caatgggcag  1260
ccggagaaca actacaagac cacgcctccc gtgctggact ccgacggctc cttcttcctc  1320
tatagcaagc tcaccgtgga caagagcagg tggcagcagg ggaacgtctt ctcatgctcc  1380
gtgatgcatg aggctctgca caaccactac acgcagaaga gcctctccct gtctccgggt  1440
aaatga                                                             1446

SEQ ID NO: 403           moltype = DNA   length = 396
FEATURE                  Location/Qualifiers
misc_feature             1..396
                         note = Description of Artificial Sequence: Synthetic
                           polynucleotide
source                   1..396
                         mol_type = other DNA
                         organism = synthetic construct
SEQUENCE: 403
caggtgcagc tgcaggagtc gggcccagga ctggtgagac cttcggagac cctgtccgtc  60
acctgcatcg tctctggggg ctccatcagc aattactact ggacttggat ccgacagtcc  120
ccaggaaagg gactggagtg gataggctat atttctgaca gagaaacaac gacttacaat  180
ccctccctca acagtcgagc cgtcatatca cgagacacgt cgaaaaacca attgtcccta  240
caattacgtt ccgtcaccac tgcggacacg gccatctatt tctgtgcgac agcgcgccga  300
ggacagagga tttatggagt ggtttcattt ggagagttct tctactacta catggac     360
gtctggggca aagggactgc ggtcaccgtc tcctca                            396

SEQ ID NO: 404           moltype = AA   length = 481
FEATURE                  Location/Qualifiers
REGION                   1..481
                         note = Description of Artificial Sequence: Synthetic
                           polypeptide
source                   1..481
                         mol_type = protein
                         organism = synthetic construct
SEQUENCE: 404
MKHLWFFLLL VAAPRWVLSQ VQLQESGPGL VRPSETLSVT CIVSGGSISN YYWTWIRQSP  60
GKGLEWIGYI SDRETTTYNP SLNSRAVISR DTSKNQLSLQ LRSVTTADTA IYFCATARRG  120
QRIYGVVSFG EFFYYYMDV WGKGTAVTVS SASTKGPSVF PLAPSSKSTS GGTAALGCLV  180

```
KDYFPEPVTV SWNSGALTSG VHTFPAVLQS SGLYSLSSVV TVPSSSLGTQ TYICNVNHKP   240
SNTKVDKRVE PKSCDKTHTC PPCPAPELLG GPSVFLFPPK PKDTLMISRT PEVTCVVVDV   300
SHEDPEVKFN WYVDGVEVHN AKTKPREEQY NSTYRVVSVL TVLHQDWLNG KEYKCKVSNK   360
ALPAPIEKTI SKAKGQPREP QVYTLPPSRE EMTKNQVSLT CLVKGFYPSD IAVEWESNGQ   420
PENNYKTTPP VLDSDGSFFL YSKLTVDKSR WQQGNVFSCS VMHEALHNHY TQKSLSLSPG   480
K                                                                 481

SEQ ID NO: 405          moltype = AA  length = 132
FEATURE                 Location/Qualifiers
REGION                  1..132
                        note = Description of Artificial Sequence: Synthetic
                         polypeptide
source                  1..132
                        mol_type = protein
                        organism = synthetic construct
SEQUENCE: 405
QVQLQESGPG LVRPSETLSV TCIVSGGSIS NYYWTWIRQS PGKGLEWIGY ISDRETTTYN    60
PSLNSRAVIS RDTSKNQLSL QLRSVTTADT AIYFCATARR GQRIYGVVSF GEFFYYYMD   120
VWGKGTAVTV SS                                                     132

SEQ ID NO: 406          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 406
NYYWT                                                               5

SEQ ID NO: 407          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 407
YISDRETTTY NPSLNS                                                  16

SEQ ID NO: 408          moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 408
ARRGQRIYGV VSFGEFFYYY YMDV                                         24

SEQ ID NO: 409          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 409
GGSISN                                                              6

SEQ ID NO: 410          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 410
YISDRETTT                                                           9

SEQ ID NO: 411          moltype = DNA  length = 702
FEATURE                 Location/Qualifiers
misc_feature            1..702
                        note = Description of Artificial Sequence: Synthetic
                         polynucleotide
source                  1..702
                        mol_type = other DNA
                        organism = synthetic construct
SEQUENCE: 411
```

```
atggcctgga tccctctcct cctcggcctc ctctctcact gcacagggtc tgtgacgtcc    60
tatgtgagcc cactgtcagt ggccctgggg gagacggcca ggattcctg tggacgacag    120
gcccttggaa gtagagctgt gcagtggtat caacataagc caggccaggc ccctatttg    180
ctcatctata ataatcaaga ccggcccca gggatcctg agcggttctc tggcacccct    240
gatattaatt ttgggaccac ggccacctg actatcagg gggtcgaagt cggggatgaa    300
gccgactatt actgtcacat gtgggactct agaagtggtt tcagttggtc tttcggcggg    360
gcgaccaggc tgaccgtcct aggtcagccc aaggctgccc cctcggtcac tctgttcccg    420
ccctcctctg aggagcttca agccaacaag gccacactgg tgtgtctcat aagtgacttc    480
tacccgggag ccgtgacagt ggcctggaag gcagatagca gccccgtcaa ggcgggagtg    540
gagaccacca cacctccaa acaaagcaac aacaagtacg cggccagcag ctatctgagc    600
ctgacgcctg agcagtggaa gtcccacaaa agctacagct gccaggtcac gcatgaaggg    660
agcaccgtgg agaagacagt ggccctaca gaatgttcat ag                        702

SEQ ID NO: 412              moltype = DNA   length = 324
FEATURE                     Location/Qualifiers
misc_feature                1..324
                            note = Description of Artificial Sequence: Synthetic
                             polynucleotide
source                      1..324
                            mol_type = other DNA
                            organism = synthetic construct
SEQUENCE: 412
tcctatgtga gcccactgtc agtggccctg ggggagacgg ccaggatttc tgtggacga    60
caggcccttg aagtagagc tgtgcagtgg tatcaacata agccaggcca ggcccctat    120
ttgctcatct ataataatca agaccggccc tcagggatcc ctgagcggtt ctctggcacc    180
cctgatatta attttgggac cacggccacc ctgactatca gcggggtcga agtcggggat    240
gaagccgact attactgtca catgtgggac tctagaagtg gtttcagttg gtcttcggc    300
ggggcgacca ggctgaccgt ccta                                          324

SEQ ID NO: 413              moltype = AA   length = 233
FEATURE                     Location/Qualifiers
REGION                      1..233
                            note = Description of Artificial Sequence: Synthetic
                             polypeptide
source                      1..233
                            mol_type = protein
                            organism = synthetic construct
SEQUENCE: 413
MAWIPLLLGL LSHCTGSVTS YVSPLSVALG ETARISCGRQ ALGSRAVQWY QHKPGQAPIL    60
LIYNNQDRPS GIPERFSGTP DINFGTTATL TISGVEVGDE ADYYCHMWDS RSGFSWSFGG   120
ATRLTVLGQP KAAPSVTLFP PSSEELQANK ATLVCLISDF YPGAVTVAWK ADSSPVKAGV   180
ETTTPSKQSN NKYAASSYLS LTPEQWKSHK SYSCQVTHEG STVEKTVAPT ECS          233

SEQ ID NO: 414              moltype = AA   length = 108
FEATURE                     Location/Qualifiers
REGION                      1..108
                            note = Description of Artificial Sequence: Synthetic
                             polypeptide
source                      1..108
                            mol_type = protein
                            organism = synthetic construct
SEQUENCE: 414
SYVSPLSVAL GETARISCGR QALGSRAVQW YQHKPGQAPI LLIYNNQDRP SGIPERFSGT    60
PDINFGTTAT LTISGVEVGD EADYYCHMWD SRSGFSWSFG GATRLTVL                108

SEQ ID NO: 415              moltype = AA   length = 11
FEATURE                     Location/Qualifiers
REGION                      1..11
                            note = Description of Artificial Sequence: Synthetic peptide
source                      1..11
                            mol_type = protein
                            organism = synthetic construct
SEQUENCE: 415
GRQALGSRAV Q                                                         11

SEQ ID NO: 416              moltype = AA   length = 12
FEATURE                     Location/Qualifiers
REGION                      1..12
                            note = Description of Artificial Sequence: Synthetic peptide
source                      1..12
                            mol_type = protein
                            organism = synthetic construct
SEQUENCE: 416
HMWDSRSGFS WS                                                        12

SEQ ID NO: 417              moltype = DNA   length = 1446
FEATURE                     Location/Qualifiers
misc_feature                1..1446
                            note = Description of Artificial Sequence: Synthetic
```

|   |   |   |
|---|---|---|
| source | 1..1446 | |
| | mol_type = other DNA | |
| | organism = synthetic construct | |

SEQUENCE: 417

```
atgaaacacc tgtggttctt ccttctcctg gtggcagctc ccagatgggg cgtgtcccag   60
gtgcatctgc aagagtcggg gccaggactg gtgacgcctt cggaaaccct gtccctcact  120
tgcactgtgt cgaatggctc cgtcagtggt cgcttctgga gctggatccg gcagtcccca  180
gggagaggac tggaatggat cggttatttt tctgacactg acaggtctga atataatcct  240
tctctcagga gtcgactcac cttatcagta gatagatcta agaaccagtt gtccctgaga  300
ttgaagtccg tgaccgctgc ggattcggcc acttattact gtgcgagagc acagcagggg  360
aagaggatct atggaatagt gtctttcgga gagttcttct attattatta catggacgcc  420
tggggcaaag ggactccggt caccgtctcc tcagcgtcga ccaagggccc atcggtcttc  480
cctctggcac catcatccaa gtcgacctct gggggcacag cggcctgggc ctgcctggtc  540
aaggactact tccccgaacc ggtgacggtg tcgtggaact caggcgccct gaccagcggc  600
gtgcacacct tcccggctgt cctacagtcc tcaggactct actccctcag cagcgtggtg  660
accgtgccct ccagcagctt gggcacccag acctacatct gcaacgtgaa tcacaagccc  720
agcaacacca aggtggacaa gagagttgag cccaaatctt gtgacaaaac tcacacatgc  780
ccaccgtgcc cagcacctga actcctgggg ggaccgtcag tcttcctctt ccccccaaaa  840
cccaaggaca cctcatgatc tcccggaccc ctgaggtca catgcgtggt ggtggacgtg  900
agccacgaag accctgaggt caagttcaac tggtacgtgg acggcgtgga ggtgcataat  960
gccaagacaa agccgcggga ggagcagtac aacagcaccg tgtgtcagcg tcctc       1020
accgtcctgc accaggactg gctgaatggc aaggagtaca gtgcaaggt ctccaacaaa   1080
gccctcccag cccccatcga gaaaaccatc tccaaagcca agggcagcc ccgagaacca   1140
caggtgtaca ccctgccccc atcccgggag gagatgacca gaaccaggt cagcctgacc   1200
tgcctggtca aaggcttcta tcccagcgac atcgccgtgg agtgggagag caatgggcag  1260
ccggagaaca actacaagac cacgcctccc gtgctggact ccgacggctc cttcttcctc  1320
tatagcaagc tcaccgtgga caagagcagg tggcagcagg gaacgtcttc tcatgctcc   1380
gtgatgcatg aggctctgca caaccactac acgcagaaga gcctctccct gtctccgggt  1440
aaatga                                                              1446
```

|   |   |   |
|---|---|---|
| SEQ ID NO: 418 | moltype = DNA  length = 396 | |
| FEATURE | Location/Qualifiers | |
| misc_feature | 1..396 | |
| | note = Description of Artificial Sequence: Synthetic polynucleotide | |
| source | 1..396 | |
| | mol_type = other DNA | |
| | organism = synthetic construct | |

SEQUENCE: 418

```
caggtgcatc tgcaagagtc ggggccagga ctggtgacgc cttcggaaac cctgtccctc   60
acttgcactg tgtcgaatgg ctccgtcagt ggtcgcttct ggagctggat ccggcagtcc  120
ccagggagag gactggaatg gatcggttat tttctgacac tgacaggtct gaatataat   180
ccttctctca ggagtcgact caccttatca gtagatagat ctaagaacca gttgtccctg  240
agattgaagt ccgtgaccgc tgcggattcg gccacttatt actgtgcgag agcacagcag  300
gggaagagga tctatggaat agtgtctttc ggagagttct tctattatta ttacatggac  360
gcctggggca aagggactcc ggtcaccgtc tcctca                             396
```

|   |   |   |
|---|---|---|
| SEQ ID NO: 419 | moltype = AA  length = 481 | |
| FEATURE | Location/Qualifiers | |
| REGION | 1..481 | |
| | note = Description of Artificial Sequence: Synthetic polypeptide | |
| source | 1..481 | |
| | mol_type = protein | |
| | organism = synthetic construct | |

SEQUENCE: 419

```
MKHLWFFLLL VAAPRWVVSQ VHLQESGPGL VTPSETLSLT CTVSNGSVSG RFWSWIRQSP   60
GRGLEWIGYF SDTDRSEYNP SLRSRLTLSV DRSKNQLSLR LKSVTAADSA TYYCARAQQG  120
KRIYGIVSFG EFFYYYYMDA WGKGTPVTVS SASTKGPSVF PLAPSSKSTS GGTAALGCLV  180
KDYFPEPVTV SWNSGALTSG VHTFPAVLQS SGLYSLSSVV TVPSSSLGTQ TYICNVNHKP  240
SNTKVDKRVE PKSCDKTHTC PPCPAPELLG GPSVFLFPPK PKDTLMISRT PEVTCVVVDV  300
SHEDPEVKFN WYVDGVEVHN AKTKPREEQY NSTYRVVSVL TVLHQDWLNG KEYKCKVSNK  360
ALPAPIEKTI SKAKGQPREP QVYTLPPSRE EMTKNQVSLT CLVKGFYPSD IAVEWESNGQ  420
PENNYKTTPP VLDSDGSFFL YSKLTVDKSR WQQGNVFSCS VMHEALHNHY TQKSLSLSPG  480
K                                                                   481
```

|   |   |   |
|---|---|---|
| SEQ ID NO: 420 | moltype = AA  length = 132 | |
| FEATURE | Location/Qualifiers | |
| REGION | 1..132 | |
| | note = Description of Artificial Sequence: Synthetic polypeptide | |
| source | 1..132 | |
| | mol_type = protein | |
| | organism = synthetic construct | |

SEQUENCE: 420

```
QVHLQESGPG LVTPSETLSL TCTVSNGSVS GRFWSWIRQS PGRGLEWIGY FSDTDRSEYN   60
PSLRSRLTLS VDRSKNQLSL RLKSVTAADS ATYYCARAQQ GKRIYGIVSF GEFFYYYYMD  120
AWGKGTPVTV SS                                                       132
```

```
SEQ ID NO: 421          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 421
GRFWS                                                                           5

SEQ ID NO: 422          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 422
YFSDTDRSEY NPSLRS                                                              16

SEQ ID NO: 423          moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 423
AQQGKRIYGI VSFGEFFYYY YMDA                                                     24

SEQ ID NO: 424          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 424
NGSVSG                                                                          6

SEQ ID NO: 425          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 425
YFSDTDRSE                                                                       9

SEQ ID NO: 426          moltype = DNA  length = 699
FEATURE                 Location/Qualifiers
misc_feature            1..699
                        note = Description of Artificial Sequence: Synthetic
                         polynucleotide
source                  1..699
                        mol_type = other DNA
                        organism = synthetic construct
SEQUENCE: 426
atggcctgga tccctctcct cctcggcctc ctctctcact gcacaggttc tgacacttcg              60
ttaaacccac tgtcgctggc cccaggagcg acggccaaaa ttccctgcgg agaaaggagc             120
cgtggaagta gggctgtcca gtggtatcag cagaagccag gccaggcccc cacattgatc             180
atttataata atcaagaccg gccccgcaggg gtctctgaac gattttctgg caatcctgac            240
gtcgctattg gggtgacggc caccctgacc atcagtcggg tcgaagtcgg ggatgaggcc             300
gactatattt gtcactattg ggacagtaga agtcccatca gctggatttt cggcggaggg             360
acccagctga ccgtcctggg tcagcccaag gctgccccct cggtcactct gttcccgccc             420
tcctctgagg agcttcaagc caacaaggcc acactggtgt gtctcataag tgacttctac             480
ccgggagccg tgacagtggc ctggaaggca gatagcagcc cgtcaaggc gggagtgag               540
accaccacac cctccaaaca aagcaacaac aagtacgcgg ccagcagcta tctgagcctg             600
acgcctgagc agtggaagtc ccacaaaagc tacagctgcc aggtcacgca tgaagggagc             660
accgtggaga agacagtggc ccctacagaa tgttcatag                                    699

SEQ ID NO: 427          moltype = DNA  length = 321
FEATURE                 Location/Qualifiers
misc_feature            1..321
                        note = Description of Artificial Sequence: Synthetic
                         polynucleotide
source                  1..321
```

```
                          mol_type = other DNA
                          organism = synthetic construct
SEQUENCE: 427
tcgttaaacc cactgtcgct ggcccccagga gcgacggcca aaattccctg cggagaaagg   60
agccgtggaa gtagggctgt ccagtggtat cagcagaagc caggccaggc ccccacattg  120
atcatttata ataatcaaga ccggcccgca ggggtctctg aacgattttc tggcaatcct  180
gacgtcgcta ttgggggtgac ggccacccctg accatcagtc gggtcgaagt cggggatgag  240
gccgactatt attgtcacta ttgggacagt agaagtccca tcagctggat tttcggcgga  300
gggacccagc tgaccgtcct g                                             321

SEQ ID NO: 428            moltype = AA length = 232
FEATURE                   Location/Qualifiers
REGION                    1..232
                          note = Description of Artificial Sequence: Synthetic
                           polypeptide
source                    1..232
                          mol_type = protein
                          organism = synthetic construct
SEQUENCE: 428
MAWIPLLLGL LSHCTGSDTS LNPLSLAPGA TAKIPCGERS RGSRAVQWYQ QKPGQAPTLI   60
IYNNQDRPAG VSERFSGNPD VAIGVTATLT ISRVEVGDEA DYYCHYWDSR SPISWIFGGG  120
TQLTVLGQPK AAPSVTLFPP SSEELQANKA TLVCLISDFY PGAVTVAWKA DSSPVKAGVE  180
TTTPSKQSNN KYAASSYLSL TPEQWKSHKS YSCQVTHEGS TVEKTVAPTE CS          232

SEQ ID NO: 429            moltype = AA length = 107
FEATURE                   Location/Qualifiers
REGION                    1..107
                          note = Description of Artificial Sequence: Synthetic
                           polypeptide
source                    1..107
                          mol_type = protein
                          organism = synthetic construct
SEQUENCE: 429
SLNPLSLAPG ATAKIPCGER SRGSRAVQWY QQKPGQAPTL IIYNNQDRPA GVSERFSGNP   60
DVAIGVTATL TISRVEVGDE ADYYCHYWDS RSPISWIFGG GTQLTVL                107

SEQ ID NO: 430            moltype = AA length = 11
FEATURE                   Location/Qualifiers
REGION                    1..11
                          note = Description of Artificial Sequence: Synthetic peptide
source                    1..11
                          mol_type = protein
                          organism = synthetic construct
SEQUENCE: 430
GERSRGSRAV Q                                                         11

SEQ ID NO: 431            moltype = AA length = 12
FEATURE                   Location/Qualifiers
REGION                    1..12
                          note = Description of Artificial Sequence: Synthetic peptide
source                    1..12
                          mol_type = protein
                          organism = synthetic construct
SEQUENCE: 431
HYWDSRSPIS WI                                                        12

SEQ ID NO: 432            moltype = DNA length = 1446
FEATURE                   Location/Qualifiers
misc_feature              1..1446
                          note = Description of Artificial Sequence: Synthetic
                           polynucleotide
source                    1..1446
                          mol_type = other DNA
                          organism = synthetic construct
SEQUENCE: 432
atgaaacacc tgtggttctt cctcctgctg gtggcagctc ccagatgggt cgtgtcccag   60
gtgcatctgc aagagtcggg gccaggactg gtgacgcctt cggaaccct gtccctcact   120
tgcactgtgt cgaatggctc cgtcagtggt cgcttctgga ctggatccg gcagtcccca  180
gggagaggac tggaatggat cggttatttt tctgacactg acaggtctga atataatcct  240
tctctcagga gtcgactcac cttatcagtc gatagatcca agaaccagtt gtccctaaaa  300
ttgaagtccg tgaccgctgc ggattcggcc acttattact gtgcgagagc acaacagggg  360
aagaggatct atgaatagt gtctttcgga gagttgttct attattatta catggacgcc  420
tggggcaaag ggactccggt caccgtctcc tcagcgtcga ccaagggccc atcggtcttc  480
cctctggcac catcatccaa gtcgacctct gggggcacag cggccctggg ctgcctggtc  540
aaggactact ccccgaacc ggtgacggtg tcgtggaact caggcgccct gaccagcggc  600
gtgcacacct tcccggctgt cctacagtc tcaggactct actccctcag cagcgtggtg  660
accgtgccct ccagcagctt gggcacccag acctacatct gcaacgtgaa tcacaagccc  720
agcaacacca aggtggacaa gagagttgag cccaaatctt gtgacaaaac tcacacatgc  780
ccaccgtgcc cagcacctga actcctgggg ggaccgtcag tcttcctctt ccccccaaaa  840
```

```
cccaaggaca ccctcatgat ctcccggacc cctgaggtca catgcgtggt ggtggacgtg    900
agccacgaag accctgaggt caagttcaac tggtacgtgg acggcgtgga ggtgcataat    960
gccaagacaa agccgcggga ggagcagtac aacagcacgt accgtgtggt cagcgtcctc   1020
accgtcctgc accaggactg gctgaatggc aaggagtaca agtgcaaggt ctccaacaaa   1080
gcccctcccag ccccatcga gaaaaccatc tccaaagcca aagggcagcc ccgagaacca   1140
caggtgtaca ccctgccccc atcccgggag agatgaccaa gaaccaggt cagcctgacc   1200
tgcctggtca aaggcttcta tcccagcgac atcgccgtgg agtgggagag caatgggcag   1260
ccggagaaca actacaagac cacgcctccc gtgctggact ccgacggctc cttcttcctc   1320
tatagcaagc tcaccgtgga caagagcagg tggcagcagg ggaacgtctt ctcatgctcc   1380
gtgatgcatg aggctctgca caaccactac acgcagaaga cctctccct gtctccgggt   1440
aaatga                                                              1446

SEQ ID NO: 433          moltype = DNA  length = 396
FEATURE                 Location/Qualifiers
misc_feature            1..396
                        note = Description of Artificial Sequence: Synthetic
                         polynucleotide
source                  1..396
                        mol_type = other DNA
                        organism = synthetic construct
SEQUENCE: 433
caggtgcatc tgcaagagtc ggggccagga ctggtgacgc cttcggaaac cctgtccctc    60
acttgcactg tgtcgaatgg ctccgtcagt ggtcgcttct ggagctggat ccggcagtcc   120
ccagggagag gactgaatg gatcggttat ttttctgaca ctgacaggtc tgaatataat    180
ccttctctca ggagtcgact caccttatca gtcgatagat ccaagaacca gttgtccta    240
aaattgaagt ccgtgaccgc tgcggattcg gccacttatt actgtgcgag agcacaaacag   300
gggaagagga tctatggaat agtgtctttc ggagagttgt tctattatta ttacatggac   360
gcctggggca aagggactcc ggtcaccgtc tcctca                              396

SEQ ID NO: 434          moltype = AA  length = 481
FEATURE                 Location/Qualifiers
REGION                  1..481
                        note = Description of Artificial Sequence: Synthetic
                         polypeptide
source                  1..481
                        mol_type = protein
                        organism = synthetic construct
SEQUENCE: 434
MKHLWFFLLL VAAPRWVVSQ VHLQESGPGL VTPSETLSLT CTVSNGSVSG RFWSWIRQSP    60
GRGLEWIGYF SDTDRSEYNP SLRSRLTLSV DRSKNQLSLK LKSVTAADSA TYYCARAQQG   120
KRIYGIVSFG ELFYYYYMDA WGKGTPVTVS SASTKGPSVF PLAPSSKSTS GGTAALGCLV   180
KDYFPEPVTV SWNSGALTSG VHTFPAVLQS SGLYSLSSVV TVPSSSLGTQ TYICNVNHKP   240
SNTKVDKRVE PKSCDKTHTC PPCPAPELLG GPSVFLFPPK PKDTLMISRT PEVTCVVVDV   300
SHEDPEVKFN WYVDGVEVHN AKTKPREEQY NSTYRVVSVL TVLHQDWLNG KEYKCKVSNK   360
ALPAPIEKTI SKAKGQPREP QVYTLPPSRE EMTKNQVSLT CLVKGFYPSD IAVEWESNGQ   420
PENNYKTTPP VLDSDGSFFL YSKLTVDKSR WQQGNVFSCS VMHEALHNHY TQKSLSLSPG   480
K                                                                   481

SEQ ID NO: 435          moltype = AA  length = 132
FEATURE                 Location/Qualifiers
REGION                  1..132
                        note = Description of Artificial Sequence: Synthetic
                         polypeptide
source                  1..132
                        mol_type = protein
                        organism = synthetic construct
SEQUENCE: 435
QVHLQESGPG LVTPSETLSL TCTVSNGSVS GRFWSWIRQS PGRGLEWIGY FSDTDRSEYN    60
PSLRSRLTLS VDRSKNQLSL KLKSVTAADS ATYYCARAQQ GKRIYGIVSF GELFYYYYMD   120
AWGKGTPVTV SS                                                       132

SEQ ID NO: 436          moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 436
AQQGKRIYGI VSFGELFYYY YMDA                                           24

SEQ ID NO: 437          moltype = DNA  length = 699
FEATURE                 Location/Qualifiers
misc_feature            1..699
                        note = Description of Artificial Sequence: Synthetic
                         polynucleotide
source                  1..699
                        mol_type = other DNA
                        organism = synthetic construct
```

```
SEQUENCE: 437
atggcctgga tccctctcct cctcggcctc ctctctcact gcacaggttc tgacacttcg    60
ttaaacccac tgtcgctggc cccgggagcg acgccaaaaa ttccctgcgg agaaaggagc   120
cgtggaagta gggctgtcca gtggtatcag cagaagccag gccaggcccc acattgatc   180
atttatataa atcaagaccg gcccgcaggg gtctctgaac gatttctgg caatcctgac   240
gtcgctattg gggtgacggc caccctgacc atcagtcggg tcgaagtcgg ggatgagggc   300
gactattatt gtcactattg ggacagtaga agtcccatca gctggatttt cgccggaggg   360
acccagttga ccgtcctggg tcagcccaag gctgccccct cggtcactct gttcccgccc   420
tcctctgagg agcttcaagc caacaaggcc acactggtgt gtctcataag tgacttctac   480
ccggagccg tgacagtggc ctggaaggca gatagcagcc ccgtcaaggc ggggagtggag   540
accaccacac cctccaaaca aagcaacaac aagtacgcgg ccagcagcta tctgagcctg   600
acgcctgagc agtggaagtc ccacaaaagc tacagctgcc aggtcacgca tgaagggagc   660
accgtggaga agacagtggc ccctacagaa tgttcatag               699

SEQ ID NO: 438          moltype = DNA   length = 321
FEATURE                 Location/Qualifiers
misc_feature            1..321
                        note = Description of Artificial Sequence: Synthetic
                         polynucleotide
source                  1..321
                        mol_type = other DNA
                        organism = synthetic construct
SEQUENCE: 438
tcgttaaacc cactgtcgct ggccccggga gcgacggcca aaattccctg cggagaaagg    60
agccgtggaa gtagggctgt ccagtggtat cagcagaagc caggccaggc ccccacattg   120
atcatttata ataatcaaga ccggcccgca ggggtctctg aacgatttc tggcaatcct   180
gacgtcgcta ttggggtgac ggccaccctg accatcagtc gggtcgaagt cggggatgag   240
ggcgactatt attgtcacta ttgggacagt agaagtccca tcagctggat tttcgccgga   300
gggacccagt tgaccgtcct g                                             321

SEQ ID NO: 439          moltype = AA    length = 232
FEATURE                 Location/Qualifiers
REGION                  1..232
                        note = Description of Artificial Sequence: Synthetic
                         polypeptide
source                  1..232
                        mol_type = protein
                        organism = synthetic construct
SEQUENCE: 439
MAWIPLLLGL LSHCTGSDTS LNPLSLAPGA TAKIPCGERS RGSRAVQWYQ QKPGQAPTLI    60
IYNNQDRPAG VSERFSGNPD VAIGVTATLT ISRVEVGDEG DYYCHYWDSR SPISWIFAGG   120
TQLTVLGQPK AAPSVTLFPP SSEELQANKA TLVCLISDFY PGAVTVAWKA DSSPVKAGVE   180
TTTPSKQSNN KYAASSYLSL TPEQWKSHKS YSCQVTHEGS TVEKTVAPTE CS           232

SEQ ID NO: 440          moltype = AA    length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 440
SLNPLSLAPG ATAKIPCGER SRGSRAVQWY QQKPGQAPTL IIYNNQDRPA GVSERFSGNP    60
DVAIGVTATL TISRVEVGDE GDYYCHYWDS RSPISWIFAG GTQLTVL                 107

SEQ ID NO: 441          moltype = DNA   length = 1437
FEATURE                 Location/Qualifiers
misc_feature            1..1437
                        note = Description of Artificial Sequence: Synthetic
                         polynucleotide
source                  1..1437
                        mol_type = other DNA
                        organism = synthetic construct
SEQUENCE: 441
atgaaacacc tgtggttctt cctcctgctg gtggcagctc ccagatgggt cctttcccag    60
gtgcaactac aggagtcggg cccaggactg gtgaagcctt cggagaccct tccctcacc   120
tgcactgtct ctggtgactc catcaacact ggtcatcact actggggctg gtccgtcag   180
gtcccaggga agggaccgga atggattgct cacatccact ataatacggc tgtcttgcac   240
aatccggccc tcaagagtcg agtcaccatt tcgattttca ccctgaagaa tctgattacc   300
ctgaggctca gtaatatgac cgccgcggac acggccgtct attttgcgt tcgatccggc   360
ggcgacttt tatactataa tgagtggcaa aaacccact ggttctatcc ctggggcccg   420
ggaattttgg tcaccgtctc gagcgcctcc accaagggcc catcggtctt ccccctggca   480
ccctcctcca agagcacctc tgggggcaca gcggccctgg gctgcctggt caaggactac   540
ttccccgaac cggtgacggt gtcgtggaac tcaggcgccc tgaccagcgg cgtgcacacc   600
ttcccggctg tcctacagtc ctcaggactc tactccctca gcagcgtggt gaccgtgccc   660
tccagcagct gggcaccca gacctacatc tgcaacgtga atcacaagcc cagcaacacc   720
aaggtggaca agagagttga gcccaaatct tgtgacaaaa ctcacacatg cccaccgtgc   780
ccagcacctg aactcctggg gggaccgtca gtcttcctct tcccccaaa acccaaggac   840
```

```
accctcatga tctcccggac ccctgaggtc acatgcgtgg tggtggacgt gagccacgaa    900
gaccctgagg tcaagttcaa ctggtacgtg gacggcgtgg aggtgcataa tgccaagaca    960
aagccgcggg aggagcagta caacagcacg taccgtgtgg tcagcgtcct caccgtcctg   1020
caccaggact ggctgaatgg caaggagtac aagtgcaagg tctccaacaa agccctccca   1080
gcccccatcg agaaaaccat ctccaaagcc aaagggcagc cccgagaacc acaggtgtac   1140
accctgcccc catcccggga ggagatgacc aagaaccagg tcagcctgac ctgcctggtc   1200
aaaggcttct atcccagcga catcgccgtg gagtgggaga gcaatgggca gccggagaac   1260
aactacaaga ccacgcctcc cgtgctggac tccgacggct ccttcttcct ctatagcaag   1320
ctcaccgtgg acaagagcag gtggcagcag gggaacgtct tctcatgctc cgtgatgcat   1380
gaggctctgc acaaccacta cacgcagaag agcctctccc tgtctccggg taaatga      1437

SEQ ID NO: 442           moltype = DNA   length = 387
FEATURE                  Location/Qualifiers
misc_feature             1..387
                         note = Description of Artificial Sequence: Synthetic
                         polynucleotide
source                   1..387
                         mol_type = other DNA
                         organism = synthetic construct
SEQUENCE: 442
caggtgcaac tacaggagtc gggcccagga ctggtgaagc cttcggagac cctttccctc     60
acctgcactg tctctggtga ctccatcaac actggtcatc actactgggg ctgggtccgt    120
caggtcccag ggaagggacc ggaatggatt gctcacatcc actataatac ggctgtcttg    180
cacaatccgg ccctcaagag tcgagtcacc atttcgattt tcaccctgaa gaatctgatt    240
accctgaggc tcagtaatat gaccgccgcg gacacggccg tctatttctg cgttcgatcc    300
ggcggcgaca ttttatacta taatgagtgg caaaaacccc actggttcta tccctgggc    360
ccgggaattt tggtcaccgt ctcgagc                                        387

SEQ ID NO: 443           moltype = AA   length = 478
FEATURE                  Location/Qualifiers
REGION                   1..478
                         note = Description of Artificial Sequence: Synthetic
                         polypeptide
source                   1..478
                         mol_type = protein
                         organism = synthetic construct
SEQUENCE: 443
MKHLWFFLLL VAAPRWVLSQ VQLQESGPGL VKPSETLSLT CTVSGDSINT GHHYWGWVRQ     60
VPGKGPEWIA HIHYNTAVLH NPALKSRVTI SIFTLKNLIT LRLSNMTAAD TAVYFCVRSG    120
GDILYYNEWQ KPHWFYPWGP GILVTVSSAS TKGPSVFPLA PSSKSTSGGT AALGCLVKDY    180
FPEPVTVSWN SGALTSGVHT FPAVLQSSGL YSLSSVVTVP SSSLGTQTYI CNVNHKPSNT    240
KVDKRVEPKS CDKTHTCPPC PAPELLGGPS VFLFPPKPKD TLMISRTPEV TCVVVDVSHE    300
DPEVKFNWYV DGVEVHNAKT KPREEQYNST YRVVSVLTVL HQDWLNGKEY KCKVSNKALP    360
APIEKTISKA KGQPREPQVY TLPPSREEMT KNQVSLTCLV KGFYPSDIAV EWESNGQPEN    420
NYKTTPPVLD SDGSFFLYSK LTVDKSRWQQ GNVFSCSVMH EALHNHYTQK SLSLSPGK      478

SEQ ID NO: 444           moltype = AA   length = 129
FEATURE                  Location/Qualifiers
REGION                   1..129
                         note = Description of Artificial Sequence: Synthetic
                         polypeptide
source                   1..129
                         mol_type = protein
                         organism = synthetic construct
SEQUENCE: 444
QVQLQESGPG LVKPSETLSL TCTVSGDSIN TGHHYWGWVR QVPGKGPEWI AHIHYNTAVL     60
HNPALKSRVT ISIFTLKNLI TLRLSNMTAA DTAVYFCVRS GGDILYYNEW QKPHWFYPWG    120
PGILVTVSS                                                            129

SEQ ID NO: 445           moltype = AA   length = 19
FEATURE                  Location/Qualifiers
REGION                   1..19
                         note = Description of Artificial Sequence: Synthetic peptide
source                   1..19
                         mol_type = protein
                         organism = synthetic construct
SEQUENCE: 445
SGGDILYYNE WQKPHWFYP                                                  19

SEQ ID NO: 446           moltype = DNA   length = 708
FEATURE                  Location/Qualifiers
misc_feature             1..708
                         note = Description of Artificial Sequence: Synthetic
                         polynucleotide
source                   1..708
                         mol_type = other DNA
                         organism = synthetic construct
SEQUENCE: 446
atggcctggg ctctgctcct cctcaccctc ctcactcagg gcacagggtc ctgggcccag     60
```

```
tctgccctga ctcagcctcc ctccgcgtcc gggtctcttg acagtcact caccatctcc   120
tgcagtggaa ccgccagtga cattggcagt tggaattttg tctcctggta tcaacaattc   180
ccaggcagag ccccccaacct cattattttt gaggtcaata ggcggcgatc agggggtccct  240
gatcgcttct ctggttccaa gtcgggcaat acggcctccc tgaccgtctc tgggctccgg   300
tctgaggatg aggctgaata ttttttgcagt tcccttttga agtgtggga cattgttttt   360
ggcggaggga ccaaggtgac cgtcctaggt cagcccaagg ctgcccccctc ggtcactctg   420
ttcccgccct cctctgagga gcttcaagcc aacaaggcca cactggtgtg tctcataagt   480
gacttctacc cggagccgt gacagtggcc tggaaggcag atagcagccc cgtcaaggcg   540
ggagtggaga ccaccacacc tccaaacaa agcaacaaca agtacgcggc cagcagctac   600
ctgagcctga cgcctgagca gtggaagtcc cacaaaagct acagctgcca ggtcacgcat   660
gaagggagca ccgtggagaa gacagtggcc cctacagaat gttcatag               708

SEQ ID NO: 447           moltype = DNA   length = 330
FEATURE                  Location/Qualifiers
misc_feature             1..330
                         note = Description of Artificial Sequence: Synthetic
                         polynucleotide
source                   1..330
                         mol_type = other DNA
                         organism = synthetic construct
SEQUENCE: 447
cagtctgccc tgactcagcc tccctccgcg tccgggtctc ttggacagtc actcaccatc   60
tcctgcagtg gaaccgccag tgacattggc agttggaatt ttgtctcctg gtatcaacaa   120
ttcccaggca gagcccccaa cctcattatt tttgaggtca ataggcggcg atcagggggtc  180
cctgatcgct tctctggttc caagtcgggc aatacggcct ccctgaccgt ctctgggctc   240
cggtctgagg atgaggctga atattttttgc agttcccttt caggcaggtg ggacattgtt   300
tttggcggag ggaccaaggt gaccgtccta                                   330

SEQ ID NO: 448           moltype = AA   length = 235
FEATURE                  Location/Qualifiers
REGION                   1..235
                         note = Description of Artificial Sequence: Synthetic
                         polypeptide
source                   1..235
                         mol_type = protein
                         organism = synthetic construct
SEQUENCE: 448
MAWALLLLTL LTQGTGSWAQ SALTQPPSAS GSLGQSLTIS CSGTASDIGS WNFVSWYQQF    60
PGRAPNLIIF EVNRRRSGVP DRFSGSKSGN TASLTVSGLR SEDEAEYFCS SLSGRWDIVF   120
GGGTKVTVLG QPKAAPSVTL FPPSSEELQA NKATLVCLIS DFYPGAVTVA WKADSSPVKA   180
GVETTTPSKQ SNNKYAASSY LSLTPEQWKS HKSYSCQVTH EGSTVEKTVA PTECS        235

SEQ ID NO: 449           moltype = AA   length = 110
FEATURE                  Location/Qualifiers
REGION                   1..110
                         note = Description of Artificial Sequence: Synthetic
                         polypeptide
source                   1..110
                         mol_type = protein
                         organism = synthetic construct
SEQUENCE: 449
QSALTQPPSA SGSLGQSLTI SCSGTASDIG SWNFVSWYQQ FPGRAPNLII FEVNRRRSGV    60
PDRFSGSKSG NTASLTVSGL RSEDEAEYFC SSLSGRWDIV FGGGTKVTVL              110

SEQ ID NO: 450           moltype = AA   length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 450
SGTASDIGSW NFVS                                                     14

SEQ ID NO: 451           moltype = DNA   length = 1455
FEATURE                  Location/Qualifiers
misc_feature             1..1455
                         note = Description of Artificial Sequence: Synthetic
                         polynucleotide
source                   1..1455
                         mol_type = other DNA
                         organism = synthetic construct
SEQUENCE: 451
atgaaacacc tgtggttctt cctcctgctg gtggcagctc ccagatgggg cctgtcccag    60
ccgcagctgc aggagtcggg gccaggactg gtgaggcttc ggagaccct gtccctcacc   120
tgcactgtgt ccggcgactc cactgctgct tgtgactatt ctggggctg gtcggcag     180
cccccaggga aggggctgga gtggattgga agtttgtcac attgtgcagg ttactacaat   240
agtggctgga cctaccacaa cccgtctctc aagagtcgac tcacgatttc actcgacacg   300
cccaagaatc aggtcttcct gaagttaaat tctgtgaccg ccgcggacac ggccatttac   360
```

```
tactgtgcgc gattcggtgg cgacgttttg gtgtaccacg attggccaaa gccggcctgg    420
gtcgacctct ggggccgggg agttttggtc accgtctcga gcgcctccac caagggccca    480
tcggtcttcc ccctggcacc ctcctccaag agcacctctg ggggcacagc ggccctgggc    540
tgcctggtca aggactactt ccccgaaccg gtgacggtgt cgtggaactc aggcgccctg    600
accagcggcg tgcacacctt cccggctgtc ctacagtcct caggactcta ctccctcagc    660
agcgtggtga ccgtgccctc cagcagcttg ggcacccaga cctacatctg caacgtgaat    720
cacaagccca gcaacaccaa ggtggacaag agagttgagc ccaaatcttg tgacaaaact    780
cacacatgcc caccgtgccc agcacctgaa ctcctggggg gaccgtcagt cttcctcttc    840
ccccccaaaac ccaaggacac cctcatgatc tcccggaccc ctgaggtcac atgcgtggtg    900
gtggacgtga gccacgaaga ccctgaggtc aagttcaact ggtacgtgga cggcgtggag    960
gtgcataatg ccaagacaaa gccgcgggag gagcagtaca acagcacgta ccgtgtggtc   1020
agcgtcctca ccgtcctgca ccaggactgg ctgaatggca aggagtacaa gtgcaaggtc   1080
tccaacaaag ccctcccagc ccccatcgag aaaaccatct ccaaagccaa agggcagccc   1140
cgagaaccac aggtgtacac cctgccccca tcccgggagg agatgaccaa gaaccaggtc   1200
agcctgacct gcctggtcaa aggcttctat cccagcgaca tcgccgtgga gtgggagagc   1260
aatgggcagc cggagaacaa ctacaagacc acgcctcccg tgctggactc cgacggctcc   1320
ttcttcctct atagcaagct caccgtggac aagagcaggt ggcagcaggg gaacgtcttc   1380
tcatgctccg tgatgcatga ggctctgcac aaccactaca cgcagaagag cctctccctg   1440
tctccgggta aatga                                                    1455

SEQ ID NO: 452         moltype = DNA  length = 405
FEATURE                Location/Qualifiers
misc_feature           1..405
                       note = Description of Artificial Sequence: Synthetic
                         polynucleotide
source                 1..405
                       mol_type = other DNA
                       organism = synthetic construct
SEQUENCE: 452
cagccgcagc tgcaggagtc ggggccagga ctggtggagg cttcggagac cctgtccctc     60
acctgcactg tgtccggcga ctccactgct gcttgtgact atttctgggg ctgggtccgg    120
cagcccccag ggaaggggct ggagtggatt ggaagtttgt cacattgtgc aggttactac    180
aatagtggct ggacctacca caacccgtct ctcaagagtc gactcacgat ttcactcgac    240
acgcccaaga atcaggtctt cctgaagtta aattctgtga ccgccgcgga cacggccatt    300
tactactgtg cgcgattcgg tggcgacgtt ttggtgtacc acgattggcc aaagccggcc    360
tgggtcgacc tctggggccg gggagttttg gtcaccgtct cgagc                   405

SEQ ID NO: 453         moltype = AA  length = 484
FEATURE                Location/Qualifiers
REGION                 1..484
                       note = Description of Artificial Sequence: Synthetic
                         polypeptide
source                 1..484
                       mol_type = protein
                       organism = synthetic construct
SEQUENCE: 453
MKHLWFFLLL VAAPRWVLSQ PQLQESGPGL VEASETLSLT CTVSGDSTAA CDYFWGWVRQ     60
PPGKGLEWIG SLSHCAGYYN SGWTYHNPSL KSRLTISLDT PKNQVFLKLN SVTAADTAIY    120
YCARFGGDVL VYHDWPKPAW VDLWGRGVLV TVSSASTKGP SVFPLAPSSK STSGGTAALG    180
CLVKDYFPEP VTVSWNSGAL TSGVHTFPAV LQSSGLYSLS SVVTVPSSSL GTQTYICNVN    240
HKPSNTKVDK RVEPKSCDKT HTCPPCPAPE LLGGPSVFLF PPKPKDTLMI SRTPEVTCVV    300
VDVSHEDPEV KFNWYVDGVE VHNAKTKPRE EQYNSTYRVV SVLTVLHQDW LNGKEYKCKV    360
SNKALPAPIE KTISKAKGQP REPQVYTLPP SREEMTKNQV SLTCLVKGFY PSDIAVEWES    420
NGQPENNYKT TPPVLDSDGS FFLYSKLTVD KSRWQQGNVF SCSVMHEALH NHYTQKSLSL    480
SPGK                                                                484

SEQ ID NO: 454         moltype = AA  length = 135
FEATURE                Location/Qualifiers
REGION                 1..135
                       note = Description of Artificial Sequence: Synthetic
                         polypeptide
source                 1..135
                       mol_type = protein
                       organism = synthetic construct
SEQUENCE: 454
QPQLQESGPG LVEASETLSL TCTVSGDSTA ACDYFWGWVR QPPGKGLEWI GSLSHCAGYY     60
NSGWTYHNPS LKSRLTISLD TPKNQVFLKL NSVTAADTAI YYCARFGGDV LVYHDWPKPA    120
WVDLWGRGVL VTVSS                                                    135

SEQ ID NO: 455         moltype = AA  length = 22
FEATURE                Location/Qualifiers
REGION                 1..22
                       note = Description of Artificial Sequence: Synthetic peptide
source                 1..22
                       mol_type = protein
                       organism = synthetic construct
SEQUENCE: 455
SLSHCAGYYN SGWTYHNPSL KS                                             22
```

| | | |
|---|---|---|
| SEQ ID NO: 456 | moltype = AA length = 19 | |
| FEATURE | Location/Qualifiers | |
| REGION | 1..19 | |
| | note = Description of Artificial Sequence: Synthetic peptide | |
| source | 1..19 | |
| | mol_type = protein | |
| | organism = synthetic construct | |
| SEQUENCE: 456 | | |
| FGGDVLVYHD WPKPAWVDL | | 19 |
| | | |
| SEQ ID NO: 457 | moltype = AA length = 15 | |
| FEATURE | Location/Qualifiers | |
| REGION | 1..15 | |
| | note = Description of Artificial Sequence: Synthetic peptide | |
| source | 1..15 | |
| | mol_type = protein | |
| | organism = synthetic construct | |
| SEQUENCE: 457 | | |
| SLSHCAGYYN SGWTY | | 15 |
| | | |
| SEQ ID NO: 458 | moltype = AA length = 9 | |
| FEATURE | Location/Qualifiers | |
| REGION | 1..9 | |
| | note = Description of Artificial Sequence: Synthetic peptide | |
| source | 1..9 | |
| | mol_type = protein | |
| | organism = synthetic construct | |
| SEQUENCE: 458 | | |
| TGNINNFVS | | 9 |
| | | |
| SEQ ID NO: 459 | moltype = AA length = 10 | |
| FEATURE | Location/Qualifiers | |
| REGION | 1..10 | |
| | note = Description of Artificial Sequence: Synthetic peptide | |
| source | 1..10 | |
| | mol_type = protein | |
| | organism = synthetic construct | |
| SEQUENCE: 459 | | |
| GSLAGNWDVV | | 10 |
| | | |
| SEQ ID NO: 460 | moltype = DNA length = 1455 | |
| FEATURE | Location/Qualifiers | |
| misc_feature | 1..1455 | |
| | note = Description of Artificial Sequence: Synthetic polynucleotide | |
| source | 1..1455 | |
| | mol_type = other DNA | |
| | organism = synthetic construct | |
| SEQUENCE: 460 | | |

```
atgaaacacc tgtggttctt cctcctgctg gtggcagctc ccagatgggt cctgtcccag   60
ccgcagctgc aggagtcggg gccaggactg gtggaggctt cggagaccct gtccctcacc  120
tgcactgtgt ccggcgactc cactgctggt tgtgactatt tctggggctg ggtccggcag  180
cccccaggga aggggctgga gtggattggg gttttgtcac attgtgcagg ttactacaat  240
actggctgga cctaccacaa cccgtctctc aagagtcgac tcacgatttc actcgacacg  300
cccaagaatc aggtcttcct gaagtttaaat tctgtgaccg ccgcggacac ggccatttac  360
tactgtgcgc gattcgacgg cgaagttttg tgtgtacaacg attggccaaa gccggcctgg  420
gtcgacctct ggggccgggg aacttttggtc accgtctcga gcgcctccac caagggccca  480
tcggtcttcc ccctggcacc ctcctccaag agcacctctg ggggcacagc ggccctgggc  540
tgcctggtca aggactactt ccccgaaccg gtgacggtgt cgtggaactc aggcgccctg  600
accagcggcg tgcacacctt cccggctgtc ctacagtcct caggactcta ctccctcagc  660
agcgtggtga ccgtgccctc cagcagcttg ggcacccaga cctacatctg caacgtgaat  720
cacaagccca gcaacaccaa ggtggacaag agagttgagc ccaaatcttg tgacaaaact  780
cacacatgcc caccgtgccc agcacctgaa ctcctggggg gaccgtcagt cttcctcttc  840
cccccaaaac ccaaggacac cctcatgatc tcccggaccc ctgaggtcac atgcgtggtg  900
gtggacgtga gccacgaaga ccctgaggtc aagttcaact ggtacgtgga cggcgtggag  960
gtgcataatg ccaagacaaa gccgcgggag gagcagtaca acagcacgta ccgtgtggtc 1020
agcgtcctca ccgtcctgca ccaggactgg ctgaatggca aggagtacaa gtgcaaggtc 1080
tccaacaaag ccctcccagc ccccatcgag aaaaccatct ccaaagccaa agggcagccc 1140
cgagaaccac aggtgtacac cctgccccca tcccgggagg agatgaccaa gaaccaggtc 1200
agcctgacct gcctggtcaa aggcttctat cccagcgaca tcgccgtgga gtgggagagc 1260
aatgggcagc cggagaacaa ctacaagacc acgcctcccg tgctggactc cgacggctcc 1320
ttcttcctct atagcaagct caccgtggac aagagcaggt ggcagcaggg gaacgtcttc 1380
tcatgctccg tgatgcatga ggctctgcac aaccactaca cgcagaagag cctctccctg 1440
tctccgggta aatga                                                  1455
```

| | | |
|---|---|---|
| SEQ ID NO: 461 | moltype = DNA length = 405 | |
| FEATURE | Location/Qualifiers | |
| misc_feature | 1..405 | |
| | note = Description of Artificial Sequence: Synthetic | |

```
                        polynucleotide
source                  1..405
                        mol_type = other DNA
                        organism = synthetic construct
SEQUENCE: 461
cagccgcagc tgcaggagtc ggggccagga ctggtggagg cttcggagac cctgtccctc    60
acctgcactg tgtccggcga ctccactgct ggttgtgact atttctgggg ctgggtccgg   120
cagcccccag ggaaggggct ggagtggatt ggggggtttgt cacattgtgc aggttactac   180
aatactggct ggacctacca caacccgtct ctcaagagtc gactcacgac ttcactcgac   240
acgcccaaga atcaggtctt cctgaagtta aattctgtga ccgccgcgga cacggccatt   300
tactactgtg cgcgattcga cggcgaagtt ttggtgtaca acgattggcc aaagccggcc   360
tgggtcgacc tctggggccg gggaactttg gtcaccgtct cgagc                   405

SEQ ID NO: 462          moltype = AA  length = 484
FEATURE                 Location/Qualifiers
REGION                  1..484
                        note = Description of Artificial Sequence: Synthetic
                         polypeptide
source                  1..484
                        mol_type = protein
                        organism = synthetic construct
SEQUENCE: 462
MKHLWFFLLL VAAPRWVLSQ PQLQESGPGL VEASETLSLT CTVSGDSTAG CDYFWGWVRQ    60
PPGKGLEWIG GLSHCAGYYN TGWTYHNPSL KSRLTISLDT PKNQVFLKLN SVTAADTAIY   120
YCARFDGEVL VYNDWPKPAW VDLWGRGTLV TVSSASTKGP SVFPLAPSSK STSGGTAALG   180
CLVKDYFPEP VTVSWNSGAL TSGVHTFPAV LQSSGLYSLS SVVTVPSSSL GTQTYICNVN   240
HKPSNTKVDK RVEPKSCDKT HTCPPCPAPE LLGGPSVFLF PPKPKDTLMI SRTPEVTCVV   300
VDVSHEDPEV KFNWYVDGVE VHNAKTKPRE EQYNSTYRVV SVLTVLHQDW LNGKEYKCKV   360
SNKALPAPIE KTISKAKGQP REPQVYTLPP SREEMTKNQV SLTCLVKGFY PSDIAVEWES   420
NGQPENNYKT TPPVLDSDGS FFLYSKLTVD KSRWQQGNVF SCSVMHEALH NHYTQKSLSL   480
SPGK                                                                484

SEQ ID NO: 463          moltype = AA  length = 135
FEATURE                 Location/Qualifiers
REGION                  1..135
                        note = Description of Artificial Sequence: Synthetic
                         polypeptide
source                  1..135
                        mol_type = protein
                        organism = synthetic construct
SEQUENCE: 463
QPQLQESGPG LVEASETLSL TCTVSGDSTA GCDYFWGWVR QPPGKGLEWI GGLSHCAGYY    60
NTGWTYHNPS LKSRLTISLD TPKNQVFLKL NSVTAADTAI YYCARFDGEV LVYNDWPKPA   120
WVDLWGRGTL VTVSS                                                    135

SEQ ID NO: 464          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 464
GCDYFWG                                                               7

SEQ ID NO: 465          moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 465
FDGEVLVYND WPKPAWVDL                                                 19

SEQ ID NO: 466          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 466
GDSTAGCD                                                              8

SEQ ID NO: 467          moltype = DNA  length = 693
FEATURE                 Location/Qualifiers
misc_feature            1..693
                        note = Description of Artificial Sequence: Synthetic
```

```
                              polynucleotide
source                        1..693
                              mol_type = other DNA
                              organism = synthetic construct
SEQUENCE: 467
atggcctggg ctctgctcct cctcaccctc ctcactcagg gcacaggggc ctgggcccag   60
tctgccctga ctcagcctcc ctccgcgtcc gggtctcctg gacagtcaat caccatctcc  120
tgcactggaa ccagcaataa ctttgtctcc tggtaccagc aacacccagc caaggccccc  180
aaactcgtca tttatggggt caataagcgc ccctcaggtg tccctgatcg ttttctggc   240
tccaagtctg gcaacacggc ctccctgacc gtctctggac tccagactga cgatgaggct  300
gtctattact gcggctcact gtaggcaac tgggatgtga ttttcggcgg agggaccaag  360
ttgaccgtcc tgggtcagcc catggctgcc cctcggtca ctctgttccc gccctcctct   420
gaggagcttc aagccaacaa ggccacactg gtgtgtctca taagtgactt ctacccggga  480
gccgtgacag tggcctggaa ggcagatagc agccccgtca aggcgggagt ggagaccacc  540
acaccctcca aacaaagcaa caacaagtac gcggccagca gctacctgag cctgacgcct  600
gagcagtgga agtcccacaa aagctacagc tgccaggtca cgcatgaagg gagcaccgtg  660
gagaagacag tggcccctac agaatgttca tag                               693

SEQ ID NO: 468              moltype = DNA   length = 315
FEATURE                     Location/Qualifiers
misc_feature                1..315
                            note = Description of Artificial Sequence: Synthetic
                              polynucleotide
source                      1..315
                            mol_type = other DNA
                            organism = synthetic construct
SEQUENCE: 468
cagtctgccc tgactcagcc tccctccgcg tccgggtctc ctggacagtc aatcaccatc   60
tcctgcactg gaaccagcaa taactttgtc tcctggtacc agcaacaccc agccaaggcc  120
cccaaactcg tcatttatgg ggtcaataag cgcccctcag gtgtccctga tcgttttct   180
ggctccaagt ctggcaacac ggcctccctg accgtctctg gactgacgat gag          240
gctgtctatt actgcggctc acttgtaggc aactgggatg tgattttcgg cggagggacc  300
aagttgaccg tcctg                                                   315

SEQ ID NO: 469              moltype = AA   length = 230
FEATURE                     Location/Qualifiers
REGION                      1..230
                            note = Description of Artificial Sequence: Synthetic
                              polypeptide
source                      1..230
                            mol_type = protein
                            organism = synthetic construct
SEQUENCE: 469
MAWALLLLTL LTQGTGAWAQ SALTQPPSAS GSPGQSITIS CTGTSNNFVS WYQQHPAKAP   60
KLVIYGVNKR PSGVPDRFSG SKSGNTASLT VSGLQTDDEA VYYCGSLVGN WDVIFGGGTK  120
LTVLGQPMAA PSVTLFPPSS EELQANKATL VCLISDFYPG AVTVAWKADS SPVKAGVETT  180
TPSKQSNNKY AASSYLSLTP EQWKSHKSYS CQVTHEGSTV EKTVAPTECS            230

SEQ ID NO: 470              moltype = AA   length = 105
FEATURE                     Location/Qualifiers
REGION                      1..105
                            note = Description of Artificial Sequence: Synthetic
                              polypeptide
source                      1..105
                            mol_type = protein
                            organism = synthetic construct
SEQUENCE: 470
QSALTQPPSA SGSPGQSITI SCTGTSNNFV SWYQQHPAKA PKLVIYGVNK RPSGVPDRFS   60
GSKSGNTASL TVSGLQTDDE AVYYCGSLVG NWDVIFGGGT KLTVL                  105

SEQ ID NO: 471              moltype = DNA   length = 1455
FEATURE                     Location/Qualifiers
misc_feature                1..1455
                            note = Description of Artificial Sequence: Synthetic
                              polynucleotide
source                      1..1455
                            mol_type = other DNA
                            organism = synthetic construct
SEQUENCE: 471
atggaattgg ggctgagctg gttttcctc gttggtctct taagaggtgt ccagtgtcgg   60
gtgcagttgg tggagtcggg gggaggcgtg gtccagcctg gaagtccgt gagctttcc   120
tgtgtagtct ccgatttccc cttcagcaag tatcctatgt attgggttcg ccaggctcca  180
ggcaaggggc tggagtgggt ggcagccatc tccggtgatg cctggcatgt ggtctactca  240
aattccgctg cagggccgatt tctcgtctcc agggacaatg tcaagaacac tctatattta  300
gaaatgaaca gcctgaaaat tgaggatacg gccgtatatc gctgcgcgag aatgttccag  360
gagtctggtc caccacgttt ggatcgttgg acggtcgaa attattacta ttattctggt   420
atggacgtct ggggccaagg gaccacggtc accgtctcga gcgcctccac caagggccca  480
tcggtcttcc ccctggcacc ctcctccaag agcacctctg gggcacagc ggccctgggc   540
tgcctggtca aggactactt ccccgaaccg gtgacggtgt cgtggaactc aggcgccctg  600
```

```
accagcggcg tgcacacctt cccggctgtc ctacagtcct caggactcta ctccctcagc    660
agcgtggtga ccgtgccctc cagcagcttg ggcacccaga cctacatctg caacgtgaat    720
cacaagccca gcaacaccaa ggtggacaag agagttgagc ccaaatcttg tgacaaaact    780
cacacatgcc caccgtgccc agcacctgaa ctcctggggg gaccgtcagt cttcctcttc    840
cccccaaaac ccaaggacac cctcatgatc tcccggaccc ctgaggtcac atgcgtggtg    900
gtggacgtga gccacgaaga ccctgaggtc aagttcaact ggtacgtgga cggcgtggag    960
gtgcataatg ccaagacaaa gccgcgggag gagcagtaca acagcacgta ccgtgtggtc   1020
agcgtcctca ccgtcctgca ccaggactgg ctgaatggca aggagtacaa gtgcaaggtc   1080
tccaacaaag cccttccagc ccccatcgag aaaaccatct ccaaagccaa agggcagccc   1140
cgagaaccac aggtgtacac cctgccccca tcccgggagg agatgaccaa gaaccaggtc   1200
agcctgacct gcctggtcaa aggcttctat cccagcgaca tcgccgtgga gtgggagagc   1260
aatgggcagc cggagaacaa ctacaagacc acgcctcccg tgctggactc cgacggctcc   1320
ttcttcctct atagcaagct caccgtggac aagagcaggt ggcagcaggg gaacgtcttc   1380
tcatgctccg tgatgcatga ggctctgcac aaccactaca cgcagaagag cctctccctg   1440
tctccgggta aatga                                                    1455

SEQ ID NO: 472         moltype = DNA  length = 405
FEATURE                Location/Qualifiers
misc_feature           1..405
                       note = Description of Artificial Sequence: Synthetic
                       polynucleotide
source                 1..405
                       mol_type = other DNA
                       organism = synthetic construct
SEQUENCE: 472
cgggtgcagt tggtggagtc gggggggaggc gtggtccagc ctgggaagtc cgtgagactt     60
tcctgtgtag tctccgattt cccccttcag aagtatccta tgtattgggt tcgccaggct    120
ccaggcaagg ggctggagtg ggtggcagcc atctccggtg atgcctggca tgtggtctac    180
tcaaattccg tgcagggccg atttctcgtc tccaggcgaca atgtcaagaa cactctatat    240
ttagaaatga acagcctgaa aattgaggat acggccgtat atcgctgcgc gagaatgttc    300
caggagtctg gtccaccacg tttggatcgt tggagcggtc gaaattatta ctattattct    360
ggtatggacg tctggggcca agggaccacg gtcaccgtct cgagc                    405

SEQ ID NO: 473         moltype = AA  length = 484
FEATURE                Location/Qualifiers
REGION                 1..484
                       note = Description of Artificial Sequence: Synthetic
                       polypeptide
source                 1..484
                       mol_type = protein
                       organism = synthetic construct
SEQUENCE: 473
MELGLSWVFL VGLLRGVQCR VQLVESGGGV VQPGKSVRLS CVVSDFPFSK YPMYWVRQAP     60
GKGLEWVAAI SGDAWHVVYS NSVQGRFLVS RDNVKNTLYL EMNSLKIEDT AVYRCARMFQ    120
ESGPPRLDRW SGRNYYYSG MDVWGQGTTV TVSSASTKGP SVFPLAPSSK STSGGTAALG    180
CLVKDYFPEP VTVSWNSGAL TSGVHTFPAV LQSSGLYSLS SVVTVPSSSL GTQTYICNVN    240
HKPSNTKVDK RVEPKSCDKT HTCPPCPAPE LLGGPSVFLF PPKPKDTLMI SRTPEVTCVV    300
VDVSHEDPEV KFNWYVDGVE VHNAKTKPRE EQYNSTYRVV SVLTVLHQDW LNGKEYKCKV    360
SNKALPAPIE KTISKAKGQP REPQVYTLPP SREEMTKNQV SLTCLVKGFY PSDIAVEWES    420
NGQPENNYKT TPPVLDSDGS FFLYSKLTVD KSRWQQGNVF SCSVMHEALH NHYTQKSLSL    480
SPGK                                                                 484

SEQ ID NO: 474         moltype = AA  length = 135
FEATURE                Location/Qualifiers
REGION                 1..135
                       note = Description of Artificial Sequence: Synthetic
                       polypeptide
source                 1..135
                       mol_type = protein
                       organism = synthetic construct
SEQUENCE: 474
RVQLVESGGG VVQPGKSVRL SCVVSDFPFS KYPMYWVRQA PGKGLEWVAA ISGDAWHVVY     60
SNSVQGRFLV SRDNVKNTLY LEMNSLKIED TAVYRCARMF QESGPPRLDR WSGRNYYYS    120
GMDVWGQGTT VTVSS                                                     135

SEQ ID NO: 475         moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 475
KYPMY                                                                  5

SEQ ID NO: 476         moltype = AA  length = 17
FEATURE                Location/Qualifiers
REGION                 1..17
                       note = Description of Artificial Sequence: Synthetic peptide
```

| | | |
|---|---|---|
| source | 1..17<br>mol_type = protein<br>organism = synthetic construct | |
| SEQUENCE: 476 | | |
| AISGDAWHVV YSNSVQG | | 17 |
| | | |
| SEQ ID NO: 477<br>FEATURE<br>REGION | moltype = AA  length = 26<br>Location/Qualifiers<br>1..26<br>note = Description of Artificial Sequence: Synthetic peptide | |
| source | 1..26<br>mol_type = protein<br>organism = synthetic construct | |
| SEQUENCE: 477 | | |
| MFQESGPPRL DRWSGRNYYY YSGMDV | | 26 |
| | | |
| SEQ ID NO: 478<br>FEATURE<br>REGION | moltype = AA  length = 6<br>Location/Qualifiers<br>1..6<br>note = Description of Artificial Sequence: Synthetic peptide | |
| source | 1..6<br>mol_type = protein<br>organism = synthetic construct | |
| SEQUENCE: 478 | | |
| DFPFSK | | 6 |
| | | |
| SEQ ID NO: 479<br>FEATURE<br>REGION | moltype = AA  length = 10<br>Location/Qualifiers<br>1..10<br>note = Description of Artificial Sequence: Synthetic peptide | |
| source | 1..10<br>mol_type = protein<br>organism = synthetic construct | |
| SEQUENCE: 479 | | |
| AISGDAWHVV | | 10 |
| | | |
| SEQ ID NO: 480<br>FEATURE<br>misc_feature | moltype = DNA  length = 720<br>Location/Qualifiers<br>1..720<br>note = Description of Artificial Sequence: Synthetic<br> polynucleotide | |
| source | 1..720<br>mol_type = other DNA<br>organism = synthetic construct | |
| SEQUENCE: 480 | | |
| atgaggctcc ctgctcagct cctggggctg ctaatgctct ggatacctga attcactgca   60<br>gacattgtga tgacccagac tcctctctct ttgtccgtca cccctggaca gccggcctcc  120<br>atctcctgca agtccagtga gagcctccga caaagtaatg gaaagacctc tttgtattgg  180<br>tatcggcaga agccaggcca gtctccacaa ctcctagtgt ttgaagtttc taatcgattc  240<br>tctggcgtgt cggataggtt tgttggcagc gggtcaggga cagacttcac actgagaatc  300<br>agccgggtag aggctgagga tgttggattt tattactgca tgcaaagtaa agacttccca  360<br>cttacatttg gcggcgggac caaggtggat ctcaaacgta cggtggctgc accatctgtc  420<br>ttcatcttcc cgccatctga tgagcagttg aaatctggaa ctgcctctgt tgtgtgcctg  480<br>ctgaataact tctatcccag agaggccaaa gtacagtgga aggtggataa cgccctccaa  540<br>tcgggtaact cccaggagag tgtcacagag caggacagca aggacagcac ctacagcctc  600<br>agcagcaccc tgacgctgag caaagcagac tacgagaaac acaaagtcta cgcctgcgaa  660<br>gtcacccatc agggcctgag ctcgcccgtc acaaagagct tcaacagggg agagtgttag  720 | | |
| | | |
| SEQ ID NO: 481<br>FEATURE<br>misc_feature | moltype = DNA  length = 336<br>Location/Qualifiers<br>1..336<br>note = Description of Artificial Sequence: Synthetic<br> polynucleotide | |
| source | 1..336<br>mol_type = other DNA<br>organism = synthetic construct | |
| SEQUENCE: 481 | | |
| gacattgtga tgacccagac tcctctctct ttgtccgtca cccctggaca gccggcctcc   60<br>atctcctgca agtccagtga gagcctccga caaagtaatg gaaagacctc tttgtattgg  120<br>tatcggcaga agccaggcca gtctccacaa ctcctagtgt ttgaagtttc taatcgattc  180<br>tctggcgtgt cggataggtt tgttggcagc gggtcaggga cagacttcac actgagaatc  240<br>agccgggtag aggctgagga tgttggattt tattactgca tgcaaagtaa agacttccca  300<br>cttacatttg gcggcgggac caaggtggat ctcaaa                             336 | | |
| | | |
| SEQ ID NO: 482<br>FEATURE<br>REGION | moltype = AA  length = 239<br>Location/Qualifiers<br>1..239<br>note = Description of Artificial Sequence: Synthetic<br> polypeptide | |

```
                        -continued source                  1..239
                        mol_type = protein
                        organism = synthetic construct
SEQUENCE: 482
MRLPAQLLGL LMLWIPEFTA DIVMTQTPLS LSVTPGQPAS ISCKSSESLR QSNGKTSLYW   60
YRQKPGQSPQ LLVFEVSNRF SGVSDRFVGS GSGTDFTLRI SRVEAEDVGF YYCMQSKDFP  120
LTFGGGTKVD LKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 483          moltype = AA   length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 483
DIVMTQTPLS LSVTPGQPAS ISCKSSESLR QSNGKTSLYW YRQKPGQSPQ LLVFEVSNRF   60
SGVSDRFVGS GSGTDFTLRI SRVEAEDVGF YYCMQSKDFP LTFGGGTKVD LK          112

SEQ ID NO: 484          moltype = AA   length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 484
KSSESLRQSN GKTSLY                                                   16

SEQ ID NO: 485          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 485
EVSNRFS                                                             7

SEQ ID NO: 486          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 486
MQSKDFPLT                                                           9

SEQ ID NO: 487          moltype = DNA   length = 1455
FEATURE                 Location/Qualifiers
misc_feature            1..1455
                        note = Description of Artificial Sequence: Synthetic
                         polynucleotide
source                  1..1455
                        mol_type = other DNA
                        organism = synthetic construct
SEQUENCE: 487
atggaattgg ggctgagctg gttttcctc gttggtctct taagaggtgt ccactgtcgg    60
gtgcagttgg tggagtcggg gggaggcgtg gtccagcctg gaagtccgt gagactttcc   120
tgtgtagtct ctgatttccc cttcagcaag tatcctatgt attgggttcg ccaggctcca   180
ggcaagggc tggagtgggt ggcagccatc tccgctgatg cctggcatgt ggtctactca   240
ggctccgtgc agggccgatt tctcgtctcc aggacaact ccaagaacat tctgtatttg   300
gaaatgaaca ccctgaaaat tgaggacacg gccgtatatc gctgcgcgag aatgttccag   360
gagtctggtc caccacgttt cgattcttgg agcggtcgaa attactacta ttactctggt   420
atggacgtct ggggccaagg gaccacggtc accgtctcga gcgcctccac caagggccca   480
tcggtcttcc ccctggcacc ctcctccaag agcacctctg ggggcacagc ggccctgggc   540
tgcctggtca aggactactt ccccgaaccg gtgacggtgt cgtggaactc aggcgccctg   600
accagcggcg tgcacacctt cccggctgtc ctacagtcct caggactcta ctccctcagc   660
agcgtggtga ccgtgccctc agcagcttg gcacccagag cctacatctg caacgtgaat   720
cacaagccca gcaacaccaa ggtggacaag agagttgagc ccaaatcttg tgacaaaact   780
cacacatgcc caccgtgccc agcacctgaa ctcctcgggg gaccgtcagt cttcctcttc   840
cccccaaaac ccaaggacac cctcatgatc tcccggaccc ctgaggtcac atgcgtggtg   900
gtggacgtga gccacgaaga ccctgaggtc aagttcaact ggtacgtgga cggcgtggag   960
gtgcataatg ccaagacaaa gccgcgggag gagcagtaca acagcacgta ccgtgtggtc  1020
agcgtcctca ccgtcctgca ccaggactgg ctgaatggca aggagtacaa gtgcaaggtc  1080
tccaacaaag ccctcccagc ccccatcgag aaaaccatct ccaaagccaa agggcagccc  1140
```

-continued

```
cgagaaccac aggtgtacac cctgcccca tcccgggagg agatgaccaa gaaccaggtc   1200
agcctgacct gcctggtcaa aggcttctat cccagcgaca tcgccgtgga gtgggagagc   1260
aatgggcagc cggagaacaa ctacaagacc acgcctcccg tgctggactc cgacggctcc   1320
ttcttcctct atagcaagct caccgtggac aagagcaggt ggcagcaggg gaacgtcttc   1380
tcatgctccg tgatgcatga ggctctgcac aaccactaca cgcagaagag cctctcctg    1440
tctccgggta aatga                                                    1455

SEQ ID NO: 488          moltype = DNA   length = 405
FEATURE                 Location/Qualifiers
misc_feature            1..405
                        note = Description of Artificial Sequence: Synthetic
                         polynucleotide
source                  1..405
                        mol_type = other DNA
                        organism = synthetic construct
SEQUENCE: 488
cgggtgcagt tggtggagtc ggggggaggc gtggtccagc ctgggaagtc cgtgagactt    60
tcctgtgtag tctctgattt ccccttcagc aagtatccta tgtattgggt tcgccaggct   120
ccaggcaagg gctggagtg ggtggcagcc atctccgctg atgcctggca tgtggtctac    180
tcaggctccg tgcagggccg atttctcgtc tccaggaca actccaagaa cattctgtat    240
ttggaaatga acaccctgaa aattgaggac acggccgtat atcgctgcgc gagaatgttc    300
caggagtctg gtccaccacg tttcgattct tggagcggtc gaaattacta ctattactct    360
ggtatggacg tctggggcca aggaccacg gtcaccgtct cgagc                   405

SEQ ID NO: 489          moltype = AA    length = 484
FEATURE                 Location/Qualifiers
REGION                  1..484
                        note = Description of Artificial Sequence: Synthetic
                         polypeptide
source                  1..484
                        mol_type = protein
                        organism = synthetic construct
SEQUENCE: 489
MELGLSWVFL VGLLRGVHCR VQLVESGGGV VQPGKSVRLS CVVSDFPFSK YPMYWVRQAP    60
GKGLEWVAAI SADAWHVVYS GSVQGRFLVS RDNSKNILYL EMNTLKIEDT AVYRCARMFQ   120
ESGPPRFDSW SGRNYYYSG MDVWGQGTTV TVSSASTKGP SVFPLAPSSK STSGGTAALG    180
CLVKDYFPEP VTVSWNSGAL TSGVHTFPAV LQSSGLYSLS SVVTVPSSSL GTQTYICNVN    240
HKPSNTKVDK RVEPKSCDKT HTCPPCPAPE LLGGPSVFLF PPKPKDTLMI SRTPEVTCVV    300
VDVSHEDPEV KFNWYVDGVE VHNAKTKPRE EQYNSTYRVV SVLTVLHQDW LNGKEYKCKV    360
SNKALPAPIE KTISKAKGQP REPQVYTLPP SREEMTKNQV SLTCLVKGFY PSDIAVEWES    420
NGQPENNYKT TPPVLDSDGS FFLYSKLTVD KSRWQQGNVF SCSVMHEALH NHYTQKSLSL    480
SPGK                                                                484

SEQ ID NO: 490          moltype = AA    length = 135
FEATURE                 Location/Qualifiers
REGION                  1..135
                        note = Description of Artificial Sequence: Synthetic
                         polypeptide
source                  1..135
                        mol_type = protein
                        organism = synthetic construct
SEQUENCE: 490
RVQLVESGGG VVQPGKSVRL SCVVSDFPFS KYPMYWVRQA PGKGLEWVAA ISADAWHVVY    60
SGSVQGRFLV SRDNSKNILY LEMNTLKIED TAVYRCARMF QESGPPRFDS WSGRNYYYS    120
GMDVWGQGTT VTVSS                                                    135

SEQ ID NO: 491          moltype = AA    length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 491
AISADAWHVV YSGSVQG                                                  17

SEQ ID NO: 492          moltype = AA    length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 492
MFQESGPPRF DSWSGRNYYY YSGMDV                                        26

SEQ ID NO: 493          moltype = AA    length = 10
FEATURE                 Location/Qualifiers
REGION                  1..10
```

```
                    note = Description of Artificial Sequence: Synthetic peptide
source              1..10
                    mol_type = protein
                    organism = synthetic construct
SEQUENCE: 493
AISADAWHVV                                                                10

SEQ ID NO: 494      moltype = DNA  length = 720
FEATURE             Location/Qualifiers
misc_feature        1..720
                    note = Description of Artificial Sequence: Synthetic
                     polynucleotide
source              1..720
                    mol_type = other DNA
                    organism = synthetic construct
SEQUENCE: 494
atgaggctcc ctgctcagct cctggggctg ctaatgctct ggatacctga atttattgcc   60
gacattgtga tgacccagac tcctctctct ttgtccgtcg accctggaca gccggcctcc  120
atctcctgca gtccagtca gagcctccga caaagtaatg gaaagacctc tttgtattgg  180
tatcagcaga agccaggcca gtctccacaa ctcctaatat ttgaagtttc taatcgattc  240
tctggcgtgt cggataggtt tgttggcagc gggtcaggga cagacttcac actgagaatc  300
agccgggtag aggctgagga tgttggattt tattactgca tgcaaagtaa agacttccca  360
ctcacctttg gcggcgggac caaggtggat ctcaaccgta cggtggctgc accatctgtc  420
ttcatcttcc cgccatctga tgagcagttg aaatctggaa ctgcctctgt tgtgtgcctg  480
ctgaataact tctatcccag agaggccaaa gtacagtgga aggtggataa cgccctccaa  540
tcgggtaact cccaggagag tgtcacagag caggacagca cctacagcct  600
agcagcaccc tgacgctgag caaagcagac tacgagaaac acaaagtcta cgcctgcgaa  660
gtcacccatc agggcctgag ctcgcccgtc acaaagagct tcaacagggg agagtgttag  720

SEQ ID NO: 495      moltype = DNA  length = 336
FEATURE             Location/Qualifiers
misc_feature        1..336
                    note = Description of Artificial Sequence: Synthetic
                     polynucleotide
source              1..336
                    mol_type = other DNA
                    organism = synthetic construct
SEQUENCE: 495
gacattgtga tgacccagac tcctctctct ttgtccgtcg accctggaca gccggcctcc   60
atctcctgca gtccagtca gagcctccga caaagtaatg gaaagacctc tttgtattgg  120
tatcagcaga agccaggcca gtctccacaa ctcctaatat ttgaagtttc taatcgattc  180
tctggcgtgt cggataggtt tgttggcagc gggtcaggga cagacttcac actgagaatc  240
agccgggtag aggctgagga tgttggattt tattactgca tgcaaagtaa agacttccca  300
ctcacctttg gcggcgggac caaggtggat ctcaac                             336

SEQ ID NO: 496      moltype = AA  length = 239
FEATURE             Location/Qualifiers
REGION              1..239
                    note = Description of Artificial Sequence: Synthetic
                     polypeptide
source              1..239
                    mol_type = protein
                    organism = synthetic construct
SEQUENCE: 496
MRLPAQLLGL LMLWIPEFIA DIVMTQTPLS LSVDPGQPAS ISCKSSQSLR QSNGKTSLYW   60
YQQKPGQSPQ LLIFEVSNRF SGVSDRFVGS GSGTDFTLRI SRVEAEDVGF YYCMQSKDFP  120
LTFGGGTKVD LNRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 497      moltype = AA  length = 112
FEATURE             Location/Qualifiers
REGION              1..112
                    note = Description of Artificial Sequence: Synthetic
                     polypeptide
source              1..112
                    mol_type = protein
                    organism = synthetic construct
SEQUENCE: 497
DIVMTQTPLS LSVDPGQPAS ISCKSSQSLR QSNGKTSLYW YQQKPGQSPQ LLIFEVSNRF   60
SGVSDRFVGS GSGTDFTLRI SRVEAEDVGF YYCMQSKDFP LTFGGGTKVD LN          112

SEQ ID NO: 498      moltype = AA  length = 16
FEATURE             Location/Qualifiers
REGION              1..16
                    note = Description of Artificial Sequence: Synthetic peptide
source              1..16
                    mol_type = protein
                    organism = synthetic construct
SEQUENCE: 498
```

KSSQSLRQSN GKTSLY                                                         16

SEQ ID NO: 499            moltype = DNA  length = 1455
FEATURE                   Location/Qualifiers
misc_feature              1..1455
                          note = Description of Artificial Sequence: Synthetic
                          polynucleotide
source                    1..1455
                          mol_type = other DNA
                          organism = synthetic construct
SEQUENCE: 499
atggaattgg ggctgagctg ggttttcctc gttgctctct taagaggtgt ccagtgtcag    60
gtgcagttgg tggagtcggg cggaggcgtg gtccagcctg gaagtccct gagactctcc   120
tgtgtagtct ctaattttct cttcaataaa cgtcacatgc actgggtccg ccaggctccg   180
ggcaagggac tagagtggat agcagtcatt tcctctgatg ccattcacgt agactacgca   240
agttccgtgc ggggccgatc cctcatctcc agagacaatt ccaaaaatag tttatatcta   300
gacatgaata acctgaaaat tgaggacacg gccacatatt attgtgcaag agatagagac   360
ggatatggtc caccacagat ccagacttgg agcggtcgat acctccacct ttattctgga   420
atagacgcct ggggcctagg gaccacggtc accgtctcga gcgcctccac caagggccca   480
tcggtcttcc ccctggcacc ctcctccaag agcacctctg gggcacagc ggccctgggc   540
tgcctggtca aggactactt ccccgaaccg gtgacggtgt cgtggaactc aggcgccctg   600
accagcggcg tgcacacctt cccggctgtc ctacagtcct caggactcta ctccctcagc   660
agcgtggtga ccgtgccctc cagcagcttg gcacccagag cctacatctg caacgtgaat   720
cacaagccca gcaacaccaa ggtggacaag agagttgagc ccaaatcttg tgacaaaact   780
cacacatgcc caccgtgccc agcacctgaa ctcctggggg gaccgtcagt cttcctcttc   840
cccccaaaac ccaaggacac cctcatgatc tcccggaccc ctgaggtcac atgcgtggtg   900
gtggacgtga gccacgaaga ccctgaggtc aagttcaact ggtacgtgga cggcgtggag   960
gtgcataatg ccaagacaaa gccgcgggag gagcagtaca acagcacgta ccgtgtggtc  1020
agcgtcctca ccgtcctgca ccaggactgg ctgaatggca aggagtacaa gtgcaaggtc  1080
tccaacaaag ccctcccagc ccccatcgag aaaaccatct ccaaagccaa agggcagccc  1140
cgagaaccac aggtgtacac cctgccccca tcccgggagg agatgaccaa gaaccaggtc  1200
agcctgacct gcctggtcaa aggcttctat cccagcgaca tcgccgtgga gtgggagagc  1260
aatgggcagc cggagaacaa ctacaagacc acgcctcccg tgctggactc cgacggctcc  1320
ttcttcctct atagcaagct caccgtggac aagagcaggt ggcagcaggg gaacgtcttc  1380
tcatgctccg tgatgcatga ggctctgcac aaccactaca cgcagaagag cctctccctg  1440
tctccgggta aatga                                                   1455

SEQ ID NO: 500            moltype = DNA  length = 405
FEATURE                   Location/Qualifiers
misc_feature              1..405
                          note = Description of Artificial Sequence: Synthetic
                          polynucleotide
source                    1..405
                          mol_type = other DNA
                          organism = synthetic construct
SEQUENCE: 500
caggtgcagt tggtggagtc gggcggaggc gtggtccagc ctgggaagtc cctgagactc    60
tcctgtgtag tctctaattt tctcttcaat aaacgtcaca tgcactgggt ccgccaggct   120
ccaggcaagg gactagagtg gatagcagtc atttcctctg atgccattca cgtagactac   180
gcaagttccg tgcggggccg atccctcatc tccagagaca attccaaaaa tagtttatat   240
ctagacatga ataacctgaa aattgaggac acggccacat attattgtgc aagagataga   300
gacggatatg gtccaccaca gatccagact tggagcggtc gatacctcca cctttattct   360
ggaatagacg cctggggcct aggaccacg gtcaccgtct cgagc                   405

SEQ ID NO: 501            moltype = AA  length = 484
FEATURE                   Location/Qualifiers
REGION                    1..484
                          note = Description of Artificial Sequence: Synthetic
                          polypeptide
source                    1..484
                          mol_type = protein
                          organism = synthetic construct
SEQUENCE: 501
MELGLSWVFL VALLRGVQCQ VQLVESGGGV VQPGKSLRLS CVVSNFLFNK RHMHWVRQAP    60
GKGLEWIAVI SSDAHVDYA SSVRGRSLIS RDNSKNSLYL DMNNLKIEDT ATYYCARDRD   120
GYGPPQIQTW SGRYLHLYSG IDAWGLGTTV TVSSASTKGP SVFPLAPSSK STSGGTAALG   180
CLVKDYFPEP VTVSWNSGAL TSGVHTFPAV LQSSGLYSLS SVVTVPSSSL GTQTYICNVN   240
HKPSNTKVDK RVEPKSCDKT HTCPPCPAPE LLGGPSVFLF PPKPKDTLMI SRTPEVTCVV   300
VDVSHEDPEV KFNWYVDGVE VHNAKTKPRE EQYNSTYRVV SVLTVLHQDW LNGKEYKCKV   360
SNKALPAPIE KTISKAKGQP REPQVYTLPP SREEMTKNQV SLTCLVKGFY PSDIAVEWES   420
NGQPENNYKT TPPVLDSDGS FFLYSKLTVD KSRWQQGNVF SCSVMHEALH NHYTQKSLSL   480
SPGK                                                                484

SEQ ID NO: 502            moltype = AA  length = 135
FEATURE                   Location/Qualifiers
REGION                    1..135
                          note = Description of Artificial Sequence: Synthetic
                          polypeptide
source                    1..135

```
                            mol_type = protein
                            organism = synthetic construct
SEQUENCE: 502
QVQLVESGGG VVQPGKSLRL SCVVSNFLFN KRHMHWVRQA PGKGLEWIAV ISSDAIHVDY    60
ASSVRGRSLI SRDNSKNSLY LDMNNLKIED TATYYCARDR DGYGPPQIQT WSGRYLHLYS   120
GIDAWGLGTT VTVSS                                                    135

SEQ ID NO: 503           moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 503
KRHMH                                                                 5

SEQ ID NO: 504           moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 504
VISSDAIHVD YASSVRG                                                   17

SEQ ID NO: 505           moltype = AA  length = 26
FEATURE                  Location/Qualifiers
REGION                   1..26
                         note = Description of Artificial Sequence: Synthetic peptide
source                   1..26
                         mol_type = protein
                         organism = synthetic construct
SEQUENCE: 505
DRDGYGPPQI QTWSGRYLHL YSGIDA                                         26

SEQ ID NO: 506           moltype = AA  length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 506
NFLFNK                                                                6

SEQ ID NO: 507           moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 507
VISSDAIHVD                                                           10

SEQ ID NO: 508           moltype = DNA  length = 720
FEATURE                  Location/Qualifiers
misc_feature             1..720
                         note = Description of Artificial Sequence: Synthetic
                          polynucleotide
source                   1..720
                         mol_type = other DNA
                         organism = synthetic construct
SEQUENCE: 508
atgaggctcc ctgctcagct cctggggctg ctaatgctct ggatacctga attcactgcg    60
gacattgtgc tgacccagag cccccctctt ctgtccgtca gtcctggaca gccggcctcc   120
atctcctgta agtctagtca gagcctccga caaagtaatg gaaagacata tttgtattgg   180
tacgtacaaa agtccggcca gtctccacaa cccctgatcc aggaagtttc cattcgcttc   240
tctggagtgc caggtagatt cgctggcagc ggatcaggga cagacttcac actgaaaatc   300
agccgggtgg aggctgaaga tgttggagtt tatttctgca tgcaaagtaa agactttcca   360
ctcactttgt gcgagggac caaggtgac ctcaatcgta cggtggctgc accatctgtc   420
ttcatcttcc cgccatctga tgagcagttg aaatctggaa ctgcctctgt tgtgtgcctg   480
ctgaataact ctatcccag agaggccaaa gtacagtgga aggtggataa cgccctccaa   540
tcgggtaact cccaggagag tgtcacagag caggacagca aggacagcac ctacagcctc   600
agcagcaccc tgacgctgag caaagcagac tacgagaaac acaaagtcta cgcctgcgaa   660
gtcacccatc agggcctgag ctcgcccgtc acaaagagct tcaacagggg agagtgttag   720
```

| SEQ ID NO: 509 | moltype = DNA length = 336 |
|---|---|
| FEATURE | Location/Qualifiers |
| misc_feature | 1..336 |
| | note = Description of Artificial Sequence: Synthetic polynucleotide |
| source | 1..336 |
| | mol_type = other DNA |
| | organism = synthetic construct |

SEQUENCE: 509

```
gacattgtgc tgacccagag cccctctttt ctgtccgtca gtcctggaca gccggcctcc  60
atctcctgta agtctagtca gagcctccga caaagtaatg gaaagacata tttgtattgg 120
tacgtacaaa agtccggcca gtctccacaa cccctgatcc aggaagtttc cattcgcttc 180
tctggagtgc caggtagatt cgctggcagc ggatcaggga cagacttcac actgaaaatc 240
agccgggtgg aggctgaaga tgttggagtt tatttctgca tgcaaagtaa agactttcca 300
ctcactttg gcggagggac caaggtggac ctcaat                           336
```

| SEQ ID NO: 510 | moltype = AA length = 239 |
|---|---|
| FEATURE | Location/Qualifiers |
| REGION | 1..239 |
| | note = Description of Artificial Sequence: Synthetic polypeptide |
| source | 1..239 |
| | mol_type = protein |
| | organism = synthetic construct |

SEQUENCE: 510

```
MRLPAQLLGL LMLWIPEFTA DIVLTQSPLF LSVSPGQPAS ISCKSSQSLR QSNGKTYLYW  60
YVQKSGQSPQ PLIQEVSIRF SGVPGRFAGS GSGTDFTLKI SRVEAEDVGV YFCMQSKDFP 120
LTFGGGTKVD LNRTVAAPSV FIFPPSDEQL KSGTASVVCL LNNFYPREAK VQWKVDNALQ 180
SGNSQESVTE QDSKDSTYSL SSTLTLSKAD YEKHKVYACE VTHQGLSSPV TKSFNRGEC  239
```

| SEQ ID NO: 511 | moltype = AA length = 112 |
|---|---|
| FEATURE | Location/Qualifiers |
| REGION | 1..112 |
| | note = Description of Artificial Sequence: Synthetic polypeptide |
| source | 1..112 |
| | mol_type = protein |
| | organism = synthetic construct |

SEQUENCE: 511

```
DIVLTQSPLF LSVSPGQPAS ISCKSSQSLR QSNGKTYLYW YVQKSGQSPQ PLIQEVSIRF  60
SGVPGRFAGS GSGTDFTLKI SRVEAEDVGV YFCMQSKDFP LTFGGGTKVD LN        112
```

| SEQ ID NO: 512 | moltype = AA length = 16 |
|---|---|
| FEATURE | Location/Qualifiers |
| REGION | 1..16 |
| | note = Description of Artificial Sequence: Synthetic peptide |
| source | 1..16 |
| | mol_type = protein |
| | organism = synthetic construct |

SEQUENCE: 512

```
KSSQSLRQSN GKTYLY                                                 16
```

| SEQ ID NO: 513 | moltype = AA length = 7 |
|---|---|
| FEATURE | Location/Qualifiers |
| REGION | 1..7 |
| | note = Description of Artificial Sequence: Synthetic peptide |
| source | 1..7 |
| | mol_type = protein |
| | organism = synthetic construct |

SEQUENCE: 513

```
EVSIRFS                                                            7
```

| SEQ ID NO: 514 | moltype = DNA length = 1455 |
|---|---|
| FEATURE | Location/Qualifiers |
| misc_feature | 1..1455 |
| | note = Description of Artificial Sequence: Synthetic polynucleotide |
| source | 1..1455 |
| | mol_type = other DNA |
| | organism = synthetic construct |

SEQUENCE: 514

```
atggaattgg ggctgagctg gttttcctc gttgctctct taagaggtgt ccagtgtcag  60
gtgcagctgg tggaatcggg aggaggcgtg tccagcctg aaagtccct cagactctca 120
tgtgtcgtct ctaatttcat cttaataaa tatcctatgt attgggtccg ccaggctcca 180
ggcaaggggc tggagtgggt ggcagccatc tccgctgatg cctggcatgt agactacga 240
gcctccgtga aggaccgatt tctcatctcc agagacaatt ccaagaatgc tctatatttg 300
gaaatgaaca ccctgagagt tgaagacacg gtatctact actgtgcgag aaatatagag 360
gagtttagtg ttccacagtt cgattcttgg agcggtcgaa gctactacca ctattttggg 420
atggacgtct ggggccaagg gaccacggtc accgtctcga gcgcctccac caagggccca 480
```

```
tcggtcttcc ccctggcacc ctcctccaag agcacctctg ggggcacagc ggccctgggc    540
tgcctggtca aggactactt ccccgaaccg tgacggtgt  cgtggaactc aggcgccctg    600
accagcggcg tgcacacctt cccggctgtc ctacagtcct caggactcta ctccctcagc    660
agcgtggtga ccgtgccctc cagcagcttg ggcacccaga cctacatctg caacgtgaat    720
cacaagccca gcaacaccaa ggtggacaag agagttgagc ccaaatcttg tgacaaaact    780
cacacatgcc caccgtgccc agcacctgaa ctcctggggg gaccgtcagt cttcctcttc    840
cccccaaaac ccaaggacac cctcatgatc tcccggaccc ctgaggtcac atgcgtggtg    900
gtggacgtga gccacgaaga ccctgaggtc aagttcaact ggtacgtgga cggcgtggag    960
gtgcataatg ccaagacaaa gccgcgggag gagcagtaca acagcacgta ccgtgtggtc   1020
agcgtcctca ccgtcctgca ccaggactgg ctgaatggca aggagtacaa gtgcaaggtc   1080
tccaacaaag ccctcccagc ccccatcgag aaaaccatct ccaaagccaa agggcagccc   1140
cgagaaccac aggtgtacac cctgccccca tcccgggagg agatgaccaa gaaccaggtc   1200
agcctgacct gcctggtcaa aggcttctat cccagcgaca tcgccgtgga gtgggagagc   1260
aatgggcagc cggagaacaa ctacaagacc acgcctcccg tgctggactc gacggctcc   1320
ttcttcctct atagcaagct caccgtggac aagagcaggt ggcagcaggg gaacgtcttc   1380
tcatgctccg tgatgcatga ggctctgcac aaccactaca cgcagaagag cctctccctg   1440
tctccgggta aatga                                                    1455

SEQ ID NO: 515         moltype = DNA  length = 405
FEATURE                Location/Qualifiers
misc_feature           1..405
                       note = Description of Artificial Sequence: Synthetic
                        polynucleotide
source                 1..405
                       mol_type = other DNA
                       organism = synthetic construct
SEQUENCE: 515
caggtgcagc tggtggaatc gggaggaggc gtggtccagc ctggaaagtc cctcagactc     60
tcatgtgtcg tctctaattt catctttaat aaatatccta tgtattgggt ccgccaggct    120
ccaggcaagg ggctggagtg ggtggcagcc atctccgctg atgcctggca tgtagactac    180
gcagcctccg tgaaggaccg atttctcatc tccagagaca attccaagaa tgctctatat    240
ttggaaatga acaccctgag agttgaagac acgggtatct actactgtgc gagaaatata    300
gaggagttta gtgttccaca gttcgattct tggagcggtc gaagctacta ccactatttt    360
gggatggacg tctggggcca aggaccacgg tcaccgtctc cgagc                     405

SEQ ID NO: 516         moltype = AA  length = 484
FEATURE                Location/Qualifiers
REGION                 1..484
                       note = Description of Artificial Sequence: Synthetic
                        polypeptide
source                 1..484
                       mol_type = protein
                       organism = synthetic construct
SEQUENCE: 516
MELGLSWVFL VALLRGVQCQ VQLVESGGGV VQPGKSLRLS CVVSNFIFNK YPMYWVRQAP     60
GKGLEWVAAI SADAWHVDYA ASVKDRFLIS RDNSKNALYL EMNTLRVEDT GIYYCARNIE    120
EFSVPQFDSW SGRSYYHYFG MDVWGQGTTV TVSSASTKGP SVFPLAPSSK STSGGTAALG    180
CLVKDYFPEP VTVSWNSGAL TSGVHTFPAV LQSSGLYSLS SVVTVPSSSL GTQTYICNVN    240
HKPSNTKVDK RVEPKSCDKT HTCPPCPAPE LLGGPSVFLF PPKPKDTLMI SRTPEVTCVV    300
VDVSHEDPEV KFNWYVDGVE VHNAKTKPRE EQYNSTYRVV SVLTVLHQDW LNGKEYKCKV    360
SNKALPAPIE KTISKAKGQP REPQVYTLPP SREEMTKNQV SLTCLVKGFY PSDIAVEWES    420
NGQPENNYKT TPPVLDSDGS FFLYSKLTVD KSRWQQGNVF SCSVMHEALH NHYTQKSLSL    480
SPGK                                                                  484

SEQ ID NO: 517         moltype = AA  length = 135
FEATURE                Location/Qualifiers
REGION                 1..135
                       note = Description of Artificial Sequence: Synthetic
                        polypeptide
source                 1..135
                       mol_type = protein
                       organism = synthetic construct
SEQUENCE: 517
QVQLVESGGG VVQPGKSLRL SCVVSNFIFN KYPMYWVRQA PGKGLEWVAA ISADAWHVDY     60
AASVKDRFLI SRDNSKNALY LEMNTLRVED TGIYYCARNI EEFSVPQFDS WSGRSYYHYF    120
GMDVWGQGTT VTVSS                                                     135

SEQ ID NO: 518         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 518
AISADAWHVD YAASVKD                                                    17

SEQ ID NO: 519         moltype = AA  length = 26
FEATURE                Location/Qualifiers
```

| | | |
|---|---|---|
| REGION | 1..26 | |
| | note = Description of Artificial Sequence: Synthetic peptide | |
| source | 1..26 | |
| | mol_type = protein | |
| | organism = synthetic construct | |

SEQUENCE: 519
NIEEFSVPQF DSWSGRSYYH YFGMDV                                        26

| | | |
|---|---|---|
| SEQ ID NO: 520 | moltype = AA  length = 6 | |
| FEATURE | Location/Qualifiers | |
| REGION | 1..6 | |
| | note = Description of Artificial Sequence: Synthetic peptide | |
| source | 1..6 | |
| | mol_type = protein | |
| | organism = synthetic construct | |

SEQUENCE: 520
NFIFNK                                                              6

| | | |
|---|---|---|
| SEQ ID NO: 521 | moltype = AA  length = 10 | |
| FEATURE | Location/Qualifiers | |
| REGION | 1..10 | |
| | note = Description of Artificial Sequence: Synthetic peptide | |
| source | 1..10 | |
| | mol_type = protein | |
| | organism = synthetic construct | |

SEQUENCE: 521
AISADAWHVD                                                          10

| | | |
|---|---|---|
| SEQ ID NO: 522 | moltype = DNA  length = 720 | |
| FEATURE | Location/Qualifiers | |
| misc_feature | 1..720 | |
| | note = Description of Artificial Sequence: Synthetic polynucleotide | |
| source | 1..720 | |
| | mol_type = other DNA | |
| | organism = synthetic construct | |

SEQUENCE: 522
atgaggctcc ctgctcagct cctggggctg ctaatgctct ggatacctga gttcgctgca   60
gacattgtga tgactcagac tcctgtctct ctgtccgtca gtcttggaca ggcggcctcc   120
atctcctgca gctccagtga gagtctcgga cgtggtgatg aaggacctat ttgcattgg   180
taccgacaga agccaggcca gactccacaa ttactcatgt atgaagtttc tactcgattc   240
tctggagtgt ccgacaggtt cgctggcagc gggtcacgta cacaattcac attgaaaatt   300
agtcgggtgg aggctgaaga tgttggcgtt tattactgca tgcaaagtag agacttccca   360
atcacttttg gcggagggac cagggtggat ctcaaacgta cggtggctgc accatctgtc   420
ttcatcttcc cgccatctga tgagcagttg aaatctggaa ctgcctctgt tgtgtgcctg   480
ctgaataact tctatcccag agaggccaaa gtacagtgga aggtggataa cgccctccaa   540
tcgggtaact cccaggagag tgtcacagag caggacagca aggacagcac ctacagcctc   600
agcagcaccc tgacgctgag caaagcagac tacgagaaac acaaagtcta cgcctgcgaa   660
gtcacccatc agggcctgag ctcgcccgtc acaaagagct tcaacagggg agagtgttag   720

| | | |
|---|---|---|
| SEQ ID NO: 523 | moltype = DNA  length = 336 | |
| FEATURE | Location/Qualifiers | |
| misc_feature | 1..336 | |
| | note = Description of Artificial Sequence: Synthetic polynucleotide | |
| source | 1..336 | |
| | mol_type = other DNA | |
| | organism = synthetic construct | |

SEQUENCE: 523
gacattgtga tgactcagac tcctgtctct ctgtccgtca gtcttggaca ggcggcctcc   60
atctcctgca gctccagtga gagtctcgga cgtggtgatg aaggacctat ttgcattgg   120
taccgacaga agccaggcca gactccacaa ttactcatgt atgaagtttc tactcgattc   180
tctggagtgt ccgacaggtt cgctggcagc gggtcacgta cacaattcac attgaaaatt   240
agtcgggtgg aggctgaaga tgttggcgtt tattactgca tgcaaagtag agacttccca   300
atcacttttg gcggagggac cagggtggat ctcaaa                             336

| | | |
|---|---|---|
| SEQ ID NO: 524 | moltype = AA  length = 239 | |
| FEATURE | Location/Qualifiers | |
| REGION | 1..239 | |
| | note = Description of Artificial Sequence: Synthetic polypeptide | |
| source | 1..239 | |
| | mol_type = protein | |
| | organism = synthetic construct | |

SEQUENCE: 524
MRLPAQLLGL LMLWIPEFAA DIVMTQTPVS LSVSLGQAAS ISCSSSESLG RGDGRTYLHW   60
YRQKPGQTPQ LLMYEVSTRF SGVSDRFAGS GSRTQFTLKI SRVEAEDVGV YYCMQSRDFP   120
ITFGGGTRVD LKRTVAAPSV FIFPPSDEQL KSGTASVVCL LNNFYPREAK VQWKVDNALQ   180
SGNSQESVTE QDSKDSTYSL SSTLTLSKAD YEKHKVYACE VTHQGLSSPV TKSFNRGEC   239

```
SEQ ID NO: 525           moltype = AA  length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 525
DIVMTQTPVS LSVSLGQAAS ISCSSSESLG RGDGRTYLHW YRQKPGQTPQ LLMYEVSTRF  60
SGVSDRFAGS GSRTQFTLKI SRVEAEDVGV YYCMQSRDFP ITFGGGTRVD LK         112

SEQ ID NO: 526           moltype = AA  length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 526
SSSESLGRGD GRTYLH                                                  16

SEQ ID NO: 527           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 527
EVSTRFS                                                            7

SEQ ID NO: 528           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 528
MQSRDFPIT                                                          9

SEQ ID NO: 529           moltype = DNA  length = 1455
FEATURE                  Location/Qualifiers
misc_feature             1..1455
                         note = Description of Artificial Sequence: Synthetic
                          polynucleotide
source                   1..1455
                         mol_type = other DNA
                         organism = synthetic construct
SEQUENCE: 529
atggaattgg ggctgagctg gttttcctc gtcgttctcc taagaggtgt ccactgtcag   60
gtgcatctgc tggagtcggg gggaggcgtg gtccaacctg gaagtccct aagactctcc  120
tgtgaaacct ctggcttcat cttcaacgaa tatcccatgt attggatccg ccaggctcca  180
ggcaagggac cggagtgggt ggccgccatc tccgctgacg cctggcatgt ggactacga   240
ggctccgtgc ggggccgatt taccgtctcc agagacaatt ctaagaattc tctatattta  300
gacatgaaga gtctgaaagt tgaagacacg gctatatatt tctgtgcgaa agatggggag  360
gaaacacaag taccacaatt gcattcctgg agcggacgaa acttatatca ctacactggt  420
tttgacgtct ggggcccagg gaccacggtc accgtctcga gcgcctccac caagggccca  480
tcggtcttcc ccctggcacc ctcctccaag agcacctctg ggggcacagc ggccctgggc  540
tgcctggtca aggactactt ccccgaaccg gtgacggtgt cgtggaactc aggcgccctg  600
accagcggcg tgcacacctt cccggctgtc ctacagtcct caggactcta ctccctcagc  660
agcgtggtga ccgtgccctc cagcagcttg ggcacccaga cctacatctg caacgtgaat  720
cacaagccca gcaacaccaa ggtggacaag agagttgagc ccaaatcttg tgacaaaact  780
cacacatgcc caccgtgccc agcacctgaa ctcctggggg gaccgtcagt cttcctcttc  840
cccccaaaac ccaaggacac cctcatgatc tcccggaccc ctgaggtcac atgcgtggtg  900
gtggacgtga gccacgaaga ccctgaggtc aagttcaact ggtacgtgga cggcgtggag  960
gtgcataatg ccaagacaaa gccgcgggag gagcagtaca acagcacgta ccgtgtggtc 1020
agcgtcctca ccgtcctgca ccaggactgg ctgaatggca aggagtacaa gtgcaaggtc 1080
tccaacaaag ccctcccagc ccccatcgag aaaaccatct ccaaagccaa agggcagccc 1140
cgagaaccac aggtgtacac cctgccccca tcccgggagg agatgaccaa gaaccaggtc 1200
agcctgacct gcctggtcaa aggcttctat cccagcgaca tcgccgtgga gtgggagagc 1260
aatgggcagc cggagaacaa ctacaagacc acgcctcccg tgctggactc cgacggctcc 1320
ttcttcctct atagcaagct caccgtggac aagagcaggt ggcagcaggg gaacgtcttc 1380
tcatgctccg tgatgcatga ggctctgcac aaccactaca cgcagaagag cctctccctg 1440
tctccgggta aatga                                                 1455

SEQ ID NO: 530           moltype = DNA  length = 405
```

```
FEATURE                 Location/Qualifiers
misc_feature            1..405
                        note = Description of Artificial Sequence: Synthetic
                         polynucleotide
source                  1..405
                        mol_type = other DNA
                        organism = synthetic construct
SEQUENCE: 530
caggtgcatc tggtggagtc ggggggaggc gtggtccaac ctgggaagtc cctaagactc   60
tcctgtgaaa cctctggctt catcttcaac gaatatccca tgtattggat ccgccaggct  120
ccaggcaagg gaccggagtg ggtggccgca atctccgctg acgcctggca tgtggactac  180
gcaggctccg tgcggggccg atttaccgtc tccagagaca attctaagaa ttctctatat  240
ttagacatga agagtctgaa agttgaagac acggctatat atttctgtgc gaaagatggg  300
gaggaacaca aggtaccaca attgcattcc tggagcggac gaaacttata tcactacact  360
ggttttgacg tctggggccc agggaccacg gtcaccgtct cgagc                  405

SEQ ID NO: 531          moltype = AA  length = 484
FEATURE                 Location/Qualifiers
REGION                  1..484
                        note = Description of Artificial Sequence: Synthetic
                         polypeptide
source                  1..484
                        mol_type = protein
                        organism = synthetic construct
SEQUENCE: 531
MELGLSWVFL VVLLRGVHCQ VHLVESGGGV VQPGKSLRLS CETSGFIFNE YPMYWIRQAP   60
GKGPEWVAAI SADAWHVDYA GSVRGRFTVS RDNSKNSLYL DMKSLKVEDT AIYFCAKDGE  120
EHKVPQLHSW SGRNLYHYTG FDVWGPGTTV TVSSASTKGP SVFPLAPSSK STSGGTAALG  180
CLVKDYFPEP VTVSWNSGAL TSGVHTFPAV LQSSGLYSLS SVVTVPSSSL GTQTYICNVN  240
HKPSNTKVDK RVEPKSCDKT HTCPPCPAPE LLGGPSVFLF PPKPKDTLMI SRTPEVTCVV  300
VDVSHEDPEV KFNWYVDGVE VHNAKTKPRE EQYNSTYRVV SVLTVLHQDW LNGKEYKCKV  360
SNKALPAPIE KTISKAKGQP REPQVYTLPP SREEMTKNQV SLTCLVKGFY PSDIAVEWES  420
NGQPENNYKT TPPVLDSDGS FFLYSKLTVD KSRWQQGNVF SCSVMHEALH NHYTQKSLSL  480
SPGK                                                               484

SEQ ID NO: 532          moltype = AA  length = 135
FEATURE                 Location/Qualifiers
REGION                  1..135
                        note = Description of Artificial Sequence: Synthetic
                         polypeptide
source                  1..135
                        mol_type = protein
                        organism = synthetic construct
SEQUENCE: 532
QVHLVESGGG VVQPGKSLRL SCETSGFIFN EYPMYWIRQA PGKGPEWVAA ISADAWHVDY   60
AGSVRGRFTV SRDNSKNSLY LDMKSLKVED TAIYFCAKDG EEHKVPQLHS WSGRNLYHYT  120
GFDVWGPGTT VTVSS                                                   135

SEQ ID NO: 533          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 533
EYPMY                                                                5

SEQ ID NO: 534          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 534
AISADAWHVD YAGSVRG                                                  17

SEQ ID NO: 535          moltype = AA  length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 535
DGEEHKVPQL HSWSGRNLYH YTGFDV                                        26

SEQ ID NO: 536          moltype = AA  length = 6
```

```
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 536
GFIFNE                                                                          6

SEQ ID NO: 537          moltype = DNA  length = 720
FEATURE                 Location/Qualifiers
misc_feature            1..720
                        note = Description of Artificial Sequence: Synthetic
                         polynucleotide
source                  1..720
                        mol_type = other DNA
                        organism = synthetic construct
SEQUENCE: 537
atgaggctcc ctgctcagct cctggggctg ctaatgctct ggataccrga acttgctgca      60
gacattgtga tgacccagtc tcctgtctct ctgtccgtca ccctcggaca gccggcctcc     120
atgtcctgca agtccagtca gagtgtccga cagagtgatg gcaagacttt cttatattgg     180
tatcgacaga agccaggcca gtctccacaa ctgttaatat atgagggttc gagtcgattc     240
tctggagtgt cagataggat tctctggcag gggtcaggga cagacttcac actgaggatc     300
agtcgagtgg aggctgagga tgctggcgtt tacttctgct tgcaaactaa agacttcccc     360
ctcacttttg gcggagggac cagggtggat ctcaaacgta cggtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct tcaacagggg agagtgttag     720

SEQ ID NO: 538          moltype = DNA  length = 336
FEATURE                 Location/Qualifiers
misc_feature            1..336
                        note = Description of Artificial Sequence: Synthetic
                         polynucleotide
source                  1..336
                        mol_type = other DNA
                        organism = synthetic construct
SEQUENCE: 538
gacattgtga tgacccagtc tcctgtctct ctgtccgtca ccctcggaca gccggcctcc      60
atgtcctgca agtccagtca gagtgtccga cagagtgatg gcaagacttt cttatattgg     120
tatcgacaga agccaggcca gtctccacaa ctgttaatat atgagggttc gagtcgattc     180
tctggagtgt cagataggat tctctggcag gggtcaggga cagacttcac actgaggatc     240
agtcgagtgg aggctgagga tgctggcgtt tacttctgct tgcaaactaa agacttcccc     300
ctcacttttg gcggagggac cagggtggat ctcaaa                               336

SEQ ID NO: 539          moltype = AA  length = 239
FEATURE                 Location/Qualifiers
REGION                  1..239
                        note = Description of Artificial Sequence: Synthetic
                         polypeptide
source                  1..239
                        mol_type = protein
                        organism = synthetic construct
SEQUENCE: 539
MRLPAQLLGL LMLWIPELAA DIVMTQSPVS LSVTLGQPAS MSCKSSQSVR QSDGKTFLYW      60
YRQKPGQSPQ LLIYEGSSRF SGVSDRISGS GSGTDFTLRI SRVEAEDAGV YFCLQTKDFP     120
LTFGGGTRVD LKRTVAAPSV FIFPPSDEQL KSGTASVVCL LNNFYPREAK VQWKVDNALQ     180
SGNSQESVTE QDSKDSTYSL SSTLTLSKAD YEKHKVYACE VTHQGLSSPV TKSFNRGEC     239

SEQ ID NO: 540          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 540
DIVMTQSPVS LSVTLGQPAS MSCKSSQSVR QSDGKTFLYW YRQKPGQSPQ LLIYEGSSRF      60
SGVSDRISGS GSGTDFTLRI SRVEAEDAGV YFCLQTKDFP LTFGGGTRVD LK              112

SEQ ID NO: 541          moltype = AA  length = 16
FEATURE                 Location/Qualifiers
REGION                  1..16
                        note = Description of Artificial Sequence: Synthetic peptide
source                  1..16
                        mol_type = protein
```

|  |  |  |
|---|---|---|
| SEQUENCE: 541 | | |
| KSSQSVRQSD GKTFLY | | 16 |
| SEQ ID NO: 542 | moltype = AA   length = 7 | |
| FEATURE | Location/Qualifiers | |
| REGION | 1..7 | |
| | note = Description of Artificial Sequence: Synthetic peptide | |
| source | 1..7 | |
| | mol_type = protein | |
| | organism = synthetic construct | |
| SEQUENCE: 542 | | |
| EGSSRFS | | 7 |
| SEQ ID NO: 543 | moltype = AA   length = 9 | |
| FEATURE | Location/Qualifiers | |
| REGION | 1..9 | |
| | note = Description of Artificial Sequence: Synthetic peptide | |
| source | 1..9 | |
| | mol_type = protein | |
| | organism = synthetic construct | |
| SEQUENCE: 543 | | |
| LQTKDFPLT | | 9 |
| SEQ ID NO: 544 | moltype = DNA   length = 1455 | |
| FEATURE | Location/Qualifiers | |
| misc_feature | 1..1455 | |
| | note = Description of Artificial Sequence: Synthetic polynucleotide | |
| source | 1..1455 | |
| | mol_type = other DNA | |
| | organism = synthetic construct | |

SEQUENCE: 544

```
atggaattgg ggctgagctg ggttttcctc gtcgttctcc taagaggtgt ccactgtcag   60
gtgcatctgg tggagtcggg ggggaggcgt tgtccaacct gaaagtccct aagactctcc  120
tgtgaaacct ctggcttcat cttcaatcaa tatcccatgt attgggtccg ccaggctcca  180
ggcaagggac cggagtgggt ggccgccatc tccgctgatg cctggcatgt ggactaccca  240
ggctccgtgc ggggccgatt taccgtctcc agagacaatt ccaagagttc tctatattta  300
gacatgaaga gtctgaaagt tgaagacacg gctatatatt tctgtgcgaa agatggggag  360
gaacacaagg taccacaatt gcattcctgg agcggacgaa acttatatca ctacactggt  420
tttgacgtct ggggcccagg gaccacggtc accgtctcga gcgcctccac caagggccca  480
tcggtcttcc ccctggcacc ctcctccaag agcacctctg gggcacagc ggccctgggc   540
tgcctggtca aggactactt ccccgaaccg gtgacggtgt cgtggaactc aggcgccctg  600
accagcggcg tgcacacctt cccggctgtc ctacagtcct caggactcta ctccctcagc  660
agcgtggtga ccgtgccctc cagcagcttg gcacccagag cctacatctg caacgtgaat  720
cacaagccca gcaacaccaa ggtggacaag agagttgagc ccaaatcttg tgacaaaact  780
cacacatgcc caccgtgccc agcacctgaa ctcctggggg gaccgtcagt cttcctcttc  840
cccccaaaac ccaaggacac cctcatgatc tcccggaccc ctgaggtcac atgcgtggtg  900
gtggacgtga gccacgaaga ccctgaggtc aagttcaact ggtacgtgga cggcgtggag  960
gtgcataatg ccaagacaaa gccgcgggag gagcagtaca acagcacgta ccgtgtggtc 1020
agcgtcctca ccgtcctgca ccaggactgg ctgaatggca aggagtacaa gtgcaaggtc 1080
tccaacaaag ccctcccagc cccatcgag aaaaccatct ccaaagccaa agggcagccc  1140
cgagaaccac aggtgtacac cctgcccca tcccgggagg agatgaccaa gaaccaggtc  1200
agcctgacct gcctggtcaa aggcttctat cccagcgaca tcgccgtgga gtgggagagc 1260
aatgggcagc cggagaacaa ctacaagacc acgcctcccg tgctggactc cgacggctcc 1320
ttcttcctct atagcaagct caccgtggac aagagcaggt ggcagcaggg gaacgtcttc 1380
tcatgctccg tgatgcatga ggctctgcac aaccactaca cgcagaagag cctctccctg 1440
tctccgggta aatga                                                  1455
```

|  |  |  |
|---|---|---|
| SEQ ID NO: 545 | moltype = DNA   length = 405 | |
| FEATURE | Location/Qualifiers | |
| misc_feature | 1..405 | |
| | note = Description of Artificial Sequence: Synthetic polynucleotide | |
| source | 1..405 | |
| | mol_type = other DNA | |
| | organism = synthetic construct | |

SEQUENCE: 545

```
caggtgcatc tggtggagtc gggggggaggc gttgtccaac ctggaaagtc cctaagactc   60
tcctgtgaaa cctctggctt catcttcaat caatatccca tgtattgggt ccgccaggct  120
ccaggcaagg gaccggagtg ggtggccgcc atctccgctg atgcctggca tgtggactac  180
ccaggctccg tgcggggccg atttaccgtc tccagagaca attccaagag ttctctatat  240
ttagacatga agagtctgaa agttgaagac acggctatat ttctgtgc gaaagatggg   300
gaggaacaca aggtaccaca attgcattcc tggagcggac gaaacttata tcactacact  360
ggttttgacg tctggggccc agggaccacg gtcaccgtct cgagc                  405
```

|  |  |  |
|---|---|---|
| SEQ ID NO: 546 | moltype = AA   length = 484 | |
| FEATURE | Location/Qualifiers | |
| REGION | 1..484 | |

```
                           note = Description of Artificial Sequence: Synthetic
                            polypeptide
source                     1..484
                           mol_type = protein
                           organism = synthetic construct
SEQUENCE: 546
MELGLSWVFL VVLLRGVHCQ VHLVESGGGV VQPGKSLRLS CETSGFIFNQ YPMYWVRQAP  60
GKGPEWVAAI SADAWHVDYP GSVRGRFTVS RDNSKSSLYL DMKSLKVEDT AIYFCAKDGE 120
EHKVPQLHSW SGRNLYHYTG FDVWGPGTTV TVSSASTKGP SVPPLAPSSK STSGGTAALG 180
CLVKDYFPEP VTVSWNSGAL TSGVHTFPAV LQSSGLYSLS SVVTVPSSSL GTQTYICNVN 240
HKPSNTKVDK RVEPKSCDKT HTCPPCPAPE LLGGPSVFLF PPKPKDTLMI SRTPEVTCVV 300
VDVSHEDPEV KFNWYVDGVE VHNAKTKPRE EQYNSTYRVV SVLTVLHQDW LNGKEYKCKV 360
SNKALPAPIE KTISKAKGQP REPQVYTLPP SREEMTKNQV SLTCLVKGFY PSDIAVEWES 420
NGQPENNYKT TPPVLDSDGS FFLYSKLTVD KSRWQQGNVF SCSVMHEALH NHYTQKSLSL 480
SPGK                                                              484

SEQ ID NO: 547             moltype = AA  length = 135
FEATURE                    Location/Qualifiers
REGION                     1..135
                           note = Description of Artificial Sequence: Synthetic
                            polypeptide
source                     1..135
                           mol_type = protein
                           organism = synthetic construct
SEQUENCE: 547
QVHLVESGGG VVQPGKSLRL SCETSGFIFN QYPMYWVRQA PGKGPEWVAA ISADAWHVDY  60
PGSVRGRFTV SRDNSKSSLY LDMKSLKVED TAIYFCAKDG EEHKVPQLHS WSGRNLYHYT 120
GFDVWGPGTT VTVSS                                                  135

SEQ ID NO: 548             moltype = AA  length = 5
FEATURE                    Location/Qualifiers
REGION                     1..5
                           note = Description of Artificial Sequence: Synthetic peptide
source                     1..5
                           mol_type = protein
                           organism = synthetic construct
SEQUENCE: 548
QYPMY                                                               5

SEQ ID NO: 549             moltype = AA  length = 17
FEATURE                    Location/Qualifiers
REGION                     1..17
                           note = Description of Artificial Sequence: Synthetic peptide
source                     1..17
                           mol_type = protein
                           organism = synthetic construct
SEQUENCE: 549
AISADAWHVD YPGSVRG                                                 17

SEQ ID NO: 550             moltype = AA  length = 6
FEATURE                    Location/Qualifiers
REGION                     1..6
                           note = Description of Artificial Sequence: Synthetic peptide
source                     1..6
                           mol_type = protein
                           organism = synthetic construct
SEQUENCE: 550
GFIFNQ                                                              6

SEQ ID NO: 551             moltype = DNA  length = 720
FEATURE                    Location/Qualifiers
misc_feature               1..720
                           note = Description of Artificial Sequence: Synthetic
                            polynucleotide
source                     1..720
                           mol_type = other DNA
                           organism = synthetic construct
SEQUENCE: 551
atgaggctcc ctgctcagct cctggggctg ctaatgctct ggatacctga acttgctgca  60
gacattgtga tgacccagtc tcctgtctct ctgtccgtca ccctcggaca gccggcctcc 120
atgtcctgca agtccagtca gactgtccga cagagtgatg gcaagacttt cttatattgg 180
tatcgacaga aggcaggcca gtctccacaa ctgttaatat atgagggttc gaatcgattc 240
tctggagtgt cagataggat ctctggcagc gggtcgggga cagatttcac actgagaatc 300
agtcgtgtgg aggctgagga tgtttggcgt tatttctgcc tgcaaactaa agactttccc 360
ctcactttg gcggagggac cagggtggat atcaaacgta cggtggctgc cccatctgtc 420
ttcatcttcc cgccatctga tgagcagttg aaatctggaa ctgcctctgt tgtgtgcctg 480
ctgaataact tctatcccag agaggccaaa gtacagtgga aggtggataa cgccctccaa 540
tcgggtaact cccaggagag tgtcacagag caggacagca aggacagcac ctacagcctc 600
agcagcaccc tgacgctgag caaagcagac tacgagaaac acaaagtcta cgcctgcgaa 660
```

```
                    gtcacccatc agggcctgag ctcgcccgtc acaaagagct tcaacagggg agagtgttag    720

SEQ ID NO: 552              moltype = DNA  length = 336
FEATURE                     Location/Qualifiers
misc_feature                1..336
                            note = Description of Artificial Sequence: Synthetic
                             polynucleotide
source                      1..336
                            mol_type = other DNA
                            organism = synthetic construct
SEQUENCE: 552
gacattgtga tgacccagtc tcctgtctct ctgtccgtca ccctcggaca gccggcctcc    60
atgtcctgca agtccagtca gactgtccga cagagtgatg gcaagacttt cttatattgg   120
tatcgacaga aggcaggcca gtctccacaa ctgttaatat atgagggttc gaatcgattc   180
tctggagtgt cagataggat ctctggcagc gggtcgggga cagatttcac actgagaatc   240
agtcgagtgg aggctgagga tgttggcgtt tatttctgcc tgcaaactaa agacttcccc   300
ctcacttttg gcggagggac cagggtggat atcaaa                             336

SEQ ID NO: 553              moltype = AA  length = 239
FEATURE                     Location/Qualifiers
REGION                      1..239
                            note = Description of Artificial Sequence: Synthetic
                             polypeptide
source                      1..239
                            mol_type = protein
                            organism = synthetic construct
SEQUENCE: 553
MRLPAQLLGL LMLWIPELAA DIVMTQSPVS LSVTLGQPAS MSCKSSQTVR QSDGKTFLYW    60
YRQKAGQSPQ LLIYEGSNRF SGVSDRISGS GSGTDFTLRI SRVEAEDVGV YFCLQTKDFP   120
LTFGGGTRVD IKRTVAAPSV FIFPPSDEQL KSGTASVVCL LNNFYPREAK VQWKVDNALQ   180
SGNSQESVTE QDSKDSTYSL SSTLTLSKAD YEKHKVYACE VTHQGLSSPV TKSFNRGEC    239

SEQ ID NO: 554              moltype = AA  length = 112
FEATURE                     Location/Qualifiers
REGION                      1..112
                            note = Description of Artificial Sequence: Synthetic
                             polypeptide
source                      1..112
                            mol_type = protein
                            organism = synthetic construct
SEQUENCE: 554
DIVMTQSPVS LSVTLGQPAS MSCKSSQTVR QSDGKTFLYW YRQKAGQSPQ LLIYEGSNRF    60
SGVSDRISGS GSGTDFTLRI SRVEAEDVGV YFCLQTKDFP LTFGGGTRVD IK           112

SEQ ID NO: 555              moltype = AA  length = 16
FEATURE                     Location/Qualifiers
REGION                      1..16
                            note = Description of Artificial Sequence: Synthetic peptide
source                      1..16
                            mol_type = protein
                            organism = synthetic construct
SEQUENCE: 555
KSSQTVRQSD GKTFLY                                                    16

SEQ ID NO: 556              moltype = AA  length = 7
FEATURE                     Location/Qualifiers
REGION                      1..7
                            note = Description of Artificial Sequence: Synthetic peptide
source                      1..7
                            mol_type = protein
                            organism = synthetic construct
SEQUENCE: 556
EGSNRFS                                                               7

SEQ ID NO: 557              moltype = DNA  length = 1455
FEATURE                     Location/Qualifiers
misc_feature                1..1455
                            note = Description of Artificial Sequence: Synthetic
                             polynucleotide
source                      1..1455
                            mol_type = other DNA
                            organism = synthetic construct
SEQUENCE: 557
atggaattgg ggctgagctg gttttcctc gtcgctctcc taagaggtgt ccactgtgaa     60
gtgcatctgg tggagtcggg gggaggcgtg gtccaacctg gaaagtccct cagactctcc   120
tgtgtaactt ctggcttcat cttcaaacaa tatcctatgt attggatccg ccaggctcca   180
ggcaggggc tggagtgggt ggccgccatc tccgctgatg cctggcatgt ggactacgca   240
ggctccgtga agggccgatt taccgtctcc agagacaact ccaagaattc tctatattta   300
gacatgaaca gtctgacagt tgaagacacg gctatatatt tctgtgcgaa agatggggaa   360
```

```
gaacacgaag taccacagtt gcactcctgg agcggacgaa atttatatca ctacactggt    420
gtggacatct ggggcccagg gaccacggtc accgtctcga gcgcctccac caagggccca    480
tcggtcttcc ccctggcacc ctcctccaag agcacctctg gggcacagcg gccctgggc     540
tgcctggtca aggactactt ccccgaaccg gtgacggtgt cgtggaactc aggcgccctg    600
accagcggcg tgcacacctt cccggctgtc ctacagtcct caggactcta tccctcagc     660
agcgtggtga ccgtgccctc agcagcttg gcacccaga cctacatctg caacgtgaat     720
cacaagccca gcaacaccaa ggtggacaag agagttgagc ccaaatcttg tgacaaaact    780
cacacatgcc caccgtgccc agcacctgaa ctcctggggg gaccgtcagt cttcctcttc    840
ccccccaaaac ccaaggacac cctcatgatc tcccggaccc ctgaggtcac atgcgtggtg    900
gtggacgtga gccacgaaga ccctgaggtc aagttcaact ggtacgtgga cggcgtggag    960
gtgcataatg ccaagacaaa gccgcgggag gagcagtaca acagcacgta ccgtgtggtc   1020
agcgtcctca ccgtcctgca ccaggactgg ctgaatggca aggagtacaa gtgcaaggtc   1080
tccaacaaag ccctcccagc ccccatcgag aaaaccatct ccaaagccaa agggcagccc   1140
cgagaaccac aggtgtacac cctgccccca tcccgggagg agatgaccaa gaaccaggtc   1200
agcctgacct gcctggtcaa aggcttctat cccagcgaca tcgccgtgga gtgggagagc   1260
aatgggcagc cggagaacaa ctacaagacc acgcctcccg tgctggactc cgacggctcc   1320
ttcttcctct atagcaagct caccgtggac aagagcaggt ggcagcaggg gaacgtcttc   1380
tcatgctccg tgatgcatga ggctctgcac aaccactaca cgcagaagag cctctccctg   1440
tctccgggta aatga                                                    1455

SEQ ID NO: 558         moltype = DNA  length = 405
FEATURE                Location/Qualifiers
misc_feature           1..405
                       note = Description of Artificial Sequence: Synthetic
                         polynucleotide
source                 1..405
                       mol_type = other DNA
                       organism = synthetic construct
SEQUENCE: 558
gaagtgcatc tggtggagtc ggggggaggc gtggtccaac ctggaaagtc cctcagactc     60
tcctgtgtaa cttctggctt catcttcaaa caatatccta tgtattggat ccgccaggct    120
ccaggcaagg ggctggagtg ggtggccgcc atctccgctg atgcctggca tgtggactac    180
gcaggctccg tgcggggccg atttaccgtc tccagagaca actccaagaa ttctctatat    240
ttagacatga acagtctgac agttgaagac acggctatat atttctgtgc gaaagatggg    300
gaagaacacg aagtaccaca gttgcactcc tggagcggga gaaatttata tcactacact    360
ggtgtggaca tctggggccc agggaccacg gtcaccgtct cgagc                    405

SEQ ID NO: 559         moltype = AA  length = 484
FEATURE                Location/Qualifiers
REGION                 1..484
                       note = Description of Artificial Sequence: Synthetic
                         polypeptide
source                 1..484
                       mol_type = protein
                       organism = synthetic construct
SEQUENCE: 559
MELGLSWVFL VALLRGVHCE VHLVESGGGV VQPGKSLRLS CVTSGFIFKQ YPMYWIRQAP     60
GKGLEWVAAI SADAWHVDYA GSVRGRFTVS RDNSKNSLYL DMNSLTVEDT AIYFCAKDGE    120
EHEVPQLHSW SGRNLYHYTG VDIWGPGTTV TVSSASTKGP SVFPLAPSSK STSGGTAALG    180
CLVKDYFPEP VTVSWNSGAL TSGVHTFPAV LQSSGLYSLS SVVTVPSSSL GTQTYICNVN    240
HKPSNTKVDK RVEPKSCDKT HTCPPCPAPE LLGGPSVFLF PPKPKDTLMI SRTPEVTCVV    300
VDVSHEDPEV KFNWYVDGVE VHNAKTKPRE EQYNSTYRVV SVLTVLHQDW LNGKEYKCKV    360
SNKALPAPIE KTISKAKGQP REPQVYTLPP SREEMTKNQV SLTCLVKGFY PSDIAVEWES    420
NGQPENNYKT TPPVLDSDGS FFLYSKLTVD KSRWQQGNVF SCSVMHEALH NHYTQKSLSL    480
SPGK                                                                 484

SEQ ID NO: 560         moltype = AA  length = 135
FEATURE                Location/Qualifiers
REGION                 1..135
                       note = Description of Artificial Sequence: Synthetic
                         polypeptide
source                 1..135
                       mol_type = protein
                       organism = synthetic construct
SEQUENCE: 560
EVHLVESGGG VVQPGKSLRL SCVTSGFIFK QYPMYWIRQA PGKGLEWVAA ISADAWHVDY     60
AGSVRGRFTV SRDNSKNSLY LDMNSLTVED TAIYFCAKDG EEHEVPQLHS WSGRNLYHYT    120
GVDIWGPGTT VTVSS                                                     135

SEQ ID NO: 561         moltype = AA  length = 26
FEATURE                Location/Qualifiers
REGION                 1..26
                       note = Description of Artificial Sequence: Synthetic peptide
source                 1..26
                       mol_type = protein
                       organism = synthetic construct
SEQUENCE: 561
DGEEHEVPQL HSWSGRNLYH YTGVDI                                          26
```

-continued

| | | |
|---|---|---|
| SEQ ID NO: 562 | moltype = AA   length = 6 | |
| FEATURE | Location/Qualifiers | |
| REGION | 1..6 | |
| | note = Description of Artificial Sequence: Synthetic peptide | |
| source | 1..6 | |
| | mol_type = protein | |
| | organism = synthetic construct | |

SEQUENCE: 562
GFIFKQ                                                                    6

| | | |
|---|---|---|
| SEQ ID NO: 563 | moltype = DNA   length = 720 | |
| FEATURE | Location/Qualifiers | |
| misc_feature | 1..720 | |
| | note = Description of Artificial Sequence: Synthetic polynucleotide | |
| source | 1..720 | |
| | mol_type = other DNA | |
| | organism = synthetic construct | |

SEQUENCE: 563
```
atgaggctcc ctgctcagct cctggggctg ctaatgctct ggatacctga acttactgca    60
gacattgtga tgacccagac tcctgtctct ctgtccgtca ccctcggaca gccggcctcc   120
atgtcctgta agtccagtca gagcctccga caaagtgatg gcaagacttt cttgtattgg   180
tatcgacaga aggcaggcca gtctccacaa ctcctaatat ctgaggcttc aatcgattc    240
tctggagtgt cagataggtt ctctggcagc ggttcaggga cagacttcac actgaaaatc   300
agtcgggtgg aggctgagga tgttggcatt tatttctgca tgcaaactaa agacttcccc   360
ctcacttttg gcggagggac caaggtggat ctcaaacgta actatccatc tgtc         420
ttcatcttcc cgccatctga tgagcagttg aaatctggaa ctgcctctgt tgtgtgcctg   480
ctgaataact tctatcccag agaggccaaa gtacagtgga aggtggataa cgccctccaa   540
tcgggtaact cccaggagag tgtcacagag caggacagca aggacagcac ctacagcctc   600
agcagcaccc tgacgctgag caaagcagac tacgagaaac acaaagtcta cgcctgcgaa   660
gtcacccatc agggcctgag ctcgcccgtc acaaagagct tcaacagggg agagtgttag   720
```

| | | |
|---|---|---|
| SEQ ID NO: 564 | moltype = DNA   length = 336 | |
| FEATURE | Location/Qualifiers | |
| misc_feature | 1..336 | |
| | note = Description of Artificial Sequence: Synthetic polynucleotide | |
| source | 1..336 | |
| | mol_type = other DNA | |
| | organism = synthetic construct | |

SEQUENCE: 564
```
gacattgtga tgacccagac tcctgtctct ctgtccgtca ccctcggaca gccggcctcc    60
atgtcctgta agtccagtca gagcctccga caaagtgatg gcaagacttt cttgtattgg   120
tatcgacaga aggcaggcca gtctccacaa ctcctaatat ctgaggcttc aatcgattc    180
tctggagtgt cagataggtt ctctggcagc ggttcaggga cagacttcac actgaaaatc   240
agtcgggtgg aggctgagga tgttggcatt tatttctgca tgcaaactaa agacttcccc   300
ctcacttttg gcggagggac caaggtggat ctcaaa                             336
```

| | | |
|---|---|---|
| SEQ ID NO: 565 | moltype = AA   length = 239 | |
| FEATURE | Location/Qualifiers | |
| REGION | 1..239 | |
| | note = Description of Artificial Sequence: Synthetic polypeptide | |
| source | 1..239 | |
| | mol_type = protein | |
| | organism = synthetic construct | |

SEQUENCE: 565
```
MRLPAQLLGL LMLWIPELTA DIVMTQTPVS LSVTLGQPAS MSCKSSQSLR QSDGKTFLYW    60
YRQKAGQSPQ LLISEASNRF SGVSDRFSGS GSGTDFTLKI SRVEAEDVGI YFCMQTKDFP   120
LTFGGGTKVD LKRTVAAPSV FIFPPSDEQL KSGTASVVCL LNNFYPREAK VQWKVDNALQ   180
SGNSQESVTE QDSKDSTYSL SSTLTLSKAD YEKHKVYACE VTHQGLSSPV TKSFNRGEC    239
```

| | | |
|---|---|---|
| SEQ ID NO: 566 | moltype = AA   length = 112 | |
| FEATURE | Location/Qualifiers | |
| REGION | 1..112 | |
| | note = Description of Artificial Sequence: Synthetic polypeptide | |
| source | 1..112 | |
| | mol_type = protein | |
| | organism = synthetic construct | |

SEQUENCE: 566
```
DIVMTQTPVS LSVTLGQPAS MSCKSSQSLR QSDGKTFLYW YRQKAGQSPQ LLISEASNRF    60
SGVSDRFSGS GSGTDFTLKI SRVEAEDVGI YFCMQTKDFP LTFGGGTKVD LK           112
```

| | | |
|---|---|---|
| SEQ ID NO: 567 | moltype = AA   length = 16 | |
| FEATURE | Location/Qualifiers | |
| REGION | 1..16 | |
| | note = Description of Artificial Sequence: Synthetic peptide | |
| source | 1..16 | |

```
                        mol_type = protein
                        organism = synthetic construct
SEQUENCE: 567
KSSQSLRQSD GKTFLY                                                     16

SEQ ID NO: 568          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 568
EASNRFS                                                                7

SEQ ID NO: 569          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 569
MQTKDFPLT                                                              9

SEQ ID NO: 570          moltype = DNA   length = 1455
FEATURE                 Location/Qualifiers
misc_feature            1..1455
                        note = Description of Artificial Sequence: Synthetic
                         polynucleotide
source                  1..1455
                        mol_type = other DNA
                        organism = synthetic construct
SEQUENCE: 570
atggaattgg ggctgagctg ggttttcctc gtcgctctcc taagaggtgt ccactgtgag    60
gtgcgtctga tggagtcggg gggaggcgtg gtccagcctg gaagtccct cagactctcc   120
tgtgtaacct ctggcttcat cttcaaaaaa tatcctatgt actggatccg ccaggctcca   180
ggcaaggggc tggagtgggt ggccgccatc tccgctgatg cctggcatgt ggactaccca   240
ggctccgtgc ggggccgatt taccgtctca agagacaact ccaagaattc tctatattta   300
gacatgaata gtctgacagt agaagacacg gctatatatt tttgtgcgaa agatggggag   360
gaacacgaag tcccacaact gcactcctgg agcggacgaa atttatatca ctacactggt   420
gtagacgtct ggggcccagg gaccacggtc accgtctcga gcgcctccac caagggccca   480
tcggtcttcc ccctggcacc ctcctccaag agcacctctg ggggcacagc ggccctgggc   540
tgcctggtca aggactactt ccccgaaccg gtgacggtgt cgtggaactc aggcgccctg   600
accagcggcg tgcacacctt cccggctgtc ctacagtcct caggactcta ctccctcagc   660
agcgtggtga ccgtgccctc cagcagcttg gcacccagac cctacatctg caacgtgaat   720
cacaagccca gcaacaccaa ggtggacaag agagttgagc ccaaatcttg tgacaaaact   780
cacacatgcc caccgtgccc agcacctgaa ctcctggggg gaccgtcagt cttcctcttc   840
cccccaaaac ccaaggacac cctcatgatc tcccggaccc ctgaggtcac atgcgtggtg   900
gtggacgtga gccacgaaga ccctgaggtc aagttcaact ggtacgtgga cggcgtggag   960
gtgcataatg ccaagacaaa gccgcgggag gagcagtaca acagcacgta ccgtgtgtgt  1020
agcgtcctca ccgtcctgca ccaggactgg ctgaatggca aggagtacaa gtgcaaggtc  1080
tccaacaaag ccctcccagc cccatcgag aaaaccatct ccaaagccaa agggcagccc   1140
cgagaaccac aggtgtacac cctgccccca tcccgggagg atgaccaa gaaccaggtc   1200
agcctgacct gcctggtcaa aggcttctat cccagcgaca tcgccgtgga gtgggagagc  1260
aatgggcagc cggagaacaa ctacaagacc acgcctcccg tgctggactc cgacggctcc  1320
ttcttcctct atagcaagct caccgtggac aagagcaggt ggcagcaggg gaacgtcttc  1380
tcatgctccg tgatgcatga ggctctgcac aaccactaca cgcagaagag cctctccctg  1440
tctccgggta aatga                                                    1455

SEQ ID NO: 571          moltype = DNA   length = 405
FEATURE                 Location/Qualifiers
misc_feature            1..405
                        note = Description of Artificial Sequence: Synthetic
                         polynucleotide
source                  1..405
                        mol_type = other DNA
                        organism = synthetic construct
SEQUENCE: 571
gaggtgcgtc tgatggagtc ggggggaggc gtggtccagc ctgggaagtc cctcagactc    60
tcctgtgtaa cctctggctt catcttcaaa aatatccta tgtactggat ccgccaggct   120
ccaggcaagg ggctggagtg ggtggccgcc atctccgctg atgcctggca tgtggactac   180
ccaggctccg tgcggggccg atttaccgtc tcaagagaca actccaagaa ttctctatat   240
ttagacatga atagtctgac agtagaagac acggctatat atttttgtgc gaaagatggg   300
gaggaacacg aagtcccaca actgcactcc tggagcggac gaaatttata tcactacact   360
ggtgtagacg tctggggccc agggaccacg gtcaccgtct cgagc                   405

SEQ ID NO: 572          moltype = AA   length = 484
FEATURE                 Location/Qualifiers
```

```
REGION                        1..484
                              note = Description of Artificial Sequence: Synthetic
                                 polypeptide
source                        1..484
                              mol_type = protein
                              organism = synthetic construct
SEQUENCE: 572
MELGLSWVFL VALLRGVHCE VRLMESGGGV VQPGKSLRLS CVTSGFIFKK YPMYWIRQAP       60
GKGLEWVAAI SADAWHVDYP GSVRGRFTVS RDNSKNSLYL DMNSLTVEDT AIYFCAKDGE      120
EHEVPQLHSW SGRNLYHYTG VDVWGPGTTV TVSSASTKGP SVFPLAPSSK STSGGTAALG      180
CLVKDYFPEP VTVSWNSGAL TSGVHTFPAV LQSSGLYSLS SVVTVPSSSL GTQTYICNVN      240
HKPSNTKVDK RVEPKSCDKT HTCPPCPAPE LLGGPSVFLF PPKPKDTLMI SRTPEVTCVV      300
VDVSHEDPEV KFNWYVDGVE VHNAKTKPRE EQYNSTYRVV SVLTVLHQDW LNGKEYKCKV      360
SNKALPAPIE KTISKAKGQP REPQVYTLPP SREEMTKNQV SLTCLVKGFY PSDIAVEWES      420
NGQPENNYKT TPPVLDSDGS FFLYSKLTVD KSRWQQGNVF SCSVMHEALH NHYTQKSLSL      480
SPGK                                                                   484

SEQ ID NO: 573                moltype = AA   length = 135
FEATURE                       Location/Qualifiers
REGION                        1..135
                              note = Description of Artificial Sequence: Synthetic
                                 polypeptide
source                        1..135
                              mol_type = protein
                              organism = synthetic construct
SEQUENCE: 573
EVRLMESGGG VVQPGKSLRL SCVTSGFIFK KYPMYWIRQA PGKGLEWVAA ISADAWHVDY       60
PGSVRGRFTV SRDNSKNSLY LDMNSLTVED TAIYFCAKDG EEHEVPQLHS WSGRNLYHYT      120
GVDVWGPGTT VTVSS                                                       135

SEQ ID NO: 574                moltype = AA   length = 26
FEATURE                       Location/Qualifiers
REGION                        1..26
                              note = Description of Artificial Sequence: Synthetic peptide
source                        1..26
                              mol_type = protein
                              organism = synthetic construct
SEQUENCE: 574
DGEEHEVPQL HSWSGRNLYH YTGVDV                                            26

SEQ ID NO: 575                moltype = AA   length = 6
FEATURE                       Location/Qualifiers
REGION                        1..6
                              note = Description of Artificial Sequence: Synthetic peptide
source                        1..6
                              mol_type = protein
                              organism = synthetic construct
SEQUENCE: 575
GFIFKK                                                                   6

SEQ ID NO: 576                moltype = DNA   length = 720
FEATURE                       Location/Qualifiers
misc_feature                  1..720
                              note = Description of Artificial Sequence: Synthetic
                                 polynucleotide
source                        1..720
                              mol_type = other DNA
                              organism = synthetic construct
SEQUENCE: 576
atgaggctcc ctgctcagct cctggggctg ctaatgctct ggatacctga agtgactgca       60
gacattgtga tgacccagac tcctgtctct gtgtccgtca ccctcggaca gccggcctcc      120
atgtcctgca agtccagtca gagcgtccga caaagtgatg gcaagacttt tttatattgg      180
tatcgacaga aggcaggcca gtctccacaa ctcttaatat atgaggcttc gaagcgattc      240
tctggagtgt cagataggtt ctctggcagc gggtcaggga cagacttcac actgaaaatc      300
agtcgggtgg gggctgagga tgttggcgtt tatttctgca tgcaaactaa agacttccca      360
cttactttgg cgcgagggac caaggtggat ctcaaacgta cggtggctgc accatctgtc      420
ttcatcttcc cgccatctga tgagcagttg aaatctggaa ctgcctctgt tgtgtgcctg      480
ctgaataact tctatcccag agaggccaaa gtacagtgga aggtggataa cgccctccaa      540
tcgggtaact cccaggagag tgtcacagag caggacagca aggacagcac ctacagcctc      600
agcagcaccc tgacgctgag caaagcagac tacgagaaac acaaagtcta cgcctgcgaa      660
gtcacccatc agggcctgag ctcgcccgtc acaaagagct tcaacagggg agagtgttag      720

SEQ ID NO: 577                moltype = DNA   length = 336
FEATURE                       Location/Qualifiers
misc_feature                  1..336
                              note = Description of Artificial Sequence: Synthetic
                                 polynucleotide
source                        1..336
                              mol_type = other DNA
```

```
                         organism = synthetic construct
SEQUENCE: 577
gacattgtga tgacccagac tcctgtctct gtgtccgtca ccctcggaca gccggcctcc    60
atgtcctgca agtccagtca gagcgtccga caaagtgatg caagactttt tttatattgg   120
tatcgacaga aggcaggcca gtctccacaa ctcttaatat atgaggcttc gaagcgattc   180
tctggagtgt cagataggtt ctctggcagc gggtcaggga cagacttcac actgaaaatc   240
agtcgggtgg gggctgagga tgttggcgtt tatttctgca tgcaaactaa agacttcccc   300
cttactttg gcggagggac caaggtggat ctcaaa                              336

SEQ ID NO: 578          moltype = AA    length = 239
FEATURE                 Location/Qualifiers
REGION                  1..239
                        note = Description of Artificial Sequence: Synthetic
                         polypeptide
source                  1..239
                        mol_type = protein
                        organism = synthetic construct
SEQUENCE: 578
MRLPAQLLGL LMLWIPEVTA DIVMTQTPVS VSVTLGQPAS MSCKSSQSVR QSDGKTFLYW    60
YRQKAGQSPQ LLIYEASKRF SGVSDRFSGS GSGTDFTLKI SRVGAEDVGV YFCMQTKDFP   120
LTFGGGTKVD LKRTVAAPSV FIFPPSDEQL KSGTASVVCL LNNFYPREAK VQWKVDNALQ   180
SGNSQESVTE QDSKDSTYSL SSTLTLSKAD YEKHKVYACE VTHQGLSSPV TKSFNRGEC    239

SEQ ID NO: 579          moltype = AA    length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 579
DIVMTQTPVS VSVTLGQPAS MSCKSSQSVR QSDGKTFLYW YRQKAGQSPQ LLIYEASKRF    60
SGVSDRFSGS GSGTDFTLKI SRVGAEDVGV YFCMQTKDFP LTFGGGTKVD LK           112

SEQ ID NO: 580          moltype = AA    length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 580
EASKRFS                                                                7

SEQ ID NO: 581          moltype = DNA    length = 693
FEATURE                 Location/Qualifiers
misc_feature            1..693
                        note = Description of Artificial Sequence: Synthetic
                         polynucleotide
source                  1..693
                        mol_type = other DNA
                        organism = synthetic construct
SEQUENCE: 581
atggcctggg ctctgctcct cctcaccctc ctcactcagg gcacaggggc ctgggcccag    60
tctgccctga ctcagcctcc ctccgcgtcc gggtctcctg gacagtcaat caccatctcc   120
tgcactggaa atatcaataa ctttgtctcc tggtaccaac aacacctgg caaggccccc    180
aaactcgtca tttatggggt caataagcgc cctcaggtg tccctgatcg ttttctggc    240
tccaagtctg gcaacgcggc ctccctgacc gtctctggac tccagactga cgatgaggcc   300
gtctattact gcggctcact tgcaggcaac tgggatgtgg ttttcggcgg agggaccaag   360
ttgactgtcc tgggtcagcc catggctgcc ccctcggtca ctctgttccc gccctcctct   420
gaggagcttc aagccaacaa ggccacactg gtgtgtctca taagtgactt ctacccggga   480
gccgtgacag tggcctggaa ggcagatagc agccccgtca aggcgggagt ggagaccacc   540
acaccctcca aacaaagcaa caacaagtac gcggccagca gctacctgag cctgacgcct   600
gagcagtgga agtccacaa aagctacagc tgccaggtca cgcatgaagg gagcaccgtg   660
gagaagacag tggcccctac agaatgttca tag                                693

SEQ ID NO: 582          moltype = DNA    length = 315
FEATURE                 Location/Qualifiers
misc_feature            1..315
                        note = Description of Artificial Sequence: Synthetic
                         polynucleotide
source                  1..315
                        mol_type = other DNA
                        organism = synthetic construct
SEQUENCE: 582
cagtctgccc tgactcagcc tcctccgcg tccgggtctc ctggacagtc aatcaccatc    60
tcctgcactg gaaatatcaa taactttgtc tcctggtacc aacaacaccc tggcaaggcc   120
ccaaactcg tcatttatgg ggtcaataag cgccctcag gtgtccctga tcgttttctct   180
```

```
ggctccaagt ctggcaacgc ggcctccctg accgtctctg gactccagac tgacgatgag    240
gctgtctatt actgcggctc acttgcaggc aactgggatg tggttttcgg cggagggacc    300
aagttgactg tcctg                                                     315

SEQ ID NO: 583          moltype = AA  length = 230
FEATURE                 Location/Qualifiers
REGION                  1..230
                        note = Description of Artificial Sequence: Synthetic
                        polypeptide
source                  1..230
                        mol_type = protein
                        organism = synthetic construct
SEQUENCE: 583
MAWALLLLTL LTQGTGAWAQ SALTQPPSAS GSPGQSITIS CTGNINNFVS WYQQHPGKAP     60
KLVIYGVNKR PSGVPDRFSG SKSGNAASLT VSGLQTDDEA VYYCGSLAGN WDVVFGGGTK    120
LTVLGQPMAA PSVTLFPPSS EELQANKATL VCLISDFYPG AVTVAWKADS SPVKAGVETT    180
TPSKQSNNKY AASSYLSLTP EQWKSHKSYS CQVTHEGSTV EKTVAPTECS               230

SEQ ID NO: 584          moltype = AA  length = 105
FEATURE                 Location/Qualifiers
REGION                  1..105
                        note = Description of Artificial Sequence: Synthetic
                        polypeptide
source                  1..105
                        mol_type = protein
                        organism = synthetic construct
SEQUENCE: 584
QSALTQPPSA SGSPGQSITI SCTGNINNFV SWYQQHPGKA PKLVIYGVNK RPSGVPDRFS     60
GSKSGNAASL TVSGLQTDDE AVYYCGSLAG NWDVVFGGGT KLTVL                   105

SEQ ID NO: 585          moltype = DNA  length = 24
FEATURE                 Location/Qualifiers
misc_feature            1..24
                        note = Description of Artificial Sequence: Synthetic
                        oligonucleotide
source                  1..24
                        mol_type = other DNA
                        organism = synthetic construct
SEQUENCE: 585
actatggact ggatttggag gatc                                            24

SEQ ID NO: 586          moltype = DNA  length = 26
FEATURE                 Location/Qualifiers
misc_feature            1..26
                        note = Description of Artificial Sequence: Synthetic
                        oligonucleotide
source                  1..26
                        mol_type = other DNA
                        organism = synthetic construct
SEQUENCE: 586
aacatgaaac acctgtggtt cttcct                                          26

SEQ ID NO: 587          moltype = DNA  length = 24
FEATURE                 Location/Qualifiers
misc_feature            1..24
                        note = Description of Artificial Sequence: Synthetic
                        oligonucleotide
source                  1..24
                        mol_type = other DNA
                        organism = synthetic construct
SEQUENCE: 587
ggaagtagtc cttgaccagg cagc                                            24

SEQ ID NO: 588          moltype = DNA  length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 588
atgaggctcc ctgctcagct                                                 20

SEQ ID NO: 589          moltype = DNA  length = 21
FEATURE                 Location/Qualifiers
misc_feature            1..21
                        note = Description of Artificial Sequence: Synthetic
                        oligonucleotide
```

```
                        -continued source                  1..21
                        mol_type = other DNA
                        organism = synthetic construct
SEQUENCE: 589
ccccagctca gcttctcttc c                                          21

SEQ ID NO: 590          moltype = DNA   length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 590
ccttggatag aagttattca gc                                         22

SEQ ID NO: 591          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 591
catggcctgg gctctgct                                              18

SEQ ID NO: 592          moltype = DNA   length = 19
FEATURE                 Location/Qualifiers
misc_feature            1..19
                        note = Description of Artificial Sequence: Synthetic
                         oligonucleotide
source                  1..19
                        mol_type = other DNA
                        organism = synthetic construct
SEQUENCE: 592
ccatggcctg gatccctct                                             19

SEQ ID NO: 593          moltype = DNA   length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 593
ccttcatgcg tgacctggca gc                                         22

SEQ ID NO: 594          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 594
ELDKWA                                                           6

SEQ ID NO: 595          moltype = AA   length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 595
AREAGGPIWH DDVKYYDFND GYYNYHYMDV                                 30

SEQ ID NO: 596          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 596
```

```
ARDRRAVPIA TDNWLDP                                                       17

SEQ ID NO: 597           moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 597
TRDRRVVPMA TDNWLDP                                                       17

SEQ ID NO: 598           moltype = AA  length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 598
AAGAVGADSG SWFDP                                                         15

SEQ ID NO: 599           moltype = AA  length = 30
FEATURE                  Location/Qualifiers
REGION                   1..30
                         note = Description of Artificial Sequence: Synthetic
                          polypeptide
source                   1..30
                         mol_type = protein
                         organism = synthetic construct
SEQUENCE: 599
VREAGGPDYR NGYNYYDFYD GYYNYHYMDV                                         30

SEQ ID NO: 600           moltype = AA  length = 110
FEATURE                  Location/Qualifiers
REGION                   1..110
                         note = Description of Artificial Sequence: Synthetic
                          polypeptide
source                   1..110
                         mol_type = protein
                         organism = synthetic construct
SEQUENCE: 600
SYELTQPPSV SVSPGQTASI TCSGSKLGDK YVSWYQLRPG QSPILVMYEN DRRPSGIPER        60
FSGSNSGDTA TLTISGTQAL DEADFYCQAW ETTTTTFVFF GGGTQLTVLG                  110

SEQ ID NO: 601           moltype = AA  length = 111
FEATURE                  Location/Qualifiers
REGION                   1..111
                         note = Description of Artificial Sequence: Synthetic
                          polypeptide
source                   1..111
                         mol_type = protein
                         organism = synthetic construct
SEQUENCE: 601
QSALTQPASV SGSPGQTITI SCNGTSSDVG GFDSVSWYQQ SPGKAPKVMV FDVSHRPSGI        60
SNRFSGSKSG NTASLTISGL HIEDEGDYFC SSLTDRSHRI FGGGTKVTVL G                111

SEQ ID NO: 602           moltype = AA  length = 111
FEATURE                  Location/Qualifiers
REGION                   1..111
                         note = Description of Artificial Sequence: Synthetic
                          polypeptide
source                   1..111
                         mol_type = protein
                         organism = synthetic construct
SEQUENCE: 602
QSALTQPASV SGSPGQSITI SCNGTSNDVG GYESVSWYQQ HPGKAPKVVI YDVSKRPSGV        60
SNRFSGSKSG NTASLTISGL QAEDEGDYYC KSLTSTRRRV FGTGTKLTVL G                111

SEQ ID NO: 603           moltype = DNA  length = 1445
FEATURE                  Location/Qualifiers
misc_feature             1..1445
                         note = Description of Artificial Sequence: Synthetic
                          polynucleotide
source                   1..1445
                         mol_type = other DNA
                         organism = synthetic construct
SEQUENCE: 603
atgaaacacc tgtggttctt ccttctcctg gtggcagctc ccagatgggt cctgtccaga        60
```

```
tgcagttaca ggagtcgggc cccggactgg tgaagccttc ggaaaccctg tccctcacgt    120
gcagtgtgtc tggtgcctcc ataagtgaca gttactggag ctggatccgg cggtccccag    180
ggaagggact tgagtggatt gggtatgtcc acaaaagcgg cgacacaaat acatcccct     240
ccctcaagag tcgagtcaac ttgtcgttag acacgtccaa aaatcaggtg tccctgagcc    300
ttgtggccgc gaccgctgcg gactcgggca aatattatcg cgcagaacca ctgcacggga    360
ggagaattta tggaatcgtt gccttcaatg agtggttcac ctacttctac atggacgtct    420
ggggcaatgg gactcaggtc accgtctcct cagcctccac caagggccca tcggtcttcc    480
ccctggcacc ctcctccaag agcacctctg ggggcacagc ggccctgggc tgcctggtca    540
aggactactt ccccgaaccg gtgacggtgt cgtggaactc aggcgccctg accagcggcg    600
tgcacacctt cccggctgtc ctacagtcct caggactcta ctccctcagc agcgtggtga    660
ccgtgccctc cagcagcttg gcacccagag cctacatctg caacgtgaat cacaagccca    720
gcaacaccaa ggtggacaag agagttgagc ccaaatcttg tgacaaaact cacacatgcc    780
caccgtgccc agcacctgaa ctcctggggg gaccgtcagt cttcctcttc cccccaaaac    840
ccaaggacac cctcatgatc tcccggaccc ctgaggtcac atgcgtggtg gtggacgtga    900
gccacgaaga ccctgaggtc aagttcaact ggtacgtgga cggcgtggag gtgcataatg    960
ccaagacaaa gccgcgggag gagcagtaca acagcacgta ccgtgtggtc agcgtcctca   1020
ccgtcctgca ccaggactgg ctgaatggca aggagtacaa gtgcaaggtc tccaacaaag   1080
ccctcccagc ccccatcgag aaaaccatct ccaaagccaa agggcagccc cgagaaccac   1140
aggtgtacac cctgccccca tcccgggagg agatgaccaa gaaccaggtc agcctgacct   1200
gcctggtcaa aggcttctat cccagcgaca tcgccgtgga gtgggagagc aatgggcagc   1260
cggagaacaa ctacaagacc acgcctcccg tgctggactc cgacggctcc ttcttcctct   1320
atagcaagct caccgtggac aagagcaggt ggcagcaggg gaacgtcttc tcatgctccg   1380
tgatgcatga ggctctgcac aaccactaca cgcagaagag cctctccctg tctccgggta   1440
aatga                                                                1445

SEQ ID NO: 604          moltype = AA   length = 481
FEATURE                 Location/Qualifiers
REGION                  1..481
                        note = Description of Artificial Sequence: Synthetic
                        polypeptide
source                  1..481
                        mol_type = protein
                        organism = synthetic construct
SEQUENCE: 604
MKHLWFFLLL VAAPRWVLSQ MQLQESGPGL VKPSETLSLT CSVSGASISD SYWSWIRRSP     60
GKGLEWIGYV HKSGDTNYIP SLKSRVNLSL DTSKNQVSLS LVAATAADSG KYYCARTLHG    120
RRIYGIVAFN EWFTYFYMDV WGNGTQVTVS SASTKGPSVF PLAPSSKSTS GGTAALGCLV    180
KDYFPEPVTV SWNSGALTSG VHTFPAVLQS SGLYSLSSVV TVPSSSLGTQ TYICNVNHKP    240
SNTKVDKRVE PKSCDKTHTC PPCPAPELLG GPSVFLFPPK PKDTLMISRT PEVTCVVVDV    300
SHEDPEVKFN WYVDGVEVHN AKTKPREEQY NSTYRVVSVL TVLHQDWLNG KEYKCKVSNK    360
ALPAPIEKTI SKAKGQPREP QVYTLPPSRE EMTKNQVSLT CLVKGFYPSD IAVEWESNGQ    420
PENNYKTTPP VLDSDGSFFL YSKLTVDKSR WQQGNVFSCS VMHEALHNHY TQKSLSLSPG    480
K                                                                    481

SEQ ID NO: 605          moltype = DNA   length = 401
FEATURE                 Location/Qualifiers
misc_feature            1..401
                        note = Description of Artificial Sequence: Synthetic
                        polynucleotide
source                  1..401
                        mol_type = other DNA
                        organism = synthetic construct
SEQUENCE: 605
cagcgattag tggagtctgg gggaggcgtg gtccagcctg gtcgtccct gagactctcc      60
tgtgcagcgt ccggattcga cttcagtaga caaggctccg actgggtccg ccaggctcca   120
ggccaggggc tggagtgggt ggcatttatt aaatatgatg gaagtgagaa atatcatgct   180
gactccgtat ggggccgact cagcatctcc agagacaatt ccaaggatac gctttatctc   240
caaatgaata gcctgagagt cgaggacacg gctacatatt tttgtgtgag agaggctggt   300
gggcccgact accgtaatgg gtacaactat tacgatttct atgatggtta tttataactac   360
cactatatgg acgtctgggg caaagggacc acggtcaccg t                        401

SEQ ID NO: 606          moltype = DNA   length = 404
FEATURE                 Location/Qualifiers
misc_feature            1..404
                        note = Description of Artificial Sequence: Synthetic
                        polynucleotide
source                  1..404
                        mol_type = other DNA
                        organism = synthetic construct
SEQUENCE: 606
caggaacaac tggtggagtc tgggggaggc gtgtccagc cggggggtc cctgagactc       60
tcctgtttag cgtctggatt cacgtttcac aaatatggca tgcactgggt ccgccaggct   120
ccaggcaagg gcctggagtg ggtggcactc atctcagatg acggaatgag gaaatatcat   180
tcagactcca tgtgggggcg agtcaccatc tccagagaca attccaagaa cactctttat   240
ctgcaattca gcagcctgaa agtcgaagac acggctatgt tcttctgtgc gagagaggct   300
ggtgggccaa tctggcatga cgacgtcaaa tattacgatt ttaatgacgg ctactacaac   360
taccactaca tggacgtctg gggcaagggg accacggtca ccgt                    404

SEQ ID NO: 607          moltype = DNA   length = 404
```

```
FEATURE            Location/Qualifiers
misc_feature       1..404
                   note = Description of Artificial Sequence: Synthetic
                   polynucleotide
source             1..404
                   mol_type = other DNA
                   organism = synthetic construct
SEQUENCE: 607
caggaacaac tggtggagtc tggggggaggc gtggtccagc cggggggggtc cctgagactc    60
tcctgtttag cgtctggatt cacgtttcac aaatatggca tgcactgggt ccgccaggct   120
ccaggcaagg gcctggagtg ggtggcactc atctcagatg acggaatgag gaaatatcat   180
tcagactcca tgtggggccg agtcaccatc tccagagaca attccaagaa cactctttat   240
ctgcaattca gcagcctgaa agtcgaagac acggctatgt tcttctgtgc gagagaggct   300
ggtgggccaa tctggcatga cgacgtcaaa tattacgatt taatgacgg ctactacaac    360
taccactaca tggacgtctg gggcaagggg accacggtca ccgt                    404

SEQ ID NO: 608     moltype = DNA  length = 404
FEATURE            Location/Qualifiers
misc_feature       1..404
                   note = Description of Artificial Sequence: Synthetic
                   polynucleotide
source             1..404
                   mol_type = other DNA
                   organism = synthetic construct
SEQUENCE: 608
caggaacaac tgttggagtc tggggggaggc gtggtccagc cggggggggtc cctgagactc    60
tcctgtttag cgtctggatt cacgtttcac aaatatggca tgcactgggt ccgccaggct   120
ccaggcaagg gcctggagtg ggtggcactc atctcagatg acggaatgag gaaatatcat   180
tcaaactcca tgtggggccg agtcaccatc tccagagaca attccaagaa cactctttat   240
ctgcaattca gcagcctgaa agtcgaagac acggctatgt tcttctgtgc gagagaggct   300
ggtgggccaa tctggcatga cgacgtcaaa tattacgatt taatgacgg ctactacaac    360
taccactaca tggacgtctg gggcaagggg accacggtca ccgt                    404

SEQ ID NO: 609     moltype = DNA  length = 404
FEATURE            Location/Qualifiers
misc_feature       1..404
                   note = Description of Artificial Sequence: Synthetic
                   polynucleotide
source             1..404
                   mol_type = other DNA
                   organism = synthetic construct
SEQUENCE: 609
cacgaacaac tggtggaggc cggggggaggc gtggtccagc cggggggggtc cctgagactc    60
tcctgtttag cgtctggatt cacgtttcac aaatatggca tgcactgggt ccgccaggct   120
ccaggcaagg gcctggagtg ggtggcactc atctcagatg acggaatgag gaaatatcat   180
tcagactcca tgtggggccg agtcaccatc tccagagaca attccaagaa cactctttat   240
ctgcaattca gcagcctgag agtcgaagac acggctatgt tcttctgtgc gagagaggcc   300
ggtgggccaa tctggcatga cgacgtcaaa tattacgatt taatgacgg ctactacaac    360
tatcactaca tggacgtctg gggcaagggg accaaggtca ccgt                    404

SEQ ID NO: 610     moltype = DNA  length = 404
FEATURE            Location/Qualifiers
misc_feature       1..404
                   note = Description of Artificial Sequence: Synthetic
                   polynucleotide
source             1..404
                   mol_type = other DNA
                   organism = synthetic construct
SEQUENCE: 610
caggaaaaac tggtggagtc tggggggaggc gtggtccagc cggggggggtc cctgagactc    60
tcctgtttag cgtctggatt caccttcac aaatatggca tgcactgggt ccgccaggct   120
ccaggcaagg gcctggagtg ggtggcactc atctcagatg acggaatgag gaaatatcat   180
tcagactcca tgtggggccg agtcaccatc tccagagaca attccaagaa cactttttat   240
ctgcaattca gcagcctgaa agtcgaagac acggctatgt tcttctgtgc gagagaggct   300
ggtgggccaa tctggcatga cgacgtcaaa tattacgatt taatgacgg ctactacaat    360
taccactaca tggacgtctg gggcaagggg accattgtca ccgt                    404

SEQ ID NO: 611     moltype = DNA  length = 404
FEATURE            Location/Qualifiers
misc_feature       1..404
                   note = Description of Artificial Sequence: Synthetic
                   polynucleotide
source             1..404
                   mol_type = other DNA
                   organism = synthetic construct
SEQUENCE: 611
caggaaaaac tggtggagtc tggggggaggc gtggtccagc cggggggggtc cctgagactc    60
tcctgtttag cgtctggatt caccttcac aaatatggca tgcactgggt ccgccaggct   120
ccaggcaagg gcctggagtg ggtggcactc atctcagatg acggaatgag gaaatatcat   180
```

```
tcagactcca tgtggggccg agtcaccatc tccagagaca attccaagaa cactctatat    240
ctgcaattca gcagcctgaa agtcgaagac acggctatgt tcttctgtgc gagagaggct    300
ggtgggccaa tctggcatga cgacgtcaaa tattacgatt ttaatgacgg ctactacaac    360
taccactaca tggacgtctg gggcaagggg accacggtca ccgt                     404

SEQ ID NO: 612          moltype = DNA  length = 325
FEATURE                 Location/Qualifiers
misc_feature            1..325
                        note = Description of Artificial Sequence: Synthetic
                         polynucleotide
source                  1..325
                        mol_type = other DNA
                        organism = synthetic construct
SEQUENCE: 612
cagtctgccc tgactcagcc tgcctccgtg tctgggtctc ctggacagtc gatcaccatc    60
tcctgcaatg gaaccagcaa tgatgttggt ggctatgaat ctgtctcctg gtaccaacaa    120
catcccggca aagcccccaa agtcgtgatt tatgatgtca gtaaacgcc ctcagggggtt    180
tctaatcgct tctctggctc caagtccggc aacacggcct ccctgaccat ctctgggctc    240
caggctgagg acgagggtga ctattactgc aagtctctga caagcacgag acgtcgggtt    300
ttcggcactg ggaccaagct gaccg                                          325

SEQ ID NO: 613          moltype = DNA  length = 325
FEATURE                 Location/Qualifiers
misc_feature            1..325
                        note = Description of Artificial Sequence: Synthetic
                         polynucleotide
source                  1..325
                        mol_type = other DNA
                        organism = synthetic construct
SEQUENCE: 613
cagtctgccc tgactcagcc tgcctccgtg tctgggtctc ctggacagac gatcaccatc    60
tcctgcaatg gaaccagcag tgacgttggt ggatttgact ctgtctcctg gtaccaacaa    120
tccccaggga aagcccccaa agtcatggtt tttgatgtca gtcatcggcc ctcaggtatc    180
tctaatcgct tctctggctc caagtccggc aacacggcct ccctgaccat ctctgggctc    240
cacattgagg acgagggcga ttatttctgc tcttcactga cagacagaag ccatcgcata    300
ttcggcggcg ggaccaaggt gaccg                                          325

SEQ ID NO: 614          moltype = DNA  length = 325
FEATURE                 Location/Qualifiers
misc_feature            1..325
                        note = Description of Artificial Sequence: Synthetic
                         polynucleotide
source                  1..325
                        mol_type = other DNA
                        organism = synthetic construct
SEQUENCE: 614
cagtctgccc tgactcagcc tgcctccgtg tctgggtctc ctggacagac gatcaccatc    60
tcctgcaatg gaaccagcag tgacgttggt ggatttgact ctgtctcctg gtatcaacaa    120
tccccaggga aagcccccaa agtcatggtt tttgatgtca gtcatcggcc ctcaggtatc    180
tctaatcgct tctctggctc caagtccggc aacacggcct ccctgaccat ctctgggctc    240
cacattgagg acgagggcga ttatttctgc tcttcactga cagacagaag ccatcgcata    300
ttcggcggcg ggaccaaggt gaccg                                          325

SEQ ID NO: 615          moltype = DNA  length = 325
FEATURE                 Location/Qualifiers
misc_feature            1..325
                        note = Description of Artificial Sequence: Synthetic
                         polynucleotide
source                  1..325
                        mol_type = other DNA
                        organism = synthetic construct
SEQUENCE: 615
cagtctgccc tgactcagcc tgcctccgtg tctgggtctc ctggacagac gatcaccatc    60
tcctgcaatg gaaccagccg tgacgttggt ggatttgact ctgtctcctg gtatcaacaa    120
tccccaggga aagcccccaa agtcatggtt tttgatgtca gtcatcggcc ctcaggtatg    180
tctaatcgct tctctggctc caagtccggc aacacggcct ccctgaccat ttctgggctc    240
cacattgagg acgagggcga ttatttctgc tcttcattga cagacagaag ccatcgcata    300
ttcggcggcg ggaccaagct gaccg                                          325

SEQ ID NO: 616          moltype = DNA  length = 325
FEATURE                 Location/Qualifiers
misc_feature            1..325
                        note = Description of Artificial Sequence: Synthetic
                         polynucleotide
source                  1..325
                        mol_type = other DNA
                        organism = synthetic construct
SEQUENCE: 616
cagtctgccc tgactcagcc tgcctccgtg tctgggtctc ctggacagac gatcaccatc    60
```

```
tcctgcaatg gaaccagaag tgacgttggt ggatttgact ctgtctcctg gtaccaacaa   120
tccccaggga gagcccccaa agtcatggtt tttgatgtca gtcatcggcc ctcaggtatc   180
tctaatcgct tctctggctc caagtccggc aacacggcct ccctgaccat ctctgggctc   240
cacattgagg acgagggcga ttatttctgc tcttcactga cagacagaag ccatcgcata   300
ttcggcggcg ggaccaagct gaccg                                        325

SEQ ID NO: 617          moltype = DNA   length = 325
FEATURE                 Location/Qualifiers
misc_feature            1..325
                        note = Description of Artificial Sequence: Synthetic
                          polynucleotide
source                  1..325
                        mol_type = other DNA
                        organism = synthetic construct
SEQUENCE: 617
cagtctgccc tgactcagcc tgcctccgtg tctgggtctc ctggacagac gatcaccatc   60
tcctgcaatg gaaccagcag tgacgttggt ggatttgact ctgtctcctg gtatcaacaa   120
tccccaggga aagcccccaa agtcatggtt tttgatgtca gtcatcggcc ctcaggtatc   180
tctaatcgct tctctggctc caagtccggc aacacggcct ccctgaccat ctctgggctc   240
cacattgagg acgagggcga ttatttctgc tcttcactga cagacagaag ccatcgcata   300
ttcggcggcg ggaccaaggt gaccg                                        325

SEQ ID NO: 618          moltype = DNA   length = 325
FEATURE                 Location/Qualifiers
misc_feature            1..325
                        note = Description of Artificial Sequence: Synthetic
                          polynucleotide
source                  1..325
                        mol_type = other DNA
                        organism = synthetic construct
SEQUENCE: 618
cagtctgccc tgactcagcc tgcctccgtg tctgggtctc ctggacagac gatcaccatc   60
tcctgcaatg gaaccagaag tgacgttggt ggatttgact ctgtctcctg gtaccaacaa   120
tccccaggga aagcccccaa agtcatggtt tttgatgtca gtcatcggcc ctcaggtatc   180
tctaatcgct tctctggctc caagtccggc aacacggcct ccctgaccat ctctgggctc   240
cacattgagg acgagggcga ttatttctgc tcttcactga cagacagaag ccatcgcata   300
ttcggcggcg ggaccaaggt gaccg                                        325

SEQ ID NO: 619          moltype = AA   length = 134
FEATURE                 Location/Qualifiers
REGION                  1..134
                        note = Description of Artificial Sequence: Synthetic
                          polypeptide
source                  1..134
                        mol_type = protein
                        organism = synthetic construct
SEQUENCE: 619
QEKLVESGGG VVQPGGSLRL SCLASGFTFH KYGMHWVRQA PGKGLEWVAL ISDDGMRKYH   60
SDSMWGRVTI SRDNSKNTLY LQFSSLKVED TAMFFCAREA GGPIWHDDVK YYDFNDGYYN   120
YHYMDVWGKG TTVT                                                    134

SEQ ID NO: 620          moltype = AA   length = 134
FEATURE                 Location/Qualifiers
REGION                  1..134
                        note = Description of Artificial Sequence: Synthetic
                          polypeptide
source                  1..134
                        mol_type = protein
                        organism = synthetic construct
SEQUENCE: 620
QEKLVESGGG VVQPGGSLRL SCLASGFTFH KYGMHWVRQA PGKGLEWVAL ISDDGMRKYH   60
SDSMWGRVTI SRDNSKNTLY LQFSSLKVED TAMFFCAREA GGPIWHDDVK YYDFNDGYYN   120
YHYMDVWGKG TIVT                                                    134

SEQ ID NO: 621          moltype = AA   length = 134
FEATURE                 Location/Qualifiers
REGION                  1..134
                        note = Description of Artificial Sequence: Synthetic
                          polypeptide
source                  1..134
                        mol_type = protein
                        organism = synthetic construct
SEQUENCE: 621
HEQLVEAGGG VVQPGGSLRL SCLASGFTFH KYGMHWVRQA PGKGLEWVAL ISDDGMRKYH   60
SDSMWGRVTI SRDNSKNTLY LQFSSLRVED TAMFFCAREA GGPIWHDDVK YYDFNDGYYN   120
YHYMDVWGKG TKVT                                                    134

SEQ ID NO: 622          moltype = AA   length = 134
FEATURE                 Location/Qualifiers
```

```
REGION                  1..134
                        note = Description of Artificial Sequence: Synthetic
                             polypeptide
source                  1..134
                        mol_type = protein
                        organism = synthetic construct
SEQUENCE: 622
QEQLLESGGG VVQPGGSLRL SCLASGFTFH KYGMHWVRQA PGKGLEWVAL ISDDGMRKYH   60
SNSMWGRVTI SRDNSKNTLY LQFSSLKVED TAMFFCAREA GGPIWHDDVK YYDFNDGYYN  120
YHYMDVWGKG TTVT                                                   134

SEQ ID NO: 623          moltype = AA  length = 134
FEATURE                 Location/Qualifiers
REGION                  1..134
                        note = Description of Artificial Sequence: Synthetic
                             polypeptide
source                  1..134
                        mol_type = protein
                        organism = synthetic construct
SEQUENCE: 623
QEQLVESGGG VVQPGGSLRL SCLASGFTFH KYGMHWVRQA PGKGLEWVAL ISDDGMRKYH   60
SDSMWGRVTI SRDNSKNTLY LQFSSLKVED TAMFFCAREA GGPIWHDDVK YYDFNDGYYN  120
YHYMDVWGKG TTVT                                                   134

SEQ ID NO: 624          moltype = AA  length = 133
FEATURE                 Location/Qualifiers
REGION                  1..133
                        note = Description of Artificial Sequence: Synthetic
                             polypeptide
source                  1..133
                        mol_type = protein
                        organism = synthetic construct
SEQUENCE: 624
QRLVESGGGV VQPGSSLRLS CAASGFDFSR QGMHWVRQAP GQGLEWVAFI KYDGSEKYHA   60
DSVWGRLSIS RDNSKDTLYL QMNSLRVEDT ATYFCVREAG GPDYRNGYNY YDFYDGYYNY  120
HYMDVWGKGT TVT                                                    133

SEQ ID NO: 625          moltype = AA  length = 108
FEATURE                 Location/Qualifiers
REGION                  1..108
                        note = Description of Artificial Sequence: Synthetic
                             polypeptide
source                  1..108
                        mol_type = protein
                        organism = synthetic construct
SEQUENCE: 625
QSALTQPASV SGSPGQSITI SCNGTSNDVG GYESVSWYQQ HPGKAPKVVI YDVSKRPSGV   60
SNRFSGSKSG NTASLTISGL QAEDEGDYYC KSLTSTRRRV FGTGTKLT               108

SEQ ID NO: 626          moltype = AA  length = 108
FEATURE                 Location/Qualifiers
REGION                  1..108
                        note = Description of Artificial Sequence: Synthetic
                             polypeptide
source                  1..108
                        mol_type = protein
                        organism = synthetic construct
SEQUENCE: 626
QSALTQPASV SGSPGQTITI SCNGTSSDVG GFDSVSWYQQ SPGKAPKVMV FDVSHRPSGI   60
SNRFSGSKSG NTASLTISGL HIEDEGDYFC SSLTDRSHRI FGGGTKVT               108

SEQ ID NO: 627          moltype = AA  length = 108
FEATURE                 Location/Qualifiers
REGION                  1..108
                        note = Description of Artificial Sequence: Synthetic
                             polypeptide
source                  1..108
                        mol_type = protein
                        organism = synthetic construct
SEQUENCE: 627
QSALTQPASV SGSPGQTITI SCNGTSRDVG GFDSVSWYQQ SPGKAPKVMV FDVSHRPSGM   60
SNRFSGSKSG NTASLTISGL HIEDEGDYFC SSLTDRSHRI FGGGTKLT               108

SEQ ID NO: 628          moltype = AA  length = 108
FEATURE                 Location/Qualifiers
REGION                  1..108
                        note = Description of Artificial Sequence: Synthetic
                             polypeptide
source                  1..108
```

```
                            mol_type = protein
                            organism = synthetic construct
SEQUENCE: 628
QSALTQPASV SGSPGQTITI SCNGTRSDVG GFDSVSWYQQ SPGRAPKVMV FDVSHRPSGI    60
SNRFSGSKSG NTASLTISGL HIEDEGDYFC SSLTDRSHRI FGGGTKLT                108

SEQ ID NO: 629              moltype = AA   length = 108
FEATURE                     Location/Qualifiers
REGION                      1..108
                            note = Description of Artificial Sequence: Synthetic
                             polypeptide
source                      1..108
                            mol_type = protein
                            organism = synthetic construct
SEQUENCE: 629
QSALTQPASV SGSPGQTITI SCNGTRSDVG GFDSVSWYQQ SPGKAPKVMV FDVSHRPSGI    60
SNRFSGSKSG NTASLTISGL HIEDEGDYFC SSLTDRSHRI FGGGTKVT                108

SEQ ID NO: 630              moltype = DNA   length = 84
FEATURE                     Location/Qualifiers
misc_feature                1..84
                            note = Description of Artificial Sequence: Synthetic
                             oligonucleotide
source                      1..84
                            mol_type = other DNA
                            organism = synthetic construct
SEQUENCE: 630
gaggctggtg ggccaatctg gcatgacgac gtcaaatatt acgatttaa tgacggctac     60
tacaattacc actacatgga cgtc                                          84

SEQ ID NO: 631              moltype = AA   length = 230
FEATURE                     Location/Qualifiers
REGION                      1..230
                            note = Description of Artificial Sequence: Synthetic
                             polypeptide
source                      1..230
                            mol_type = protein
                            organism = synthetic construct
SEQUENCE: 631
MAWTFLLLGL LSHCTASVTS DISVAPGETA RISCGEKSLG SRAVQWYQHR AGQAPSLIIY    60
NNQDRPSGIP ERFSGSPDSP FGTTATLTIT SVEAGDEADY YCHIWDSRVP TKWVFGGGTT   120
LTVLGQPKAA PSVTLFPPSS EELQANKATL VCLISDFYPG AVTVAWKADS SPVKAGVETT   180
TPSKQSNNKY AASSYLSLTP EQWKSHKSYS CQVTHEGSTV EKTVAPTECS              230

SEQ ID NO: 632              moltype = AA   length = 6
FEATURE                     Location/Qualifiers
REGION                      1..6
                            note = Description of Artificial Sequence: Synthetic 6xHis
                             tag
source                      1..6
                            mol_type = protein
                            organism = synthetic construct
SEQUENCE: 632
HHHHHH                                                              6

SEQ ID NO: 633              moltype = DNA   length = 480
FEATURE                     Location/Qualifiers
misc_feature                1..480
                            note = Description of Artificial Sequence: Synthetic
                             polynucleotide
source                      1..480
                            mol_type = other DNA
                            organism = synthetic construct
SEQUENCE: 633
atggactgga tttggaggat cctcttcttg gtggcagcag ttgcaagtgc ccactcgcag    60
gtgcagctgg tgcagtctgg gccggaggtg aagaagcctg gtcctcagt gaaggtctcc   120
tgcaaggcct ctggaaacac cttcagtaaa tatgatgtcc actgggtacg acaggccact   180
ggacagggc ttgaatgggt gggatggatg agtcatgagg gtgataagac agaatctgca   240
cagagattta agggccgagt caccttcacg agggacactt ccgcaagcac agcctacatg   300
gaactgcgcg gcctgacatc tgacgacacg gccatctatt attgtacgag aggctcaaaa   360
catcgttttgc gagactacgt tctctacgat gactacggct taattaatta tcaagagtgg   420
aatgactacc ttgaatttttt ggacgtctgg ggccatggaa ccgcggtcac cgtctcctca   480

SEQ ID NO: 634              moltype = DNA   length = 480
FEATURE                     Location/Qualifiers
misc_feature                1..480
                            note = Description of Artificial Sequence: Synthetic
                             polynucleotide
source                      1..480
```

```
                      mol_type = other DNA
                      organism = synthetic construct
SEQUENCE: 634
atggactgga tttggaggat cctcttcttg gtggcagcag ttgcaagtgc ccactcgcag   60
gtgcagctgg tgcagtctgg gcctgaggtg aagaagcctg ggtcctcagt gaaggtctcc  120
tgcaaggcct ctggaaacac cttcagtaaa tatgatgtcc actgggtacg acaggccact  180
ggacaggggc ttgaatgggt gggatggatt agtcatgagc gtgataagac agaatctgca  240
cagagattta agggccgagt caccttcacg agggacactt ccgcaaccac agcctacatg  300
gaactgcgcg gcctgacatc tgacgacacg gccatttatt attgtacgag aggctcaaaa  360
catcgcttgc gagactacgt tctctacgat gactacggct taattaatta tcaagagtgg  420
aatgactacc ttgaattttt ggacgtctgg ggccatggaa ccgcggtcac cgtctcctca  480

SEQ ID NO: 635       moltype = DNA   length = 480
FEATURE              Location/Qualifiers
misc_feature         1..480
                     note = Description of Artificial Sequence: Synthetic
                      polynucleotide
source               1..480
                     mol_type = other DNA
                     organism = synthetic construct
SEQUENCE: 635
atggactgga tttggaggat cctcttcttg gtggcagcag ttgcaagtgc ccacgcgcag   60
gtgcagctgg agcagtctgg ggctgaggtg aagaagcctg ggtcctcagt gaaggtctcc  120
tgcaaggcct ctggaaacac cttcagtaaa tatgatgtcc actgggtacg acaggccact  180
ggacaggggc ttgaatgggt gggatggatg agtcatgagg tgataagac agaatctgca  240
cagagattta agggccgagt caccttcacg agggacactt ccgcaagcac agcctacatg  300
gaactgcgcg gcctgacatc tgacgacacg gccatttatt attgtacgag aggttcaaaa  360
catcgcttgc gagactacgt tctctacgat gactacggct taattaatta tcaagagtgg  420
aatgactacc ttgaattttt ggacgtctgg ggccatggaa ccgcggtcac cgtctcctca  480

SEQ ID NO: 636       moltype = DNA   length = 480
FEATURE              Location/Qualifiers
misc_feature         1..480
                     note = Description of Artificial Sequence: Synthetic
                      polynucleotide
source               1..480
                     mol_type = other DNA
                     organism = synthetic construct
SEQUENCE: 636
atggactgga tttggaggat cctcttcttg gtggcagcag ttgcaagtgc ccactcgcag   60
gtgcagctgg tgcagtctgg ggctgaggtg aagaagcctg ggtcctcagt gaaggtctcc  120
tgcaaggcct ctggaaacac cttcaggaaa tatgatgtcc actgggtacg acaggccact  180
ggacaggggc ttgaatgggt gggatggatg agtcatgagg gtgataagac agaatctgca  240
cagagattta agggccgagt ctctttcacg agggacaatt ccgcaagcac agcctacatt  300
gaactgcgcg gcctgacatc tgacgacacg gccatttatt attgtaccgg aggctcaaaa  360
catcgcttgc gagactacgt tctctacgat gattacggcc taataaatca gcaagagtgg  420
aatgactacc ttgaattttt ggacgtctgg ggccatggaa ccgcggtcac cgtctcctca  480

SEQ ID NO: 637       moltype = DNA   length = 396
FEATURE              Location/Qualifiers
misc_feature         1..396
                     note = Description of Artificial Sequence: Synthetic
                      polynucleotide
source               1..396
                     mol_type = other DNA
                     organism = synthetic construct
SEQUENCE: 637
atgaggctcc ctgctcagct cctggggctg ctaatgctct gggtctctgg atccagtgcg   60
gatactgtcg tgactcagtc tccactctcc ctgcccgtca cccctggaga ggcggcctcc  120
atgtcctgtt cgtcgactca gagcctccgt catagtaatg agccaacta tttggcttgg  180
tatcagcaca aaccgggca gtctccacga ctcctaatcc gtttaggttc tcaacgggcc  240
tccggggtcc ctgacagatt cagtggcagt ggatcaggca ctcatttac actgaaaatc  300
agtagagtgg aggctgaaga tgctgcaatt tattattgca tgcaaggtct gaaccgtccc  360
tggacgttcg gcaaggggac caagttggaa atcaaa                            396

SEQ ID NO: 638       moltype = DNA   length = 396
FEATURE              Location/Qualifiers
misc_feature         1..396
                     note = Description of Artificial Sequence: Synthetic
                      polynucleotide
source               1..396
                     mol_type = other DNA
                     organism = synthetic construct
SEQUENCE: 638
atgaggctcc ctgctcagct cctggggctg ctaatgctct gggtctctgg atccagtgcg   60
gatactgtcg tgactcagtc tccactctcc ctgcccgtca cccctggaga ggcggcctcc  120
atgtcctgta cgtcgactca gagcctccgt catagtaatg agccaacta tttggcttgg  180
taccagcaca aaccagggca gtctccacga ctcctaatcc gtttaggttc tcaacgggcc  240
tccggggtcc ctgacagatt cagtggcagt ggatcaggca ctcatttac actgaaaatc  300
```

```
                                                -continued
agtcgagtgg agcctgaaga tgctgcaatt tattattgca tgcaaggtct gaaccgtccc    360
tggacgttcg gcaaggggac caagttggaa atcaaa                              396

SEQ ID NO: 639          moltype = DNA  length = 396
FEATURE                 Location/Qualifiers
misc_feature            1..396
                        note = Description of Artificial Sequence: Synthetic
                         polynucleotide
source                  1..396
                        mol_type = other DNA
                        organism = synthetic construct
SEQUENCE: 639
atgaggctcc ctgctcagct cctggggctg ctaatgctct ggtctctgga atccagtgcg    60
gatactgtcg tgactcagtc tccactctcc ctgtccgtca cccctggaga ggcggcctcc    120
atgtcctgta cgtcgactca gagcctccgg catagtaatg gagccaacta tttggcttgg    180
taccagcaca aaccagggca gtctccacga ctcctaatcc gtttaggttc tcaacgggcc    240
tccggggtcc ctgacagatt cagtggcagt ggatcaggca ctcatttac actgaaaatc     300
agtagagtgg aggctgacga tgctgcaatt tattattgca tgcaaggtct gaaccgtccc    360
tggacgttcg gcaaggggac caagttggag atcaaa                              396

SEQ ID NO: 640          moltype = DNA  length = 405
FEATURE                 Location/Qualifiers
misc_feature            1..405
                        note = Description of Artificial Sequence: Synthetic
                         consensus sequence
source                  1..405
                        mol_type = other DNA
                        organism = synthetic construct
SEQUENCE: 640
caggaacaac tggtggagtc tgggggaggc gtggtccagc cggggggggtc cctgagactc    60
tcctgtttag cgtctggatt cacatttcac aaatatggca tgcactgggt ccgccaggct    120
ccaggcaagg gcctgagtg gtggcactc atctcagatg acggaagtga ggaaatatca      180
ttcagactcc atgtggggcc gagtcaccat ctccagagac aattccaaga acactcttta    240
tctgcaattc agcagcctga aagtcgaaga cacggctatg ttcttctgtg cgagagaggc    300
tggtgggcca atctggcatg acgacgtcaa atattacgat tttaatgacg gctactacaa    360
ctaccactac atggacgtct ggggcaaggg gaccacggtc accgt                    405

SEQ ID NO: 641          moltype = DNA  length = 325
FEATURE                 Location/Qualifiers
misc_feature            1..325
                        note = Description of Artificial Sequence: Synthetic
                         consensus sequence
source                  1..325
                        mol_type = other DNA
                        organism = synthetic construct
SEQUENCE: 641
cagtctgccc tgactcagcc tgcctccgtg tctgggtctc ctggacagac gatcaccatc    60
tcctgcaatg gaaccagcag tgacgttggt ggatttgact ctgtctcctg gtaccaacaa    120
tccccaggga aagcccccaa agtcatggtt tttgatgtca gtcatcggcc tcaggtatc     180
tctaatcgct tctctggctc caagtccggc aacacggcct ccctgaccat ctctgggctc    240
cacattgagg acgagggcga ttatttctgc tcttcactga cagacagaag ccatcgcata    300
ttcggcggcg ggaccaagst gaccg                                          325

SEQ ID NO: 642          moltype = AA  length = 134
FEATURE                 Location/Qualifiers
REGION                  1..134
                        note = Description of Artificial Sequence: Synthetic
                         consensus sequence
source                  1..134
                        mol_type = protein
                        organism = synthetic construct
VARIANT                 3
                        note = X can be K, Q or R
SEQUENCE: 642
QEXLVESGGG VVQPGGSLRL SCLASGFTFH KYGMHWVRQA PGKGLEWVAL ISDDGMRKYH     60
SDSMWGRVTI SRDNSKNTLY LQFSSLKVED TAMFFCAREA GGPIWHDDVK YYDFNDGYYN    120
YHYMDVWGKG TTVT                                                      134

SEQ ID NO: 643          moltype = AA  length = 108
FEATURE                 Location/Qualifiers
REGION                  1..108
                        note = Description of Artificial Sequence: Synthetic
                         consensus sequence
source                  1..108
                        mol_type = protein
                        organism = synthetic construct
VARIANT                 107
                        note = X can be L or V
SEQUENCE: 643
```

```
QSALTQPASV SGSPGQTITI SCNGTSSDVG GFDSVSWYQQ SPGKAPKVMV FDVSHRPSGI    60
SNRFSGSKSG NTASLTISGL HIEDEGDYFC SSLTDRSHRI FGGGTKXT                108
```

| SEQ ID NO: 644 | moltype = DNA   length = 444 |
|---|---|
| FEATURE | Location/Qualifiers |
| misc_feature | 1..444 |
| | note = Description of Artificial Sequence: Synthetic consensus sequence |
| source | 1..444 |
| | mol_type = other DNA |
| | organism = synthetic construct |

```
SEQUENCE: 644
cagytgcagy tgcaggagtc gggcccagga ctggtgaagc cttcggagac cctgtccctc    60
acktgcastg tgtctggtgm ctccatragg ggyrscgact ggggcgakaa tgattattac   120
tggggctgga tccgscagtc cccagggaag ggrctggagt ggattgggag tttgtcatat   180
stcgcagagt cattasagsg gsggstmcac cmactacaac ccgtccctca agagtcgagt   240
caccttgtcg wtmgacacgt ccaaraatca ggtctccctg aggctkabyt ctgtgaccgc   300
cgcggacacg gccatmtact attgtgcgcg awcactdcac ggacggagaa wtcatggtrt   360
wtttgccttc aaagagtggt yccymtwccg ggctggwtca acgtctgggg ccaggaath   420
chggtcaccg tctccwsctc ctca                                         444
```

| SEQ ID NO: 645 | moltype = AA   length = 147 |
|---|---|
| FEATURE | Location/Qualifiers |
| REGION | 1..147 |
| | note = Description of Artificial Sequence: Synthetic consensus sequence |
| source | 1..147 |
| | mol_type = protein |
| | organism = synthetic construct |
| VARIANT | 2 |
| | note = X can be V,L,S,P or M |
| VARIANT | 23 |
| | note = X can be S,T,N |
| VARIANT | 27 |
| | note = X can be A,T,D,E or G |
| VARIANT | 30 |
| | note = X can be S,R,N,A or G |
| VARIANT | 32 |
| | note = X can be G,T or not present |
| VARIANT | 33 |
| | note = X can be E,D or not present |
| VARIANT | 36 |
| | note = X can be A,T,D,E or not present |
| VARIANT | 37 |
| | note = X can be G,K,N,C or not present |
| VARIANT | 39 |
| | note = X can be S,N,A,Y or F |
| VARIANT | 40 |
| | note = X can be Y,H or F |
| VARIANT | 57 |
| | note = X can be Y,G,S or H |
| VARIANT | 58 |
| | note = X can be V,L or I |
| VARIANT | 60 |
| | note = X can be K,D,H,Y or W |
| VARIANT | 61 |
| | note = X can be S,C,T or R |
| VARIANT | 63 |
| | note = X can be G,S,R or not present |
| VARIANT | 65 |
| | note = X can be Y,W or not present |
| VARIANT | 64 |
| | note = X can be Y,F or not present |
| VARIANT | 66 |
| | note = X can be N,G or not present |
| VARIANT | 67 |
| | note = X can be S,T or not present |
| VARIANT | 69 |
| | note = X can be D,W,A or T |
| VARIANT | 71 |
| | note = X can be N,Y,F,L or H |
| VARIANT | 73 |
| | note = X can be S,I,N or K |
| VARIANT | 82 |
| | note = X can be L,F,I or M |
| VARIANT | 90 |
| | note = X can be Q,L,E,R or W |
| VARIANT | 94 |
| | note = X can be S,R,K or T |

```
VARIANT                 96
                        note = X can be V,T,N,S or A
VARIANT                 97
                        note = X can be A,G,D,S,N or F
VARIANT                 105
                        note = X can be K,I,V or T
VARIANT                 111
                        note = X can be T,A,F,S or H
VARIANT                 112
                        note = X can be L,K,D,G or R
VARIANT                 115
                        note = X can be R,K,H or not present
VARIANT                 116
                        note = X can be R,D or not present
VARIANT                 118
                        note = X can be Y,F or not present
VARIANT                 119
                        note = X can be E,G,D,M or R
VARIANT                 120
                        note = X can be I,V or L
VARIANT                 122
                        note = X can be A,V,Y or P
VARIANT                 123
                        note = X can be F,L,Y,I or V
VARIANT                 124
                        note = X can be N,K,G,H,Y or A
VARIANT                 125
                        note = X can be E,D,H or G
VARIANT                 137
                        note = X can be N,K,R,P or Q
VARIANT                 139
                        note = X can be T,I or not present
VARIANT                 140
                        note = X can be L,P or not present
VARIANT                 141
                        note = X can be T,V,I or L
VARIANT                 142
                        note = X can be Q,S,A,T,H or L
SEQUENCE: 645
QXQLQESGPG LVKPSETLSL TCXVSGXSIX GXXWGXXDXX WGWIRQSPGK GLEWIGXXHX   60
XGXXXXXGXT XYXPSLKSRV TXSLDTSKNX VSLXLXXVTA ADTAXYYCAR XXHGXXIXXX  120
VXXXXWFTYF YMDVWGXGXX XXVTVSS                                     147

SEQ ID NO: 646          moltype = DNA  length = 354
FEATURE                 Location/Qualifiers
misc_feature            1..354
                        note = Description of Artificial Sequence: Synthetic
                         consensus sequence
source                  1..354
                        mol_type = other DNA
                        organism = synthetic construct
SEQUENCE: 646
gaaattgtga tgacgcagtc tccmsmcwcc stgtctgtgt ctccaggaga gacagccacr   60
atctcctgta gggmcagwca gcattgacat tggcggtagb aarwmtgtak cctggtacca  120
acasaarccw ggccaggccc ccasrctcat catytttgat amywataacc ggccckcagg  180
trtccctgas cgrttctctg gctccctga ctccsgttct gggacmacgg ccactctgac   240
catcaccagt gtccagkccg argatgaggc mgactattac tgcagttcay mtataggaag  300
agtggmgktc ccaccaatyg gatsttcggc ggagggacca agtgaccgt cwta          354

SEQ ID NO: 647          moltype = AA  length = 116
FEATURE                 Location/Qualifiers
REGION                  1..116
                        note = Description of Artificial Sequence: Synthetic
                         consensus sequence
source                  1..116
                        mol_type = protein
                        organism = synthetic construct
VARIANT                 9
                        note = X can be S,T,P or D
VARIANT                 10
                        note = X can be D,F,S or T
VARIANT                 11
                        note = X can be I,V,M,A or L
VARIANT                 24
                        note = X can be G,T,N or R
VARIANT                 25
                        note = X can be E,K,G or A
VARIANT                 26
                        note = X can be K,E,T or S
```

```
VARIANT         28
                note = X can be L,I,N,T or S
VARIANT         29
                note = X can be G,D,I,V or not present
VARIANT         30
                note = X can be S,I,N,L or not present
VARIANT         34
                note = X can be R,N or K
VARIANT         35
                note = X can be A,S,F or N
VARIANT         37
                note = X can be Q,I,S or A
VARIANT         41
                note = X can be H,Q,Y or L
VARIANT         42
                note = X can be R,K,H or F
VARIANT         48
                note = X can be S,K or R
VARIANT         53
                note = X can be N,G,E or D
VARIANT         54
                note = X can be N,V,T or A
VARIANT         55
                note = X can be Q,N,D,Y or S
VARIANT         56
                note = X can be D,K or S
VARIANT         59
                note = X can be S,A,P or G
VARIANT         61
                note = X can be I,V or F
VARIANT         63
                note = X can be E,D,G or A
VARIANT         69
                note = X can be P,K,R or G
VARIANT         70
                note = X can be D,G,S or Y
VARIANT         72
                note = X can be P,T,R or not present
VARIANT         82
                note = X can be T,S or N
VARIANT         83
                note = X can be S,N,G or R
VARIANT         86
                note = X can be A,T or S
VARIANT         87
                note = X can be G,E or D
VARIANT         95
                note = X can be H,S,G or Q
VARIANT         96
                note = X can be I,S or Q
VARIANT         97
                note = X can be W,Y or L
VARIANT         98
                note = X can be D,V,F or E
VARIANT         99
                note = X can be S,A,G or E
VARIANT         100
                note = X can be R,N or W
VARIANT         101
                note = X can be V,R,G,P or not present
VARIANT         104
                note = X can be K,N,D or not present
VARIANT         105
                note = X can be W,V or R
VARIANT         106
                note = X can be V,I or not T
VARIANT         109
                note = X can be G,E,R or Q
SEQUENCE: 647
EIVMTQSPXX XSVSPGETAT ISCXXXSXXX GGWXXVXWYQ XXPGQAPXLI IFXXXXRPXG    60
XPXRFSGSXX SXFGTTATLT IXXVQXXDEA DYYCXXXXXX XPTXXXFGXG TKLTVL       116

SEQ ID NO: 648         moltype = DNA  length = 480
FEATURE                Location/Qualifiers
misc_feature           1..480
                       note = Description of Artificial Sequence: Synthetic
                        consensus sequence
source                 1..480
                       mol_type = other DNA
```

```
                        organism = synthetic construct
SEQUENCE: 648
atggactgga tttggaggat cctcttcttg gtggcagcag ttgcaagtgc ccactcgcag    60
gtgcagctgg tgcagtctgg gcctgaggtg aagaagcctg gtcctcagt gaaggtctcc   120
tgcaaggcct ctggaaacac cttcagtaaa tatgatgtcc actgggtacg acaggcccact  180
ggacaggggc ttgaatgggg gggatggatg agtcatgagg gtgataagac agaatctgca   240
cagagattta agggccgagt caccttcacg agggacactt ccgcaagcac agcctacatg   300
gaactgcgcg gcctgacatc tgacgacacg gccatttatt attgtacgag aggctcaaaa   360
catcgcttgc gagactacgt tctctacgat gactacggct aattaatta tcaagagtgg    420
aatgactacc ttgaattttt ggacgtctgg ggccatggaa ccgcggtcac cgtctcctca    480

SEQ ID NO: 649         moltype = AA  length = 141
FEATURE                Location/Qualifiers
REGION                 1..141
                       note = Description of Artificial Sequence: Synthetic
                         consensus sequence
source                 1..141
                       mol_type = protein
                       organism = synthetic construct
SEQUENCE: 649
QVQLVQSGPE VKKPGSSVKV SCKASGNTFS KYDVHWVRQA TGQGLEWVGW MSHEGDKTES    60
AQRFKGRVTF TRDTSASTAY MELRGLTSDD TAIYYCTRGS KHRLRDYVLY DDYGLINYQE   120
WNDYLEFLDV WGHGTAVTVS S                                             141

SEQ ID NO: 650         moltype = DNA  length = 396
FEATURE                Location/Qualifiers
misc_feature           1..396
                       note = Description of Artificial Sequence: Synthetic
                         consensus sequence
source                 1..396
                       mol_type = other DNA
                       organism = synthetic construct
SEQUENCE: 650
atgaggctcc ctgctcagct cctggggctg ctaatgctct gggtctctgg atccagtgcg    60
gatactgtcg tgactcagtc tccactctcc ctgcccgtca cccctggaga ggcggcctcc   120
atgtcctgtt cgtcgactca gagcctccgg catagtaatg gagccaacta tttggcttgg   180
tatcagcaca aaccggggca gtctccacga ctcctaatcc gtttaggttc tcaacgggcc   240
tccgggtcc ctgacagatt cagtggcagt ggatcaggca ctcattttac actgaaaatc    300
agtagagtgg aggctgaaga tgctgcaatt tattattgca tgcaaggtct gaaccgtccc   360
tggacgttcg gcaaggggac caagttggaa atcaaa                             396

SEQ ID NO: 651         moltype = AA  length = 112
FEATURE                Location/Qualifiers
REGION                 1..112
                       note = Description of Artificial Sequence: Synthetic
                         consensus sequence
source                 1..112
                       mol_type = protein
                       organism = synthetic construct
SEQUENCE: 651
DTVVTQSPLS LPVTPGEAAS MSCSSTQSLR HSNGANYLAW YQHKPGQSPR LLIRLGSQRA    60
SGVPDRFSGS GSGTHFTLKI SRVEAEDAAI YYCMQGLNRP WTFGKGTKLE IK           112

SEQ ID NO: 652         moltype = DNA  length = 71
FEATURE                Location/Qualifiers
source                 1..71
                       mol_type = other DNA
                       organism = synthetic construct
modified_base          30
                       mod_base = i
modified_base          49
                       mod_base = i
SEQUENCE: 652
gtattcgccg accagtgcac gtttaattgn gacggtgcag atggcaatnt cgaacgatgg    60
tacctttttt a                                                         71

SEQ ID NO: 653         moltype = DNA  length = 405
FEATURE                Location/Qualifiers
source                 1..405
                       mol_type = other DNA
                       organism = synthetic construct
SEQUENCE: 653
caggaacaac tggtggagtc tgggggaggc gtggtccagc cggggggggtc cctgagactc    60
tcctgtttag cgtctggatt cacatttcac aaatatggca tgcactgggt ccgccaggct   120
ccaggcaagg gcctggagtg ggtggcactc atctcagatg acggaagtga ggaaatatca   180
ttcagactcc atgtggggcc gagtcaccat ctccagagac aattccaaga acactctta    240
tctgcaattc agcagcctga aagtcgaaga cacggctatg ttcttctgtg cgagagaggc   300
tggtgggcca atctggcatg acgacgtcaa atattacgat tttaatgacg gctactacaa   360
ctaccactac atggacgtct ggggcaaggg gaccacggtc accgt                   405
```

```
SEQ ID NO: 654          moltype = DNA  length = 41
FEATURE                 Location/Qualifiers
source                  1..41
                        mol_type = other DNA
                        organism = synthetic construct
SEQUENCE: 654
ttcaacatcc gaaaaggtgg ctcaaagtag cgagggtact c                          41

SEQ ID NO: 655          moltype = DNA  length = 324
FEATURE                 Location/Qualifiers
source                  1..324
                        mol_type = other DNA
                        organism = synthetic construct
SEQUENCE: 655
cagtctgccc tgactcagcc tgcctccgtg tctgggtctc ctggacagac gatcaccatc      60
tcctgcaatg gaaccagcat gacgttggtg gatttgactc tgtctcctgg taccaacaat    120
ccccagggaa agccccaaa gtcatggttt ttgatgtcag tcatcggccc tcaggtatct     180
ctaatcgctt ctctggctcc aagtccggca cacggcccc cctgaccatc tctgggctcc    240
acattgagga cgagggcgat tatttctgct cttcactgac agacagaagc catcgcatat    300
tcggcggcgg gaccaagstg accg                                            324

SEQ ID NO: 656          moltype = AA  length = 5
FEATURE                 Location/Qualifiers
source                  1..5
                        mol_type = protein
                        organism = synthetic construct
SEQUENCE: 656
HQARK                                                                   5

SEQ ID NO: 657          moltype = AA  length = 32
FEATURE                 Location/Qualifiers
source                  1..32
                        mol_type = protein
                        organism = synthetic construct
SEQUENCE: 657
RSADSRQQFK YSEAVLSDMN RTYVDYRNGY NY                                    32

SEQ ID NO: 658          moltype = AA  length = 134
FEATURE                 Location/Qualifiers
source                  1..134
                        mol_type = protein
                        organism = synthetic construct
VARIANT                 3
                        note = X can be any Amino Acid
SEQUENCE: 658
QEXLVESGGG VVQPGGSLRL SCIASGFTFH KYGMHWVRQA PGKGLEWVAI ISDDGMRKYH      60
SDSMWGRVTL SRDNSKNTLY LQFSSLKVED TAMFFCAREA GGPIWHDDVK YYDFNDGYYN     120
YHYMDVWGKG TTVT                                                       134

SEQ ID NO: 659          moltype = AA  length = 21
FEATURE                 Location/Qualifiers
source                  1..21
                        mol_type = protein
                        organism = synthetic construct
SEQUENCE: 659
SNYEHVIYKV QAYKSTRRVT L                                                21

SEQ ID NO: 660          moltype = AA  length = 108
FEATURE                 Location/Qualifiers
source                  1..108
                        mol_type = protein
                        organism = synthetic construct
VARIANT                 107
                        note = X can be any Amino Acid
SEQUENCE: 660
QSALTQPASV SGSPGQTITI SCNGTSSDVG GFDSVSWYQQ SPGKAPKVMV FDVSHRPSGI      60
SNRFSGSKSG NTASLTISGL HIEDEGDYFC SSLTDRSHRI FGGGTKXT                  108

SEQ ID NO: 661          moltype = AA  length = 19
FEATURE                 Location/Qualifiers
source                  1..19
                        mol_type = protein
                        organism = synthetic construct
SEQUENCE: 661
FGGEVVVYRD WPKPAWVDL                                                   19

SEQ ID NO: 662          moltype = DNA  length = 396
FEATURE                 Location/Qualifiers
```

```
source                  1..396
                        mol_type = other DNA
                        organism = synthetic construct
SEQUENCE: 662
cagatgcagt tacaggagtc gggccccgga ctggtgaagc cttcggaaac cctgtccctc    60
acgtgcagtg tgtctggtgc ctccataagt gacagttact ggagctggat ccggcggtcc   120
ccagggaagg gacttgagtg gattgggtat gtccacaaaa gcggcgacac aaattacagc   180
ccctccctca agagtcgagt caacttgtcg ttagacacgt ccaaaaatca ggtgtccctg   240
agccttgtgg ccgcgaccgc tgcggactcg ggcaaatatt attgcgcgag aacactgcac   300
gggaggagaa tttatggaat cgttgccttc aatgagtggt tcacctactt ctacatggac   360
gtctggggca atgggactca ggtcaccgtc tcctca                             396

SEQ ID NO: 663          moltype = DNA  length = 396
FEATURE                 Location/Qualifiers
source                  1..396
                        mol_type = other DNA
                        organism = synthetic construct
SEQUENCE: 663
cagatgcagt tacaggagtc gggccccgga ctggtgaagc cttcggaaac cctgtccctc    60
acgtgcagtg tgtctggtgc ctccataagt gacagttact ggagctggat ccggcggtcc   120
ccagggaagg gacttgagtg gattgggtat gtccacaaaa gcggcgacac aaattacatc   180
ccctccctca agagtcgagt caacttgtcg ttagacacgt ccaaaaatca ggtgtccctg   240
agccttgtgg ccgcgaccgc tgcggactcg ggcaaatatt attgcgcgag aacactgcac   300
gggaggagaa tttatggaat cgttgccttc aatgagtggt tcacctactt ctacatggac   360
gtctggggca atgggactca ggtcaccgtc tcctca                             396

SEQ ID NO: 664          moltype = DNA  length = 396
FEATURE                 Location/Qualifiers
source                  1..396
                        mol_type = other DNA
                        organism = synthetic construct
SEQUENCE: 664
caggttcatc tgcaggagtc gggccccgga ctggtgaagc cttcggagac cctgtccctc    60
acgtgcaatg tgtctgggac cctcgtgcgt gataactact ggagctggat cagacaaccc   120
ctcggggaagc aacctgagtg gattggctat gtccatgaca gcggggacac gaattacaac   180
ccctccctga agagtcgagt ccacttatcg ttggacaagt ccaaaaacct ggtgtccctg   240
aggctgaccg gcgtgaccgc cgcggactcg gccatatatt attgcgcgac aacaaaacac   300
gggaggagga tttatggcgt cgttgccttc aaagagtggt tcacctattt ctacatggac   360
gtctggggca aagggacttc ggtcaccgtc tcctca                             396

SEQ ID NO: 665          moltype = DNA  length = 396
FEATURE                 Location/Qualifiers
source                  1..396
                        mol_type = other DNA
                        organism = synthetic construct
SEQUENCE: 665
cagctgcacc tgcaggagtc gggcccaggg ctggtgaagc ctccggagac cctgtccctc    60
acgtgtagtg tgtctggcgc ctccatcaat gatgccattt ggagttggat tcggcagtcc   120
ccagggaagc ggcctgagtg ggttggatat gtccatcaca gcggtgacac aaattataat   180
ccctcactca agaggcgcgt cacgttttca ttagacacgg ccaagaatga agtgtccctg   240
aaattagtag acctgaccgc tgcggactcg gccacatatt tttgtgcgcg agcacttcac   300
gggaagagga tttatgggat agttgccctc ggagagttgt tcacctactt ctacatggac   360
gtctggggca aggggactgc ggtcaccgtc tcctca                             396

SEQ ID NO: 666          moltype = DNA  length = 411
FEATURE                 Location/Qualifiers
source                  1..411
                        mol_type = other DNA
                        organism = synthetic construct
SEQUENCE: 666
cagccgcagc tgcaggagtc ggggccagga ctggtgaggg cttcggagac cctgtccctc    60
acctgcactg tgtccggcga ctccactgct gcttgtgact atttctgggg ctgggtccgg   120
cagccccag ggaagggcct ggagtggatt ggggtttgt cacattgtgg aggttactac     180
aatactggct ggacctacca caacccgtct ctcaagagtc ggctcacgat ttcactcgac   240
accccaaga atcaggtctt cctgaagtta aattctgtga ccgccgcgga cacggccatt   300
tactactgtg cgcgattcga cggcgaagtt ttggtgtacc acgattggcc aaagccggcc   360
tgggtggacc tctgggccg gggaactttg gtcaccgtca ccgtctcctc a             411

SEQ ID NO: 667          moltype = DNA  length = 412
FEATURE                 Location/Qualifiers
source                  1..412
                        mol_type = other DNA
                        organism = synthetic construct
SEQUENCE: 667
cagtcgcagc tgcaggagtc gggcccacga ctggtgaggg cctcggagac cctgtcactc    60
acgtgcaatg tgtccggcga gtccactggt gcctgtactt atttctgggg ctgggtccgg   120
caggccccag gaaggggct ggagtggatc gggagtttgt cccattgtca gagtttctgg   180
ggttccggtt ggaccttcca caaccgtctc tcaagagtc gactcacgat ttcactcgac   240
acgcccaaga atcaggtctt cctcaagctc acttctctga ctgccgcgga cacggccact   300
```

```
tactactgtg cgcgattcga cggcgaagtc ttggtctata atcattggcc aaagccggcc    360
tgggtcgacc tcttggggcc gcggaatacc ggtcaccgtc accgtctcct ca            412

SEQ ID NO: 668          moltype = DNA   length = 387
FEATURE                 Location/Qualifiers
source                  1..387
                        mol_type = other DNA
                        organism = synthetic construct
SEQUENCE: 668
caggtgcagc tgcaggagtc gggcccagga ctggtgaagc ctgcggagac cctgtccctc    60
acctgcagtg tctctggaga atctatcaat actggtcatt actactgggg ctgggtccgt    120
caggtcccag ggaagggact tgagtggata ggtcatatcc attatacgac ggctgtcctg    180
cacaacccgt ccctcaagag tcgactcacc atcaaaattt cacgttgag aaaccagatt     240
accctgaggc tcagtaatgt gacggccgcg gacacggccg tctatcactg cgtacgatcc    300
ggcggcgaca tcttatatta ttatgagtgg caaaagccgc actggttctc tccctggggc    360
ccgggaatcc acgtcaccgt ctcgagc                                        387

SEQ ID NO: 669          moltype = DNA   length = 399
FEATURE                 Location/Qualifiers
source                  1..399
                        mol_type = other DNA
                        organism = synthetic construct
SEQUENCE: 669
cagttgcaga tgcaggagtc gggcccagga ctggtgaagc cttcggagac cctgtctctg    60
agttgcactg tctctggtga ctccataagg ggtggcgagt ggggcgataa agattatcat    120
tggggctggg tccgccactc agcaggaaag ggcctggag ggattgggag tatccattgg     180
aggggaccca cccactacaa agagtccctc aggagaagag tgagtatgtc gatcgacacg    240
tccaggaatt ggttctccct gaggctggcc tctgtgaccg ccgcggacac ggccgtctac    300
ttttgtgcga gacaccgaca tcatgatgtt ttcatgttgg tccctattgc gggctggttc    360
gacgtctggg gcccgggagt ccaggtcacc gtctcgagc                           399

SEQ ID NO: 670          moltype = DNA   length = 365
FEATURE                 Location/Qualifiers
source                  1..365
                        mol_type = other DNA
                        organism = synthetic construct
SEQUENCE: 670
cagttgcaga tgcaggagtc gggcccagga ctggtgaagc cttcggagac cctgtctctg    60
agttgcactg tctctggtga ctccataagg ggtggcgagt ggggcgataa agattatcat    120
tggggctggg tccgccactc agcaggaaag ggaccaccca ctacaaagag tccctcagga    180
gaagagtgag tatgtcgatc gacacgtcca ggaattggtt ctccctgagg ctggcctctg    240
tgaccgccgc ggacacggcc gtctactttt gtgcgagaca ccgacatcat gatgtttca    300
tgttggtccc tattgcgggc tggttcgacg tctggggccc gggagtccag gtcaccgtct    360
cgagc                                                                365

SEQ ID NO: 671          moltype = DNA   length = 401
FEATURE                 Location/Qualifiers
source                  1..401
                        mol_type = other DNA
                        organism = synthetic construct
SEQUENCE: 671
cagctgcagt tgcaggaatc gggccaggac tggtgaagcc ttcggagacc ctgtccctga    60
cttgcacagt ttctggtggc tccatgaggg gcaccgactg gggcgagaat gacttccact    120
acggctggat ccgccagtcc tccgcaaagg ggctggagtg gattgggagc atccattgga    180
ggggaggac cacccactac aagacgtcct tcaggagtcg ggcccacctt gctagcac        240
cgtccaataa tcgcttctcc ctgacgttta gttttgtgca cgccgcggac acggccgtct    300
actattgtgc gagacataaa tatcatgata ttttcagggt ggtccctgtt gcgggctggt    360
tcgaccctg gggccaggga ttactggtca ccgtctcgag c                         401

SEQ ID NO: 672          moltype = DNA   length = 498
FEATURE                 Location/Qualifiers
source                  1..498
                        mol_type = other DNA
                        organism = synthetic construct
SEQUENCE: 672
cagctgcagt tgcaggaatc gggcccagga ctcgtgaagc cttcggagac cctgtccctg    60
acttgcacag tttctggtgg ctccatgagg ggcaccgact ggggcgagaa tgacttccac    120
tacggctgga tccgccagtc ctccgcaaag gggctggagt ggacagttc tgctggctcc    180
atgaggggca cccgactggg cgagaatgac ttccactgga tcggatccg ccagtcctcc    240
gcaaagggc tggagtggat tgggagcatc cattggaggg ggaggaccac ccactacaag    300
acgtccttca ggagtcgggc caccttgtcg atagacacgt ccaataatcg cttctccctg    360
acgtttagtt ttgtgaccgc cgcggacacg gccgtctact attgtgcgag acataaatat    420
catgatattt tcagggtggt ccctgttgcg ggctggttcg accctggggg ccagggatta    480
ctggtcaccg tctcgagc                                                  498

SEQ ID NO: 673          moltype = DNA   length = 448
FEATURE                 Location/Qualifiers
source                  1..448
                        mol_type = other DNA
```

-continued

```
                        organism = synthetic construct
SEQUENCE: 673
cagytgcagy tgcaggagtc gggcccagga ctggtgaagc cttcggagac cctgtccctc    60
acktgcastg tgtctggtgm ctccatragg ggyrscgact ggggcgakaa tgattattac   120
tggggctgga tccgscagtc cccagggaag ggrctgagtg ggattgggag tttgtcatat   180
stcgcagagt cattasagsg gsgggstmca cmactacaac ccgtccctca agagtcgagt   240
caccttgtcg wtmgacacgt ccaaraatca ggtctccctg aggctkabyt ctgtgaccgc   300
cgcggacacg gccatmtact attgtgcgcg awcgawcact acacggacgg agaawtcatg   360
gtrtwtttgc cttcaaagag tggtyccymt wccgggctgg wtcgacgtct ggggccaggg   420
aathchggtc accgtctgcw sctcctca                                      448

SEQ ID NO: 674          moltype = AA   length = 132
FEATURE                 Location/Qualifiers
source                  1..132
                        mol_type = protein
                        organism = synthetic construct
SEQUENCE: 674
QMQLQESGPG LVKPSETLSL TCSVSGASIS DSYWSWIRRS PGKGLEWIGY VHKSGDTNYS    60
PSLKSRVNLS LDTSKNQVSL SLYAATAADS GKYYCARTLH GRRIYGIVAF NEWFTYFYMD   120
VWGNGTQVTV SS                                                       132

SEQ ID NO: 675          moltype = AA   length = 132
FEATURE                 Location/Qualifiers
source                  1..132
                        mol_type = protein
                        organism = synthetic construct
SEQUENCE: 675
QMQLQESGPG LVKPSETLSL TCSVSGASIS DSYWSWIRRS PGKGLEWIGY VHKSGDTNYI    60
PSLKSRVNLS LDTSKNQVSL SLVAATAADS GKYYCARTLH GRRIYGIVAF NEWFTYFYMD   120
VWGNGTQVTV SS                                                       132

SEQ ID NO: 676          moltype = AA   length = 132
FEATURE                 Location/Qualifiers
source                  1..132
                        mol_type = protein
                        organism = synthetic construct
SEQUENCE: 676
QVHLQESGPG LVKPSETLSL TCNVSGTLVR DNYWSWIRQP LGKQPEWIGY VHDSGDTNYN    60
PSLKSRVHLS LDKSKNLVSL RLTGVTAADS AIYYCATTKH GRRIYGVVAF KEWFTYFYMD   120
VWGKGTSVTV SS                                                       132

SEQ ID NO: 677          moltype = AA   length = 132
FEATURE                 Location/Qualifiers
source                  1..132
                        mol_type = protein
                        organism = synthetic construct
SEQUENCE: 677
QLHLQESGPG LVKPPETLSL TCSVSGASIN DAYWSWIRQS PGKRPEWVGY VHHSGDTNYN    60
PSLKRRVTFS LDTAKNEVSL KLVDLTAADS ATYFCARALH GKRIYGIVAL GELFTYFYMD   120
VWGKGTAVTV SS                                                       132

SEQ ID NO: 678          moltype = AA   length = 137
FEATURE                 Location/Qualifiers
source                  1..137
                        mol_type = protein
                        organism = synthetic construct
SEQUENCE: 678
QPQLQESGPG LVEASETLSL TCTVSGDSTA ACDYFWGWVR QPPGKGLEWI GGLSHCAGYY    60
NTGWTYHNPS LKSRLTISLD TPKNQVFLKL NSVTAADTAI YYCARFDGEV LVYHDWPKPA   120
WVDLWGRGTL VTVTVSS                                                  137

SEQ ID NO: 679          moltype = AA   length = 137
FEATURE                 Location/Qualifiers
source                  1..137
                        mol_type = protein
                        organism = synthetic construct
SEQUENCE: 679
QSQLQESGPR LVEASETLSL TCNVSGESTG ACTYFWGWVR QAPGKGLEWI GSLSHCQSFW    60
GSGWTFHNPS LKSRLTISLD TPKNQVFLKL TSLTAADTAT YYCARFDGEV LVYNHWPKPA   120
WVDLWGRGIP VTVTVSS                                                  137

SEQ ID NO: 680          moltype = AA   length = 129
FEATURE                 Location/Qualifiers
source                  1..129
                        mol_type = protein
                        organism = synthetic construct
SEQUENCE: 680
QVQLQESGPG LVKPAETLSL TCSVSGESIN TGHYYWGWVR QVPGKGLEWI GHIHYTTAVL    60
HNPSLKSRLT IKIYTLRNQI TLRLSNVTAA DTAVYHCVRS GGDILYYYEW QKPHWFSPWG   120
```

```
PGIHVTVSS                                                                    129

SEQ ID NO: 681          moltype = AA  length = 133
FEATURE                 Location/Qualifiers
source                  1..133
                        mol_type = protein
                        organism = synthetic construct
SEQUENCE: 681
QLQMQESGPG LVKPSETLSL SCTVSGDSIR GGEWGDKDYH WGWVRHSAGK GLEWIGSIHW            60
RGTTHYKESL RRRVSMSIDT SRNWFSLRLA SVTAADTAVY FCARHRHHDV FMLVPIAGWF           120
DVWGPGVQVT VSS                                                              133

SEQ ID NO: 682          moltype = AA  length = 134
FEATURE                 Location/Qualifiers
source                  1..134
                        mol_type = protein
                        organism = synthetic construct
SEQUENCE: 682
QLQLQESGPG LVKPSETLSL TCTVSQGSMR GTDWGENDFH YQWIRQSSAK GLEWIGSIHW            60
RGRTTHYKTS FRSRATLSID TSNNRFSLTF SFVTAADTAV YYCARHKYHD IFRVVPVAGW           120
FDPWGQGLLV TVSS                                                             134

SEQ ID NO: 683          moltype = AA  length = 134
FEATURE                 Location/Qualifiers
source                  1..134
                        mol_type = protein
                        organism = synthetic construct
SEQUENCE: 683
QLQLQESGPG LVKPSETLSL TCTVSGGSMR GTDWGENDFH YGWIRQSSAK GLEWIGSIHW            60
RGRTTHYKTS FRSRATLSID TSNNRFSLTF SFVTAADTAV YYCARHKYHD IFRVVPVAGW           120
FDPWGQGLLV TVSS                                                             134

SEQ ID NO: 684          moltype = AA  length = 147
FEATURE                 Location/Qualifiers
source                  1..147
                        mol_type = protein
                        organism = synthetic construct
VARIANT                 2
                        note = X can be any Amino Acid
VARIANT                 23
                        note = X can be any Amino Acid
VARIANT                 27
                        note = X can be any Amino Acid
VARIANT                 30
                        note = X can be any Amino Acid
VARIANT                 32..33
                        note = X can be any Amino Acid
VARIANT                 36..37
                        note = X can be any Amino Acid
VARIANT                 39..40
                        note = X can be any Amino Acid
VARIANT                 57..58
                        note = X can be any Amino Acid
VARIANT                 60..61
                        note = X can be any Amino Acid
VARIANT                 63..67
                        note = X can be any Amino Acid
VARIANT                 69
                        note = X can be any Amino Acid
VARIANT                 71
                        note = X can be any Amino Acid
VARIANT                 73
                        note = X can be any Amino Acid
VARIANT                 82
                        note = X can be any Amino Acid
VARIANT                 90
                        note = X can be any Amino Acid
VARIANT                 94
                        note = X can be any Amino Acid
VARIANT                 96..97
                        note = X can be any Amino Acid
VARIANT                 105
                        note = X can be any Amino Acid
VARIANT                 111..112
                        note = X can be any Amino Acid
VARIANT                 115..116
                        note = X can be any Amino Acid
VARIANT                 118..120
                        note = X can be any Amino Acid
```

```
VARIANT                    122..125
                           note = X can be any Amino Acid
VARIANT                    137
                           note = X can be any Amino Acid
VARIANT                    139..142
                           note = X can be any Amino Acid
SEQUENCE: 684
QXQIQESGPG LVKPSETLSL ICXVSGXSIX GXXWGXXDXX WGWIRQSPGK GIEWIGXXHX      60
XGXXXXXGXI XYXPSIKSRV TXSIDTSKNX VSLXIXXVTA ADTAXYYCAR XXHGXXIXXX     120
VXXXXWFTYF YMDVWGXGXX XXVTVSS                                        147

SEQ ID NO: 685             moltype = DNA   length = 321
FEATURE                    Location/Qualifiers
source                     1..321
                           mol_type = other DNA
                           organism = synthetic construct
SEQUENCE: 685
gaaattgtga tgacgcagtc tcccgacacc ctgtctgtct ctccagggga gacagtcaca      60
ctctcctgca gggccagtca gaatattaac aagaatttag cctggtacca atacaaacct    120
ggccagtctc ccaggctcgt aattttgaa acatatagca agatcgctgc tttccctgcc     180
aggttcgttg ccagtggttc tgggacagag ttcactctca ccatcaacaa catgcagtct    240
gaagatgttg cagtttatta ctgtcaacaa tatgaagagt ggcctcggac gttcgggcaa    300
gggaccaagg tggatatcaa a                                              321

SEQ ID NO: 686             moltype = DNA   length = 321
FEATURE                    Location/Qualifiers
source                     1..321
                           mol_type = other DNA
                           organism = synthetic construct
SEQUENCE: 686
gaaattgtga tgacgcagtc tcccgacacc ctgtctgtct ctccagggga gacagtcaca      60
ctctcctgca gggccagtca gaatattaac aagaatttag cctggtacca atacaaacct    120
ggccagtctc ccaggctcgt aattttgaa acatatagca agatcgctgc tttccctgcc     180
aggttcgttg ccagtggttc tgggacagag ttcactctca ccatcaacaa catgcagtct    240
gaagatgttg cagtttatta ctgtcaacaa tatgaagagt ggcctcggac gttcgggcaa    300
gggaccaagg tggatatcaa a                                              321

SEQ ID NO: 687             moltype = DNA   length = 321
FEATURE                    Location/Qualifiers
source                     1..321
                           mol_type = other DNA
                           organism = synthetic construct
SEQUENCE: 687
gaaatagtga tgacgcagtc tccacccacc ctgtctgtgt ctccagggga aacagccaca      60
ctctcctgta gggccagtca gaatgttaag aataatttag cctggtacca gctgaaacct    120
ggccaggctc ccaggctgct catctttgat gcgtccagca gggccggtgg tattcctgac    180
aggttcagtg gcagcggtta tgggacagac ttcactctca ccgtcaacag tgtgcagtcc    240
gaagattttg gagattattt ttgtcagcaa tatgaagagt ggcctcggac gttcggccaa    300
gggaccaagg tggatatcaa a                                              321

SEQ ID NO: 688             moltype = DNA   length = 321
FEATURE                    Location/Qualifiers
source                     1..321
                           mol_type = other DNA
                           organism = synthetic construct
SEQUENCE: 688
gaaatagtga tgacgcagtc tccacccacc ctgtctgtgt ctccagggga aacagccaca      60
ctctcctgta gggccagtca gaatgttaag aataatttag cctggtacca gctgaaacct    120
ggccaggctc ccaggctcct catctttgat gcgtccagca gggccggtgg tattcctgac    180
aggttcagtg gcagcggtta tgggacagac ttcactctca ccgtcaacag tgtgcagtcc    240
gaagattttg gagattattt ttgtcagcaa tatgaagagt ggcctcggac gttcggccaa    300
gggaccaagg tggatatcaa a                                              321

SEQ ID NO: 689             moltype = DNA   length = 315
FEATURE                    Location/Qualifiers
source                     1..315
                           mol_type = other DNA
                           organism = synthetic construct
SEQUENCE: 689
tccgatatat ctgtggcccc aggagagacg gccaggattt cctgtgggga aaagagcctt      60
ggaagtagag ctgtacaatg gtatcaacac agggccggcc aggcccctc tttaatcata     120
tataataatc aggaccggcc ctcagggatc cctgagcgat tctctggctc ccctgactcc    180
ccttttggga ccacggccac cctgaccatc accagtgtcg aagccgggga tgaggccgac    240
tattactgtc atatatggga tagtagagtt cccaccaaat gggtcttcgg cggagggacc    300
acgctgaccg tgtta                                                     315

SEQ ID NO: 690             moltype = DNA   length = 315
FEATURE                    Location/Qualifiers
source                     1..315
```

```
                           mol_type = other DNA
                           organism = synthetic construct
SEQUENCE: 690
tccgatatat ctgtgcccc aggagagacg gccaggattt cctgtgggga aaagagcctt    60
ggaagtagag ctgtacaatg gtatcaacac agggccggcc aggcccctc tttaatcata    120
tataataatc aggaccggcc ctcagggatc cctgagcgat tctctggctc ccctgactcc   180
cctttggga ccacggccac cctgaccatc accagtgtcg aagccgggga tgaggccgac    240
tattactgtc atatatggga tagtagagtt cccaccaaat gggtcttcgg cggagggacc   300
acgctgaccg tgtta                                                    315

SEQ ID NO: 691              moltype = DNA    length = 315
FEATURE                     Location/Qualifiers
source                      1..315
                            mol_type = other DNA
                            organism = synthetic construct
SEQUENCE: 691
acctttgtgt cagtggcccc aggacagacg gccaggcagg cttgtgggga agagagcctt   60
ggaagtagat ctgttatttg gtatcaacag aggccaggcc agcccccttc attaatcatc   120
tataataata atgaccggcc ctcagggatt cctgaccgat tttctgggtc ccctggctcc   180
acttttggga ccacggccac cctgaccatc accagtgtcg aagccgggga tgaggccgac   240
tattattgtc atatatggga tagtagacga ccaaccaatt gggtcttcgg cgaagggacc   300
acactgatcg tgtta                                                    315

SEQ ID NO: 692              moltype = DNA    length = 315
FEATURE                     Location/Qualifiers
source                      1..315
                            mol_type = other DNA
                            organism = synthetic construct
SEQUENCE: 692
tcctctatgt ccgtgtcccc gggggagacg gccaagatct cctgtggaaa agagagcatt   60
ggtagcagag ctgtgcaatg gtatcagcag aagccaggcc agcccccctc attgattatc   120
tataataatc aggaccgccc cgcagggggtc cctgagcgat tctctgcctc ccctgacttc   180
cgtcctggga ccacggccac cctgaccatc accaatgtcg acgccgagga tgaggccgac   240
tattactgtc atatctatga tgctagaggt ggcaccaatt gggtcttcga cagagggacc   300
acactgaccg tctta                                                    315

SEQ ID NO: 693              moltype = DNA    length = 315
FEATURE                     Location/Qualifiers
source                      1..315
                            mol_type = other DNA
                            organism = synthetic construct
SEQUENCE: 693
cagtctgccc tgactcagcc tccctccgcg tccgggtctc ctggacagtc aatctccatc   60
tcctgcactg gaaccagcaa taggtttgtc tcctggtacc agcaacaccc aggcaaggcc   120
cccaaactcg tcatttatgg ggtcaataag cgccctcag gtgtccctga tcgttttctct   180
ggctccaagt ctggcaacac ggcctcctg accgtctctg ggctcagac tgacgatgag    240
gctgtctatt actgcagctc acttgtaggc aactgggatg tgattttcgg cggagggacc   300
aagttgaccg tcctg                                                    315

SEQ ID NO: 694              moltype = DNA    length = 317
FEATURE                     Location/Qualifiers
source                      1..317
                            mol_type = other DNA
                            organism = synthetic construct
SEQUENCE: 694
cagtctgccc tgactcagcc tccctccgcg tccgggtctc ctggacagtc aatcaccatc   60
tcctgcaatg gaaccgccac taactttgtc tcctggtacc aacaattccc agacaaggcc   120
cccaaactca tcatttatgg ggtcgataag cgcccccccg tgtcccccga tcgtttctct   180
ggctcccggt ctggcacgac ggcctccctt accgtctctc ccgactccag actgacgatg   240
aggctgtcta ttattgcggt tcacttgtcg gcaactggga tgtgattttc ggcggaggga   300
ccaccttgac cgtccta                                                  317

SEQ ID NO: 695              moltype = DNA    length = 326
FEATURE                     Location/Qualifiers
source                      1..326
                            mol_type = other DNA
                            organism = synthetic construct
SEQUENCE: 695
cagtctgccc tgactcagcc tccctccgcg tccgggtctc ttggacagtc agtcaccatc   60
tcctgcaatg gaaccagcag tgacattggc ggttggaatt tgtctcctgg tatcaacagt   120
tcccgggcag agccccagag ctcattattt ttgaggtcaa taagcggccc tcaggggtcc   180
ctggtcgttc tctggctcca agtctgggca attcggcctc cctgaccgtc tctggctcc    240
agtctgacga tgagggtcaa tatttctgca gttcactttt cggcaggtgg gatgttgttt   300
ttgggggac caagctgacc gtccta                                         326

SEQ ID NO: 696              moltype = DNA    length = 354
FEATURE                     Location/Qualifiers
source                      1..354
                            mol_type = other DNA
```

```
                        organism = synthetic construct
SEQUENCE: 696
gaaattgtga tgacgcagtc tccmsmcwcc stgtctgtgt ctccaggaga gacagccact    60
atctcctgta gggmcagwca gcattgacat tggcggtagb aadwmtgtab cctggtacca   120
acasaarccw ggccaggccc ccasrctcat catytttgat amyhataacc ggccckcagg   180
tttccctgab cgtttctctg gctcccctga ctccsgttct gggacmacgg ccaccctgac   240
catcaccagt gtccagkccg argatgaggc mgactattac tgcagttcay mtataggaag   300
agtggmgktc ccaccaatyg gatsttcggc ggagggacca agstgaccgt cwta         354

SEQ ID NO: 697          moltype = DNA   length = 354
FEATURE                 Location/Qualifiers
source                  1..354
                        mol_type = other DNA
                        organism = synthetic construct
SEQUENCE: 697
gaaattgtga tgacgcagtc tccmsmcwcc stgtctgtgt ctccaggaga gacagccact    60
atctcctgta gggmcagwca gcattgacat tggcggtagb astwmtgtak cctggtacca   120
acasaarccw ggccaggccc ccasrctcat catytttgat amyhataacc ggccckcagg   180
tttccctgas cgrttctctg gctcccctga ctccsgttct gggacmacgg ccaccctgac   240
catcaccagt gtccagkccg argatgaggc mgactattac tgcagttcay mtataggaag   300
agtggmgktc ccaccaatyg gatsttcggc ggagggacca agstgaccgt cwta         354

SEQ ID NO: 698          moltype = AA    length = 105
FEATURE                 Location/Qualifiers
source                  1..105
                        mol_type = protein
                        organism = synthetic construct
SEQUENCE: 698
SDISVAPGET ARISCGEKSL GSRAVQWYQH RAGQAPSLII YNNQDRPSGI PERFSGSPDS    60
PFGTTATLTI TSVEAGDEAD YYCHIWDSRV PTKWVFGGGT TLTVL                   105

SEQ ID NO: 699          moltype = AA    length = 105
FEATURE                 Location/Qualifiers
source                  1..105
                        mol_type = protein
                        organism = synthetic construct
SEQUENCE: 699
TFVSVAPGQT ARITCGEESL GSRSVIWYQQ RPGQAPSLII YNNNDRPSGI PDRFSGSPGS    60
TFGTTATLTI TSVEAGDEAD YYCHIWDSRR PTNWVFGEGT TLIVL                   105

SEQ ID NO: 700          moltype = AA    length = 89
FEATURE                 Location/Qualifiers
source                  1..89
                        mol_type = protein
                        organism = synthetic construct
SEQUENCE: 700
SSMSVSPGET AKISCGKESI GSRAVQWYQQ KPGQPPSLII YNNQDRPAGV PERFSASPDF    60
RPGTTATLTI TNVDAEDEAD YYCHIYDAR                                      89

SEQ ID NO: 701          moltype = AA    length = 105
FEATURE                 Location/Qualifiers
source                  1..105
                        mol_type = protein
                        organism = synthetic construct
SEQUENCE: 701
QSALTQPPSA SGSPGQSISI SCTGTSNRFV SWYQQHPGKA PKLVIYGVNK RPSGVPDRFS    60
GSKSGNTASL TVSGLQTDDE AVYYCSSLVG NWDVIFGGGT KLTVL                   105

SEQ ID NO: 702          moltype = AA    length = 105
FEATURE                 Location/Qualifiers
source                  1..105
                        mol_type = protein
                        organism = synthetic construct
SEQUENCE: 702
QSALTQPPSA SGSPGQSITI SCNGTATNFV SWYQQFPDKA PKLIIFGVDK RPPGVPDRFS    60
GSRSGTTASL TVSRLQTDDE AVYYCGSLVG NWDVIFGGGT TLTVL                   105

SEQ ID NO: 703          moltype = AA    length = 110
FEATURE                 Location/Qualifiers
source                  1..110
                        mol_type = protein
                        organism = synthetic construct
SEQUENCE: 703
QSALTQPPSA SGSLGQSVTI SCNGTSSDIG GWNFVSWYQQ FPGRAPRLII FEVNKRPSGV    60
PGRFSGSKSG NSASLTVSGL QSDDEGQYFC SSLFGRWDVV FGGGTKLTVL              110

SEQ ID NO: 704          moltype = AA    length = 107
FEATURE                 Location/Qualifiers
source                  1..107
```

```
                            mol_type = protein
                            organism = synthetic construct
SEQUENCE: 704
EIVMTQSPDT LSVSPGETVT LSCRASQNIN KNLAWYQYKP GQSPRLVIFE TYSKIAAFPA   60
RFVASGSGTE FTLTINNMQS EDVAVYYCQQ YEEWPRTFGQ GTKVDIK                107

SEQ ID NO: 705          moltype = AA  length = 107
FEATURE                 Location/Qualifiers
source                  1..107
                        mol_type = protein
                        organism = synthetic construct
SEQUENCE: 705
EIVMTQSPPT LSVSPGETAT LSCRASQNVK NNLAWYQLKP GQAPRLLIFD ASSRAGGIPD   60
RFSGSGYGTD FTLTVNSVQS EDFGDYFCQQ YEEWPRTFGQ GTKVDIK                107

SEQ ID NO: 706          moltype = AA  length = 116
FEATURE                 Location/Qualifiers
source                  1..116
                        mol_type = protein
                        organism = synthetic construct
VARIANT                 9..11
                        note = X can be any Amino Acid
VARIANT                 24..26
                        note = X can be any Amino Acid
VARIANT                 28..30
                        note = X can be any Amino Acid
VARIANT                 34..35
                        note = X can be any Amino Acid
VARIANT                 37
                        note = X can be any Amino Acid
VARIANT                 41..42
                        note = X can be any Amino Acid
VARIANT                 48
                        note = X can be any Amino Acid
VARIANT                 53..56
                        note = X can be any Amino Acid
VARIANT                 59
                        note = X can be any Amino Acid
VARIANT                 61
                        note = X can be any Amino Acid
VARIANT                 63
                        note = X can be any Amino Acid
VARIANT                 69..70
                        note = X can be any Amino Acid
VARIANT                 72
                        note = X can be any Amino Acid
VARIANT                 82..83
                        note = X can be any Amino Acid
VARIANT                 86..87
                        note = X can be any Amino Acid
VARIANT                 95..101
                        note = X can be any Amino Acid
VARIANT                 104..106
                        note = X can be any Amino Acid
VARIANT                 109
                        note = X can be any Amino Acid
SEQUENCE: 706
EIVMTQSPXX XSVSPGETAT ISCXXXSXXX GGWXXVXWYQ XXPGGAPXLI IFXXXXRPXG   60
XPXRFSGSXX SXFGTTATLT IXXVQXXDEA DYYCXXXXXX XPTXXXFGXG TKLTVL      116

SEQ ID NO: 707          moltype = DNA  length = 480
FEATURE                 Location/Qualifiers
source                  1..480
                        mol_type = other DNA
                        organism = synthetic construct
SEQUENCE: 707
atggactgga tttggaggat cctcttcttg gtggcagcag ttgcaagtgc ccactcgcag   60
gtgcagctgg tgcagtctgg gccggaggtg aagaagcctg gtcctcagt gaaggtctcc   120
tgcaaggcct ctggaaacac cttcagtaaa tatgatgtcc actgggtacg acaggccact   180
ggacaggggc ttgaatgggt gggatggatg agtcatgagg gtgataagac agaatctgca   240
cagagattta aggccgagt caccttcacg agggacactt ccgcaagcac agcctacatg   300
gaactgcgcg gcctgacatc tgacgacacg gccatctatt attgtacgag aggctcaaaa   360
catcgtttgc gagactacgt tctctacgat gactacggct aattaatta tcaagagtgg   420
aatgactacc ttgaattttt ggacgtctgg ggccatgaa ccgcggtcac cgtctcctca   480

SEQ ID NO: 708          moltype = DNA  length = 480
FEATURE                 Location/Qualifiers
source                  1..480
                        mol_type = other DNA
```

```
                      organism = synthetic construct
SEQUENCE: 708
atggactgga tttggaggat cctcttcttg gtggcagcag ttgcaagtgc ccactcgcag   60
gtgcagctgt tgcagtctgg gccggaggtg aagaagcctg gtcctcagt gaaggtctcc   120
tgcaaggcct ctggaaacac cttcagtaaa tatgatgtcc actgggtacg acaggccact  180
ggacaggggc ttgaatgggt gggatggatg agtcatgagg gtgataagac agaatctgca  240
cagagattta agggccgagt caccttcacg agggacactt ccgcaagcac agcctacatg  300
gaactgcgcg gcctgacatc tgacgacacg gccatttatt attgtacgag aggctcaaaa  360
catcgcttgc gagactacgt tctctacgat gactatggct taattaatta tcaagagtgg  420
aatgactacc ttgaattttt ggacgtctgg ggccatggaa ccgcggtcac cgtctcctca  480

SEQ ID NO: 709           moltype = DNA   length = 480
FEATURE                  Location/Qualifiers
source                   1..480
                         mol_type = other DNA
                         organism = synthetic construct
SEQUENCE: 709
atggactgga tttggaggat cctcttcttg gtggcagcag ttgcaagtgc ccactcgcag   60
gtgcagctgg tgcagtctgg gccggaggtg aagaagcctg gtcctcagt gaaggtctcc    120
tgcaaggcct ctggaaacac cttcagtaaa tatgatgtcc actgggtacg acaggccact  180
ggacaggggc ttgaatgggt gggatggatt agtcatgagc gtgataagac agaatctgca  240
cagagattta agggccgagt caccttcacg agggacactt ccgcaaccac agcctacatg  300
gaactgcgcg gcctgacatc tgacgacacg gccatttatt attgtacgag aggctcaaaa  360
catcgcttgc gagactacgt tctctacgat gactacggct taattaatta tcaagagtgg  420
aatgactacc ttgaattttt ggacgtctgg ggccatggaa ccgcggtcac cgtctcctca  480

SEQ ID NO: 710           moltype = DNA   length = 480
FEATURE                  Location/Qualifiers
source                   1..480
                         mol_type = other DNA
                         organism = synthetic construct
SEQUENCE: 710
atggactgga tttggaggat cctcttcttg gtggcagcag ttgcaagtgc ccacgcgcag   60
gtgcagctgg agcagtctgg gccggaggtg aagaagcctg gtcctcagt gaaggtctcc    120
tgcaaggcct ctggaaacac cttcagtaaa tatgatgtcc actgggtacg acaggccact  180
ggacaggggc ttgaatgggt gggatggatg agtcatgagg gtgataagac agaatctgca  240
cagagattta aggggcgagt caccttcacg agggacactt ccgcaagcac agcctacatg  300
gaactgcgcg gcctgacatc tgacgacacg gccatttatt attgtacgag aggttcaaaa  360
catcgcttgc gagactacgt tctctacgat gactacggct taattaatta tcaagagtgg  420
aatgactacc ttgaattttt ggacgtctgg ggccatggaa ccgcggtcac cgtctcctca  480

SEQ ID NO: 711           moltype = DNA   length = 480
FEATURE                  Location/Qualifiers
source                   1..480
                         mol_type = other DNA
                         organism = synthetic construct
SEQUENCE: 711
atggactgga tttggaggat cctcttcttg gtggcagcag ttgcaagtgc ccactcgcag   60
gtgcagctgg tgcagtctgg gccggaggtg aagaagcctg gtcctcagt gaaggtctcc    120
tgcaaggcct ctggaaacac cttcaggaaa tatgatgtcc actgggtacg acaggccact  180
ggacaggggc ttgaatgggt gggatggatg agtcatgagg gtgataagac agaatctgca  240
cagagattta agggccgagt ctctttcacg agggacaatt ccgcaagcac agcctacatg  300
gaactgcgcg gcctgacatc tgacgacacg gccatttatt attgtaccgg aggctcaaaa  360
catcgcttgc gagactacgt tctctacgat gattacggcc taataaatca gcaagagtag  420
aatgactacc ttgaattttt ggacgtctgg ggccatggaa ccgcggtcac cgtctcctca  480

SEQ ID NO: 712           moltype = DNA   length = 480
FEATURE                  Location/Qualifiers
source                   1..480
                         mol_type = other DNA
                         organism = synthetic construct
SEQUENCE: 712
atggactgga tttggaggat cctcttcttg gtggcagcag ttgcaagtgc ccactcgcag   60
gtgcagctgg tgcagtctgg gccggaggtg aagaagcctg gtcctcagt gaaggtctcc    120
tgcaaggcct ctggaaacac cttcagtaaa tatgatgtcc actgggtacg acaggccact  180
ggacaggggc ttgaatgggt gggatggatg agtcatgagg gtgataagac agaatctgca  240
cagagattta agggccgagt caccttcacg agggacactt ccgcaagcac agcctacatg  300
gaactgcgcg gcctgacatc tgacgacacg gccatctatt attgtaggag aggctcaaaa  360
catcgcttgc gagactacgt tctctacgat gactacggct taattaatta tcaagagtgg  420
aatgactacc ttgaattttt ggacgtctgg ggccatggaa ccgcggtcac cgtctcctca  480

SEQ ID NO: 713           moltype = DNA   length = 396
FEATURE                  Location/Qualifiers
source                   1..396
                         mol_type = other DNA
                         organism = synthetic construct
SEQUENCE: 713
atgaggctcc tgctcagct cctggggctg ctaatgctct gggtctctgg atccagtgcg    60
gatactgtct tgactcagtc tccactctcc ctgcccgtca ccctggaga ggcggcctcc    120
```

```
atgtcctgtt cgtcgactca gagcctccgg catagtaatg gagccaacta tttggcttgg    180
taccagcaca aaccggggca gtctccacga ctcctaatcc gtttaggttc tcaacgggcc    240
tccggggtcc ctgacagatt cagtggcagt ggatcaggca ctcattttac actgaaaatc    300
agtagagtgg aggctgaaga tgctgcaatt tattattgca tgcaaggtct gaaccgtccc    360
tggacgttcg gcaaggggac caagttggaa atcaaa                              396

SEQ ID NO: 714         moltype = DNA   length = 396
FEATURE                Location/Qualifiers
source                 1..396
                       mol_type = other DNA
                       organism = synthetic construct
SEQUENCE: 714
atgaggctcc ctgctcagct cctggggctg ctaatgctct gggtctctgg atccagtgcg    60
gatactgtcg tgactcagtc tccactctcc ctgcccgtca cccctggaga ggcggcctcc   120
atgtcctgta cgtcgactca gagcctccgt catagtaatg gagccaacta tttggcttgg   180
taccagcaca aaccgggca  gtctccacga ctcctaatcc gtttaggttc tcaacgggcc   240
tccggggtcc ctgacagatt cagtggcagt ggatcaggca ctcattttac actgaaaatc   300
agtcgagtgg aggctgaaga tgctgcaatt tattattgca tgcaaggtct gaaccgtccc   360
tggacgttcg gcaaggggac caagttggaa atcaaa                              396

SEQ ID NO: 715         moltype = DNA   length = 396
FEATURE                Location/Qualifiers
source                 1..396
                       mol_type = other DNA
                       organism = synthetic construct
SEQUENCE: 715
atgaggctcc ctgctcagct cctggggctg ctaatgctct gggtctctgg atccagtgcg    60
gatactgtcg tgactcagtc tccactctcc ctgcccgtca cccctggaga ggcggcctcc   120
atgtcctgta cgtcgactca gagcctccgg catagtaatg gagccaacta tttggcttgg   180
taccagcaca aaccggggca gtctccacga ctcctaatcc gtttaggttc tcaacgggcc   240
tccggggtcc ctgacagatt cagtggcagt ggatcaggca ctcattttac actgaaaatc   300
agtcgagtgg aggctgaaga tgctgcaatt tattattgca tgcaaggtct gaaccgtccc   360
tggacgttcg gcaaggggac caagttggag atcaaa                              396

SEQ ID NO: 716         moltype = DNA   length = 372
FEATURE                Location/Qualifiers
source                 1..372
                       mol_type = other DNA
                       organism = synthetic construct
SEQUENCE: 716
atgaggctcc ctgctcagct cctggggctg ctaatgctct gggtctctgg atccagtgcg    60
gatactgtcg tgactcagtc tccactctcc ctgcccgtca cccctggaga ggcggcctcc   120
atgtcctgtt cgtcgactca gagcctccgg catagtaatg gagccaacta tttggcttgg   180
taccagcaca aaccggggca gtctccacga ctcctaatcc gtttaggttc tcaacgggcc   240
tccggggtcc ctgacagatt cagtggcagt ggatcaggca ctcattttac actgaaaatc   300
agtagagtgg aggctgaaga tgctgcaatt tattattgca tgcaaggtct gaaccgtccc   360
tggacgttcg gc                                                        372

SEQ ID NO: 717         moltype = AA   length = 141
FEATURE                Location/Qualifiers
source                 1..141
                       mol_type = protein
                       organism = synthetic construct
SEQUENCE: 717
QVQLVQSGPE VKKPGSSVKV SCKASGNTFS KYDVHWVRQA TGQGLEWVGW MSHEGDKTES     60
AQRFKGRVTF TRDTSASTAY MELRGLTSDD TAIYYCTRGS KHRLRDYVLY DDYGLINYQE    120
WNDYLEFLDV WGHGTAVTVS S                                              141

SEQ ID NO: 718         moltype = AA   length = 141
FEATURE                Location/Qualifiers
source                 1..141
                       mol_type = protein
                       organism = synthetic construct
SEQUENCE: 718
QVQLVQSGPE VKKPGSSVKV SCKASGNTFS KYDVHWVRQA TGQGLEWVGW ISHERDKTES     60
AQRFKGRVTF TRDTSASTAY MELRGLTSDD TAIYYCTRGS KHRLRDYVLY DDYGLINYQE    120
WNDYLEFLDV WGHGTAVTVS S                                              141

SEQ ID NO: 719         moltype = AA   length = 141
FEATURE                Location/Qualifiers
source                 1..141
                       mol_type = protein
                       organism = synthetic construct
SEQUENCE: 719
QVQLVQSGAE VKKPGSSVKV SCKASGNTFS KYDVHWVRQA TGQGLEWVGW MSHEGDKTES     60
AQRFKGRVTF TRDTSASTAY MELRGLTSDD TAIYYCTRGS KHRLRDYVLY DDYGLINYQE    120
WNDYLEFLDV WGHGTAVTVS S                                              141

SEQ ID NO: 720         moltype = AA   length = 141
```

```
FEATURE             Location/Qualifiers
source              1..141
                    mol_type = protein
                    organism = synthetic construct
SEQUENCE: 720
QVQLVQSGAE VKKPGSSVKV SCKASGNTFS KYDVHWVRQA TGQGLEWVGW MSHEGDKTES    60
AQRFKGRVSF TRDNSASTAY IELRGLTSDD TAIYYCTGGS KHRLRDYVLY DDYGLINQQE   120
WNDYLEFLDV WGHGTAVTVS S                                             141

SEQ ID NO: 721      moltype = AA  length = 112
FEATURE             Location/Qualifiers
source              1..112
                    mol_type = protein
                    organism = synthetic construct
SEQUENCE: 721
DTVVTQSPLS LPVTPGEAAS MSCSSTQSLR HSNGANYLAW YQHKPGQSPR LLIRLGSQRA    60
SGVPDRFSGS GSGTHFTLKI SRVEAEDAAI YYCMQGLNRP WTFGKGTKLE IK           112

SEQ ID NO: 722      moltype = AA  length = 112
FEATURE             Location/Qualifiers
source              1..112
                    mol_type = protein
                    organism = synthetic construct
SEQUENCE: 722
DTVVTQSPLS LPVTPGEAAS MSCSSTQSLR HSNGANYLAW YQHKPGQSPR LLIRLGSQRA    60
SGVPDRFSGS GSGTHFTLKI SRVEDEDAAI YYCMQGLNRP WTFGKGTKLE IK           112

SEQ ID NO: 723      moltype = AA  length = 112
FEATURE             Location/Qualifiers
source              1..112
                    mol_type = protein
                    organism = synthetic construct
SEQUENCE: 723
DTVVTQSPLS LSVTPGEAAS MSCTSTQSLR HSNGANYLAW YQHKPGQSPR LLIRLGSQRA    60
SGVPDRFSGS GSGTHFTLKI SRVEAEDAAI YYCMQGLNRP WTFGKGTKLE IK           112

SEQ ID NO: 724      moltype = AA  length = 112
FEATURE             Location/Qualifiers
source              1..112
                    mol_type = protein
                    organism = synthetic construct
SEQUENCE: 724
DTVVTQSPLS LPVTPGEAAS MSCSSTQSLR HSNGANYLAW YQHKPGQSPR LLIRLGSQRA    60
SGVPDRFSGS GSGTHFTLKI SRVEADDAAI YYCMQGLNRP WTFGKGTKLE IK           112
```

What is claimed is:

1. A non-naturally occurring PGT-124 monoclonal antibody comprising (a) a light chain variable region comprising three complementarity determining regions having the amino acid sequences of SEQ ID NOs: 415, 151, and 416 and (b) a heavy chain variable region comprising three complementarity determining regions having the amino acid sequences of SEQ ID NOs: 406, 407, and 408, wherein the CDRs are per Kabat definition, wherein the antibody comprises an engineered Fc region incorporating a salvage receptor binding epitope, thereby exhibiting increased serum half-life through enhanced interaction with the neonatal Fc receptor (FcRn).

2. The antibody of claim 1, comprising a light chain variable region having the amino acid sequence of SEQ ID NO: 414 and a heavy chain variable region having the amino acid sequence of SEQ ID NO: 405.

3. The antibody of claim 1, comprising a light chain having the amino acid sequence of SEQ ID NO: 413 and a heavy chain having the amino acid sequence of SEQ ID NO: 404.

4. An antigen-binding fragment of the antibody according to claim 1.

5. The antigen-binding fragment of the antibody according to claim 4, which is selected from the group consisting of the Fab, Fab', F(ab')2, Fv, single chain Fv, diabody, and domain antibody (dAb) fragments.

6. A nucleic acid molecule encoding the antibody according to claim 1, wherein the nucleic acid molecule encodes a light chain variable region comprising the nucleic acid sequence of SEQ ID NO: 412 and a heavy chain variable region comprising the nucleic acid sequence of SEQ ID NO: 403.

7. A nucleic acid molecule encoding the antibody according to claim 1, wherein the nucleic acid molecule encodes a light chain sequence comprising the nucleic acid sequence of SEQ ID NO: 411 and a heavy chain sequence comprising the nucleic acid sequence of SEQ ID NO: 402.

8. The nucleic acid molecule according to claim 6, which is selected from the group consisting of cDNA, hnRNA, and mRNA.

9. A vector comprising the nucleic acid molecule according to claim 6.

10. A cell comprising the vector according to claim 8.

11. An immortalized B cell clone expressing the antibody according to claim 1.

12. A pharmaceutical composition comprising the antibody of claim 1 and a pharmaceutically acceptable carrier.

13. A pharmaceutical composition comprising the nucleic acid molecule of claim 6 and a pharmaceutically acceptable carrier.

14. A method of treating an HIV-1 infection, or for post-exposure prophylaxis comprising administering a pharmaceutical composition, in an effective amount, comprising the antibody of claim 1 to a patient in need thereof.

15. A method of treating an HIV-1 infection, or for post-exposure prophylaxis comprising administering a pharmaceutical composition, in an effective amount comprising the nucleic acid molecule of claim 6 to a patient in need thereof;
   wherein the nucleic acid molecule comprises a DNA expression system comprising a promoter and leader sequence operably linked to the variable region sequence, and/or operably linked to an origin of replication, and/or operably linked to one or more selectable markers, and/or operably linked to one or more control elements/regulatory sequences.

16. A method for producing the antibody of claim 1, comprising the steps of (i) culturing a host cell that expresses the antibody of claim 1 and (ii) isolating the antibody.

* * * * *